US008048862B2

(12) United States Patent
Seiwert et al.

(10) Patent No.: US 8,048,862 B2
(45) Date of Patent: Nov. 1, 2011

(54) MACROCYCLIC INHIBITORS OF HEPATITIS C VIRUS REPLICATION

(75) Inventors: Scott D. Seiwert, Pacifica, CA (US); Leonid Beigelman, San Mateo, CA (US); Brad Buckman, Oakland, CA (US); Antitsa Dimitrova Stoycheva, Half Moon Bay, CA (US); Steven B. Porter, Mill Valley, CA (US); Williamson Ziegler Bradford, Ross, CA (US); Vladimir Serebryany, Burlingame, CA (US)

(73) Assignee: InterMune, Inc., Brisbane, CA (US)

( * ) Notice: Subject to any disclaimer, the term of this patent is extended or adjusted under 35 U.S.C. 154(b) by 122 days.

(21) Appl. No.: 12/423,681

(22) Filed: Apr. 14, 2009

(65) Prior Publication Data

US 2009/0269305 A1 Oct. 29, 2009

Related U.S. Application Data

(60) Provisional application No. 61/045,220, filed on Apr. 15, 2008, provisional application No. 61/105,736, filed on Oct. 15, 2008, provisional application No. 61/105,751, filed on Oct. 15, 2008, provisional application No. 61/143,728, filed on Jan. 9, 2009, provisional application No. 61/150,693, filed on Feb. 6, 2009.

(51) Int. Cl.

| | |
|---|---|
| ***A61K 38/21*** | (2006.01) |
| ***A61K 31/4709*** | (2006.01) |
| ***A61K 31/7056*** | (2006.01) |
| ***A61K 31/4738*** | (2006.01) |
| ***A61K 31/407*** | (2006.01) |
| ***A61K 31/4725*** | (2006.01) |
| ***A61K 31/517*** | (2006.01) |
| ***A61K 31/403*** | (2006.01) |
| ***C07D 245/04*** | (2006.01) |
| ***C07D 209/02*** | (2006.01) |

(52) U.S. Cl. .......... 514/43; 514/312; 514/285; 514/411; 514/309; 514/266.2; 514/336; 514/365; 514/414; 540/460; 424/85.5; 424/85.7; 548/465

(58) Field of Classification Search .................. 514/365, 514/336, 414; 548/465
See application file for complete search history.

(56) References Cited

U.S. PATENT DOCUMENTS

| | | | |
|---|---|---|---|
| 5,034,394 | A | 7/1991 | Daluge |
| 5,232,928 | A | 8/1993 | Skiles |
| 5,624,949 | A | 4/1997 | Heath et al. |
| 5,656,627 | A | 8/1997 | Bemis et al. |
| 5,756,466 | A | 5/1998 | Bemis et al. |
| 5,847,135 | A | 12/1998 | Bemis et al. |
| 5,968,895 | A | 10/1999 | Gefter et al. |
| 6,329,417 | B1 | 12/2001 | Llinas-Brunet et al. |
| 6,608,027 | B1 | 8/2003 | Tsantrizos et al. |
| 6,642,204 | B2 | 11/2003 | Llinas-Brunet et al. |
| 6,693,072 | B2 | 2/2004 | Gallion et al. |
| 6,767,991 | B1 | 7/2004 | Llinas-Brunet et al. |
| 6,846,802 | B2 | 1/2005 | Chen et al. |
| 6,858,600 | B2 | 2/2005 | Hamilton et al. |
| 6,867,303 | B2 | 3/2005 | Grela |
| 6,909,000 | B2 | 6/2005 | Farmer et al. |
| 6,919,423 | B2 | 7/2005 | Llinas-Brunet |
| 7,012,066 | B2 | 3/2006 | Saksena et al. |
| 7,041,698 | B2 | 5/2006 | Ripka et al. |
| 7,132,504 | B2 | 11/2006 | Scola et al. |
| 7,157,424 | B2 | 1/2007 | Chen et al. |
| 7,173,057 | B2 | 2/2007 | Chen et al. |
| 7,208,600 | B2 | 4/2007 | Cottrell et al. |
| 7,273,885 | B2 | 9/2007 | Pitlik et al. |
| 7,491,794 | B2 | 2/2009 | Blatt et al. |
| 7,829,665 | B2 | 11/2010 | Blatt et al. |
| 2002/0016294 | A1 | 2/2002 | Venkatraman et al. |
| 2002/0016442 | A1 | 2/2002 | Llinas-Brunet et al. |
| 2002/0037998 | A1 | 3/2002 | Llinas-Brunet et al. |
| 2002/0107181 | A1 | 8/2002 | Chen et al. |
| 2002/0111313 | A1 | 8/2002 | Campbell et al. |
| 2003/0181363 | A1 | 9/2003 | Llinas-Brunet et al. |
| 2003/0186895 | A1 | 10/2003 | Llinas-Brunet et al. |
| 2003/0191067 | A1 | 10/2003 | Llinas-Brunet et al. |
| 2003/0195228 | A1 | 10/2003 | Chen et al. |
| 2003/0224977 | A1 | 12/2003 | Llinas-Brunet et al. |
| 2003/0236242 | A1 | 12/2003 | Perni et al. |
| 2004/0002448 | A1 | 1/2004 | Tsantrizos et al. |
| 2004/0018986 | A1 | 1/2004 | Pitlik et al. |
| 2004/0038872 | A1 | 2/2004 | Campbell et al. |
| 2004/0048802 | A1 | 3/2004 | Ripka et al. |
| 2004/0072761 | A1 | 4/2004 | Campbell et al. |

(Continued)

FOREIGN PATENT DOCUMENTS

| | | |
|---|---|---|
| CA | 2370400 | 8/2003 |

(Continued)

OTHER PUBLICATIONS

Wu and Farrelly, Toxicology 236:1-6, 2007.* Beaulieu et al., Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease., J. Org. Chem., 2005, 70: 5869-5879.

Bedossa et al.—The French Metavir Cooperative Study Group, "Intraobserver and Interobserver Variations in Liver Biopsy Interpretation in Patients with Chronic Hepatitis C" Hepatology, 1994, 20:15-20.

Belokon et al., A General Method for the Asymmetric Synthesis of anti-Diastereoisomers of b-Substituted L-2-Aminobutanoic Acids via Chiral Nickel Schiffs Base Complexes of Dehydroaminobutanoic Acid. X-Ray Crystal and Molecular Structure of the Nickel Complex of the Schiff's Base from [(Benzylprolyl)amino]benzophenone and Dehydroaminobutanoic Acid. , (1990) 8: 2301-2310., J. Chem. Soc. Perkin Trans. 1, 1990, 8: 2301-2310.

(Continued)

*Primary Examiner* — Yong Chu
(74) *Attorney, Agent, or Firm* — Knobbe Martens Olson & Bear LLP

(57) ABSTRACT

The embodiments provide compounds of the general Formulae I, II, III, IV, V, VI, VII, and X, as well as compositions, including pharmaceutical compositions, comprising a subject compound. The embodiments further provide treatment methods, including methods of treating a hepatitis C virus infection and methods of treating liver fibrosis, the methods generally involving administering to an individual in need thereof an effective amount of a subject compound or composition.

40 Claims, No Drawings

U.S. PATENT DOCUMENTS

| | | | |
|---|---|---|---|
| 2004/0077551 | A1 | 4/2004 | Campbell et al. |
| 2004/0106559 | A1 | 6/2004 | Wang et al. |
| 2004/0138109 | A1 | 7/2004 | Chen et al. |
| 2004/0180815 | A1 | 9/2004 | Nakajima et al. |
| 2004/0229776 | A1 | 11/2004 | Chen et al. |
| 2004/0229777 | A1 | 11/2004 | Cerreta et al. |
| 2004/0229848 | A1 | 11/2004 | Demuth et al. |
| 2004/0259804 | A1 | 12/2004 | Karanewsky |
| 2005/0049187 | A1 | 3/2005 | Brandenburg et al. |
| 2005/0065073 | A1 | 3/2005 | Wu et al. |
| 2005/0080017 | A1 | 4/2005 | Cottrell et al. |
| 2005/0090432 | A1 | 4/2005 | McPhee et al. |
| 2005/0119189 | A1 | 6/2005 | Cottrell et al. |
| 2005/0119453 | A1 | 6/2005 | Brenner et al. |
| 2005/0136400 | A1 | 6/2005 | Lin et al. |
| 2005/0143316 | A1 | 6/2005 | Tu et al. |
| 2005/0153877 | A1 | 7/2005 | Miao et al. |
| 2005/0153900 | A1 | 7/2005 | Velazquez et al. |
| 2005/0192212 | A1 | 9/2005 | Llinas-Brunet et al. |
| 2005/0197301 | A1 | 9/2005 | Njoroge et al. |
| 2005/0209135 | A1 | 9/2005 | Busacca et al. |
| 2005/0215486 | A1 | 9/2005 | Cottrell et al. |
| 2005/0215513 | A1 | 9/2005 | Boojamra et al. |
| 2005/0215525 | A1 | 9/2005 | Boojamra et al. |
| 2005/0222047 | A1 | 10/2005 | Chen et al. |
| 2005/0245458 | A1 | 11/2005 | Arasappan et al. |
| 2005/0261200 | A1 | 11/2005 | Miao et al. |
| 2005/0267018 | A1 | 12/2005 | Blatt et al. |
| 2005/0267043 | A1 | 12/2005 | Bogen et al. |
| 2005/0267151 | A1 | 12/2005 | Busacca et al. |
| 2005/0272663 | A1 | 12/2005 | Arasappan et al. |
| 2006/0009667 | A1 | 1/2006 | Herweck et al. |
| 2006/0019905 | A1 | 1/2006 | Bailey et al. |
| 2006/0046956 | A1 | 3/2006 | Sannigrahi et al. |
| 2006/0063915 | A1 | 3/2006 | Gallou et al. |
| 2006/0063916 | A1 | 3/2006 | Gallou |
| 2006/0069099 | A1 | 3/2006 | Fu et al. |
| 2006/0122123 | A1 | 6/2006 | Chaudhary et al. |
| 2006/0128692 | A1 | 6/2006 | Chen et al. |
| 2006/0183694 | A1 | 8/2006 | Sin et al. |
| 2006/0198824 | A1 | 9/2006 | Malcolm et al. |
| 2006/0205638 | A1 | 9/2006 | Busacca et al. |
| 2006/0210969 | A1 | 9/2006 | Rice et al. |
| 2006/0269516 | A1 | 11/2006 | Presta et al. |
| 2006/0275366 | A1 | 12/2006 | Malcolm et al. |
| 2006/0276405 | A1 | 12/2006 | Albrecht |
| 2007/0010455 | A1 | 1/2007 | Hewawasam et al. |
| 2007/0027071 | A1 | 2/2007 | Holloway et al. |
| 2007/0032433 | A1 | 2/2007 | Saksena et al. |
| 2007/0054842 | A1 | 3/2007 | Blatt et al. |
| 2007/0054864 | A1 | 3/2007 | Graupe et al. |
| 2007/0072809 | A1 | 3/2007 | Cho et al. |
| 2007/0078081 | A1 | 4/2007 | Casarez et al. |
| 2007/0093414 | A1 | 4/2007 | Carini et al. |
| 2007/0112001 | A1 | 5/2007 | Anselm et al. |
| 2007/0161574 | A1 | 7/2007 | Rosenquist et al. |
| 2007/0197448 | A1 | 8/2007 | Velazquez et al. |
| 2007/0231262 | A1 | 10/2007 | Lin et al. |
| 2007/0281885 | A1 | 12/2007 | Sun et al. |
| 2007/0299078 | A1 | 12/2007 | Niu et al. |
| 2008/0014173 | A1 | 1/2008 | Scola et al. |
| 2008/0019942 | A1 | 1/2008 | Seiwert et al. |
| 2008/0032936 | A1 | 2/2008 | Gai et al. |
| 2008/0038225 | A1 | 2/2008 | Sun et al. |
| 2008/0039470 | A1 | 2/2008 | Niu et al. |
| 2008/0057031 | A1* | 3/2008 | Casarez et al. ............... 424/85.7 |
| 2008/0107624 | A1 | 5/2008 | D'Andrea et al. |
| 2008/0107625 | A1 | 5/2008 | D'Andrea et al. |
| 2008/0119461 | A1 | 5/2008 | Sin et al. |
| 2008/0125444 | A1 | 5/2008 | Sun et al. |
| 2008/0267916 | A1 | 10/2008 | Gai et al. |
| 2008/0267917 | A1 | 10/2008 | Niu et al. |
| 2008/0267918 | A1 | 10/2008 | Gai et al. |
| 2008/0269228 | A1 | 10/2008 | Moore et al. |
| 2008/0269502 | A1 | 10/2008 | Gantz et al. |
| 2008/0274080 | A1 | 11/2008 | Or et al. |
| 2008/0274082 | A1 | 11/2008 | Gai et al. |
| 2008/0279821 | A1 | 11/2008 | Niu et al. |
| 2008/0286230 | A1 | 11/2008 | Sommadossi et al. |
| 2008/0317712 | A1 | 12/2008 | Niu et al. |
| 2009/0005387 | A1 | 1/2009 | Niu et al. |
| 2009/0035267 | A1 | 2/2009 | Moore et al. |
| 2009/0035268 | A1 | 2/2009 | Sun et al. |
| 2009/0035272 | A1 | 2/2009 | Moore et al. |
| 2009/0041721 | A1 | 2/2009 | Niu et al. |
| 2009/0047244 | A1 | 2/2009 | Parsy et al. |
| 2009/0047248 | A1 | 2/2009 | Sun et al. |
| 2009/0048297 | A1 | 2/2009 | Phadke et al. |
| 2009/0053175 | A1 | 2/2009 | Or et al. |
| 2009/0060874 | A1 | 3/2009 | Qiu et al. |
| 2009/0062311 | A1 | 3/2009 | Simmen et al. |
| 2009/0075869 | A1 | 3/2009 | Holloway et al. |
| 2009/0082261 | A1 | 3/2009 | Chen et al. |
| 2009/0082366 | A1 | 3/2009 | Czarnik |
| 2009/0093533 | A1 | 4/2009 | Beigelman et al. |
| 2009/0098085 | A1 | 4/2009 | Sun et al. |
| 2009/0105471 | A1 | 4/2009 | Blatt et al. |
| 2009/0111757 | A1 | 4/2009 | Lin et al. |
| 2009/0111969 | A1 | 4/2009 | Blatt et al. |
| 2009/0111982 | A1 | 4/2009 | Blatt et al. |
| 2009/0123423 | A1 | 5/2009 | Gai et al. |
| 2009/0123425 | A1 | 5/2009 | Moore et al. |
| 2009/0130059 | A1 | 5/2009 | Sun et al. |
| 2009/0148407 | A1 | 6/2009 | Blatt et al. |
| 2009/0149491 | A1 | 6/2009 | Liu et al. |
| 2009/0155209 | A1 | 6/2009 | Blatt et al. |
| 2009/0155210 | A1 | 6/2009 | Gai et al. |
| 2009/0163706 | A1 | 6/2009 | Hildbrand et al. |
| 2009/0169510 | A1 | 7/2009 | Blatt et al. |
| 2009/0180983 | A1 | 7/2009 | Moore et al. |
| 2009/0180985 | A1 | 7/2009 | Liu et al. |
| 2009/0202480 | A1 | 8/2009 | Parsy et al. |
| 2009/0203008 | A1 | 8/2009 | Ludmerer et al. |
| 2009/0203629 | A1 | 8/2009 | Holsinger |
| 2009/0269305 | A1 | 10/2009 | Seiwert et al. |
| 2009/0274657 | A1 | 11/2009 | Gai et al. |
| 2009/0275714 | A1 | 11/2009 | Puentener et al. |
| 2009/0285773 | A1 | 11/2009 | Sun et al. |
| 2009/0285774 | A1 | 11/2009 | Sin et al. |
| 2009/0286814 | A1 | 11/2009 | Lin et al. |
| 2009/0286843 | A1 | 11/2009 | Blatt et al. |
| 2009/0297472 | A1 | 12/2009 | Wang et al. |
| 2009/0297476 | A1 | 12/2009 | Seiwert et al. |
| 2010/0003217 | A1 | 1/2010 | Cretton-Scott et al. |
| 2010/0022578 | A1 | 1/2010 | Raboisson et al. |
| 2010/0068176 | A1 | 3/2010 | Belema et al. |
| 2010/0074867 | A1 | 3/2010 | Venkatraman et al. |
| 2010/0074890 | A1 | 3/2010 | Hagel et al. |
| 2010/0080770 | A1 | 4/2010 | Hiebert et al. |
| 2010/0080771 | A1 | 4/2010 | Hiebert et al. |
| 2010/0081700 | A1 | 4/2010 | Wang et al. |
| 2010/0087382 | A1 | 4/2010 | Bailey et al. |
| 2010/0119479 | A1 | 5/2010 | Buckman et al. |
| 2010/0124545 | A1 | 5/2010 | Zhang et al. |
| 2010/0150866 | A1 | 6/2010 | Wang et al. |
| 2010/0152103 | A1 | 6/2010 | Phadke et al. |
| 2010/0160403 | A1 | 6/2010 | Link et al. |
| 2010/0168384 | A1* | 7/2010 | Mcdaniel et al. ............. 530/330 |
| 2010/0173939 | A1 | 7/2010 | Link |
| 2010/0196321 | A1 | 8/2010 | Cooper et al. |
| 2010/0215616 | A1 | 8/2010 | Romine et al. |
| 2010/0221217 | A1 | 9/2010 | Porter et al. |
| 2010/0260710 | A1 | 10/2010 | Parsy et al. |

FOREIGN PATENT DOCUMENTS

| | | |
|---|---|---|
| CL | 01958-96 | 7/1997 |
| CL | 2703-97 | 12/1997 |
| CL | REG. 39715 | 6/1998 |
| CL | 01184-98 | 3/1999 |
| CL | 1797-99 | 8/1999 |
| CL | 1804-99 | 8/1999 |
| CL | 795-00 | 4/2000 |
| CL | 766-01 | 10/2001 |
| CL | 144-03 | 1/2003 |
| CL | 167-03 | 1/2003 |
| CL | 168-03 | 1/2003 |
| CL | 1161-04 | 12/2004 |

| | | | |
|---|---|---|---|
| CL | 120-05 | | 1/2005 |
| EA | 2006 07738 | B1 | 12/2006 |
| EP | 0206497 | A2 | 12/1986 |
| EP | 0349242 | A2 | 1/1990 |
| JP | 2002/542160 | | 10/2000 |
| RU | 2247126 | C2 | 2/2005 |
| WO | WO 97/18207 | | 5/1997 |
| WO | WO 97/43310 | | 11/1997 |
| WO | WO 98/17679 | | 4/1998 |
| WO | WO 98/46630 | | 10/1998 |
| WO | WO 98/51665 | | 11/1998 |
| WO | WO 99/07733 | | 2/1999 |
| WO | WO 99/07734 | | 2/1999 |
| WO | WO 99/47545 | | 9/1999 |
| WO | WO 00/09543 | | 2/2000 |
| WO | WO 00/09558 | | 2/2000 |
| WO | WO 00/23421 | | 4/2000 |
| WO | WO 00/59929 | | 10/2000 |
| WO | WO 01/74768 | | 10/2001 |
| WO | WO 01/81325 | | 11/2001 |
| WO | WO 02/18369 | | 3/2002 |
| WO | WO 02/060926 | | 8/2002 |
| WO | WO 03/002518 | | 1/2003 |
| WO | WO 03/053349 | | 7/2003 |
| WO | WO 03/062228 | | 7/2003 |
| WO | WO 03/062265 | | 7/2003 |
| WO | WO 03/064416 | | 8/2003 |
| WO | WO 03/064455 | | 8/2003 |
| WO | WO 03/064456 | | 8/2003 |
| WO | WO 03/066103 | | 8/2003 |
| WO | WO 03/099274 | | 12/2003 |
| WO | WO 2004/009121 | | 1/2004 |
| WO | WO 2004/026896 | | 4/2004 |
| WO | WO 2004/037855 | | 5/2004 |
| WO | WO 2004/039833 | | 5/2004 |
| WO | WO 2004/072243 | | 8/2004 |
| WO | WO 2004/089974 | | 10/2004 |
| WO | WO 2004/092162 | | 10/2004 |
| WO | WO 2004/092203 | | 10/2004 |
| WO | WO 2004/093798 | | 11/2004 |
| WO | WO 2004/093915 | | 11/2004 |
| WO | WO 2004/094452 | | 11/2004 |
| WO | WO 2004/096286 | | 11/2004 |
| WO | WO 2004094452 | A2 * | 11/2004 |
| WO | WO 2004/103996 | | 12/2004 |
| WO | WO 2004/113365 | | 12/2004 |
| WO | WO 2005/003147 | | 1/2005 |
| WO | WO 2005/010029 | | 2/2005 |
| WO | WO 2005/021584 | | 3/2005 |
| WO | WO 2005/028501 | | 3/2005 |
| WO | WO 2005/035525 | | 4/2005 |
| WO | WO 2005/037214 | | 4/2005 |
| WO | WO 2005/039552 | | 5/2005 |
| WO | WO 2005/046712 | | 5/2005 |
| WO | WO 2005/051410 | | 6/2005 |
| WO | WO 2005/051980 | | 6/2005 |
| WO | WO 2005/056182 | | 6/2005 |
| WO | WO 2005/070955 | | 8/2005 |
| WO | WO 2005/073195 | | 8/2005 |
| WO | WO 2005/073216 | | 8/2005 |
| WO | WO 2005/075502 | | 8/2005 |
| WO | WO 2005/095403 | | 10/2005 |
| WO | WO 2005/097820 | | 10/2005 |
| WO | WO 2005/107745 | | 11/2005 |
| WO | WO 2005/113581 | | 12/2005 |
| WO | WO 2006/000085 | | 1/2006 |
| WO | WO 2006/020276 | | 2/2006 |
| WO | WO 2006/043145 | | 4/2006 |
| WO | WO 2006/045096 | | 4/2006 |
| WO | WO 2006/075021 | | 7/2006 |
| WO | WO 2006/113942 | | 10/2006 |
| WO | WO 2006/119061 | | 11/2006 |
| WO | WO 2006/122188 | | 11/2006 |
| WO | WO 2007/011658 | | 1/2007 |
| WO | WO 2007/011777 | | 1/2007 |
| WO | WO 2007/014919 | | 2/2007 |
| WO | WO 2007/014922 | | 2/2007 |
| WO | WO 2007/014926 | | 2/2007 |
| WO | WO 2007/014927 | | 2/2007 |
| WO | WO 2007/015824 | | 2/2007 |
| WO | WO 2007/016441 | | 2/2007 |
| WO | WO 2007/016476 | | 2/2007 |
| WO | WO 2007/017144 | | 2/2007 |
| WO | WO 2007/022459 | | 2/2007 |
| WO | WO 2007/030656 | | 3/2007 |
| WO | WO 2007/044893 | | 4/2007 |
| WO | WO 2007/044933 | | 4/2007 |
| WO | WO 2007/056120 | | 5/2007 |
| WO | WO 2007/089618 | | 8/2007 |
| WO | WO 2007/092616 | | 8/2007 |
| WO | WO 2007/104162 | | 9/2007 |
| WO | WO 2007/106317 | | 9/2007 |
| WO | WO 2007/111866 | | 10/2007 |
| WO | WO 2007/130499 | | 11/2007 |
| WO | WO 2007/133865 | | 11/2007 |
| WO | WO 2007/143694 | | 12/2007 |
| WO | WO 2007/146695 | | 12/2007 |
| WO | WO 2007/148135 | | 12/2007 |
| WO | WO 2008/005565 | | 1/2008 |
| WO | WO 2008/019266 | | 2/2008 |
| WO | WO 2008/019289 | | 2/2008 |
| WO | WO 2008/019303 | | 2/2008 |
| WO | WO 2008/021733 | | 2/2008 |
| WO | WO 2008/021871 | | 2/2008 |
| WO | WO 2008/021960 | | 2/2008 |
| WO | WO 2008/022006 | | 2/2008 |
| WO | WO 2008/033389 | | 3/2008 |
| WO | WO 2008/033466 | | 3/2008 |
| WO | WO 2008/046860 | | 4/2008 |
| WO | WO 2008/051475 | | 5/2008 |
| WO | WO 2008/051477 | | 5/2008 |
| WO | WO 2008/051514 | | 5/2008 |
| WO | WO 2008/057208 | | 5/2008 |
| WO | WO 2008/057209 | | 5/2008 |
| WO | WO 2008/057995 | | 5/2008 |
| WO | WO 2008/060927 | | 5/2008 |
| WO | WO 2008/064057 | | 5/2008 |
| WO | WO 2008/064061 | | 5/2008 |
| WO | WO 2008/064066 | | 5/2008 |
| WO | WO 2008/064218 | | 5/2008 |
| WO | WO 2008/070358 | | 6/2008 |
| WO | WO 2008/073282 | | 6/2008 |
| WO | WO 2008/086161 | | 7/2008 |
| WO | WO 2008/095058 | | 8/2008 |
| WO | WO 2008/095999 | | 8/2008 |
| WO | WO 2008/096001 | | 8/2008 |
| WO | WO 2008/098368 | | 8/2008 |
| WO | WO 2008/101665 | | 8/2008 |
| WO | WO 2010/015545 | | 8/2008 |
| WO | WO 2008/106058 | | 9/2008 |
| WO | WO 2008/106130 | | 9/2008 |
| WO | WO 2008/106139 | | 9/2008 |
| WO | WO 2008/118332 | | 10/2008 |
| WO | WO 2008/124384 | | 10/2008 |
| WO | WO 2008/128121 | | 10/2008 |
| WO | WO 2008/128921 | | 10/2008 |
| WO | WO 2008/134397 | | 11/2008 |
| WO | WO 2008/134398 | | 11/2008 |
| WO | WO 2008/137126 | | 11/2008 |
| WO | WO 2008/137779 | | 11/2008 |
| WO | WO 2008/141227 | | 11/2008 |
| WO | WO 2009/003009 | | 12/2008 |
| WO | WO 2009/005676 | | 1/2009 |
| WO | WO 2009/005677 | | 1/2009 |
| WO | WO 2009/005690 | | 1/2009 |
| WO | WO 2009/008913 | | 1/2009 |
| WO | WO 2009/035540 | | 3/2009 |
| WO | WO 2009/046098 | | 4/2009 |
| WO | WO 2009/051840 | | 4/2009 |
| WO | WO 2009/053828 | | 4/2009 |
| WO | WO 2009/064955 | | 5/2009 |
| WO | WO 2009/064975 | | 5/2009 |
| WO | WO 2009/067225 | | 5/2009 |
| WO | WO 2009/070692 | | 6/2009 |
| WO | WO 2009/073713 | | 6/2009 |
| WO | WO 2009/073719 | | 6/2009 |
| WO | WO 2009/073780 | | 6/2009 |
| WO | WO 2009/076173 | | 6/2009 |

| | | |
|---|---|---|
| WO | WO 2009/079352 | 6/2009 |
| WO | WO 2009/079353 | 6/2009 |
| WO | WO 2009/080542 | 7/2009 |
| WO | WO 2009/082697 | 7/2009 |
| WO | WO 2009/082701 | 7/2009 |
| WO | WO 2009/085659 | 7/2009 |
| WO | WO 2009/094438 | 7/2009 |
| WO | WO 2009/094443 | 7/2009 |
| WO | WO 2009/108507 | 9/2009 |
| WO | WO 2009/112592 | 9/2009 |
| WO | WO 2009/124853 | 10/2009 |
| WO | WO 2009/129109 | 10/2009 |
| WO | WO 2009/134624 | 11/2009 |
| WO | WO 2009/137432 | 11/2009 |
| WO | WO 2009/142842 | 11/2009 |
| WO | WO 2009/143359 | 11/2009 |
| WO | WO 2009/143361 | 11/2009 |
| WO | WO 2009/146347 | 12/2009 |
| WO | WO 2009/149377 | 12/2009 |
| WO | WO 2009/152051 | 12/2009 |
| WO | WO 2010/011566 | 1/2010 |
| WO | WO 2010/017178 | 2/2010 |
| WO | WO 2010/017432 | 2/2010 |
| WO | WO 2010/028236 | 3/2010 |
| WO | WO 2010/030359 | 3/2010 |
| WO | WO 2010/033443 | 3/2010 |
| WO | WO 2010/033444 | 3/2010 |
| WO | WO 2010/033466 | 3/2010 |
| WO | WO 2010/034105 | 4/2010 |
| WO | WO 2010/048468 | 4/2010 |
| WO | WO 2010/059667 | 5/2010 |
| WO | WO 2010/065577 | 6/2010 |
| WO | WO 2010/068760 | 6/2010 |
| WO | WO 2010/085638 | 7/2010 |
| WO | WO 2010/107965 | 9/2010 |
| WO | WO 2010/115981 | 10/2010 |
| WO | WO 2010/116248 | 10/2010 |
| WO | WO 2010/118009 | 10/2010 |

OTHER PUBLICATIONS

Farina, Efficient Synthesis of BILN 2061, a Potent HCV Protease inhibitor, by a Convergent Approach Based on Ring-Closing Metathesis, ACS ProSpectives Conference Series, Process Chemistry in the Pharmaceutical Industry, Feb. 6-9, 2005, pp. 28.
Faucher et al., Synthesis of BILN 2061, an HCV NS3 Protease Inhibitor with Proven Antiviral Effect in Humans, Organic Letters (2004), 6(17): 2901-2904.
Foster, FRCP, Ph.D., Past, Present, and Future Hepatitis C, Seminars in Liver Disease, (2004) 24(Supp 2): 97-104.
Franciscus, ¿Que Hemos Aprendido sobre la Hepatitis C en la Conferencia AASLD de 2002? HCV Advocate at http://www.hcvadvocate.org/pdf/AASLD_2002_sp-3.pdf, 8 pages.
Galgoci et al., A convenient synthesis of methyl (Z)-1-carbamoyl-2-ethenylcyclopropanecarboxylate and (Z)-1-carbamoyl-2-ethenylcyclopropanecarboxylic acid, Synth. Commun., (1994) 24(17): 2477-2483.
Gonzalez et al., Synthetic studies on L-Proline and (4R)-hydroxy-L-proline derivatives Synthesis (2004) 8: 1171-1182.
Goodman & Gilman Pharmacological Basis of Therapeutics, 9th Edition, vol. I, McGraw-Hill, Interamericana, Mexico (1996) p. 47, 2 pages.
Goudreau et al., Potent Inhibitors of the Hepatitis C Virus NS3 Protease: Design and Synthesis of Macrocyclic Substrate-Based (-Strand Mimics, J. Org. Chem. (2004) 69(19): 6185-6201.
Goudreau et al., The Therapeutic Potential of NS3 Protease Inhibitors in HCV Infection, Expert Opin. Investig. Drugs (2005) 1129-1144.
Hinrichsen et al., Short-term antiviral efficacy of BILN 2061, a hepatitis C virus serine protease inhibitor, in hepatitis C genotype 1 patients, Gastroenterology (2004), 127(5), 1347-1355.
Khan et al., "Diastereoselective Synthesis of trans-2-(1-Triphenylmethyl-1H-imidazol-4-yl)Cyclopropanecarboxylic Acids: Key Intermediates for the Preparation of Potent and Chiral Histamine H3 Receptor Agents" Bioorg. Med. Chem. Lett., 1997, 7(23):3017-3022.
LaPlante et al., Dynamics and structure-based design of drugs targeting the critical serine protease of the hepatitis C virus from a peptidic substrate to BILN 2061., Current Medicinal Chemistry: Anti-Infective Agents, 2005, 4(2): 111-132 (Abstract Only).
Lin et al., Combination of a hepatitis C virus NS3-NS4A protease inhibitor and alpha interferon synergistically inhibits viral RNA replication and facilitates viral RNA clearance in replicon cells., Antimicrobal Agents & Chemo., 2004, 48(12): 4784-4792.
Llinas-Brunet et al., Structure-Activity Study on a Novel Series of Macrocyclic Inhibitors fo the Hepatitis C Virus NS3 Protease Leading to the Discovery of BILN 2061, J. Med. Chem. 2004, 47, 1605-1608.
Lu et al., Mutations conferring resistance to a potent hepatitis C virus serine protease inhibitor in vitro, Antimicrobial Agents and Chemotherapy (2004), 48(6): 2260-2266.
Ma et al., Accelerating Effect Induced by the Structure of a-Amino Acid in the Copper-Catalyzed Coupling Reaction of Aryl Halides with a-Amino Acids. Synthesis of Benzolactam-V8. , J Amer Chem Soc., 1998, 120: 12459-12467.
Marchetti et al., Synthesis of Two Novel Cyclic Biphenyl Ether Analogs of an Inhibitor of HCV NS3 Protease, Synlett. (1999), S1, 1000-1002.
McKenna et al., The scope and limitations of the Suzuki-Miyaura cross-coupling reactions of 6- and 8-substituted 1,2,3,4-tetrahydroisoquinoline-3-carboxylates, Tetrahedron Lett., 2001, 42, 5797-5800.
Ni et al., Progress and development of small molecule HCV antivirals, Curr. Opin. Drug Disc. Devel. (2004) 7(4): 446-459 (Abstract only).
Perni et al., Inhibitors of Hepatitis C Virus NS3•4A protease 1. Non-Charged Tetrapeptide Variants, Bioorg. Med. Chem. Lett. (2003) 13(22): 4059-4063.
Perni et al., Inhibitors of hepatitis C virus NS3•4A protease 2. Warhead SAR and optimization, Bioorg. Med. Chem. Lett., 2004, 14(6): 1441-6.
Perni et al., Inhibitors of hepatitis C virus NS3•4A protease. Part 3. P2 proline variants, Bioorg. Med. Chem. Lett. (2004) 14(8): 1939-1942.
Raboisson et al., Discovery of Novel Potent and Selective Dipeptide Hepatitis C Virus NS3/4A Serine Protease Inhibitors, Bioorg & Med Chem Letters, 18(18): 5095-5100, Sep. 15, 2008.
Ronn et al., Exploration of Acyl Sulfonamides as Carboxylic Acid Replacements in Protease Inhibitors of the Hepatitis C Virus Full-length NS3, Bioorg & Med Chem., 14(2): 544-559, Jan. 15, 2006.
Seiwert et al., Preclinical Characteristics of the Hepatitis C Virus NS3/4A Protease Inhibitor ITMN-191 (R7227), Antimicro Agents Chemother., Dec. 2008, 52(12): 4432-4441.
Simmen et al., "Preclinical characterization of TMC435350, a novel macrocyclic inhibitor of the HCV NS3/4A serine protease", Tibotec Poster, Mechelen, Belgium, 14th International Symposium on Hepatitis O Virus & Related Viruses, Glasgow, UK, Sep. 9, 2007, 1 page.
Sulkowski, "Orally available Hepatitis C Virus (HCV) protease inhibitor (BILN 2061) demonstrates potent anti-viral activity in persons infected with HCV genotype 1" AASLD Conference Report (2002) 1 page, Link: www.natap.org/2002/AASLD/day14.htm.
Sun et al., P4 cap modified tetrapeptidyl (-ketoamides as potent HCV NS3 protease inhibitors, Bioorg. Med. Chem. Lett. (2004) 14(16): 4333-4338.
The Merck Index, An Encyclopedia of Chemicals, Drugs, and Biologicals, "Abacavir", 14th Edition, 2006, p. 1.
The Merck Index, An Encyclopedia of Chemicals, Drugs, and Biologicals, "Didanosine", 14th Edition, 2006, p. 525.
Thibeault et al., Sensitivity of NS3 serine proteases from hepatitis C virus genotypes 2 and 3 to the inhibitor BILN 2061, J. Virol., (2004) 78(14): 7352-7359.
Thorstensson et al., Synthesis of Novel Potent Hepatitis C Virus NS3 Protease Inhibitors. Discovery of 4-Hydroxy-cyclopent-2ene-1,2-dicarboxylic Acid as a N-Acyl-L-Hydroxy-proline Bioisostere, Bioorg. Med. Chem. (2006), 15: 827-838.
Tsantrizos et al., Macrocyclic Inhibitors of the NS3 Protease as Potential Therapeutic Agents of Hepatitis C Virus Infection., Angew. Chem. Int. Ed. (2003), 42(12):1356-1360.
Tsantrizos, The design of a potent inhibitor of the hepatitis C virus NS3 protease: BILN 2061—From the NMR tube to the clinic, Biopolymers (2004), 76(4): 309-323 (Abstract Only).

www.medknowledge.de/neu/2002/IV-2002-32-biln-2061-pipeline.htm, pp. 1-4.

Yao et al., "Molecular views of viral polyprotein processing revealed by the crystal structure of the hepatitis C virus bifunctional protease—helicase," Structure, 1999, 7(11):1353-1363.

Zhou et al., Phenotypic and Structural Analyses of Hepatitis C Virus NS3 Protease Arg155 Variants, Jun. 6, 2007, J Bio Chem., 282(31): 22619-22628.

Zucca et al., Regioselective Solid-phase 4-Amino-de-chlorination of 2,3,6-Trichloropyrimidine by Resin-supported N-Potassium Carbamates, Tetra Lttr., 2001, 42: 1033-1035.

International Search Report and Written Opinion dated Feb. 5, 2010 in PCT/US2009/040565, filed Apr. 14, 2009.

Beers, et al. (Eds), "The Merck Manual of Diagnosis and Therapy", 18th Ed. 2006, Merck Research Laboratories, pp. 214-215.

Falchi et al., 4-(4,6-Dimethoxy[1,3,5]triazin-2-yl)-4-methylmorpholinium Chloride (DMTMM): A valuable Alternative to PyBOP for Solid Phase Peptide Synthesis, (Jan. 2000) 2: 275-277.

Foster, Deuterium isotope effects in the metabolism of drugs and Xenobiotics: Implications for drug design, Advances in Drug Research, Academic Press, London, UK, (1985) 14: 2-40.

Kwong et al., Hepatitis C virus NS3/4A protease, Antiviral Res. (Jul. 1998) 40: 1-18.

Lamarre et al., An NS3 Protease Inhibitor with Antiviral Effects in Humans Infected with Hepatitis C Virus, Nature, (Nov. 2003) 426(6963): 186-189.

Pause et al., An NS3 Serine Protease Inhibitor Abrogates Replication of Subgenomic Hepatititis C Virus RNA, J Bio Chem., (Mar. 2003) 278(22): 20374-20380.

Šebestík et al., Acridin-9-yl Exchange: A Proposal for the Action of Some 9-Aminoacridine Drugs, Biopolymers (Peptide Science) (Aug. 2006) 84: 605-614.

Shibnev et al., 2-Methoxy-6,9-Dichloroacridine in Peptide Synthesis as a Fluorescent Label, Bioorganicheskaya Khimiuya (1984) 10(5): 610-617.

Thibeault et al., Use of the fused NS4A peptide-NS3 protease domain to study the importance of the helicase domain for protease inhibitor binding to hepatitis C virus NS3-NS4A, Biochemistry (Feb. 2009) 48(4): 744-753.

International Preliminary Report on Patentability and Written Opinion dated Oct. 28, 2010 in Application No. PCT/US2009/040565, filed Apr. 14, 2009.

Kwong et al., Recent Progress in the Development of Selected Hepatitis C Virus NS3-4A Protease and NS5B Polymerase Inhibitors, Curr Opin Pharmaco. Oct. 1, 2008, 8(5): 522-531.

Lalezari et al., Potent Antiviral Activity of the HCV Nucleoside Polymerase Inhibitor R7128 with Peg-IFN and Ribavirin: Interim Results of R7128 500MG BID for 28 Days, XP026661792, J Hepatol. 48, Jan. 1, 2008, S29, 66, Abstract only.

Reddy et al., Antiviral Activity, Pharmacokinetics, Safety and Tolerability of R7128, a Novel Nucleoside HCV RNA Polymerase Inhibitor, Following Multiple, Ascending, Oral Doses in Patients with HCV Genotype 1 Infection who have Failed Prior Interferon Therapy, Hepatology 46(4): Suppl. S, 862A-863A, Oct. 2007, AASLD LB9, Abstract Only.

Rodriguez-Torres et al., Potent Antiviral Response to the HCV Nucleoside Polymerase Inhibitor R7128 for 28 Days with PEG-IFN and Ribavirin: Subanalysis by Race/Ethnicity, Weight and HCV Genotype, XP-002580352, Hepatology, 48(4) #1899, Suppl. 1160A, AASLD, Abstract Only, (2008).

Rodriguez-Torres et al., Potent Antiviral Response to the HCV Nucleoside Polymerase Inhibitor R7128 for 28 Days with PEG-IFN and Ribavirin: Subanalysis by Race/Ethnicity, Weight and HCV Genotype, XP002580353, Online Oct. 31, 2008, URL:http://www.pharmasset.com/download/Phase_1_Subanalysis_Cohrts_1_2_3.pdf, 1 page.

Tan et al., Combination of the NS3/4A Protease Inhibitor ITMN-191 (R7227) with the Active Moiety of the NS5B Inhibitors R1626 or R7128 Enhances Replicon Clearance and Reduces the Emergence of Drug Resistant Variant, Oct. 31, 2008, XP002580351, URL:http://wwww.pharmasset.com/download/Tan_PSI7851_AASLD%20Oct08.pdf, 1 page.

Tan et al., Combination of the NS3/4A Protease Inhibitor ITMN-191 9R7227) with the Active Moiety of the NS5B Inhibitors R1626 or R7128 Enhances Replicon Clearance and Reduces the Emergence of Drug Resistant Variants, XP-002580350, Hepatology, Oct. 2008, 48(4) Suppl. 1153A, AASLD, Abstract Only.

Anonymous, View of NCT00801255 on Feb. 17, 2009, XP002580349 ClinicalTrials, Retrieved from the Internet: URL:http://clinicaltrials.gov/archive/NCTO0801255/2009_02_17.

Blatt et al., ITMN-191 Concentrations Achieved in the Liver of Animals Promote HCV Replicon Clearance in Vitro and this Effect is Enhanced by PEG-IFN Alpha-2a, XP022087916, J Hepatol., Apr. 1, 2007, 46: S219, Abstract #576, 1 page.

Gane et al., Antiviral Activity of the HCV Nucleoside Polymerase Inhibitor R7128 in HCV Genotype 2 and 3 prior Non-Responders: Interim Results of R7128 1500mg Bid with PEG-IFN and Ribavirin for 28 Days, Online Oct. 31, 2008 XP002580355, URL:http://www.pharmasset.com/download/Phase_I_Analysis_Cohort_4.pdf, 1 page.

Gane et al., Antiviral Activity of the HCV Nucleoside Polymerase Inhibitor R7128 in HCV Genotype 2 and 3 prior Non-Responders: Interim Results of R7128 1500mg BID with PEG-IFN and Ribavirin for 28 Days, XP 002580354, Hepatology, 48(4) Suppl, 1024A, LB10, Oct. 2008, AASLD, Abstract Only.

* cited by examiner

MACROCYCLIC INHIBITORS OF HEPATITIS C VIRUS REPLICATION

RELATED APPLICATIONS

This application claims the benefit of U.S. Provisional Application Nos. 61/045,220, filed Apr. 15, 2008; 61/105,736, filed Oct. 15, 2008; 61/105,751, filed Oct. 15, 2008; 61/143,728, filed Jan. 9, 2009; and 61/150,693, filed Feb. 6, 2009; all of which are incorporated herein by reference in their entirety.

SEQUENCE LISTING

The present application is being filed along with a Sequence Listing in electronic format. The Sequence Listing is provided as a file entitled INTMU-049A.TXT, created Apr. 13, 2009, which is 4 Kb in size. The information in the electronic format of the Sequence Listing is incorporated herein by reference in its entirety.

BACKGROUND OF THE INVENTION

1. Field of the Invention

The present invention relates to compounds, processes for their synthesis, compositions and methods for the treatment of hepatitis C virus (HCV) infection.

2. Description of the Related Art

Hepatitis C virus (HCV) infection is the most common chronic blood borne infection in the United States. Although the numbers of new infections have declined, the burden of chronic infection is substantial, with Centers for Disease Control estimates of 3.9 million (1.8%) infected persons in the United States. Chronic liver disease is the tenth leading cause of death among adults in the United States, and accounts for approximately 25,000 deaths annually, or approximately 1% of all deaths. Studies indicate that 40% of chronic liver disease is HCV-related, resulting in an estimated 8,000-10,000 deaths each year. HCV-associated end-stage liver disease is the most frequent indication for liver transplantation among adults.

Antiviral therapy of chronic hepatitis C has evolved rapidly over the last decade, with significant improvements seen in the efficacy of treatment. Nevertheless, even with combination therapy using pegylated IFN-α plus ribavirin, 40% to 50% of patients fail therapy, i.e., are nonresponders (NR) or relapsers. These patients currently have no effective therapeutic alternative. In particular, patients who have advanced fibrosis or cirrhosis on liver biopsy are at significant risk of developing complications of advanced liver disease, including ascites, jaundice, variceal bleeding, encephalopathy, and progressive liver failure, as well as a markedly increased risk of hepatocellular carcinoma.

The high prevalence of chronic HCV infection has important public health implications for the future burden of chronic liver disease in the United States. Data derived from the National Health and Nutrition Examination Survey (NHANES III) indicate that a large increase in the rate of new HCV infections occurred from the late 1960s to the early 1980s, particularly among persons between 20 to 40 years of age. It is estimated that the number of persons with long-standing HCV infection of 20 years or longer could more than quadruple from 1990 to 2015, from 750,000 to over 3 million. The proportional increase in persons infected for 30 or 40 years would be even greater. Since the risk of HCV-related chronic liver disease is related to the duration of infection, with the risk of cirrhosis progressively increasing for persons infected for longer than 20 years, this will result in a substantial increase in cirrhosis-related morbidity and mortality among patients infected between the years of 1965-1985.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins of the virus. In the case of HCV, the generation of mature non-structural proteins (NS2, NS3, NS4, NS4A, NS4B, NS5A, and NS5B) is effected by two viral proteases. The first viral protease cleaves at the NS2-NS3 junction of the polyprotein. The second viral protease is serine protease contained within the N-terminal region of NS3 (herein referred to as "NS3 protease"). NS3 protease mediates all of the subsequent cleavage events at sites downstream relative to the position of NS3 in the polyprotein (i.e., sites located between the C-terminus of NS3 and the C-terminus of the polyprotein). NS3 protease exhibits activity both in cis, at the NS3-NS4 cleavage site, and in trans, for the remaining NS4A-NS4B, NS4B-NS5A, and NS5A-NS5B sites. The NS4A protein is believed to serve multiple functions, acting as a cofactor for the NS3 protease and possibly assisting in the membrane localization of NS3 and other viral replicase components. Apparently, the formation of the complex between NS3 and NS4A is necessary for NS3-mediated processing events and enhances proteolytic efficiency at all sites recognized by NS3. The NS3 protease also exhibits nucleoside triphosphatase and RNA helicase activities. NS5B is an RNA-dependent RNA polymerase involved in the replication of HCV RNA.

SUMMARY OF THE INVENTION

The present embodiments provide compounds of the general Formula I:

(I)

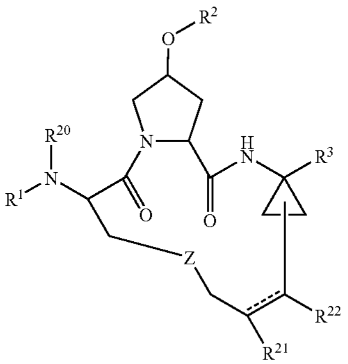

or a pharmaceutically acceptable salt or prodrug thereof wherein:

$R^1$ is —$(CR^5R^6)_nR^4$;

n is 0, 1 or 2;

$R^2$ is selected from the group consisting of aryl, heteroaryl and polycyclic moiety, each optionally substituted with one or more substituents each independently selected from the group consisting of halo, cyano, nitro, hydroxy, cyanoamino, —SH, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —NHC(O)NR$^{1a}$R$^{1b}$, —NHC(S)NR$^{1a}$R$^{1b}$, —C(O)NR$^{1a}$R$^{1b}$, —NR$^{1a}$R$^{1b}$, —C(O)R$^{2a}$, —C(O)OR$^{2a}$, —NHC(O)R$^{2a}$, —NHC(O)OR$^{2a}$, —SO$_m$R$^{2a}$, —NHS(O)$_2$R$^{2a}$, —NR$^{2a}$[(CH$_2$)$_p$OH], —O[(CH$_2$)$_p$NR$^{3a}$R$^{3b}$], —S[(CH$_2$)$_p$NR$^{3a}$R$^{3b}$], —(CH$_2$)$_p$NR$^{3a}$R$^{3b}$, —(CH$_2$)$_p$R$^{4a}$, —O(CH$_2$)$_p$R$^{4a}$, and C$_{1-6}$ alkyl optionally substituted with up to 5 fluoro; said aryl and heteroaryl as an optional substituent are each further optionally substituted with one or more substituents each independently selected from the group consisting of halo, cyano, nitro, hydroxy, C$_{1-6}$ alkyl, C$_{1-6}$ alkoxy, aryl, heteroaryl, —NR$^{1a}$R$^{1b}$, C$_{1-6}$ alkyl optionally substituted with up to 5 fluoro, and C$_{1-6}$ alkoxy optionally substituted with up to 5 fluoro;

R$^4$ is selected from the group consisting of aryl and heteroaryl, each optionally substituted with one or more substituents each independently selected from the group consisting of halo, cyano, nitro, hydroxy, cyanoamino, —SH, C$_{1-6}$ alkyl optionally substituted with up to 5 fluoro, C$_{1-6}$ alkoxy optionally substituted with up to 5 fluoro, C$_{2-6}$ alkenyl, C$_{2-6}$ alkynyl, —(CH$_2$)$_q$C$_{3-7}$cycloalkyl, C$_{3-6}$ heterocycloalkyl, aryl, heteroaryl, aryloxy, arylthio, C$_{1-6}$ alkylthio, —N[(CH$_2$)$_p$OH][(CH$_2$)$_r$OH], —S(O)$_2$NR$^{1a}$R$^{1b}$, —NHC(O)NR$^{1a}$R$^{1b}$, —NHC(S)NR$^{1a}$R$^{1b}$, —C(O)NR$^{1a}$R$^{1b}$, —NR$^{1a}$R$^{1b}$, —C(O)R$^{2a}$, —C(O)OR$^{2a}$, —NHC(O)R$^{2a}$, —NHC(O)OR$^{2a}$, —SO$_m$R$^{2a}$, —NHS(O)$_2$R$^{2a}$, —NR$^{2a}$[(CH$_2$)$_p$OH], —O[(CH$_2$)$_p$NR$^{3a}$R$^{3b}$], —S[(CH$_2$)$_p$NR$^{3a}$R$^{3b}$], —(CH$_2$)$_p$ NR$^{3a}$R$^{3b}$, —(CH$_2$)$_p$R$^{4a}$ and —O(CH$_2$)$_p$R$^{4a}$;

R$^{1a}$ and R$^{1b}$ are each separately a hydrogen atom, or separately selected from the group consisting of C$_{1-6}$ alkyl, C$_{3-7}$ cycloalkyl, and phenyl, each optionally substituted with one or more substituents each independently selected from the group consisting of halo, cyano, nitro, hydroxy, C$_{1-6}$ alkyl, —(CH$_2$)$_q$C$_{3-7}$cycloalkyl, C$_{2-6}$ alkenyl, hydroxy-C$_{1-6}$ alkyl, C$_{1-6}$ alkyl optionally substituted with up to 5 fluoro, and C$_{1-6}$ alkoxy optionally substituted with up to 5 fluoro; or R$^{1a}$ and R$^{1b}$ are taken together with the nitrogen to which they are attached to form indolinyl, pyrrolidinyl, piperidinyl, piperazinyl, or morpholinyl;

each R$^{2a}$ is separately selected from the group consisting of C$_{1-6}$ alkyl, C$_{3-7}$ cycloalkyl, and C$_{6\ or\ 10}$ aryl, each optionally substituted with one or more substituents each independently selected from the group consisting of halo, cyano, nitro, hydroxy, C$_{1-6}$ alkyl, C$_{2-6}$ alkenyl, —(CH$_2$)$_q$C$_{3-7}$cycloalkyl, C$_{1-6}$ alkoxy, phenyl, and hydroxy-C$_{1-6}$ alkyl; or R$^{2a}$ is a tetrahydrofuran ring linked through the C$_3$ or C$_4$ position of the tetrahydrofuran ring; or R$^{2a}$ is a tetrahydropyran ring linked through the C$_4$ position of the tetrahydropyran ring;

R$^{3a}$ and R$^{3b}$ are each separately selected from the group consisting of hydrogen and C$_{1-6}$ alkyl; or R$^{3a}$ and R$^{3b}$ are taken together with the nitrogen to which they are attached to form indolinyl, pyrrolidinyl, piperidinyl, piperazinyl, or morpholinyl;

each R$^{4a}$ is separately imidazolyl or pyrazolyl;

each m is separately 0, 1 or 2;

each p is separately an integer selected from 1-6;

each q is separately 0, 1 or 2;

each r is separately an integer selected from 1-6;

R$^3$ is —C(O)NHS(O)$_2$R$^9$, where R$^9$ is selected from the group consisting of C$_{1-6}$ alkyl, —(CH$_2$)$_q$C$_{3-7}$cycloalkyl, —(CH$_2$)$_q$C$_{6\ or\ 10}$ aryl, and a heteroaromatic ring, each optionally substituted with one or more substituents each independently selected from the group consisting of halo, cyano, nitro, hydroxy, —COOH, C$_{1-6}$ alkyl, —(CH$_2$)$_t$C$_{3-7}$cycloalkyl, C$_{2-6}$ alkenyl, C$_{1-6}$ alkoxy, hydroxy-C$_{1-6}$ alkyl, C$_{1-6}$ alkyl optionally substituted with up to 5 fluoro, and C$_{1-6}$ alkoxy optionally substituted with up to 5 fluoro, or R$^9$ is —NR$^{9a}$R$^{9b}$; or R$^3$ is a —CONHO(CH$_2$)$_m$R$^{10}$ where R$^{10}$ is selected from the group consisting of C$_{1-6}$ alkyl, —(CH$_2$)$_q$C$_{3-7}$cycloalkyl, optionally substituted aryl and optionally substituted heteroaryl; or R$^3$ is a carboxylic acid;

wherein R$^{9a}$ and R$^{9b}$ are each separately a hydrogen atom, or separately selected from the group consisting of C$_{1-6}$ alkyl, —(CH$_2$)$_q$C$_{3-7}$cycloalkyl, and C$_{6\ or\ 10}$ aryl, each optionally substituted with one or more substituents each independently selected from the group consisting of halo, cyano, nitro, hydroxy, C$_{1-6}$ alkyl, —(CH$_2$)$_t$C$_{3-7}$ cycloalkyl, C$_{2-6}$ alkenyl, C$_{1-6}$ alkoxy, hydroxy-C$_{1-6}$ alkyl, phenyl, C$_{1-6}$ alkyl substituted with up to 5 fluoro, and C$_{1-6}$ alkoxy substituted with up to 5 fluoro, or R$^{9a}$ and R$^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or R$^{9a}$ and R$^{9b}$ are each separately selected from the group consisting of a hydrogen atom and a heteroaryl group;

or —NR$^{9a}$R$^{9b}$ is a three- to six-membered alkyl cyclic secondary amine, which optionally has one to three additional hetero atoms incorporated in the ring, and which is optionally substituted with one or more substituents each independently selected from the group consisting of halo, cyano, nitro, C$_{1-6}$ alkyl, C$_{1-6}$ alkoxy, and phenyl;

or R$^{9a}$ and R$^{9b}$ are taken together with the nitrogen to which they are attached to form a heteroaryl, optionally substituted with one or more substituents each independently selected from the group consisting of a halogen, cyano, nitro, hydroxy, C$_{1-6}$ alkyl, —(CH$_2$)$_q$C$_{3-7}$cycloalkyl, C$_{1-6}$ alkoxy, C$_{3-6}$ cycloalkoxy, —NH(CO)OR$^{1e}$, wherein R$^{1e}$ is C$_{1-6}$ alkyl, or —(CH$_2$)$_q$C$_{3-7}$cycloalkyl, —N(R$^{1d}$)$_2$, —NH(CO)R$^{1d}$, and —NH(CO)NHR$^{1d}$, wherein each R$^{1d}$ is separately selected from the group consisting of a hydrogen atom, C$_{1-6}$ alkyl, and —(CH$_2$)$_q$C$_{3-7}$cycloalkyl;

each t is separately 0, 1 or 2;

R$^5$ and R$^6$ are each separately a hydrogen, or separately selected from the group consisting of alkyl and arylalkyl, each optionally substituted with one or more substituents each independently selected from the group consisting of halo, cyano, nitro, hydroxy, C$_{1-6}$ alkyl, —(CH$_2$)$_u$C$_{3-7}$cycloalkyl, C$_{2-6}$ alkenyl, C$_{1-6}$ alkoxy, hydroxyl-C$_{1-6}$ alkyl, phenyl, C$_{1-6}$ alkyl substituted with up to 5 fluoro, and C$_{1-6}$ alkoxy substituted with up to 5 fluoro; or R$^5$ and R$^6$ are taken together with the carbon to which they are attached to form a C$_{3-7}$ cycloalkyl, optionally substituted with one or more substituents each independently selected from the group consisting of halo, cyano, nitro, hydroxy, C$_{1-6}$ alkyl, —(CH$_2$)$_u$C$_{3-7}$ cycloalkyl, C$_{2-6}$ alkenyl, C$_{1-6}$ alkoxy, hydroxy-C$_{1-6}$ alkyl, phenyl, C$_{1-6}$ alkyl substituted with up to 5 fluoro, and C$_{1-6}$ alkoxy substituted with up to 5 fluoro;

each u is separately 0, 1 or 2;

Z is selected from the group consisting of

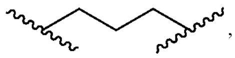
,
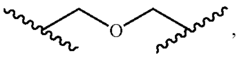
,

-continued

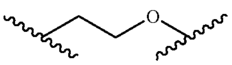
,
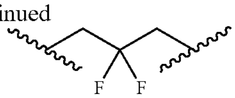
,
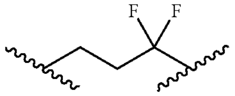
,
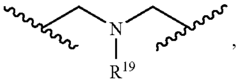
,
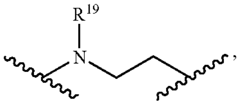
,
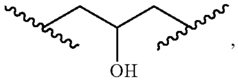
, and
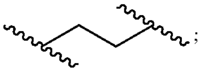
;

$R^{19}$ is hydrogen, $C_{1-6}$ alkyl optionally substituted with up to 5 fluoro, or —$SO_mR^{2a}$;

$R^{20}$ is selected from the group consisting of hydrogen, —$SO_mR^{2a}$, —C(O)$OR^{2a}$, —C(O)$R^{2a}$, —C(O)$NR^{1a}R^{1b}$, and —C(S)$NR^{1a}R^{1b}$;

$R^{21}$ and $R^{22}$ are each hydrogen or together with the carbon atoms to which they are attached form an optionally substituted cyclopropyl; and the dashed line represents an optional double bond;

with the proviso that the compound of formula I is not

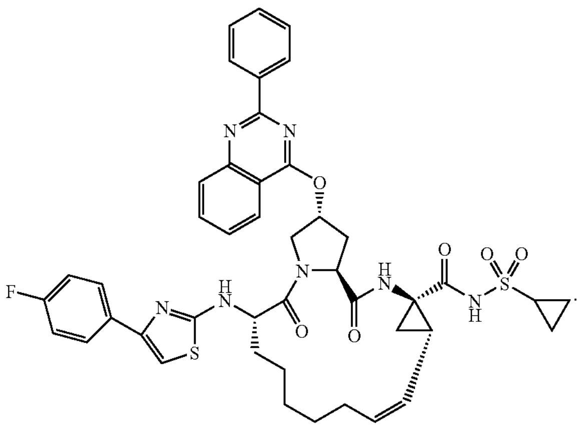
.

The present embodiments also provide compounds of the general Formula I wherein:

(a) $R^1$ is hydrogen;

(b) $R^2$ is hydrogen, —C(O)$R^4$ or selected from the group consisting of $C_{1-6}$ alkyl, aryl, heteroaryl and polycyclic moiety, each optionally substituted with one or more substituents each separately selected from the group consisting of halo, cyano, nitro, hydroxy, cyanoamino, —SH, $C_{1-6}$ alkyl, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —N[$(CH_2)_p$OH][$(CH_2)_r$OH], —S$(O)_2NR^{1a}R^{1b}$, —NHC(O)$NR^{1a}R^{1b}$, —NHC(S)$NR^{1a}R^{1b}$, —C(O)$NR^{1a}R^{1b}$, —$NR^{1a}R^{1b}$, —C(O)$R^{2a}$, —C(O)$OR^{2a}$, —NHC(O)$R^{2a}$, —NHC(O)$OR^{2a}$, —$SO_mR^{2a}$, —NHS$(O)_2R^{2a}$, —$NR^{2a}$[$(CH_2)_p$OH], —O[$(CH_2)_pNR^{3a}R^{3b}$], —S[$(CH_2)_pNR^{3a}R^{3b}$], —$(CH_2)_pNR^{3a}R^{3b}$, —$(CH_2)R^{4a}$ and —O$(CH_2)_pR^{4a}$;

(c) $R^4$ is $C_{1-6}$ alkyl or polycyclic moiety optionally substituted with one or more substituents each separately selected from the group consisting of halo, cyano, nitro, hydroxy, $C_{1-6}$ alkyl, —$(CH_2)_qC_{3-7}$cycloalkyl, $C_{2-6}$ alkenyl, hydroxyl-$C_{1-6}$ alkyl, $C_{1-6}$ alkyl optionally substituted with up to 5 fluoro, and $C_{1-6}$ alkoxy optionally substituted with up to 5 fluoro;

or $R^4$ is —$NR^{90a}R^{90b}$ or $C_{1-6}$ alkyl optionally substituted with up to 5 fluoro;

wherein $R^{90a}$ and $R^{90b}$ are each separately a hydrogen atom or $C_{1-6}$ alkyl; or $R^{90a}$ and $R^{90b}$ are taken together with the nitrogen to which they are attached to form a three- to six-membered heterocycle, which optionally has one to three additional hetero atoms incorporated in the ring;

(d) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each separately selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(e) $R^{2a}$ is selected from the group consisting of $C_{1-6}$ alkyl, $C_{3-7}$ cycloalkyl, and $C_{6\ or\ 10}$ aryl, each optionally substituted with one or more substituents each separately selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

(f) $R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

(g) $R^{4a}$ is imidazolyl or pyrazolyl;

(h) each m is separately 0, 1 or 2;

(i) each p is separately an integer selected from 1-6;

(j) each q is separately 0, 1 or 2;

(k) each r is separately an integer selected from 1-6;

(l) $R^3$ is —C(O)NHS$(O)_2R^9$, where $R^9$ is selected from the group consisting of —$(CH_2)_r$C(O)$NHR^{9c}$, —$(CH_2)_r$C(O)$OR^{9c}$, and —$(CH_2)_qR^{9d}$;

wherein $R^{9c}$ is $C_{6\ or\ 10}$ aryl optionally substituted with one or more substituents each separately selected from the group consisting of —O$(CH_2)_q$C(O)$NHR^{9e}$ and —NH$(CH_2)_q$C(O)$NHR^{9e}$;

wherein $R^{9d}$ is $C_{6\ or\ 10}$ aryl substituted with one or more substituents each separately selected from the group consisting of —O$(CH_2)_q$C(O)$NHR^{9e}$ and —NH$(CH_2)_q$C(O)$NHR^{9e}$;

wherein $R^{9e}$ is selected from the group consisting of hydrogen, $C_{6\ or\ 10}$ aryl, and $C_{1-6}$ alkyl optionally substituted with up to 5 fluoro;

or $R^3$ is a —$CONR^{100a}R^{100b}$;

(m) $R^{100a}$ is —$(CH_2)_vCONR^{200a}R^{200b}$, and $R^{100b}$ is a hydrogen or —$(CH_2)_vCONR^{200a}R^{200b}$; or $R^{100a}$ and $R^{100b}$ are optionally taken together with the nitrogen to which they are attached to form a three- to six-membered heterocycle, which optionally has one to three additional hetero atoms incorporated in the ring, and which is optionally substituted with —$(CH_2)_vCONR^{300a}R^{300b}$;

(n) each v is separately 0, 1, 2, 3, 4, 5, or 6;

(o) $R^{200a}$ and $R^{200b}$ are each separately hydrogen or $—(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(p) $R^{300a}$ and $R^{300b}$ are each separately hydrogen or $—(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(q) Z is selected from the group consisting of

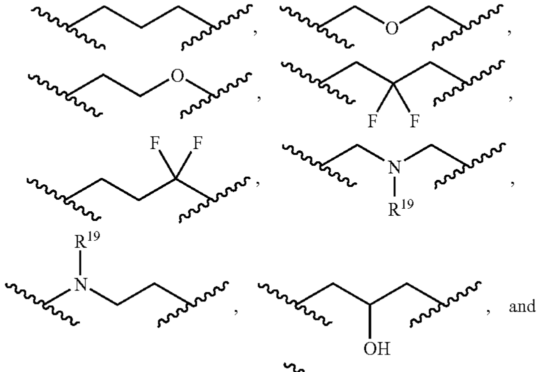

and

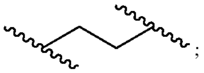

;

(r) $R^{19}$ is hydrogen, $—SO_mR^{2a}$, or $C_{1-6}$ alkyl optionally substituted with up to 5 fluoro;

(s) $R^{20}$ is selected from the group consisting of $—SO_mR^{2a}$, $—C(O)OR^{2a}$, $—C(O)R^{2a}$, $—C(O)NR^{1a}R^{1b}$, and $—C(S)NR^{1a}R^{1b}$;

(t) $R^{21}$ and $R^{21}$ are each hydrogen or together with the carbon atoms to which they are attached form an optionally substituted cyclopropyl; and (u) the dashed line represents an optional double bond.

The present embodiments also provide compounds of the general Formula I wherein:

(a) $R^1$ is hydrogen;

(b) $R^2$ is $—C(O)R^4$, hydrogen, or $C_{1-6}$ alkyl optionally substituted with up to 5 fluoro;

(c) $R^4$ is $—NR^{90a}R^{90b}$, or $C_{1-6}$ alkyl optionally substituted with up to 5 fluoro;

(d) $R^{90a}$ and $R^{90b}$ are each separately a hydrogen atom, or $C_{1-6}$ alkyl; or $R^{90a}$ and $R^{90b}$ are taken together with the nitrogen to which they are attached to form a three- to six-membered heterocycle, which optionally has one to three additional hetero atoms incorporated in the ring;

(e) $R^3$ is $—C(O)NHS(O)_2R^9$, where $R^9$ is $—(CH_2)_qC_{3-7}$ cycloalkyl substituted with methyl;

or $R^9$ is selected from the group consisting of $—(CH_2)_rC(O)NHR^{9c}$, $—(CH_2)_rC(O)OR^{9c}$, and $—(CH_2)_qR^{9d}$;

wherein $R^{9c}$ is $C_{6\ or\ 10}$ aryl optionally substituted with one or more substituents each separately selected from the group consisting of $—O(CH_2)_qC(O)NHR^{9e}$ and $—NH(CH_2)_qC(O)NHR^{9e}$;

wherein $R^{9d}$ is $C_{6\ or\ 10}$ aryl substituted with one or more substituents each separately selected from the group consisting of $—O(CH_2)_qC(O)NHR^{9e}$ and $—NH(CH_2)_qC(O)NHR^{9e}$;

wherein $R^{9e}$ is selected from the group consisting of hydrogen, $C_{6\ or\ 10}$ aryl, and $C_{1-6}$ alkyl optionally substituted with up to 5 fluoro;

or $R^3$ is a $—CONHO(CH_2)_mR^{10}$ where $R^{10}$ is selected from the group consisting of $C_{1-6}$ alkyl, $—(CH_2)_qC_{3-7}$cycloalkyl, optionally substituted aryl and optionally substituted heteroaryl;

or $R^3$ is a $—CONR^{100a}R^{100b}$;

(f) each m is separately 0, 1 or 2;

(g) each q is separately 0, 1 or 2;

(h) each t is separately 0, 1 or 2;

(i) each r is separately an integer selected from 1-6;

(j) $R^{100a}$ is hydrogen, and $R^{100b}$ is a hydrogen, or $—(CH_2)_vCONR^{200a}R^{200b}$; or $R^{100a}$ and $R^{100b}$ are optionally taken together with the nitrogen to which they are attached to form a three- to six-membered heterocycle, which optionally has one to three hetero atoms incorporated in the ring, and which is optionally substituted with $—(CH_2)_vCONR^{300a}R^{300b}$;

(k) each v is separately 0, 1, 2, 3, 4, 5, or 6;

(l) $R^{200a}$ and $R^{200b}$ are each separately hydrogen or $—(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(m) each p is separately an integer selected from 1-6;

(n) $R^{300a}$ and $R^{300b}$ are each separately hydrogen or $—(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(o) Z is selected from the group consisting of

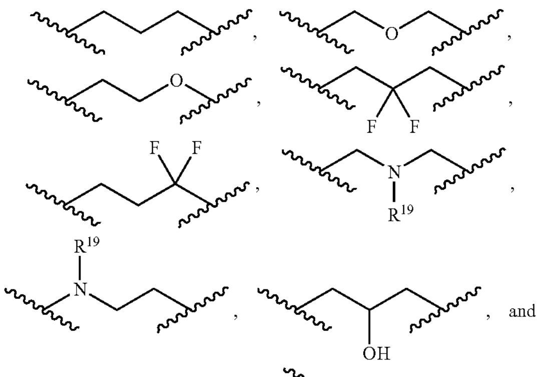

and

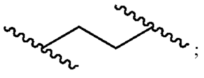

;

(p) $R^{19}$ is hydrogen, $—SO_mR^{2a}$, or $C_{1-6}$ alkyl optionally substituted with up to 5 fluoro;

(q) $R^{20}$ is selected from the group consisting of $—SO_mR^{2a}$, $—C(O)OR^{2a}$, $—C(O)R^{2a}$, $—C(O)NR^{1a}R^{1b}$, and $—C(S)NR^{1a}R^{1b}$;

(r) $R^{21}$ and $R^{21}$ are each hydrogen or together with the carbon atoms to which they are attached form an optionally substituted cyclopropyl; and (s) the dashed line represents an optional double bond.

The present embodiments also provide compounds of the general Formula I wherein:

(a) $R^1$ is $—(CR^5R^6)_nR^4$;

(b) n is 0, 1 or 2;

(c) $R^2$ is selected from the group consisting of aryl, heteroaryl and polycyclic moiety, each optionally substituted with one or more substituents each independently selected from the group consisting of halo, cyano, nitro, hydroxy, cyanoamino, —SH, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_pNR^{3a}R^{3b}$, —$(CH_2)_pR^{4a}$, —$O(CH_2)_pR^{4a}$, and $C_{1-6}$ alkyl optionally substituted with up to 5 fluoro; said aryl and heteroaryl as an optional substituent are each further optionally substituted with one or more substituents each independently selected from the group consisting of halo, cyano, nitro, hydroxy, $C_{1-6}$ alkyl, $C_{1-6}$ alkoxy, aryl, heteroaryl, —$NR^{1a}R^{1b}$, $C_{1-6}$ alkyl optionally substituted with up to 5 fluoro, and $C_{1-6}$ alkoxy optionally substituted with up to 5 fluoro;

(d) $R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_p NR^{3a}R^{3b}$, —$(CH_2)_pR^{4a}$ and —$O(CH_2)_pR^{4a}$;

(e) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(f) each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

(g) $R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

(h) each $R^{4a}$ is separately imidazolyl or pyrazolyl;

(i) each m is separately 0, 1 or 2;

(j) each p is separately an integer selected from 1-6;

(k) each q is separately 0, 1 or 2;

(l) each r is separately an integer selected from 1-6;

(m) $R^3$ is —$P(O)R^{10a}R^{10b}$, wherein $R^{10a}$ and $R^{10b}$ are each separately selected from the group consisting of hydroxy, —$(O)_v$—$C_{1-6}$ alkyl, —$(O)_v$—$(CH_2)_qC_{3-7}$cycloalkyl, —$(O)_v$-aryl, and —$(O)_v$-heteroaryl, each optionally substituted with one or more substituents each independently selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro;

(n) wherein each v is separately 0 or 1;

(o) each t is separately 0, 1 or 2;

(p) $R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

(q) each u is separately 0, 1 or 2;

(r) Z is selected from the group consisting of

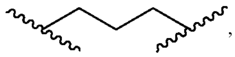,
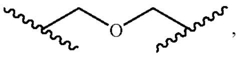,
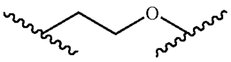,
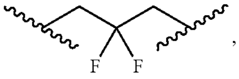,
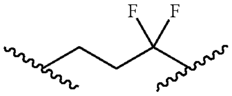,
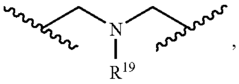,
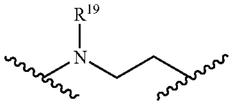,
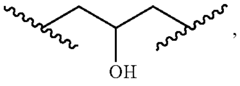, and
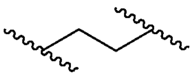;

(s) $R^{19}$ is hydrogen, $C_{1-6}$ alkyl optionally substituted with up to 5 fluoro, or —$SO_mR^{2a}$;

(t) $R^{20}$ is selected from the group consisting of hydrogen, —$SO_mR^{2a}$, —$C(O)OR^{2a}$, —$C(O)R^{2a}$, —$C(O)NR^{1a}R^{1b}$, and —$C(S)NR^{1a}R^{1b}$;

(u) $R^{21}$ and $R^{22}$ are each hydrogen or together with the carbon atoms to which they are attached form an optionally substituted cyclopropyl; and (v) the dashed line represents an optional double bond.

The present embodiments provide compounds of the general Formula II:

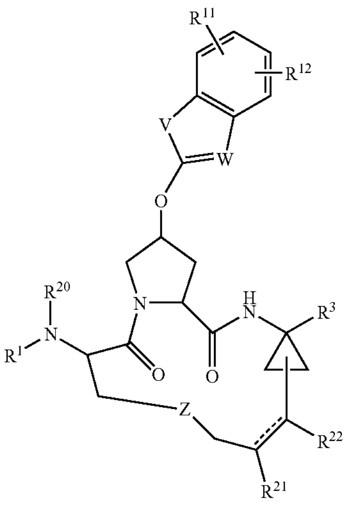

II or a pharmaceutically acceptable salt or prodrug thereof wherein:

$R^1$ is $-(CR^5R^6)_nR^4$;

n is 0, 1 or 2;

$R^3$ is $-C(O)NHS(O)_2R^9$, where $R^9$ is selected from the group consisting of $C_{1-6}$ alkyl, $-(CH_2)_qC_{3-7}$cycloalkyl, $C_{6\ or\ 10}$ aryl, and a heteroaromatic ring, each optionally substituted with one or more substituents each independently selected from the group consisting of halo, cyano, nitro, hydroxy, —COOH, $C_{1-6}$ alkyl, $-(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is $-NR^{9a}R^{9b}$; or $R^3$ is a $-CONHO(CH_2)_mR^{10}$ where $R^{10}$ is selected from the group consisting of $C_{1-6}$ alkyl, $-(CH_2)_qC_{3-7}$cycloalkyl, optionally substituted aryl and optionally substituted heteroaryl; or $R^3$ is a carboxylic acid;

wherein $R^{9a}$ and $R^{9b}$ are each separately a hydrogen atom, or separately selected from the group consisting of $C_{1-6}$ alkyl, $-(CH_2)_qC_{3-7}$cycloalkyl, and $C_{6\ or\ 10}$ aryl, each optionally substituted with one or more substituents each independently selected from the group consisting of halo, cyano, nitro, hydroxy, $C_{1-6}$ alkyl, $-(CH_2)_tC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or $-NR^{9a}R^{9b}$ is a three- to six-membered alkyl cyclic secondary amine, which optionally has one to three hetero atoms incorporated in the ring, and which is optionally substituted with one or more substituents each independently selected from the group consisting of halo, cyano, nitro, $C_{1-6}$ alkyl, $C_{1-6}$ alkoxy, and phenyl;

or $R^{9a}$ and $R^{9b}$ are taken together with the nitrogen to which they are attached to form a heteroaryl, optionally substituted with one or more substituents each independently selected from the group consisting of a halogen, cyano, nitro, hydroxy, $C_{1-6}$ alkyl, $-(CH_2)_qC_{3-7}$cycloalkyl, $C_{1-6}$ alkoxy, $C_{3-6}$ cycloalkoxy, $-NH(CO)OR^{1e}$, wherein $R^{1e}$ is $C_{1-6}$ alkyl, or $-(CH_2)_qC_{3-7}$cycloalkyl, $-N(R^{1d})_2$, $-NH(CO)R^{1d}$, and $-NH(CO)NHR^{1d}$, wherein each $R^{1d}$ is separately selected from the group consisting of a hydrogen atom, $C_{1-6}$ alkyl, and $-(CH_2)_qC_{3-7}$cycloalkyl;

each m is separately 0, 1 or 2;

each q is separately 0, 1 or 2;

each t is separately 0, 1 or 2;

$R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, $-(CH_2)_qC_{3-7}$cycloalkyl, $C_{3-6}$ heterocycloalkyl, aryl, heteroaryl, aryloxy, arylthio, $C_{1-6}$ alkylthio, $-N[(CH_2)_pOH][(CH_2)_rOH]$, $-S(O)_2NR^{1a}R^{1b}$, $NHC(O)NR^{1a}R^{1b}$, $-NHC(S)NR^{1a}R^{1b}$, $-C(O)NR^{1a}R^{1b}$, $-NR^{1a}R^{1b}$, $-C(O)R^{2a}$, $-C(O)OR^{2a}$, $-NHC(O)R^{2a}$, $-NHC(O)OR^{2a}$, $-SO_mR^{2a}$, $-NHS(O)_2R^{2a}$, $-NR^{2a}[(CH_2)_pOH]$, $-O[(CH_2)_pNR^{3a}R^{3b}]$, $-S[(CH_2)_pNR^{3a}R^{3b}]$, $-(CH_2)_pNR^{3a}R^{3b}$, $-(CH_2)_pR^{4a}$ and $-O(CH_2)_pR^{4a}$;

$R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, $-(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, $-(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

$R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

each $R^{4a}$ is separately imidazolyl or pyrazolyl;

each p is separately an integer selected from 1-6;

each r is separately an integer selected from 1-6;

$R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, $-(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, $—(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

$R^{11}$ and $R^{12}$ are each separately selected from the group consisting of hydrogen, halo, cyano, nitro, hydroxy, cyanoamino, —SH, $C_{1-6}$ alkoxy, $C_{2-6}$ alkenyl, $C_{2-6}$ alkynyl, $—(CH_2)_qC_{3-7}$cycloalkyl, $C_{3-6}$ heterocycloalkyl, aryl, heteroaryl, aryloxy, arylthio, $C_{1-6}$ alkylthio, $—N[(CH_2)_pOH][(CH_2)_rOH]$, $—S(O)_2NR^7R^8$, $—NHC(O)NR^7R^8$, $—NHC(S)NR^7R^8$, $—C(O)NR^7R^8$, $—NR^7R^8$, $—C(O)R^{13}$, $—C(O)OR^{13}$, $—NHC(O)R^{13}$, $—NHC(O)OR^{13}$, $—SO_mR^{13}$, $—NHS(O)_2R^{13}$, $—NR^{13}[(CH_2)_pOH]$, $—O[(CH_2)_pNR^{14}R^{15}]$, $—S[(CH_2)_pNR^{14}R^{15}]$, $—(CH_2)_pNR^{14}R^{15}$, $—(CH_2)_pR^{16}$, $—O(CH_2)_pR^{16}$, and $C_{1-6}$ alkyl optionally substituted with up to 5 fluoro;

$R^7$ and $R^3$ are each separately a hydrogen, or separately selected from the group consisting of $C_{1-6}$ alkyl, $—(CH_2)_qC_{3-7}$cycloalkyl, and phenyl, each optionally substituted with one or more substituents each independently selected from the group consisting of halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^7$ and $R^8$ are taken together with the nitrogen to which they are attached to form indolinyl, pyrrolidinyl, piperidinyl, piperazinyl, or morpholinyl;

$R^{13}$ is selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, $—(CH_2)_qC_{3-7}$cycloalkyl, $C_{1-6}$ alkoxy, phenyl, and hydroxy-$C_{1-6}$ alkyl; or $R^{13}$ is a tetrahydrofuran ring linked through the $C_3$ or $C_4$ position of the tetrahydrofuran ring; or $R^{13}$ is a tetrahydropyran ring linked through the $C_4$ position of the tetrahydropyran ring;

$R^{14}$ and $R^{15}$ are each separately selected from hydrogen and $C_{1-6}$ alkyl; or $R^{14}$ and $R^{15}$ are taken together with the nitrogen to which they are attached to form indolinyl, pyrrolidinyl, piperidinyl, piperazinyl, or morpholinyl;

each $R^{16}$ is separately imidazolyl or pyrazolyl;

V is selected from the group consisting of —O—, —S—, and $—NR^{15}—$;

W is —N— or $—CR^{15}—$;

wherein $R^{15}$ is H, or selected from the group consisting of $C_{1-6}$ alkyl, $(CH_2)_qC_{3-7}$cycloalkyl, aryl, and heteroaryl, each optionally substituted with one or more substituents each independently selected from the group consisting of halo, cyano, nitro, $C_{1-6}$ alkyl, $C_{1-6}$ alkoxy, or phenyl;

each u is separately 0, 1 or 2;

Z is selected from the group consisting of

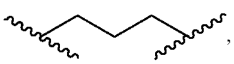,
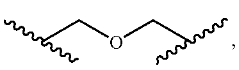,
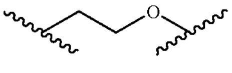,
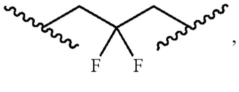,

-continued

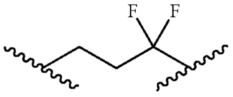,
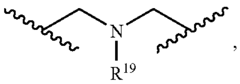,
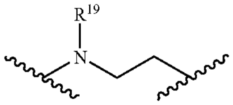,
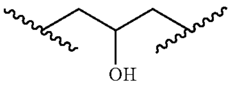, and
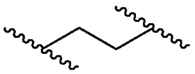;

$R^{19}$ is hydrogen, $C_{1-6}$ alkyl optionally substituted with up to 5 fluoro, or $—SO_mR^{2a}$;

$R^{20}$ is selected from the group consisting of hydrogen, $—SO_mR^{2a}$, $—C(O)OR^{2a}$, $—C(O)R^{2a}$, $—C(O)NR^{1a}R^{1b}$, and $—C(S)NR^{1a}R^{1b}$;

$R^{21}$ and $R^{22}$ are each hydrogen or together with the carbon atoms to which they are attached form an optionally substituted cyclopropyl; and the dashed line represents an optional double bond.

The present embodiments also provide compounds of the general Formula II wherein:

(a) $R^1$ is hydrogen;

(b) each m is separately 0, 1 or 2;

(c) each p is separately an integer selected from 1-6;

(d) each q is separately 0, 1 or 2;

(e) each r is separately an integer selected from 1-6;

(f) $R^3$ is $—C(O)NHS(O)_2R^9$, where $R^9$ is selected from the group consisting of $C_{1-6}$ alkyl, $—(CH_2)_qC_{3-7}$cycloalkyl, $C_{6\ or\ 10}$ aryl, and a heteroaryl, each optionally substituted with one or more substituents each separately selected from the group consisting of halo, cyano, nitro, hydroxy, —COOH, $C_{1-6}$ alkyl, $—(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is $NR^{9a}R^{9b}$;

wherein $R^{9a}$ and $R^{9b}$ are each separately a hydrogen atom, or separately selected from the group consisting of $C_{1-6}$ alkyl, $—(CH_2)_qC_{3-7}$cycloalkyl, and $C_{6\ or\ 10}$ aryl, each optionally substituted with one or more substituents each separately selected from the group consisting of halo, cyano, nitro, hydroxy, $C_{1-6}$ alkyl, $—(CH_2)_tC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or $R^{9a}$ and $R^{9b}$ are taken together with the nitrogen to which they are attached to form a three- to six-membered heterocycle, which optionally has one to three hetero atoms incorporated in the ring, and which is optionally substituted with one or more substituents each separately selected from the group consisting of halo, cyano, nitro, $C_{1-6}$ alkyl, $C_{1-6}$ alkoxy, and phenyl, or $R^{9a}$ and $R^{9b}$ are taken together with the nitrogen to which they are attached to form a heteroaryl, optionally substituted with one or more substituents each separately selected from the group consisting of a halogen, cyano, nitro, hydroxy, $C_{1-6}$ alkyl, —$(CH_2)_q$ $C_{3-7}$cycloalkyl, $C_{1-6}$ alkoxy, $C_{3-6}$ cycloalkoxy, —NH(CO)$OR^{1e}$, wherein $R^{1e}$ is $C_{1-6}$ alkyl, or —$(CH_2)_q$ $C_{3-7}$ cycloalkyl, —$N(R^{1d})_2$, —NH(CO)$R^{1d}$, and —NH(CO)$NHR^{1d}$, wherein each $R^{1d}$ is separately selected from the group consisting of a hydrogen atom, $C_{1-6}$ alkyl, and —$(CH_2)_qC_{3-7}$cycloalkyl;

or $R^9$ is selected from the group consisting of —$(CH_2)_r$C(O)$NHR^{9c}$, —$(CH_2)_r$C(O)$OR^{9c}$, and —$(CH_2)_qR^{9d}$;

wherein $R^{9c}$ is $C_{6\ or\ 10}$ aryl optionally substituted with one or more substituents each separately selected from the group consisting of —$O(CH_2)_q$C(O)$NHR^{9c}$ and —$NH(CH_2)_q$C(O)$NHR^{9e}$;

wherein $R^{9d}$ is $C_{6\ or\ 10}$ aryl substituted with one or more substituents each separately selected from the group consisting of —$O(CH_2)_q$C(O)$NHR^{9e}$ and —NH$(CH_2)_q$C(O)$NHR^{9e}$;

wherein $R^{9e}$ is selected from the group consisting of hydrogen, $C_{6\ or\ 10}$ aryl, and $C_{1-6}$ alkyl optionally substituted with up to 5 fluoro;

or $R^3$ is a —$CONHO(CH_2)_mR^{10}$ where $R^{10}$ is selected from the group consisting of $C_{1-6}$ alkyl, —$(CH_2)_qC_{3-7}$cycloalkyl, optionally substituted aryl and optionally substituted heteroaryl;

or $R^3$ is a —$CONR^{100a}R^{100b}$;

or $R^3$ is a carboxylic acid;

(g) each t is separately 0, 1 or 2;

(h) $R^{100a}$ is —$(CH_2)_vCONR^{200a}R^{200b}$, and $R^{100b}$ is a hydrogen or —$(CH_2)_vCONR^{200a}R^{200b}$; or $R^{100a}$ and $R^{100b}$ are optionally taken together with the nitrogen to which they are attached to form a three- to six-membered heterocycle, which optionally has one to three hetero atoms incorporated in the ring, and which is optionally substituted with —$(CH_2)_vCONR^{300a}R^{300b}$;

(i) each v is separately 0, 1, 2, 3, 4, 5, or 6;

(j) $R^{200a}$ and $R^{200b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(k) $R^{300a}$ and $R^{300b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(l) $R^{11}$ and $R^{12}$ are each separately selected from the group consisting of hydrogen, halo, cyano, nitro, hydroxy, cyanoamino, —SH, $C_{1-6}$ alkyl, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —N[$(CH_2)_p$OH][$(CH_2)_r$OH], —$S(O)_2NR^7R^8$, —NHC(O)$NR^7R^8$, —NHC(S)$NR^7R^8$, —C(O)$NR^7R^8$, —$NR^7R^8$, —C(O)$R^{13}$, —C(O)$OR^{13}$, —NHC(O)$R^{13}$, —NHC(O)$OR^{13}$, —$SO_mR^{13}$, —$NHS(O)_2R^{13}$, —$NR^{13}$, —[$(CH_2)_p$OH], —O[$(CH_2)_pNR^{14}R^{15}$], —S[$(CH_2)_pNR^{14}R^{15}$], —$(CH_2)_pNR^{14}R^{15}$, —$(CH_2)R^{16}$ and —$O(CH_2)_pR^{16}$;

(m) $R^7$ and $R^8$ are each separately a hydrogen, or separately selected from the group consisting of $C_{1-6}$ alkyl, —$(CH_2)_qC_{3-7}$cycloalkyl, and phenyl, each optionally substituted with one or more substituents each separately selected from the group consisting of halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^7$ and $R^8$ are taken together with the nitrogen to which they are attached to form indolinyl, pyrrolidinyl, piperidinyl, piperazinyl, or morpholinyl;

(n) $R^{13}$ is selected from the group consisting of $C_{1-6}$ alkyl, $C_{3-7}$ cycloalkyl, and $C_{6\ or\ 10}$ aryl, each optionally substituted with one or more substituents each separately selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{13}$ is a tetrahydrofuran ring linked through the $C_3$ or $C_4$ position of the tetrahydrofuran ring; or $R^{13}$ is a tetrahydropyran ring linked through the $C_4$ position of the tetrahydropyran ring;

(o) $R^{14}$ and $R^{15}$ are each separately selected from hydrogen and $C_{1-6}$ alkyl; or $R^{14}$ and $R^{15}$ are taken together with the nitrogen to which they are attached to form indolinyl, pyrrolidinyl, piperidinyl, piperazinyl, or morpholinyl;

(p) $R^{16}$ is imidazolyl or pyrazolyl;

(q) V is selected from the group consisting of —O—, —S—, and —$NR^{23}$—;

(r) $R^{23}$ is H, or selected from the group consisting of $C_{1-6}$ alkyl, —$(CH_2)_qC_{3-7}$cycloalkyl, arylalkyl, heteroarylalkyl, aryl, and heteroaryl, each optionally substituted with one or more substituents each separately selected from the group consisting of halo, cyano, nitro, $C_{1-6}$ alkyl, $C_{1-6}$ alkoxy, or phenyl; wherein said phenyl as an optional substituent is further optionally substituted with one or more substituents each separately selected from the group consisting of halo, cyano, $C_{1-6}$ alkyl optionally substituted with up to 5 fluoro, and $C_{1-6}$ alkoxy optionally substituted with up to 5 fluoro;

(s) W is —N— or —$CR^{30}$—;

(t) $R^{30}$ is H, or selected from the group consisting of $C_{1-6}$ alkyl, —$(CH_2)_qC_{3-7}$cycloalkyl, arylalkyl, heteroarylalkyl, aryl, and heteroaryl, each optionally substituted with one or more substituents each separately selected from the group consisting of halo, cyano, nitro, $C_{1-6}$ alkyl, $C_{1-6}$ alkoxy, or phenyl;

(u) Z is selected from the group consisting of

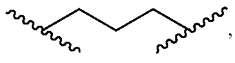, 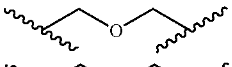, 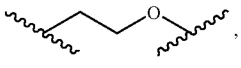, 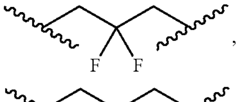, 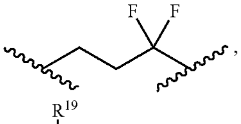, 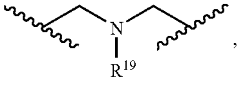, 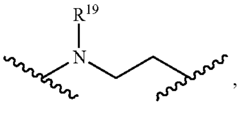, 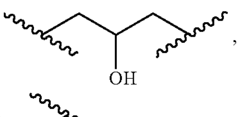, and 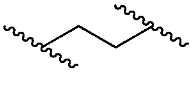;

(v) $R^{19}$ is hydrogen, —$SO_mR^{2a}$, or $C_{1-6}$ alkyl optionally substituted with up to 5 fluoro;

(w) $R^{20}$ is selected from the group consisting of —$SO_mR^{2a}$, —$C(O)OR^{2a}$, —$C(O)R^{2a}$, —$C(O)NR^{1a}R^{1b}$, and —$C(S)NR^{1a}R^{1b}$;

(x) $R^{21}$ and $R^{21}$ are each hydrogen or together with the carbon atoms to which they are attached form an optionally substituted cyclopropyl;

(y) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each separately selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(z) $R^{2a}$ is selected from the group consisting of $C_{1-6}$ alkyl, $C_{3-7}$ cycloalkyl, and $C_{6\ or\ 10}$ aryl, each optionally substituted with one or more substituents each separately selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring; and (aa) the dashed line represents an optional double bond.

The present embodiments provide compounds of the general Formula III or IV:

III

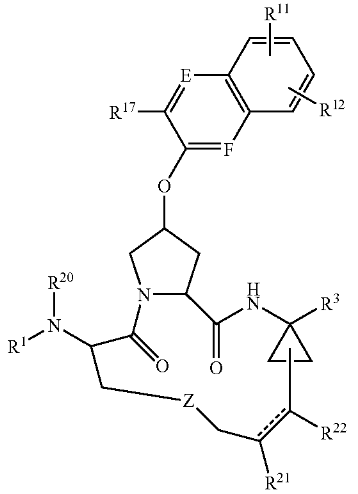

or

IV

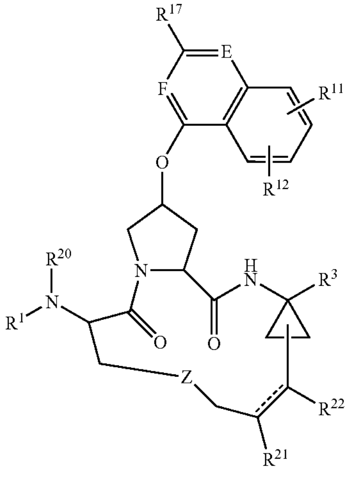

or a pharmaceutically acceptable salt or prodrug thereof wherein:

$R^1$ is —$(CR^5R^6)_nR^4$;

n is 0, 1 or 2;

$R^3$ is —$C(O)NHS(O)_2R^9$, where $R^9$ is selected from the group consisting of $C_{1-6}$ alkyl, —$(CH_2)_qC_{3-7}$cycloalkyl, $C_{6\ or\ 10}$ aryl, and a heteroaromatic ring, each optionally substituted with one or more substituents each independently selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is —$NR^{9a}R^{9b}$; or $R^3$ is a —$CONHO(CH_2)_mR^{10}$ where $R^{10}$ is selected from the group consisting of $C_{1-6}$ alkyl, —$(CH_2)_qC_{3-7}$cycloalkyl, optionally substituted aryl and optionally substituted heteroaryl; or $R^3$ is a carboxylic acid;

wherein $R^{9a}$ and $R^{9b}$ are each separately a hydrogen atom, or separately selected from the group consisting of $C_{1-6}$ alkyl, —$(CH_2)_qC_{3-7}$cycloalkyl, and $C_{6\ or\ 10}$ aryl, each optionally substituted with one or more substituents each independently selected from the group consisting of halo, cyano, nitro, hydroxy, $C_{1-6}$ alkyl, —$(CH_2)_tC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or —$NR^{9a}R^{9b}$ is a three- to six-membered alkyl cyclic secondary amine, which optionally has one to three hetero atoms incorporated in the ring, and which is optionally substituted with one or more substituents each independently selected from the group consisting of halo, cyano, nitro, $C_{1-6}$ alkyl, $C_{1-6}$ alkoxy, and phenyl;

or $R^{9a}$ and $R^{9b}$ are taken together with the nitrogen to which they are attached to form a heteroaryl, optionally substituted with one or more substituents each independently selected from the group consisting of a halogen, cyano, nitro, hydroxy, $C_{1-6}$ alkyl, —$(CH_2)_qC_{3-7}$cycloalkyl, $C_{1-6}$ alkoxy, $C_{3-6}$ cycloalkoxy, —$NH(CO)OR^{1e}$, wherein $R^{1e}$ is $C_{1-6}$ alkyl, or —$(CH_2)_qC_{3-7}$cycloalkyl, —$N(R^{1d})_2$, —$NH(CO)R^{1d}$, and —$NH(CO)NHR^{1d}$, wherein each $R^{1d}$ is separately selected from the group consisting of a hydrogen atom, $C_{1-6}$ alkyl, and $(CH_2)_qC_{3-7}$cycloalkyl;

each m is separately 0, 1 or 2;

each q is separately 0, 1 or 2;

each t is separately 0, 1 or 2;

$R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, $NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_p$ $NR^{3a}R^{3b}$, —$(CH_2)_pR^{4a}$ and —$O(CH_2)_pR^{4a}$;

$R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

$R^{2a}$ is selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

$R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

each $R^{4a}$ is separately imidazolyl or pyrazolyl;

each p is separately an integer selected from 1-6;

each r is separately an integer selected from 1-6;

$R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

$R^{11}$ and $R^{12}$ are each separately selected from the group consisting of hydrogen, halo, cyano, nitro, hydroxy, cyanoamino, —SH, $C_{1-6}$ alkyl, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^7R^8$, —$NHC(O)NR^7R^8$, —$NHC(S)NR^7R^8$, —$C(O)NR^7R^8$, —$NR^7R^8$, —$C(O)R^{13}$, —$C(O)OR^{13}$, —$NHC(O)R^{13}$, —$NHC(O)OR^{13}$, —$SO_mR^{13}$, —$NHS(O)_2R^{13}$, —$NR^{13}[(CH_2)_pOH]$, —$O[(CH_2)_pNR^{14}R^{15}]$, —$S[(CH_2)_pNR^{14}R^{15}]$, —$(CH_2)_pNR^{14}R^{15}$, —$(CH_2)R^{16}$ and —$O(CH_2)_pR^{16}$;

$R^7$ and $R^8$ are each separately a hydrogen, or separately selected from the group consisting of $C_{1-6}$ alkyl, —$(CH_2)_qC_{3-7}$cycloalkyl, and phenyl, each optionally substituted with one or more substituents each independently selected from the group consisting of halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^7$ and $R^8$ are taken together with the nitrogen to which they are attached to form indolinyl, pyrrolidinyl, piperidinyl, piperazinyl, or morpholinyl;

$R^{13}$ is selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{13}$ is a tetrahydrofuran ring linked through the $C_3$ or $C_4$ position of the tetrahydrofuran ring; or $R^{13}$ is a tetrahydropyran ring linked through the $C_4$ position of the tetrahydropyran ring;

$R^{14}$ and $R^{15}$ are each separately selected from hydrogen and $C_{1-6}$ alkyl; or $R^{14}$ and $R^{15}$ are taken together with the nitrogen to which they are attached to form indolinyl, pyrrolidinyl, piperidinyl, piperazinyl, or morpholinyl;

each $R^{16}$ is separately imidazolyl or pyrazolyl;

$R^{17}$ is a hydrogen, or selected from the group consisting of $C_{1-6}$ alkyl, —$(CH_2)_qC_{3-7}$cycloalkyl, aryl, and heteroaryl, each optionally substituted with one or more substituents each independently selected from the group consisting of halo, cyano, nitro, $C_{1-6}$ alkyl, $C_{1-6}$ alkoxy, phenyl, and —$NR^{1a}R^{1b}$;

E and F are independently —N— or —$CR^{18}$—;

when E is —$CR^{18}$—, F is —N—; when F is —$CR^{18}$—, E is —N—;

each $R^{18}$ is separately a hydrogen, or selected from the group consisting of $C_{1-6}$ alkyl, $(CH_2)_qC_{3-7}$cycloalkyl, aryl, and heteroaryl, each optionally substituted with one or more substituents each independently selected from the group consisting of halo, cyano, nitro, $C_{1-6}$ alkyl, $C_{1-6}$ alkoxy, and phenyl;

each u is independently 0, 1 or 2;

Z is selected from the group consisting of

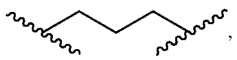,
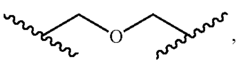,
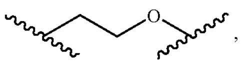,
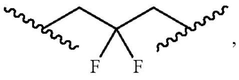,
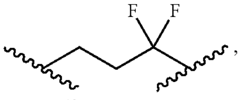,
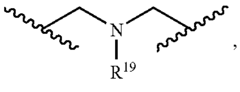,
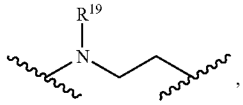,
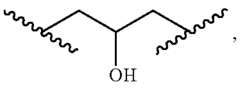, and -continued

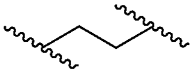

;

$R^{19}$ is hydrogen, $C_{1-6}$ alkyl optionally substituted with up to 5 fluoro, or —$SO_mR^{2a}$;

$R^{20}$ is selected from the group consisting of hydrogen, —$SO_mR^{2a}$, —$C(O)OR^{2a}$, —$C(O)R^{2a}$, —$C(O)NR^{1a}R^{1b}$, and —$C(S)NR^{1a}R^{1b}$;

$R^{21}$ and $R^{22}$ are each hydrogen or together with the carbon atoms to which they are attached form an optionally substituted cyclopropyl; and the dashed line represents an optional double bond.

The present embodiments provide compounds of the general Formula V or VI:

(V)

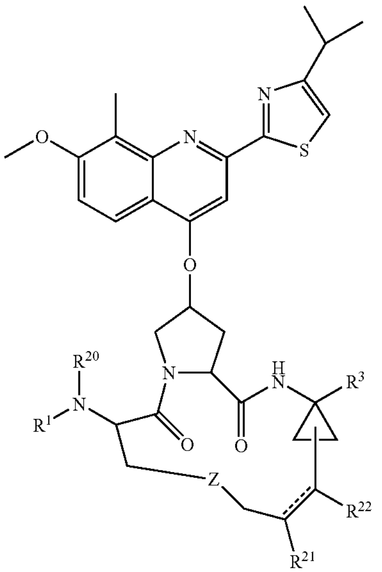

or (VI)

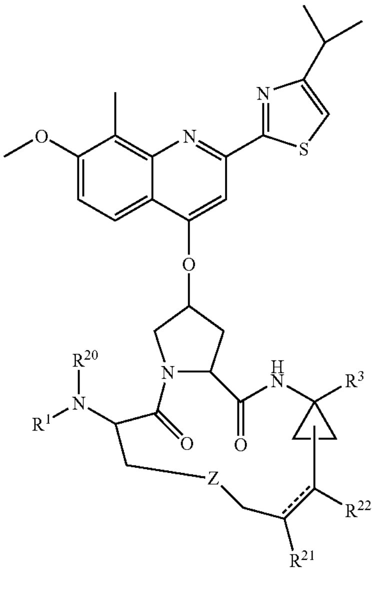

or a pharmaceutically acceptable salt or prodrug thereof wherein:

$R^1$ is —$(CR^5R^6)_nR^4$;

n is 0, 1 or 2;

$R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_pNR^{3a}R^{3b}$, —$(CH_2)_pR^{4a}$ and —$O(CH_2)_pR^{4a}$;

$R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

$R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

each $R^{4a}$ is separately imidazolyl or pyrazolyl;

each m is separately 0, 1 or 2;

each p is separately an integer selected from 1-6;

each q is separately 0, 1 or 2;

each r is separately an integer selected from 1-6;

$R^3$ is —$C(O)NHS(O)_2R^9$, where $R^9$ is selected from the group consisting of $C_{1-6}$ alkyl, —$(CH_2)_qC_{3-7}$cycloalkyl, $C_{6\ or\ 10}$ aryl, and a heteroaromatic ring, each optionally substituted with one or more substituents each independently selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is —$NR^{9a}R^{9b}$; or $R^3$ is a —$CONHO(CH_2)_mR^{10}$ where $R^{10}$ is selected from the group consisting of $C_{1-6}$ alkyl, —$(CH_2)_qC_{3-7}$cycloalkyl, optionally substituted aryl and optionally substituted heteroaryl; or $R^3$ is a carboxylic acid;

wherein $R^{9a}$ and $R^{9b}$ are each separately a hydrogen atom, or separately selected from the group consisting of $C_{1-6}$ alkyl, —$(CH_2)_qC_{3-7}$cycloalkyl, and $C_{6\ or\ 10}$ aryl, each optionally substituted with one or more substituents each independently selected from the group consisting of halo, cyano, nitro, hydroxy, $C_{1-6}$ alkyl, —$(CH_2)_tC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or —$NR^{9a}R^{9b}$ is a three- to six-membered alkyl cyclic secondary amine, which optionally has one to three hetero atoms incorporated in the ring, and which is optionally substituted with one or more substituents each independently selected from the group consisting of halo, cyano, nitro, $C_{1-6}$ alkyl, $C_{1-6}$ alkoxy, and phenyl, or $R^{9a}$ and $R^{9b}$ are taken together with the nitrogen to which they are attached to form a heteroaryl, optionally substituted with one or more substituents each independently selected from the group consisting of a halogen, cyano, nitro, hydroxy, $C_{1-6}$ alkyl, —$(CH_2)_qC_{3-7}$cycloalkyl, $C_{1-6}$ alkoxy, $C_{3-6}$ cycloalkoxy, —NH(CO)$OR^{1e}$, wherein $R^{1e}$ is $C_{1-6}$ alkyl, or —$(CH_2)_qC_{3-7}$cycloalkyl, —$N(R^{1d})_2$, —NH(CO)$R^{1d}$, and —NH(CO)$NHR^{1d}$, wherein each $R^{1d}$ is separately selected from the group consisting of a hydrogen atom, $C_{1-6}$ alkyl, and —$(CH_2)_qC_{3-7}$cycloalkyl;

each t is separately 0, 1 or 2;

$R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each u is separately 0, 1 or 2;

Z is selected from the group consisting of

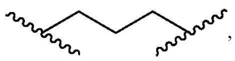 , 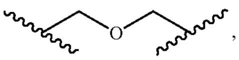 ,

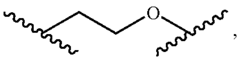 , 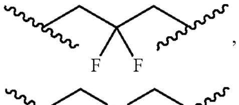 ,

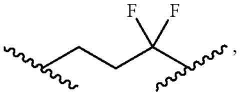 , 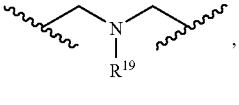 ,

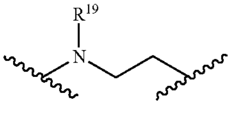 , 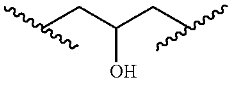 , and

-continued

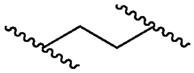 ;

$R^{19}$ is hydrogen, $C_{1-6}$ alkyl optionally substituted with up to 5 fluoro, or —$SO_mR^{2a}$;

$R^{20}$ is selected from the group consisting of hydrogen, —$SO_mR^{2a}$, —C(O)$OR^{2a}$, —C(O)$R^{2a}$, —C(O)$NR^{1a}R^{1b}$, and —C(S)$NR^{1a}R^{1b}$;

$R^{21}$ and $R^{22}$ are each hydrogen or together with the carbon atoms to which they are attached form an optionally substituted cyclopropyl; and the dashed line represents an optional double bond.

The present embodiments also provide compounds of the general Formula V or VI wherein:

(a) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each separately selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(b) $R^{2a}$ is selected from the group consisting of $C_{1-6}$ alkyl, $C_{3-7}$ cycloalkyl, and $C_{6\ or\ 10}$ aryl, each optionally substituted with one or more substituents each separately selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

(c) each m is separately 0, 1 or 2;

(d) each p is separately an integer selected from 1-6;

(e each q is separately 0, 1 or 2;

(f) $R^3$ is —C(O)$NHS(O)_2R^9$, where $R^9$ is selected from the group consisting of $C_{1-6}$ alkyl, —$(CH_2)_qC_{3-7}$cycloalkyl, $C_{6\ or\ 10}$ aryl, and a heteroaryl, each optionally substituted with one or more substituents each separately selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is $NR^{9a}R^{9b}$;

wherein $R^{9a}$ and $R^{9b}$ are each separately a hydrogen atom, or separately selected from the group consisting of $C_{1-6}$ alkyl, —$(CH_2)_qC_{3-7}$cycloalkyl, and $C_{6\ or\ 10}$ aryl, each optionally substituted with one or more substituents each separately selected from the group consisting of halo, cyano, nitro, hydroxy, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or $R^{9a}$ and $R^{9b}$ are taken together with the nitrogen to which they are attached to form a three- to six-membered heterocycle, which optionally has one to three hetero atoms incorporated in the ring, and which is optionally substituted with one or more substituents each separately selected from the group consisting of halo, cyano, nitro, $C_{1-6}$ alkyl, $C_{1-6}$ alkoxy, and phenyl, or $R^{9a}$ and $R^{9b}$ are taken together with the nitrogen to which they are attached to form a heteroaryl, optionally substituted with one or more substituents each separately selected from the group consisting of a halogen, cyano, nitro, hydroxy, $C_{1-6}$ alkyl, $—(CH_2)_qC_{3-7}$cycloalkyl, $C_{1-6}$ alkoxy, $C_{3-6}$ cycloalkoxy, $—NH(CO)OR^{1e}$, wherein $R^{1e}$ is $C_{1-6}$ alkyl, or $—(CH_2)_qC_{3-7}$ cycloalkyl, $—N(R^{1d})_2$, $—NH(CO)R^{1d}$, and $—NH(CO)NHR^{1d}$, wherein each $R^{1d}$ is separately selected from the group consisting of a hydrogen atom, $C_{1-6}$ alkyl, and $—(CH_2)_qC_{3-7}$cycloalkyl;

or $R^3$ is a $—CONHO(CH_2)_mR^{10}$ where $R^{10}$ is selected from the group consisting of $C_{1-6}$ alkyl, $—(CH_2)_qC_{3-7}$cycloalkyl, optionally substituted aryl and optionally substituted heteroaryl;

or $R^3$ is a $—CONR^{100a}R^{100b}$;

or $R^3$ is a carboxylic acid;

(g) each t is separately 0, 1 or 2;

(h) $R^{100a}$ is $—(CH_2)_vCONR^{200a}R^{200b}$, and $R^{100b}$ is a hydrogen or $—(CH_2)_vCONR^{200a}R^{200b}$; or $R^{100a}$ and $R^{100b}$ are optionally taken together with the nitrogen to which they are attached to form a three- to six-membered heterocycle, which optionally has one to three additional hetero atoms incorporated in the ring, and which is optionally substituted with $—(CH_2)_vCONR^{300a}R^{300b}$ (i) each v is separately 0, 1, 2, 3, 4, 5, or 6;

(j) $R^{200a}$ and $R^{200b}$ are each separately hydrogen or $—(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(k) $R^{300a}$ and $R^{300b}$ are each separately hydrogen or $—(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(l) Z is selected from the group consisting of

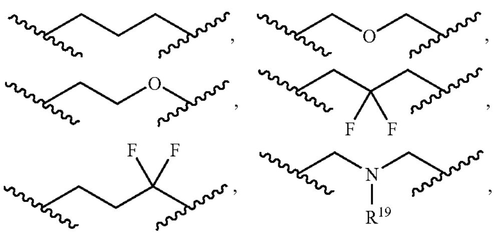

-continued

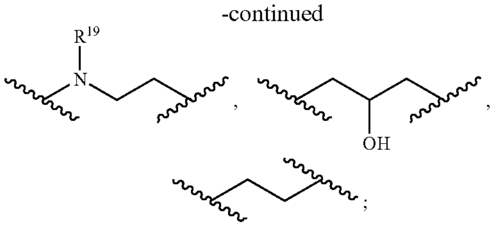

, and ;

(m) $R^{19}$ is hydrogen, $—SO_mR^{2a}$, or $C_{1-6}$ alkyl optionally substituted with up to fluoro;

(n) $R^{20}$ is selected from the group consisting of $—SO_mR^{2a}$, $—C(O)OR^{2a}$, $—C(O)R^{2a}$, $—C(O)NR^{1a}R^{1b}$, and $—C(S)NR^{1a}R^{1b}$;

(o) $R^{21}$ and $R^{21}$ are each hydrogen or together with the carbon atoms to which they are attached form an optionally substituted cyclopropyl; and (p) the dashed line represents an optional double bond.

The present embodiments provide compounds of the general Formula VII:

VII

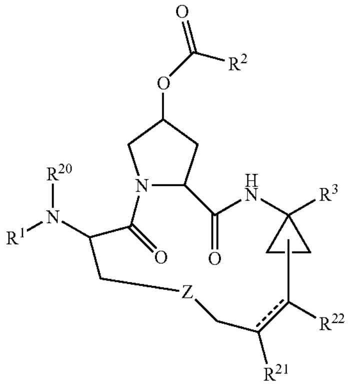

or a pharmaceutically acceptable salt or prodrug thereof wherein:

(a) $R^1$ is hydrogen;

(b) $R^2$ is selected from the group consisting of:

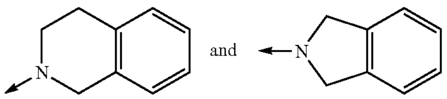

and , each optionally substituted with one or more substituents each separately selected from the group consisting of halo, cyano, nitro, hydroxy, cyanoamino, —SH, $C_{1-6}$ alkyl, $C_{1-6}$ alkoxy, $C_{2-6}$ alkenyl, $C_{2-6}$ alkynyl, $—(CH_2)_qC_{3-7}$cycloalkyl, $C_{3-6}$ heterocycloalkyl, aryl, heteroaryl, aryloxy, arylthio, $C_{1-6}$ alkylthio, $—N[(CH_2)_pOH][(CH_2)_rOH]$, $—S(O)_2NR^{1a}R^{1b}$, $—NHC(O)NR^{1a}R^{1b}$, $—NHC(S)NR^{1a}R^{1b}$, $—C(O)NR^{1a}R^{1b}$, $—NR^{1a}R^{1b}$, $—C(O)R^{2a}$, $—C(O)OR^{2a}$, $—NHC(O)R^{2a}$, $—NHC(O)OR^{2a}$, $—SO_mR^{2a}$, $—NHS(O)_2R^{2a}$, $—NR^{2a}[(CH_2)_pOH]$, $—O[(CH_2)_pNR^{3a}R^{3b}]$, $—S[(CH_2)_pNR^{3a}R^{3b}]$, $—(CH_2)_pNR^{3a}R^{3b}$, $—(CH_2)_pR^{4a}$ and $—O(CH_2)_pR^{4a}$;

(c) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each separately selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(d) each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl;

(e) $R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

(f) $R^{4a}$ is imidazolyl or pyrazolyl;

(g) each m is separately 0, 1 or 2;

(h) each p is separately an integer selected from 1-6;

(i) each q is separately 0, 1 or 2;

(j) each r is separately an integer selected from 1-6;

(k) $R^{20}$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_p\ NR^{3a}R^{3b}$, —$(CH_2)_pR^{4a}$ and —$O(CH_2)_pR^{4a}$;

(l) $R^3$ is —$C(O)NHS(O)_2R^9$, where $R^9$ is selected from the group consisting of —$(CH_2)_rC(O)NHR^{9c}$, —$(CH_2)_rC(O)OR^{9c}$, and —$(CH_2)_qR^{9d}$;

wherein $R^{9c}$ is $C_{6\ or\ 10}$ aryl optionally substituted with one or more substituents each separately selected from the group consisting of —$O(CH_2)_qC(O)NHR^{9e}$ and —$NH(CH_2)_qC(O)NHR^{9e}$;

wherein $R^{9d}$ is $C_{6\ or\ 10}$ aryl substituted with one or more substituents each separately selected from the group consisting of —$O(CH_2)_qC(O)NHR^{9e}$ and —$NH(CH_2)_qC(O)NHR^{9e}$;

wherein $R^{9e}$ is selected from the group consisting of hydrogen, $C_{6\ or\ 10}$ aryl, and $C_{1-6}$ alkyl optionally substituted with up to 5 fluoro;

or $R^3$ is —$C(O)NHS(O)_2R^9$, where $R^9$ is —$(CH_2)_qC_{3-7}$cycloalkyl substituted with methyl;

or $R^3$ is a —$CONHO(CH_2)_mR^{10}$ where $R^{10}$ is selected from the group consisting of $C_{1-6}$ alkyl, —$(CH_2)_qC_{3-7}$cycloalkyl, optionally substituted aryl and optionally substituted heteroaryl;

or $R^3$ is a —$CONR^{100a}R^{100b}$;

or $R^3$ is carboxylic acid;

(m) each t is separately 0, 1 or 2;

(n) $R^{100a}$ is —$(CH_2)_vCONR^{200a}R^{200b}$, and $R^{100b}$ is a hydrogen or —$(CH_2)_vCONR^{200a}R^{200b}$; or $R^{100a}$ and $R^{100b}$ are optionally taken together with the nitrogen to which they are attached to form a three- to six-membered heterocycle, which optionally has one to three additional hetero atoms incorporated in the ring, and which is optionally substituted with —$(CH_2)_vCONR^{300a}R^{300b}$;

(o) each v is separately 0, 1, 2, 3, 4, 5, or 6;

(p) $R^{200a}$ and $R^{200b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(q) $R^{300a}$ and $R^{300b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(r) Z is selected from the group consisting of

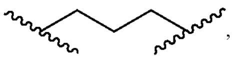,
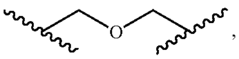,
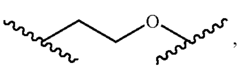,
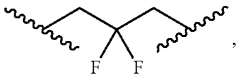,
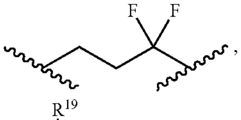,
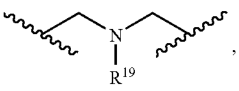,
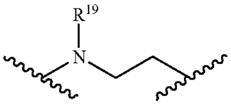,
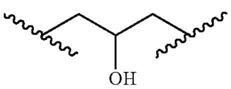, and
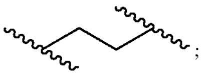;

(s) $R^{19}$ is hydrogen, —$SO_mR^{2a}$, or $C_{1-6}$ alkyl optionally substituted with up to 5 fluoro;

(t) $R^{21}$ and $R^{21}$ are each hydrogen or together with the carbon atoms to which they are attached form an optionally substituted cyclopropyl; and (u) the dashed line represents an optional double bond.

The present embodiments provide compounds of the general Formula X:

(X)

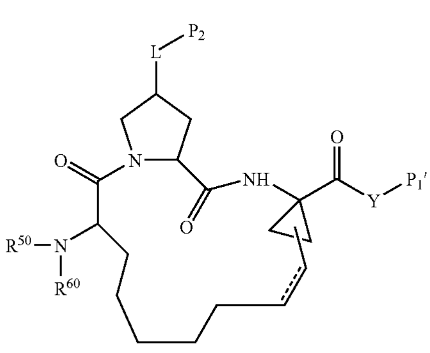

or a pharmaceutically acceptable salt, prodrug, or ester thereof wherein:

(a) Y is a moiety having a size and configuration such that, upon binding of the compound to NS3 protease, at least one atom of Y is within 4 Å or less of at least one moiety selected from NS3 protease His57 imidazole moiety and NS3 protease Gly137 nitrogen atom;

(b) $P_1$' is a moiety, different from Y, having a size and configuration such that, upon binding of the compound to NS3 protease, at least one atom of $P_1$' is within 6 Å or less of at least one NS3 protease S1' pocket moiety selected from the group consisting of Lys136, Gly137, Ser139, His57, Gly58, Gln41, Ser42, and Phe43;

(c) L is a moiety consisting of from 1 to 5 atoms selected from the group consisting of carbon, oxygen, nitrogen, hydrogen, and sulfur;

(d) $P_2$ is a moiety selected from the group consisting of unsubstituted aryl, substituted aryl, unsubstituted heteroaryl, substituted heteroaryl, unsubstituted heterocyclic and substituted heterocyclic;

(e) the dashed line represents an optional double bond;

(f) $P_2$ is positioned by L such that, upon binding of the compound to NS3 protease, at least one atom of $P_2$ is within 5 Å or less of any backbone or side chain atom of at least one NS3 protease residue selected from the group consisting of Tyr56, His57, Val78, Asp79, Gln80, Asp81, Arg155 and Ala156;

(g) $R^{50}$ is H and $R^{60}$ is selected from the group consisting of unsubstituted aryl, substituted aryl, unsubstituted heteroaryl, substituted heteroaryl, unsubstituted heterocyclic and substituted heterocyclic; or $R^{50}$ and $R^{60}$ taken together with the nitrogen to which they are attached form a moiety selected from the group consisting of unsubstituted heteroaryl, substituted heteroaryl, unsubstituted heterocyclic and substituted heterocyclic; and (h) $R^{50}$ and $R^{60}$ are positioned such that, upon binding of the compound to NS3 protease, at least one atom of $R^{50}$ or $R^{60}$ is within 5 Å or less of any backbone or side chain atom of at least one NS3 protease residue selected from the group consisting of Arg123, Ala156, Ala157, Val158, Cys159, and Asp168.

DETAILED DESCRIPTION OF THE EMBODIMENTS

Definitions

As used herein, common organic abbreviations are defined as follows:

Ac Acetyl
$Ac_2O$ Acetic anhydride
aq. Aqueous
Bn Benzyl
Bz Benzoyl
BOC or Boc tert-Butoxycarbonyl
Bu n-Butyl
cat. Catalytic
Cbz Carbobenzyloxy
CDI 1,1'-carbonyldiimidazole
Cy ($c\text{-}C_6H_{11}$) Cyclohexyl
° C. Temperature in degrees Centigrade
DBU 1,8-Diazabicyclo[5.4.0]undec-7-ene
DCE 1,2-Dichloroethane
DCM methylene chloride
DIEA Diisopropylethylamine
DMA Dimethylacetamide
DMAP 4-(Dimethylamino)pyridine
DME Dimethoxyethane
DMF N,N'-Dimethylformamide
DMSO Dimethylsulfoxide
Et Ethyl
EtOAc Ethyl acetate
g Gram(s)
h Hour (hours)
HATU 2-(1H-7-azabenzotriazol-1-yl)-1,1,3,3-tetramethyl uronium hexafluorophosphate
HOBT 1-Hydroxybenzotriazole
HPLC High performance liquid chromatography
iPr Isopropyl
IU International Units
LCMS Liquid chromatography-mass spectrometry
LDA Lithium diisopropylamide
mCPBA meta-Chloroperoxybenzoic Acid
MeOH Methanol
MeCN Acetonitrile
mL Milliliter(s)
MTBE Methyl tertiary-butyl ether
$NH_4OAc$ Ammonium acetate
PG Protecting group
Pd/C Palladium on activated carbon
ppt Precipitate
PyBOP (Benzotriazol-1-yloxy)tripyrrolidinophosphonium hexafluorophosphate
RCM Ring closing metathesis
rt Room temperature
sBuLi sec-Butylithium
TEA Triethylamine
TCDI 1,1'-Thiocarbonyl diimidazole
Tert, t tertiary
TFA Trifluoracetic acid
THF Tetrahydrofuran
TLC Thin-layer chromatography
TMEDA Tetramethylethylenediamine
μL Microliter(s)

As used herein, the term "hepatic fibrosis," used interchangeably herein with "liver fibrosis," refers to the growth of scar tissue in the liver that can occur in the context of a chronic hepatitis infection.

The terms "individual," "host," "subject," and "patient" are used interchangeably herein, and refer to a mammal, including, but not limited to, primates, including simians and humans.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

The term "sustained viral response" (SVR; also referred to as a "sustained response" or a "durable response"), as used herein, refers to the response of an individual to a treatment regimen for HCV infection, in terms of serum HCV titer. Generally, a "sustained viral response" refers to no detectable HCV RNA (e.g., less than about 500, less than about 200, or less than about 100 genome copies per milliliter serum) found in the patient's serum for a period of at least about one month, at least about two months, at least about three months, at least about four months, at least about five months, or at least about six months following cessation of treatment.

"Treatment failure patients" as used herein generally refers to HCV-infected patients who failed to respond to previous therapy for HCV (referred to as "non-responders") or who initially responded to previous therapy, but in whom the therapeutic response was not maintained (referred to as "relapsers"). The previous therapy generally can include treatment with IFN-α monotherapy or IFN-α combination therapy, where the combination therapy may include administration of IFN-α and an antiviral agent such as ribavirin.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, murines, simians, humans, mammalian farm animals, mammalian sport animals, and mammalian pets.

As used herein, the term "a Type I interferon receptor agonist" refers to any naturally occurring or non-naturally occurring ligand of human Type I interferon receptor, which binds to and causes signal transduction via the receptor. Type I interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

As used herein, the term "Type II interferon receptor agonist" refers to any naturally occurring or non-naturally occurring ligand of human Type II interferon receptor that binds to and causes signal transduction via the receptor. Type II interferon receptor agonists include native human interferon-γ, recombinant IFN-γ species, glycosylated IFN-γ species, pegylated IFN-γ species, modified or variant IFN-γ species, IFN-γ fusion proteins, antibody agonists specific for the receptor, non-peptide agonists, and the like.

As used herein, the term "a Type III interferon receptor agonist" refers to any naturally occurring or non-naturally occurring ligand of humanIL-28 receptor α ("IL-28R"), the amino acid sequence of which is described by Sheppard, et al., infra., that binds to and causes signal transduction via the receptor.

As used herein, the term "interferon receptor agonist" refers to any Type I interferon receptor agonist, Type II interferon receptor agonist, or Type III interferon receptor agonist.

The term "dosing event" as used herein refers to administration of an antiviral agent to a patient in need thereof, which event may encompass one or more releases of an antiviral agent from a drug dispensing device. Thus, the term "dosing event," as used herein, includes, but is not limited to, installation of a continuous delivery device (e.g., a pump or other controlled release injectible system); and a single subcutaneous injection followed by installation of a continuous delivery system.

"Continuous delivery" as used herein (e.g., in the context of "continuous delivery of a substance to a tissue") is meant to refer to movement of drug to a delivery site, e.g., into a tissue in a fashion that provides for delivery of a desired amount of substance into the tissue over a selected period of time, where about the same quantity of drug is received by the patient each minute during the selected period of time.

"Controlled release" as used herein (e.g., in the context of "controlled drug release") is meant to encompass release of substance (e.g., a Type I or Type III interferon receptor agonist, e.g., IFN-α) at a selected or otherwise controllable rate, interval, and/or amount, which is not substantially influenced by the environment of use. "Controlled release" thus encompasses, but is not necessarily limited to, substantially continuous delivery, and patterned delivery (e.g., intermittent delivery over a period of time that is interrupted by regular or irregular time intervals).

"Patterned" or "temporal" as used in the context of drug delivery is meant delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug delivery device" is meant to encompass any device wherein the release (e.g., rate, timing of release) of a drug or other desired substance contained therein is controlled by or determined by the device itself and not substantially influenced by the environment of use, or releasing at a rate that is reproducible within the environment of use.

By "substantially continuous" as used in, for example, the context of "substantially continuous infusion" or "substantially continuous delivery" is meant to refer to delivery of drug in a manner that is substantially uninterrupted for a pre-selected period of drug delivery, where the quantity of drug received by the patient during any 8 hour interval in the pre-selected period never falls to zero. Furthermore, "substantially continuous" drug delivery can also encompass delivery of drug at a substantially constant, pre-selected rate or range of rates (e.g., amount of drug per unit time, or volume of drug formulation for a unit time) that is substantially uninterrupted for a pre-selected period of drug delivery.

By "substantially steady state" as used in the context of a biological parameter that may vary as a function of time, it is meant that the biological parameter exhibits a substantially constant value over a time course, such that the area under the curve defined by the value of the biological parameter as a function of time for any 8 hour period during the time course (AUC8 hr) is no more than about 20% above or about 20% below, and preferably no more than about 15% above or about 15% below, and more preferably no more than about 10% above or about 10% below, the average area under the curve of the biological parameter over an 8 hour period during the time course (AUC8 hr average). The AUC8 hr average is defined as the quotient (q) of the area under the curve of the biological parameter over the entirety of the time course (AUCtotal) divided by the number of 8 hour intervals in the time course (total/3 days), i.e., q=(AUCtotal)/(total/3 days). For example, in the context of a serum concentration of a drug, the serum concentration of the drug is maintained at a substantially steady state during a time course when the area under the curve of serum concentration of the drug over time for any 8 hour period during the time course (AUC8 hr) is no more than about 20% above or about 20% below the average area under the curve of serum concentration of the drug over an 8 hour period in the time course (AUC8 hr average), i.e., the AUC8 hr is no more than 20% above or 20% below the AUC8 hr average for the serum concentration of the drug over the time course.

The term "alkyl" as used herein refers to a radical of a fully saturated hydrocarbon, including, but not limited to, methyl, ethyl, n-propyl, isopropyl, n-butyl, isobutyl, tert-butyl, n-hexyl,

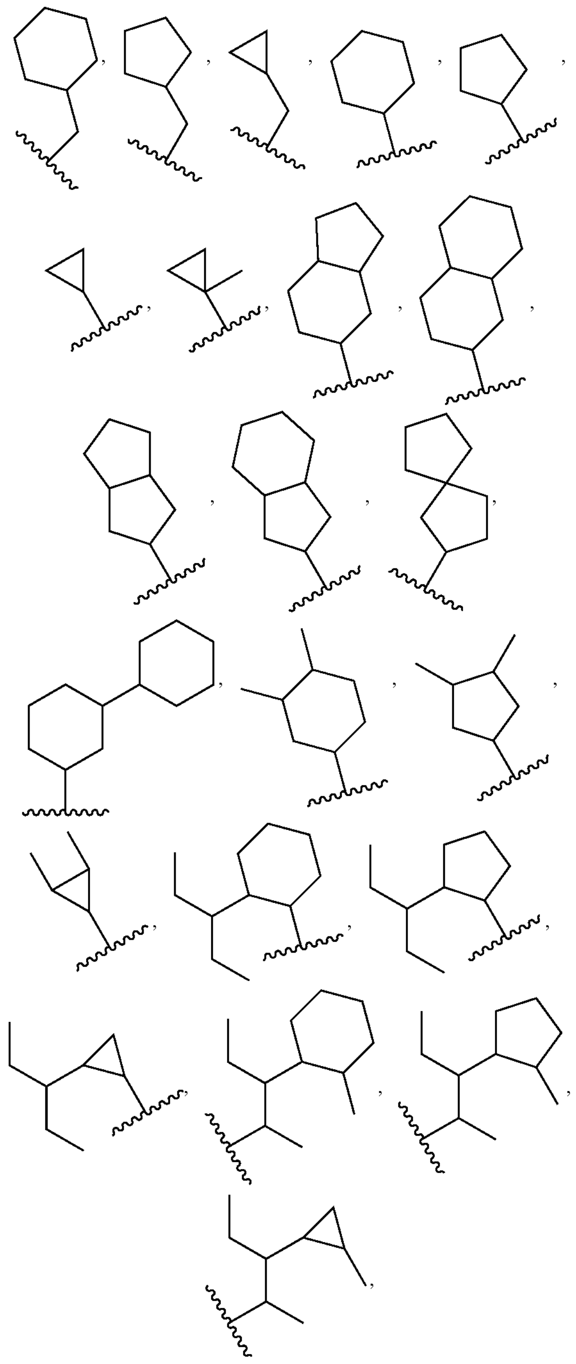

and the like. For example, the term "alkyl" as used herein includes radicals of fully saturated hydrocarbons defined by the following general formula's: the general formula for linear or branched fully saturated hydrocarbons not containing a cyclic structure is $C_nH_{2n+2}$; the general formula for a fully saturated hydrocarbon containing one ring is $C_nH_{2n}$; the general formula for a fully saturated hydrocarbon containing two rings is $C_nH_{2(n-1)}$; the general formula for a saturated hydrocarbon containing three rings is $C_nH_{2(n-2)}$.

The term "halo" used herein refers to fluoro, chloro, bromo, or iodo.

The term "alkoxy" used herein refers to straight or branched chain alkyl radical covalently bonded to the parent molecule through an —O-linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "polycyclic moiety" used herein refers a bicyclic moiety or tricyclic moiety optionally containing one or more heteroatoms wherein at least one of the rings is not an aryl or heteroaryl ring. The bicyclic moiety contains two rings wherein the rings are fused, the bicyclic moiety can be appended at any position of the two rings. For example, bicyclic moiety may refer to a radical including but not limited to:

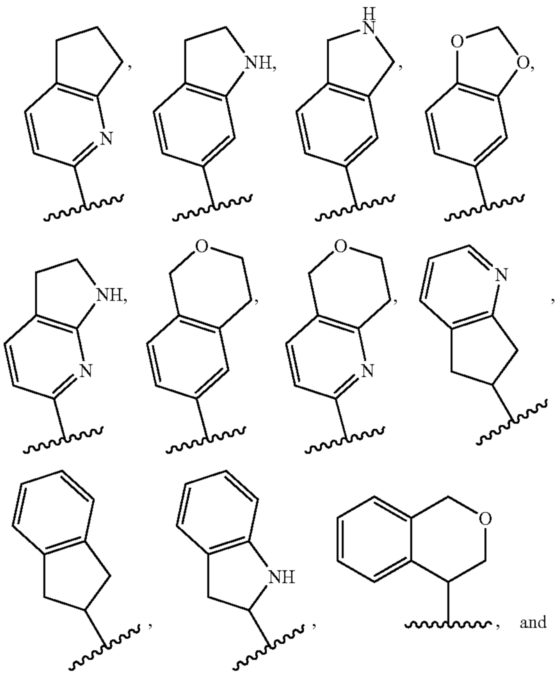

and

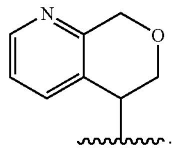

The tricyclic moiety contains a bicyclic moiety with an additional fused ring, the tricyclic moiety can be appended at any position of the three rings. For example, tricyclic moiety may refer to a radical including but not limited to:

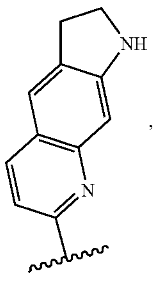, 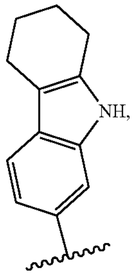, 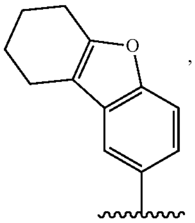,

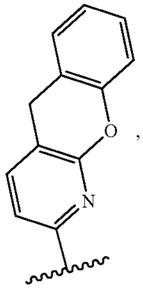, 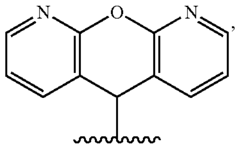,

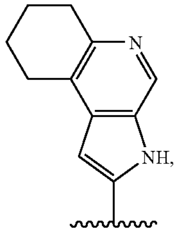 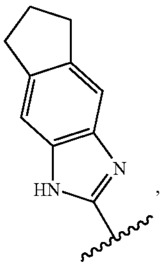, 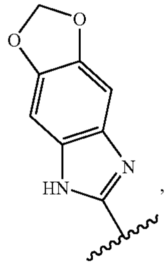,

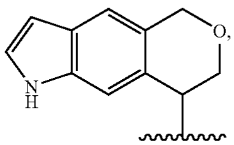 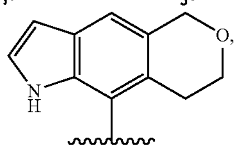

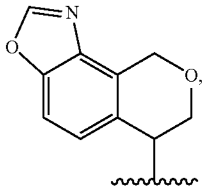 and 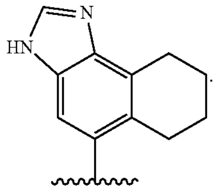.

The term "aryl" used herein refers to homocyclic aromatic radical whether one ring or multiple fused rings. Examples of aryl groups include, but are not limited to, phenyl, naphthyl, phenanthrenyl, naphthacenyl, and the like.

The term "cycloalkyl" used herein refers to saturated aliphatic ring system radical having three to twenty carbon atoms including, but not limited to, cyclopropyl, cyclopentyl, cyclohexyl, cycloheptyl, and the like.

The term "cycloalkenyl" used herein refers to aliphatic ring system radical having three to twenty carbon atoms having at least one carbon-carbon double bond in the ring. Examples of cycloalkenyl groups include, but are not limited to, cyclopropenyl, cyclopentenyl, cyclohexenyl, cycloheptenyl, bicyclo [3.1.0]hexyl, and the like.

The term "polycycloalkyl" used herein refers to saturated aliphatic ring system radical having at least two rings that are fused with or without bridgehead carbons. Examples of polycycloalkyl groups include, but are not limited to, bicyclo [4.4.0]decanyl, bicyclo[2.2.1]heptanyl, adamantyl, norbornyl, and the like.

The term "polycycloalkenyl" used herein refers to aliphatic ring system radical having at least two rings that are fused with or without bridgehead carbons in which at least one of the rings has a carbon-carbon double bond. Examples of polycycloalkenyl groups include, but are not limited to, norbornylenyl, 1,1'-bicyclopentenyl, and the like.

The term "polycyclic hydrocarbon" used herein refers to a ring system radical in which all of the ring members are carbon atoms. Polycyclic hydrocarbons can be aromatic or can contain less than the maximum number of non-cumulative double bonds. Examples of polycyclic hydrocarbon include, but are not limited to, naphthyl, dihydronaphthyl, indenyl, fluorenyl, and the like.

The term "heterocyclic" or "heterocyclyl" or "heterocycloalkyl" used herein refers to cyclic non-aromatic ring system radical having at least one ring in which one or more ring atoms are not carbon, namely heteroatom. In fused ring systems, the one or more heteroatoms may be present in only one of the rings. Examples of heterocyclic groups include, but are not limited to, morpholinyl, tetrahydrofuranyl, dioxolanyl, pyrrolidinyl, pyranyl, piperidyl, piperazyl, and the like.

The term "heteroaryl" used herein refers to an aromatic heterocyclic group, whether one ring or multiple fused rings. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridinyl, pyrrolyl, oxazolyl, indolyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "cycloalkylalkyl" used herein refers to one or more cycloalkyl groups appended to an alkyl radical. Examples of cycloalkylalkyl include, but are not limited to, cyclohexylmethyl, cyclohexylethyl, cyclopentylmethyl, cyclopentylethyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "heterocyclylalkyl" used herein refers to one or more heterocyclyl groups appended to an alkyl radical. Examples of heterocyclylalkyl include, but are not limited to, morpholinylmethyl, morpholinylethyl, morpholinylpropyl, tetrahydrofuranylmethyl, pyrrolidinylpropyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S-linkage. Examples of alkoxy groups include, but are not limited to, methoxy, ethoxy, propoxy, isopropoxy, butoxy, n-butoxy, sec-butoxy, t-butoxy and the like.

The term "arylthio" used herein refers to an aryl radical covalently bonded to the parent molecule through an —S— linkage.

The term "alkylamino" used herein refers to nitrogen radical with one or more alkyl groups attached thereto. Thus, monoalkylamino refers to nitrogen radical with one alkyl group attached thereto and dialkylamino refers to nitrogen radical with two alkyl groups attached thereto.

The term "cyanoamino" used herein refers to nitrogen radical with nitrile group attached thereto.

The term "carbamyl" used herein refers to RNHC(O)O—.

The term "keto" and "carbonyl" used herein refers to C═O.

The term "carboxy" used herein refers to —COOH.

The term "sulfamyl" used herein refers to $—SO_2NH_2$.

The term "sulfonyl" used herein refers to $—SO_2—$.

The term "sulfinyl" used herein refers to —SO—.

The term "thiocarbonyl" used herein refers to C═S.

The term "thiocarboxy" used herein refers to CSOH.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the terms "group" and "moiety."

As used herein, a substituted group is derived from the unsubstituted parent structure in which there has been an exchange of one or more hydrogen atoms for another atom or group. Unless otherwise indicated, when substituted, the substituent group(s) is (are) one or more group(s) individually and independently selected from $C_1$-$C_6$ alkyl, $C_1$-$C_6$ alkenyl, $C_1$-$C_6$ alkynyl, $C_3$-$C_7$ cycloalkyl (optionally substituted with halo, alkyl, alkoxy, carboxyl, CN, $—SO_2$-alkyl, $—CF_3$, and $—OCF_3$), $C_3$-$C_6$ heterocycloalkyl (e.g., tetrahydrofuryl) (optionally substituted with halo, alkyl, alkoxy, carboxyl, CN, $—SO_2$-alkyl, $—CF_3$, and $—OCF_3$), aryl (optionally substituted with halo, alkyl, alkoxy, carboxyl, CN, $—SO_2$-alkyl, $—CF_3$, and $—OCF_3$), heteroaryl (optionally substituted with halo, alkyl, alkoxy, carboxyl, CN, $—SO_2$-alkyl, $—CF_3$, and $—OCF_3$), halo (e.g., chloro, bromo, iodo and fluoro), cyano, hydroxy, $C_1$-$C_6$ alkoxy, aryloxy, sulfhydryl (mercapto), $C_1$-$C_6$ alkylthio, arylthio, mono- and di-($C_1$-$C_6$)alkylamino, quaternary ammonium salts, amino($C_1$-$C_6$)alkoxy, hydroxy ($C_1$-$C_6$)alkylamino, amino($C_1$-$C_6$)alkylthio, cyanoamino, nitro, carbamyl, keto (oxo), carbonyl, carboxy, glycolyl, glycyl, hydrazino, guanyl, sulfamyl, sulfonyl, sulfinyl, thiocarbonyl, thiocarboxy, and combinations thereof. The protecting groups that can form the protective derivatives of the above substituents are known to those of skill in the art and can be found in references such as Greene and Wuts *Protective Groups in Organic Synthesis*; John Wiley and Sons: New York, 1999. Wherever a substituent is described as "optionally substituted" that substituent can be substituted with the above substituents unless the context clearly dictates otherwise.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Isotopes may be present in the compounds described. Each chemical element as represented in a compound structure may include any isotope of said element. For example, in a compound structure a hydrogen atom may be explicitely disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by salvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound. A prodrug is a compound that undergoes biotransformation (chemical conversion) before exhibiting its pharmacological effects. For example, a prodrug can thus be viewed as a drug containing specialized protective groups used in a transient manner to alter or to eliminate undesirable properties in the parent molecule. Thus, reference herein to a compound includes all of the aforementioned forms unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein can also be used in the practice or testing of the embodiments, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The present embodiments provide compounds of Formulae I, II, III, IV, V, VI, VII, and X, as well as pharmaceutical compositions and formulations comprising any compound of Formulae I, II, III, IV, V, VI, VII, and X. A subject compound is useful for treating HCV infection and other disorders, as discussed below.

Formula I

The embodiments provide a compound having the structure of Formula I:

(I)

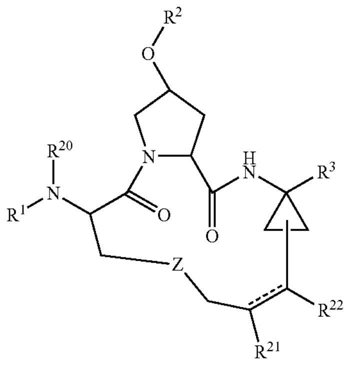

or a pharmaceutically acceptable salt or prodrug thereof wherein:

$R^1$ is —$(CR^5R^6)_nR^4$;

n is 0, 1 or 2;

$R^2$ is selected from the group consisting of aryl, heteroaryl and polycyclic moiety, each optionally substituted with one or more substituents each independently selected from the group consisting of halo, cyano, nitro, hydroxy, cyanoamino, —SH, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_pNR^{3a}R^{3b}$, —$(CH_2)_pR^{4a}$, —$O(CH_2)_pR^{4a}$, and $C_{1-6}$ alkyl optionally substituted with up to 5 fluoro; said aryl and heteroaryl as an optional substituent are each further optionally substituted with one or more substituents each independently selected from the group consisting of halo, cyano, nitro, hydroxy, $C_{1-6}$ alkyl, $C_{1-6}$ alkoxy, aryl, heteroaryl, —$NR^{1a}R^{1b}$, $C_{1-6}$ alkyl optionally substituted with up to 5 fluoro, and $C_{1-6}$ alkoxy optionally substituted with up to 5 fluoro;

$R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_pNR^{3a}R^{3b}$, —$(CH_2)_pR^{4a}$ and —$O(CH_2)_pR^{4a}$;

$R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

$R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

each $R^{4a}$ is separately imidazolyl or pyrazolyl;

each m is separately 0, 1 or 2;

each p is separately an integer selected from 1-6;

each q is separately 0, 1 or 2;

each r is separately an integer selected from 1-6;

$R^3$ is —$C(O)NHS(O)_2R^9$, where $R^9$ is selected from the group consisting of $C_{1-6}$ alkyl, —$(CH_2)_qC_{3-7}$cycloalkyl, —$(CH_2)_qC_{6\ or\ 10}$ aryl, and a heteroaromatic ring, each optionally substituted with one or more substituents each independently selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is —$NR^{9a}R^{9b}$; or $R^3$ is a —$CONHO(CH_2)_mR^{10}$ where $R^{10}$ is selected from the group consisting of $C_{1-6}$ alkyl, —$(CH_2)_qC_{3-7}$cycloalkyl, optionally substituted aryl and optionally substituted heteroaryl; or $R^3$ is a carboxylic acid;

wherein $R^{9a}$ and $R^{9b}$ are each separately a hydrogen atom, or separately selected from the group consisting of $C_{1-6}$ alkyl, —$(CH_2)_qC_{3-7}$cycloalkyl, and $C_{6\ or\ 10}$ aryl, each optionally substituted with one or more substituents each independently selected from the group consisting of halo, cyano, nitro, hydroxy, $C_{1-6}$ alkyl, —$(CH_2)_tC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or —$NR^{9a}R^{9b}$ is a three- to six-membered alkyl cyclic secondary amine, which optionally has one to three additional hetero atoms incorporated in the ring, and which is optionally substituted with one or more substituents each independently selected from the group consisting of halo, cyano, nitro, $C_{1-6}$ alkyl, $C_{1-6}$ alkoxy, and phenyl;

or $R^{9a}$ and $R^{9b}$ are taken together with the nitrogen to which they are attached to form a heteroaryl, optionally substituted with one or more substituents each independently selected from the group consisting of a halogen, cyano, nitro, hydroxy, $C_{1-6}$ alkyl, —$(CH_2)_qC_{3-7}$cycloalkyl, $C_{1-6}$ alkoxy, $C_{3-6}$ cycloalkoxy, —NH(CO)OR$^{1e}$, wherein R$^{1e}$ is $C_{1-6}$ alkyl, or —$(CH_2)_qC_{3-7}$cycloalkyl, —N(R$^{1d}$)$_2$, —NH(CO)R$^{1d}$, and —NH(CO)NHR$^{d}$, wherein each R$^{1d}$ is separately selected from the group consisting of a hydrogen atom, $C_{1-6}$ alkyl, and —$(CH_2)_qC_{3-7}$cycloalkyl;

each t is separately 0, 1 or 2;

R$^5$ and R$^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or R$^5$ and R$^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each u is separately 0, 1 or 2;

Z is selected from the group consisting of

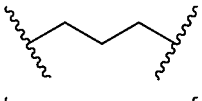,
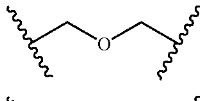,
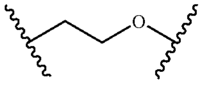,
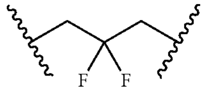,
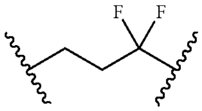,
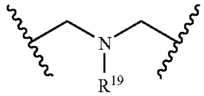,
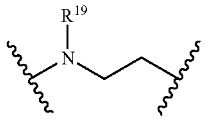,
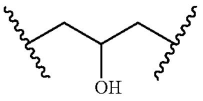, and
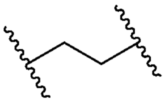;

R$^{19}$ is hydrogen, $C_{1-6}$ alkyl optionally substituted with up to 5 fluoro, or —SO$_m$R$^{2a}$;

R$^{20}$ is selected from the group consisting of hydrogen, —SO$_m$R$^{2a}$, —C(O)OR$^{2a}$, —C(O)R$^{2a}$, —C(O)NR$^{1a}$R$^{1b}$, and —C(S)NR$^{1a}$R$^{1b}$;

R$^{21}$ and R$^{22}$ are each hydrogen or together with the carbon atoms to which they are attached form an optionally substituted cyclopropyl; and the dashed line represents an optional double bond;

with the proviso that the compound of formula I is not

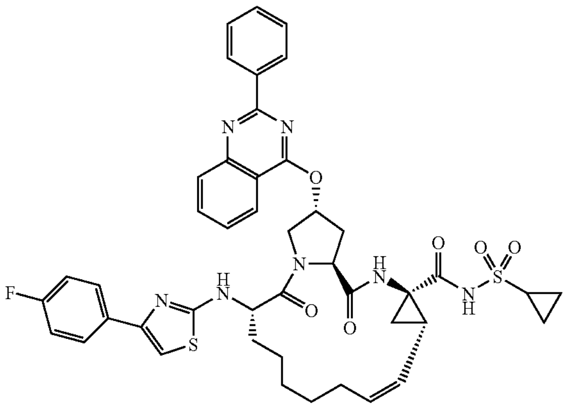.

Some embodiments include compounds of Formula I having the structure:

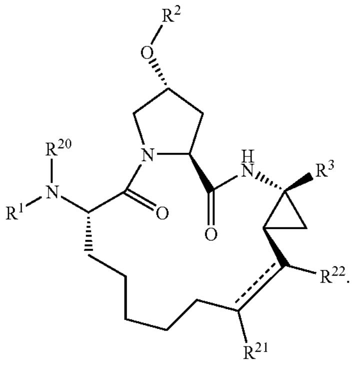

In some embodiments, R$^{20}$ is selected from the group consisting of hydrogen, —SO$_m$R$^{2a}$, and —C(O)R$^{2a}$.

In another embodiment, R$^4$ is selected from the group consisting of aryl and heteroaryl, each substituted with one or more substituents each independently selected from the group consisting of halo, cyano, nitro, hydroxy, cyanoamino, —SH, $C_{1-6}$ alkyl optionally substituted with up to 5 fluoro, and $C_{1-6}$ alkoxy optionally substituted with up to 5 fluoro; n is 0; and R$^3$ is —C(O)NHS(O)$_2$R$^9$ where R$^9$ is $C_{3-7}$cycloalkyl optionally substituted with $C_{1-6}$ alkyl.

In another embodiment, R$^4$ is selected from the group consisting of aryl and heteroaryl, each substituted with one or more substituents each independently selected from the group consisting of halo, $C_{1-6}$ alkyl optionally substituted with up to 5 fluoro, and $C_{1-6}$ alkoxy optionally substituted with up to 5 fluoro.

In some embodiments, R$^4$ is aryl substituted with one or more substituents each independently selected from the group consisting of halo, $C_{1-6}$ alkyl optionally substituted with up to 5 fluoro.

In another embodiment, wherein R$^4$ is aryl substituted with one or more substituents each independently selected from the group consisting of fluorine and $CF_3$.

In another embodiment, R$^2$ is selected from the group consisting of thiazole, oxazole, imidazole, benzothiazole, benzoxazole, benzoimidazole, quinoline, isoquinoline, quinazoline, quinoxaline, imidazopyridine, and imidazopyrazine, each optionally substituted with one or more substituents each independently selected from the group consisting of halo, cyano, nitro, hydroxy, cyanoamino, —SH, $C_{1-6}$ alkoxy, $C_{2-6}$ alkenyl, $C_{2-6}$ alkynyl, $-(CH_2)_qC_{3-7}$cycloalkyl, $C_{3-6}$ heterocycloalkyl, aryl, heteroaryl, aryloxy, arylthio, $C_{1-6}$ alkylthio, $-N[(CH_2)_pOH][(CH_2)_rOH]$, $-S(O)_2NR^{1a}R^{1b}$, $-NHC(O)NR^{1a}R^{1b}$, $-NHC(S)NR^{1a}R^{1b}$, $-C(O)NR^{1a}R^{1b}$, $-NR^{1a}R^{1b}$, $-C(O)R^{2a}$, $-C(O)OR^{2a}$, $-NHC(O)R^{2a}$ NHC(O)OR$^{2a}$, $-SO_mR^{2a}$, $-NHS(O)_2R^{2a}$, $-NR^{2a}[(CH_2)_pOH]$, $-O[(CH_2)_pNR^{3a}R^{3b}]$, $-S[(CH_2)_pNR^{3a}R^{3b}]$, $-(CH_2)_pNR^{3a}R^{3b}$, $-(CH_2)_pR^{4a}$, $-O(CH_2)_pR^{4a}$, and $C_{1-6}$ alkyl optionally substituted with up to 5 fluoro; said aryl and heteroaryl as an optional substituent are each further optionally substituted with one or more substituents each independently selected from the group consisting of halo, cyano, nitro, hydroxy, $C_{1-6}$ alkyl, $C_{1-6}$ alkoxy, aryl, heteroaryl, $-NR^{1a}R^{1b}$, $C_{1-6}$ alkyl optionally substituted with up to 5 fluoro, and $C_{1-6}$ alkoxy optionally substituted with up to 5 fluoro.

In still another embodiment, $R^2$ is selected from the group consisting of thiazole, oxazole, imidazole, benzothiazole, benzoxazole, benzoimidazole, quinoline, isoquinoline, quinazoline, quinoxaline, imidazopyridine, and imidazopyrazine, each optionally substituted with one or more substituents each independently selected from the group consisting of halo, $C_{1-6}$ alkoxy, $-(CH_2)_qC_{3-7}$cycloalkyl, aryl and heteroaryl; wherein said aryl and heteroaryl as an optional substituent are each further optionally substituted with one or more substituents each independently selected from the group consisting of $C_{1-6}$ alkyl, and $-NR^{1a}R^{1b}$, wherein q is 0 and $R^{1a}$ and $R^{1b}$ are each separately a hydrogen atom or $C_{1-6}$ alkyl.

In some embodiments, $R^2$ is selected from the group consisting of thiazole, oxazole, imidazole, benzothiazole, benzoxazole, benzoimidazole, quinoline, isoquinoline, quinazoline, quinoxaline, imidazopyridine, and imidazopyrazine, each optionally substituted with one or more substituents each independently selected from the group consisting of halo, $C_{1-6}$ alkoxy, $-(CH_2)_qC_{3-7}$cycloalkyl, phenyl, thiazole, oxazole, thiophene, and pyridine; wherein said thiazole and oxazole as an optional substituent are each further optionally substituted with one or more substituents each independently selected from the group consisting of $C_{1-6}$ alkyl, and $-NR^{1a}R^{1b}$, wherein q is 0 and $R^{1a}$ and $R^{1b}$ are each separately a hydrogen atom or $C_{1-6}$ alkyl.

In another embodiment, n is 0 or 1; $R^5$ and $R^6$ are each hydrogen; $R^4$ is phenyl, thiazole, oxazole, benzoxazole, benzothiazole, pyridine, or naphthyl, each optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen, $-C(O)CH_3$, or $-SO_2CH_3$.

In another embodiment, n is 0 or 1; $R^5$ and $R^6$ are each hydrogen; $R^4$ is phenyl optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen.

In still another embodiment, n is 0 or 1; $R^5$ and $R^6$ are each hydrogen; $R^4$ is phenyl substituted with one or more substituents each independently selected from the group consisting of halo and $C_{1-6}$ alkyl optionally substituted with up to 5 fluoro; and $R^{20}$ is hydrogen.

In another embodiment, n is 0 or 1; $R^5$ and $R^6$ are each hydrogen; $R^4$ is phenyl substituted with one or more fluoro and optionally substituted with $CF_3$; and $R^{20}$ is hydrogen.

In some embodiments, Z is propyl.

In another embodiment, $R^3$ is carboxylic acid.

In another embodiment, $R^3$ is $-C(O)NHS(O)_2R^9$, where $R^9$ is $C_{3-7}$cycloalkyl optionally substituted with $C_{1-6}$ alkyl or $C_{1-6}$ alkoxy.

In another embodiment, $R^3$ is a $-CONHO(CH_2)_mR^{10}$ where $R^{10}$ is $C_{1-6}$ alkyl, $-(CH_2)_qC_{3-7}$cycloalkyl or phenyl optionally substituted with $CF_3$; m is 0 or 1; and q is 0 or 1.

In another embodiment, $R^3$ is $-C(O)NHS(O)_2R^9$, where $R^9$ is $-NR^{9a}R^{9b}$ and $R^{9a}$ and $R^{9b}$ are each independently a hydrogen atom or $C_{1-6}$ alkyl or $-NR^{9a}R^{9b}$ is a pyrrolidine or piperidine.

Formula I (Alternative 1)

In an alternative embodiment of Formula I:

(a) $R^1$ is hydrogen;

(b) $R^2$ is hydrogen, $-C(O)R^4$ or selected from the group consisting of $C_{1-6}$ alkyl, aryl, heteroaryl and polycyclic moiety, each optionally substituted with one or more substituents each separately selected from the group consisting of halo, cyano, nitro, hydroxy, cyanoamino, $-SH$, $C_{1-6}$ alkyl, $C_{1-6}$ alkoxy, $C_{2-6}$ alkenyl, $C_{2-6}$ alkynyl, $-(CH_2)_qC_{3-7}$cycloalkyl, $C_{3-6}$ heterocycloalkyl, aryl, heteroaryl, aryloxy, arylthio, $C_{1-6}$ alkylthio, $-N[(CH_2)_pOH][(CH_2)_rOH]$, $-S(O)_2NR^{1a}R^{1b}$, $-NHC(O)NR^{1a}R^{1b}$, $-NHC(S)NR^{1a}R^{1b}$, $-C(O)NR^{1a}R^{1b}$, $-NR^{1a}R^{1b}$, $-C(O)R^{2a}$, $-C(O)OR^{2a}$, $-NHC(O)R^{2a}$, $-NHC(O)OR^{2a}$, $-SO_mR^{2a}$, $-NHS(O)_2R^{2a}$, $-NR^{2a}[(CH_2)_pOH]$, $-O[(CH_2)_pNR^{3a}R^{3b}]$, $-S[(CH_2)_pNR^{3a}R^{3b}]$, $-(CH_2)_pNR^{3a}R^{3b}$, $-(CH_2)_pR^{4a}$ and $-O(CH_2)_pR^{4a}$;

(c) $R^4$ is $C_{1-6}$ alkyl or polycyclic moiety optionally substituted with one or more substituents each separately selected from the group consisting of halo, cyano, nitro, hydroxy, $C_{1-6}$ alkyl, $-(CH_2)_qC_{3-7}$cycloalkyl, $C_{2-6}$ alkenyl, hydroxyl-$C_{1-6}$ alkyl, $C_{1-6}$ alkyl optionally substituted with up to 5 fluoro, and $C_{1-6}$ alkoxy optionally substituted with up to 5 fluoro;

or $R^4$ is $-NR^{90a}R^{90b}$ or $C_{1-6}$ alkyl optionally substituted with up to 5 fluoro;

wherein $R^{90a}$ and $R^{90b}$ are each separately a hydrogen atom or $C_{1-6}$ alkyl; or $R^{90a}$ and $R^{90b}$ are taken together with the nitrogen to which they are attached to form a three- to six-membered heterocycle, which optionally has one to three additional hetero atoms incorporated in the ring;

(d) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each separately selected from the group consisting of halo, cyano, nitro, hydroxy, $C_{1-6}$ alkyl, $-(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(e) $R^{2a}$ is selected from the group consisting of $C_{1-6}$ alkyl, $C_{3-7}$ cycloalkyl, and $C_{6\ or\ 10}$ aryl, each optionally substituted with one or more substituents each separately selected from the group consisting of halo, cyano, nitro, hydroxy, $C_{1-6}$ alkyl, $C_{2-6}$ alkenyl, $-(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

(f) $R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

(g) $R^{4a}$ is imidazolyl or pyrazolyl;

(h) each m is separately 0, 1 or 2;

(i) each p is separately an integer selected from 1-6;

(j) each q is separately 0, 1 or 2;

(k) each r is separately an integer selected from 1-6;

(l) $R^3$ is —$C(O)NHS(O)_2R^9$, where $R^9$ is selected from the group consisting of —$(CH_2)_rC(O)NHR^{9c}$, —$(CH_2)_rC(O)OR^{9c}$, and —$(CH_2)_qR^{9d}$;

wherein $R^{9c}$ is $C_{6\ or\ 10}$ aryl optionally substituted with one or more substituents each separately selected from the group consisting of —$O(CH_2)_qC(O)NHR^{9e}$ and —$NH(CH_2)_qC(O)NHR^{9e}$;

wherein $R^{9d}$ is $C_{6\ or\ 10}$ aryl substituted with one or more substituents each separately selected from the group consisting of —$O(CH_2)_qC(O)NHR^{9e}$ and —$NH(CH_2)_qC(O)NHR^{9e}$;

wherein $R^{9e}$ is selected from the group consisting of hydrogen, $C_{6\ or\ 10}$ aryl, and $C_{1-6}$ alkyl optionally substituted with up to 5 fluoro;

or $R^3$ is a —$CONR^{100a}R^{100b}$;

(m) $R^{100a}$ is —$(CH_2)_vCONR^{200a}R^{200b}$, and $R^{100b}$ is a hydrogen or —$(CH_2)_vCONR^{200a}R^{200b}$; or $R^{100a}$ and $R^{100b}$ are optionally taken together with the nitrogen to which they are attached to form a three- to six-membered heterocycle, which optionally has one to three additional hetero atoms incorporated in the ring, and which is optionally substituted with —$(CH_2)_vCONR^{300a}R^{300b}$;

(n) each v is separately 0, 1, 2, 3, 4, 5, or 6;

(o) $R^{200a}$ and $R^{200b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(p) $R^{300a}$ and $R^{300b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(q) Z is selected from the group consisting of

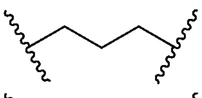, 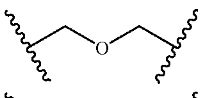,

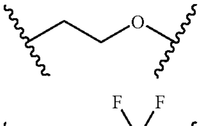, 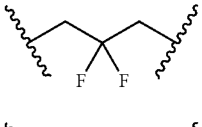,

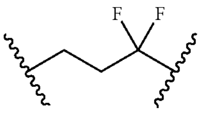, 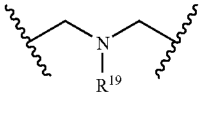,

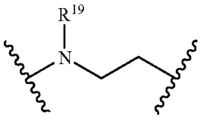, 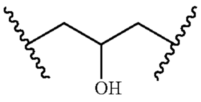, and

-continued

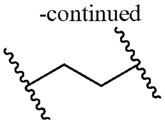;

(r) $R^{19}$ is hydrogen, —$SO_mR^{2a}$, or $C_{1-6}$ alkyl optionally substituted with up to 5 fluoro;

(s) $R^{20}$ is selected from the group consisting of —$SO_mR^{2a}$, —$C(O)OR^{2a}$, —$C(O)R^{2a}$, —$C(O)NR^{1a}R^{1b}$, and —$C(S)NR^{1a}R^{1b}$;

(t) $R^{21}$ and $R^{21}$ are each hydrogen or together with the carbon atoms to which they are attached form an optionally substituted cyclopropyl; and (u) the dashed line represents an optional double bond.

In another embodiment, $R^{20}$ is selected from the group consisting of —$SO_mR^{2a}$, and —$C(O)R^{2a}$.

In another embodiment, $R^{20}$ is —$C(O)OR^{2a}$.

In another embodiment, $R^{2a}$ is $C_{1-6}$ alkyl.

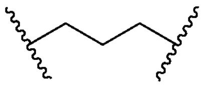.

In another embodiment, Z is

In another embodiment, $R^3$ is —$C(O)NHS(O)_2R^9$, where $R^9$ is —$(CH_2)_qC_{3-7}$cycloalkyl substituted with methyl.

In another embodiment, $R^3$ is —$CONR^{100a}R^{100b}$.

In another embodiment, $R^{100a}$ and $R^{100b}$ are taken together with the nitrogen to which they are attached to form a three- to six-membered heterocycle substituted with —$(CH_2)_vCONR^{300a}R^{300b}$.

In another embodiment, $R^{300a}$ and $R^{300b}$ are each separately hydrogen or —$(CH_2)_pC_{6\ or\ 10}$ aryl; v is 0; and p is 1.

In another embodiment, $R^{100a}$ is —$(CH_2)_vCONR^{200a}R^{200b}$, and $R^{100b}$ is a hydrogen, or —$(CH_2)_vCONR^{200a}R^{200b}$.

In another embodiment, $R^2$ is hydrogen.

In another embodiment, $R^2$ is —$C(O)R^4$ where $R^4$ is a dihydroisoindole optionally substituted with one or more substituents each separately selected from the group consisting of halo, cyano, nitro, hydroxy, $C_{1-6}$ alkyl, —$(CH_2)_qC_{3-7}$ cycloalkyl, $C_{2-6}$ alkenyl, hydroxyl-$C_{1-6}$ alkyl, $C_{1-6}$ alkyl optionally substituted with up to 5 fluoro, and $C_{1-6}$ alkoxy optionally substituted with up to 5 fluoro.

In another embodiment, $R^4$ is a dihydroisoindole optionally substituted with one or more substituents each separately selected from the group consisting of halo, $C_{1-6}$ alkyl, $C_{1-6}$ alkyl optionally substituted with up to 5 fluoro, and $C_{1-6}$ alkoxy optionally substituted with up to 5 fluoro.

In another embodiment, $R^2$ is —$C(O)R^4$ where $R^4$ is $C_{1-6}$ alkyl.

In another embodiment, $R^2$ is $C_{1-6}$ alkyl.

In another embodiment, $R^2$ is —$C(O)R^4$ where $R^4$ is —$NR^{90a}R^{90b}$; wherein $R^{90a}$ and $R^{90b}$ are each separately a hydrogen atom or $C_{1-6}$ alkyl; or $R^{90a}$ and $R^{90b}$ are taken together with the nitrogen to which they are attached to form a three- to six-membered heterocycle, which optionally has one to three additional hetero atoms incorporated in the ring.

In another embodiment, $R^{90a}$ and $R^{90b}$ are each separately a hydrogen atom or $C_{1-6}$ alkyl.

Formula I (Alternative 2)

In an alternative embodiment of Formula I:

(a) $R^1$ is hydrogen;

(b) $R^2$ is —C(O)$R^4$, hydrogen, or $C_{1-6}$ alkyl optionally substituted with up to 5 fluoro;

(c) $R^4$ is —$NR^{90a}R^{90b}$, or $C_{1-6}$ alkyl optionally substituted with up to 5 fluoro;

(d) $R^{90a}$ and $R^{90b}$ are each separately a hydrogen atom, or $C_{1-6}$ alkyl; or $R^{90a}$ and $R^{90b}$ are taken together with the nitrogen to which they are attached to form a three- to six-membered heterocycle, which optionally has one to three additional hetero atoms incorporated in the ring;

(e) $R^3$ is —C(O)NHS(O)$_2R^9$, where $R^9$ is —$(CH_2)_qC_{3-7}$ cycloalkyl substituted with methyl;

or $R^9$ is selected from the group consisting of —$(CH_2)_r$C(O)NH$R^{9c}$, —$(CH_2)_r$C(O)O$R^{9c}$, and —$(CH_2)_qR^{9d}$;

wherein $R^{9c}$ is $C_{6\ or\ 10}$ aryl optionally substituted with one or more substituents each separately selected from the group consisting of —O$(CH_2)_q$C(O)NH$R^{9e}$ and —NH$(CH_2)_q$C(O)NH$R^{9e}$;

wherein $R^{9d}$ is $C_{6\ or\ 10}$ aryl substituted with one or more substituents each separately selected from the group consisting of —O$(CH_2)_q$C(O)NH$R^{9e}$ and —NH$(CH_2)_q$C(O)NH$R^{9e}$;

wherein $R^{9e}$ is selected from the group consisting of hydrogen, $C_{6\ or\ 10}$ aryl, and $C_{1-6}$ alkyl optionally substituted with up to 5 fluoro;

or $R^3$ is a —CONHO$(CH_2)_m R^{10}$ where $R^{10}$ is selected from the group consisting of $C_{1-6}$ alkyl, —$(CH_2)_qC_{3-7}$cycloalkyl, optionally substituted aryl and optionally substituted heteroaryl;

or $R^3$ is a —CON$R^{100a}R^{100b}$;

(f) each m is separately 0, 1 or 2;

(g) each q is separately 0, 1 or 2;

(h) each t is separately 0, 1 or 2;

(i) each r is separately an integer selected from 1-6;

(j) $R^{100a}$ is hydrogen, and $R^{100b}$ is a hydrogen, or —$(CH_2)_v$CON$R^{200a}R^{200b}$; or $R^{100a}$ and $R^{100b}$ are optionally taken together with the nitrogen to which they are attached to form a three- to six-membered heterocycle, which optionally has one to three hetero atoms incorporated in the ring, and which is optionally substituted with —$(CH_2)_v$CON$R^{300a}R^{300b}$;

(k) each v is separately 0, 1, 2, 3, 4, 5, or 6;

(l) $R^{200a}$ and $R^{200b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(m) each p is separately an integer selected from 1-6;

(n) $R^{300a}$ and $R^{300b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(o) Z is selected from the group consisting of

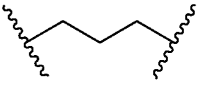 , 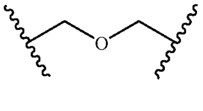 ,

-continued

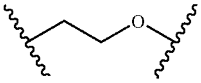 , 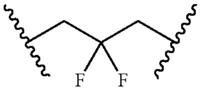 ,

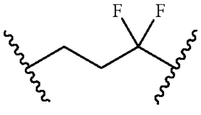 , 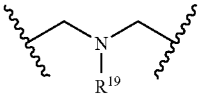 ,

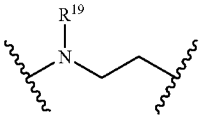 , 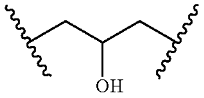 , and

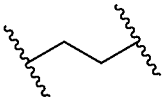 ;

(p) $R^{19}$ is hydrogen, —$SO_mR^{2a}$, or $C_{1-6}$ alkyl optionally substituted with up to 5 fluoro;

(q) $R^{20}$ is selected from the group consisting of —$SO_mR^{2a}$, —C(O)O$R^{2a}$, —C(O)$R^{2a}$, —C(O)N$R^{1a}R^{1b}$, and —C(S)N$R^{1a}R^{1b}$;

(r) $R^{21}$ and $R^{21}$ are each hydrogen or together with the carbon atoms to which they are attached form an optionally substituted cyclopropyl; and (s) the dashed line represents an optional double bond.

In another embodiment, $R^{20}$ is —C(O)O$R^{2a}$.

In another embodiment, $R^{2a}$ is $C_{1-6}$ alkyl.

In another embodiment, Z is

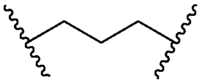 .

In another embodiment, $R^3$ is —C(O)NHS(O)$_2R^9$, where $R^9$ is —$(CH_2)_qC_{3-7}$cycloalkyl substituted with methyl.

In another embodiment, $R^3$ is —CON$R^{100a}R^{100b}$.

In another embodiment, $R^{100a}$ and $R^{100b}$ are taken together with the nitrogen to which they are attached to form a three- to six-membered heterocycle substituted with —$(CH_2)_v$CON$R^{300a}R^{300b}$.

In another embodiment, $R^{300a}$ and $R^{300b}$ are each separately hydrogen or —$(CH_2)_pC_{6\ or\ 10}$ aryl; v is 0; and p is 1.

In another embodiment, $R^{100a}$ is hydrogen, and $R^{100b}$ is a hydrogen or —$(CH_2)_v$CON$R^{200a}R^{200b}$.

In another embodiment, $R^2$ is $C_{1-6}$ alkyl.

In another embodiment, $R^2$ is —C(O)$R^4$; $R^4$ is —N$R^{90a}R^{90b}$ or $C_{1-6}$ alkyl; and $R^{90a}$ and $R^{90b}$ are each separately a hydrogen atom, or $C_{1-6}$ alkyl; or $R^{90a}$ and $R^{90b}$ are taken together with the nitrogen to which they are attached to form a three- to six-membered heterocycle.

In another embodiment, $R^{90a}$ and $R^{90b}$ are each separately a hydrogen atom or $C_{1-6}$ alkyl.

In another embodiment, $R^{90a}$ and $R^{90b}$ are taken together with the nitrogen to which they are attached to form a three- to six-membered heterocycle.

Formula I (Alternative 3)

In an alternative embodiment of Formula I:

(a) $R^1$ is —$(CR^5R^6)_nR^4$;

(b) n is 0, 1 or 2;

(c) $R^2$ is selected from the group consisting of aryl, heteroaryl and polycyclic moiety, each optionally substituted with one or more substituents each independently selected from the group consisting of halo, cyano, nitro, hydroxy, cyanoamino, —SH, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_pNR^{3a}R^{3b}$; —$(CH_2)_pR^{4a}$, —$O(CH_2)_pR^{4a}$, and $C_{1-6}$ alkyl optionally substituted with up to 5 fluoro; said aryl and heteroaryl as an optional substituent are each further optionally substituted with one or more substituents each independently selected from the group consisting of halo, cyano, nitro, hydroxy, $C_{1-6}$ alkyl, $C_{1-6}$ alkoxy, aryl, heteroaryl, —$NR^{1a}R^{1b}$, $C_{1-6}$ alkyl optionally substituted with up to 5 fluoro, and $C_{1-6}$ alkoxy optionally substituted with up to 5 fluoro;

(d) $R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_p NR^{3a}R^{3b}$, —$(CH_2)_pR^{4a}$ and —$O(CH_2)_pR^{4a}$;

(e) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(f) each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

(g) $R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

(h) each $R^{4a}$ is separately imidazolyl or pyrazolyl;

(i) each m is separately 0, 1 or 2;

(j) each p is separately an integer selected from 1-6;

(k) each q is separately 0, 1 or 2;

(l) each r is separately an integer selected from 1-6;

(m) $R^1$ is —$P(O)R^{10a}R^{10b}$, wherein $R^{10a}$ and $R^{10b}$ are each separately selected from the group consisting of hydroxy, —$(O)_v$—$C_{1-6}$ alkyl, —$(O)_v$—$(CH_2)_qC_{3-7}$cycloalkyl, —$(O)_v$-aryl, and —$(O)_v$-heteroaryl, each optionally substituted with one or more substituents each independently selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro;

(n) wherein each v is separately 0 or 1;

(o) each t is separately 0, 1 or 2;

(p) $R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

(q) each u is separately 0, 1 or 2;

(r) Z is selected from the group consisting of

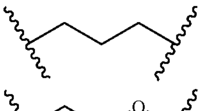,
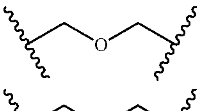,
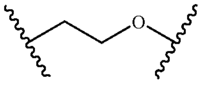,
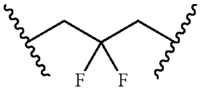,
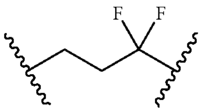,
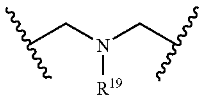,
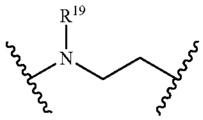,
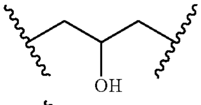, and
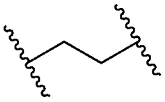;

(s) $R^{19}$ is hydrogen, $C_{1-6}$ alkyl optionally substituted with up to 5 fluoro, or —$SO_mR^{2a}$;

(t) $R^{20}$ is selected from the group consisting of hydrogen, —$SO_mR^{2a}$, —$C(O)OR^{2a}$, —$C(O)R^{2a}$, —$C(O)NR^{1a}R^{1b}$, and —$C(S)NR^{1a}R^{1b}$;

(u) $R^{21}$ and $R^{22}$ are each hydrogen or together with the carbon atoms to which they are attached form an optionally substituted cyclopropyl; and (v) the dashed line represents an optional double bond.

In another embodiment, $R^{10a}$ is hydroxy.

In another embodiment, $R^{10b}$ is —O—$C_{1-6}$ alkyl.

In another embodiment, $R^{10b}$ is —O-methyl or —O-ethyl.

In another embodiment, $R^{10b}$ is —$C_{1-6}$ alkyl.

In another embodiment, $R^{10b}$ is methyl or ethyl.

In another embodiment, $R^{10a}$ is hydroxy or —O—$C_{1-6}$ alkyl and $R^{10b}$ is $C_{1-6}$ alkyl.

Formula II

The embodiments provide a compound of Formula II:

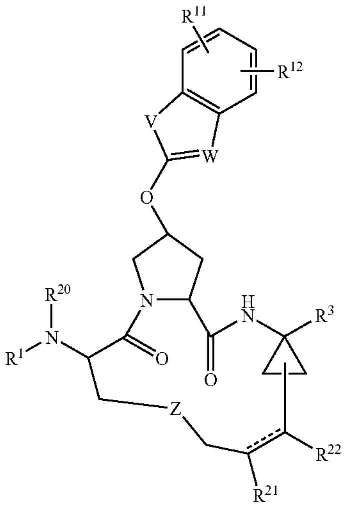

II or a pharmaceutically acceptable salt or prodrug thereof wherein:

$R^1$ is —$(CR^5R^6)_nR^4$;

n is 0, 1 or 2;

$R^3$ is —$C(O)NHS(O)_2R^9$, where $R^9$ is selected from the group consisting of $C_{1-6}$ alkyl, —$(CH_2)_qC_{3-7}$cycloalkyl, $C_{6\ or\ 10}$ aryl, and a heteroaromatic ring, each optionally substituted with one or more substituents each independently selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is —$NR^{9a}R^{9b}$; or $R^3$ is a —$CONHO(CH_2)_mR^{10}$ where $R^{10}$ is selected from the group consisting of $C_{1-6}$ alkyl, —$(CH_2)_qC_{3-7}$cycloalkyl, optionally substituted aryl and optionally substituted heteroaryl; or $R^3$ is a carboxylic acid;

wherein $R^{9a}$ and $R^{9b}$ are each separately a hydrogen atom, or separately selected from the group consisting of $C_{1-6}$ alkyl, —$(CH_2)_qC_{3-7}$cycloalkyl, and $C_{6\ or\ 10}$ aryl, each optionally substituted with one or more substituents each independently selected from the group consisting of halo, cyano, nitro, hydroxy, $C_{1-6}$ alkyl, —$(CH_2)_tC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or —$NR^{9a}R^{9b}$ is a three- to six-membered alkyl cyclic secondary amine, which optionally has one to three hetero atoms incorporated in the ring, and which is optionally substituted with one or more substituents each independently selected from the group consisting of halo, cyano, nitro, $C_{1-6}$ alkyl, $C_{1-6}$ alkoxy, and phenyl;

or $R^{9a}$ and $R^{9b}$ are taken together with the nitrogen to which they are attached to form a heteroaryl, optionally substituted with one or more substituents each independently selected from the group consisting of a halogen, cyano, nitro, hydroxy, $C_{1-6}$ alkyl, —$(CH_2)_qC_{3-7}$cycloalkyl, $C_{1-6}$ alkoxy, $C_{3-6}$ cycloalkoxy, —$NH(CO)OR^{1e}$, wherein $R^{1e}$ is $C_{1-6}$ alkyl, or —$(CH_2)_qC_{3-7}$cycloalkyl, —$N(R^{1d})_2$, —$NH(CO)R^{1d}$, and —$NH(CO)NHR^{1d}$, wherein each $R^{1d}$ is separately selected from the group consisting of a hydrogen atom, $C_{1-6}$ alkyl, and —$(CH_2)_qC_{3-7}$cycloalkyl;

each m is separately 0, 1 or 2;

each q is separately 0, 1 or 2;

each t is separately 0, 1 or 2;

$R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_pNR^{3a}R^{3b}$, —$(CH_2)_pR^{4a}$ and —$O(CH_2)_pR^{4a}$;

$R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

$R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

each $R^{4a}$ is separately imidazolyl or pyrazolyl;

each p is separately an integer selected from 1-6;

each r is separately an integer selected from 1-6;

$R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

$R^{11}$ and $R^{12}$ are each separately selected from the group consisting of hydrogen, halo, cyano, nitro, hydroxy, cyanoamino, —SH, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^7R^8$, —$NHC(O)NR^7R^8$, —$NHC(S)NR^7R^8$, —$C(O)NR^7R^8$, —$NR^7R^8$, —$C(O)R^{13}$, —$C(O)OR^{13}$, —$NHC(O)R^{13}$, —$NHC(O)OR^{13}$, —$SO_mR^{13}$, —$NHS(O)_2R^{13}$, —$NR^{13}[(CH_2)_pOH]$, —$O[(CH_2)_pNR^{14}R^{15}]$, —$S[(CH_2)_pNR^{14}R^{15}]$, —$(CH_2)_pNR^{14}R^{15}$, —$(CH_2)_pR^{16}$, —$O(CH_2)_pR^{16}$, and $C_{1-6}$ alkyl optionally substituted with up to 5 fluoro;

$R^7$ and $R^8$ are each separately a hydrogen, or separately selected from the group consisting of $C_{1-6}$ alkyl, —$(CH_2)_qC_{3-7}$cycloalkyl, and phenyl, each optionally substituted with one or more substituents each independently selected from the group consisting of halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^7$ and $R^8$ are taken together with the nitrogen to which they are attached to form indolinyl, pyrrolidinyl, piperidinyl, piperazinyl, or morpholinyl;

$R^{13}$ is selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{13}$ is a tetrahydrofuran ring linked through the $C_3$ or $C_4$ position of the tetrahydrofuran ring; or $R^{13}$ is a tetrahydropyran ring linked through the $C_4$ position of the tetrahydropyran ring;

$R^{14}$ and $R^{15}$ are each separately selected from hydrogen and $C_{1-6}$ alkyl; or $R^{14}$ and $R^{15}$ are taken together with the nitrogen to which they are attached to form indolinyl, pyrrolidinyl, piperidinyl, piperazinyl, or morpholinyl;

each $R^{16}$ is separately imidazolyl or pyrazolyl;

V is selected from the group consisting of —O—, —S—, and —$NR^{15}$—;

W is —N— or —$CR^{15}$—;

wherein $R^{15}$ is H, or selected from the group consisting of $C_{1-6}$ alkyl, $(CH_2)_qC_{3-7}$cycloalkyl, aryl, and heteroaryl, each optionally substituted with one or more substituents each independently selected from the group consisting of halo, cyano, nitro, $C_{1-6}$ alkyl, $C_{1-6}$ alkoxy, or phenyl;

each u is separately 0, 1 or 2;

Z is selected from the group consisting of

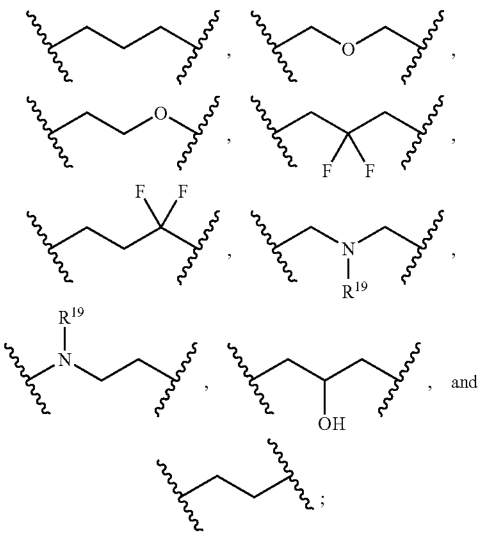

, , , , , , , and ;

$R^{19}$ is hydrogen, $C_{1-6}$ alkyl optionally substituted with up to 5 fluoro, or $SO_mR^{2a}$;

$R^{20}$ is selected from the group consisting of hydrogen, —$SO_mR^{2a}$, —$C(O)OR^{2a}$, —$C(O)R^{2a}$, —$C(O)NR^{1a}R^{1b}$, and —$C(S)NR^{1a}R^{1b}$;

$R^{21}$ and $R^{22}$ are each hydrogen or together with the carbon atoms to which they are attached form an optionally substituted cyclopropyl; and the dashed line represents an optional double bond.

In some embodiments, the compound of Formula II has the structure:

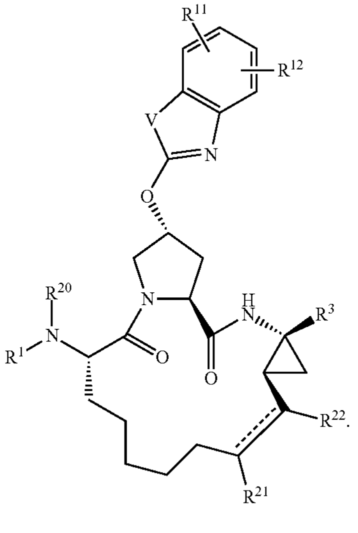

In some embodiments, $R^{20}$ is selected from the group consisting of hydrogen, —$SO_mR^{2a}$, and —$C(O)R^{2a}$.

In another embodiment, $R^4$ is selected from the group consisting of aryl and heteroaryl, each substituted with one or more substituents each independently selected from the group consisting of halo, cyano, nitro, hydroxy, cyanoamino, —SH, $C_{1-6}$ alkyl optionally substituted with up to 5 fluoro, and $C_{1-6}$ alkoxy optionally substituted with up to 5 fluoro; n is 0; and $R^3$ is —$C(O)NHS(O)_2R^9$ where $R^9$ is $C_{3-7}$cycloalkyl optionally substituted with $C_{1-6}$ alkyl.

In another embodiment, $R^4$ is selected from the group consisting of aryl and heteroaryl, each substituted with one or more substituents each independently selected from the group consisting of halo, $C_{1-6}$ alkyl optionally substituted with up to 5 fluoro, and $C_{1-6}$ alkoxy optionally substituted with up to 5 fluoro.

In another embodiment, $R^4$ is aryl substituted with one or more substituents each independently selected from the group consisting of halo, $C_{1-6}$ alkyl optionally substituted with up to 5 fluoro.

In another embodiment, $R^4$ is aryl substituted with one or more substituents each independently selected from the group consisting of fluorine and $CF_3$.

In another embodiment, $R^{11}$ and $R^{12}$ are each separately selected from the group consisting of hydrogen, halo, $C_{1-6}$ alkyl optionally substituted with up to 5 fluoro, $C_{1-6}$ alkoxy, and —$(CH_2)_qC_{3-7}$cycloalkyl where q is 0.

In another embodiment, n is 0 or 1; $R^5$ and $R^6$ are each hydrogen; $R^4$ is phenyl, thiazole, oxazole, benzoxazole, benzothiazole, pyridine, or naphthyl, each optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen, —$C(O)CH_3$, or —$SO_2CH_3$.

In another embodiment, n is 0 or 1; $R^5$ and $R^6$ are each hydrogen; $R^4$ is phenyl optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen.

In another embodiment, n is 0 or 1; $R^5$ and $R^6$ are each hydrogen; $R^4$ is phenyl substituted with one or more substituents each independently selected from the group consisting of halo and $C_{1-6}$ alkyl optionally substituted with up to 5 fluoro; and $R^{20}$ is hydrogen.

In another embodiment, n is 0 or 1; $R^5$ and $R^6$ are each hydrogen; $R^4$ is phenyl substituted with one or more fluoro and optionally substituted with $CF_3$; and $R^{20}$ is hydrogen.

In another embodiment, Z is propyl.

In another embodiment, $R^3$ is carboxylic acid.

In another embodiment, $R^3$ is —$C(O)NHS(O)_2R^9$, where $R^9$ is $C_{3-7}$cycloalkyl optionally substituted with $C_{1-6}$ alkyl or $C_{1-6}$ alkoxy.

In another embodiment, $R^3$ is a —$CONHO(CH_2)_mR^{10}$ where $R^{10}$ is $C_{1-6}$ alkyl, —$(CH_2)_qC_{3-7}$cycloalkyl or phenyl optionally substituted with $CF_3$; m is 0 or 1; and q is 0 or 1.

In another embodiment, $R^3$ is —$C(O)NHS(O)_2R^9$, where $R^9$ is —$NR^{9a}R^{9b}$ and $R^{9a}$ and $R^{9b}$ are each independently a hydrogen atom or $C_{1-6}$ alkyl or —$NR^{9a}R^{9b}$ is a pyrrolidine or piperidine.

Formula II (Alternative)

In an alternative embodiment of Formula II:

(a) $R^1$ is hydrogen;

(b) each m is separately 0, 1 or 2;

(c) each p is separately an integer selected from 1-6;

(d) each q is separately 0, 1 or 2;

(e) each r is separately an integer selected from 1-6;

(f) $R^3$ is —$C(O)NHS(O)_2R^9$, where $R^9$ is selected from the group consisting of $C_{1-6}$ alkyl, —$(CH_2)_qC_{3-7}$cycloalkyl, $C_{6\ or\ 10}$ aryl, and a heteroaryl, each optionally substituted with one or more substituents each separately selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is —$NR^{9a}R^{9b}$;

wherein $R^{9a}$ and $R^{9b}$ are each separately a hydrogen atom, or separately selected from the group consisting of $C_{1-6}$ alkyl, —$(CH_2)_qC_{3-7}$cycloalkyl, and $C_{6\ or\ 10}$ aryl, each optionally substituted with one or more substituents each separately selected from the group consisting of halo, cyano, nitro, hydroxy, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or $R^{9a}$ and $R^{9b}$ are taken together with the nitrogen to which they are attached to form a three- to six-membered heterocycle, which optionally has one to three hetero atoms incorporated in the ring, and which is optionally substituted with one or more substituents each separately selected from the group consisting of halo, cyano, nitro, $C_{1-6}$ alkyl, $C_{1-6}$ alkoxy, and phenyl, or $R^{9a}$ and $R^{9b}$ are taken together with the nitrogen to which they are attached to form a heteroaryl, optionally substituted with one or more substituents each separately selected from the group consisting of a halogen, cyano, nitro, hydroxy, $C_{1-6}$ alkyl, —$(CH_2)_qC_{3-7}$cycloalkyl, $C_{1-6}$ alkoxy, $C_{3-6}$ cycloalkoxy, —NH(CO)$OR^{1e}$, wherein $R^{1e}$ is $C_{1-6}$ alkyl, or —$(CH_2)_qC_{3-7}$ cycloalkyl, —$N(R^{1d})_2$, —NH(CO)$R^{1d}$, and —NH(CO)NH$R^{1d}$, wherein each $R^{1d}$ is separately selected from the group consisting of a hydrogen atom, $C_{1-6}$ alkyl, and —$(CH_2)_qC_{3-7}$cycloalkyl;

or $R^9$ is selected from the group consisting of —$(CH_2)_rC(O)NHR^{9c}$, —$(CH_2)_rC(O)OR^{9c}$, and —$(CH_2)_qR^{9d}$;

wherein $R^{9c}$ is $C_{6\ or\ 10}$ aryl optionally substituted with one or more substituents each separately selected from the group consisting of —$O(CH_2)_qC(O)NHR^{9e}$ and —$NH(CH_2)_qC(O)NHR^{9e}$;

wherein $R^{9d}$ is $C_{6\ or\ 10}$ aryl substituted with one or more substituents each separately selected from the group consisting of —$O(CH_2)_qC(O)NHR^{9e}$ and —NH$(CH_2)_qC(O)NHR^{9e}$;

wherein $R^{9e}$ is selected from the group consisting of hydrogen, $C_{6\ or\ 10}$ aryl, and $C_{1-6}$ alkyl optionally substituted with up to 5 fluoro;

or $R^{9e}$ is a —$CONHO(CH_2)_mR^{10}$ where $R^{10}$ is selected from the group consisting of $C_{1-6}$ alkyl, —$(CH_2)_qC_{3-7}$ cycloalkyl, optionally substituted aryl and optionally substituted heteroaryl;

or $R^3$ is a —$CONR^{100a}R^{100b}$;

or $R^3$ is a carboxylic acid;

(g) each t is separately 0, 1 or 2;

(h) $R^{100a}$ is —$(CH_2)_vCONR^{200a}R^{200b}$, and $R^{100b}$ is a hydrogen or —$(CH_2)_vCONR^{200a}R^{200b}$; or $R^{100a}$ and $R^{100b}$ are optionally taken together with the nitrogen to which they are attached to form a three- to six-membered heterocycle, which optionally has one to three hetero atoms incorporated in the ring, and which is optionally substituted with —$(CH_2)_vCONR^{300a}R^{300b}$;

(i) each v is separately 0, 1, 2, 3, 4, 5, or 6;

(j) $R^{200a}$ and $R^{200b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(k) $R^{300a}$ and $R^{300b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(l) $R^{11}$ and $R^{12}$ are each separately selected from the group consisting of hydrogen, halo, cyano, nitro, hydroxy, cyanoamino, —SH, $C_{1-6}$ alkyl, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^7R^8$, —$NHC(O)NR^7R^8$, —$NHC(S)NR^7R^8$, —$C(O)NR^7R^8$, —$NR^7R^8$, —$C(O)R^{13}$, —$C(O)OR^{13}$, —$NHC(O)R^{13}$, —$NHC(O)OR^{13}$, —$SO_mR^{13}$, —$NHS(O)_2R^{13}$, —$NR^{13}[(CH_2)_pOH]$, —$O[(CH_2)_pNR^{14}R^{15}]$, —$S[(CH_2)_pNR^{14}R^{15}]$, —$(CH_2)_pNR^{14}R^{15}$, —$(CH_2)_pR^{16}$ and —$O(CH_2)_pR^{16}$;

(m) $R^7$ and $R^8$ are each separately a hydrogen, or separately selected from the group consisting of $C_{1-6}$ alkyl, —$(CH_2)_qC_{3-7}$cycloalkyl, and phenyl, each optionally substituted with one or more substituents each separately selected from the group consisting of halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^7$ and $R^8$ are taken together with the nitrogen to which they are attached to form indolinyl, pyrrolidinyl, piperidinyl, piperazinyl, or morpholinyl;

(n) $R^{13}$ is selected from the group consisting of $C_{1-6}$ alkyl, $C_{3-7}$ cycloalkyl, and $C_{6\ or\ 10}$ aryl, each optionally substituted with one or more substituents each separately selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{13}$ is a tetrahydrofuran ring linked through the $C_3$ or $C_4$ position of the tetrahydrofuran ring; or $R^{13}$ is a tetrahydropyran ring linked through the $C_4$ position of the tetrahydropyran ring;

(o) $R^{14}$ and $R^{15}$ are each separately selected from hydrogen and $C_{1-6}$ alkyl; or $R^{14}$ and $R^{15}$ are taken together with the nitrogen to which they are attached to form indolinyl, pyrrolidinyl, piperidinyl, piperazinyl, or morpholinyl;

(p) $R^{16}$ is imidazolyl or pyrazolyl;

(q) V is selected from the group consisting of —O—, —S—, and —$NR^{23}$—;

(r) $R^{23}$ is H, or selected from the group consisting of $C_{1-6}$ alkyl, —$(CH_2)_qC_{3-7}$cycloalkyl, arylalkyl, heteroarylalkyl, aryl, and heteroaryl, each optionally substituted with one or more substituents each separately selected from the group consisting of halo, cyano, nitro, $C_{1-6}$ alkyl, $C_{1-6}$ alkoxy, or phenyl; wherein said phenyl as an optional substituent is further optionally substituted with one or more substituents each separately selected from the group consisting of halo, cyano, $C_{1-6}$ alkyl optionally substituted with up to 5 fluoro, and $C_{1-6}$ alkoxy optionally substituted with up to 5 fluoro;

(s) W is —N— or —$CR^{30}$—;

(t) $R^{30}$ is H, or selected from the group consisting of $C_{1-6}$ alkyl, —$(CH_2)_qC_{3-7}$cycloalkyl, arylalkyl, heteroarylalkyl, aryl, and heteroaryl, each optionally substituted with one or more substituents each separately selected from the group consisting of halo, cyano, nitro, $C_{1-6}$ alkyl, $C_{1-6}$ alkoxy, or phenyl;

(u) Z is selected from the group consisting of

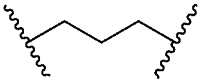, 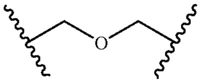, 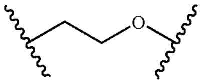, 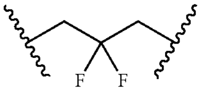, 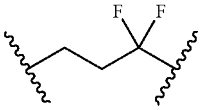, 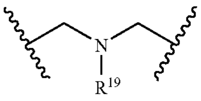, 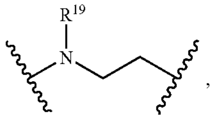, 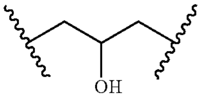, and 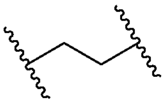;

(v) $R^{19}$ is hydrogen, —$SO_mR^{2a}$, or $C_{1-6}$ alkyl optionally substituted with up to 5 fluoro;

(w) $R^{20}$ is selected from the group consisting of —$SO_mR^{2a}$, —$C(O)OR^{2a}$, $C(O)R^{2a}$, —$C(O)NR^{1a}R^{1b}$, and —$C(S)NR^{1a}R^{1b}$;

(x) $R^{21}$ and $R^{21}$ are each hydrogen or together with the carbon atoms to which they are attached form an optionally substituted cyclopropyl;

(y) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each separately selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(z) $R^{2a}$ is selected from the group consisting of $C_{1-6}$ alkyl, $C_{3-7}$ cycloalkyl, and $C_{6\ or\ 10}$ aryl, each optionally substituted with one or more substituents each separately selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring; and (aa) the dashed line represents an optional double bond.

In another embodiment, $R^{20}$ is selected from the group consisting of —$SO_mR^{2a}$, and —$C(O)R^{2a}$.

In another embodiment, $R^{20}$ is —$C(O)OR^{2a}$.

In another embodiment, $R^{2a}$ is $C_{1-6}$ alkyl.

In another embodiment, Z is

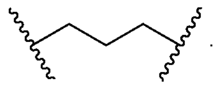

In another embodiment, $R^3$ is an acylsulfonamide of the formula $—C(O)NHS(O)_2R^9$, where $R^9$ is $—(CH_2)_qC_{3-7}$cycloalkyl optionally substituted with $C_{1-6}$ alkyl.

In another embodiment, $R^3$ is a $—CONHO(CH_2)_mR^{10}$ where $R^{10}$ is optionally substituted aryl and m is 0.

In another embodiment, $R^3$ is $—C(O)NHS(O)_2R^9$ where $R^9$ is $—NR^{9a}R^{9b}$ and $R^{9a}$ and $R^{9b}$ are each independently a hydrogen atom or $C_{1-6}$ alkyl or $—NR^{9a}R^{9b}$ is pyrrolidine or piperidine.

In another embodiment, V is selected from the group consisting of —O— and —S—; and W is —N—.

In another embodiment, V is $—NR^{21}—$; $R^{21}$ is H, $C_{1-6}$ alkyl, or arylalkyl; and W is —N—.

In another embodiment, $R^{11}$ and $R^{12}$ are each separately selected from the group consisting of hydrogen, halo, $C_{1-6}$ alkyl optionally substituted with up to 5 fluoro, $C_{1-6}$ alkoxy, and $—(CH_2)_qC_{3-7}$cycloalkyl where q is 0.

Formulas III and IV

The embodiments provide a compound having the structure of Formula III or Formula IV:

III

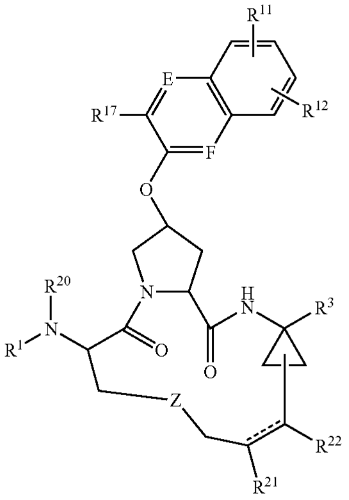

or

IV

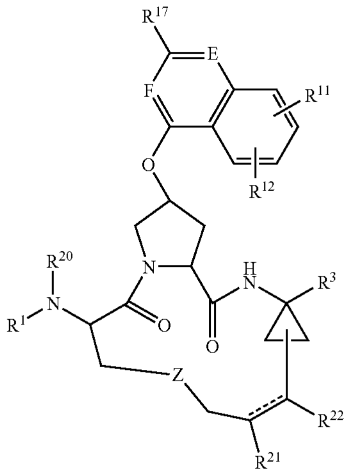

or a pharmaceutically acceptable salt or prodrug thereof wherein:

$R^1$ is $—(CR^5R^6)_nR^4$;

n is 0, 1 or 2;

$R^3$ is $—C(O)NHS(O)_2R^9$, where $R^9$ is selected from the group consisting of $C_{1-6}$ alkyl, $—(CH_2)_qC_{3-7}$cycloalkyl, $C_{6\ or\ 10}$ aryl, and a heteroaromatic ring, each optionally substituted with one or more substituents each independently selected from the group consisting of halo, cyano, nitro, hydroxy, —COOH, $C_{1-6}$ alkyl, $—(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is $—NR^{9a}R^{9b}$; or $R^3$ is a $—CONHO(CH_2)_mR^{10}$ where $R^{10}$ is selected from the group consisting of $C_{1-6}$ alkyl, $—(CH_2)_qC_{3-7}$cycloalkyl, optionally substituted aryl and optionally substituted heteroaryl; or $R^3$ is a carboxylic acid;

wherein $R^{9a}$ and $R^{9b}$ are each separately a hydrogen atom, or separately selected from the group consisting of $C_{1-6}$ alkyl, $—(CH_2)_qC_{3-7}$cycloalkyl, and $C_{6\ or\ 10}$ aryl, each optionally substituted with one or more substituents each independently selected from the group consisting of halo, cyano, nitro, hydroxy, $C_{1-6}$ alkyl, $—(CH_2)_tC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or $—NR^{9a}R^{9b}$ is a three- to six-membered alkyl cyclic secondary amine, which optionally has one to three hetero atoms incorporated in the ring, and which is optionally substituted with one or more substituents each independently selected from the group consisting of halo, cyano, nitro, $C_{1-6}$ alkyl, $C_{1-6}$ alkoxy, and phenyl;

or $R^{9a}$ and $R^{9b}$ are taken together with the nitrogen to which they are attached to form a heteroaryl, optionally substituted with one or more substituents each independently selected from the group consisting of a halogen, cyano, nitro, hydroxy, $C_{1-6}$ alkyl, $—(CH_2)_qC_{3-7}$cycloalkyl, $C_{1-6}$ alkoxy, $C_{3-6}$ cycloalkoxy, $—NH(CO)OR^{1e}$, wherein $R^{1e}$ is $C_{1-6}$ alkyl, or $—(CH_2)_qC_{3-7}$cycloalkyl, $—N(R^{1d})_2$, $—NH(CO)R^{1d}$, and $—NH(CO)NHR^{1d}$, wherein each $R^{1d}$ is separately selected from the group consisting of a hydrogen atom, $C_{1-6}$ alkyl, and $(CH_2)_qC_{3-7}$cycloalkyl;

each m is separately 0, 1 or 2;

each q is separately 0, 1 or 2;

each t is separately 0, 1 or 2;

$R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, $—(CH_2)_qC_{3-7}$cycloalkyl, $C_{3-6}$ heterocycloalkyl, aryl, heteroaryl, aryloxy, arylthio, $C_{1-6}$ alkylthio, $—N[(CH_2)_pOH][(CH_2)_rOH]$, $—S(O)_2NR^{1a}R^{1b}$, $—NHC(O)NR^{1a}R^{1b}$, $—NHC(S)NR^{1a}R^{1b}$, $—C(O)NR^{1a}R^{1b}$, $—NR^{1a}R^{1b}$, $—C(O)R^{2a}$, $—C(O)OR^{2a}$, $—NHC(O)R^{2a}$, $—NHC(O)OR^{2a}$, $—SO_mR^{2a}$, $—NHS(O)_2R^{2a}$, $—NR^{2a}[(CH_2)_pOH]$, $—O[(CH_2)_pNR^{3a}R^{3b}]$, $—S[(CH_2)_pNR^{3a}R^{3b}]$, $—(CH_2)_p NR^{3a}R^{3b}$, $—(CH_2)_pR^{4a}$ and $—O(CH_2)_pR^{4a}$;

$R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, $—(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

$R^{2a}$ is selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, $—(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

$R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

each $R^{4a}$ is separately imidazolyl or pyrazolyl;

each p is separately an integer selected from 1-6;

each r is separately an integer selected from 1-6;

$R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, $—(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, $—(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

$R^{11}$ and $R^{12}$ are each separately selected from the group consisting of hydrogen, halo, cyano, nitro, hydroxy, cyanoamino, —SH, $C_{1-6}$ alkyl, $C_{1-6}$ alkoxy, $C_{2-6}$ alkenyl, $C_{2-6}$ alkynyl, $—(CH_2)_qC_{3-7}$cycloalkyl, $C_{3-6}$ heterocycloalkyl, aryl, heteroaryl, aryloxy, arylthio, $C_{1-6}$ alkylthio, $—N[(CH_2)_pOH][(CH_2)_rOH]$, $—S(O)_2NR^7R^8$, $—NHC(O)NR^7R^8$, $—NHC(S)NR^7R^8$, $—C(O)NR^7R^8$, $—NR^7R^8$, $—C(O)R^{13}$, $—C(O)OR^{13}$, $—NHC(O)R^{13}$, $—NHC(O)OR^{13}$, $—SO_mR^{13}$, $—NHS(O)_2R^{13}$, $—NR^{13}[(CH_2)_pOH]$, $—O[(CH_2)_pNR^{14}R^{15}]$, $—S[(CH_2)_pNR^{14}R^{15}]$, $—(CH_2)_pNR^{14}R^{15}$, $—(CH_2)_pR^{16}$ and $—O(CH_2)_pR^{16}$;

$R^7$ and $R^8$ are each separately a hydrogen, or separately selected from the group consisting of $C_{1-6}$ alkyl, $—(CH_2)_qC_{3-7}$cycloalkyl, and phenyl, each optionally substituted with one or more substituents each independently selected from the group consisting of halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^7$ and $R^8$ are taken together with the nitrogen to which they are attached to form indolinyl, pyrrolidinyl, piperidinyl, piperazinyl, or morpholinyl;

$R^{13}$ is selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, $—(CH_2)_qC_{3-7}$cycloalkyl, $C_{1-6}$ alkoxy, phenyl, and hydroxy-$C_{1-6}$ alkyl; or $R^{13}$ is a tetrahydrofuran ring linked through the $C_3$ or $C_4$ position of the tetrahydrofuran ring; or $R^{13}$ is a tetrahydropyran ring linked through the $C_4$ position of the tetrahydropyran ring;

$R^{14}$ and $R^{15}$ are each separately selected from hydrogen and $C_{1-6}$ alkyl; or $R^{14}$ and $R^{15}$ are taken together with the nitrogen to which they are attached to form indolinyl, pyrrolidinyl, piperidinyl, piperazinyl, or morpholinyl;

each $R^{16}$ is separately imidazolyl or pyrazolyl;

$R^{17}$ is a hydrogen, or selected from the group consisting of $C_{1-6}$ alkyl, $—(CH_2)_qC_{3-7}$cycloalkyl, aryl, and heteroaryl, each optionally substituted with one or more substituents each independently selected from the group consisting of halo, cyano, nitro, $C_{1-6}$ alkyl, $C_{1-6}$ alkoxy, phenyl, and $—NR^{1a}R^{1b}$;

E and F are independently —N— or $—CR^{18}—$;

when E is $—CR^{18}—$, F is —N—; when F is $—CR^{18}—$, E is —N—;

each $R^{18}$ is separately a hydrogen, or selected from the group consisting of $C_{1-6}$ alkyl, $(CH_2)_qC_{3-7}$cycloalkyl, aryl, and heteroaryl, each optionally substituted with one or more substituents each independently selected from the group consisting of halo, cyano, nitro, $C_{1-6}$ alkyl, $C_{1-6}$ alkoxy, and phenyl;

each u is independently 0, 1 or 2;

Z is selected from the group consisting of

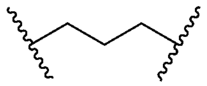,
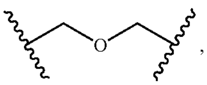,
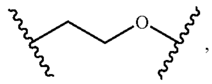,
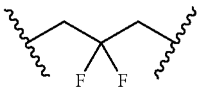,
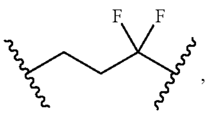,
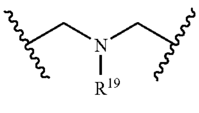,
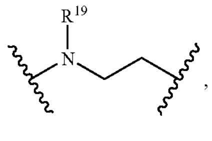,
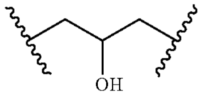, and
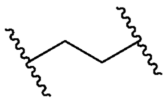;

$R^{19}$ is hydrogen, $C_{1-6}$ alkyl optionally substituted with up to 5 fluoro, or $—SO_mR^{2a}$;

$R^{20}$ is selected from the group consisting of hydrogen, $—SO_mR^{2a}$, $—C(O)OR^{2a}$, $—C(O)R^{2a}$, $—C(O)NR^{1a}R^{1b}$, and $—C(S)NR^{1a}R^{1b}$;

$R^{21}$ and $R^{22}$ are each hydrogen or together with the carbon atoms to which they are attached form an optionally substituted cyclopropyl; and the dashed line represents an optional double bond.

Some embodiments include a compound of Formula III having the structure:

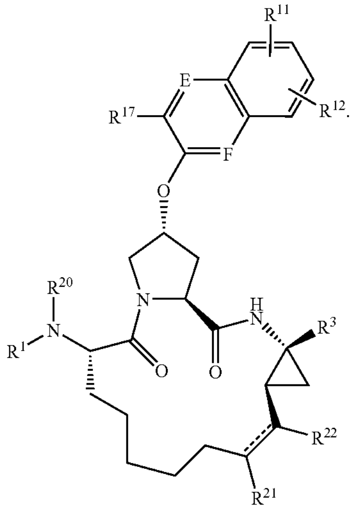

Some embodiments include a compound of Formula IV having the structure:

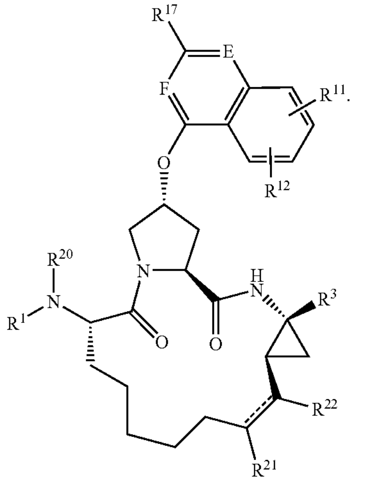

In another embodiment, $R^{20}$ is selected from the group consisting of hydrogen, —$SO_mR^{2a}$, and —$C(O)R^{2a}$.

In another embodiment, $R^4$ is selected from the group consisting of aryl and heteroaryl, each substituted with one or more substituents each independently selected from the group consisting of halo, cyano, nitro, hydroxy, cyanoamino, —SH, $C_{1-6}$ alkyl optionally substituted with up to 5 fluoro, and $C_{1-6}$ alkoxy optionally substituted with up to 5 fluoro; n is 0; and $R^3$ is —$C(O)NHS(O)_2R^9$ where $R^9$ is $C_{3-7}$cycloalkyl optionally substituted with $C_{1-6}$ alkyl.

In another embodiment, $R^4$ is selected from the group consisting of aryl and heteroaryl, each substituted with one or more substituents each independently selected from the group consisting of halo, $C_{1-6}$ alkyl optionally substituted with up to 5 fluoro, and $C_{1-6}$ alkoxy optionally substituted with up to 5 fluoro.

In another embodiment, $R^4$ is aryl substituted with one or more substituents each independently selected from the group consisting of halo, $C_{1-6}$ alkyl optionally substituted with up to 5 fluoro.

In another embodiment, $R^4$ is aryl substituted with one or more substituents each independently selected from the group consisting of fluorine and $CF_3$.

In another embodiment, $R^{11}$ and $R^{12}$ are each separately selected from the group consisting of hydrogen, $C_{1-6}$ alkyl, and $C_{1-6}$ alkoxy.

In another embodiment, $R^{11}$ and $R^{12}$ are each separately selected from the group consisting of hydrogen, methyl and methoxy.

In another embodiment, $R^{17}$ is a hydrogen, or selected from the group consisting of phenyl, thiazole, thiophene, oxazole and pyridine, each optionally substituted with one or more substituents each independently selected from the group consisting $C_{1-6}$ alkyl and —$NR^{1a}R^{1b}$, wherein $R^{1a}$ and $R^{1b}$ are each separately a hydrogen atom or $C_{1-6}$ alkyl.

In another embodiment, n is 0 or 1; $R^5$ and $R^6$ are each hydrogen; $R^4$ is phenyl, thiazole, oxazole, benzoxazole, benzothiazole, pyridine, or naphthyl, each optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen, —$C(O)CH_3$, or —$SO_2CH_3$.

In another embodiment, n is 0 or 1; $R^5$ and $R^6$ are each hydrogen; $R^4$ is phenyl optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen.

In another embodiment, n is 0 or 1; $R^5$ and $R^6$ are each hydrogen; $R^4$ is phenyl substituted with one or more substituents each independently selected from the group consisting of halo and $C_{1-6}$ alkyl optionally substituted with up to 5 fluoro; and $R^{20}$ is hydrogen.

In another embodiment, n is 0 or 1; $R^5$ and $R^6$ are each hydrogen; $R^4$ is phenyl substituted with one or more fluoro and optionally substituted with $CF_3$; and $R^{20}$ is hydrogen.

In another embodiment, Z is propyl.

In another embodiment, $R^3$ is carboxylic acid.

In another embodiment, $R^3$ is —$C(O)NHS(O)_2R^9$, where $R^9$ is $C_{3-7}$cycloalkyl optionally substituted with $C_{1-6}$ alkyl or $C_{1-6}$ alkoxy.

In another embodiment, $R^3$ is a —$CONHO(CH_2)_mR^{10}$ where $R^{10}$ is $C_{1-6}$ alkyl, —$(CH_2)_qC_{3-7}$cycloalkyl or phenyl optionally substituted with $CF_3$; m is 0 or 1; and q is 0 or 1.

In another embodiment, $R^3$ is —$C(O)NHS(O)_2R^9$, where $R^9$ is —$NR^{9a}R^{9b}$ and $R^{9a}$ and $R^{9b}$ are each independently a hydrogen atom or $C_{1-6}$ alkyl or —$NR^{9a}R^{9b}$ is a pyrrolidine or piperidine.

Formulas V and VI

The embodiments provide a compound having the structure of Formula V or VI:

(V)

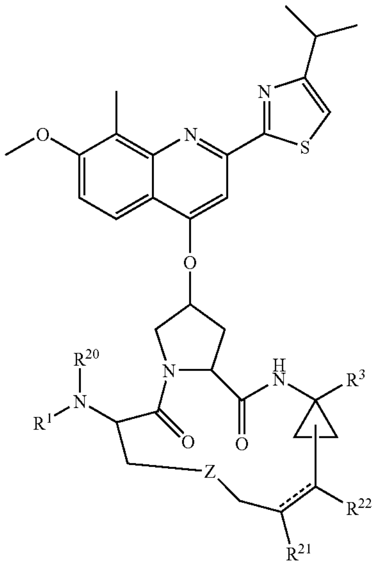

or (VI)

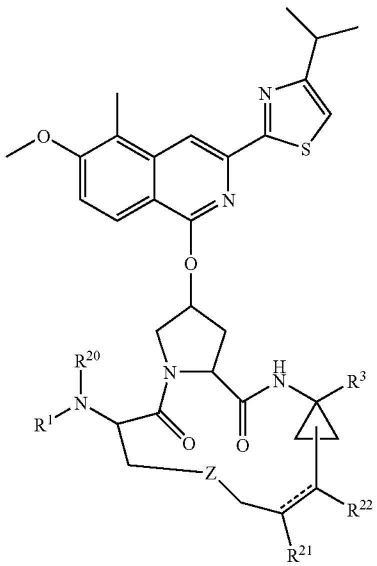

or a pharmaceutically acceptable salt or prodrug thereof wherein:

$R^1$ is —$(CR^5R^6)_nR^4$;

n is 0, 1 or 2;

$R^4$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_pNR^{3a}R^{3b}$, —$(CH_2)_pR^{4a}$ and —$O(CH_2)_pR^{4a}$;

$R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

$R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

each $R^{4a}$ is separately imidazolyl or pyrazolyl;

each m is separately 0, 1 or 2;

each p is separately an integer selected from 1-6;

each q is separately 0, 1 or 2;

each r is separately an integer selected from 1-6;

$R^3$ is —$C(O)NHS(O)_2R^9$, where $R^9$ is selected from the group consisting of $C_{1-6}$ alkyl, —$(CH_2)_qC_{3-7}$cycloalkyl, $C_{6\ or\ 10}$ aryl, and a heteroaromatic ring, each optionally substituted with one or more substituents each independently selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is —$NR^{9a}R^{9b}$; or $R^3$ is a —$CONHO(CH_2)_mR^{10}$ where $R^{10}$ is selected from the group consisting of $C_{1-6}$ alkyl, —$(CH_2)_qC_{3-7}$cycloalkyl, optionally substituted aryl and optionally substituted heteroaryl; or $R^3$ is a carboxylic acid;

wherein $R^{9a}$ and $R^{9b}$ are each separately a hydrogen atom, or separately selected from the group consisting of $C_{1-6}$ alkyl, —$(CH_2)_qC_{3-7}$cycloalkyl, and $C_{6\ or\ 10}$ aryl, each optionally substituted with one or more substituents each independently selected from the group consisting of halo, cyano, nitro, hydroxy, $C_{1-6}$ alkyl, —$(CH_2)_tC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or —$NR^{9a}R^{9b}$ is a three- to six-membered alkyl cyclic secondary amine, which optionally has one to three hetero atoms incorporated in the ring, and which is optionally substituted with one or more substituents each independently selected from the group consisting of halo, cyano, nitro, $C_{1-6}$ alkyl, $C_{1-6}$ alkoxy, and phenyl, or $R^{9a}$ and $R^{9b}$ are taken together with the nitrogen to which they are attached to form a heteroaryl, optionally substituted with one or more substituents each independently selected from the group consisting of a halogen, cyano, nitro, hydroxy, $C_{1-6}$ alkyl, —$(CH_2)_qC_{3-7}$cycloalkyl, $C_{1-6}$ alkoxy, $C_{3-6}$ cycloalkoxy, —NH(CO)$OR^{1e}$, wherein $R^{1e}$ is $C_{1-6}$ alkyl, or —$(CH_2)_qC_{3-7}$cycloalkyl, —$N(R^{1d})_2$, —NH(CO)$R^{1d}$, and —NH(CO)$NHR^{d}$, wherein each $R^{1d}$ is separately selected from the group consisting of a hydrogen atom, $C_{1-6}$ alkyl, and —$(CH_2)_qC_{3-7}$cycloalkyl;

each t is separately 0, 1 or 2;

$R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more substituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each u is separately 0, 1 or 2;

Z is selected from the group consisting of

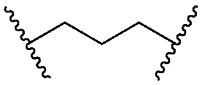,
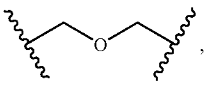,
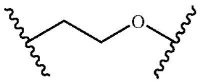,
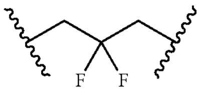,
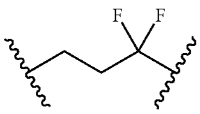,
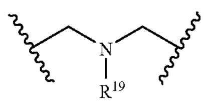,
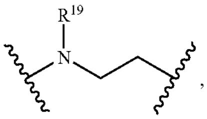,
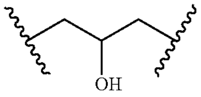, and
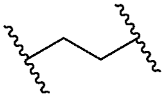;

$R^{19}$ is hydrogen, $C_{1-6}$ alkyl optionally substituted with up to 5 fluoro, or —$SO_mR^{2a}$;

$R^{20}$ is selected from the group consisting of hydrogen, —$SO_mR^{2a}$, —C(O)$OR^{2a}$, —C(O)$R^{2a}$, —C(O)$NR^{1a}R^{1b}$, and —C(S)$NR^{1a}R^{1b}$;

$R^{21}$ and $R^{22}$ are each hydrogen or together with the carbon atoms to which they are attached form an optionally substituted cyclopropyl; and the dashed line represents an optional double bond.

In another embodiment, n is 0 or 1; $R^5$ and $R^6$ are each hydrogen; $R^4$ is phenyl, thiazole, oxazole, benzoxazole, benzothiazole, pyridine, or naphthyl, each optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen, —$C(O)CH_3$, or —$SO_2CH_3$.

In another embodiment, n is 0 or 1; $R^5$ and $R^6$ are each hydrogen; $R^4$ is phenyl optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen.

In another embodiment, n is 0 or 1; $R^5$ and $R^6$ are each hydrogen; $R^4$ is phenyl substituted with one or more substituents each independently selected from the group consisting of halo and $C_{1-6}$ alkyl optionally substituted with up to 5 fluoro; and $R^{20}$ is hydrogen.

In another embodiment, n is 0 or 1; $R^5$ and $R^6$ are each hydrogen; $R^4$ is phenyl substituted with one or more fluoro and optionally substituted with $CF_3$; and $R^{20}$ is hydrogen.

In another embodiment, Z is propyl.

In another embodiment, $R^3$ is carboxylic acid.

In another embodiment, $R^3$ is —C(O)NHS$(O)_2R^9$, where $R^9$ is $C_{3-7}$cycloalkyl optionally substituted with $C_{1-6}$ alkyl or $C_{1-6}$ alkoxy.

In another embodiment, $R^3$ is a —CONHO$(CH_2)_mR^{10}$ where $R^{10}$ is $C_{1-6}$ alkyl, —$(CH_2)_qC_{3-7}$cycloalkyl or phenyl optionally substituted with $CF_3$; m is 0 or 1; and q is 0 or 1.

In another embodiment, $R^3$ is —C(O)NHS$(O)_2R^9$, where $R^9$ is —$NR^{9a}R^{9b}$ and $R^{9a}$ and $R^{9b}$ are each independently a hydrogen atom or $C_{1-6}$ alkyl or —$NR^{9a}R^{9b}$ is a pyrrolidine or piperidine.

Formulas V and VI (Alternative)

In some alternative embodiments of Formulas V and VI:

(a) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each separately selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(b) $R^{2a}$ is selected from the group consisting of $C_{1-6}$ alkyl, $C_{3-7}$ cycloalkyl, and $C_{6\ or\ 10}$ aryl, each optionally substituted with one or more substituents each separately selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

(c) each m is separately 0, 1 or 2;

(d) each p is separately an integer selected from 1-6;

(e) each q is separately 0, 1 or 2;

(f) $R^3$ is —C(O)NHS$(O)_2R^9$, where $R^9$ is selected from the group consisting of $C_{1-6}$ alkyl, —$(CH_2)_qC_{3-7}$cycloalkyl, $C_{6\ or\ 10}$ aryl, and a heteroaryl, each optionally substituted with one or more substituents each separately selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro, or $R^9$ is $NR^{9a}R^{9b}$;

wherein $R^{9a}$ and $R^{9b}$ are each separately a hydrogen atom, or separately selected from the group consisting of $C_{1-6}$ alkyl, —$(CH_2)_qC_{3-7}$cycloalkyl, and $C_{6\ or\ 10}$ aryl, each optionally substituted with one or more substituents each separately selected from the group consisting of halo, cyano, nitro, hydroxy, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, or $R^{9a}$ and $R^{9b}$ are each separately selected from the group consisting of a hydrogen atom and a heterocycle, which is a five-, six-, or seven-membered, saturated or unsaturated heterocyclic group, containing from one to four heteroatoms selected from the group consisting of nitrogen, oxygen, and sulfur, or $R^{9a}$ and $R^{9b}$ are each separately selected from the group consisting of a hydrogen atom and a heteroaryl group;

or $R^{9a}$ and $R^{9b}$ are taken together with the nitrogen to which they are attached to form a three- to six-membered heterocycle, which optionally has one to three hetero atoms incorporated in the ring, and which is optionally substituted with one or more substituents each separately selected from the group consisting of halo, cyano, nitro, $C_{1-6}$ alkyl, $C_{1-6}$ alkoxy, and phenyl, or $R^{9a}$ and $R^{9b}$ are taken together with the nitrogen to which they are attached to form a heteroaryl, optionally substituted with one or more substituents each separately selected from the group consisting of a halogen, cyano, nitro, hydroxy, $C_{1-6}$ alkyl, —$(CH_2)_qC_{3-7}$cycloalkyl, $C_{1-6}$ alkoxy, $C_{3-6}$ cycloalkoxy, —NH(CO)$OR^{1e}$, wherein $R^{1e}$ is $C_{1-6}$ alkyl, or —$(CH_2)_qC_{3-7}$ cycloalkyl, —$N(R^{1d})_2$, —NH(CO)$R^{1d}$, and —NH(CO)$NHR^{1d}$, wherein each $R^{1d}$ is separately selected from the group consisting of a hydrogen atom, $C_{1-6}$ alkyl, and —$(CH_2)_qC_{3-7}$cycloalkyl;

or $R^3$ is a —$CONHO(CH_2)_mR^{10}$ where $R^{10}$ is selected from the group consisting of $C_{1-6}$ alkyl, —$(CH_2)_qC_{3-7}$cycloalkyl, optionally substituted aryl and optionally substituted heteroaryl;

or $R^3$ is a —$CONR^{100a}R^{100b}$;

or $R^3$ is a carboxylic acid;

(g) each t is separately 0, 1 or 2;

(h) $R^{100a}$ is —$(CH_2)_vCONR^{200a}R^{200b}$, and $R^{100b}$ is a hydrogen or —$(CH_2)_vCONR^{200a}R^{200b}$; or $R^{100a}$ and $R^{100b}$ are optionally taken together with the nitrogen to which they are attached to form a three- to six-membered heterocycle, which optionally has one to three additional hetero atoms incorporated in the ring, and which is optionally substituted with —$(CH_2)_vCONR^{300a}R^{300b}$;

(i) each v is separately 0, 1, 2, 3, 4, 5, or 6;

(j) $R^{200a}$ and $R^{200b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(k) $R^{300a}$ and $R^{300b}$ are each separately hydrogen or —$(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(l) Z is selected from the group consisting of

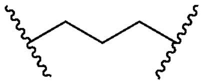, 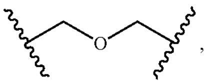,

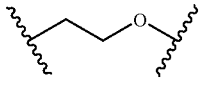, 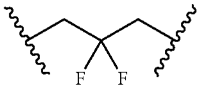,

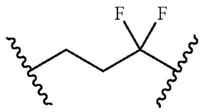, 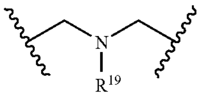,

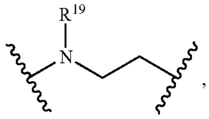, 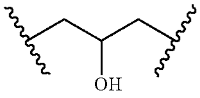, and

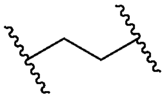;

(m) $R^{19}$ is hydrogen, —$SO_mR^{2a}$, or $C_{1-6}$ alkyl optionally substituted with up to 5 fluoro;

(n) $R^{20}$ is selected from the group consisting of —$SO_mR^{2a}$, —C(O)$OR^{2a}$, —C(O)$R^{2a}$, —C(O)$NR^{1a}R^{1b}$, and —C(S)$NR^{1a}R^{1b}$;

(o) $R^{21}$ and $R^{21}$ are each hydrogen or together with the carbon atoms to which they are attached form an optionally substituted cyclopropyl; and (p) the dashed line represents an optional double bond.

In another embodiment, $R^{20}$ is selected from the group consisting of —$SO_mR^{2a}$, and —C(O)$R^{2a}$.

In another embodiment, $R^{20}$ is —C(O)$OR^{2a}$.

In another embodiment, wherein $R^{2a}$ is $C_{1-6}$ alkyl.

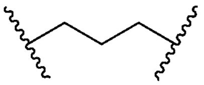.

In another embodiment, Z is

In another embodiment, $R^3$ is —C(O)NHS$(O)_2R^9$, where $R^9$ is —$(CH_2)_qC_{3-7}$cycloalkyl optionally substituted with $C_{1-6}$ alkyl.

In another embodiment, $R^3$ is carboxylic acid.

In another embodiment, $R^3$ is —C(O)$NHO(CH_2)_mR^{10}$ where $R^{10}$ is $C_{1-6}$alkyl, —$(CH_2)_qC_{3-7}$cycloalkyl, or phenyl optionally substituted with $CF_3$; m is 0 or 1; and q is 0 or 1.

In another embodiment, $R^3$ is —C(O)NHS$(O)_2R^9$ where $R^9$ is —$NR^{9a}R^{9b}$ and $R^{9a}$ and $R^{9b}$ are each independently a hydrogen atom or $C_{1-6}$ alkyl or —$NR^{9a}R^{9b}$ is a pyrrolidine or piperidine.

Formula VII

Some embodiments provide a compound having the structure of Formula VII:

VII

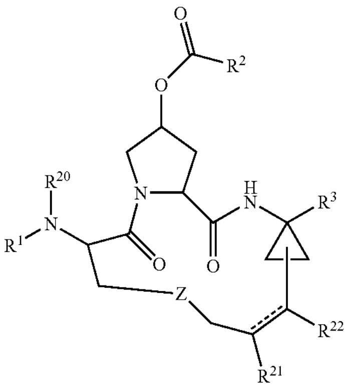

or a pharmaceutically acceptable salt or prodrug thereof wherein:

(a) $R^1$ is hydrogen;

(b) $R^2$ is selected from the group consisting of:

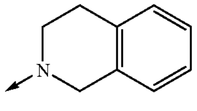
and
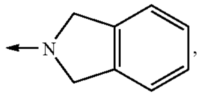
, each optionally substituted with one or more substituents each separately selected from the group consisting of halo, cyano, nitro, hydroxy, cyanoamino, —SH, $C_{1-6}$ alkyl, $C_{1-6}$ alkoxy, $C_{2-6}$ alkenyl, $C_{2-6}$ alkynyl, $—(CH_2)_q C_{3-7}$cycloalkyl, $C_{3-6}$ heterocycloalkyl, aryl, heteroaryl, aryloxy, arylthio, $C_{1-6}$ alkylthio, $—N[(CH_2)_pOH][(CH_2)_rOH]$, $—S(O)_2NR^{1a}R^{1b}$, $—NHC(O)NR^{1a}R^{1b}$, $—NHC(S)NR^{1a}R^{1b}$, $—C(O)NR^{1a}R^{1b}$, $—NR^{1a}R^{1b}$, $—C(O)R^{2a}$, $—C(O)OR^{2a}$, $—NHC(O)R^{2a}$, $—NHC(O)OR^{2a}$, $—SO_mR^{2a}$, $—NHS(O)_2R^{2a}$, $—NR^{2a}[(CH_2)_pOH]$, $—O[(CH_2)_pNR^{3a}R^{3b}]$, $—S[(CH_2)_pNR^{3a}R^{3b}]$, $—(CH_2)_pNR^{3a}R^{3b}$; $—(CH_2)_pR^{4a}$ and $—O(CH_2)_pR^{4a}$;

(c) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each separately selected from the group consisting of halo, cyano, nitro, hydroxy, $C_{1-6}$ alkyl, $—(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(d) each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, $—(CH_2)_qC_{3-7}$cycloalkyl, $C_{1-6}$ alkoxy, phenyl, and hydroxy-$C_{1-6}$ alkyl;

(e) $R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

(f) $R^{4a}$ is imidazolyl or pyrazolyl;

(g) each m is separately 0, 1 or 2;

(h) each p is separately an integer selected from 1-6;

(i) each q is separately 0, 1 or 2;

(j) each r is separately an integer selected from 1-6;

(k) $R^{20}$ is selected from the group consisting of aryl and heteroaryl, each optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, $—(CH_2)_qC_{3-7}$cycloalkyl, $C_{3-6}$ heterocycloalkyl, aryl, heteroaryl, aryloxy, arylthio, $C_{1-6}$ alkylthio, $—N[(CH_2)_pOH][(CH_2)_rOH]$, $—S(O)_2NR^{1a}R^{1b}$, $NHC(O)NR^{1a}R^{1b}$, $—NHC(S)NR^{1a}R^{1b}$, $—C(O)NR^{1a}R^{1b}$, $—NR^{1a}R^{1b}$, $—C(O)R^{2a}$, $—C(O)OR^{2a}$, $—NHC(O)R^{2a}$, $—NHC(O)OR^{2a}$, $—SO_mR^{2a}$, $—NHS(O)_2R^{2a}$, $—NR^{2a}[(CH_2)_pOH]$, $—O[(CH_2)_pNR^{3a}R^{3b}]$, $—S[(CH_2)_pNR^{3a}R^{3b}]$, $—(CH_2)_p NR^{3a}R^{3b}$, $—(CH_2)_pR^{4a}$ and $—O(CH_2)_pR^{4a}$;

(l) $R^3$ is $—C(O)NHS(O)_2R^9$, where $R^9$ is selected from the group consisting of $—(CH_2)_rC(O)NHR^{9c}$, $—(CH_2)_rC(O)OR^{9c}$, and $—(CH_2)_qR^{9d}$;

wherein $R^{9c}$ is $C_{6\ or\ 10}$ aryl optionally substituted with one or more substituents each separately selected from the group consisting of $—O(CH_2)_qC(O)NHR^{9e}$ and $—NH(CH_2)_qC(O)NHR^{9e}$;

wherein $R^{9d}$ is $C_{6\ or\ 10}$ aryl substituted with one or more substituents each separately selected from the group consisting of $—O(CH_2)_qC(O)NHR^{9e}$ and $—NH(CH_2)_qC(O)NHR^{9e}$;

wherein $R^{9e}$ is selected from the group consisting of hydrogen, $C_{6\ or\ 10}$ aryl, and $C_{1-6}$ alkyl optionally substituted with up to 5 fluoro;

or $R^3$ is $—C(O)NHS(O)_2R^9$, where $R^9$ is $—(CH_2)_qC_{3-7}$cycloalkyl substituted with methyl;

or $R^3$ is a $—CONHO(CH_2)_mR^{10}$ where $R^{10}$ is selected from the group consisting of $C_{1-6}$ alkyl, $—(CH_2)_qC_{3-7}$cycloalkyl, optionally substituted aryl and optionally substituted heteroaryl;

or $R^3$ is a $—CONR^{100a}R^{100b}$;

or $R^3$ is carboxylic acid;

(m) each t is separately 0, 1 or 2;

(n) $R^{100a}$ is $—(CH_2)_vCONR^{200a}R^{200b}$, and $R^{100b}$ is a hydrogen or $—(CH_2)_vCONR^{200a}R^{200b}$; or $R^{100a}$ and $R^{100b}$ are optionally taken together with the nitrogen to which they are attached to form a three- to six-membered heterocycle, which optionally has one to three additional hetero atoms incorporated in the ring, and which is optionally substituted with $—(CH_2)_vCONR^{300a}R^{300b}$;

(o) each v is separately 0, 1, 2, 3, 4, 5, or 6;

(p) $R^{200a}$ and $R^{200b}$ are each separately hydrogen or $—(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(q) $R^{300a}$ and $R^{300b}$ are each separately hydrogen or $—(CH_2)_pC_{6\ or\ 10}$ aryl optionally substituted with one or more substituents each separately selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

(r) Z is selected from the group consisting of

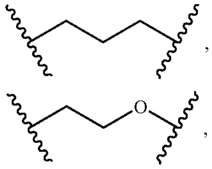 , 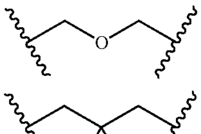 ,

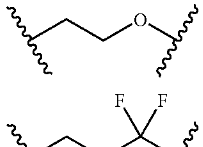 , 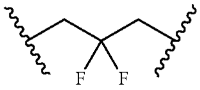 ,

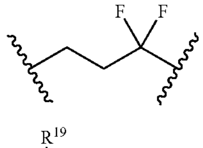 , 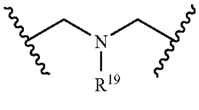 ,

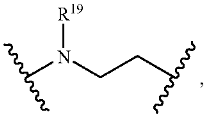 , 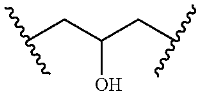 , and

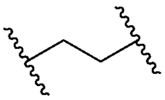 ;

(s) $R^{19}$ is hydrogen, —$SO_mR^{2a}$, or $C_{1-6}$ alkyl optionally substituted with up to 5 fluoro;

(t) $R^{21}$ and $R^{21}$ are each hydrogen or together with the carbon atoms to which they are attached form an optionally substituted cyclopropyl; and (u) the dashed line represents an optional double bond.

In another embodiment, $R^2$ is selected from the group consisting of

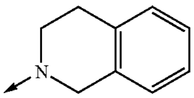 and 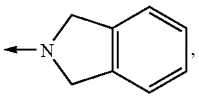 , each optionally substituted with one or more substituents each separately selected from the group consisting of halo, hydroxy, $C_{1-6}$ alkyl, and $C_{1-6}$ alkoxy.

In another embodiment, $R^3$ is —$C(O)NHS(O)_2R^9$, where $R^9$ is —$(CH_2)_qC_{3-7}$cycloalkyl substituted with methyl.

In another embodiment, $R^3$ is —$CONR^{100a}R^{100b}$.

In another embodiment, $R^{100a}$ and $R^{100b}$ are taken together with the nitrogen to which they are attached to form a three- to six-membered heterocycle substituted with —$(CH_2)_vCONR^{300a}R^{300b}$.

In another embodiment, $R^{300a}$ and $R^{300b}$ are each separately hydrogen or —$(CH_2)_pC_{6\ or\ 10}$ aryl; v is 0; and p is 1.

In another embodiment, $R^{100a}$ is hydrogen, and $R^{100b}$ is a hydrogen or —$(CH_2)_vCONR^{200a}R^{200b}$.

In another embodiment, $R^{20}$ is selected from the group consisting of phenyl, thiazole, oxazole, benzoxazole, benzothiazole, pyridine, or naphthyl, each optionally substituted with one or more substitutents each independently selected from the group consisting of halo, cyano, $C_{1-6}$ alkyl optionally substituted with up to 5 fluoro, $C_{1-6}$ alkoxy optionally substituted with up to 5 fluoro, and phenyl.

In another embodiment, $R^{20}$ is phenyl optionally substituted with one or more substitutents each independently selected from the group consisting of halo, cyano, $C_{1-6}$ alkyl optionally substituted with up to 5 fluoro, $C_{1-6}$ alkoxy optionally substituted with up to 5 fluoro, and phenyl.

In another embodiment, $R^{20}$ is phenyl substituted with one or more substitutents each independently selected from the group consisting of halo and $C_{1-6}$ alkyl optionally substituted with up to 5 fluoro.

In another embodiment, $R^{20}$ is phenyl substituted with one or more fluoro and optionally substituted with $CF_3$.

In another embodiment, Z is

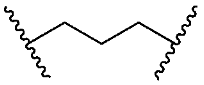 .

Formula X

Some embodiments provide a compound of Formula X:

(X)

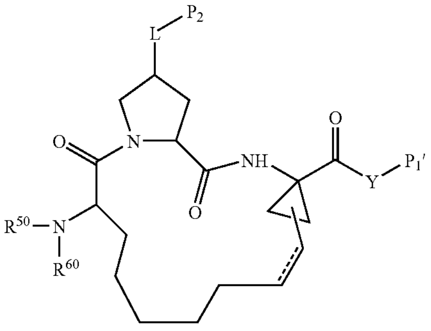

or a pharmaceutically acceptable salt, prodrug, or ester thereof.

Some embodiments of the compound of Formula X have the structure of Formula Xa:

(Xa)

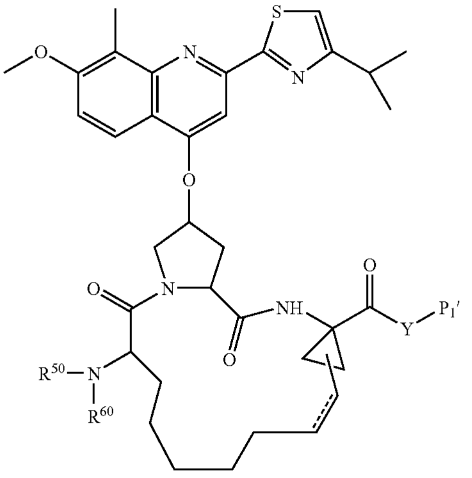

or a pharmaceutically acceptable salt, prodrug, or ester thereof.

As used herein, an NS3 protease S1' pocket moiety refers to a moiety of the NS3 protease that interacts with the amino acid positioned one residue C-terminal to the cleavage site of the substrate polypeptide cleaved by NS3 protease (e.g., the NS3 protease moieties that interact with amino acid S in the polypeptide substrate DLEVVT-STWVLV, SEQ ID NO: 1). Exemplary moieties include, but are not limited to, atoms of the peptide backbone or side chains of amino acids Lys136, Gly137, Ser139, His57, Gly58, Gln41, Ser42, and Phe43, see Yao. et. al., Structure 1999, 7, 1353.

As used herein, an NS3 protease S2 pocket moiety refers to a moiety of the NS3 protease that interacts with the amino acid positioned two residues N-terminal to the cleavage site of the substrate polypeptide cleaved by NS3 protease (e.g., the NS3 protease moieties that interact with amino acid V in the polypeptide substrate DLEVVT-STWVLV, SEQ ID NO: 1). Exemplary moieties include, but are not limited to, atoms of the peptide backbone or side chains of amino acids His57, Arg155, Val78, Asp79, Gln80 and Asp81, see Yao. et. al., Structure 1999, 7, 1353.

Embodiments described herein include compounds containing moieties having a size, configuration and/or position selected to interact and/or be in proximity to particular regions, particular amino acid residues, and/or particular atoms of NS3 protease, upon binding of the compound to NS3 protease. For example, in an embodiment of the compound of the general formulae (X) and (Xa), Y is a moiety having a size and configuration such that, upon binding of the compound to NS3 protease, at least one atom of Y is within 4 Å or less of at least one moiety selected from NS3 protease His57 imidazole moiety and NS3 protease Gly137 nitrogen atom. In another embodiment of the compound of the general formulae (X) and (Xa), Y is a moiety having a size and configuration such that, upon binding of the compound to NS3 protease, at least one atom of Y forms a hydrogen bond with a peptide backbone atom or side chain moiety located in the substrate binding pocket of NS3 protease, including, but not limited to, NS3 protease His57 imidazole moiety and NS3 protease Gly137 nitrogen atom. In some instances, Y may be configured to form a hydrogen bond with both the NS3 protease His57 imidazole moiety and the NS3 protease Gly137 nitrogen atom. The moiety —NH—$SO_2$— is an example of a Y moiety.

In a similar fashion, in an embodiment of the compound of the general formulae (X) and (Xa), the $P_1$' moiety, different from Y, has a size and configuration such that, upon binding of the compound to NS3 protease, at least one atom of $P_1$' is within 6 Å or less of at least one NS3 protease S1' pocket moiety selected from the group consisting of Lys136, Gly137, Ser139, His57, Gly58, Gln41, Ser42, and Phe43. In another embodiment of the compound of the general formulae (X) and (Xa), the $P_1$' moiety, different from Y, has a size and configuration such that, upon binding of the compound to NS3 protease, at least one atom of $P_1$' forms a non-polar interaction with peptide backbone or side chain atom or atoms located in the substrate binding pocket of NS3 protease, including, but not limited to amino acid residues that form the NS3 protease S1' pocket. For example the $P_1$' moiety may form a non-polar interaction with at least one amino acid selected from Lys136, Gly137, Ser139, His57, Gly58, Gln41, Ser42, and Phe43. The moieties $C_{3-7}$ cycloalkyl, $C_{4-10}$ alkylcycloalkyl and di($C_{1-4}$ alkyl)amine are examples of $P_1$' moieties. Examples of Y—$P_1$' include —NH—$SO_2$-methylcyclopropyl and —NH—$SO_2$—$N(CH_3)_2$.

In a similar fashion, in an embodiment of the compound of the general formulae (X) and (Xa), the $P_2$ moiety has a size and configuration such that, upon binding of the compound to NS3 protease, at least one atom of $P_2$ is within 5 Å or less of any backbone or side chain atom of at least one NS3 protease residue selected from the group consisting of Tyr56, His57, Val78, Asp79, Gln80, Asp81, Arg155 and Ala156. In an embodiment of the compound of the general formulae (X) and (Xa), $P_2$ is positioned by L to provide this configuration, where L is a moiety consisting of from 1 to 5 atoms selected from the group consisting of carbon, oxygen, nitrogen, hydrogen, and sulfur. In an embodiment, L is an oxygen atom. In another embodiment, L may contain 2 to 5 atoms selected from the group consisting of carbon, oxygen, nitrogen, hydrogen, and sulfur. For example, L may contain a moiety having the formula —W—C(═V)—, where V and W are each individually selected from O, S or NH. Specific exemplary moieties for L include, but are not limited to, ester, amide, carbamate, thioester, and thioamide. In some embodiments, $P_2$ may be selected from the group consisting of unsubstituted aryl, substituted aryl, unsubstituted heteroaryl, substituted heteroaryl, unsubstituted heterocyclic and substituted heterocyclic.

In another embodiment of the compound of the general formulae (X) and (Xa), the $P_2$ moiety has a size and configuration such that, upon binding of the compound to NS3 protease, at least one atom of $P_2$ forms a non-polar interaction with peptide backbone or side chain atom or atoms located in the substrate binding pocket of NS3 protease, including, but not limited to amino acid residues that form the NS3 protease S2 pocket. For example the $P_2$ moiety may form a non-polar interaction with at least one amino acid selected from His57, Arg155, Val78, Asp79, Gln80 and Asp81. The $P_2$ moiety also may be configured to form a hydrogen bond with peptide backbone or side chain atom or atoms located in the substrate binding pocket of NS3 protease, including, but not limited to amino acid residues that form the NS3 protease S2 pocket. For example the $P_2$ moiety may form a hydrogen bond with at least one amino acid selected from His57, Arg155, Val78, Asp79, Gln80 and Asp81. In some instances, $P_2$ may form both a non-polar interaction and a hydrogen bond with peptide backbone or side chain moieties or atoms located in the substrate binding pocket of NS3 protease, such amino acids selected from His57, Arg155, Val78, Asp79, Gln80 and Asp81. Such hydrogen bond and non-polar interactions may occur with the same amino acid residue or with different amino acid residues in the NS3 protease S2 pocket. In an embodiment of the compound of the general formulae (X) and (Xa), $P_2$ is positioned by L to provide this configuration, where L is a moiety as described above. In some embodiments, $P_2$ may be selected from the group consisting of unsubstituted aryl, substituted aryl, unsubstituted heteroaryl, substituted heteroaryl, unsubstituted heterocyclic and substituted heterocyclic.

In another embodiment of the compound of the general formulae (X) and (Xa), the $R^{50}$ and $R^{60}$ moieties have a size, configuration and/or positioning such that, upon binding of the compound to NS3 protease, at least one atom of $R^{50}$ or $R^{60}$ is within 5 Å or less of any backbone or side chain atom of at least one NS3 protease residue selected from the group consisting of Arg123, Ala156, Ala157, Val158, Cys159, and Asp168. In an embodiment, $R^{50}$ is H and $R^{60}$ is selected from the group consisting of unsubstituted aryl, substituted aryl, unsubstituted heteroaryl, substituted heteroaryl, unsubstituted heterocyclic and substituted heterocyclic; or $R^{50}$ and $R^{60}$ taken together with the nitrogen to which they are attached form a moiety selected from the group consisting of unsubstituted heteroaryl, substituted heteroaryl, unsubstituted heterocyclic and substituted heterocyclic.

Compositions

The present embodiments further provide compositions, including pharmaceutical compositions, comprising compounds of the general Formulae I, II, III, IV, V, VI, VII, or X.

A subject pharmaceutical composition comprises a subject compound; and a pharmaceutically acceptable excipient. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The present embodiments provide for a method of inhibiting NS3/NS4 protease activity comprising contacting a NS3/NS4 protease with a compound disclosed herein.

The present embodiments provide for a method of treating hepatitis by modulating NS3/NS4 protease comprising contacting a NS3/NS4 protease with a compound disclosed herein.

Example compounds of Formulae I, II, III, IV, V, VI, and VII include Compound Numbers 101-492, 701, 1001-1075, and 1077-1147 as set forth herein.

Preferred embodiments provide a method of treating a hepatitis C virus infection in an individual, the method comprising administering to the individual an effective amount of a composition comprising a preferred compound.

Preferred embodiments provide a method of treating liver fibrosis in an individual, the method comprising administering to the individual an effective amount of a composition comprising a preferred compound.

Preferred embodiments provide a method of increasing liver function in an individual having a hepatitis C virus infection, the method comprising administering to the individual an effective amount of a composition comprising a preferred compound.

In many embodiments, a subject compound inhibits the enzymatic activity of a hepatitis virus C(HCV) NS3 protease. Whether a subject compound inhibits HCV NS3 protease can be readily determined using any known method. Typical methods involve a determination of whether an HCV polyprotein or other polypeptide comprising an NS3 recognition site is cleaved by NS3 in the presence of the agent. In many embodiments, a subject compound inhibits NS3 enzymatic activity by at least about 10%, at least about 15%, at least about 20%, at least about 25%, at least about 30%, at least about 40%, at least about 50%, at least about 60%, at least about 70%, at least about 80%, or at least about 90%, or more, compared to the enzymatic activity of NS3 in the absence of the compound.

In many embodiments, a subject compound inhibits enzymatic activity of an HCV NS3 protease with an $IC_{50}$ of less than about 50 μM, e.g., a subject compound inhibits an HCV NS3 protease with an $IC_{50}$ of less than about 40 μM, less than about 25 μM, less than about 10 μM, less than about 1 μM, less than about 100 nM, less than about 80 nM, less than about 60 nM, less than about 50 nM, less than about 25 nM, less than about 10 nM, or less than about 1 nM, or less.

In many embodiments, a subject compound inhibits the enzymatic activity of a hepatitis virus C(HCV) NS3 helicase. Whether a subject compound inhibits HCV NS3 helicase can be readily determined using any known method. In many embodiments, a subject compound inhibits NS3 enzymatic activity by at least about 10%, at least about 15%, at least about 20%, at least about 25%, at least about 30%, at least about 40%, at least about 50%, at least about 60%, at least about 70%, at least about 80%, or at least about 90%, or more, compared to the enzymatic activity of NS3 in the absence of the compound.

In many embodiments, a subject compound inhibits HCV viral replication. For example, a subject compound inhibits HCV viral replication by at least about 10%, at least about 15%, at least about 20%, at least about 25%, at least about 30%, at least about 40%, at least about 50%, at least about 60%, at least about 70%, at least about 80%, or at least about 90%, or more, compared to HCV viral replication in the absence of the compound. Whether a subject compound inhibits HCV viral replication can be determined using methods known in the art, including an in vitro viral replication assay.

Treating a Hepatitis Virus Infection

The methods and compositions described herein are generally useful in treatment of an of HCV infection.

Whether a subject method is effective in treating an HCV infection can be determined by a reduction in viral load, a reduction in time to seroconversion (virus undetectable in patient serum), an increase in the rate of sustained viral response to therapy, a reduction of morbidity or mortality in clinical outcomes, or other indicator of disease response.

In general, an effective amount of a compound of Formulae I, II, III, IV, V, VI, VII, or X, and optionally one or more additional antiviral agents, is an amount that is effective to reduce viral load or achieve a sustained viral response to therapy.

Whether a subject method is effective in treating an HCV infection can be determined by measuring viral load, or by measuring a parameter associated with HCV infection, including, but not limited to, liver fibrosis, elevations in serum transaminase levels, and necroinflammatory activity in the liver. Indicators of liver fibrosis are discussed in detail below.

The method involves administering an effective amount of a compound of Formulae I, II, III, IV, V, VI, VII, or X, optionally in combination with an effective amount of one or more additional antiviral agents. In some embodiments, an effective amount of a compound of Formulae I, II, III, IV, V, VI, VII, or X, and optionally one or more additional antiviral agents, is an amount that is effective to reduce viral titers to undetectable levels, e.g., to about 1000 to about 5000, to about 500 to about 1000, or to about 100 to about 500 genome copies/mL serum. In some embodiments, an effective amount of a compound of Formulae I, II, III, IV, V, VI, VII, or X, and optionally one or more additional antiviral agents, is an amount that is effective to reduce viral load to lower than 100 genome copies/mL serum.

In some embodiments, an effective amount of a compound of Formulae I, II, III, IV, V, VI, VII, or X, and optionally one or more additional antiviral agents, is an amount that is effective to achieve a 1.5-log, a 2-log, a 2.5-log, a 3-log, a 3.5-log, a 4-log, a 4.5-log, or a 5-log reduction in viral titer in the serum of the individual.

In many embodiments, an effective amount of a compound of Formulae I, II, III, IV, V, VI, VII, or X, and optionally one or more additional antiviral agents, is an amount that is effective to achieve a sustained viral response, e.g., non-detectable or substantially non-detectable HCV RNA (e.g., less than about 500, less than about 400, less than about 200, or less than about 100 genome copies per milliliter serum) is found in the patient's serum for a period of at least about one month, at least about two months, at least about three months, at least about four months, at least about five months, or at least about six months following cessation of therapy.

As noted above, whether a subject method is effective in treating an HCV infection can be determined by measuring a parameter associated with HCV infection, such as liver fibrosis. Methods of determining the extent of liver fibrosis are discussed in detail below. In some embodiments, the level of a serum marker of liver fibrosis indicates the degree of liver fibrosis.

As one non-limiting example, levels of serum alanine aminotransferase (ALT) are measured, using standard assays. In general, an ALT level of less than about 45 international units is considered normal. In some embodiments, an effective amount of a compound of Formulae I, II, III, IV, V, VI, VII, or X, and optionally one or more additional antiviral agents, is an amount effective to reduce ALT levels to less than about 45 IU/mL serum.

A therapeutically effective amount of a compound of Formulae I, II, III, IV, V, VI, VII, or X, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Methods of measuring serum markers include immunological-based methods, e.g., enzyme-linked immunosorbent assays (ELISA), radioimmunoassays, and the like, using antibody specific for a given serum marker.

In many embodiments, an effective amount of a compound of Formulae I, II, III, IV, V, VI, VII, or X and an additional antiviral agent is a synergistic amount. The additional antiviral agent may itself be a combination of antiviral agents, e.g., a combination of pegylated interferon-alfa and ribavirin. As used herein, a "synergistic combination" or a "synergistic amount" of a compound of Formulae I, II, III, IV, V, VI, VII, or X and an additional antiviral agent is a combined dosage that is more effective in the therapeutic or prophylactic treatment of an HCV infection than the incremental improvement in treatment outcome that could be predicted or expected from a merely additive combination of (i) the therapeutic or prophylactic benefit of the compound of Formulae I, II, III, IV, V, VI, VII, or X when administered at that same dosage as a monotherapy and (ii) the therapeutic or prophylactic benefit of the additional antiviral agent when administered at the same dosage as a monotherapy.

In some embodiments, a selected amount of a compound of Formulae I, II, III, IV, V, VI, VII, or X and a selected amount of an additional antiviral agent are effective when used in combination therapy for a disease, but the selected amount of the compound of Formulae I, II, III, IV, V, VI, VII, or X and/or the selected amount of the additional antiviral agent is ineffective when used in monotherapy for the disease. Thus, the embodiments encompass (1) regimens in which a selected amount of the additional antiviral agent enhances the therapeutic benefit of a selected amount of the compound of Formulae I, II, III, IV, V, VI, VII, or X when used in combination therapy for a disease, where the selected amount of the additional antiviral agent provides no therapeutic benefit when used in monotherapy for the disease (2) regimens in which a selected amount of the compound of Formulae I, II, III, IV, V, VI, VII, or X enhances the therapeutic benefit of a selected amount of the additional antiviral agent when used in combination therapy for a disease, where the selected amount of the compound of Formulae I, II, III, IV, V, VI, VII, or X provides no therapeutic benefit when used in monotherapy for the disease and (3) regimens in which a selected amount of the compound of Formulae I, II, III, IV, V, VI, VII, or X and a selected amount of the additional antiviral agent provide a therapeutic benefit when used in combination therapy for a disease, where each of the selected amounts of the compound of Formulae I, II, III, IV, V, VI, VII, or X and the additional antiviral agent, respectively, provides no therapeutic benefit when used in monotherapy for the disease. As used herein, a "synergistically effective amount" of a compound of Formulae I, II, III, IV, V, VI, VII, or X and an additional antiviral agent, and its grammatical equivalents, shall be understood to include any regimen encompassed by any of (1)-(3) above.

Fibrosis

The embodiments provides methods for treating liver fibrosis (including forms of liver fibrosis resulting from, or associated with, HCV infection), generally involving administering a therapeutic amount of a compound of Formulae I, II, III, IV, V, VI, VII, or X, and optionally one or more additional antiviral agents. Effective amounts of compounds of Formulae I, II, III, IV, V, VI, VII, or X, with and without one or more additional antiviral agents, as well as dosing regimens, are as discussed below.

Whether treatment with a compound of Formulae I, II, III, IV, V, VI, VII, or X, and optionally one or more additional antiviral agents, is effective in reducing liver fibrosis is determined by any of a number of well-established techniques for measuring liver fibrosis and liver function. Liver fibrosis reduction is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score:

2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of anti-fibrotic therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

In some embodiments, a therapeutically effective amount of a compound of Formulae I, II, III, IV, V, VI, VII, or X, and optionally one or more additional antiviral agents, is an amount that effects a change of one unit or more in the fibrosis stage based on pre- and post-therapy liver biopsies. In particular embodiments, a therapeutically effective amount of a compound of Formulae I, II, III, IV, V, VI, VII, or X, and optionally one or more additional antiviral agents, reduces liver fibrosis by at least one unit in the METAVIR, the Knodell, the Scheuer, the Ludwig, or the Ishak scoring system.

Secondary, or indirect, indices of liver function can also be used to evaluate the efficacy of treatment with a compound of Formulae I, II, III, IV, V, VI, VII, or X. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score.

An effective amount of a compound of Formulae I, II, III, IV, V, VI, VII, or X, and optionally one or more additional antiviral agents, is an amount that is effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

A therapeutically effective amount of a compound of Formulae I, II, III, IV, V, VI, VII, or X, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Quantitative tests of functional liver reserve can also be used to assess the efficacy of treatment with an interferon receptor agonist and pirfenidone (or a pirfenidone analog). These include: indocyanine green clearance (ICG), galactose elimination capacity (GEC), aminopyrine breath test (ABT), antipyrine clearance, monoethylglycine-xylidide (MEG-X) clearance, and caffeine clearance.

As used herein, a "complication associated with cirrhosis of the liver" refers to a disorder that is a sequellae of decompensated liver disease, i.e., or occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

A therapeutically effective amount of a compound of Formulae I, II, III, IV, V, VI, VII, or X, and optionally one or more additional antiviral agents, is an amount that is effective in reducing the incidence (e.g., the likelihood that an individual will develop) of a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with a compound of Formulae I, II, III, IV, V, VI, VII, or X, and optionally one or more additional antiviral agents, is effective in reducing the incidence of a disorder associated with cirrhosis of the liver can readily be determined by those skilled in the art.

Reduction in liver fibrosis increases liver function. Thus, the embodiments provide methods for increasing liver function, generally involving administering a therapeutically effective amount of a compound of Formulae I, II, III, IV, V, VI, VII, or X, and optionally one or more additional antiviral agents. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splanchnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Those skilled in the art know the normal ranges for such serum proteins. The following are non-limiting examples. The normal level of alanine transaminase is about 45 IU per milliliter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

A therapeutically effective amount of a compound of Formulae I, II, III, IV, V, VI, VII, or X, and optionally one or more additional antiviral agents, is one that is effective to increase liver function by at least about 10%, at least about 20%, at least about 30%, at least about 40%, at least about 50%, at least about 60%, at least about 70%, at least about 80%, or more. For example, a therapeutically effective amount of a compound of Formulae I, II, III, IV, V, VI, VII, or X, and optionally one or more additional antiviral agents, is an amount effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. A therapeutically effective amount of a compound of Formulae I, II, III, IV, V, VI, VII, or X, and optionally one or more additional antiviral agents, is also an amount effective to increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

Dosages, Formulations, and Routes of Administration

In the subject methods, the active agent(s) (e.g., compound of Formulae I, II, III, IV, V, VI, VII, or X, and optionally one or more additional antiviral agents) may be administered to the host using any convenient means capable of resulting in the desired therapeutic effect. Thus, the agent can be incorporated into a variety of formulations for therapeutic administration. More particularly, the agents of the embodiments can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations

The above-discussed active agent(s) can be formulated using well-known reagents and methods. Compositions are provided in formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," $20^{th}$ edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., 3 ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, an agent is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

As such, administration of the agents can be achieved in various ways, including oral, buccal, rectal, parenteral, intraperitoneal, intradermal, subcutaneous, intramuscular, transdermal, intratracheal, etc., administration. In many embodiments, administration is by bolus injection, e.g., subcutaneous bolus injection, intramuscular bolus injection, and the like.

The pharmaceutical compositions of the embodiments can be administered orally, parenterally or via an implanted reservoir. Oral administration or administration by injection is preferred.

Subcutaneous administration of a pharmaceutical composition of the embodiments is accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a pharmaceutical composition of the embodiments to a patient through the port is referred to herein as "a subcutaneous injection port delivery system." In many embodiments, subcutaneous administration is achieved by bolus delivery by needle and syringe.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents can be made into suppositories by mixing with a variety of bases such as emulsifying bases or water-soluble bases. The compounds of the embodiments can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the embodiments calculated in an amount sufficient to produce the desired effect in association with a pharmaceutically acceptable diluent, carrier or vehicle. The specifications for the novel unit dosage forms of the embodiments depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Other Antiviral or Antifibrotic Agents

As discussed above, a subject method will in some embodiments be carried out by administering an NS3 inhibitor that is a compound of Formulae I, II, III, IV, V, VI, VII, or X, and optionally one or more additional antiviral agent(s).

In some embodiments, the method further includes administration of one or more interferon receptor agonist(s). Interferon receptor agonists are described herein.

In other embodiments, the method further includes administration of pirfenidone or a pirfenidone analog. Pirfenidone and pirfenidone analogs are described herein.

Additional antiviral agents that are suitable for use in combination therapy include, but are not limited to, nucleotide and nucleoside analogs. Non-limiting examples include azidothymidine (AZT) (zidovudine), and analogs and derivatives thereof; 2',3'-dideoxyinosine (DDI) (didanosine), and analogs and derivatives thereof; 2',3'-dideoxycytidine (DDC) (dideoxycytidine), and analogs and derivatives thereof; 2',3'-didehydro-2',3'-dideoxythymidine (D4T) (stavudine), and analogs and derivatives thereof; combivir; abacavir; adefovir dipoxil; cidofovir; ribavirin; ribavirin analogs; and the like.

In some embodiments, the method further includes administration of ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. Some embodiments also involve use of derivatives of ribavirin (see, e.g., U.S. Pat. No. 6,277,830). The ribavirin may be administered orally in capsule or tablet form, or in the same or different administration form and in the same or different route as the NS-3 inhibitor compound. Of course, other types of administration of both medicaments, as they become available are contemplated, such as by nasal spray, transdermally, intravenously, by suppository, by sustained release dosage form, etc. Any form of administration will work so long as the proper dosages are delivered without destroying the active ingredient.

In some embodiments, the method further includes administration of ritonavir. Ritonavir, 10-hydroxy-2-methyl-5-(1-methylethyl)-1-[2-(1-methylethyl)-4-thiazolyl]-3,6-dioxo-8,11-bis(phenylmethyl)-2,4,7,12-tetraazamidecan-13-oic acid, 5-thiazolylmethyl ester[5S-(5R*,8R*,10R*,11R*)], available from Abbott Laboratories, is an inhibitor of the protease of the human immunodeficiency virus and also of the cytochrome P450 3A and P450 2D6 liver enzymes frequently involved in hepatic metabolism of therapeutic molecules in man. Because of its strong inhibitory effect on cytochrome P450 3A and the inhibitory effect on cytochrome P450 2D6, ritonavir at doses below the normal therapeutic dosage may be combined with other protease inhibitors to achieve therapeutic levels of the second protease inhibitor while reducing the number of dosage units required, the dosing frequency, or both.

Coadministration of low-dose ritonavir may also be used to compensate for drug interactions that tend to decrease levels of a protease inhibitor metabolized by CYP3A. Its structure, synthesis, manufacture and formulation are described in U.S. Pat. Nos. 5,541,206 5,635,523 5,648,497 5,846,987 and 6,232,333. The ritonavir may be administered orally in capsule or tablet or oral solution form, or in the same or different administration form and in the same or different route as the NS-3 inhibitor compound. Of course, other types of administration of both medicaments, as they become available are contemplated, such as by nasal spray, transdermally, intravenously, by suppository, by sustained release dosage form, etc. Any form of administration will work so long as the proper dosages are delivered without destroying the active ingredient.

In some embodiments, an additional antiviral agent is administered during the entire course of NS3 inhibitor compound treatment. In other embodiments, an additional antiviral agent is administered for a period of time that is overlapping with that of the NS3 inhibitor compound treatment, e.g., the additional antiviral agent treatment can begin before the NS3 inhibitor compound treatment begins and end before the NS3 inhibitor compound treatment ends; the additional antiviral agent treatment can begin after the NS3 inhibitor compound treatment begins and end after the NS3 inhibitor compound treatment ends; the additional antiviral agent treatment can begin after the NS3 inhibitor compound treatment begins and end before the NS3 inhibitor compound treatment ends; or the additional antiviral agent treatment can begin before the NS3 inhibitor compound treatment begins and end after the NS3 inhibitor compound treatment ends.

Methods of Treatment

Monotherapies

The NS3 inhibitor compounds described herein may be used in acute or chronic therapy for HCV disease. In many embodiments, the NS3 inhibitor compound is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The NS3 inhibitor compound can be administered 5 times per day, 4 times per day, tid, bid, qd, qod, biw, tiw, qw, qow, three times per month, or once monthly. In other embodiments, the NS3 inhibitor compound is administered as a continuous infusion.

In many embodiments, an NS3 inhibitor compound of the embodiments is administered orally.

In connection with the above-described methods for the treatment of HCV disease in a patient, an NS3 inhibitor compound as described herein may be administered to the patient at a dosage from about 0.01 mg to about 100 mg/kg patient bodyweight per day, in 1 to 5 divided doses per day. In some embodiments, the NS3 inhibitor compound is administered at a dosage of about 0.5 mg to about 75 mg/kg patient bodyweight per day, in 1 to 5 divided doses per day.

The amount of active ingredient that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific NS3 inhibitor compound, the severity of the symptoms and the susceptibility of the subject to side effects. Preferred dosages for a given NS3 inhibitor compound are readily determinable by those of skill in the art by a variety of means. A preferred means is to measure the physiological potency of a given interferon receptor agonist.

In many embodiments, multiple doses of NS3 inhibitor compound are administered. For example, an NS3 inhibitor compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapies with Ribavirin

In some embodiments, the methods provide for combination therapy comprising administering an NS3 inhibitor compound as described above, and an effective amount of ribavirin. Ribavirin can be administered in dosages of about 400 mg, about 800 mg, about 1000 mg, or about 1200 mg per day.

One embodiment provides any of the above-described methods modified to include co-administering to the patient a therapeutically effective amount of ribavirin for the duration of the desired course of NS3 inhibitor compound treatment.

Another embodiment provides any of the above-described methods modified to include co-administering to the patient about 800 mg to about 1200 mg ribavirin orally per day for the duration of the desired course of NS3 inhibitor compound treatment. In another embodiment, any of the above-described methods may be modified to include co-administering to the patient (a) 1000 mg ribavirin orally per day if the patient has a body weight less than 75 kg or (b) 1200 mg ribavirin orally per day if the patient has a body weight greater than or equal to 75 kg, where the daily dosage of ribavirin is optionally divided into to 2 doses for the duration of the desired course of NS3 inhibitor compound treatment.

Combination Therapies with Levovirin

In some embodiments, the methods provide for combination therapy comprising administering an NS3 inhibitor compound as described above, and an effective amount of levovirin. Levovirin is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, levovirin is administered orally in dosages of about 400, about 800, about 1000, or about 1200 mg per day for the desired course of NS3 inhibitor compound treatment.

Combination Therapies with Viramidine

In some embodiments, the methods provide for combination therapy comprising administering an NS3 inhibitor compound as described above, and an effective amount of viramidine. Viramidine is generally administered in an amount ranging from about 30 mg to about 60 mg, from about 60 mg to about 125 mg, from about 125 mg to about 200 mg, from about 200 mg to about 300 mg, from about 300 mg to about 400 mg, from about 400 mg to about 1200 mg, from about 600 mg to about 1000 mg, or from about 700 to about 900 mg per day, or about 10 mg/kg body weight per day. In some embodiments, viramidine is administered orally in dosages of about 800 mg, or about 1600 mg per day for the desired course of NS3 inhibitor compound treatment.

Combination Therapies with Ritonavir

In some embodiments, the methods provide for combination therapy comprising administering an NS3 inhibitor compound as described above, and an effective amount of ritonavir. Ritonavir is generally administered in an amount ranging from about 50 mg to about 100 mg, from about 100 mg to about 200 mg, from about 200 mg to about 300 mg, from about 300 mg to about 400 mg, from about 400 mg to about 500 mg, or from about 500 mg to about 600 mg, twice per day. In some embodiments, ritonavir is administered orally in dosages of about 300 mg, or about 400 mg, or about 600 mg twice per day for the desired course of NS3 inhibitor compound treatment.

Combination Therapies with Alpha-glucosidase Inhibitors

Suitable α-glucosidase inhibitors include any of the above-described imino-sugars, including long-alkyl chain derivatives of imino sugars as disclosed in U.S. Patent Publication No. 2004/0110795; inhibitors of endoplasmic reticulum-associated α-glucosidases; inhibitors of membrane bound α-glucosidase; miglitol (Glyset®), and active derivatives, and analogs thereof; and acarbose (Precose®), and active derivatives, and analogs thereof.

In many embodiments, the methods provide for combination therapy comprising administering an NS3 inhibitor compound as described above, and an effective amount of an α-glucosidase inhibitor administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

An α-glucosidase inhibitor can be administered 5 times per day, 4 times per day, tid (three times daily), bid, qd, qod, biw, tiw, qw, qow, three times per month, or once monthly. In other embodiments, an α-glucosidase inhibitor is administered as a continuous infusion.

In many embodiments, an α-glucosidase inhibitor is administered orally.

In connection with the above-described methods for the treatment of a flavivirus infection, treatment of HCV infection, and treatment of liver fibrosis that occurs as a result of an HCV infection, the methods provide for combination therapy comprising administering an NS3 inhibitor compound as described above, and an effective amount of α-glucosidase inhibitor administered to the patient at a dosage of from about 10 mg per day to about 600 mg per day in divided doses, e.g., from about 10 mg per day to about 30 mg per day, from about 30 mg per day to about 60 mg per day, from about 60 mg per day to about 75 mg per day, from about 75 mg per day to about 90 mg per day, from about 90 mg per day to about 120 mg per day, from about 120 mg per day to about 150 mg per day, from about 150 mg per day to about 180 mg per day, from about 180 mg per day to about 210 mg per day, from about 210 mg per day to about 240 mg per day, from about 240 mg per day to about 270 mg per day, from about 270 mg per day to about 300 mg per day, from about 300 mg per day to about 360 mg per day, from about 360 mg per day to about 420 mg per day, from about 420 mg per day to about 480 mg per day, or from about 480 mg to about 600 mg per day.

In some embodiments, the methods provide for combination therapy comprising administering an NS3 inhibitor compound as described above, and an effective amount of α-glucosidase inhibitor administered in a dosage of about 10 mg three times daily. In some embodiments, an α-glucosidase inhibitor is administered in a dosage of about 15 mg three times daily. In some embodiments, an α-glucosidase inhibitor is administered in a dosage of about 20 mg three times daily. In some embodiments, an α-glucosidase inhibitor is administered in a dosage of about 25 mg three times daily. In some embodiments, an α-glucosidase inhibitor is administered in a dosage of about 30 mg three times daily. In some embodiments, an α-glucosidase inhibitor is administered in a dosage of about 40 mg three times daily. In some embodiments, an α-glucosidase inhibitor is administered in a dosage of about 50 mg three times daily. In some embodiments, an α-glucosidase inhibitor is administered in a dosage of about 100 mg three times daily. In some embodiments, an α-glucosidase inhibitor is administered in a dosage of about 75 mg per day to about 150 mg per day in two or three divided doses, where the individual weighs 60 kg or less. In some embodiments, an α-glucosidase inhibitor is administered in a dosage of about 75 mg per day to about 300 mg per day in two or three divided doses, where the individual weighs 60 kg or more.

The amount of active ingredient (e.g., α-glucosidase inhibitor) that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific α-glucosidase inhibitor, the severity of the symptoms and the susceptibility of the subject to side effects. Preferred dosages for a given α-glucosidase inhibitor are readily determinable by those of skill in the art by a variety of means. A typical means is to measure the physiological potency of a given active agent.

In many embodiments, multiple doses of an α-glucosidase inhibitor are administered. For example, the methods provide for combination therapy comprising administering an NS3 inhibitor compound as described above, and an effective amount of α-glucosidase inhibitor administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapies with Thymosin-α

In some embodiments, the methods provide for combination therapy comprising administering an NS3 inhibitor compound as described above, and an effective amount of thymosin-α. Thymosin-α (Zadaxin™) is generally administered by subcutaneous injection. Thymosin-α can be administered tid, bid, qd, qod, biw, tiw, qw, qow, three times per month, once monthly, substantially continuously, or continuously for the desired course of NS3 inhibitor compound treatment. In many embodiments, thymosin-α is administered twice per week for the desired course of NS3 inhibitor compound treatment. Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

Thymosin-α can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In one embodiment, thymosin-α is administered for the desired course of NS3 inhibitor compound treatment.

Combination Therapies with Interferon(s)

In many embodiments, the methods provide for combination therapy comprising administering an NS3 inhibitor compound as described above, and an effective amount of an interferon receptor agonist. In some embodiments, a compound of Formulae I, II, III, IV, V, VI, VII, or X and a Type I or III interferon receptor agonist are co-administered in the treatment methods described herein. Type I interferon receptor agonists suitable for use herein include any interferon-α (IFN-α). In certain embodiments, the interferon-α is a PEGylated interferon-α. In certain other embodiments, the interferon-α is a consensus interferon, such as INFERGEN® interferon alfacon-1. In still other embodiments, the interferon-α is a monoPEG (30 kD, linear)-ylated consensus interferon.

Effective dosages of an IFN-α range from about 3 μg to about 27 μg, from about 3 MU to about 10 MU, from about 90 μg to about 180 μg, or from about 18 μg to about 90 μg. Effective dosages of Infergen® consensus IFN-α include about 3 μg, about 6 μg, about 9 μg, about 12 μg, about 15 μg, about 18 μg, about 21 μg, about 24 μg, about 27 μg, or about 30 μg, of drug per dose. Effective dosages of IFN-α2a and IFN-α2b range from 3 million Units (MU) to 10 MU per dose. Effective dosages of PEGASYS®PEGylated IFN-α2a contain an amount of about 90 μg to 270 μg, or about 180 μg, of drug per dose. Effective dosages of PEG-INTRON®PEGylated IFN-α2b contain an amount of about 0.5 μg to 3.0 μg of drug per kg of body weight per dose. Effective dosages of PEGylated consensus interferon (PEG-CIFN) contain an amount of about 18 μg to about 90 μg, or from about 27 μg to about 60 μg, or about 45 μg, of CIFN amino acid weight per dose of PEG-CIFN. Effective dosages of monoPEG (30 kD, linear)-ylated CIFN contain an amount of about 45 μg to about 270 μg, or about 60 μg to about 180 μg, or about 90 μg to about 120 μg, of drug per dose. IFN-α can be administered daily, every other day, once a week, three times a week, every other week, three times per month, once monthly, substantially continuously or continuously.

In many embodiments, the Type I or Type III interferon receptor agonist and/or the Type II interferon receptor agonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. Dosage regimens can include tid, bid, qd, qod, biw, tiw, qw, qow, three times per month, or monthly administrations. Some embodiments provide any of the above-described methods in which the desired dosage of IFN-α is administered subcutaneously to the patient by bolus delivery qd, qod, tiw, biw, qw, qow, three times per month, or monthly, or is administered subcutaneously to the patient per day by substantially continuous or continuous delivery, for the desired treatment duration. In other embodiments, any of the above-described methods may be practiced in which the desired dosage of PEGylated IFN-α (PEG-IFN-α) is administered subcutaneously to the patient by bolus delivery qw, qow, three times per month, or monthly for the desired treatment duration.

In other embodiments, an NS3 inhibitor compound and a Type II interferon receptor agonist are co-administered in the treatment methods of the embodiments. Type II interferon receptor agonists suitable for use herein include any interferon-γ (IFN-γ).

Effective dosages of IFN-γ can range from about 0.5 $\mu g/m^2$ to about 500 $\mu g/m^2$, usually from about 1.5 $\mu g/m^2$ to 200 $\mu g/m^2$, depending on the size of the patient. This activity is based on 106 international units (U) per 50 μg of protein. IFN-γ can be administered daily, every other day, three times a week, or substantially continuously or continuously.

In specific embodiments of interest, IFN-γ is administered to an individual in a unit dosage form of from about 25 μg to about 500 μg, from about 50 μg to about 400 μg, or from about 100 μg to about 300 μg. In particular embodiments of interest, the dose is about 200 μg IFN-γ. In many embodiments of interest, IFN-γ1b is administered.

Where the dosage is 200 μg IFN-γ per dose, the amount of IFN-γ per body weight (assuming a range of body weights of from about 45 kg to about 135 kg) is in the range of from about 4.4 μg IFN-γ per kg body weight to about 1.48 μg IFN-γ per kg body weight.

The body surface area of subject individuals generally ranges from about 1.33 $m^2$ to about 2.50 $m^2$. Thus, in many embodiments, an IFN-γ dosage ranges from about 150 $\mu g/m^2$ to about 20 $\mu g/m^2$. For example, an IFN-γ dosage ranges from about 20 $\mu g/m^2$ to about 30 $\mu g/m^2$, from about 30 $\mu g/m^2$ to about 40 $\mu g/m^2$, from about 40 $\mu g/m^2$ to about 50 $\mu g/m^2$, from about 50 $\mu g/m^2$ to about 60 $\mu g/m^2$, from about 60 $\mu g/m^2$ to about 70 $\mu g/m^2$, from about 70 $\mu g/m^2$ to about 80 $\mu g/m^2$, from about 80 $\mu g/m^2$ to about 90 $\mu g/m^2$, from about 90 $\mu g/m^2$ to about 100 $\mu g/m^2$, from about 100 $\mu g/m^2$ to about 110 $\mu g/m^2$, from about 110 $\mu g/m^2$ to about 120 $\mu g/m^2$, from about 120 $\mu g/m^2$ to about 130 $\mu g/m^2$, from about 130 $\mu g/m^2$ to about 140 $\mu g/m^2$, or from about 140 $\mu g/m^2$ to about 150 $\mu g/m^2$. In some embodiments, the dosage groups range from about 25 $\mu g/m^2$ to about 100 $\mu g/m^2$. In other embodiments, the dosage groups range from about 25 $\mu g/m^2$ to about 50 $\mu g/m^2$.

In some embodiments, a Type I or a Type III interferon receptor agonist is administered in a first dosing regimen, followed by a second dosing regimen. The first dosing regimen of Type I or a Type III interferon receptor agonist (also referred to as "the induction regimen") generally involves administration of a higher dosage of the Type I or Type III interferon receptor agonist. For example, in the case of Infergen® consensus IFN-α (CIFN), the first dosing regimen comprises administering CIFN at about 9 μg, about 15 μg, about 18 μg, or about 27 μg. The first dosing regimen can encompass a single dosing event, or at least two or more dosing events. The first dosing regimen of the Type I or Type III interferon receptor agonist can be administered daily, every other day, three times a week, every other week, three times per month, once monthly, substantially continuously or continuously.

The first dosing regimen of the Type I or Type III interferon receptor agonist is administered for a first period of time, which time period can be at least about 4 weeks, at least about 8 weeks, or at least about 12 weeks.

The second dosing regimen of the Type I or Type III interferon receptor agonist (also referred to as "the maintenance dose") generally involves administration of a lower amount of the Type I or Type III interferon receptor agonist. For example, in the case of CIFN, the second dosing regimen comprises administering CIFN at a dose of at least about 3 μg, at least about 9 μg, at least about 15 μg, or at least about 18 μg. The second dosing regimen can encompass a single dosing event, or at least two or more dosing events.

The second dosing regimen of the Type I or Type III interferon receptor agonist can be administered daily, every other day, three times a week, every other week, three times per month, once monthly, substantially continuously or continuously.

In some embodiments, where an "induction"/"maintenance" dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase.

In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, the Type II interferon receptor agonist treatment is discontinued once Type I or a Type III interferon receptor agonist treatment begins.

In other embodiments, the Type I or Type III interferon receptor agonist is administered in single dosing regimen. For example, in the case of CIFN, the dose of CIFN is generally in a range of from about 3 μg to about 15 μg, or from about 9 μg to about 15 μg. The dose of Type I or a Type III interferon receptor agonist is generally administered daily, every other day, three times a week, every other week, three times per month, once monthly, or substantially continuously. The dose of the Type I or Type III interferon receptor agonist is administered for a period of time, which period can be, for example, from at least about 24 weeks to at least about 48 weeks, or longer.

In some embodiments, where a single dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase. In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with the Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, Type II interferon receptor agonist treatment is discontinued once Type I or a Type III interferon receptor agonist treatment begins.

In additional embodiments, an NS3 inhibitor compound, a Type I or III interferon receptor agonist, and a Type II interferon receptor agonist are co-administered for the desired duration of treatment in the methods described herein. In some embodiments, an NS3 inhibitor compound, an interferon-α, and an interferon-γ are co-administered for the desired duration of treatment in the methods described herein.

In some embodiments, the invention provides methods using an amount of a Type I or Type III interferon receptor agonist, a Type II interferon receptor agonist, and an NS3 inhibitor compound, effective for the treatment of HCV infection in a patient. Some embodiments provide methods using an effective amount of an IFN-α, IFN-γ, and an NS3 inhibitor compound in the treatment of HCV infection in a patient. One embodiment provides a method using an effective amount of a consensus IFN-α, IFN-γ and an NS3 inhibitor compound in the treatment of HCV infection in a patient.

In general, an effective amount of a consensus interferon (CIFN) and IFN-γ suitable for use in the methods of the embodiments is provided by a dosage ratio of 1 μg CIFN: 10 μg IFN-γ, where both CIFN and IFN-γ are unPEGylated and unglycosylated species.

In one embodiment, the invention provides any of the above-described methods modified to use an effective amount of INFERGEN® consensus IFN-α and IFN-γ in the treatment of HCV infection in a patient comprising administering to the patient a dosage of INFERGEN® containing an amount of about 1 μg to about 30 μg, of drug per dose of INFERGEN®, subcutaneously qd, qod, tiw, biw, qw, qow, three times per month, once monthly, or per day substantially continuously or continuously, in combination with a dosage of IFN-γ containing an amount of about 10 μg to about 300 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of virus infection in a patient comprising administering to the patient a dosage of INFERGEN® containing an amount of about 1 μg to about 9 μg, of drug per dose of INFERGEN®, subcutaneously qd, qod, tiw, biw, qw, qow, three times per month, once monthly, or per day substantially continuously or continuously, in combination with a dosage of IFN-γ containing an amount of about 10 μg to about 100 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of virus infection in a patient comprising administering to the patient a dosage of INFERGEN® containing an amount of about 1 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 10 μg to about 50 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of a virus infection in a patient comprising administering to the patient a dosage of INFERGEN® containing an amount of about 9 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 90 μg to about 100 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of a virus infection in a patient comprising administering to the patient a dosage of INFERGEN® containing an amount of about 30 μg of drug per dose of INFERGEN®, subcutaneously qd, qod, tiw, biw, qw, qow, three times per month, once monthly, or per day substantially continuously or continuously, in combination with a dosage of IFN-γ containing an amount of about 200 μg to about 300 μg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of PEGylated consensus IFN-α and IFN-γ in the treatment of a virus infection in a patient comprising administering to the patient a dosage of PEGylated consensus IFN-α (PEG-CIFN) containing an amount of about 4 μg to about 60 μg of CIFN amino acid weight per dose of PEG-CIFN, subcutaneously qw, qow, three times per month, or monthly, in combination with a total weekly dosage of IFN-γ containing an amount of about 30 μg to about 1,000 μg of drug per week in divided doses administered subcutaneously qd, qod, tiw, biw, or administered substantially continuously or continuously, for the desired duration of treatment with an NS3 inhibitor compound.

Another embodiment provides any of the above-described methods modified to use an effective amount of PEGylated consensus IFN-α and IFN-γ in the treatment of a virus infection in a patient comprising administering to the patient a dosage of PEGylated consensus IFN-α (PEG-CIFN) containing an amount of about 18 μg to about 24 μg of CIFN amino acid weight per dose of PEG-CIFN, subcutaneously qw, qow, three times per month, or monthly, in combination with a total weekly dosage of IFN-γ containing an amount of about 100 μg to about 300 μg of drug per week in divided doses administered subcutaneously qd, qod, tiw, biw, or substantially continuously or continuously, for the desired duration of treatment with an NS3 inhibitor compound.

In general, an effective amount of IFN-α2a or 2b or 2c and IFN-γ suitable for use in the methods of the embodiments is provided by a dosage ratio of 1 million Units (MU) IFN-α2a or 2b or 2c:30 μg IFN-γ, where both IFN-α2a or 2b or 2c and IFN-γ are unPEGylated and unglycosylated species.

Another embodiment provides any of the above-described methods modified to use an effective amount of IFN-α2a or 2b or 2c and IFN-γ in the treatment of a virus infection in a patient comprising administering to the patient a dosage of IFN-α2a, 2b or 2c containing an amount of about 1 MU to about 20 MU of drug per dose of IFN-α2a, 2b or 2c subcutaneously qd, qod, tiw, biw, or per day substantially continuously or continuously, in combination with a dosage of IFN-γ containing an amount of about 30 μg to about 600 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of IFN-α2a or 2b or 2c and IFN-γ in the treatment of a virus infection in a patient comprising administering to the patient a dosage of IFN-α2a, 2b or 2c containing an amount of about 3 MU of drug per dose of IFN-α2a, 2b or 2c subcutaneously qd, qod, tiw, biw, or per day substantially continuously or continuously, in combination with a dosage of IFN-γ containing an amount of about 100 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of IFN-α2a or 2b or 2c and IFN-γ in the treatment of a virus infection in a patient comprising administering to the patient a dosage of IFN-α2a, 2b or 2c containing an amount of about 10 MU of drug per dose of IFN-α2a, 2b or 2c subcutaneously qd, qod, tiw, biw, or per day substantially continuously or continuously, in combination with a dosage of IFN-γ containing an amount of about 300 μg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of PEGASYS®PEGylated IFN-α2a and IFN-γ in the treatment of a virus infection in a patient comprising administering to the patient a dosage of PEGASYS® containing an amount of about 90 μg to about 360 μg, of drug per dose of PEGASYS®, subcutaneously qw, qow, three times per month, or monthly, in combination with a total weekly dosage of IFN-γ containing an amount of about 30 μg to about 1,000 μg, of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEGASYS®PEGylated IFN-α2a and IFN-γ in the treatment of a virus infection in a patient comprising administering to the patient a dosage of PEGASYS® containing an amount of about 180 μg of drug per dose of PEGASYS®, subcutaneously qw, qow, three times per month, or monthly, in combination with a total weekly dosage of IFN-γ containing an amount of about 100 μg to about 300 μg, of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEG-INTRON®PEGylated IFN-α2b and IFN-γ in the treatment of a virus infection in a patient comprising administering to the patient a dosage of PEG-INTRON® containing an amount of about 0.75 μg to about 3.0 μg of drug per kilogram of body weight per dose of PEG-INTRON®, subcutaneously qw, qow, three times per month, or monthly, in combination with a total weekly dosage of IFN-γ containing an amount of about 30 μg to about 1,000 μg of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEG-INTRON®PEGylated IFN-α2b and IFN-γ in the treatment of a virus infection in a patient comprising administering to the patient a dosage of PEG-INTRON® containing an amount of about 1.5 μg of drug per kilogram of body weight per dose of PEG-INTRON®, subcutaneously qw, qow, three times per month, or monthly, in combination with a total weekly dosage of IFN-γ containing an amount of about 100 μg to about 300 μg of drug per week administered in divided doses subcutaneously qd, qod, tiw, or biw, or administered substantially continuously or continuously, for the desired duration of treatment with an NS3 inhibitor compound.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 100 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 25 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 200 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 25 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 200 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 100 μg monoPEG (30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 μg monoPEG (30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 μg monoPEG (30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 μg monoPEG (30 kD, linear)-ylated consensus IFN-α administered subcutaneously every 10 days or qw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 100 μg monoPEG (30 kD, linear)-ylated consensus IFN-α administered subcutaneously every 10 days or qw; and 100 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 150 μg monoPEG (30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 μg monoPEG (30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 μg monoPEG (30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 μg monoPEG (30 kD, linear)-ylated consensus IFN-α administered subcutaneously every 10 days or qw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 150 μg monoPEG (30 kD, linear)-ylated consensus IFN-α administered subcutaneously every 10 days or qw; and 100 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 200 μg monoPEG (30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 μg monoPEG (30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 μg monoPEG (30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 μg monoPEG (30 kD, linear)-ylated consensus IFN-α administered subcutaneously every 10 days or qw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 200 μg monoPEG (30 kD, linear)-ylated consensus IFN-α administered subcutaneously every 10 days or qw; and 100 μg Actimmune® human IFN-γ1b administered subcutaneously tiw, where the duration of therapy is 48 weeks.

Any of the above-described methods involving administering an NS3 inhibitor, a Type I interferon receptor agonist (e.g., an IFN-α), and a Type II interferon receptor agonist (e.g., an IFN-γ), can be augmented by administration of an effective amount of a TNF-α antagonist (e.g., a TNF-α antagonist other than pirfenidone or a pirfenidone analog). Exemplary, non-limiting TNF-α antagonists that are suitable for use in such combination therapies include ENBREL®, REMICADE®, and HUMIRA™.

One embodiment provides a method using an effective amount of ENBREL®; an effective amount of IFN-α; an effective amount of IFN-γ; and an effective amount of an NS3 inhibitor in the treatment of an HCV infection in a patient, comprising administering to the patient a dosage ENBREL® containing an amount of from about 0.1 μg to about 23 mg per dose, from about 0.1 μg to about 1 μg, from about 1 μg to about 10 μg, from about 10 μg to about 100 μg, from about 100 μg to about 1 mg, from about 1 mg to about 5 mg, from about 5 mg to about 10 mg, from about 10 mg to about 15 mg, from about 15 mg to about 20 mg, or from about 20 mg to about 23 mg of ENBREL®, subcutaneously qd, qod, tiw, biw, qw, qow, three times per month, once monthly, or once every other month, or per day substantially continuously or continuously, for the desired duration of treatment.

One embodiment provides a method using an effective amount of REMICADE®, an effective amount of IFN-αc; an effective amount of IFN-γ; and an effective amount of an NS3 inhibitor in the treatment of an HCV infection in a patient, comprising administering to the patient a dosage of REMICADE® containing an amount of from about 0.1 mg/kg to about 4.5 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, or from about 4.0 mg/kg to about 4.5 mg/kg per dose of REMICADE®, intravenously qd, qod, tiw, biw, qw, qow, three times per month, once monthly, or once every other month, or per day substantially continuously or continuously, for the desired duration of treatment.

One embodiment provides a method using an effective amount of HUMIRA™, an effective amount of IFN-α; an effective amount of IFN-γ; and an effective amount of an NS3 inhibitor in the treatment of an HCV infection in a patient, comprising administering to the patient a dosage of HUMIRA™ containing an amount of from about 0.1 μg to about 35 mg, from about 0.1 μg to about 1 μg, from about 1 μg to about 10 μg, from about 10 μg to about 100 μg, from about 100 μg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, or from about 30 mg to about 35 mg per dose of a HUMIRA™, subcutaneously qd, qod, tiw, biw, qw, qow, three times per month, once monthly, or once every other month, or per day substantially continuously or continuously, for the desired duration of treatment.

Combination Therapies with Pirfenidone

In many embodiments, the methods provide for combination therapy comprising administering an NS3 inhibitor compound as described above, and an effective amount of pirfenidone or a pirfenidone analog. In some embodiments, an NS3 inhibitor compound, one or more interferon receptor agonist(s), and pirfenidone or pirfenidone analog are co-administered in the treatment methods of the embodiments. In certain embodiments, an NS3 inhibitor compound, a Type I interferon receptor agonist, and pirfenidone (or a pirfenidone analog) are co-administered. In other embodiments, an NS3 inhibitor compound, a Type I interferon receptor agonist, a Type II interferon receptor agonist, and pirfenidone (or a pirfenidone analog) are co-administered. Type I interferon receptor agonists suitable for use herein include any IFN-α, such as interferon alfa-2a, interferon alfa-2b, interferon alfacon-1, and PEGylated IFN-αc's, such as peginterferon alfa-2a, peginterferon alfa-2b, and PEGylated consensus interferons, such as monoPEG (30 kD, linear)-ylated consensus interferon. Type II interferon receptor agonists suitable for use herein include any interferon-γ.

Pirfenidone or a pirfenidone analog can be administered once per month, twice per month, three times per month, once per week, twice per week, three times per week, four times per week, five times per week, six times per week, daily, or in divided daily doses ranging from once daily to 5 times daily over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Effective dosages of pirfenidone or a specific pirfenidone analog include a weight-based dosage in the range from about 5 mg/kg/day to about 125 mg/kg/day, or a fixed dosage of about 400 mg to about 3600 mg per day, or about 800 mg to about 2400 mg per day, or about 1000 mg to about 1800 mg per day, or about 1200 mg to about 1600 mg per day, administered orally in one to five divided doses per day. Other doses and formulations of pirfenidone and specific pirfenidone analogs suitable for use in the treatment of fibrotic diseases are described in U.S. Pat. Nos. 5,310,562; 5,518,729; 5,716,632; and 6,090,822.

One embodiment provides any of the above-described methods modified to include co-administering to the patient a therapeutically effective amount of pirfenidone or a pirfenidone analog for the duration of the desired course of NS3 inhibitor compound treatment.

Combination Therapies with TNF-α Antagonists

In many embodiments, the methods provide for combination therapy comprising administering an effective amount of an NS3 inhibitor compound as described above, and an effective amount of TNF-α antagonist, in combination therapy for treatment of an HCV infection.

Effective dosages of a TNF-α antagonist range from 0.1 μg to 40 mg per dose, e.g., from about 0.1 μg to about 0.5 μg per dose, from about 0.5 μg to about 1.0 μg per dose, from about 1.0 μg per dose to about 5.0 μg per dose, from about 5.0 μg to about 10 μg per dose, from about 10 μg to about 20 μg per dose, from about 20 μg per dose to about 30 μg per dose, from about 30 μg per dose to about 40 μg per dose, from about 40 μg per dose to about 50 μg per dose, from about 50 μg per dose to about 60 μg per dose, from about 60 μg per dose to about 70 μg per dose, from about 70 μg to about 80 μg per dose, from about 80 μg per dose to about 100 μg per dose, from about 100 μg to about 150 μg per dose, from about 150 μg to about 200 μg per dose, from about 200 μg per dose to about 250 μg per dose, from about 250 μg to about 300 μg per dose, from about 300 μg to about 400 μg per dose, from about 400 μg to about 500 μg per dose, from about 500 μg to about 600 μg per dose, from about 600 μg to about 700 μg per dose, from about 700 μg to about 800 μg per dose, from about 800 μg to about 900 μg per dose, from about 900 μg to about 1000 μg per dose, from about 1 mg to about 10 mg per dose, from about 10 mg to about 15 mg per dose, from about 15 mg to about 20 mg per dose, from about 20 mg to about 25 mg per dose, from about 25 mg to about 30 mg per dose, from about 30 mg to about 35 mg per dose, or from about 35 mg to about 40 mg per dose.

In some embodiments, effective dosages of a TNF-α antagonist are expressed as mg/kg body weight. In these embodiments, effective dosages of a TNF-α antagonist are from about 0.1 mg/kg body weight to about 10 mg/kg body weight, e.g., from about 0.1 mg/kg body weight to about 0.5 mg/kg body weight, from about 0.5 mg/kg body weight to about 1.0 mg/kg body weight, from about 1.0 mg/kg body weight to about 2.5 mg/kg body weight, from about 2.5 mg/kg body weight to about 5.0 mg/kg body weight, from about 5.0 mg/kg body weight to about 7.5 mg/kg body weight, or from about 7.5 mg/kg body weight to about 10 mg/kg body weight.

In many embodiments, a TNF-α antagonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The TNF-α antagonist can be administered tid, bid, qd, qod, biw, tiw, qw, qow, three times per month, once monthly, substantially continuously, or continuously.

In many embodiments, multiple doses of a TNF-α antagonist are administered. For example, a TNF-α antagonist is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A TNF-α antagonist and an NS3 inhibitor are generally administered in separate formulations. A TNF-α antagonist and an NS3 inhibitor may be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

One embodiment provides a method using an effective amount of a TNF-α antagonist and an effective amount of an NS3 inhibitor in the treatment of an HCV infection in a patient, comprising administering to the patient a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

One embodiment provides a method using an effective amount of ENBREL® and an effective amount of an NS3 inhibitor in the treatment of an HCV infection in a patient, comprising administering to the patient a dosage ENBREL® containing an amount of from about 0.1 μg to about 23 mg per dose, from about 0.1 μg to about 1 μg, from about 1 μg to about 10 μg, from about 10 μg to about 100 μg, from about 100 μg to about 1 mg, from about 1 mg to about 5 mg, from about 5 mg to about 10 mg, from about 10 mg to about 15 mg, from about 15 mg to about 20 mg, or from about 20 mg to about 23 mg of ENBREL®, subcutaneously qd, qod, tiw, biw, qw, qow, three times per month, once monthly, or once every other month, or per day substantially continuously or continuously, for the desired duration of treatment with an NS3 inhibitor compound.

One embodiment provides a method using an effective amount of REMICADE® and an effective amount of an NS3 inhibitor in the treatment of an HCV infection in a patient, comprising administering to the patient a dosage of REMICADE® containing an amount of from about 0.1 mg/kg to about 4.5 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, or from about 4.0 mg/kg to about 4.5 mg/kg per dose of REMICADE®, intravenously qd, qod, tiw, biw, qw, qow, three times per month, once monthly, or once every other month, or per day substantially continuously or continuously, for the desired duration of treatment with an NS3 inhibitor compound.

One embodiment provides a method using an effective amount of HUMIRA™ and an effective amount of an NS3 inhibitor in the treatment of an HCV infection in a patient, comprising administering to the patient a dosage of HUMIRA™ containing an amount of from about 0.1 μg to about 35 mg, from about 0.1 μg to about 1 μg, from about 1 μg to about 10 μg, from about 10 μg to about 100 μg, from about 100 μg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, or from about 30 mg to about 35 mg per dose of a HUMIRA™, subcutaneously qd, qod, tiw, biw, qw, qow, three times per month, once monthly, or once every other month, or per day substantially continuously or continuously, for the desired duration of treatment with an NS3 inhibitor compound.

Combination Therapies with Thymosin-α

In many embodiments, the methods provide for combination therapy comprising administering an effective amount of an NS3 inhibitor compound as described above, and an effective amount of thymosin-α, in combination therapy for treatment of an HCV infection.

Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

One embodiment provides a method using an effective amount of ZADAXIN™ thymosin-α and an effective amount of an NS3 inhibitor in the treatment of an HCV infection in a patient, comprising administering to the patient a dosage of ZADAXIN™ containing an amount of from about 1.0 mg to about 1.6 mg per dose, subcutaneously twice per week for the desired duration of treatment with the NS3 inhibitor compound.

Combination Therapies with a TNF-α Antagonist and an Interferon

Some embodiments provide a method of treating an HCV infection in an individual having an HCV infection, the method comprising administering an effective amount of an NS3 inhibitor, and effective amount of a TNF-α antagonist, and an effective amount of one or more interferons.

One embodiment provides any of the above-described methods modified to use an effective amount of IFN-γ and an effective amount of a TNF-α antagonist in the treatment of HCV infection in a patient comprising administering to the patient a dosage of IFN-γ containing an amount of about 10 μg to about 300 μg of drug per dose of IFN-γ, subcutaneously qd, qod, tiw, biw, qw, qow, three times per month, once monthly, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of IFN-γ and an effective amount of a TNF-α antagonist in the treatment of HCV infection in a patient comprising administering to the patient a dosage of IFN-γ containing an amount of about 10 μg to about 100 μg of drug per dose of IFN-γ, subcutaneously qd, qod, tiw, biw, qw, qow, three times per month, once monthly, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-γ and an effective amount of a TNF-α antagonist in the treatment of a virus infection in a patient comprising administering to the patient a total weekly dosage of IFN-γ containing an amount of about 30 μg to about 1,000 μg of drug per week in divided doses administered subcutaneously qd, qod, tiw, biw, or administered substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-γ and an effective amount of a TNF-α antagonist in the treatment of a virus infection in a patient comprising administering to the patient a total weekly dosage of IFN-γ containing an amount of about 100 μg to about 300 μg of drug per week in divided doses administered subcutaneously qd, qod, tiw, biw, or administered substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of INFERGEN® consensus IFN-α and a TNF-α antagonist in the treatment of HCV infection in a patient comprising administering to the patient a dosage of INFERGEN® containing an amount of about 1 μg to about 30 μg, of drug per dose of INFERGEN®, subcutaneously qd, qod, tiw, biw, qw, qow, three times per month, once monthly, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of INFERGEN® consensus IFN-α and a TNF-α antagonist in the treatment of HCV infection in a patient comprising administering to the patient a dosage of INFERGEN® containing an amount of about 1 μg to about 9 μg, of drug per dose of INFERGEN®, subcutaneously qd, qod, tiw, biw, qw, qow, three times per month, once monthly, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGylated consensus IFN-α and an effective amount of a TNF-α antagonist in the treatment of a virus infection in a patient comprising administering to the patient a dosage of PEGylated consensus IFN-α (PEG-CIFN) containing an amount of about 4 μg to about 60 μg of CIFN amino acid weight per dose of PEG-CIFN, subcutaneously qw, qow, three times per month, or monthly, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGylated consensus IFN-α and an effective amount of a TNF-α antagonist in the treatment of a virus infection in a patient comprising administering to the patient a dosage of PEGylated consensus IFN-α (PEG-CIFN) containing an amount of about 18 μg to about 24 μg of CIFN amino acid weight per dose of PEG-CIFN, subcutaneously qw, qow, three times per month, or monthly, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α2a or 2b or 2c and an effective amount of a TNF-α antagonist in the treatment of a virus infection in a patient comprising administering to the patient a dosage of IFN-α2a, 2b or 2c containing an amount of about 1 MU to about 20 MU of drug per dose of IFN-α2a, 2b or 2c subcutaneously qd, qod, tiw, biw, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α2a or 2b or 2c and an effective amount of a TNF-α antagonist in the treatment of a virus infection in a patient comprising administering to the patient a dosage of IFN-α2a, 2b or 2c containing an amount of about 3 MU of drug per dose of IFN-α2a, 2b or 2c subcutaneously qd, qod, tiw, biw, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α2a or 2b or 2c and an effective amount of a TNF-α antagonist in the treatment of a virus infection in a patient comprising administering to the patient a dosage of IFN-α2a, 2b or 2c containing an amount of about 10 MU of drug per dose of IFN-α2a, 2b or 2c subcutaneously qd, qod, tiw, biw, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGASYS®PEGylated IFN-α2a and an effective amount of a TNF-α antagonist in the treatment of a virus infection in a patient comprising administering to the patient a dosage of PEGASYS® containing an amount of about 90 μg to about 360 μg, of drug per dose of PEGASYS®, subcutaneously qw, qow, three times per month, or monthly, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGASYS®PEGylated IFN-α2a and an effective amount of a TNF-α antagonist in the treatment of a virus infection in a patient comprising administering to the patient a dosage of PEGASYS® containing an amount of about 180 μg, of drug per dose of PEGASYS®, subcutaneously qw, qow, three times per month, or monthly, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEG-INTRON®PEGylated IFN-α2b and an effective amount of a TNF-α antagonist in the treatment of a virus infection in a patient comprising administering to the patient a dosage of PEG-INTRON® containing an amount of about 0.75 μg to about 3.0 μg of drug per kilogram of body weight per dose of PEG-INTRON®, subcutaneously qw, qow, three times per month, or monthly, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEG-INTRON®PEGylated IFN-α2b and an effective amount of a TNF-α antagonist in the treatment of a virus infection in a patient comprising administering to the patient a dosage of PEG-INTRON® containing an amount of about 1.5 μg of drug per kilogram of body weight per dose of PEG-INTRON®, subcutaneously qw, qow, three times per month, or monthly, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Combination Therapies with Other Antiviral Agents

Other agents such as inhibitors of HCV NS3 helicase are also attractive drugs for combinational therapy, and are contemplated for use in combination therapies described herein. Ribozymes such as Heptazyme™ and phosphorothioate oligonucleotides which are complementary to HCV protein sequences and which inhibit the expression of viral core proteins are also suitable for use in combination therapies described herein.

In some embodiments, the additional antiviral agent(s) is administered during the entire course of treatment with the NS3 inhibitor compound described herein, and the beginning and end of the treatment periods coincide. In other embodiments, the additional antiviral agent(s) is administered for a period of time that is overlapping with that of the NS3 inhibitor compound treatment, e.g., treatment with the additional antiviral agent(s) begins before the NS3 inhibitor compound treatment begins and ends before the NS3 inhibitor compound treatment ends; treatment with the additional antiviral agent(s) begins after the NS3 inhibitor compound treatment begins and ends after the NS3 inhibitor compound treatment ends; treatment with the additional antiviral agent(s) begins after the NS3 inhibitor compound treatment begins and ends before the NS3 inhibitor compound treatment ends; or treatment with the additional antiviral agent(s) begins before the NS3 inhibitor compound treatment begins and ends after the NS3 inhibitor compound treatment ends.

The NS3 inhibitor compound can be administered together with (i.e., simultaneously in separate formulations; simultaneously in the same formulation; administered in separate formulations and within about 48 hours, within about 36 hours, within about 24 hours, within about 16 hours, within about 12 hours, within about 8 hours, within about 4 hours, within about 2 hours, within about 1 hour, within about 30 minutes, or within about 15 minutes or less) one or more additional antiviral agents.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 100 μg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 150 μg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 200 μg of drug per dose, subcutaneously once weekly, once every 8 days, or once every 10 days for the desired treatment duration with an NS3 inhibitor compound.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 9 μg of drug per dose, subcutaneously once daily or three times per week for the desired treatment duration with an NS3 inhibitor compound.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 15 μg of drug per dose, subcutaneously once daily or three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 25 μg of drug per dose, subcutaneously three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 50 μg of drug per dose, subcutaneously three times per week for the desired treatment duration with an NS3 inhibitor compound.

As non-limiting examples, any of the above-described methods featuring an IFN-γ regimen can be modified to replace the subject IFN-γ regimen with a regimen of IFN-γ comprising administering a dosage of IFN-γ containing an amount of 100 μg of drug per dose, subcutaneously three times per week for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b)

administering a dosage of IFN-γ containing an amount of 50 μg of drug per dose, subcutaneously three times per week; for the desired treatment duration with an NS3 inhibitor compound.

As non-limiting examples, any of the above-described methods featuring a TNF antagonist regimen can be modified to replace the subject TNF antagonist regimen with a TNF antagonist regimen comprising administering a dosage of a TNF antagonist selected from the group of: (a) etanercept in an amount of 25 mg of drug per dose subcutaneously twice per week, (b) infliximab in an amount of 3 mg of drug per kilogram of body weight per dose intravenously at weeks 0, 2 and 6, and every 8 weeks thereafter, or (c) adalimumab in an amount of 40 mg of drug per dose subcutaneously once weekly or once every 2 weeks; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously once daily; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously three times per week; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen can be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 μg of drug per dose, subcutaneously once daily; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of INFERGEN® interferon alfacon-1 containing an amount of 9 μg of drug per dose, subcutaneously once daily or three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen can be modified to replace the subject IFN-α and TNF antagonist combination regimen with an IFN-α and TNF antagonist combination regimen comprising: (a) administering a dosage of INFERGEN® interferon alfacon-1 containing an amount of 15 μg of drug per dose, subcutaneously once daily or three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 25 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 50 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen can be modified to replace the subject IFN-γ and TNF antagonist combination regimen with an IFN-γ and TNF antagonist combination regimen comprising: (a) administering a dosage of IFN-γ containing an amount of 100 μg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods that includes a regimen of monoPEG (30 kD, linear)-ylated consensus IFN-α can be modified to replace the regimen of monoPEG (30 kD, linear)-ylated consensus IFN-α with a regimen of peginterferon alfa-2a comprising administering a dosage of peginterferon alfa-2a containing an amount of 180 μg of drug per dose, subcutaneously once weekly for the desired treatment duration with an NS3 inhibitor compound.

As non-limiting examples, any of the above-described methods that includes a regimen of monoPEG (30 kD, linear)-ylated consensus IFN-α can be modified to replace the regimen of monoPEG (30 kD, linear)-ylated consensus IFN-α with a regimen of peginterferon alfa-2b comprising administering a dosage of peginterferon alfa-2b containing an amount of 1.0 μg to 1.5 μg of drug per kilogram of body weight per dose, subcutaneously once or twice weekly for the desired treatment duration with an NS3 inhibitor compound.

As non-limiting examples, any of the above-described methods can be modified to include administering a dosage of ribavirin containing an amount of 400 mg, 800 mg, 1000 mg or 1200 mg of drug orally per day, optionally in two or more divided doses per day, for the desired treatment duration with an NS3 inhibitor compound.

As non-limiting examples, any of the above-described methods can be modified to include administering a dosage of ribavirin containing (i) an amount of 1000 mg of drug orally per day for patients having a body weight of less than 75 kg or (ii) an amount of 1200 mg of drug orally per day for patients having a body weight of greater than or equal to 75 kg, optionally in two or more divided doses per day, for the desired treatment duration with an NS3 inhibitor compound.

As non-limiting examples, any of the above-described methods can be modified to replace the subject NS3 inhibitor regimen with an NS3 inhibitor regimen comprising administering a dosage of 0.01 mg to 0.1 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 0.1 mg to 1 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 1 mg to 10 mg of drug per kilogram of body weight orally daily, optionally in two or more divided doses per day, for the desired treatment duration with the NS3 inhibitor compound.

As non-limiting examples, any of the above-described methods can be modified to replace the subject NS3 inhibitor regimen with an NS3 inhibitor regimen comprising administering a dosage of 10 mg to 100 mg of drug per kilogram of body weight orally daily, optionally in two or more divided doses per day, for the desired treatment duration with the NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 0.01 mg to 0.1 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 0.1 mg to 1 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 1 mg to 10 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen can be modified to replace the subject NS5B inhibitor regimen with an NS5B inhibitor regimen comprising administering a dosage of 10 mg to 100 mg of drug per kilogram of body weight orally daily, optionally in two or more divided doses per day, for the desired treatment duration with an NS3 inhibitor compound.

The present embodiments provide for a method of treating a hepatitis C virus infection comprising administering to a human dosages of peginterferon alfa-2a and ribavirin under a standard of care protocol (SOC) in combination with ITMN-191 or a pharmaceutically acceptable salt thereof. The chemical structure of ITMN-191 is shown below. In some embodiments, the peginterferon alfa-2a and ribavirin in combination with ITMN-191 or a pharmaceutically acceptable salt thereof are administered in combination and provide HCV RNA levels below about 43 IU/mL, below about 25 IU/mL, or below about 9.3 IU/mL after 14 days of treatment. In some embodiments, the dosage of peginterferon alfa-2a can be about 180 μg of peginterferon alfa-2a per dose, administered subcutaneously once weekly for the desired treatment duration. In some embodiments, the dosage of peginterferon alfa-2a can be an amount in the range of about 1.0 μg to about 1.5 μg of drug per kilogram of body weight per dose, subcutaneously once or twice weekly for the desired treatment duration with the ITMN-191 and the ribavarin. In some embodiments, the dosage of ribavirin can be about 400 mg, about 800 mg, about 1000 mg or about 1200 mg of drug orally per day, optionally in two or more divided doses per day, for the desired treatment duration with the peginterferon alfa-2a and ITMN-191. In some embodiments, the dosage of ribavirin can be an amount of about 1000 mg of drug orally per day for patients having a body weight of less than 75 kg or an amount of about 1200 mg of drug orally per day for patients having a body weight of greater than or equal to 75 kg, optionally in two or more divided doses per day, for the desired treatment duration with the peginterferon alfa-2a and ITMN-191.

In some embodiments, the amounts of peginterferon alfa-2a and ribavirin administered in the SOC protocol can be lowered due to combination with ITMN-191. For example, the amounts of peginterferon alfa-2a and ribavirin can be reduced below the SOC by about 10% to about 75% during the combination treatment.

Patient Identification

In certain embodiments, the specific regimen of drug therapy used in treatment of the HCV patient is selected according to certain disease parameters exhibited by the patient, such as the initial viral load, genotype of the HCV infection in the patient, liver histology and/or stage of liver fibrosis in the patient.

Thus, some embodiments provide any of the above-described methods for the treatment of HCV infection in which the subject method is modified to treat a treatment failure patient for a duration of 48 weeks.

Other embodiments provide any of the above-described methods for HCV in which the subject method is modified to treat a non-responder patient, where the patient receives a 48 week course of therapy.

Other embodiments provide any of the above-described methods for the treatment of HCV infection in which the subject method is modified to treat a relapser patient, where the patient receives a 48 week course of therapy.

Other embodiments provide any of the above-described methods for the treatment of HCV infection in which the subject method is modified to treat a naïve patient infected with HCV genotype 1, where the patient receives a 48 week course of therapy.

Other embodiments provide any of the above-described methods for the treatment of HCV infection in which the subject method is modified to treat a naïve patient infected with HCV genotype 4, where the patient receives a 48 week course of therapy.

Other embodiments provide any of the above-described methods for the treatment of HCV infection in which the subject method is modified to treat a naïve patient infected with HCV genotype 1, where the patient has a high viral load (HVL), where "HVL" refers to an HCV viral load of greater than $2\times10^6$ HCV genome copies per mL serum, and where the patient receives a 48 week course of therapy.

One embodiment provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per mL of patient serum and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per mL of patient serum and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per mL of patient serum and no or early stage liver fibrosis as measured by a Knodell score of 0, 1, or 2 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per mL of patient serum and no or early stage liver fibrosis as measured by a Knodell score of 0, 1, or 2 and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per mL of patient serum and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per mL of patient serum and then (2) administering to the patient the drug therapy of the subject method for a time period of about 20 weeks to about 24 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per mL of patient serum and then (2) administering to the patient the drug therapy of the subject method for a time period of about 24 weeks to about 48 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 24 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of at least about 24 weeks.

Another embodiment provides any of the above-described methods for the treatment of an HCV infection, where the subject method is modified to include the steps of (1) identifying a patient having an HCV genotype 1 or 4 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of about 20 weeks to about 50 weeks.

Another embodiment provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of at least about 24 weeks and up to about 48 weeks.

Subjects Suitable for Treatment

Any of the above treatment regimens can be administered to individuals who have been diagnosed with an HCV infection. Any of the above treatment regimens can be administered to individuals who have failed previous treatment for HCV infection ("treatment failure patients," including non-responders and relapsers).

Individuals who have been clinically diagnosed as infected with HCV are of particular interest in many embodiments. Individuals who are infected with HCV are identified as having HCV RNA in their blood, and/or having anti-HCV antibody in their serum. Such individuals include anti-HCV ELISA-positive individuals, and individuals with a positive recombinant immunoblot assay (RIBA). Such individuals may also, but need not, have elevated serum ALT levels.

Individuals who are clinically diagnosed as infected with HCV include naïve individuals (e.g., individuals not previously treated for HCV, particularly those who have not previously received IFN-α-based and/or ribavirin-based therapy) and individuals who have failed prior treatment for HCV ("treatment failure" patients). Treatment failure patients include non-responders (i.e., individuals in whom the HCV titer was not significantly or sufficiently reduced by a previous treatment for HCV, e.g., a previous IFN-α monotherapy, a previous IFN-α and ribavirin combination therapy, or a previous pegylated IFN-α and ribavirin combination therapy); and relapsers (i.e., individuals who were previously treated for HCV, e.g., who received a previous IFN-α monotherapy, a previous IFN-α and ribavirin combination therapy, or a previous pegylated IFN-α and ribavirin combination therapy, whose HCV titer decreased, and subsequently increased).

In particular embodiments of interest, individuals have an HCV titer of at least about $10^5$, at least about $5\times10^5$, or at least about $10^6$, or at least about $2\times10^6$, genome copies of HCV per milliliter of serum. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

Also of interest are HCV-positive individuals (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment with IFN-α-based therapies or who cannot tolerate IFN-α-based therapies, or who have a contraindication to such therapies. In particular embodiments of interest, HCV-positive individuals with stage 3 or 4 liver fibrosis according to the METAVIR scoring system are suitable for treatment with the methods described herein. In other embodiments, individuals suitable for treatment with the methods of the embodiments are patients with decompensated cirrhosis with clinical manifestations, including patients with far-advanced liver cirrhosis, including those awaiting liver transplantation. In still other embodiments, individuals suitable for treatment with the methods described herein include patients with milder degrees of fibrosis including those with early fibrosis (stages 1 and 2 in the METAVIR, Ludwig, and Scheuer scoring systems; or stages 1, 2, or 3 in the Ishak scoring system).

Preparation of NS3 Inhibitors

Methodology

The HCV protease inhibitors in the following sections can be prepared according to the procedures and schemes shown in each section. The numberings in each of the following Preparation of NS3 Inhibitor sections including the General Method or General Procedure designations, are meant for that specific section only, and should not be construed or confused with the same numberings, if any, in other sections.

Preparation of NS3 Inhibitors: Section I

EXAMPLE 1

General Synthesis A

Scheme I

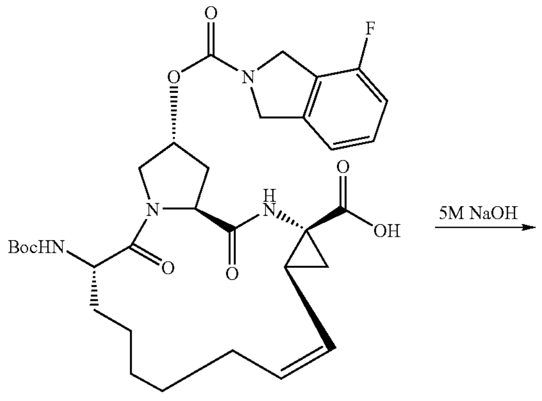

1

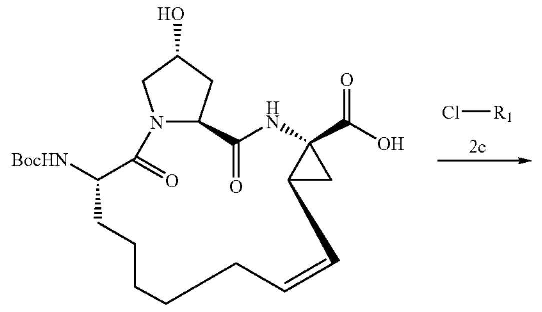

2

-continued

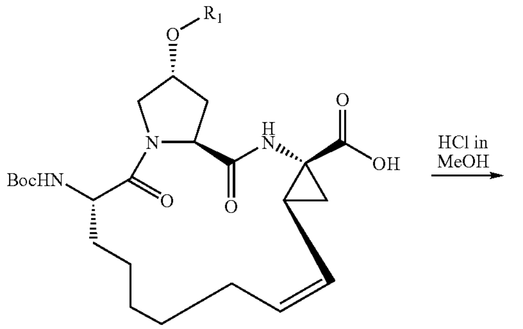

I-A

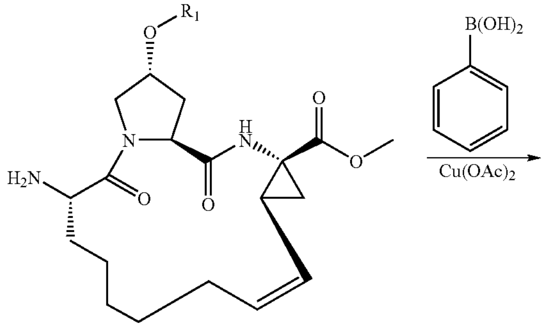

I-B

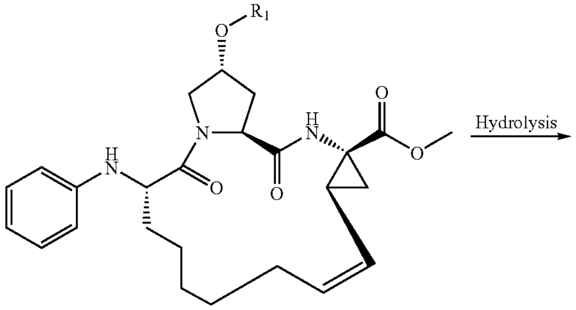

I-C

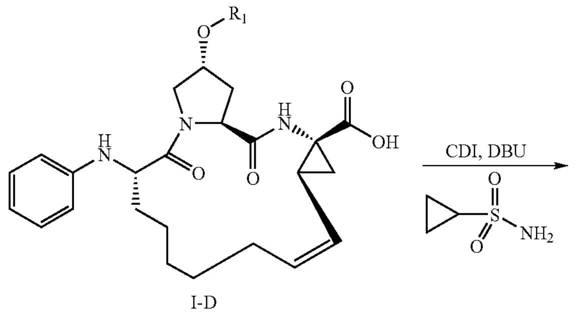

I-D

-continued

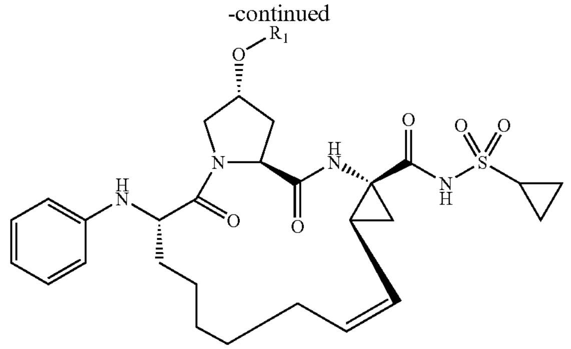

I-E

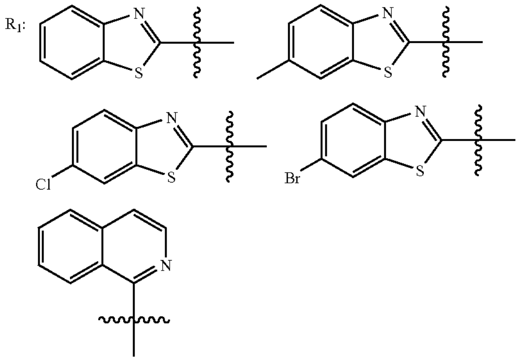

Macrocyclics of general structures I-D and I-E can be synthesized as shown in Scheme I. The isoindoline carbamate 1 can be treated under basic conditions to hydrolyse the isoindoline carbamate thereby providing alcohol 2. The alcohol 2 can be treated with a heteroaryl chloride, such as 2-chlorobenzothiazole, 2-chloro-6-methylbenzothiazole, 2,6-dichlorobenzothiazole, 6-bromo-2-chlorobenzothiazole, 1-chloroisoquinoline and the like, under basic conditions to afford a compound of general structure I-A. The compound of general structure I-A can be treated with acid in methanol to remove the Boc protecting group and form a methyl ester thereby providing a compound of general structure I-B. The compound of general structure I-B can be treated with optionally substituted aryl boronic acids under $Cu^{2+}$-catalyzed conditions thereby providing N-aryl compounds of general structure I-C. The compounds of general structure I-C can be treated under basic conditions to hydrolyse the methyl ester thereby providing carboxylic acids of general structure I-D. Finally, acids of general structure I-D can be coupled with sulfonamides (or sulfamides, not shown) thereby providing compounds of general structure I-E.

Example 1-1

General Procedure A

Compound 1 (10 g, 15.9 mmol.) was dissolved in methanol (100 mL), 5 M NaOH solution (95 mL) was added, the resulting mixture was heated to 50° C. and stirred overnight, after completion of the reaction. The mixture was cooled by ice water, 2 M HCl was added to acidify the mixture to pH=3-4, then the mixture was extracted by EtOAc, the organic layers were combined, washed by brine, dried, the solvent was removed under reduced pressure, the crude compound 2 (7.5 g) was used directly in the next step.

Example 1-2

General Procedure B

A solution of Compound 2 (5 g, 1 mL/100 mg) in DMF was added slowly to a mixture of NaH was dissolved in DMF (1.5 mL/100 mg NaH), cooled to 0-5° C. The mixture was stirred for 2 h at 0-5° C., then heteroaryl halide (2c) was added, the resulting mixture was warmed to room temperature and stirred for 12 h. The mixture was cooled to 0° C. (ice water bath), then 2 M HCl was carefully added to lower the pH (pH=3-4). The acidic mixture was extracted by EtOAc. The combined organic layers were washed by brine and dried. The solvent was removed under reduced pressure and the crude product was purified by column chromatography to afford general compound I-A (3.0 g, 60-70% yield).

Example 1-3

General Procedure C

General compound I-A (3.0 g) was dissolved in HCl in MeOH (25 mL/g, compound I-A), the resulting mixture was stirred at room temperature for 12 h. The solvent was removed then aqueous $NaHCO_3$ was added to neutralize any remaining acid. The basic mixture was extracted by EtOAc. The EtOAc layer was dried and then the solvent was removed to afford a crude residue. Crude general compound I-B (2.8 g) was used without further purification in the next step.

Example 1-4

General Procedure D

A mixture of general compound I-B (400 mg, 0.80 mmol.), phenylboronic acid (146.8 mg, 1.2 mmol.), $Cu(OAc)_2$ (188 mg, 1.0 mmol.), pyridine (316 mg, 4 mmol.), pyridine N-Oxide (76 mg, 0.8 mmol.) and molecular sieves 4 Å in dichloromethane (10 mL) was stirred for 12 h at room temperature in a vessel opened to the air. During this time period, the reaction was monitored by LC-MS. Subsequently, another 1.5 eq boronic acid was added with continued stirring. After completion of the reaction, the solvent was removed and the crude mixture was purified by prep-HPLC to give the pure general compound I-C (80 mg, isolated yield 15%). If excessive boronic acid was used, N,N diphenyl product was obtained.

Example 1-5

General Procedure E

General compound I-C was dissolved in methanol (10 mL/1 g compound I-C), 2 M aqueous NaOH (8 mL/1 g compound I-C) was added to the methanol solution and the resulting mixture was stirred at room temperature overnight. The mixture was cooled to 0° C. (ice water bath), then 2 M HCl was carefully added to lower the pH (pH=3-4). The acidic mixture was extracted by EtOAc. The combined organic layers were washed by brine and dried. The solvent was removed under reduced pressure and the crude product was purified by prep-TLC (EtOAc/methanol=10:1) to afford general compound I-D (yield, 90-100%).

Example 1-6

General Procedure F

General compound I-D (60 mg, 0.14 mmol. in 2 mL dichloromethane) was added to CDI (45.6 mg, 0.28 mmol.) dissolved in dichloromethane (1 mL) and then stirred 1 h. Subsequently, cyclopropyl sulfonamide (25.4 mg, 0.21 mmol.) and DBU (0.2 mL, 5.0 eq) were added, the resulting mixture was stirred at room temperature for another 12 h monitoring by LCMS. The solvent was then removed and the crude product was purified by prep-HPLC to give the pure general compound I-E as a white solid (~50% yield).

Example 1-7

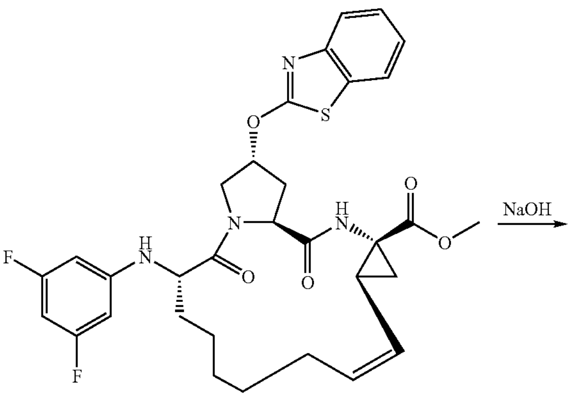

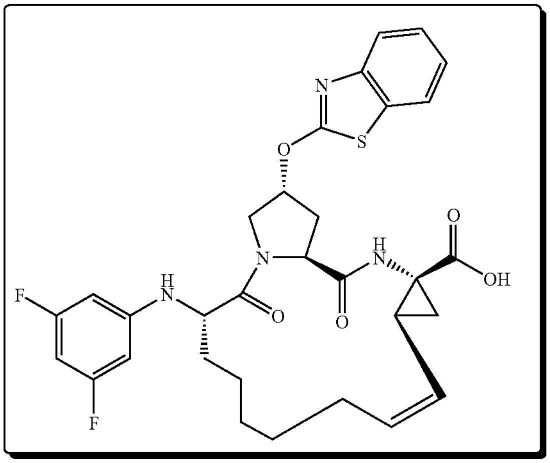

324

Compound 324 was prepared in a manner analogous to General Procedure E, and the yield was 85%. MS (ESI) m/e ($M+H^+$) 610.7.
Example 1-8
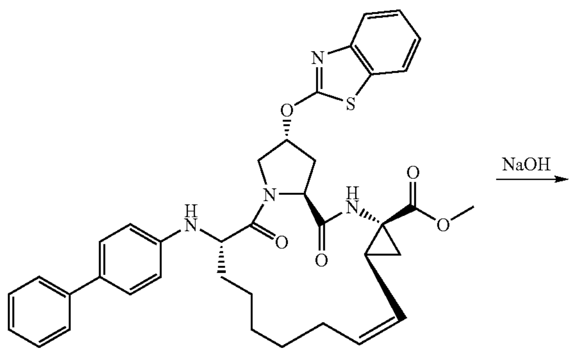
-continued
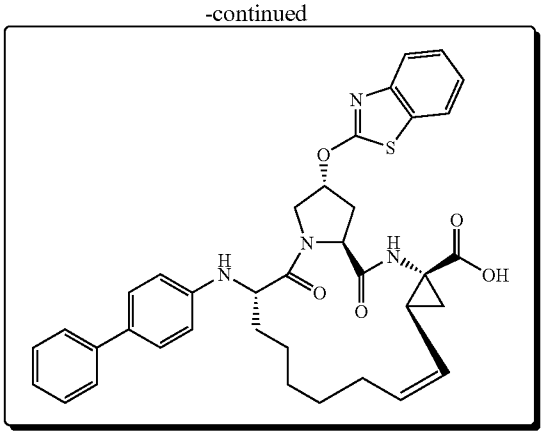
325
Compound 325 was prepared in a manner analogous to General Procedure E, and the yield was 85%. MS (ESI) m/e ($M+H^+$) 650.8.
Example 1-9
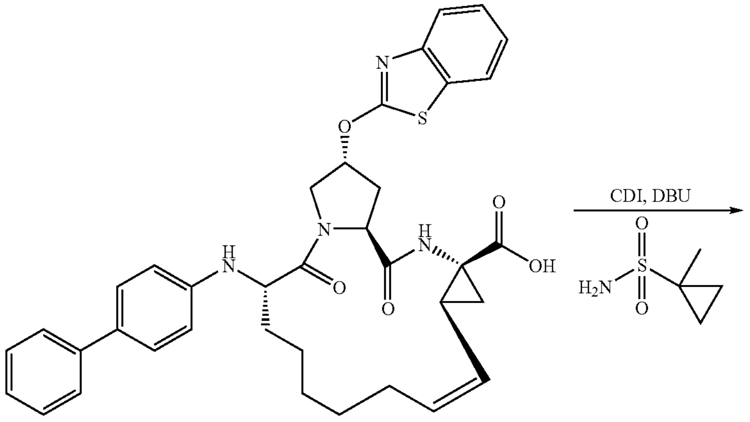
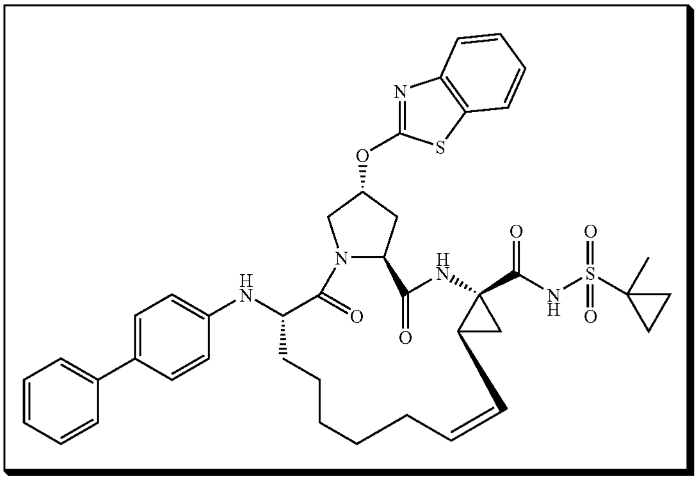
326

Compound 326 was prepared in a manner analogous to General Procedure F, and the yield was 50%. MS (ESI) m/e ($M+H^+$) 767.9.
Example 1-10
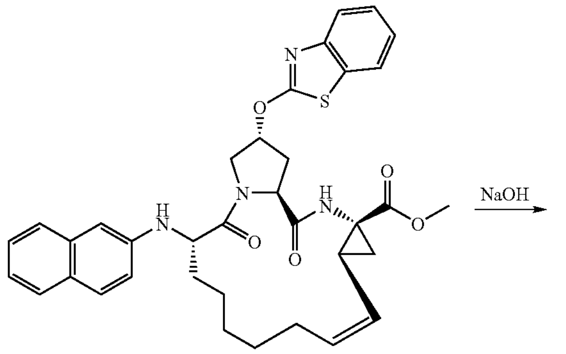
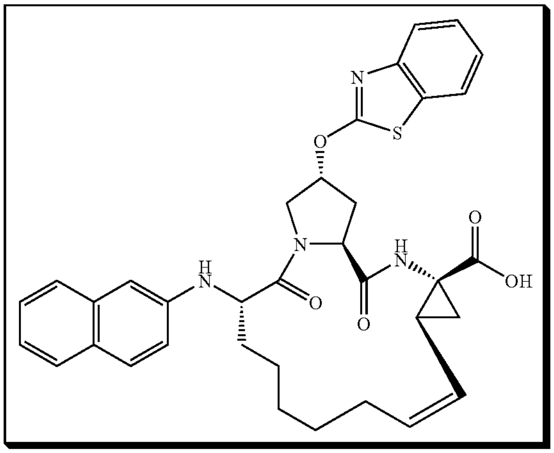
327
Compound 327 was prepared in a manner analogous to General Procedure E, and the yield was 85%. MS (ESI) m/e ($M+H^+$) 624.7.
Example 1-11
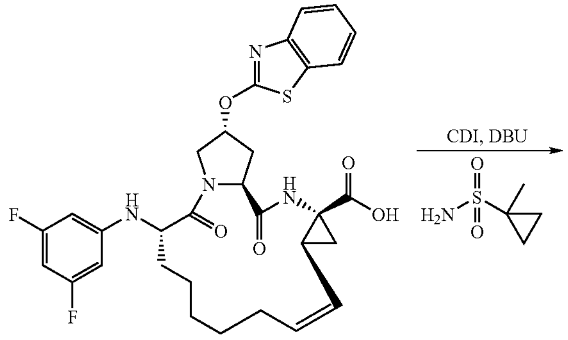
-continued
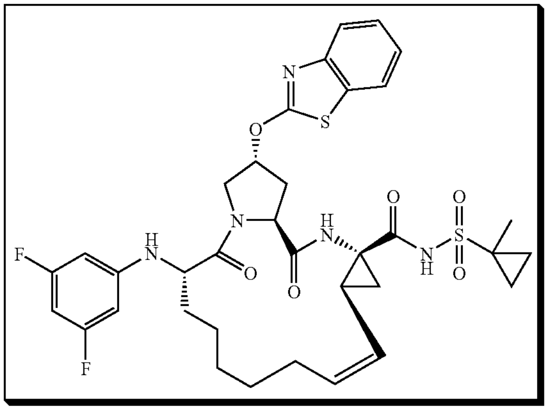
328
Compound 328 was prepared in a manner analogous to General Procedure F, and the yield was 50%. MS (ESI) m/e ($M+H^+$) 727.8.
Example 1-12
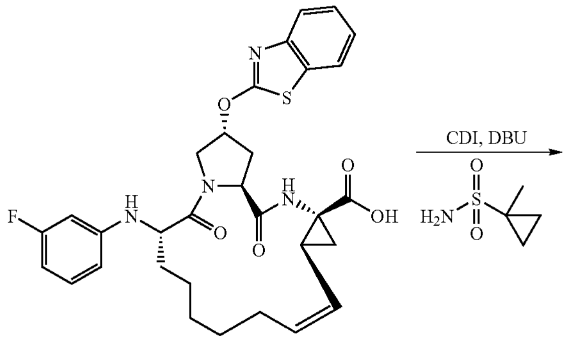
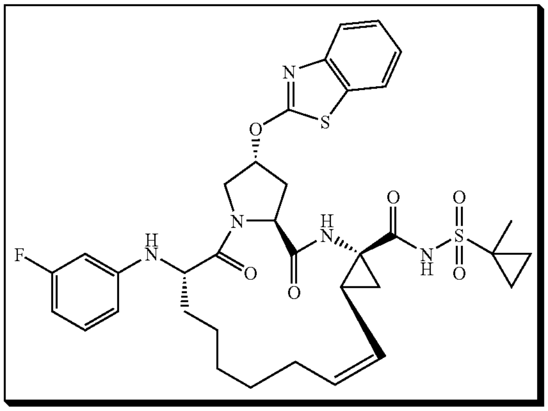
235

Compound 235 was prepared in a manner analogous to General Procedure F, and the yield was 50%. MS (ESI) m/e ($M+H^+$) 709.8.
Example 1-13
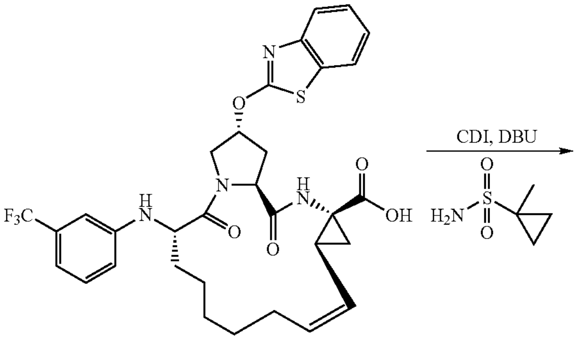
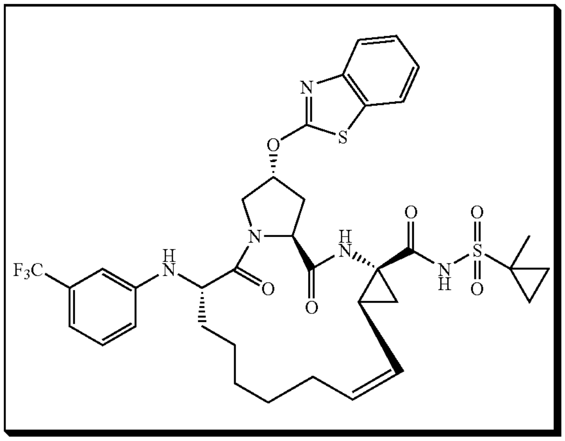
222
Compound 222 was prepared in a manner analogous to General Procedure F, and the yield was 50%. MS (ESI) m/e ($M+H^+$) 759.8.
Example 1-14
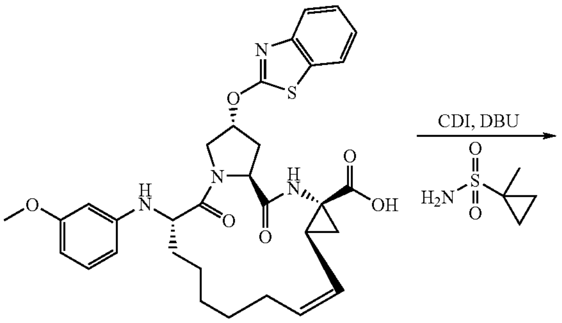
-continued
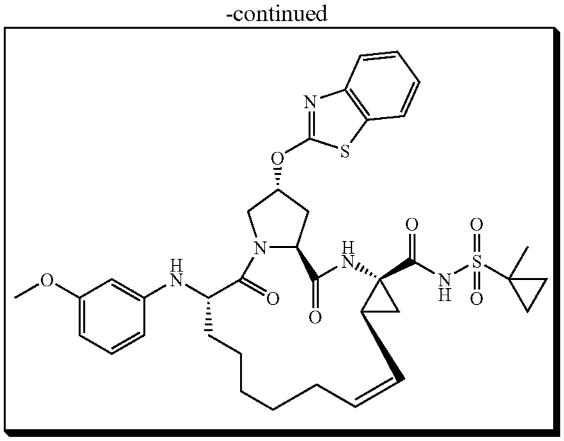
244
Compound 244 was prepared in a manner analogous to General Procedure F, and the yield was 50%. MS (ESI) m/e ($M+H^+$) 721.9.
Example 1-15
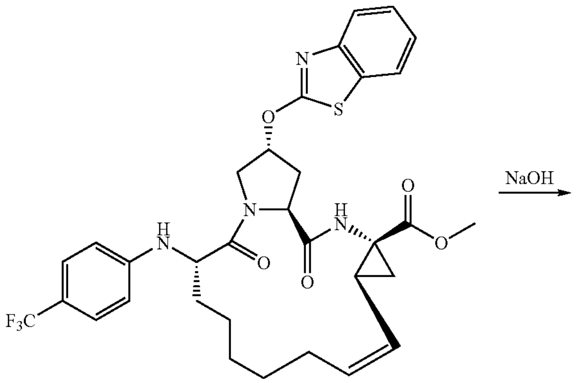
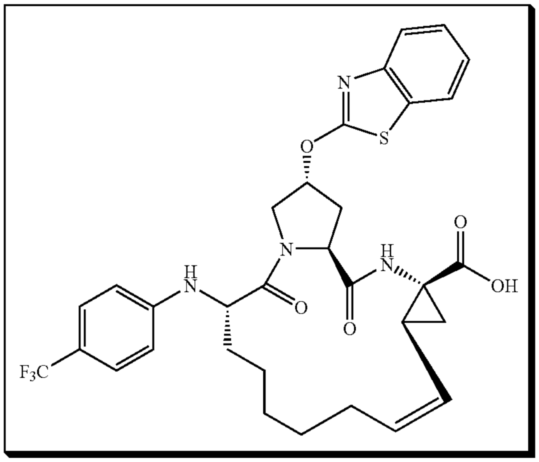
329

Compound 329 was prepared in a manner analogous to General Procedure E, and the yield was 85%. MS (ESI) m/e ($M+H^+$) 642.7.
Example 1-16
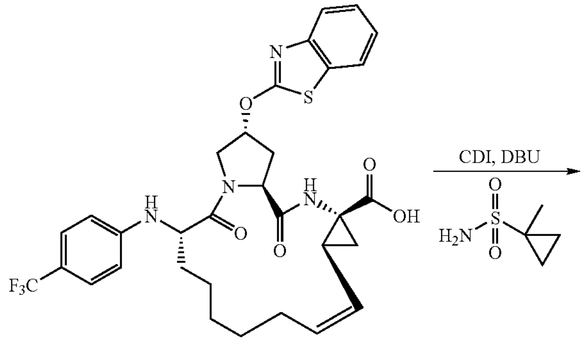
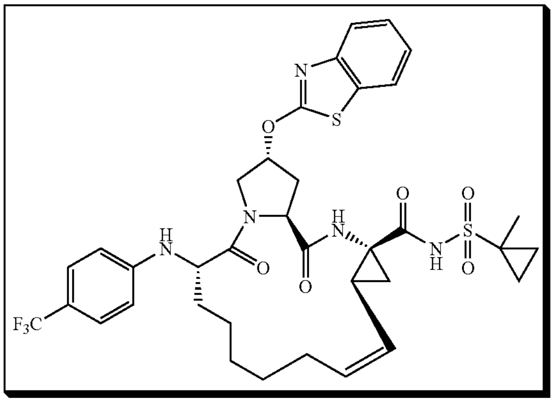
330
Compound 330 was prepared in a manner analogous to General Procedure F, and the yield was 50%. MS (ESI) m/e ($M+H^+$) 759.8.
Example 1-17
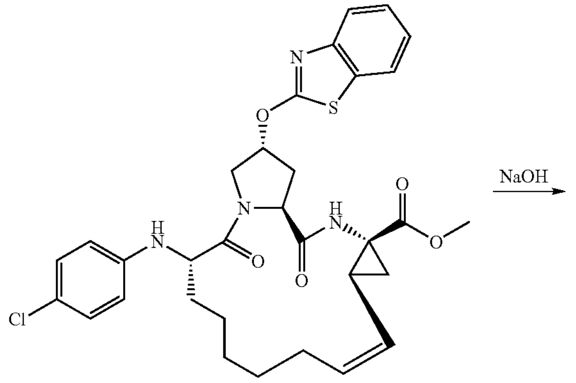
-continued
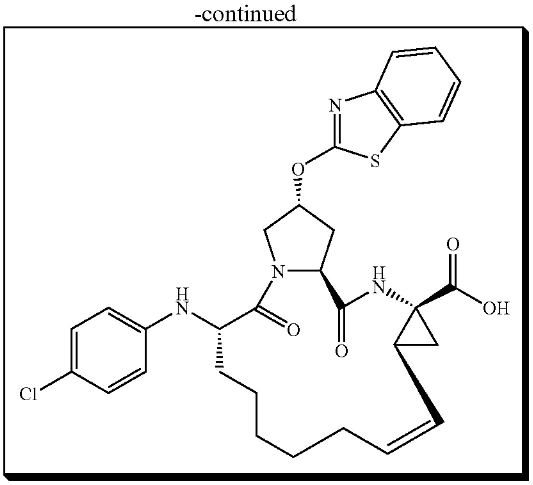
331
Compound 331 was prepared in a manner analogous to General Procedure E, and the yield was 85%. MS (ESI) m/e ($M+H^+$) 609.1.
Example 1-18
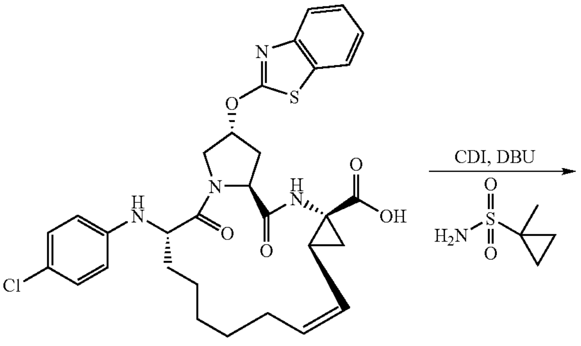
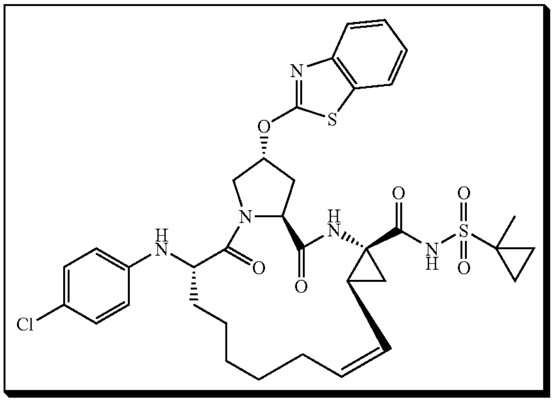
332

Compound 332 was prepared in a manner analogous to General Procedure F, and the yield was 50%. MS (ESI) m/e (M+H+) 726.3.
Example 1-19
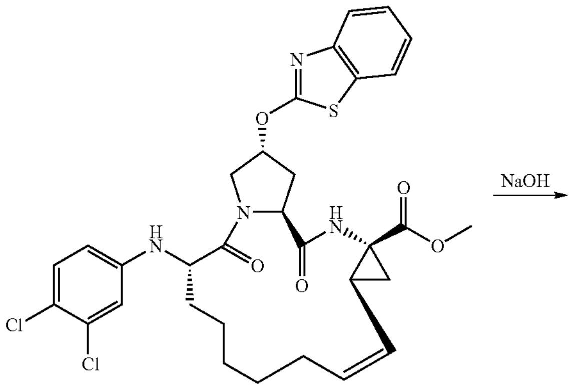
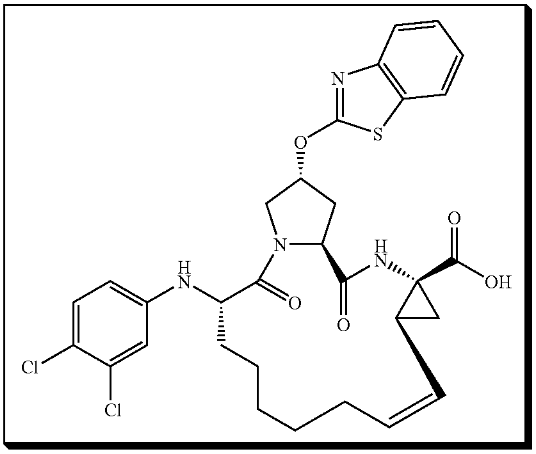
333
Compound 333 was prepared in a manner analogous to General Procedure E, and the yield was 85%. MS (ESI) m/e (M+H+) 643.6.
Example 1-20
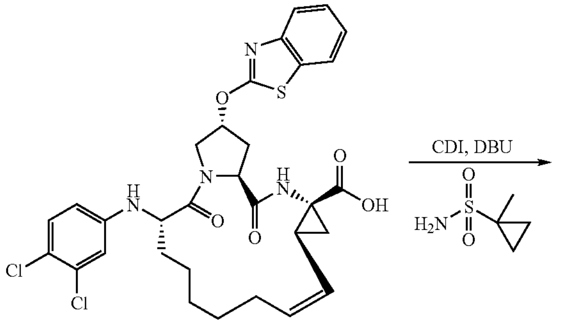
-continued
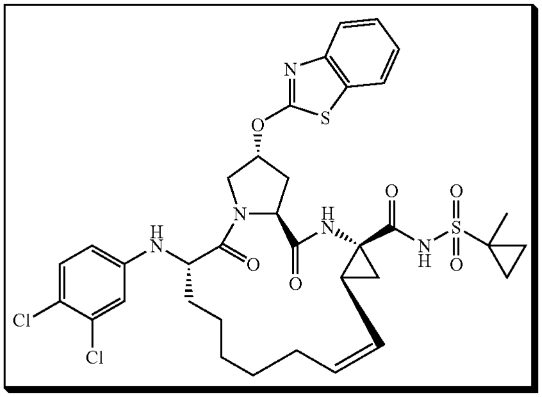
334
Compound 334 was prepared in a manner analogous to General Procedure F, and the yield was 50%. MS (ESI) m/e (M+H+) 760.8.
Example 1-21
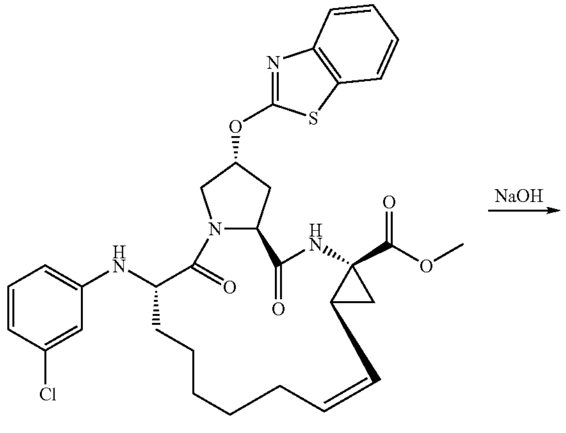
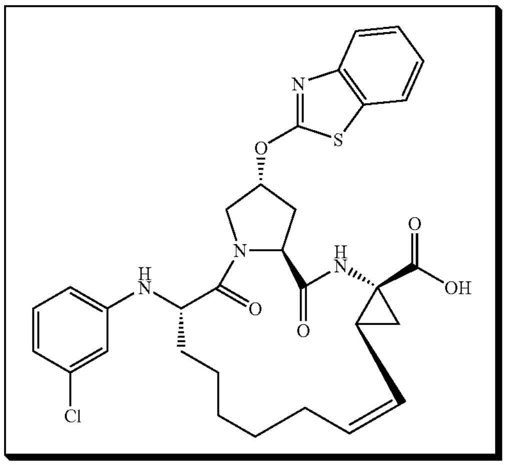
335

Compound 335 was prepared in a manner analogous to General Procedure E, and the yield was 85%. MS (ESI) m/e $(M+H^+)$ 609.1.
Example 1-22
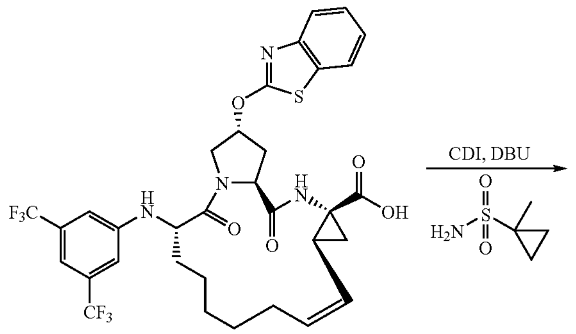
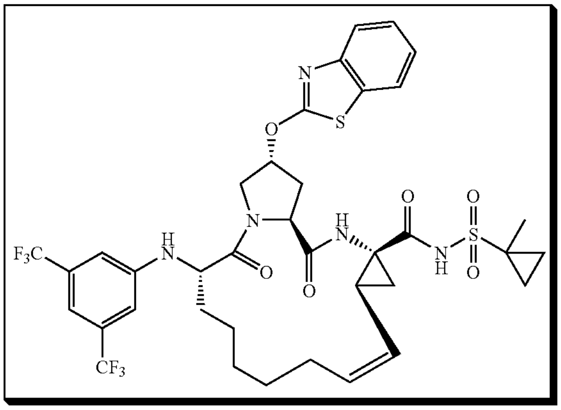
336
Compound 336 was prepared in a manner analogous to General Procedure F, and the yield was 50%. MS (ESI) m/e $(M+H^+)$ 827.8.
Example 1-23
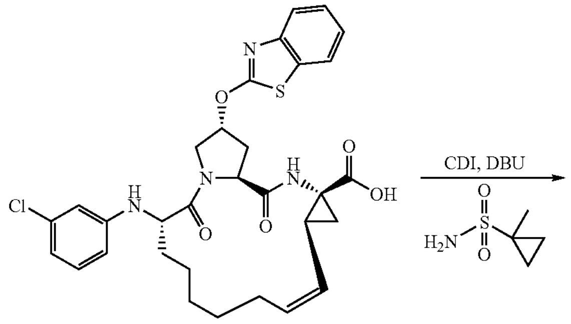
-continued
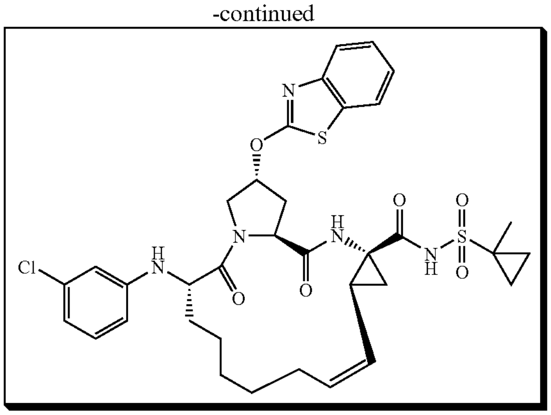
337
Compound 337 was prepared in a manner analogous to General Procedure F, and the yield was 50%. MS (ESI) m/e $(M+H^+)$ 726.3.
Example 1-24
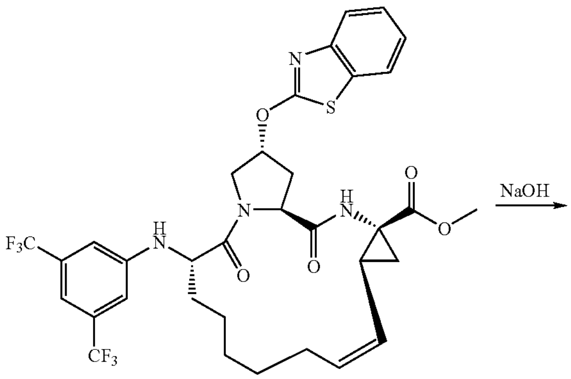
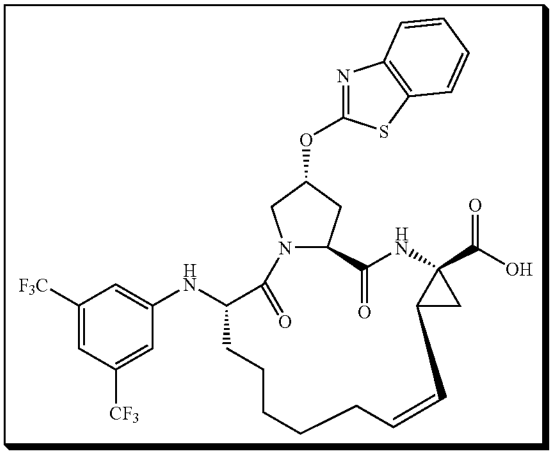
338

Compound 338 was prepared in a manner analogous to General Procedure E, and the yield was 85%. MS (ESI) m/e (M+H+) 710.7.

Example 1-25

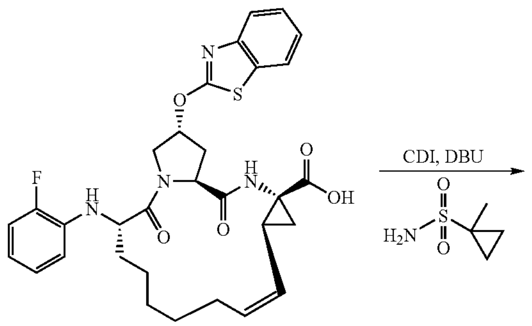

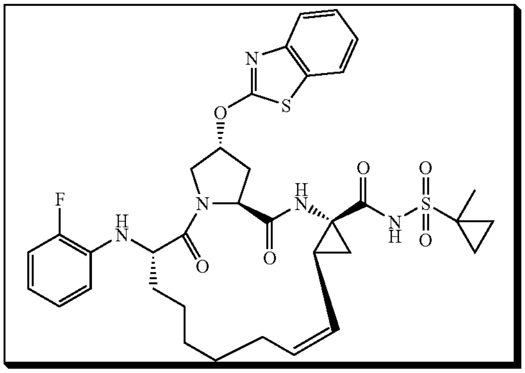

339

Compound 339 was prepared in a manner analogous to General Procedure F, and the yield was 85%. MS (ESI) m/e (M+H+) 709.9.

Example 1-26

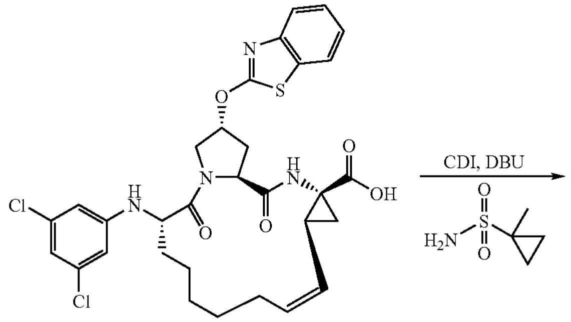

-continued

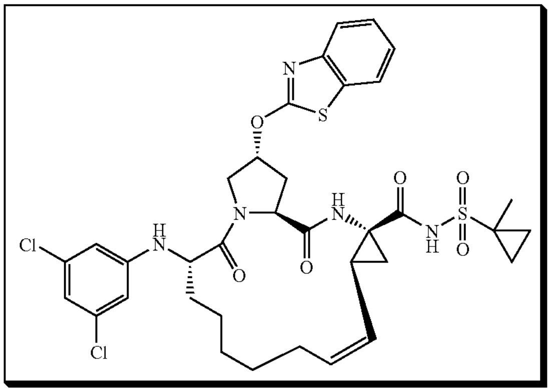

340

Compound 340 was prepared in a manner analogous to General Procedure F, and the yield was 50%. MS (ESI) m/e (M+H+) 760.8.

Example 1-27

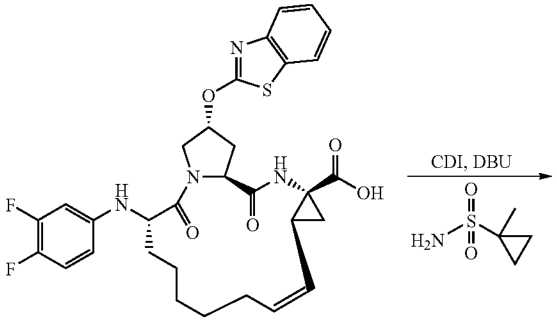

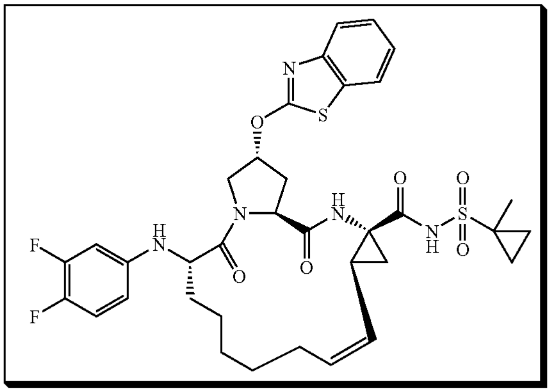

341

Compound 341 was prepared in a manner analogous to General Procedure F, and the yield was 50%. MS (ESI) m/e (M+H+) 727.8.

Example 1-28
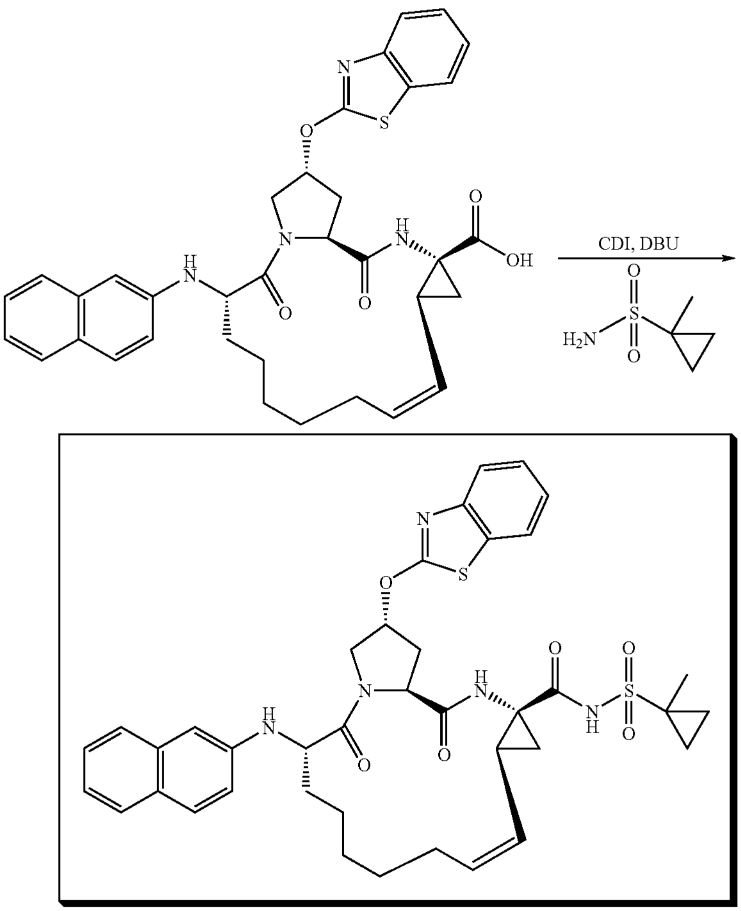
342
Compound 342 was prepared in a manner analogous to General Procedure F, and the yield was 50%. MS (ESI) m/e $(M+H^+)$ 741.9.
Example 1-29
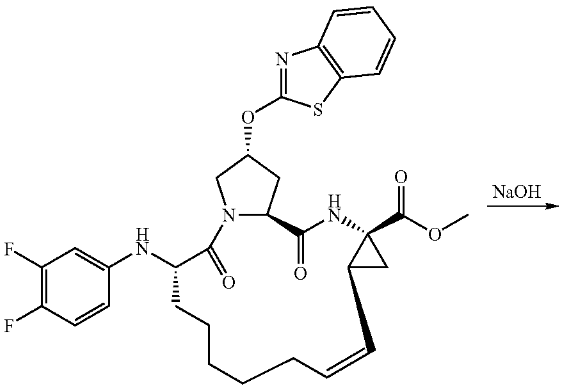
-continued
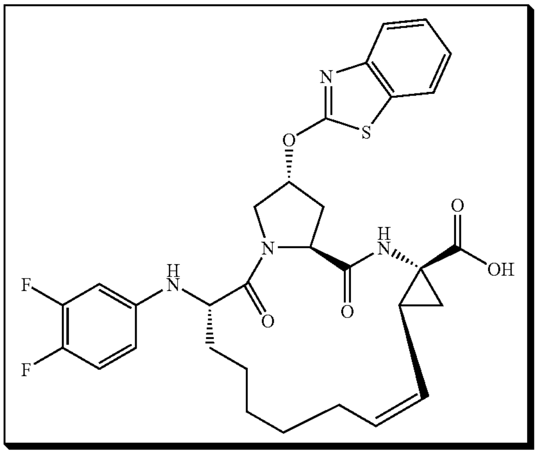
343
Compound 343 was prepared in a manner analogous to General Procedure E, and the yield was 85%. MS (ESI) m/e $(M+H^+)$ 610.7.

Example 1-30
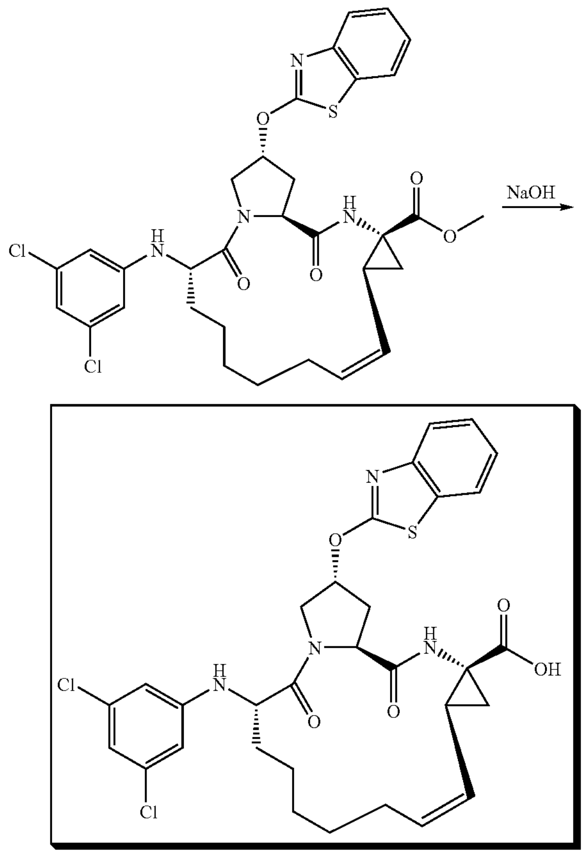
344
Compound 344 was prepared in a manner analogous to General Procedure E, and the yield was 85%. MS (ESI) m/e (M+H$^+$) 643.6.
Example 1-31
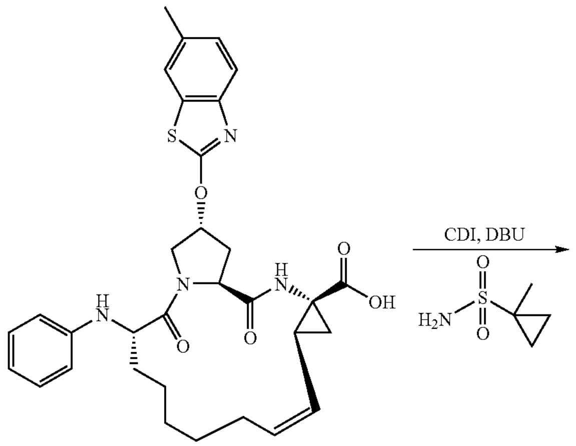
-continued
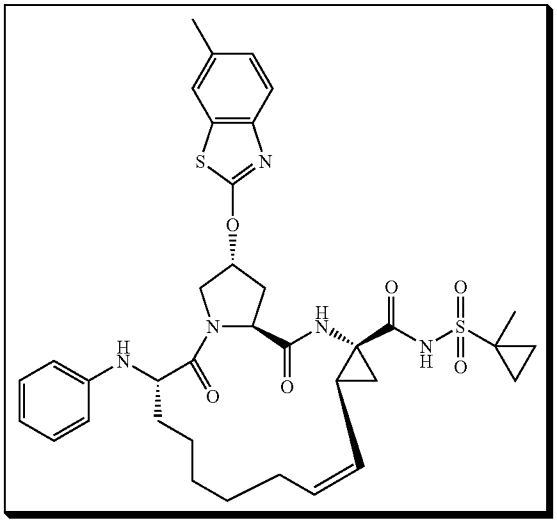
218
Compound 218 was prepared in a manner analogous to General Procedure F, and the yield was 50%. MS (ESI) m/e (M+H$^+$) 705.9.
Example 1-32
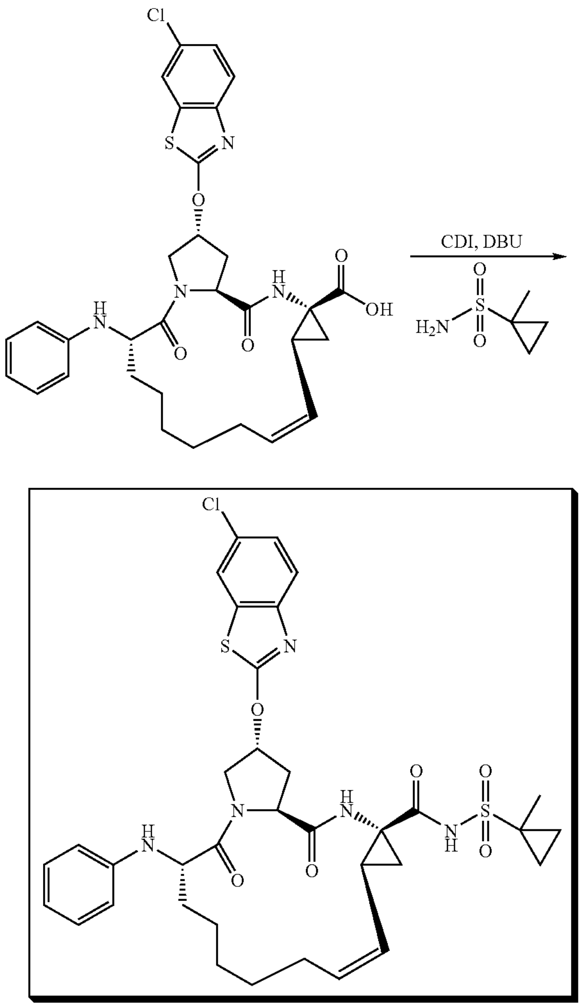
217

Compound 217 was prepared in a manner analogous to General Procedure F, and the yield was 50%. MS (ESI) m/e (M+H$^+$) 726.3.
Example 1-33
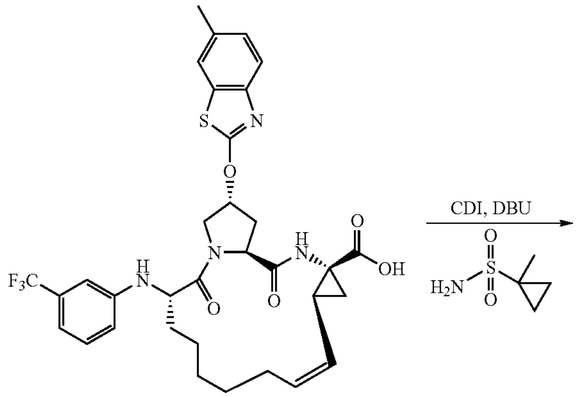
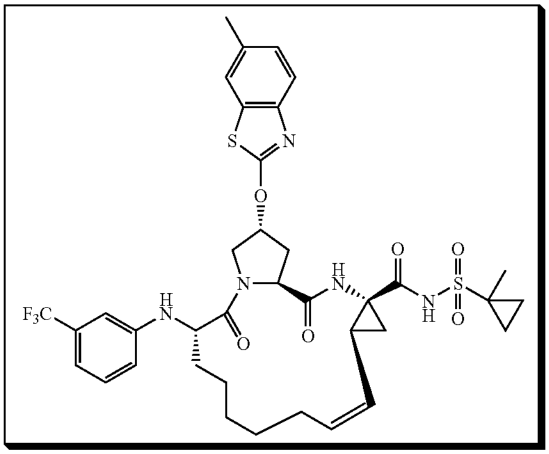
227
Compound 227 was prepared in a manner analogous to General Procedure F, and the yield was 50%. MS (ESI) m/e (M+H$^+$) 773.9.
Example 1-34
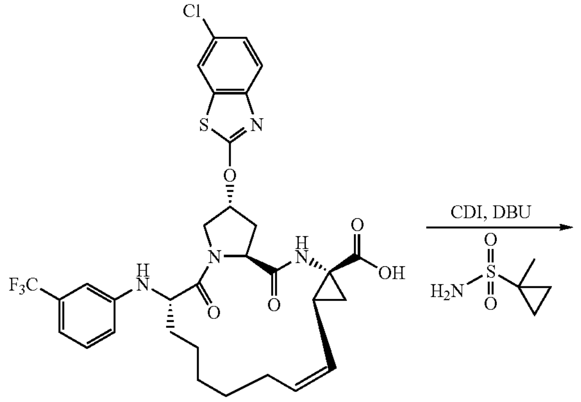
-continued
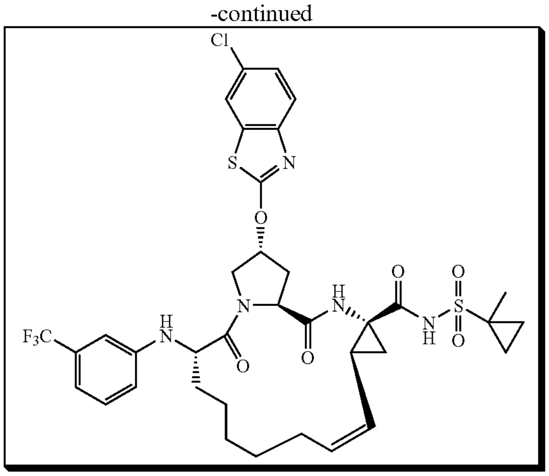
226
Compound 226 was prepared in a manner analogous to General Procedure F, and the yield was 50%. MS (ESI) m/e (M+H$^+$) 794.3.
Example 1-35
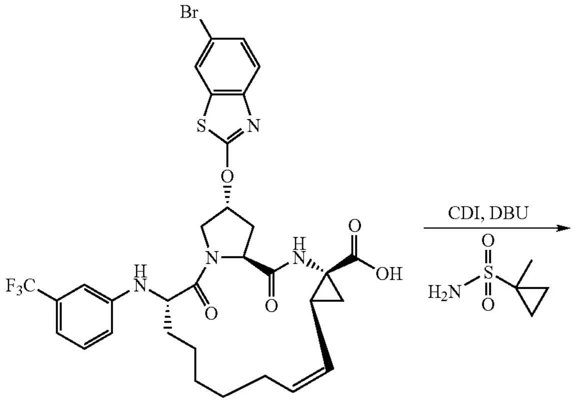
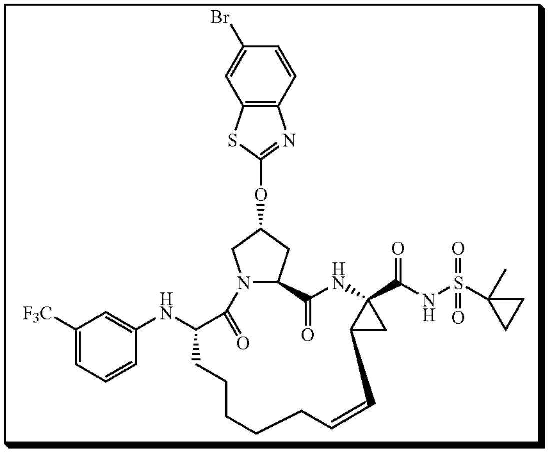
223

Compound 223 was prepared in a manner analogous to General Procedure F, and the yield was 50%. MS (ESI) m/e ($M+H^+$) 838.8.
Example 1-36
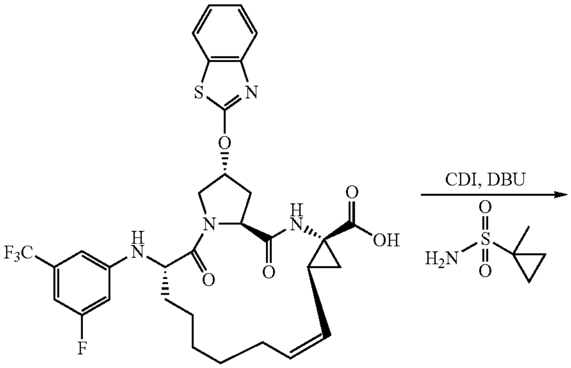
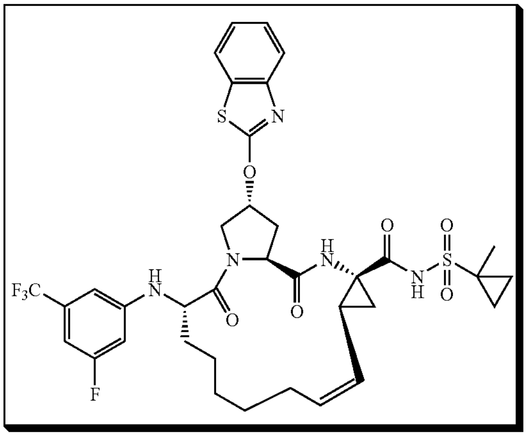
345
Compound 345 was prepared in a manner analogous to General Procedure F, and the yield was 50%. MS (ESI) m/e ($M+H^+$) 777.8.
Example 1-37
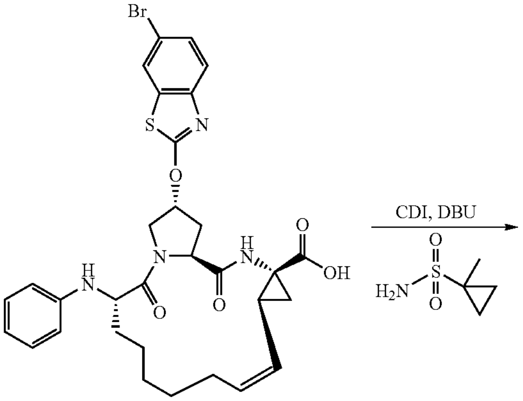
-continued
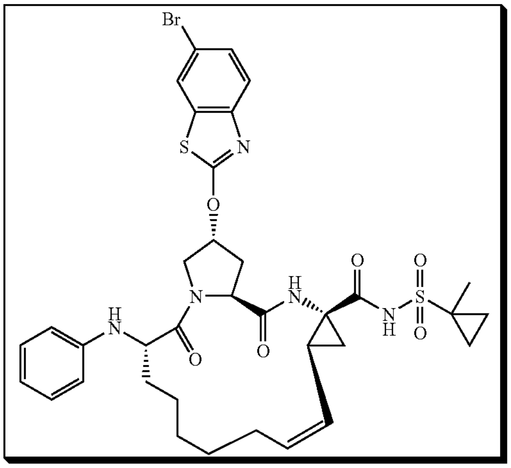
214
Compound 214 was prepared in a manner analogous to General Procedure F, and the yield was 50%. MS (ESI) m/e ($M+H^+$) 770.8.
Example 1-38
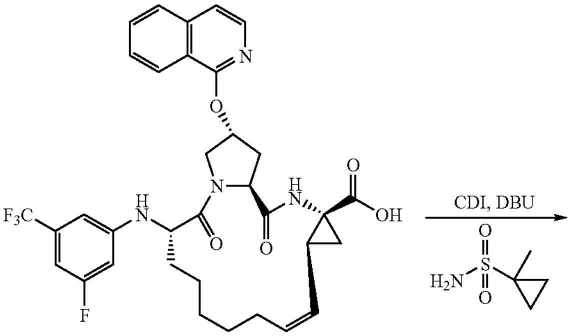
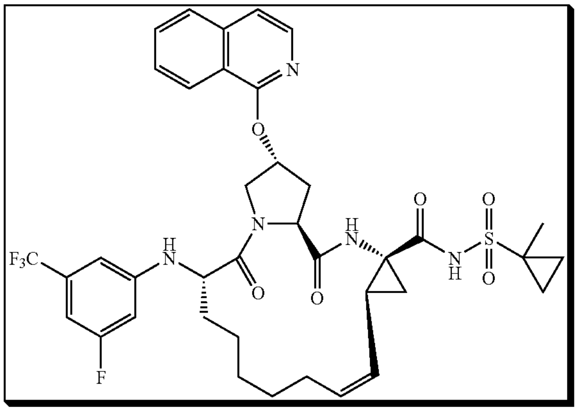
346

Compound 346 was prepared in a manner analogous to General Procedure F, and the yield was ~45%. MS (ESI) m/e $(M+H^+)$ 772.2.
Example 1-39
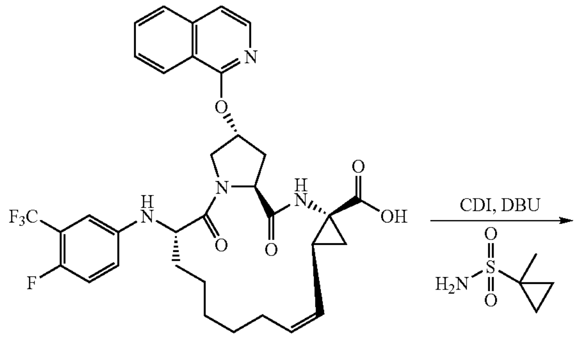
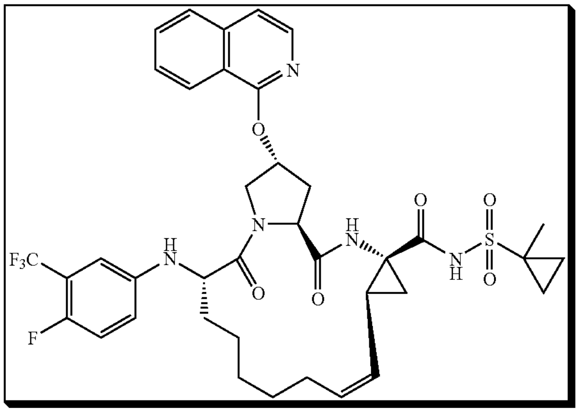
347
Compound 347 was prepared in a manner analogous to General Procedure F, and the yield was ~45%. MS (ESI) m/e $(M+H^+)$ 772.2.
Example 1-40
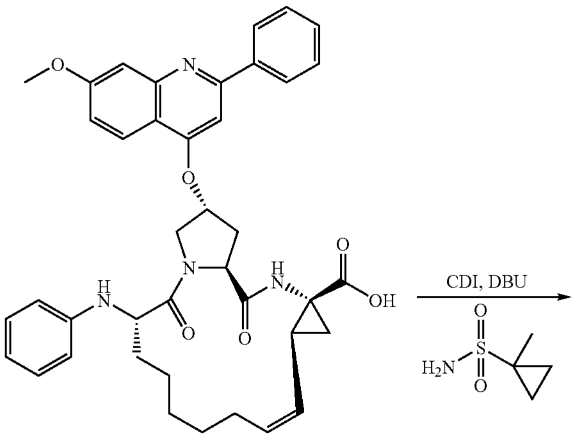
-continued
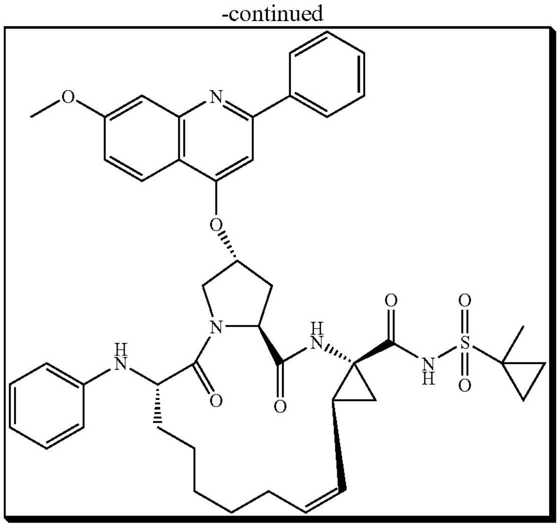
220
Compound 220 was prepared in a manner analogous to General Procedure F, and the yield was 50%. MS (ESI) m/e $(M+H^+)$ 791.9.
Example 1-41
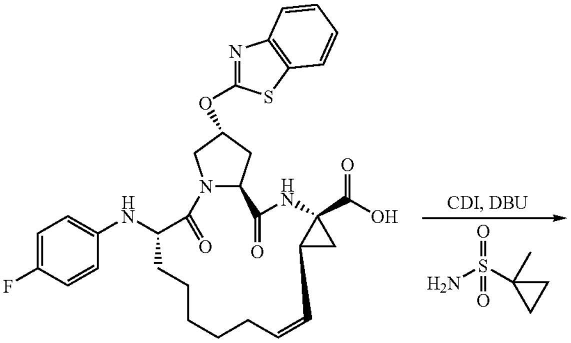
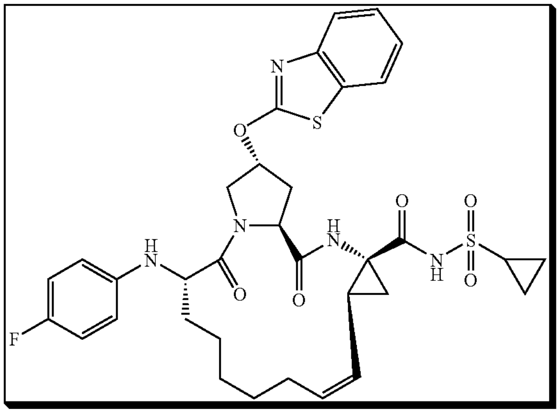
348

Compound 348 was prepared in a manner analogous to General Procedure F, and the yield was 50%. MS (ESI) m/e ($M+H^+$) 695.

Example 1-42

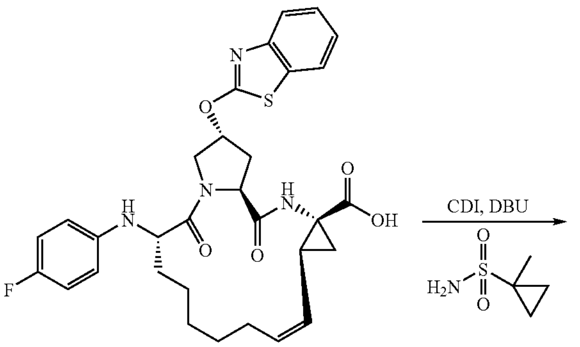

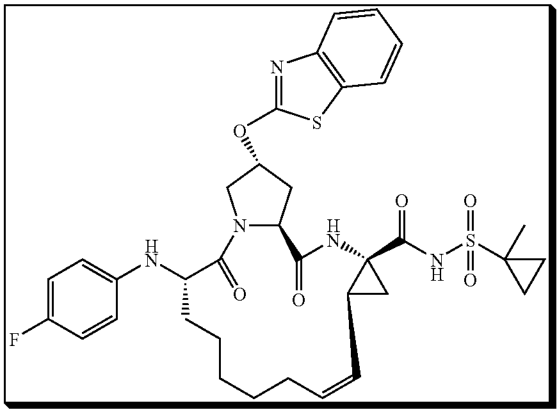

349

Compound 349 was prepared in a manner analogous to General Procedure F, and the yield was 50%. MS (ESI) m/e ($M+H^+$) 709.

Preparation of NS3 Inhibitors: Section II

EXAMPLE 2

Scheme II

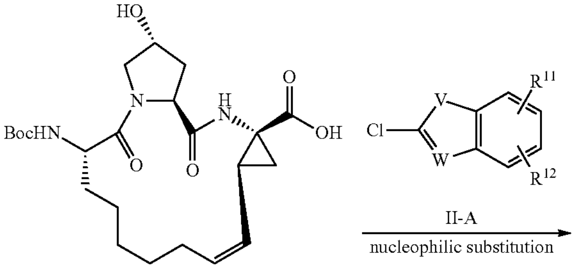

2

-continued

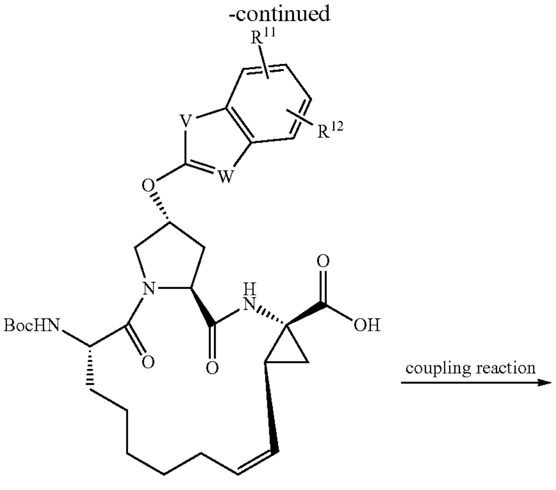

II-B

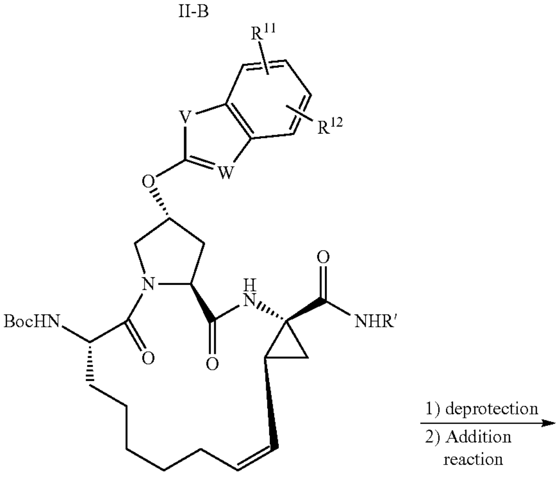

II-C

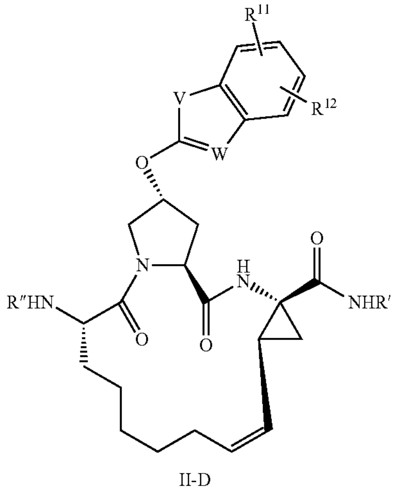

II-D

R'=O-aryl or $SO_2$cycloalkyl; R'=O-aryl or $SO_2$cycloalkyl; R"=$(CH_2)_n$aryl or $(CH_2)_n$heteroaryl; and n=0, 1, or 2. $R^{11}$, $R^{12}$, V, and W are as defined above.

Macrocyclics of general structures II-D can be synthesized as shown in Scheme II. The alcohol 2 can be treated with a heteroaryl chloride of formula II-A, such as 2-chlorobenzothiazole, 2-chloro-6-methylbenzothiazole, 2,6-dichlorobenzothiazole, 6-bromo-2-chlorobenzothiazole, and the like, under basic conditions to afford a compound of general structure II-B. The compound of general structure II-B can be coupled with sulfonamides (or sulfamides not shown) or optionally substituted O-alkyl or aryl hydroxylamines thereby providing compounds of general structure II-C. The Boc protected compounds of general structure II-C can be treated with acid in an appropriate solvent to remove the Boc protecting group to provide the free amine. The free amine can then be coupled under appropriate conditions providing an N-substituted compound of general structure I-D.

Example 2-1

General Method A

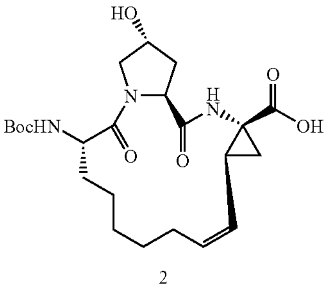

2

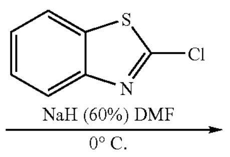

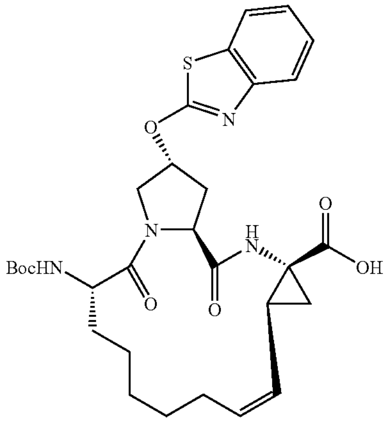

3-B

To a solution of compound 2 (1 g, 2.2 mmol.) in 10 mL of dry DMF was added sodium hydride (0.53 g, 13.2 mmol.) at 0° C. The resulting mixture was stirred at this temperature for 1 h before the addition of 2-chloro-benzothiazole, the mixture was then allowed to slowly warm to room temperature and stirred overnight. The reaction was quenched by careful addition of methanol (10 mL) and water (30 mL). The resulting solution was stirred for 15 min, extracted with ethyl acetate, washed with brine, dried over $Na_2SO_4$, and concentrated under reduced pressure to afford a residue. The residue was purified by Prep-HPLC to afford compound 3-B as a white solid 0.78 g (yield 60.5%). $^1$H NMR (400 MHz, DMSO-$d_6$) δ 12.22 (bra, 1 H), 8.61 (s, 2 H), 7.83 (d, J=7.6 Hz, 1 H), 7.67 (d, J=7.6 Hz, 1 H), 7.36 (t, J=7.2 Hz, 1 H), 7.24 (t, J=7.2 Hz, 1 H), 6.94 (d, J=6.8 Hz, 1 H), 5.74 (s, 1 H), 5.46 (q, J=8 Hz, 1 H), 5.25 (t, J=9.2 Hz, 1 H), 4.51 (d, J=12.8 Hz, 1 H), 4.41 (t, J=8 Hz, 1 H), 4.00 (t, J=10 Hz, 1 H), 3.87 (d, J=9.6 Hz, 1 H), 2.29-2.30 (m, 1 H), 2.14-2.16 (m, 1 H), 1.43-1.47 (m, 2 H), 1.29-1.14 (m, 16H). MS (ESI) m/e (M+H$^+$) 598.7.

EXAMPLE 3

General Method C

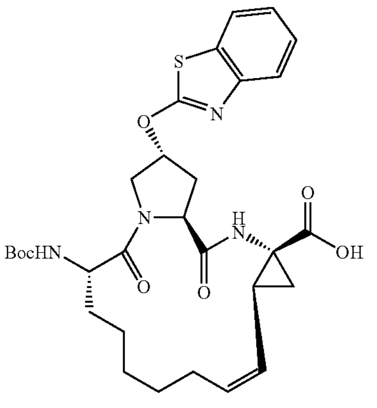

3-B

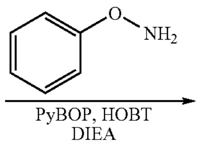

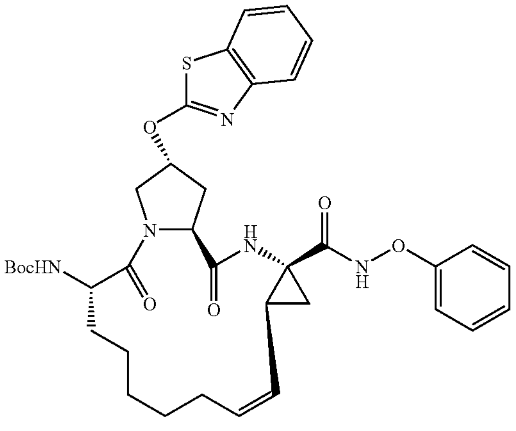

3-E

To a solution of compound 3-B (100 mg, 0.17 mmol.) in 5 mL of dry DMF was added PyBOP (177 mg, 0.34 mmol.) and HOBT (46 mg, 0.34 mmol.) at room temperature, the resulting mixture was stirred 2 h at the same temperature. Subsequently, the stirring mixture was treated with O-phenylhydroxylamine hydrochloride (26.9 mg, 0.19 mmol.) and DIEA (88 mg, 0.68 mmol.), the resulting mixture was stirred overnight at rt. The reaction was quenched by adding water (20 mL) and extracted with ethyl acetate (3×15 mL). The combined organic layers were washed with brine, dried over $Na_2SO_4$, and concentrated to get a residue, which was purified by Prep-HPLC to give compound 3-E as white solid 50 mg (yield 32.5%). MS (ESI) m/e ($M+H^+$) 690.3.

EXAMPLE 4

General Method D

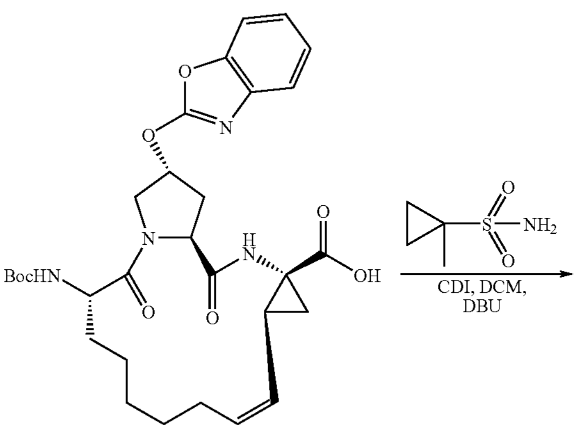

4-B

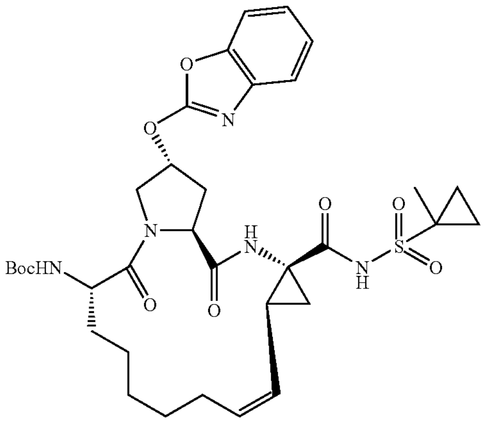

4-C

To a solution of compound 4-B (100 mg, 0.17 mmol.) in dry DCM (3 mL) was added CDI (55 mg, 0.34 mmol.) at 25° C., the mixture was stirred 1 h at the same temperature. Subsequently, the stirring mixture was treated with methylcyclopropanyl sulfonamide (46 mg, 0.34 mmol.) and DBU (0.1 mL, 0.85 mmol.), the resulting mixture was stirred overnight at 25° C. The solvent was removed to afford a residue which was purified by Prep-HPLC to give 4-C as white solid 50 mg (yield 43%). MS (ESI) m/e ($M+H^+$) 700.3.

EXAMPLE 5

Synthesis of N-Substituted Aryl Ethers

Scheme III

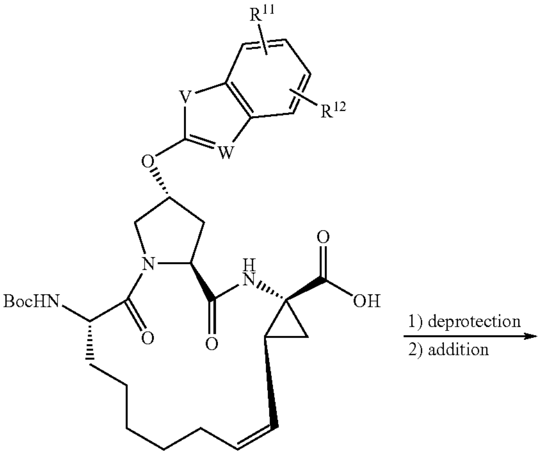

III-A

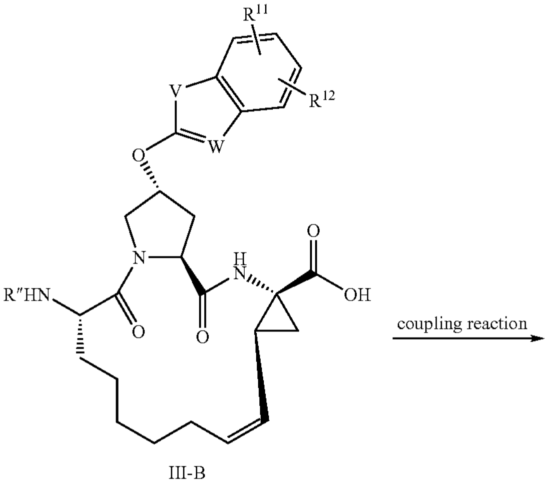

III-B

-continued

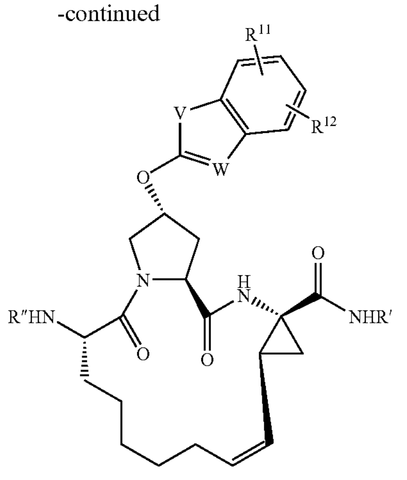

III-C

R"=$(CH_2)_n$aryl or $(CH_2)_n$heteroaryl; n=0, 1, or 2; and R'=O-aryl or $SO_2$cycloalkyl. $R^{11}$, $R^{12}$, V, and W are as defined above.

Macrocyclics of general structures III-C can be synthesized as shown in Scheme III. The Boc protected carboxylic acids of the general structure III-A can be treated with an acid in an appropriate solvent to remove the Boc protecting group to provide the free amine. The free amine can then be coupled under appropriate conditions providing an N-substituted compound of general structure III-B. The compound of general structure III-B can be coupled with sulfonamides (or sulfamides; not shown) or optionally substituted O-alkyl or aryl hydroxylamines thereby providing compounds of general structure III-C.

Example 5-1

General Method E

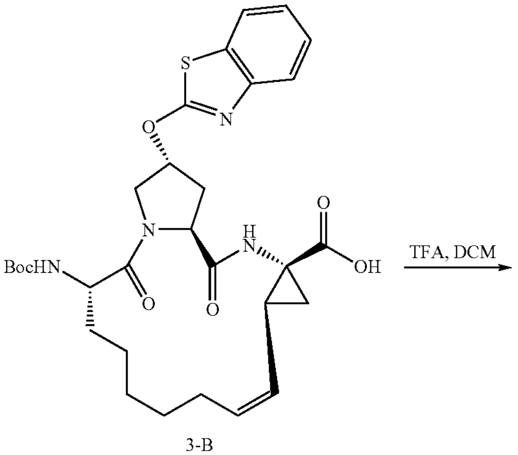

3-B

-continued

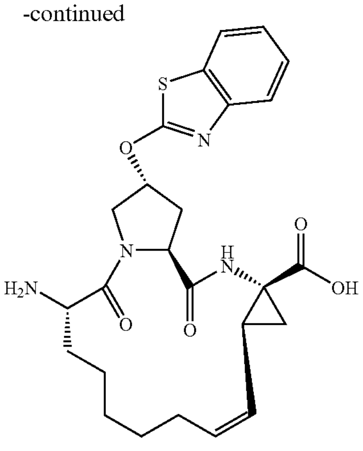

5

A solution of compound 3-B (1 g, 1.67 mmol.) in DCM (5 mL) was treated with TFA (5 mL) at 25° C. After stirring 2 h, the solvent was removed to afford a residue of 5 (1.0 g, 100%), which was used in the next step without further purification. MS (ESI) m/e ($M+H^+$) 499.2.

Example 5-2

General Method F

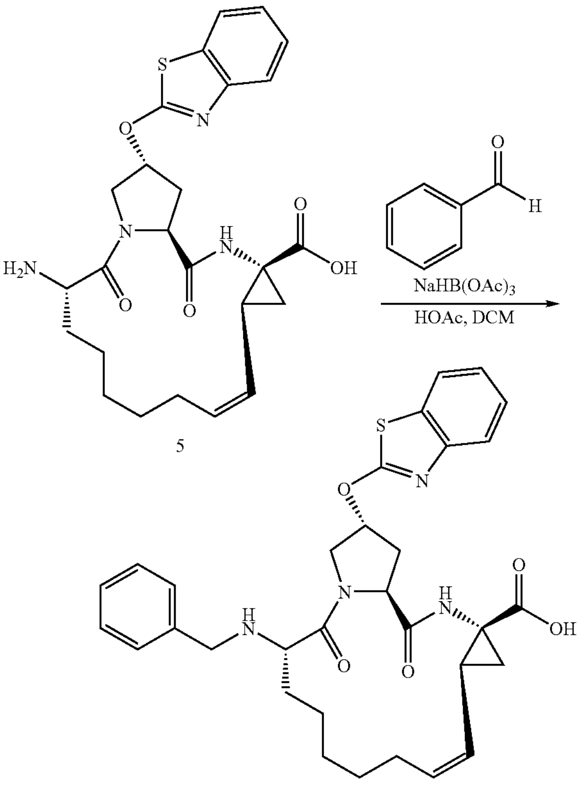

5

141

To a solution of compound 5 (100 mg, 0.2 mmol.) in DCM (5 mL) was added benzaldehyde (13 mg, 0.24 mmol.), $NaHB(OAc)_3$ (81 mg, 0.38 mmol.), and AcOH (0.02 mL) at 25° C.

The resulting mixture was stirred overnight at 25° C. The solvent was removed to afford a residue, which was purified by Prep-HPLC to give 141 as white solid 50 mg (yield 43.2%). $^{1}$H NMR (400 MHz, DMSO-$d_6$) δ 12.43 (br, 1H), 9.29 (br, 1 H), 9.16 (br, 1 H), 8.89 (s, 1 H), 7.90 (d, 1 H), 7.70 (d, J=8.0 Hz, 1 H), 7.42 (t, J=7.2 Hz, 1 H), 7.36-7.23 (m, 6 H), 5.83 (s, 1 H), 5.49 (q, J=10.4 Hz, 1 H), 5.33 (t, J=10 Hz, 1 H), 4.44 (t, J=8.0 Hz, 1 H), 4.25 (s, 1 H), 4.00 (m, 2 H), 3.87 (m, 1 H), 2.34-2.30 (m, 4 H), 2.04-1.97 (m, 3 H), 1.77 (br, 3 H), 1.47-1.23 (m, 9H). MS (ESI) m/e (M+H$^+$) 589.4

Example 5-3

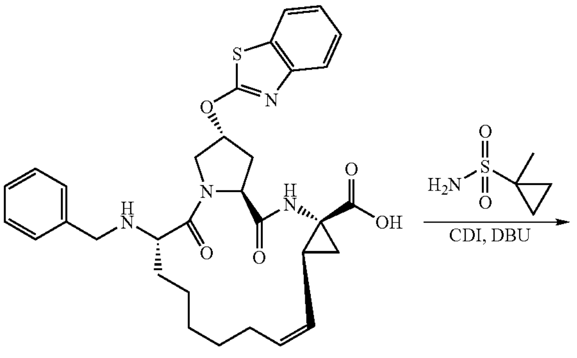

141

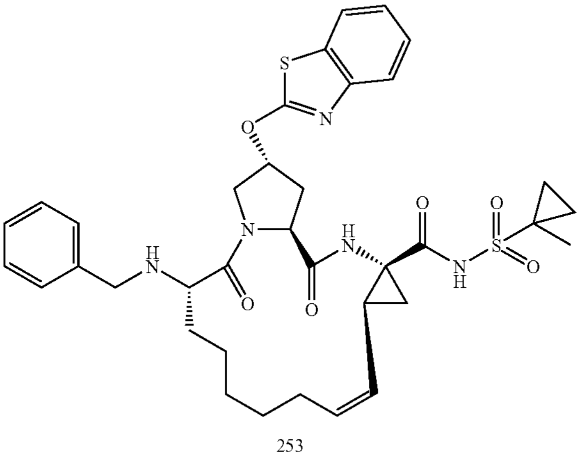

253

The acylsulfonamide 253 was prepared following General Method D, the product was isolated as a white solid. Yield=45.3%. MS (ESI) m/e (M+H$^+$) 706.3.

Example 5-4

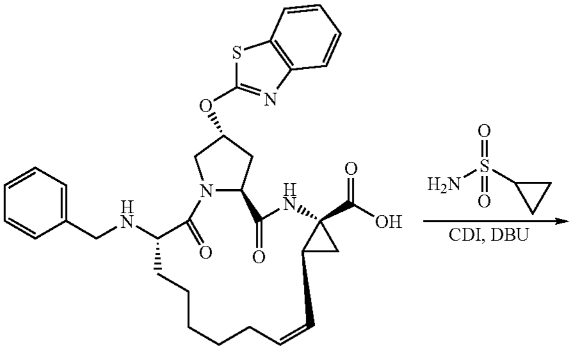

141

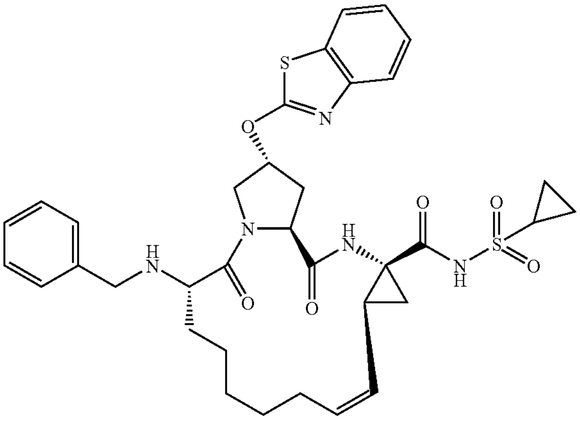

197

The acylsulfonamide 197 was prepared following General Method D, the product was isolated as a white solid. Yield=43%. MS (ESI) m/e (M+H$^+$) 792.3.

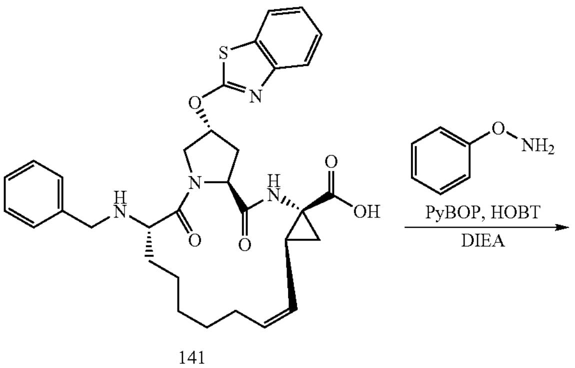

141

-continued

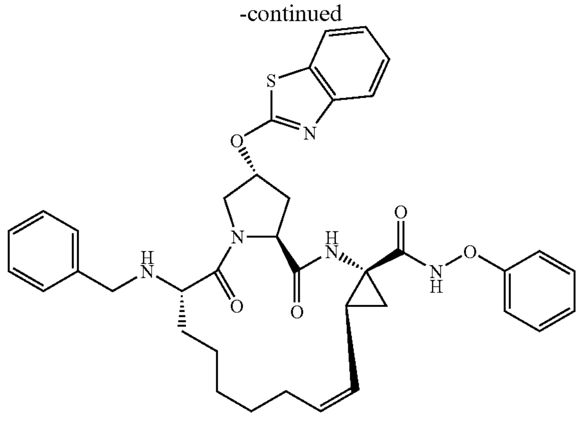

309

The hydroxamate 309 was prepared following General Method C.

Example 5-5

General Method G

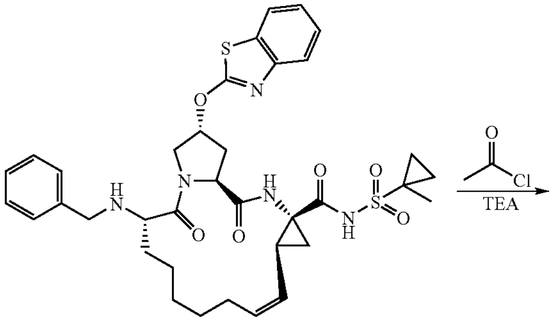

253

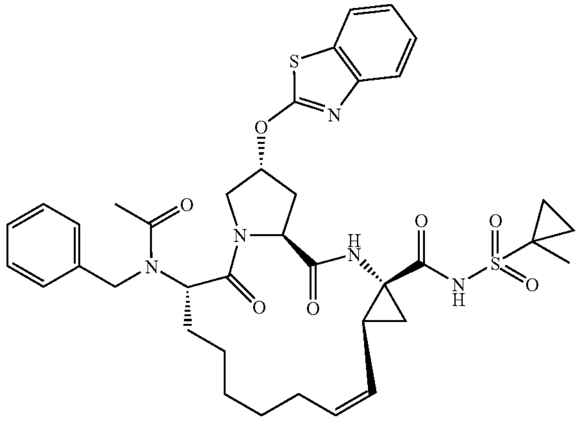

315

A solution of compound 253 (100 mg, 0.14 mmol.) in DCM (5 mL) was cooled to 0° C., then $Et_3N$ (85 mg, 0.84 mmol.) was added, followed by slow addition acetyl chloride (55 mg, 0.7 mmol.). After complete addition, the mixture was allowed to reach room temperature and stirred overnight. The mixture was diluted with EtOAc (20 mL), then washed with 5% $NaHCO_3$, water and brine. The organic solvent mixture was dried over $Na_2SO_4$ and then the solid was removed by filtration. The organic solvent was removed to afford a crude product mixture, which was applied to Prep-HPLC to afford compound 315 as a white solid 19 mg (isolated yield 20%). MS (ESI) m/e ($M+H^+$) 748.3.

Example 5-6

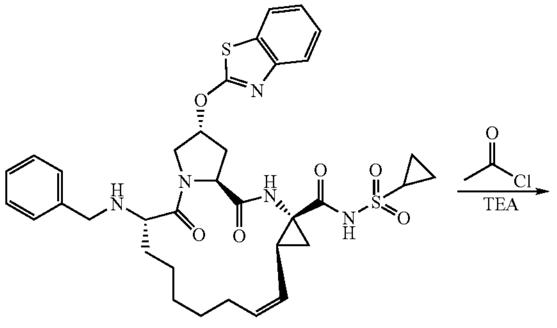

197

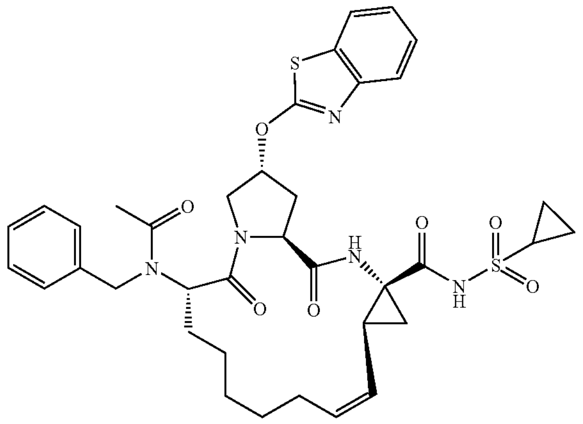

316

The amide 316 was prepared following General Method G. Isolated Yield=16%. MS (ESI) m/e ($M+H^+$) 734.3.

Example 5-7

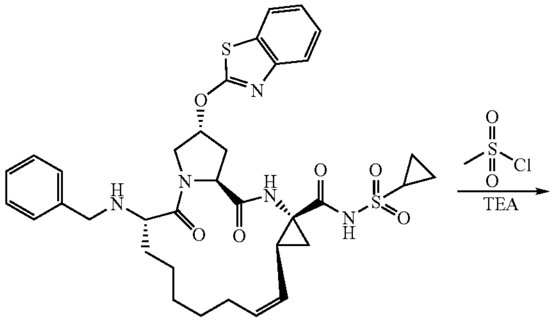

197

-continued

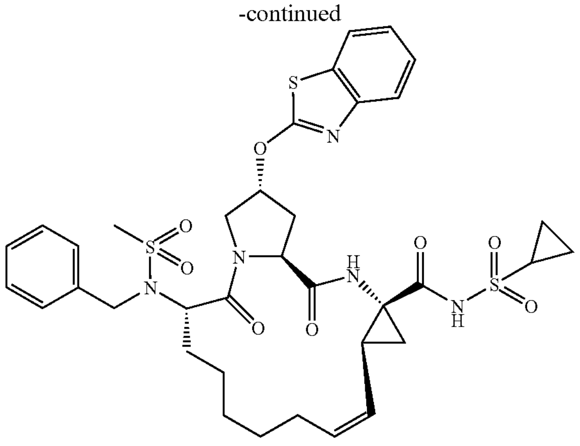

317

The sulfonamide 317 was prepared following General Method G, using methansulfonyl chloride in place of acetyl chloride. Isolated Yield=15%. MS (ESI) m/e (M+H$^+$) 770.2.

EXAMPLE 6

General Method H

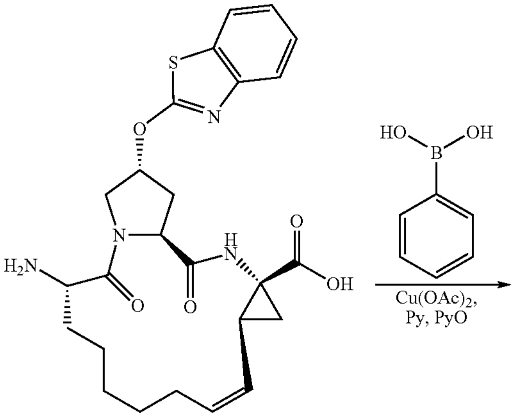

5

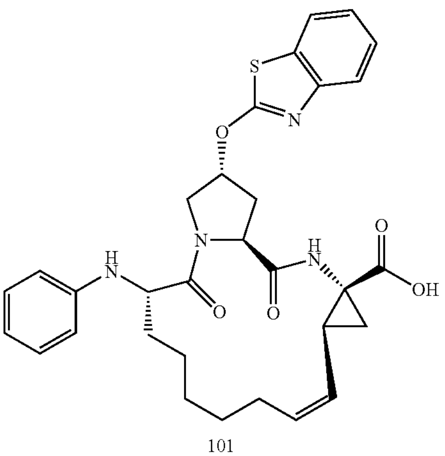

101

A mixture of compound 5 (400 mg, 0.80 mmol.), phenylboronic acid (147 mg, 1.2 mmol.), $Cu(OAc)_2$ (188 mg, 1.0 mmol.), pyridine (316 mg, 4 mmol.), pyridine N-Oxide (76 mg, 0.8 mmol.) and molecular sieves 4 Å in dichloromethane (10 mL) was stirred for 12 h at room temperature opened to the air. The reaction was monitored by LC-MS. Another 1.5 eq boronic acid was added and stirred. After completion of the reaction, the solvent was removed and the crude mixture was purified by prep-HPLC to afford compound 101. (80 mg, isolated yield 15%) $^1$H-NMR (400 MHz, $CDCl_3$): δ 8.60 (s, 1 H), 7.91 (d, J=8 Hz, 1 H), 7.71 (d, J=8 Hz, 1 H), 7.41 (t, J=7.6 Hz, 1 H), 7.29 (t, J=7.6 Hz, 2 H), 6.92 (t, J=8 Hz, 2 H), 6.59 (d, J=8 Hz, 2 H), 6.52 (d, 1 H), 5.84 (s, 1 H), 5.54-5.47 (q, 1 H), 5.32-5.27 (t, 1 H), 4.48-4.41 (t, 1 H), 4.35-4.32 (m, 1 H), 4.01-3.82 (m, 2 H), 2.53-2.11 (m, 2 H), 2.26-2.11 (t, 1 H), 2.08-1.18 (br, 11 H). MS-ESI: m/z=575[M+1]$^+$.

Example 6-1

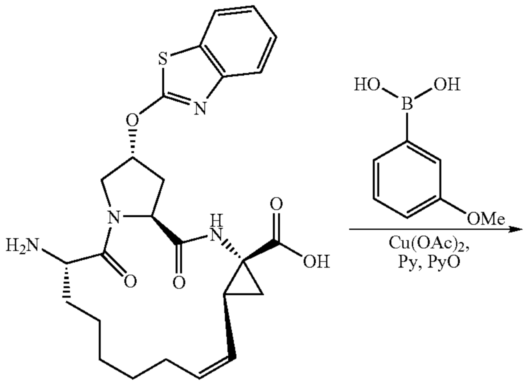

5

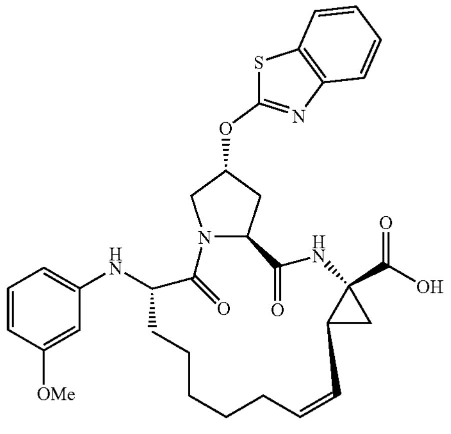

132

The acid 132 was prepared following General Method H. Isolated yield=18%. MS-ESI: m/z=605[M+1]$^+$ Example 6-2

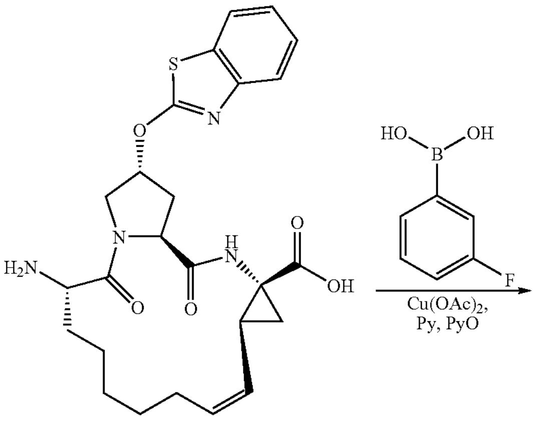

5

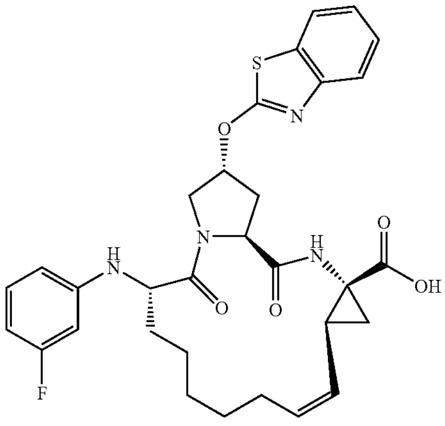

123

The acid 123 was prepared following General Method H. Isolated yield 12% MS-ESI: m/z=593[M+1]$^+$.

Example 6-3

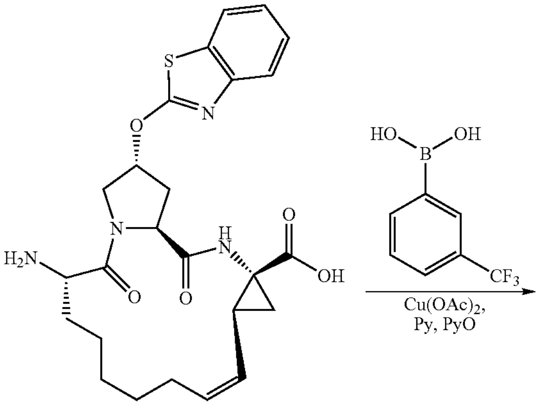

5

-continued

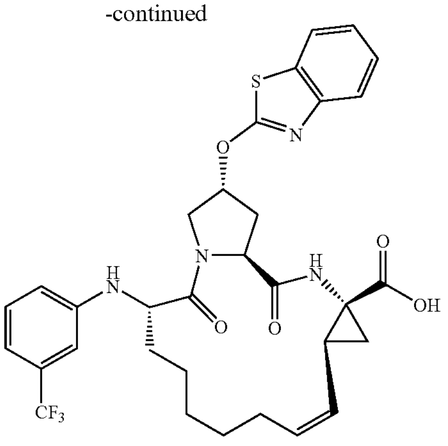

110

The acid 110 was prepared following General Method H. Isolated yield 16% MS-ESI: m/z=643[M+1]$^+$.

EXAMPLE 7

General Method I

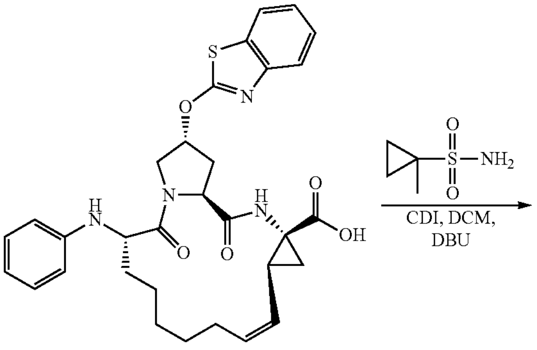

101

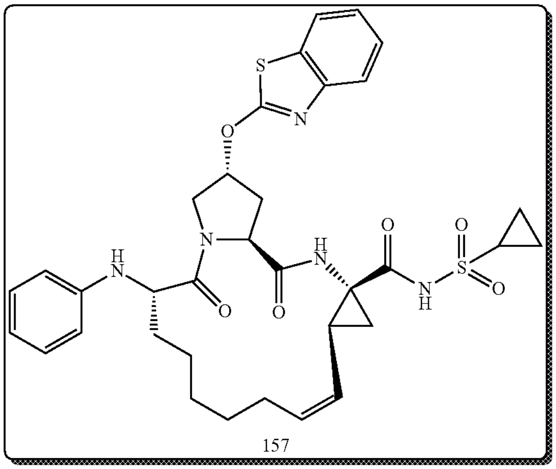

157

The compound 101 (60 mg, 0.14 mmol.) in dichloromethane (2 mL) was added to CDI (46 mg, 0.28 mmol.) in dichloromethane (1 mL), the resulting mixture was stirred at room temperature for 1 h. Subsequently, the mixture was treated with cyclopropyl sulfonamide (25 mg, 0.21 mmol.)

and DBU (0.2 mL, 5.0 eq), the resulting mixture was stirred at room temperature for another 12 h and the reaction was monitored by LCMS. After completion of the reaction, the solvent was removed and the crude was purified by prep-HPLC to afford the pure compound 157 as a white solid. Yield=20%. MS-ESI: m/z=678.2 [M+1]$^+$.

Example 7-1

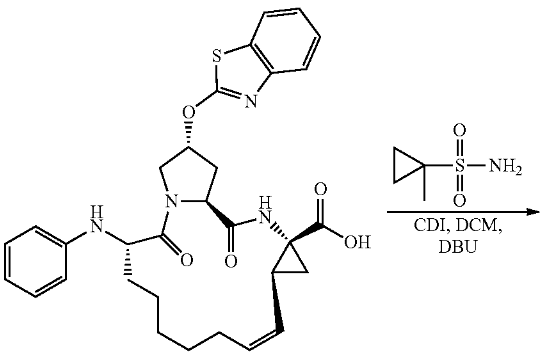

101

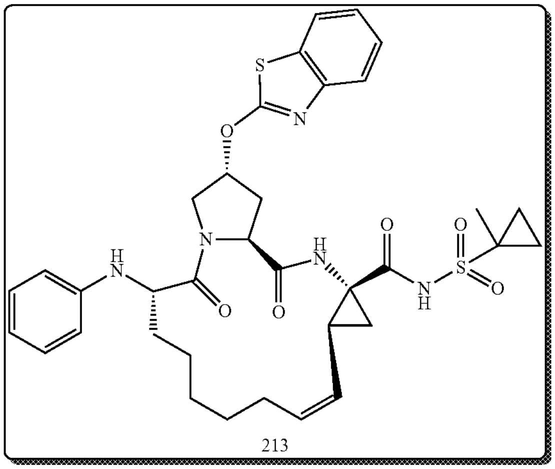

213

Compound 213 was prepared in a manner analogous to General Method I, and the yield was ~45%. MS (ESI) m/e (M+H$^+$) 692.0.

Example 7-2

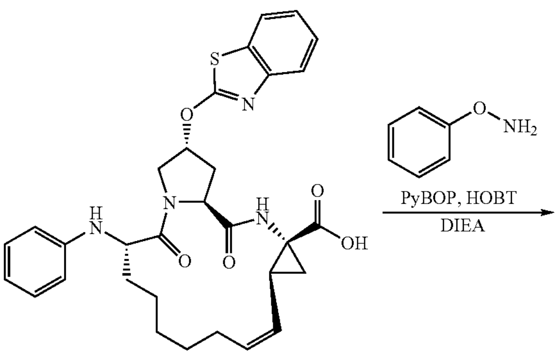

101

-continued

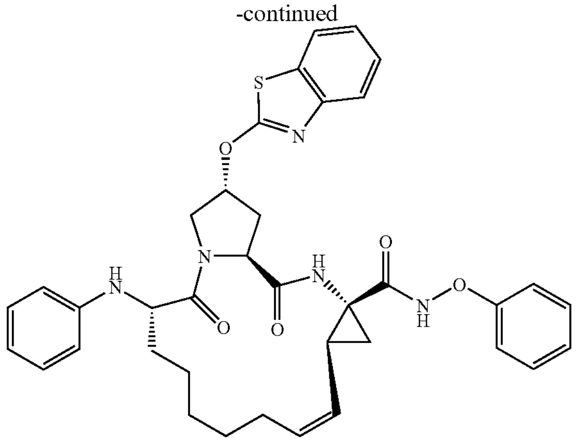

269

The hydroxamate 269 is prepared following General Method C.

EXAMPLE 8

Alternative Synthesis of Aryl Ethers

Scheme IV

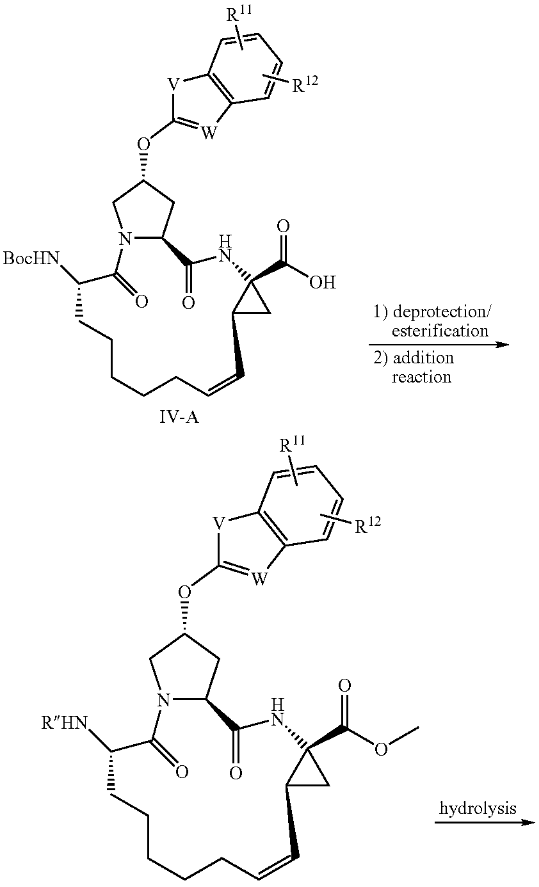

IV-A

IV-B

-continued

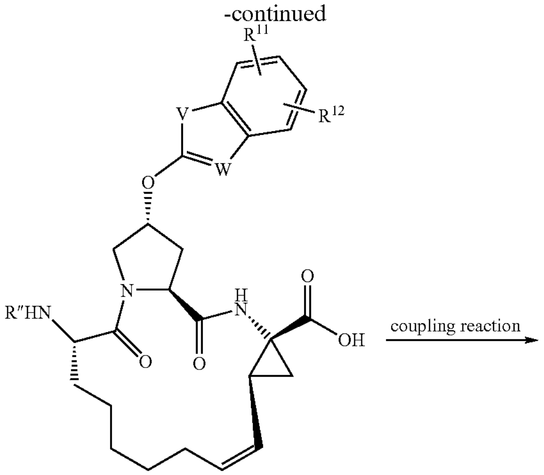

IV-C

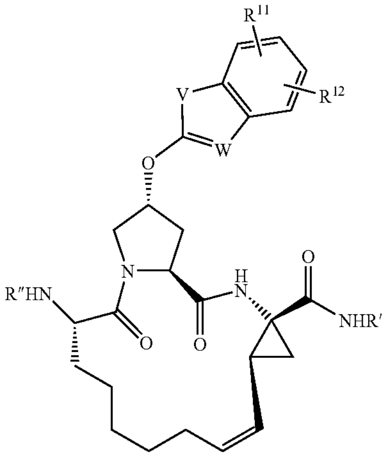

IV-D

R'=O-aryl or $SO_2$cycloalkyl; R"=$(CH_2)_n$aryl or $(CH_2)_n$heteroaryl; and n=0, 1, or 2. $R^{11}$, $R^{12}$, V, and W are as defined above.

Macrocyclics of general structures IV-D can be synthesized as shown in Scheme IV. The Boc protected carboxylic acid of general structure IV-A can be treated with acid in methanol to remove the Boc protecting group and esterify the carboxylic acid to provide a free amine and a methyl ester. The amino ester can then be coupled under appropriate conditions providing an N-substituted compound of general structure IV-B. The methyl esters of general structure IV-B can be treated under basic conditions to hydrolyse the methyl ester thereby providing carboxylic acids of general structure IV-C. Finally, acids of general structure IV-C can be coupled with sulfonamides (or sulfamides; not shown) or optionally substituted O-alkyl or aryl hydroxylamines thereby providing compounds of general structure IV-D.

Example 8-1

General Method J

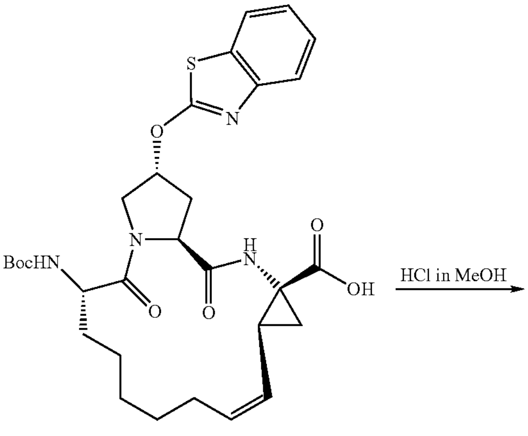

3-B

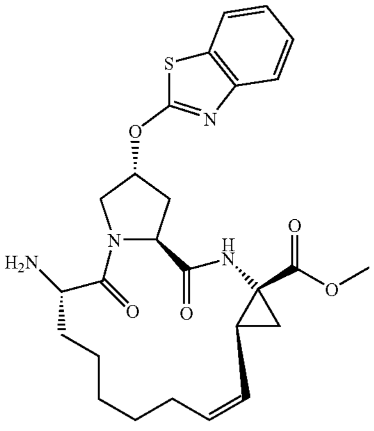

6-A

Compound 3-B was dissolved in HCl in MeOH (25 mL/g compound 14), the resulting mixture was stirred at room temperature for 12 h, after that, the solvent was removed, aqueous $NaHCO_3$ was added to neutralize the acid, then, EtOAc was added to extract the mixture, the organic layer was dried, the solvent was removed, the crude compound 6-A was used in the next step without further purification.

Example 8-2

General Method K

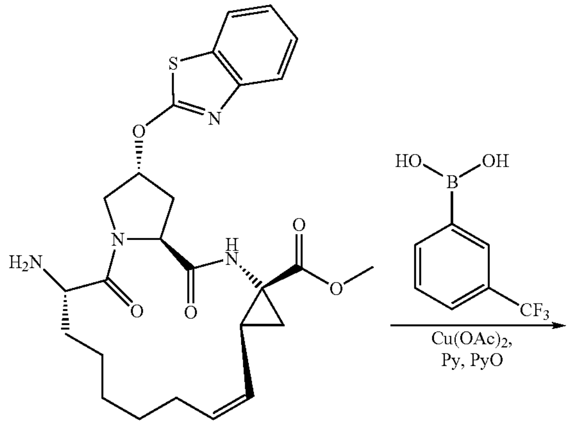

6-A

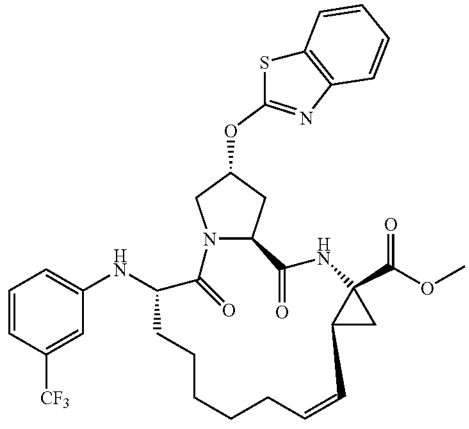

7-A

A mixture of crude compound 6-A (500 mg, 0.98 mmol.), phenylboronic acid (371 mg, 1.95 mmol.), $Cu(OAc)_2$ (249 mg, 1.37 mmol.), pyridine (387 mg, 5 mmol.), pyridine N-Oxide (93 mg, 0.98 mmol.) and molecular sieves 4 Å in dichloromethane (10 mL) was stirred for 12 h at room temperature opened to the air. The reaction was monitored by LC-MS. After completion of the reaction, the solvent was removed and the crude mixture was purified by Prep-HPLC to give the pure compound 7-A. (400 mg, isolated yield 60%).

MS-ESI: m/z=657 $[M+1]^+$ If excessive boronic acid is used, N,N diphenyl product may be obtained.

Example 8-3

General Method L

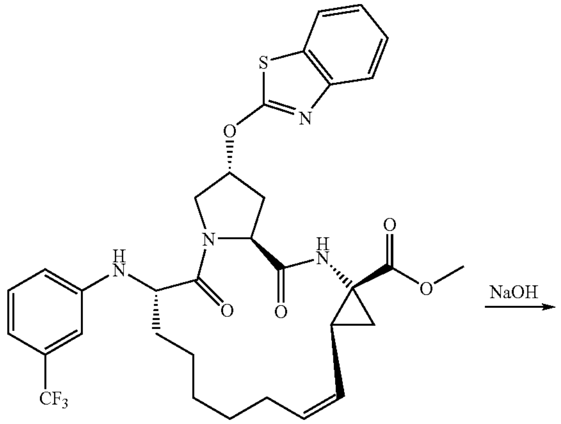

7-A

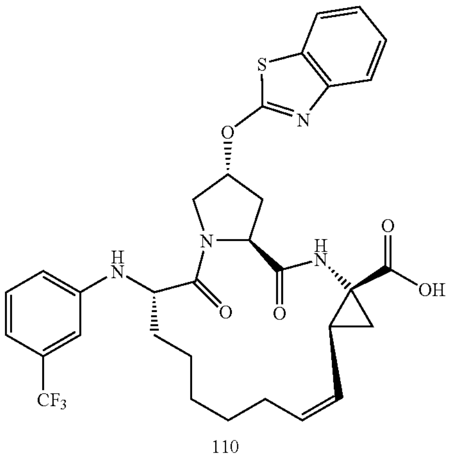

110

The compound 7-A (400 mg, 0.61 mmol.) was dissolved in methanol (5 mL), then NaOH (488 mg, 12.2 mmol.) and water (1 mL) were added, the resulting mixture was stirred at rt for 12 h, after completion of the reaction, 2M HCl was added to acidify the mixture to pH=4-5, EtOAc was added toextract the mixture, the organic layer was dried, and the solvent was removed to afford the acid 110.

Preparation of NS3 Inhibitors: Section III
EXAMPLE 9
Scheme V: General Route for Synthesis of Aryl amine precursors
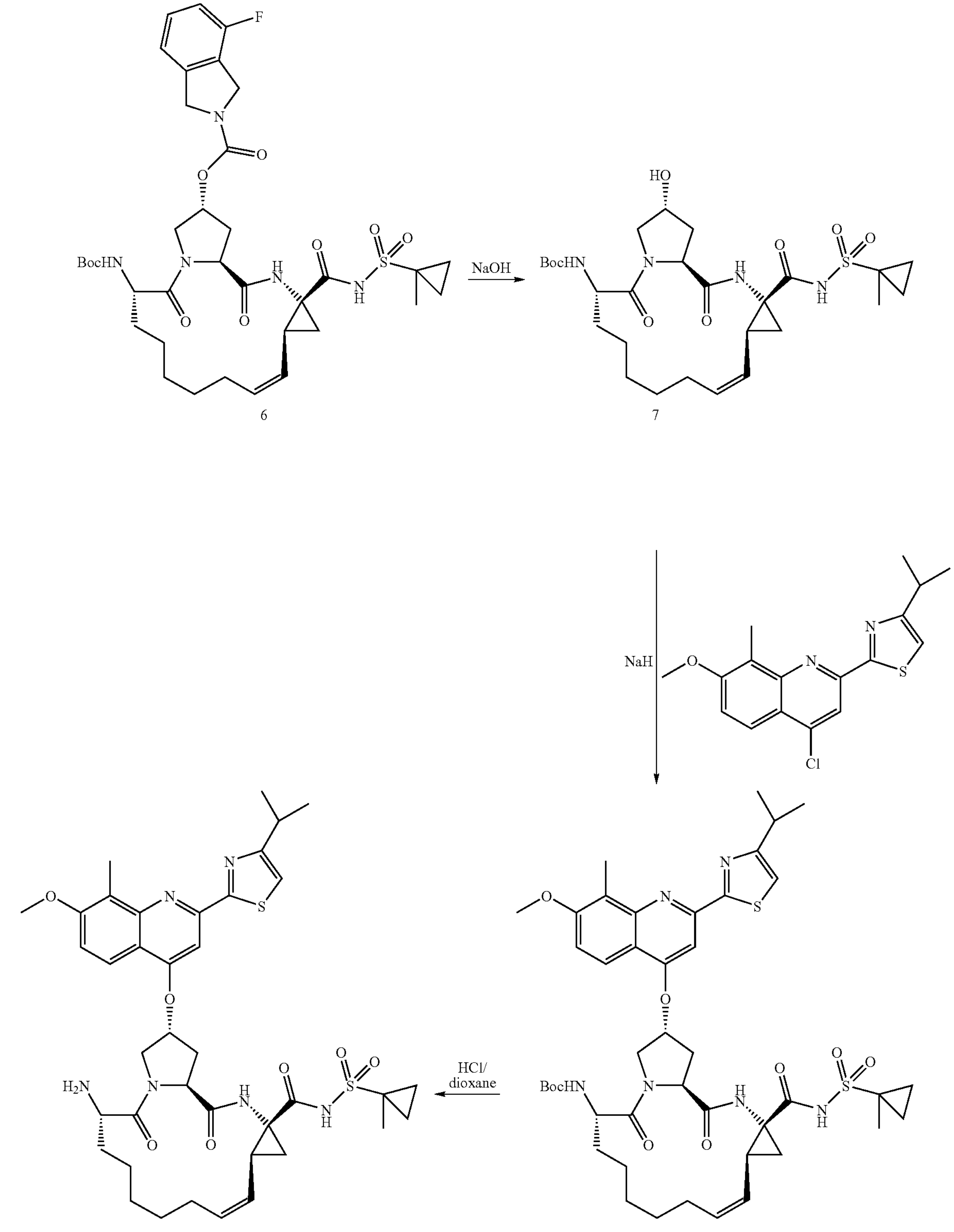
6
7
8
9

Compound 9 can be synthesized as shown in Scheme V. The isoindoline carbamate 6 can be treated under basic conditions, for example sodium hydroxide in ethanol, to hydrolyse the isoindoline carbamate thereby providing alcohol 7. The alcohol 7 can be treated with 2-(4-isopropylthiazol-2-yl)-4-chloro-7-methoxy-8-methyl-quinoline under basic conditions, for example sodium hydride in DMF, to afford compound 8. Compound 8 can be treated under acidic conditions, for example HCl in dioxane, to remove the Boc protecting group thereby forming compound 9.

Example 9-1

General Method M

7

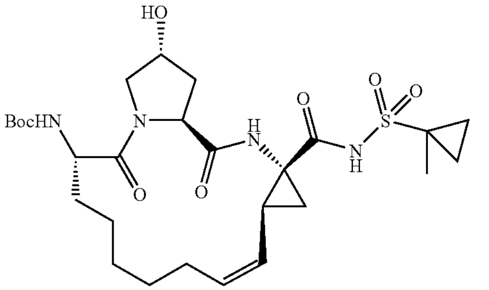

A mixture of carbamate 6 (8.4 g, 11.3 mmol.), ethanol (60 mL) and 2 N aqueous sodium hydroxide (57 mL) was refluxed for 4 h. Ethanol was removed by evaporation and the residue was dissolved in water. Hydrochloric acid (2N) was added to pH 2-3 and the precipitated compound was extracted with ethyl acetate. The organic phase was dried over magnesium sulfate and evaporated. The residue was crystallized from methanol (30 mL) to give the target hydroxy compound 7 as a white solid. Yield 5.12 g (77.7%). $^1$H-NMR (DMSO-d$^6$), δ: 10.87 (s, 1 H), 8.98 (s, 1 H), 6.99 (d, 1 H), 5.61 (dt, 1 H), 5.14 (d, 1 H), 4.95 (dd, 1 H), 4.44 (m, 1 H), 4.36 (dd, 1 H), 4.05-4.18 (m, 2 H), 3.74-3.77 (m, 1 H), 3.67 (dd, 1 H), 2.39-2.48 (m, 1 H), 2.31 (dd, 1 H), 1.94-2.08 (m, 2 H), 1.70-1.90 (m, 2 H), 1.60 (dd, 1 H), 1.10-1.52 (m, 21 H), 0.84-0.92 (m, 2 H).

Example 9-2

General Method MA

8

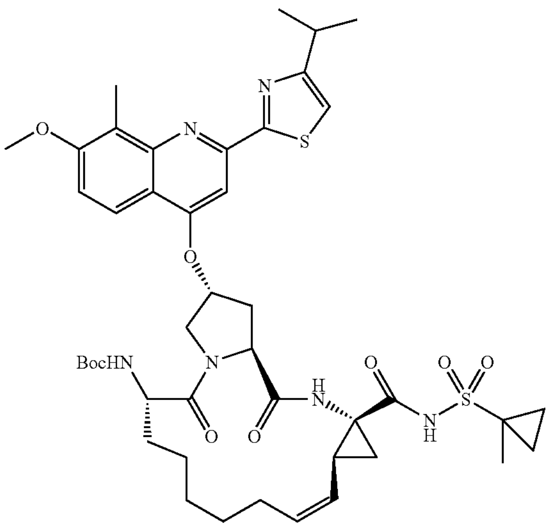

Compound 7 (292 mg, 0.5 mmol.) was co-evaporated with DMF and then dissolved in anhydrous DMF (5 mL). After cooling to 0° C. sodium hydride (80 mg, 60% mineral oil dispersion, 2 mmol.) was added and the reaction mixture was stirred at room temperature until hydrogen formation subsided (15-20 min). 2-(4-isopropylthiazol-2-yl)-4-chloro-7-methoxy-8-methyl-quinoline (200 mg, 0.6 mmol.) was added and the reaction was stirred overnight at room temperature. The reaction mixture was diluted with water, acidified to pH 2-3 with 2N hydrochloric acid and extracted with ethyl acetate. The organic phase was washed with water, dried over magnesium sulfate, and evaporated. Compound 8 was isolated by column chromatography in 25% acetone-hexane. Yield 220 mg (50.1%). Pale-yellow foam. $^1$H-NMR (DMSO-d$^6$), δ: 10.85 (s, 1 H), 9.00 (s, 1 H), 8.08 (d, 1 H), 7.53 (s, 1 H), 7.46 (s, 1 H), 7.28 (d, 1 H), 7.15 (d, 1 H), 5.66 (m, 1 H), 5.60 (dt, 1 H), 5.05 (dd, 1 H), 4.70 (d, 1 H), 4.46 (dd, 1 H), 4.01-4.06 (m, 1 H), 3.93 (s, 3 H), 3.91 (m, 1 H), 3.18 (m, 1 H), 2.62-2.70 (m, 2 H), 2.58 (s, 3 H), 2.30-2.46 (m, 2 H), 1.62-1.80 (m, 2 H), 1.48-1.60 (m, 2 H), 1.25-1.46 (m, 16 H), 1.10-1.22 (m, 11 H), 0.80-0.92 (m, 2 H).

Example 9-3

General Method MB

9

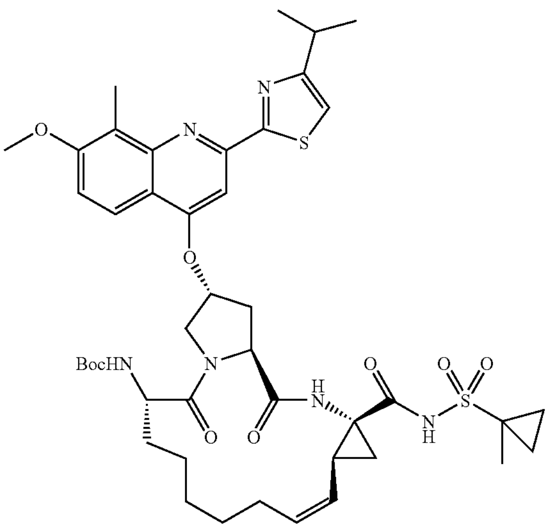

Compound 8 (220 mg, 0.25 mmol.) was dissolved in DCM (5 mL) and treated with 4N HCl-dioxane (1 mL, 4 mmol.). After stirring for 2 h at room temperature the solid was filtered off, washed with ethyl acetate, and dried in vacuo to provide to desired product compound 9. Yield: 170 mg (83.4%; HCl salt). Yellow solid. $^1$H-NMR (DMSO-d$^6$), δ: 10.86 (s, 1 H), 9.26 (s, 1 H), 8.29 (m, 3 H), 8.09 (d, 1 H), 7.58 (s, 1 H), 7.49 (s, 1 H), 7.44 (d, 1 H), 5.72 (m, 1 H), 5.62 (dt, 1 H), 5.11 (dd, 1 H), 4.55 (dd, 1 H), 4.32 (d, 1 H), 4.26 (m, 1 H), 4.08 (dd, 1 H), 3.87 (s, 3 H), 3.17 (m, 1 H), 2.74 (dd, 1 H), 2.56 (s, 3 H), 2.40-2.59 (m, 2 H), 2.21 (dt, 1 H), 1.82-1.94 (m, 1 H), 1.64-1.82 (m, 2 H), 1.61 (dd, 1 H), 1.53 (dd, 1 H), 1.16-1.50 (m, 17 H), 0.88 (m, 2 H).

EXAMPLE 10

Scheme VI

Synthesis of Acylsulfonamide Alcohol Precursor

General Method N

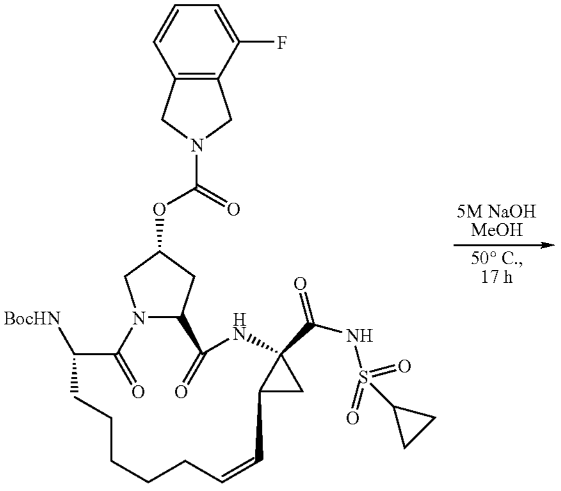

10

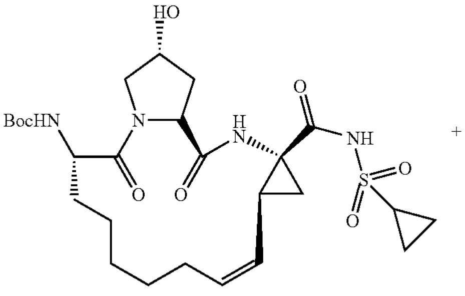

11

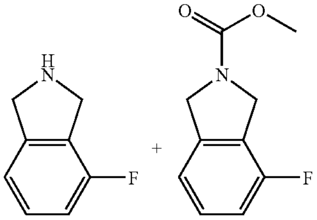

12 13

Example 10-1

To a solution of the carbamate 10 (1.00 g, 1.37 mmol.) in methanol (10 mL) was added aqueous NaOH (5 M, 8.6 mL). The mixture was heated to 50° C., additional methanol (10.0 mL) was added to fully dissolve remaining solids. The resulting clear solution was stirred at 50° C. for 17 h, HPLC showed complete reaction: Shimadzu MS 17 3 minute method ELSD 0.23 mins (50%) MH+ 138; 1.90 mins (44%) MH+ 569.

Example 10-2

11

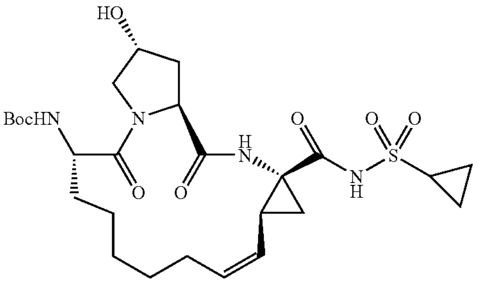

The solution was cooled below 10° C. and 2 M aqueous hydrochloric was added slowly until pH 4, significant product had precipitated at this stage. The resulting gum and aqueous solution was stirred with ethyl acetate (30 mL) until all was in solution. The aqueous layer was further extracted with ethyl acetate (3x30 mL). The combined organic layers were washed twice with brine, dried over $Na_2SO_4$ and evaporated under reduced pressure to give the crude product 11 as a beige solid—0.88 g. HPLC—ELSD 1.90 mins (99.1%) MH+ 569.

Example 10-3

13

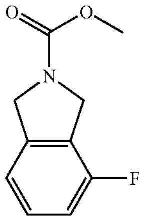

The crude solid 11 was dissolved in dichloromethane and columned on 25 g of silica gel. The solvent was changed to TBME which rapidly eluted a non-polar impurity, 82 mg, pale brown solid, found to be the methylcarbamate derivative 13 of the isoindoline—31% yield. HPLC—ELSD no signal, UV 1.76 mins (96%) MH+ 196. $^1H$ NMR (250 MHz, $CDCl_3$) δ ppm 7.19-7.33 (m, 1 H), 6.88-7.10 (m, 2 H), 4.74 (dd, J=9.9, 3.8 Hz, 4 H), 3.79 (s, 3 H).

Example 10-4

11

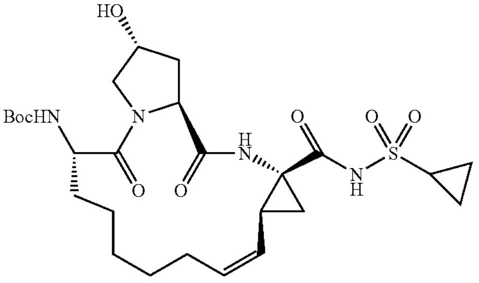

Further elution gave product 11 as a very pale beige solid. Yield 480 mg (62%). Additional product was still eluting slowly. $^1H$ NMR (250 MHz, $CDCl_3$) δ ppm 10.60 (br. s, 0.2 H), 10.46 (s, 0.8 H), 8.48 (br. s, 0.2 H), 7.74 (s, 0.8 H), 6.60 (br. s, 0.2 H), 5.56-5.81 (m, 1 H), 5.34 (m, 0.8 H), 4.85-5.03 (m, 1 H), 4.41-4.73 (m, 2 H), 4.28 (br. s, 1 H), 3.39-4.10 (m, 3 H), 2.73-2.98 (m, 1 H), 2.06-2.63 (m, 4 H), 1.68-2.05 (m, 3 H), 1.20-1.67 (m, 17 H), 0.65-1.13 (m, 4 H).

EXAMPLE 11

Scheme VII

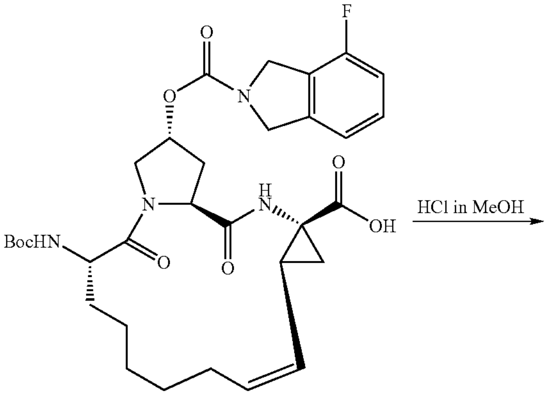

1

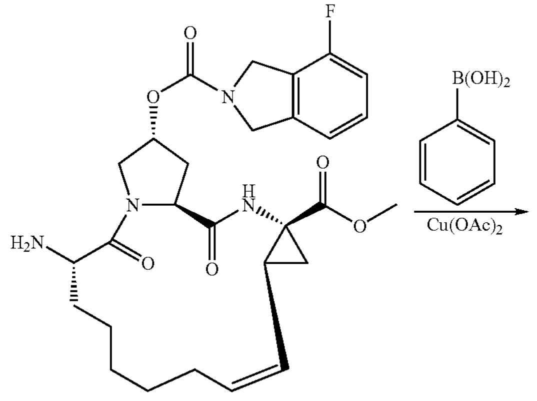

12

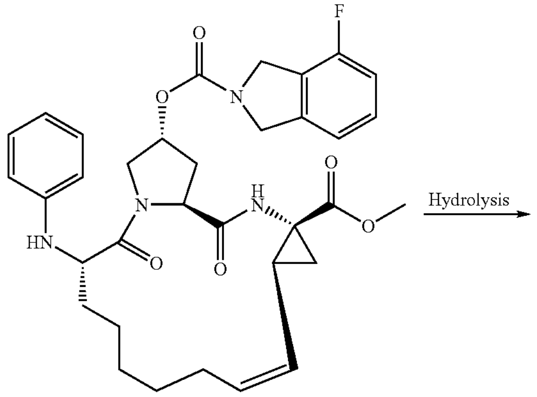

13

-continued

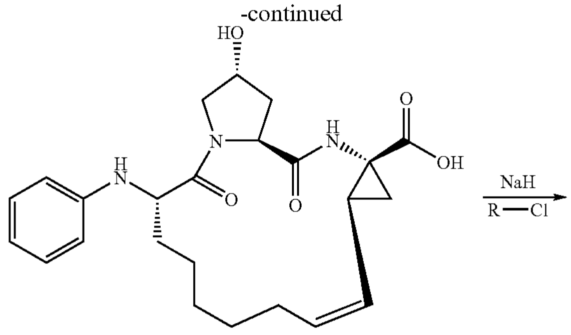

14

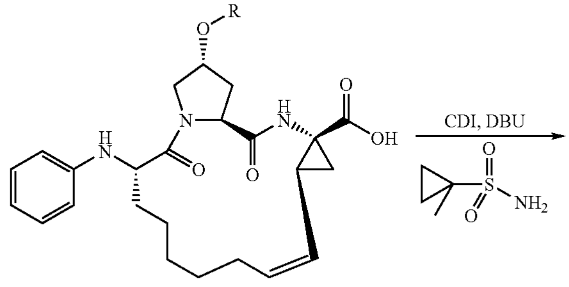

VII-A

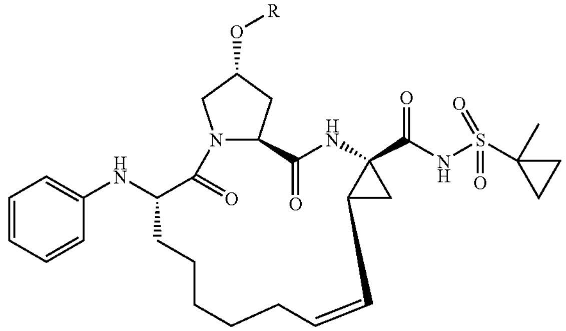

VII-B

Macrocyclics of general structures VII-A and VII-B can be synthesized as shown in Scheme VII. The isoindoline carbamate 1 can be treated with acid in methanol to remove the Boc protecting group and form a methyl ester thereby providing compound 12. Compound 12 can be treated with optionally substituted aryl boronic acids, for example phenyl boranic acid, under $Cu^{2+}$- catalyzed conditions thereby providing N-aryl compounds, such as compound 13. Compound 13 can be treated under basic conditions to hydrolyse the methyl ester and the isoindoline carbamate thereby providing hydroxy acid 14. The hydroxy acid 14 can be treated with a heteroaryl chloride, such as 2-chlorobenzothiazole, 2-chloro-6-methylbenzothiazole, 6-bromo-2-chlorobenzothiazole, 2,6-dichlorobenzothiazole, 2-chlorobenzoxazole, 2-chloro-1-ethyl-1H-benzoimidazole, and 2-chloro-1-isopropyl-1H-benzoimidazole and the like, under basic conditions to afford a compound of general structure VII-A. Finally, acids of general structure VII-A can be coupled with sulfonamides (or sulfamides, not shown) thereby providing compounds general structure VII-B.

Example 11-1

General Procedure G

Compound 1 (3.0 g) was dissolved in HCl in MeOH (25 mL/g compound 1), the resulting mixture was stirred at room temperature for 12 h. The solvent was removed then aqueous $NaHCO_3$ was added to neutralize any remaining acid. The basic mixture was extracted by EtOAc. The EtOAc layer was dried and then the solvent was removed to afford a crude residue. The crude compound 12 (2.8 g) was used in the next step without further purification.

Example 11-2

General Procedure O

A mixture of compound 12 (400 mg, 0.80 mmol.), phenylboronic acid (146.8 mg, 1.2 mmol.), $Cu(OAc)_2$ (188 mg, 1.0 mmol.), pyridine (316 mg, 4 mmol.), pyridine N-Oxide (76 mg, 0.8 mmol.) and molecular sieves 4 Å in dichloromethane (10 mL) was stirred for 12 h at room temperature opened to the air. Another 1.5 eq boronic acid was added and the reaction was stirred until completion of the reaction. The reaction was monitored by LC-MS. After completion of the reaction, the solvent was removed and the crude mixture was purified by Prep-HPLC to afford pure compound 13, (400 mg, isolated yield 75%).

Example 11-3

General Procedure P

To a stirring solution of compound 13 (400 mg, 0.56 mmol) in methanol (10 mL) was added 5 M NaOH solution (2 mL), the resulting mixture was heated to 50° C. and continued stirring overnight. Subsequently, the mixture was cooled to 0° C. (ice water bath), then 2 M HCl was carefully added to lower the pH (pH=3-4). The acidic mixture was extracted by EtOAc. The combined organic layers were washed by brine and dried. The solvent was removed under reduced pressure and the crude compound 14 (380 mg) was used without further purification in the next step.

Example 11-4

General Procedure Q

A solution of compound 14 (380 g, 1 mL/100 mg compound 14) in DMF was added slowly to a mixture of NaH was dissolved in DMF (1.5 mL/100 mg NaH), cooled to 0-5° C. The mixture was stirred for 2 h at 0-5° C., then heteroaryl halide (R—Cl) was added, the resulting mixture was warmed to room temperature and stirred for 12 h. The mixture was cooled to 0° C. (ice water bath), then 2 M HCl was carefully added to lower the pH (pH=3-4). The acidic mixture was extracted by EtOAc. The combined organic layers were washed by brine and dried. The solvent was removed under reduced pressure and the crude product was purified by column chromatography to afford general compound VII-A (150 mg, 40-70% yield).

Example 11-5

General Procedure R

General compound VII-A (1 eq. in 2 mL dichloromethane) was added to CDI (2-6 equiv.) dissolved in dichloromethane (1 mL) and then stirred 1 h. Subsequently, 1-methylcyclopropane-1-sulfonamide (2-6 equiv.) and DBU (0.1 mL) were added, the resulting mixture was stirred at room temperature for another 12 h monitoring by LCMS. After completion of the reaction, the solvent was then removed and the crude product was purified by prep-TLC to give the general compound VII-B as a white solid (~20-50% yield).

Example 11-6

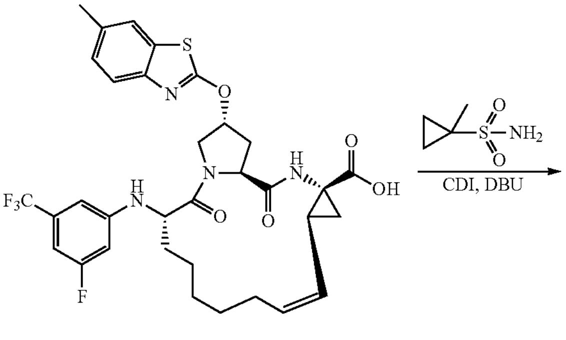

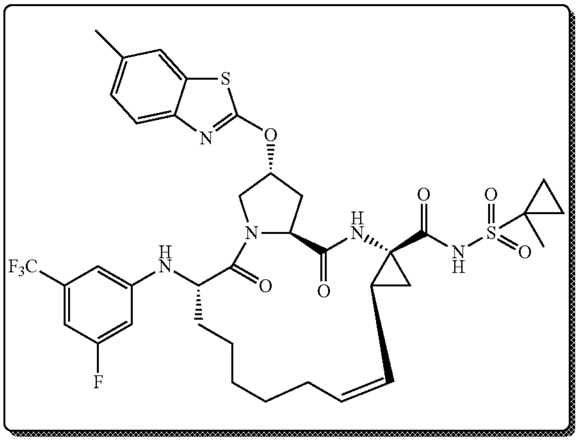

350

Compound 350 was prepared in a manner analogous to General Procedure R, and the yield is 50%. MS (ESI) m/e ($M+H^+$) 792.2.

Example 11-7

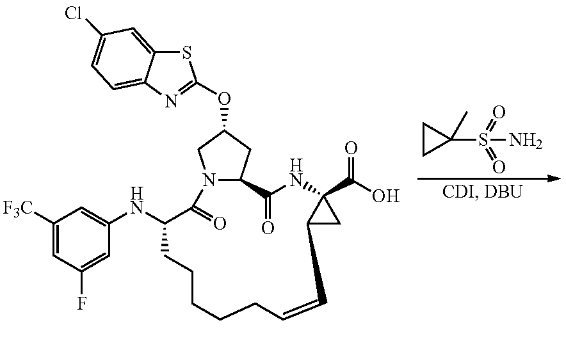

-continued
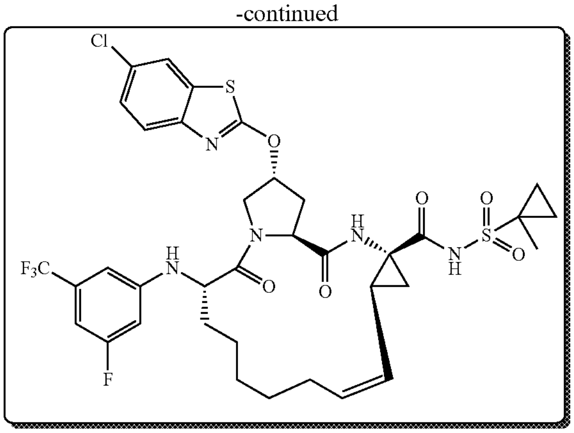
351
Compound 351 was prepared in a manner analogous to General Procedure R, and the yield is 50%. MS (ESI) m/e (M+H+) 812.2.
Example 11-8
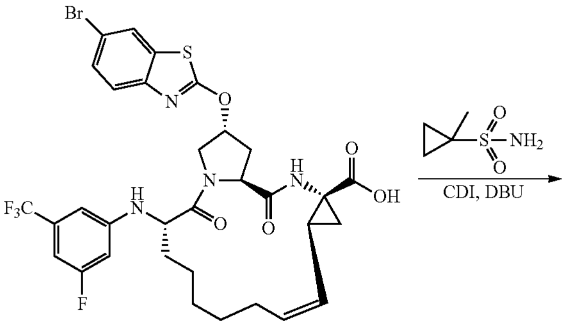
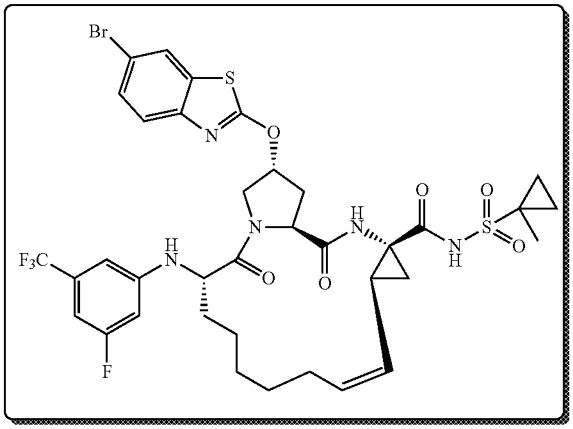
352
Compound 352 was prepared in a manner analogous to General Procedure R, and the yield is 50%. MS (ESI) m/e (M+H+) 856.
Example 11-9
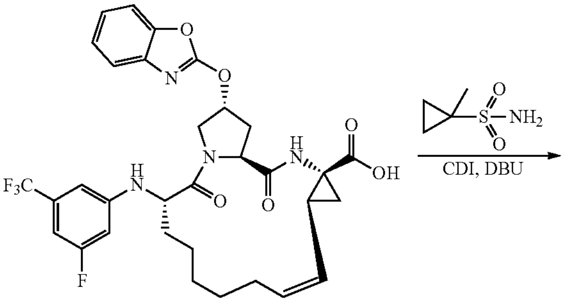
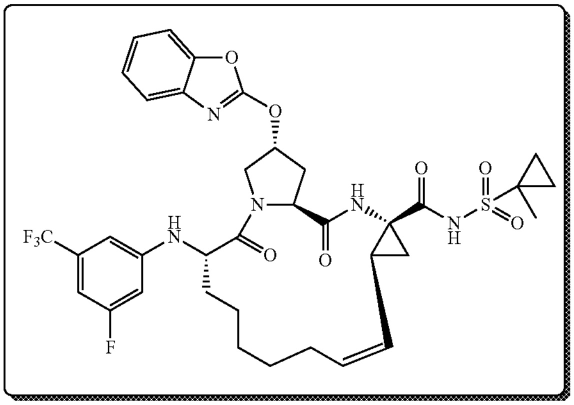
353
Compound 353 was prepared in a manner analogous to General Procedure R, and the yield is 50%. MS (ESI) m/e (M+H+) 761.
Example 11-10
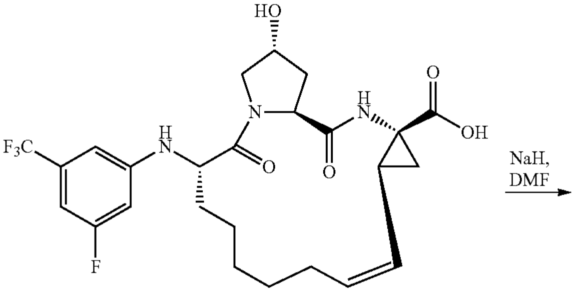
15

-continued
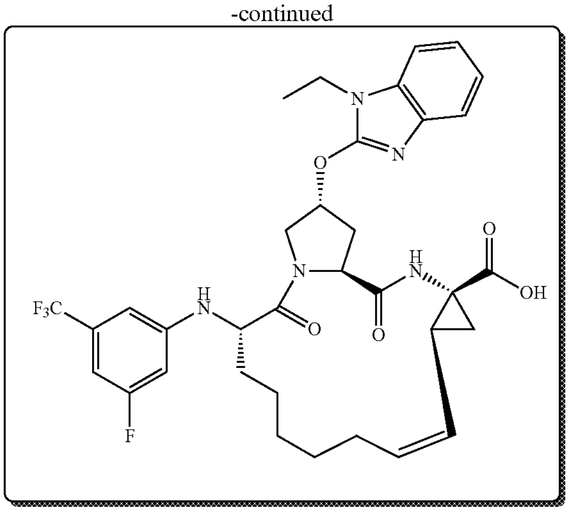
318
Compound 318 was prepared in a manner analogous to General Procedure Q, and the yield is 60%. MS (ESI) m/e (M+H$^+$) 671.3.
Example 11-11
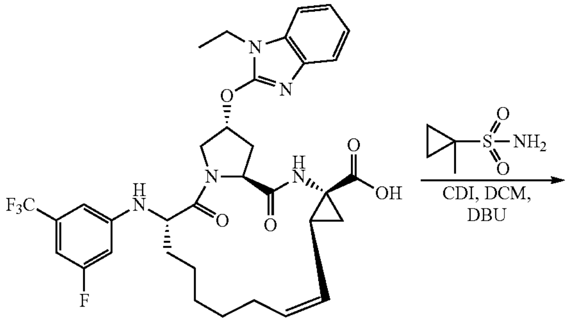
318
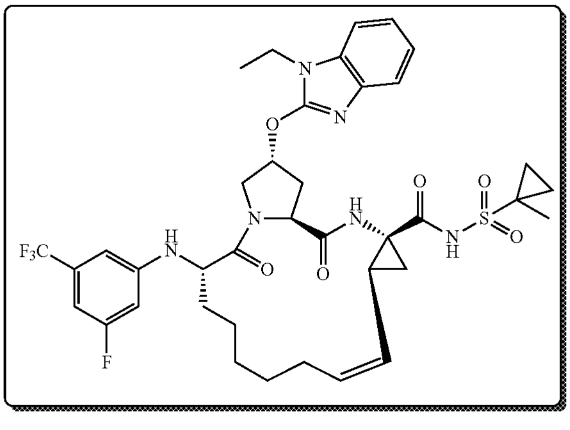
319
Compound 319 was prepared in a manner analogous to General Procedure R, and the yield is 45%. MS (ESI) m/e (M+H$^+$) 788.3.
Example 11-12
388
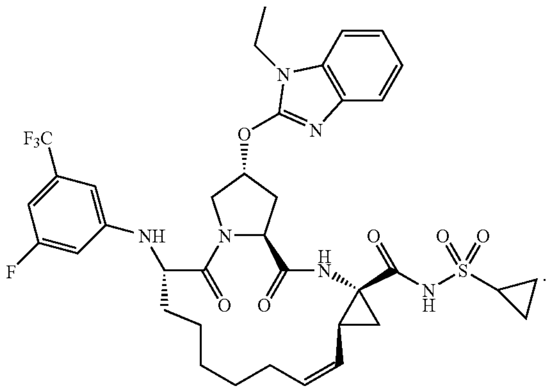
Compound 388 was prepared in a manner analogous to General Procedure R, to afford 22 mg (22.7%). MS (ESI) m/z (M+H)$^+$ 775.3.
Example 11-13
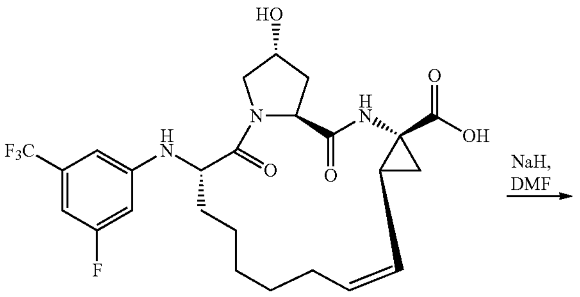
15
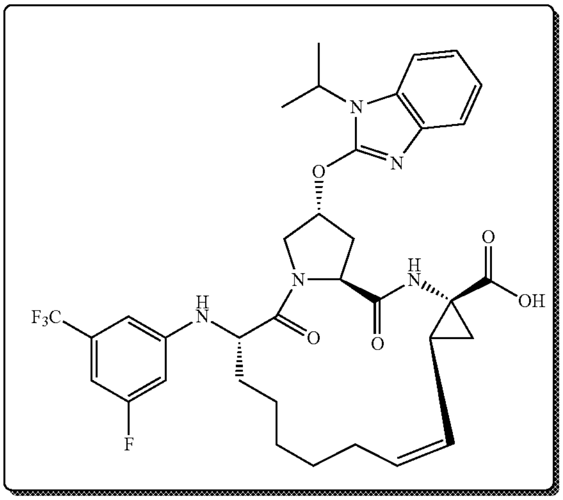
320

Compound 320 was prepared in a manner analogous to General Procedure Q, and the yield is 61%. MS (ESI) m/e $(M+H^+)$ 685.3.

Example 11-14

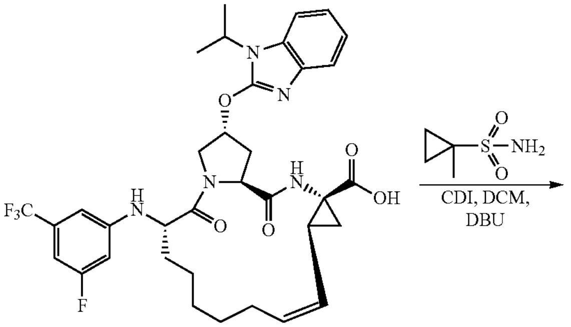

320

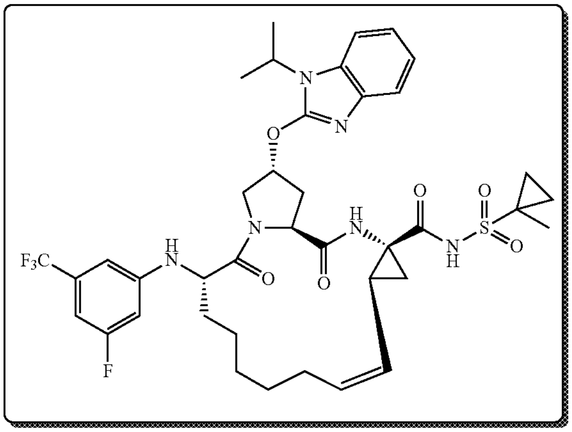

376

Compound 376 was prepared in a manner analogous to General Procedure R, and the yield was ~45%. MS (ESI) m/e $(M+H^+)$ 803.3.

Example 11-15

393

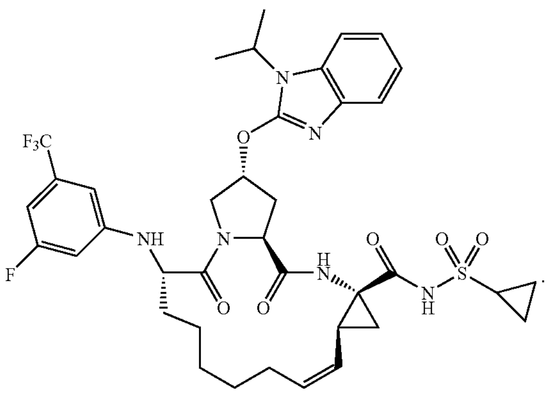

Compound 393 was prepared in a manner analogous to General Procedure F, to afford 39.2 mg (49%). MS (ESI) m/z $(M+H)^+$ 789.1.

Example 11-16

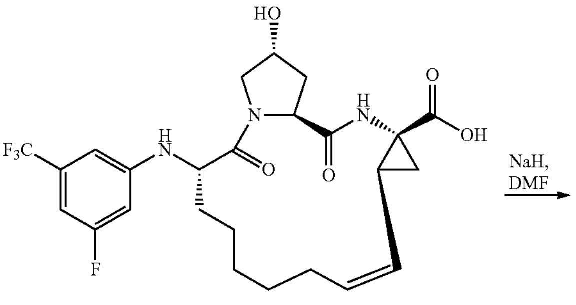

15

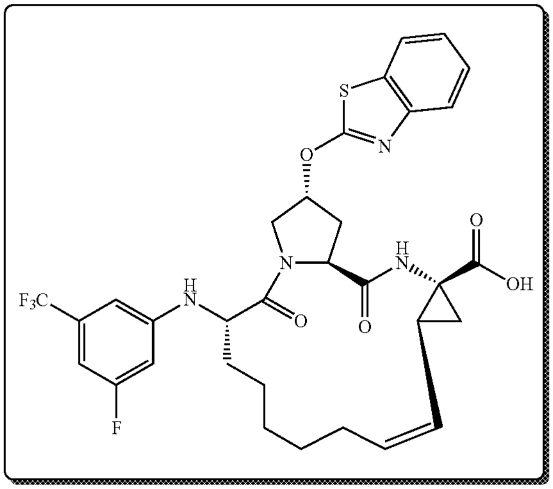

321

Compound 321 was prepared in a manner analogous to General Procedure Q, and the yield is 45%. MS (ESI) m/e $(M+H^+)$ 661.3.

Example 11-17

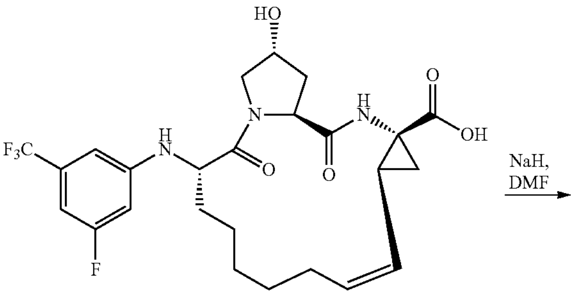

15

-continued

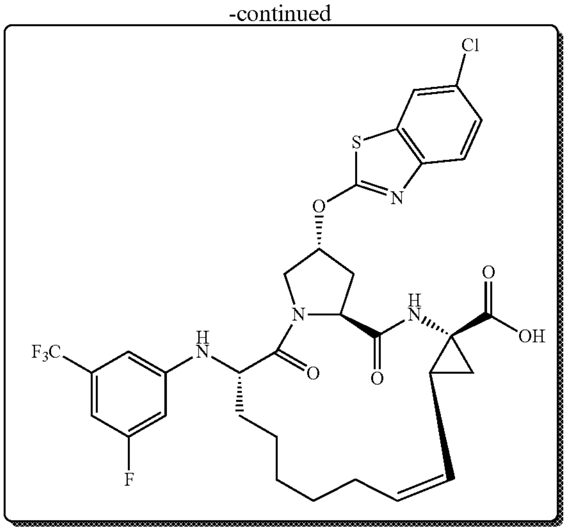

322

Compound 322 was prepared in a manner analogous to General Procedure Q, and the yield is 52%. MS (ESI) m/e ($M+H^+$) 694.2.

Example 11-18

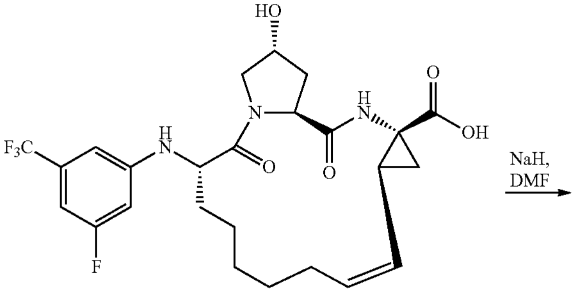

15

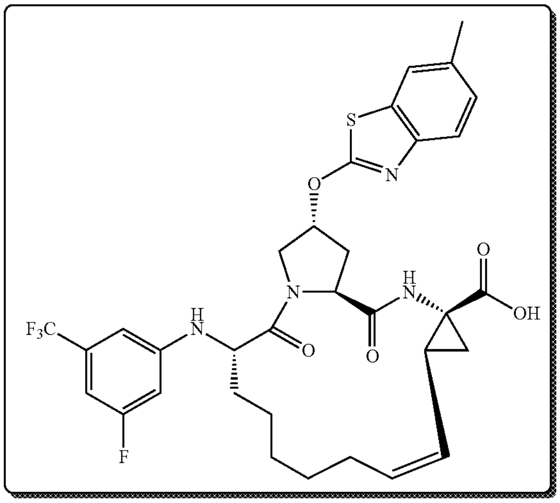

323

Compound 323 was prepared in a manner analogous to General Procedure Q, and the yield is 53%. MS (ESI) m/e ($M+H^+$) 674.2.

Example 11-19

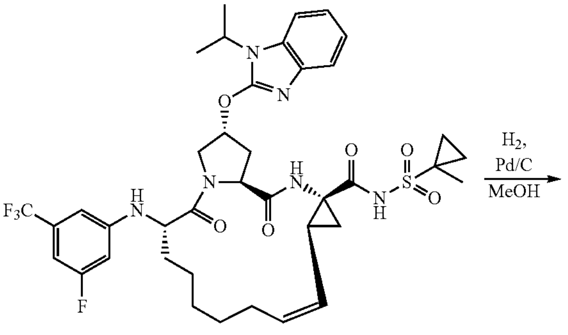

376

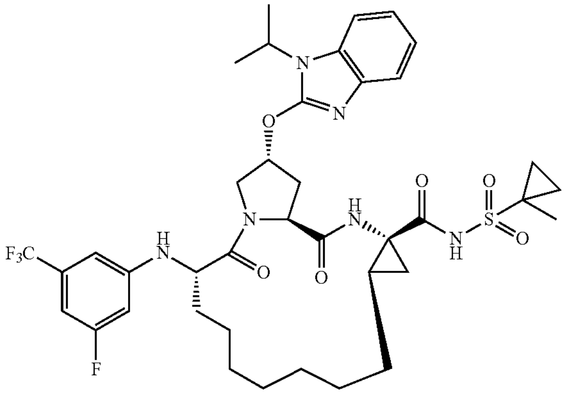

465

General Procedure RH22

To a solution of compound 376 (47 mg, 0.059 mmol.) in 3 mL of EtOAc was added catalyst (Pd/C, 10 mg, 20% wt), the mixture was degassed with hydrogen for 3 times, then the resulting mixture was stirred at room temperature under hydrogen atmosphere for 1.5 h, the reaction was monitored by LCMS. After completion of the reaction, the solid was removed by filtration, the solvent was evaporated and the crude product was purified by prep-HPLC to afford compound 465 (2.5 mg, 5.3%). MS (ESI) m/z $(M+H)^+$ 805.5.

Example 11-20

466

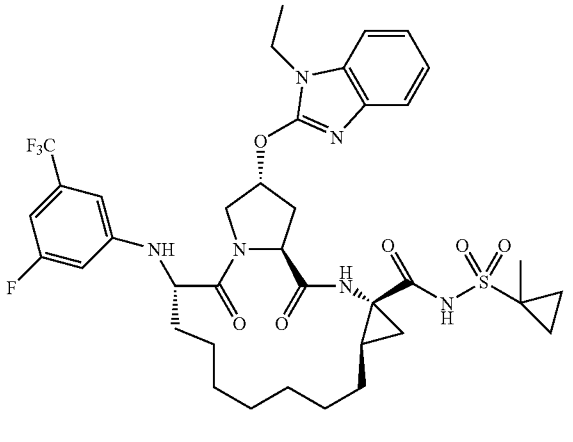

Compound 466 was prepared in a manner analogous to General Procedure RH2 to afford 90.6 mg (48%), MS (ESI) m/z $(M+H)^+$ 791.3.

Preparation of NS3 Inhibitors: Section IV

EXAMPLE 12

Scheme VIII

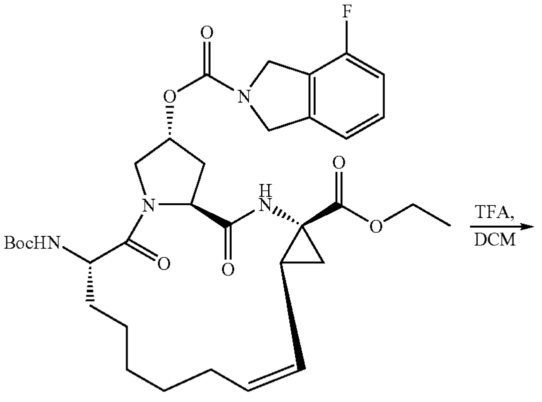

16

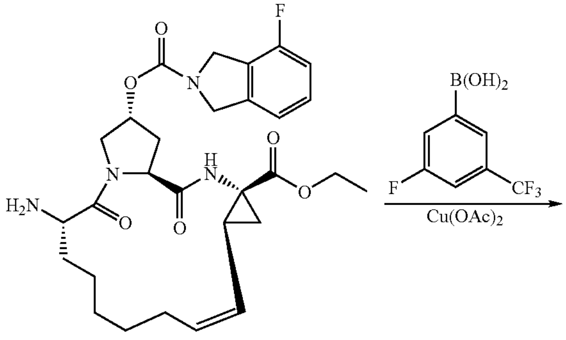

17

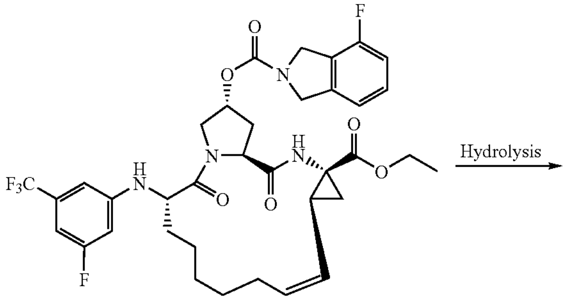

18

-continued

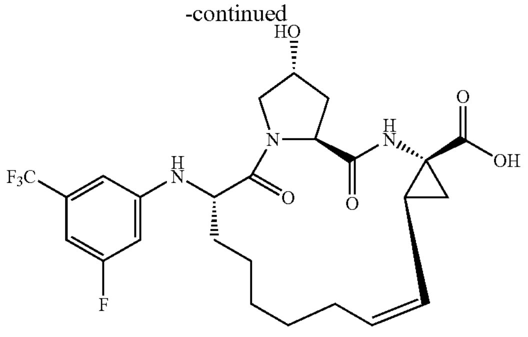

15

N-aryl amines, such as compound 15, can be synthesized as shown in Scheme VIII. The isoindoline carbamate 16 can be treated with acid, for example TFA in DCM, to remove the Boc protecting group thereby providing compound 17. Compound 17 can be treated with optionally substituted aryl boronic acids, for example 3-fluoro-5-(trifluoromethyl)phenyl boronic acid, under $Cu^{2+}$-catalyzed conditions thereby providing N-aryl compounds, such as compound 18. Finally, compound 18 can be treated under basic conditions to hydrolyse the ethyl ester and the isoindoline carbamate thereby providing hydroxy acid 15. The hydroxy acid 15 can be used to synthesize the macrocycles by further methods disclosed herein.

Example 12-1

General Procedure S

To a solution of compound 16 (100 mg, 0.15 mmol.) in 3 mL of DCM was added 3 mL of TFA, stirring was continued at rt for 2 h. The solvent was removed afford a residue. The residue was treated with water (30 mL) and then aqueous sat. $NaHCO_3$ was added to adjust the pH (pH~10). The basic aqueous solution was extracted with ethyl acetate (3×20 mL). combined organic layers were washed with brine, dried over $Na_2SO_4$, filtered and concentrated to afford compound 17 as white solid (84.7 mg, yield 100%). MS (ESI) m/e $(M+H^+)$ 556.2.

Example 12-2

General Procedure T

To a solution of compound 17 (1 g, 1.8 mmol.) in 15 mL of DCM was added 4 Å molecular sieves, $Cu(OAc)_2$ (0.9 g, 4.5 mmol.), 3-fluoro-5-(trifluoromethyl)phenylboronic acid (0.75 g, 3.6 mmol.), pyridine (2.8 g, 36 mmol.) and pyridine N-Oxide (0.4 g, 4.5 mmol.) sequentially at 25° C. The resulting mixture was stirred at same temperature for 48 h. The mixture was concentrated to afford a residue, which was purified by Prep-TLC to afford 18 as white solid (760 mg, yield 58.9%). MS (ESI) m/e $(M+H^+)$ 718.3.

Example 12-3

General Procedure U

To a solution of compound 18 (100 mg, 0.14 mmol.) in 5 mL of ethanol was added 5 mL of aq. NaOH (20%) at 50° C. The resulting mixture was stirred at the same temperature overnight. The ethanol was removed under reduced pressure to afford a residue. The residue was treated with water (30 mL), and then aqueous diluted HCl was added to adjust the pH (pH-3). The acidic aqueous layer was extracted with ethyl acetate (3×30 mL). The combined organic layers were washed with brine, dried over $Na_2SO_4$, filtered, and concentrated to afford compound 15 as a white solid (73 mg, yield 100%). MS (ESI) m/e ($M+H^+$) 527.
Example 12-4
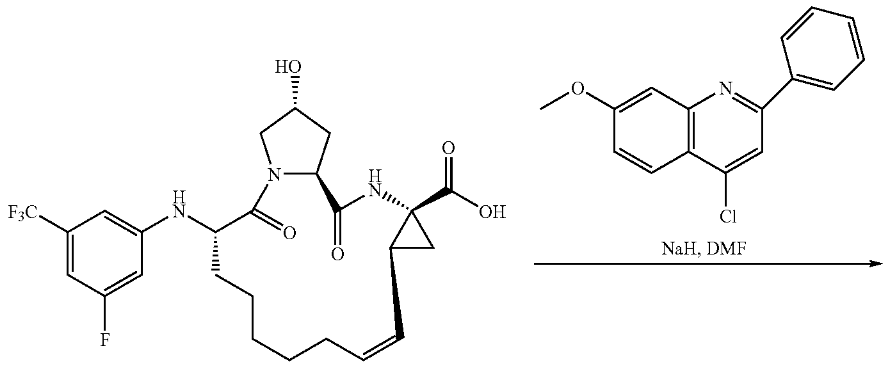
15
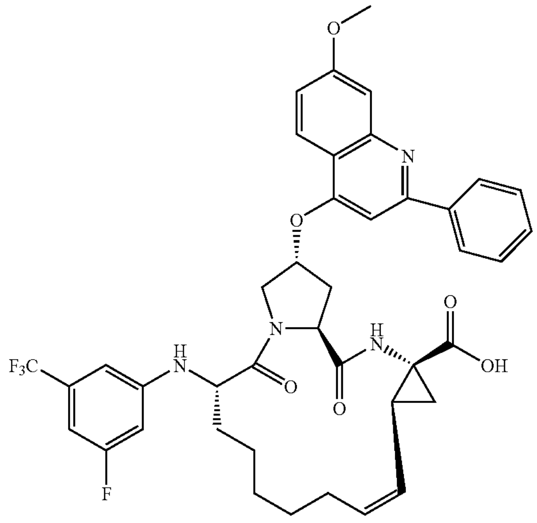
354

Compound 354 was prepared in a manner analogous to General Procedure B, and the yield is 20%. MS (ESI) m/e $(M+H^+)$ 760.7.
Example 12-5
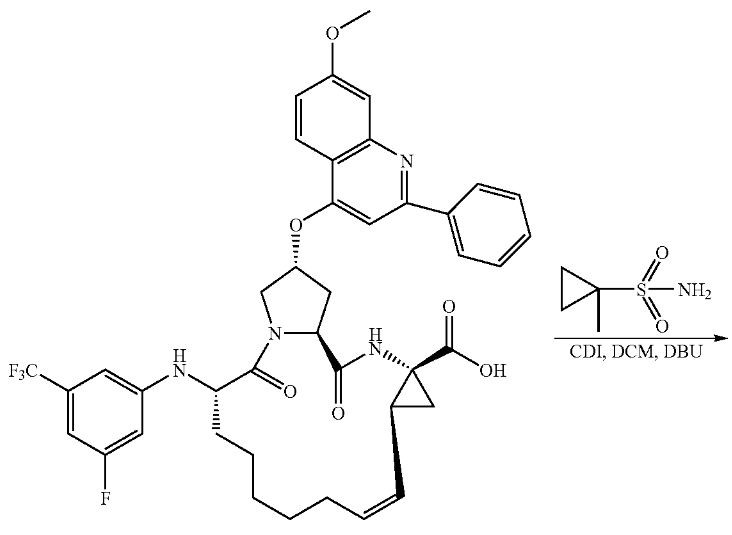
354
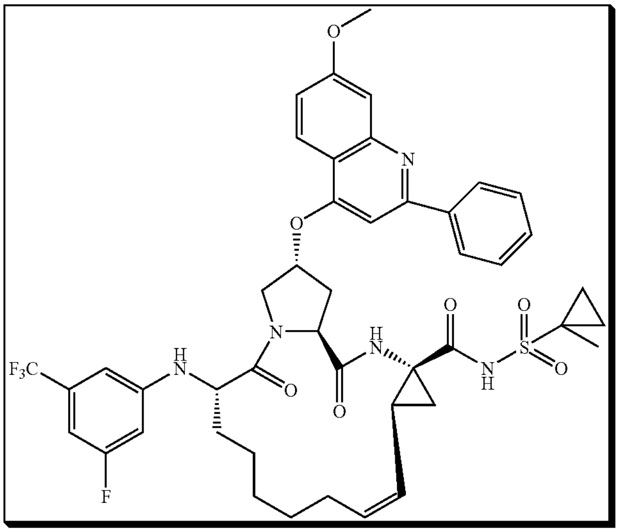
355

Compound 355 was prepared in a manner analogous to General Procedure F, and the yield is 30%. MS (ESI) m/e $(M+H^+)$ 877.9.

Preparation of NS3 Inhibitors: Section V

EXAMPLE 13

Scheme IX: Synthesis of O-Benzothiazole N- Thiazole Acylsulfonamides

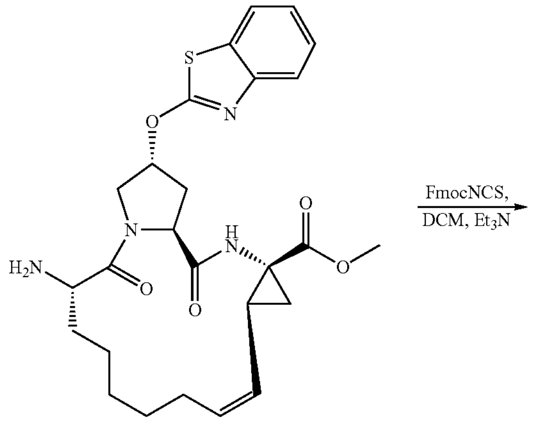

19

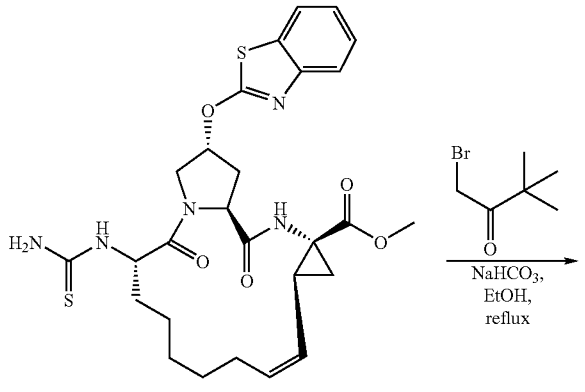

20

-continued

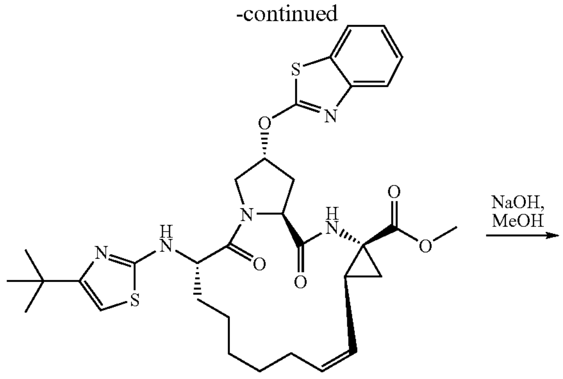

21

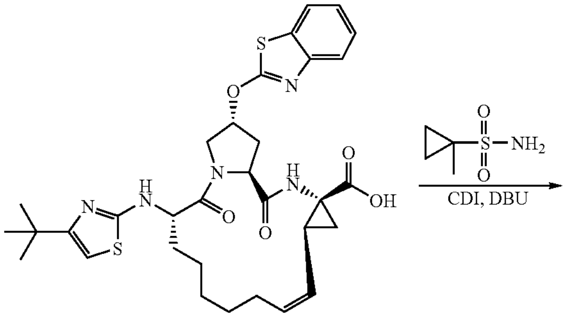

119

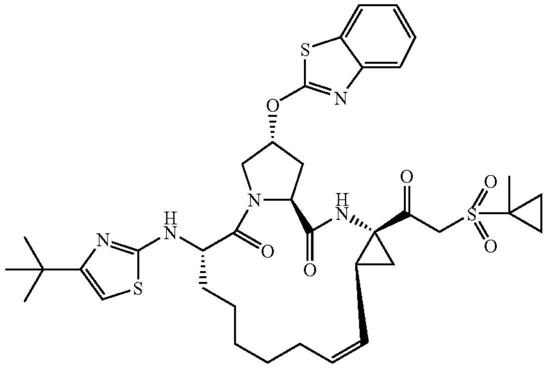

231

N-thiazole amines, such as compound 231, can be synthesized as shown in Scheme IX. Compound 19 can be treated with 9-fluorenylmethoxycarbonyl isothiocyanate (Fmoc-NCS) to afford thiourea 20. Thiourea 20 can be treated with α-bromoketones, for example 1-bromo-3,3-dimethylbutan-2-one, under basic conditions thereby providing N-thiazole esters, such as compound 21. Compound 21 can be treated under basic conditions to hydrolyse the ethyl ester thereby providing carboxylic acids, such as compound 119. Finally, carboxylic acids, for example compound 119, can be coupled with sulfonamides (or sulfamides, not shown) thereby providing acyl sulfonamides, such as compound 231.

Example 13-1

General Procedure

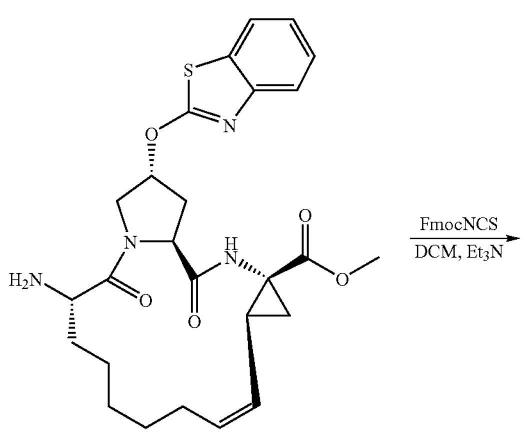

19

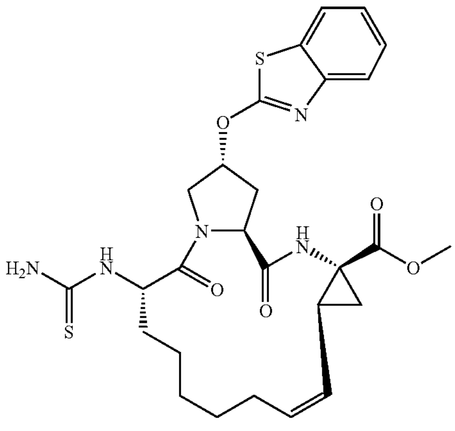

20

To a solution of compound 19 (512 mg, 1 mmol.) and FmocNCS (281 mg, 1 mmol.) in DCM (5 mL) at 0° C. was added $Et_3N$ (5 mL, 3 mmol.) in one portion. The reaction mixture was allowed to rt and stirred 0.5 hour. Subsequently, the reaction was purified by prep-TLC to afford 400 mg of desired product 20 as white solid (70% yield).

Example 13-2

General Procedure I

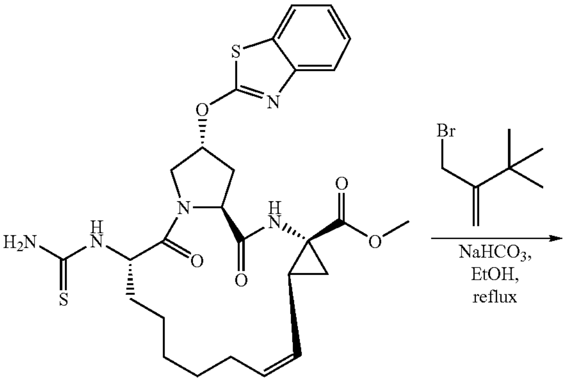

20

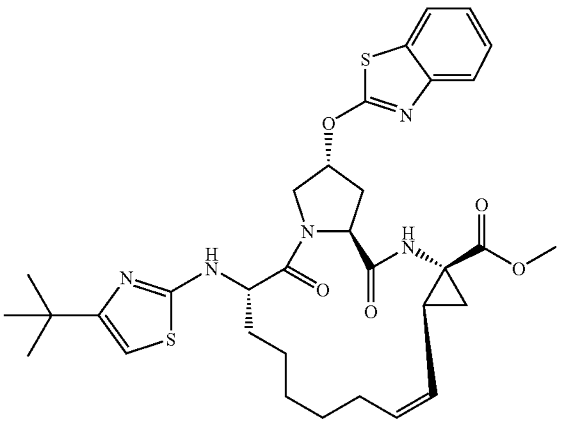

21

A mixture of compound 20 (400 mg, 0.7 mmol.), $NaHCO_3$ (120 mg, 1.4 mmol.) and 1-bromo-3,3-dimethylbutan-2-one (2.5 mL, 1.4 mmol.) in 6 mL of EtOH was refluxed for 1 hour.

The reaction mixture was cooled down and purified by prep-TLC to afford 350 mg of desired product 21 as white solid (77% yield).

Example 13-3

General Procedure J

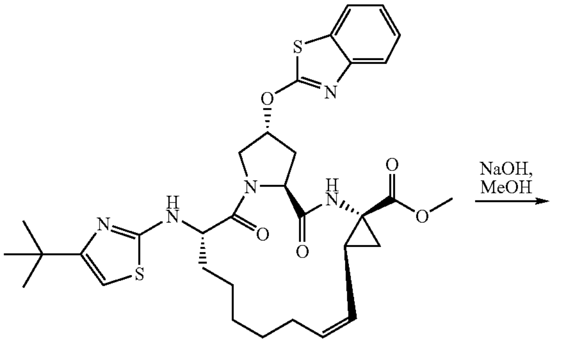

21

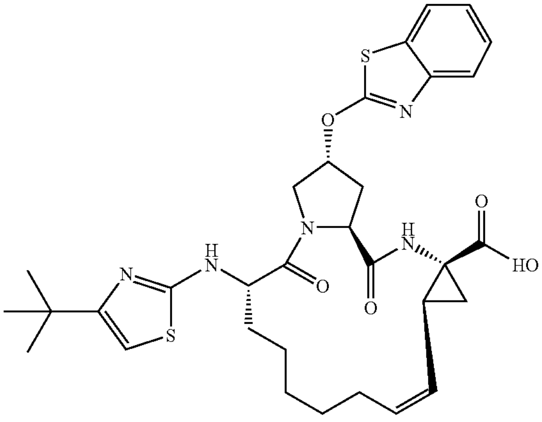

119

A mixture of compound 21 (350 mg, 0.5 mmol.), NaOH (100 mg, 2.5 mmol.), $H_2O$ (1 mL), and methanol (5 mL) was stirred at rt for 24 hours. The volatiles were removed and the remaining aqueous solution was acidified at 0° C. Subsequently, the acidic solution was extracted with ethyl acetate.

The combined organics were dried over $Na_2SO_4$, filtered and concentrated under reduced pressure to afford 258 mg of compound 119 as white solid. MS (ESI) m/e $(M+H^+)$ 638.2.

Example 13-4

General Procedure K

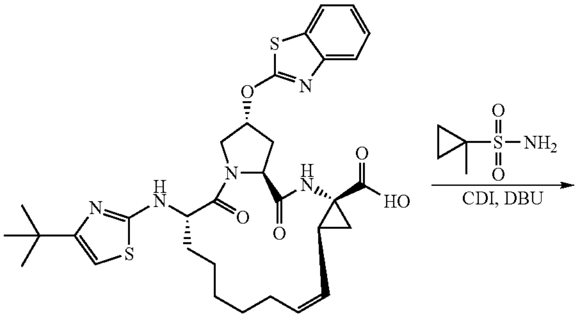

119

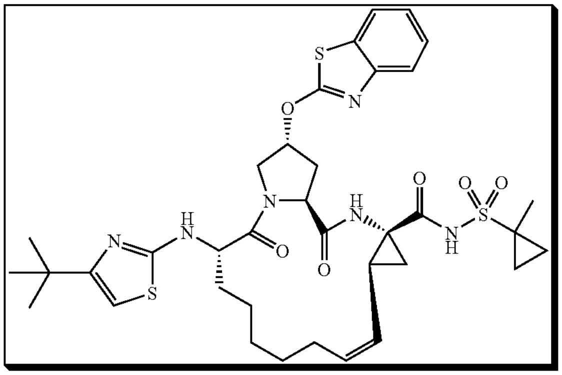

231

To the solution of compound 119 (360 mg) in DCM (5 mL) was added CDI (324 mg, 2 mmol.) at rt in one portion. The resulting mixture was stirred at rt for 2 hrs. Subsequently, 1-methylcyclopropane-1-sulfonamide (270 mg, 2 mmol.) and DBU (1 mL) were successively added. Stirring was continued for another 20 hrs. After purification, 80 mg of compound 231 was obtained as white solid (yield 21%). MS (ESI) m/e $(M+H^+)$ 755.2.

Preparation of NS3 Inhibitors: Section VI

EXAMPLE 14

Scheme X: Preparation of 2-phenyl-4-chloro-7-methoxy-quinoline

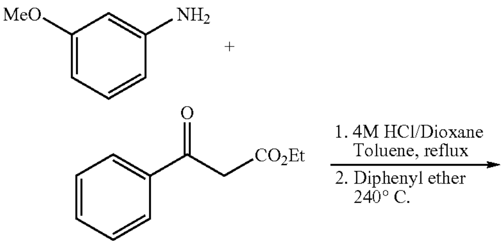

-continued

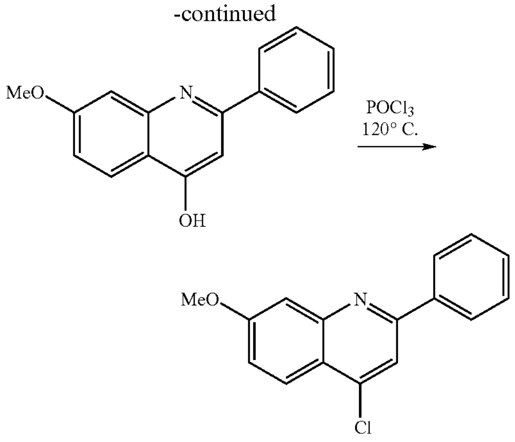

Optionally substituted 2-phenyl-4-chloro-7-alkoxy-quinolines, such as 2-phenyl-4-chloro-7-methoxy-quinoline, can be synthesized as shown in Scheme X. A β-keto ester, such as ethyl benzoylacetate, can reacted with an optionally substituted aniline to provide an optionally substituted 2-phenyl-4-hydroxy-7-alkoxy-quinolines, such as 2-phenyl-4-hydroxy-7-methoxy-quinoline. An optionally substituted 2-phenyl-4-hydroxy-7-alkoxy-quinolines, such as 2-phenyl-4-hydroxy-7-methoxy-quinoline, can be treated with a chlorinating agent, for example oxalyl chloride, thionyl chloride, phosphorus oxychloride and the like, thereby providing optionally substituted 2-phenyl-4-chloro-7-alkoxy-quinolines, such as 2-phenyl-4-chloro-7-methoxy-quinoline.

Example 14-1

General Procedure V

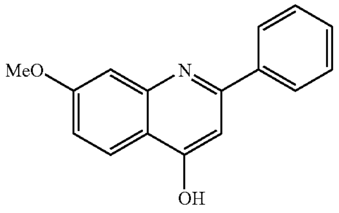

Preparation of 2-phenyl-4-hydroxy-7-methoxy-quinoline

To a solution of ethyl benzoylacetate (10.00 g, 52.0 mmol., 1 eq) and m-anisidine (7.05 g, 57.2 mmol., 1.1 eq) in toluene (85 mL) was added 4M HCl in dioxane (0.520 mL, 2.08 mmol., 0.04 eq) dropwise. The reaction mixture was refluxed for 15 hours while water was collected in a Dean-Stark apparatus. The reaction mixture was left to cool to ambient temperature and the solvent removed under vacuum. The residue was suspended in diphenyl ether (28 mL) and the mixture was heated for 2 h at 240° C. The reaction mixture was then left to cool to ambient temperature and dichloromethane (55 mL) was added, leading to the precipitation of a yellow solid. Stirring was continued at ambient temperature for a further 30 min and the solid collected by filtration, rinsing the cake with a small amount of dichloromethane. The solid was transferred to a 100 mL round bottom flask and stirred with dichloromethane (50 mL) for another 45 min at ambient temperature. After filtration and drying under high vacuum, 2.85 g (22%) of the title compound was isolated as a pale yellow solid. $^1$H NMR (250 MHz, DMSO-d$_6$) δ ppm 11.54 (s, 1 H), 7.99 (d, J=8.91 Hz, 1 H), 7.73-7.90 (m, 2 H), 7.48-7.64 (m, 3 H), 7.20 (d, J=2.32 Hz, 1 H), 6.94 (dd, J=2.34, 8.97 Hz, 1 H), 6.26 (s, 1 H), 3.86 (s, 3 H). LC-MS: purity 98% (UV), t$_R$ 1.52 min, m/z [M+1]$^+$ 252.10.

Example 14-2

General Procedure WA

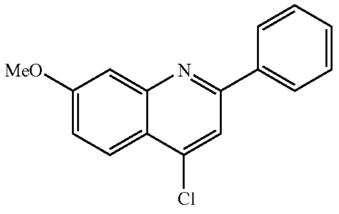

Preparation of 2-phenyl-4-chloro-7-methoxy-quinoline 2-phenyl-4-hydroxy-7-methoxy-quinoline (2.73 g, 10.9 mmol., 1 eq) was suspended in neat phosphorus oxychloride (30 mL). The reaction mixture was heated under reflux. After 2 h, LCMS analysis showed full consumption of the starting material. The reaction mixture was left to cool to ambient temperature and the solvent removed under vacuum. The residue was partitioned between ethyl acetate (100 mL) and 2M aqueous sodium hydroxide solution (80 mL). The mixture was stirred at ambient temperature for a further 10 min, and then the two layers were separated. The organic phase was washed with water (2×50 mL) and saturated aqueous sodium chloride solution (50 mL), dried over sodium sulfate, filtered and the solvent removed under vacuum. The obtained beige solid was further dried under high vacuum for 2 hours to give 2.66 g (91%) of the title compound. $^1$H NMR (250 MHz, DMSO-d$_6$) δ ppm 8.25-8.35 (m, 2H), 8.21 (s, 1 H), 8.09 (d, J=9.14 Hz, 1 H), 7.47-7.61 (m, 4H), 7.38 (dd, J=2.55, 9.18 Hz, 1 H), 3.97 (s, 3 H). LC-MS: purity 100% (UV), t$_R$ 2.58 min, m/z [M+1]$^+$ 270.00.

EXAMPLE 15

Preparation of 2-(4'-isopropyl-thiazol-2-yl)-4-chloro-7-methoxy-8-methyl-quinoline Scheme XI: Preparation of 1-Bromo-3-methyl-but-2-one:

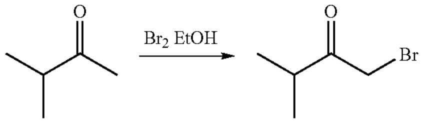

Example 15-1

General Procedure WB

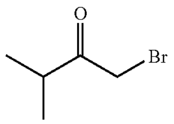

Preparation of 1-Bromo-3-methyl-but-2-one

To a solution of 3-methyl-butan-2-one (20 g, 232 mmol., 1.0 eq.) in dry methanol (200 mL) previously cooled to 0° C., bromine (37.11 g, 232 mmol., 1.0 eq.) was added in a rapid fashion, with vigorous stirring, keeping the temperature below 10° C. Stirring was continued at 10° C. for 2 hours. Water (40 mL) was added and the reaction mixture was left to stir at ambient temperature for 15 hours. A second portion of water (80 mL) was added and the resulting mixture was extracted with diethyl ether (3×400 mL). The organic extracts were combined, washed with 10% aqueous potassium carbonate solution (150 mL), dried over sodium sulphate, filtered, and the solvent removed under vacuum to give 27.5 g (72%) of the title compound as a yellow oil which was used in the next step without any further purification. $^1$H NMR (250 MHz, $CDCl_3$) δ ppm 3.99 (s, 2 H) 2.99 (spt, J=6.93 Hz, 1 H) 1.17 (d, J=6.85 Hz, 6 H).

EXAMPLE 16

Scheme XII: Preparation of 4-isopropylthiazole-2-carbonyl chloride:

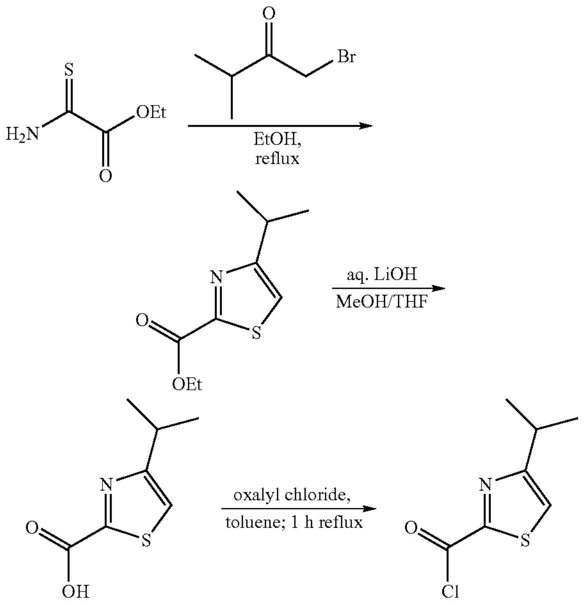

Optionally substituted thiazole-2-carboxylic acid chlorides, such as 4-isopropylthiazole-2-carbonyl chloride, can be synthesized as shown in Scheme XII. Ethyl thioxamate can react with an optionally substituted α-bromo ketone, such as 1-bromo-3-methyl-but-2-one thereby providing an optionally substituted thiazole-2-carboxylic ethyl ester, such as ethyl 4-isopropyl-thiazole-2 carboxylate. The optionally substituted thiazole-2-carboxylic ethyl ester, such as ethyl 4-isopropyl-thiazole-2 carboxylate, can then be treated under basic conditions, for example lithium hydroxide in methanol/THF, to provide an optionally substituted thiazole-2-carboxylic acids, such as 4-isopropyl-thiazole-2-carboxylic acid. Finally, the optionally substituted thiazole-2-carboxylic acids, such as 4-isopropyl-thiazole-2-carboxylic acid, can be reacted with a chlorinating agent, for example oxalyl chloride, thionyl chloride and the like, to provide an optionally substituted thiazole-2-carboxylic acid chloride, such as 4-isopropylthiazole-2-carbonyl chloride.

Example 16-1

General Procedure X

Preparation of Ethyl 4-isopropyl-thiazole-2 carboxylate

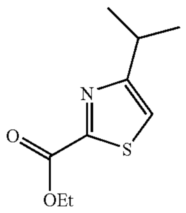

1-Bromo-3-methyl-but-2-one (17.5 g, 106.2 mmol., 1.2 eq.) was added dropwise to a boiling solution of ethyl thioxamate (11.8 g, 88.7 mmol., 1.0 eq.) in ethanol (100 mL). The reaction mixture was stirred under reflux for a further 4 hours by when LCMS analysis showed the reaction to be complete. The reaction mixture was left to cool to ambient temperature and made alkaline by addition of a few drops of concentrated aqueous ammonia. The reaction mixture was then partitioned between water (100 mL) and ethyl acetate (100 mL). The organic layer was collected and the aqueous phase further extracted with ethyl acetate (2×300 mL). The organic extracts were combined, washed with brine (100 mL), dried over sodium sulphate, filtered and the solvent removed under vacuum. The residue was purified by flash column chromatography using a gradient of heptanes:ethyl acetate (9:1 to 85:15). After combining the relevant fractions and solvent removal, 11.1 g (74%) of the title compound was isolated as a yellow solid. $^1$H NMR (500 MHz, $CDCl_3$) δ ppm 7.19 (s, 1 H), 4.48 (q, J=7.17 Hz, 2 H), 3.25 (spt, J=6.89 Hz, 1 H), 1.43

(t, J=7.10 Hz, 3 H), 1.35 (d, J=7.02 Hz, 6 H). LC-MS: 90% (UV), $t_R$ 1.87 min, m/z $[M+1]^+$ 200.05

Example 16-2

General Procedure Y

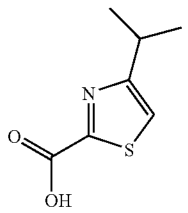

Preparation of 4-Isopropyl-thiazole-2-carboxylic acid

Lithium hydroxide monohydrate (0.947 g, 22.6 mmol., 1.1 eq.) was added to a solution of ethyl 4-isopropyl-thiazole-2 carboxylate (4.08 g, 20.5 mmol., 1.0 eq.) in tetrahydrofuran (45 mL) and methanol (15 mL). The reaction mixture was stirred at ambient temperature for 15 hours. LCMS analysis of the reaction mixture showed a small amount of methyl ester remaining (trans-esterification from ethyl to methyl ester occurred) so lithium hydroxide monohydrate (86 mg, 2.0 mmol., 0.1 eq.) was added and the reaction mixture stirred for a further 3 hours. The reaction mixture was diluted with water (15 mL) and washed with diethyl ether (40 mL). The aqueous phase was cooled to 0° C., and acidified to pH 3 by slow addition of 1M hydrochloric acid. The aqueous layer was extracted with diethyl ether (3×50 mL). The organic extracts were combined, dried over sodium sulphate, filtered and the solvent removed under vacuum to give a mixture of the title product 2.5 g (71%) and 0.6 g of the decarboxylated by product. The mixture was used in the next step without further purification. $^1$H NMR (250 MHz, $CDCl_3$) δ ppm 7.29 (s, 1 H) 3.15-3.30 (spt, J=6.85 Hz, 1 H), 1.35 (d, J=6.85 Hz, 6 H). LC-MS: 72% (UV), $t_R$ 1.21 min, m/z $[M+1]^+$ 171.95.

Analysis for Decarboxylated By-Product:

$^1$H NMR (250 MHz, $CDCl_3$) δ ppm 8.91 (d, J=1.98 Hz, 1 H), 6.97 (dd, J=1.98, 0.76 Hz, 1 H), 3.15-3.30 (spt, J=6.85 Hz, 1 H), 1.35 (d, J=6.85 Hz, 6 H). LC-MS: 25% (UV), $t_R$ 1.37 min, m/z $[M+1-CO_2]^+$ 128.05.

Example 16-3

General Procedure YA

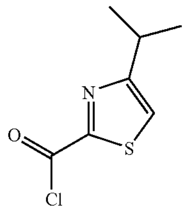

Preparation of 4-isopropylthiazole-2-carbonyl chloride

Oxalyl chloride (5.71 g, 45 mmol., 3.0 eq) was added dropwise, at ambient temperature, to a solution of 4-isopropyl-thiazole-2-carboxylic acid (3.85 g, 22.5 mmol., 1.5 eq) in toluene (40 mL). Stirring was continued at ambient temperature until the bubbling stopped. The reaction mixture was then heated under reflux for a further 1 hour. LCMS analysis of an aliquot quenched with methanol revealed full conversion of the acid to the acid chloride. The reaction mixture was left to cool to ambient temperature and the solvent removed under vacuum. The crude material was used directly in the next step without further purification.

EXAMPLE 17

Scheme XIII: Preparation of 2-(4-isopropylthiazol-2-yl)-4-chloro-7-methoxy-8-methyl-quinoline:

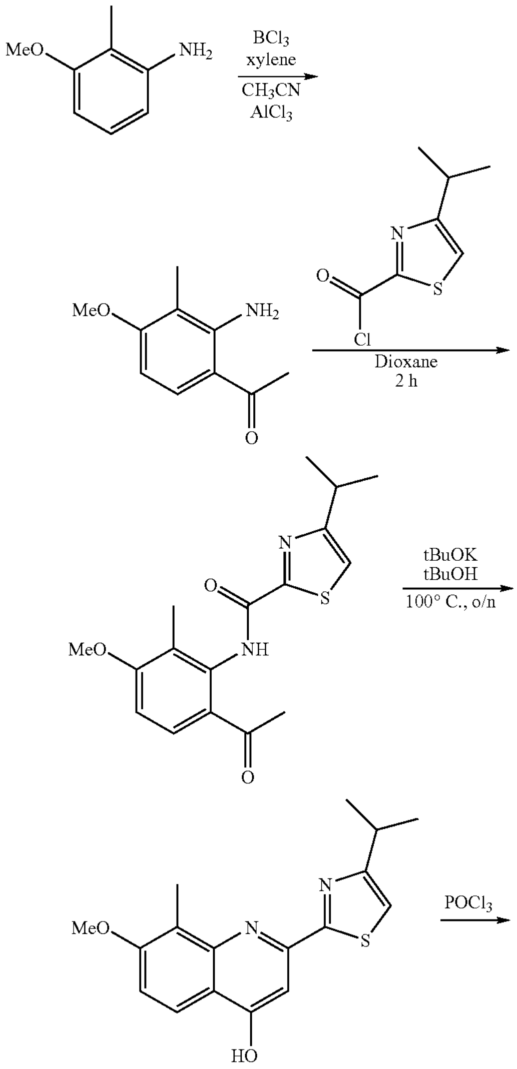

-continued

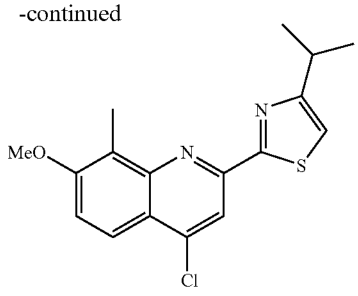

Optionally substituted 2-(thiazol-2-yl)-4-chloro-7-alkoxy-8-alkyl-quinoline 2-phenyl-4-chloro-7-alkoxy-quinolines, such as 2-(4-isopropylthiazol-2-yl)-4-chloro-7-methoxy-8-methyl-quinoline, can be synthesized as shown in Scheme XIII. 3-Alkoxy-2-alkyl-anilines, such as 3-methoxy-2-methyl-aniline, can react with acetonitrile ($CH_3CN$) in the presence of Lewis acids, for example boron trichloride and aluminum trichloride, to provide 2-alkyl-3-alkoxy-6-acetyl-anilines such as 2-methyl-3-methoxy-6-acetyl-aniline. The 2-alkyl-3-alkoxy-6-acetyl-anilines, such as 2-methyl-3-methoxy-6-acetyl-aniline, can be coupled to an an optionally substituted thiazole-2-carboxylic acid chloride, such as 4-isopropylthiazole-2-carbonyl chloride to provide an optionally substituted 1-acetyl-2-[(thiazol-2-yl)-carbonylamino]-3-alkyl-4-alkoxy-benzene, such as 1-acetyl-2-[(4-isopropyl-thiazol-2-yl)-carbonylamino]-3-methyl-4-methoxy-benzene. The optionally substituted 1-acetyl-2-[(thiazol-2-yl)-carbonylamino]-3-alkyl-4-alkoxy-benzene, such as 1-acetyl-2-[(4-isopropyl-thiazol-2-yl)-carbonylamino]-3-methyl-4-methoxy-benzene, can be cyclized under basic conditions, for example sodium tert-butoxide in tert-butanol, to provide an optionally substituted 2-(thiazol-2-yl)-4-hydroxy-7-alkoxy-8-alkyl-quinoline, such as 2-(4-isopropylthiazol-2-yl)-4-hydroxy-7-methoxy-8-methyl-quinoline. Finally, an optionally substituted 2-(thiazol-2-yl)-4-hydroxy-7-alkoxy-8-alkyl-quinoline, such as 2-(4-isopropylthiazol-2-yl)-4-hydroxy-7-methoxy-8-methyl-quinoline can be reacted with a chlorinating agent, for example phosphorous oxychloride, oxalyl chloride, thionyl chloride and the like, to provide an optionally substituted 2-(thiazol-2-yl)-4-chloro-7-alkoxy-8-alkyl-quinoline 2-phenyl-4-chloro-7-alkoxy-quinolines, such as 2-(4-isopropylthiazol-2-yl)-4-chloro-7-methoxy-8-methyl-quinoline.

Example 17-1

General Procedure Z

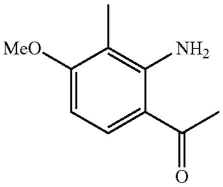

Preparation of 2-Methyl-3-methoxy-6-acetyl-aniline

Boron trichloride (1M solution in dichloromethane, 31.4 mL, 31.4 mmol., 1.05 eq.) was added dropwise, over 20 minutes, at 0° C., to a solution of 3-methoxy-2-methyl-aniline (4.10 g, 29.9 mmol., 1.0 eq.) in xylenes (48 mL). The reaction mixture was stirred for 30 minutes at 0° C., then acetonitrile (4.06 mL, 77.71 mmol., 2.6 eq.) was added dropwise keeping the reaction mixture in the range 0-10° C. Stirring was continued for a further 30 minutes keeping the temperature bellow 10° C. The reaction mixture was transferred to a dropping funnel, using dichloromethane (20 mL) to rinse the initial reaction flask. This solution was added dropwise to a stirred suspension of aluminium trichloride (4.18 g, 31.38 mmol., 1.05 eq.) in dichloromethane (10 mL) at 0° C. The resulting reaction mixture was then heated under reflux for 15 hours. The reaction mixture was cooled to 0° C. and ice cold 2M hydrochloric acid (120 mL) was slowly added giving a light yellow suspension. The suspension was then stirred at 80° C. for around 90 minutes until a clear yellow solution was obtained. The reaction mixture was left to cool to ambient temperature and extracted with dichloromethane (3×100 mL). The organic extracts were combined, dried over sodium sulphate, filtered and the solvent removed under vacuum. The obtained solid was washed with diethyl ether (2×5 mL) and collected by filtration to give 2.31 g (43%) of the title compound as a beige solid. $^1H$ NMR (250 MHz, $CDCl_3$) δ ppm 7.66 (d, J=8.98 Hz, 1 H), 6.45 (br. s, 2 H), 6.31 (d, J=9.14 Hz, 1 H), 3.88 (s, 3 H), 2.55 (s, 3 H), 2.02 (s, 3 H). LC-MS: 97% (UV), $t_R$ 1.16 min, m/z $[M+1]^+$ 180.10.

Example 17-2

General Procedure AA

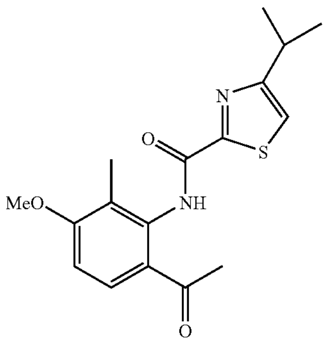

Preparation of 1-Acetyl-2-[(4-isopropyl-thiazol-2-yl)-carbonylamino]-3-methyl-4-methoxy-benzene Oxalyl chloride (5.71 g, 45 mmol., 3.0 eq) was added dropwise, at ambient temperature, to a solution of 4-isopropyl-thiazole-2-carboxylic acid (3.85 g, 22.5 mmol., 1.5 eq) in toluene (40 mL). Stirring was continued at ambient temperature until the bubbling stopped. The reaction mixture was then heated under reflux for a further 1 hour. LCMS analysis of an aliquot quenched with methanol revealed full conversion of the acid to the acid chloride. The reaction mixture was left to cool to ambient temperature and the solvent removed under vacuum. The residue was diluted with dry dioxane (40 mL). Diisopropylethylamine (3.9 g, 30 mmol., 2 eq.) was added dropwise followed by 2-methyl-3-methoxy-6-acetyl-aniline (2.7 g, 15.0 mmol., 1.0 eq). The reaction mixture was stirred at ambient temperature for 15 hours. LCMS analysis showed full conversion of the starting material to product. The solvent was removed under vacuum and the residue dissolved with ethyl acetate (75 mL). The organic layer was washed with saturated aqueous sodium hydrogen carbonate (50 mL), water (50 mL), and brine (50 mL), dried over sodium sulphate, filtered and the solvent removed under vacuum. The residue was purified by flash column chromatography using a gradient of heptanes:ethyl acetate (4:1 to 6:4). The relevant fractions were combined and the solvent removed under vacuum to give 4.55 g (91%) of the title compound as a pale yellow solid. $^1$H NMR (500 MHz, $CDCl_3$) δ ppm 11.28 (br. s, 1 H), 7.76 (d, J=8.70 Hz, 1 H), 7.17 (s, 1 H), 6.79 (d, J=8.70 Hz, 1 H), 3.94 (s, 3 H), 3.23 (spt, J=6.89 Hz, 1 H), 2.59 (s, 3 H), 2.17 (s, 3 H), 1.42 (d, J=6.87 Hz, 6 H). LC-MS: 99% (UV), $t_R$ 2.24 min, m/z $[M+1]^+$ 333.05.

Example 17-3

General Procedure BB

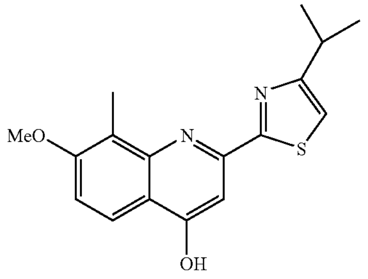

Preparation of 2-(4-isopropylthiazol-2-yl)-4-hydroxy-7-methoxy-8-methyl-quinoline Sodium tert-butoxide (3.20 g, 28.6 mmol., 2.1 eq.) was added portion wise, at ambient temperature, to a solution of 1-acetyl-2-[(4-isopropyl-thiazol-2-yl)-carbonylamino]-3-methyl-4-methoxy-benzene (4.52 g, 13.6 mmol., 1.0 eq.) in dry tert-butanol (45 mL). The reaction mixture was stirred at 90° C. for 4 hours. LCMS analysis showed the reaction to be complete. The reaction mixture was left to cool to ambient temperature and then diluted with ethyl acetate (100 mL). The organic layer was washed with 1M aqueous potassium hydrogen sulphate (75 mL), water (50 mL), brine (50 mL), dried over sodium sulphate, filtered and the solvent removed under vacuum to give 4.63 g (99%) of the title compound as an off white solid. $^1$H NMR (500 MHz, $CDCl_3$) δ ppm 9.59 (br. s, 1 H), 8.26 (d, J=9.16 Hz, 1 H), 7.10 (s, 1 H), 7.03 (d, J=9.16 Hz, 1 H), 6.77 (s, 1 H), 3.98 (s, 3 H), 3.20 (spt, J=6.87 Hz, 1 H), 2.43 (s, 3 H), 1.39 (d, J=7.02 Hz, 6 H). LC-MS: 95% (UV), $t_R$ 2.24 min, m/z $[M+1]^+$ 315.15.

Example 17-4

General Procedure CC

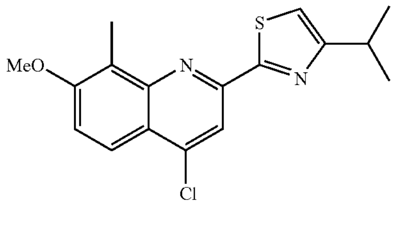

Preparation of 2-(4-isopropylthiazol-2-yl)-4-chloro-7-methoxy-8-methyl-quinoline 2-(4-isopropylthiazol-2-yl)-4-hydroxy-7-methoxy-8-methyl-quinoline (4.63 g, 13.6 mmol., 1.0 eq.) was charged into a 100 mL round bottom flask. Phosphorous oxychloride (45 mL) was added and the reaction mixture stirred at 90° C. for 3 hours. Monitoring the reaction mixture by $^1$H NMR showed full consumption of the starting material. The reaction mixture was left to cool to ambient temperature and the solvent removed under vacuum. The residue was diluted with ethyl acetate (80 mL) and the reaction mixture cooled to 0° C. 2M aqueous sodium hydroxide solution was added portion wise until the pH of the aqueous phase was 14 (stir reaction mixture for 1 min between every NaOH addition). The two layers were separated and the organic layer was further washed with water (50 mL) and brine (50 mL). The organic layer was dried over sodium sulphate, filtered and the solvent removed under vacuum to give 4.11 g (91%) of the title compound as a pale brown solid. $^1$H NMR (500 MHz, $CDCl_3$) δ ppm 8.28 (s, 1 H), 8.09 (d, J=9.16 Hz, 1 H), 7.38 (d, J=9.16 Hz, 1 H), 7.06 (s, 1 H), 4.02 (s, 3 H), 3.20 (spt, J=6.87 Hz, 1 H), 2.73 (s, 3 H), 1.40 (d, J=6.87 Hz, 6 H).

EXAMPLE 18

Synthesis of RCM precursor (1R,2R)-1-amino-2-vinyl-cyclopropane-1-carbonyl-(1'-methyl)-cyclopropane-sulfonamide hydrochloride salt Scheme XIV: General Route for synthesis of (1R, 2R)-1-amino-2-vinyl-cyclopropane-1-carbonyl-(1'-methyl)-cyclopropane-sulfonamide hydrochloride salt

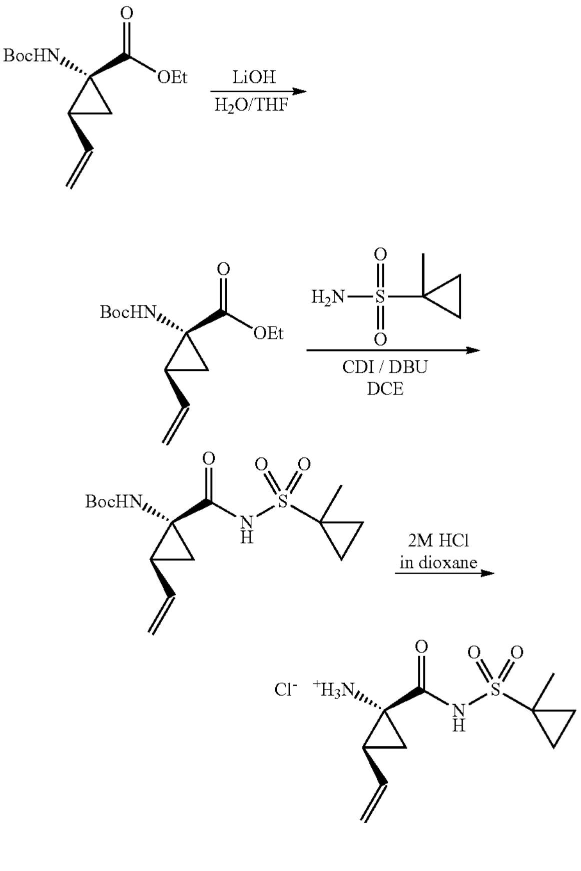

(1R,2R)-1-amino-2-vinyl-cyclopropane-1-carbonyl-(1'-methyl)-cyclopropane-sulfonamide hydrochloride salt can be synthesized as shown in Scheme XIV. Ethyl (1R,2R)-1-(tert-butoxycarbonylamino)-2-vinyl-cyclopropane-1-carboxylate can be treated under basic conditions, for example lithium hydroxide in a water-THF mixture, to hydrolyse the ethyl ester thereby providing (1R,2R)-1-(tert-butoxycarbonylamino)-2-vinyl-cyclopropane-1-carboxylic acid. (1R, 2R)-1-(tert-butoxycarbonylamino)-2-vinyl-cyclopropane-1-carboxylic acid can be coupled with 1-methyl-cyclopropanesulfonamide, for example using 1,1'-Carbonyldiimidazole in the presence of DBU, to provide (1R,2R)-1-(tert-butoxycarbonylamino)-2-vinyl-cyclopropane-1-carbonyl-(1'-methyl)-cyclopropane sulfonamide. (1R,2R)-1-(tert-butoxycarbonylamino)-2-vinyl-cyclopropane-1-carbonyl-(1'-methyl)-cyclopropanesulfonamide can be treated under acidic conditions, for example using a mixture of hydrochloric acid and dioxane, to remove the Boc protecting group thereby providing (1R,2R)-1-amino-2-vinyl-cyclopropane-1-carbonyl-(1'-methyl)-cyclopropane-sulfonamide hydrochloride salt.

Example 18-1

General Procedure DD

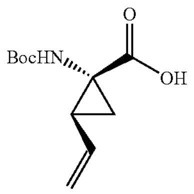

Preparation of (1R,2R)-1-(tert-butoxycarbonylamino)-2-vinyl-cyclopropane-1-carboxylic acid Ethyl (1R,2R)-1-(tert-butoxycarbonylamino)-2-vinyl-cyclopropane-1-carboxylate (2.0 g, 7.84 mmol., 1.0 eq.), water (60 mL) and tetrahydrofuran (50 mL) were charged into a 250 mL round bottom flask placed in ice/water bath. Lithium hydroxide monohydrate (0.523 g, 12.94 mmol., 1.65 eq.) was added portion wise and the reaction mixture heated at 80° C. for 15 hours. TLC analysis of the reaction mixture (heptanes: ethyl acetate, 1:1) showed full consumption of the starting material. The reaction mixture was left to cool down to ambient temperature and diluted with ethyl acetate (50 mL). The organic phase was discarded, and the aqueous phase washed further with ethyl acetate (50 mL). The aqueous phase was acidified to pH 3 by slow addition of 1M hydrochloric acid then extracted with ethyl acetate (2×80 mL). The organic extracts were pooled, washed with brine (50 mL), dried over sodium sulphate, filtered and concentrated to dryness to give 1.72 g (96%) of the title compound as a pale yellow solid. $^1$H NMR (500 MHz, $CDCl_3$) δ ppm 5.67-5.86 (m, 1 H), 5.31 (d, J=17.10 Hz, 1 H), 5.18-5.28 (m, 1 H), 5.15 (d, J=10.32 Hz, 1 H), 2.20 (q, J=8.86 Hz, 1 H), 1.70-1.92 (m, 1 H), 1.50-1.65 (m, 1 H), 1.46 (s, 9 H). LC-MS: purity 100% (ELS), $t_R$ 1.56 min, m/z [M−H]-226.10.

Example 18-2

General Procedure DDLS

Ethyl (1R,2S)-1-(tert-butoxycarbonylamino)-2-vinyl-cyclopropane-1-carboxylate (61 g, 0.239 mol, 1.0 eq.) and tetrahydrofuran (700 mL) were charged into a 2 L round bottom flask placed in ice/water bath. Lithium hydroxide monohydrate (30 g, 0.714 mol, 3.0 eq.) was dissolved in water (800 mL) and added slowly to the mixture. The reaction mixture was heated at 50° C. for 18 hours. Monitoring the reaction conversion by LCMS showed some residual starting material so lithium hydroxide (20 g, 0.476 mol, 2 eq.) was added. The reaction was stirred further for 5 hours and then stirred at room temperature for 2 days. Monitoring the reaction conversion by LCMS showed complete conversion. The reaction mixture was acidified to pH 3 by slow addition of 1M hydrochloric acid then extracted with ethyl acetate (4×900 mL). The organic extracts were pooled, washed with brine (600 mL), dried over sodium sulfate, filtered and concentrated to dryness. Cyclohexane (100 mL) was added to the dried crude material and concentrated to afford 71.44 g (54.0 g, 100%, corrected for residual solvent) of (1R,2R)-1-(tert-butoxycarbonylamino)-2-vinyl-cyclopropane-1-carboxylic acid as a pale yellow solid which contained residual cyclohexane (24.5% w/was calculated from $^1$H NMR). The compound was used in the next step without further purification. $^1$H NMR (500 MHz, $CDCl_3$) δ ppm 5.79 (dt, J=17.01, 9.65 Hz, 1 H), 5.27 (br. s, 1 H), 5.30 (d, J=17.09 Hz, 1 H), 5.14 (d, J=10.38 Hz, 1 H), 2.20 (q, J=8.85 Hz, 1 H), 1.70-1.90 (m, 1 H), 1.52-1.63 (m, 1 H), 1.45 (s, 9 H). LC-MS: purity 100% (UV), $t_R$ 1.60 min, m/z $[M+Na]^+$ 250.00.

Example 18-3

General Procedure EE

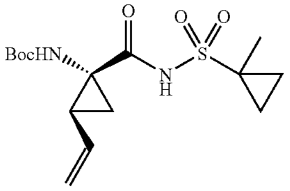

Preparation of (1R,2R)-1-(tert-butoxycarbonylamino)-2-vinyl-cyclopropane-1-carbonyl-(1'-methyl)-cyclopropanesulfonamide (1R,2R)-1-(tert-Butoxycarbonylamino)-2-vinyl-cyclopropane-1-carboxylic acid (3.80 g, 16.72 mmol., 1.0 eq.) and dichloroethane (60 mL) were charged into a 100 mL round bottom flask. 1,1'-Carbonyldiimidazole (3.80 g, 23.40 mmol., 1.4 eq.) was added portionwise and the reaction mixture stirred at 50° C. for 15 hours. 1-Methyl-cyclopropanesulfonamide (6.10 g, 45.14 mmol., 2.7 eq.) was added portionwise followed by dropwise addition of DBU (6.834 g, 45.14 mmol., 2.7 eq.). Stirring was continued at 50° C. for a further 15 hours by when LCMS analysis of the reaction mixture showed full consumption of the starting material. The solvent was removed under vacuum. The residue was partitioned between dichloromethane (100 mL) and 0.5 M hydrochloric acid (60 mL). The organic phase was washed with brine (60 mL), dried over sodium sulfate, filtered and the solvent removed under vacuum. The residue was purified by flash column chromatography using heptanes:ethyl acetate gradient (9:1 to 6:4) as eluent. After combining the relevant fractions and removing the solvent under vacuum, 4.0 g (70%) of the title compound was isolated as an off-white solid. $^1$H NMR (250 MHz, $CDCl_3$) δ ppm 9.56 (br. s, 1 H), 5.46-5.78 (m, 1 H), 5.11-5.41 (m, 3 H), 2.16 (q, J=8.53 Hz, 1 H), 1.91 (dd, J=5.94, 8.07 Hz, 1 H), 1.59-1.79 (m, 3 H), 1.54 (s, 3 H), 1.50 (s, 9 H), 1.20-1.39 (m, 2 H). LC-MS: purity 100% (ELS), $t_R$ 1.81 min, m/z $[M+Na]^+$ 367.05.

Example 18-4

General Procedure EELS (1R,2S)-1-(tert-Butoxycarbonylamino)-2-vinyl-cyclopropane-1-carboxylic acid (54.0 g, 0.239 mol, 1.0 eq., dichloroethane (700 mL) and molecular sieves were charged into a 2.50 L round bottom flask. The mixture was stirred at room temperature for 15 minutes. The molecular sieves were filtered off and washed with dichloromethane (2×40 mL). 1,1'-Carbonyldiimidazole (54.3 g, 0.334 mol, 1.4 eq.) was added portionwise and the reaction mixture stirred vigorously at 50° C. for 3 hours until no more gas evolution was noticed. 1-Methyl-cyclopropanesulfonamide (48.5 g, 0.358 mol, 1.5 eq.) was added portionwise followed by dropwise addition of DBU (91.0 g, 0.598 mol, 2.5 eq.). Stirring was continued at 50° C. for a further 20 hours by which time LCMS analysis of the reaction mixture showed full consumption of the starting material. The reaction mixture was washed with 0.05M citric acid (2×540 mL) and brine (500 mL), dried over sodium sulfate and filtered. After the solvent was removed under vacuum, 75.6 g (92%) of (1R,2R)-1-(tert-butoxycarbonylamino)-2-vinyl-cyclopropane-1-carbonyl-(1'-methyl)-cyclopropanesulfonamide was isolated as a pale yellow solid. The compound was used in the next step without further purification. $^1$H NMR (500 MHz, $CDCl_3$) δ ppm 9.57 (br. s, 1 H), 5.51-5.69 (m, 1 H), 5.41 (br. s, 1 H), 5.31 (d, J=17.09 Hz, 1 H), 5.16 (d, J=10.38 Hz, 1H), 2.16 (q, J=8.54 Hz, 1 H), 1.91 (dd, J=7.78, 5.95 Hz, 1 H), 1.71 (dd, J=10.53, 5.04 Hz, 1 H), 1.60-1.67 (m, 1 H), 1.53 (s, 3 H), 1.46-1.51 (m, 9 H), 1.27-1.37 (m, 1 H), 0.80-0.92 (m, 2 H). LC-MS: purity 95% (UV), $t_R$ 1.96 min, m/z $[M+Na]^+$ 367.35.

Example 18-5

General Procedure FF

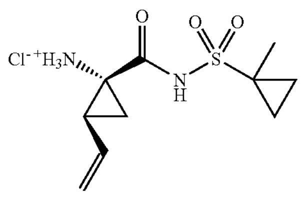

Preparation of (1R,2R)-1-amino-2-vinyl-cyclopropane-1-carbonyl-(1'-methyl)-cyclopropane-sulfonamide hydrochloride salt (1R,2R)-1-(tert-Butoxycarbonylamino)-2-vinyl-cyclopropane-1-acyl-(1'-methyl)-cyclopropanesulfonamide (4.00 g, 11.6 mmol., 1.0 eq.) and dioxane (20 mL) were charged into a 50 mL round bottom flask. 4 M HCl in dioxane (10 mL) was added dropwise over 5 minutes and the reaction mixture stirred at ambient temperature for 15 hours. LCMS analysis showed full consumption of the starting material. The solvent was removed under vacuum and the residue further dried under high vacuum for 4 hours to give 2.80 g (86%, corrected for solvent content) of the title compound as a white foamy solid which contained residual dioxane (25% w/was calculated from NMR). The compound was used in the next step without further purification. $^1$H NMR (500 MHz, DMSO-$d_6$) δ ppm 9.06 (br. s, 3H), 5.50-5.63 (m, 1 H), 5.35 (d, J=16.51 Hz, 1 H), 5.21 (d, J=11.37 Hz, 1 H), 2.35 (q, 1 H), 2.02 (t, J=6.97 Hz, 1 H), 1.67 (dd, J=6.79, 9.72 Hz, 1 H), 1.45-1.48 (m, 1 H), 1.43 (s, 3 H), 1.30-1.38 (m, 1 H), 0.84-0.98 (m, 2 H). LC-MS: purity 100% (UV), $t_R$ 0.80 min, m/z $[M+H]^+$ 245.00.

Example 18-6

General Procedure FFLS (1R,2S)-1-(tert-Butoxycarbonylamino)-2-vinyl-cyclopropane-1-carbonyl-(1'-methyl)-cyclopropanesulfonamide (18.0 g, 52.3 mmol., 1.0 eq.) was charged into a 500 mL round bottom flask placed on top of an ice/water bath, and 4 M HCl in dioxane (180 mL) was added dropwise over 5 min with rapid stirring. The reaction mixture was then stirred at ambient temperature for 15 hours. LCMS analysis showed full consumption of the starting material. The solvent was removed under vacuum and the residue further evaporated from dichloromethane (2×100 mL). The crude product was dried further under high vacuum for 4 hours to give 13.98 g (95%) of (1R,2R)-1-amino-2-vinyl-cyclopropane-1-carbonyl-(1'-methyl)-cyclopropane-sulfonamide hydrochloride salt as a beige solid. The compound was used in the next step without further purification. $^1$H NMR (500 MHz, DMSO-$d_6$) δ ppm 9.06 (br. s, 3H), 5.50-5.63 (m, 1 H), 5.35 (d, J=16.51 Hz, 1 H), 5.21 (d, J=11.37 Hz, 1 H), 2.35 (q, 1 H), 2.02 (t, J=6.97 Hz, 1 H), 1.67 (dd, J=6.79, 9.72 Hz, 1 H), 1.45-1.48 (m, 1 H), 1.43 (s, 3 H), 1.30-1.38 (m, 1 H), 0.84-0.98 (m, 2 H). LC-MS: purity 99% (UV), $t_R$ 0.85 min, m/z $[M+H]^+$ 245.10.

Example 18-7

General Procedure GG

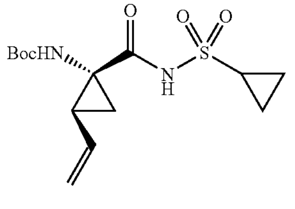

Preparation of (1R,2R)-1-(tert-butoxycarbonylamino)-2-vinyl-cyclopropane-1-carbonyl-cyclopropanesulfonamide (1R,2R)-1-(tert-Butoxycarbonylamino)-2-vinyl-cyclopropane-1-carboxylic acid (1.72 g, 7.57 mmol., 1.0 eq.) and dichloroethane (38 mL) were charged into a 100 mL round bottom flask. 1,1'-Carbonyldiimidazole (1.72 g, 10.61 mmol., 1.4 eq.) was added portionwise and the reaction mixture stirred at 50° C. for 15 hours. Cyclopropanesulfonamide (2.47 g, 20.4 mmol., 2.7 eq.) was added portionwise followed by dropwise addition of DBU (3.11 g, 20.4 mmol., 2.7 eq.). Stirring was continued at 50° C. for a further 15 hours by when LCMS analysis of the reaction mixture showed full consumption of the starting material. The solvent was removed under vacuum. The residue was partitioned between dichloromethane (50 mL) and 0.5 M hydrochloric acid (20 mL). The organic phase was washed with brine (20 mL), dried over sodium sulfate, filtered and the solvent removed under vacuum. The residue was purified by flash column chromatography using heptanes:ethyl acetate gradient (60:50 to 50:50) as eluent. After combining the relevant fractions and removing the solvent under vacuum, 1.12 g (45%) of the title compound was isolated as a yellow semi solid. $^1$H NMR (500 MHz, $CDCl_3$) δ ppm 9.71 (br. s, 1 H), 5.61 (br. s, 1 H), 5.32 (d, J=16.87 Hz, 1 H), 5.20-5.28 (m, 1 H), 5.18 (d, J=10.27 Hz, 1 H), 2.88-3.00 (m, 1 H), 2.16 (q, J=8.44 Hz, 1 H), 1.87-1.96 (m, 1 H), 1.51 (s, 9 H), 1.40-1.47 (m, 1 H), 1.24-1.36 (m, 2 H), 1.07-1.16 (m, 1 H), 0.99-1.07 (m, 1 H). LC-MS: purity 100% (ELS), $t_R$ 1.74 min, m/z [M−H]-329.10.

Example 18-8

General Procedure HH

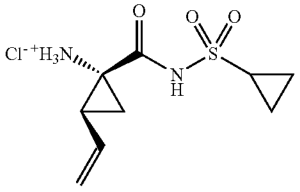

Preparation of (1R,2R)-1-amino-2-vinyl-cyclopropane-1-carbonyl-cyclopropane-sulfonamide hydrochloride salt (1R,2R)-1-(tert-Butoxycarbonylamino)-2-vinyl-cyclopropane-1-acyl-cyclopropane-sulfo-namide (1.12 g, 3.4 mmol., 1.0 eq.) and dioxane (8.5 mL) were charged into a 25 mL round bottom flask. 4M HCl in dioxane (8.5 mL) was added dropwise over 5 minutes and the reaction mixture stirred at ambient temperature for 15 hours. LCMS analysis showed full consumption of the starting material. The solvent was removed under vacuum and the residue further dried under high vacuum for 4 hours to give 1.25 g (99% corrected for solvent content) of the title compound as a white foamy solid which contained residual dioxane (25% w/was calculated from NMR). The compound was used in the next step without further purification. $^1$H NMR (500 MHz, $CD_3OD$) δ ppm 5.73 (ddd, J=7.34, 10.13, 17.19 Hz, 1 H), 5.44 (d, J=17.06 Hz, 1 H), 5.35 (d, J=10.27 Hz, 1 H), 2.95-3.13 (m, 1 H), 2.28-2.46 (m, 1 H), 2.20 (t, J=7.98 Hz, 1 H), 1.69 (dd, J=7.89, 10.09 Hz, 1 H), 1.26-1.34 (m, 1 H), 1.20-1.27 (m, 1 H), 1.12 (d, J=8.07 Hz, 2 H). LC-MS: purity 100% (ELS), $t_R$ 0.55 min, m/z [M+H]$^+$ 231.00.

Example 18-9

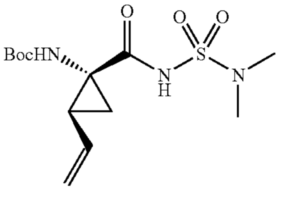

Preparation of (1R,2S)-1-(tert-Butoxycarbonylamino)-2-vinyl-cyclopropane-1-carbonyl-N,N-dimethylsulfamide (1R,2S)-1-(tert-Butoxycarbonylamino)-2-vinyl-cyclopropane-1-carboxylic acid (1.3 g, 5.72 mmol, 1.0 eq.), dichloroethane (30 mL) and molecular sieves were charged into a 100 mL round bottom flask. The mixture was stirred at room temperature for 15 minutes. The molecular sieves were filtered off and washed with dichloroethane (2×5 mL). 1,1'-Carbonyldiimidazole (1.29 g, 8.01 mmol, 1.4 eq.) was added portionwise and the reaction mixture stirred vigorously at 50° C. for 1 hour until no more gas evolution was noticed. Dimethylsulfamide (1.70 g, 13.62 mmol, 1.7 eq.) was added portionwise followed by dropwise addition of DBU (3.2 mL, 21.63 mmol, 2.7 eq.). Stirring was continued at 50° C. for a further 15 hours by which time LCMS analysis of the reaction mixture showed full consumption of the starting material. The reaction mixture was washed with 0.5 M hydrochloric acid (3×50 mL) and brine (50 mL), dried over sodium sulfate and filtered. The residue was purified by flash column chromatography, using a methanol:dichloromethane gradient (from neat dichloromethane to 2% methanol in dichloromethane). After combining the relevant fractions and solvent removal, 1.5 g (78%) of (1R,2S)-1-(tert-Butoxycarbonylamino)-2-vinyl-cyclopropane-1-carbonyl-N,N-dimethylsulfamide was isolated as a white solid. $^1$H NMR (500 MHz, $CDCl_3$) δ ppm 8.90-9.88 (m, 1 H) 5.46-5.73 (m, 2 H) 5.14 (d, J=10.38 Hz, 1 H) 2.90 (s, 6 H) 2.12 (q, J=8.70 Hz, 1 H) 1.87 (dd, J=7.93, 5.80 Hz, 1 H) 1.45 (br. s, 9 H) 1.23-1.38 (m, 1 H). LC-MS: purity 99% (UV), m/z [M+Na]$^+$ 356.35.

EXAMPLE 19

Scheme XV: General Route for synthesis of 2-(3-trifluoromethyl-5-fluoro-phenylamino)-non-8-enoic acid

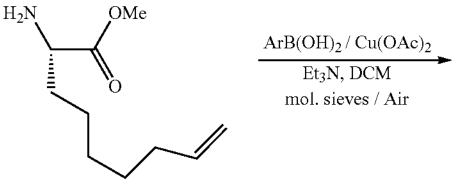

-continued

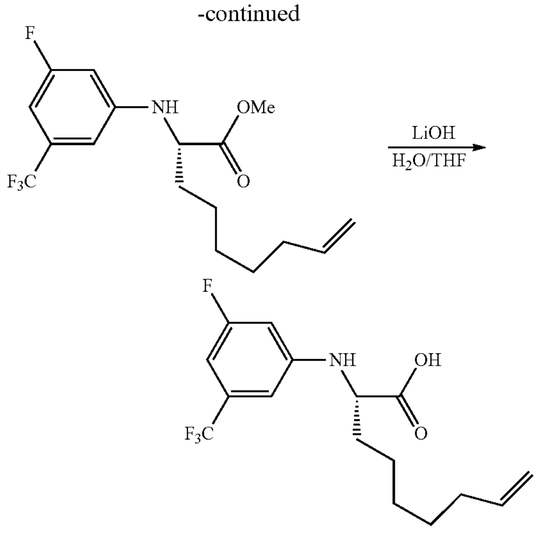

N-aryl amino acids, such as 2-(3-trifluoromethyl-5-fluoro-phenylamino)-non-8-enoic acid, can be synthesized as shown in Scheme XV. 2-Amino-non-8-enoic acid methyl ester can be treated with an optionally substituted aryl boronic acids, for example 3-fluoro-5-(trifluoromethyl)phenyl boronic acid, under $Cu^{2+}$-catalyzed conditions to provide N-aryl amino esters, such as 2-(3-trifluoromethyl-5-fluoro-phenylamino)-non-8-enoic acid methyl ester. Finally, N-aryl amino esters, such as 2-(3-trifluoromethyl-5-fluoro-phenylamino)-non-8-enoic acid methyl ester can be treated under basic conditions to hydrolyse the methyl ester thereby providing N-aryl amino acids, such as 2-(3-trifluoromethyl-5-fluoro-phenylamino)-non-8-enoic acid. The N-aryl amino acids can be used to synthesize macrocycles by further methods disclosed herein.

Example 19-1

General Procedure II

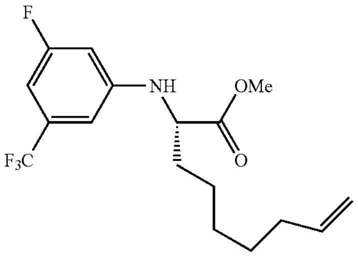

Preparation of 2-(3-trifluoromethyl-5-fluoro-phenylamino)-non-8-enoic acid methyl ester Reaction performed in parallel in 8×50 mL reaction flasks. Copper (II) acetate (270 mg, 1.48 mmol., 1.1 eq.) and 4 Å molecular sieves (700 mg) were charged in 50 mL round bottom flask. Dichloromethane (10 mL, previously saturated with air) was added a single portion. 2-amino-non-8-enoic acid methyl ester (250 mg, 1.35 mmol., 1.0 eq.) was added and the reaction mixture was stirred for a further 5 min by when the initial light blue solution had turned dark blue. 3-fluoro-5-trifluoromethylbenzene boronic acid (560 mg, 2.70 mmol., 2 eq.) was added followed by triethylamine (218 mg, 2.70 mmol., 2 eq.). The reaction mixture was stirred over night under an air atmosphere. The 8 reaction mixtures were combined together and 1M hydrochloric acid (150 mL) was added. The mixture was stirred for a further 5 min until the aqueous layer turned pale blue and the organic layer turned pale yellow. The organic layer was collected, dried over sodium sulfate and the solvent removed under vacuum. The residue was purified by flash column chromatography, using a dichloromethane:heptanes gradient (from neat heptane to 50% dichloromethane in heptanes). After combining the relevant fractions and solvent removal, 970 mg (26%) of the title compound was isolated as a yellow oil. $^1H$ NMR (500 MHz, $CDCl_3$) δ ppm 6.66 (d, J=8.54 Hz, 1 H), 6.61 (s, 1 H), 6.42 (d, J=10.83 Hz, 1 H), 5.72-5.87 (m, J=6.71, 6.71, 10.26, 17.05 Hz, 1 H), 5.00 (dd, J=1.83, 17.09 Hz, 1 H), 4.95 (dt, J=0.95, 10.15 Hz, 1 H), 4.48 (d, J=8.54 Hz, 1 H), 4.05 (dt, J=6.45, 8.32 Hz, 1 H), 3.76 (s, 3H), 2.05 (q, J=6.92 Hz, 2 H), 1.82-1.93 (m, 1 H), 1.71-1.82 (m, 1 H), 1.30-1.45 (m, 6 H). LC-MS: purity 94% (UV), $t_R$ 2.63 min, m/z $[M+H]^+$ 348.00.

Intermediates Synthesized According to the Preceding General Methods

Example 19-2

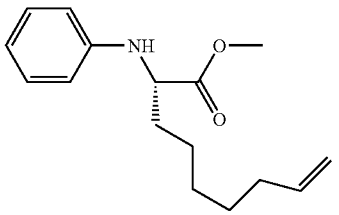

2-phenylamino-non-8-enoic acid methyl ester was prepared in a manner analogous to General Procedure II, to afford 817 mg (58%), yellow oil. $^1H$ NMR (250 MHz, $CDCl_3$) δ ppm 7.21-7.34 (m, 2 H), 6.84 (t, J=7.31 Hz, 1 H), 6.72 (d, J=8.22 Hz, 2 H), 5.91 (m, J=16.98, 10.20, 6.66, 6.66 Hz, 1 H), 4.94-5.22 (m, 2 H), 4.24 (br. s, 1 H), 4.09-4.22 (m, 1 H), 3.80 (s, 3 H), 2.06-2.28 (m, 2 H), 1.67-2.06 (m, 2 H), 1.29-1.66 (m, 6 H). LC-MS: purity 92% (UV), $t_R$ 2.41 min, m/z $[M+H]^+$ 262.20.

Example 19-3

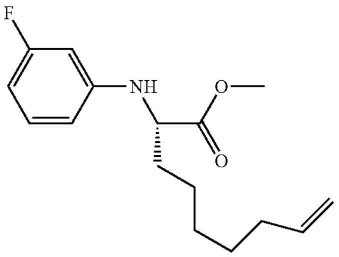

Preparation of (S)-2-(3-fluoro-phenylamino)-non-8-enoic acid methyl ester

General Procedure IILS 2-(3-fluoro-phenylamino)-non-8-enoic acid methyl ester was also prepared in the following manner. The reaction was performed in parallel in 45×50 mL reaction flasks. Copper (II) acetate anhydrous (381 mg, 2.07 mmol, 1.1 eq.), 4 Å molecular sieves (350 mg) and dichloromethane (20 mL, previously saturated with air) were charged in 50 mL round bottom flask. 2-amino-non-8-enoic acid methyl ester (350 mg, 1.88 mmol, 1.0 eq.) was added and the reaction mixture was stirred for a further 5 min. 3-fluorobenzene boronic acid (545 mg, 3.77 mmol, 2 eq.) was added followed by triethylamine (386 mg, 3.77 mmol, 2 eq.). The reaction mixture was stirred for 18 hours under an air atmosphere. The 45 reaction mixtures were combined together. Sieves was filtered off and washed twice with dichloromethane (30 mL×2). 2M hydrochloric acid (800 mL) was added. The mixture was stirred for a further 5 min. The organic layer was collected, dried over sodium sulfate and the solvent removed under vacuum. The residue was purified by dry flash chromatography, using a ethylacetate:heptanes gradient (from neat heptanes to 10% ethylacetate in heptanes). After combining the relevant fractions and solvent removal, 10.27 g (43%, not corrected) of the title compound was isolated as a yellow oil. $^1$H NMR (500 MHz, $CDCl_3$) δ ppm 7.06-7.14 (m, 1 H) 6.40-6.46 (m, 1 H) 6.35-6.40 (m, 1 H) 6.30 (dt, J=11.44, 2.21 Hz, 1 H) 5.80 (m, J=16.99, 10.24, 6.68, 6.68 Hz, 1 H) 5.00 (dd, J=17.17, 1.60 Hz, 1 H) 4.95 (d, J=10.07 Hz, 1 H) 4.15-4.29 (m, 1 H) 3.98-4.07 (m, 1 H) 3.74 (s, 3 H) 2.05 (q, J=6.87 Hz, 2 H) 1.80-1.91 (m, 1 H) 1.75 (dq, J=14.21, 7.17 Hz, 1 H) 1.30-1.47 (m, 6 H). LC-MS: purity 94% (UV), $t_R$ 5.14 min, m/z $[M+H]^+$ 280.40

Example 19-4

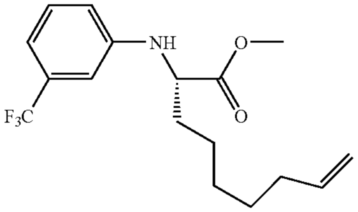

2-(3-trifluoromethyl-phenylamino)-non-8-enoic acid methyl ester was prepared in a manner analogous to General Procedure II, to afford 931 mg (52%) as a clear oil. $^1$H NMR (250 MHz, $CDCl_3$) δ ppm 7.14-7.40 (m, 1 H), 6.97 (d, J=7.61 Hz, 1 H), 6.82 (s, 1 H), 6.75 (dd, J=7.92, 2.44 Hz, 1 H), 5.80 (m, J=17.06, 10.36, 6.70, 6.70 Hz, 1 H), 4.86-5.09 (m, 2 H), 4.33 (br. s, 1 H), 4.09 (t, J=6.24 Hz, 1 H), 3.75 (s, 3 H), 2.05 (d, J=7.01 Hz, 2 H), 1.69-1.97 (m, 2 H), 1.23-1.52 (m, 6 H). LC-MS: purity 99% (UV), $t_R$ 2.57 min, m/z $[M+H]^+$ 330.50.

Example 19-5

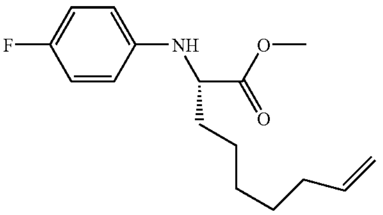

2-(4-Fluoro-phenyl)-amino-non-8-enoic acid methyl ester was prepared in a manner analogous to General Procedure II, to afford 1.47 g (49%), yellow oil. $^1$H NMR (500 MHz, $CDCl_3$) δ ppm 6.88 (t, J=8.70 Hz, 2 H), 6.49-6.63 (m, 2 H), 5.80 (m, J=17.03, 10.28, 6.71, 6.71 Hz, 1 H), 5.00 (dd, J=17.09, 1.53 Hz, 1 H), 4.95 (d, J=10.22 Hz, 1 H), 3.98 (d, J=4.27 Hz, 2 H), 3.72 (s, 3 H), 2.05 (q, J=6.82 Hz, 2 H), 1.79-1.87 (m, 1 H), 1.71-1.78 (m, 1 H), 1.38-1.45 (m, 4 H), 1.34-1.38 (m, 2 H). LC-MS: 94% (UV), $t_R$ 2.44 min, m/z $[M+H]^+$ 280.20.

Example 19-6

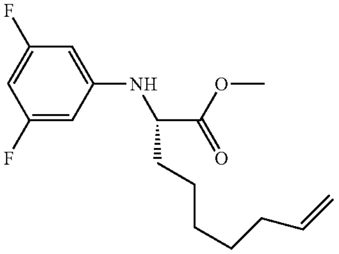

2-(3,5-difluoro-phenyl-amino)-non-8-enoic acid methyl ester was prepared in a manner analogous to General Procedure II, to afford 630 mg (19%), yellow oil. $^1$H NMR (500 MHz, $CDCl_3$) δ ppm 6.17 (tt, J=9.16, 2.14 Hz, 1 H), 6.06-6.13 (m, 2 H), 5.75-5.85 (m, 1 H), 5.00 (dd, J=17.09, 1.83 Hz, 1 H), 4.95 (d, J=10.38 Hz, 1 H), 4.34 (d, J=8.54 Hz, 1 H), 3.96-4.02 (m, 1 H), 3.76 (s, 3 H), 2.85 (t, J=7.32 Hz, 1 H), 2.02-2.08 (m, 3 H), 1.79-1.90 (m, 1 H), 1.69-1.79 (m, 1 H), 1.60-1.69 (m, 1 H), 1.38-1.43 (m, 2 H), 1.36 (dd, J=7.02, 3.05 Hz, 1 H). LC-MS: purity 86% (UV), $t_R$ 2.52 min, m/z $[M+H]^+$ 298.10.

Example 19-7

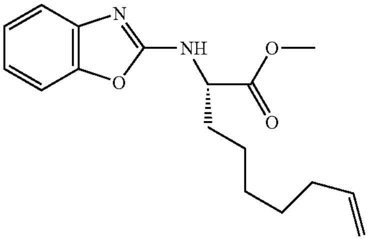

2-(2-benzoxazyl-amino)-non-8-enoic acid methyl ester was prepared in a manner analogous to General Procedure II, to afford 2.28 g (70%), yellow oil. $^1$H NMR (500 MHz, $CDCl_3$) δ ppm 7.39 (d, J=7.78 Hz, 1 H), 7.25-7.28 (m, 1 H), 7.18 (t, J=7.55 Hz, 1 H), 7.04-7.08 (m, 1 H), 5.78 (m, J=17.03, 10.24, 6.66, 6.66 Hz, 1 H), 5.64 (br. s, 1 H), 4.98 (dd, J=17.09, 1.53 Hz, 1 H), 4.93 (d, J=10.07 Hz, 1 H), 4.61-4.66 (m, 1 H), 3.79 (s, 3 H), 1.99-2.06 (m, 3 H), 1.79-1.87 (m, 1 H), 1.43-1.51 (m, 1 H), 1.32-1.43 (m, 5 H). LC-MS: purity 87% (UV), $t_R$ 4.67 min, m/z $[M+H]^+$ 303.45.

Example 19-8

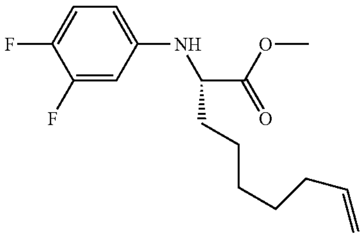

2-(3,4-Difluoro-phenyl-amino)-non-8-enoic acid methyl ester was prepared in a manner analogous to General Procedure II, to afford 522 mg (16%), yellow oil. $^1$H NMR (250 MHz, $CDCl_3$) δ ppm 6.95 (dt, J=10.13, 8.87 Hz, 1 H), 6.40 (ddd, J=12.49, 6.62, 2.82 Hz, 1 H), 6.28 (m, J=8.85, 3.11, 3.11, 1.68 Hz, 1 H), 5.80 (m, J=17.02, 10.24, 6.70, 6.70 Hz, 1 H), 4.86-5.10 (m, 2 H), 3.87-4.19 (m, 2 H), 3.73 (s, 3 H), 1.96-2.13 (m, 2 H), 1.64-1.94 (m, 2 H), 1.30-1.42 (m, 6 H). LC-MS: purity 98% (UV), $t_R$ 2.47 min, m/z $[M+H]^+$ 298.45.

Example 19-9

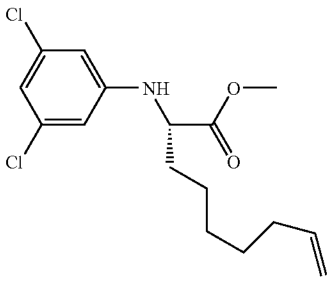

2-(3,5-Dichloro-phenyl-amino)-non-8-enoic acid methyl ester was prepared in a manner analogous to General Procedure II, to afford 1.70 g (42%), yellow oil. $^1$H NMR (250 MHz, $CDCl_3$) δ ppm 6.71 (t, J=1.75 Hz, 1 H), 6.46 (d, J=1.68 Hz, 1 H), 5.80 (d, J=6.85 Hz, 1 H), 5.03 (d, J=1.68 Hz, 1 H), 4.94-4.99 (m, 1 H), 4.21-4.38 (m, 1 H), 3.93-4.10 (m, 1 H), 3.87 (s, 1 H), 3.76 (s, 3 H), 2.04-2.13 (m, 2 H), 1.71-1.93 (m, 2 H), 1.32-1.41 (m, 6 H). LC-MS: purity 97% (UV), $t_R$ 2.74 min, m/z $[M+H]^+$ 330.10.

Example 19-10

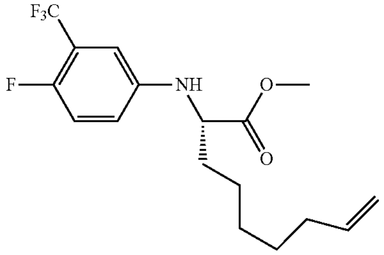

2-(3-Trifluoromethyl-4-fluoro-phenylamino)-non-8-enoic acid methyl ester was prepared in a manner analogous to General Procedure II, to afford 550 mg (14%), pale yellow solid. $^1$H NMR (500 MHz, $CDCl_3$) δ ppm 7.00 (t, J=9.38 Hz, 1 H), 6.77 (dd, J=5.34, 3.05 Hz, 1 H), 6.66-6.74 (m, 1 H), 5.72-5.87 (m, 1 H), 5.00 (dd, J=17.17, 1.30 Hz, 1 H), 4.95 (d, J=10.07 Hz, 1 H), 4.18 (d, J=6.71 Hz, 1 H), 4.01 (q, J=6.41 Hz, 1 H), 3.74 (s, 3 H), 2.05 (q, J=6.92 Hz, 2 H), 1.80-1.92 (m, 1 H), 1.69-1.80 (m, 1 H), 1.25-1.52 (m, 6 H). LC-MS: purity 100% (UV), $t_R$ 2.36 min, m/z $[M+H]^+$ 348.50.

Example 19-11

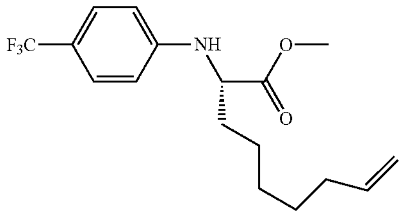

2-(4-Trifluoromethyl-phenylamino)-non-8-enoic acid methyl ester was prepared in a manner analogous to General Procedure II, to afford 1.21 g (23%), pale yellow solid. $^1$H NMR (500 MHz, $CDCl_3$) δ ppm 7.41 (d, J=8.54 Hz, 2 H), 6.62 (d, J=8.54 Hz, 2 H), 5.71-5.89 (m, 1 H), 5.00-5.10 (m, 1 H), 4.95 (d, J=10.22 Hz, 1 H), 4.45 (d, J=8.54 Hz, 1 H), 4.07-4.15 (m, 1 H), 3.75 (s, 3 H), 2.00-2.10 (m, 2 H), 1.83-

1.93 (m, 1 H), 1.77 (dq, J=14.13, 7.19 Hz, 1 H), 1.32-1.48 (m, 6 H). LC-MS: purity 100% (UV), $t_R$ 2.71 min, m/z $[M+H]^+$ 330.20.

Example 19-12

General Procedure JJ

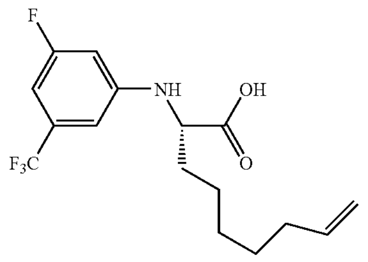

Preparation of 2-(3-trifluoromethyl-5-fluoro-phenylamino)-non-8-enoic acid 2-(3-Trifluoromethyl-5-fluoro-phenylamino)-non-8-enoic acid methyl ester (1.643 g, 4.73 mmol., 1 eq.) was dissolved in tetrahydrofuran (40 mL). A solution of lithium hydroxide monohydrate (0.596 g, 14.19 mmol., 3 eq.) in water (40 mL) was added dropwise and the reaction mixture stirred for a further 3 hours at ambient temperature by when LCMS analysis of an aliquot showed the reaction to be complete. The reaction mixture volume was reduced by half in vacuo to remove most of the tetrahydrofuran and the obtained solution was diluted with 1.5M hydrochloric acid (40 mL). The solution was extracted with dichloromethane (2×60 mL). The organic extracted were combined, dried over sodium sulfate and the solvent removed in vacuo to give 1.41 g (90%) of the title compound as a yellow oil. $^1$H NMR (500 MHz, $CDCl_3$) δ ppm 6.68 (d, J=8.54 Hz, 1 H), 6.63 (s, 1 H), 6.44 (dd, J=1.98, 10.68 Hz, 1 H), 5.72-5.85 (m, J=6.64, 6.64, 10.28, 17.03 Hz, 1 H), 5.00 (dq, J=1.66, 17.15 Hz, 1 H), 4.95 (dt, J=0.97, 10.11 Hz, 1 H), 4.07 (dd, J=5.80, 6.87 Hz, 1 H), 2.19 (s, 2 H), 2.05 (q, J=6.87 Hz, 2 H), 1.90-1.99 (m, 1 H), 1.74-1.86 (m, 1 H), 1.43-1.51 (m, 2 H), 1.32-1.43 (m, 3 H). LC-MS: purity 98% (UV), $t_R$ 2.33 min, m/z $[M+H]^+$334.10

Example 19-13

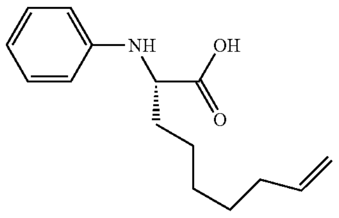

2-phenylamino-non-8-enoic acid was prepared in a manner analogous to General Procedure JJ, to afford 630 mg (89%), yellow solid. $^1$H NMR (500 MHz, $CDCl_3$) δ ppm 7.21 (dd, J=8.54, 7.32 Hz, 2 H), 6.80 (t, J=7.32 Hz, 1 H), 6.65 (d, J=7.93 Hz, 2 H), 5.80 (m, J=17.01, 10.22, 6.68, 6.68 Hz, 1 H), 5.00 (dq, J=17.13, 1.72 Hz, 1 H), 4.92-4.96 (m, 1 H), 4.03 (dd, J=7.48, 5.65 Hz, 1 H), 2.05 (q, J=7.02 Hz, 2 H), 1.88-1.98 (m, 1 H), 1.74-1.83 (m, 1 H), 1.48 (td, J=6.87, 2.75 Hz, 2 H), 1.38-1.43 (m, 2 H), 1.32-1.38 (m, 2 H). LC-MS: purity 92% (UV), $t_R$ 2.09 min, m/z $[M+H]^+$ 248.20.

Example 19-14

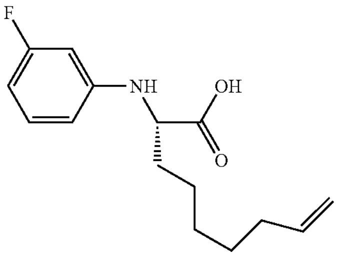

2-(3-fluoro-phenylamino)-non-8-enoic acid was prepared in a manner analogous to General Procedure JJ, to afford 259 mg (94%), yellow solid. $^1$H NMR (500 MHz, $CDCl_3$) δ ppm 7.09-7.15 (m, 1 H), 6.46 (td, J=8.35, 2.21 Hz, 1 H), 6.40 (dd, J=8.16, 2.06 Hz, 1 H), 6.33 (dt, J=11.29, 2.29 Hz, 1 H), 5.79 (m, J=17.03, 10.24, 6.66, 6.66 Hz, 1 H), 5.00 (dd, J=17.09, 1.83 Hz, 1 H), 4.92-4.97 (m, 1 H) 4.03 (dd, J=7.02, 5.80 Hz, 1 H), 2.05 (q, J=6.97 Hz, 2 H), 1.88-1.97 (m, 1 H), 1.74-1.84 (m, 1 H), 1.43-1.52 (m, 2 H), 1.34-1.43 (m, 4 H). LC-MS: purity 97% (UV), $t_R$ 2.14 min, m/z $[M+H]^+$ 266.15.

General Procedure JJLS

The preceding compound was also prepared in the following manner. (3-Fluorophenylamino)-non-8-enoic acid methyl ester (9.9 g, 35 mmol, 1 eq.) was dissolved in tetrahydrofuran (300 mL). A solution of lithium hydroxide monohydrate (4.47 g, 106 mmol, 3 eq.) in water (300 mL) was added dropwise and the reaction mixture stirred for 18 hours at ambient temperature by when LCMS analysis of an aliquot showed the reaction to be complete. The reaction mixture volume was reduced by half under vacuum to remove most of the tetrahydrofuran and the obtained solution was diluted with 1.0M hydrochloric acid. The solution was extracted with dichloromethane (2×50 mL). The organic extracted were combined, dried over sodium sulfate and the solvent removed under vacuum to give 9 g (95%) of the title compound as a yellow solid which contained unknown impurities. $^1$H NMR (500 MHz, $CDCl_3$) δ ppm 7.12 (q, 1 H) 6.45 (td, J=8.35, 2.06 Hz, 1 H) 6.40 (dd, J=8.16, 1.60 Hz, 1 H) 6.32 (dt, J=11.29, 2.14 Hz, 1 H) 5.80 (m, J=17.01, 10.26, 6.66, 6.66 Hz, 1 H) 4.93-5.02 (m, 2 H) 4.03 (t, J=6.41 Hz, 1 H) 2.05 (q, J=6.82 Hz, 2 H) 1.89-1.96 (m, 1 H) 1.74-1.83 (m, 1 H) 1.33-1.51 (m, 6 H). LC-MS: purity 100% (UV), $t_R$ 4.74 min, m/z $[M+H]^+$ 266.05.

Example 19-15

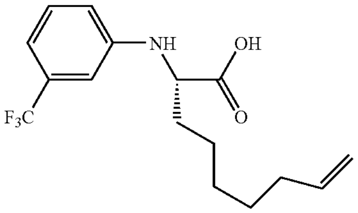

2-(3-trifluoromethyl-phenylamino)-non-8-enoic acid was prepared in a manner analogous to General Procedure JJ, to afford 820 mg (92%), beige solid. $^1$H NMR (500 MHz, $CDCl_3$) δ ppm 7.28 (t, J=7.93 Hz, 1 H), 7.00 (d, J=7.63 Hz, 1 H), 6.84 (s, 1 H), 6.76 (dd, J=8.24, 2.14 Hz, 1 H), 5.73-5.85 (m, 1 H), 5.00 (dq, J=17.09, 1.73 Hz, 1 H), 4.95 (m, J=10.19, 2.10, 1.18, 1.18 Hz, 1 H), 4.10 (dd, J=7.02, 5.80 Hz, 1 H), 2.05 (q, J=7.02 Hz, 2 H), 1.89-1.98 (m, 1 H), 1.80 (dq, J=14.61, 7.24 Hz, 1 H), 1.44-1.52 (m, 2 H), 1.31-1.44 (m, 4 H). LC-MS: purity 97% (UV), $t_R$ 2.30 min, m/z $[M+H]^+$ 316.10.

Example 19-16

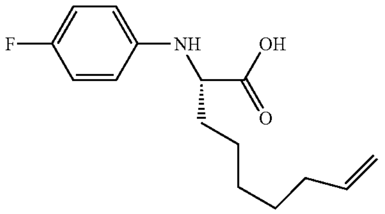

2-(4-Fluoro-phenyl)-amino-non-8-enoic acid was prepared in a manner analogous to General Procedure JJ, to afford 1.11 g (74%), yellow solid. $^1$H NMR (500 MHz, $CDCl_3$) δ ppm 6.91 (t, J=8.59 Hz, 2 H), 6.59 (dd, J=8.83, 4.26 Hz, 2 H), 5.80 (m, J=17.04, 10.31, 6.66, 6.66 Hz, 1 H), 5.00 (dd, J=17.10, 1.50 Hz, 1 H), 4.95 (d, J=9.93 Hz, 1 H), 3.95 (t, J=6.31 Hz, 1 H), 2.05 (q, J=6.94 Hz, 2 H), 1.85-1.96 (m, 2 H), 1.69-1.85 (m, 2 H), 1.45-1.52 (m, 2 H), 1.34-1.43 (m, 4 H). LC-MS: 93% (UV), $t_R$ 2.15 min, m/z $[M+H]^+$ 266.10

Example 19-17

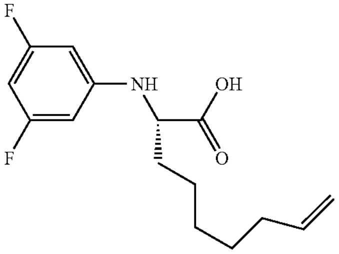

2-(3,5-difluoro-phenylamino)-non-8-enoic acid was prepared in a manner analogous to General Procedure JJ, to afford 667 mg (92%, corrected for residual solvent), yellow solid. $^1$H NMR (500 MHz, $CDCl_3$) δ ppm 6.03-6.28 (m, 2 H), 5.70-5.90 (m, 1 H), 4.82-5.08 (m, 2 H), 4.01 (t, J=6.26 Hz, 1 H), 2.05 (q, =6.92 Hz, 2 H), 1.89-1.98 (m, 1 H), 1.72-1.84 (m, 1 H), 1.58-1.72 (m, 1 H), 1.15-1.55 (m, 6 H). LC-MS: 96% (UV), $t_R$ 2.24 min, m/z $[M+H]^+$ 284.15.

Example 19-18

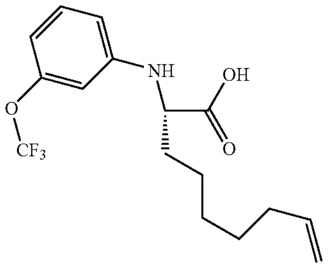

(S)-2-(3-(trifluoromethoxy)phenylamino)-non-8-enoic acid was prepared in a manner analogous to General Procedure JJ, to afford 1.21 g (95%), pale yellow solid. $^1$H NMR (500 MHz, $CDCl_3$) δ ppm 7.17 (t, J=8.09 Hz, 1 H), 6.61 (d, J=7.93 Hz, 1H), 6.53 (dd, J=8.24, 1.83 Hz, 1 H), 6.46 (s, 1 H), 5.72-5.88 (m, 1 H), 4.89-5.07 (m, 2 H), 4.05 (dd, J=7.02, 5.80 Hz, 1 H), 2.00-2.14 (m, 2 H), 1.87-1.99 (m, 1 H), 1.72-1.85 (m, 1H), 1.31-1.58 (m, 6 H). LC-MS: purity 95% (UV), $t_R$ 2.35 min, m/z $[M+H]^+$ 332.50.

Example 19-19

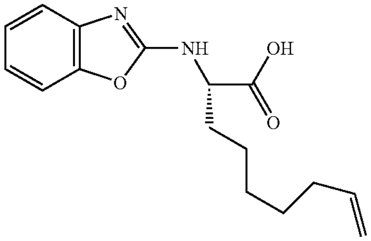

2-(2-benzoxazyl-amino)-non-8-enoic acid was prepared in a manner analogous to General Procedure JJ, to afford 2.05 g (96%), pale yellow oil. $^1$H NMR (500 MHz, $CDCl_3$) δ ppm 8.96 (br. s, 1 H), 7.32 (t, J=7.25 Hz, 2 H), 7.22 (t, J=7.63 Hz, 1 H), 7.06-7.13 (m, 1 H), 5.81 (m, J=17.05, 10.26, 6.71, 6.71 Hz, 1 H), 5.31 (s, 1 H), 4.99 (dd, J=17.17, 1.45 Hz, 1 H), 4.93 (d, J=10.22 Hz, 1 H), 4.59 (t, J=5.19 Hz, 1 H), 2.11-2.22 (m, 1 H), 1.98-2.11 (m, 3 H), 1.62 (dd, J=11.67, 6.48 Hz, 1 H), 1.51 (dd, J=11.44, 6.10 Hz, 1 H), 1.35-1.48 (m, 4 H). LC-MS: purity 83% (UV), $t_R$ 4.30 min, m/z $[M+H]^+$ 289.50.

Example 19-20

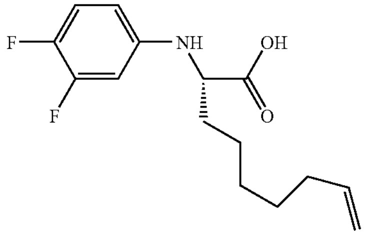

2-(3,4-Difluoro-phenyl-amino)-non-8-enoic acid was prepared in a manner analogous to General Procedure JJ, to afford 618 mg (92%), yellow solid. $^1$H NMR (500 MHz, $CDCl_3$) δ ppm 6.89-7.06 (m, 1 H), 6.43 (ddd, J=12.37, 6.54, 2.84 Hz, 1 H), 6.25-6.36 (m, 1 H), 5.80 (m, J=17.00, 10.27, 6.70, 6.70 Hz, 1 H), 4.87-5.07 (m, 2 H), 3.95 (dd, J=6.94, 5.83 Hz, 1 H), 1.98-2.10 (m, 2 H), 1.83-1.95 (m, 1 H), 1.77 (d, J=7.41 Hz, 1 H), 1.23-1.56 (m, 8 H). LC-MS: purity 89% (UV), $t_R$ 2.21 min, m/z $[M+H]^+$ 284.10.

Example 19-21

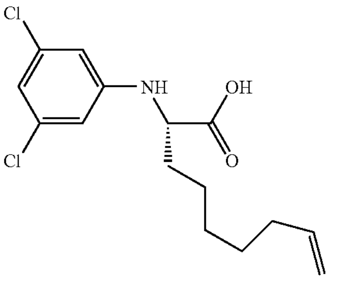

2-(3,5-Dichloro-phenyl-amino)-non-8-enoic acid was prepared in a manner analogous to General Procedure JJ, to afford 561 mg (34%), yellow solid. $^1$H NMR (500 MHz, $CDCl_3$) δ ppm 6.73 (s, 1 H), 6.49 (s, 1 H), 5.74-5.86 (m, 1 H), 5.00 (d, J=18.76 Hz, 1 H), 4.95 (d, J=10.09 Hz, 1 H), 4.03 (br. s, 1 H), 2.37 (t, J=7.57 Hz, 1 H), 2.02-2.08 (m, 2 H), 1.85-1.98 (m, 1 H), 1.71-1.84 (m, 1 H), 1.59-1.71 (m, 1 H), 1.28-1.52 (m, 7 H). LC-MS: purity 97% (UV), $t_R$ 2.44 min, m/z $[M+H]^+$ 316.00.

Example 19-22

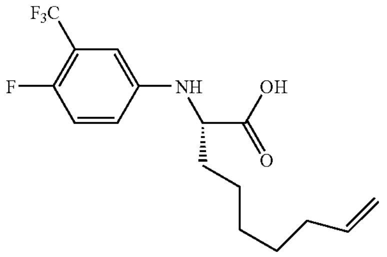

2-(3-Trifluoromethyl-4-fluoro-phenylamino)-non-8-enoic acid was prepared in a manner analogous to General Procedure JJ, to afford 520 mg (98%), pale yellow solid. $^1$H NMR (500 MHz, $CDCl_3$) δ ppm 7.02 (t, J=9.31 Hz, 1 H), 6.80 (dd, J=5.34, 2.90 Hz, 1 H), 6.70-6.75 (m, 1 H), 5.79 (m, J=17.05, 10.26, 6.71, 6.71 Hz, 1 H), 5.00 (dd, J=17.17, 1.60 Hz, 1 H), 4.95 (d, J=10.22 Hz, 1 H), 4.02 (t, J=6.41 Hz, 1 H), 2.05 (q, J=6.97 Hz, 2 H), 1.86-1.96 (m, 1 H), 1.75-1.83 (m, 1 H), 1.44-1.52 (m, 2 H), 1.33-1.43 (m, 4 H). LC-MS: purity 96% (UV), $t_R$ 5.00 min, m/z $[M+H]^+$ 334.45.

Example 19-23

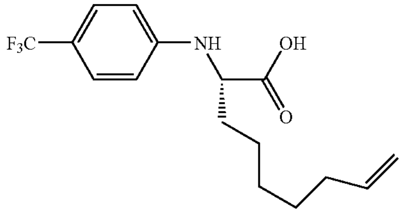

2-(4-Trifluoromethyl-phenylamino)-non-8-enoic acid was prepared in a manner analogous to General Procedure JJ, to afford 1.16 g (97%), pale yellow oily solid. $^1$H NMR (250 MHz, $CDCl_3$) δ ppm 7.42 (d, J=8.68 Hz, 2 H), 6.64 (d, J=8.68 Hz, 2 H), 5.79 (m, J=17.04, 10.26, 6.68, 6.68 Hz, 2 H), 4.87-5.08 (m, 3 H), 4.11 (dd, J=6.85, 5.79 Hz, 1 H), 3.71-3.85 (m, 2 H), 1.97-2.14 (m, 3 H), 1.83-1.92 (m, 3 H). LC-MS: purity 100% (UV), $t_R$ 2.43 min, m/z $[M+H]^+$ 316.50.

Example 19-24

Scheme XVI: General Route for synthesis of Macrocycle.

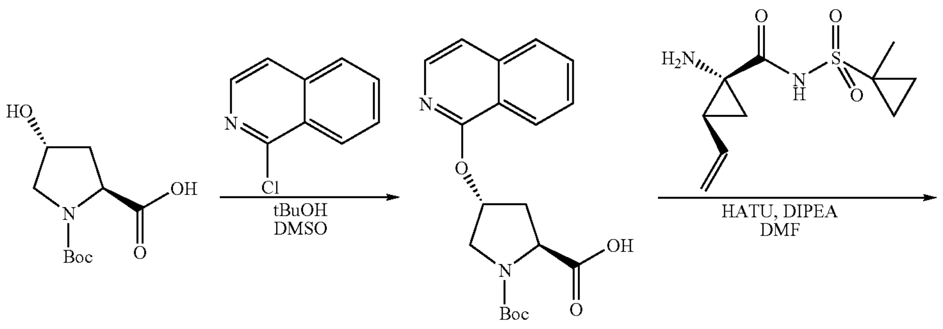

-continued
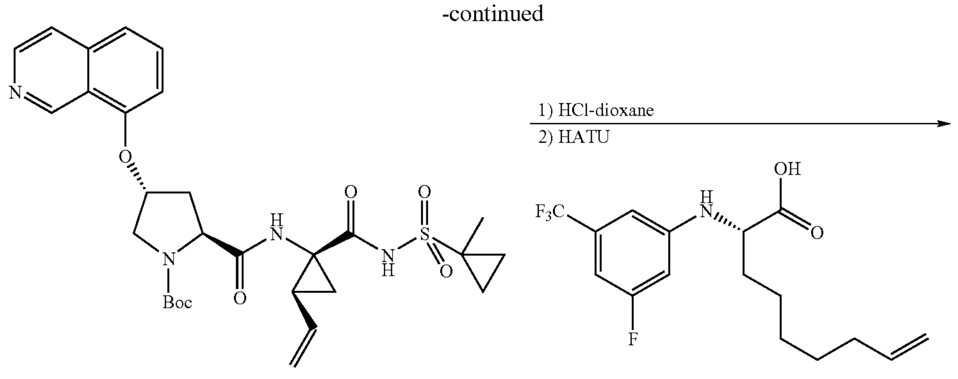
22
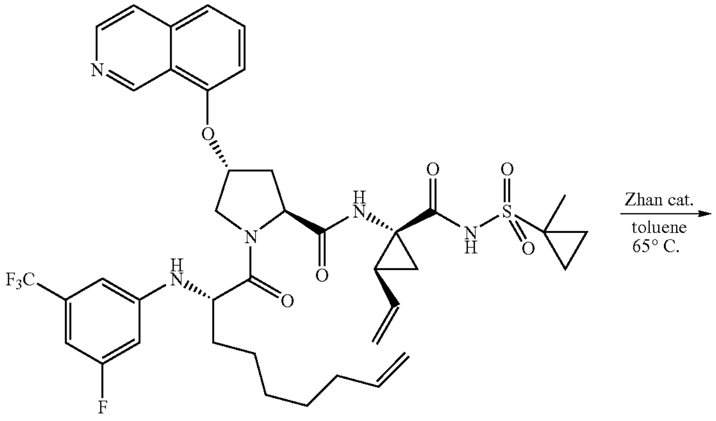
24
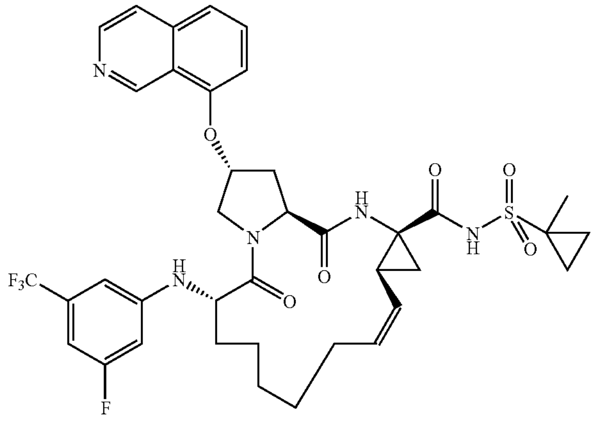
346

Macrocycles, such as compound 346, can be synthesized as shown in Scheme XVI. (2S,4R)-1-(tert-Butoxycarbonylamino)-4-hydroxy-proline can be treated with a heteroaryl chloride, such as 2-phenyl-4-chloro-7-methoxy-quinoline, 1-chloro-isoquinoline and the like, under basic conditions, for example potassium tert-butoxide in DMSO, to provide heteroaryl ethers, such as (2S,4R)-1-(tert-butoxycarbonylamino)-4-(1-isoquinolin-1-oxy)-proline. The heteroaryl ethers, such as (2S,4R)-1-(tert-butoxycarbonylamino)-4-(1-isoquinolin-1-oxy)-proline, can be coupled with amino acylsulfonamides, such as (1R,2R)-1-Amino-2-vinyl-cyclopropane-1-acyl-(1'-methyl)cyclopropanesulfonamide, using a coupling agent, for example using HATU in DMF in the presence of DIPEA, to provide dipeptides such as compound 22. Compound 22 can be treated under acidic conditions, for example HCl in dioxane, to remove the Boc protecting group thereby forming free amines, such as compound 23. Free amines, such as compound 23, can be coupled with N-aryl amino acids, such as 2-(3-trifluoromethyl-5-fluoro-phenylamino)-non-8-enoic acid, using a coupling agent, for example using HATU in DMF in the presence of DIPEA, to provide macrocyclization precursors, such as compound 24. Finally, the macrocyclization precursors, such as compound 24, can be cyclized in the presence of a catalyst, for example a Zhan catalyst, to provide macrocycles, such as compound 346.

Example 19-25

General Procedure KK

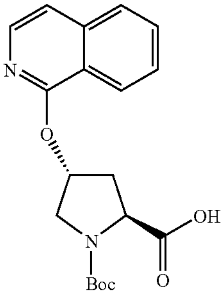

Preparation of (2S,4R)-1-(tert-butoxycarbonylamino)-4-(1-isoquinolin-1-oxy)-proline (2S,4R)-1-(tert-Butoxycarbonylamino)-4-hydroxy-proline (1.00 g, 4.64 mmol., 1.0 eq.) and dimethylsulfoxide (40 mL) were charged into a 100 mL round bottom flask. Potassium tert-butoxide (1.04 g, 9.3 mmol., 2.0 eq.) was added portionwise over 10 minutes at ambient temperature followed by 1-chloro-isoquinoline (0.836 g, 5.11 mmol., 1.1 eq.). Stirring was continued at ambient temperature for a further 15 hrs by when LCMS analysis of the reaction mixture showed the reaction to be complete. The reaction mixture was partitioned between ethyl acetate (80 mL) and water (40 mL). The phases were separated and the aqueous phase further extracted with ethyl acetate (40 mL). The organic phases were combined to give "organic phase 1". The aqueous phase was acidified to pH 3 with 1M hydrochloric acid and extracted with ethyl acetate (2×50 mL). The organic extracts were combined to give "organic phase 2". Organic phase 1, being contaminated with traces of chloroisoquinoline, was extracted with 1M aqueous sodium hydrogen carbonate solution (50 mL). The aqueous phase (pH 8) was washed with ethyl acetate (2×40 mL) and acidified to pH 3 with 1M hydrochloric acid. The aqueous phase was then extracted with ethyl acetate (2×80 mL). The organic extracts were pooled and combined with "organic phase 2". The resulting solution was dried over sodium sulfate, filtered and the solvent removed under vacuum to give 1.86 g (92% corrected for solvent) of the title compound which contained residual dimethylsulfoxide (18% w/w). $^1$H NMR (500 MHz, $CDCl_3$) δ ppm 8.19 (dd, J=8.44, 13.39 Hz, 1 H), 7.91-8.04 (m, 1 H), 7.71-7.82 (m, 1 H), 7.68 (t, J=7.24 Hz, 1 H), 7.55 (t, J=7.43 Hz, 1 H), 7.21-7.27 (m, 1 H), 5.82 (br. s, 1 H), 4.42-4.75 (m, 1 H), 3.77-4.00 (m, 2 H), 2.67-2.80 (m, 1 H), 2.41-2.65 (m, 1 H), 1.46 (s, 9 H). LC-MS: purity 100% (ELS) 92% (UV), $t_R$ 1.97 min, m/z $[M+H]^+$ 359.05.

Example 19-26

General Procedure LL

22

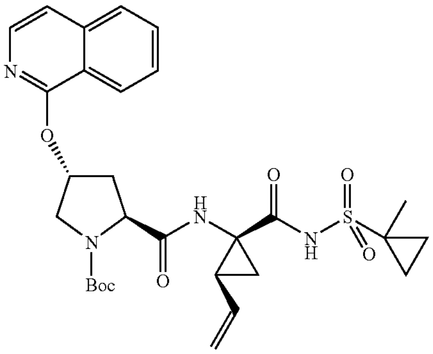

Preparation of Boc Protected Heteroaryl Ether Intermediate (2S,4R)-1-(tert-Butoxycarbonylamino)-4-(1-isoquinolin-1-oxy)-proline (2.17 g, 6.0 mmol., 1.0 eq.) and N,N-dimethylformamide (25 mL) were charged into a 50 mL round bottom flask under nitrogen. HATU (2.76 g, 7.3 mmol., 1.2 eq.) and diisopropylethylamine (2.34 g, 18.1 mmol., 3.0 eq.) were added and the reaction mixture stirred at ambient temperature for a further 20 minutes. (1R,2R)-1-Amino-2-vinyl-cyclopropane-1-acyl-(1'-methyl)cyclopropanesulfonamide hydrochloride salt (1.78 g, 6.35 mmol., 1.05 eq.) was added as a single portion and stirring was continued at ambient temperature for a further 15 hours. Monitoring the reaction extent by LCMS showed full disappearance of the starting material. The solvent was removed under vacuum and the residue partitioned between ethyl acetate (30 mL) and water (20 mL). The organic phase was further washed with water (10 mL), brine (10 mL), dried over sodium sulfate, filtered and the solvent removed under vacuum. The residue was purified by flash column chromatography, using a heptanes:ethyl acetate gradient (from 7:3 to 4:6). After combining the relevant fractions and solvent removal, 3.48 g (98%) of compound 22 was isolated as a pale yellow foamy solid. $^{1}$H NMR (500 MHz, $CDCl_3$) δ ppm 9.88 (br. s, 1 H), 8.14 (d, J=8.44 Hz, 1 H), 7.98 (d, J=5.87 Hz, 1 H), 7.72-7.82 (m, 1 H), 7.68 (t, J=7.52 Hz, 1 H), 7.54 (t, J=7.70 Hz, 1 H), 7.26 (d, J=5.50 Hz, 1 H), 7.22 (br. s, 1 H), 5.81-5.94 (m, 1 H), 5.67-5.82 (m, 1 H), 5.30 (d, J=17.24 Hz, 1 H), 5.16 (d, J=10.27 Hz, 1 H), 4.42 (t, J=7.89 Hz, 1 H), 3.67-3.96 (m, 2 H), 2.39-2.65 (m, 2 H), 2.13 (q, J=8.56 Hz, 1 H), 1.98 (dd, J=8.07, 5.50 Hz, 1 H), 1.58-1.71 (m, 2 H), 1.51 (s, 3 H), 1.47 (s, 9 H), 1.38-1.44 (m, 1 H), 0.86-0.92 (m, 1 H), 0.79-0.86 (m, 1 H). LC-MS: purity 100% (UV), $t_R$ 2.29 min, m/z $[M+H]^+$ 585.25.

Example 19-27

General Procedure MM

23

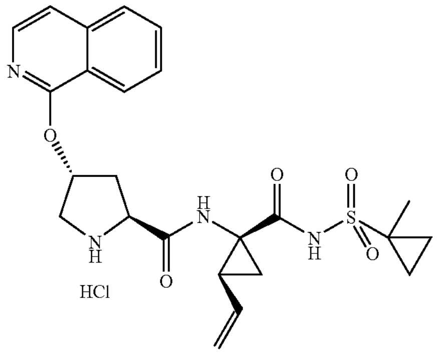

Preparation of Deprotected Heteroaryl Ether Intermediate Hydrochloride Salt

Boc protected heteroaryl ether intermediate compound 22 (3.48 g, 5.95 mmol., 1.0 eq.) and dioxane (2.5 mL) were charged into a 25 mL round bottom flask. 4M HCl in dioxane (12.5 mL) was added dropwise over 5 minutes and the reaction mixture stirred at ambient temperature for 2 hours. LCMS analysis showed full consumption of the starting material. The solvent was removed under vacuum and the residue further dried under high vacuum for 4 hours to give 2.70 g (94%) of compound 23 which was used in the next step without further purification. $^{1}$H NMR (500 MHz, DMSO-$d_6$) δ ppm 10.57-10.86 (m, 1H), 9.17 (s, 1 H), 8.87-9.01 (m, 1 H), 8.36 (d, J=7.70 Hz, 1 H), 8.03 (d, J=5.87 Hz, 1 H), 7.93 (d, J=8.44 Hz, 1 H), 7.80 (td, J=7.61, 1.28 Hz, 1 H), 7.65 (td, J=7.70, 1.10 Hz, 1 H), 7.47 (d, J=5.87 Hz, 1 H), 5.82 (t, J=3.85 Hz, 1 H), 5.46-5.55 (m, 1 H), 5.27 (dd, J=17.24, 1.47 Hz, 1 H), 5.10 (dd, J=10.27, 1.83 Hz, 1 H), 4.54-4.67 (m, 1 H), 3.67-3.77 (m, 1 H), 3.59-3.67 (m, 1 H), 3.52-3.55 (m, 1 H), 2.75 (dd, J=14.31, 7.34 Hz, 1 H), 2.29 (q, J=8.93 Hz, 1 H), 2.22 (ddd, J=14.12, 11.19, 4.40 Hz, 1 H), 1.80 (dd, J=7.89, 4.95 Hz, 1 H), 1.33-1.43 (m, 5 H), 1.27 (dd, J=9.35, 4.95 Hz, 1 H), 0.85-0.94 (m, 2 H). LC-MS: purity 92% (UV), $t_R$ 1.43 min, m/z $[M+H]^+$ 485.25.

Example 19-28

General Procedure NN

24

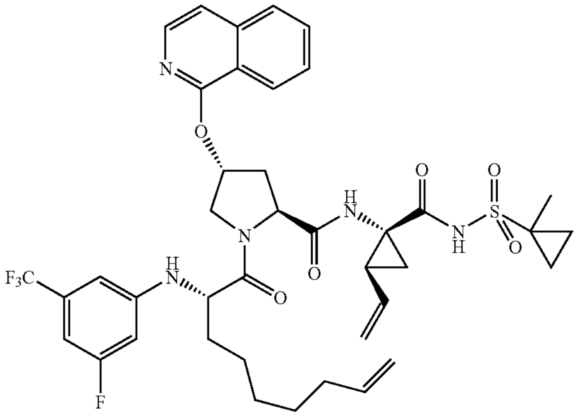

Preparation of Macrocyclization Precursor:

Deprotected heteroaryl ether intermediate compound 23 (HCl salt, 500 mg, 1.03 mmol., 1.0 eq.) and N,N-dimethylformamide (9 mL) were charged into a 25 mL round bottom flask under nitrogen. HATU (505 mg, 1.33 mmol., 1.3 eq.) and diisopropylethylamine (665 mg, 5.15 mmol., 5.0 eq.) were added and the reaction mixture stirred at ambient temperature for a further 15 minutes. 2-(3-trifluoromethyl-5-fluoro-phenylamino)-non-8-enoic acid (376 mg, 1.13 mmol., 1.1 eq.) was added as a single portion and stirring was continued at ambient temperature for a further 15 hours. Monitoring the reaction extent by LCMS showed full consumption of the starting material. The solvent was removed under vacuum and the residue partitioned between dichloromethane (20 mL) and water (20 mL). The organic phase was washed with water (10 mL), brine (10 mL), dried over sodium sulfate, filtered and concentrated to dryness. The residue was purified by flash column chromatography, using a heptanes:ethyl acetate gradient (from 95:5 to 50:50). After combining the relevant fractions and solvent removal, 531 mg (65%) of compound 24 was isolated as a yellow glassy solid. $^{1}$H NMR (500 MHz, $CDCl_3$) δ ppm 10.21 (br. s, 1 H), 8.06 (d, J=8.24 Hz, 1 H), 7.99 (d, J=5.95 Hz, 1 H), 7.78 (d, J=8.24 Hz, 1 H), 7.66-7.73 (m, 1 H), 7.54 (t, J=7.55 Hz, 1 H), 7.30 (d, J=5.80 Hz, 1 H), 6.87 (s, 1 H), 6.61 (d, J=8.39 Hz, 1 H), 6.58 (s, 1 H), 6.38 (d, J=10.83 Hz, 1 H), 6.04 (br. s, 1 H), 5.73-5.85 (m, 2 H), 5.24 (dd, J=17.17, 0.99 Hz, 1 H), 5.13 (dd, J=10.38, 1.22 Hz, 1 H), 5.08 (d, J=9.77 Hz, 1 H), 4.99 (dd, J=17.17, 1.75 Hz, 1 H), 4.94 (dt, J=10.19, 0.93 Hz, 1 H), 4.50 (t, J=8.39 Hz, 1 H), 4.05-4.17 (m, 3 H), 2.53-2.65 (m, 2 H), 2.02-2.09 (m, 4 H), 1.77-1.87 (m, 2 H), 1.68-1.75 (m, 2 H), 1.51 (s, 3 H), 1.44-

1.49 (m, 2 H), 1.32-1.43 (m, 4 H), 0.82-0.96 (m, 3 H). LC-MS: purity 92% (UV), $t_R$ 2.79 min, m/z $[M+H]^+$ 800.35.

Example 19-29

General Procedure OO

346

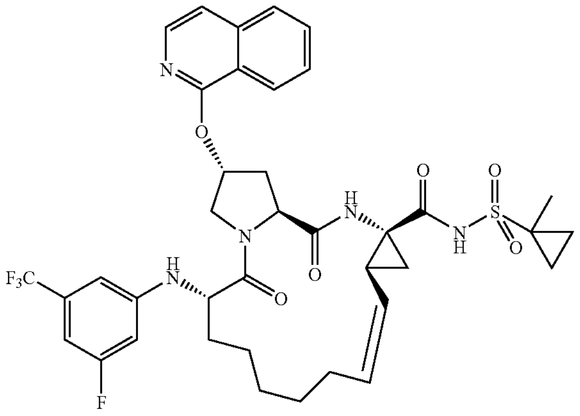

Preparation of Compound 346:

The macrocyclization precursor compound 24 (200 mg, 0.250 mmol., 1.0 eq.) and toluene (10 mL, previously degassed by bubbling nitrogen through the solvent for 30 min) were charged in a 25 mL round bottom flask previously flushed with nitrogen gas (It is important to keep the reaction mixture under a protective nitrogen atmosphere as much as possible). Zhan catalyst (1.6 mg, 2 mol %) was added and the reaction mixture heated at 65° C. for 1 hour with constant nitrogen gas bubbling through the reaction mixture (via needle). LCMS analysis showed 80% conversion, so a further 1 mol % catalyst was added and the stirring continued at 65° C. After one 1 hour all starting material had been consumed so heating was stopped and the reaction mixture left to cool down to ambient temperature. N-methyl-ethylenediamine (24 mg, 10 times the catalyst weight) was added and the reaction mixture stirred for a further 15 minutes. The solvent was removed under vacuum and the residue partitioned between ethyl acetate (20 mL) and water (10 mL). The organic layer was collected and the pH of the aqueous phase adjusted to 6-7 with 0.5M hydrochloric acid. The aqueous phase was further extracted with ethyl acetate (2×20 mL). The organic phases were combined, dried over sodium sulfate, filtered and concentrated under vacuum. The residue was purified by flash column chromatography, using a methanol: dichloromethane gradient (from 0.5% to 1% methanol in dichloromethane). After combining the relevant fractions and solvent removal, 40.7 mg (21%) of compound 346 was isolated as a glassy solid. $^1$H NMR (500 MHz, $CDCl_3$) δ ppm 10.09 (br. s, 1 H), 8.05 (d, J=8.24 Hz, 1 H), 7.98 (d, J=5.80 Hz, 1 H), 7.74 (d, J=8.24 Hz, 1 H), 7.63-7.68 (m, 1 H), 7.49 (t, J=7.63 Hz, 1 H), 7.26 (s, 2 H), 7.00 (br. s, 1 H), 6.55 (s, 1 H), 6.52 (d, J=8.39 Hz, 1 H), 6.30 (d, J=10.68 Hz, 1 H), 5.98 (br. s, 1 H), 5.65-5.74 (m, 1 H), 4.98 (t, J=9.69 Hz, 1 H), 4.78 (d, J=8.70 Hz, 1 H), 4.70 (t, J=7.86 Hz, 1 H), 4.23 (td, J=3.43, 8.66 Hz, 1 H), 4.13-4.20 (m, 2 H), 2.69 (dd, J=3.43, 7.71 Hz, 2 H), 2.36-2.45 (m, 1 H), 2.27 (q, J=8.80 Hz, 1 H), 2.00-2.07 (m, 1 H), 1.84-1.92 (m, 2 H), 1.74-1.82 (m, 2 H), 1.48-1.52 (m, 4 H), 1.39-1.48 (m, 4 H), 1.28-1.35 (m, 2 H), 0.80-0.85 (m, 2 H). LC-MS: purity 93% (UV), $t_R$ 5.53 min, m/z $[M+H]^+$ 772.40.

Example 19-30

375

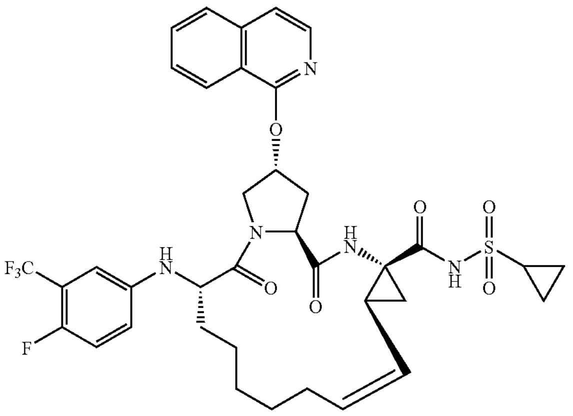

Compound 375 was prepared in a manner analogous to General Procedure OO, and the yield was 27%. $^1$H NMR (500 MHz, $CDCl_3$) δ 10.16 (br. s, 1 H), 8.00 (dd, 2 H), 7.79 (d, J=8.07 Hz, 1 H), 7.71 (t, J=7.43 Hz, 1 H), 7.52 (t, J=7.61 Hz, 1 H), 7.31 (d, J=5.87 Hz, 1 H), 6.76 (s, 1 H), 6.71 (dd, J=2.57, 5.14 Hz, 1 H), 6.35-6.41 (m, 1 H), 6.29 (t, 1 H), 5.97 (br. s, 1 H), 5.75 (q, 1 H), 5.01 (t, J=9.45 Hz, 1 H), 4.66-4.73 (m, 1 H), 4.31 (d, J=9.54 Hz, 1 H), 4.24 (d, J=11.55 Hz, 1 H), 4.09-4.18 (m, 2 H), 2.93 (br. s, 1 H), 2.62-2.76 (m, 2 H), 2.46-2.56 (m, 1 H), 2.25 (d, J=8.99 Hz, 1 H), 1.93-2.04 (m, 2 H), 1.73-1.88 (m, 2 H), 1.42-1.55 (m, 6 H), 1.28-1.38 (m, 3 H), 1.08-1.21 (m, 2 H). LC-MS: purity 99% (ELS) 96% (UV), $t_R$ 5.29 min, m/z $[M+H]^+$ 758.30.

Example 19-31

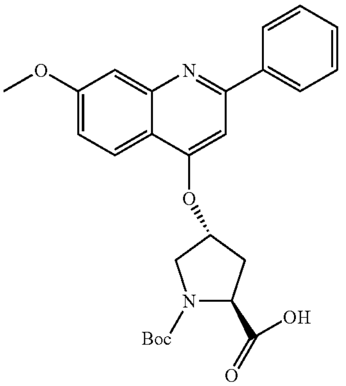

(2S,4R)-1-(tert-butoxycarbonylamino)-4-(2-phenyl-7-methoxy-quinoline-4-oxy)-proline was prepared in a manner analogous to General Procedure KK, to afford 17.39 g (70%), beige solid. $^1$H NMR (250 MHz, $CD_3OD$) δ ppm 7.94-8.16 (m, 3 H) 7.50-7.65 (m, 3 H) 7.36-7.48 (m, 1 H) 7.25-7.32 (m, 1 H) 7.14-7.25 (m, 1 H) 5.36-5.61 (m, 1 H) 4.37-4.61 (m, 1 H) 3.97 (s, 3 H) 3.85-3.94 (m, 2 H) 2.70-2.88 (m, 1 H) 2.35-2.54

(m, 1 H) 1.34-1.53 (m, 9 H). LC-MS: purity 96% (UV), $t_R$ 1.53 min m/z $[M+H]^+$ 465.60.

Example 19-32

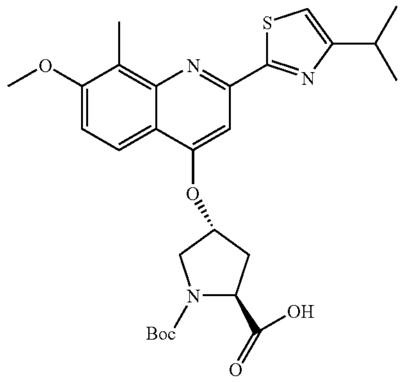

(2S,4R)-1-(tert-butoxycarbonylamino)-4-[2-(3'-isopropyl-thiazol-2-yl)-7-methoxy-8-methyl-quinoline-4-oxy]-proline was prepared in a manner analogous to General Procedure KK, to afford 6.40 g (99%), yellow solid. $^1H$ NMR (500 MHz, $CDCl_3$) δ ppm 7.89-8.03 (m, 1 H) 7.44-7.56 (m, 1 H) 7.24 (d, J=9.16 Hz, 1 H) 7.04 (br. s, 1 H) 5.39 (br. s, 1 H) 4.69 (s, 1 H) 4.47-4.60 (m, 1 H) 4.00 (s, 3 H) 3.98 (br. s, 1 H) 3.78-3.88 (m, 1 H) 3.18-3.25 (m, 1 H) 2.71 (s, 3 H) 1.47 (s, 9 H) 1.42-1.45 (m, 1 H) 1.40 (d, J=6.71 Hz, 6 H) 1.36-1.38 (m, 1 H). LC-MS: purity 100% (UV), $t_R$ 2.65 min, m/z $[M+H]^+$ 528.30.

General Procedure KKLS

A preparation of (2S,4R)-1-(tert-butoxycarbonylamino)-4-[2-(3'-isopropyl-thiazol-2-yl)-7-methoxy-8-methyl-quinoline-4-oxy]-proline was also completed using the following procedure: (2S,4R)-1-(tert-Butoxycarbonylamino)-4-hydroxy-proline (24.25 g, 105 mmol, 1.0 eq.) and dimethylsulfoxide (350 mL) were charged into a 2 L round bottom flask. Potassium tert-butoxide (23.56 g, 210 mmol, 2.0 eq.) was added portionwise over 10 minutes at ambient temperature. The reaction mixture was stirred for 1 hour at ambient temperature while the colour changed from pale yellow to dark orange. 2-(4-isopropylthiazol-2-yl)-4-chloro-7-methoxy-8-methyl-quinoline (35.00 g, 105 mmol, 1.0 eq.) was added portionwise leading to the formation of a brown sticky residue. Further dimethylsulfoxide (150 mL) was added to help solubilizing the reagents and the stirring was continued at 35° C. for a further 20 min. As the reaction mixture remained very thick more dimethylsulfoxide (300 mL) was added. The resulting mixture was stirred at 28° C. for 15 hours by which time LCMS analysis of the reaction mixture showed the reaction to be complete. The reaction mixture was diluted with methanol (300 mL) and stirred for 30 min. The reaction mixture was left to cool to ambient temperature and split into two portions to ease the work up. Both fractions were treated in the same way as follows. The mixture was diluted with ethyl acetate (500 mL) and water (300 mL). The aqueous phase was acidified to pH 3 with 1M hydrochloric acid (~80 mL) and extracted with ethyl acetate (3×200 mL). The organic extracts were combined, washed with water (5×350 mL) and brine (300 mL), dried over sodium sulfate, filtered and the solvent removed under vacuum to give 24 g and 25 g of crude product respectively. Each solid was purified separately by dry flash chromatography onto 500 g of silica and eluting with a dichloromethane:methanol gradient (from neat dichloromethane to 5% methanol in dichloromethane). After combining the relevant fractions and solvent removal 20.6 g (37%) and 21.7 g (39%) of the desired product were isolated as a yellow solid. The combined yield was 42.3 g (76%). $^1H$ NMR (500 MHz, $CDCl_3$) δ ppm 7.89-8.03 (m, 1 H) 7.44-7.56 (m, 1 H) 7.24 (d, J=9.16 Hz, 1 H) 7.04 (br. s, 1 H) 5.39 (br. s, 1 H) 4.69 (s, 1 H) 4.47-4.60 (m, 1 H) 4.00 (s, 3 H) 3.98 (br. s, 1 H) 3.78-3.88 (m, 1 H) 3.18-3.25 (m, 1 H) 2.71 (s, 3 H) 1.47 (s, 9 H) 1.42-1.45 (m, 1 H) 1.40 (d, J=6.71 Hz, 6 H) 1.36-1.38 (m, 1 H). LC-MS: purity 98% (UV), m/z $[M+Na]^+$ 550.15.

Example 19-33

25

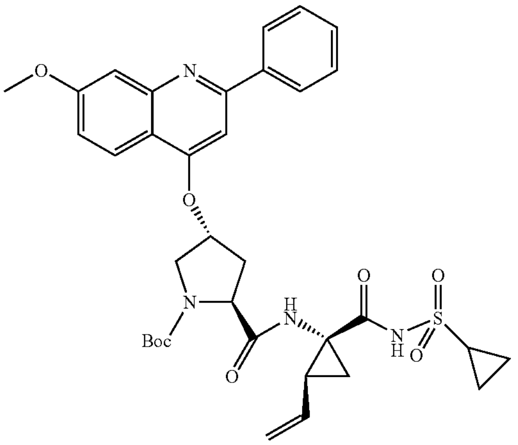

The preceding compound was prepared in a manner analogous to General Procedure LL, to afford 4.27 g (%), cream solid. $^1H$ NMR (250 MHz, $CDCl_3$) δ ppm 10.03 (br. s, 1 H) 8.05 (dd, J=7.99, 1.45 Hz, 2 H), 7.97 (d, J=9.14 Hz, 1 H), 7.39-7.62 (m, 4 H), 7.25 (s, 1 H), 7.13 (dd, J=9.14, 2.28 Hz, 1 H), 7.00 (s, 1 H), 5.63-5.92 (m, 1 H), 5.22-5.39 (m, 2 H), 5.16 (d, J=10.36 Hz, 1 H), 4.37 (t, J=7.84 Hz, 1 H), 3.97 (s, 3 H), 3.88 (br. s, 2 H), 2.90-3.01 (m, 1 H), 2.42-2.75 (m, 2 H), 2.13 (q, J=8.58 Hz, 1 H), 2.00 (dd, J=7.99, 5.56 Hz, 1 H), 1.56-1.88 (m, 1 H), 1.46 (s, 9 H), 1.27-1.39 (m, 2 H), 1.05 (d, J=8.07 Hz, 2 H). LC-MS: purity 100% (UV), $t_R$ 3.70 min, m/z $[M+H]^+$ 677.40.

Example 19-34

26

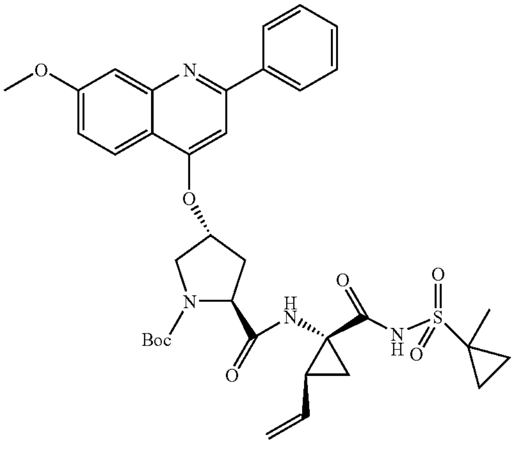

The preceding compound was prepared in a manner analogous to General Procedure LL, to afford 2.32 g (86%), yellow solid. $^1$H NMR (500 MHz, $CD_3OD$) δ ppm 8.65 (dd, J=4.40, 1.28 Hz, 1 H), 8.34 (dd, J=8.44, 1.28 Hz, 1 H), 8.12 (d, J=9.17 Hz, 1 H), 8.05 (d, J=7.89 Hz, 2 H), 7.57-7.60 (m, 3 H), 7.45-7.47 (m, 1 H), 7.36 (s, 1 H), 7.27 (dd, J=9.17, 2.38 Hz, 1 H), 5.69-5.80 (m, 1 H), 5.61 (br. s, 1 H), 5.31 (d, J=17.06 Hz, 1 H), 5.13 (d, J=10.64 Hz, 1 H), 4.37-4.46 (m, 1 H), 3.99 (s, 3 H), 3.92-3.96 (m, 1 H) 2.65 (dd, J=13.85, 6.69 Hz, 1 H), 2.38 (ddd, J=13.98, 9.86, 4.22 Hz, 1 H), 2.25 (q, J=8.68 Hz, 1 H), 1.81-1.89 (m, 1 H), 1.56-1.64 (m, 1 H), 1.50 (s, 3 H), 1.47 (s, 9 H), 1.44-1.46 (m, 1 H), 1.37-1.44 (m, 2 H). LC-MS: purity 95% (UV), $t_R$ 1.79 min, m/z $[M+H]^+$ 691.80.

Example 19-35

Preparation of compound 27

27

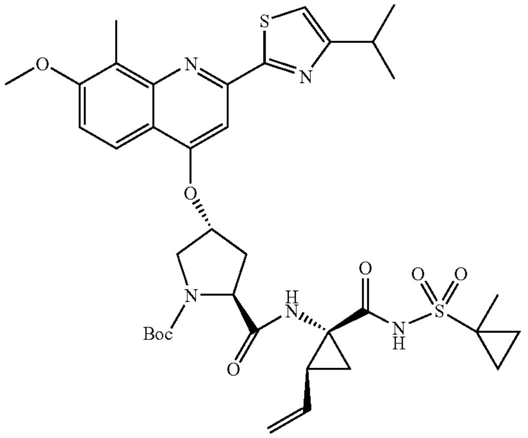

General Procedure LLLS (2S,4R)-1-(tert-Butoxycarbonylamino)-4-[2-(3'-isopropyl-thiazol-2-yl)-7-methoxy-8-methyl-quinoline-4-oxy]-proline (25.00 g, 47.38 mmol., 1.0 eq.) and N,N-dimethylformamide (200 mL) were charged into a 1 L round bottom flask under nitrogen. HATU (21.62 g, 56.86 mmol., 1.2 eq.) and diisopropylethylamine (50 mL, 284.3 mmol., 6.0 eq.) were added at 0° C. and the reaction mixture stirred at ambient temperature for a further 30 minutes. (1R,2S)-1-Amino-2-vinyl-cyclopropane-1-carbonyl-(1'-methyl)cyclopropane-sulfonamide hydrochloride salt (13.98 g, 49.75 mmol., 1.05 eq.), previously dissolved in N,N-dimethylformamide (50 mL) was added dropwise over 15 minutes at 0° C. and stirring was continued for 2 hours ambient temperature. Monitoring the reaction conversion by LCMS showed complete consumption of the starting material. The solvent was removed under vacuum and the residue partitioned between water (0.5 L) and ethyl acetate (0.5 L) leading to the precipitation of a solid. The phases were separated and the solid partitioned between ethyl acetate (1.5 L) and water (3 L). The organic phases were combined, washed with water (2×1 L), dried over sodium sulfate, filtered and the solvent removed under vacuum. The residue was purified by dry flash chromatography, using a heptanes:ethyl acetate gradient (from 4:1 to neat EtOAc). After combining the relevant fractions and solvent removal, 21.0 g (59%) of compound 27 was isolated as a yellow solid. $^1$H NMR (500 MHz, $CDCl_3$) δ ppm 9.79 (br. s, 1 H) 7.93 (d, J=9.00 Hz, 1 H) 7.51 (br. s, 1 H) 7.24 (d, J=9.16 Hz, 1 H) 7.16 (br. s, 1 H) 7.05 (s, 1 H) 5.65-5.88 (m, 1 H) 5.37-5.48 (m, 1 H) 5.30 (d, J=17.09 Hz, 1 H) 5.17 (d, J=10.38 Hz, 1 H) 4.40 (t, J=7.78 Hz, 1 H) 4.00 (s, 3 H) 3.92 (br. s, 2 H) 3.12-3.30 (m, 1 H) 2.71 (s, 3 H) 2.54-2.68 (m, 2 H) 2.12 (q, J=8.70 Hz, 1 H) 1.99 (dd, J=8.09, 5.80 Hz, 1 H) 1.61-1.78 (m, 3 H) 1.52 (s, 2 H) 1.44-1.50 (m, 9 H) 1.33-1.43 (m, 7 H) 0.76-0.95 (m, 2 H). LC-MS: purity 98% (UV), m/z $[M+H]^+$ 754.45.

Example 19-36

28

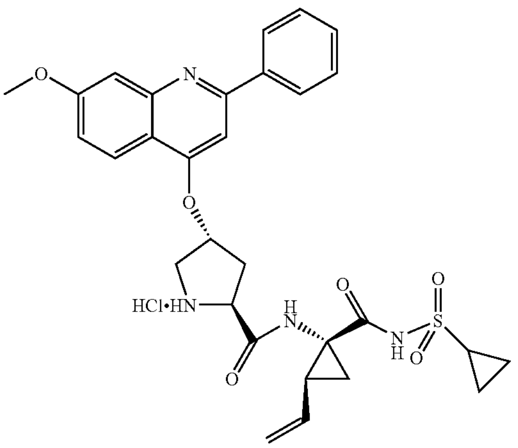

The preceding compound was prepared in a manner analogous to General Procedure MM, to afford 571 mg (99%), yellow solid. $^1$H NMR (500 MHz, $CD_3OD$) δ ppm 8.56 (d, J=9.31 Hz, 1 H), 8.11 (d, J=7.17 Hz, 2 H), 7.71-7.81 (m, 3 H), 7.66 (s, 1 H), 7.61 (d, J=2.29 Hz, 1 H), 7.51 (dd, J=9.31, 2.29 Hz, 1 H), 6.01 (br. s, 1 H), 5.64 (ddd, J=17.13, 10.19, 8.70 Hz, 1 H), 5.34 (dd, J=17.17, 0.99 Hz, 1 H), 5.16 (dd, J=10.38, 1.22 Hz, 1 H), 4.81-4.84 (m, 1 H), 4.08 (s, 3 H), 4.01 (s, 2 H), 3.11 (dd, J=14.65, 7.48 Hz, 1 H), 2.91-2.99 (m, 1 H), 2.57 (ddd, J=14.57, 10.68, 4.20 Hz, 1 H), 2.40 (q, J=8.65 Hz, 1 H), 1.96 (dd, J=7.93, 5.65 Hz, 1 H), 1.39 (dd, J=9.46, 5.49 Hz, 1 H), 1.24-1.31 (m, 1 H), 0.99-1.19 (m, 3 H). LC-MS: purity 99% (UV), $t_R$ 1.24 min, m/z $[M+H]^+$ 577.30.

Example 19-37

29

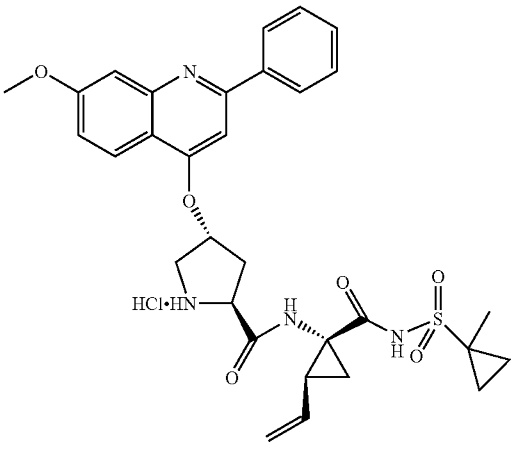

The preceding compound was prepared in a manner analogous to General Procedure MM, to afford 2.24 g (99%), beige solid. $^1$H NMR (500 MHz, $CD_3OD$) δ ppm 8.61 (dd, J=4.43, 1.37 Hz, 1 H), 8.39 (d, J=9.16 Hz, 1 H), 8.30 (dd, J=8.39, 1.37 Hz, 1 H), 7.95-7.98 (m, 2 H), 7.58-7.66 (m, 3 H), 7.52 (s, 1 H), 7.46 (d, J=2.14 Hz, 1 H), 7.36-7.41 (m, 2 H), 5.86 (t, J=3.81 Hz, 1 H), 5.44-5.53 (m, 1 H), 5.21 (dd, J=17.24, 1.37 Hz, 1 H), 5.03 (dd, J=10.38, 1.53 Hz, 1 H), 4.68 (dd, J=10.68, 7.32 Hz, 1 H), 3.95 (s, 3 H), 3.83-3.88 (m, 2 H), 2.97 (dd, J=15.11, 7.48 Hz, 1 H), 2.42 (ddd, J=14.80, 10.53, 4.27 Hz, 1 H), 2.25 (q, J=8.65 Hz, 1 H), 1.82 (dd, J=8.09, 5.65 Hz, 1 H), 1.44-1.49 (m, 1 H), 1.37-1.41 (m, 1 H), 1.37 (s, 3 H), 1.24 (dd, J=9.61, 5.65 Hz, 1 H), 0.70-0.82 (m, 2 H). LC-MS: purity 78% (UV), $t_R$ 1.27 min, m/z $[M+H]^+$ 591.30.

Example 19-38

30

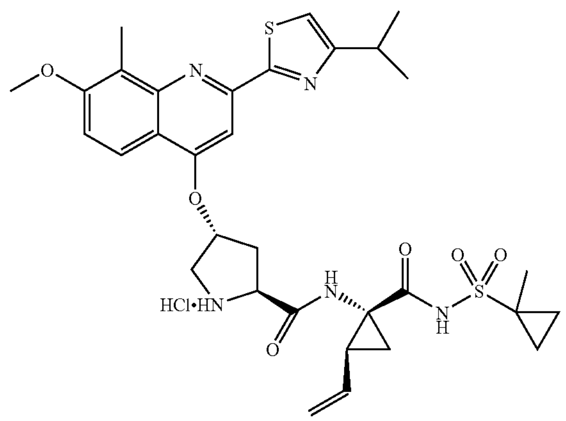

The preceding compound was prepared in a manner analogous to General Procedure MM, to afford 3.16 g (96%), brown solid. $^1$H NMR (500 MHz, $CD_3OD$) δ ppm 8.41 (d, J=9.31 Hz, 1 H), 7.78 (s, 1 H), 7.66 (s, 1 H), 7.61 (d, J=9.46 Hz, 1 H), 5.88 (br. s, 1 H), 5.57-5.67 (m, 1 H), 5.33 (d, J=16.94 Hz, 1 H), 5.16 (d, J=11.14 Hz, 1 H), 4.81 (dd, J=10.60, 7.55 Hz, 1 H), 4.08 (s, 3 H), 3.97 (br. s, 2 H), 3.25-3.30 (m, 1 H), 3.06 (dd, J=14.42, 7.40 Hz, 1 H), 2.64 (s, 3 H), 2.55 (ddd, J=14.65, 10.60, 4.35 Hz, 1 H), 2.37 (q, J=8.70 Hz, 1 H), 1.95 (dd, J=7.93, 5.65 Hz, 1 H), 1.56-1.62 (m, 1 H), 1.51-1.54 (m, 1 H), 1.50 (s, 3 H), 1.44 (d, J=7.02 Hz, 6 H), 1.38 (dd, J=9.46, 5.65 Hz, 1 H), 0.85-0.94 (m, 2 H). LC-MS: purity 99% (UV), $t_R$ 1.94 min, m/z $[M+H]^+$ 654.10.

Example 19-39

31

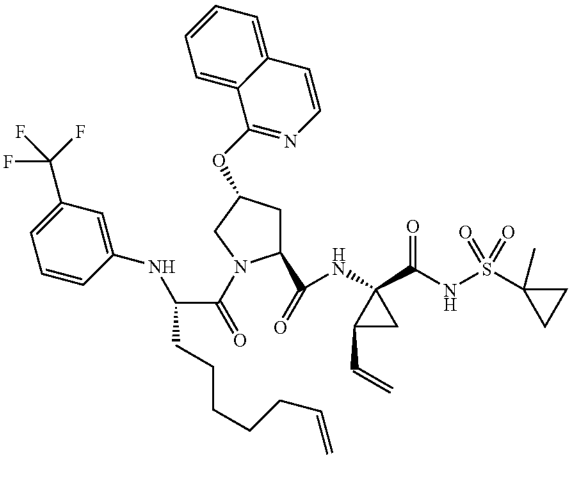

The preceding compound was prepared in a manner analogous to General Procedure NN, to afford 55.0 mg (26%), beige foamy solid. $^1$H NMR (500 MHz, $CDCl_3$) δ ppm 10.19 (br. s, 1 H), 8.01-8.07 (m, 1 H), 7.96-8.01 (m, 1 H), 7.74-7.83 (m, 1 H), 7.71 (t, J=7.52 Hz, 1 H), 7.61-7.68 (m, 1 H), 7.46-7.60 (m, 2 H), 7.30 (d, J=5.87 Hz, 1 H), 6.98-7.09 (m, 1 H), 6.89 (d, J=4.77 Hz, 1 H), 6.75 (s, 1 H), 6.65 (d, J=8.07 Hz, 1 H), 6.03 (d, J=2.20 Hz, 1 H), 5.73-5.85 (m, 3 H), 5.24 (d, J=16.87 Hz, 1 H), 5.08-5.18 (m, 1 H), 4.99 (d, J=15.77 Hz, 1 H), 4.94 (d, J=10.64 Hz, 1 H), 4.83 (br. s, 1 H), 4.44-4.57 (m, 1 H), 4.12-4.22 (m, 1 H), 4.04-4.12 (m, 1 H), 2.59 (d, J=8.80 Hz, 1 H), 1.96-2.11 (m, 3 H), 1.67-1.87 (m, 3 H), 1.51 (s, 3 H), 1.44-1.49 (m, 2 H), 1.31-1.43 (m, 5 H), 1.17-1.29 (m, 2 H), 0.83-0.98 (m, 2 H). LC-MS: purity 75% (UV), $t_R$ 2.77 min, m/z $[M+H]^+$ 782.45.

Example 19-40

32

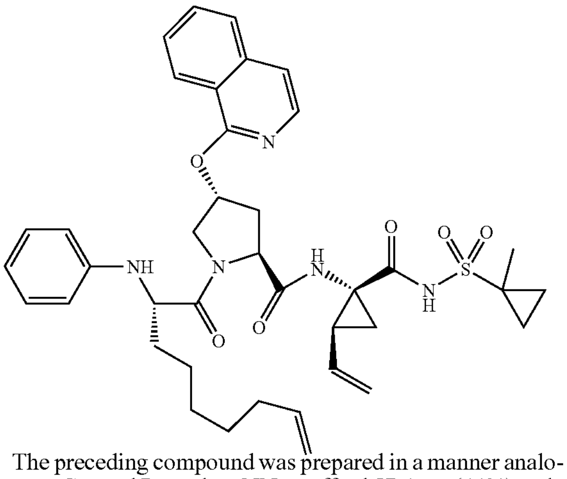

The preceding compound was prepared in a manner analogous to General Procedure NN, to afford 57.4 mg (44%), pale yellow solid. $^1$H NMR (500 MHz, $CDCl_3$) δ ppm 10.17 (br. s, 1 H), 8.06 (d, J=8.44 Hz, 1 H), 8.00 (d, J=5.87 Hz, 1 H), 7.75-7.80 (m, 1 H), 7.67-7.73 (m, 1 H), 7.48-7.54 (m, 1 H), 7.29 (d, J=5.87 Hz, 1 H), 7.19 (s, 1 H), 6.94 (t, J=7.89 Hz, 2 H), 6.61 (t, J=7.34 Hz, 1 H), 6.49 (d, J=7.89 Hz, 2 H), 5.99 (d, J=2.93 Hz, 1 H), 5.71-5.84 (m, 2 H) 5.25 (d, J=17.06 Hz, 1 H), 5.13 (d, J=10.27 Hz, 1 H), 4.99 (dd, J=17.06, 1.65 Hz, 1 H), 4.93 (dd, J=10.18, 0.83 Hz, 1 H), 4.52 (t, J=8.34 Hz, 1 H), 4.17 (d, J=11.92 Hz, 1 H), 4.09-4.14 (m, 1 H) 4.06 (dd, J=11.74, 3.67 Hz, 1 H), 2.55 (dd, J=8.34, 2.66 Hz, 2 H), 1.98-2.09 (m, 4 H), 1.74-1.81 (m, 2 H), 1.72 (dd, J=10.73, 5.04 Hz, 1 H), 1.65-1.70 (m, 1 H), 1.51 (s, 3 H), 1.41-1.47 (m, 2 H), 1.28-1.41 (m, 5 H), 0.79-0.95 (m, 3 H). LC-MS: purity 100% (UV), $t_R$ 2.64 min, m/z $[M+H]^+$ 714.40.

Example 19-41

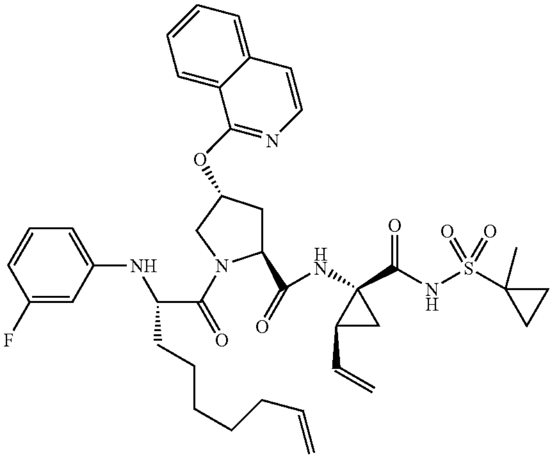

The preceding compound was prepared in a manner analogous to General Procedure NN, to afford 432 mg (61%), pale yellow solid. $^{1}$H NMR (500 MHz, $CDCl_3$) δ ppm 10.14 (br. s, 1 H), 8.07 (d, J=8.24 Hz, 1 H), 7.99 (d, J=5.80 Hz, 1 H), 7.75-7.82 (m, 1 H), 7.66-7.74 (m, 1 H), 7.49-7.60 (m, 1 H), 7.30 (d, J=5.80 Hz, 1 H), 6.99 (s, 1 H) 6.84-6.94 (m, 1 H), 6.18-6.38 (m, 3 H), 6.01 (s, 1 H), 5.70-5.87 (m, 2 H), 5.24 (dd, J=17.09, 1.22 Hz, 1 H), 5.13 (dd, J=10.38, 1.37 Hz, 1 H), 4.90-5.04 (m, 2 H), 4.70 (br. s, 1 H), 4.51 (t, J=8.39 Hz, 1 H), 4.01-4.21 (m, 3 H), 2.58 (dd, J=8.39, 2.59 Hz, 2 H), 1.98-2.10 (m, 4 H), 1.75-1.83 (m, 2 H), 1.62-1.75 (m, 4 H), 1.56 (d, J=6.41 Hz, 1 H), 1.51 (s, 2 H) 1.43-1.48 (m, 1 H), 1.29-1.42 (m, 4 H), 0.80-0.97 (m, 2 H). LC-MS: purity 97% (UV), $t_R$ 2.65 min, m/z $[M+H]^+$ 732.50.

Example 19-42

34

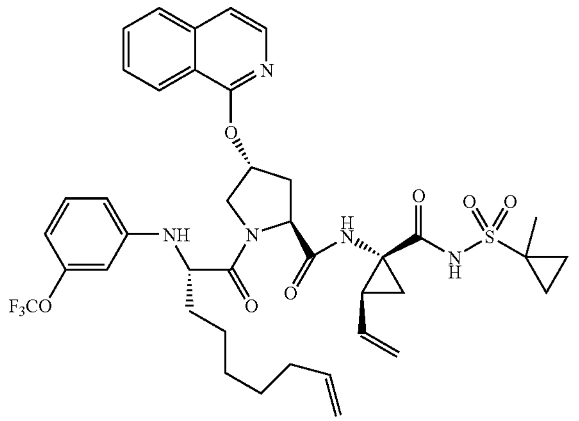

The preceding compound was prepared in a manner analogous to General Procedure NN, to afford 528 mg (42%), yellow solid. $^{1}$H NMR (500 MHz, $CDCl_3$) δ ppm 10.21 (br. s, 1 H), 8.06 (d, J=8.39 Hz, 1 H), 7.99 (d, J=5.80 Hz, 1 H), 7.78 (d, 1 H), 7.70 (t, J=7.55 Hz, 1 H), 7.52 (t, J=7.63 Hz, 1 H), 7.30 (d, J=5.95 Hz, 1 H), 7.09 (br. s, 1 H), 6.92 (t, J=8.16 Hz, 1 H), 6.48 (d, J=8.09 Hz, 1 H), 6.40 (d, J=8.24 Hz, 1 H), 6.36 (s, 1 H), 6.01 (d, J=2.44 Hz, 1 H), 5.78 (dd, J=10.22, 6.71 Hz, 1 H), 5.24 (d, J=17.09 Hz, 1 H), 5.13 (d, J=10.53 Hz, 1 H), 4.99 (dd, J=17.09, 1.68 Hz, 1 H), 4.93 (d, J=10.22 Hz, 1 H), 4.52 (t, J=8.32 Hz, 1 H), 4.13 (q, J=7.12 Hz, 3 H), 4.09 (d, J=3.36 Hz, 1 H), 2.55-2.60 (m, 2 H), 2.01-2.07 (m, 7 H), 1.65-1.84 (m, 5 H), 1.44-1.48 (m, 2 H), 1.31-1.42 (m, 5 H), 0.88-0.95 (m, 1 H), 0.79-0.87 (m, 1 H). LC-MS: purity 100% (UV), $t_R$ 5.72 min, m/z $[M+H]^+$ 798.50.

Example 19-43

35

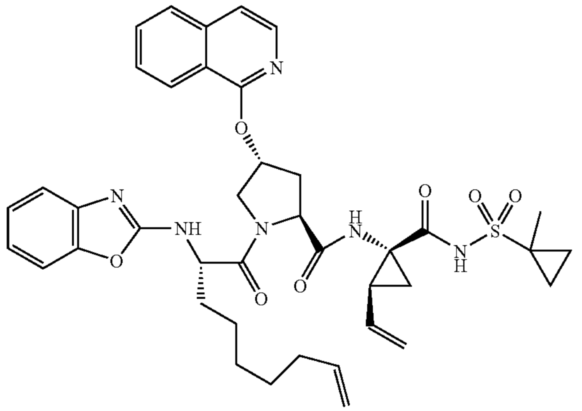

The preceding compound was prepared in a manner analogous to General Procedure NN, to afford 209 mg (42%), yellow solid. $^{1}$H NMR (500 MHz, $CDCl_3$) δ ppm 10.19 (br. s, 1 H), 8.07 (d, J=8.24 Hz, 1 H), 8.00 (d, J=5.80 Hz, 1 H), 7.76 (d, J=8.09 Hz, 1 H), 7.66 (t, J=7.55 Hz, 1 H), 7.44 (t, J=7.71 Hz, 1 H), 7.29 (d, J=5.80 Hz, 1 H), 7.18 (d, J=7.78 Hz, 1 H), 7.04-7.11 (m, 3 H), 6.99 (d, J=7.32 Hz, 1 H), 6.14 (br. s, 1 H), 6.01 (br. s, 1 H), 5.73-5.86 (m, 3 H), 5.25 (d, J=17.09 Hz, 1 H), 5.14 (d, J=10.38 Hz, 1 H), 4.87-5.03 (m, 4 H), 4.72 (br. s, 1 H), 4.55 (t, J=8.16 Hz, 1 H), 4.34 (d, J=11.75 Hz, 1 H), 4.09-4.14 (m, 1 H), 2.55-2.64 (m, 2 H), 2.07-2.13 (m, 1 H), 2.03 (d, J=5.80 Hz, 2 H), 1.89-1.97 (m, 2 H), 1.72-1.78 (m, 2 H), 1.65-1.71 (m, 1 H), 1.55 (s, 1 H), 1.47 (dd, J=9.08, 5.57 Hz, 2 H), 1.30-1.39 (m, 4 H), 0.88-0.95 (m, 1 H), 0.81-0.88 (m, 1 H). LC-MS: purity 98% (UV), $t_R$ 2.16 min, m/z $[M+H]^+$ 755.40.

Example 19-44

36

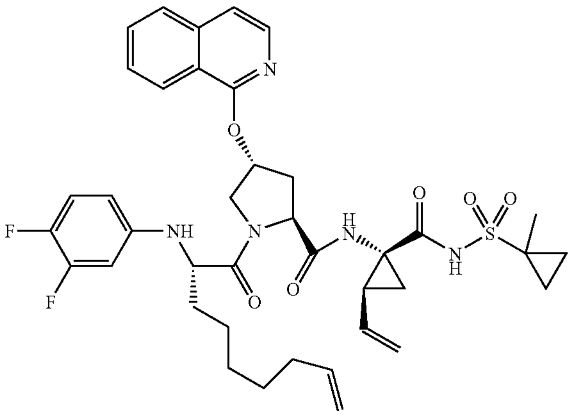

The preceding compound was prepared in a manner analogous to General Procedure NN, to afford 103 mg (48%), pale yellow oil. $^{1}$H NMR (500 MHz, $CDCl_3$) δ ppm 10.20 (br. s, 1 H), 8.02 (d, J=8.24 Hz, 1 H), 7.97 (d, J=5.80 Hz, 1 H), 7.74-7.78 (m, 1 H), 7.68 (t, J=7.48 Hz, 1 H), 7.50 (t, J=7.63 Hz, 1 H), 7.24-7.30 (m, 1 H), 6.60-6.70 (m), 6.32 (ddd, J=12.44, 6.49, 2.75 Hz), 6.13 (d, J=8.85 Hz), 5.98 (br. s), 5.69-5.83 (m, 2 H), 5.23 (d, J=17.39 Hz, 1 H), 5.10 (d, J=10.99 Hz, 1 H), 4.98 (dd, J=17.09, 1.53 Hz, 1 H), 4.92 (d, J=10.38 Hz, 1 H), 4.52 (dd, J=9.61, 7.17 Hz, 1 H), 4.08-4.14 (m, 1 H), 4.03-4.08 (m, 1 H), 3.99 (dd, J=8.54, 3.97 Hz, 1 H), 2.54-2.62 (m, 1 H), 2.46-2.54 (m, 1 H), 1.95-2.11 (m, 4 H), 1.59-1.83 (m, 4 H), 1.50-1.58 (m, 1 H), 1.49 (s, 3 H), 1.17-1.47 (m, 8 H), 0.95-1.18 (m, 1 H), 0.85-0.93 (m, 1 H), 0.76-0.84 (m, 1 H). LC-MS: purity 100% (UV), $t_R$ 2.23 min, m/z $[M+H]^+$ 750.40.

Example 19-45

37

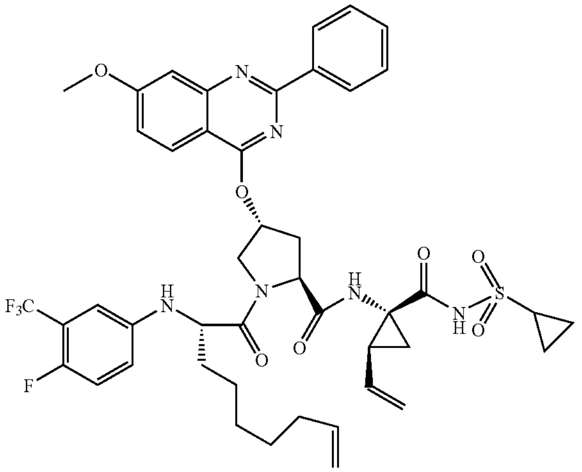

The preceding compound was prepared in a manner analogous to General Procedure NN, to afford 142.5 mg (60%), yellow solid. $^1$H NMR (250 MHz, $CDCl_3$) δ ppm 10.36 (s, 1 H), 8.00-8.14 (m, 2 H), 7.82 (d, J=8.98 Hz, 1 H), 7.42-7.62 (m, 4 H), 7.11 (dd, J=2.44, 9.14 Hz, 1 H), 7.04 (s, 1 H), 6.98 (s, 1 H), 6.78-6.92 (m, 1 H), 6.73 (dd, J=2.66, 5.41 Hz, 1 H), 6.52-6.68 (m, 1 H), 5.67-5.93 (m, 2 H), 5.41-5.62 (m, 1 H), 5.23 (dd, J=1.29, 17.28 Hz, 1 H), 5.12 (dd, J=1.45, 10.28 Hz, 1 H), 4.87-5.05 (m, 2 H), 4.69 (d, J=10.05 Hz, 1 H), 4.46 (t, J=8.30 Hz, 1 H), 4.03-4.22 (m, 3 H), 3.98 (s, 3 H), 3.50 (s, 1 H), 2.55-2.67 (m, 2 H), 1.95-2.13 (m, 4 H), 1.65-1.87 (m, 2 H), 1.29-1.49 (m, 8 H), 1.01-1.17 (m, 2 H), 0.79-0.95 (m, 1 H). LC-MS: purity 93% (UV), $t_R$ 4.58 min, m/z $[M+H]^+$ 892.10.

Example 19-46

38

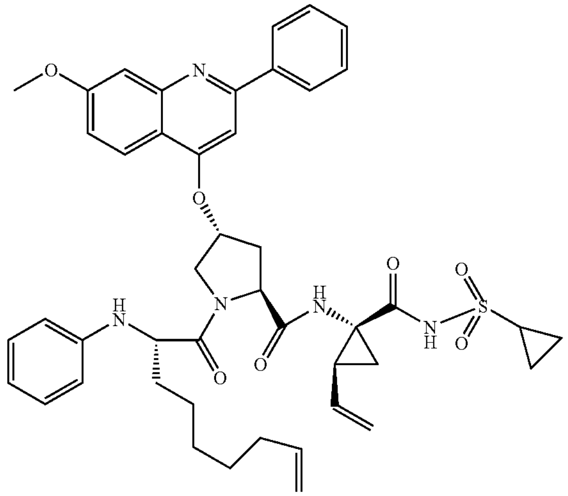

The preceding compound was prepared in a manner analogous to General Procedure NN, to afford 297 mg (50%), pale yellow solid. $^1$H NMR (500 MHz, $CDCl_3$) δ ppm 10.28 (br. s, 1 H) 8.07 (d, J=7.17 Hz, 2 H) 7.85 (d, J=9.16 Hz, 1 H) 7.52-7.58 (m, 2 H) 7.50 (d, J=7.02 Hz, 1 H) 7.48 (d, J=2.44 Hz, 1 H) 7.11 (dd, J=9.16, 2.44 Hz, 1 H) 7.07 (t, J=7.86 Hz, 2 H) 7.05 (s, 1 H) 6.94 (s, 1 H) 6.72 (t, J=7.32 Hz, 1 H) 6.55 (d, J=7.93 Hz, 2 H) 5.69-5.85 (m, 2 H) 5.50 (br. s, 1 H) 5.23 (d, J=16.94 Hz, 1 H) 5.13 (d, J=11.14 Hz, 1 H) 4.99 (dd, J=17.17, 1.60 Hz, 1 H) 4.93 (d, J=10.07 Hz, 1 H) 4.36-4.50 (m, 2 H) 4.23 (d, J=11.75 Hz, 1 H) 4.14-4.21 (m, 1 H) 4.06 (dd, J=11.67, 3.43 Hz, 1 H) 3.99 (s, 3 H) 2.90-2.99 (m, 1 H) 2.55-2.67 (m, 2 H) 1.97-2.08 (m, 4 H) 1.73-1.83 (m, 2 H) 1.44-1.54 (m, 2 H) 1.32-1.43 (m, 7 H) 1.06 (s, 2 H). LC-MS: purity 100% (UV), $t_R$ 2.64 min, m/z $[M+H]^+$ 714.40.

Example 19-47

39

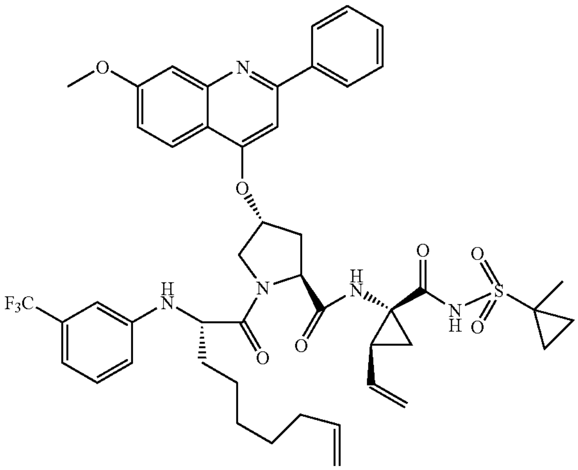

The preceding compound was prepared in a manner analogous to General Procedure NN, to afford 240 mg (32%), beige solid. $^1$H NMR (500 MHz, $CD_3OD$) δ ppm 8.06 (d, J=6.71 Hz, 1 H), 7.92 (d, J=9.16 Hz, 1 H), 7.48-7.60 (m, 3 H), 7.43 (d, J=2.44 Hz, 1 H), 7.30 (s, 1 H), 7.10 (dd, J=9.16, 2.44 Hz, 1 H), 6.93-7.03 (m, 1 H), 6.88 (s, 1 H), 6.77 (d, J=7.32 Hz, 1 H), 6.69 (dd, J=8.24, 1.83 Hz, 1 H), 5.70-5.86 (m, 2 H), 5.61-5.68 (m, 1 H), 5.30 (dd, J=17.24, 1.37 Hz, 1 H), 5.12 (dd, J=10.53, 1.37 Hz, 1 H), 4.93-4.99 (m, 1 H), 4.87-4.91 (m, 1 H), 4.56 (dd, J=10.22, 6.87 Hz, 1 H), 4.41 (d, J=12.51 Hz, 1 H), 4.33 (dd, J=8.09, 5.04 Hz, 1 H), 4.07 (dd, J=12.36, 3.20 Hz, 1 H), 3.98 (s, 3 H), 2.63 (dd, J=13.73, 6.41 Hz, 1 H), 2.36 (ddd, J=13.96, 10.45, 3.97 Hz, 1 H), 2.22 (q, J=8.85 Hz, 1 H), 1.98-2.04 (m, 2 H), 1.78-1.91 (m, 2 H), 1.67-1.77 (m, 1 H), 1.54-1.64 (m, 2 H), 1.52 (s, 3 H), 1.42-1.51 (m, 3 H), 1.35-

1.41 (m, 3 H), 1.26-1.35 (m, 3 H), 0.86-0.95 (m, 2 H). LC-MS: purity 92% (UV), $t_R$ 2.27 min m/z $[M+H]^+$ 888.45.

Example 19-48

40

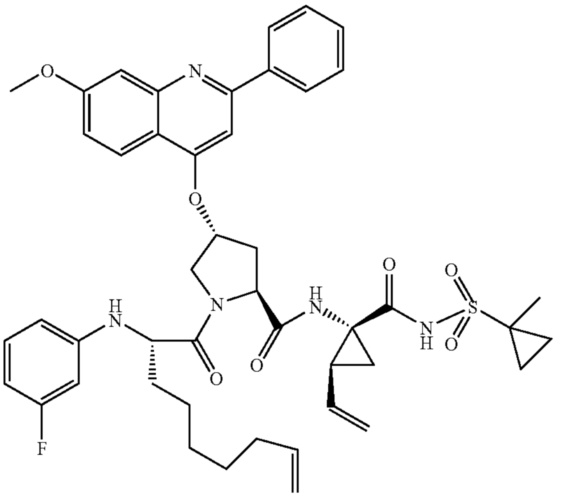

The preceding compound was prepared in a manner analogous to General Procedure NN, to afford 220 mg (31%), yellow waxy solid. $^1H$ NMR (500 MHz, $CD_3OD$) δ ppm 8.02 (d, J=7.02 Hz, 2 H), 7.86 (d, J=9.16 Hz, 1 H), 7.43-7.55 (m, 3 H), 7.35 (d, J=2.44 Hz, 1 H), 7.18 (s, 1 H), 7.05 (dd, J=9.16, 2.14 Hz, 1 H), 6.76-6.87 (m, 1 H), 6.18-6.31 (m, 3 H), 5.65-5.82 (m, 2 H), 5.50 (br. s, 1 H), 5.26 (d, J=17.70 Hz, 1 H), 5.07 (d, J=11.29 Hz, 1 H), 4.95 (dd, J=17.24, 1.68 Hz, 1 H), 4.88 (d, J=10.38 Hz, 1 H), 4.49 (dd, J=9.92, 7.17 Hz, 1 H), 4.27 (d, J=12.21 Hz, 1 H), 4.17 (dd, J 7.78, 5.34 Hz, 1 H), 4.00 (dd, J=12.21, 3.05 Hz, 1 H), 3.91 (s, 3 H), 2.56 (dd, J=12.36, 7.17 Hz, 1 H), 2.27-2.38 (m, 1 H), 2.17 (q, J=8.85 Hz, 1 H), 1.99 (q, J=7.22 Hz, 2 H), 1.83 (dd, J=7.93, 5.49 Hz, 1 H), 1.72-1.81 (m, 1 H), 1.61-1.72 (m, 1 H), 1.50-1.61 (m, 2 H), 1.48 (s, 3 H), 1.38-1.47 (m, 2 H), 1.31-1.37 (m, 3 H), 1.24-1.28 (m, 2 H), 0.76-0.94 (m, 3 H). LC-MS: purity 98% (UV), $t_R$ 2.13 min, m/z $[M+H]^+$ 838.45.

Example 19-49

41

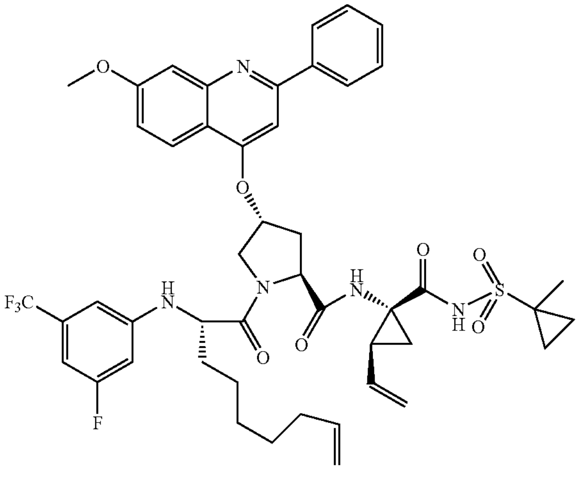

The preceding compound was prepared in a manner analogous to General Procedure NN, to afford 191 mg (25%), yellow waxy solid. $^1H$ NMR (500 MHz, $CD_3OD$) δ ppm 8.03 (d, J=7.02 Hz, 2 H), 7.90 (d, J=9.16 Hz, 1 H), 7.46-7.55 (m, 3 H), 7.38 (d, J=2.44 Hz, 1 H), 7.22 (s, 1 H), 7.06 (dd, J=9.16, 2.44 Hz, 1 H), 6.71 (s, 1 H), 6.51 (d, J=8.54 Hz, 1 H), 6.46 (d, J=11.44 Hz, 1 H), 5.67-5.82 (m, 2 H), 5.57 (br. s, 1 H), 5.28 (dd, J=17.17, 0.84 Hz, 1 H), 5.10 (d, J=11.75 Hz, 1 H), 4.95 (dd, J=17.17, 1.75 Hz, 1 H), 4.88-4.90 (m, 1 H), 4.54 (dd, J=10.07, 7.02 Hz, 1 H), 4.27-4.38 (m, 2 H), 4.04 (dd, J=12.05, 3.20 Hz, 1 H), 3.93 (s, 3 H), 2.59 (dd, J=14.04, 7.02 Hz, 1 H), 2.34 (ddd, J=13.92, 10.26, 3.89 Hz, 1 H), 2.19 (q, J=8.95 Hz, 1 H), 2.01 (q, J=6.87 Hz, 2 H), 1.79-1.88 (m, 2 H), 1.67-1.77 (m, 1 H), 1.53-1.62 (m, 2 H), 1.50 (s, 3 H), 1.43-1.49 (m, 2 H), 1.34-1.39 (m, 3 H), 1.28-1.34 (m, 3 H), 0.82-0.94 (m, 2 H). LC-MS: purity 95% (UV), $t_R$ 2.29 min, m/z $[M+H]^+$ 906.45.

Example 19-50

42

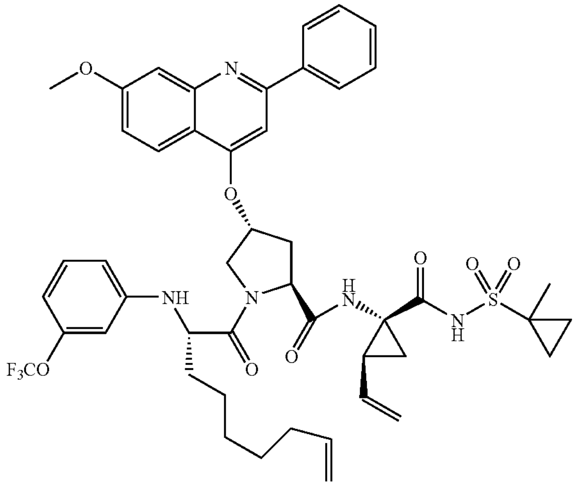

m

Compound 42 was prepared in a manner analogous to General Procedure NN, to afford 267 mg (62%), white solid. $^1H$ NMR (500 MHz, $CDCl_3$) δ ppm 10.09 (br. s, 1 H), 8.05 (d, J=7.48 Hz, 2 H), 7.85 (d, J=9.16 Hz, 1 H), 7.51-7.56 (m, 2 H), 7.49 (d, J=7.02 Hz, 1 H), 7.47 (d, J=1.83 Hz, 1 H), 7.08-7.14 (m, 2 H), 6.99-7.04 (m, 2 H), 6.55 (d, J=7.93 Hz, 1 H), 6.40-6.45 (m, 2 H), 5.69-5.83 (m, 2 H), 5.49 (br. s, 1 H), 5.22 (d, J=17.09 Hz, 1 H), 5.11 (d, J=10.38 Hz, 1 H), 4.90-5.00 (m, 2 H), 4.75 (br. s, 1 H), 4.47 (t, J=8.09 Hz, 1 H), 4.11-4.19 (m, 2 H), 4.05-4.11 (m, 1 H), 3.97 (s, 3 H), 2.59 (d, J=7.48 Hz, 2 H), 2.03 (dd, J=13.12, 5.65 Hz, 4 H), 1.83-1.97 (m, 2 H), 1.78 (d, J=5.49 Hz, 2 H), 1.49 (s, 4 H), 1.29-1.43 (m, 6 H), 0.86-

0.93 (m, 1 H), 0.81-0.87 (m, 1 H). LC-MS: purity 99% (UV), $t_R$ 1.88 min, m/z $[M+H]^+$ 904.90.

Example 19-51

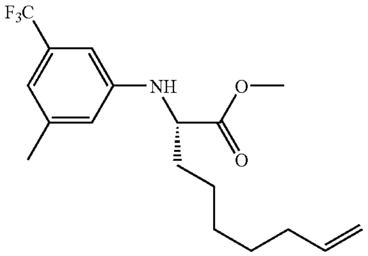

(S)-2-(3-methyl-5-trifluoromethyl-phenylamino)-non-8-enoic acid methyl ester was prepared in a manner analogous to General Procedure II to afford 271 mg (64%). $^1H$ NMR (500 MHz, $CDCl_3$) δ ppm 6.80 (s, 1 H) 6.63 (s, 1 H) 6.57 (s, 1 H) 5.75-5.85 (m, 1H) 4.93-5.03 (m, 2 H) 4.08 (t, J=6.41 Hz, 1 H) 3.74 (s, 3 H) 2.31 (s, 3 H) 2.02-2.08 (m, 2H) 1.85 (s, 1 H) 1.76 (s, 1 H) 1.33-1.46 (m, 7 H). LC-MS: purity 98% (UV), $t_R$ 5.65 min, m/z $[M+H]^+$ 344.20.

Example 19-52

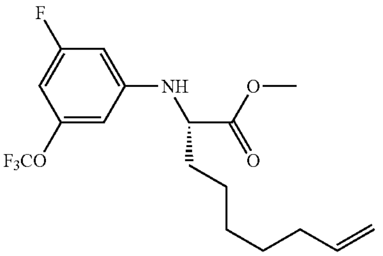

(S)-2-(3-Fluoro-5-trifluoromethoxy-phenylamino)-non-8-enoic acid methyl ester was prepared in a manner analogous to General Procedure II to afford 225 mg (41%). $^1H$ NMR (500 MHz, $CDCl_3$) δ ppm 6.31 (d, J=9.16 Hz, 1 H) 6.19-6.25 (m, 2 H) 5.74-5.85 (m, 1 H) 4.91-5.05 (m, 2 H) 4.41 (d, J=8.39 Hz, 1 H) 3.96-4.04 (m, 1 H) 3.76 (s, 3 H) 2.00-2.10 (m, 2 H) 1.81-1.90 (m, 1 H) 1.75 (dq, J=14.13, 7.14 Hz, 1 H) 1.29-1.46 (m, 6 H). LC-MS: purity 98% (UV), $t_R$ 2.69 min m/z $[M+H]^+$ 364.10.

Example 19-53

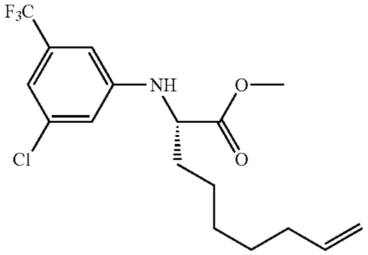

(S)-2-(3-chloro-5-trifluoromethyl-phenylamino)-non-8-enoic acid methyl ester was prepared in a manner analogous to General Procedure II to afford 346 mg (20%). $^1H$ NMR (500 MHz, $CDCl_3$) δ ppm 6.94 (s, 1 H) 6.70 (d, J=8.70 Hz, 2 H) 5.80 (m, J=16.98, 10.22, 6.69, 6.69 Hz, 1 H) 4.91-5.04 (m, 2 H) 4.44 (d, J=8.54 Hz, 1 H) 4.02-4.10 (m, 1 H) 3.76 (s, 3 H) 2.00-2.11 (m, 2 H) 1.82-1.92 (m, 1 H) 1.72-1.81 (m, 1 H) 1.30-1.46 (m, 6 H). LC-MS: purity 98% (UV), $t_R$ 2.78 min, m/z $[M+H]^+$ 363.95.

Example 19-54

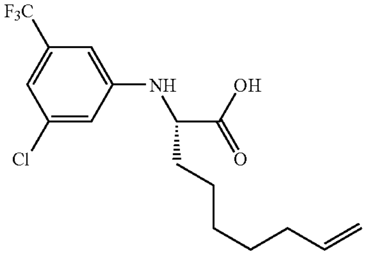

(S)-2-(3-chloro-5-trifluoromethyl-phenylamino)-non-8-enoic acid was prepared in a manner analogous to General Procedure JJ to afford 312 mg (94%). $^1H$ NMR (500 MHz, $CDCl_3$) δ ppm 6.97 (s, 1 H) 6.73 (s, 1 H) 6.71 (s, 1 H) 5.73-5.85 (m, 1 H) 4.91-5.04 (m, 2 H) 4.51 (br. s., 1 H) 4.09 (t, J=6.26 Hz, 1 H) 3.73-3.81 (m, 1 H) 2.05 (q, J=6.71 Hz, 2 H) 1.90-1.98 (m, 1 H) 1.88 (dt, J=6.48, 3.32 Hz, 1 H) 1.80 (dq, J=14.34, 7.32 Hz, 1H) 1.32-1.51 (m, 5 H). LC-MS: purity 100% (UV), $t_R$ 2.51 min, m/z $[M+H]^+$ 349.90.

Example 19-55

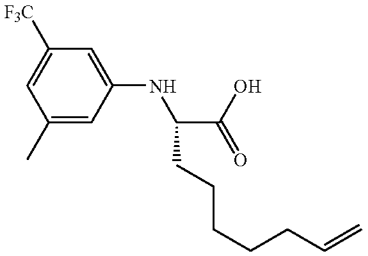

(S)-2-(3-methyl-5-trifluoromethyl-phenylamino)-non-8-enoic acid was prepared in a manner analogous to General Procedure JJ to afford 236 mg (91%). $^1H$ NMR (500 MHz, $CDCl_3$) δ ppm 6.83 (s, 1 H) 6.65 (s, 1 H) 6.59 (s, 1 H) 5.80 (m, J=17.03, 10.28, 6.71, 6.71 Hz, 1 H) 4.97-5.03 (m, 1 H) 4.95 (dd, J=10.22, 0.92 Hz, 1 H) 4.03-4.14 (m, 1 H) 2.32 (s, 3 H) 2.05 (q, J=6.82 Hz, 2 H) 1.92 (d, J=5.65 Hz, 1 H) 1.73-1.85

(m, 1 H) 1.43-1.52 (m, 2 H) 1.32-1.43 (m, 4 H). LC-MS: purity 97% (UV), $t_R$ 2.43 min, m/z $[M+H]^+$ 330.45.

Example 19-56

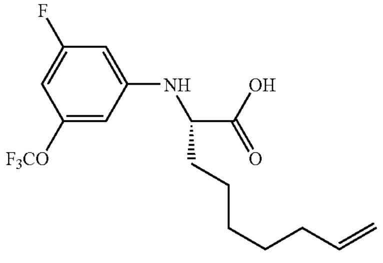

(S)-2-(3-(trifluoromethoxy)phenylamino)non-8-enoic acid was prepared in a manner analogous to General Procedure JJ to afford 257 mg (92%). $^1$H NMR (500 MHz, $CDCl_3$) δ ppm 6.34 (d, J=9.16 Hz, 1 H) 6.20-6.26 (m, 2 H) 5.73-5.85 (m, 1 H) 4.90-5.05 (m, 2 H) 4.02 (t, J=6.33 Hz, 1 H) 3.75-3.84 (m, 1 H) 2.94 (t, J=7.25 Hz) 1.99-2.10 (m, 2 H) 1.85-1.98 (m, 1 H) 1.79 (dq, J=14.50, 7.27 Hz, 1 H) 1.62-1.73 (m, 1 H) 1.31-1.51 (m, 6 H) LC-MS: purity 93% (UV), $t_R$ 5.14 min, m/z $[M+H]^+$ 350.05.

Example 19-57

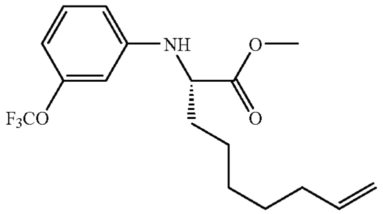

(S)-methyl 2-(3-(trifluoromethoxy)phenylamino)non-8-enoate was prepared in a manner analogous to General Procedure II to afford 160 mg (39%). $^1$H NMR (500 MHz, $CDCl_3$) δ ppm 7.15 (t, J=8.16 Hz, 1 H) 6.58 (d, J=8.09 Hz, 1 H) 6.52 (dd, J=8.16, 1.91 Hz, 1 H) 6.43 (br. s, 1 H) 5.80 (m, J=16.98, 10.22, 6.69, 6.69 Hz, 1 H) 5.00 (dd, J=17.17, 1.75 Hz, 1 H) 4.95 (d, J=10.22 Hz, 1 H) 4.27 (br. s, 1 H) 4.01-4.07 (m, 1 H) 3.74 (s, 3 H) 2.01-2.09 (m, 2 H) 1.81-1.90 (m, 1 H) 1.76 (dq, J=14.17, 7.18 Hz, 1 H) 1.30-1.46 (m, 6 H). LC-MS: purity 100% (UV), $t_R$ 2.73 min, m/z $[M+H]^+$ 743.30.

Example 19-58

78

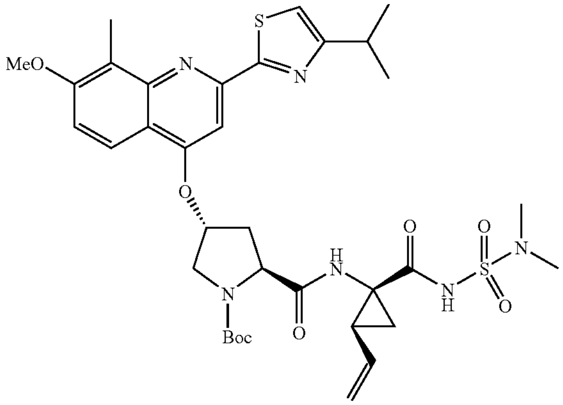

(1R,2S)-1-(tert-butoxycarbonylamino)-2-vinyl-cyclopropane-1-carbonyl-(1'-methyl)-dimethylsulfonamide (1.5 g, 4.50 mmol, 1.0 eq.) and dioxane (3 mL) were charged into a 50 mL round bottom flask and the reaction mixture cooled on top of an ice bath. 4M HCl in dioxane (15 mL) was added and the reaction mixture stirred at ambient temperature for 1 hour. After this time, LCMS analysis of an aliquot showed the reaction to be complete. The solvent was removed under vacuum and the residue azeotroped with dichloromethane (2×30 mL) twice. The residue was used in the next step without further purification.

(2S,4R)-1-(tert-butoxycarbonyl)-4-(2-(4-isopropylthiazol-2-yl)-7-methoxy-8-methylquinolin-4-yloxy)pyrrolidine-2-carboxylic acid (2.05 g, 4.05 mmol, 0.9 eq.) and N,N-dimethylformamide (20 mL) were charged into a 50 mL round bottom flask and the reaction mixture cooled to 0° C. HATU (2.2 g, 5.85 mmol, 1.3 eq.) was added portion wise followed by diisopropylethylamine (4 mL, 22.5 mmol, 5.0 eq.). Stirring was continued at 0° C. for a further 15 minutes. A solution of the amino acid residue in N,N-dimethylformamide (5 mL) was then added to the reaction mixture. The reaction mixture was stirred at ambient temperature for a further 2 hours by which time LCMS analysis of an aliquot showed the reaction to be complete. The solvent was removed under vacuum and the residue dissolved in ethyl acetate (100 mL). The organic phase was washed with water (2×100 mL), dried over sodium sulfate, filtered and the solvent removed under vacuum. The residue was purified by flash column chromatography, using a ethyl acetate:heptanes gradient (from 1:9 to 7:3 ethyl acetate/heptanes). After combining the relevant fractions and solvent removal, 2.40 g (83%) of compound 79 was isolated as a pale yellow solid. $^1$H NMR (500 MHz, $CDCl_3$) δ ppm 9.82 (s, 1 H) 7.92 (d, J=9.16 Hz, 1 H) 7.51 (s, 1 H) 7.24 (d, J=9.16 Hz, 1 H) 7.07 (br. s, 1H) 7.05 (s, 1 H) 5.71-5.85 (m, 1 H) 5.43 (br. s, 1 H) 5.30 (d, J=17.09 Hz, 1 H) 5.17 (d, J=10.38 Hz, 1 H) 4.38 (t, J=7.93 Hz, 1 H) 4.00 (s, 3 H) 3.82-3.96 (m, 2 H) 3.20 (spt, J=6.82 Hz, 1 H) 2.93 (s, 6 H) 2.70 (s, 3 H) 2.60 (d, J=6.10 Hz, 2 H) 2.11 (q, J=8.65 Hz, 1 H) 1.97 (dd, J=8.01, 5.87 Hz, 1 H) 1.47 (s, 9 H) 1.40-1.44 (m, 1 H) 1.39 (d, J=7.78 Hz, 6 H). LC-MS: purity 100% (UV), $t_R$ 2.48 min, m/z $[M+H]^+$ 743.30.

Example 19-59

79

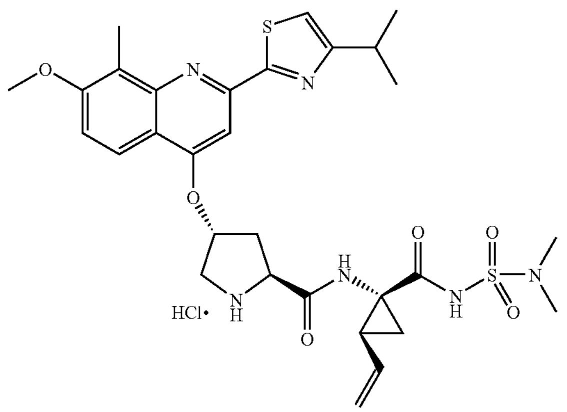

Compound 78 (1.4 g, 1.884 mmol, 1 eq.) and dioxane (3 mL) were charged into a 50 mL round bottom flask and the reaction mixture cooled on top of an ice bath. 4M HCl in dioxane (15 mL) was added and the reaction mixture stirred at ambient temperature for 1.5 hour. After this time, LCMS analysis of an aliquot showed the reaction to be complete. The solvent was removed under vacuum and the residue azeotroped with dichloromethane (2×30 mL) twice to give 1.41 g (99%) of compound 79 as a beige solid which was used in the next step without further purification. $^1$H NMR (250 MHz, MeOD) δ ppm 9.19 (s, 1 H) 8.41 (d, J=9.44 Hz, 1 H) 7.77 (s, 1 H) 7.67 (s, 1 H) 7.58 (d, J=9.44 Hz, 1 H) 5.86 (br. s, 1 H) 5.49-5.71 (m, 1 H) 5.22-5.37 (m, 1 H) 5.14 (dd, J=10.36, 1.22 Hz, 1 H) 4.70-4.83 (m, 1 H) 4.05 (s, 3 H) 3.96 (s, 2 H) 3.03 (br. s, 1 H) 2.78-2.93 (m, 6 H) 2.60 (s, 4 H) 2.31 (s, 1 H) 1.84-1.98 (m, 1 H) 1.42 (d, J=6.85 Hz, 6 H) 1.34 (dd, J=9.44, 5.63 Hz, 1 H). LC-MS: purity 100% (UV), $t_R$ 1.55 min, m/z $[M+H]^+$ 643.25.
EXAMPLE 20
Scheme XVII: Olefin Metathesis route to N-Aryl Acylsulfonamides
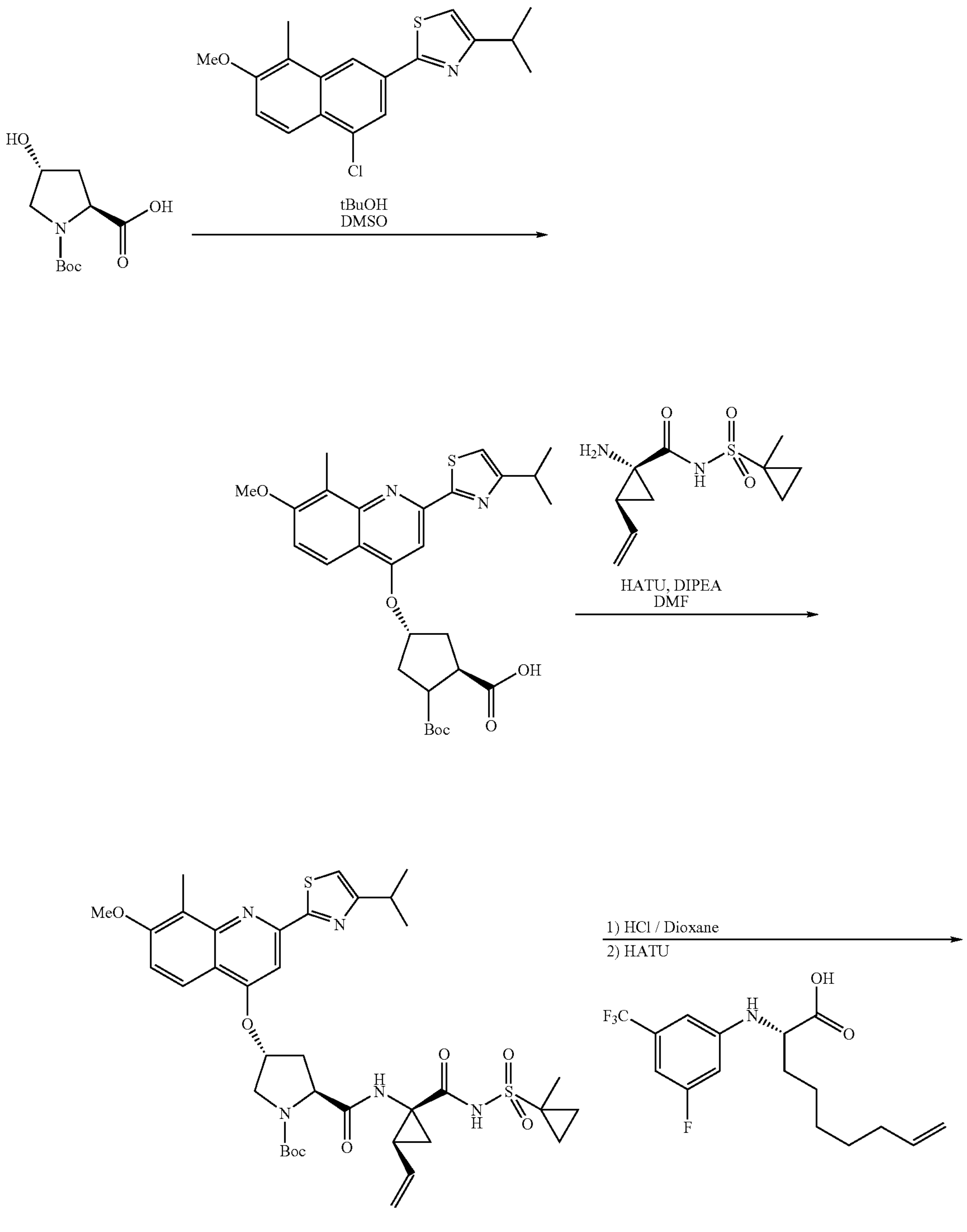

-continued
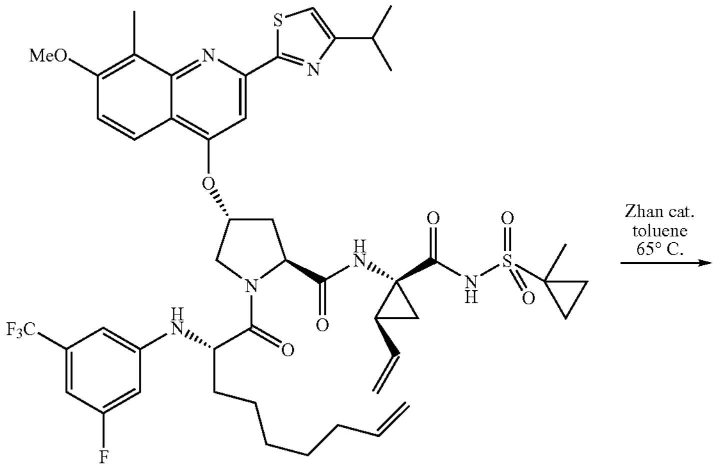
45
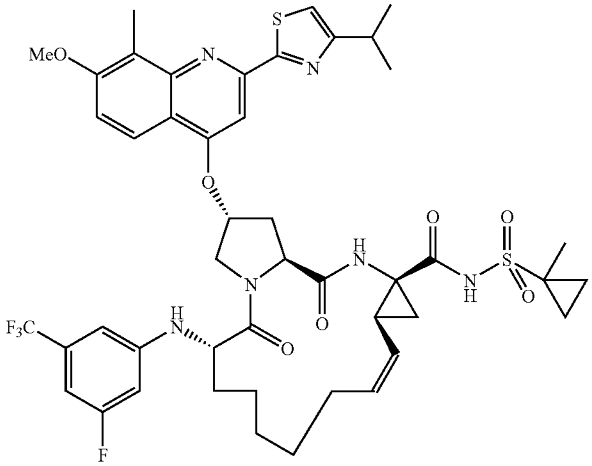
358

Macrocycles, such as compound 358, can be synthesized as shown in Scheme XVII. (2S,4R)-1-(tert-Butoxycarbonylamino)-4-hydroxy-proline can be treated with a heteroaryl chloride, such as 2-(4-isopropylthiazol-2-yl)-4-chloro-7-methoxy-8-methyl-quinoline and the like, under basic conditions, for example potassium tert-butoxide in DMSO, to provide heteroaryl ethers, such as (2S,4R)-1-(tert-butoxycarbonylamino)-4-[2-(3'-isopropyl-thiazol-2-yl)-7-methoxy-8-methyl-quinoline-4-oxy]-proline. The heteroaryl ethers, such as (2S,4R)-1-(tert-butoxycarbonylamino)-4-[2-(3'-isopropyl-thiazol-2-yl)-7-methoxy-8-methyl-quinoline-4-oxy]-proline, can be coupled with amino acylsulfonamides, such as (1R,2R)-1-amino-2-vinyl-cyclopropane-1-acyl-(1'-methyl)cyclopropanesulfonamide, using a coupling agent, for example using HATU in DMF in the presence of DIPEA, to provide dipeptides such as compound 43. Compound 43 can be treated under acidic conditions, for example HCl in dioxane, to remove the Boc protecting group thereby forming amines, such as compound 44. Amines, such as compound 44, can be coupled with N-aryl amino acids, such as 2-(3-trifluoromethyl-5-fluoro-phenylamino)-non-8-enoic acid, using a coupling agent, for example using HATU in DMF in the presence of DIPEA, to provide macrocyclization precursors, such as compound 45. Finally, the macrocyclization precursors, such as compound 45, can be cyclized in the presence of a catalyst, for example a Zhan catalyst, to provide macrocycles, such as compound 358.

Example 20-1

General Procedure PP

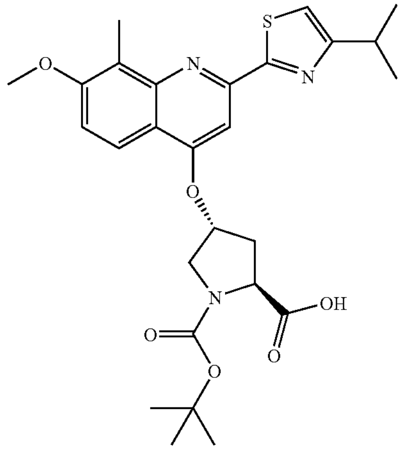

Synthesis of (2S,4R)-1-(tert-butoxycarbonylamino)-4-[2-(3'-isopropyl-thiazol-2-yl)-7-methoxy-8-methyl-quinoline-4-oxy]-proline (2S,4R)-1-(tert-Butoxycarbonylamino)-4-hydroxy-proline (24.25 g, 105 mmol., 1.0 eq.) and dimethylsulfoxide (350 mL) were charged into a 2 L round bottom flask. Potassium tert-butoxide (23.56 g, 210 mmol., 2.0 eq.) was added portionwise over 10 min at ambient temperature. The reaction mixture was stirred for 1 hour at ambient temperature while the color changed from pale yellow to dark orange. 2-(4-isopropylthiazol-2-yl)-4-chloro-7-methoxy-8-methyl-quinoline (35.00 g, 105 mmol., 1.0 eq.) was added portionwise leading to the formation of a brown sticky residue.

Further dimethylsulfoxide (150 mL) was added to help solubilizing the reagents and the stirring was continued at 35° C. for a further 20 min. As the reaction mixture remained very thick more dimethylsulfoxide (300 mL) was added. The resulting mixture was stirred at 28° C. for 15 hours by which time LCMS analysis of the reaction mixture showed the reaction to be complete. The reaction mixture was diluted with methanol (300 mL) and stirred for 30 min. The reaction mixture was left to cool to ambient temperature and split into two portions to ease the work up. Both fractions were treated in the same way as follows. The mixture was diluted with ethyl acetate (500 mL) and water (300 mL). The aqueous phase was acidified to pH 3 with 1M hydrochloric acid (~80 mL) and extracted with ethyl acetate (3×200 mL). The organic extracts were combined, washed with water (5×350 mL) and brine (300 mL), dried over sodium sulfate, filtered and the solvent removed under vacuum to give 24 g and 25 g of crude product respectively. Each solid was purified separately by dry flash chromatography onto 500 g of silica and eluting with a dichloromethane:methanol gradient (from neat dichloromethane to 5% methanol in dichloromethane). After combining the relevant fractions and solvent removal 20.6 g (37%) and 21.7 g (39%) of the desired product were isolated as a yellow solid. The combined yield was 42.3 g (76%). $^1$H NMR (500 MHz, $CDCl_3$) δ ppm 7.89-8.03 (m, 1 H), 7.44-7.56 (m, 1 H), 7.24 (d, J=9.16 Hz, 1 H), 7.04 (br. s, 1 H), 5.39 (br. s, 1 H), 4.69 (s, 1 H), 4.47-4.60 (m, 1 H), 4.00 (s, 3 H), 3.98 (br. s, 1 H), 3.78-3.88 (m, 1 H), 3.18-3.25 (m, 1 H), 2.71 (s, 3 H), 1.47 (s, 9 H), 1.42-1.45 (m, 1 H), 1.40 (d, J=6.71 Hz, 6 H), 1.36-1.38 (m, 1 H). LC-MS: purity 100% (UV), $t_R$ 2.65 min, m/z $[M+Na]^+$ 550.20.

Example 20-2

General Procedure QQ

43

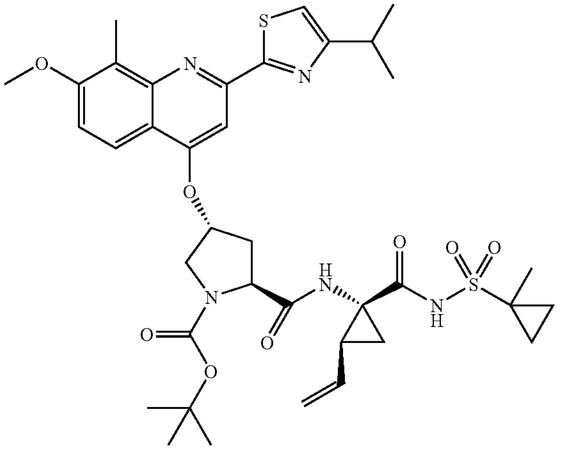

Synthesis of Compound 43

(2S,4R)-1-(tert-Butoxycarbonylamino)-4-[2-(3'-isopropyl-thiazol-2-yl)-7-methoxy-8-methyl-quinoline-4-oxy]-proline (25.00 g, 47.38 mmol., 1.0 eq.) and N,N-dimethylformamide (200 mL) were charged into a 1 L round bottom flask under nitrogen. HATU (21.62 g, 56.86 mmol., 1.2 eq.) and diisopropylethylamine (50 mL, 284.3 mmol., 6.0 eq.) were added at 0° C. and the reaction mixture stirred at ambient temperature for a further 30 minutes. (1R,2S)-1-Amino-2-vinyl-cyclopropane-1-carbonyl-(1'-methyl)cyclopropane-sulfonamide hydrochloride salt (13.98 g, 49.75 mmol., 1.05 eq.), previously dissolved in N,N-dimethylformamide (50 mL) was added dropwise over 15 minutes at 0° C. and stirring was continued for 2 hours ambient temperature. Monitoring the reaction conversion by LCMS showed complete consumption of the starting material. The solvent was removed under vacuum and the residue partitioned between water (0.5 L) and ethyl acetate (0.5 L) leading to the precipitation of a solid. The phases were separated and the solid partitioned between ethyl acetate (1.5 L) and water (3 L). The organic phases were combined, washed with water (2×1 L), dried over sodium sulfate, filtered and the solvent removed under vacuum. The residue was purified by dry flash chromatography, using a heptanes:ethyl acetate gradient (from 4:1 to neat EtOAc). After combining the relevant fractions and solvent removal, 21.0 g (59%) of compound 43 was isolated as a yellow solid. $^1$H NMR (500 MHz, $CDCl_3$) δ ppm 9.79 (br. s, 1 H), 7.93 (d, J=9.00 Hz, 1 H), 7.51 (br. s, 1 H), 7.24 (d, J=9.16 Hz, 1 H), 7.16 (br. s, 1 H), 7.05 (s, 1 H), 5.65-5.88 (m, 1 H), 5.37-5.48 (m, 1 H), 5.30 (d, J=17.09 Hz, 1 H), 5.17 (d, J=10.38 Hz, 1 H), 4.40 (t, J=7.78 Hz, 1 H), 4.00 (s, 3 H), 3.92 (br. s, 2 H), 3.12-3.30 (m, 1 H), 2.71 (s, 3 H), 2.54-2.68 (m, 2 H), 2.12 (q, J=8.70 Hz, 1 H), 1.99 (dd, J=8.09, 5.80 Hz, 1 H), 1.61-1.78 (m, 3 H), 1.52 (s, 2 H), 1.44-1.50 (m, 9 H), 1.33-1.43 (m, 7 H), 0.76-0.95 (m, 2 H). LC-MS: purity 98% (UV), $t_R$ 2.50 min, m/z $[M+H]^+$ 754.45.

Example 20-3

General Procedure RR

44

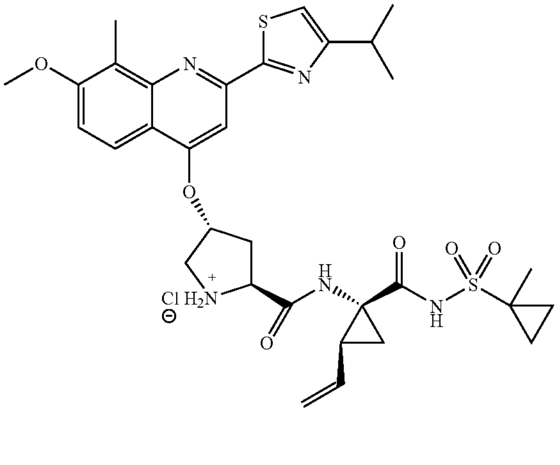

Synthesis of Compound 44

Compound 43 (3.61 g, 4.78 mmol., 1.0 eq.) and dichloromethane (45 mL) were charged into a 100 mL round bottom flask. 4M HCl in dioxane (30 mL) was added dropwise over 5 minutes and the dark orange reaction mixture stirred at ambient temperature for 2 hours. LCMS analysis showed full consumption of the starting material. The solvent was removed under vacuum and the residue dried further under high vacuum for 4 hours to give 3.70 g (96%, 3.16 g corrected for solvent content) of compound 44 as a brown solid which contained residual dioxane (15% w/w). The product was used in the next step without further purification. $^1$H NMR (500 MHz, $CD_3OD$) δ ppm 8.41 (d, J=9.31 Hz, 1 H), 7.78 (s, 1 H), 7.66 (s, 1 H), 7.61 (d, J=9.46 Hz, 1 H), 5.88 (br. s, 1 H), 5.57-5.67 (m, 1 H), 5.33 (d, J=16.94 Hz, 1 H), 5.16 (d, J=11.14 Hz, 1 H), 4.81 (dd, J=10.60, 7.55 Hz, 1 H), 4.08 (s, 3H), 3.97 (br. s, 2 H), 3.25-3.30 (m, 1 H), 3.06 (dd, J=14.42, 7.40 Hz, 1 H), 2.64 (s, 3 H), 2.55 (ddd, J=14.65, 10.60, 4.35 Hz, 1 H), 2.37 (q, J=8.70 Hz, 1 H), 1.95 (dd, J=7.93, 5.65 Hz, 1 H), 1.56-1.62 (m, 1 H), 1.51-1.54 (m, 1 H), 1.50 (s, 3 H), 1.44 (d, J=7.02 Hz, 6 H), 1.38 (dd, J=9.46, 5.65 Hz, 1 H), 0.85-0.94 (m, 2 H). LC-MS: purity 99% (UV), $t_R$ 1.95 min, m/z $[M+H]^+$ 654.10.

Example 20-4

General Procedure SS

45

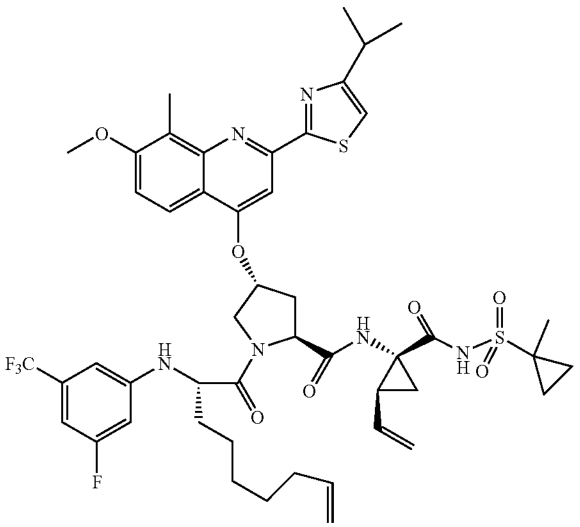

Synthesis of Compound 45

Compound 44 (HCl salt, 670 mg, 0.97 mmol., 1.0 eq.) and N,N-dimethylformamide (10 mL) were charged into a 25 mL round bottom flask under nitrogen. HATU (443 mg, 1.16 mmol., 1.2 eq.) and diisopropylethylamine (1.01 mL, 5.82 mmol., 6.0 eq.) were added at 0° C. and the reaction mixture stirred at ambient temperature for a further 15 minutes. (2S)-2-(3-fluoro-5-trifluoromethyl-phenylamino)-non-8-enoic acid (376 mg, 1.13 mmol., 1.1 eq.) was added as a single portion and stirring was continued at ambient temperature for a further 1.5 hours. Monitoring the reaction conversion by LCMS showed full consumption of the starting material. The solvent was removed under vacuum and the residue partitioned between ethyl acetate (50 mL) and water (30 mL). The organic phase was further washed with water (30 mL), dried over sodium sulfate, filtered and concentrated to dryness. The residue was purified by flash column chromatography, using a heptanes:ethyl acetate gradient (from 9:1 to 1:1). After combining the relevant fractions and solvent removal, 688 mg (73%) of compound 45 was isolated as a pale yellow solid. $^1$H NMR (250 MHz, $CDCl_3$) δ ppm 10.13 (s, 1 H), 7.82 (d, J=9.14 Hz, 1 H), 7.56 (s, 1 H), 7.20 (d, J=9.29 Hz, 1 H), 7.06

(d, J=0.91 Hz, 1 H), 6.84 (s, 1 H), 6.58-6.72 (m, 2 H), 6.40 (dt, J=10.89, 1.94 Hz, 1 H), 5.68-5.89 (m, 2 H), 5.55-5.66 (m, 1 H), 5.22 (dd, J=17.21, 1.37 Hz, 1 H), 5.05-5.16 (m, 2 H), 4.88-5.05 (m, 2 H), 4.38-4.51 (m, 1 H), 4.09-4.25 (m, 3H), 3.99 (s, 3 H), 3.10-3.29 (m, 1 H), 2.71 (s, 3 H), 2.59-2.69 (m, 2 H), 1.99-2.10 (m, 4H), 1.76-1.89 (m, 2 H), 1.67-1.76 (m, 2 H), 1.53-1.60 (m, 1 H), 1.50 (s, 3 H), 1.45 (br. s, 1 H), 1.36-1.45 (m, 10 H), 1.30-1.36 (m, 1 H), 0.82-0.97 (m, 2 H). LC-MS: purity 100% (UV), $t_R$ 2.55 min, m/z $[M+H]^+$ 969.40.

Example 20-5

46

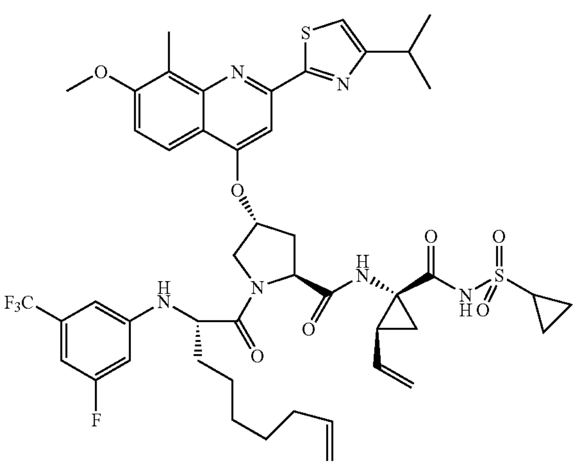

Synthesis of Compound 46

Compound 46 was prepared in a manner analogous to General Procedure NN, to afford 346 mg (54%), pale yellow solid. $^1H$ NMR (500 MHz, $CDCl_3$) δ ppm 10.38 (br. s, 1 H), 7.82 (d, J=9.00 Hz, 1 H), 7.55 (s, 1 H), 7.20 (d, J=9.16 Hz, 1 H), 7.06 (s, 1 H), 6.79 (s, 1 H), 6.65 (d, J=8.39 Hz, 1 H), 6.62 (s, 1 H), 6.38 (d, J=10.68 Hz, 1 H), 5.80 (ddd, J=17.09, 10.15, 6.94 Hz, 2 H), 5.61 (br. s, 1 H), 5.23 (d, J=17.09 Hz, 1 H), 5.12 (d, J=10.53 Hz, 1 H), 5.06 (d, J=9.61 Hz, 1 H), 4.99 (dd, J=17.01, 1.30 Hz, 1 H), 4.94 (d, J=10.22 Hz, 1 H), 4.44 (dd, J=9.38, 7.25 Hz, 1 H), 4.14-4.23 (m, 2 H), 4.08-4.13 (m, 1 H), 3.99 (s, 3 H), 3.20 (spt, J=6.76 Hz, 1 H), 2.88-3.01 (m, 1 H), 2.71 (s, 3 H), 2.56-2.69 (m, 2 H), 1.99-2.09 (m, 4 H), 1.80-1.89 (m, 1 H), 1.71-1.80 (m, 1 H), 1.58-1.72 (m, 1 H), 1.43-1.58 (m, 3 H), 1.39-1.41 (m, 7 H), 1.26-1.38 (m, 4 H), 1.08 (t, J=7.86 Hz, 2 H). LC-MS: purity 100% (UV), $t_R$ 2.74 min, m/z $[M+H]^+$ 955.30.

Example 20-6

47

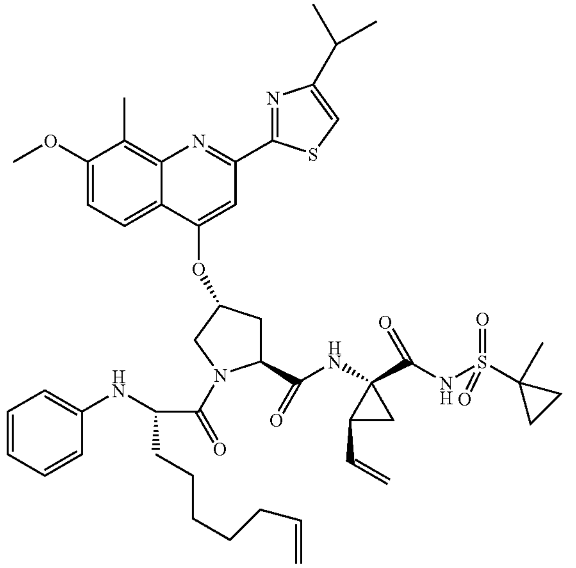

Synthesis of Compound 47

The preceding compound was prepared in a manner analogous to General Procedure NN, to afford 1.26 g (67%), pale yellow solid. $^1H$ NMR (500 MHz, $CDCl_3$) δ ppm 10.08 (s, 1 H), 7.81 (d, J=9.16 Hz, 1 H), 7.56 (s, 1 H), 7.17 (d, J=9.16 Hz, 1 H), 7.06 (s, 1 H), 6.98-7.05 (m, 2 H), 6.68 (t, J=7.32 Hz, 1 H), 6.53 (d, J=7.63 Hz, 2 H), 5.70-5.84 (m, 2 H), 5.58 (d, J=2.75 Hz, 1 H), 5.24 (d, J=17.09 Hz, 1 H), 5.09-5.15 (m, 1 H), 4.98 (dd, J=17.09, 1.83 Hz, 1 H), 4.93 (d, J=10.07 Hz, 1 H), 4.48 (t, J=8.24 Hz, 2 H), 4.22 (d, J=11.90 Hz, 1 H), 4.10-4.18 (m, 1 H), 4.05 (dd, J=11.60, 3.36 Hz, 1 H), 4.00 (s, 3 H), 3.21 (spt, J=6.92 Hz, 1 H), 2.72 (s, 3 H), 2.57-2.65 (m, 2 H), 1.96-2.06 (m, 4 H), 1.74-1.82 (m, 2 H), 1.68-1.75 (m, 2 H), 1.67 (s, 1 H), 1.58 (tt, J=13.96, 7.25 Hz, 1 H), 1.51 (s, 3 H), 1.43-1.49 (m, 1 H), 1.40 (d, J=6.71 Hz, 6 H), 1.23-1.38 (m, 5

H), 0.87-0.95 (m, 1 H), 0.81-0.87 (m, 1 H). LC-MS: purity 100% (UV), $t_R$ 2.43 min, m/z $[M+H]^+$ 883.35.

Example 20-7

48

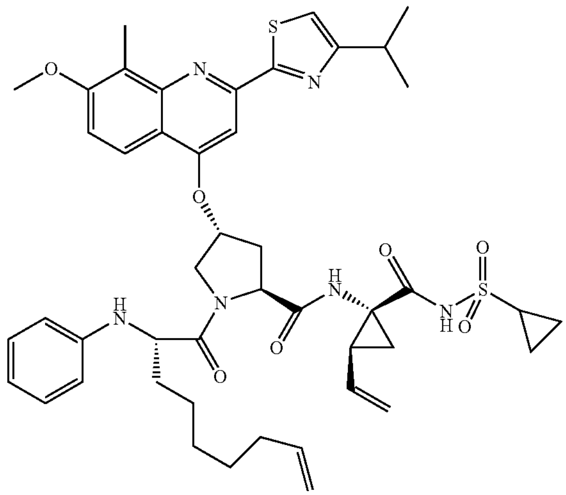

Synthesis of Compound 48

Compound 48 was prepared in a manner analogous to General Procedure NN, to afford 2.07 g (60%), white solid. $^1H$ NMR (250 MHz, $CDCl_3$) δ ppm 10.33 (br. s, 1 H), 7.81 (d, J=9.14 Hz, 1 H), 7.55 (s, 1 H), 7.17 (d, J=9.29 Hz, 1 H), 6.95-7.09 (m, 4 H), 6.60-6.74 (m, 1 H), 6.52 (d, J=7.61 Hz, 2 H), 5.68-5.88 (m, 2 H), 5.58 (d, J=2.13 Hz, 1 H), 5.24 (dd, J=17.06, 1.37 Hz, 1 H), 5.13 (dd, J=10.36, 1.52 Hz, 1 H), 4.84-5.07 (m, 2 H), 4.47 (t, J=8.22 Hz, 2 H), 4.18-4.27 (m, 1 H), 4.10-4.18 (m, 1 H), 4.02-4.10 (m, 1 H), 3.99 (s, 3 H), 3.21 (spt, J=6.73 Hz, 1 H), 2.87-3.02 (m, 1 H), 2.71 (s, 3 H), 2.55-2.65 (m, 2 H), 1.94-2.10 (m, 5 H), 1.68-1.84 (m, 3 H), 1.44-1.61 (m, 2 H), 1.40 (d, J=6.85 Hz, 6 H), 1.34 (d, J=6.40 Hz, 5 H), 1.00-1.10 (m, 2 H). LC-MS: purity 84% (UV), $t_R$ 2.71 min, m/z $[M+H]^+$ 869.00.

Example 20-8

Synthesis of Compound 49

49

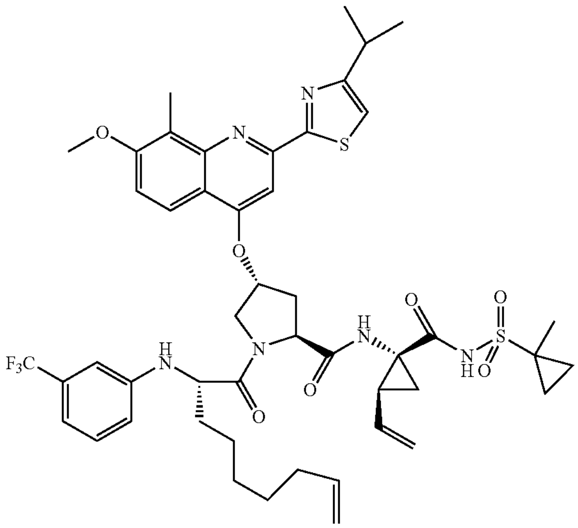

General Procedure SSLS

Compound 44 (HCl salt, 4 g, 5.3 mmol, 1.0 eq.) and N,N-dimethylformamide (80 mL) were charged into a 250 mL round bottom flask under nitrogen. HATU (2.65 g, 6.4 mmol, 1.2 eq.) and diisopropylethylamine (6 mL, 32 mmol, 6.0 eq.) were added at 0° C. and the reaction mixture stirred at ambient temperature for a further 15 minutes. (2S)-2-(3-trifluoromethyl-phenylamino)-non-8-enoic acid (2.01 g, 6.4 mmol, 1.2 eq.) was added as a single portion and stirring was continued at ambient temperature for a further 2 hours. Monitoring the reaction conversion by LCMS showed full consumption of the starting material. The solvent was removed under vacuum and the residue partitioned between ethyl acetate (80 mL) and water (80 mL). The organic phase was further washed with water (80 mL×4), dried over sodium sulfate, filtered and concentrated to dryness. The residue was purified by flash column chromatography, using a dichloromethane: ethyl acetate gradient (from neat dichloromethane to 10% ethylacetate in dichloromethane). After combining the relevant fractions the solvent was removed under vacuum to give 3.08 g (61%) of compound 49 as a yellow solid.

The residue was dissolved in toluene (300 mL) and decolorizing charcoal (924 mg, ~30 wt % of the residue mass) was added. The slurry was heated at 65° C. for 30 minutes and the charcoal removed by filtration while still hot. The mixture was used in the next step. $^1H$ NMR (500 MHz, $CDCl_3$) δ ppm 10.12 (s, 1 H) 7.80 (d, J=9.14 Hz, 1 H) 7.56 (br. s, 1 H) 7.17 (d, J=9.30 Hz, 1 H) 7.07-7.12 (m, 1 H) 7.06 (s, 1 H) 6.88-6.95 (m, 2 H) 6.80 (s, 1 H) 6.67 (d, J=8.04 Hz, 1 H) 5.71-5.83 (m, 2 H) 5.60 (br. s, 1 H) 5.23 (d, J=17.18 Hz, 1 H) 5.12 (d, J=10.40 Hz, 1 H) 4.98 (d, J=17.18 Hz, 1 H) 4.93 (d, J=10.09 Hz, 1 H) 4.86 (d, J=9.14 Hz, 1 H) 4.46 (t, J=8.28 Hz, 1 H) 4.19 (d, J=11.35 Hz, 2 H) 4.06-4.15 (m, 1 H) 3.99 (s, 3 H) 3.21 (spt, J=6.78 Hz, 1 H) 2.71 (s, 3 H) 2.64 (d, J=7.25 Hz, 2 H) 1.97-2.08 (m, 4 H) 1.75-1.88 (m, 2 H) 1.71 (br. s, 2 H) 1.62-1.70 (m, 1 H) 1.54-1.62 (m, 1 H) 1.51 (s, 3 H) 1.29-1.45 (m, 10 H) 1.23-1.29 (m, 1 H) 0.89-0.95 (m, 1 H) 0.82-0.87 (m, 1 H). LC-MS: purity 100% (UV), $t_R$ 5.60 min, m/z $[M+H]^+$ 951.31.

Example 20-9

50

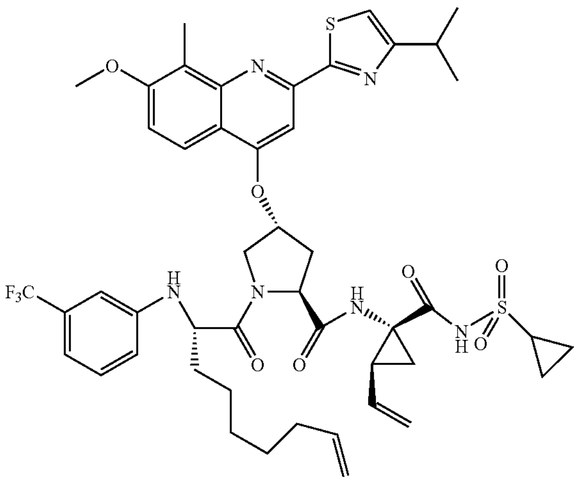

Synthesis of Compound 50

The preceding compound was prepared in a manner analogous to General Procedure NN, to afford 385 mg (61%), pale yellow solid. $^1$H NMR (500 MHz, $CDCl_3$) δ ppm 10.38 (s, 1 H), 7.80 (d, J=9.16 Hz, 1 H), 7.56 (s, 1 H), 7.17 (d, J=9.16 Hz, 1 H), 7.09 (t, 1 H), 7.06 (s, 1 H), 6.93 (d, J=7.63 Hz, 1 H), 6.86 (s, 1 H), 6.79 (s, 1 H), 6.66 (d, J=8.24 Hz, 1 H), 5.74-5.84 (m, 2 H), 5.61 (br. s, 1 H), 5.23 (d, J=17.09 Hz, 1 H), 5.12 (d, J=10.53 Hz, 1 H), 4.99 (d, J=15.72 Hz, 1 H), 4.93 (d, J=10.22 Hz, 1 H), 4.83 (d, J=9.77 Hz, 1 H), 4.42-4.48 (m, 1 H), 4.20 (d, J=11.60 Hz, 2 H), 4.07-4.11 (m, 1 H), 3.99 (s, 3 H), 3.20 (spt, J=6.82 Hz, 1 H), 2.91-2.99 (m, 1 H), 2.71 (s, 3 H), 2.60-2.67 (m, 2 H), 1.98-2.05 (m, 2 H), 1.79-1.88 (m, 1 H), 1.71-1.79 (m, 1 H), 1.47-1.60 (m, 2 H), 1.45 (dd, J=8.39, 4.58 Hz, 1 H), 1.40 (d, J=6.87 Hz, 8 H), 1.32-1.38 (m, 4 H), 1.30 (d, J=7.48 Hz, 1H), 1.03-1.11 (m, 2 H), 0.79-0.87 (m, 1 H). LC-MS: purity 100% (UV), $t_R$ 2.72 min, m/z $[M+H]^+$ 937.35.

Example 20-10

51

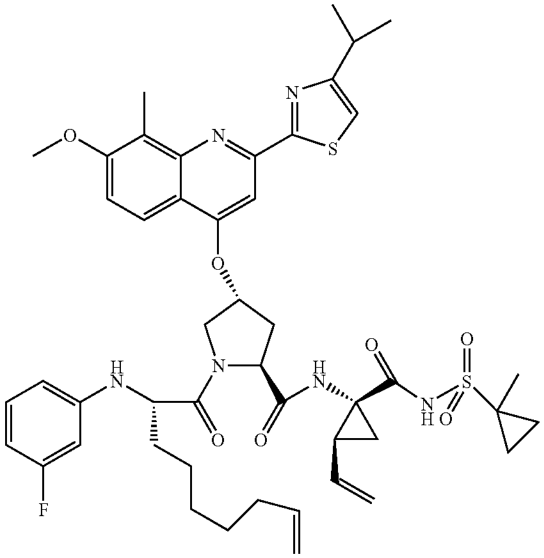

Synthesis of Compound 51

The preceding compound was prepared in a manner analogous to General Procedure NN, to afford 344 mg (50%), pale yellow solid. $^1$H NMR (500 MHz, $CDCl_3$) δ ppm 10.09 (br. s, 1 H) 7.83 (d, J=9.16 Hz, 1 H), 7.56 (s, 1 H), 7.20 (d, J=9.16 Hz, 1 H), 7.06 (s, 1 H), 6.97 (q, J=7.83 Hz, 1 H), 6.90 (s, 1 H), 6.40 (td, J=8.39, 1.68 Hz, 1 H), 6.33 (dd, J=8.16, 1.30 Hz, 1 H), 6.27 (d, J=11.29 Hz, 1 H), 5.77 (dd, J=17.09, 7.02 Hz, 2 H), 5.60 (d, J=2.14 Hz, 1 H), 5.23 (d, J=17.09 Hz, 1 H), 5.12 (d, J=10.68 Hz, 1 H), 4.99 (dd, J=17.09, 1.37 Hz, 1 H), 4.93 (d, J=9.92 Hz, 1 H), 4.69 (d, J=9.77 Hz, 1 H), 4.46 (t, J=8.32 Hz, 1 H), 4.20 (d, J=11.75 Hz, 1 H), 4.13 (q, J=6.87 Hz, 1 H), 4.07 (dd, J=11.75, 3.20 Hz, 1 H), 4.00 (s, 3 H) 3.21 (spt, J=6.71 Hz, 1 H), 2.71 (s, 3 H), 2.65 (d, J=8.24 Hz, 2H), 1.95-2.08 (m, 4 H), 1.79 (d, J=6.87 Hz, 2 H), 1.71 (s, 2 H) 1.53-1.58 (m, 1 H), 1.51 (s, 3 H), 1.45-1.49 (m, 1 H), 1.42-1.46 (m, 1 H), 1.40 (d, J=6.87 Hz, 6 H), 1.28-1.37 (m, 4 H), 0.91-0.95 (m, 1 H), 0.81-0.87 (m, 1 H). LC-MS: purity 99% (UV), $t_R$ 2.48 min, m/z $[M+H]^+$ 901.45.

Example 20-11

52

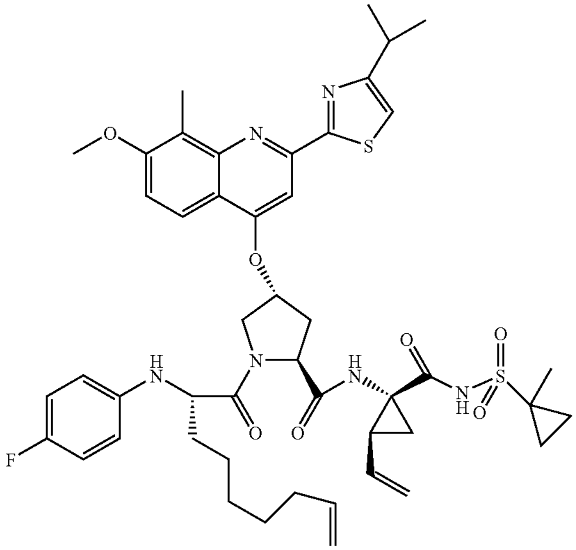

Synthesis of Compound 52

The preceding compound was prepared in a manner analogous to General Procedure NN, to afford 754 mg (58%), yellow solid. $^1$H NMR (500 MHz, $CDCl_3$) δ ppm 10.10 (br. s, 1 H), 7.80 (d, J=9.00 Hz, 1 H), 7.54 (s, 1 H), 7.19 (d, J=9.31 Hz, 1 H), 7.14 (s, 1 H), 7.06 (s, 1 H), 6.62-6.68 (m, 2 H), 6.39-6.44 (m, 2 H), 6.03 (br. s, 1 H), 5.72-5.83 (m, 2 H), 5.58 (d, J=3.81 Hz, 1 H), 5.26 (d, J=16.94 Hz, 1 H), 5.09-5.14 (m, 1 H), 4.97 (dd, J=17.09, 1.68 Hz, 1 H), 4.92 (dd, J=10.07, 0.76 Hz, 1 H), 4.52 (dd, J=9.92, 6.87 Hz, 1 H), 4.13-4.19 (m, 1 H), 4.07 (d, J=3.20 Hz, 1 H), 4.01-4.05 (m, 1 H), 4.00 (s, 3 H), 3.89-3.98 (m, 1 H), 3.64-3.74 (m, 4 H), 3.19-3.24 (m, 1 H), 3.17 (q, J=7.48 Hz, 3 H), 2.71 (s, 3 H), 2.61-2.69 (m, 1 H), 2.52-2.60 (m, 1 H), 2.11 (q, J=8.85 Hz, 1 H), 2.00-2.05 (m, 3 H), 1.61-1.68 (m, 1 H), 1.52-1.60 (m, 1 H), 1.51 (s, 3 H), 1.44 (d, J=7.48 Hz, 6 H), 1.25-1.29 (m, 1 H), 0.93 (dt, J=8.96, 6.12 Hz, 1 H), 0.80-0.89 (m, 1 H). LC-MS: purity 91% (UV), $t_R$ 2.66 min, m/z $[M+H]^+$ 901.45.

Example 20-12

53

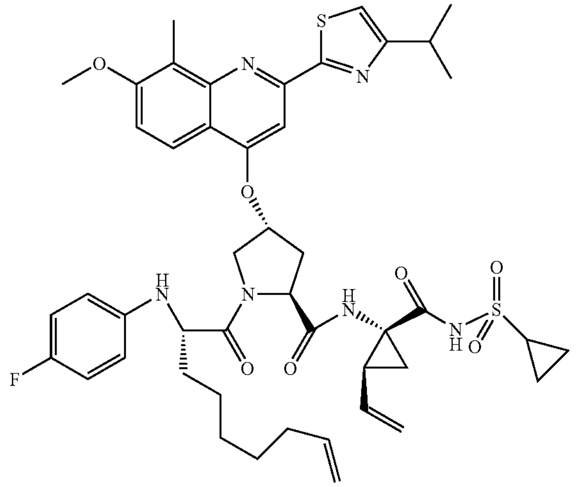

Synthesis of Compound 53

The preceding compound was prepared in a manner analogous to General Procedure NN, to afford 685 mg (52%), pale yellow solid. [1] H NMR (500 MHz, $CDCl_3$) δ ppm 10.34 (br. s, 1 H), 7.74 (d, J=8.99 Hz, 1 H), 7.56 (s, 1 H), 7.07 (s, 1 H), 6.86 (s, 1 H), 6.69 (t, J=8.67 Hz, 2 H), 6.44 (dd, J=8.91, 4.33 Hz, 2 H), 5.71-5.86 (m, 2 H), 5.60 (br. s, 1 H), 5.24 (d, J=17.18 Hz, 1 H), 5.13 (d, J=10.40 Hz, 1 H), 4.99 (dd, J=17.18, 1.89 Hz, 1H), 4.93 (dd, J=10.09, 0.95 Hz, 1 H), 4.45 (t, J=8.35 Hz, 1 H), 4.30-4.41 (m, 1 H), 4.19 (d, J=11.82 Hz, 1 H), 4.02-4.10 (m, 2 H), 4.01 (s, 3 H), 3.21 (spt, J=6.88 Hz, 1 H), 2.90-2.99 (m, 1 H), 2.72 (s, 3 H), 2.62 (d, J=8.51 Hz, 2 H), 1.99-2.09 (m, 4 H), 1.74 (d, J=4.89 Hz, 2 H), 1.53-1.59 (m, 1 H), 1.48-1.53 (m, 1 H), 1.45 (dt, J=8.63, 4.28 Hz, 2 H), 1.40 (m, J=6.94 Hz, 8 H), 1.30-1.37 (m, 4 H), 1.07 (d, J=8.04 Hz, 2 H). LC-MS: purity 100% (UV), $t_R$ 2.63 min, m/z $[M+H]^+$ 887.40.

Example 20-13

54

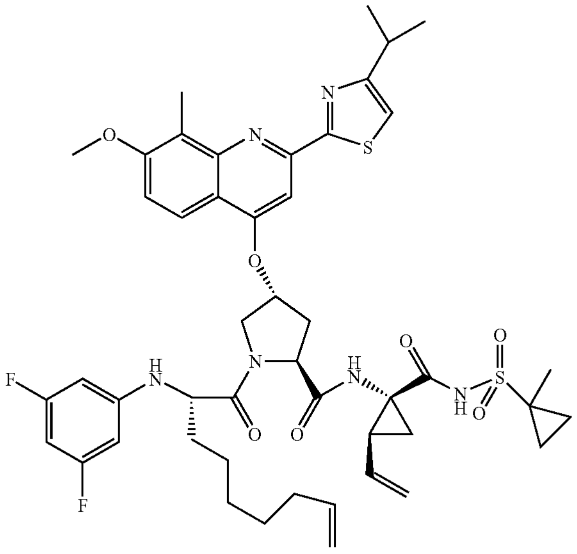

Synthesis of Compound 54

The preceding compound was prepared in a manner analogous to General Procedure NN, to afford 272 mg (51%), beige solid. [1] H NMR (500 MHz, $CDCl_3$) δ ppm 10.09 (br. s, 1 H), 7.84 (d, J=9.14 Hz, 1 H), 7.56 (s, 1 H), 7.21 (d, J=9.14 Hz, 1 H), 7.06 (s, 1 H), 6.93 (s, 1 H), 6.17 (tt, J=9.08, 2.03 Hz, 1 H), 6.05-6.13 (m, 2 H), 5.70-5.85 (m, 2 H), 5.60 (br. s, 1 H), 5.22 (dd, J=17.02, 0.79 Hz, 1 H), 5.09-5.15 (m, 1 H), 4.99 (dd, J=17.10, 1.81 Hz, 1 H), 4.92 (t, J=10.01 Hz, 2 H), 4.43-4.49 (m, 1 H), 4.16-4.21 (m, 1 H), 4.06-4.10 (m, 1 H), 4.00 (s, 3 H), 3.20 (spt, J=6.86 Hz, 1 H), 2.71 (s, 3 H), 2.59-2.69 (m, 2 H), 1.95-2.04 (m, 3 H), 1.75-1.85 (m, 2 H), 1.68-1.74 (m, 2 H), 1.53-1.60 (m, 2 H), 1.50 (s, 3 H), 1.46-1.49 (m, 1 H), 1.42-1.46 (m, 2 H), 1.38-1.42 (m, 8 H), 1.34-1.38 (m, 2 H), 1.29-1.34 (m, 2 H). LC-MS: 100% (UV), $t_R$ 2.49 min, m/z $[M+H]^+$ 919.35.

Example 20-14

55

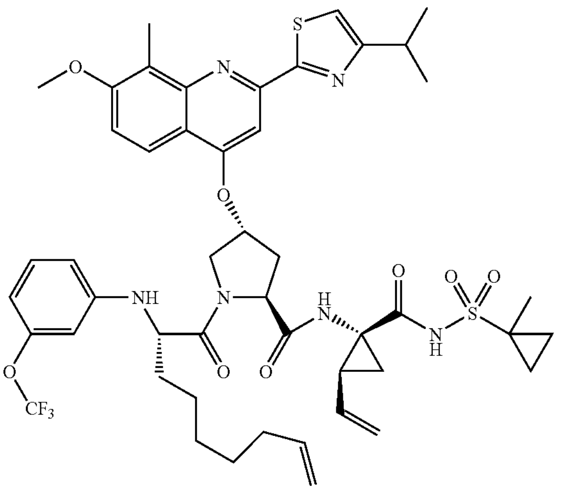

Synthesis of Compound 55

The preceding compound was prepared in a manner analogous to General Procedure NN, to afford 359 mg (64%), orange oil. [1] H NMR (500 MHz, $CDCl_3$) δ ppm 10.10 (br. s, 1 H), 7.81 (d, J=9.00 Hz, 1 H), 7.56 (s, 1 H), 7.19 (d, J=9.31 Hz, 1 H), 7.06 (s, 1 H), 7.00 (t, J=8.09 Hz, 1 H), 6.93 (br. s, 1 H), 6.54 (d, J=8.24 Hz, 1 H), 6.38-6.47 (m, 2H), 5.69-5.85 (m, 2 H), 5.60 (br. s, 1 H), 5.23 (d, J=17.09 Hz, 1 H), 5.12 (d, J=10.68 Hz, 1 H), 4.98 (d, J=17.09 Hz, 1 H), 4.93 (d, J=10.07 Hz, 1 H), 4.80 (br. s, 1 H), 4.47 (t, J=8.32 Hz, 1 H), 4.05-4.22 (m, 3 H), 3.99 (s, 3 H), 3.21 (spt, J=6.82 Hz, 1 H), 2.71 (s, 3 H), 2.64 (d, J=7.78 Hz, 2 H), 1.98-2.07 (m, 4 H), 1.75-1.88 (m, 3 H), 1.62-1.69 (m, 2 H), 1.53-1.61 (m, 2 H), 1.51 (s, 3 H), 1.42-1.45 (m, 1 H), 1.40 (d, J=6.87 Hz, 6 H), 1.37-1.39 (m, 1 H), 1.30-1.36 (m, 2 H), 0.82-0.95 (m, 2 H). LC-MS: purity 98% (UV), $t_R$ 2.56 min, m/z $[M+H]^+$ 967.40.

Example 20-15

56

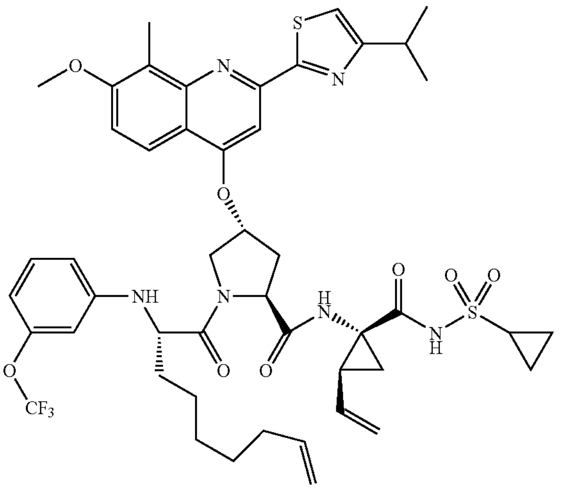

Synthesis of Compound 56

The preceding compound was prepared in a manner analogous to General Procedure NN, to afford 266 mg (42%), pale yellow solid. [1] H NMR (500 MHz, $CDCl_3$) δ ppm 10.38 (br. s, 1 H), 7.81 (d, J=9.16 Hz, 1 H), 7.56 (s, 1 H), 7.19 (d, J=9.16 Hz, 1 H), 7.06 (s, 1 H), 7.00 (t, J=8.16 Hz, 1 H), 6.84 (s, 1 H), 6.54 (d, J=8.09 Hz, 1 H), 6.42 (d, J=8.24 Hz, 1 H), 6.40 (s, 1 H), 5.72-5.86 (m, 2 H), 5.61 (br. s, 1 H), 5.23 (d, J=17.24 Hz, 1 H), 5.13 (d, J=10.38 Hz, 1 H), 4.99 (dd, J=17.09, 1.53 Hz, 1 H), 4.93 (d, J=10.22 Hz, 1 H), 4.77 (d, J=9.61 Hz, 1 H), 4.45 (t, J=8.32 Hz, 1 H), 4.17-4.20 (m, 1 H), 4.12-4.17 (m, 1 H), 4.06-4.12 (m, 1 H), 3.99 (s, 3 H), 3.21 (spt, J=6.74 Hz, 1 H), 2.89-3.01 (m, 1 H), 2.71 (s, 3 H), 2.58-2.68 (m, 2 H), 2.00-2.10 (m, 4 H), 1.78-1.86 (m, 1 H), 1.68-1.78 (m, 1 H), 1.48-1.58 (m, 2 H), 1.43-1.48 (m, 2 H), 1.39-1.41 (m, 7 H), 1.29-1.38 (m, 4 H), 1.02-1.12 (m, 2 H). LC-MS: purity 100% (UV), $t_R$ 2.73 min, m/z $[M+H]^+$ 953.25.

Example 20-16

57

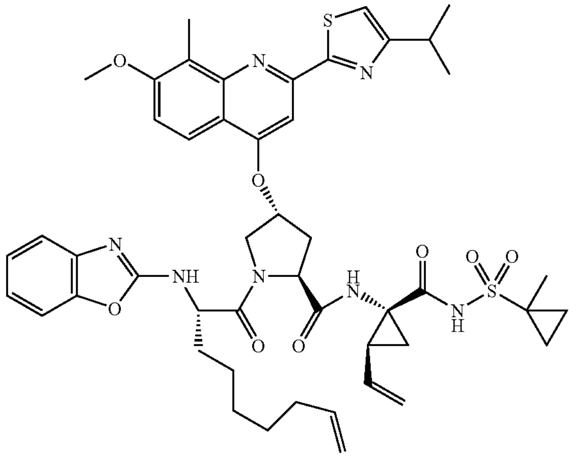

Synthesis of Compound 57

The preceding compound was prepared in a manner analogous to General Procedure NN, to afford 996 mg (73%), yellow solid. [1] H NMR (500 MHz, $CDCl_3$) δ ppm 10.11 (s, 1 H), 7.81 (d, J=9.14 Hz, 1 H), 7.55 (s, 1 H), 7.20 (d, J=7.88 Hz, 1 H), 7.07-7.13 (m, 2 H), 7.04-7.07 (m, 1 H), 6.94-7.03 (m, 3 H), 6.02 (d, J=7.57 Hz, 1 H), 5.68-5.90 (m, 2 H), 5.54-5.64 (m, 1 H), 5.23 (d, J=16.87 Hz, 1 H), 5.13 (d, J=11.35 Hz, 1 H), 4.98 (dd, J=17.02, 1.58 Hz, 1 H), 4.92 (dd, J=10.17, 1.02 Hz, 1 H), 4.76 (td, J=8.28, 5.36 Hz, 1 H), 4.48-4.52 (m, 1 H), 4.43-4.48 (m, 1 H), 4.12 (dd, J=11.66, 3.47 Hz, 1 H), 3.92 (s, 3 H), 3.17-3.22 (m, 1 H), 2.69 (s, 3 H), 2.53-2.68 (m, 2 H), 1.97-2.10 (m, 4 H), 1.81-1.96 (m, 2 H), 1.67-1.80 (m, 2 H), 1.52 (s, 5 H), 1.43-1.47 (m, 1 H), 1.35-1.43 (m, 10 H), 0.89-0.97 (m, 1 H), 0.81-0.89 (m, 1 H). LC-MS: purity 99% (UV), $t_R$ 2.49 min, m/z $[M+H]^+$ 924.55.

Example 20-17

58

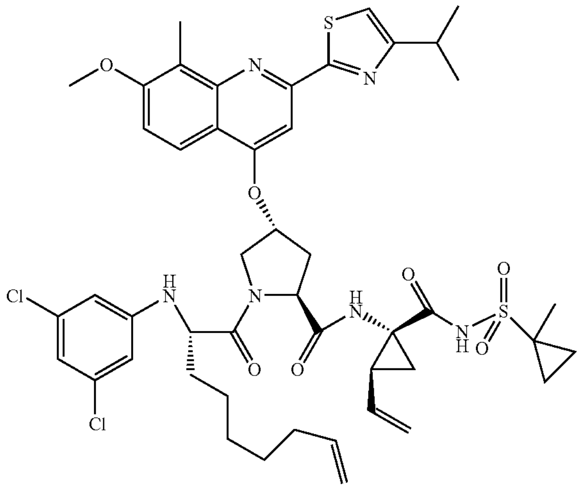

Synthesis of Compound 58

The preceding compound was prepared in a manner analogous to General Procedure NN, to afford 96 mg (23%), yellow solid. [1] H NMR (500 MHz, $CDCl_3$) δ ppm 10.15 (br. s, 1 H), 7.84 (d, J=9.16 Hz, 1 H), 7.56 (s, 1 H), 7.19 (d, J=9.16 Hz, 1 H), 7.06 (s, 1 H) 6.99 (br. s, 1 H), 6.67 (s, 1 H), 6.47-6.51 (m, 1 H), 6.45 (d, J=1.68 Hz, 2 H), 5.72-5.84 (m, 2 H), 5.56-5.62 (m, 1 H), 5.22 (d, J=17.24 Hz, 1 H), 5.12 (d, J=10.38 Hz, 1 H), 4.99 (dd, J=17.17, 1.60 Hz, 1 H), 4.94 (dd, J=10.22, 1.07 Hz, 1 H), 4.81-4.92 (m, 1 H), 4.45 (t, 1 H), 4.05-4.20 (m, 4 H), 3.98 (s, 4 H), 3.20 (spt, J=6.87 Hz, 1 H), 2.70 (s, 3 H), 2.59-2.67 (m, 2 H), 2.01-2.06 (m, 5 H), 1.82-1.97 (m, 2 H), 1.76-1.81 (m, 2 H), 1.71 (br. s, 2 H), 1.52-1.61 (m, 1 H), 1.50 (s, 3 H), 1.42-1.48 (m, 1 H), 1.28-1.38 (m, 3 H), 0.77-0.96 (m, 2 H). LC-MS: purity 90% (UV), $t_R$ 2.63 min, m/z $[M+H]^+$ 951.30.

Example 20-18

59

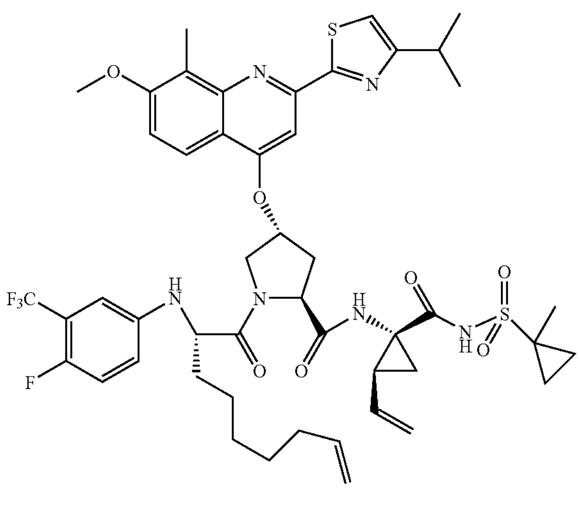

Synthesis of Compound 59

The preceding compound was prepared in a manner analogous to General Procedure SS, to afford 920 mg (66%), pale yellow solid. [1] H NMR (500 MHz, $CDCl_3$) δ ppm 10.12 (s, 1 H), 7.75 (d, J=9.16 Hz, 1 H), 7.56 (s, 1 H), 7.19 (d, J=9.16 Hz, 1 H), 7.07 (s, 1 H), 6.84 (s, 1 H), 6.74-6.80 (m, 2 H), 6.57-6.62 (m, 1 H), 5.73-5.83 (m, 2 H), 5.62 (br. s, 1 H), 5.22 (d, J=17.09 Hz, 1 H), 5.13 (d, J=10.38 Hz, 1 H), 4.99 (d, J=17.09 Hz, 1 H), 4.93 (d, J=10.22 Hz, 1 H), 4.72 (d, J=10.38 Hz, 1 H), 4.45 (t, J=8.32 Hz, 1 H), 4.17 (d, 1 H), 4.08 (d, J=6.56 Hz, 1 H), 4.00 (s, 3 H), 3.20 (quin, J=6.90 Hz, 1 H), 2.72 (s, 3 H), 2.61-2.65 (m, 2 H), 1.98-2.08 (m, 4 H), 1.75-1.82 (m, 2 H), 1.72 (br. s, 2 H), 1.50 (s, 3 H), 1.43 (d, J=5.34 Hz, 2 H), 1.40 (d, J=6.87 Hz, 6 H), 1.30-1.38 (m, 3 H), 1.24-1.30 (m, 3 H), 0.86-0.91 (m, 2 H). LC-MS: purity 89% (UV), $t_R$ 5.57 min, m/z $[M+H]^+$ 969.39.

Example 20-19

60

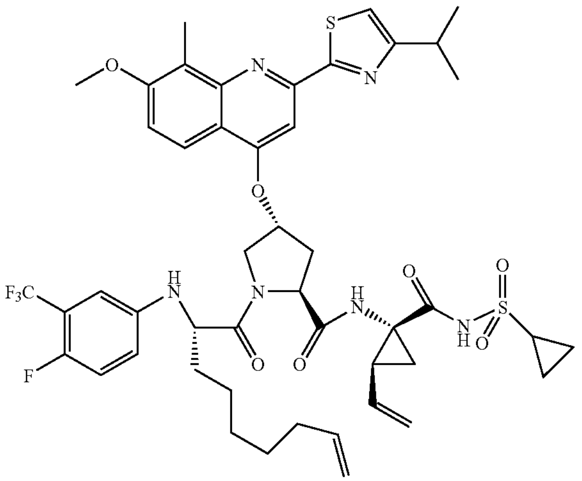

Synthesis of Compound 60

The preceding compound was prepared in a manner analogous to General Procedure NN, to afford 310 mg (48%), pale yellow solid. [1] H NMR (500 MHz, $CDCl_3$) δ ppm 10.38 (br. s, 1 H), 7.75 (d, J=9.16 Hz, 1 H), 7.56 (s, 1 H), 7.19 (d, J=9.31 Hz, 1 H), 7.07 (s, 1 H), 6.74-6.80 (m, 3 H), 6.56-6.60 (m, 1 H), 5.75-5.84 (m, 2 H), 5.62 (br. s, 1 H), 5.23 (d, J=17.09 Hz, 1 H), 5.13 (d, J=10.68 Hz, 1 H), 4.99 (dd, J=17.17, 1.45 Hz, 1 H), 4.92-4.95 (m, 1 H), 4.68 (d, J=9.16 Hz, 1 H), 4.45 (t, J=8.39 Hz, 1 H), 4.16-4.19 (m, 1 H), 4.06-4.11 (m, 2 H), 4.00 (s, 3 H), 3.17-3.25 (m, 1 H), 2.93-2.99 (m, 1 H), 2.72 (s, 3 H), 2.59-2.69 (m, 2 H), 1.99-2.09 (m, 4 H), 1.78-1.85 (m, 1 H), 1.69-1.77 (m, 1 H), 1.42-1.54 (m, 4 H), 1.39-1.41 (m, 7 H), 1.28-1.38 (m, 4 H), 1.09 (dd, J=8.62, 3.89 Hz, 2 H). LC-MS: purity 96% (UV), $t_R$ 5.45 min, m/z $[M+H]^+$ 955.11.

Example 20-20

61

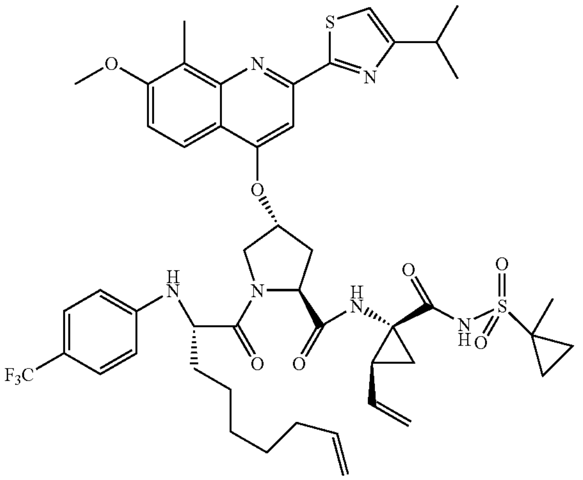

Synthesis of Compound 61

The preceding compound was prepared in a manner analogous to General Procedure NN, to afford 499 mg (60%), pale yellow solid. [1] H NMR (500 MHz, $CDCl_3$) δ ppm 10.04 (br. s, 1 H), 7.81 (d, J=9.16 Hz, 1 H), 7.58 (s, 1 H), 7.16-7.20 (m, 2 H), 7.07 (s, 1 H), 6.93 (s, 1 H), 6.49 (d, J=8.39 Hz, 2 H), 5.77 (dd, J=10.15, 7.10 Hz, 2 H), 5.63 (br. s, 1 H), 5.23 (d, J=17.09 Hz, 1 H), 5.12 (d, J=10.38 Hz, 1 H), 4.98 (d, J=17.09 Hz, 1 H), 4.93 (d, J=10.07 Hz, 1 H), 4.85 (d, J=9.61 Hz, 1 H), 4.48 (t, J=8.39 Hz, 1 H), 4.23 (d, J=11.75 Hz, 1 H), 4.10-4.19 (m, 1 H), 4.06 (dd, J=11.75, 2.59 Hz, 1 H), 3.99 (s, 3 H), 3.21 (spt, J=6.84 Hz, 1 H), 2.72 (s, 3 H), 2.64 (d, J=7.93 Hz, 2 H), 1.99-2.08 (m, 4 H), 1.77-1.85 (m, 2 H), 1.68-1.73 (m, 2 H), 1.53-1.60 (m, 2 H), 1.50 (s, 3 H), 1.39-1.42 (m, 8 H), 1.34-1.37 (m, 2 H), 0.82-0.95 (m, 4 H). LC-MS: purity 94% (UV), $t_R$ 2.72 min, m/z $[M+H]^+$ 951.40.

Example 20-21

62

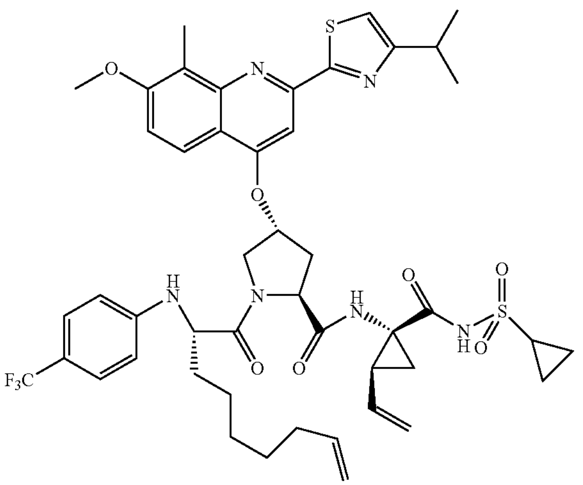

Synthesis of Compound 62

The preceding compound was prepared in a manner analogous to General Procedure NN, to afford 245 mg (67%), pale yellow solid. [1] H NMR (500 MHz, $CDCl_3$) δ ppm 10.29 (br. s, 1 H), 7.80 (d, J=9.16 Hz, 1 H), 7.57 (s, 1 H), 7.16-7.24 (m, 3 H), 7.07 (s, 1 H), 6.90 (s, 1 H), 6.47 (d, J=8.39 Hz, 2 H), 5.70-5.85 (m, 2 H), 5.62 (br. s, 1 H), 5.23 (d, J=17.09 Hz, 1 H), 5.12 (d, J=10.38 Hz, 1 H), 4.99 (d, J=17.09 Hz, 1 H), 4.93 (d, J=10.22 Hz, 1 H), 4.81 (d, J=9.31 Hz, 1 H), 4.47 (t, J=8.39 Hz, 1 H), 4.23 (d, J=11.75 Hz, 1 H), 4.12-4.20 (m, 1 H), 4.06 (dd, J=11.75, 2.59 Hz, 1 H), 3.99 (s, 3 H), 3.21 (spt, J=6.79 Hz, 1 H), 2.89-2.99 (m, 1 H), 2.72 (s, 3 H), 2.57-2.67 (m, 2 H), 1.99-2.08 (m, 4 H), 1.75-1.84 (m, 2 H), 1.51-1.61 (m, 1 H), 1.43-1.50 (m, 2 H), 1.39-1.42 (m, 7 H), 1.28-1.38 (m, 5 H), 1.06 (dd, J=8.24, 2.90 Hz, 2 H). LC-MS: purity 100% (UV), $t_R$ 2.71 min, m/z $[M+H]^+$ 937.30.

Example 20-22

230

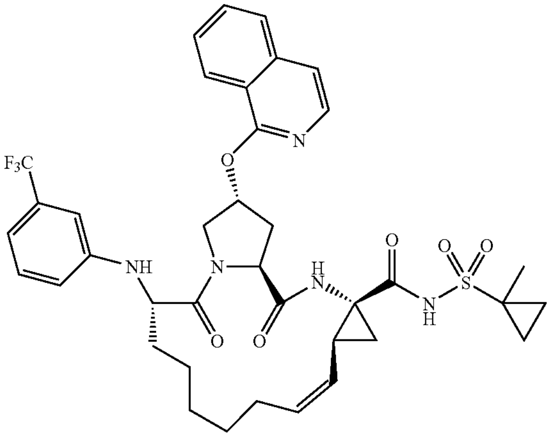

Compound 230 was prepared in a manner analogous to General Procedure OO, to afford 13.4 mg (38%), brown solid. [1] H NMR (500 MHz, $CDCl_3$) δ ppm 10.10 (s, 1 H), 8.02 (d, J=8.24 Hz, 1 H), 8.00 (d, J=5.95 Hz, 1 H), 7.77 (d, J=8.09 Hz, 1 H), 7.65-7.72 (m, 1 H), 7.45-7.52 (m, 1 H), 7.29 (d, J=5.95 Hz, 1 H), 6.97 (br. s, 1 H), 6.66-6.79 (m, 2 H), 6.49 (d, J=7.48 Hz, 1 H), 5.97 (br. s, 1 H), 5.68-5.77 (m, 1 H), 5.01 (t, J=9.61 Hz, 1 H), 4.69 (t, J=7.86 Hz, 1 H), 4.52 (d, J=8.85 Hz, 1 H), 4.24-4.28 (m, 1 H), 4.20-4.25 (m, 1 H), 4.12-4.20 (m, 1 H), 2.68-2.75 (m, 1 H), 2.60-2.68 (m, 1 H), 2.42-2.55 (m, 1 H), 2.27 (q, J=8.65 Hz, 1 H), 1.94-2.08 (m, 2 H), 1.74-1.94 (m, 4 H), 1.41-1.57 (m, 7 H), 1.22-1.38 (m, 4 H), 0.80-0.86 (m, 2 H). LC-MS: purity 85% (UV), $t_R$ 5.41 min, m/z $[M+H]^+$ 754.40.

Example 20-23

230

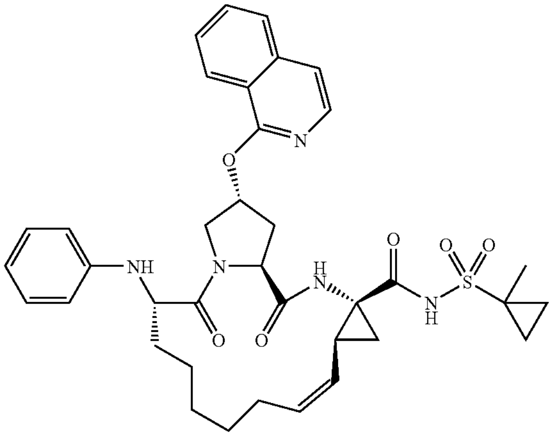

Compound 221 was prepared in a manner analogous to General Procedure OO, to afford 15.1 mg (33%), brown solid. [1] H NMR (500 MHz, $CDCl_3$) δ ppm 10.19 (s, 1 H), 8.05 (d, J=8.25 Hz, 1 H), 8.01 (d, J=5.87 Hz, 1 H), 7.76 (d, J=8.07 Hz, 1 H), 7.65 (t, J=7.98 Hz, 1 H), 7.47 (t, J=7.52 Hz, 1 H), 7.39 (br. s, 1 H), 7.29 (d, J=5.87 Hz, 1 H), 6.73 (t, J=7.89 Hz, 2 H), 6.46 (t, J=7.34 Hz, 1 H), 6.38 (d, J=7.70 Hz, 2 H), 5.95 (br. s, 1 H), 5.70-5.79 (m, 1 H), 5.03 (t, J=9.54 Hz, 1 H), 4.52 (t, J=7.70 Hz, 1 H), 4.27 (d, J=11.74 Hz, 1 H), 4.19 (br. s, 1 H), 4.11-4.17 (m, 2 H), 2.52-2.62 (m, 2 H), 2.42-2.50 (m, 1 H), 2.19 (q, J=8.56 Hz, 1 H), 1.92-1.98 (m, 1 H), 1.89 (dd, J=5.87, 7.89 Hz, 1 H), 1.74-1.86 (m, 3 H), 1.40-1.61 (m, 8 H), 1.22-1.40 (m, 3 H), 0.82-0.86 (m, 2 H). LC-MS: purity 93% (UV), $t_R$ 5.16 min, m/z $[M+H]^+$ 686.40.

Example 20-24

243

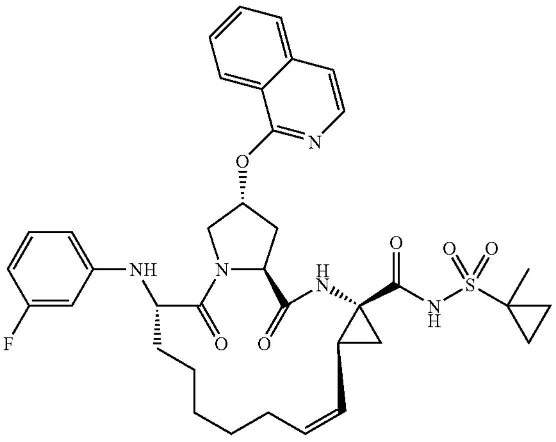

Compound 243 was prepared in a manner analogous to General Procedure OO, to afford 97 mg (53%), grey solid. [1] H NMR (500 MHz, $CDCl_3$) δ ppm 10.17 (s, 1 H), 8.04 (d, J=8.24 Hz, 1 H), 7.98 (d, J=5.80 Hz, 1 H), 7.74 (d, J=8.24 Hz, 1 H), 7.64 (t, J=7.48 Hz, 1 H), 7.47 (t, J=7.55 Hz, 1 H), 7.32 (s, 1 H), 7.26 (s, 1 H), 6.63-6.71 (m, 1 H), 6.12-6.23 (m, 3 H), 5.94 (br. s, 1 H), 5.65-5.74 (m, 1 H), 4.98 (t, J=9.61 Hz, 1 H), 4.59 (t, J=7.71 Hz, 1 H), 4.40 (d, J=8.54 Hz, 1 H), 4.19-4.24 (m, 1 H), 4.12-4.19 (m, 2 H), 2.53-2.63 (m, 2 H), 2.43-2.53 (m, 1 H), 2.21 (q, J=8.70 Hz, 1 H), 1.91-2.01 (m, 1 H), 1.72-1.88 (m, 5 H), 1.41-1.50 (m, 7 H), 1.22-1.41 (m, 3 H), 0.77-0.85 (m, 2 H). LC-MS: purity 100% (UV), $t_R$ 5.28 min, m/z $[M+H]^+$ 704.45.

Example 20-25

356

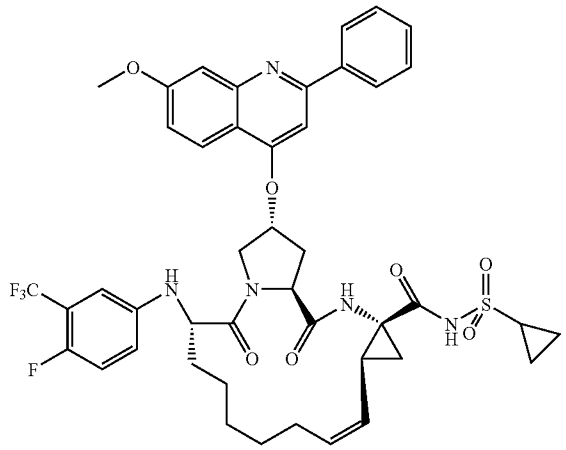

Compound 356 was prepared in a manner analogous to General Procedure OO, to afford 24.2 mg (21%), yellow solid. [1] H NMR (500 MHz, $CDCl_3$) δ ppm 10.46 (br. s, 1 H), 7.91 (d, J=9.17 Hz, 1 H), 7.80 (d, J=7.34 Hz, 2 H), 7.65 (br. s, 2 H), 7.28-7.37 (m, 2 H), 7.22-7.27 (m, 1 H), 7.11 (s, 1 H), 6.90 (t, J=8.71 Hz, 1 H), 6.75-6.81 (m, 1 H), 6.69-6.75 (m, 1 H), 5.78 (br. s, 1 H), 5.63-5.74 (m, 1 H), 4.98 (t, J=9.63 Hz, 1 H), 4.75 (t, J=7.34 Hz, 1 H), 4.18-4.35 (m, 2 H), 4.06-4.19 (m, 1 H), 3.97 (s, 3 H), 2.79-2.95 (m, 1 H), 2.57-2.76 (m, 2 H), 2.32-2.45 (m, 1 H), 2.28 (q, J=9.11 Hz, 1 H), 1.97-2.06 (m, 1 H), 1.68-1.97 (m, 2 H), 1.27-1.58 (m, 9 H), 1.02-1.14 (m, 2 H), 0.80-1.00 (m, 2 H). LC-MS: purity 100% (UV), $t_R$ 4.40 min, m/z $[M+H]^+$ 864.20.

Example 20-26

164

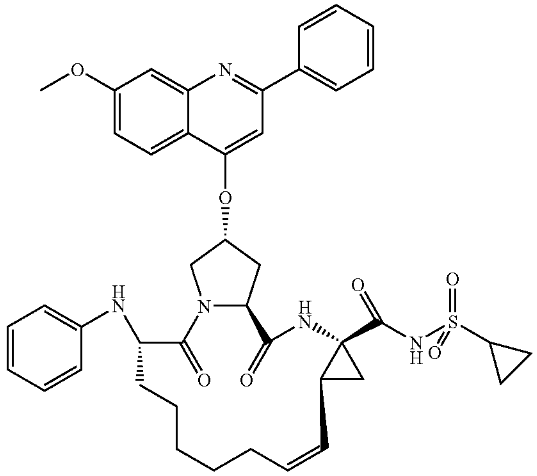

Compound 164 was prepared in a manner analogous to General Procedure OO, to afford 45 mg (31%), beige solid. [1] H NMR (500 MHz, $CDCl_3$) δ ppm 8.09 (d, J=7.32 Hz, 2 H), 7.81 (d, J=9.16 Hz, 1 H), 7.52-7.59 (m, 2 H), 7.46-7.51 (m, 1 H), 7.45 (d, J=1.83 Hz, 1 H), 7.29 (br. s, 1 H), 7.04 (dd, J=2.44, 9.16 Hz, 1 H), 7.01 (s, 1 H), 6.95 (t, J=7.78 Hz, 2 H), 6.59 (t, J=7.32 Hz, 1 H), 6.50 (d, J=7.93 Hz, 2 H), 5.68-5.79 (m, 1 H), 5.46 (br. s, 1 H), 5.01 (t, J=9.31 Hz, 1 H), 4.51 (t, J=5.65 Hz, 1 H), 4.10-4.29 (m, 4 H), 3.94 (s, 3 H), 2.86-2.96 (m, 1 H), 2.43-2.65 (m, 3 H), 2.14-2.23 (m, 1 H), 1.93-2.01 (m, 1 H), 1.91 (dd, J=6.26, 7.78 Hz, 1 H), 1.80-1.87 (m, 2 H), 1.54 (dd, J=5.95, 9.31 Hz, 2 H), 1.41-1.52 (m, 4 H), 1.24-1.39 (m, 2 H), 1.05-1.19 (m, 2 H), 0.89-0.99 (m, 1 H). LC-MS: purity 100% (UV), $t_R$ 4.03 min, m/z $[M+H]^+$ 778.50.

Example 20-27

229

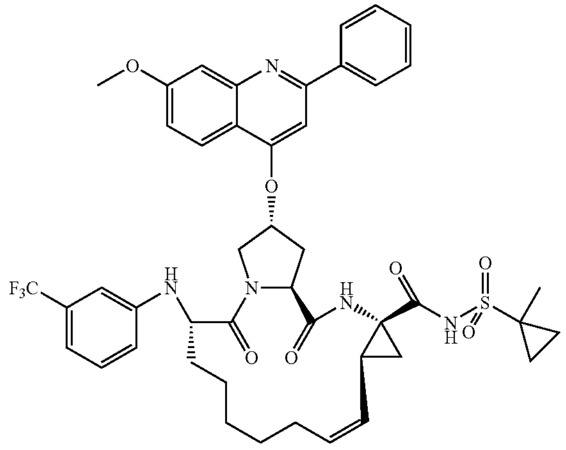

Compound 229 was prepared in a manner analogous to General Procedure OO, to afford 23 mg (14%), yellow solid. [1] H NMR (500 MHz, $CDCl_3$) δ ppm 10.36 (br. s, 1 H), 7.81-7.98 (m, 3 H), 7.76 (br. s, 2 H), 7.36 (br. s, 3 H), 7.14-7.24 (m, 2 H), 7.11 (br. s, 1 H), 6.92 (d, J=7.63 Hz, 1 H), 6.80 (br. s, 1 H), 6.75 (d, J=7.63 Hz, 1 H), 5.75 (br. s, 1 H), 5.63-5.72 (m, 1 H), 4.97 (t, J=9.69 Hz, 1 H), 4.75 (br. s, 1 H), 4.23-4.39 (m, 2 H), 4.17 (d, J=10.83 Hz, 1 H), 3.97 (s, 3 H), 2.53-2.73 (m, 2 H), 2.19-2.42 (m, 2 H), 2.04-2.11 (m, 1 H), 1.99-2.01 (m, 4 H), 1.87-1.98 (m, 1 H), 1.76-1.85 (m, 2 H), 1.66-1.76 (m, 1 H), 1.43-1.49 (m, 4 H), 1.28-1.41 (m, 4 H), 0.74-0.85 (m, 2 H). LC-MS: purity 100% (UV), $t_R$ 4.41 min, m/z $[M+H]^+$ 860.45.

Example 20-28

242

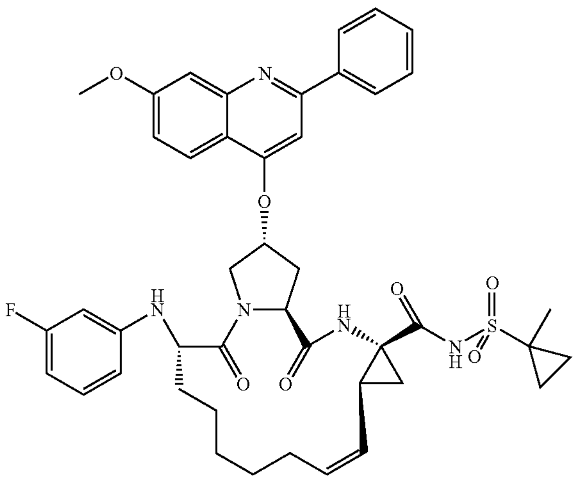

Compound 242 was prepared in a manner analogous to General Procedure OO, to afford 54 mg (31%), grey solid. $^1$H NMR (500 MHz, $CDCl_3$) δ ppm 10.11 (br. s, 1 H), 8.08 (d, J=7.32 Hz, 2 H), 7.82 (d, J=9.16 Hz, 1 H), 7.52-7.58 (m, 2 H), 7.45-7.51 (m, 1 H), 7.44 (d, J=2.29 Hz, 1 H), 7.12 (s, 1 H), 7.06 (dd, J=2.44, 9.16 Hz, 1 H), 7.00 (s, 1 H), 6.87-6.95 (m, 1 H), 6.34 (td, J 2.06, 8.35 Hz, 1 H), 6.21-6.31 (m, 2 H), 5.67-5.77 (m, 1 H), 5.46 (br. s, 1 H), 4.99 (t, J=9.61 Hz, 1 H), 4.60 (t, J=7.55 Hz, 1 H), 4.41 (d, J=9.00 Hz, 1 H), 4.18-4.25 (m, 1 H), 4.11-4.18 (m, 1 H), 3.95 (s, 3 H), 2.59-2.70 (m, 2 H), 2.40-2.53 (m, 1 H), 2.22 (q, J=8.85 Hz, 1 H), 1.93-2.02 (m, 1 H), 1.76-1.91 (m, 4 H), 1.39-1.51 (m, 9 H), 1.25-1.37 (m, 3 H), 0.78-0.86 (m, 2 H). LC-MS: purity 100% (UV), $t_R$ 4.18 min, m/z $[M+H]^+$ 810.40.

Example 20-29

357

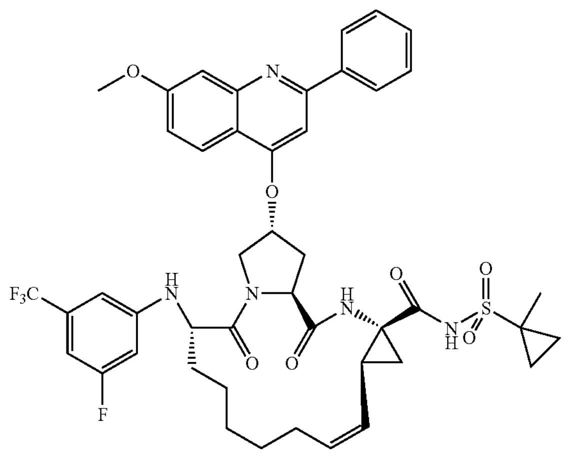

Compound 357 was prepared in a manner analogous to General Procedure OO, to afford 72 mg (49%), brown solid. $^1$H NMR (500 MHz, $CDCl_3$) δ ppm 10.10 (br. s, 1 H), 8.06 (d, J=7.48 Hz, 2 H), 7.83 (d, J=9.16 Hz, 1 H), 7.51-7.57 (m, 2 H), 7.45-7.50 (m, 1 H), 7.44 (d, J=2.14 Hz, 1 H), 7.12 (s, 1 H), 7.06 (dd, J=2.29, 9.00 Hz, 1 H), 7.00 (s, 1 H), 6.58-6.68 (m, 2 H), 6.38 (d, J=10.83 Hz, 1 H), 5.64-5.74 (m, 1 H), 5.47 (br. s, 1 H), 4.96 (t, J=9.69 Hz, 1 H), 4.81 (d, J=8.54 Hz, 1 H), 4.67 (t, J=7.55 Hz, 1 H), 4.26 (td, J=2.44, 8.16 Hz, 1 H), 4.13-4.20 (m, 2 H), 3.95 (s, 3 H), 2.59-2.73 (m, 2 H), 2.30-2.42 (m, 1 H), 2.25 (q, J=8.90 Hz, 1 H), 1.99-2.09 (m, 1 H), 1.83-1.93 (m, 2 H), 1.76-1.82 (m, 2 H), 1.71-1.74 (m, 1 H), 1.49-1.57 (m, 1 H), 1.48 (s, 3 H), 1.37-1.46 (m, 4 H), 1.25-1.34 (m, 2 H), 0.81 (s, 2 H) LC-MS: purity 97% (UV), $t_R$ 3.48 min, m/z $[M+H]^+$ 878.57.

Example 20-30

392

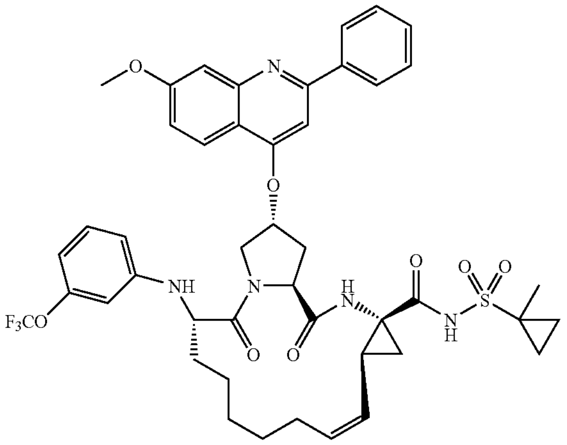

Compound 392 was prepared in a manner analogous to General Procedure NN, to afford 59 mg (48%), pale yellow glassy solid. $^1$H NMR (500 MHz, $CDCl_3$) δ ppm 9.93 (br. s, 1 H), 8.06 (d, J=7.63 Hz, 2 H), 7.81 (d, J=9.00 Hz, 1 H), 7.50-7.58 (m, 2 H), 7.48 (d, J=7.17 Hz, 1 H), 7.44 (d, J=2.14 Hz, 1 H), 7.05 (dd, J=9.08, 2.37 Hz, 1 H), 6.99 (s, 1 H), 6.93 (t, J=8.09 Hz, 1 H), 6.50 (d, J=8.09 Hz, 1 H), 6.43 (s, 1 H), 6.39 (d, J=8.24 Hz, 1 H), 5.68 (q, J=8.70 Hz, 1 H), 5.45 (br. s, 1 H), 4.95 (t, J=9.77 Hz, 1 H), 4.63 (t, J=7.55 Hz, 1 H), 4.54 (d, J=8.85 Hz, 1 H), 4.19-4.26 (m, 1 H), 4.11-4.19 (m, 2 H), 3.95 (s, 3 H), 2.55-2.70 (m, 2 H), 2.35-2.47 (m, 1 H), 2.23 (q, J=8.80 Hz, 1 H), 1.92-2.03 (m, 1 H), 1.79-1.92 (m, 3 H), 1.70-1.79 (m, 2 H), 1.47-1.52 (m, 1 H), 1.46 (s, 3 H), 1.39-

1.45 (m, 5 H), 1.22-1.35 (m, 2 H), 0.73-0.84 (m, 2 H). LC-MS: purity 96% (UV), $t_R$ 4.62 min, m/z $[M+H]^+$ 876.30.

Example 20-31

General Procedure TT

358

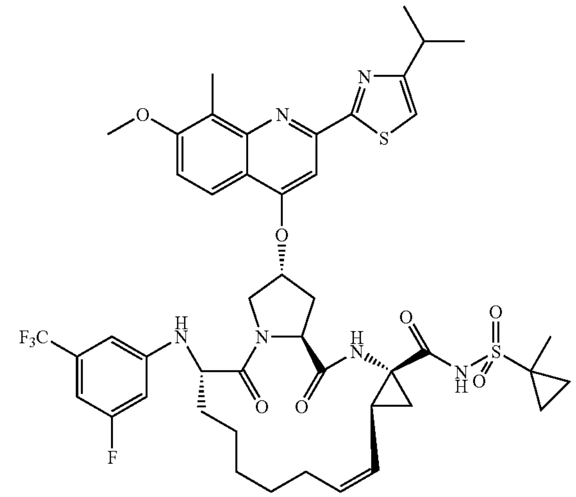

Compound 45 (552 mg, 0.541 mmol., 1.0 eq.) and toluene (83 mL, previously degassed by bubbling nitrogen through the solvent for 30 min) were charged in a 250 mL round bottom flask previously flushed with nitrogen gas and the reaction mixture heated to 65° C. (it is important to keep the reaction mixture under a protective nitrogen atmosphere). Zhan catalyst (1.8 mg, 0.5 mol %) was added and the reaction mixture heated at 65° C. for a further 20 minutes with constant nitrogen gas bubbling through the reaction mixture (via needle). During this time the reaction mixture color turned from pale yellow to pale orange. LCMS analysis showed 35% conversion of starting material to product, so further catalyst (1.8 mg, 0.5 mol %) was added and stirring continued for a further 25 minutes. LCMS analysis showed 80% conversion of starting material to product, so further catalyst (1.8 mg, 0.5 mol %) was added and stirring continued for a further 25 minutes. LCMS analysis showed 96% conversion of starting material to product so the reaction so the heating was stopped and the reaction mixture left to cool down to ambient temperature. The solvent was removed under vacuum. The residue was purified by flash column chromatography, using a methanol:dichloromethane gradient (from neat dichloromethane to 0.5% methanol in dichloromethane). After combining the relevant fractions and solvent removal, 308 mg (60%) of the title compound was isolated as a beige solid. $^1$H NMR (500 MHz, $CDCl_3$) δ ppm 10.14 (s, 1 H), 7.76 (d, J=9.16 Hz, 1 H), 7.49 (s, 1 H), 7.24-7.35 (m, 1 H), 7.11 (d, J=9.46 Hz, 1 H), 7.03 (s, 1 H), 6.61 (s, 1 H), 6.58 (d, J=8.24 Hz, 1 H), 6.33 (d, J=10.99 Hz, 1 H), 5.57-5.67 (m, 1 H), 5.52 (br. s, 1 H), 4.83-4.93 (m, 2 H), 4.66 (t, J=7.78 Hz, 1 H), 4.18-4.25 (m, 1 H), 4.12-4.17 (m, 2 H), 3.94 (s, 3 H), 3.21 (spt, J=6.92 Hz, 1 H), 2.70-2.78 (m, 1 H), 2.67 (s, 3 H), 2.57-2.65 (m, 1 H), 2.29-2.41 (m, 1 H), 2.21 (q, J=8.95 Hz, 1 H), 2.16 (br. s, 1 H), 1.92-2.03 (m, 1 H), 1.79-1.90 (m, 1 H), 1.65-1.79 (m, 3 H), 1.43-1.51 (m, 3 H), 1.37-1.42 (m, 6 H), 1.33-1.51 (m, 4 H), 1.17-1.33 (m, 3 H), 0.70-0.81 (m, 2 H). LC-MS: purity 100% (UV), $t_R$ 5.45 min, m/z $[M+H]^+$ 941.08.

Example 20-32

359

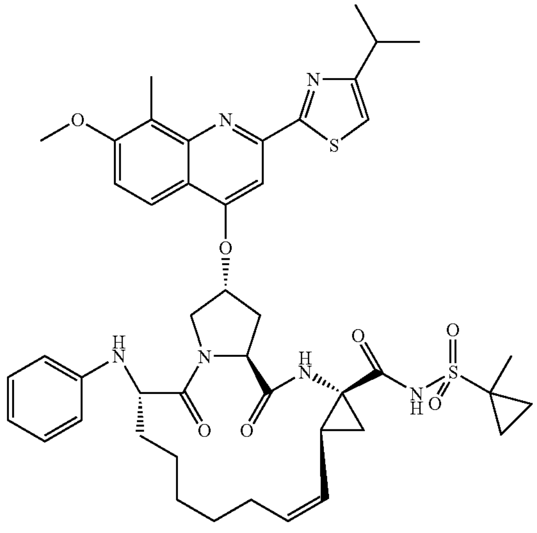

Compound 359 was prepared in a manner analogous to General Procedure TT, to afford 644 mg (73%), pale yellow solid. $^1$H NMR (500 MHz, $CDCl_3$) δ ppm 10.14 (br. s, 1 H), 7.72 (d, J=9.14 Hz, 1 H), 7.52 (s, 1 H), 7.21 (br. s, 1 H), 7.08 (d, J=9.30 Hz, 1 H), 7.06 (s, 1 H), 6.90 (t, 2 H), 6.61 (t, J=7.25 Hz, 1 H), 6.46 (d, J=7.72 Hz, 2 H), 5.76 (q, 1 H), 5.55 (br. s, 1 H), 5.04 (t, 1 H), 4.55 (t, J=7.72 Hz, 1 H), 4.26 (d, J=11.51 Hz, 1 H), 4.20 (dd, J=12.45, 5.83 Hz, 2 H), 4.14 (dd, J=11.66, 3.63 Hz, 1 H), 3.92 (s, 3 H), 3.23 (spt, 1 H), 2.69 (s, 3 H), 2.66 (dd, J=8.20, 5.52 Hz, 1 H), 2.51-2.60 (m, 2 H), 2.19 (q, J=8.62 Hz, 1 H), 1.94-2.00 (m, 1 H), 1.92 (dd, J=8.04, 5.99 Hz, 1 H), 1.86 (dt, J=6.66, 3.21 Hz, 1 H), 1.78-1.85 (m, 3 H), 1.62 (s, 3 H), 1.53-1.57 (m, 2 H), 1.52 (s, 3 H), 1.49 (d, J=8.99 Hz, 2 H), 1.41 (d, J=6.94 Hz, 6 H), 0.82-0.87 (m, 2 H). LC-MS: purity 100% (UV), $t_R$ 5.15 min, m/z $[M+H]^+$ 855.29.

Example 20-33

407

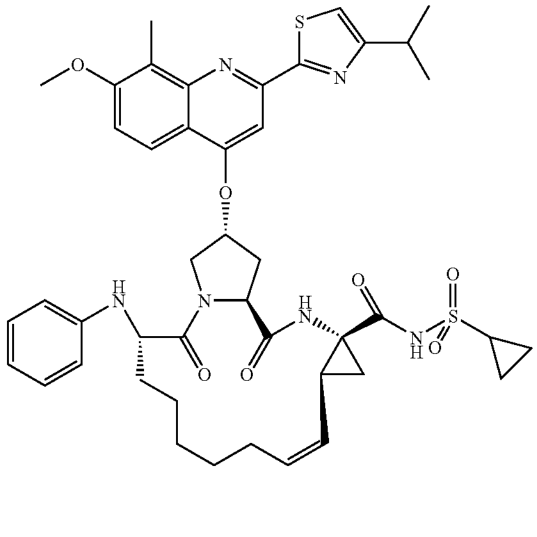

Compound 407 was prepared in a manner analogous to General Procedure TT, to afford 342 mg (42%), pale yellow solid. $^1$H NMR (500 MHz, $CDCl_3$) δ ppm 10.19 (br. s, 1 H), 7.76 (d, J=9.31 Hz, 1 H), 7.54 (s, 1 H), 7.13 (d, J=9.00 Hz, 1 H), 7.06 (s, 1 H), 6.83-6.90 (m, 1 H), 6.55-6.61 (m, 1 H), 6.48 (d, J=8.09 Hz, 1 H), 5.72-5.83 (m, 1 H), 5.58 (br. s, 1 H), 5.02 (t, J=9.61 Hz, 1 H), 4.64 (t, J=8.24 Hz, 1 H), 4.29 (s, 1 H), 4.21 (br. s, 1 H), 4.14 (dd, J=11.75, 3.97 Hz, 1 H), 3.97 (s, 3 H), 3.23 (quin, J=6.79 Hz, 1 H), 2.89-2.97 (m, 1 H), 2.73-2.82 (m, 1 H), 2.69-2.73 (m, 3 H), 2.62-2.69 (m, 1 H), 2.50-2.63 (m, 1 H), 2.22 (q, J=8.49 Hz, 1 H), 1.90-2.01 (m, 2 H), 1.83 (d, J=9.31 Hz, 2 H), 1.58 (s, 3 H), 1.46-1.54 (m, 7 H), 1.41 (d, J=6.87 Hz, 6 H), 1.29-1.38 (m, 3 H), 1.26 (s, 4 H), 1.06-1.21 (m, 3 H), 0.91-1.01 (m, 2 H), 0.89 (t, J=6.87 Hz, 1 H). LC-MS: purity 99% (UV), $t_R$ 5.04 min, m/z $[M+H]^+$ 841.30.

Example 20-34

Synthesis of Compound 360

360

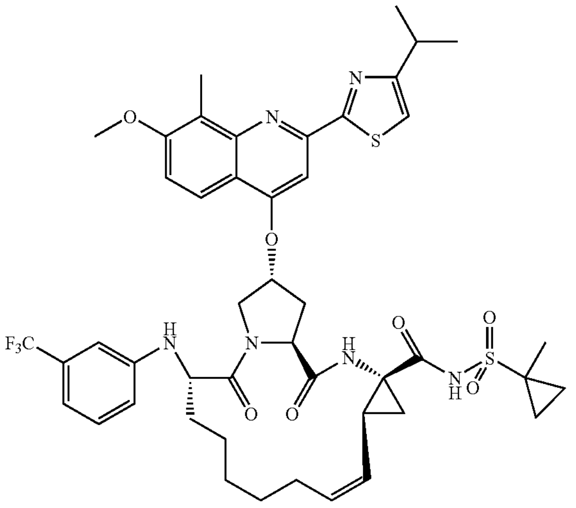

General Procedure TTLS

Compound 49 as a solution in toluene (3.08 g, 3.24 mmol, 1.0 eq.) and toluene (162 mL, previously degassed by bubbling nitrogen through the solvent for 30 min) were charged in a 500 mL round bottom flask previously flushed with nitrogen gas and the reaction mixture heated to 65° C. to give a clear yellow solution (it is important to keep the reaction mixture under a protective nitrogen atmosphere). Zhan catalyst (10.7 mg, 0.5 mol %) was added and the reaction mixture heated at 65° C. for a further 20 min with constant nitrogen gas bubbling through the reaction mixture (via needle). During this time the reaction mixture color turned from pale yellow to pale orange (56% conversion by LCMS-UV). Another catalyst aliquot (10.7 mg, 0.5 mol %) was added and the reaction mixture stirred for a further 20 min. As LCMS analysis showed some residual starting material (97% conversion by LCMS-UV) a third catalyst aliquot was added (10.7 mg, 0.5 mol %) and the reaction mixture was stirred for a further 20 min. LCMS-UV analysis showed full consumption of the starting material. The solvent was removed under vacuum. The residue was purified by flash column chromatography, using a methanol:dichloromethane gradient (from neat dichloromethane to 0.65% methanol in dichloromethane). After combining the relevant fractions and solvent removal, 1.44 mg (48%) of compound 360 was isolated as a beige solid. $^1$H NMR (500 MHz, $CDCl_3$) δ ppm 10.08 (s, 1 H) 7.73 (d, J=9.16 Hz, 1 H) 7.54 (s, 1 H) 7.11 (d, J=9.31 Hz, 1 H) 7.01-7.07 (m, 2 H) 6.76-6.87 (m, 3 H) 6.53 (d, J=7.48 Hz, 1 H) 5.72 (q, 1 H) 5.58 (br. s, 1 H) 5.00 (t, J=9.61 Hz, 1 H) 4.67 (t, J=7.78 Hz, 1 H) 4.54 (d, J=9.16 Hz, 1 H) 4.25-4.29 (m, 1 H) 4.13-4.25 (m, 2 H) 3.96 (s, 3 H) 3.22 (spt, J=6.87 Hz, 1 H) 2.71-2.77 (m, 2 H) 2.70 (s, 3 H) 2.42-2.53 (m, 1 H) 2.24 (q, J=8.70 Hz, 1 H) 1.93-2.04 (m, 1 H) 1.83-1.92 (m, 2 H) 1.73-1.83 (m, 2 H) 1.50 (s, 3 H) 1.43-1.54 (m, 6 H) 1.41 (d, J=6.87 Hz, 6 H) 1.31 (dd, J=13.12, 6.71 Hz, 2 H) 0.78-0.87 (m, 2 H). LC-MS: purity 100% (UV), $t_R$ 5.38 min, m/z $[M+H]^+$ 923.28.

Example 20-35

361

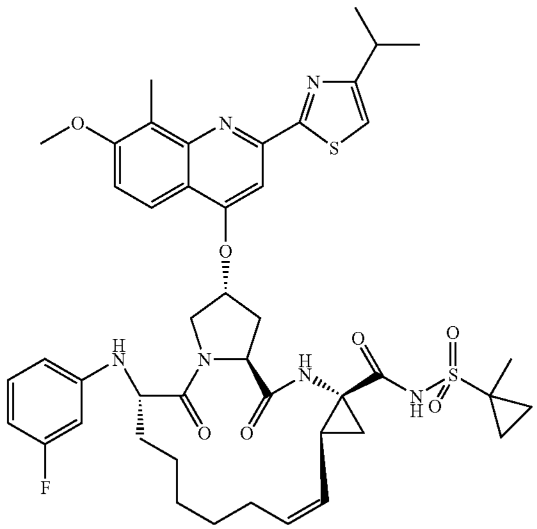

Compound 361 was prepared in a manner analogous to General Procedure TT, to afford 136 mg (44%), beige solid. $^1$H NMR (500 MHz, $CDCl_3$) δ ppm 10.18 (br. s, 1 H), 7.70 (d, J=9.00 Hz, 1 H), 7.50 (s, 1 H), 7.45 (s, 1 H), 7.01-7.08 (m, 2 H), 6.79-6.89 (m, 1 H), 6.33 (td, J=1.83, 8.32 Hz, 1 H), 6.23 (dd, J=1.45, 8.16 Hz, 1 H), 6.17 (d, J=11.14 Hz, 1 H), 5.64-5.78 (m, 1 H), 5.52 (br. s, 1 H), 4.99 (t, J=9.61 Hz, 1 H), 4.55 (t, J=7.78 Hz, 1 H), 4.39 (d, J=8.70 Hz, 1 H), 4.07-4.22 (m, 3 H), 3.88 (s, 3 H), 3.23 (spt, J=6.82 Hz, 1 H), 2.66 (s, 3 H), 2.54-2.64 (m, 2 H), 2.41-2.52 (m, 1 H), 2.17 (q, J=8.75 Hz, 1 H), 1.91-2.03 (m, 1 H), 1.85 (dd, J=6.10, 7.63 Hz, 3 H), 1.79 (dd, J=6.79, 10.76 Hz, 2 H), 1.50-1.55 (m, 2 H), 1.50 (s, 3 H), 1.42-1.47 (m, 2 H), 1.41 (d, J=7.02 Hz, 6 H), 1.37-1.40 (m, 1

H), 1.25-1.37 (m, 2 H), 0.82 (br. s, 2 H). LC-MS: purity 100% (UV), $t_R$ 5.19 min, m/z $[M+H]^+$ 873.71.

Example 20-36

362

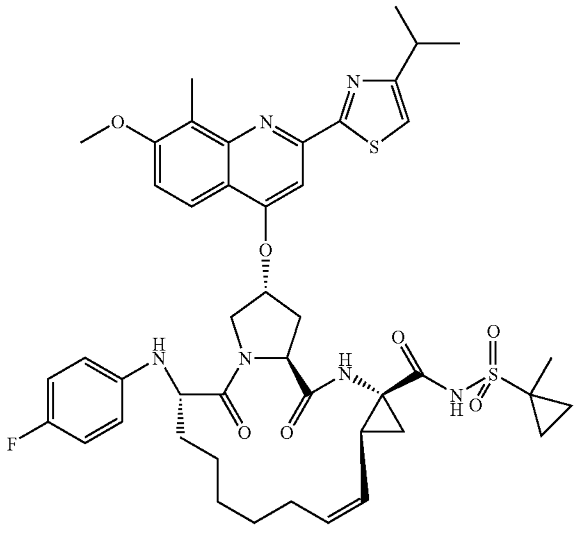

Compound 362 was prepared in a manner analogous to General Procedure TT, to afford 413 mg (59%), pale brown glassy solid. [1] H NMR (500 MHz, $CDCl_3$) δ ppm 10.15 (s, 1 H), 7.65 (d, J=9.00 Hz, 1 H), 7.52 (s, 1 H), 7.28 (s, 1 H), 7.09 (d, J=9.16 Hz, 1 H), 7.06 (s, 1 H), 6.54 (t, J=8.62 Hz, 2 H), 6.38 (dd, J=8.85, 4.27 Hz, 2 H), 5.68-5.78 (m, 1 H), 5.55 (br. s, 1 H), 5.30 (s, 1 H), 5.02 (t, J=9.54 Hz, 1 H), 4.57 (t, J=7.93 Hz, 1 H), 4.23 (d, J=11.60 Hz, 1 H), 4.02-4.18 (m, 3 H), 3.92 (s, 3 H), 3.23 (spt, J=6.87 Hz, 1 H), 2.70-2.73 (m, 1 H), 2.68 (s, 3 H), 2.57-2.64 (m, 1 H), 2.51-2.58 (m, 1 H), 2.17 (q, J=8.70 Hz, 1 H), 1.97-2.09 (m, 1 H), 1.93 (br. s, 1 H), 1.87-1.91 (m, 1 H), 1.73-1.82 (m, 5 H), 1.51-1.56 (m, 2 H), 1.50 (s, 3 H), 1.41 (d, J=6.87 Hz, 6 H), 1.27-1.36 (m, 2 H), 0.78-0.86 (m, 2 H). LC-MS: purity 98% (UV), $t_R$ 5.12 min, m/z $[M+H]^+$ 873.29.

Example 20-37

409

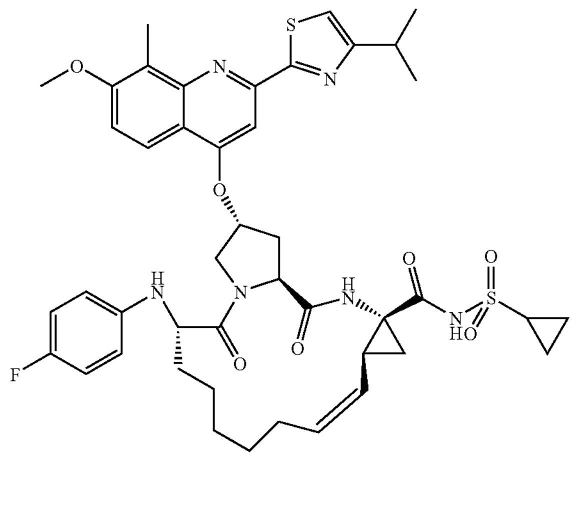

Compound 409 was prepared in a manner analogous to General Procedure TT, to afford 320 mg (58%), white solid. [1] H NMR (500 MHz, $CDCl_3$) δ ppm 10.24 (s, 1 H), 7.67 (d, J=9.16 Hz, 1 H), 7.52 (s, 1 H), 7.13 (s, 1 H), 7.06 (d, J=0.76 Hz, 1 H), 6.49-6.56 (m, 2 H), 6.40 (dd, J=8.85, 4.27 Hz, 2 H), 5.70-5.79 (m, 1 H), 5.59 (dd, J=6.03, 1.91 Hz, 1 H), 5.56 (br. s, 1 H), 4.96-5.03 (m, 1 H), 4.61 (t, J=7.86 Hz, 1 H), 4.35 (t, J=7.02 Hz, 1 H), 4.25 (d, J=11.60 Hz, 1 H), 4.12-4.16 (m, 1 H), 4.10 (dd, J=11.60, 3.36 Hz, 1 H), 3.96-4.02 (m, 1 H), 3.95 (s, 3 H), 3.90-3.94 (m, 1 H), 3.17-3.28 (m, 1 H), 2.91 (s, 1 H), 2.70-2.75 (m, 1 H), 2.70 (s, 3 H), 2.61-2.68 (m, 1 H), 2.52-2.60 (m, 1 H), 2.47-2.52 (m, 1 H), 2.22-2.30 (m, 1 H), 2.00-2.10 (m, 1 H), 1.92 (dd, J=7.93, 6.10 Hz, 2 H), 1.50-1.55 (m, 3 H), 1.45-1.48 (m, 1 H), 1.38-1.43 (m, 7 H), 1.30-1.34 (m, 2 H), 1.12-1.19 (m, 1 H), 1.05-1.12 (m, 1 H). LC-MS: purity 95% (UV), $t_R$ 2.51 min, m/z $[M+H]^+$ 859.40.

Example 20-38

363

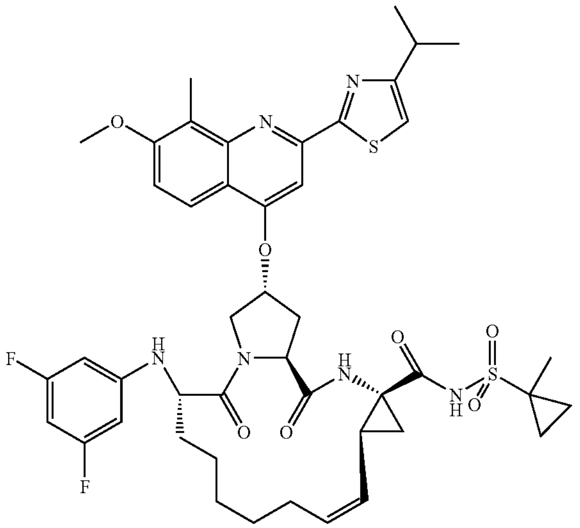

Compound 363 was prepared in a manner analogous to General Procedure TT, to afford 100 mg (40%), beige solid. [1] H NMR (500 MHz, $CDCl_3$) δ ppm 10.09 (s, 1 H), 7.79 (d, J=9.16 Hz, 1 H), 7.51 (s, 1 H), 7.14 (d, J=9.16 Hz, 1 H), 7.06 (br. s, 1 H), 7.04 (s, 1 H), 6.07-6.13 (m, 1 H), 6.04 (d, J=7.63 Hz, 2 H), 5.64-5.75 (m, 1 H), 5.55 (br. s, 1 H) 4.97 (t, J=9.61 Hz, 1 H), 4.60-4.69 (m, 2 H), 4.12-4.22 (m, 3 H), 3.95 (s, 3 H), 3.22 (spt, J=6.87 Hz, 1 H), 2.69-2.78 (m, 2 H), 2.68 (s, 3 H), 2.35-2.48 (m, 1 H), 2.23 (q, J=8.90 Hz, 1 H), 1.95-2.07 (m, 1 H), 1.81-1.88 (m, 2 H), 1.71-1.81 (m, 2 H), 1.50-1.56 (m, 1 H), 1.48 (s, 3 H), 1.44 (dd, J=9.38, 6.03 Hz, 4 H), 1.40 (d, J=6.87 Hz, 6 H), 1.23-1.36 (m, 3 H), 0.76-0.85 (m, 2 H). LC-MS: purity 100% (UV), $t_R$ 5.28 min, m/z $[M+H]^+$ 891.60.

Example 20-39

378

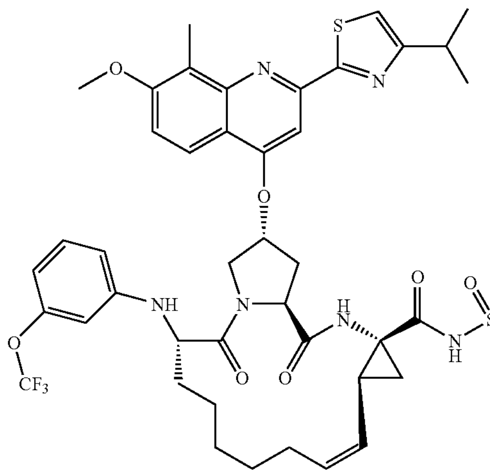

Compound 378 was prepared in a manner analogous to General Procedure TT, to afford 103 mg (40%), beige solid. $^1$H NMR (500 MHz, $CDCl_3$) δ 10.09 (s, 1 H), 7.76 (d, J=9.16 Hz, 1 H), 7.52 (s, 1 H), 7.12 (d, J=9.16 Hz, 1 H), 7.05 (s, 2 H), 6.76 (t, J=8.16 Hz, 1 H), 6.43 (d, J=8.39 Hz, 1 H), 6.40 (s, 1 H), 6.31 (dd, J=1.83, 8.24 Hz, 1 H), 5.67-5.76 (m, 1 H), 5.57 (d, J=2.90 Hz, 1 H), 4.99 (t, J=9.61 Hz, 1 H), 4.66 (t, J=7.86 Hz, 1 H), 4.48 (d, J=8.85 Hz, 1 H), 4.13-4.26 (m, 3 H), 3.95 (s, 3 H), 3.22 (spt, 1 H), 2.71-2.74 (m, 1 H), 2.70 (s, 3 H), 2.66-2.69 (m, 1 H), 2.41-2.53 (m, 1 H), 2.23 (q, J=8.75 Hz, 1 H), 1.93-2.04 (m, 1 H), 1.88 (dd, J=6.26, 7.93 Hz, 1 H), 1.70-1.87 (m, 4 H), 1.51-1.56 (m, 1 H), 1.49 (s, 3 H), 1.46 (dd, J=5.65, 9.46 Hz, 3 H), 1.41 (d, J=7.02 Hz, 6 H), 1.23-1.36 (m, 3 H), 0.77-0.86 (m, 2 H). LC-MS: purity 100% (UV), $t_R$ 5.39 min, m/z $[M+H]^+$ 939.33.

Example 20-40

379

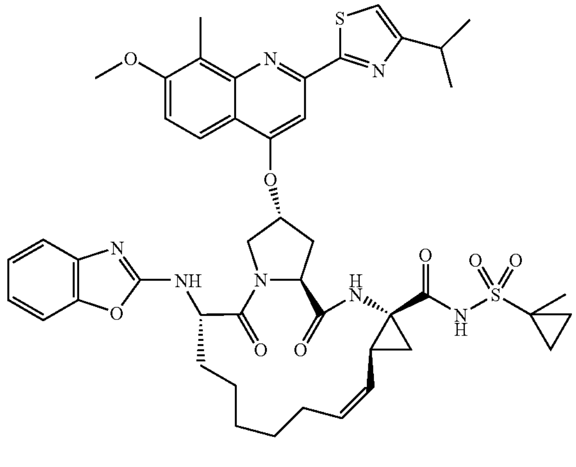

Compound 379 was prepared in a manner analogous to General Procedure TT, to afford 670 mg (72%), beige glassy solid. $^1$H NMR (500 MHz, $CDCl_3$) δ ppm 10.38 (br. s, 1 H), 7.58 (d, J=9.00 Hz, 1 H), 7.54 (s, 1 H), 7.08 (d, J=7.93 Hz, 1 H), 7.06 (d, J=0.46 Hz, 1 H), 7.04 (d, J=7.48 Hz, 1 H), 6.98-7.02 (m, 1 H), 6.91-6.97 (m, 1 H), 6.69 (d, J=9.16 Hz, 1 H), 5.69-5.79 (m, 1 H), 5.59 (br. s, 1 H), 4.99-5.05 (m, 1 H), 4.88-4.99 (m, 1 H), 4.75 (td, J=8.93, 2.90 Hz, 1 H), 4.45-4.64 (m, 1 H), 4.26 (dd, J=11.37, 3.43 Hz, 1 H), 3.72-3.79 (m, 5 H), 3.24 (spt, 1 H), 2.71-2.85 (m, 2 H), 2.62 (s, 3 H), 2.53-2.61 (m, 1 H), 2.34 (q, J=8.75 Hz, 1 H), 2.04-2.14 (m, 1 H), 1.92-2.01 (m, 1 H), 1.86 (dt, J=6.75, 3.26 Hz, 3 H), 1.77-1.83 (m, 2 H), 1.75 (br. s, 1 H), 1.55-1.64 (m, 1 H), 1.52 (s, 3 H), 1.46 (dd, J=9.54, 5.87 Hz, 2 H), 1.42 (d, J=6.87 Hz, 6 H), 1.31-1.39 (m, 2 H), 0.83 (dd, J=3.74, 2.52 Hz, 2 H). LC-MS: purity 100% (UV), $t_R$ 5.09 min, m/z $[M+H]^+$ 896.31.

Example 20-41

380

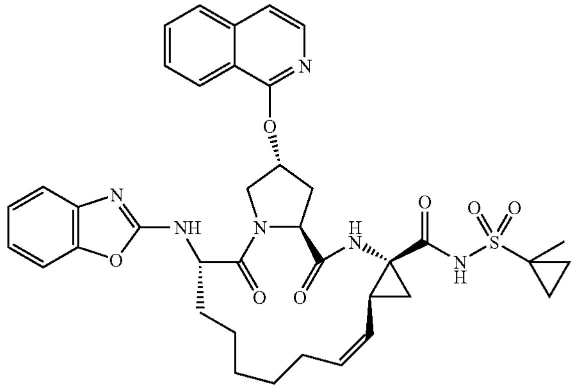

Compound 380 was prepared in a manner analogous to General Procedure OO, to afford 30.8 mg (16%), beige solid. $^1$H NMR (500 MHz, $CDCl_3$) δ 10.36 (br. s, 1 H), 8.00 (d, J=6.10 Hz, 1 H), 7.93 (d, J=8.54 Hz, 1 H), 7.69 (d, J=7.93 Hz, 1 H), 7.56 (t, J=7.32 Hz, 1 H), 7.20-7.29 (m, 2 H), 6.98-7.12 (m, 3 H), 6.90-6.97 (m, 1 H), 6.00 (br. s, 1 H), 5.67-5.77 (m, 1 H), 5.01 (t, J=9.61 Hz, 1 H), 4.90-4.98 (m, 1 H), 4.68-4.78 (m, 1 H), 4.39-4.51 (m, 1 H), 4.26 (dd, J=4.42, 11.44 Hz, 1 H), 2.71-2.81 (m, 1 H), 2.63-2.71 (m, 1 H), 2.47-2.62 (m, 1 H), 2.36 (q, J=8.75 Hz, 1 H), 1.93-2.14 (m, 2 H), 1.76-1.89 (m, 3 H), 1.71 (br. s, 2 H), 1.41-1.62 (m, 9 H), 1.28-1.41 (m, 3 H), 0.77-0.94 (m, 1 H). LC-MS: purity 100% (UV), $t_R$ 2.05 min, m/z $[M+H]^+$ 727.25.

Example 20-42

381

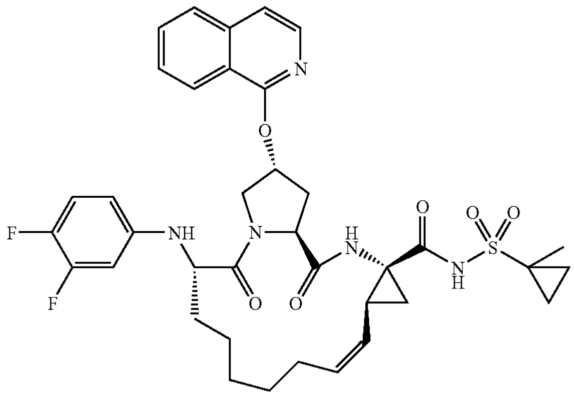

Compound 381 was prepared in a manner analogous to General Procedure OO, to afford 103 mg (48%), white solid. [1] H NMR (500 MHz, $CDCl_3$) δ ppm 10.05 (s, 1 H), 8.00-8.01 (m, 1 H), 7.99 (s, 1 H), 7.79 (d, J=8.09 Hz, 1 H), 7.70 (t, J=7.48 Hz, 1 H), 7.52 (t, J=7.63 Hz, 1 H), 7.30 (d, J=5.80 Hz, 1 H), 6.79 (s, 1 H), 6.28-6.37 (m, 2 H), 6.01 (d, J=9.31 Hz, 1 H), 5.96 (br. s, 1 H), 5.75 (q, 1 H), 5.03 (t, J=9.61 Hz, 1 H), 4.68 (t, J=8.01 Hz, 1 H), 4.26 (d, J=11.60 Hz, 1 H), 4.14-4.19 (m, 1 H), 4.11 (dd, J=11.52, 3.74 Hz, 2H), 2.70-2.77 (m, 1 H), 2.63-2.70 (m, 1 H), 2.48-2.57 (m, 1 H), 2.21-2.28 (m, 1 H), 1.92-2.01 (m, 2 H), 1.76-1.84 (m, 3 H), 1.52-1.56 (m, 2 H), 1.51 (s, 3 H), 1.47-1.50 (m, 3 H), 1.32 (d, J=7.32 Hz, 2 H), 1.26 (s, 1 H), 0.83-0.85 (m, 2 H). LC-MS: purity 98% (UV), $t_R$ 5.31 min, m/z $[M+H]^+$ 722.0.

Example 20-43

444

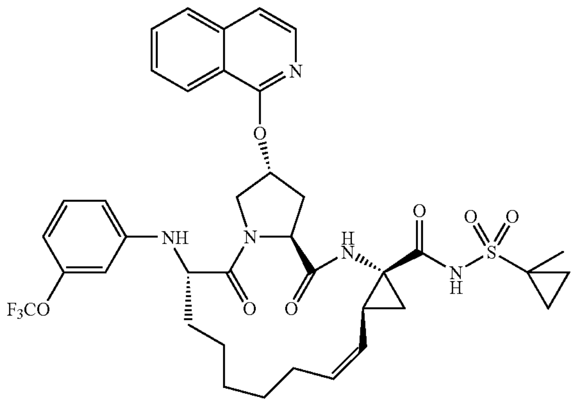

Compound 444 was prepared in a manner analogous to General Procedure OO, to afford 216 mg (44%), beige solid. [1] H NMR (500 MHz, $CDCl_3$) δ ppm 10.18 (br. s, 1H), 8.05 (d, J=7.93 Hz, 1 H), 8.00 (d, J=4.43 Hz, 1 H), 7.78 (d, J=8.09 Hz, 1 H), 7.71 (t, 1 H), 7.52 (t, J=7.32 Hz, 1 H), 7.32 (d, J=3.81 Hz, 1 H), 6.68 (t, J=8.01 Hz, 1 H), 6.40 (s, 1 H), 6.30-6.36 (m, 2 H), 6.03 (br. s, 1 H), 5.71 (q, J=8.75 Hz, 1 H), 5.00 (t, J=9.61 Hz, 1 H), 4.71 (t, J=7.17 Hz, 1 H), 4.21 (br. s, 3 H), 2.65-2.70 (m, 2 H), 2.42-2.52 (m, 1 H), 2.26 (q, J=8.80 Hz, 1 H), 1.95-2.04 (m, 1 H), 1.81-1.91 (m, 3 H), 1.78 (d, J=10.68 Hz, 1 H), 1.52-1.56 (m, 1 H), 1.38-1.57 (m, 10 H), 1.28-1.35 (m, 3 H), 0.77-0.93 (m, 1 H). LC-MS: purity 99% (UV), $t_R$ 5.55 min, m/z $[M+H]^+$ 770.3.

Example 20-44

382

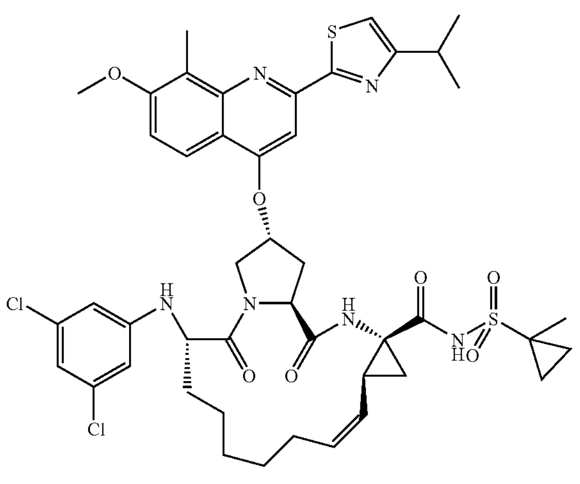

Compound 382 was prepared in a manner analogous to General Procedure TT, to afford 34 mg (40%), off white solid. [1] H NMR (500 MHz, $CDCl_3$) δ ppm 10.01 (br. s, 1 H), 7.77 (d, J=9.16 Hz, 1 H), 7.53 (s, 1 H), 7.16 (d, J=9.16 Hz, 1 H), 7.05 (s, 1 H), 6.74 (d, J=5.49 Hz, 1 H), 6.61 (s, 1 H), 6.41 (d, J=1.53 Hz, 2 H), 5.75 (q, 1 H), 5.60 (br. s, 1 H), 5.01 (t, J=9.69 Hz, 1 H), 4.67 (t, J=7.86 Hz, 1 H), 4.54 (d, J=9.00 Hz, 1 H), 4.21 (td, J=8.54, 3.20 Hz, 1 H), 4.18 (br. s, 2 H), 3.97 (s, 3 H), 3.22 (quin, J=6.75 Hz, 1 H), 2.75 (dd, J=7.78, 2.14 Hz, 2 H), 2.70 (s, 3 H), 2.40-2.49 (m, 1 H), 2.26 (q, J=8.95 Hz, 1 H), 1.98-2.07 (m, 1 H), 1.93 (t, J=6.94 Hz, 1 H), 1.83-1.91 (m, 1 H), 1.80 (d, J=10.99 Hz, 2 H), 1.54 (br. s, 1 H), 1.51 (s, 4 H), 1.48 (dd, J=9.69, 6.03 Hz, 2 H), 1.44 (d, J=6.41 Hz, 2 H), 1.41 (d, J=6.87 Hz, 6 H), 1.28-1.37 (m, 2 H), 0.84 (t, J=2.82 Hz, 2 H). LC-MS: purity 100% (UV), $t_R$ 5.60 min, m/z $[M+H]^+$ 923.31.

Example 20-45

374

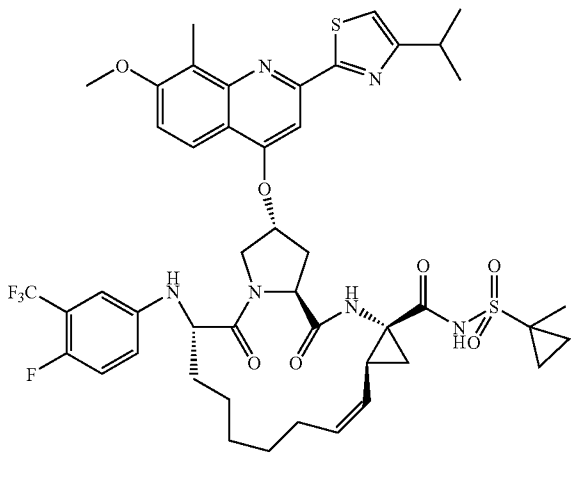

Compound 374 was prepared in a manner analogous to General Procedure TT, to afford 276 mg (33%), pale yellow solid. [1] H NMR (500 MHz, $CDCl_3$) δ ppm 10.03 (br. s, 1 H), 7.69 (d, J=9.16 Hz, 1 H), 7.53 (s, 1 H), 7.15 (d, J=9.16 Hz, 1 H), 7.06 (s, 1 H), 6.81-6.85 (m, 1 H), 6.76 (dd, J=5.49, 2.59 Hz, 1 H), 6.35-6.43 (m, 2 H), 5.74 (q, 1 H), 5.59 (br. s, 1 H), 5.02 (t, J=9.54 Hz, 1 H), 4.67 (t, J=7.93 Hz, 1 H), 4.35 (d, J=9.77 Hz, 1 H), 4.23 (d, 1 H), 4.12-4.20 (m, 2 H), 3.98 (s, 3 H), 3.22 (spt, J=6.84 Hz, 1 H), 2.73-2.81 (m, 2 H) 2.71 (s, 3 H), 2.50 (br. s, 1 H), 2.21 (quin, 1 H), 1.90-2.02 (m, 2 H), 1.77-1.84 (m, 3 H), 1.63 (s, 2 H), 1.52-1.56 (m, 1 H), 1.50 (s, 3 H), 1.44-1.49 (m, 3 H), 1.41 (d, J=6.87 Hz, 6 H), 1.26-1.36 (m, 2 H), 0.80-0.87 (m, 2 H). LC-MS: purity 100% (UV), $t_R$ 5.38 min, m/z $[M+H]^+$ 941.30.

Example 20-46

445

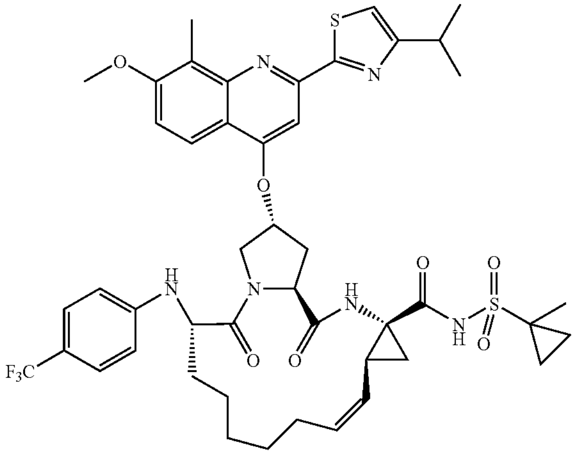

Compound 445 was prepared in a manner analogous to General Procedure TT, to afford 253 mg (57%), cream solid. [1] H NMR (500 MHz, $CDCl_3$) δ ppm 10.12 (s, 1 H), 7.77 (d, J=9.16 Hz, 1 H), 7.55 (s, 1 H), 7.22 (s, 1 H), 7.09 (d, J=9.16 Hz, 1 H), 7.06 (s, 1 H), 7.03 (d, J=8.24 Hz, 2 H), 6.36 (d, J=8.54 Hz, 2 H), 5.71-5.80 (m, 1 H), 5.56-5.62 (m, 1 H), 5.03 (t, J=9.61 Hz, 1 H), 4.63 (t, J=7.93 Hz, 1 H), 4.51 (d, J=7.93 Hz, 1 H), 4.34 (d, J=11.90 Hz, 1 H), 4.16-4.24 (m, 1 H), 4.12 (dd, J=11.60, 3.05 Hz, 1 H), 3.90 (s, 3 H), 3.23 (spt, J=7.02 Hz, 1 H), 2.69-2.77 (m, 1 H), 2.68 (s, 3 H), 2.60-2.67 (m, 1 H), 2.48-2.59 (m, 1 H), 2.15 (q, J=8.75 Hz, 1 H), 1.93-2.02 (m, 1 H), 1.90 (dd, J=7.93, 6.10 Hz, 1 H), 1.76-1.87 (m, 3 H), 1.51 (s, 3 H), 1.44-1.60 (m, 6 H), 1.41 (d, J=7.02 Hz, 6 H), 1.21-1.38 (m, 2 H), 0.74-0.87 (m, 2 H). LC-MS: purity 100% (UV), $t_R$ 5.34 min, m/z $[M+H]^+$ 923.30.

Example 20-47

369

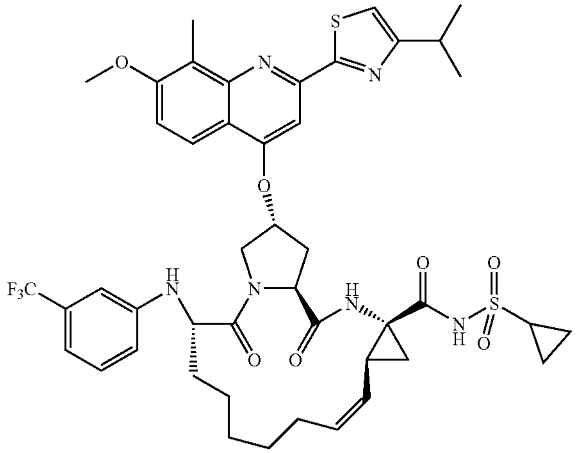

Compound 369 was prepared in a manner analogous to General Procedure TT, to afford 297 mg (84%), off-white glassy solid. [1] H NMR (500 MHz, $CDCl_3$) δ ppm 10.16 (s, 1 H), 7.73 (d, J=9.00 Hz, 1 H), 7.54 (s, 1 H), 7.12 (d, J=9.31 Hz, 1 H), 7.06 (s, 1 H), 6.82 (s, 1 H), 6.77-6.82 (m, 3 H), 6.48-6.56 (m, 1 H), 5.74 (q, 1 H), 5.59 (br. s, 1 H), 5.00 (t, J=9.54 Hz, 1 H), 4.66 (t, J=7.78 Hz, 1 H), 4.50 (br. s, 1 H), 4.20-4.29 (m, 2 H), 4.10-4.20 (m, 1 H), 3.96 (s, 3 H), 3.22 (spt, 1 H), 2.87-2.96 (m, 1 H), 2.72-2.78 (m, 1 H), 2.71 (s, 3 H), 2.44-2.56 (m, 1 H), 2.20-2.29 (m, 1 H), 1.96-2.05 (m, 1 H), 1.93 (t, 1 H), 1.74-1.91 (m, 2 H), 1.43-1.57 (m, 6 H), 1.41 (d, J=6.87 Hz, 6 H), 1.28-1.37 (m, 2 H), 1.06-1.20 (m, 2 H), 0.92-0.99 (m, 1 H), 0.80-0.92 (m, 1 H). LC-MS: purity 100% (UV), $t_R$ 5.37 min, m/z $[M+H]^+$ 909.24.

Example 20-48

439

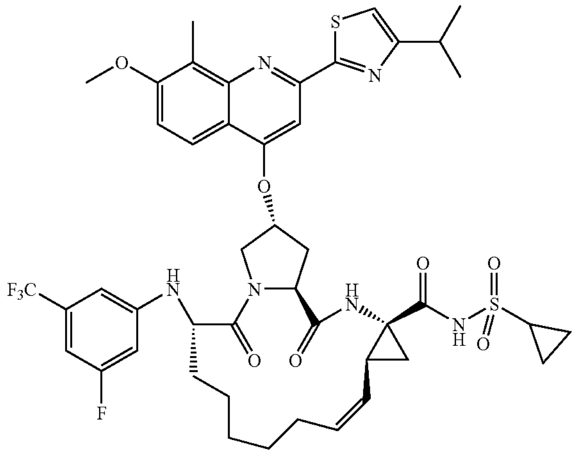

Compound 439 was prepared in a manner analogous to General Procedure TT, to afford 151 mg (47%), off-white glassy solid. [1] H NMR (500 MHz, $CDCl_3$) δ ppm 10.12 (br. s, 1 H), 7.78 (d, J=9.16 Hz, 1 H), 7.54 (s, 1 H), 7.15 (d, J=9.31 Hz, 1 H), 7.05 (s, 1 H), 6.81 (s, 1 H), 6.56-6.63 (m, 2 H), 6.35 (d, J=10.68 Hz, 1 H), 5.70-5.79 (m, 1 H), 5.60 (br. s, 1 H), 4.98 (t, J=9.54 Hz, 1 H), 4.76 (d, J=8.54 Hz, 1 H), 4.67 (t, J=7.71 Hz, 1 H), 4.26 (td, J=8.43, 2.37 Hz, 1 H), 4.19 (s, 1 H), 3.96 (s, 2 H), 3.22 (spt, J=6.87 Hz, 1 H), 2.87-2.95 (m, 1 H), 2.74 (dd, J=7.55, 2.37 Hz, 1 H), 2.69 (s, 3 H), 2.38-2.49 (m, 1 H), 2.25 (q, J=8.85 Hz, 1 H), 2.03 (dd, J=15.03, 6.18 Hz, 1 H), 1.84-1.96 (m, 2 H), 1.80 (br. s, 1 H), 1.52-1.59 (m, 1 H), 1.23-1.52 (m, 16 H), 1.06-1.21 (m, 2 H), 0.91-1.00 (m, 1 H). LC-MS: purity 100% (UV), $t_R$ 5.37 min, m/z $[M+H]^+$ 927.23.

Example 20-48A

439

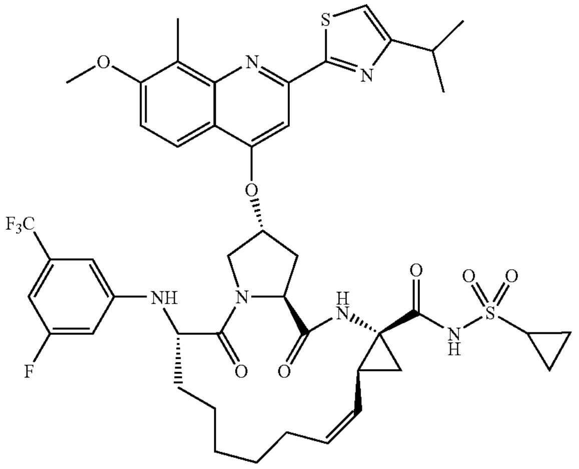

Compound 439 was also prepared in a manner analogous to General Procedure D, to afford 112 mg, 21%. MS (ESI) m/z $(M+H)^+$ 927.6.

Example 20-49

446

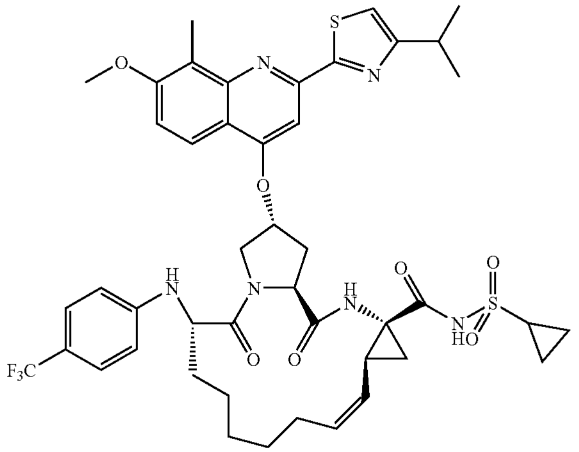

Compound 446 was prepared in a manner analogous to General Procedure TT, to afford 148 mg (67%), beige solid. [1] H NMR (500 MHz, $CDCl_3$) δ ppm 10.24 (s, 1 H), 7.77 (d, J=9.16 Hz, 1 H), 7.54 (s, 1 H), 7.15 (br. s, 1 H), 7.09 (d, J=9.16 Hz, 1 H), 7.06 (s, 1 H), 7.04 (d, J=8.24 Hz, 2 H), 6.36 (d, J=8.54 Hz, 2 H), 5.69-5.82 (m, 1 H), 5.59 (br. s, 1 H) 5.00 (t, J=9.46 Hz, 1 H), 4.61 (t, J=7.93 Hz, 1 H), 4.50 (d, J=8.54 Hz, 1 H), 4.33 (d, J=11.90 Hz, 1 H), 4.15-4.22 (m, 1 H), 4.10 (dd, J=11.60, 3.05 Hz, 1 H), 3.89 (s, 3 H), 3.16-3.28 (m, 1 H), 2.86-2.95 (m, 1 H), 2.69-2.75 (m, 1 H), 2.68 (s, 3 H), 2.59-2.67 (m, 1 H), 2.49-2.60 (m, 1 H), 2.14 (q, J=8.65 Hz, 1 H), 1.93-2.01 (m, 1 H), 1.89-1.93 (m, 1 H), 1.75-1.88 (m, 2 H), 1.44-1.60 (m, 6 H), 1.41 (d, J=6.71 Hz, 6 H), 1.24-1.38 (m, 2 H), 1.12-1.19 (m, 1 H), 1.05-1.12 (m, 1 H), 0.88-0.99 (m, 1 H). LC-MS: purity 100% (UV), $t_R$ 5.21 min, m/z $[M+H]^+$ 909.25.

Example 20-50

377

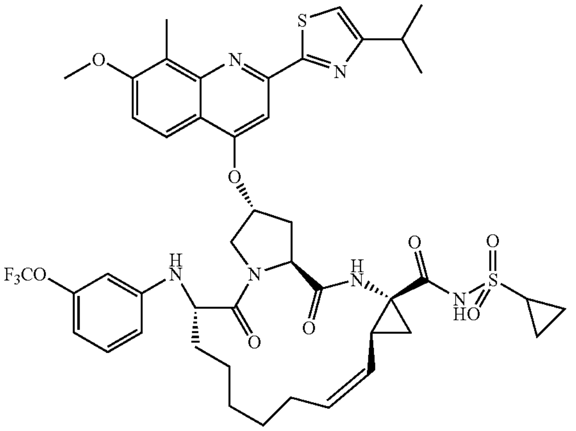

Compound 377 was prepared in a manner analogous to General Procedure TT, to afford 137 mg (58%), beige solid. [1] H NMR (500 MHz, $CDCl_3$) δ ppm 10.15 (br. s, 1 H), 7.76 (d, J=9.16 Hz, 1 H), 7.53 (s, 1 H), 7.14 (d, J=9.16 Hz, 1 H), 7.05 (s, 1 H), 6.80 (s, 1 H), 6.75 (t, J=8.09 Hz, 1 H), 6.43 (d, J=8.24 Hz, 1 H), 6.40 (s, 1 H), 6.30 (dd, J=8.24, 1.83 Hz, 1 H), 5.70-5.79 (m, 1 H), 5.59 (br. s, 1 H), 5.00 (t, J=9.46 Hz, 1 H), 4.66 (t, J=7.63 Hz, 1 H), 4.43 (d, J=8.85 Hz, 1 H), 4.18-4.26 (m, 2 H), 4.12-4.18 (m, 1 H), 3.96 (s, 3 H), 3.16-3.27 (m, 1 H), 2.88-2.95 (m, 1 H), 2.72-2.78 (m, 1 H), 2.70 (s, 3 H), 2.45-2.56 (m, 1 H), 2.24 (q, J=8.54 Hz, 1 H), 1.96-2.03 (m, 1 H), 1.94 (dd, J=7.93, 6.10 Hz, 1 H), 1.75-1.89 (m, 2 H), 1.43-1.57 (m, 6 H), 1.41 (d, J=7.02 Hz, 6 H), 1.24-1.37 (m, 3 H), 1.04-1.21 (m, 2 H), 0.90-1.00 (m, 1 H). LC-MS: purity 100% (UV), $t_R$ 5.31 min, m/z $[M+H]^+$ 925.32.

Example 20-51

447

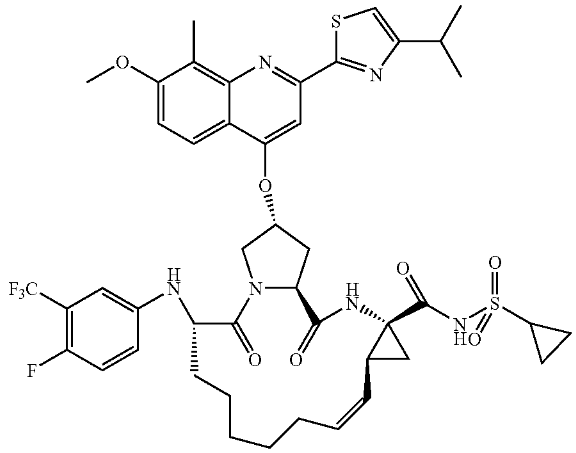

Compound 447 was prepared in a manner analogous to General Procedure TT, to afford 145 mg (52%), beige solid. $^1H$ NMR (500 MHz, $CDCl_3$) δ ppm 10.22 (s, 1 H), 7.68 (d, J=9.00 Hz, 1 H), 7.51 (s, 1 H), 7.13 (d, J=9.31 Hz, 1 H), 7.08 (s, 1 H), 7.05 (s, 1 H), 6.77 (d, J=4.12 Hz, 1 H), 6.36-6.42 (m, 2 H), 5.69 (q, J=8.75 Hz, 1 H), 5.55 (br. s, 1 H), 4.95 (t, J=9.46 Hz, 1 H), 4.66 (t, J=7.86 Hz, 1 H), 4.41-4.46 (m, 1 H), 4.21 (d, 1 H), 4.10-4.17 (m, 2 H), 3.96 (s, 3 H), 3.22 (spt, 1 H), 2.85-2.91 (m, 1 H), 2.71-2.76 (m, 1 H), 2.70 (s, 3 H), 2.44-2.53 (m, 1 H), 2.20 (q, J=8.65 Hz, 1 H), 1.90-1.99 (m, 1 H), 1.85 (t, 1 H), 1.74-1.82 (m, 3 H), 1.42-1.53 (m, 6 H), 1.40 (d, J=6.87 Hz, 6 H), 1.25-1.32 (m, 2 H), 1.09-1.15 (m, 1 H), 1.03-1.08 (m, 1 H), 0.88-0.95 (m, 1 H). LC-MS: purity 100% (UV), $t_R$ 5.29 min, m/z $[M+H]^+$ 927.25.

Example 20-52

75

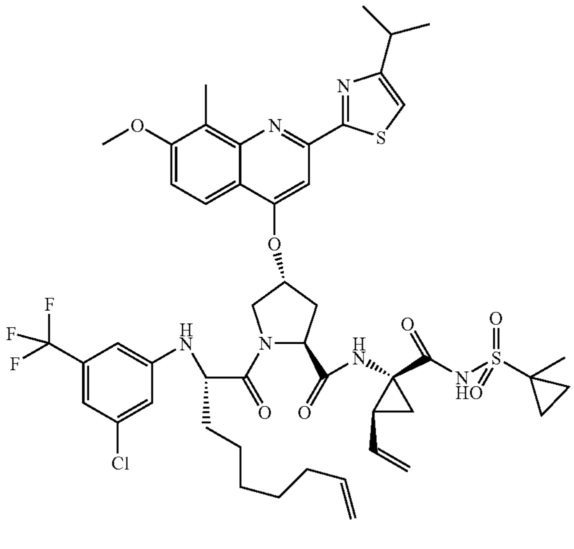

Compound 75 was prepared in a manner analogous to General Procedure SS to afford 370 mg (52%). $^1H$ NMR (500 MHz, $CDCl_3$) δ ppm 10.14 (s, 1 H) 7.82 (d, J=9.00 Hz, 1 H) 7.57 (br. s., 1 H) 7.15-7.22 (m, 2 H) 7.06 (s, 1 H) 6.93 (s, 1 H) 6.79-6.86 (m, 1 H) 6.70 (d, J=15.87 Hz, 2 H) 5.73-5.85 (m, 2 H) 5.63 (br. s., 1 H) 5.22 (d, J=17.24 Hz, 1 H) 5.06-5.15 (m, 2 H) 4.91-5.03 (m, 2 H) 4.45 (t, J=8.24 Hz, 1 H) 4.15-4.23 (m, 2 H) 4.09-4.16 (m, 1 H) 3.99 (s, 3 H) 3.21 (spt, J=7.02 Hz, 1 H) 2.68-2.73 (m, 3 H) 2.60-2.68 (m, 2 H) 1.97-2.04 (m, 2 H) 1.77-1.89 (m, 2 H) 1.66-1.77 (m, 2 H) 1.53 (br. s., 2 H) 1.51 (s, 3 H) 1.44 (dd, J=9.00, 5.19 Hz, 2 H) 1.40 (d, J=6.87 Hz, 6 H) 1.31-1.38 (m, 2 H) 1.26 (s, 2 H) 0.90-0.96 (m, 1 H) 0.83-0.90 (m, 1 H). LC-MS: purity 96% (UV), $t_R$ 5.73 min, m/z $[M+H]^+$ 965.00.

Example 20-53

76

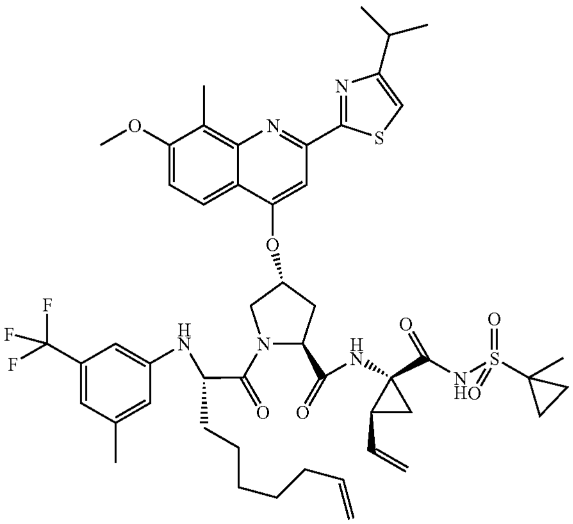

Compound 76 was prepared in a manner analogous to General Procedure SS to afford 300 mg. $^1H$ NMR (500 MHz, $CDCl_3$) δ ppm 10.16 (br. s, 1 H) 7.80 (d, J=9.16 Hz, 1 H) 7.57 (br. s, 1 H) 7.17 (d, J=9.31 Hz, 1 H) 7.07 (s, 1 H) 6.89 (br. s, 1 H) 6.77 (s, 1 H) 6.60 (s, 1 H) 6.55 (s, 1 H) 5.73-5.84 (m, 2 H) 5.61 (br. s, 1 H) 5.22 (dd, J=17.09, 0.92 Hz, 1 H) 5.12 (dd, J=10.38, 1.22 Hz, 1 H) 4.99 (dq, J=17.09, 1.63 Hz, 1 H) 4.93 (dt, J=10.15, 0.95 Hz, 1 H) 4.77-4.83 (m, 1 H) 4.45 (t, J=8.32 Hz, 1 H) 4.18-4.23 (m, 2 H) 4.14 (br. s, 1 H) 3.99 (s, 3 H) 3.17-3.25 (m, 1 H) 2.80 (s, 3 H) 2.70 (s, 3 H) 2.64 (dd, J=8.16, 1.91 Hz, 2 H) 2.20 (s, 3 H) 1.97-2.07 (m, 4 H) 1.77-1.87 (m, 2 H) 1.71-1.73 (m, 2 H) 1.51 (s, 3 H) 1.41-1.45 (m, 2 H) 1.40

(d, J=6.87 Hz, 6 H) 1.35-1.39 (m, 2 H) 0.82-0.95 (m, 2 H). LC-MS: purity 97% (UV), $t_R$ 5.66 min, m/z $[M+H]^+$ 965.34.

Example 20-54

77

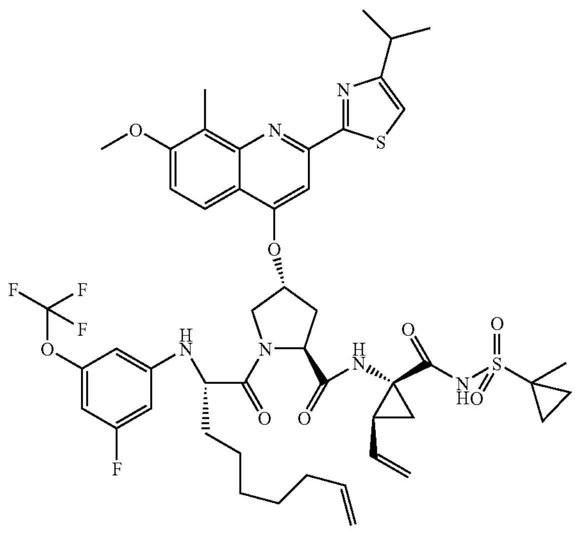

Compound 77 was prepared in a manner analogous to General Procedure SS to afford 252 mg (39%). [1] H NMR (500 MHz, $CDCl_3$) δ ppm 10.13 (s, 1 H) 7.83 (d, J=9.16 Hz, 1 H) 7.55 (s, 1 H) 7.21 (d, J=9.16 Hz, 1 H) 7.06 (s, 1 H) 6.91 (s, 1 H) 6.22-6.28 (m, 1 H) 6.16-6.34 (m, 2 H) 5.72-5.84 (m, 2 H) 5.60 (br. s, 1 H) 5.23 (d, J=17.09 Hz, 1 H) 5.12 (d, J=10.53 Hz, 1 H) 4.89-5.06 (m, 3 H) 4.41-4.51 (m, 1 H) 4.05-4.20 (m, 3 H) 3.99 (s, 3 H) 3.20 (spt, J=6.79 Hz, 1 H) 2.71 (s, 3 H) 2.58-2.69 (m, 2 H) 1.98-2.08 (m, 5 H) 1.75-1.87 (m, 3 H) 1.66-1.74 (m, 2 H) 1.56 (dd, J=14.34, 8.85 Hz, 1 H) 1.42-1.48 (m, 2 H) 1.40 (d, J=6.87 Hz, 6 H) 1.31-1.34 (m, 1 H) 1.29-1.38 (m, 3 H) 0.80-0.94 (m, 3 H). LC-MS: purity 100% (UV), $t_R$ 2.74 min, m/z $[M+H]^+$ 985.15.

Example 20-55

487

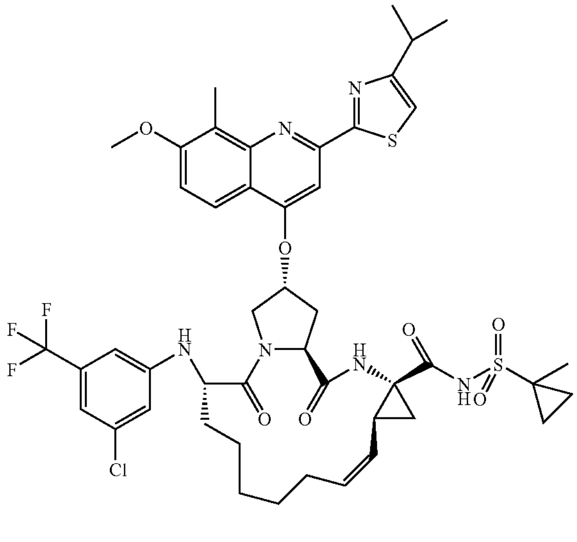

Compound 487 was prepared in a manner analogous to General Procedure TT to afford 185 mg (54%). [1] H NMR (500 MHz, $CDCl_3$) δ ppm 10.00 (s, 1 H) 7.76 (d, J=9.00 Hz, 1 H) 7.54 (s, 1 H) 7.15 (d, J=9.31 Hz, 1 H) 7.05 (s, 1 H) 6.87 (s, 1 H) 6.77 (s, 1 H) 6.66 (d, J=19.53 Hz, 2 H) 5.70-5.80 (m, 1 H) 5.61 (br. s, 1 H) 5.01 (t, J=9.61 Hz, 1 H) 4.75 (d, J=8.70 Hz, 1 H) 4.68 (t, J=7.86 Hz, 1 H) 4.24-4.32 (m, 1 H) 4.14-4.24 (m, 2 H) 3.96 (s, 3 H) 3.22 (spt, J=6.71 Hz, 1 H) 2.75 (dd, J=7.71, 2.37 Hz, 2 H) 2.69 (s, 3 H) 2.36-2.49 (m, 1 H) 2.26 (q, J=8.65 Hz, 1 H) 1.98-2.11 (m, 1 H) 1.85-1.97 (m, 2 H) 1.74-1.85 (m, 2 H) 1.50-1.53 (m, 3 H) 1.40 (d, 6 H) 1.37-1.58 (m, 6 H) 1.28-1.37 (m, 2 H) 0.84 (br. s, 2 H). LC-MS: purity 100% (UV), $t_R$ 5.60 min, m/z $[M+H]^+$ 957.25.

Example 20-56

488

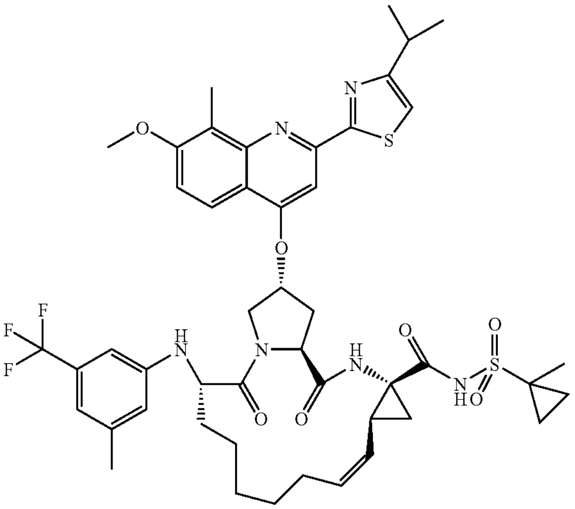

Compound 488 was prepared in a manner analogous to General Procedure TT to afford 185 mg (67%). [1] H NMR (500 MHz, $CDCl_3$) δ ppm 10.05 (br. s., 1 H) 7.69 (d, J=9.16 Hz, 1 H) 7.54 (br. s, 1 H) 7.11 (d, J=9.16 Hz, 1 H) 7.05 (s, 1 H) 6.85 (br. s, 1 H) 6.70 (s, 1 H) 6.62 (s, 1 H) 6.49 (s, 1 H) 5.70-5.77 (m, 1 H) 5.60 (br. s, 1 H) 5.01 (t, 1 H) 4.66 (t, J=7.78 Hz, 1 H) 4.51 (d, J=6.26 Hz, 1 H) 4.30 (br. s, 1 H) 4.20 (br. s, 2 H) 3.95 (s, 3 H) 3.18-3.27 (m, 1 H) 2.70-2.77 (m, 2 H) 2.69 (s, 3 H) 2.41-2.51 (m, 1 H) 2.27 (q, J=8.80 Hz, 1 H) 2.10 (s, 3 H) 1.97-2.06 (m, 1 H) 1.74-1.95 (m, 4 H) 1.51-1.58 (m, 2 H) 1.50 (s, 3 H) 1.43-1.49 (m, 3 H) 1.41 (d, J=6.87 Hz, 6 H) 1.24-1.38 (m, 3 H) 0.80-0.86 (m, 2 H). LC-MS: purity 100% (UV), $t_R$ 5.50 min, m/z $[M+H]^+$ 937.31.

Example 20-57

489

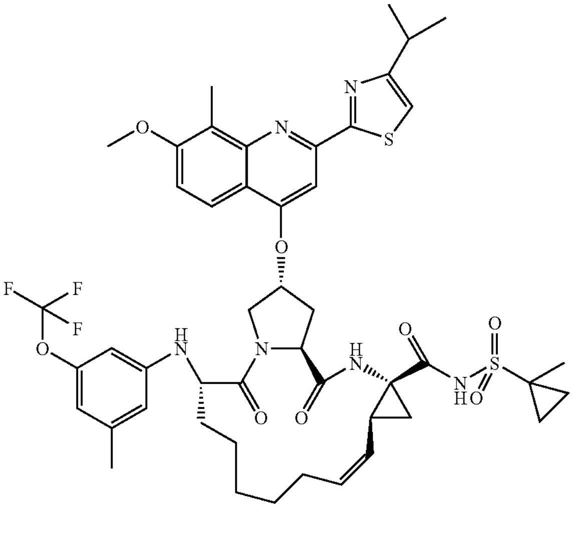

Compound 489 was prepared in a manner analogous to General Procedure TT to afford 53 mg (23%). [1] H NMR (500 MHz, $CDCl_3$) δ ppm 10.02 (s, 1 H) 7.80 (d, J=9.16 Hz, 1 H) 7.54 (s, 1 H) 7.16 (d, J=9.31 Hz, 1 H) 7.05 (s, 1 H) 6.81 (s, 1 H) 6.25 (d, J=8.85 Hz, 1 H) 6.21 (s, 1 H) 6.15 (d, J=10.53 Hz, 1 H) 5.69-5.80 (m, 1 H) 5.60 (br. s, 1 H) 5.01 (t, J=9.61 Hz, 1 H) 4.62-4.74 (m, 2 H) 4.22 (td, J=8.47, 2.90 Hz, 1 H) 4.19 (s, 2 H) 3.97 (s, 3 H) 3.22 (spt, J=6.94 Hz, 1 H) 2.75 (dd, J=7.86, 2.37 Hz, 2 H) 2.69 (s, 3 H) 2.38-2.51 (m, 1 H) 2.25 (q, J=8.90 Hz, 1 H) 1.97-2.08 (m, 1 H) 1.93 (dd, J=7.93, 6.10 Hz, 1 H) 1.84-1.91 (m, 1 H) 1.74-1.84 (m, 2 H) 1.53-1.59 (m, 2 H) 1.51 (s, 3 H) 1.42-1.50 (m, 4 H) 1.40 (d, J=6.87 Hz, 6 H) 1.28-1.37 (m, 2 H) 0.84 (dd, J=3.59, 2.52 Hz, 2 H). LC-MS: purity 100% (UV), $t_R$ 5.60 min, m/z $[M+H]^+$ 951.31.

Example 20-58

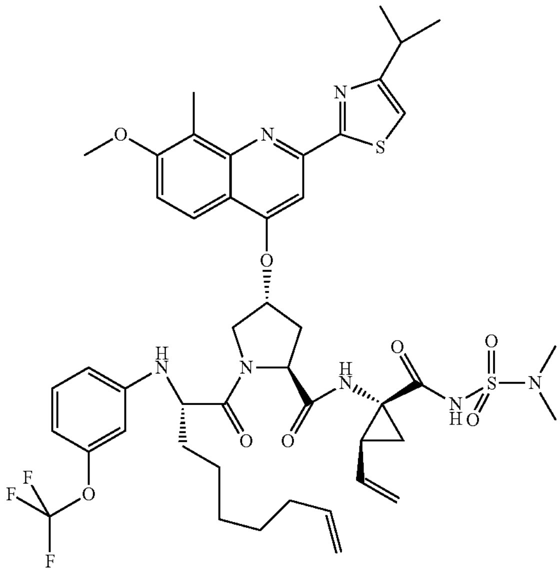

Compound 80 was prepared in a manner analogous to General Procedure SS to afford 340 mg (49%). [1] H NMR (500 MHz, $CDCl_3$) δ ppm 10.15 (s, 1 H) 7.81 (d, J=9.16 Hz, 1 H) 7.56 (s, 1 H) 7.18 (d, J=9.16 Hz, 1 H) 7.06 (s, 1 H) 6.99 (t, J=8.09 Hz, 1 H) 6.87 (br. s, 1 H) 6.54 (d, J=8.09 Hz, 1 H) 6.40-6.44 (m, 2 H) 5.70-5.83 (m, 5 H) 5.60 (d, J=2.14 Hz, 1 H) 5.23 (dd, J=17.09, 0.92 Hz, 1 H) 5.12-5.15 (m, 1 H) 4.99 (dd, J=17.09, 1.68 Hz, 1 H) 4.93 (dd, J=10.15, 0.84 Hz, 1 H) 4.79 (d, J=9.46 Hz, 1 H) 4.46 (t, J=8.32 Hz, 1 H) 3.99 (br. s, 3 H) 3.20 (spt, J=6.87 Hz, 1 H) 2.93 (s, 6 H) 2.71 (s, 3 H) 2.62-2.65 (m, 2 H) 1.96-2.06 (m, 5 H) 1.73-1.86 (m, 2 H) 1.51-1.60 (m, 1 H) 1.44-1.51 (m, 1 H) 1.41-1.44 (m, 1 H) 1.40 (d, J=6.87 Hz, 6 H) 1.29-1.38 (m, 3 H). LC-MS: purity 100% (UV), $t_R$ 2.72 min, m/z $[M+H]^+$ 956.35.

Example 20-59

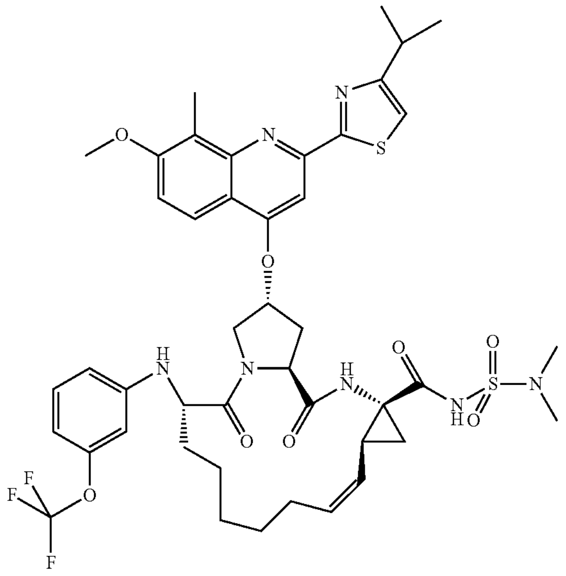

Compound 490 was prepared in a manner analogous to General Procedure TT to afford 82 mg (28%). [1] H NMR (500 MHz, $CDCl_3$) δ ppm 10.15 (s, 1 H) 7.81 (d, J=9.16 Hz, 1 H) 7.56 (s, 1 H) 7.18 (d, J=9.16 Hz, 1 H) 7.06 (s, 1 H) 6.99 (t, J=8.09 Hz, 1 H) 6.87 (br. s, 1 H) 6.54 (d, J=8.09 Hz, 1 H) 6.40-6.44 (m, 2 H) 5.70-5.83 (m, 5 H) 5.60 (d, J=2.14 Hz, 1 H) 5.23 (dd, J=17.09, 0.92 Hz, 1 H) 5.12-5.15 (m, 1 H) 4.99 (dd, J=17.09, 1.68 Hz, 1 H) 4.93 (dd, J=10.15, 0.84 Hz, 1 H) 4.79 (d, J=9.46 Hz, 1 H) 4.46 (t, J=8.32 Hz, 1 H) 3.99 (br. s, 3 H) 3.20 (spt, J=6.87 Hz, 1 H) 2.93 (s, 6 H) 2.71 (s, 3 H) 2.62-2.65 (m, 2 H) 1.96-2.06 (m, 5 H) 1.73-1.86 (m, 2 H) 1.51-1.60 (m, 1 H) 1.44-1.51 (m, 1 H) 1.41-1.44 (m, 1 H) 1.40 (d, J=6.87 Hz, 6 H) 1.29-1.38 (m, 3 H). LC-MS: purity 100% (UV), $t_R$ 2.72 min, m/z $[M+H]^+$ 956.35.

EXAMPLE 21

Scheme XVIII: General Route for the Preparation of Macrocyclic Acylsulfonamides and Acysulfamides
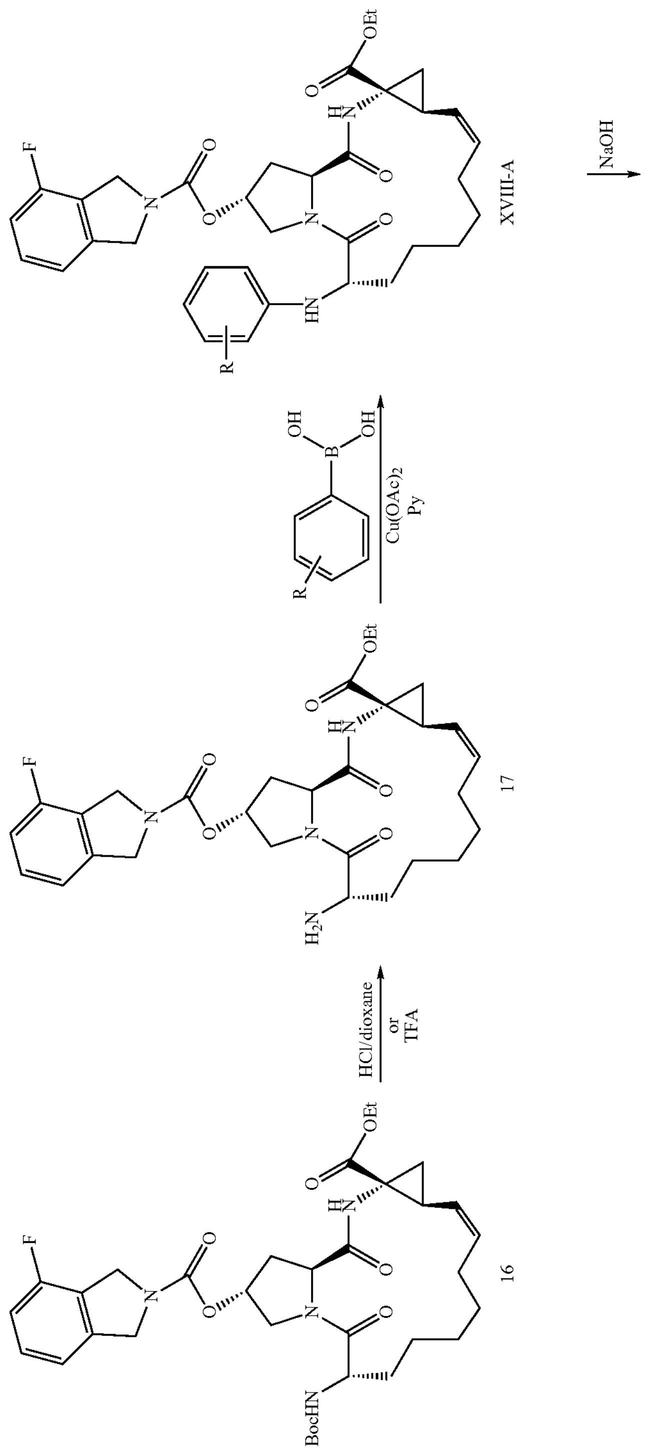
16
17
XVIII-A -continued
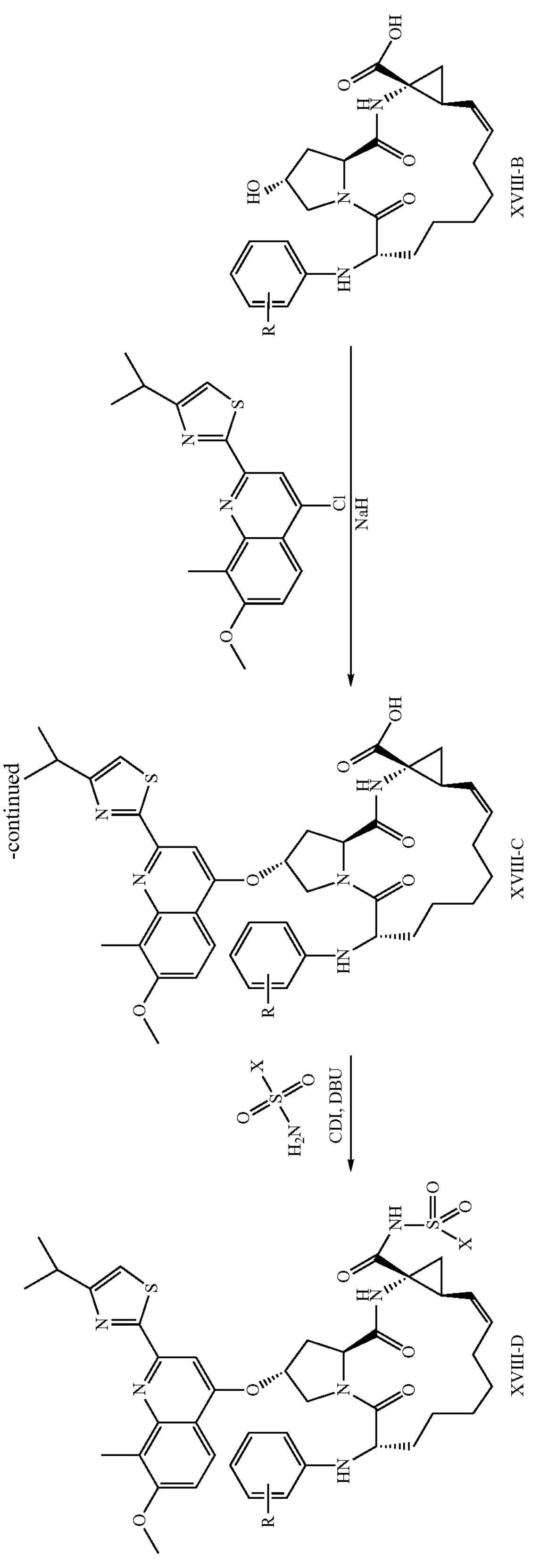
XVIII-B
XVIII-C
XVIII-D Macrocyclic protease inhibitors of general structures XXVIII-C and XXVIII-D were synthesized as shown on Scheme XVIII from synthetic precursor 16 ("RCM Ester). Compound 16 was treated under acidic conditions, for example with HCl-dioxane, to generate free amino derivative 17. Next, this compound was arylated with an optionally substituted boronic acids under $Cu^{2+}$-catalyzed conditions to yield N-aryl intermediates of general structure XXVIII-A. Simultaneous basic hydrolysis of carbamate and ester functions, for example aqueous sodium hydroxide in ethanol, afforded hydroxy carboxylic acids of general structure XXVIII-B, which were then reacted with a heteroaryl chloride, such as 2-(4-isopropylthiazol-2-yl)-4-chloro-7-methoxy-8-methyl-quinoline and the like, under basic conditions, for example sodium hydride in DMF, to furnish acids of the general structure XXVIII-C. Finally, these acids were coupled with sulfonamides or sulfamides, for example using CDI in the presence of DBU, to give the target compounds of general structure XXVIII-D.

Example 21-1

General Procedure UU

17

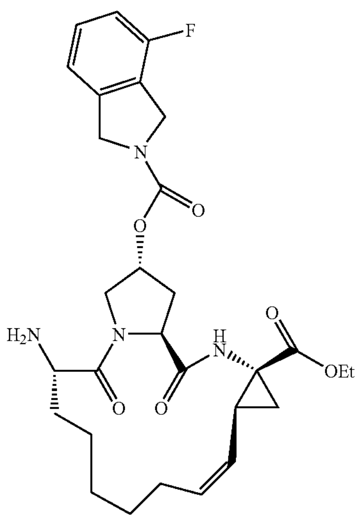

To a solution of N-Boc compound 16 (13.2 g, 20 mmol.) in DCM (80 mL) was added 4N HCl-dioxane solution (50 mL, 200 mmol.) and the reaction was allowed to proceed overnight at room temperature. After evaporation in vacuo the residue was re-dissolved in DCM and the solution was washed with saturated aqueous sodium bicarbonate, dried over sodium sulfate, evaporated, and dried under high vacuum to afford amino intermediate 17 as off-white foam which was used in the next step without further purification. Yield 12.42 g (~100%), ~90% purity. [1] H-NMR ($CDCl_3$), δ: 7.22-7.32 (m, 1 H), 6.95-7.08 (m, 3 H), 5.46-5.54 (m, 1 H), 5.30-5.36 (m, 1 H), 5.23 (dd, 1 H), 4.87-4.90 (m, 1 H), 4.71-4.78 (m, 2 H), 4.70 (d, 2 H), 4.07-4.20 (m, 2 H), 3.90-3.97 (m, 1 H), 3.69-3.80 (m, 2 H), 2.85-2.95 (m, 1 H), 2.00-2.30 (m, 4 H), 1.60 (dd, 1 H), 1.70-1.85 (m, 1 H), 1.45-1.68 (m, 5 H), 1.35-1.42 (m, 5 H), 1.24 (t, 3 H).

Example 21-2

General Procedure VV

63

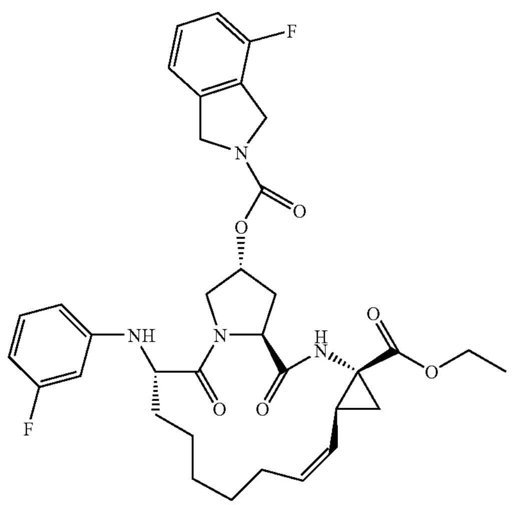

To a solution of amino compound 17 (3.8 g, ~6.1 mmol. based on ~90% purity) in DCM (60 mL) were added 3-fluorophenyl boronic acid (1.29 g, 9.2 mmol.), pyridine (1.7 mL, 21 mmol.), copper(II) acetate (0.4 g, 2.2 mmol.) and molecular sieves 4 A (~8 g). The mixture was stirred opened to the air for 2 days and then quenched by addition of 10% ammonium hydroxide (150 mL). Solids were filtered off and washed with DCM. Organic layer was separated, additionally washed with 10% aqueous ammonium hydroxide, dried over sodium sulfate and evaporated. The residue was purified by flash chromatography in 40 to 70% ethyl acetate-hexane to give the target compound 63 as white foam. Yield 2.18 g (55%). [1] H-NMR (DMSO-$d^6$), δ: 8.75 (s, 1 H), 7.37 (dd, 1 H), 7.21 (d, 1 H), 6.88-6.69 (m, 1 H), 6.41-6.49 (m, 2 H), 6.05-6.18 (dt, 1 H), 5.88 (d, 1 H), 5.53 (dd, 1 H), 5.40 (br. s, 1 H), 5.31 (dd, 1 H), 4.31-4.70 (m, 6 H), 4.07 (m, 4 H), 3.81-3.87 (m, 1 H), 2.12-2.40 (m, 4 H), 1.90-2.00 (m, 1 H), 1.69-1.82 (m, 1 H), 1.55-1.65 (m, 1 H), 1.18-1.53 (m, 9 H), 1.13 (t, 2 H).

Example 21-3

64

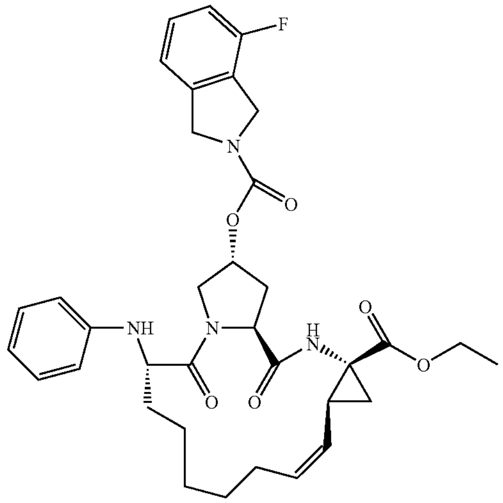

Compound 64 was prepared in a manner analogous to General Procedure VV, and the yield is 49.7%; white foam.

Example 21-4

65

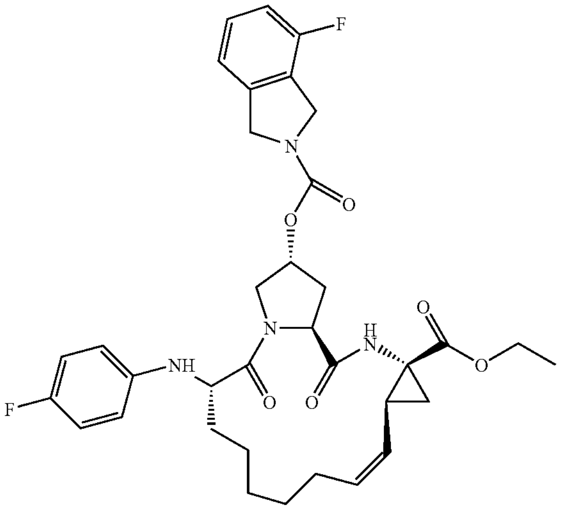

Compound 65 was prepared in a manner analogous to General Procedure VV, and the yield is 62%; white foam. [1] H-NMR ($CDCl_3$), δ: 7.23-7.27 (m, 1 H), 6.95-7.08 (m, 3 H), 6.78-6.83 (m, 2 H), 6.53-6.58 (m, 2 H), 5.52 (dt, 1 H), 5.35 (m, 1 H), 5.25 (dd, 1 H), 4.85 (m, 1 H), 4.75 (m, 2 H), 4.52-4.68 (m, 2 H), 4.32-4.41 (m, 2 H), 4.10-4.21 (m, 3 H), 3.95 (m, 1 H), 3.85 (dd, 1 H), 2.83 (m, 1 H), 2.07-2.26m, 4 H), 1.93 (m, 1 H), 1.88 (dd, 1 H), 1.73 (dd, 1 H), 1.57 (m, 2 H), 1.42 (m, 3 H), 1.22-1.28 (m, 6 H).

Example 21-5

66

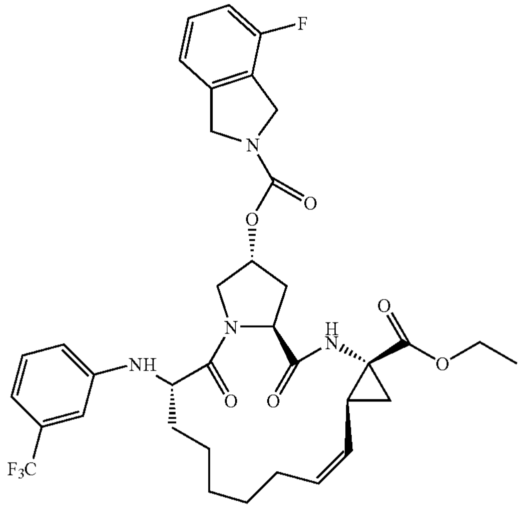

Compound 66 was prepared in a manner analogous to General Procedure VV, and the yield is 65%. White foam. [1] H-NMR ($CDCl_3$), δ: 7.23-7.28 (m, 1 H), 6.93-7.09 (m, 2 H), 6.87-6.92 (m, 2 H), 6.80 (br. s, 1 H), 6.73 (d, 1 H), 5.51 (dt, 1 H), 5.39 (m, 1 H), 5.26 (dd, 1 H), 4.87 (m, 1 H), 4.75-4.80 (m, 3 H), 4.63 (m, 2 H), 4.42 (m, 1 H), 4.13-4.20 (m, 2 H), 4.04 (m, 1 H), 3.84 (dd, 1 H), 2.87 (m, 1 H), 1.96-2.28 (m, 5 H), 1.88 (dd, 1 H), 1.75 (dd, 1 H), 1.54-1.60 (m, 2 H), 1.38-1.47 (m, 3 H), 1.22-1.36 (m, 6 H).

Example 21-6

67

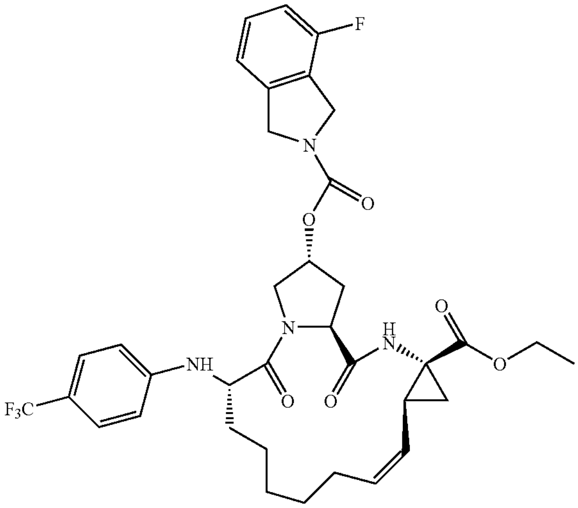

Compound 67 was prepared in a manner analogous to General Procedure VV, and the yield is 70%. White foam. [1]

H-NMR ($CDCl_3$), δ: 7.34 (d, 2 H), 7.29 (m, 1 H), 6.96-7.06 (m, 2 H), 6.90 (d, 1 H), 6.60 (d, 2 H), 5.52 (dt, 1 H), 5.38 (m, 1 H), 5.26 (dd, 1 H), 4.87-4.93 (m, 2 H), 4.73-4.77 (m, 2 H), 4.68 (m, 2 H), 4.43 (m, 1 H), 4.11-4.20 (m, 2 H), 4.15 (dd, 1 H), 3.87 (dd, 1 H), 2.88 (m, 1 H), 1.95-2.27 (m, 5 H), 1.88 (dd, 1 H), 1.75 (dd, 1H), 1.56 (dd, 1 H), 1.35-1.47 (m, 3 H), 1.20-1.35 (m, 6 H).

Example 21-7

68

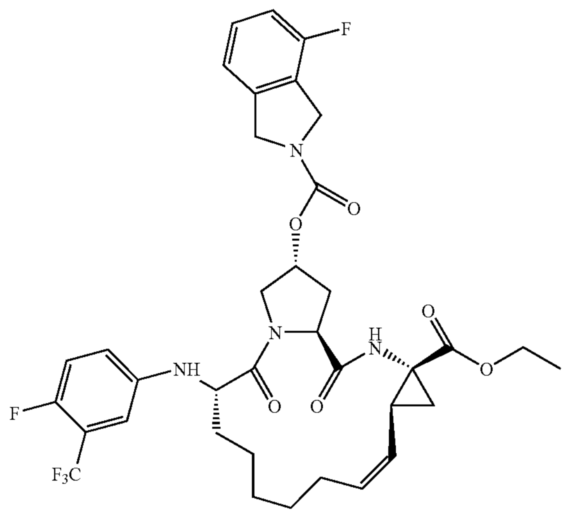

Compound 68 was prepared in a manner analogous to General Procedure VV, and the yield is 67%. White foam. [1] H-NMR ($CDCl_3$), δ: 7.28 (m, 1 H), 6.87-7.08 (m, 4H), 6.75 (m, 1 H), 6.71 (m, 1 H), 5.52 (dt, 1 H), 5.38 (m, 1 H), 5.26 (dd, 1 H), 4.86 (m, 1 H), 4.76 (m, 2 H), 4.61-4.71 (m, 3 H), 4.34 (m, 1 H), 4.10-4.20 (m, 2 H), 4.05 (dd, 1 H), 3.81 (dd, 1 H), 2.85 (m, 1 H), 2.05-2.26 (m, 4 H), 1.95-2.03 (m, 1 H), 1.88 (dd, 1 H), 1.75 (dd, 1H), 1.56 (dd, 1 H), 1.35-1.50 (m, 3 H), 1.18-1.28 (m, 6 H).

Example 21-8

69

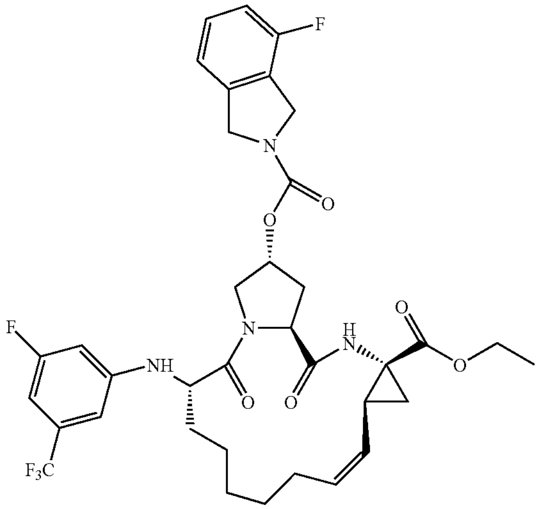

Compound 69 was prepared in a manner analogous to General Procedure VV, and the yield is 69.6%. White foam. [1] H-NMR ($CDCl_3$), δ: 7.28 (m, 1 H), 6.92-7.06 (m, 2 H), 6.84 (d, 1 H), 6.56-6.61 (m, 2 H), 6.39 (dd, 1 H), 5.52 (dt, 1 H), 5.40 (m, 1 H), 5.27 (dd, 1 H), 4.87 (m, 1 H), 4.76 (d, 2 H), 4.60-4.71 (m, 2 H), 4.36 dd, 1 H), 4.10-4.20 (m, 2 H), 4.01-4.07 (m, 1 H), 3.83-3.86 (m, 1 H), 2.84-2.88 (m, 1 H), 2.06-2.30 (m, 4 H), 1.95-2.00 (m, 1 H), 1.87 (dd, 1 H), 1.71-1.80 (m, 1 H), 1.57 (dd, 1 H), 1.35-1.50 (m, 3 H), 1.20-1.31 (m, 6H).

EXAMPLE 22

Scheme XIX: General Route for Synthesis of 411

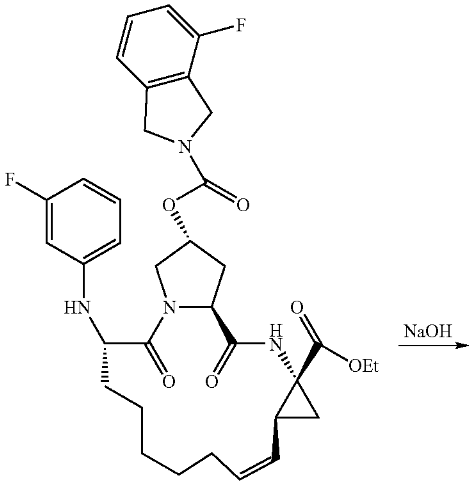

63

-continued
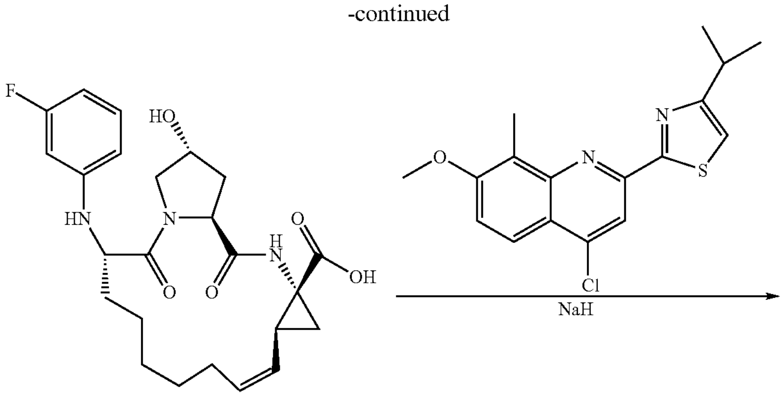
70
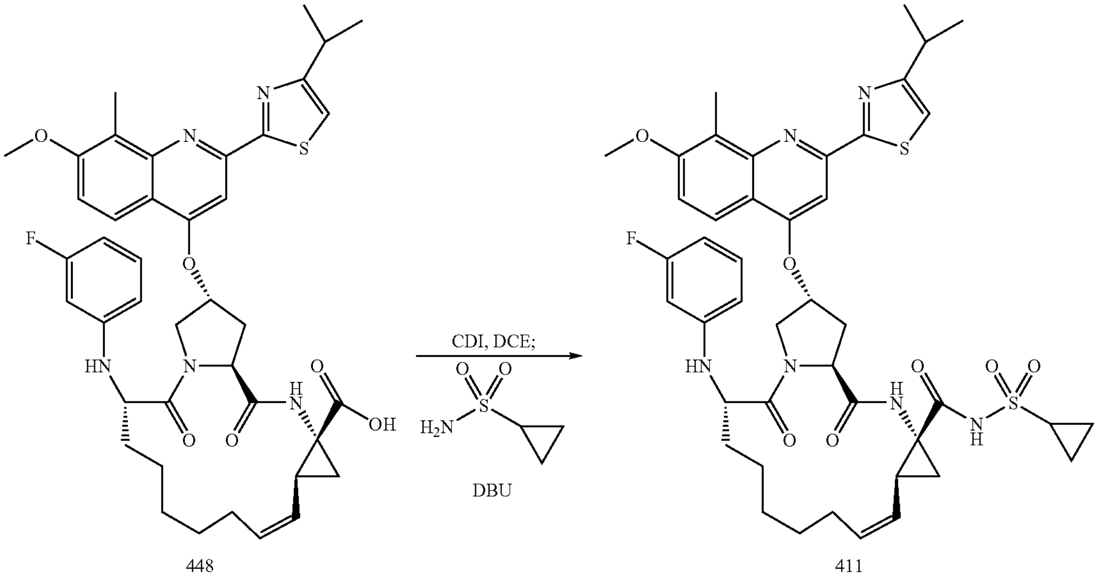
448
411

Compound 63 can be treated under basic conditions, for example aqueous sodium hydroxide in ethanol, can simultaneous hydrolyze the carbamate and ethyl ester functions thereby providing hydroxy carboxylic acids, for example compound 70. The hydroxy carboxylic acids, for example compound 70, can then reacted with a heteroaryl chloride, such as 2-(4-isopropylthiazol-2-yl)-4-chloro-7-methoxy-8-methyl-quinoline and the like, under basic conditions, for example sodium hydride in DMF, to furnish acids, such as compound 448. Finally, these acids can be coupled, for example using CDI in the presence of DBU, with sulfonamides (e.g. cyclopropylsulfonamide) or sulfamides to provide macrocycles such as compound 411.

Example 22-1

General Procedure WW

448

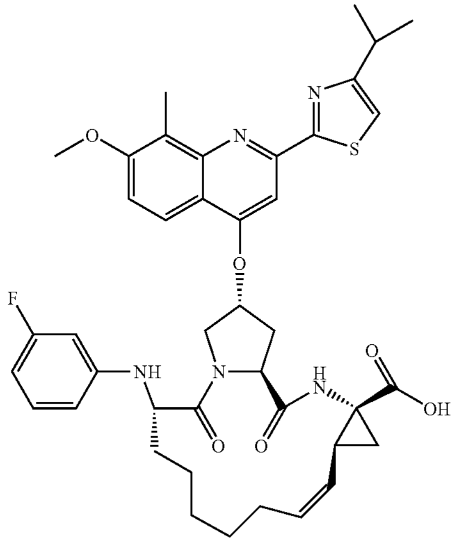

To a mixture of compound 63 (2.18 g, 3.35 mmol.) and ethanol (20 mL) was added aqueous sodium hydroxide (2N, 10 mL, 20 mmol.) and reaction mixture was stirred overnight at 70° C. Solvent was removed in vacuo and the residue was dissolved in water. The aqueous solution was acidified with 2N hydrochloric acid to pH ~3 and then extracted with ethyl acetate. Organic phase was dried over magnesium sulfate and evaporated to give crude intermediate 70 as a beige foam (~1.7 g), used on the next step without any further purification.

Crude compound 70 from the previous step (1.7 g) was co-evaporated twice with DMF and then dissolved in anhydrous DMF (10 mL). This solution was cooled down to 0° C. and sodium hydride (60% dispersion in mineral oil, 536 mg, 13.4 mmol.) was added in one portion. The reaction was stirred at room temperature until hydrogen evolution subsided (30-40 min), then 4-chloro-2-(4-isopropylthiazol-2-yl)-7-methoxy-8-methylquinoline (1.12 g, 3.35 mmol.) was added to the stirring mixture. The reaction was allowed to proceed overnight at 40° C. After addition of water and 2N hydrochloric acid the reaction mixture was extracted with ethyl acetate. Organic phase was washed with water, dried over magnesium sulfate, and evaporated. The desired acid (448) was isolated by flash chromatography in 2-4% methanol in DCM to afford 1.88 g (74% over two steps), pale yellow foam. $^1$H-NMR (DMSO-d$^6$), δ: 12.3 (br. s, 1 H), 8.68 (s, 1 H), 7.88 (d, 1 H), 7.58 (s, 1 H), 7.48 (s, 1 H), 6.68 (dd, 1 H), 6.44 (d, 1 H), 6.33 (d, 1 H), 6.21 (dd, 1 H), 5.88 (d, 1 H), 5.73 (m, 1 H), 5.52 (m, 1 H), 5.33 dd, 1 H), 4.51 (dd, 1 H), 4.34-4.40 (m, 2 H), 3.98-4.05 (m, 1 H), 3.95 (s, 3 H), 3.17 (m, 1 H), 2.49 (m, 1 H), 2.59 (s, 3 H), 2.43 (m, 1 H), 2.15 (dd, 1 H), 1.99 (m, 1 H), 1.75 (m, 1 H), 1.65 (m, 1 H), 1.15-1.49 (m, 13 H).

Example 22-2

449

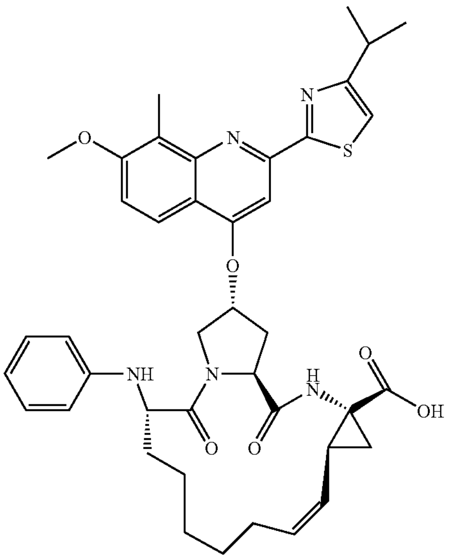

Compound 449 was prepared in a manner analogous to General Procedure WW, and the yield is 58.5% (two steps). Beige foam. $^1$H-NMR ($CDCl_3$), δ: 7.80 (d, 1 H), 7.50 (s, 1 H), 6.85-7.16 (m, 5 H), 6.69 (dd, 1 H), 6.59 (d, 2 H), 5.50-5.60 (m, 1 H), 5.48 (m, 1 H), 5.35 (dd, 1 H), 4.70 (dd, 1 H), 4.38 (d, 1 H), 4.29 (m, 1 H), 4.09 (d, 1 H), 3.95 (s, 3 H), 3.26 (m, 1 H), 2.87 (m, 1 H), 2.67 (s, 3 H), 2.47 (m, 1 H), 2.28 (m, 2 H), 2.17 (m, 1 H), 1.96 (m, 1 H), 1.82 (m, 2 H), 1.65 (dd, 1 H), 1.26-1.53 (m, 13 H).

Example 22-3

450

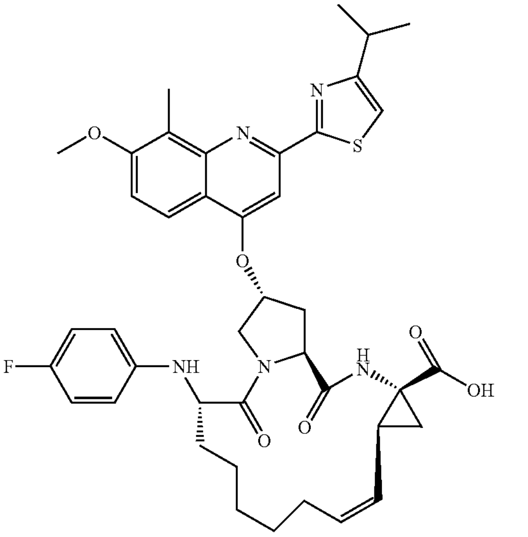

Compound 450 was prepared in a manner analogous to General Procedure WW, and the yield is 61.9% (two steps). Tan foam. [1] H-NMR ($CDCl_3$), δ: 7.71 (d, 1 H), 7.48 (s, 1 H), 7.15 (d, 1 H), 7.08 (br. s, 1 H), 7.03 (s, 1 H), 6.75 (m, 2 H), 6.52 (m, 2 H), 5.53 (m, 1 H), 5.45 (m, 1 H), 5.33 (dd, 1 H), 4.68 (dd, 1 H), 4.29 (d, 1 H), 4.22 (m, 1 H), 4.10 (d, 1 H), 3.97 (s, 3 H), 3.23 (m, 1 H), 2.87 (m, 1 H), 2.67 (s, 3 H), 2.49 (dd, 1 H), 2.28 (m, 2 H), 2.13 (m, 1 H), 1.93 (m, 1 H), 1.80 (m, 2 H), 1.62 (dd, 1 H), 1.25-1.55 (13 H).

451

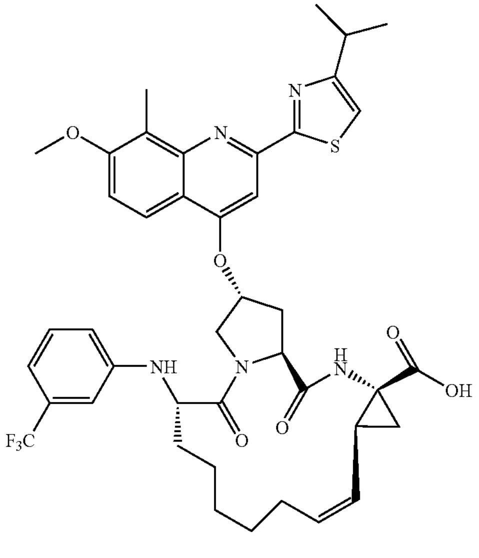

Example 22-4

Compound 451 was prepared in a manner analogous to General Procedure WW, and the yield is 71% (two steps). Yellow foam. [1] H-NMR ($CDCl_3$), δ: 7.79 (d, 1 H), 7.51 (s, 1 H), 7.13-7.17 (m, 2 H), 7.04 (s, 1 H), 6.92 (d, 1 H), 6.84 (m, 2 H), 6.70 (d, 1 H), 5.45-5.60 (m, 2 H), 5.38 (dd, 1 H), 4.80 (m, 1 H), 4.72 (dd, 1 H), 4.43 (m, 1 H), 4.35 (dd, 1 H), 4.06 (d, 1 H), 3.96 (s, 3 H), 3.29 (m, 1 H), 2.88 (m, 1 H), 2.67 (s, 3 H), 2.49 (m, 1 H), 2.31 (dd, 1 H), 2.21 (m, 2 H), 2.05 (m, 1 H), 1.80-1.93 (m, 2 H), 1.65 (dd, 1 H), 1.26-1.59 (m, 13 H).

Example 22-5

452

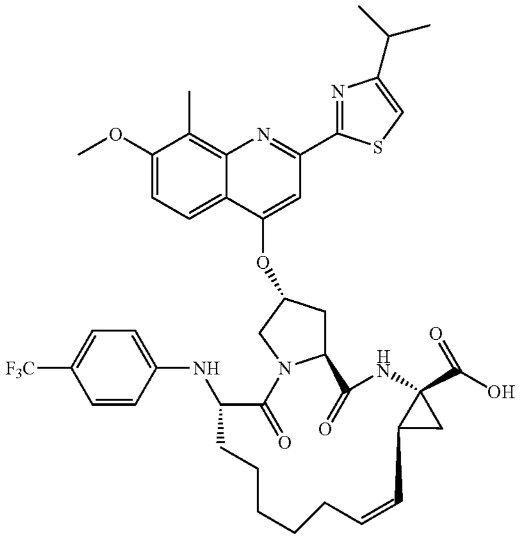

Compound 452 was prepared in a manner analogous to General Procedure WW, and the yield is 38% (two steps). Brown foam. [1] H-NMR ($CDCl_3$), δ: 7.83 (d, 1 H), 7.50 (s, 1 H), 7.29 (d, 2 H), 7.16 (d, 1 H), 6.97-7.07 (m, 2 H), 6.56 (d, 2 H), 5.34 (m, 1 H), 5.49 (m, 1 H), 5.34 (dd, 1 H), 4.85 (m, 1 H), 4.71 (dd, 1 H), 4.39 (m, 1 H), 4.28 (m, 1 H), 3.95 (s, 3 H), 3.23 (m, 1 H), 2.88 (m, 1 H), 2.67 (s, 3 H), 2.52 (dd, 1 H), 2.28 (m, 2 H), 2.15 (m, 1 H), 1.97 (m, 1 H), 1.85 (m, 1 H), 1.79 (dd, 1 H), 1.61 (dd, 1 H), 1.48 (m, 3 H), 1.25-1.39 (m, 10H).

453

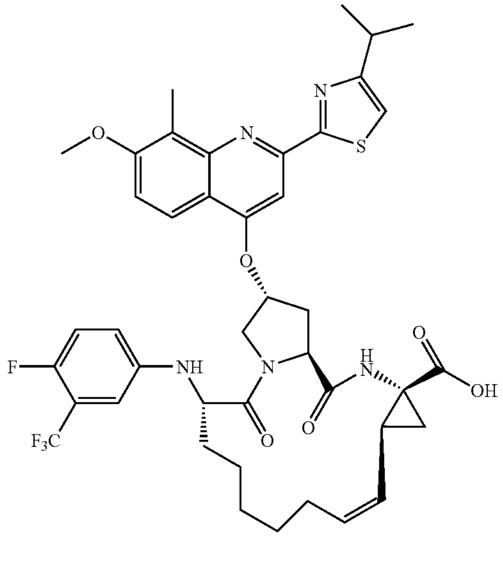

Example 22-6

Compound 453 was prepared in a manner analogous to General Procedure WW, and the yield is 51.1% (two steps). Tan foam. $^1$H-NMR ($CDCl_3$), δ: 7.73 (d, 1 H), 7.49 (s, 1 H), 7.15 (d, 1 H), 7.04 (s, 1 H), 6.88 (br. s, 1 H), 6.81 (m, 2 H), 6.63 (m, 1 H), 5.54 (m, 1 H), 5.48 (m, 1 H), 5.37 (dd, 1 H), 4.70 (m, 1 H), 4.55-4.65 (m, 1 H), 4.28-4.34 (m, 2 H), 4.05 (d, 1 H), 3.97 (s, 3 H), 3.27 (m, 1 H), 2.86 (m, 1 H), 2.67 (s, 3 H), 2.49 (m, 1 H), 2.15-2.25 (m, 3 H), 1.95 (m, 1 H), 1.79-1.85 (m, 2 H), 1.64 (dd, 1 H), 1.25-1.55 (m, 13 H).

Example 22-7

454

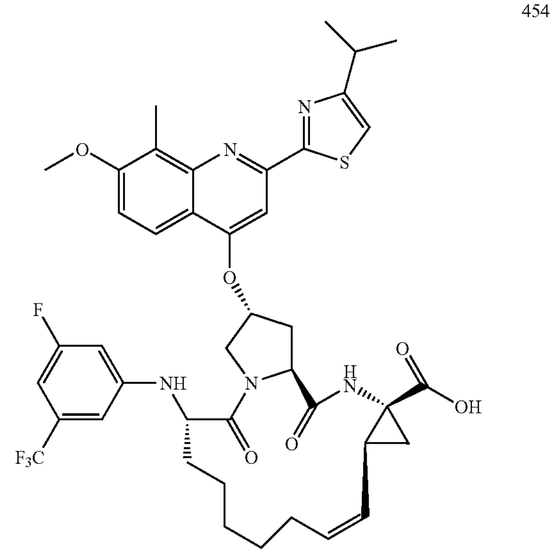

Compound 454 was prepared in a manner analogous to General Procedure WW, and the yield is 37.8% (two steps). Pale-yellow foam. $^1$H-NMR ($CDCl_3$), δ: 7.84 (d, 1 H), 7.50 (s, 1 H), 7.18 (d, 1 H), 7.04 (s, 1 H), 6.72 (br. s, 1 H), 6.66 (s, 1 H), 6.65 (d, 1 H), 6.42 (d, 1 H), 5.54 (m, 1 H), 5.50 (m, 1 H), 5.41 (dd, 1 H), 4.99 (d, 1 H), 4.68 (dd, 1 H), 4.39 (m, 2 H), 4.02 (d, 1 H), 3.96 (s, 3 H), 3.29 (m, 1 H), 2.85 (m, 1 H), 2.67 (s, 3 H), 2.50 (m, 1 H), 2.32 (dd, 1 H), 2.20 (m, 2 H), 2.05 (m, 1 H), 1.87 (m, 1 H), 1.81 (dd, 1 H), 1.65 (dd, 1 H), 1.25-1.55 (m, 13 H).

Example 22-8

General Procedure XX

411

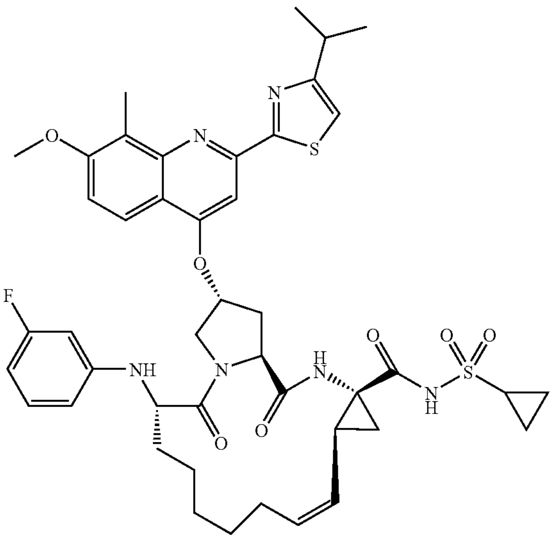

To a solution of carboxylic acid 448 (151 mg, 0.2 mmol.) in anhydrous dichloroethane (5 mL) was added carbonyldiimidazole (49 mg, 0.3 mmol.). After stirring for 3 h at room temperature cyclopropylsulfonamide (39 mg, 0.32 mmol.) was added, followed by DBU (48 μL, 0.32 mmol.). The reaction was stirred overnight at 40° C. Water and 2N hydrochloric acid (0.5 mL) were added and the mixture was extracted with ethyl acetate. Organic phase was washed with water, dried over magnesium sulfate, and evaporated. Compound 411 was isolated by column chromatography in 40-50% ethyl acetate-hexane to afford 120 mg (70%). Pale yellow foam. m/z $[M+1]^+$ 859.2. $^1$H-NMR ($CDCl_3$), δ: 10.31 (br. s, 1 H), 7.70 (d, 1 H), 7.57 (br. s, 1 H), 7.48 (s, 1 H), 7.05 (d, 1 H), 7.03 (s, 1 H), 6.81 (dd, 1 H), 6.31 (dd, 1 H), 6.14-6.22 (m, 2 H), 5.64-5.71 (m, 1 H), 5.48 (br. d, 1 H), 4.90-4.96 (m, 2 H), 4.55 (dd, 1 H), 4.06-4.15-(m, 3 H), 3.87 (s, 3 H), 3.21 (m, 1 H), 2.88 (m, 1 H), 2.65 (s, 3 H), 2.56-2.58 (m, 2 H), 2.40-2.55 (m, 1 H), 2.15 (dd, 1 H), 1.90-2.02 (m, 1 H), 1.68-1.84 (m, 3H), 1.36-1.55 (m, 11 H), 1.20-1.35 (m, 2 H), 1.00-1.18 (m, 2 H), 0.85-1.00 (m, 2 H).

Example 22-9

417

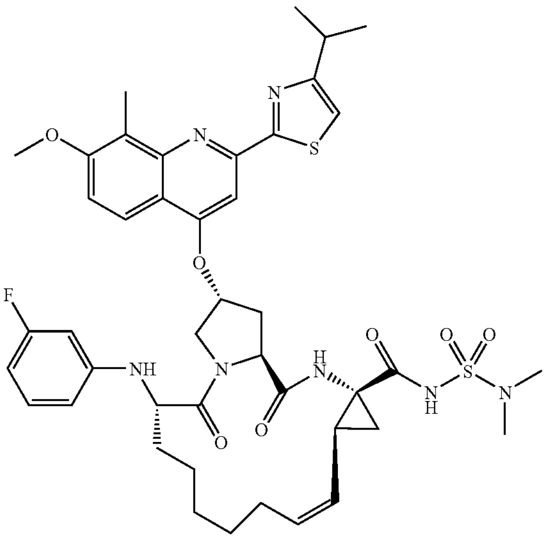

Compound 417 was prepared in a manner analogous to General Procedure XX, and the yield is 79%. Pale yellow foam. m/z $[M+1]^+$ 862.6. $^1$H-NMR (DMSO-$d^6$), δ: 10.76 (s, 1 H), 8.91 (s, 1 H), 7.81 (d, 1 H), 7.59 (s, 1 H), 7.48 (s, 1 H), 7.32 (d, 1 H), 6.67 (dd, 1 H), 6.47 (ddd, 1 H), 6.35 (dd, 1 H), 6.24 (dd, 1 H), 6.01 (d, 1 H), 5.75 (m, 1 H), 5.63 (m, 1 H), 5.10 (dd, 1 H), 4.35-4.45 (m, 3 H), 4.02 (dd, 1 H), 3.96 (s, 3 H), 3.18 (m, 1 H), 3.741 (s, 6 H), 2.55-2.70 (m, 5 H), 2.40-2.49

(m, 1 H), 2.28 (dd, 1 H), 1.70-1.85 (m, 2 H), 1.40-1.65 (m, 7 H), 1.36 (d, 3 H), 1.34 (d, 3 H), 1.20-1.30 (m, 2 H).

Example 22-10

412

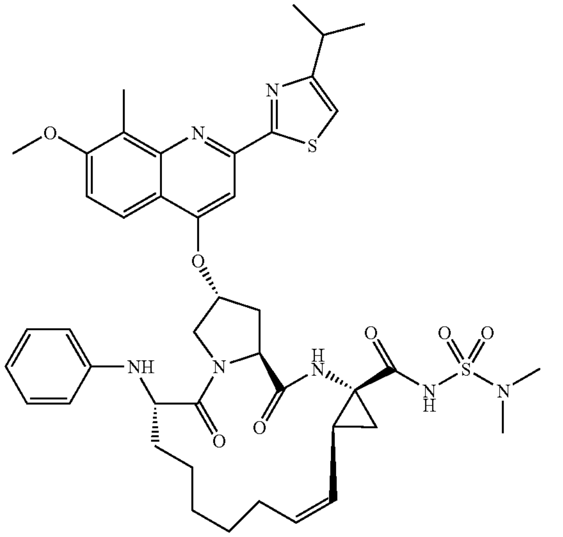

Compound 412 was prepared in a manner analogous to General Procedure XX, and the yield is 79%. Yellow foam. m/z $[M+1]^+$ 844.3. $^1$H-NMR (DMSO-$d^6$), δ: 10.76 (s, 1 H), 8.90 (s, 1 H), 7.82 (d, 1 H), 7.60 (s, 1 H), 7.48 (s, 1 H), 7.34 (d, 1 H), 6.71 (dd, 2 H), 6.52 (d, 2 H), 6.42 (dd, 1 H), 5.74 (m, 1 H), 5.59-5.70 (m, 2 H), 5.09 (dd, 1 H), 4.41-4.60 (m, 2 H), 4.31 (dd, 1 H), 4.01 (dd, 1 H), 3.97 (s, 3 H), 3.18 (m, 1 H), 2.74 (s, 6 H), 2.52-2.68 (m, 5 H), 2.40-2.48 (m, 1 H), 2.27 (dd, 1 H), 1.72-1.85 (m, 2 H), 1.39-1.65 (m, 7 H), 1.36 (d, 3 H), 1.34 (d, 3 H), 1.15-1.30 (m, 2 H).

Example 22-11

455

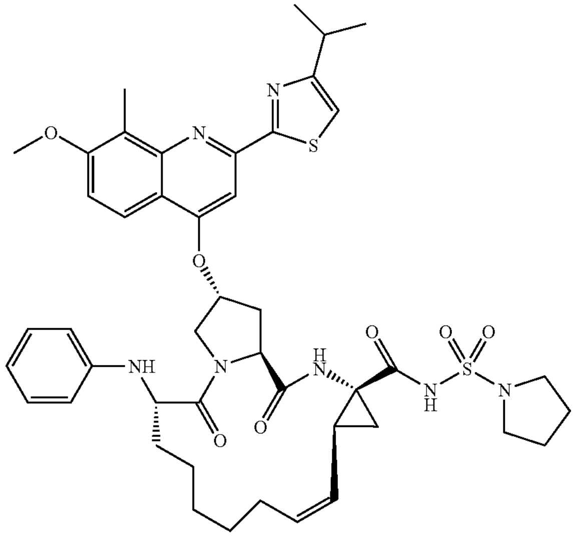

Compound 455 was prepared in a manner analogous to General Procedure XX, and the yield is 54%. Yellow foam. m/z $[M+1]^+$ 870.1. $^1$H-NMR ($CDCl_3$), δ: 9.97 (br. s, 1 H), 7.72 (d, 1 H), 7.50 (s, 1 H), 7.48 (br. s, 1 H), 7.06 (d, 1 H), 7.04 (s, 1 H), 6.88 (dd, 2 H), 6.56 (t, 1 H), 6.43 (d, 2 H), 5.71 (dt, 1 H), 5.51 (m, 1 H), 5.02 (dd, 1 H), 4.52 (m, 1 H), 4.10-4.22 (m, 2 H), 3.90 (s, 3 H), 3.60-3.65 (m, 2 H), 3.20-3.25 (m, 4 H), 2.68 (s, 3 H), 2.44-2.64 (m, 2 H), 2.13 (dd, 1 H), 1.72-1.92 (m, 11 H), 1.20-1.60 (m, 12 H).

Example 22-12

456

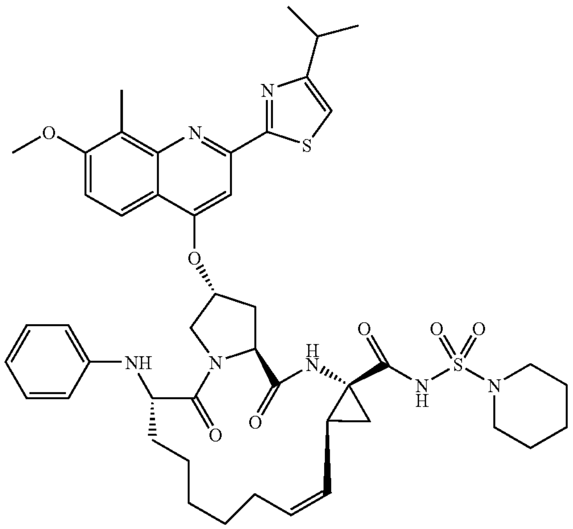

Compound 456 was prepared in a manner analogous to General Procedure XX, and the yield is 35%. Yellow foam. m/z $[M+1]^+$ 884.2. $^1$H-NMR ($CDCl_3$), δ: 9.95 (br. s, 1 H), 7.70 (d, 1 H), 7.50 (s, 1 H), 7.32 (br. s, 1 H), 7.06 (d, 1 H), 7.05 (s, 1 H), 6.90 (dd, 2 H), 6.60 (t, 1 H), 6.44 (d, 2 H), 5.76 (dt, 1 H), 5.51 (m, 1 H), 5.06 (dd, 1 H), 4.48 (dd, 1 H), 4.09-4.25 (m, 3 H), 3.90 (s, 3 H), 3.20-3.35 (m, 4 H), 2.67 (s, 3 H), 2.40-2.65 (m, 2 H), 2.12 (dd, 1 H), 1.75-1.95 (m, 4 H), 1.25-1.68 (22 H).

Example 22-13

415

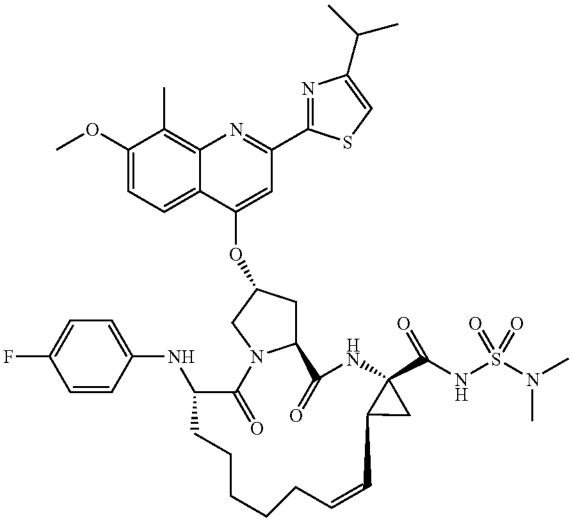

Compound 415 was prepared in a manner analogous to General Procedure XX, and the yield is 74.8%. Pale yellow foam. m/z $[M+1]^+$ 862.3. $^1$H-NMR (DMSO-$d^6$), δ: 10.78 (s, 1 H), 8.95 (s, 1 H), 7.75 (d, 1 H), 7.59 (s, 1 H), 7.48 (s, 1 H), 7.34 (d, 1 H), 6.48-6.55 (m, 2 H), 6.38-6.43 (m, 2 H), 5.74 m, 1 H), 5.65 (dt, 1 H), 5.55 (d, 1 H), 5.09 (dd, 1 H), 4.38-4.49 (m, 2 H), 4.30 (dd, 1 H), 4.00 (m, 1 H), 3.96 (s, 3 H), 3.18 (m, 1 H), 2.74 (s, 6 H), 2.65 (m, 2 H), 2.61 (s, 3 H), 2.45 (m, 1 H), 2.27

(dd, 1 H), 1.65-1.82 (m, 2 H), 1.40-1.60 (m, 7 H), 1.36 (d, 3 H), 1.34 (d, 3 H), 1.15-1.30 (m, 2 H).

Example 22-14

457

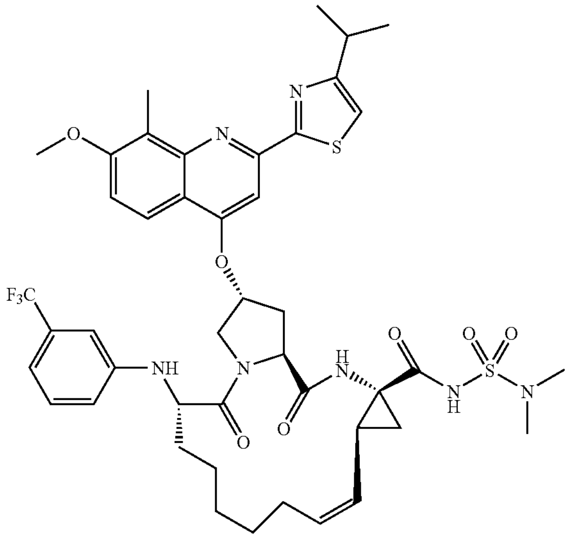

Compound 457 was prepared in a manner analogous to General Procedure XX, and the yield is 79%. Pale yellow foam. m/z $[M+1]^+$ 912.3. $^1$H-NMR (DMSO-$d^6$), δ: 10.76 (s, 1 H), 8.92 (s, 1 H), 7.74 (d, 1 H), 7.60 (s, 1 H), 7.48 (s, 1 H), 7.32 (d, 1 H), 7.04 (s, 1 H), 6.67-6.75 (m, 3 H), 6.16 (d, 1 H), 5.75 (s, 1 H), 5.63 (dt, 1 H), 5.10 (dd, 1 H), 4.40-4.50 (m, 3 H), 4.04 (dd, 1 H), 3.96 (s, 3 H), 3.17 (m, 1 H), 2.74 (s, 6 H), 2.63 (m, 2 H), 2.60 (s, 3 H), 2.44 (m, 1 H), 2.27 (dd, 1 H), 1.75-1.85 (m, 2 H), 1.37-1.60 (m, 7 H), 1.36 (d, 3 H), 1.34 (d, 3 H), 1.18-1.27 (m, 2 H).

Example 22-15

458

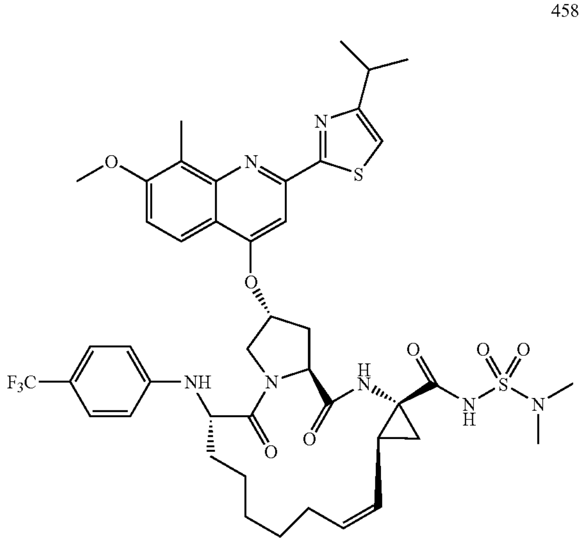

Compound 458 was prepared in a manner analogous to General Procedure XX, and the yield is 85%. Pale yellow foam. m/z $[M+1]^+$ 912.3. $^1$H-NMR (DMSO-$d^6$), δ: 10.78 (s, 1 H), 8.96 (s, 1 H), 7.88 (d, 1 H), 7.62 (s, 1 H), 7.49 (s, 1 H), 7.34 (d, 1 H), 6.72 (d, 2 H), 6.50 (d, 1 H), 6.42 (d, 2 H), 5.78 (m, 1 H), 5.64 (dt, 1 H), 5.10 (dd, 1 H), 4.52-5.70 (m, 2 H), 4.34 (m, 1 H), 3.97 (dd, 1 H), 3.94 (s, 3 H), 3.18 (m, 1 H), 2.75 (s, 6 H), 2.63 (m, 2 H), 2.61 (s, 3 H), 2.38 (dd, 1 H) 1.72-1.84 (m, 2 H), 1.39-1.62 (m, 7 H), 1.36 (d, 3 H), 1.34 (d, 3 H), 1.23 (m, 2 H).

459

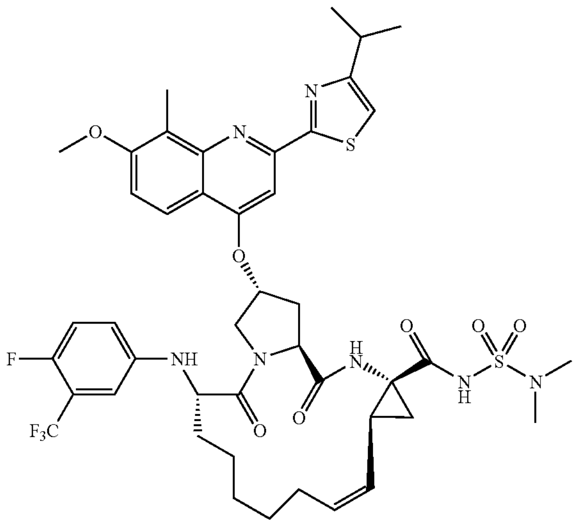

Example 22-16

Compound 459 was prepared in a manner analogous to General Procedure XX, and the yield is 83%. Pale yellow foam. m/z $[M+1]^+$ 930.3. $^1$H-NMR (DMSO-$d^6$), δ: 10.78 (s, 1 H), 8.95 (s, 1 H), 7.69 (d, 1 H), 7.59 (s, 1 H), 7.48 (s, 1 H), 7.30 (d, 1 H), 7.04 (m, 1 H), 6.70 (m, 1 H), 6.42 (dd, 1 H), 6.05 (d, 1 H), 5.76 (m, 1 H), 5.64 (dt, 1 H), 5.09 (dd, 1 H), 4.37-4.49 (m, 3 H), 4.03 (dd, 1 H), 3.94 (s, 3 H), 3.36 (m, 1 H), 2.74 (s, 6 H), 2.60-2.64 (m, 1 H), 2.60 (s, 3 H), 2.40-2.49 (m, 1 H), 2.25 (dd, 1 H), 1.70-1.86 (m, 2 H), 1.38-1.60 (m, 7 H), 1.36 (d, 3 H), 1.34 (d, 3 H), 1.18-1.28 (m, 2 H).

460

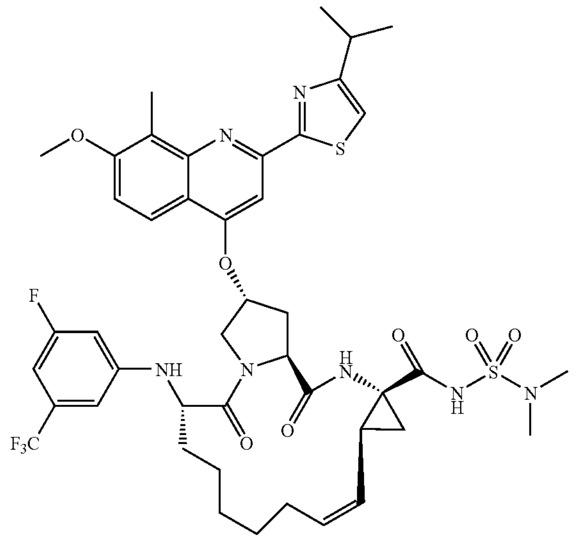

Example 22-17

Compound 460 was prepared in a manner analogous to General Procedure XX, and the yield is 83.8%. Pale yellow foam. m/z $[M+1]^+$ 930.3. $^1$H-NMR (DMSO-$d^6$), δ: 10.77 (s, 1 H), 8.97 (s, 1 H), 7.75 (d, 1 H), 7.59 (s, 1 H), 7.48 (s, 1 H), 7.27 (d, 1 H), 6.95 (s, 1 H), 6.74 (d, 1 H), 6.60 (d, 1 H), 6.54 (d, 1 H), 5.76 (s, 1 H), 5.64 (dt, 1 H), 5.11 (dd, 1 H), 4.55 (m, 1 H), 4.38-4.46 (m, 2 H), 4.05 (dd, 1 H), 3.83 (s, 3 H), 3.17 (m, 1 H), 2.74 (s, 6 H), 2.58-2.68 (m, 2 H), 2.58 (s, 3 H), 2.40-2.49 (m, 1 H), 2.28 (dd, 1 H), 1.74-1.83 (m, 2 H), 1.40-1.63 (m, 7 H), 1.35 (d, 3 H), 1.34 (d, 3 H), 1.16-1.30 (m, 2 H).

Example 22-18

391

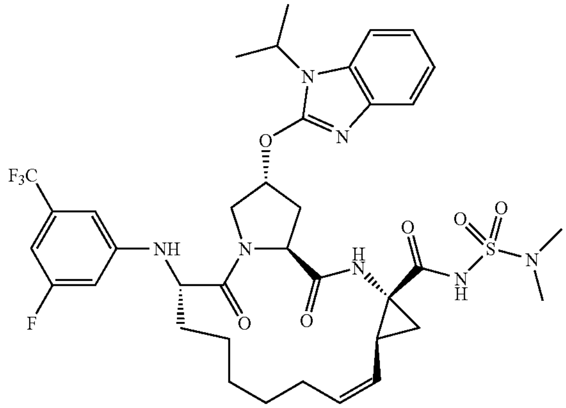

Compound 391 was prepared in a manner analogous to General Procedure R, to afford 39.7 mg (23.9%). MS (ESI) m/z $(M+H)^+$ 792.3.

EXAMPLE 23

Scheme XX: General Route for synthesis of Acylsulfonamides

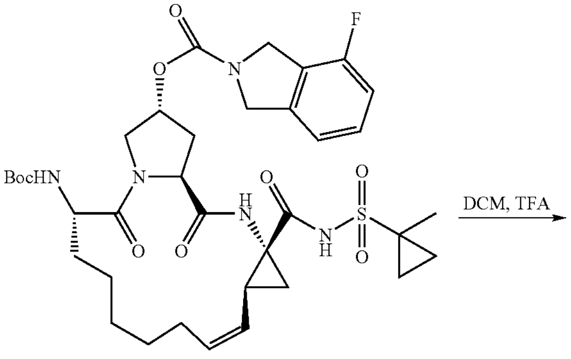

6

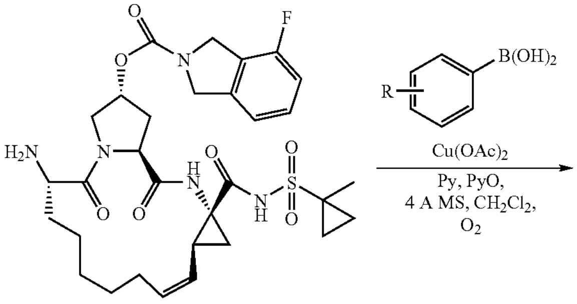

71

-continued

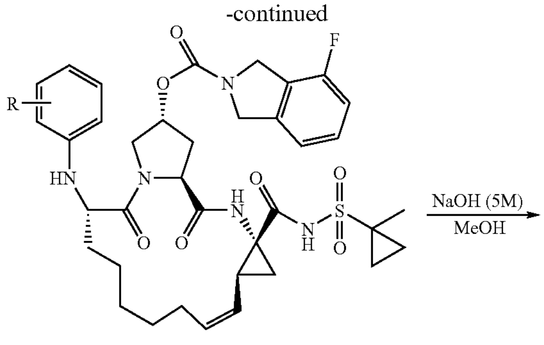

XX-A

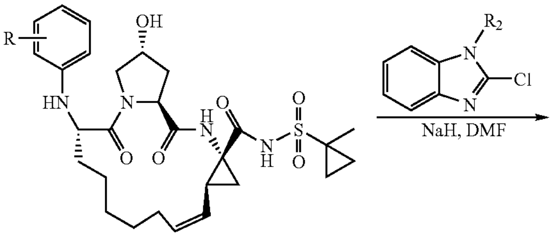

XX-B

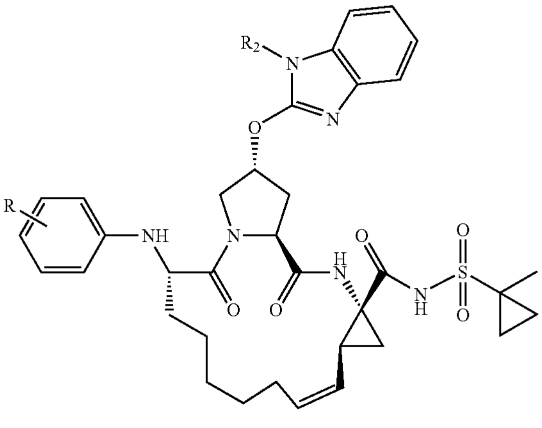

XX-C

N-aryl amines having a general structure XX-C, can be synthesized as shown in Scheme XX. The isoindoline carbamate 6 can be treated with acid, for example TFA in DCM, to remove the Boc protecting group thereby providing compound 71. Compound 71 can be treated with optionally substituted aryl boronic acids under $Cu^{2+}$-catalyzed conditions thereby providing isoindoline carbamates having general structure XX-A. The isoindoline carbamate having general structure XX-A can be treated under basic conditions, for example aqueos sodium hydroxide in methanol, to hydrolyse the isoindoline carbamate thereby providing alcohols having general structure XX-B. The alcohol having general structure XX-B can be treated with a heteroaryl chloride, such as 2-chloro-1-ethyl-benzoimidazole, 2-chloro-1-isobutyl-benzoimidazole, 2-chloro-1-isopropyl-6-methyl-benzoimidazole, 2-chloro-1-isopropyl-6-methyl-benzoimidazole, and the like, under basic conditions to afford a compound of general structure XX-C.

Example 23-1

71

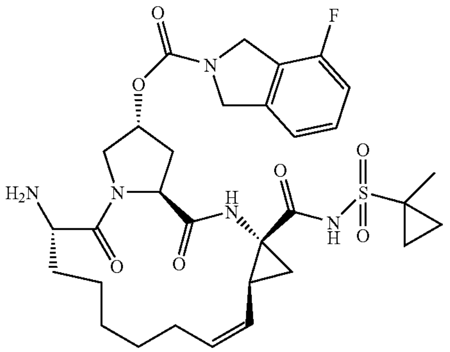

Compound 71 can be prepared in a manner analogous to General Procedure S.

Example 23-2

XX-A

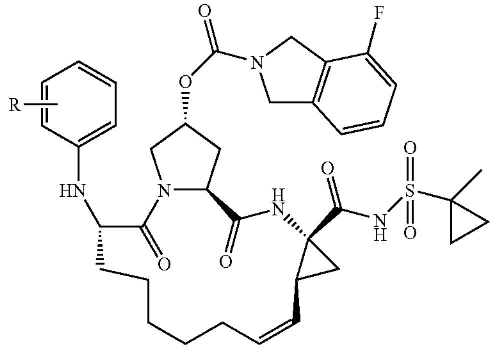

Compounds of general structure XX-A can be prepared in a manner analogous to General Procedure 0.

Example 23-2

XX-B

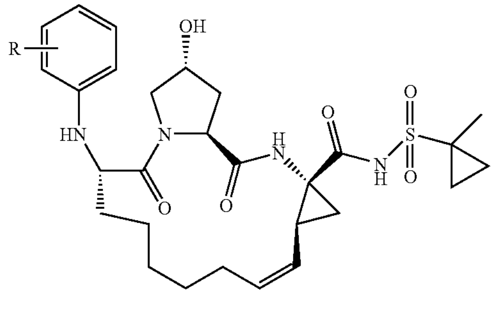

Compounds of general structure XX-B can be prepared in a manner analogous to General Procedure P.

Example 23-3

XX-C

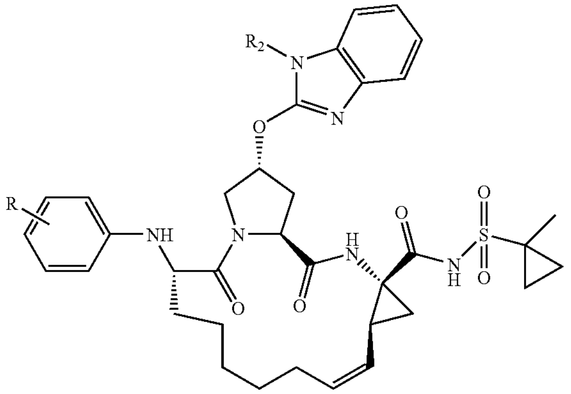

Compounds of general structure XX-C can be prepared in a manner analogous to General Procedure F.

Example 23-4

402

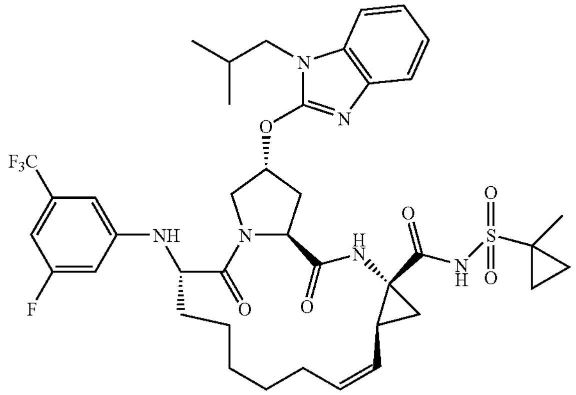

Compound 402 was prepared in a manner analogous to General Procedure F, to afford 5.1 mg (9.8%). MS (ESI) m/z $(M+H)^+$ 817.4.

Example 23-5

401

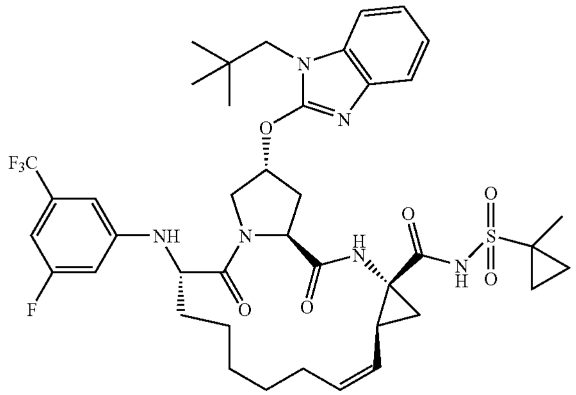

Compound 401 was prepared in a manner analogous to General Procedure F, to afford 5.1 mg (3.6%). MS (ESI) m/z $(M+Na)^+$ 853.3.

Example 23-6

365

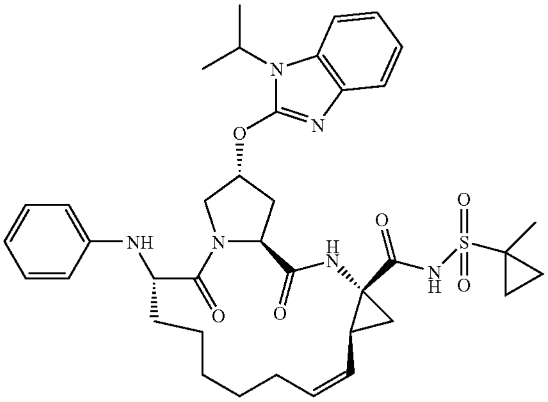

Compound 365 was prepared in a manner analogous to General Procedure F, to afford 50.7 mg, 28.3%. MS (ESI) m/z $(M+H)^+$ 717.3.

Example 23-7

461

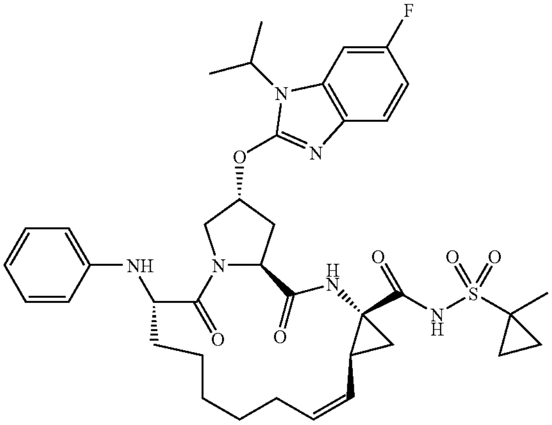

Compound 461 was prepared in a manner analogous to General Procedure F, to afford 40 mg, 28%. MS (ESI) m/z $(M+H)^+$ 735.4.

Example 23-8

462

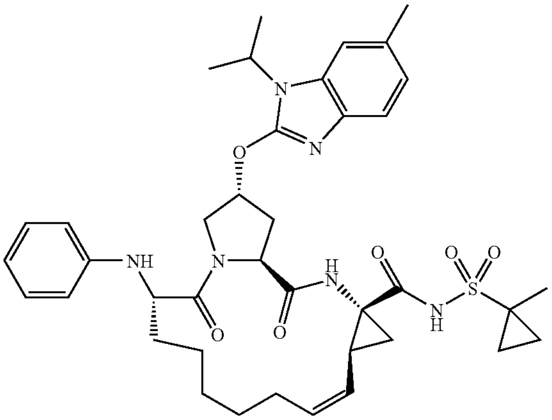

Compound 462 was prepared in a manner analogous to General Procedure F, to afford 32.6 mg, 15%. MS (ESI) m/z $(M+H)^+$ 731.4.

Example 23-9

Synthesis of substituted 2-chloro-benzoimidazoles

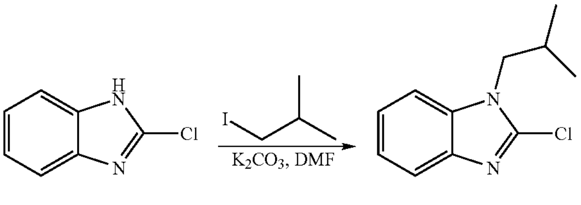

To a solution of 2-chloro-benzoimidazole (1.0 eq.) in DMF was added $K_2CO_3$ (2.0 eq.) and isobutyl iodide (1.5 eq.). The reaction mixture was stirred at room temperature for 3 days. The reaction mixture was poured into ice-water. The mixture was extracted with ethyl acetate (3×100 mL), washed with brine, dried over $Na_2SO_4$, concentrated to get a residue, which was purified by column chromatography to afford 4 g (96%) of 2-chloro-1-isobutyl-benzoimidazole.

Example 23-10

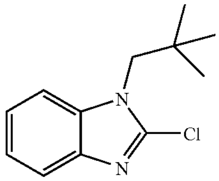

2-Chloro-1-neopentyl-benzoimidazole was prepared in a manner analogous to Example 23-9, to afford 1.1 g, 75.3%.

Example 23-11

Scheme XXI: Synthesis of substituted 2-chloro-N-(2-propyl)-benzoimidazoles:

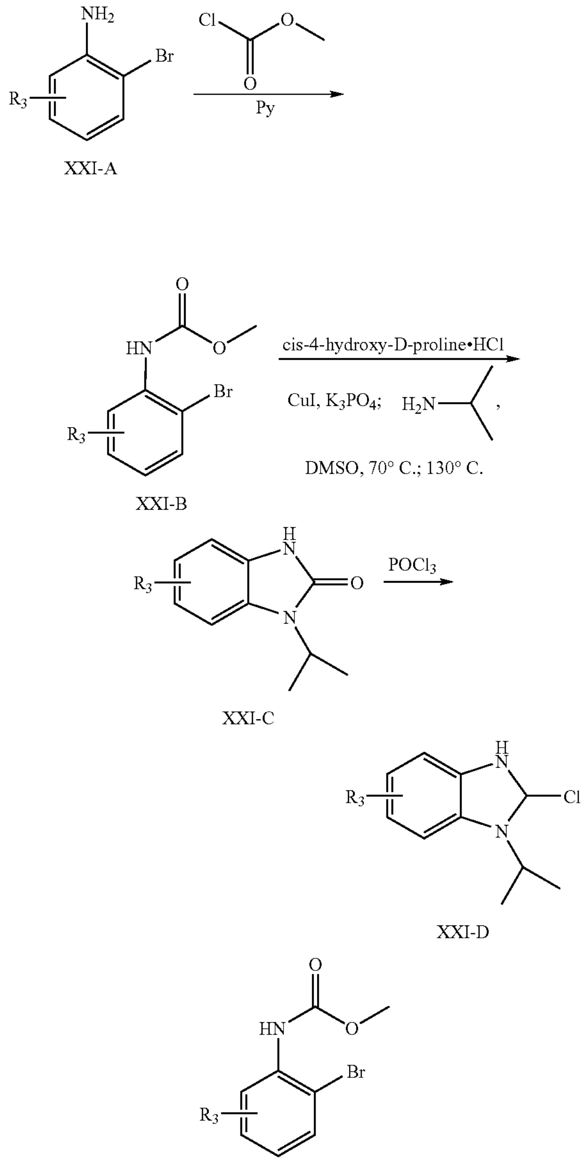

XXI-A

XXI-B

XXI-C

XXI-D

XXI-B

To a solution of a compound having the general structure XXI-A (1.0 eq.) in 15 mL of pyridine was added methyl chloroformate (1.5 eq.) at 0° C. The reaction mixture was stirred at 0° C. for 2 h. The resulting solution was filtered and concentrated. The residue was dissolved in ethyl acetate, washed with HCl (1M) and brine. The organic was dried over $Na_2SO_4$, concentrated and purified by column chromatography on silica gel using petroleum ether/ethyl acetate (10:1) to afford a compound having the general structure XXI-B.

Example 23-12

XXI-C

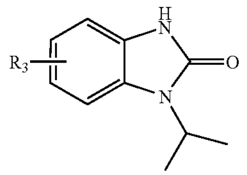

A schlenk tube was charged with a compound having the general structure XXI-B (1 eq.), CuI (0.2 eq.), trans-4-hydroxy-L-proline (0.4 eq.) and $K_3PO_4$ (2.0 eq.), evacuated and backfilled with argon. isopropylamine (2.0 eq.) and DMSO were added successively. The reaction mixture was stirred at 70° C. for 12 h and then at 130° C. for 6 h. The reaction mixture was poured into saturated $NH_4Cl$ solution. The mixture was extracted with ethyl acetate. The organic was dried over $Na_2SO_4$, concentrated and purified by column chromatography on silica gel using DCM/MeOH (80:1) to afford a compound having the general structure XXI-C.

Example 23-13

XXI-D

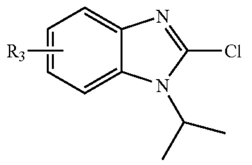

A mixture of a compound having the general structure XXI-C in $POCl_3$ was refluxed for 6 h. Most of the $POCl_3$ was removed in vacuo and the residue was quenched with ice water and treated with aq. NaOH (5M) until pH=7-8. The mixture was extracted with ethyl acetate. The organic layer was dried over $Na_2SO_4$ and evaporated to afford crude product. Crude product was purified by column chromatography on silica gel using DCM/MeOH (40:1) to afford a compound having the general structure XXI-D.

Example 23-14

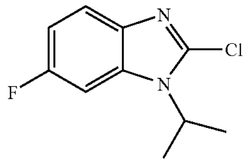

2-Chloro-6-fluoro-1-isopropyl-benzoimidazole was prepared in a manner analogous to Example 23-13, to afford 0.76 g (63%). $^1$H NMR (400 MHz, DMSO-$d_6$) δ 7.79 (m, 1 H), 7.42 (m, 1 H), 7.13 (m, 1H), 4.95 (m, 1 H), 1.52 (d, J=6.8 Hz, 6 H).

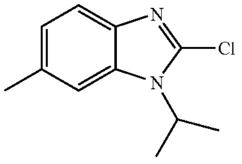

Example 23-15

2-chloro-1-isopropyl-6-methyl-benzoimidazole was prepared in a manner analogous to Example 23-13, to afford 0.87 g (53%).

Example 23-16

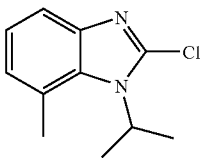

2-chloro-1-isopropyl-7-methyl-benzoimidazole was prepared in a manner analogous to Example 23-13

Example 23-17

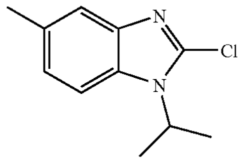

2-chloro-1-isopropyl-5-methyl-benzoimidazole was prepared in a manner analogous to Example 23-13

Example 23-18

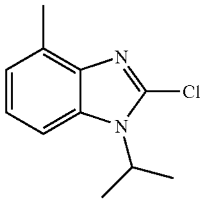

2-chloro-1-isopropyl-4-methyl-benzoimidazole was prepared in a manner analogous to Example 23-13

Example 23-18

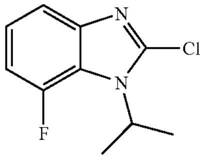

2-chloro-1-isopropyl-7-fluoro-benzoimidazole was prepared in a manner analogous to Example 23-13. $^1$H NMR (400 MHz, DMSO-$d_6$) δ 7.5 (d, J=8.0 Hz, 1 H), 7.15-7.27 (m, 2 H), 5.0 (m, 1 H), 1.52 (d, J=13.6 Hz, 6 H).

Example 23-19

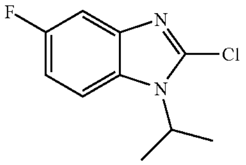

2-chloro-1-isopropyl-5-fluoro-benzoimidazole was prepared in a manner analogous to Example 23-13

Example 23-20

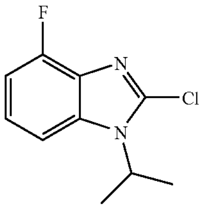

2-chloro-1-isopropyl-4-fluoro-benzoimidazole was prepared in a manner analogous to Example 23-13. $^1$H NMR (400 MHz, DMSO-$d_6$) δ 7.71 (m, 1 H), 7.16 (m, 1H), 7.08 (m, 1 H), 4.90 (m, 1H), 1.57 (d, J=8.0 Hz, 6 H).

Example 23-20

467

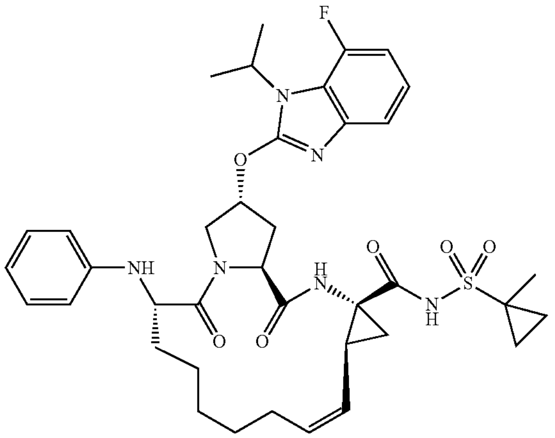

Compound 467 was prepared in a manner analogous to General Procedure F, to afford 60.9 mg (30.9%). MS (ESI) m/z $(M+H)^+$ 735.3.

Example 23-21

468

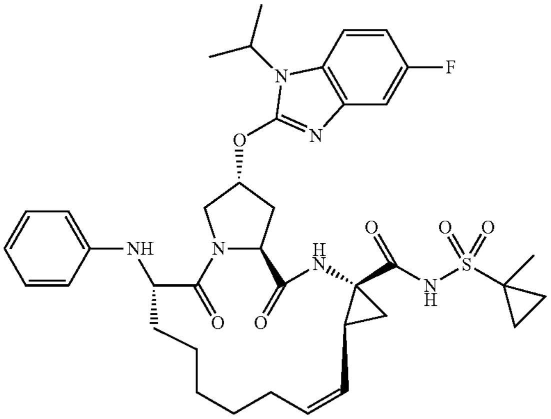

Compound 468 was prepared in a manner analogous to General Procedure F, to afford 45 mg (22.8%). MS (ESI) m/z $(M+H)^+$ 735.3.

Example 23-22

469

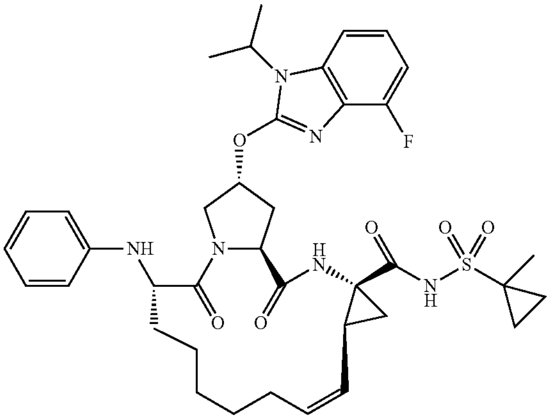

Compound 469 was prepared in a manner analogous to General Procedure F, to afford 25.5 mg (12.9%). MS (ESI) m/z $(M+H)^+$ 735.3.

Example 23-23

General Procedure DDD

To a solution of general compound XX-B (1 eq) in 3 ml of DMSO was added t-BuOK (6 eq) with ice water bath. The resulting mixture was stirred at this temperature for 0.5 h before the addition of compound 5 (1.1 eq), and it was allowed to warm to room temperature slowly and stirred overnight. The reaction was quenched by water (10 mL), extracted with ethyl acetate, washed with brine, dried over $Na_2SO_4$, concentrated to get a residue, which was purified by prep-HPLC to give target general compound XX-C.

Example 23-24

470

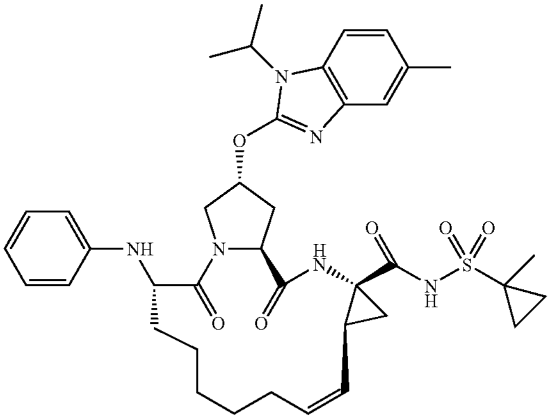

Compound 470 was prepared in a manner analogous to General Procedure DDD, to afford 5.9 mg (3.0%). MS (ESI) m/z $(M+H)^+$ 731.4.

Example 23-25

471

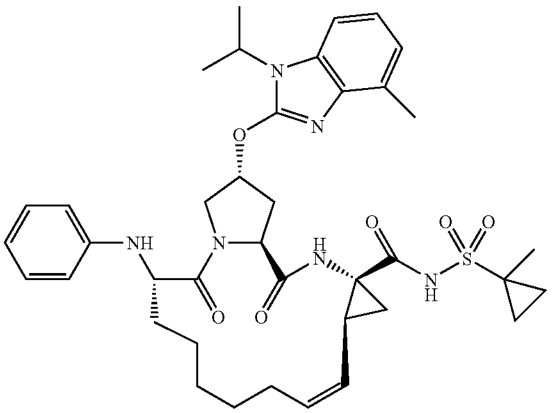

Compound 471 was prepared in a manner analogous to General Procedure DDD, to afford 25.2 mg (10%). MS (ESI) m/z $(M+H)^+$ MS: 731.3.

Example 23-26
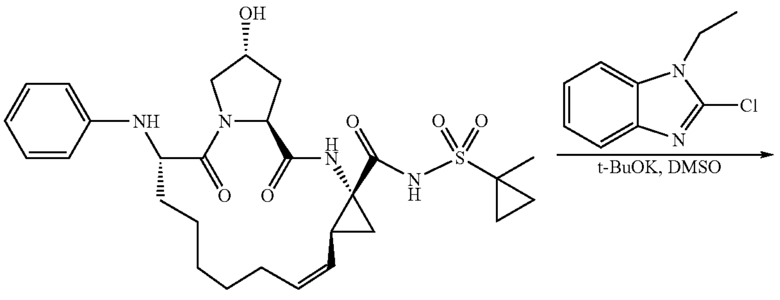
1
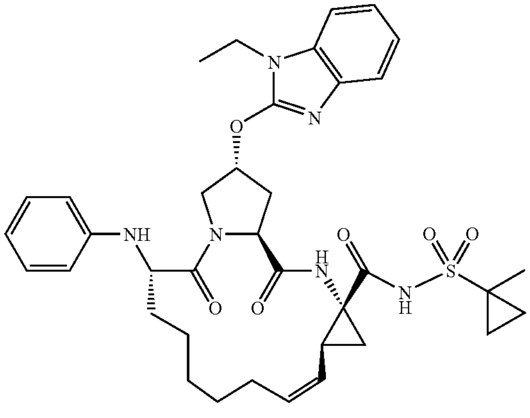
364
Compound 364 was prepared in a manner analogous to General Procedure DDD, to afford 25.2 mg (10%). MS (ESI) m/z $(M+H)^+$ MS: 731.3.
Example 23-26
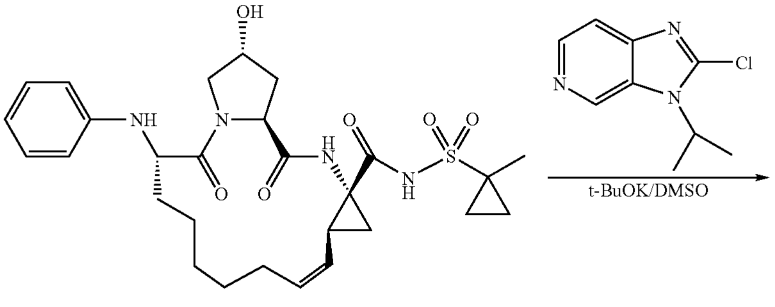
78
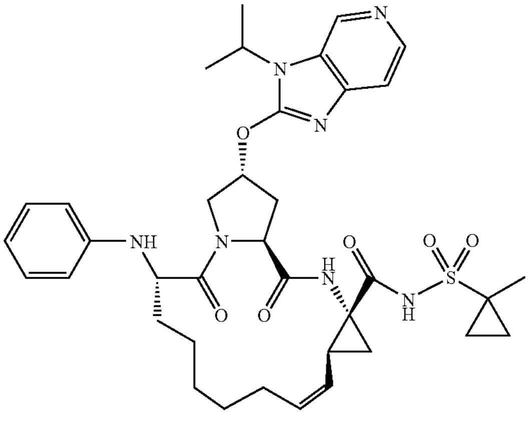
491

General Method DDDA

To a solution of compound 78 (150 mg, 0.27 mmol) in 3 mL of DMSO was added t-BuOK (182 mg, 1.62 mmol.) with ice water bath. The resulting mixture was stirred at this temperature for 0.5 h before the addition of 2-chloro-3-isopropyl-3 H-imidazo[4,5-c]pyridine (59 mg, 0.30 mmol.), and it was allowed to warm to room temperature slowly and stirred overnight. The reaction was quenched by water (10 mL), extracted with ethyl acetate, washed with brine, dried over $Na_2SO_4$, concentrated to get a residue, which was purified by Prep-HPLC to afford compound 491 (56.5 mg, 29%). MS (ESI) m/z $(M+H)^+$ 718.2.

Example 24

Scheme XXII: Synthesis of Compound 396

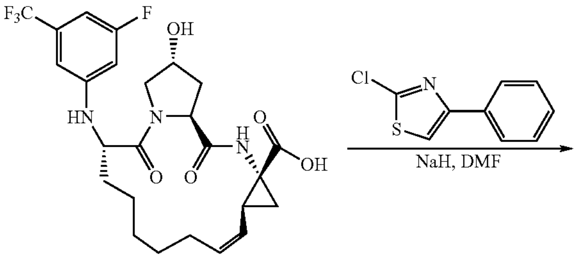

17

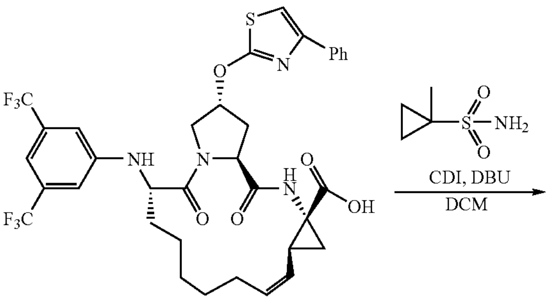

463

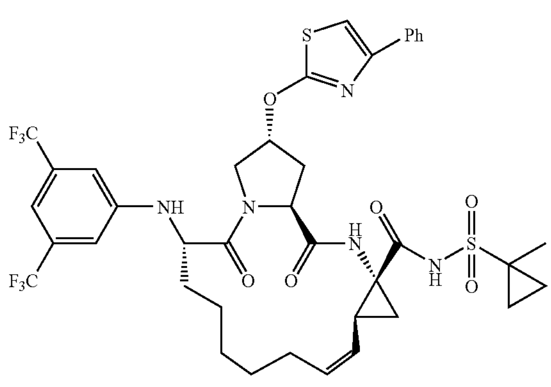

396

Compound 17 can be treated with a heteroaryl chloride, such as 2-chloro-4-phenylthiazole and the like, under basic conditions, for example sodium hydride in DMF, to afford compound 463. Compound 463 can be coupled with sulfonamides, (or sulfamides, not shown) to provide macrocycles, such compound 396.

Example 24-1

463

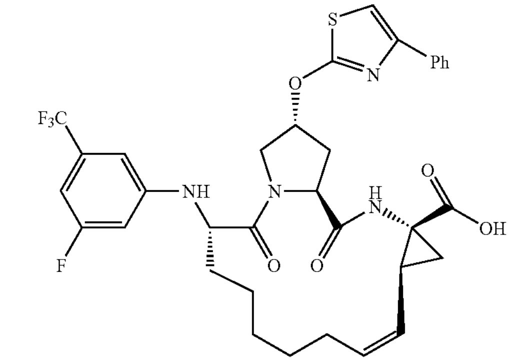

Compound 463 was prepared in a manner analogous to General Procedure B, to afford the desired product in 13.9% yield.

Example 24-2

396

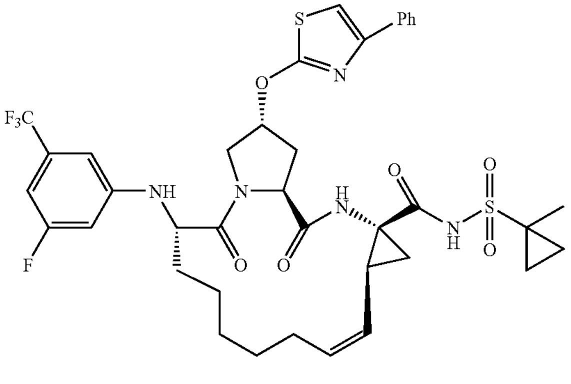

Compound 396 was prepared in a manner analogous to General Procedure F, to afford 5.6 mg (12.6%). MS (ESI) m/z $(M+H)^+$ 804.3.

EXAMPLE 25
Scheme XXIII: General Route for synthesis of Acylsulfonamides
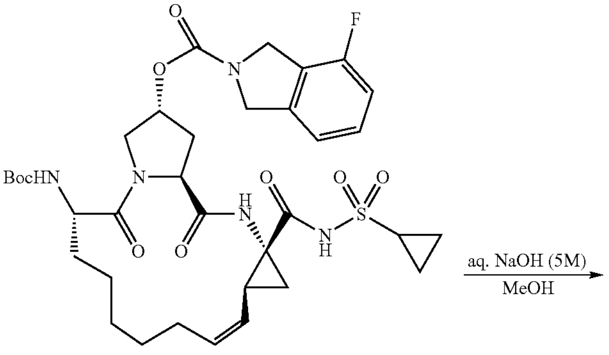
10
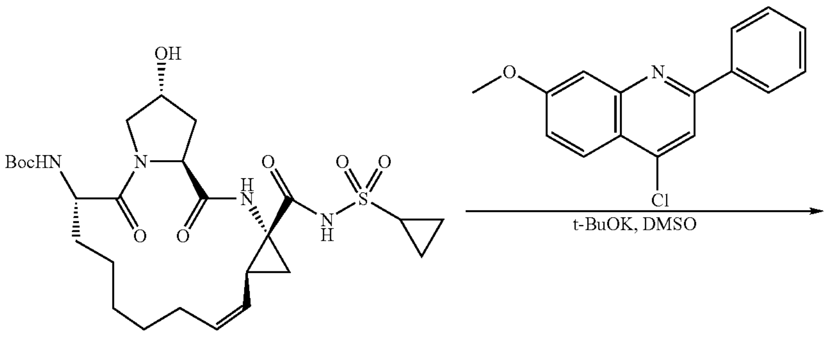
11
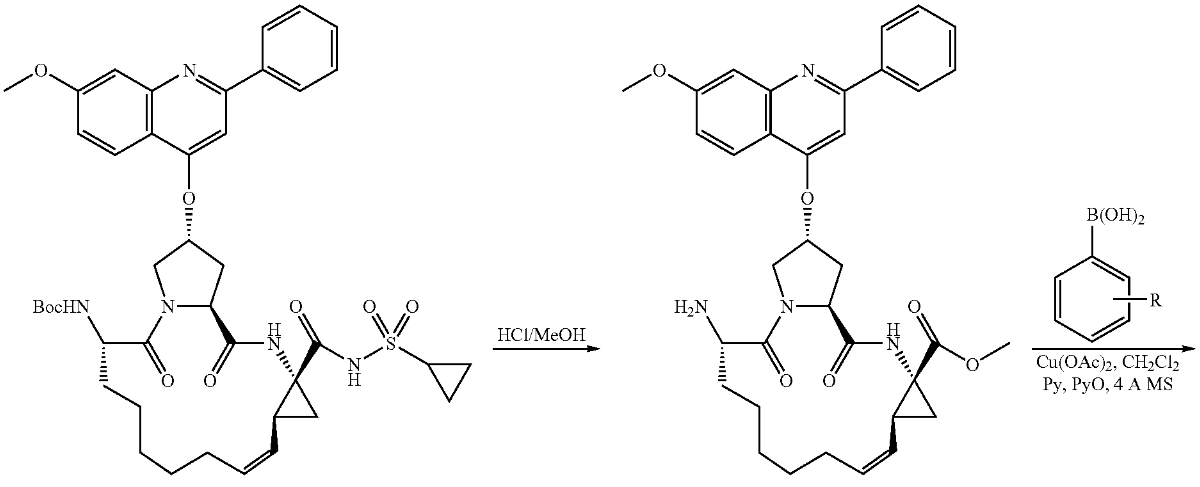
72
73

-continued

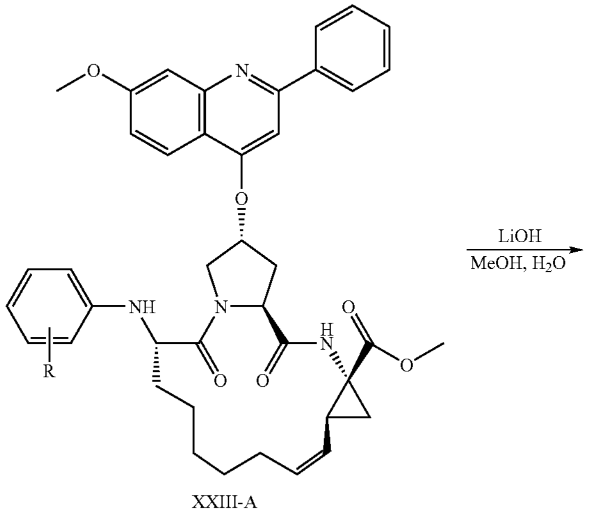

XXIII-A

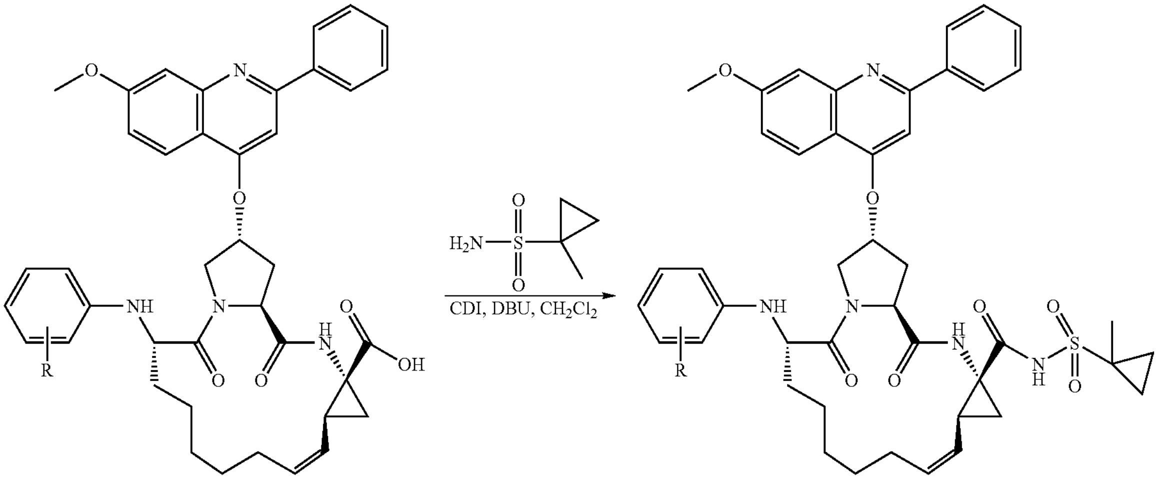

XXIII-B

XXIII-C

Macrocyclics of general structures XXIII-B and XXIII-C can be synthesized as shown in Scheme XXIII. The isoindoline carbamate 10 can be treated under basic conditions to hydrolyse the isoindoline carbamate thereby providing alcohol 11. The alcohol 11 can be treated with a heteroaryl chloride, such as 4-chloro-7-methoxy-2-phenylquinoline and the like, under basic conditions, for example sodium tert-butoxide in DMSO, to afford an heteroaryl ether, such as compound 72. The heteroaryl ether, such as compound 72 can be treated with acid in methanol to remove the Boc protecting group and form a methyl ester thereby providing an amino ester, such as compound 73. The an amino ester, such as compound 73, can be treated with optionally substituted aryl boronic acids under $Cu^{2+}$-catalyzed conditions thereby providing N-aryl compounds of general structure XXIII-A. The compounds of general structure XXIII-A can be treated under basic conditions, for example lithium hydroxide in methanol and water, to hydrolyse the methyl ester thereby providing carboxylic acids of general structure XXIII-B. Finally, acids of general structure XXIII-B can be coupled with sulfonamides (or sulfamides, not shown) thereby providing compounds general structure XXIII-C.

Example 25-1

General Procedure YY

11

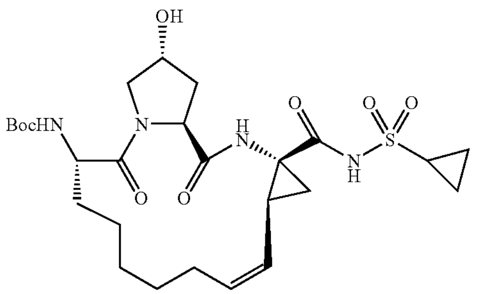

To a solution of compound 10 (10 g, 15.9 mmol.) in 100 mL of methanol was added aq. NaOH (5 M, 95 mL), the resulting mixture was heated to 50° C. and stirred overnight, The reaction was monitored by LCMS. After completion of the reaction, the mixture was cooled by ice water, acidified by aq. HCl (2 M) to pH=3-4, then the mixture was extracted by ethyl acetate (3×200 mL), the organic layers were combined, washed by brine, dried over anhydrous sodium sulfate, the solvent was removed under reduced pressure, the crude compound 11 was used directly in the next step (7.5 g, 83%).

Example 25-2

General Procedure ZZ

72

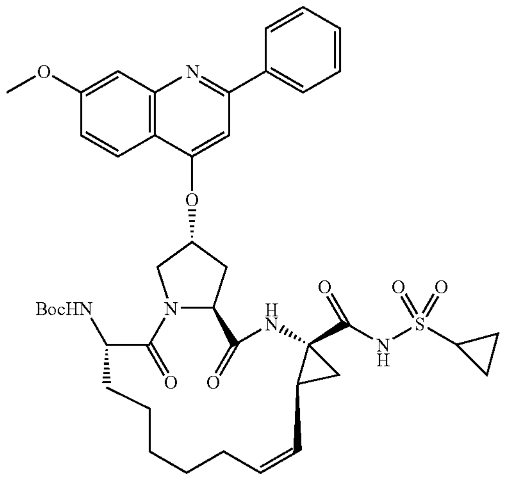

To a solution of compound 11 (4.0 g, 7 mmol.) in 4 mL of DMSO was added t-BuOK (6.0 g, 42 mmol.) in portions at ambient temperature, then the mixture was stirred for 2 h at ambient temperature. After that, 4-chloro-7-methoxy-2-phenylquinoline (2.8 g, 10.5 mmol.) was added, the resulting mixture was stirred at ambient temperature for 12 h, the reaction was monitored by LCMS. After completion of the reaction, the mixture was cooled by ice water, acidified by aq. HCl (2 M) to pH=8, then the mixture was extracted by ethyl acetate (3×100 mL), the organic layers were combined, washed by brine, dried over anhydrous sodium sulfate, solvent was removed under reduced pressure, the crude product was purified by column chromatography to afford compound 72 (3.0 g, 54%).

Example 25-3

General Procedure AAA

73

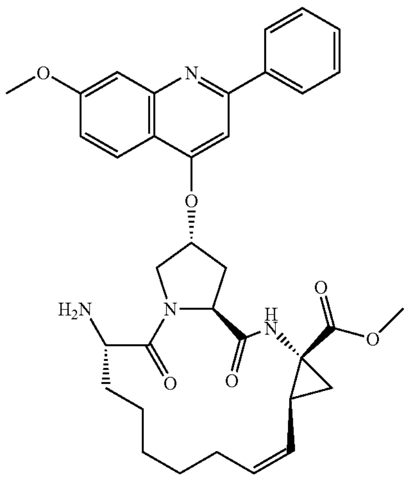

Compound 72 (1.2 g, 1.5 mmol.) was dissolved in a solution of HCl (gas) in MeOH (4 mol./L, 100 mL), the resulting mixture was stirred at room temperature for 12 h. After that, the solvent was evaporated, the mixture was basified by saturated aqueous $NaHCO_3$, then extract with ethyl acetate (3×50 mL), the organic layer was dried over anhydrous sodium sulfate, solvent was removed under reduced pressure, the crude compound 73 (910 mg, 99%) was used directly in the next step.

Example 25-4

6

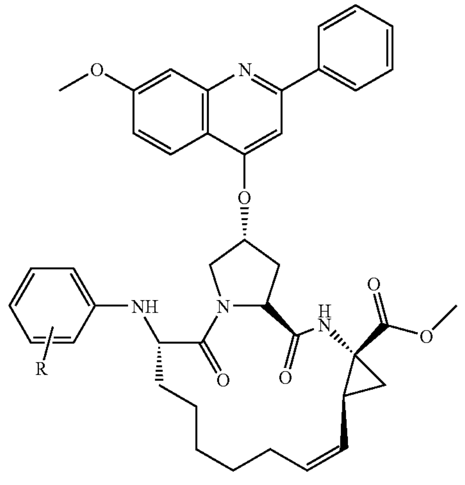

Aryl amines of general structure XXIII-A can be prepared, by coupling an optionally substituted arylboronic acid with compound 73 using a copper catalyst, as depicted in Scheme XXIII.

Example 25-5

7

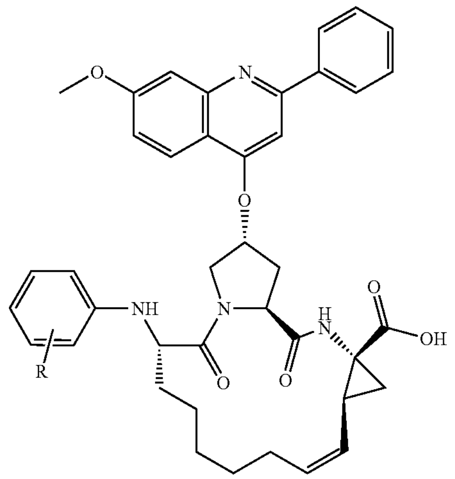

Carbocyclic acids of general structure XXIII-B can be prepared, by base catalyzed hydrolysis of the methyl ester of general structure XXIII-A, as depicted in Scheme XXIII.

Example 25-6

8

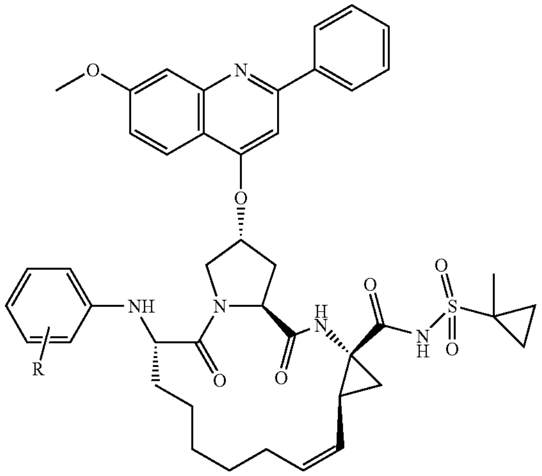

Acyl sulfonamides of general structure XXIII-C can be prepared, by coupling 1-methylcyclopropane-1-sulfonamide with carbocyclic acids of general structure XXIII-B as depicted in Scheme XXIII.

Example 25-7

229

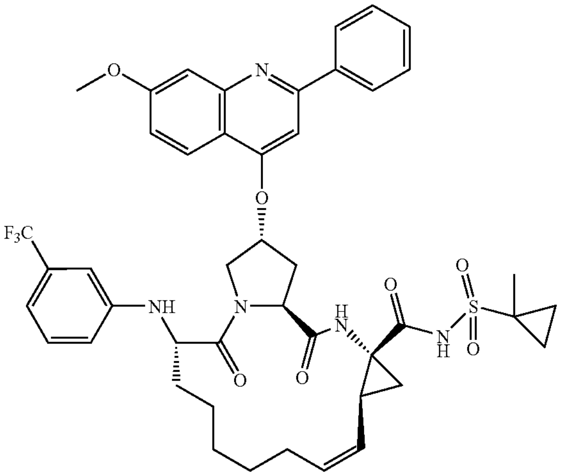

Compound 229 was prepared in a manner analogous to General Procedure F, to afford 58 mg (45%) of the desired compound. MS (ESI) m/z $(M+H)^+$ 860.2.

Example 25-8

355

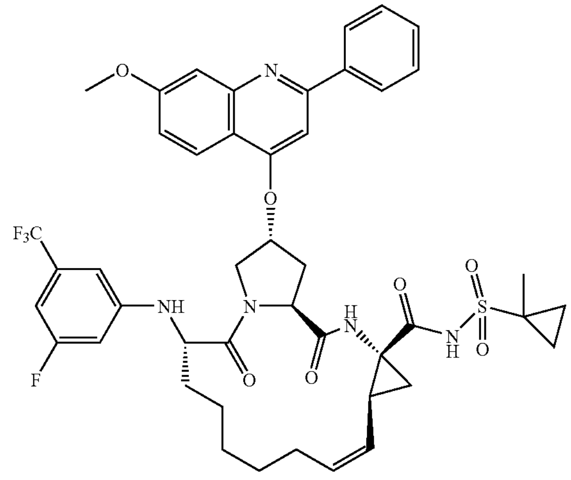

Compound 355 was prepared in a manner analogous to General Procedure F, to afford 127 mg (45%) of the desired compound. MS (ESI) m/z $(M+H)^+$ 878.2.

EXAMPLE 26

Scheme XXIV: General Route for synthesis of Acylsulfonamides

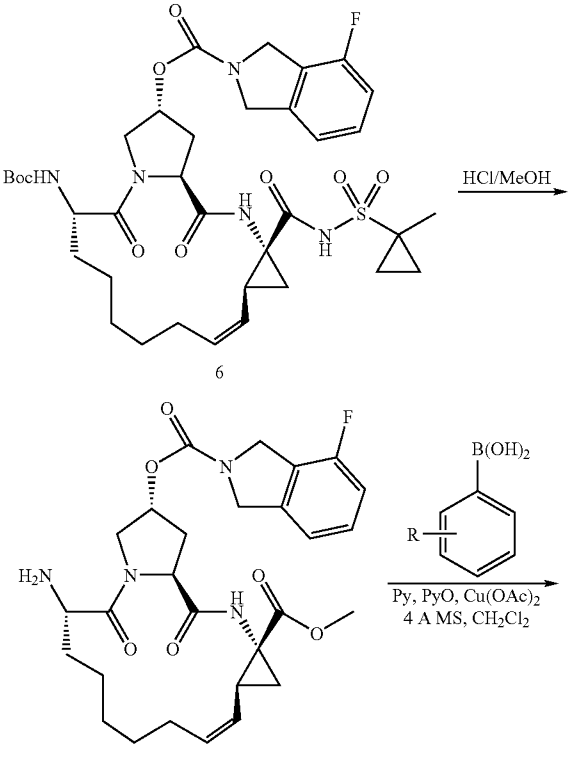

6

12

-continued

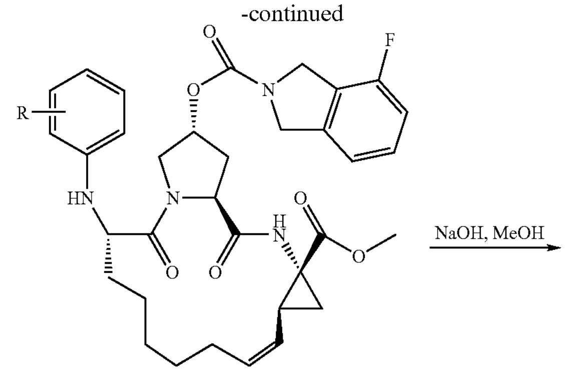

XXIV-A

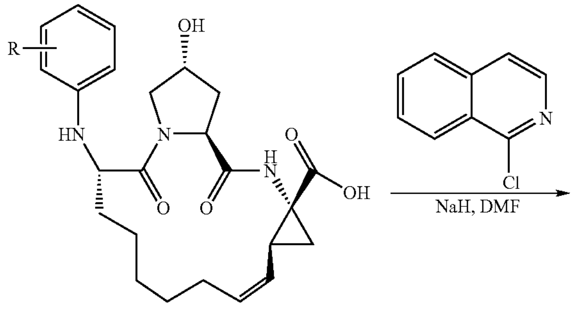

XXIV-B

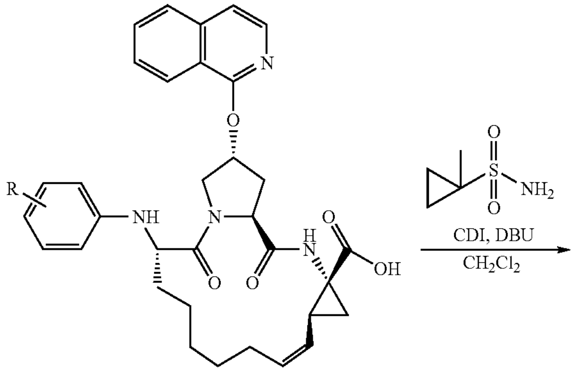

XXIV-C

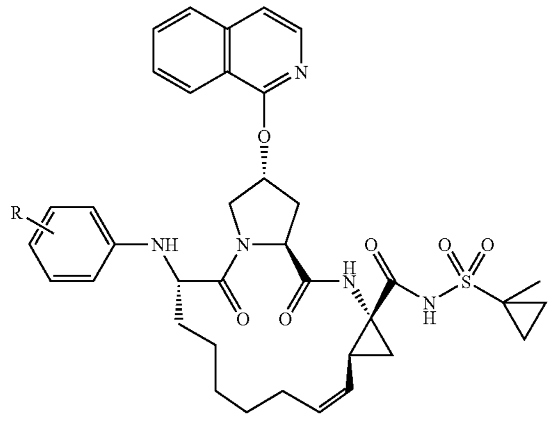

XXIV-D

Macrocyclics of general structures XXIV-C and XXIV-D can be synthesized as shown in Scheme XXIV. The isoindoline carbamate 6 can be treated with under acidic conditions, for example hydrochloric acid in methanol, to remove the Boc protecting group and form a methyl ester thereby providing compound 12. Compound 12 can be treated with optionally substituted aryl boronic acids under $Cu^{2+}$-catalyzed conditions thereby providing N-aryl compounds, such as compound having general structure XXIV-A. Compounds having general structure XXIV-A can be treated under basic conditions, for example aqueous sodium hydroxide in methanol, to hydrolyse the methyl ester and the isoindoline carbamate thereby providing a hydroxy acid having general structure XXIV-B. The hydroxy acid having general structure XXIV-B can be treated with a heteroaryl chloride, such as 1-chloro-isoquinoline and the like, under basic conditions, such as sodium hydride in DMF, to afford carboxylic acids having general structure XXIV-C. Finally, carboxylic acids having general structure XXIV-C can be coupled with sulfonamides (or sulfamides, not shown) thereby providing compounds general structure XXIV-D.

Example 26-1

12

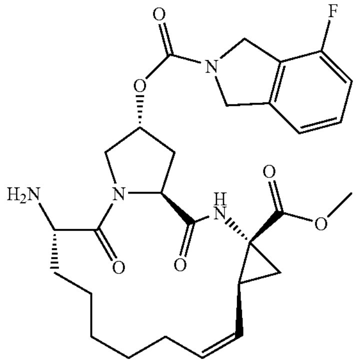

General Procedure BBB

Compound 6 (3 g) was dissolved in a solution HCl in MeOH (4 M, 100 mL), the resulting mixture was stirred at 25° C., the reaction was monitored by LCMS, after completion of the reaction, the solvent was removed, the HCl salt of amino ester 12 was obtained.

Example 26-2

XXIV-A

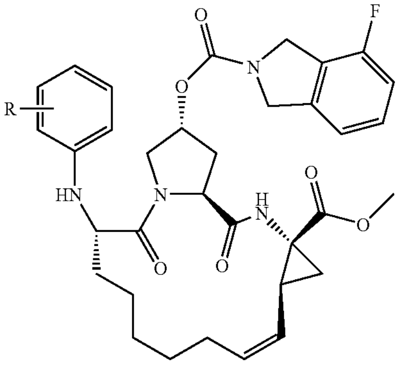

Aryl amines of general structure XXIV-A can be prepared, by coupling an optionally substituted arylboronic acid with compound 12 using a copper catalyst, as depicted in Scheme XXIV.

Example 26-3

XXIV-B

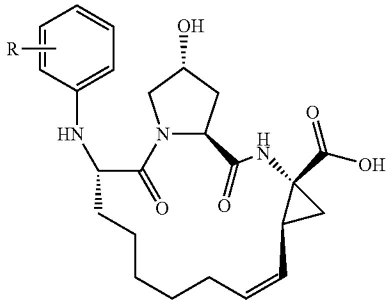

Carboxylic acid alcohols of general structure XXIV-B can be prepared, by base catalyzed hydrolysis of both the isoindoline carbamate and methyl ester of general structure XXIV-A, as depicted in Scheme XXIV.

Example 26-4

XXIV-C

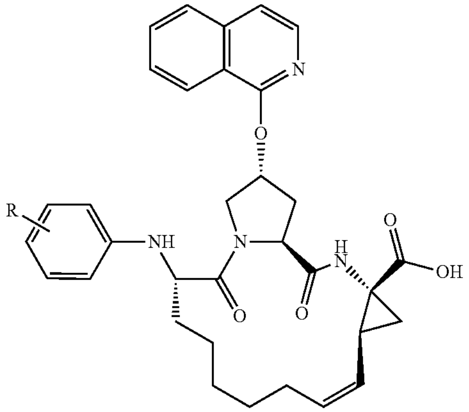

Carboxylic acids of general structure XXIV-C can be prepared, by base catalyzed coupling of carboxylic acid alcohols of general structure XXIV-B with 1-chloroisoquinoline, as depicted in Scheme XXIV.

Example 26-5

XXIV-D

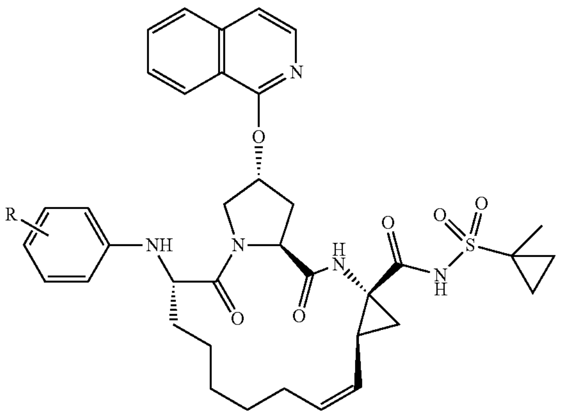

Acyl sulfonamides of general structure XXIV-D can be prepared, by coupling 1-methylcyclopropane-1-sulfonamide with carbocyclic acids of general structure XXIV-C, as depicted in Scheme XXIV.

Example 26-6

346

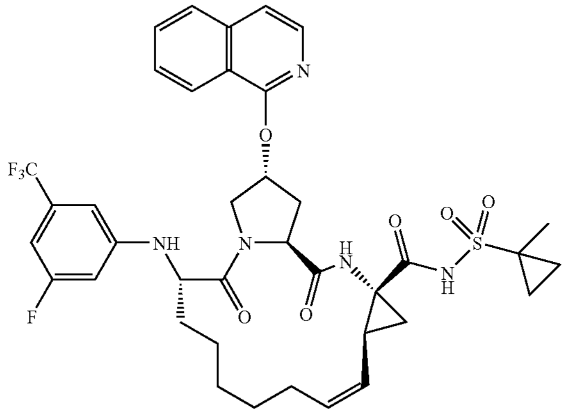

Compound 346 was prepared in a manner analogous to General Procedure F, to afford 45 mg (26%) of the desired compound. MS (ESI) m/z $(M+H)^+$ 772.2.

Example 26-7

444

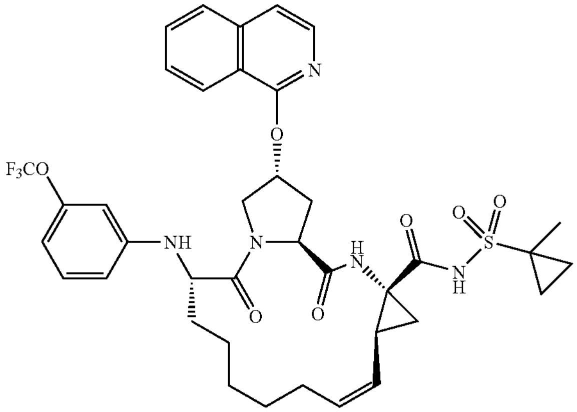

Compound 444 was prepared in a manner analogous to General Procedure F, to afford 28.1 mg (16%) of the desired compound. MS (ESI) m/z $(M+H)^+$ 770.1.

EXAMPLE 27
Scheme XXV: General Route for synthesis of Acylsulfonamides
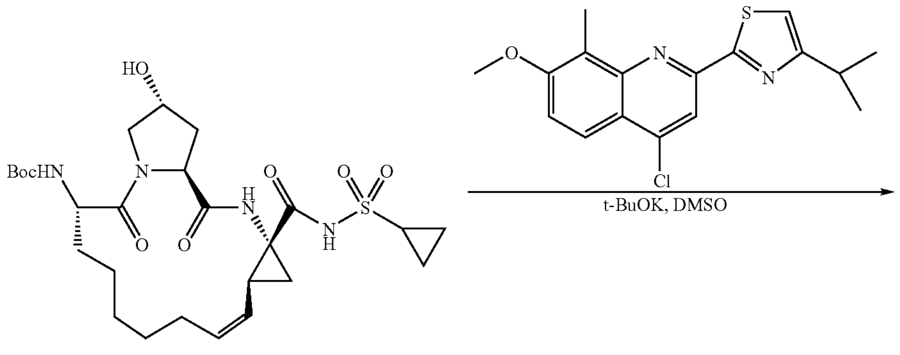
11
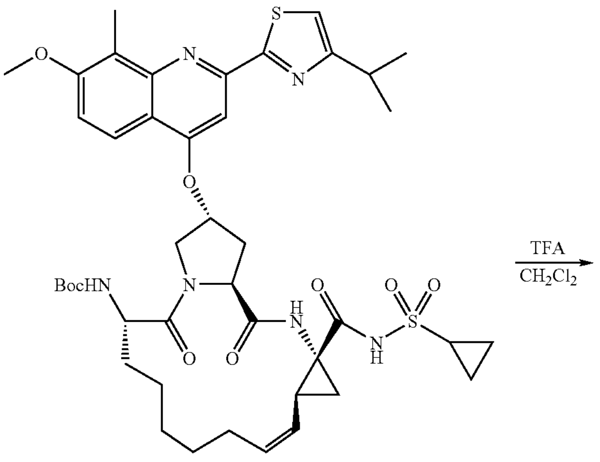
75
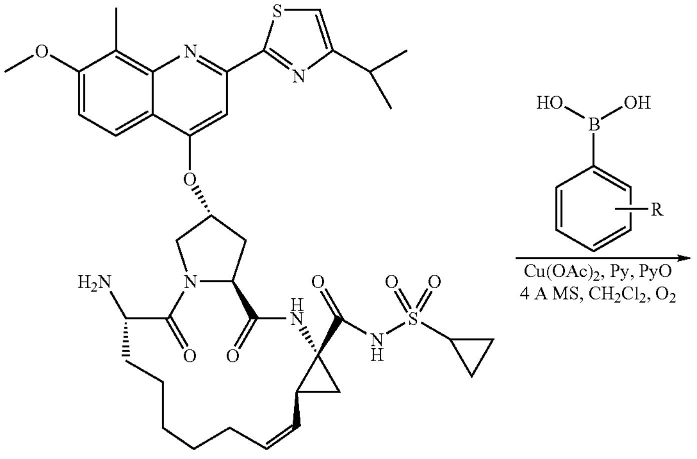
76

-continued

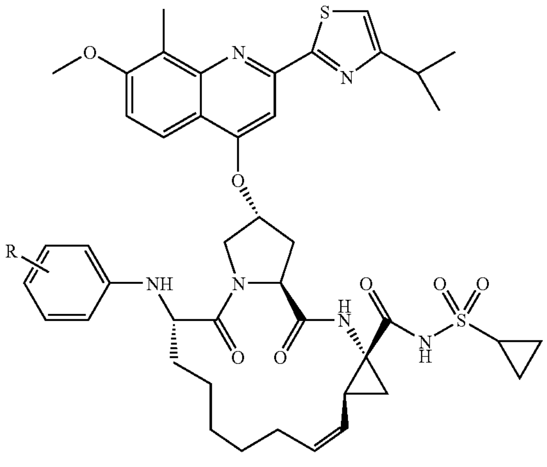

XXV-A

Macrocyclics of general structures XXV-A can be synthesized as shown in Scheme XXV. Alcohol 11 can be treated with a heteroaryl chloride, such as 4-chloro-2-(4-isopropylthiazol-2-yl)-7-methoxy-8-methylquinoline and the like, under basic conditions, for example sodium tert-butoxide in DMSO, to afford a heteroaryl ether, such as compound 75. The heteroaryl ether, such as compound 75, can be treated under acidic conditions, for example TFA in DCM, to remove the Boc protecting group thereby providing an amino acylsulfonamide, such as compound 76. The amino acylsulfonamide, such as compound 76, can be treated with optionally substituted aryl boronic acids under $Cu^{2+}$-catalyzed conditions thereby providing macrocycles of general structure XXV-A.

Example 27-1

General Procedure CCC

75

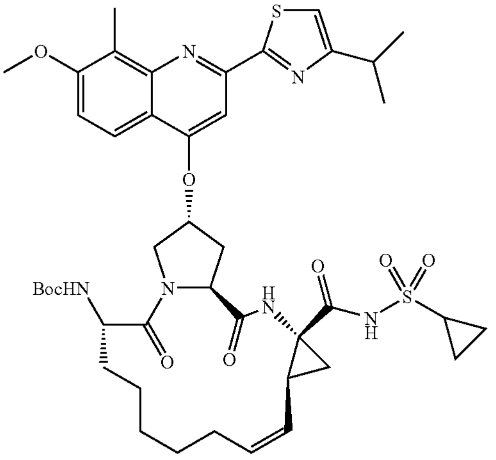

To a solution of compound 11 (570 mg, 1 mmol.) in 4 mL of DMSO was added t-BuOK (732 mg, 6 mmol.) portionwise at ambient temperature, then the mixture was stirred for 2 h at ambient temperature, after that, compound 4-chloro-2-(4-isopropylthiazol-2-yl)-7-methoxy-8-methylquinoline (400 mg, 1.2 mmol.) was added, the resulting mixture was stirred at ambient temperature for 12 h. The reaction was monitored by LCMS, after completion of the reaction, The mixture was cooled by ice water, acidified by aq. HCl (2 M) to pH=8, then the mixture was extracted by ethyl acetate (3×50 mL), the organic layers were combined, washed by brine, dried over anhydrous sodium sulfate, solvent was removed under reduced pressure, the crude product was purified by column chromatography, 430 mg (85% purity) of compound 75 was obtained (yield 42%).

Example 27-2

76

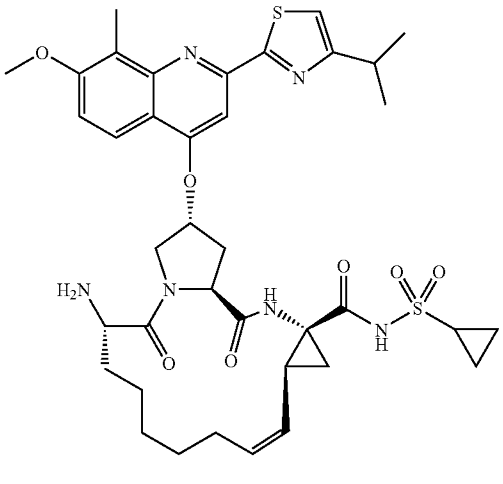

Compound 76 is prepared in a manner analogous to General Procedure S.

464

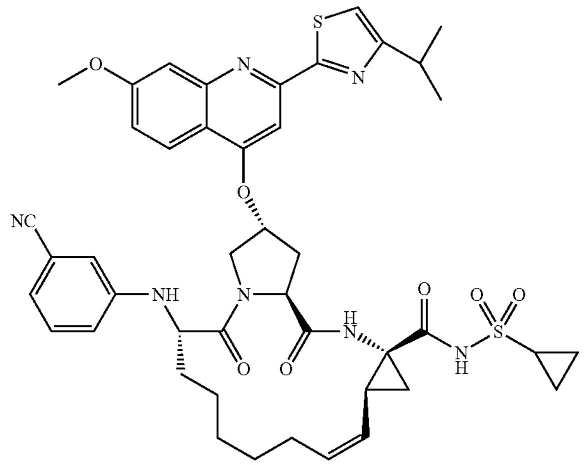

Example 27-3

Compound 464 was prepared in a manner analogous to General Procedure D, to afford 154 mg (32%). MS (ESI) m/z $(M+H)^+$ 866.4.

EXAMPLE 28

Scheme XXVI

Synthesis of N-aryl & P4 Quinoline Analogs

General Procedure EEE

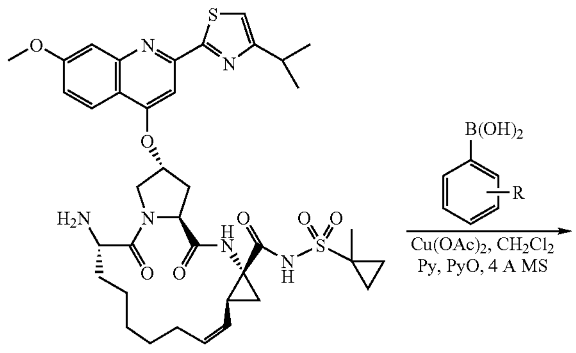

9

-continued

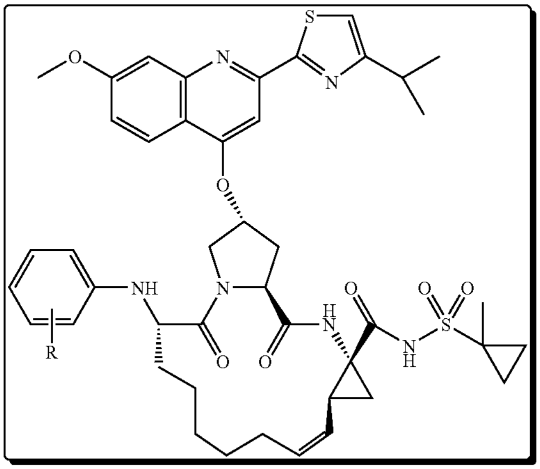

XXVI-A

A mixture of compound 9 (1 eq.), boronic acid (3 eq.), $Cu(OAc)_2$ (2 eq.), pyridine (10 eq.), pyridine N-Oxide (2 eq.) and molecular sieves 4 A in dichloromethane (5 mL) was stirred for 12 h at room temperature under an atmosphere of oxygen. The reaction was monitored by LC-MS. After completion of the reaction, the reaction mixture was diluted with ethyl acetate and filtered. The filtrate was washed with brine, dried over anhydrous sodium sulfate, concentrated in vacuo. The residue was purified by prep-HPLC to give general compound XXVI-A.

Example 28-1

472

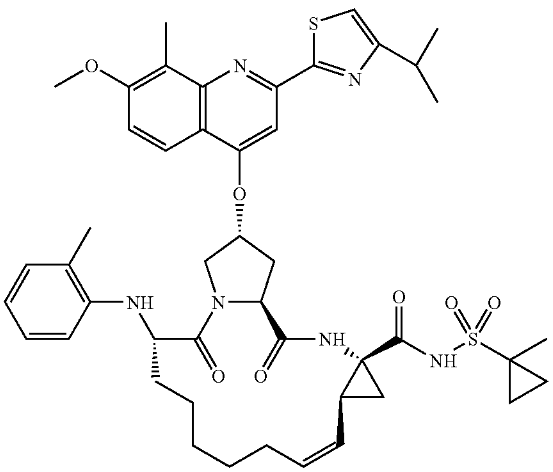

Compound 472 was prepared in a manner analogous to General Procedure EEE, to afford 5.5 mg (9.8%). MS (ESI) m/z $(M+H)^+$ 869.3.

473

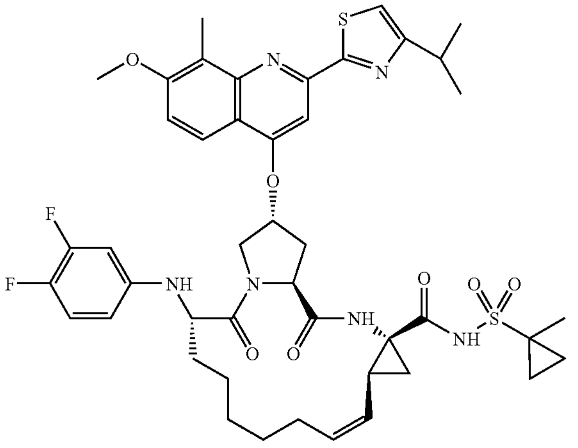

Example 28-2

Compound 473 was prepared in a manner analogous to General Procedure EEE, to afford 8.0 mg (14%). MS (ESI) m/z $(M+H)^+$ 891.3.

Example 28-3

474

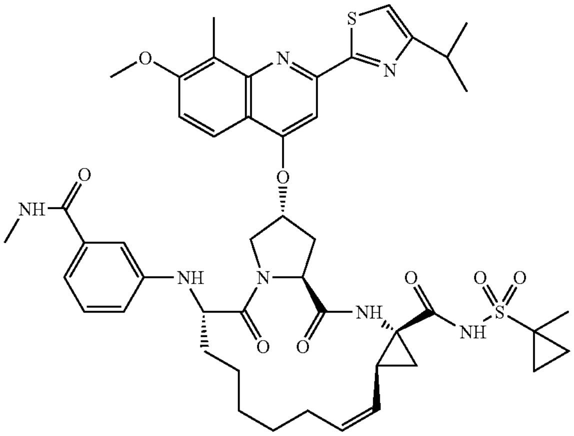

Compound 474 was prepared in a manner analogous to General Procedure EEE, to afford 5.5 mg (9.4%). MS (ESI) m/z $(M+H)^+$ 912.3.

475

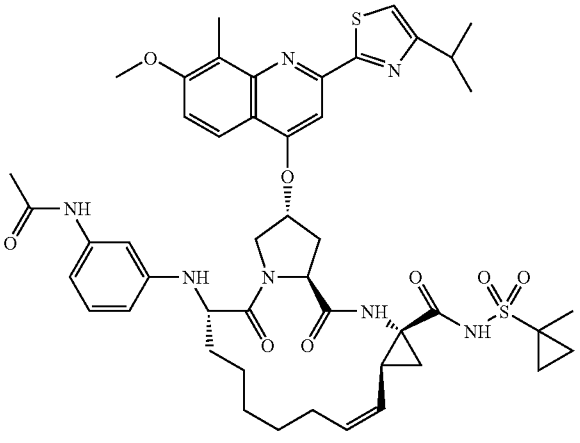

Example 28-4

Compound 475 was prepared in a manner analogous to General Procedure EEE, to afford 5.6 mg (9.6%). MS (ESI) m/z $(M+H)^+$ 912.3.

476

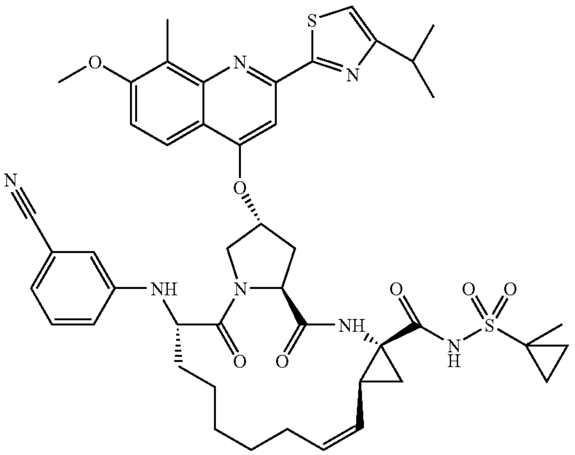

Example 28-5

Compound 476 was prepared in a manner analogous to General Procedure EEE, to afford 5.6 mg (6.4%). MS (ESI) m/z $(M+H)^+$ 880.1.

477

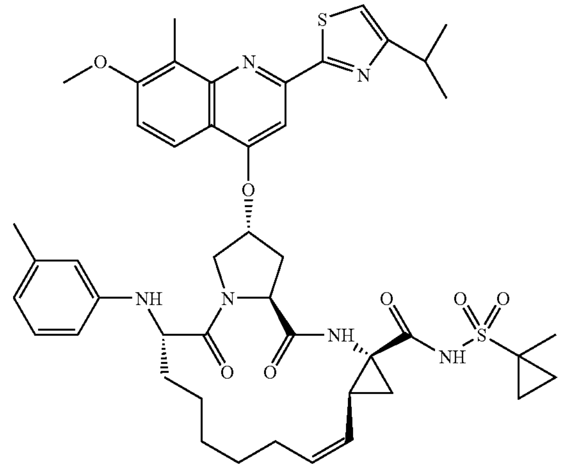

Example 28-6

Compound 477 was prepared in a manner analogous to General Procedure EEE, to afford 5.4 mg (9.7%). MS (ESI) m/z $(M+H)^+$ 869.2.

Example 28-7

478

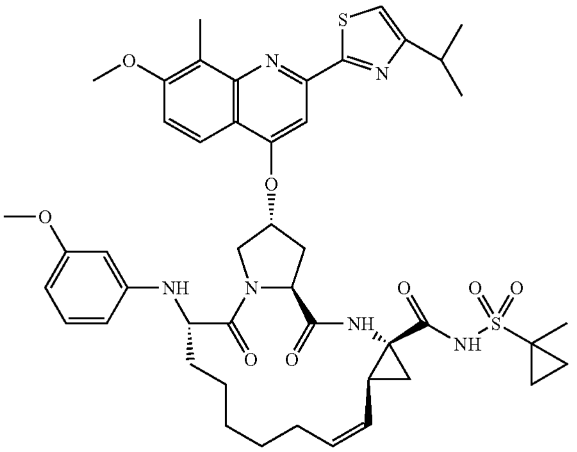

Compound 478 was prepared in a manner analogous to General Procedure EEE, to afford 5.5 mg (9.7%). MS (ESI) m/z $(M+H)^+$ 885.3.

Example 28-8

479

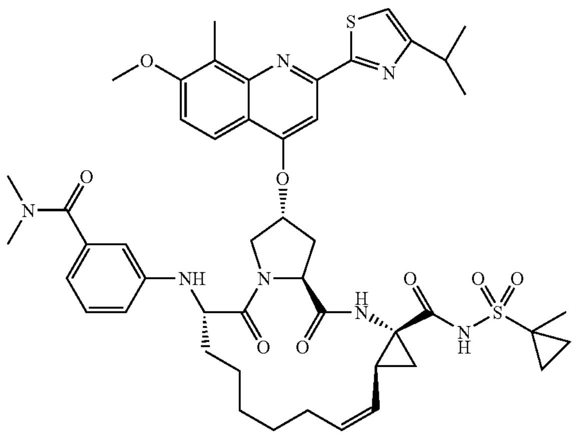

Compound 479 was prepared in a manner analogous to General Procedure EEE, to afford 22 mg (37%). MS (ESI) m/z $(M+H)^+$ 926.3.

480

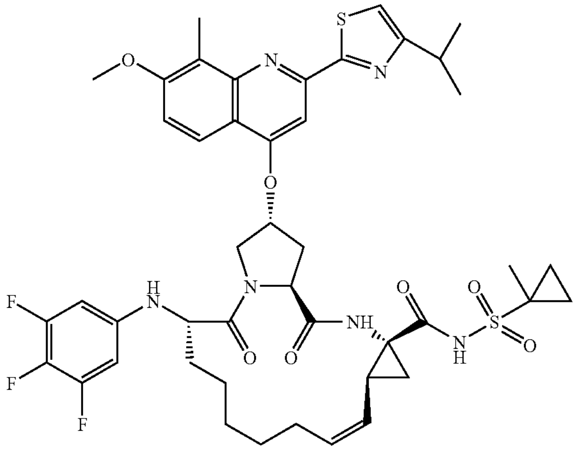

Example 28-9

Compound 480 was prepared in a manner analogous to General Procedure EEE, to afford 14.6 mg (17%). MS (ESI) m/z $(M+H)^+$ 908.9.

481

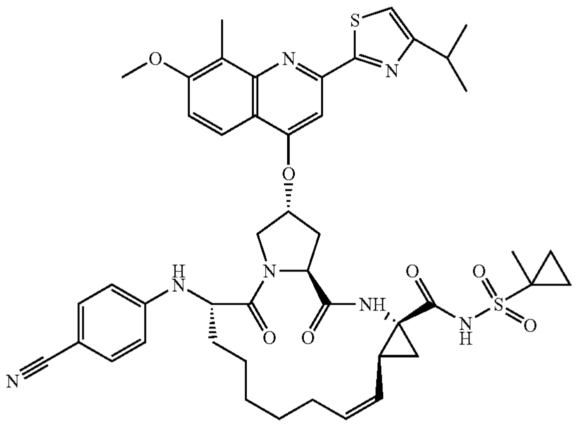

Example 28-10

Compound 481 was prepared in a manner analogous to General Procedure EEE, to afford 19.7 mg (23%). MS (ESI) m/z $(M+H)^+$ 879.9.

Example 28-11

482

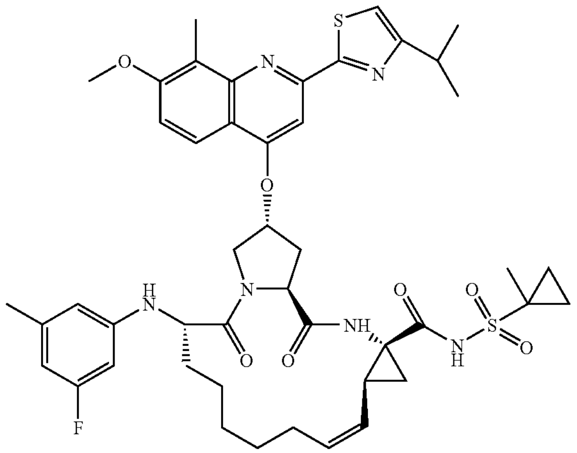

Compound 482 was prepared in a manner analogous to General Procedure EEE, to afford 17.6 mg, 22%. MS (ESI) m/z $(M+H)^+$ 887.

Example 28-12

483

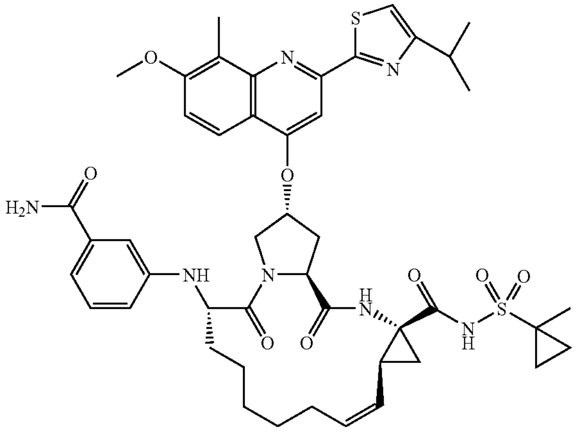

Compound 483 was prepared in a manner analogous to General Procedure EEE, to afford 9 mg (15%). MS (ESI) m/z $(M+H)^+$ 898.4.

Example 28-13

484

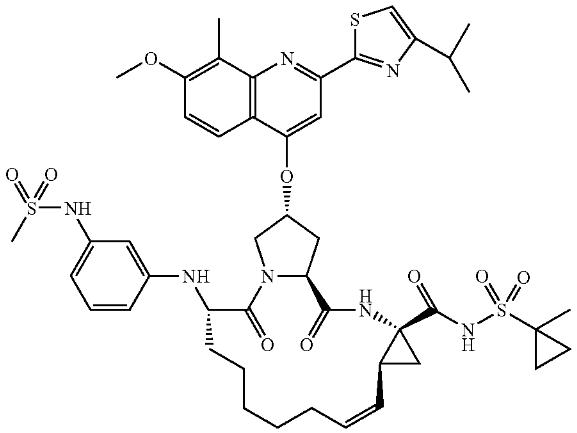

Compound 484 was prepared in a manner analogous to General Procedure EEE, to afford 29.1 mg (48%). MS (ESI) m/z $(M+H)^+$ 947.9.

Example 28-14

485

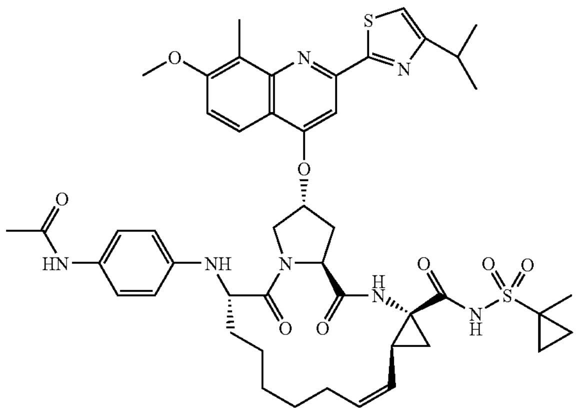

Compound 485 was prepared in a manner analogous to General Procedure EEE, to afford 20.1 mg, (34%). MS (ESI) m/z $(M+H)^+$ 912.

Example 28-15

492

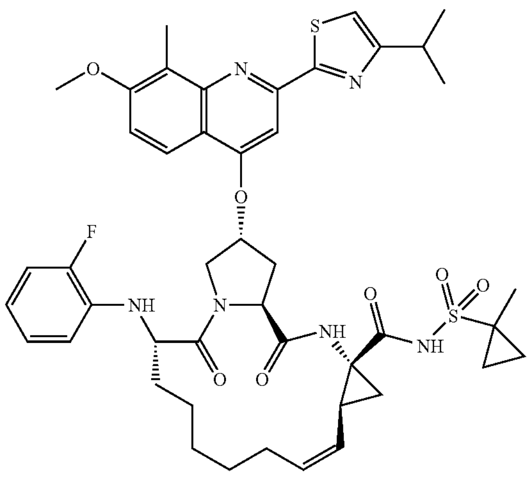

Compound 492 was prepared in a manner analogous to General Procedure EEE, to afford 12.9 mg (15% yield). MS (ESI) m/z $(M+H)^+$ 873.4.

Example 28-16

493

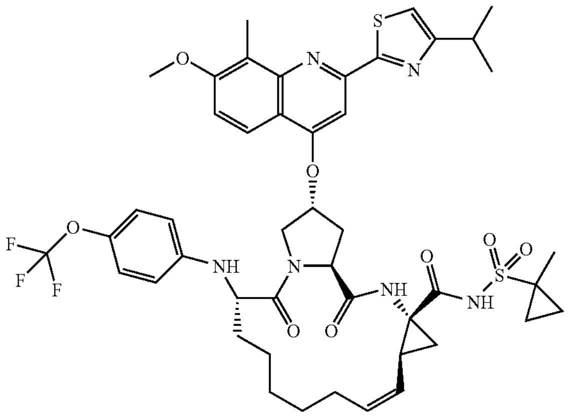

Compound 493 was prepared in a manner analogous to General Procedure EEE, to afford 5.8 mg (6.4% yield). MS (ESI) m/z $(M+H)^+$ 939.3.

EXAMPLE 29

Scheme XXVII

Synthesis Quinoxalene Analogs

Example 29-1

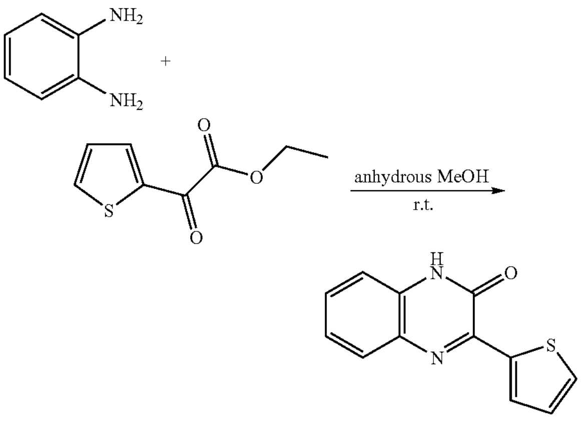

A mixture of o-phenylenediamine (2.16 g, 20 mmol) and ethyl thiophene-2-glyoxylate (3.68 g, 20 mmol.) in anhydrous methanol (60 mL) was stirred at room temperature for 12 hours under nitrogen atmosphere. The precipitate formed during this time was collected and washed with methanol to give a crude yellow solid, which was recrystallized from ethanol to give pure 3(2-thienyl)quinoxalin-2(1 H)-one (3.2 g, 70%). $^1H$ NMR (400 MHz, DMSO-$d_6$) δ 12.7 (s, 1 H), 8.39

(d, J=4.4 Hz, 1 H), 7.83 (d, J=5.2 Hz, 1 H), 7.77 (d, J=8.0 Hz, 1H), 7.50 (t, J=7.6 Hz, 1H), 7.35~7.29 (m, 1 H), 7.22 (t, J=4.8 Hz, 1 H).

Example 29-2

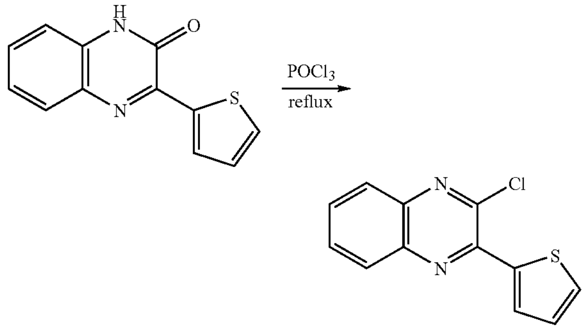

A mixture of 3-(2-thienyl)quinoxalin-2(1 H)-one (500 mg, 2.19 mmol.) and $POCl_3$ (6 mL) was heated to reflux at 120° C. After the material was consumed, the reaction mixture was taken up with water and ice. The solid was collected and dried in vacuo to give 2-chloro-3-(2-thienyl)quinoxaline (400 mg, 74%). $^1$H NMR (400 MHz, $CDCl_3$) δ 8.22 (d, J=4.8 Hz, 1 H), 8.00 (d, J=10.4 Hz, 1 H), 7.91 (d, J=10.4 Hz, 1 H), 7.72~7.61 (m, 2 H), 7.52 (d, J=6.8 Hz, 1 H), 7.13 (t, J=6.0 Hz, 1 H).

Example 29-4

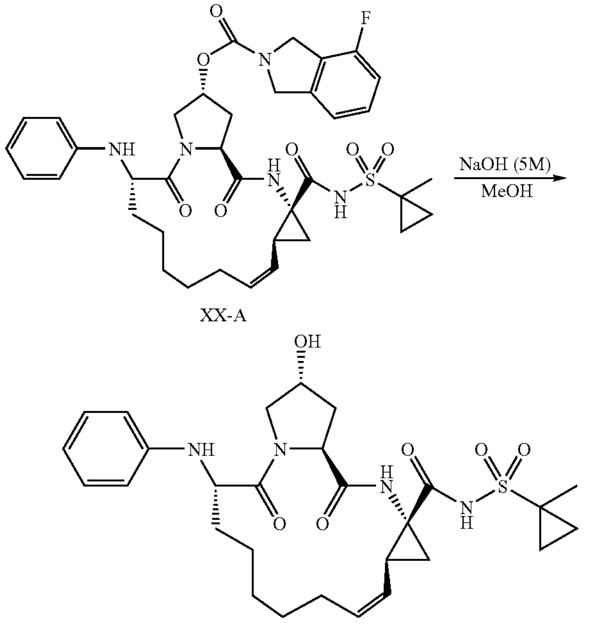

XX-A

74

Compound 74 can be formed in a manner analogous to the procedure for forming general compound XX-B.

Example 29-4

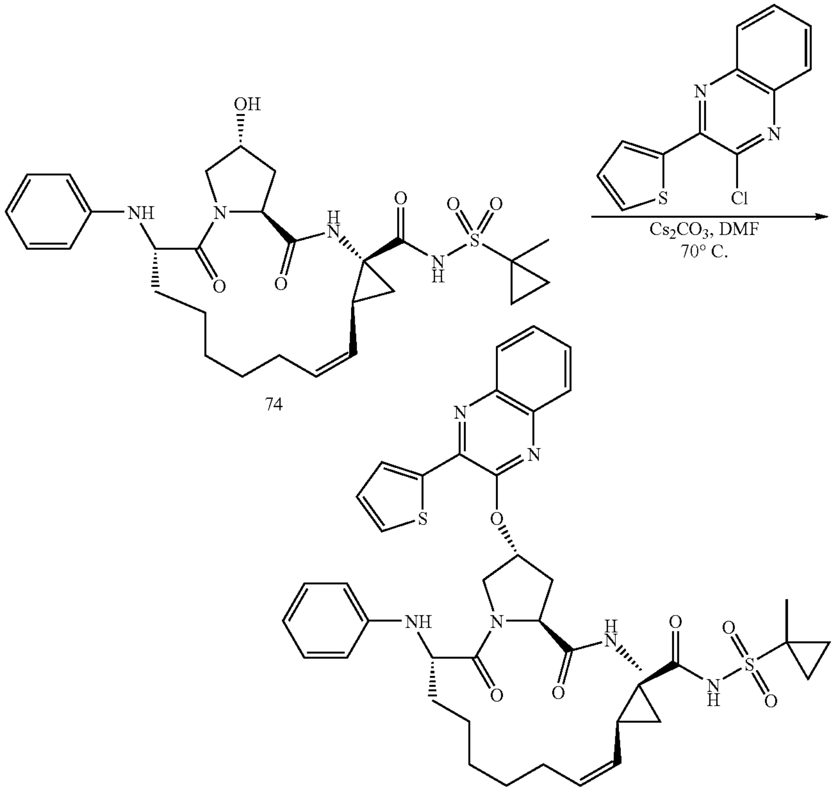

74

486

To a solution of intermediate 74 (140 mg, 0.25 mmol) in 3 ml of dry DMF was added $Cs_2CO_3$ (407 mg, 1.25 mmol) and 2-chloro-3-(2-thienyl)quinoxaline (74 mg, 0.3 mmol). The resulting mixture was stirred at 70° C. overnight. The reaction was quenched by water (10 ml), extract by ethyl acetate, washed with brine 70° C., dried over $Na_2SO_4$, concentrated to get a residue, which was purified by prep-HPLC to give compound 486 (56.4 mg, 27.4%). $^1$H NMR (400 MHz, $CDCl_3$+$D_2O$) δ 10.84 (d, J=8.8 Hz, 2 H), 7.71 (d, J=12.0 Hz, 1 H), 7.56 (m, 2 H), 7.34 (d, J=8.2 Hz, 2 H), 7.0 (m, 1 H), 6.76 (t, J=10.6 Hz, 2 H), 6.42 (m, 3 H), 5.98 (s, 1 H), 5.68 (m, 1 H), 4.95 (t, J=12.6 Hz, 1 H), 4.55 (d, J=12 Hz, 1 H), 4.57 (t, J=10.0 Hz, 1 H), 4.16 (m, 3 H), 2.50 (m, 3 H), 2.14 (m, 1 H), 1.72-1.93 (m, 5 H), 1.18-1.51 (m, 1 H). MS (ESI) m/z $(M+H)^+$ 768.9.

TABLE 1

Examples of compounds that can be prepared according to Examples 1-29

| Compound | Structure |
| --- | --- |
| 101 | 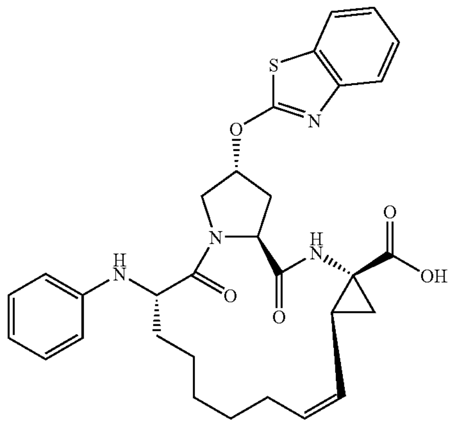 |
| 102 | 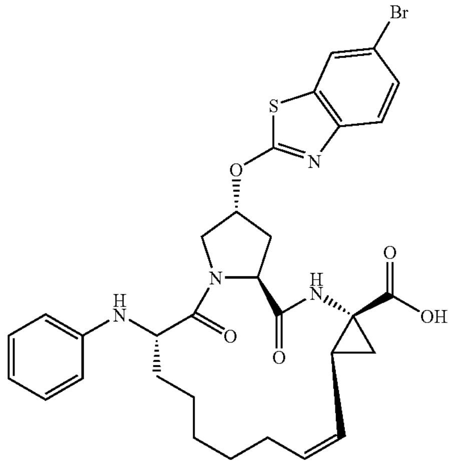 |
| 103 | 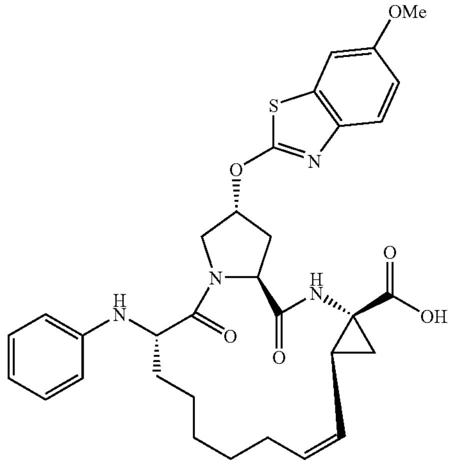 |

TABLE 1-continued
| Examples of compounds that can be prepared according to Examples 1-29 | |
|---|---|
| Compound | Structure |
| 104 | 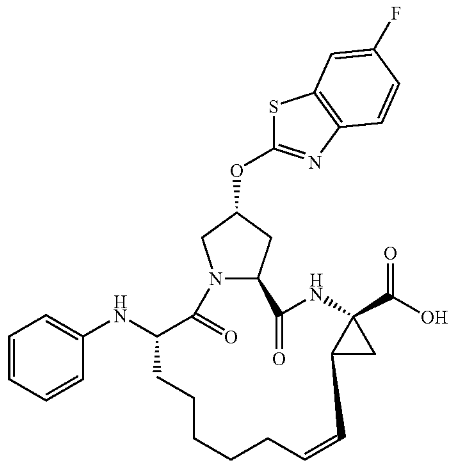 |
| 105 | 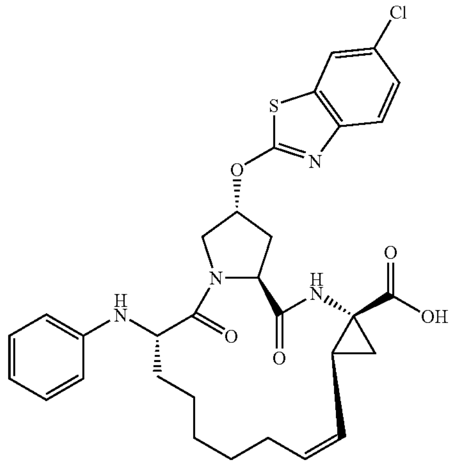 |
| 106 | 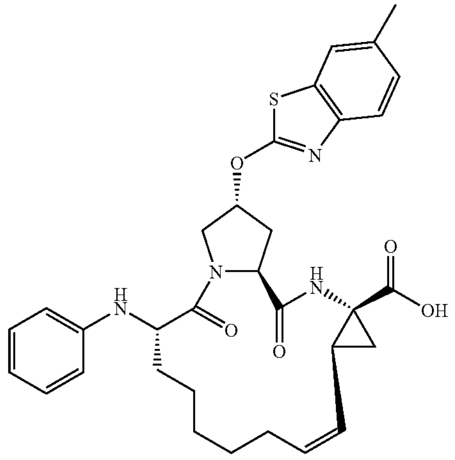 |

TABLE 1-continued
| Examples of compounds that can be prepared according to Examples 1-29 | |
|---|---|
| Compound | Structure |
| 107 | 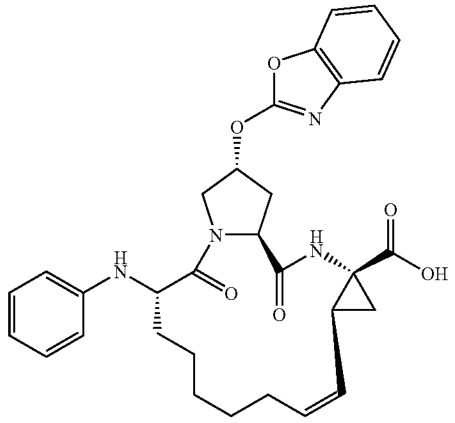 |
| 108 | 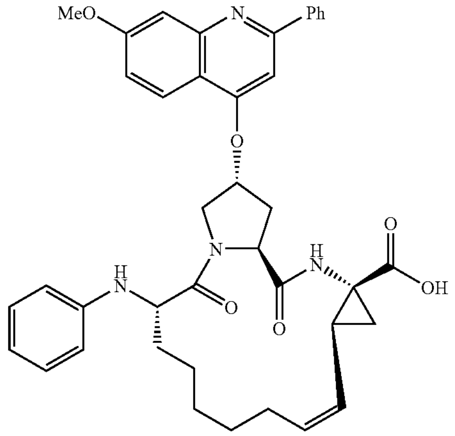 |
| 109 | 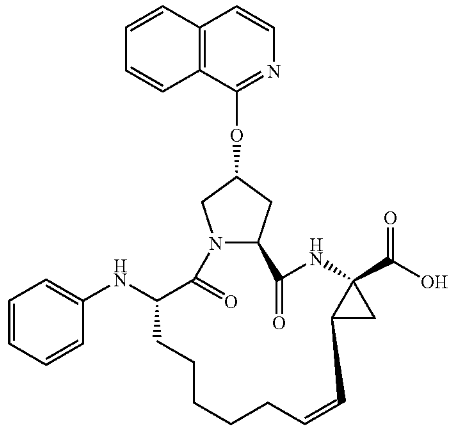 |

TABLE 1-continued
Examples of compounds that can be prepared according to Examples 1-29
| Compound | Structure |
| --- | --- |
| 110 | 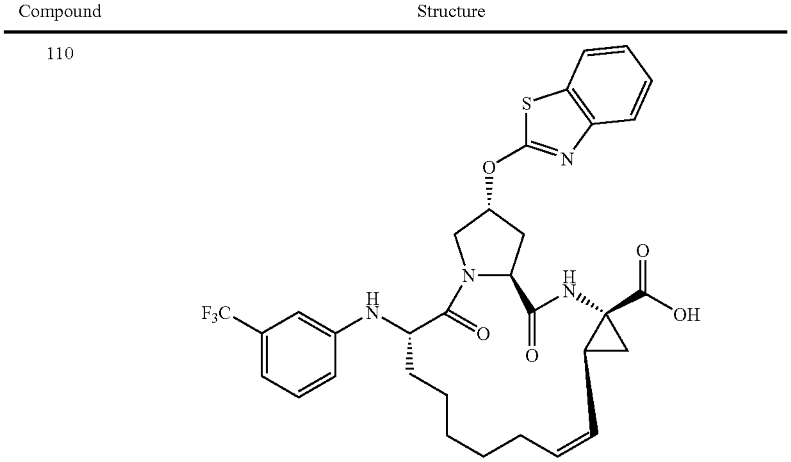 |
| 111 | 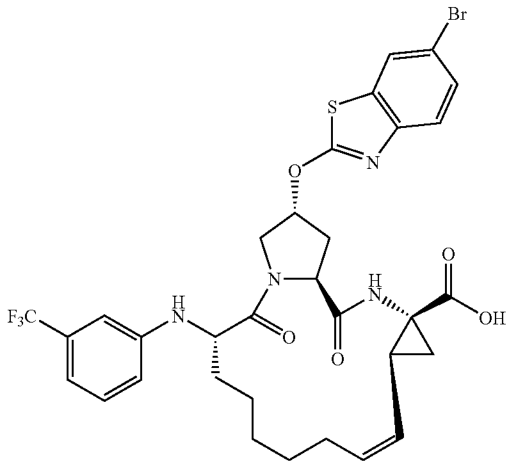 |
| 112 | 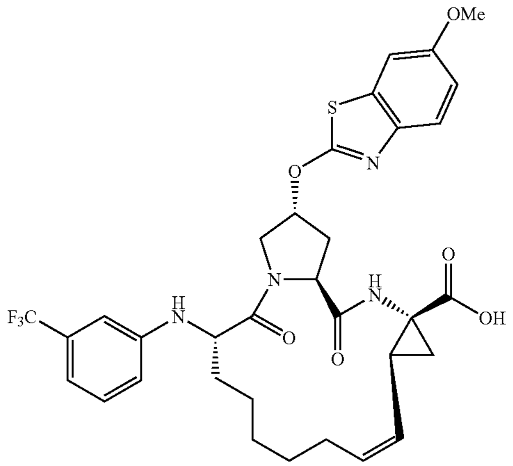 |

TABLE 1-continued
| Examples of compounds that can be prepared according to Examples 1-29 | |
|---|---|
| Compound | Structure |
| 113 | 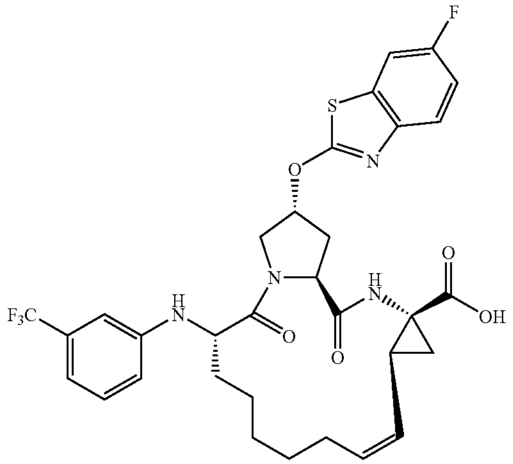 |
| 114 | 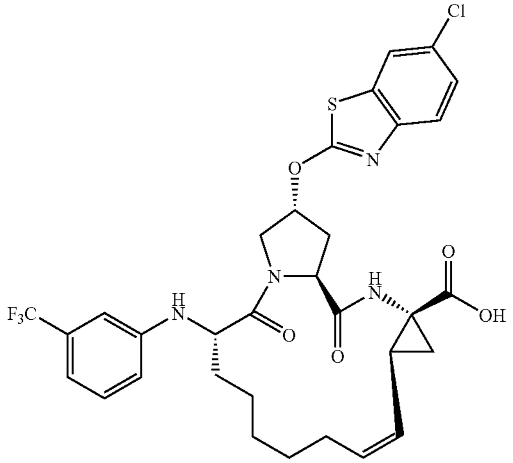 |
| 115 | 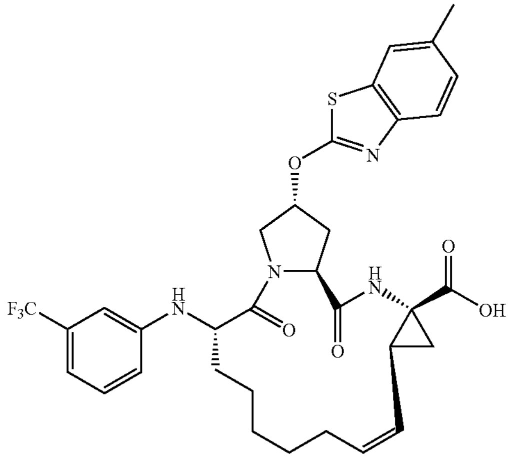 |

TABLE 1-continued
| Examples of compounds that can be prepared according to Examples 1-29 | |
|---|---|
| Compound | Structure |
| 116 | 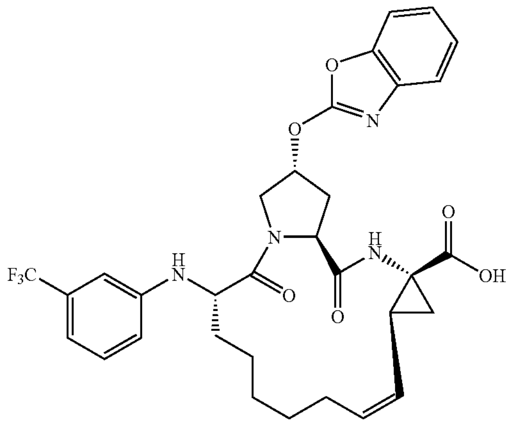 |
| 117 | 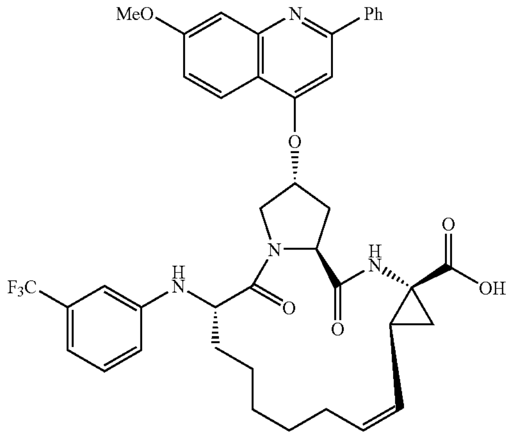 |
| 118 | 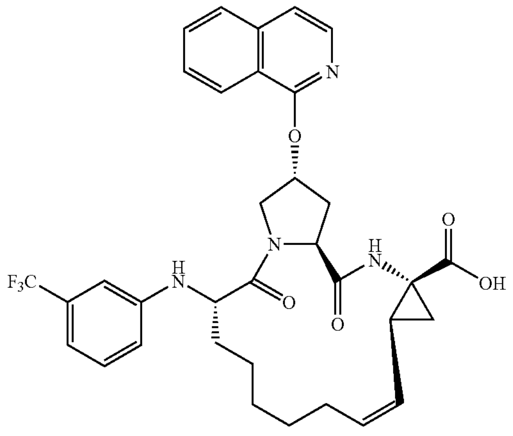 |

TABLE 1-continued
| Examples of compounds that can be prepared according to Examples 1-29 | |
|---|---|
| Compound | Structure |
| 119 | 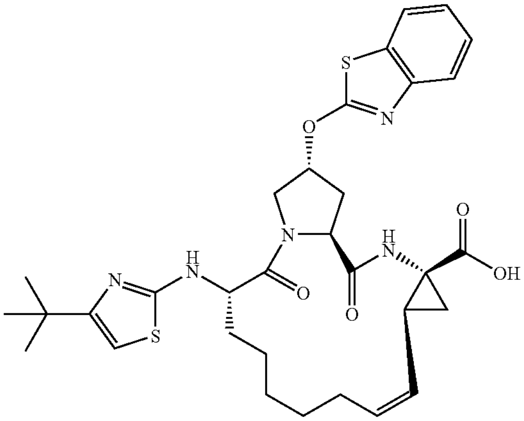 |
| 120 | 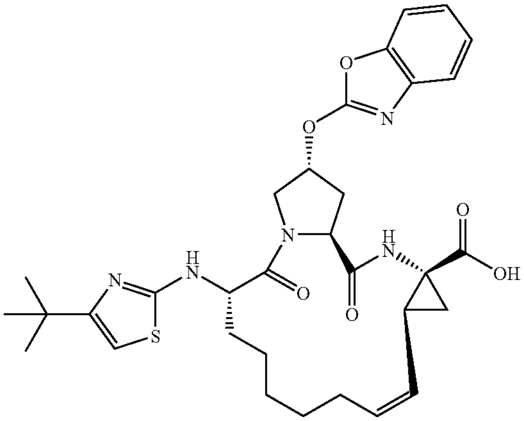 |
| 121 | 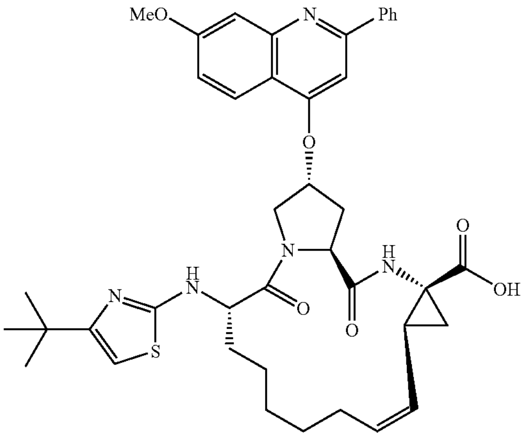 |

TABLE 1-continued
| Compound | Structure |
| --- | --- |
| 122 | 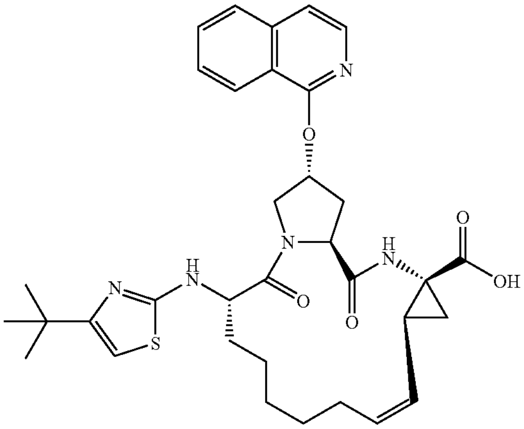 |
| 123 | 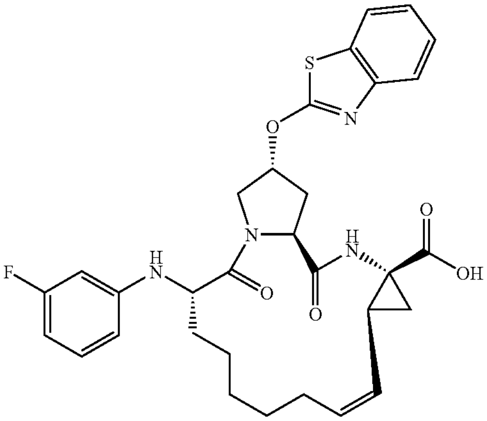 |
| 124 | 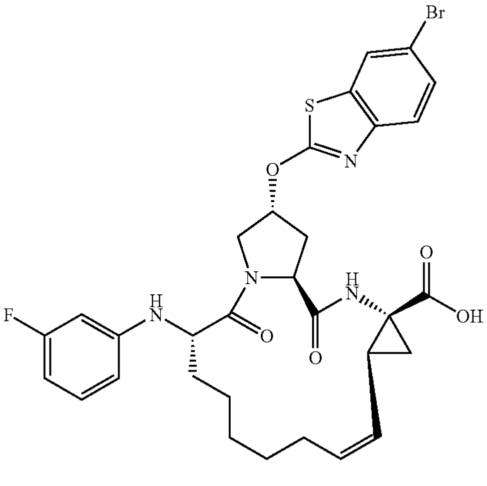 |
Examples of compounds that can be prepared according to Examples 1-29

TABLE 1-continued
| Examples of compounds that can be prepared according to Examples 1-29 | |
|---|---|
| Compound | Structure |
| 125 | 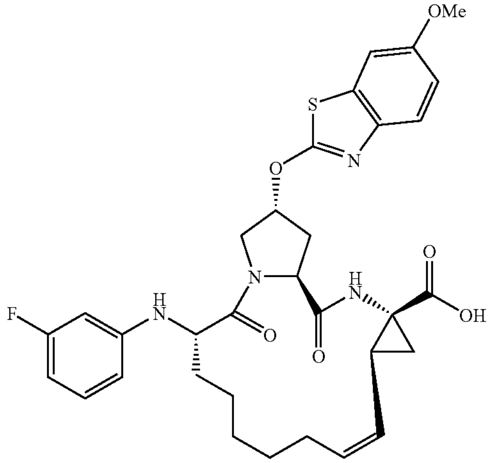 |
| 126 | 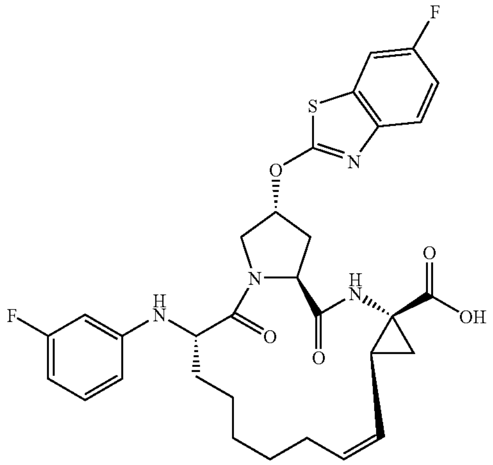 |
| 127 | 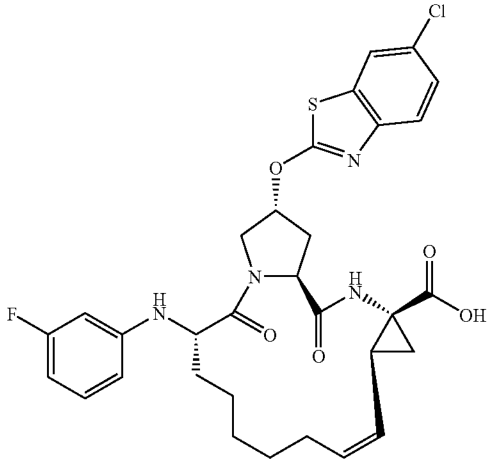 |

TABLE 1-continued
| Examples of compounds that can be prepared according to Examples 1-29 | |
|---|---|
| Compound | Structure |
| 128 | 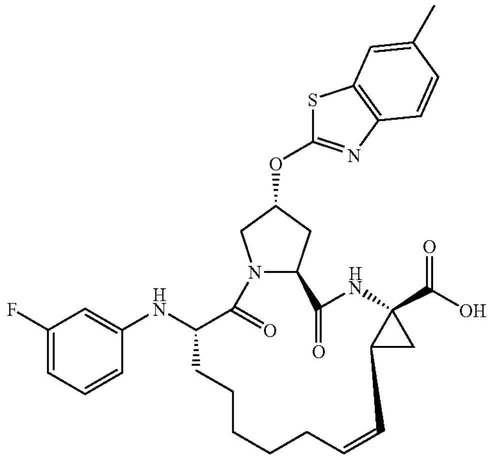 |
| 129 | 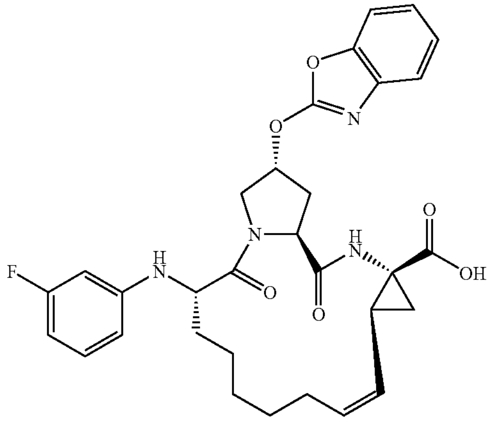 |
| 130 | 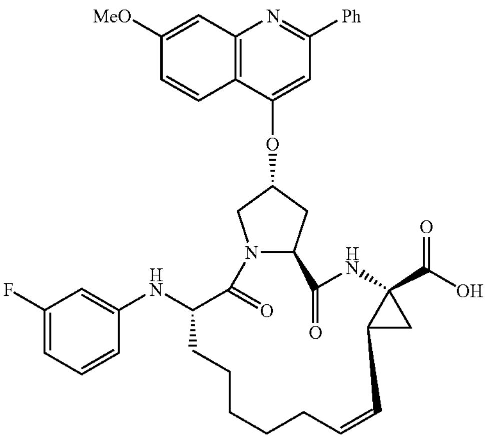 |

TABLE 1-continued
| Examples of compounds that can be prepared according to Examples 1-29 | |
|---|---|
| Compound | Structure |
| 131 | 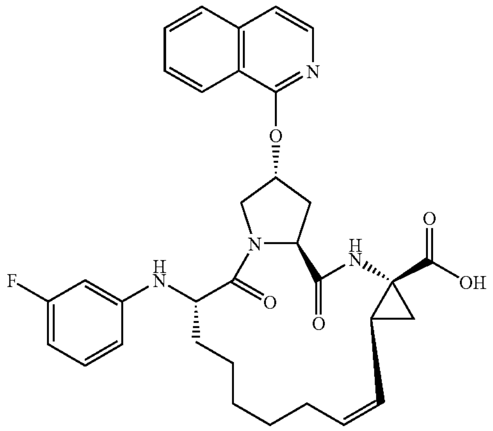 |
| 132 | 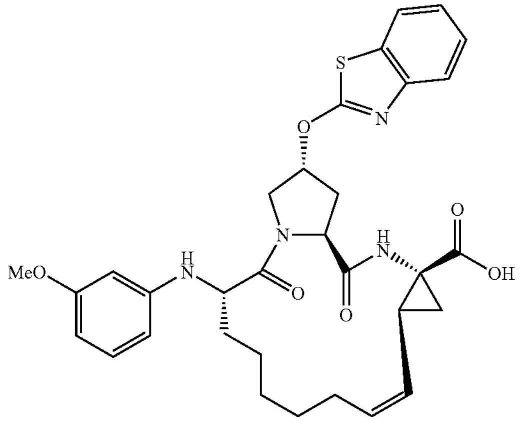 |
| 133 | 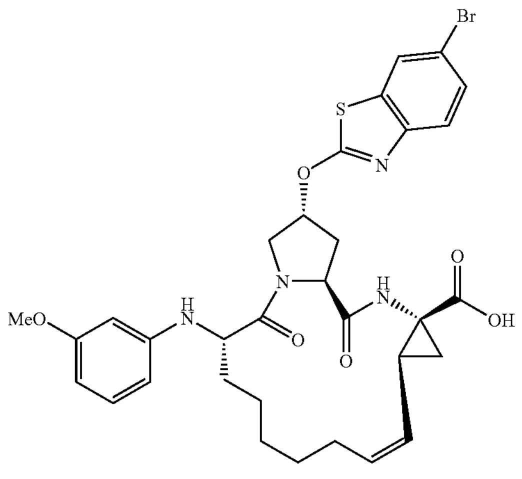 |

TABLE 1-continued
| Examples of compounds that can be prepared according to Examples 1-29 | |
|---|---|
| Compound | Structure |
| 134 | 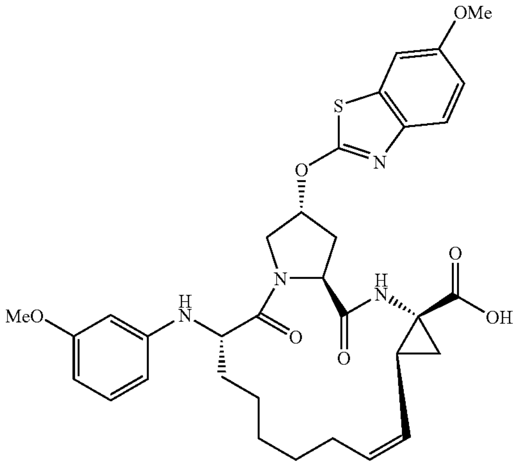 |
| 135 | 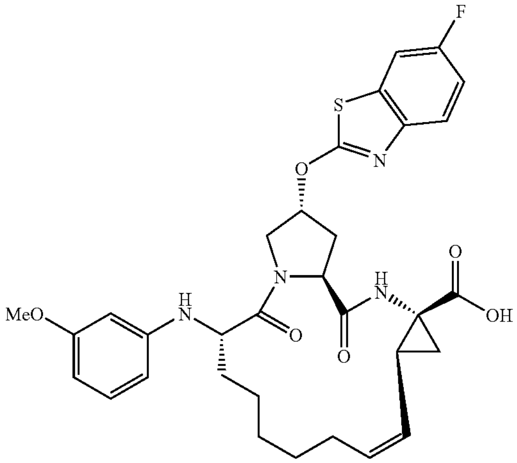 |
| 136 | 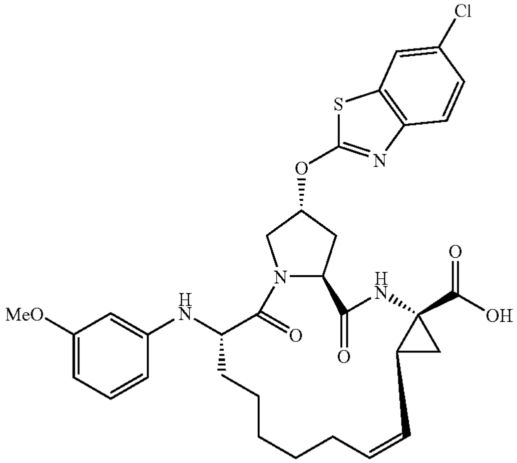 |

TABLE 1-continued
| Examples of compounds that can be prepared according to Examples 1-29 | |
|---|---|
| Compound | Structure |
| 137 | 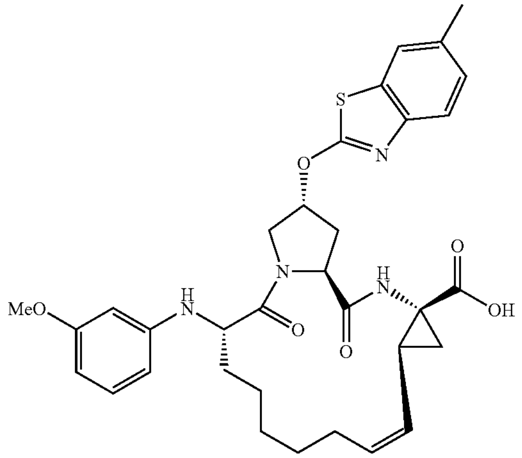 |
| 138 | 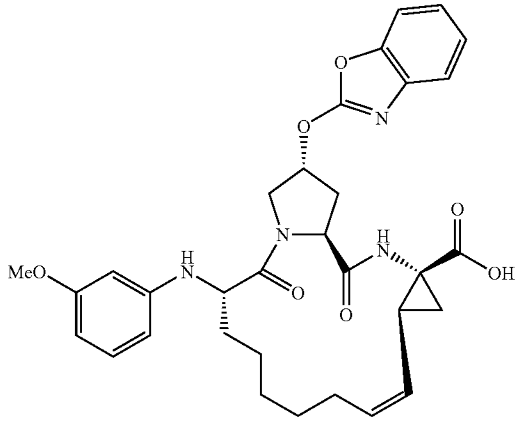 |
| 139 | 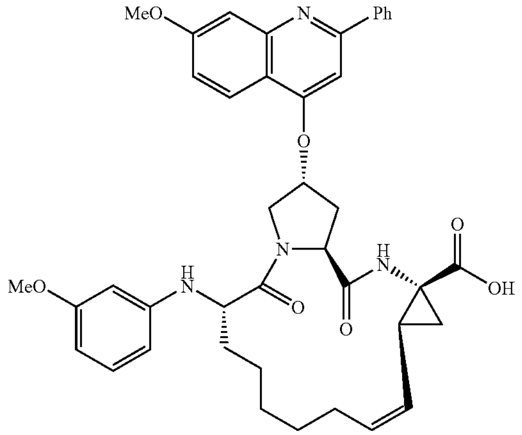 |

TABLE 1-continued
| Examples of compounds that can be prepared according to Examples 1-29 | |
|---|---|
| Compound | Structure |
| 140 | 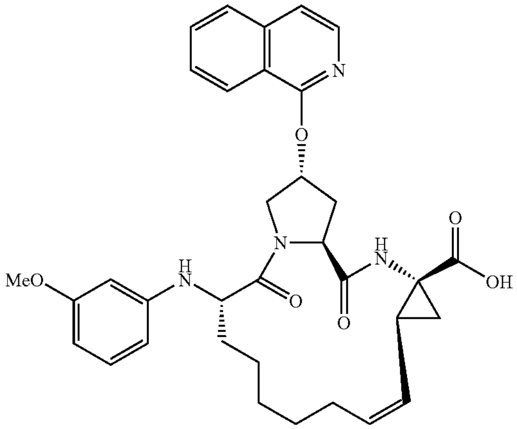 |
| 141 | 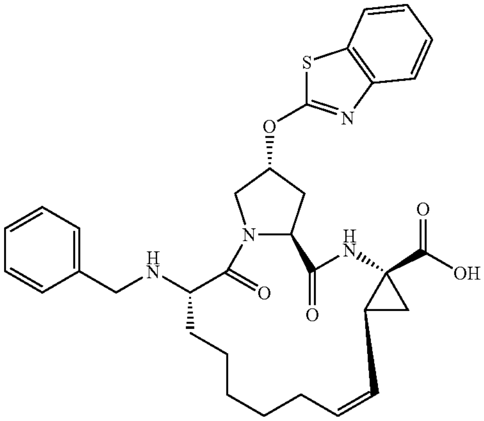 |
| 142 | 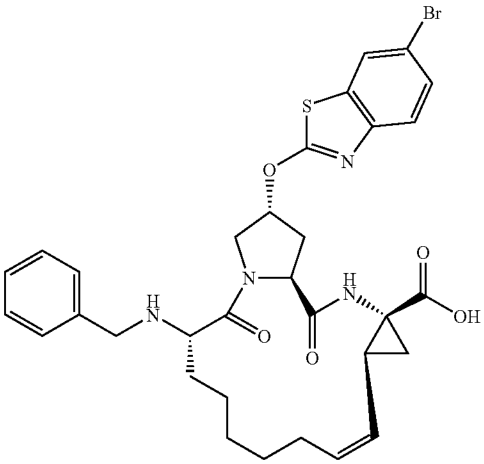 |

TABLE 1-continued
| Examples of compounds that can be prepared according to Examples 1-29 | |
|---|---|
| Compound | Structure |
| 143 | 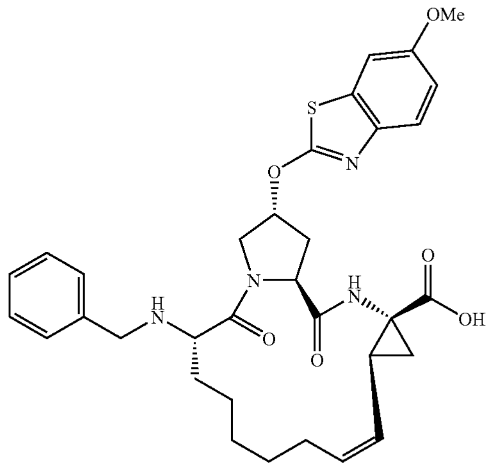 |
| 144 | 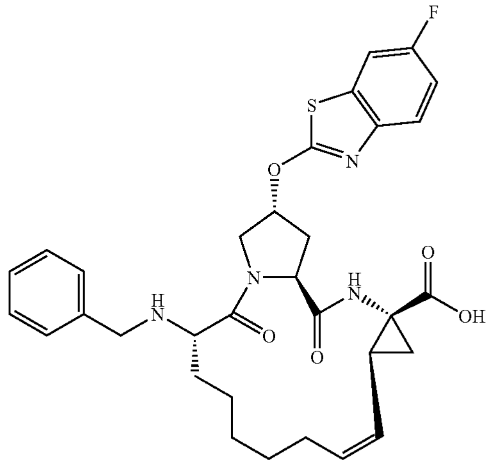 |
| 145 | 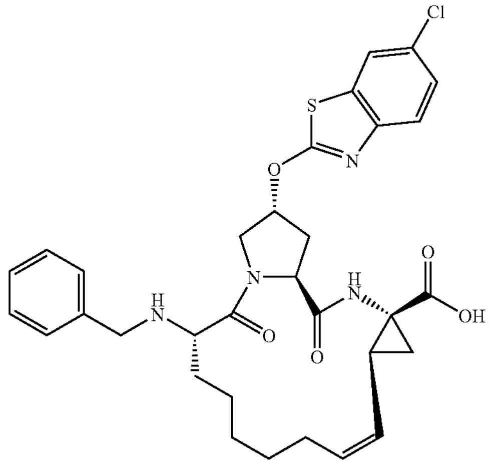 |

TABLE 1-continued
| Examples of compounds that can be prepared according to Examples 1-29 | |
|---|---|
| Compound | Structure |
| 146 | 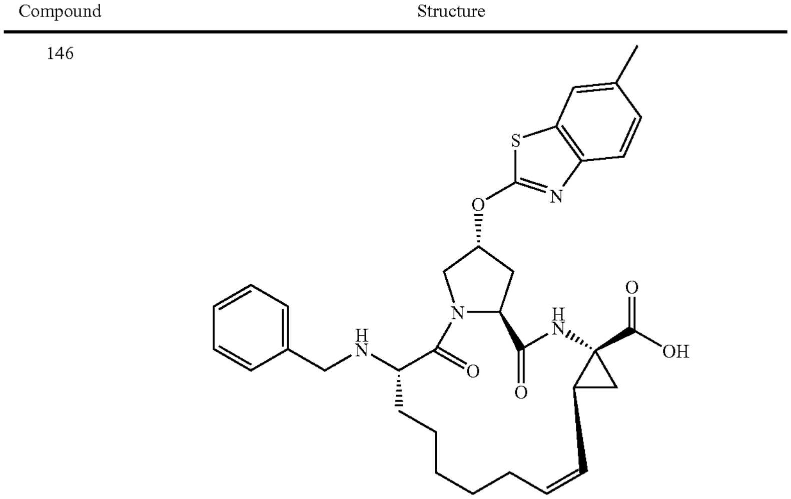 |
| 147 | 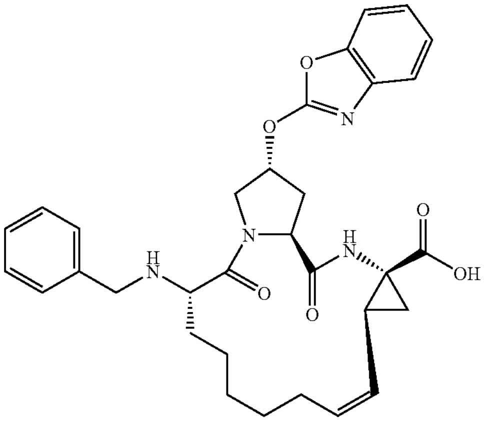 |
| 148 | 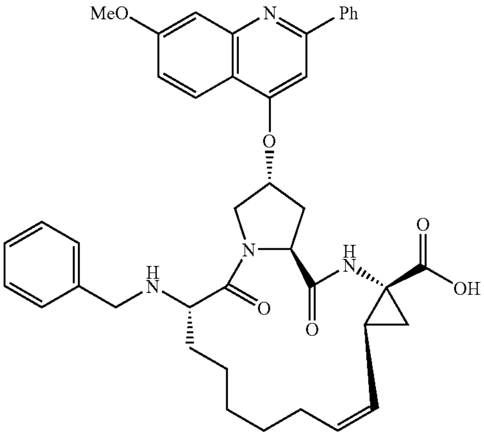 |

TABLE 1-continued
Examples of compounds that can be prepared according to Examples 1-29
| Compound | Structure |
| --- | --- |
| 149 | 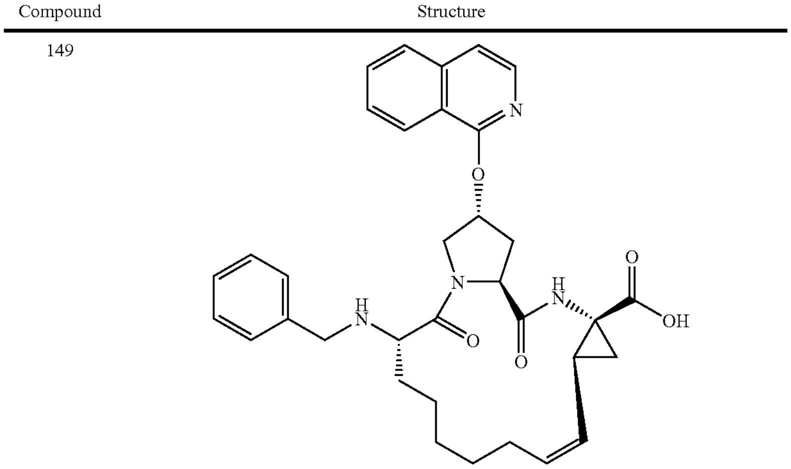 |
| 150 | 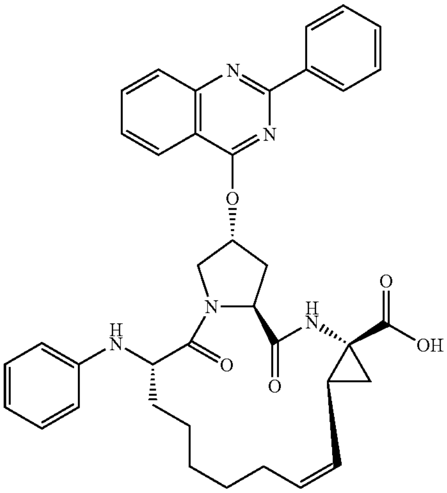 |
| 151 | 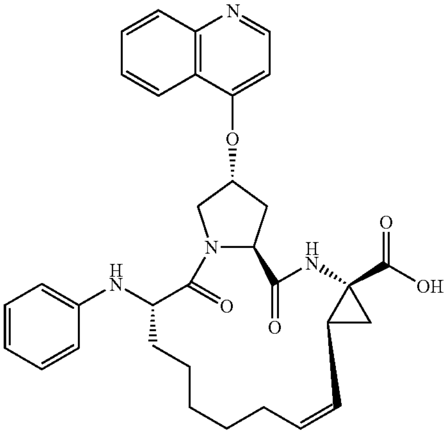 |

TABLE 1-continued
| Compound | Structure |
| --- | --- |
| Examples of compounds that can be prepared according to Examples 1-29 | |
| 152 | 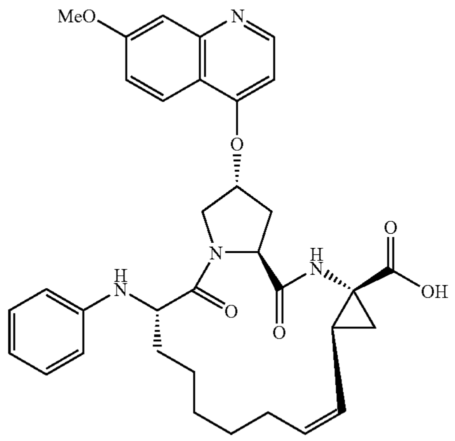 |
| 153 | 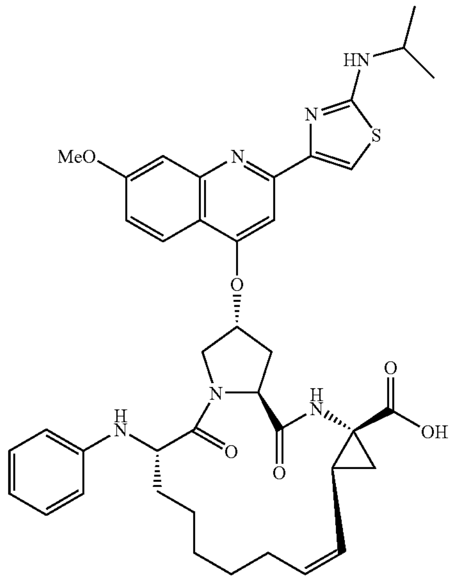 |
| 154 | 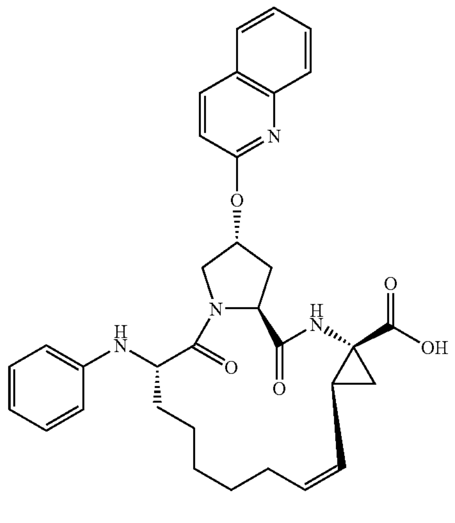 |

TABLE 1-continued
Examples of compounds that can be prepared according to Examples 1-29
| Compound | Structure |
| --- | --- |
| 155 | 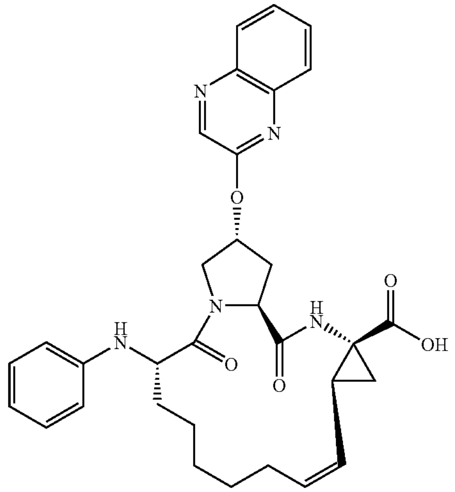 |
| 156 | 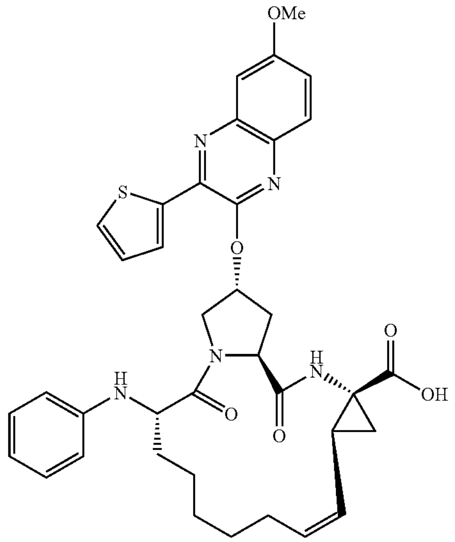 |
| 157 | 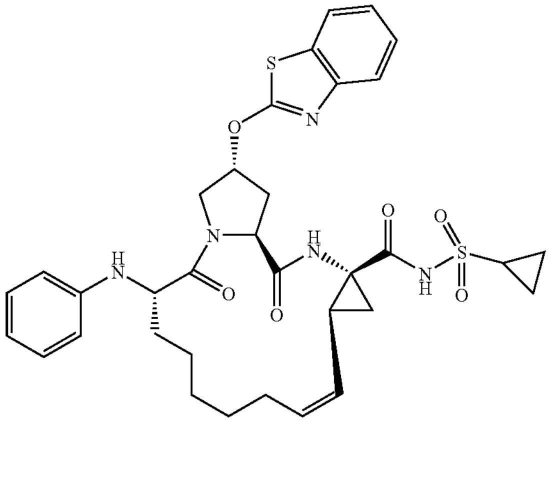 |

TABLE 1-continued
| Examples of compounds that can be prepared according to Examples 1-29 | |
|---|---|
| Compound | Structure |
| 158 | 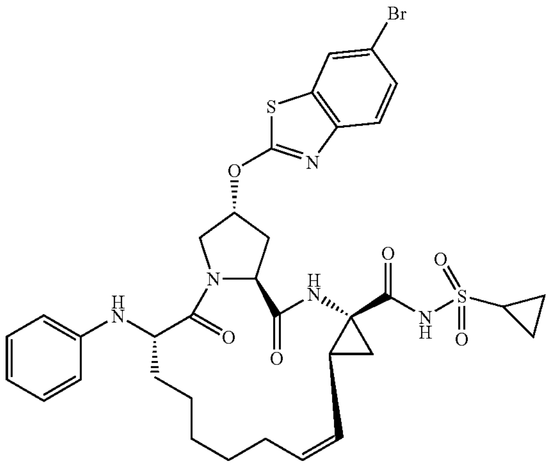 |
| 159 | 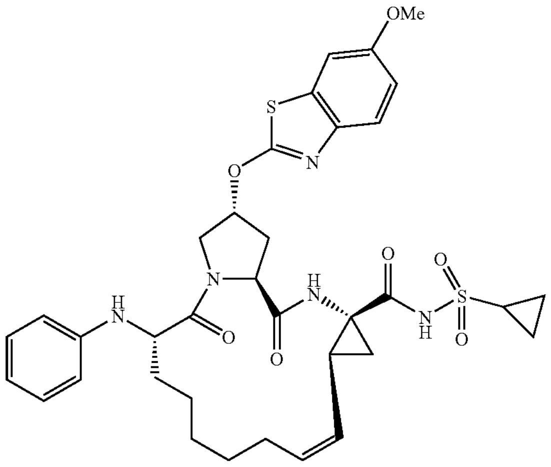 |
| 160 | 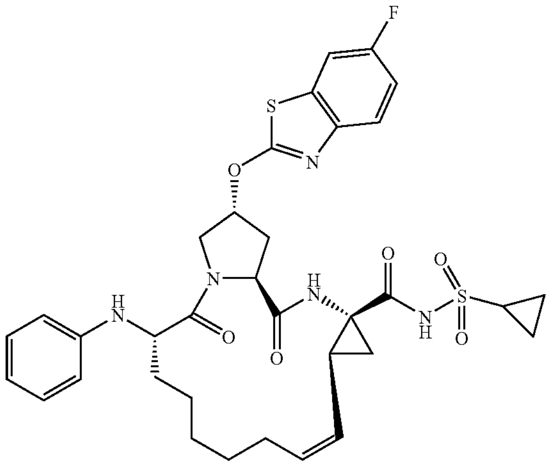 |

TABLE 1-continued
| Examples of compounds that can be prepared according to Examples 1-29 | |
|---|---|
| Compound | Structure |
| 161 | 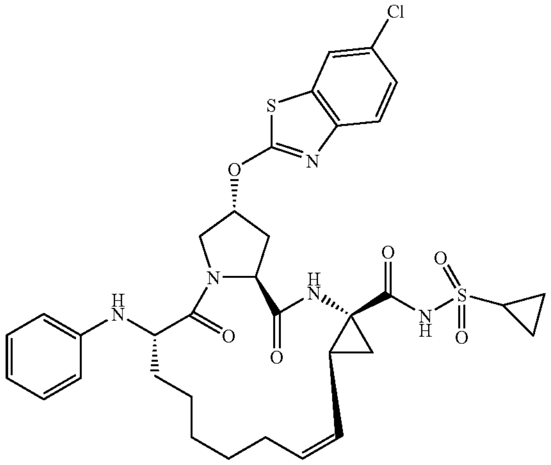 |
| 162 | 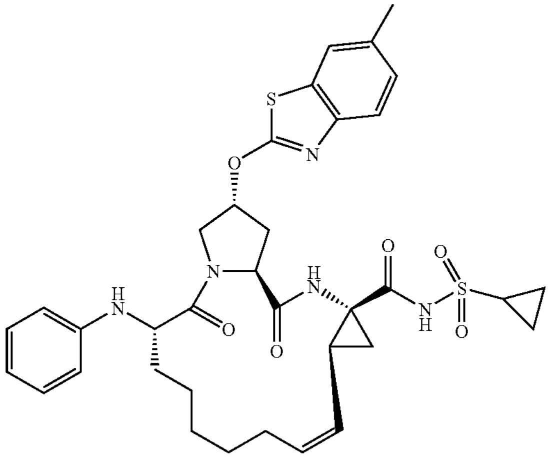 |
| 163 | 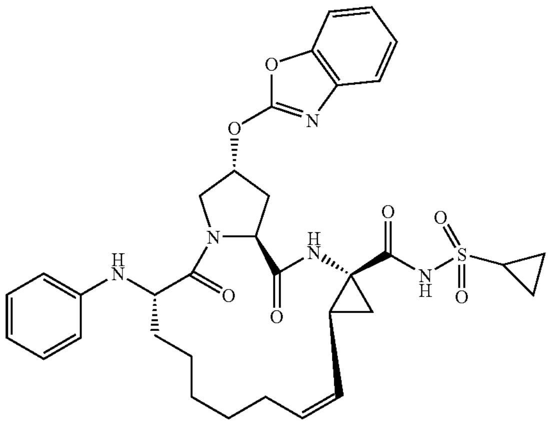 |

TABLE 1-continued
| Examples of compounds that can be prepared according to Examples 1-29 | |
|---|---|
| Compound | Structure |
| 164 | 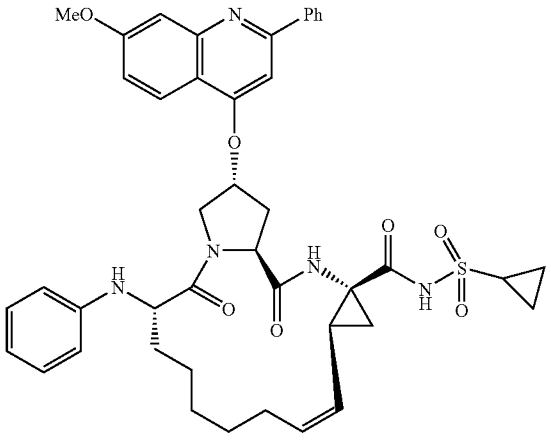 |
| 165 | 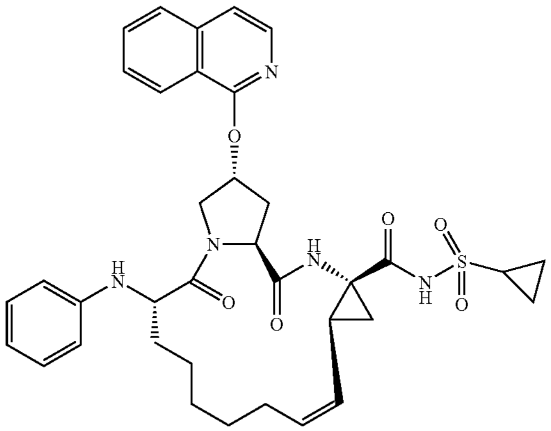 |
| 166 | 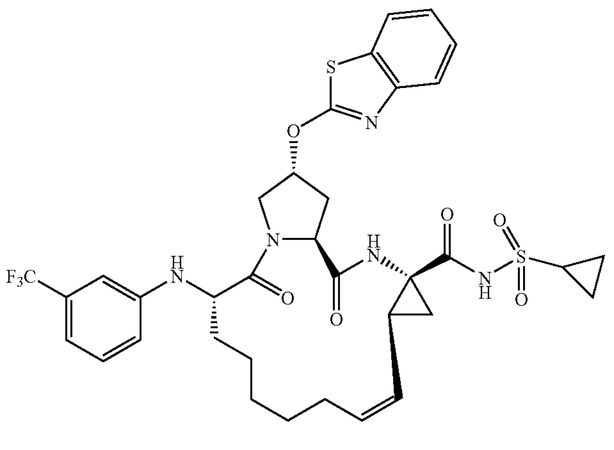 |

TABLE 1-continued
| Compound | Structure |
| --- | --- |
| Examples of compounds that can be prepared according to Examples 1-29 | |
| 167 | 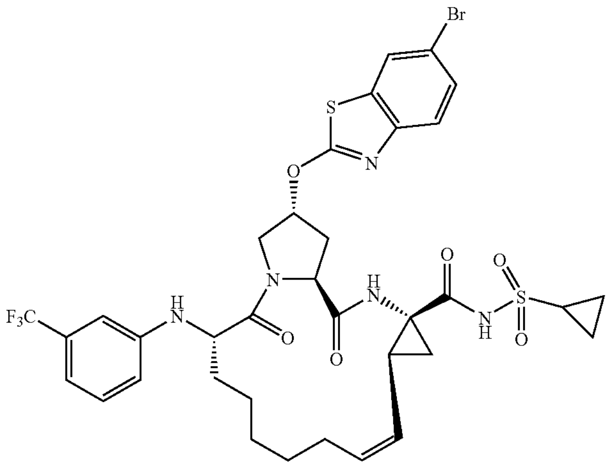 |
| 168 | 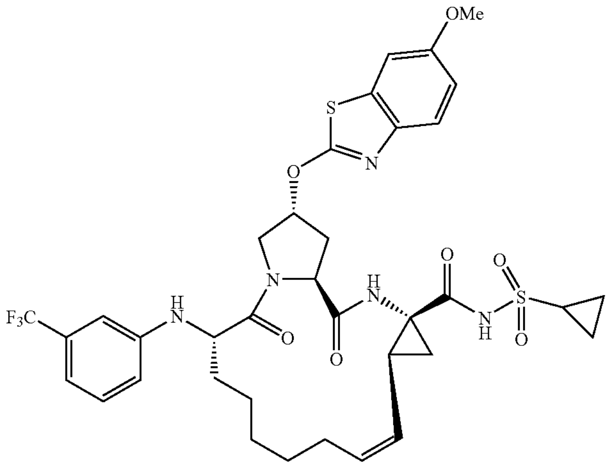 |
| 169 | 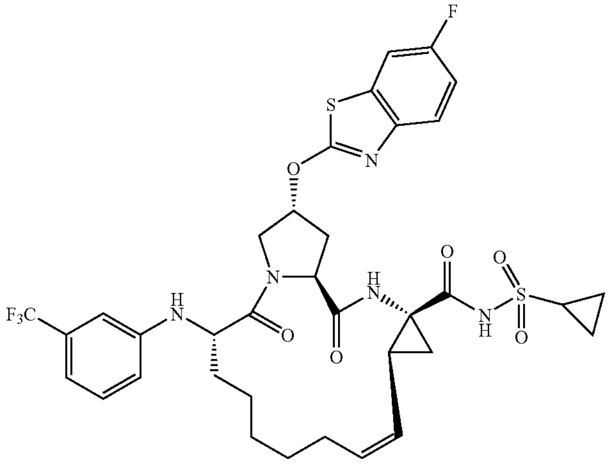 |

TABLE 1-continued
| Examples of compounds that can be prepared according to Examples 1-29 | |
|---|---|
| Compound | Structure |
| 170 | 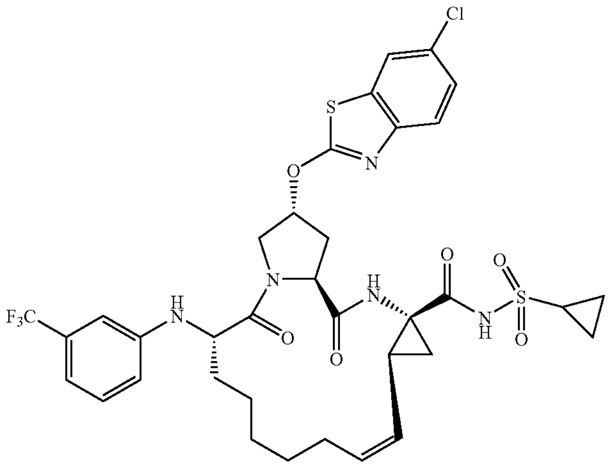 |
| 171 | 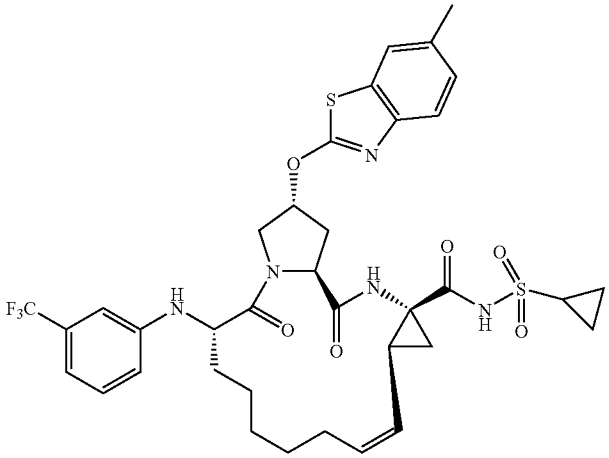 |
| 172 | 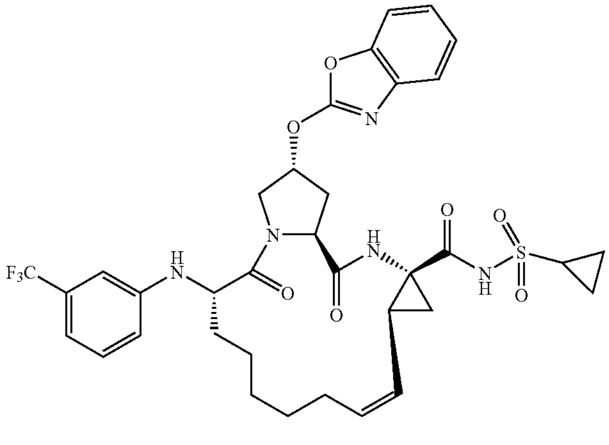 |

TABLE 1-continued
| Examples of compounds that can be prepared according to Examples 1-29 | |
|---|---|
| Compound | Structure |
| 173 | 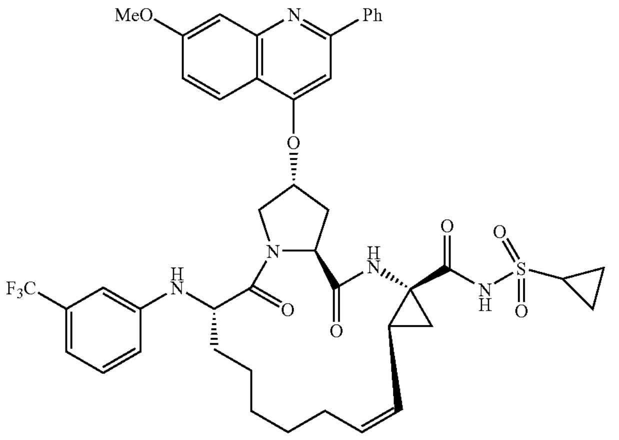 |
| 174 | 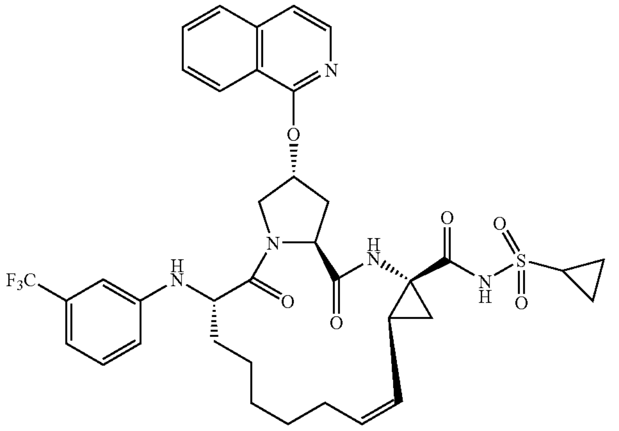 |
| 175 | 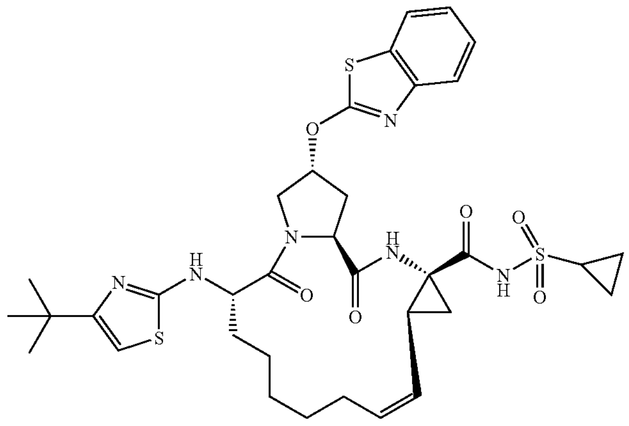 |

TABLE 1-continued
| Examples of compounds that can be prepared according to Examples 1-29 | |
|---|---|
| Compound | Structure |
| 176 | 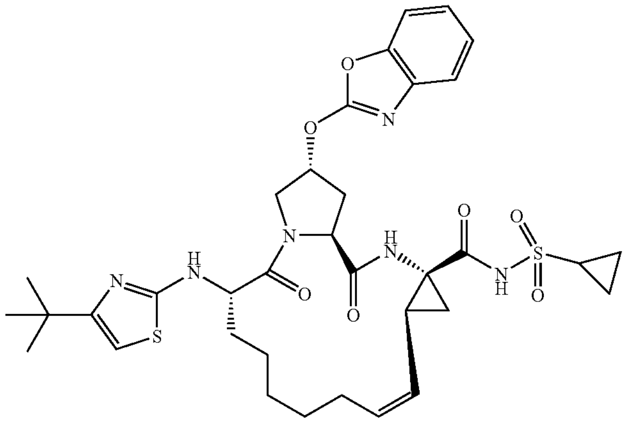 |
| 177 | 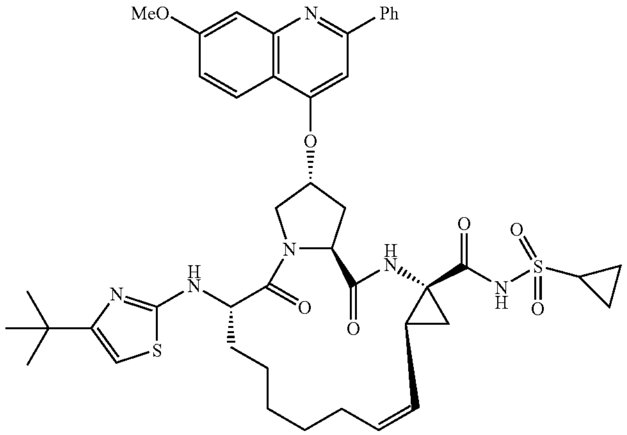 |
| 178 | 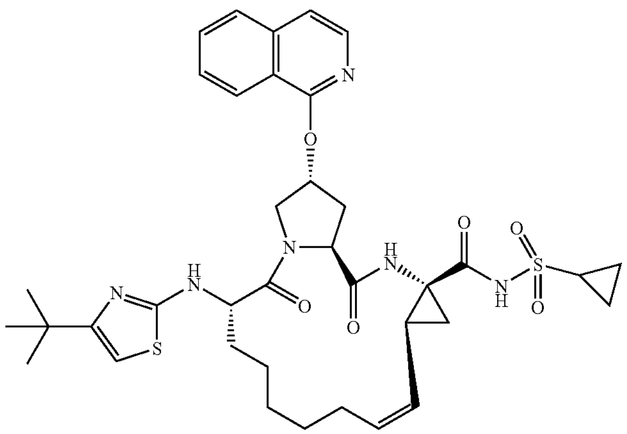 |

TABLE 1-continued
| Examples of compounds that can be prepared according to Examples 1-29 | |
|---|---|
| Compound | Structure |
| 179 | 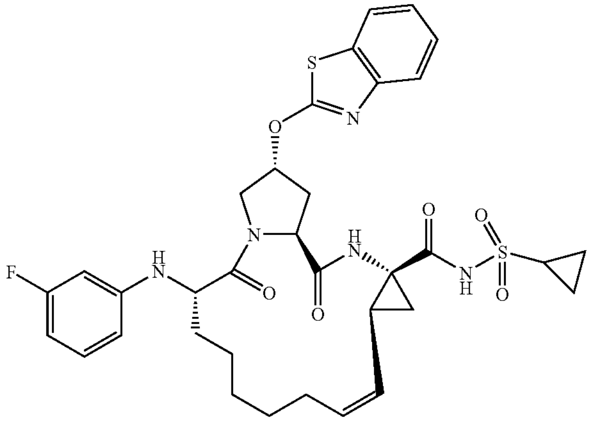 |
| 180 | 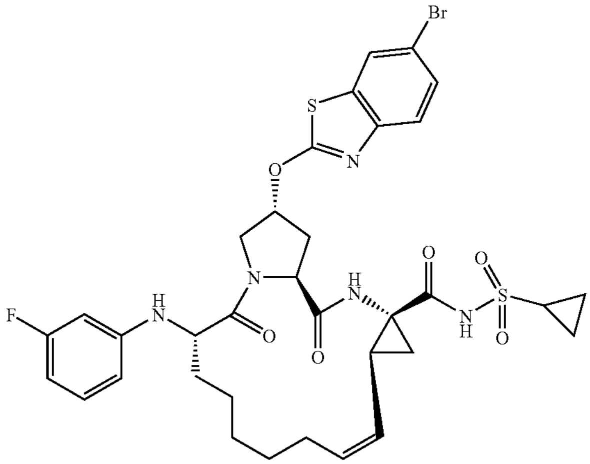 |
| 181 | 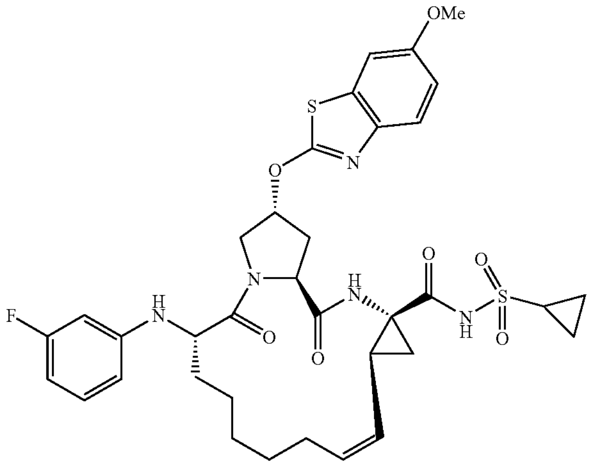 |

TABLE 1-continued
Examples of compounds that can be prepared according to Examples 1-29
| Compound | Structure |
| --- | --- |
| 182 | 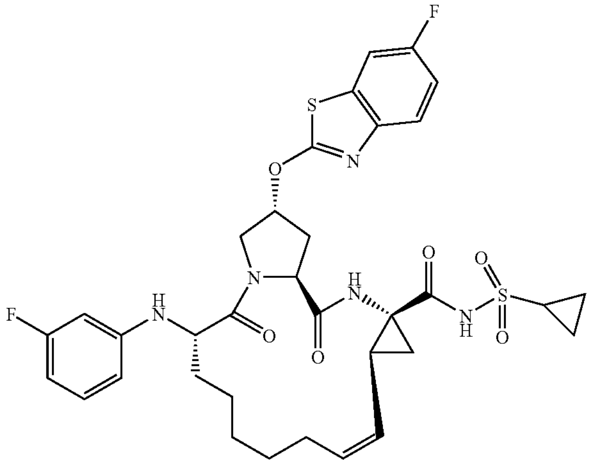 |
| 183 | 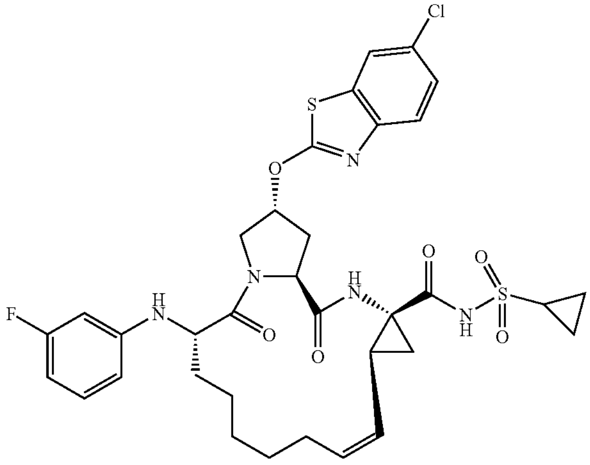 |
| 184 | 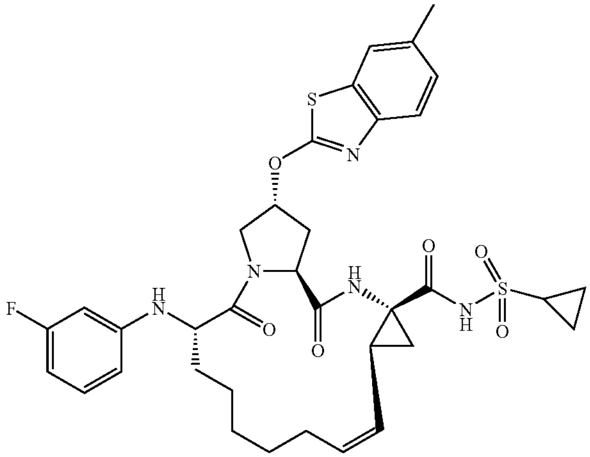 |

TABLE 1-continued
| Examples of compounds that can be prepared according to Examples 1-29 | |
|---|---|
| Compound | Structure |
| 185 | 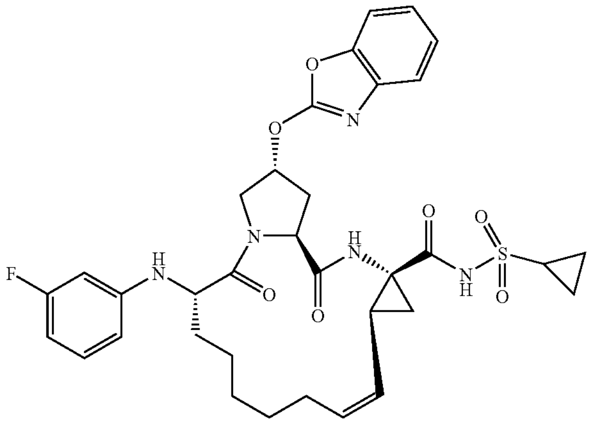 |
| 186 | 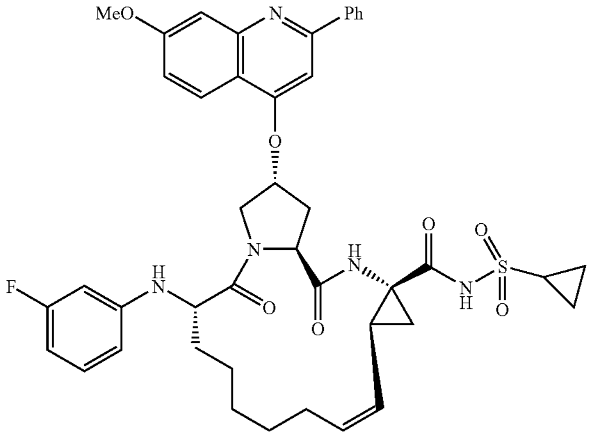 |
| 187 | 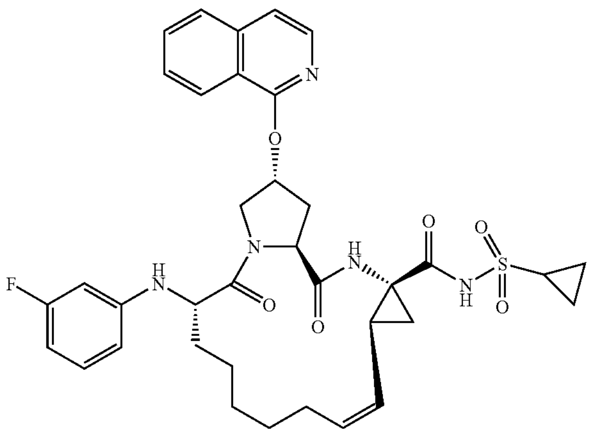 |

TABLE 1-continued
| Examples of compounds that can be prepared according to Examples 1-29 | |
|---|---|
| Compound | Structure |
| 188 | 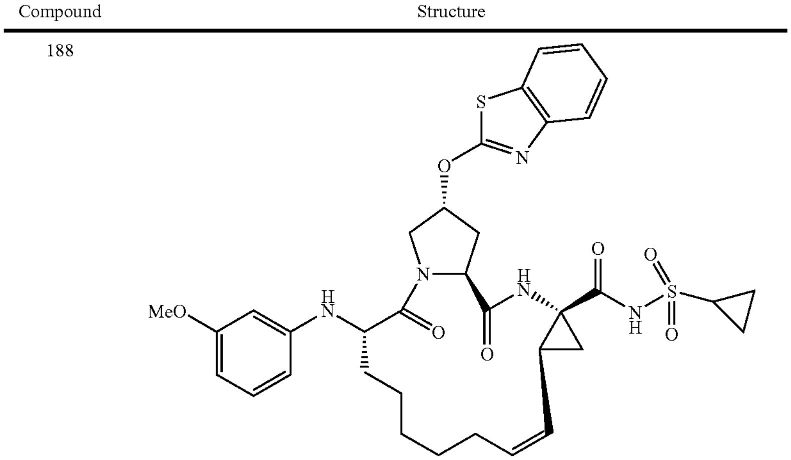 |
| 189 | 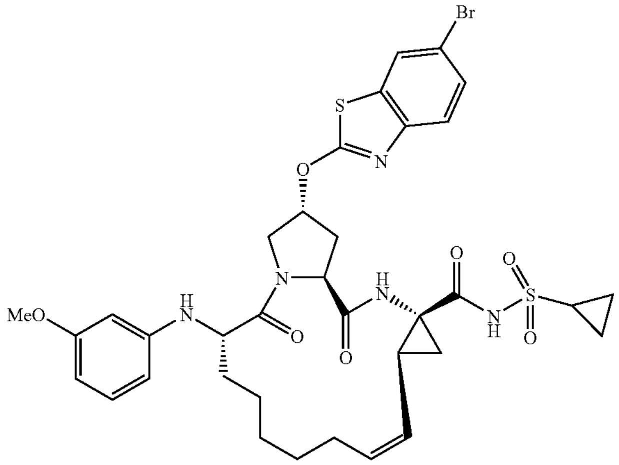 |
| 190 | 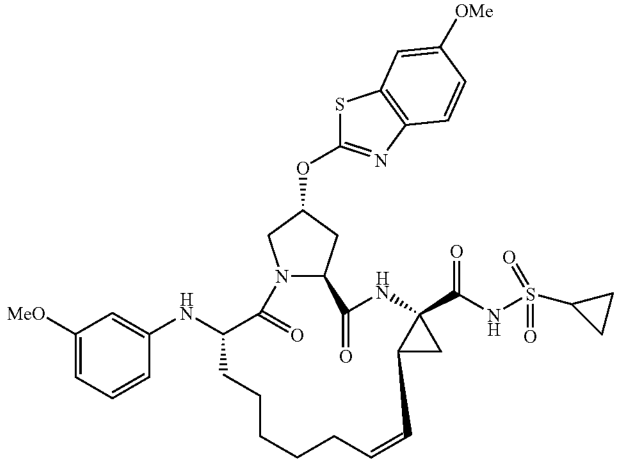 |

TABLE 1-continued
| Examples of compounds that can be prepared according to Examples 1-29 | |
|---|---|
| Compound | Structure |
| 191 | 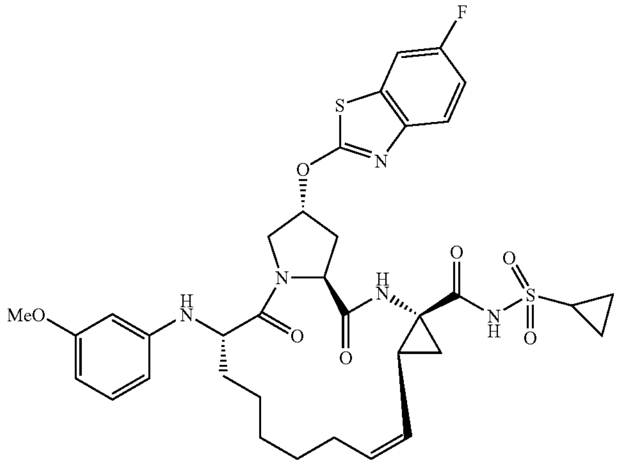 |
| 192 | 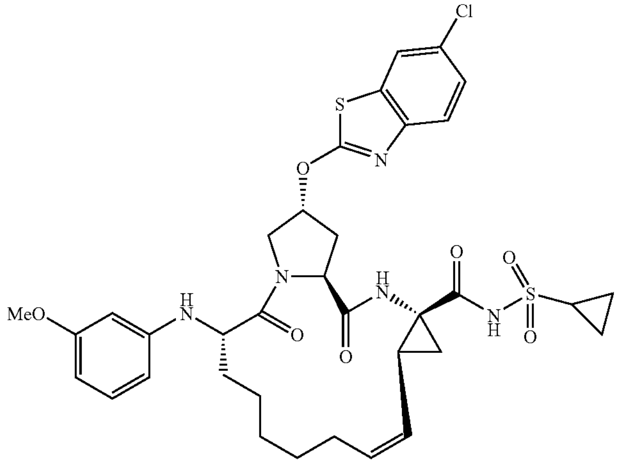 |
| 193 | 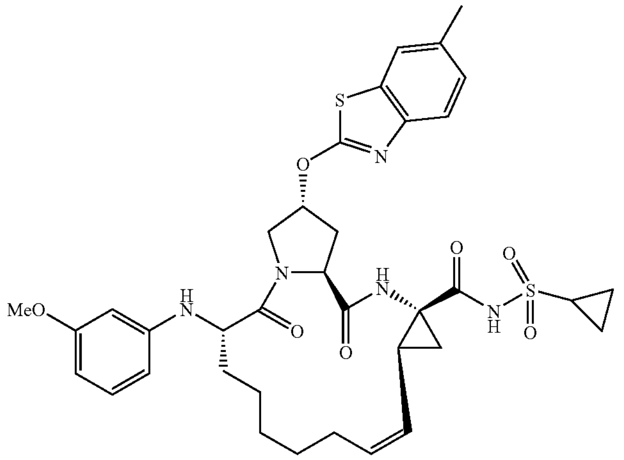 |

TABLE 1-continued
| Examples of compounds that can be prepared according to Examples 1-29 | |
|---|---|
| Compound | Structure |
| 194 | 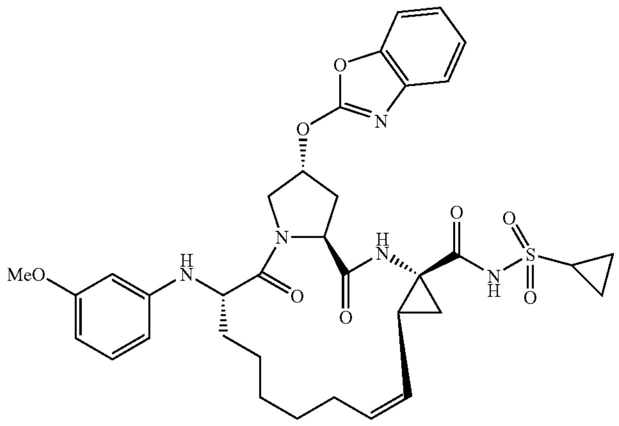 |
| 195 | 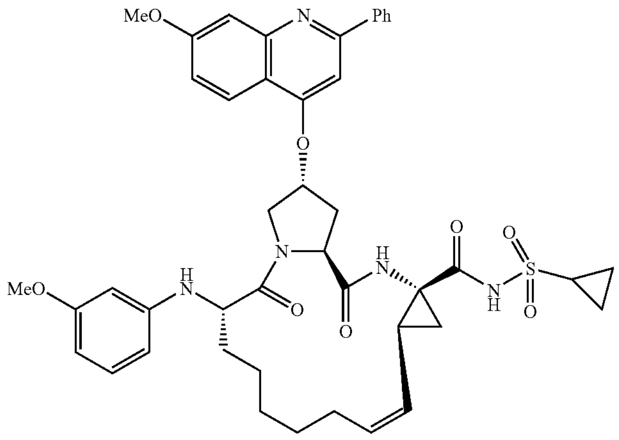 |
| 196 | 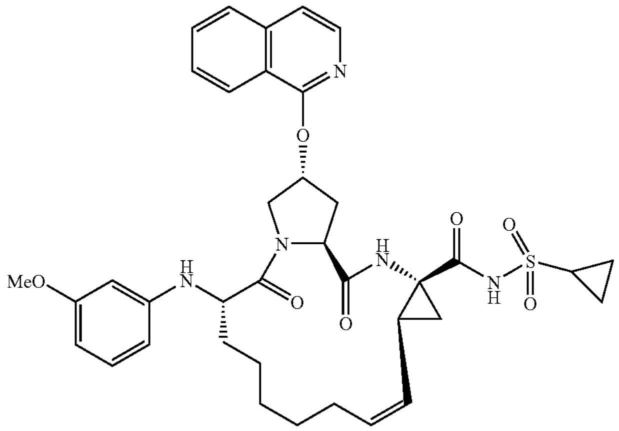 |

TABLE 1-continued
Examples of compounds that can be prepared according to Examples 1-29
| Compound | Structure |
| --- | --- |
| 197 | 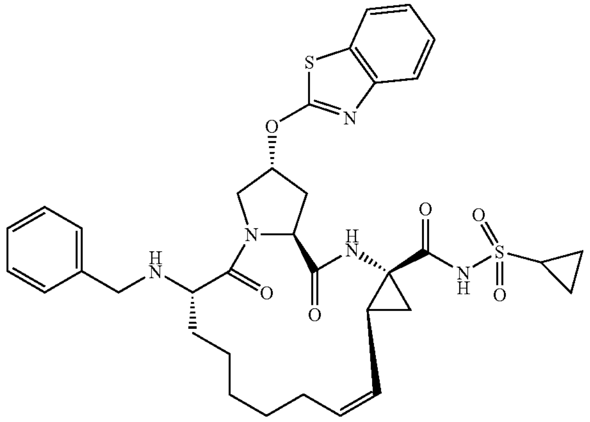 |
| 198 | 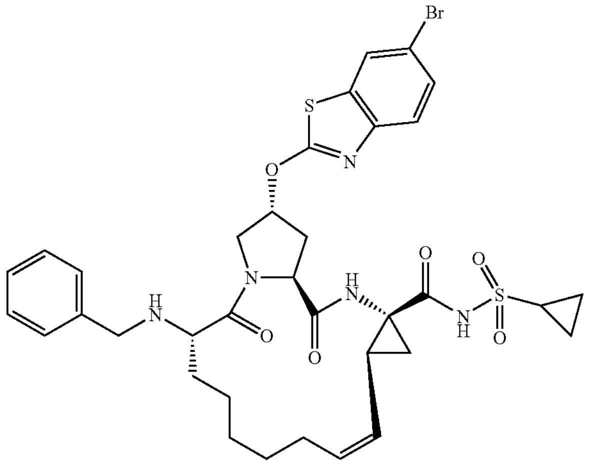 |
| 199 | 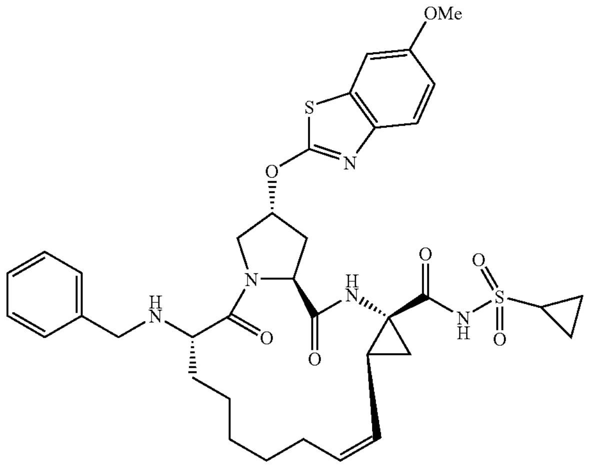 |

TABLE 1-continued
| Compound | Structure |
| --- | --- |
| Examples of compounds that can be prepared according to Examples 1-29 | |
| 200 | 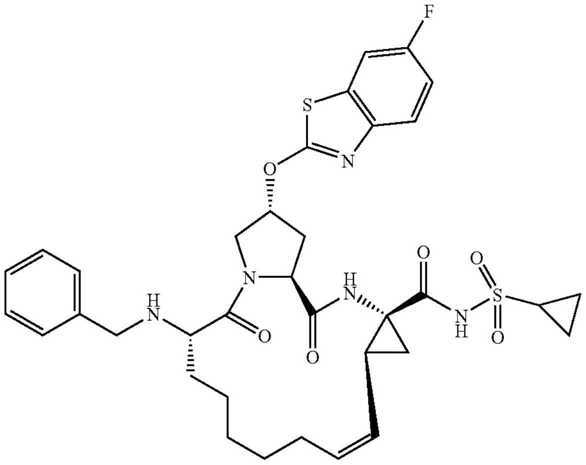 |
| 201 | 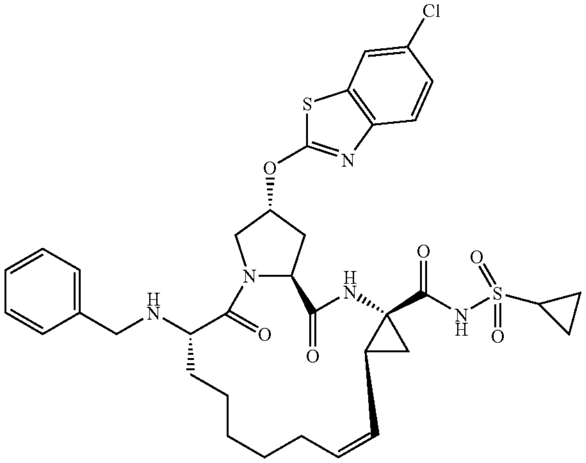 |
| 202 | 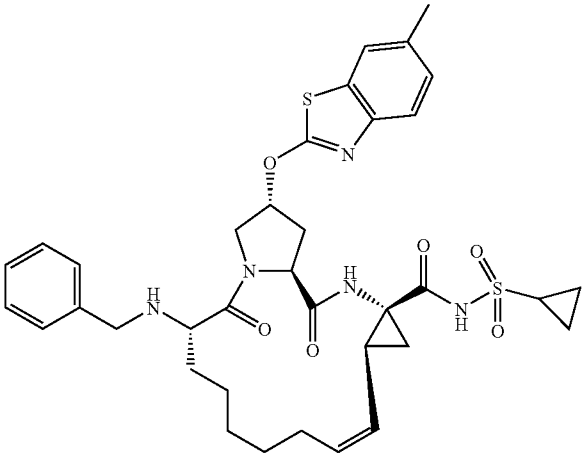 |

TABLE 1-continued
| Examples of compounds that can be prepared according to Examples 1-29 | |
|---|---|
| Compound | Structure |
| 203 | 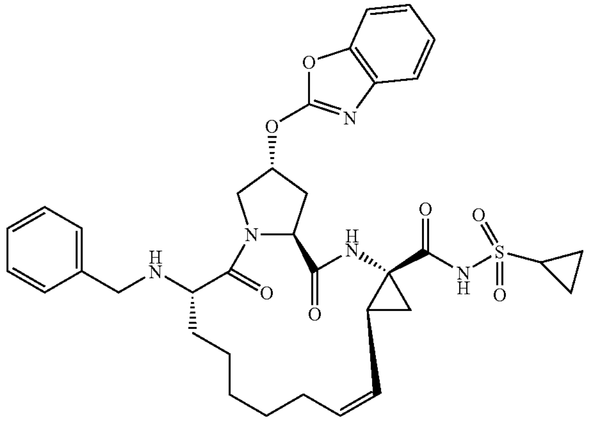 |
| 204 | 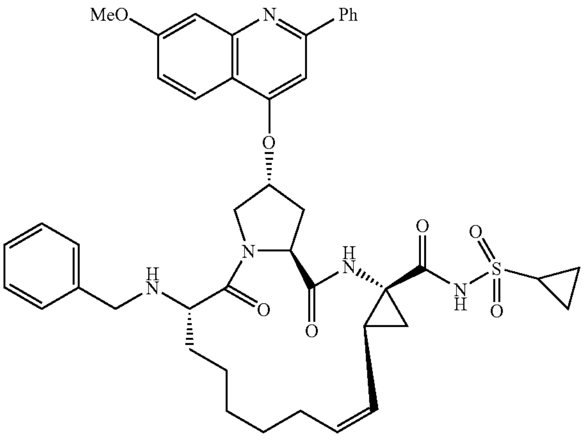 |
| 205 | 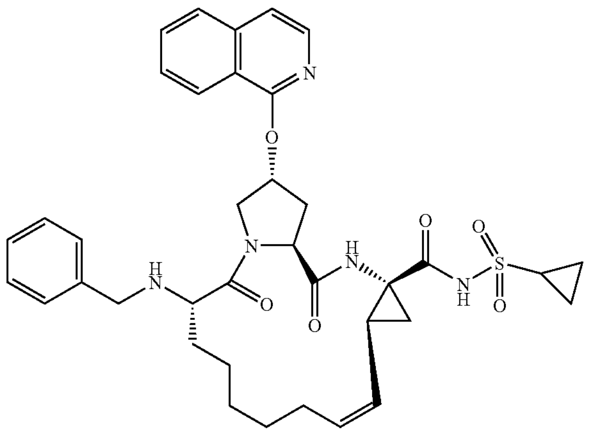 |

TABLE 1-continued
Examples of compounds that can be prepared according to Examples 1-29
| Compound | Structure |
| --- | --- |
| 206 | 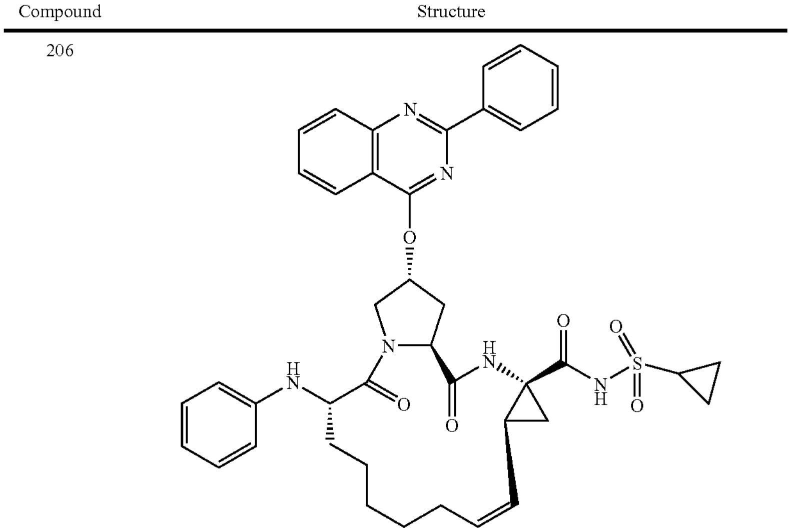 |
| 207 | 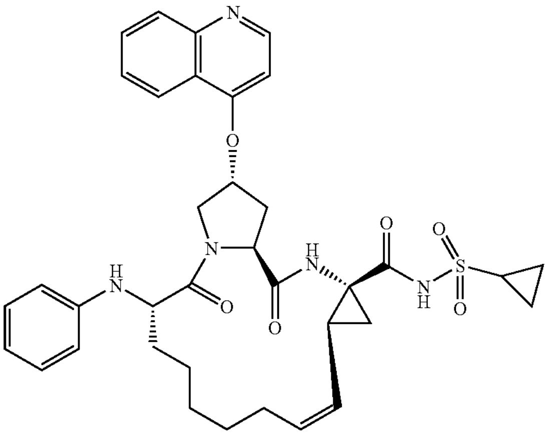 |
| 208 | 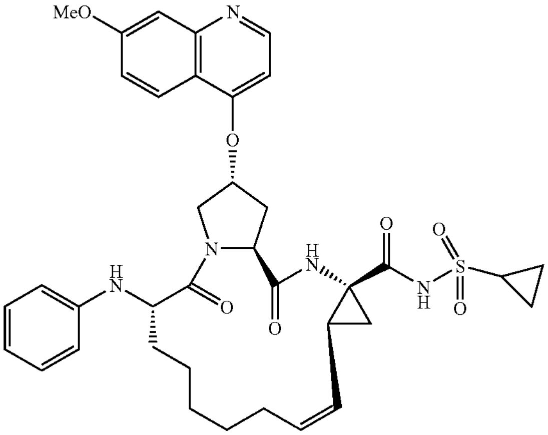 |

TABLE 1-continued
| Examples of compounds that can be prepared according to Examples 1-29 | |
|---|---|
| Compound | Structure |
| 209 | 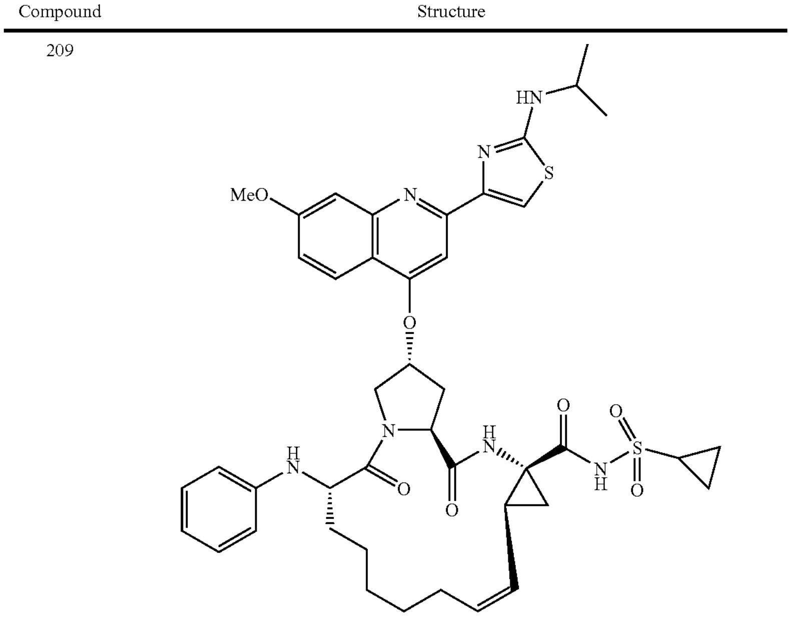 |
| 210 | 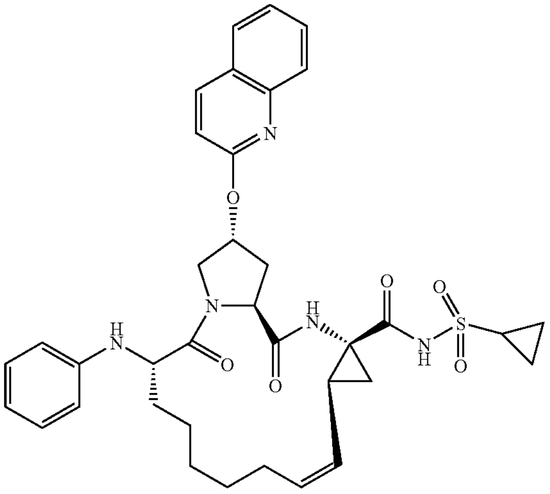 |
| 211 | 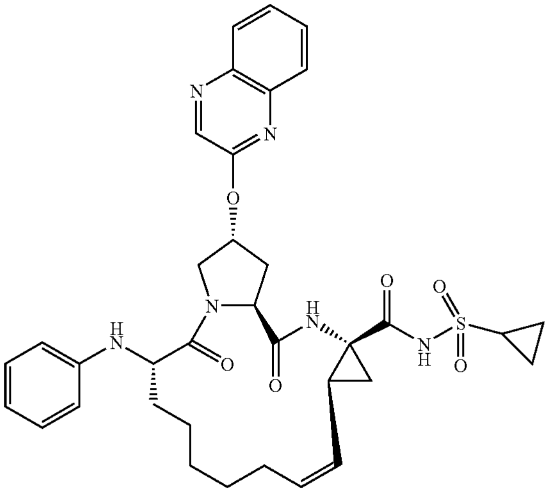 |

TABLE 1-continued
| Compound | Structure |
| --- | --- |
| Examples of compounds that can be prepared according to Examples 1-29 | |
| 212 | 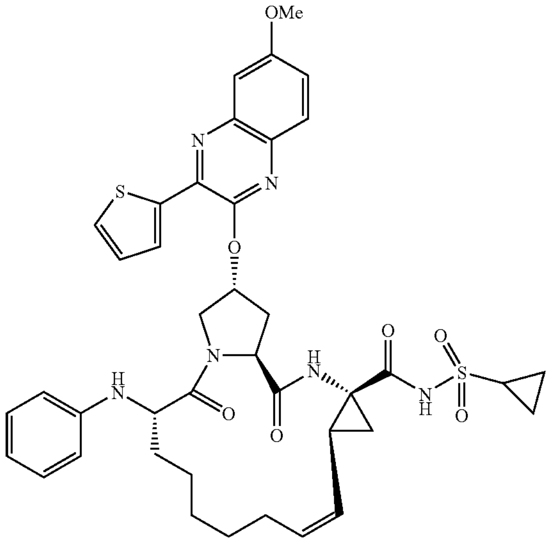 |
| 213 | 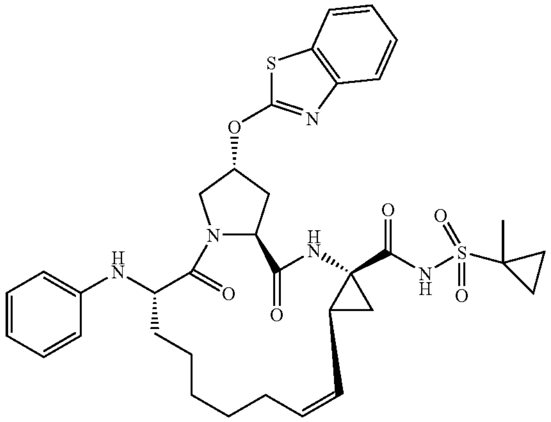 |
| 214 | 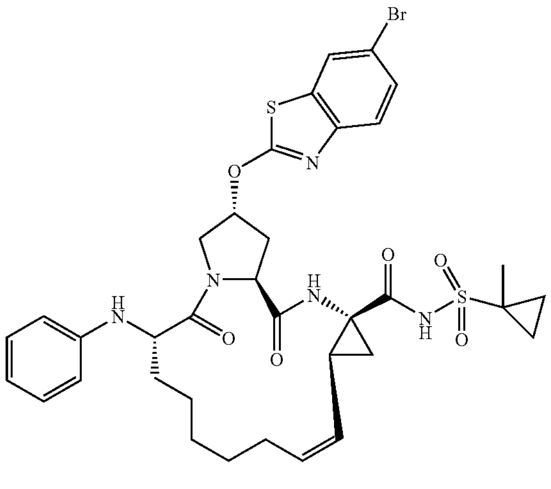 |

TABLE 1-continued
| Examples of compounds that can be prepared according to Examples 1-29 | |
|---|---|
| Compound | Structure |
| 215 | 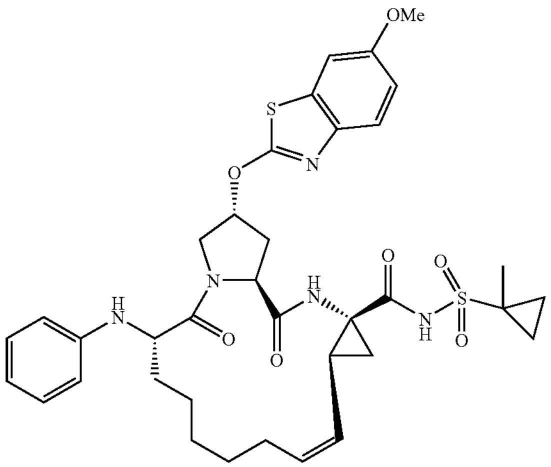 |
| 216 | 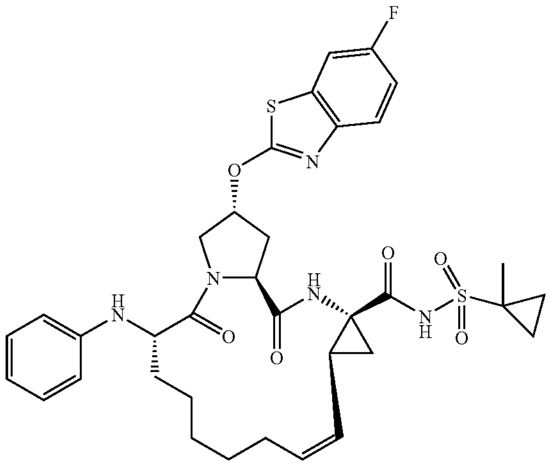 |
| 217 | 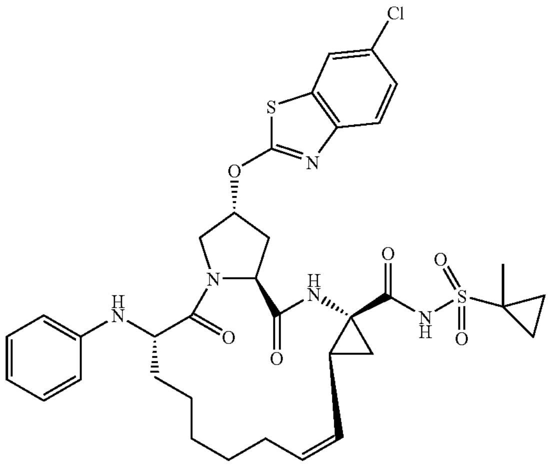 |

TABLE 1-continued
| Examples of compounds that can be prepared according to Examples 1-29 | |
|---|---|
| Compound | Structure |
| 218 | 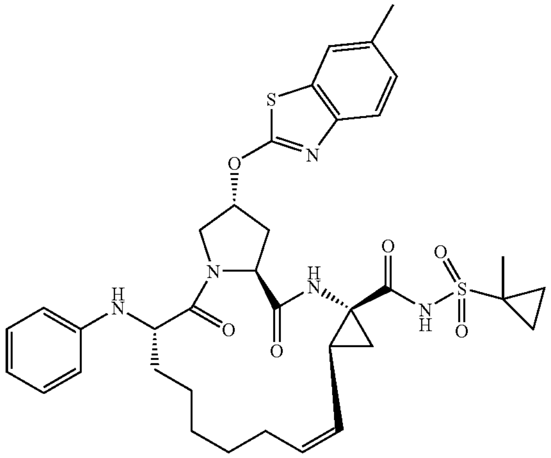 |
| 219 | 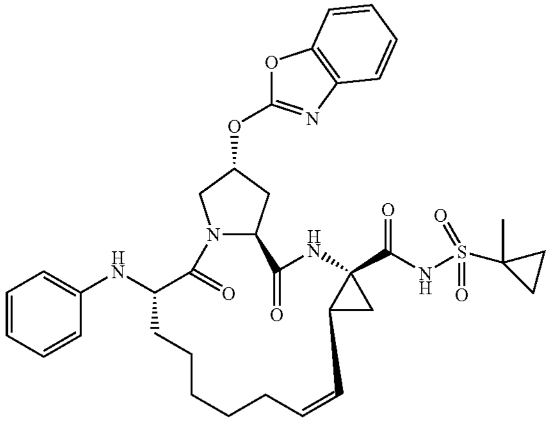 |
| 220 | 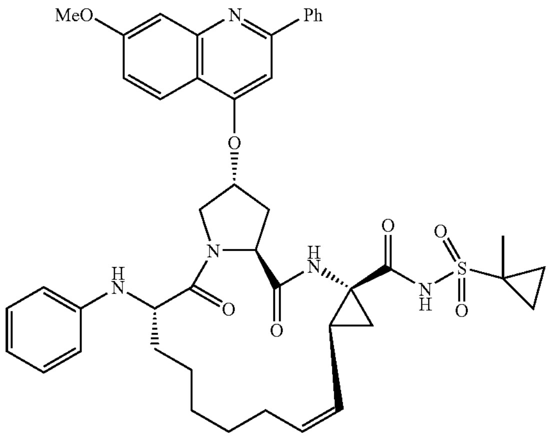 |

TABLE 1-continued
| Examples of compounds that can be prepared according to Examples 1-29 | |
|---|---|
| Compound | Structure |
| 221 | 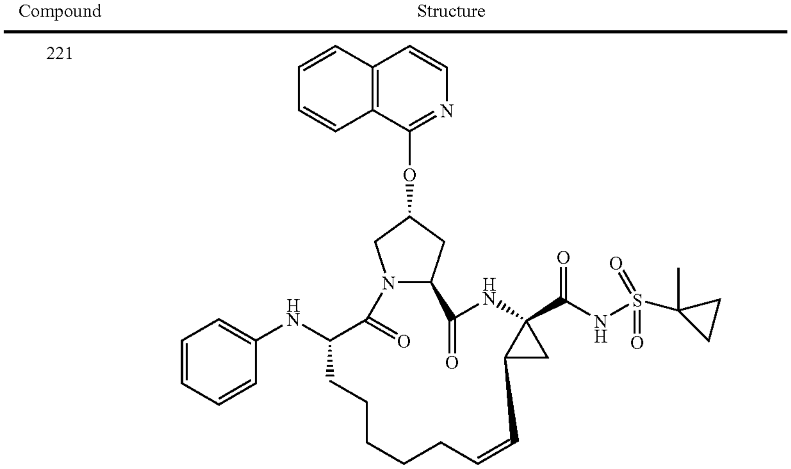 |
| 222 | 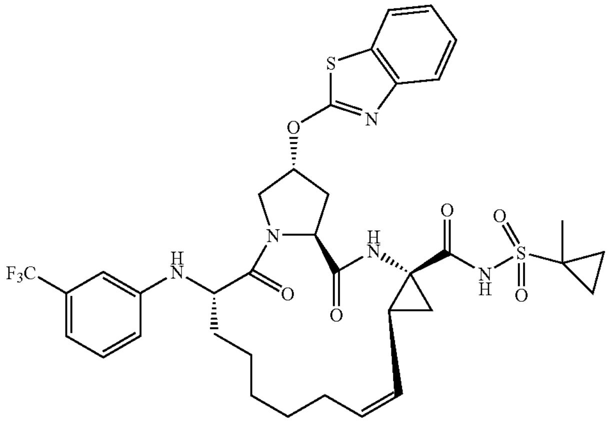 |
| 223 | 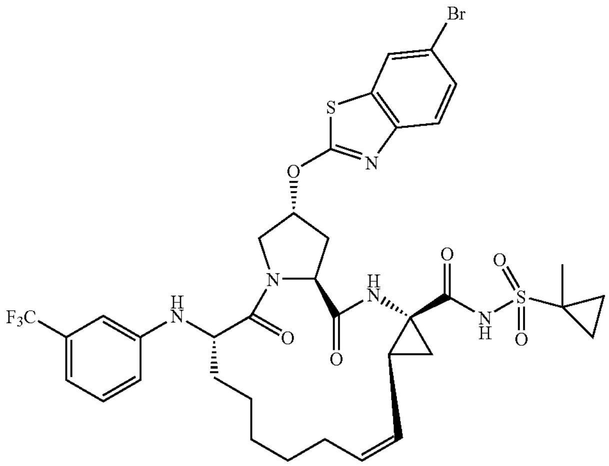 |

TABLE 1-continued
| Compound | Structure |
|---|---|
| | Examples of compounds that can be prepared according to Examples 1-29 |
| 224 | 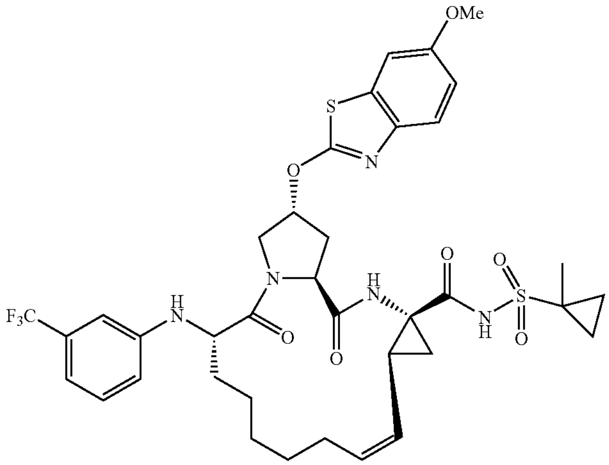 |
| 225 | 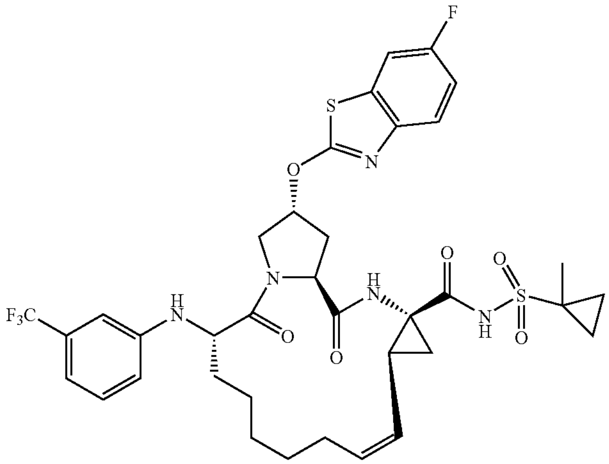 |
| 226 | 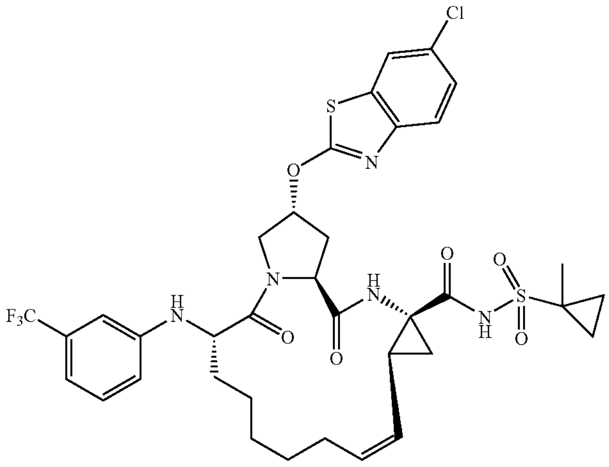 |

TABLE 1-continued
| Examples of compounds that can be prepared according to Examples 1-29 | |
|---|---|
| Compound | Structure |
| 227 | 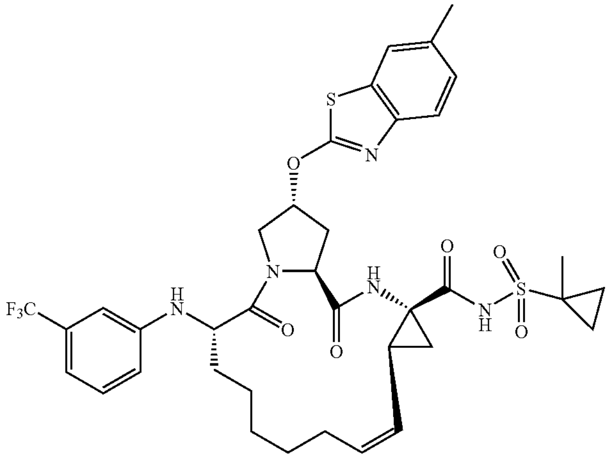 |
| 228 | 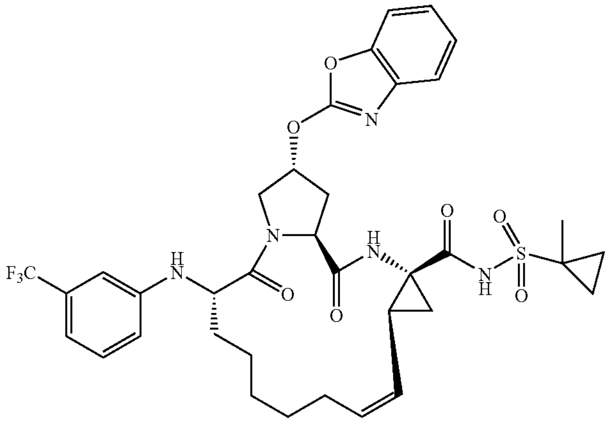 |
| 229 | 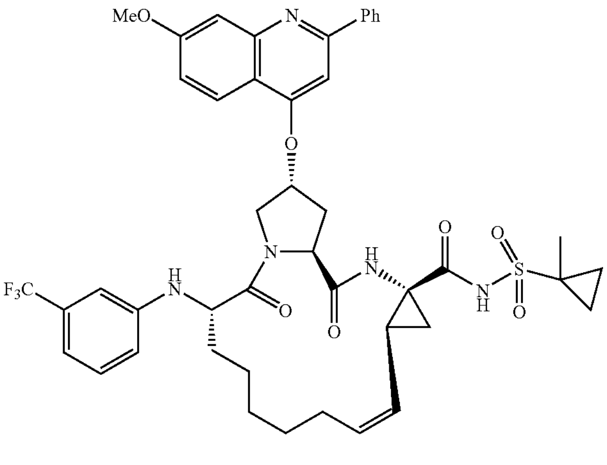 |

TABLE 1-continued
| Compound | Structure |
| --- | --- |
| Examples of compounds that can be prepared according to Examples 1-29 | |
| 230 | 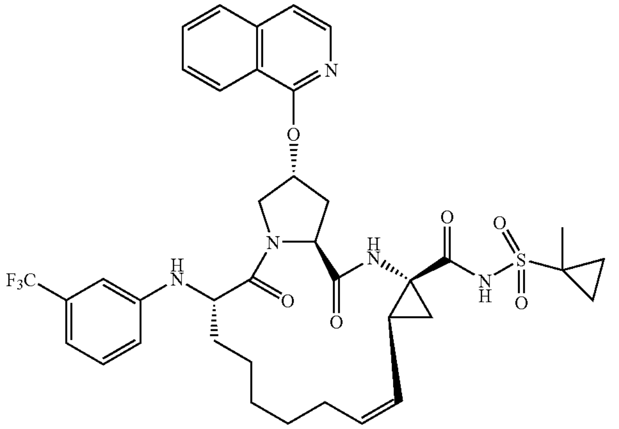 |
| 231 | 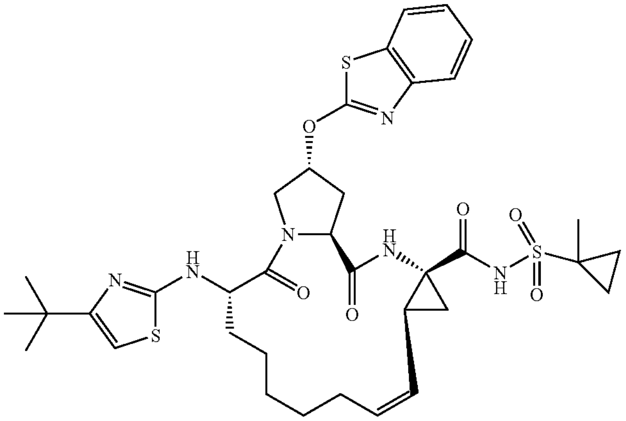 |
| 232 | 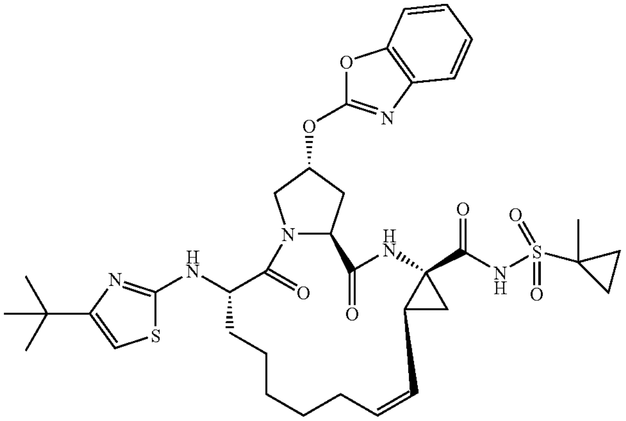 |

TABLE 1-continued
| Examples of compounds that can be prepared according to Examples 1-29 | |
|---|---|
| Compound | Structure |
| 233 | 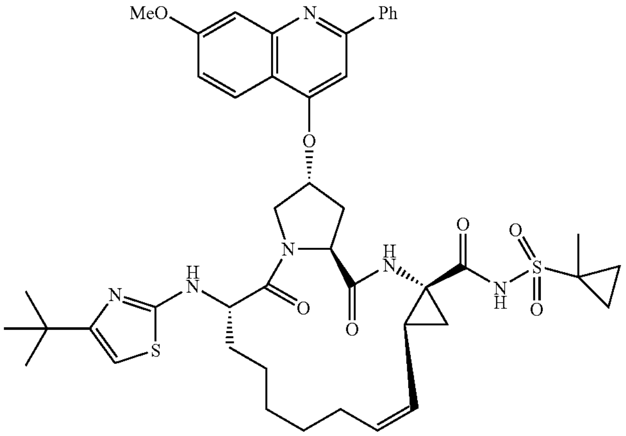 |
| 234 | 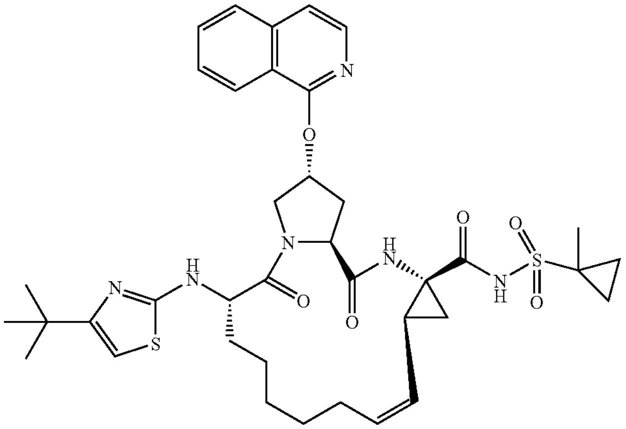 |
| 235 | 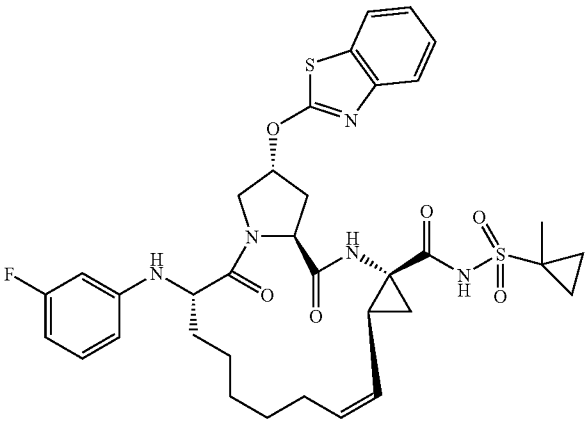 |

TABLE 1-continued
Examples of compounds that can be prepared according to Examples 1-29
| Compound | Structure |
| --- | --- |
| 236 | 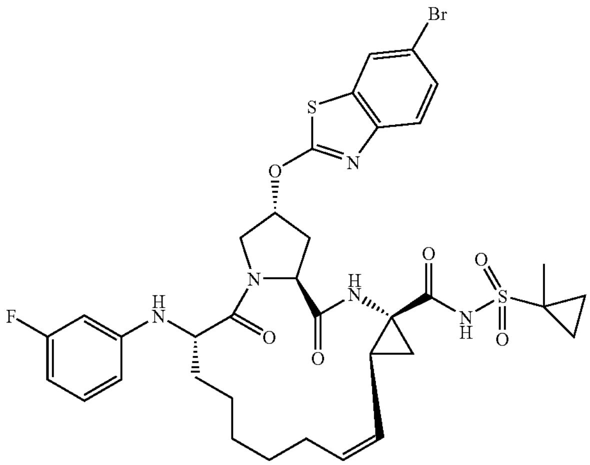 |
| 237 | 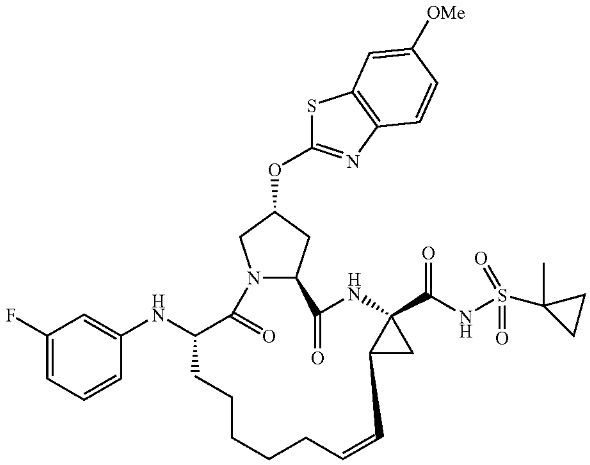 |
| 238 | 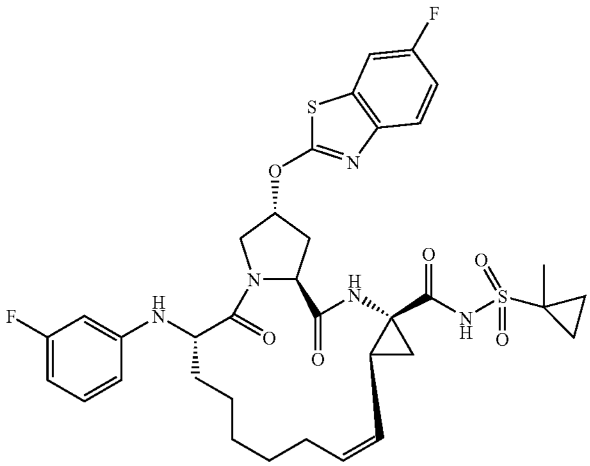 |

TABLE 1-continued
| Compound | Structure |
| --- | --- |
| Examples of compounds that can be prepared according to Examples 1-29 | |
| 239 | 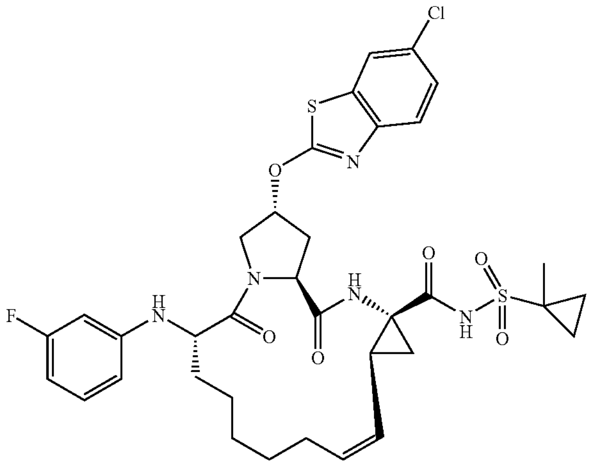 |
| 240 | 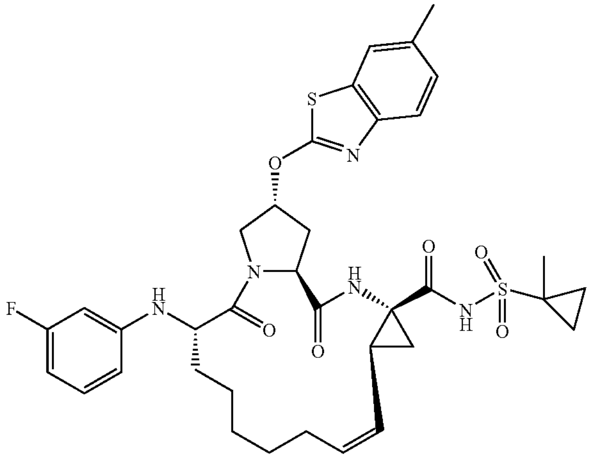 |
| 241 | 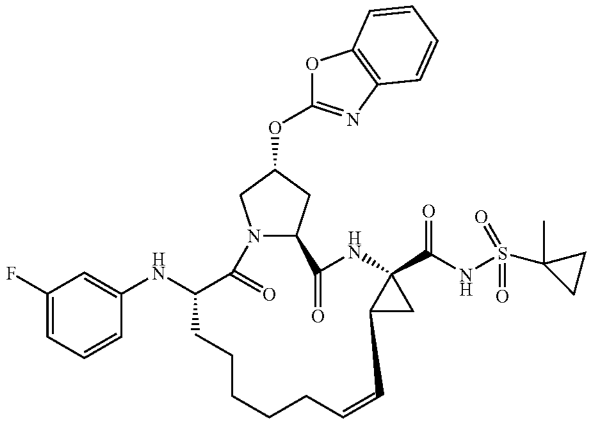 |

TABLE 1-continued
Examples of compounds that can be prepared according to Examples 1-29
| Compound | Structure |
| --- | --- |
| 242 | 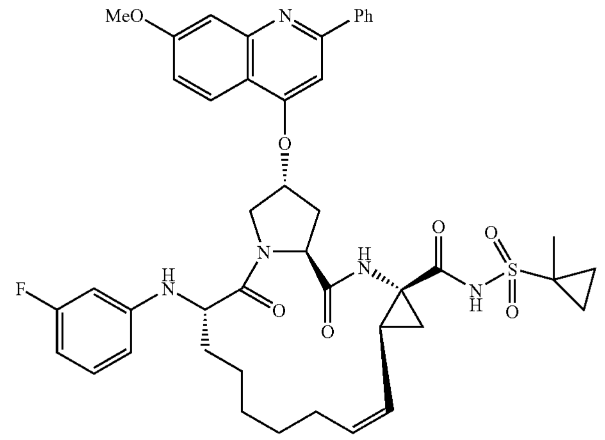 |
| 243 | 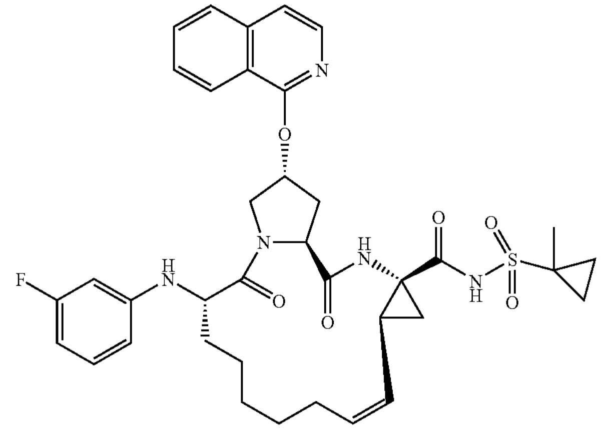 |
| 244 | 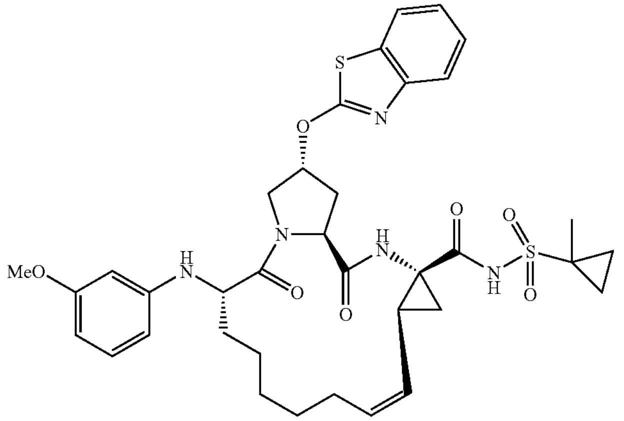 |

TABLE 1-continued
| Examples of compounds that can be prepared according to Examples 1-29 | |
|---|---|
| Compound | Structure |
| 245 | 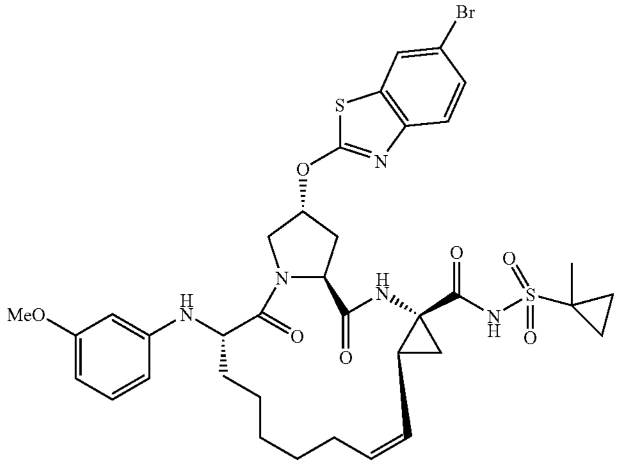 |
| 246 | 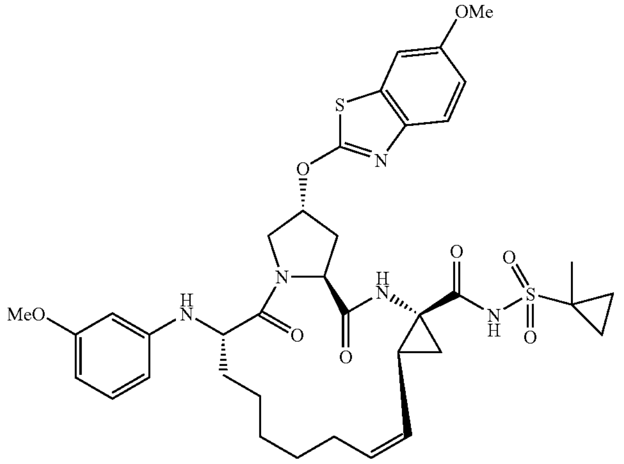 |
| 247 | 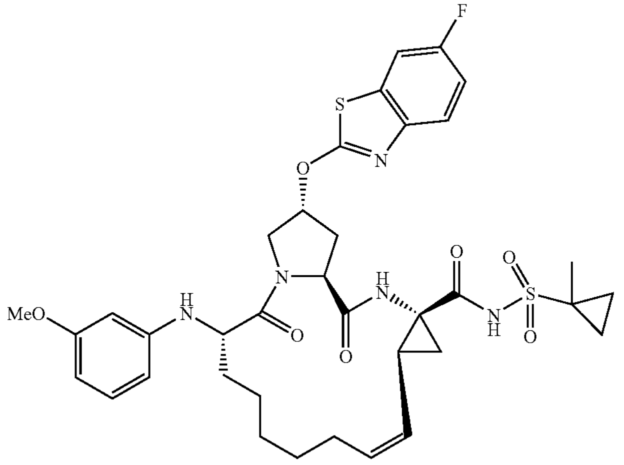 |

TABLE 1-continued
| Compound | Structure |
| --- | --- |
| 248 | 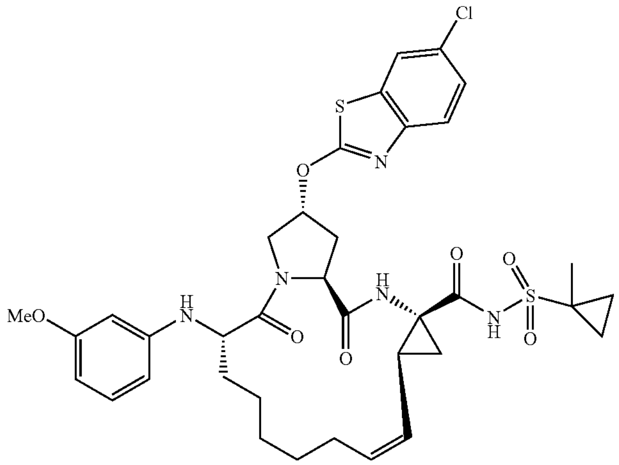 |
| 249 | 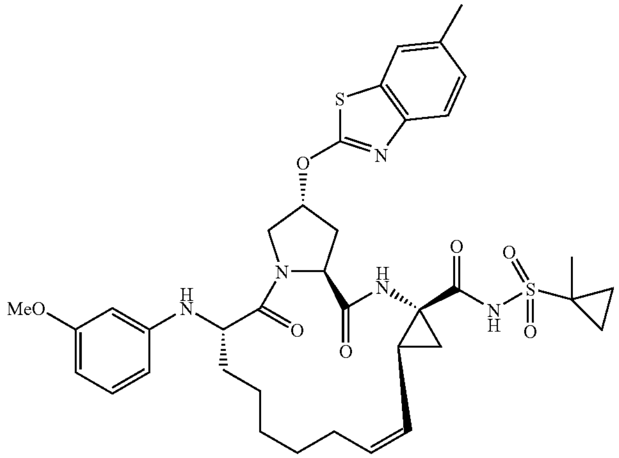 |
| 250 | 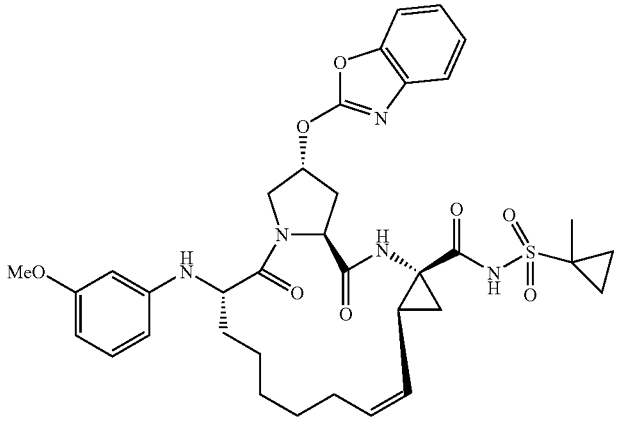 |
Examples of compounds that can be prepared according to Examples 1-29

TABLE 1-continued
| Compound | Structure |
| --- | --- |
| Examples of compounds that can be prepared according to Examples 1-29 | |
| 251 | 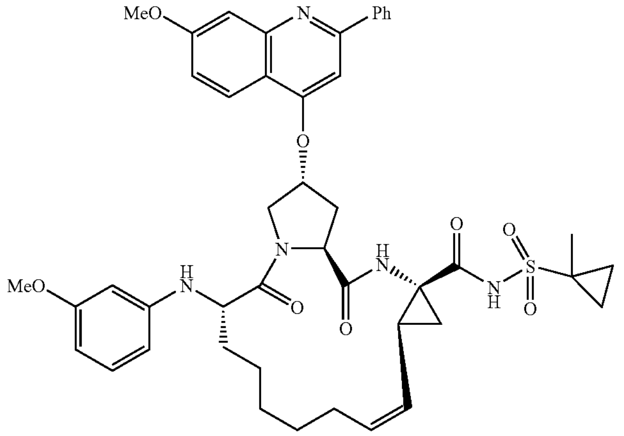 |
| 252 | 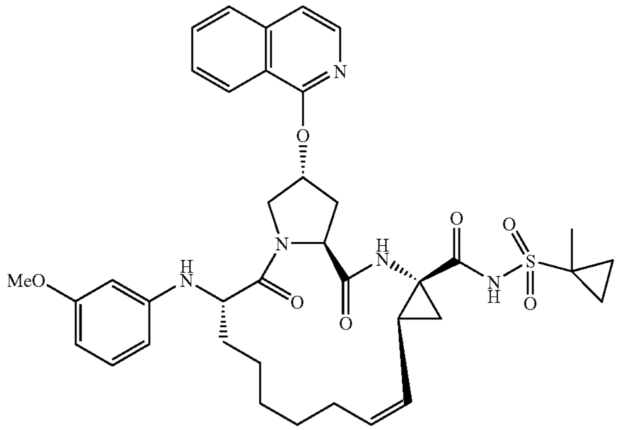 |
| 253 | 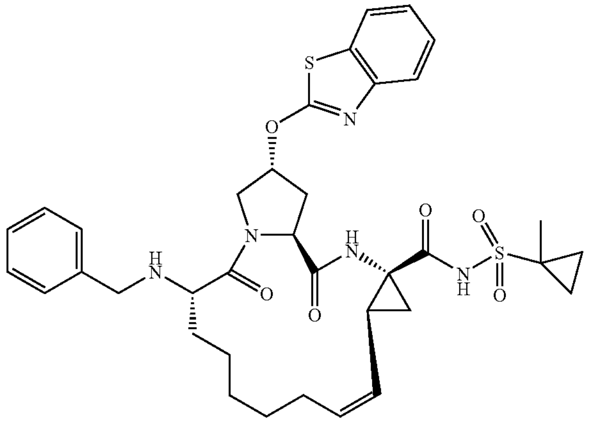 |

TABLE 1-continued
| Examples of compounds that can be prepared according to Examples 1-29 | |
|---|---|
| Compound | Structure |
| 254 | 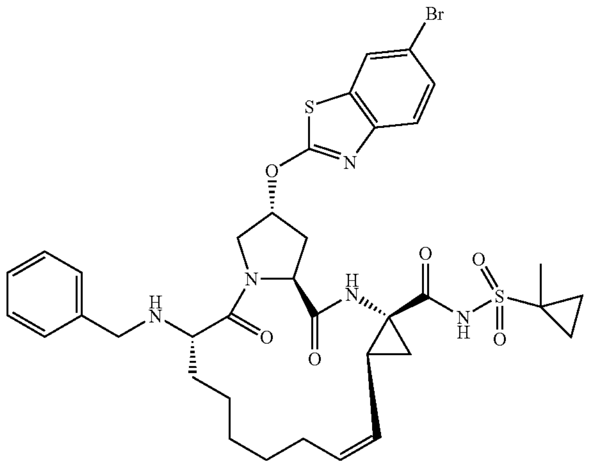 |
| 255 | 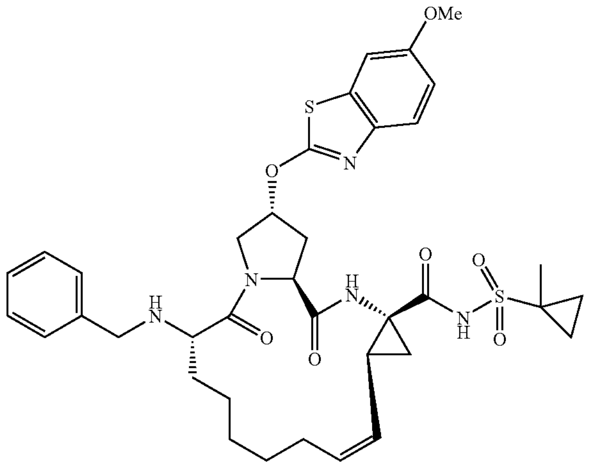 |
| 256 | 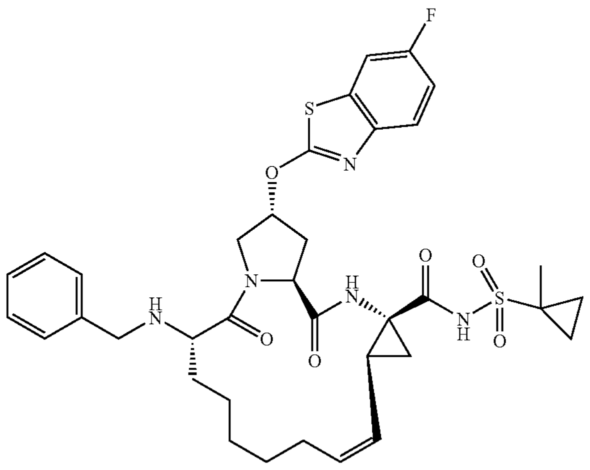 |

TABLE 1-continued
Examples of compounds that can be prepared according to Examples 1-29
| Compound | Structure |
| --- | --- |
| 257 | 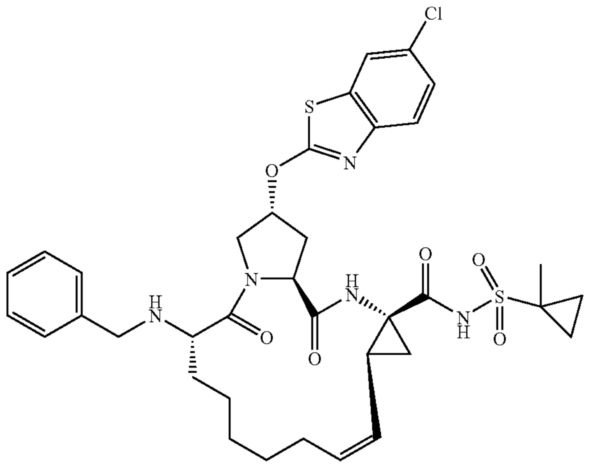 |
| 258 | 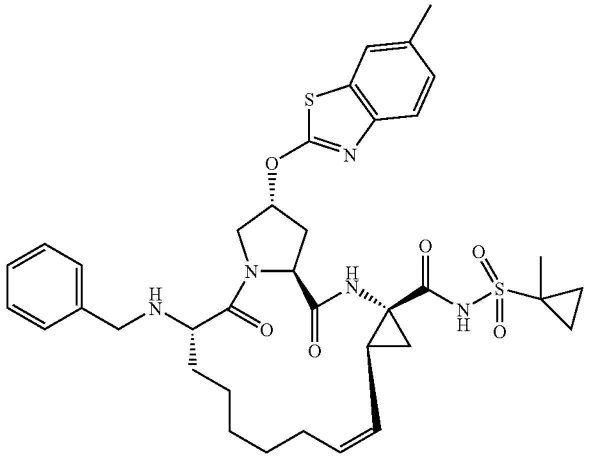 |
| 259 | 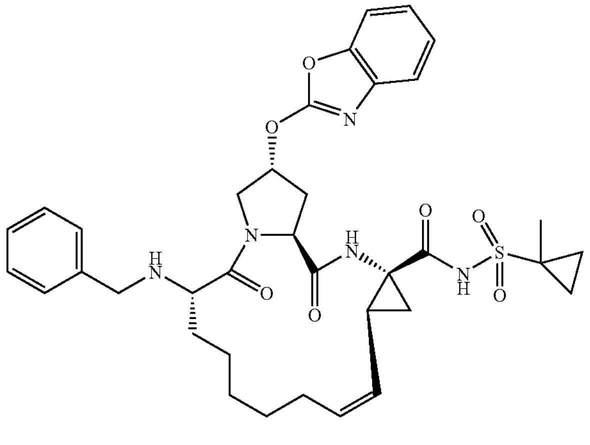 |

TABLE 1-continued
| Examples of compounds that can be prepared according to Examples 1-29 | |
|---|---|
| Compound | Structure |
| 260 | 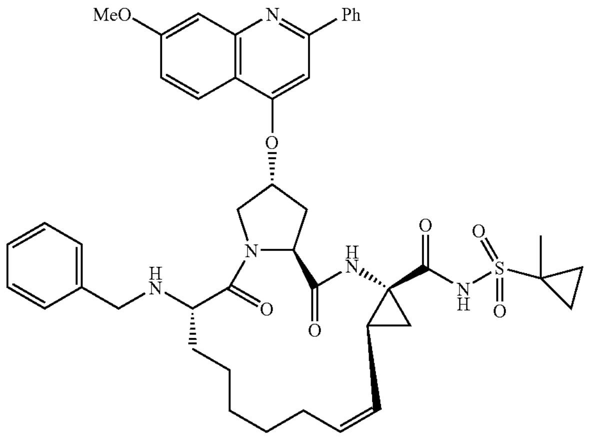 |
| 261 | 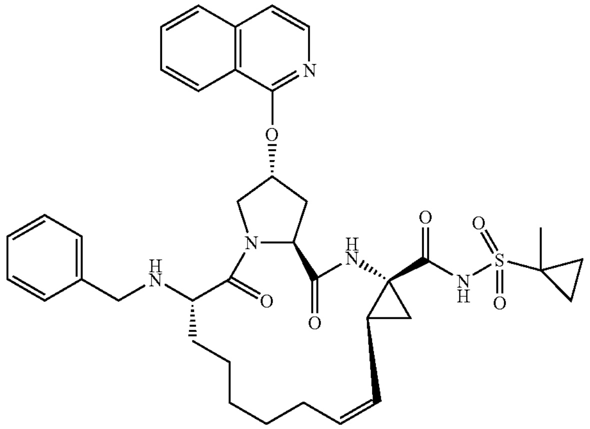 |
| 262 | 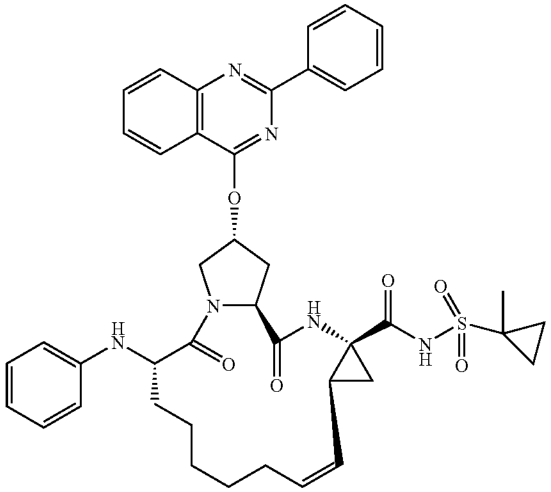 |

TABLE 1-continued
| Examples of compounds that can be prepared according to Examples 1-29 | |
|---|---|
| Compound | Structure |
| 263 | 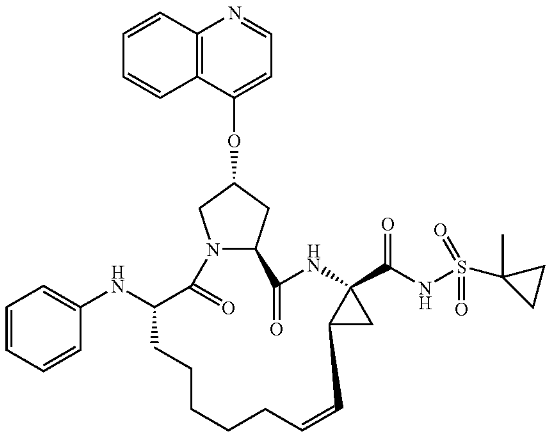 |
| 264 | 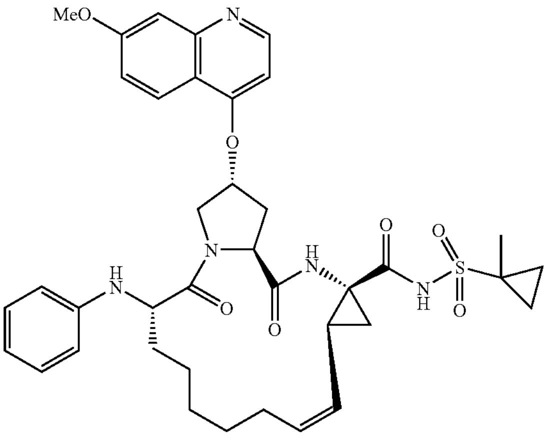 |
| 265 | 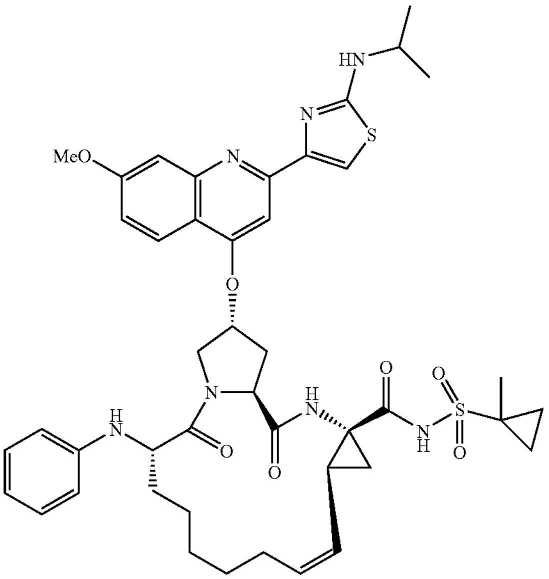 |

TABLE 1-continued
| Examples of compounds that can be prepared according to Examples 1-29 | |
|---|---|
| Compound | Structure |
| 266 | 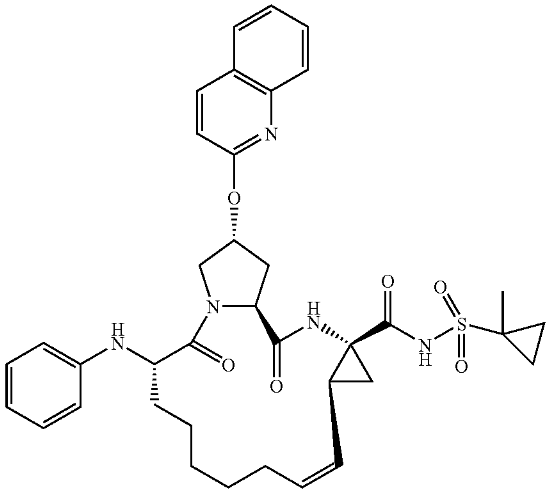 |
| 267 | 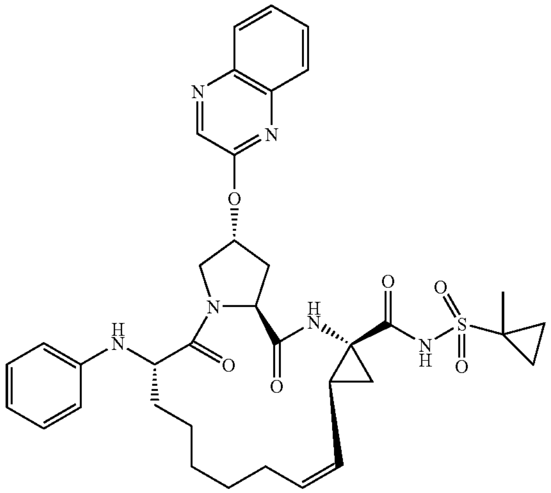 |
| 268 | 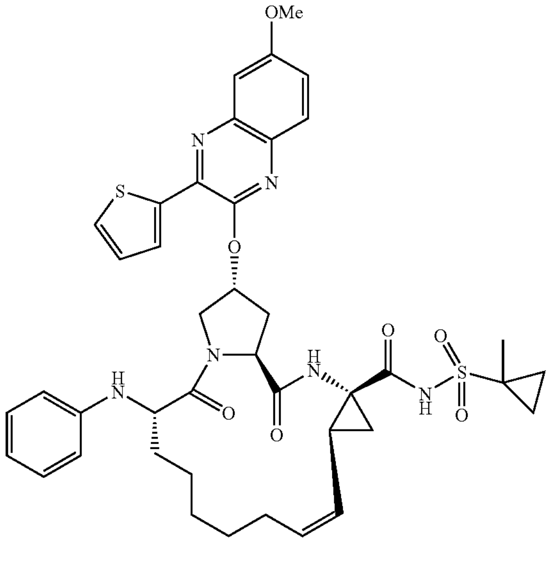 |

TABLE 1-continued
Examples of compounds that can be prepared according to Examples 1-29
| Compound | Structure |
| --- | --- |
| 269 | 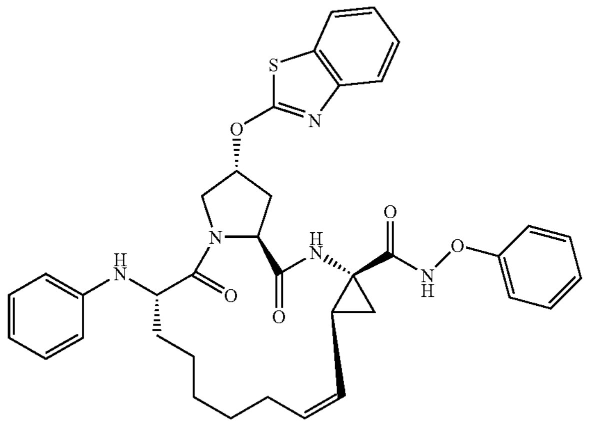 |
| 270 | 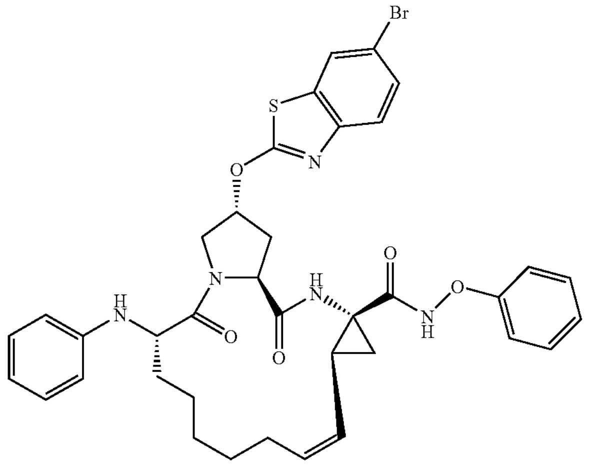 |
| 271 | 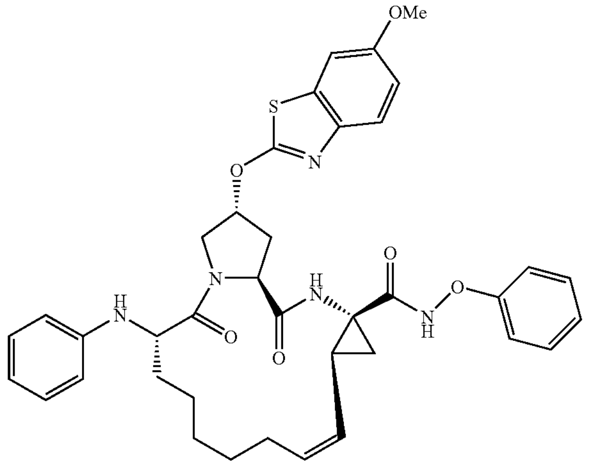 |

TABLE 1-continued
| Examples of compounds that can be prepared according to Examples 1-29 | |
|---|---|
| Compound | Structure |
| 272 | 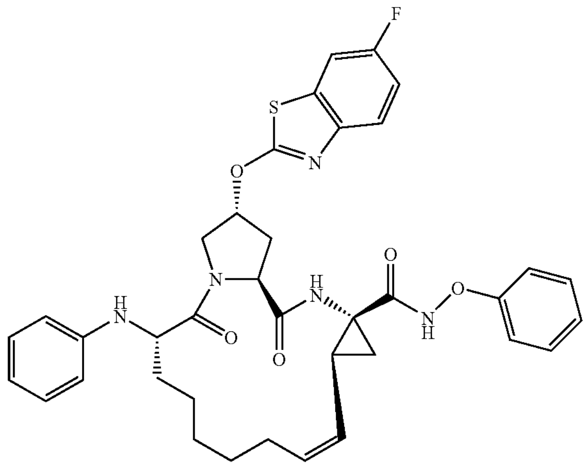 |
| 273 | 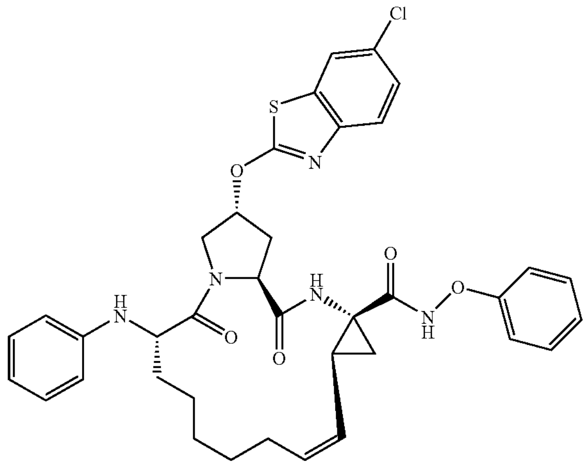 |
| 274 | 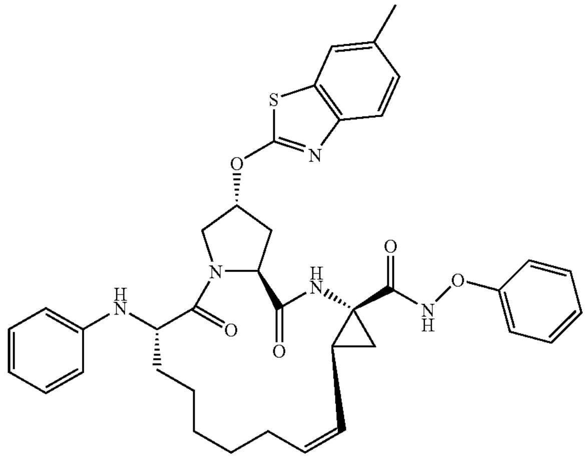 |

TABLE 1-continued
| Examples of compounds that can be prepared according to Examples 1-29 | |
|---|---|
| Compound | Structure |
| 275 | 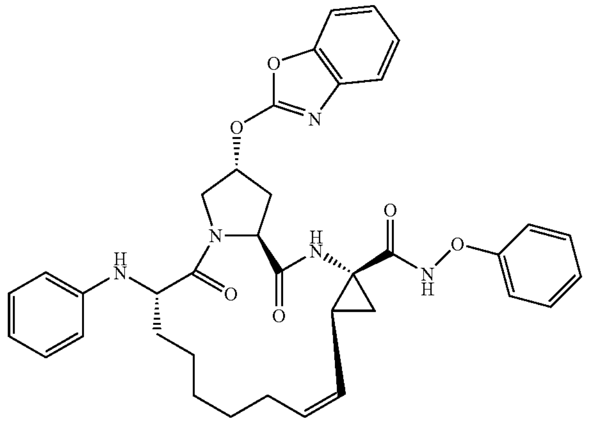 |
| 276 | 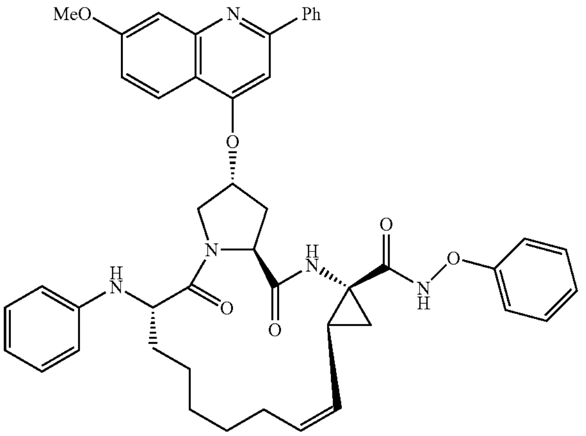 |
| 277 | 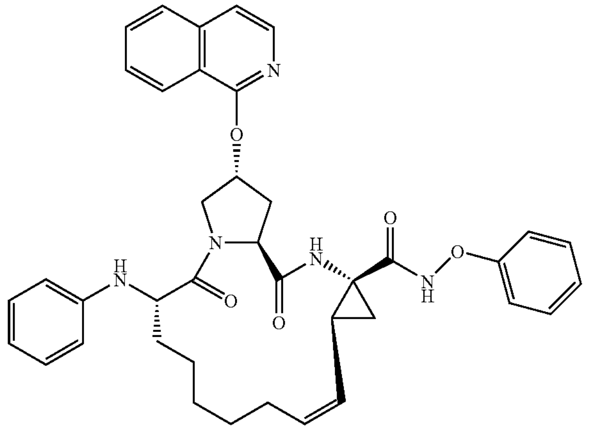 |

TABLE 1-continued
Examples of compounds that can be prepared according to Examples 1-29
| Compound | Structure |
| --- | --- |
| 278 | 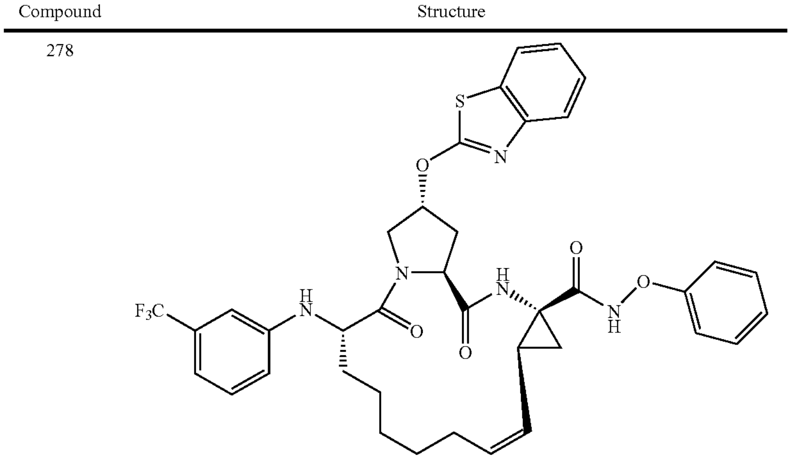 |
| 279 | 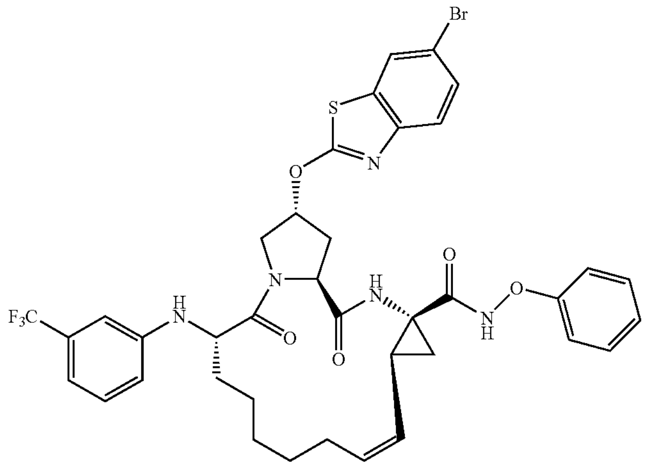 |
| 280 | 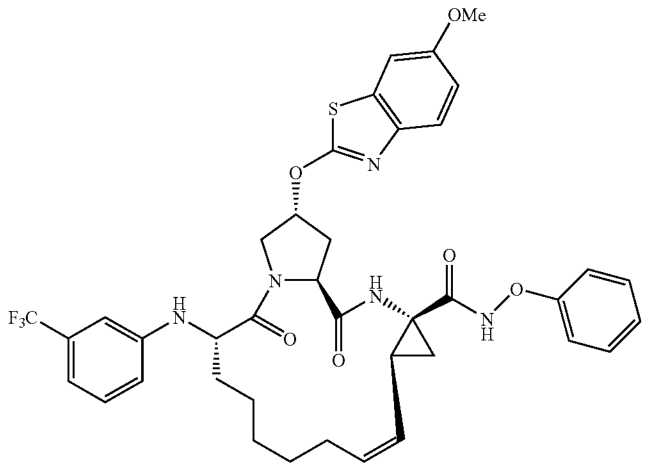 |

TABLE 1-continued
| Examples of compounds that can be prepared according to Examples 1-29 | |
|---|---|
| Compound | Structure |
| 281 | 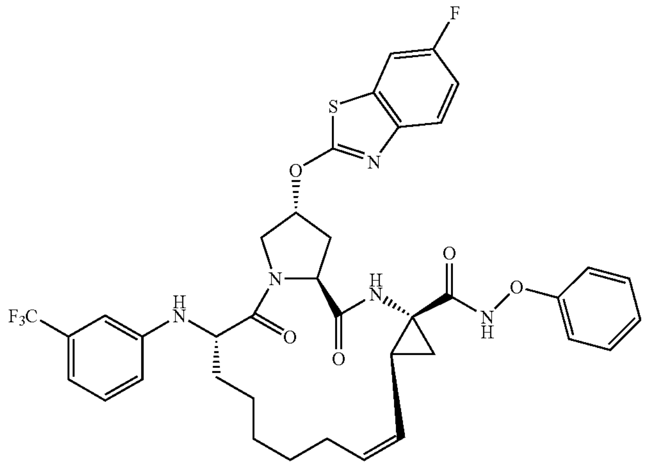 |
| 282 | 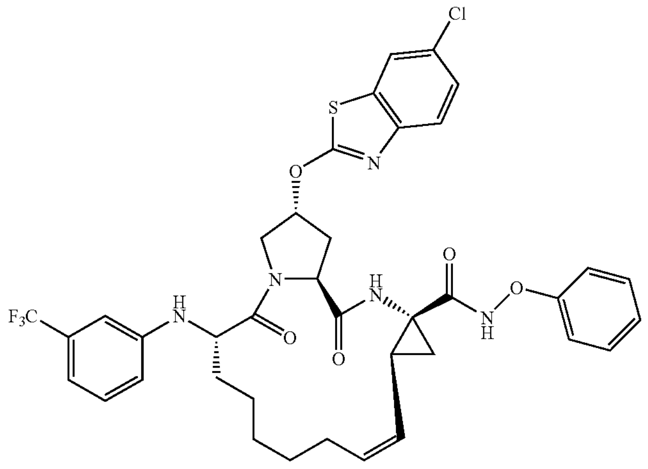 |
| 283 | 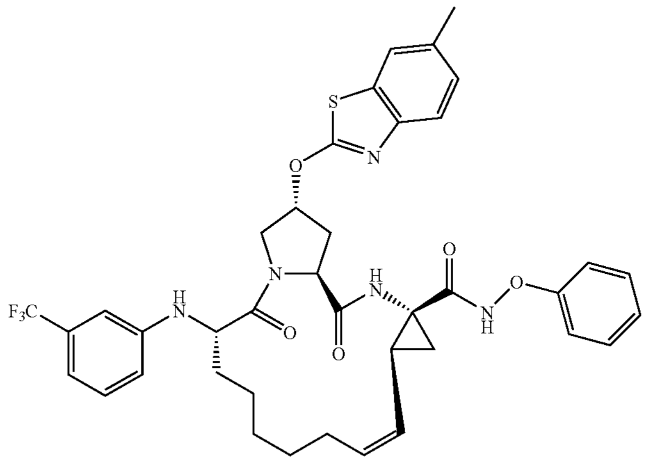 |

TABLE 1-continued
| Examples of compounds that can be prepared according to Examples 1-29 | |
|---|---|
| Compound | Structure |
| 284 | 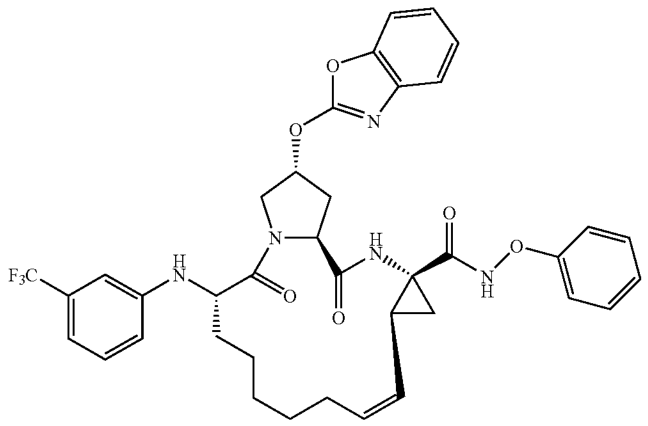 |
| 285 | 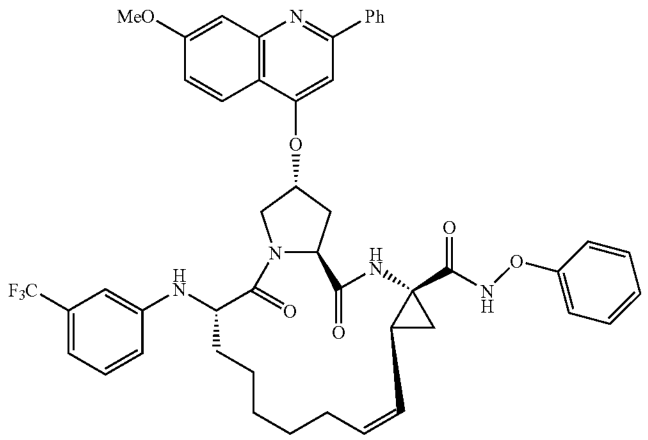 |
| 286 | 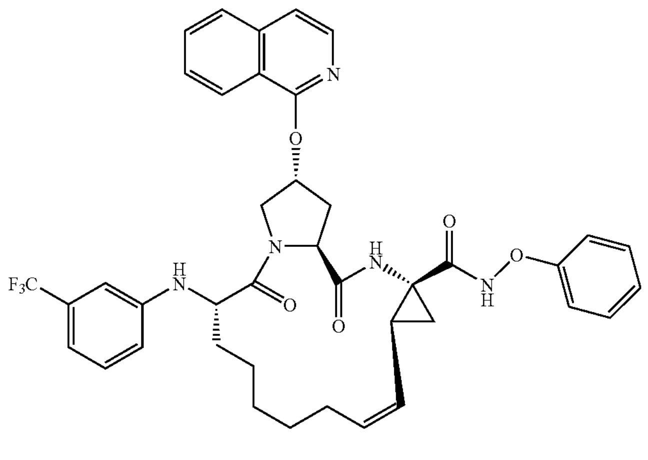 |

TABLE 1-continued
| Examples of compounds that can be prepared according to Examples 1-29 | |
|---|---|
| Compound | Structure |
| 287 | 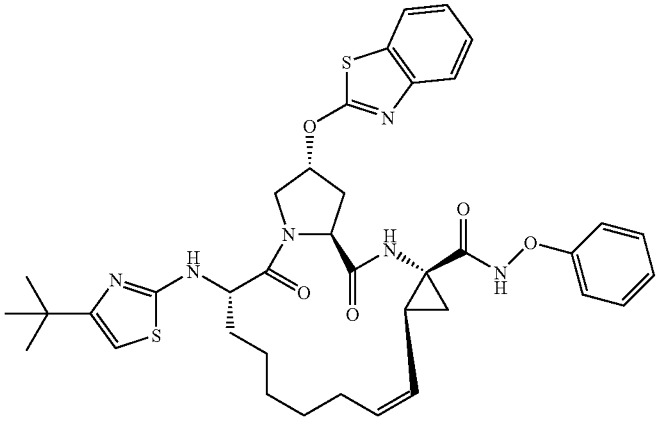 |
| 288 | 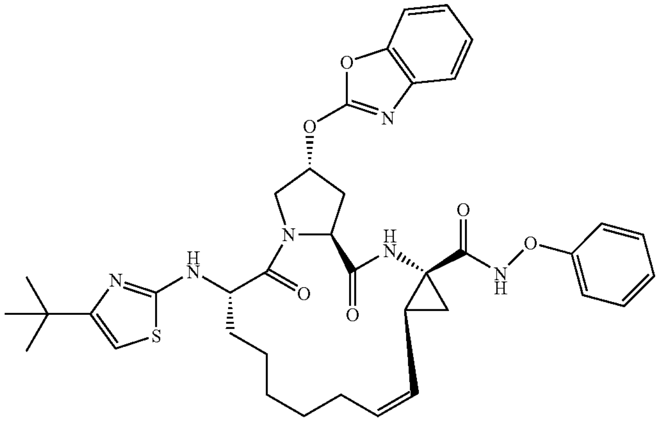 |
| 289 | 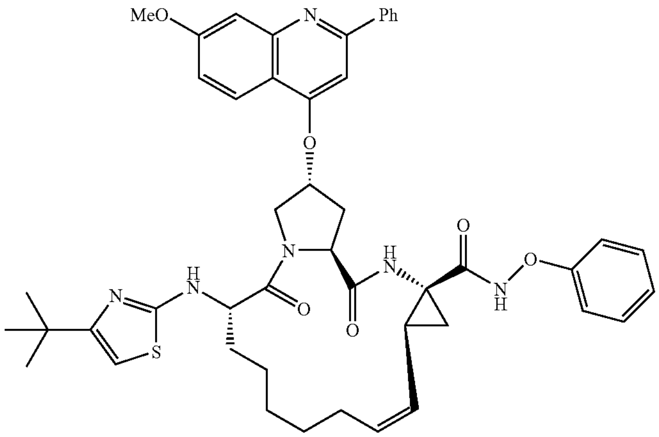 |

TABLE 1-continued
| Examples of compounds that can be prepared according to Examples 1-29 | |
|---|---|
| Compound | Structure |
| 290 | 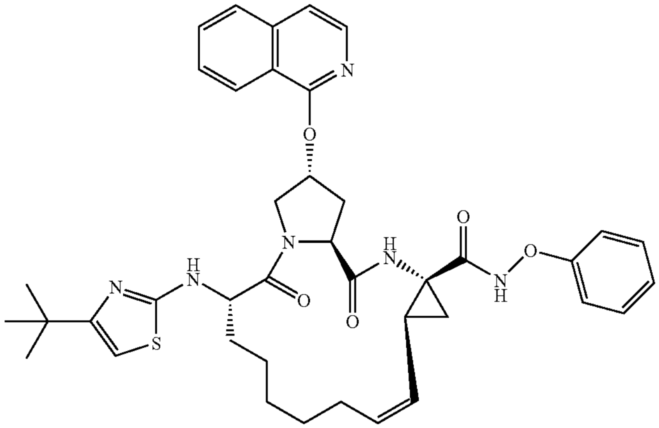 |
| 291 | 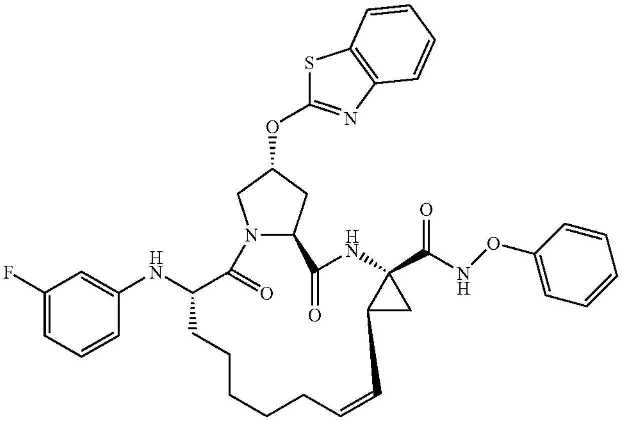 |
| 292 | 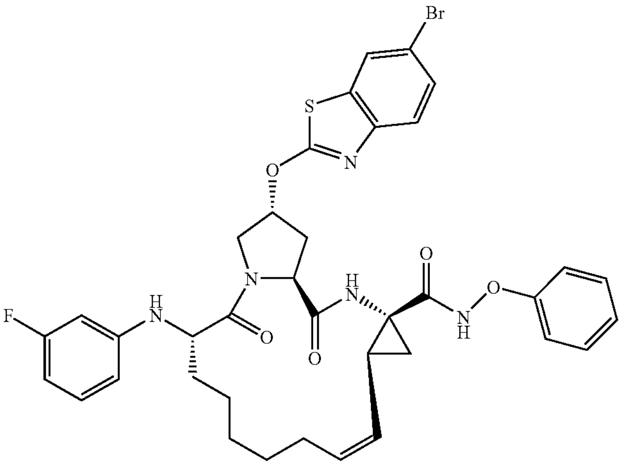 |

TABLE 1-continued
| Examples of compounds that can be prepared according to Examples 1-29 | |
|---|---|
| Compound | Structure |
| 293 | 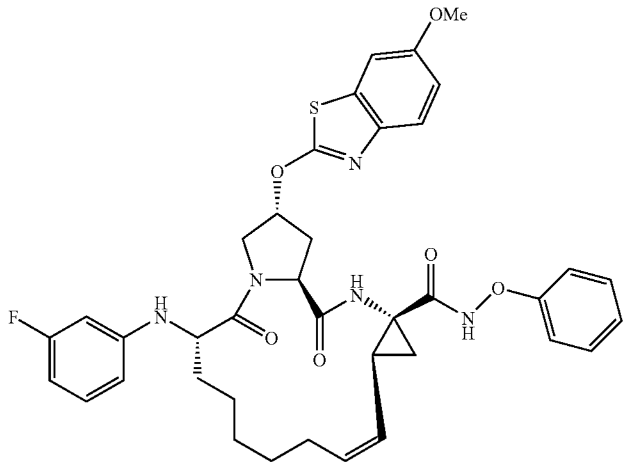 |
| 294 | 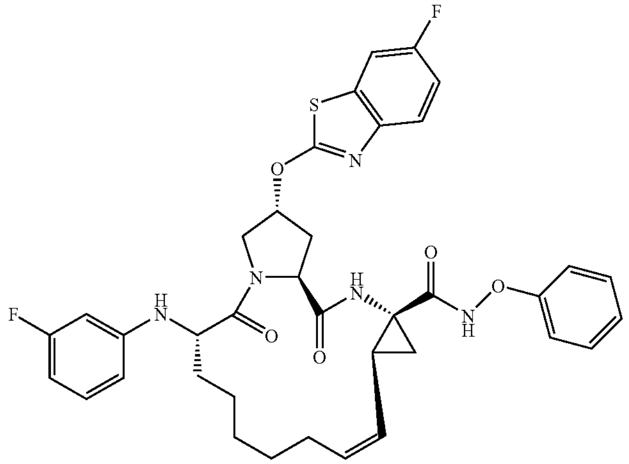 |
| 295 | 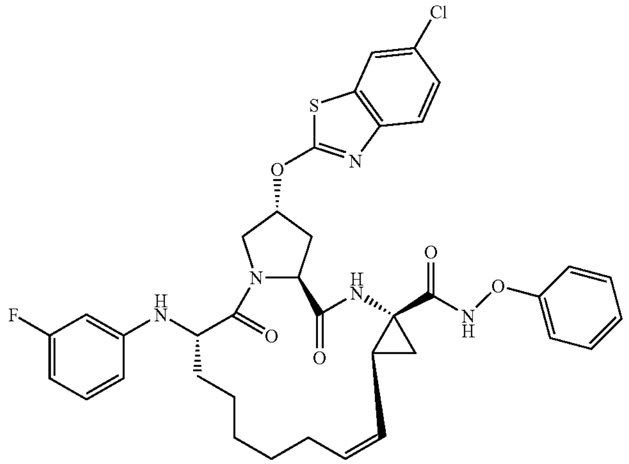 |

TABLE 1-continued
| Examples of compounds that can be prepared according to Examples 1-29 | |
|---|---|
| Compound | Structure |
| 296 | 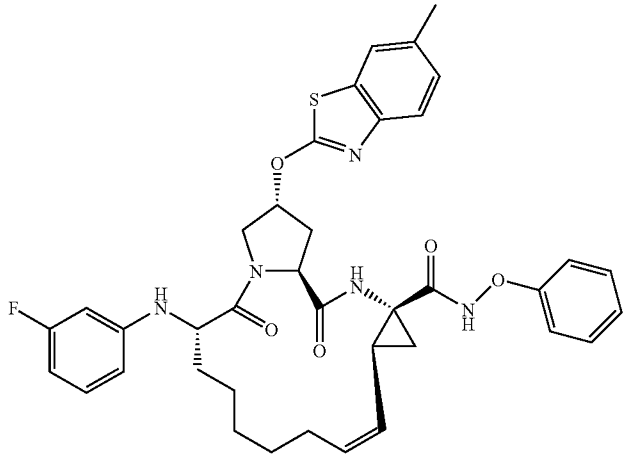 |
| 297 | 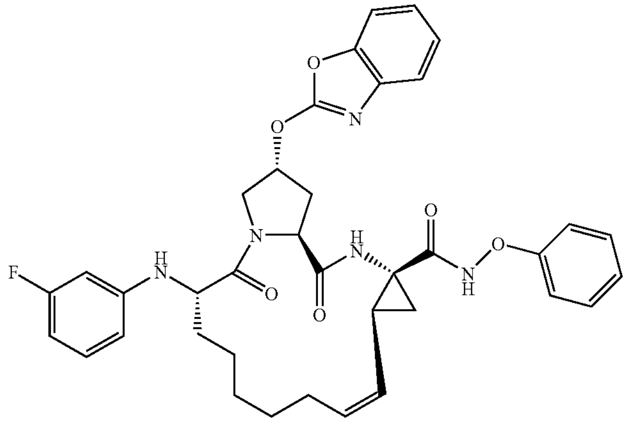 |
| 298 | 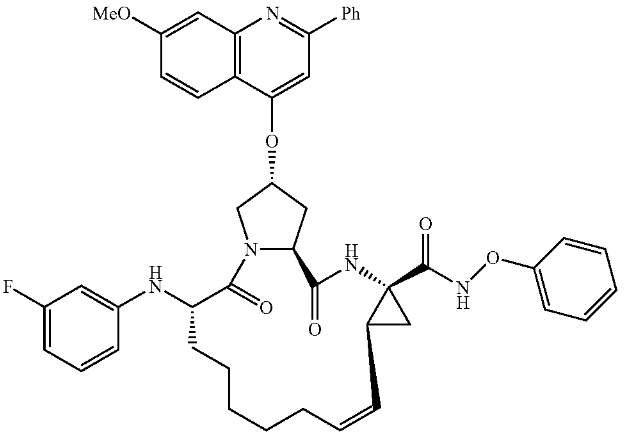 |

TABLE 1-continued
Examples of compounds that can be prepared according to Examples 1-29
| Compound | Structure |
|---|---|
| 299 | 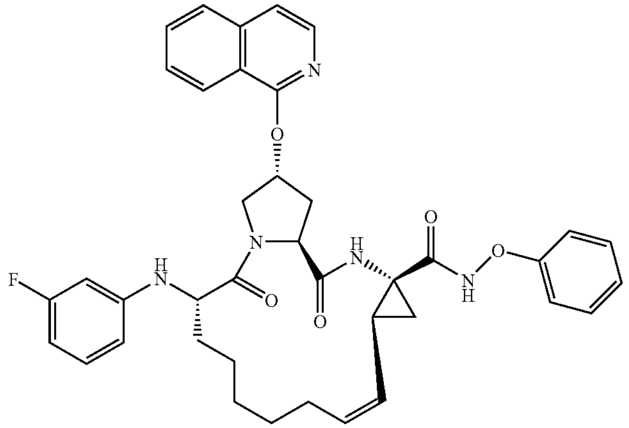 |
| 300 | 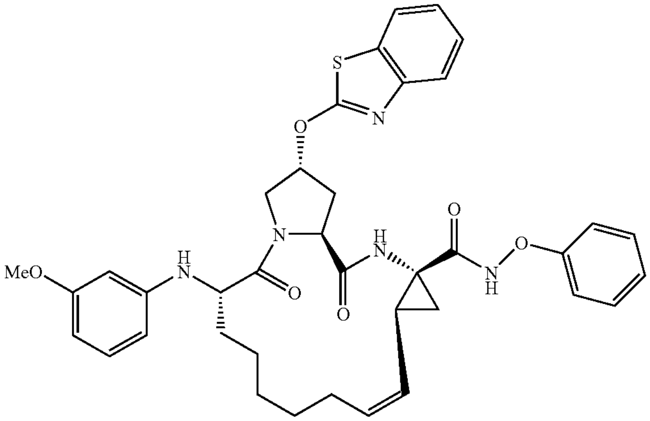 |
| 301 | 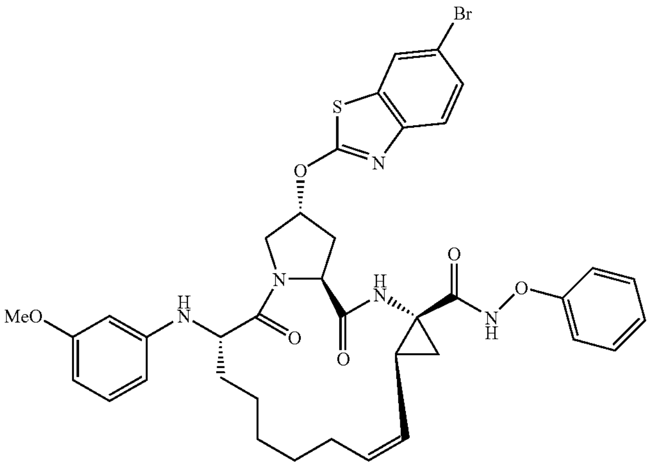 |

TABLE 1-continued
| Examples of compounds that can be prepared according to Examples 1-29 | |
|---|---|
| Compound | Structure |
| 302 | 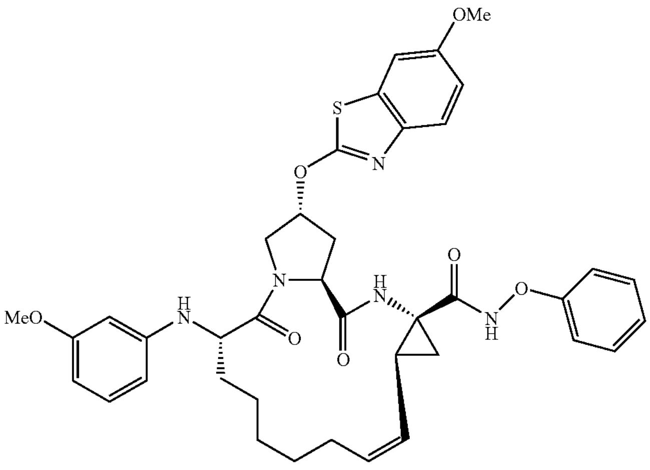 |
| 303 | 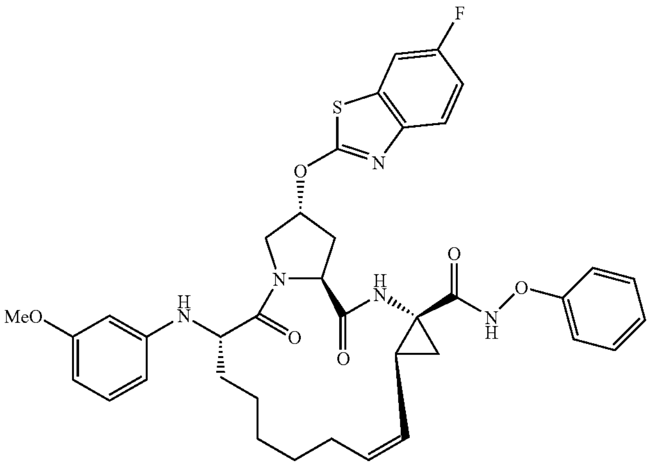 |
| 304 | 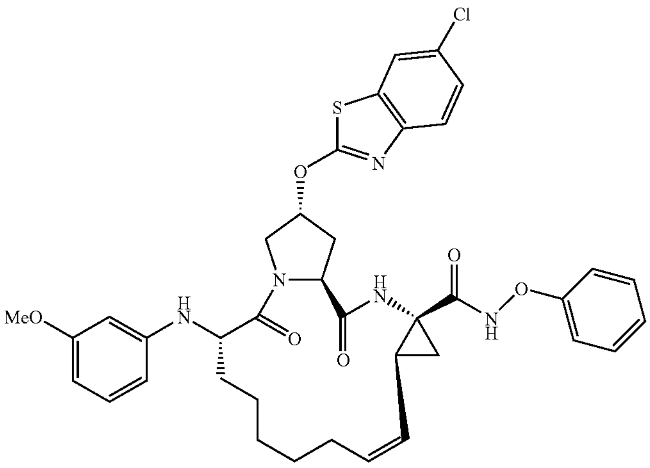 |

TABLE 1-continued
| Examples of compounds that can be prepared according to Examples 1-29 | |
|---|---|
| Compound | Structure |
| 305 | 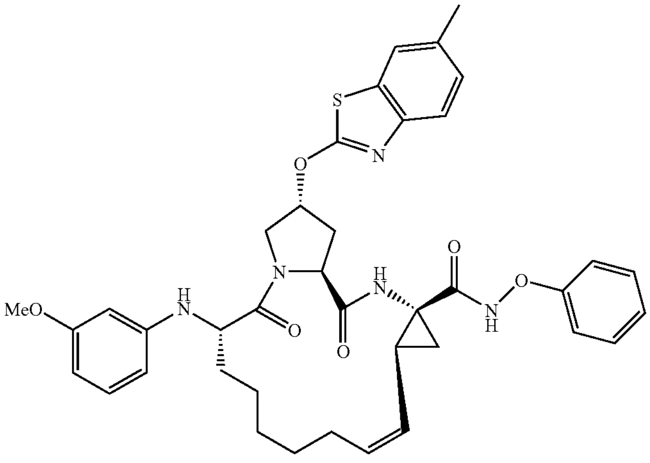 |
| 306 | 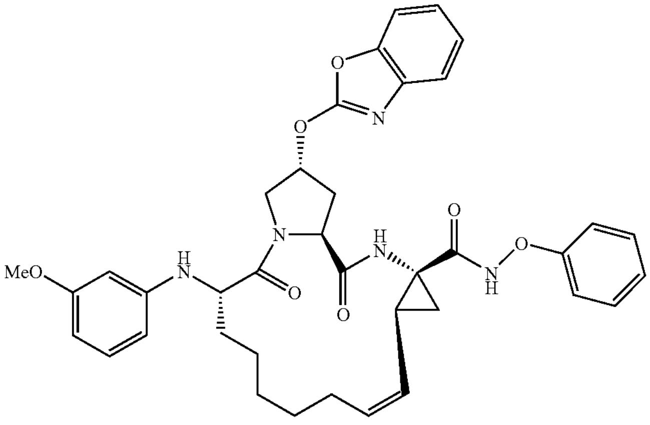 |
| 307 | 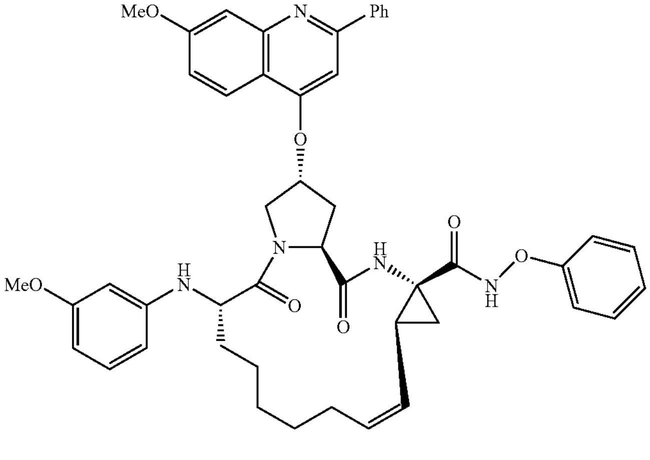 |

TABLE 1-continued
| Compound | Structure |
|---|---|
| Examples of compounds that can be prepared according to Examples 1-29 | |
| 308 | 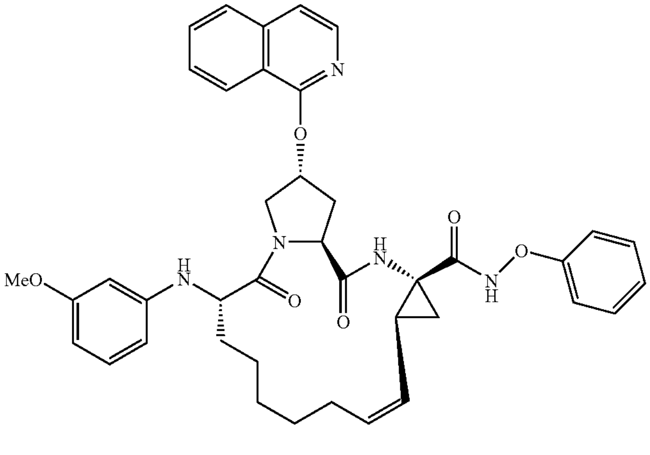 |
| 309 | 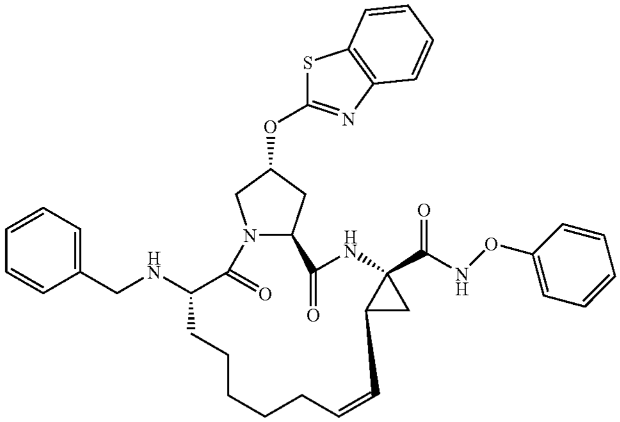 |
| 310 | 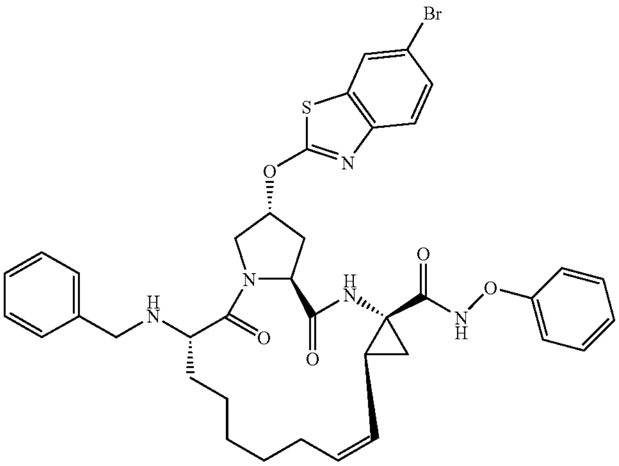 |

TABLE 1-continued
| Examples of compounds that can be prepared according to Examples 1-29 | |
|---|---|
| Compound | Structure |
| 311 | 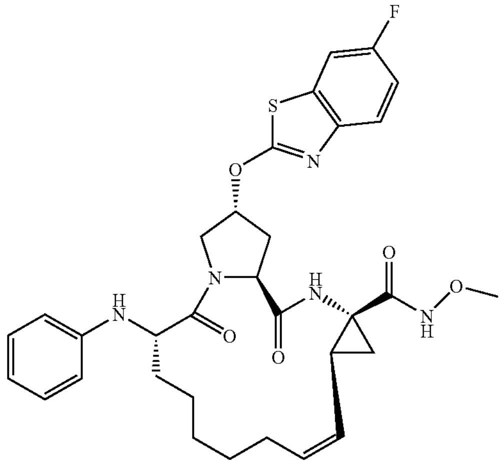 |
| 312 | 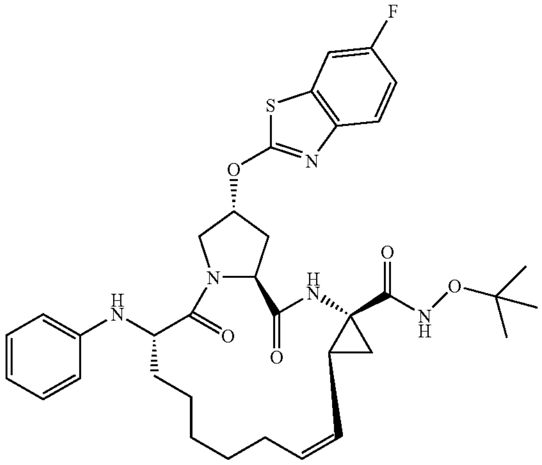 |
| 313 | 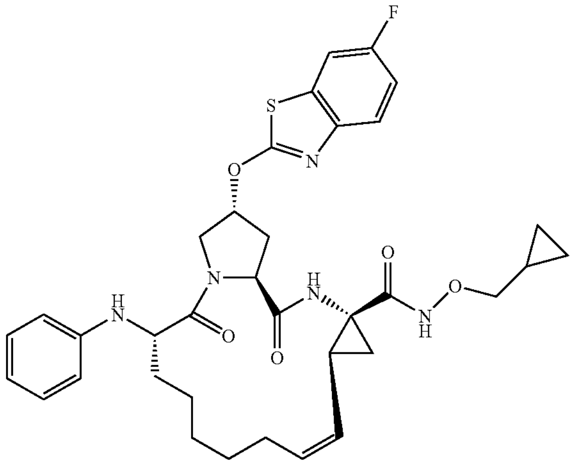 |

TABLE 1-continued
| Examples of compounds that can be prepared according to Examples 1-29 | |
|---|---|
| Compound | Structure |
| 314 | 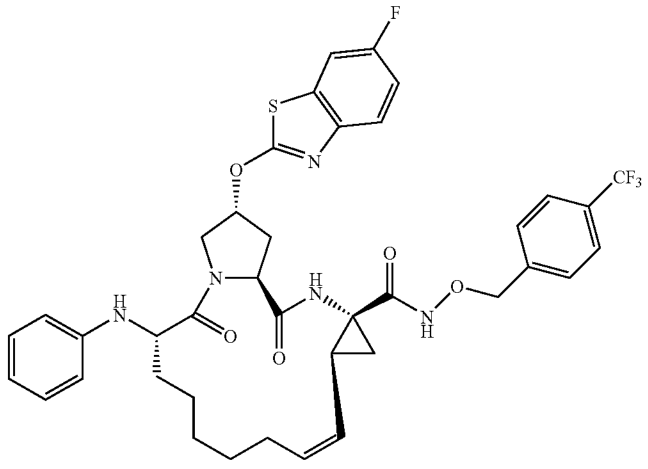 |
| 315 | 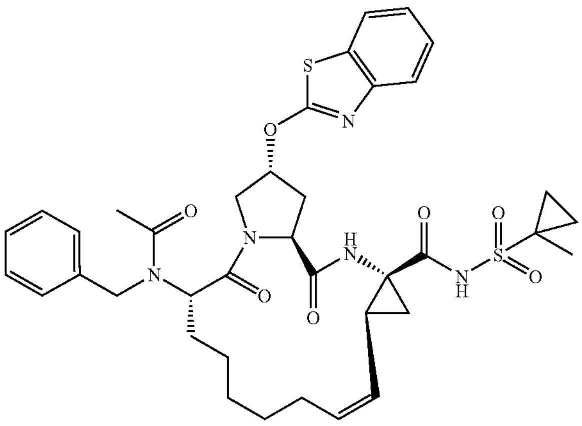 |
| 316 | 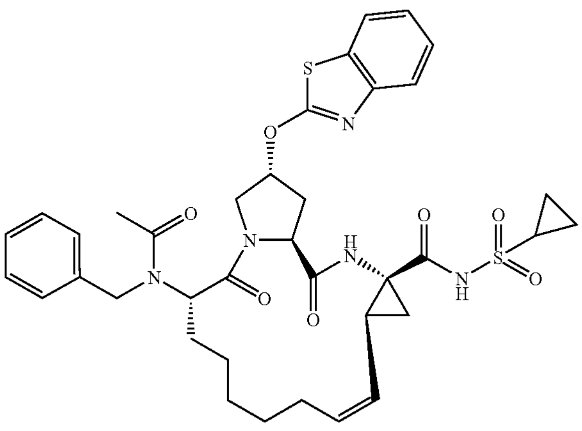 |

TABLE 1-continued
| Examples of compounds that can be prepared according to Examples 1-29 | |
|---|---|
| Compound | Structure |
| 317 | 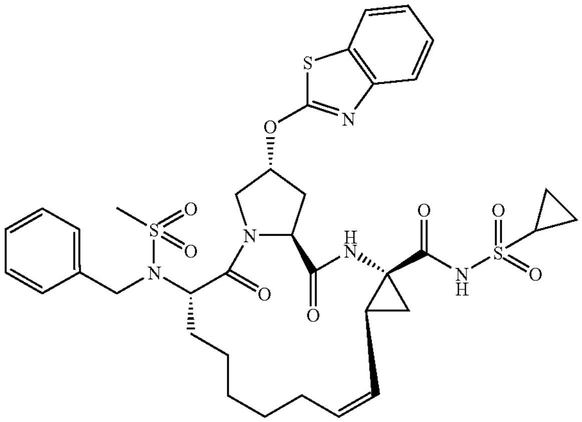 |
| 318 | 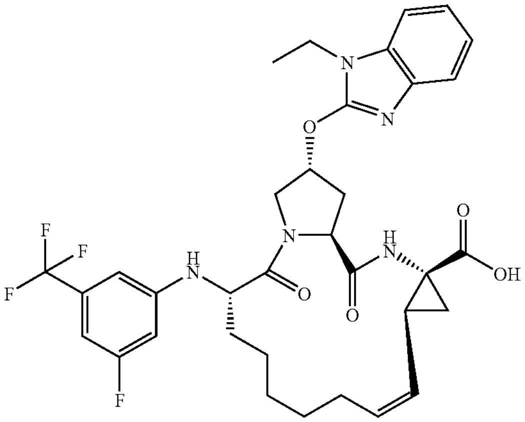 |
| 319 | 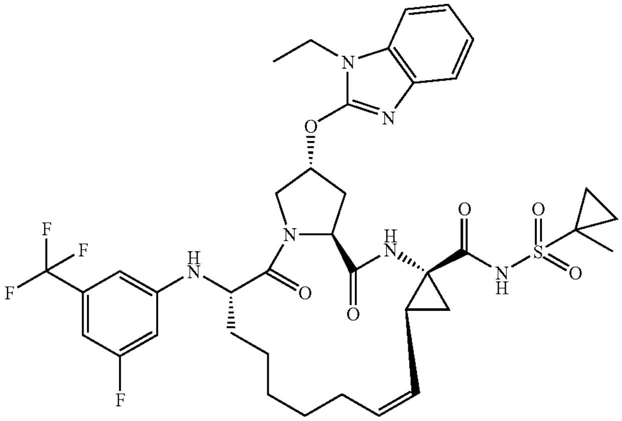 |

TABLE 1-continued
| Examples of compounds that can be prepared according to Examples 1-29 | |
|---|---|
| Compound | Structure |
| 320 | 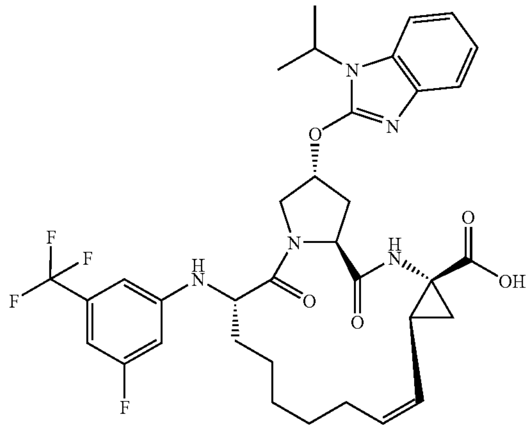 |
| 321 | 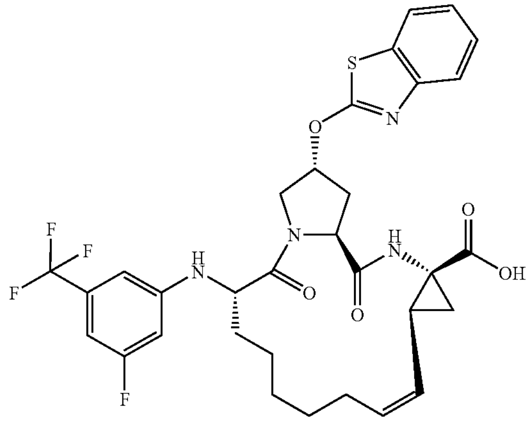 |
| 322 | 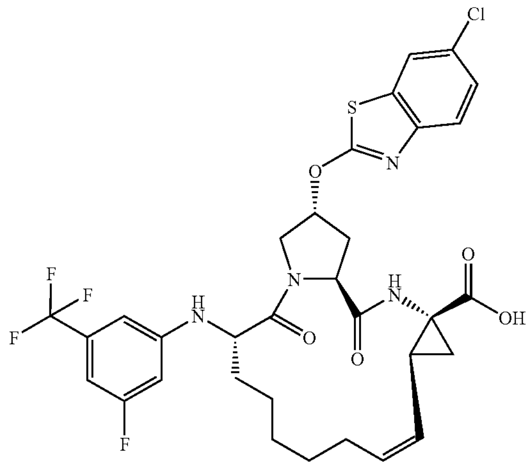 |

TABLE 1-continued
| Examples of compounds that can be prepared according to Examples 1-29 | |
|---|---|
| Compound | Structure |
| 323 | 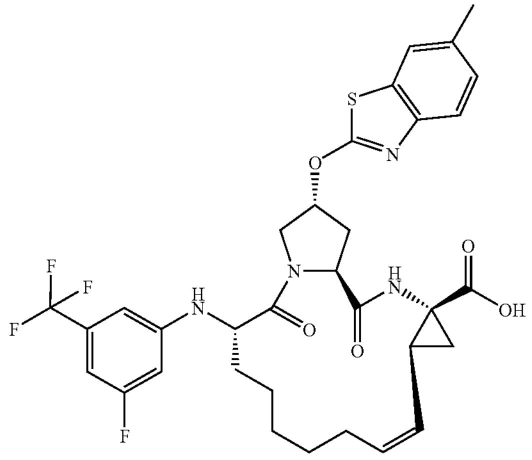 |
| 324 | 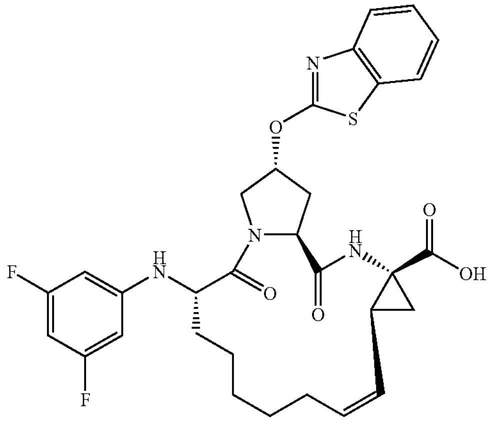 |
| 325 | 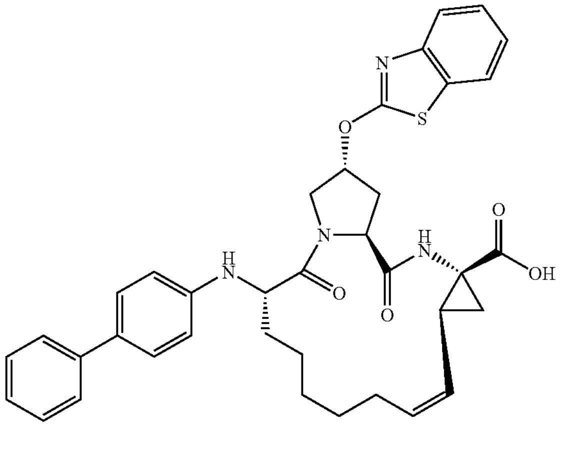 |

TABLE 1-continued
| Examples of compounds that can be prepared according to Examples 1-29 | |
|---|---|
| Compound | Structure |
| 326 | 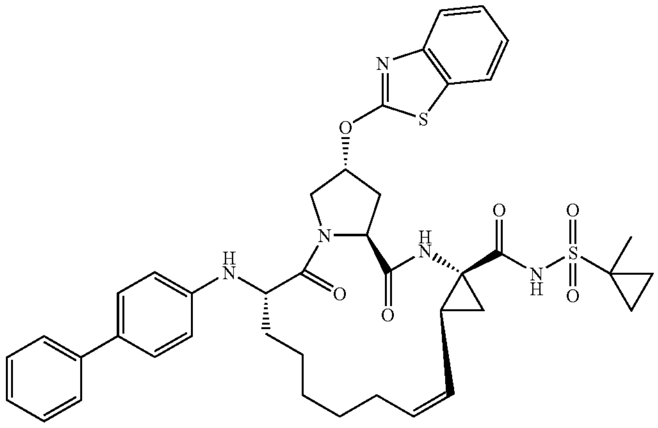 |
| 327 | 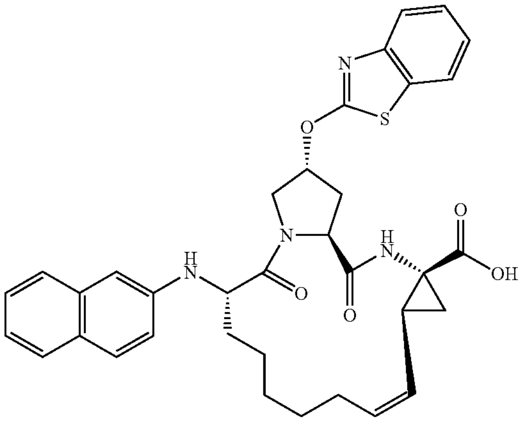 |
| 328 | 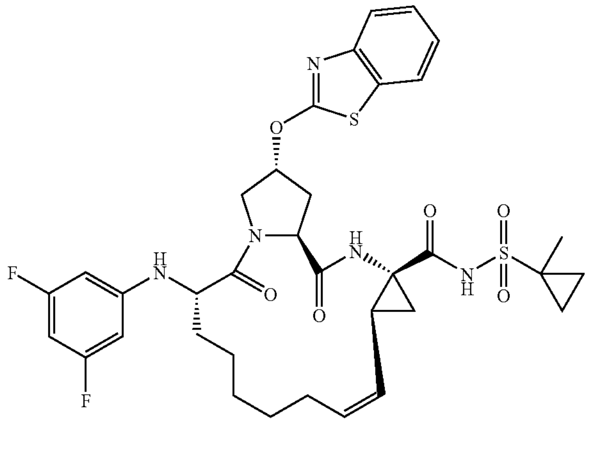 |

TABLE 1-continued
| Compound | Structure |
|---|---|
| 329 | 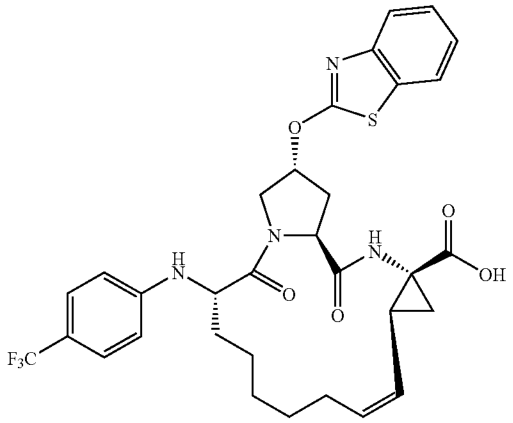 |
| 330 | 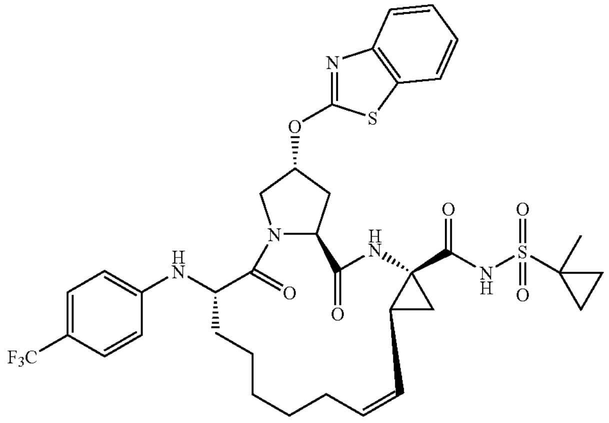 |
| 331 | 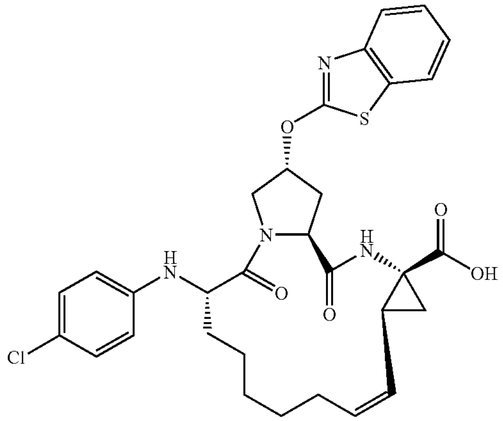 |
Examples of compounds that can be prepared according to Examples 1-29

TABLE 1-continued
| Examples of compounds that can be prepared according to Examples 1-29 | |
|---|---|
| Compound | Structure |
| 332 | 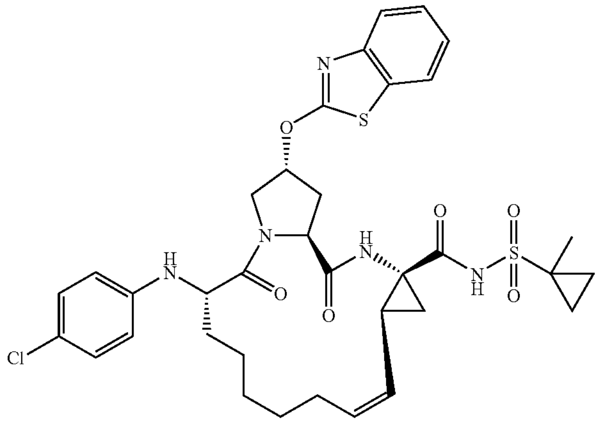 |
| 333 | 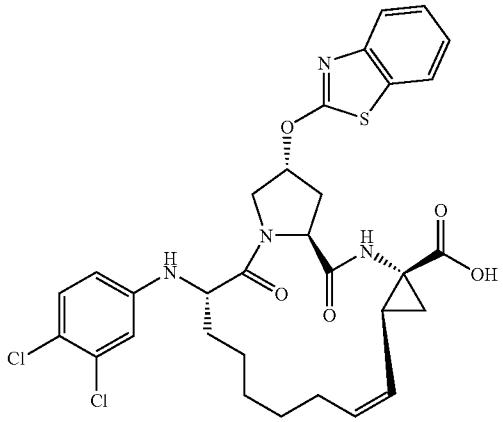 |
| 334 | 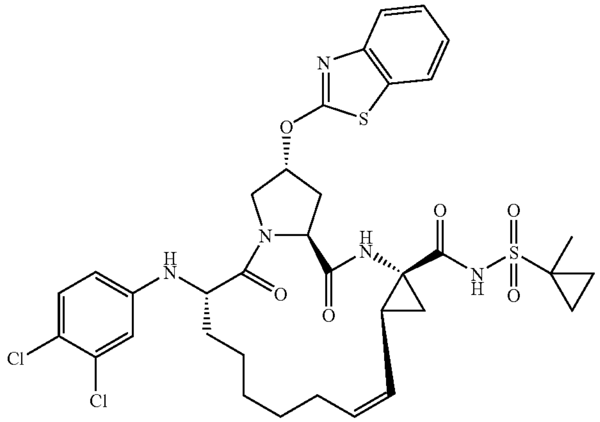 |

TABLE 1-continued
| Examples of compounds that can be prepared according to Examples 1-29 | |
|---|---|
| Compound | Structure |
| 335 | 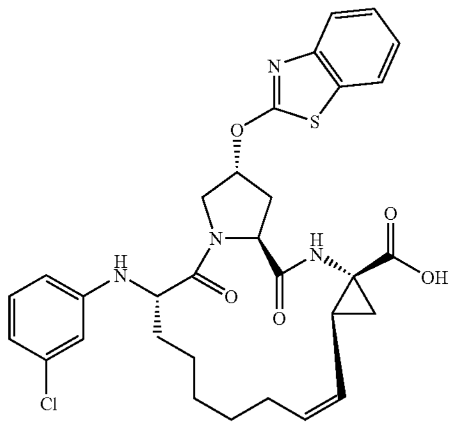 |
| 336 | 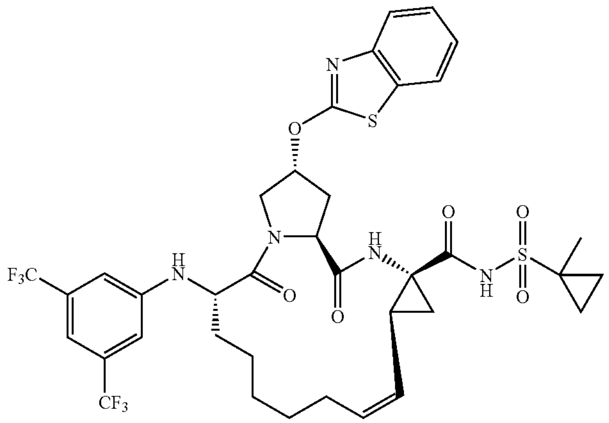 |
| 337 | 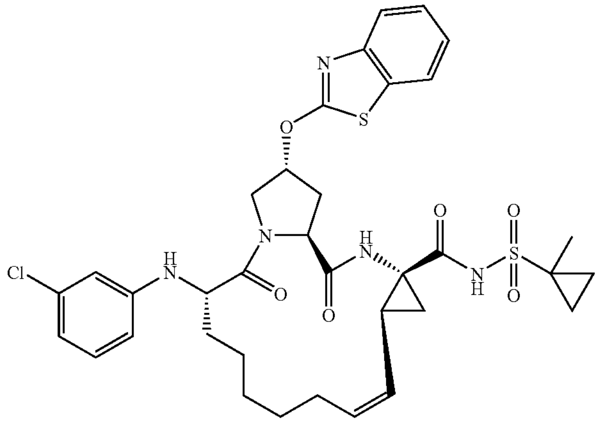 |

TABLE 1-continued
| Examples of compounds that can be prepared according to Examples 1-29 | |
|---|---|
| Compound | Structure |
| 338 | 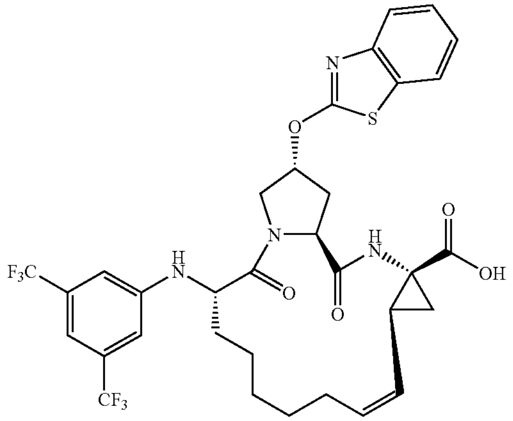 |
| 339 | 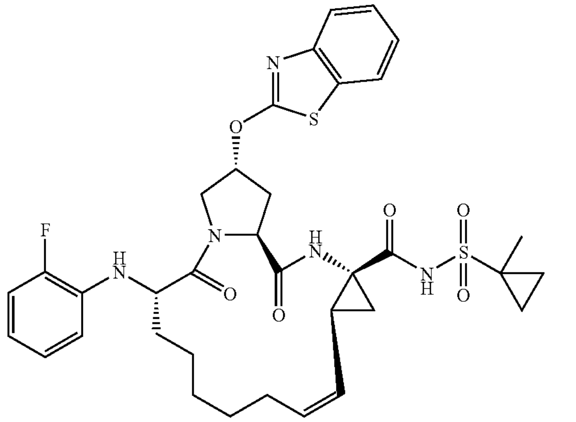 |
| 340 | 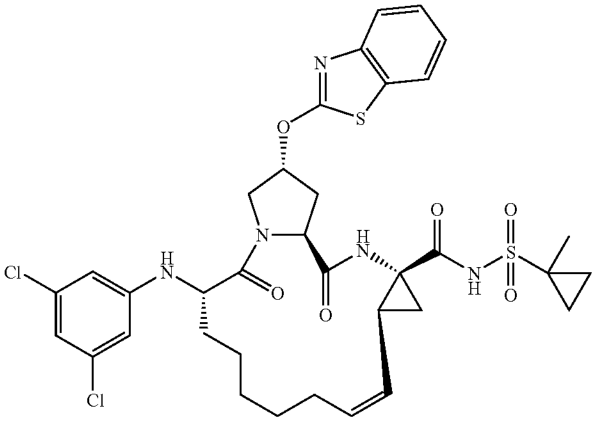 |

TABLE 1-continued
| Examples of compounds that can be prepared according to Examples 1-29 | |
|---|---|
| Compound | Structure |
| 341 | 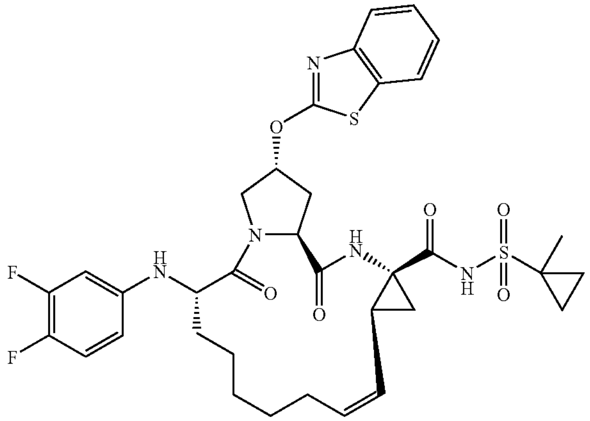 |
| 342 | 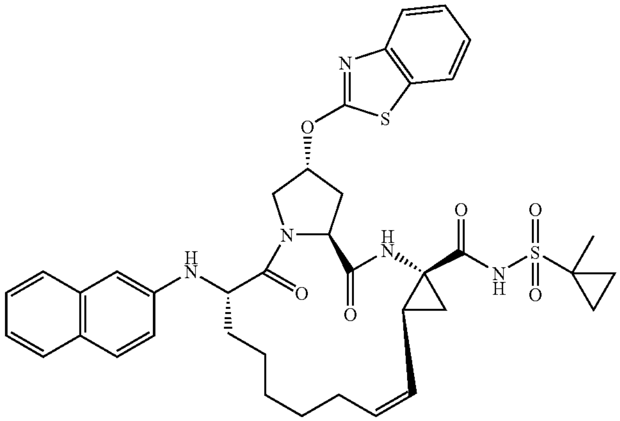 |
| 343 | 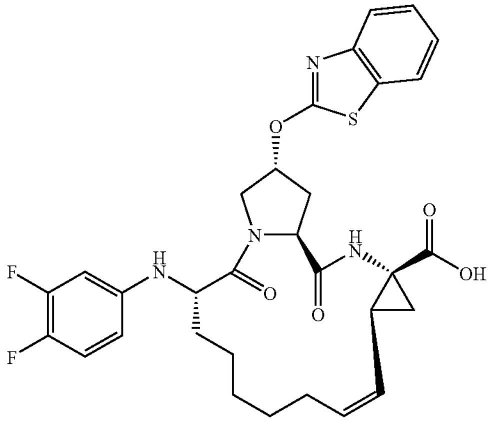 |

TABLE 1-continued
| Examples of compounds that can be prepared according to Examples 1-29 | |
|---|---|
| Compound | Structure |
| 344 | 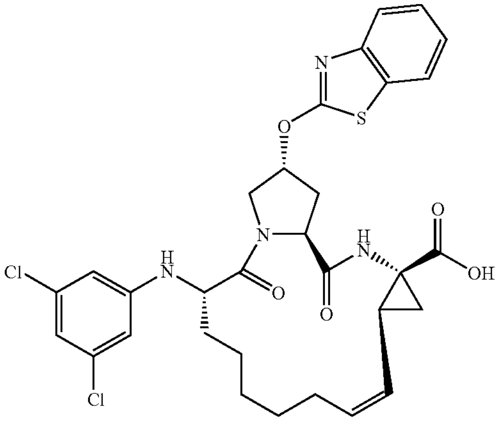 |
| 345 | 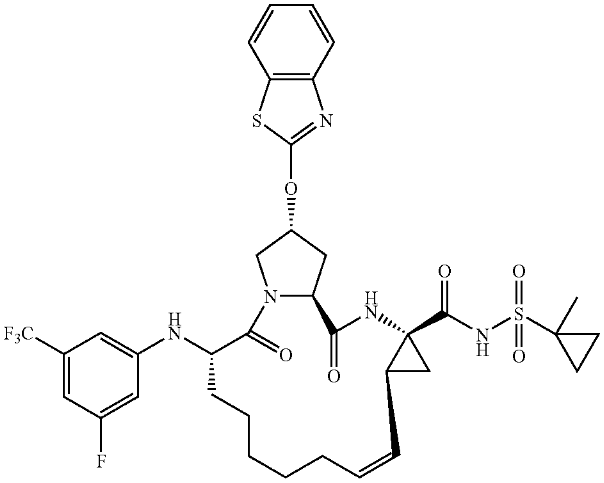 |
| 346 | 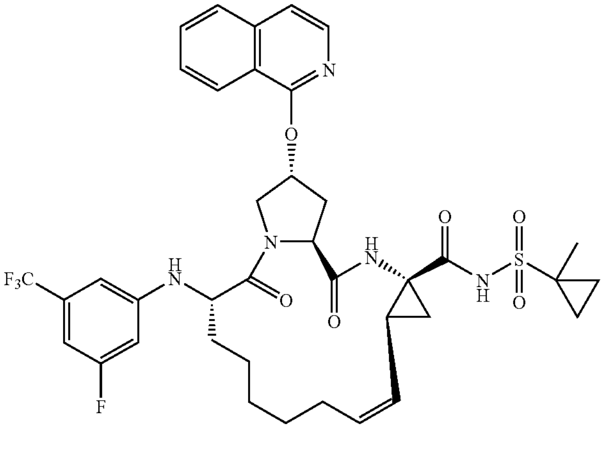 |

TABLE 1-continued
Examples of compounds that can be prepared according to Examples 1-29
| Compound | Structure |
| --- | --- |
| 347 | 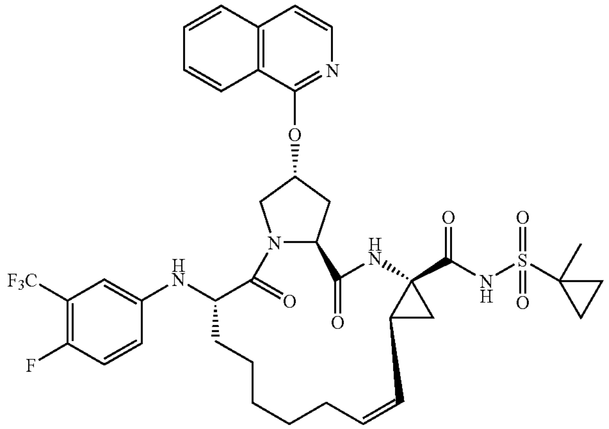 |
| 348 | 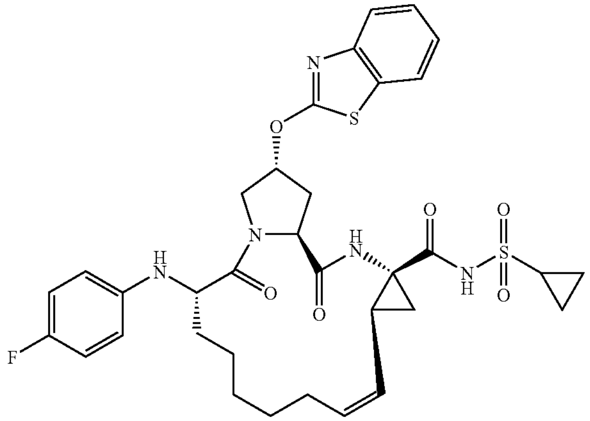 |
| 349 | 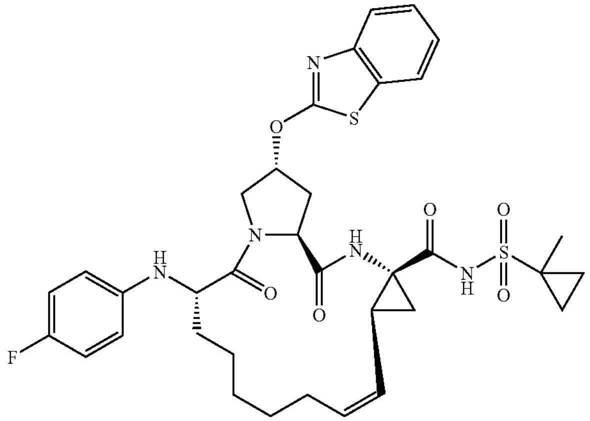 |

TABLE 1-continued
| Examples of compounds that can be prepared according to Examples 1-29 | |
|---|---|
| Compound | Structure |
| 350 | 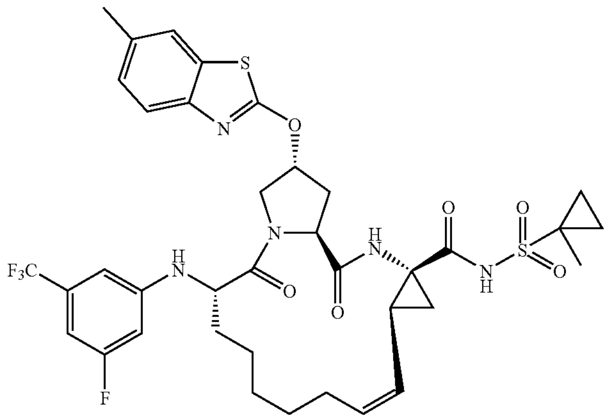 |
| 351 | 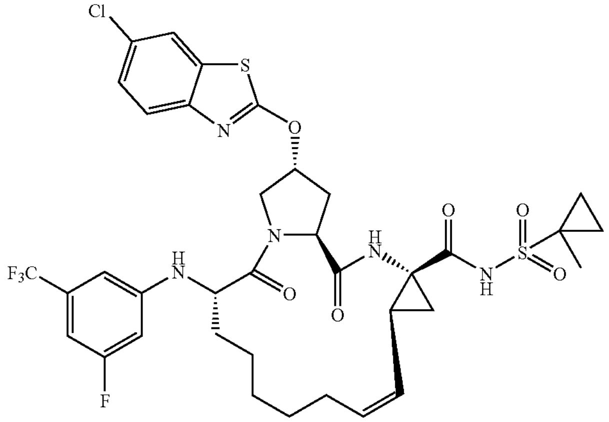 |
| 352 | 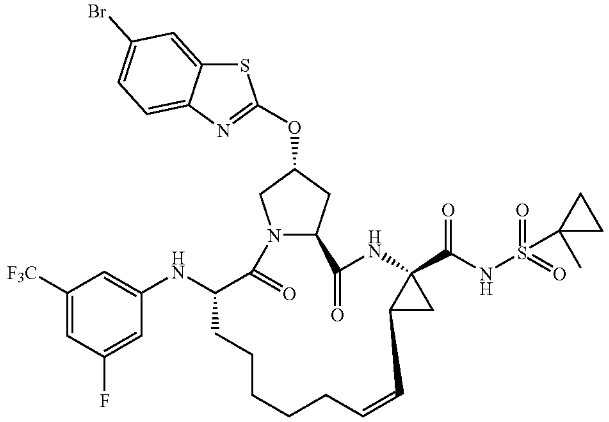 |

TABLE 1-continued
| Examples of compounds that can be prepared according to Examples 1-29 | |
|---|---|
| Compound | Structure |
| 353 | 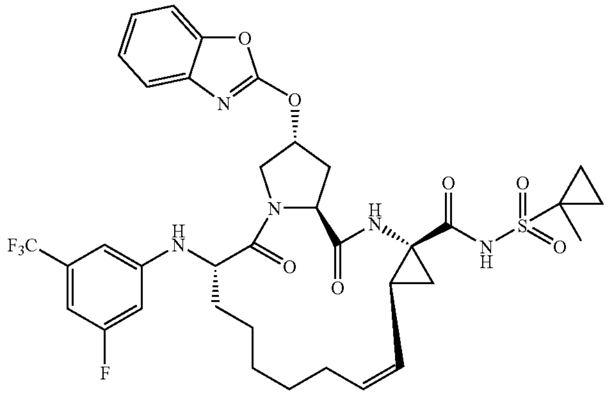 |
| 354 | 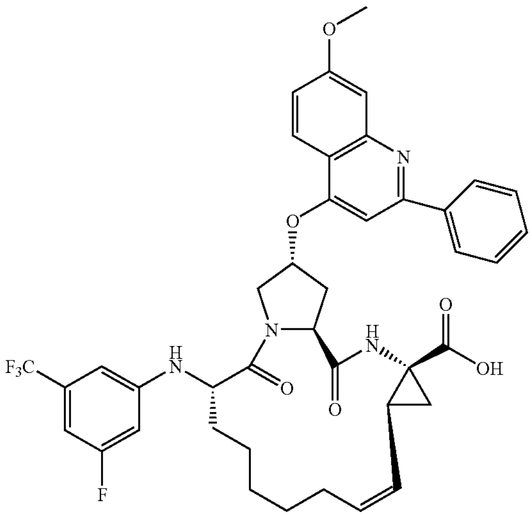 |
| 355 | 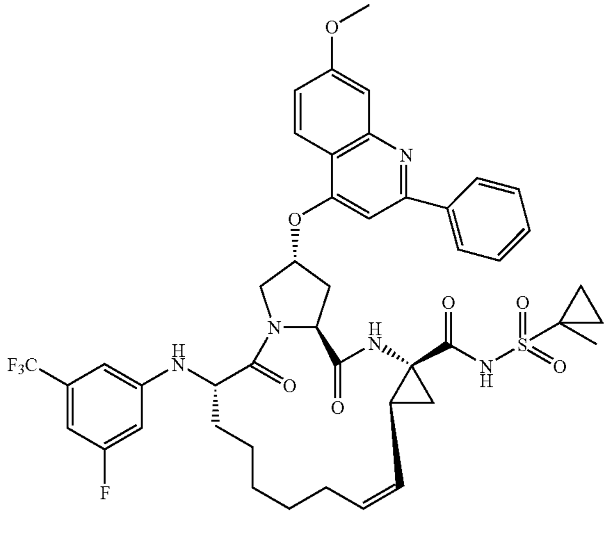 |

TABLE 1-continued
| Compound | Structure |
|---|---|
| 356 | 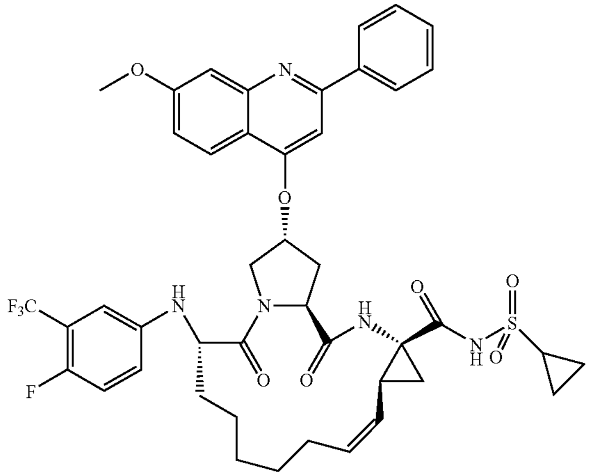 |
| 357 | 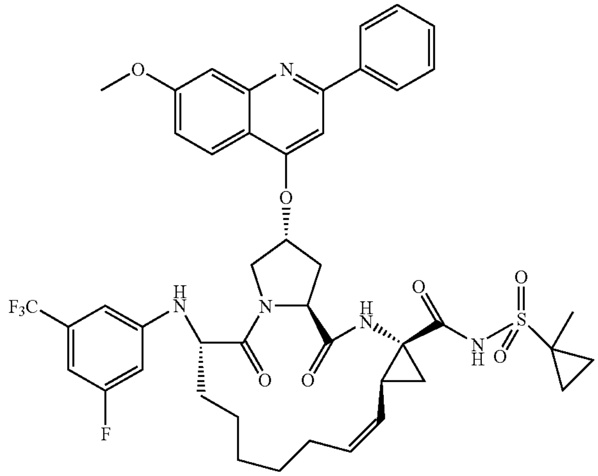 |
| 358 | 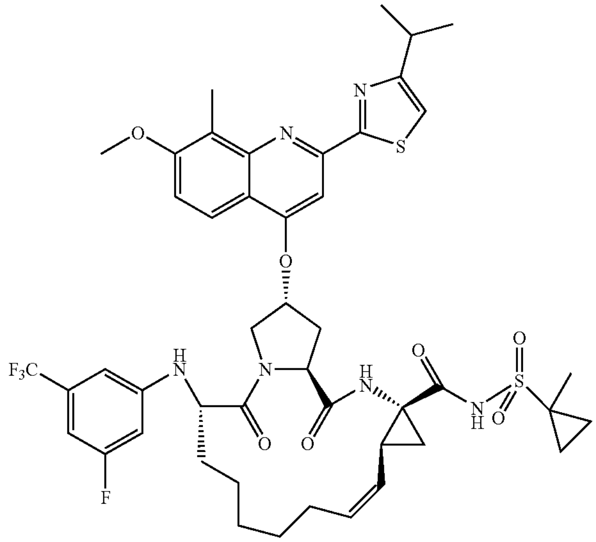 |
Examples of compounds that can be prepared according to Examples 1-29

TABLE 1-continued
| Examples of compounds that can be prepared according to Examples 1-29 | |
|---|---|
| Compound | Structure |
| 359 | 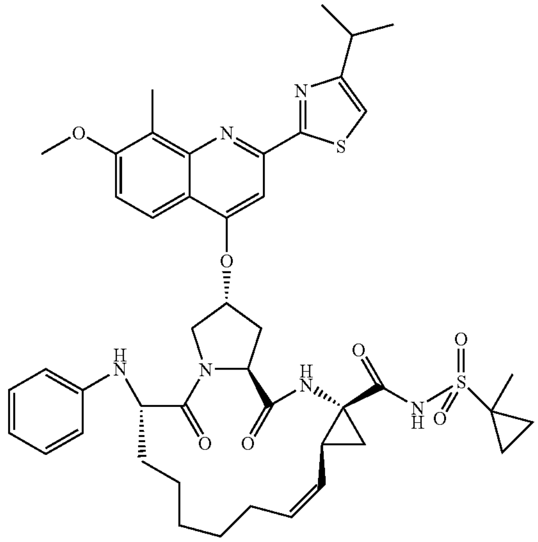 |
| 360 | 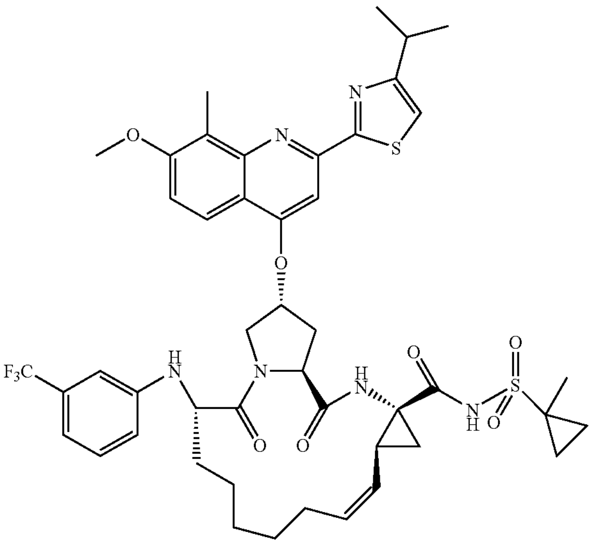 |

TABLE 1-continued
| Examples of compounds that can be prepared according to Examples 1-29 | |
|---|---|
| Compound | Structure |
| 361 | 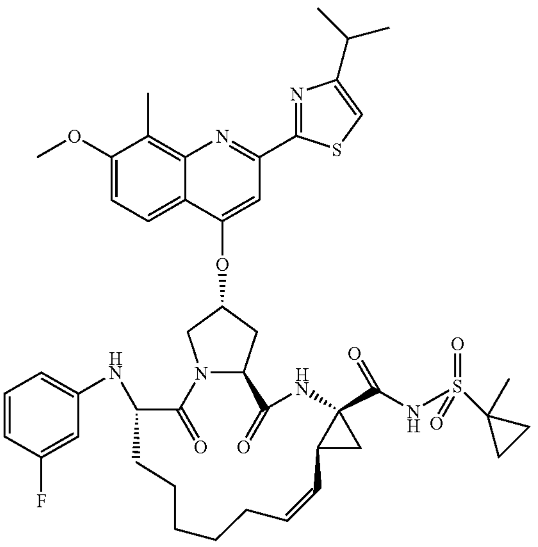 |
| 362 | 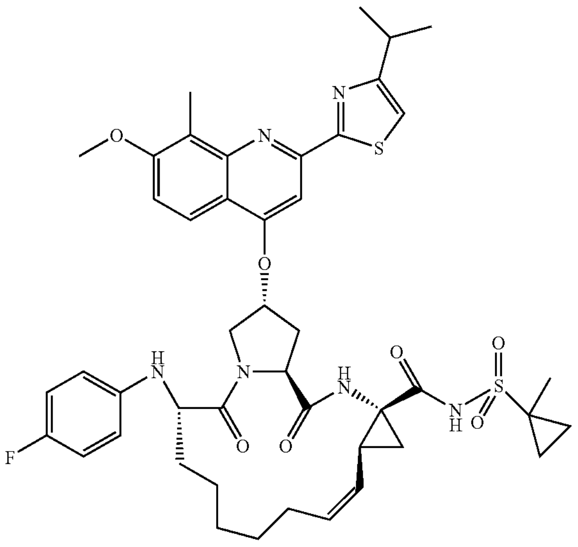 |

TABLE 1-continued
| Examples of compounds that can be prepared according to Examples 1-29 | |
|---|---|
| Compound | Structure |
| 363 | 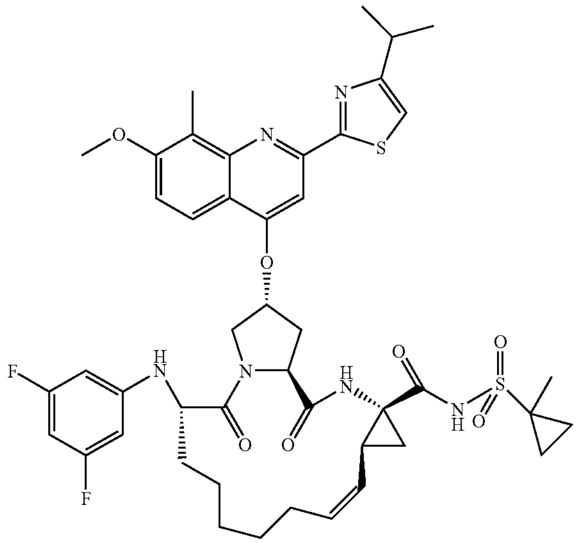 |
| 364 | 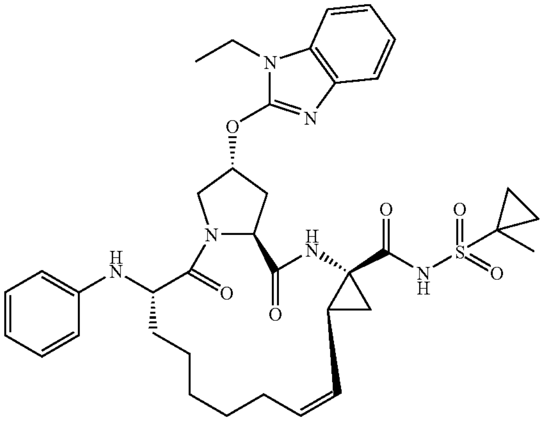 |
| 365 | 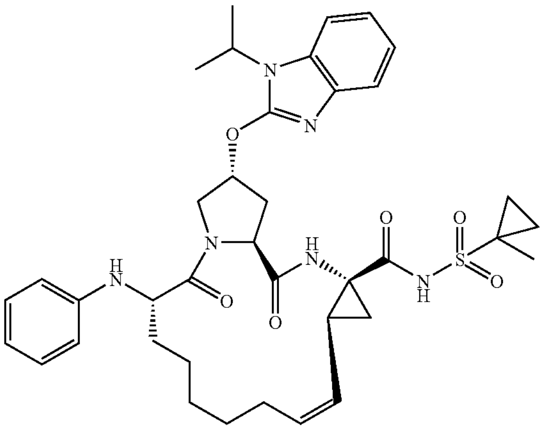 |

TABLE 1-continued
| Compound | Structure |
|---|---|
| 366 | 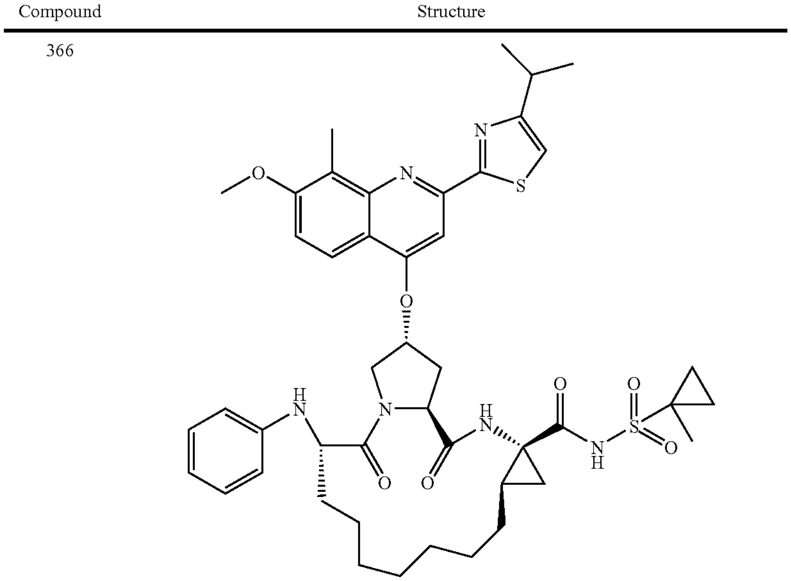 |
| 367 | 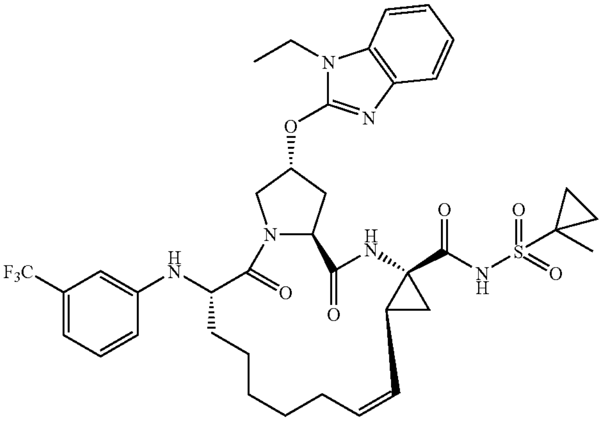 |
| 368 | 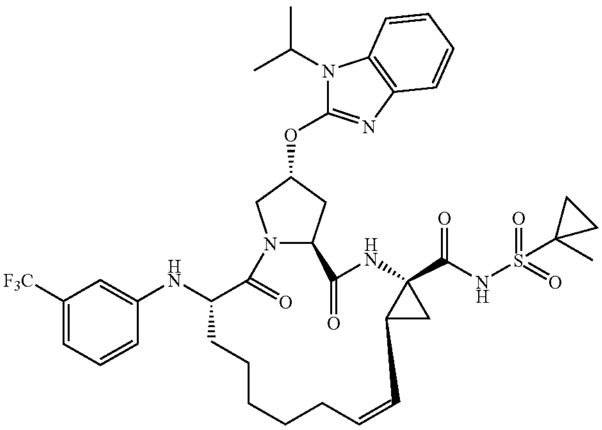 |
Examples of compounds that can be prepared according to Examples 1-29

TABLE 1-continued
| Compound | Structure |
|---|---|
| Examples of compounds that can be prepared according to Examples 1-29 | |
| 369 | 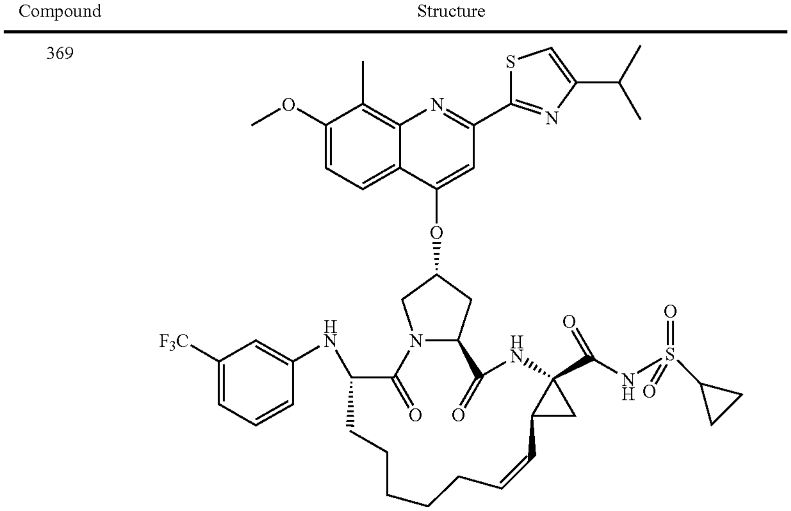 |
| 370 | 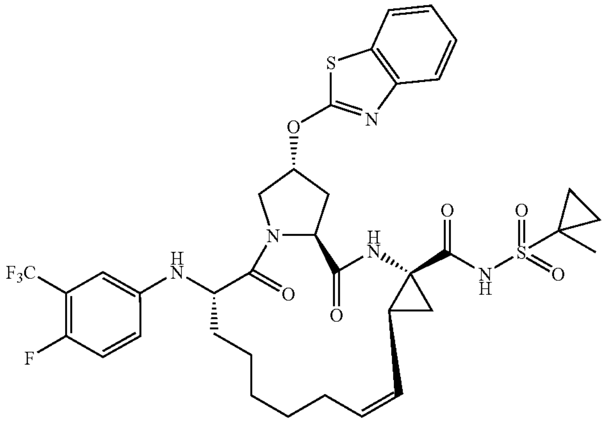 |
| 371 | 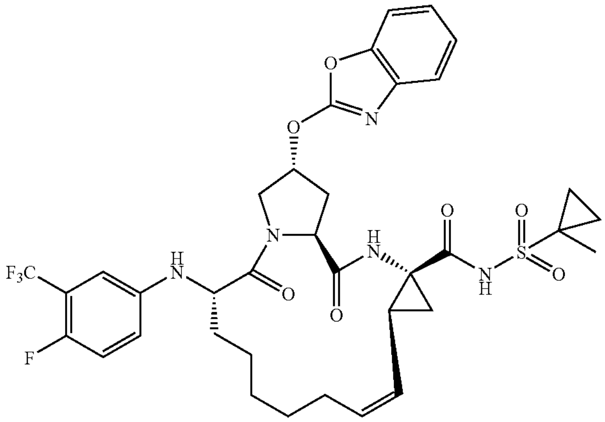 |

TABLE 1-continued
| Compound | Structure |
| --- | --- |
| Examples of compounds that can be prepared according to Examples 1-29 | |
| 372 | 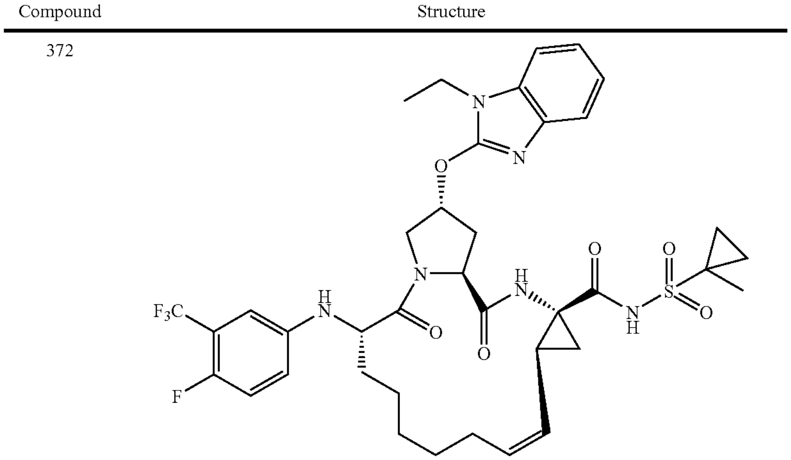 |
| 373 | 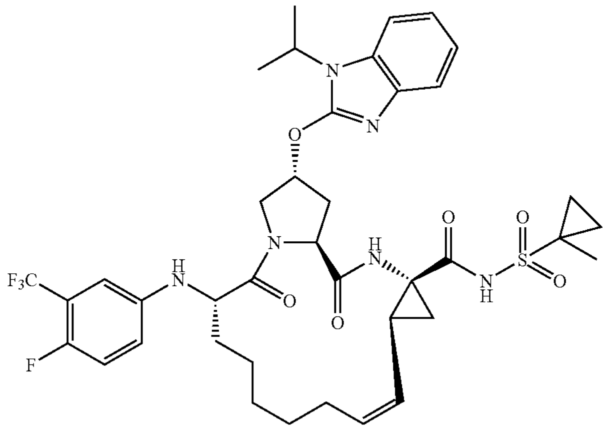 |
| 374 | 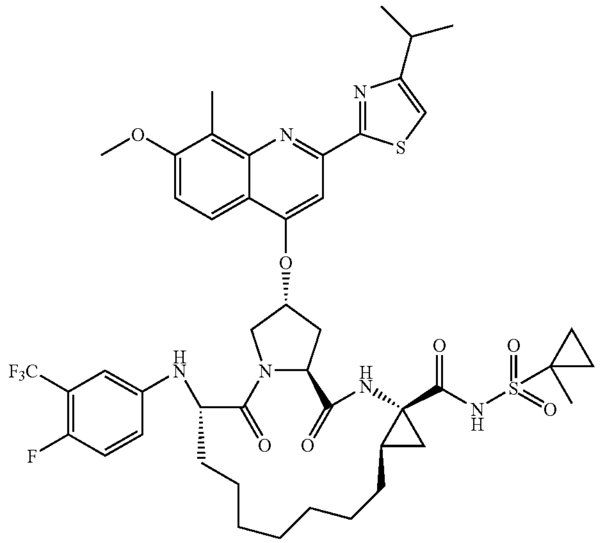 |

TABLE 1-continued
| Examples of compounds that can be prepared according to Examples 1-29 | |
|---|---|
| Compound | Structure |
| 375 | 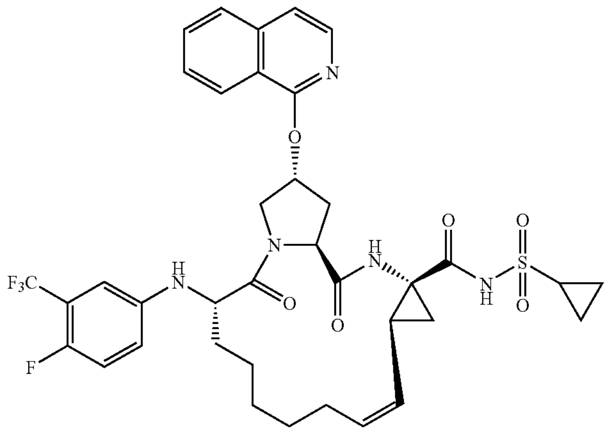 |
| 376 | 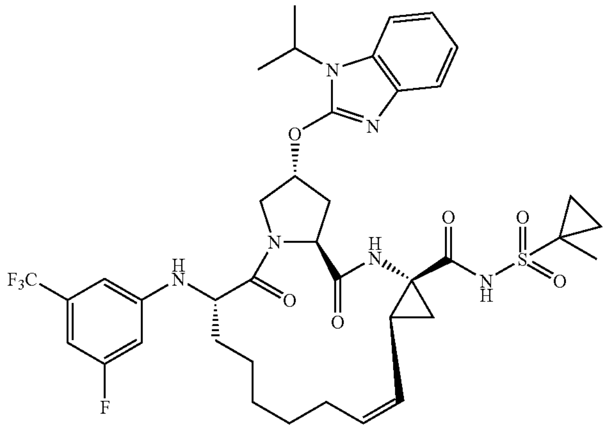 |
| 377 | 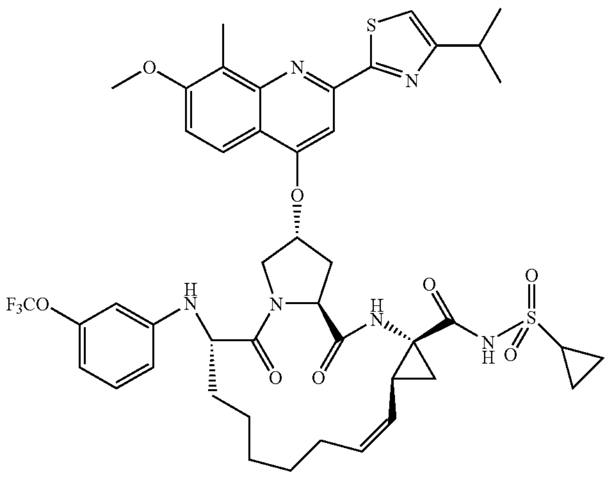 |

TABLE 1-continued
| Examples of compounds that can be prepared according to Examples 1-29 | |
|---|---|
| Compound | Structure |
| 378 | 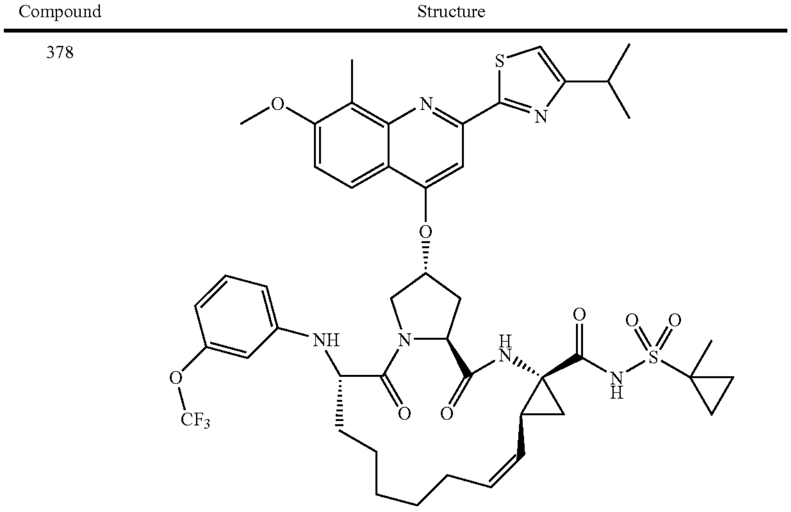 |
| 379 | 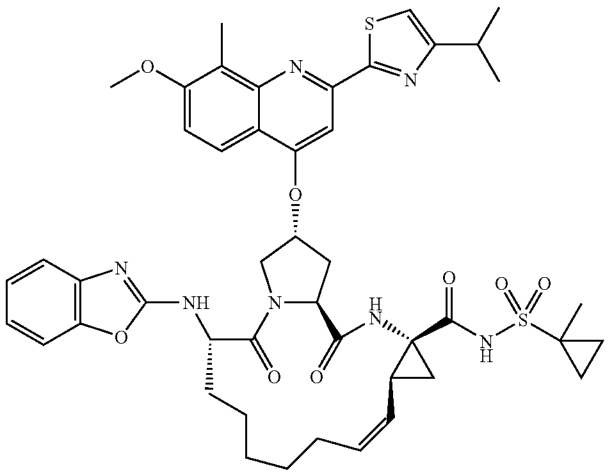 |
| 380 | 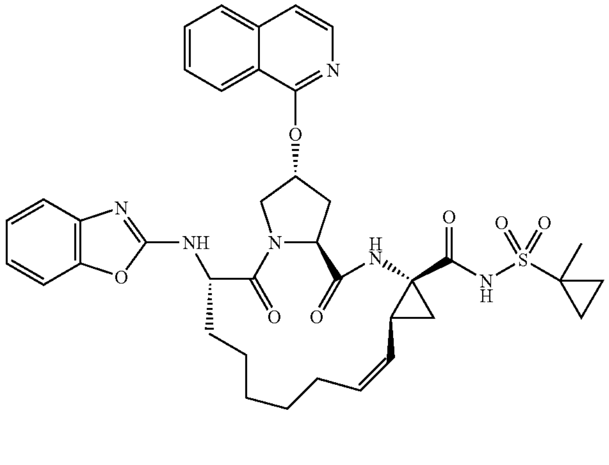 |

TABLE 1-continued
| Examples of compounds that can be prepared according to Examples 1-29 | |
|---|---|
| Compound | Structure |
| 381 | 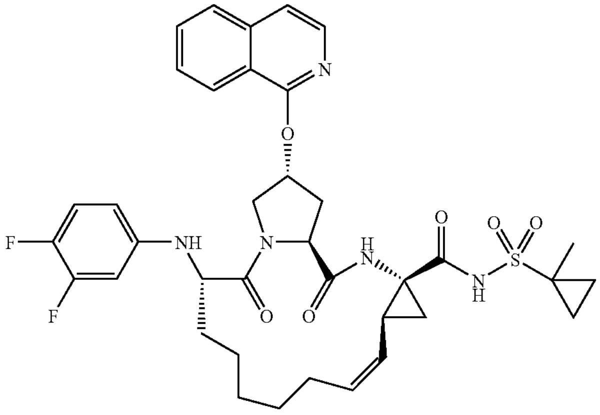 |
| 382 | 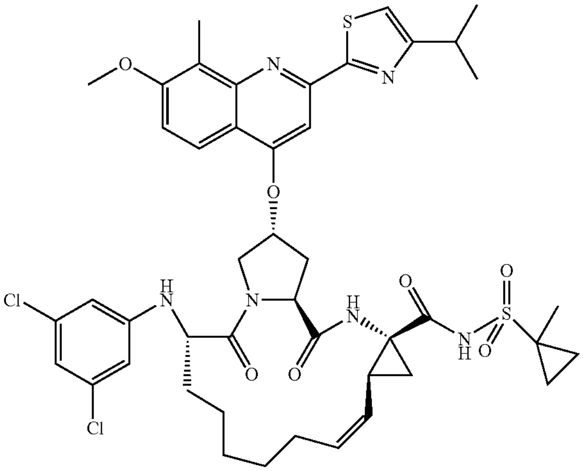 |
| 383 | 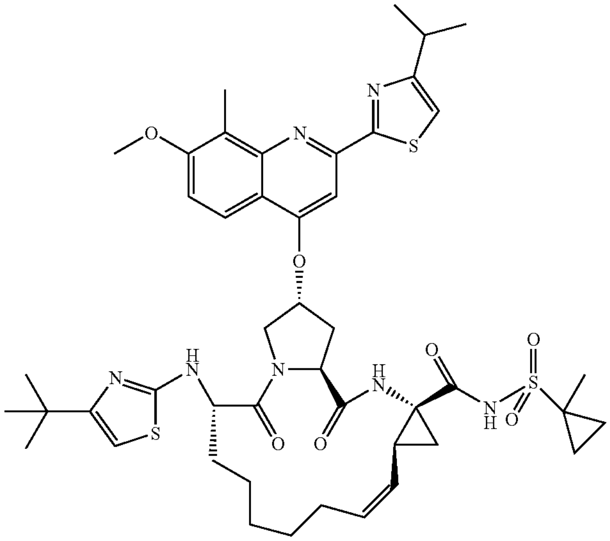 |

TABLE 1-continued
| Compound | Structure |
|---|---|
| Examples of compounds that can be prepared according to Examples 1-29 | |
| 384 | 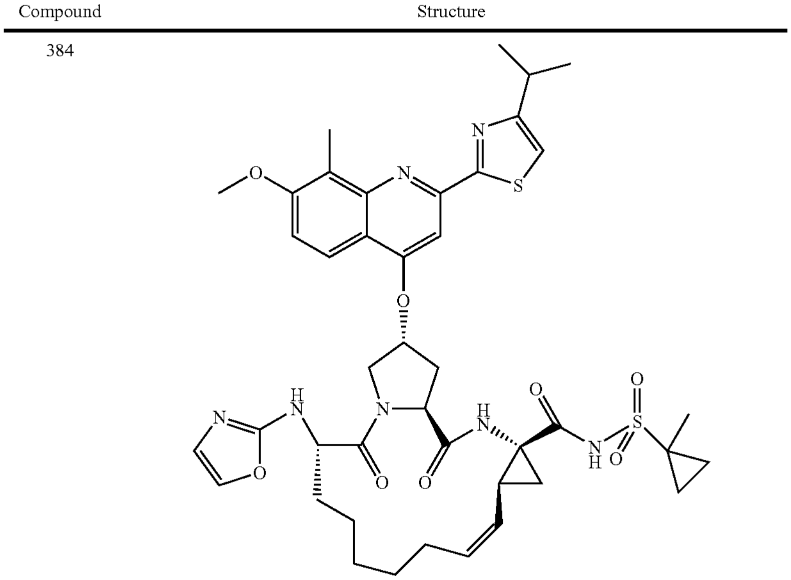 |
| 385 | 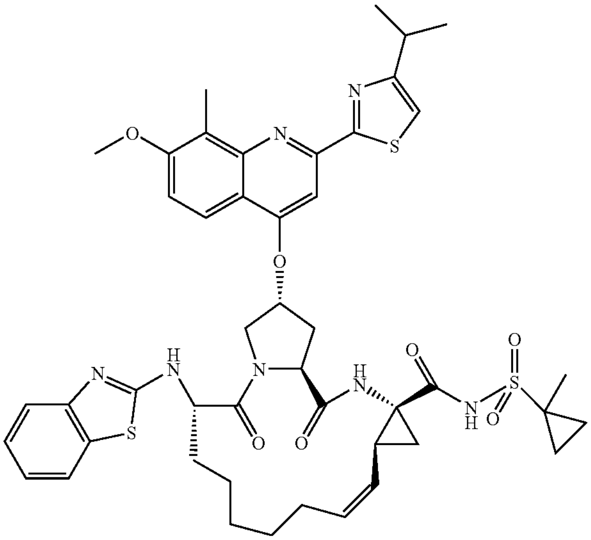 |

TABLE 1-continued
| Examples of compounds that can be prepared according to Examples 1-29 | |
|---|---|
| Compound | Structure |
| 386 | 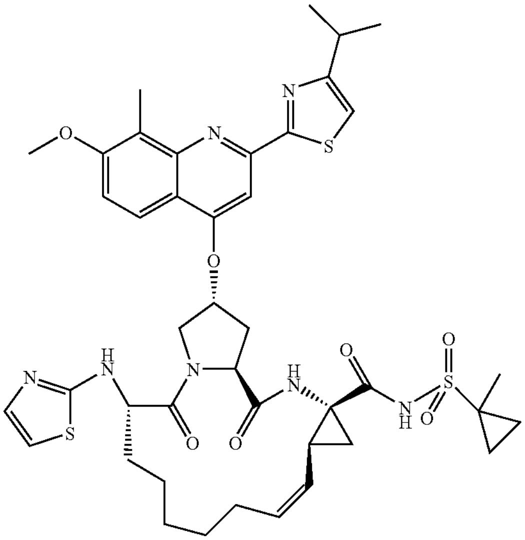 |
| 387 | 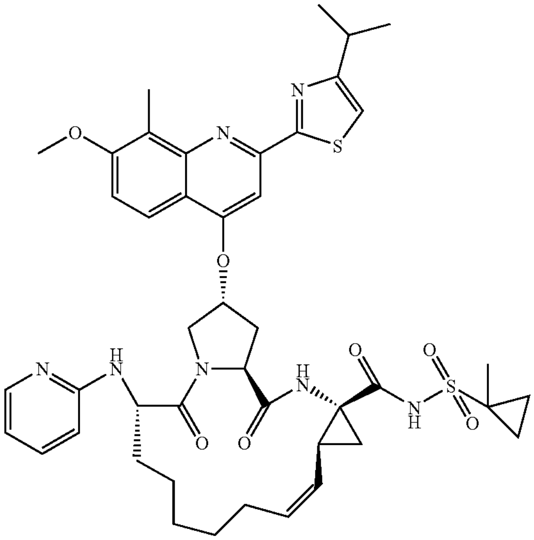 |
| 388 | 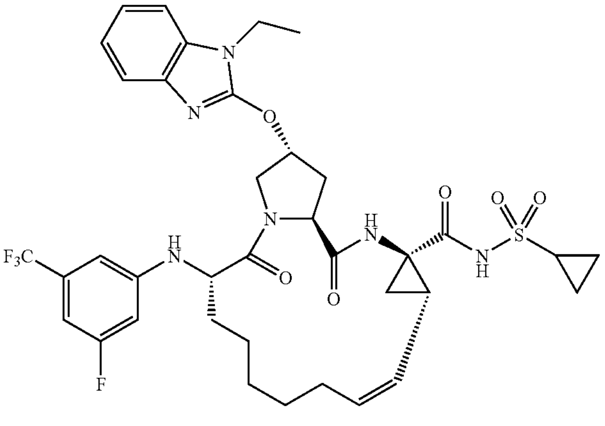 |

TABLE 1-continued
| Examples of compounds that can be prepared according to Examples 1-29 | |
|---|---|
| Compound | Structure |
| 389 | 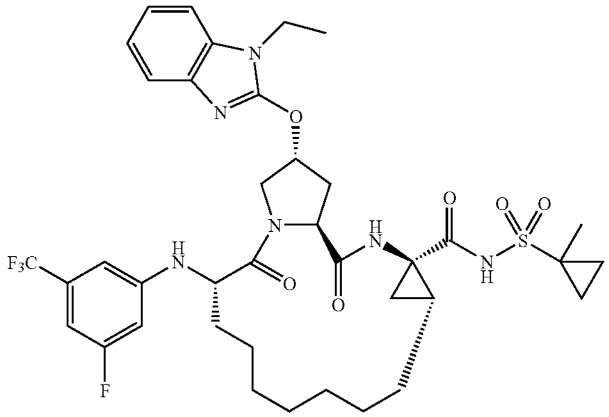 |
| 390 | 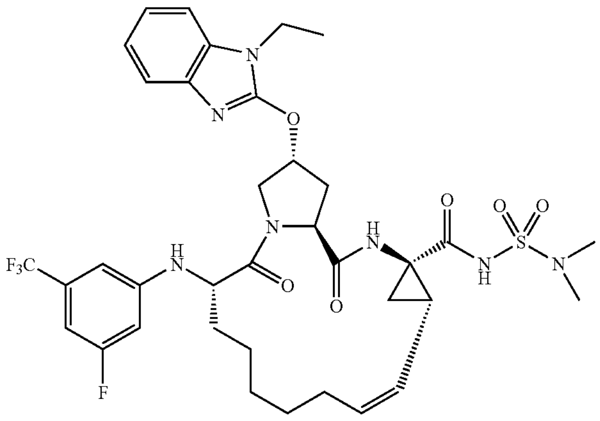 |
| 391 | 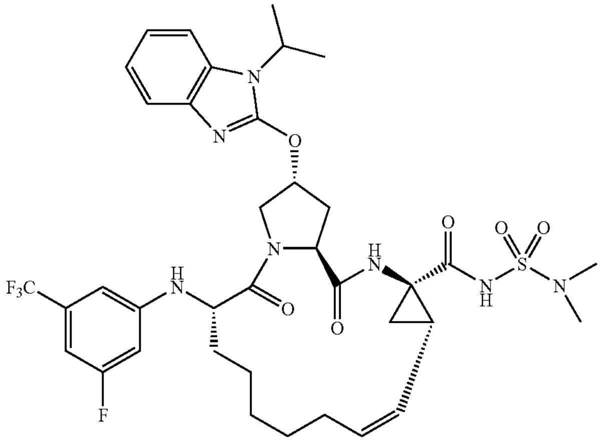 |

TABLE 1-continued
| Compound | Structure |
|---|---|
| 392 | 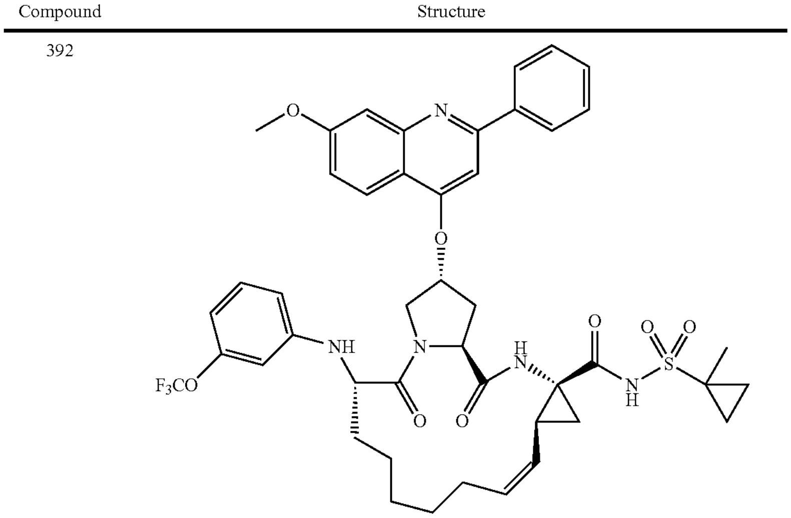 |
| 393 | 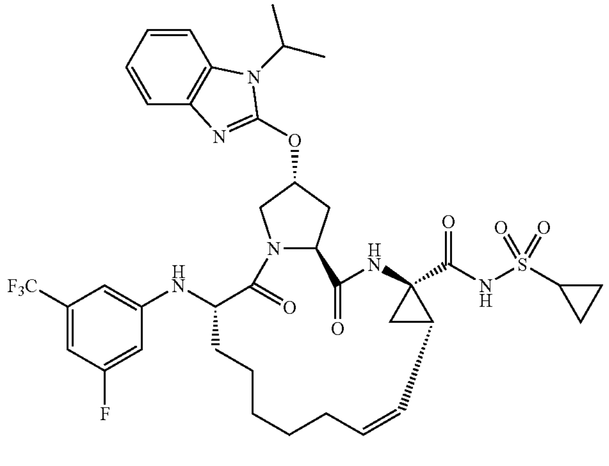 |
| 394 | 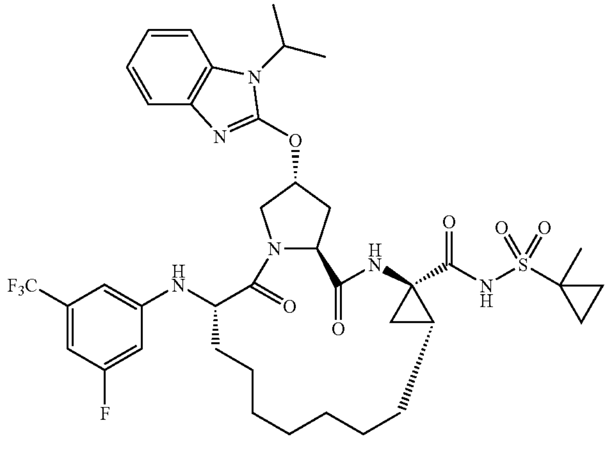 |
Examples of compounds that can be prepared according to Examples 1-29

TABLE 1-continued
| Examples of compounds that can be prepared according to Examples 1-29 | |
|---|---|
| Compound | Structure |
| 395 | 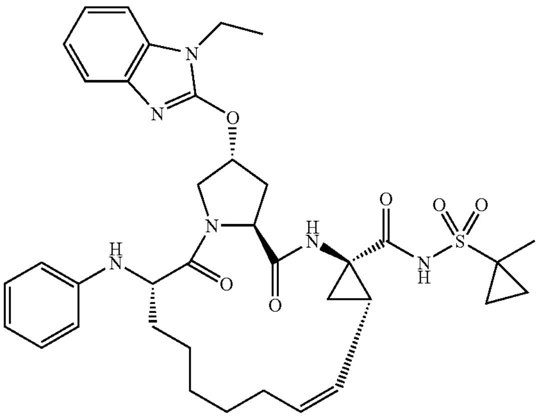 |
| 396 | 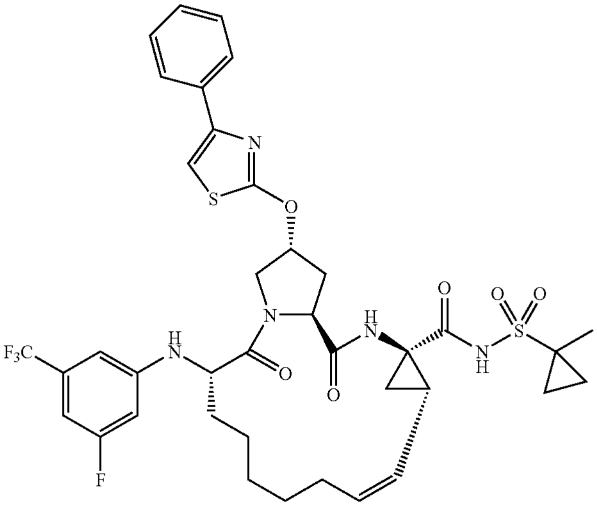 |
| 397 | 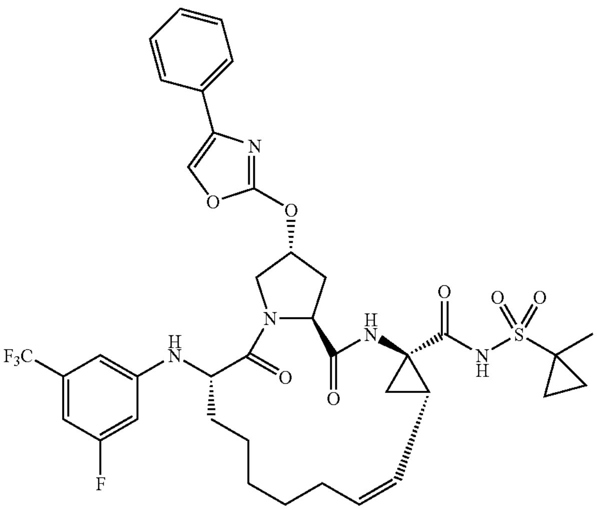 |

TABLE 1-continued
| Examples of compounds that can be prepared according to Examples 1-29 | |
|---|---|
| Compound | Structure |
| 398 | 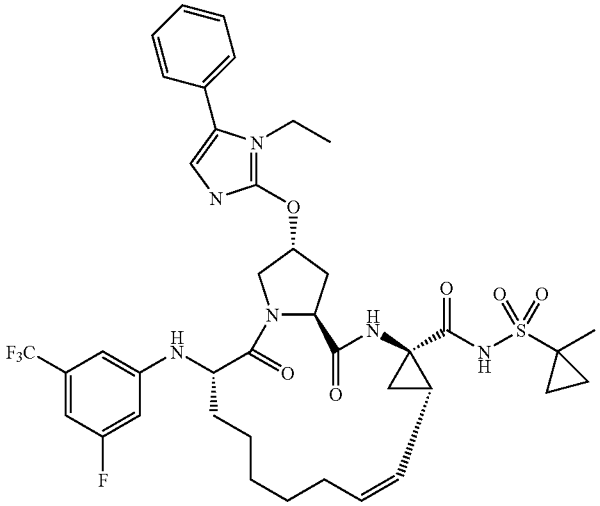 |
| 399 | 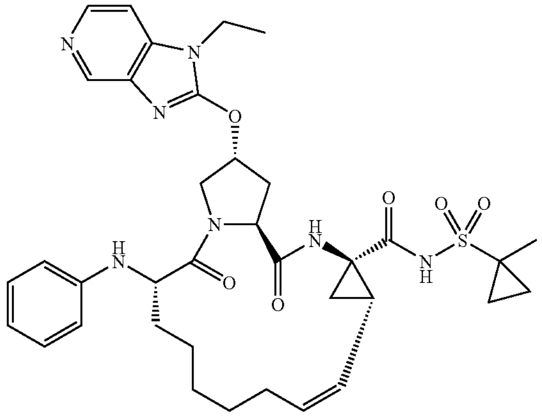 |
| 400 | 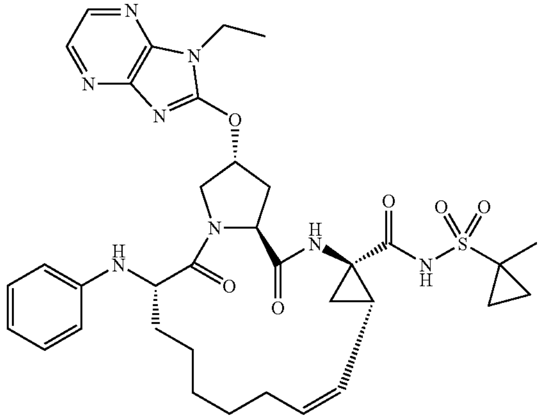 |

TABLE 1-continued
Examples of compounds that can be prepared according to Examples 1-29
| Compound | Structure |
|---|---|
| 401 | 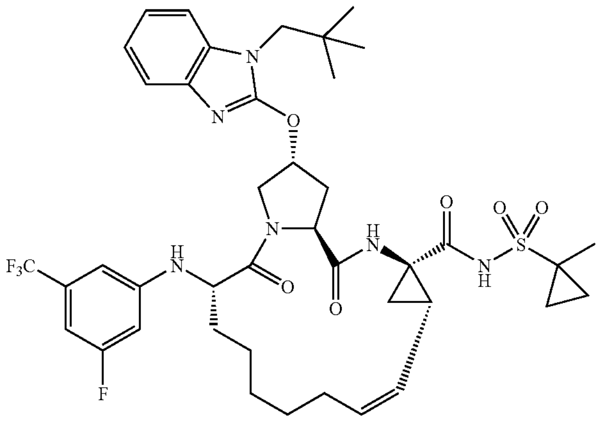 |
| 402 | 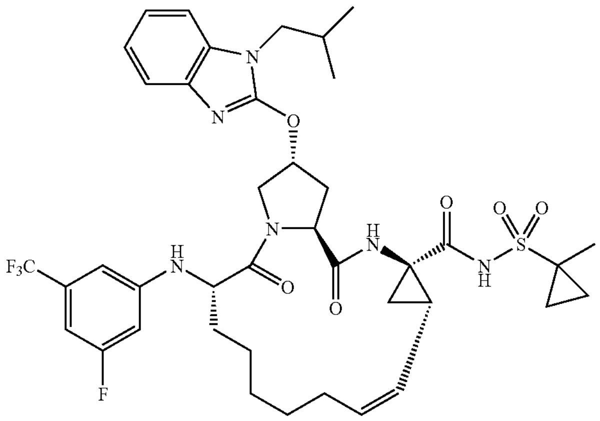 |
| 403 | 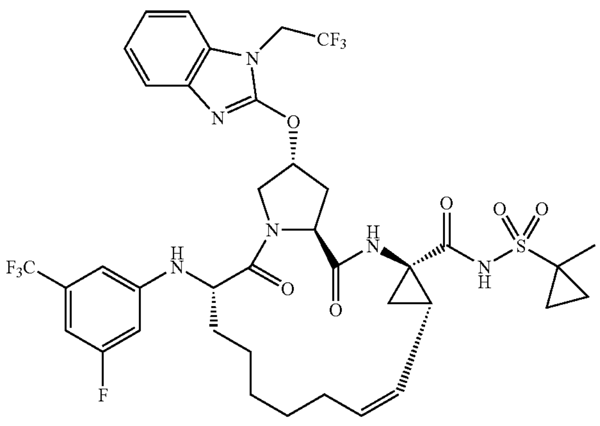 |

TABLE 1-continued
Examples of compounds that can be prepared according to Examples 1-29
| Compound | Structure |
| --- | --- |
| 404 | 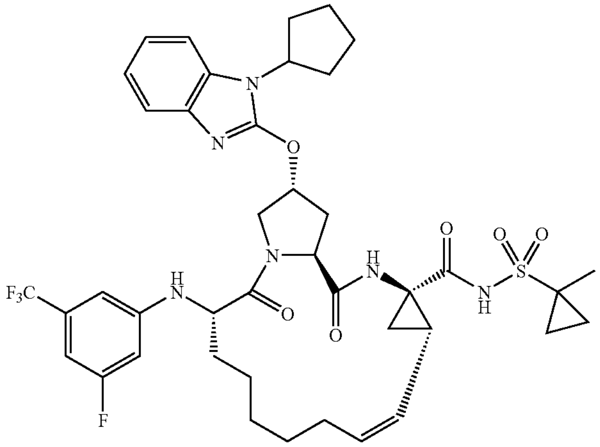 |
| 405 | 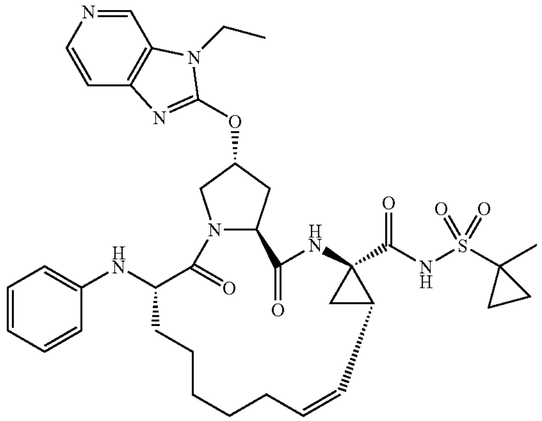 |
| 406 | 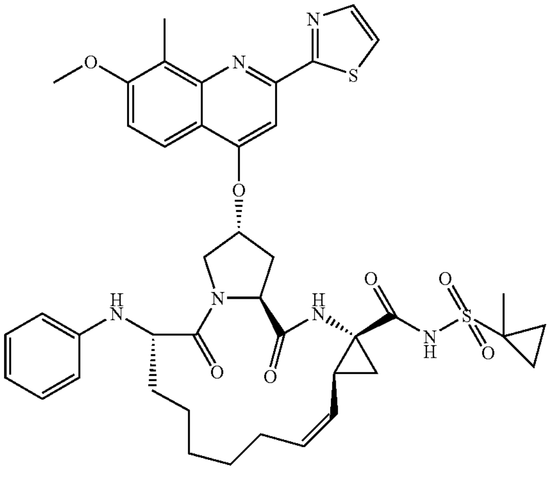 |

TABLE 1-continued
| Examples of compounds that can be prepared according to Examples 1-29 | |
|---|---|
| Compound | Structure |
| 407 | 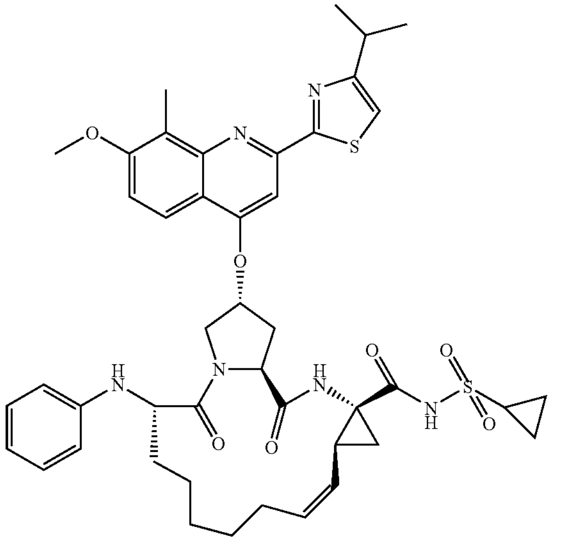 |
| 408 | 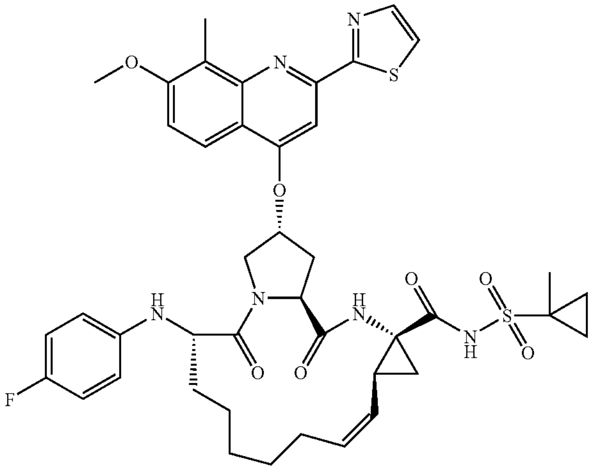 |
| 409 | 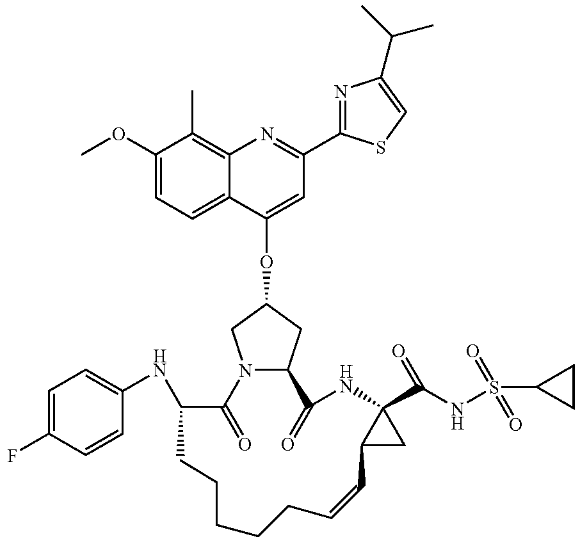 |

TABLE 1-continued
| Examples of compounds that can be prepared according to Examples 1-29 | |
|---|---|
| Compound | Structure |
| 410 | 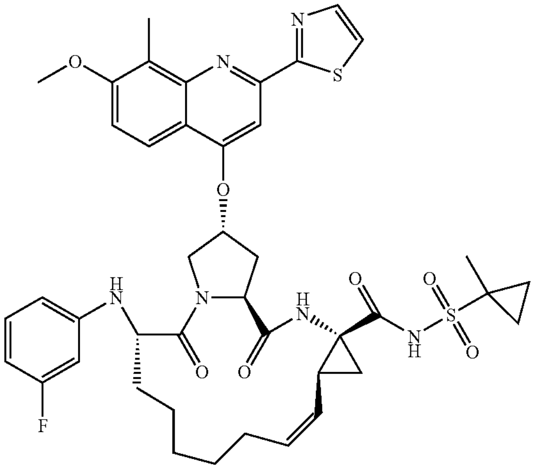 |
| 411 | 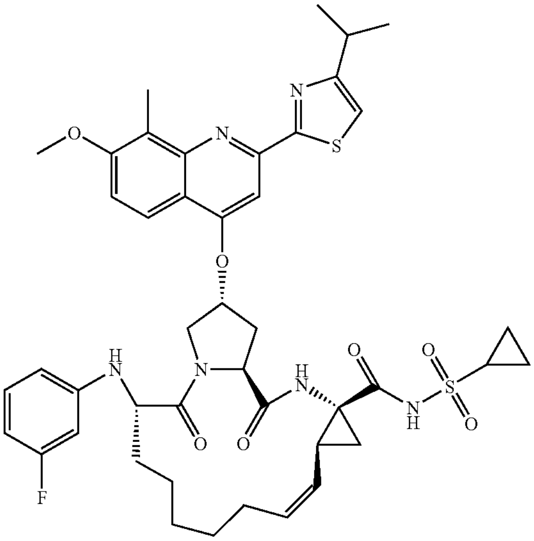 |
| 412 | 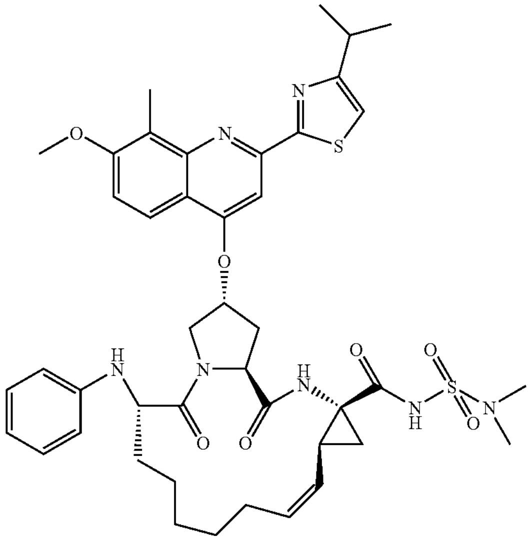 |

TABLE 1-continued
| Examples of compounds that can be prepared according to Examples 1-29 | |
|---|---|
| Compound | Structure |
| 413 | 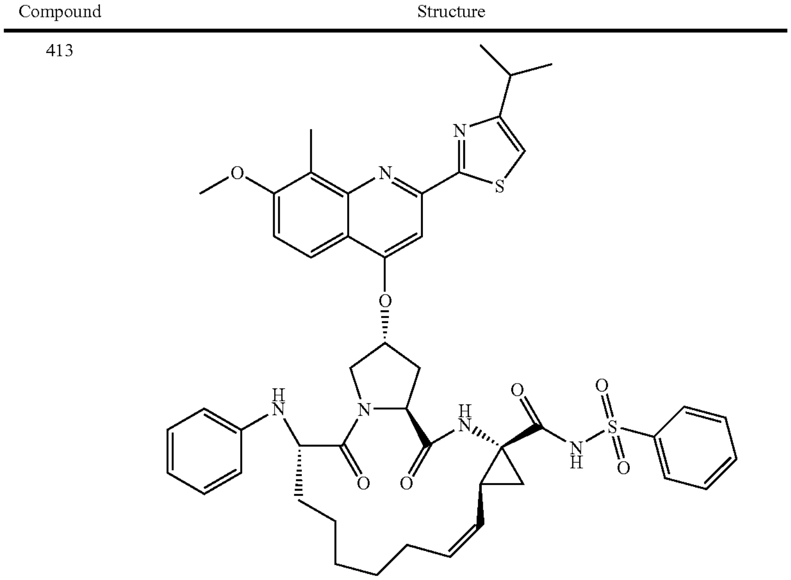 |
| 414 | 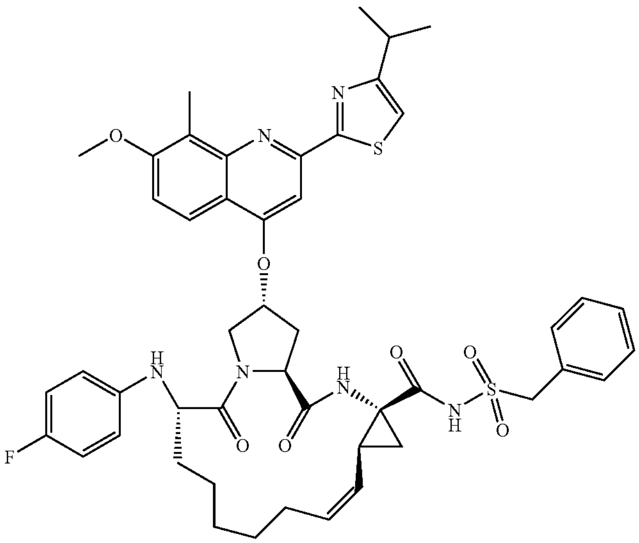 |

TABLE 1-continued
| Compound | Structure |
| --- | --- |
| Examples of compounds that can be prepared according to Examples 1-29 | |
| 415 | 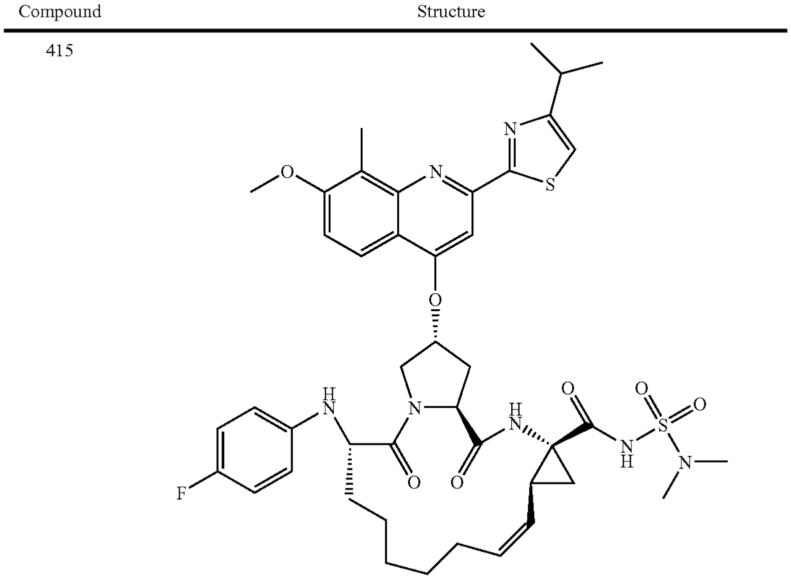 |
| 416 | 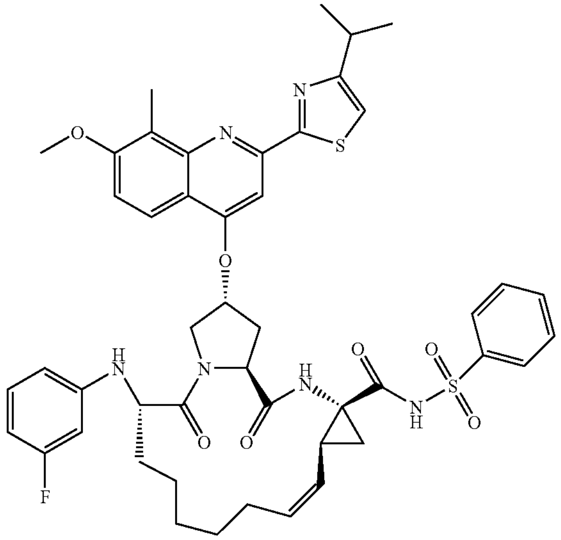 |

TABLE 1-continued
| Examples of compounds that can be prepared according to Examples 1-29 | |
|---|---|
| Compound | Structure |
| 417 | 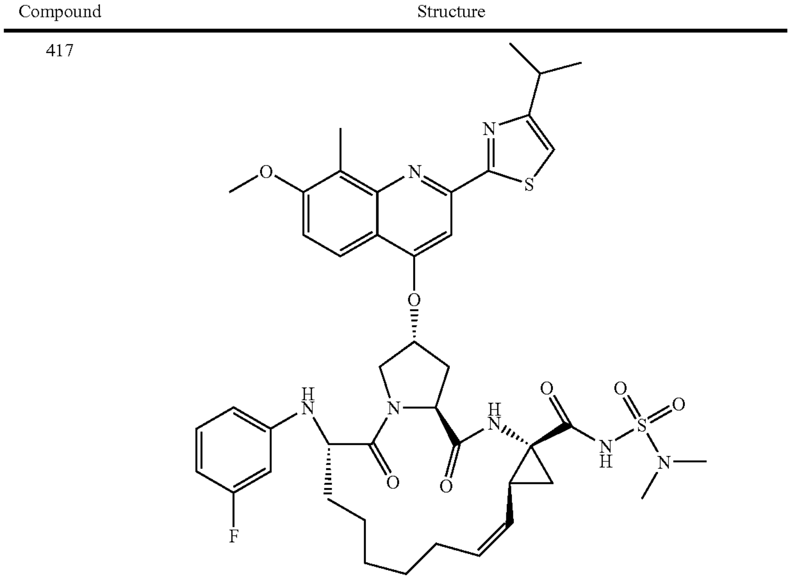 |
| 418 | 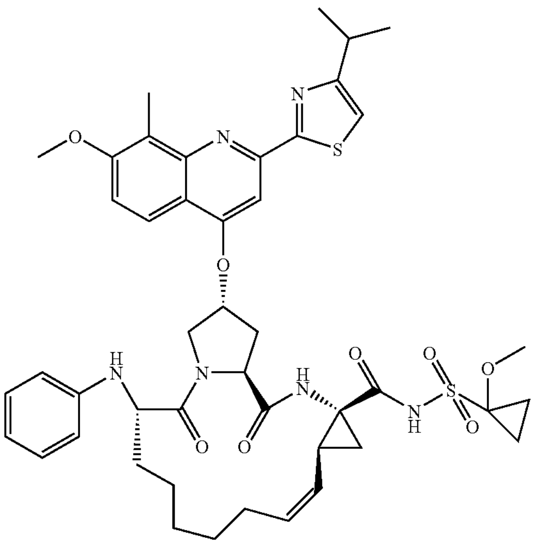 |

TABLE 1-continued
| Examples of compounds that can be prepared according to Examples 1-29 | |
|---|---|
| Compound | Structure |
| 419 | 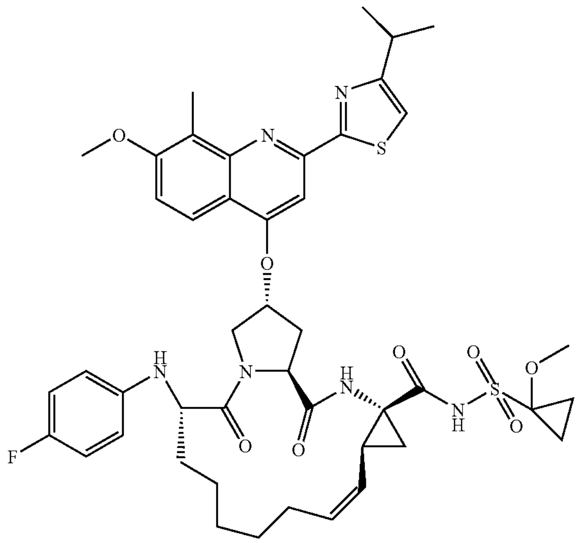 |
| 420 | 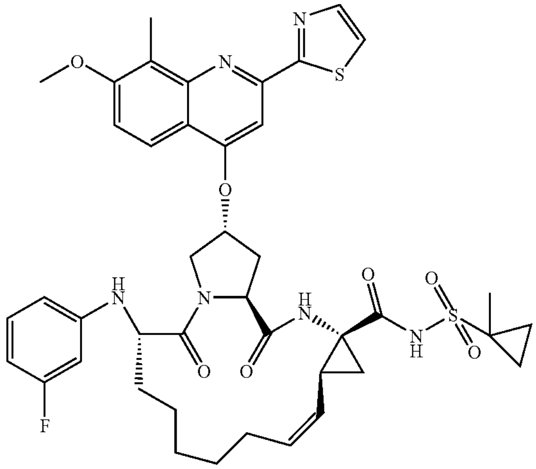 |
| 421 | 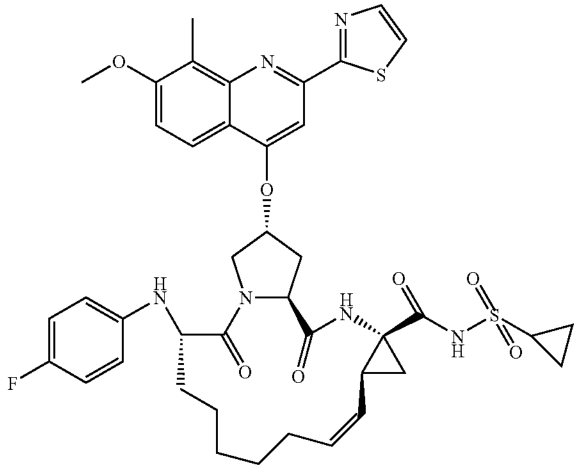 |

TABLE 1-continued
| Examples of compounds that can be prepared according to Examples 1-29 | |
|---|---|
| Compound | Structure |
| 422 | 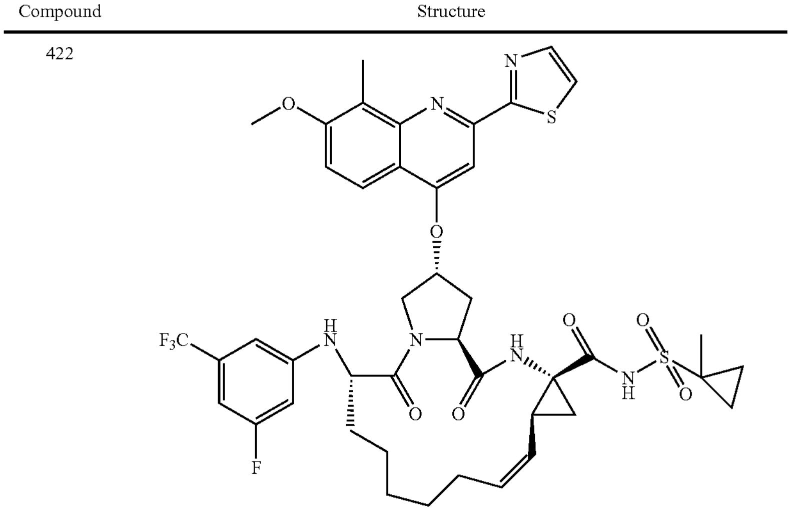 |
| 423 | 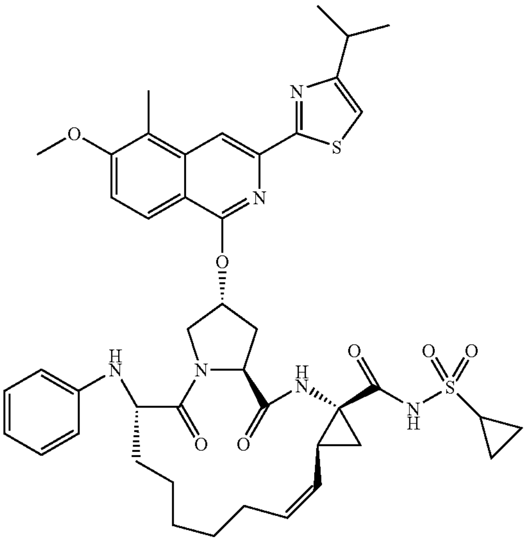 |
| 424 | 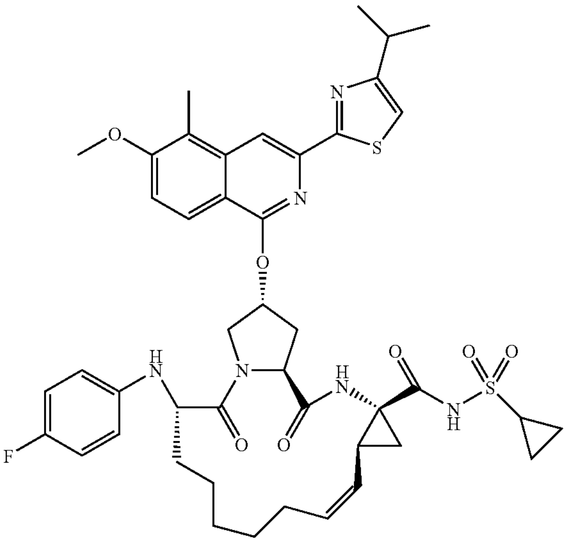 |

TABLE 1-continued
| Examples of compounds that can be prepared according to Examples 1-29 | |
|---|---|
| Compound | Structure |
| 425 | 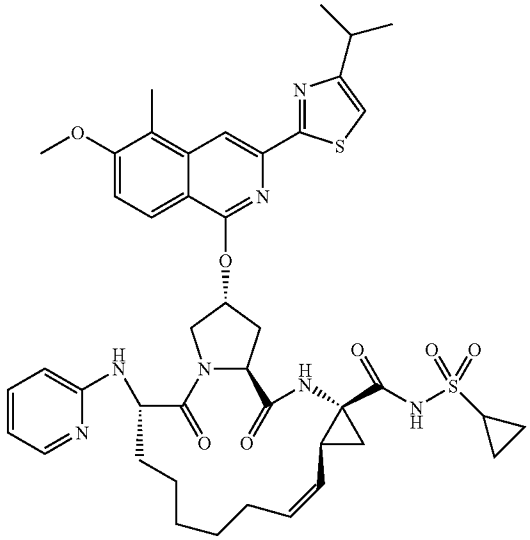 |
| 426 | 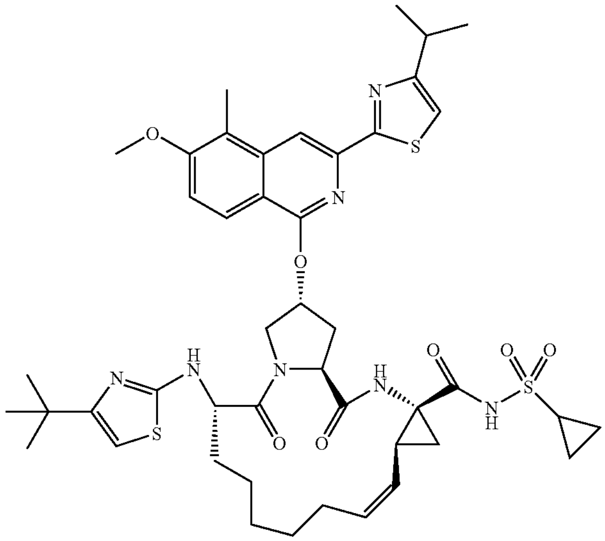 |

TABLE 1-continued
| Examples of compounds that can be prepared according to Examples 1-29 | |
|---|---|
| Compound | Structure |
| 427 | 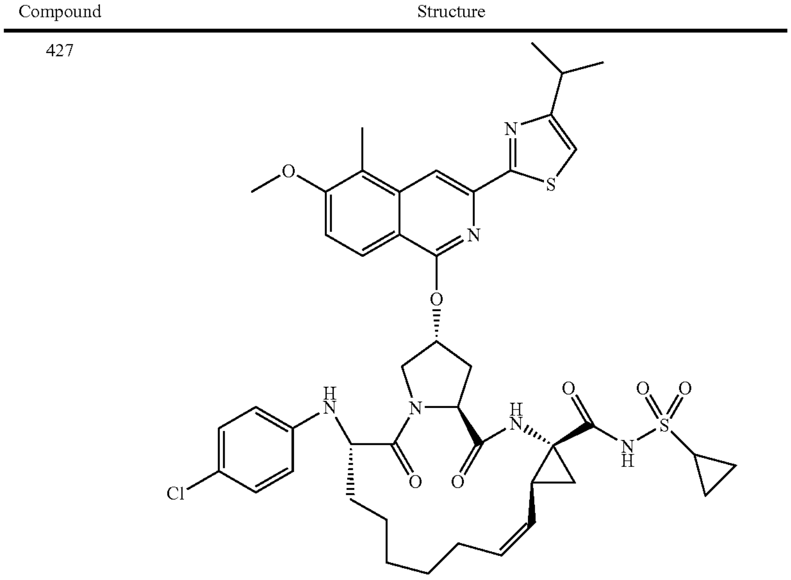 |
| 428 | 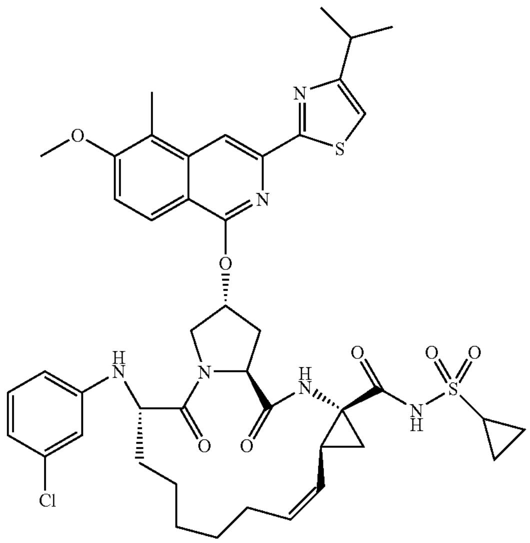 |

TABLE 1-continued
| Examples of compounds that can be prepared according to Examples 1-29 | |
| --- | --- |
| Compound | Structure |
| 429 | 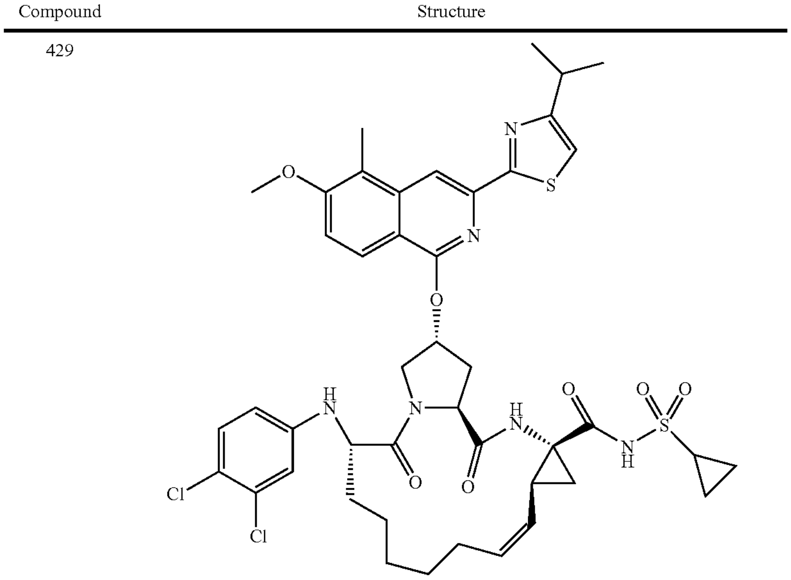 |
| 430 | 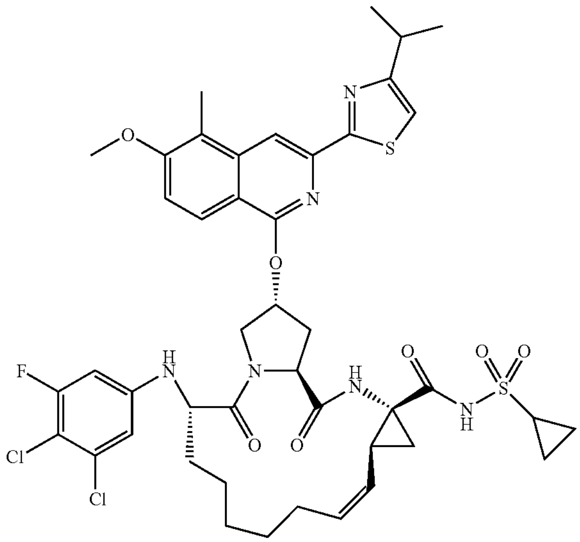 |

TABLE 1-continued
| Examples of compounds that can be prepared according to Examples 1-29 | |
|---|---|
| Compound | Structure |
| 431 | 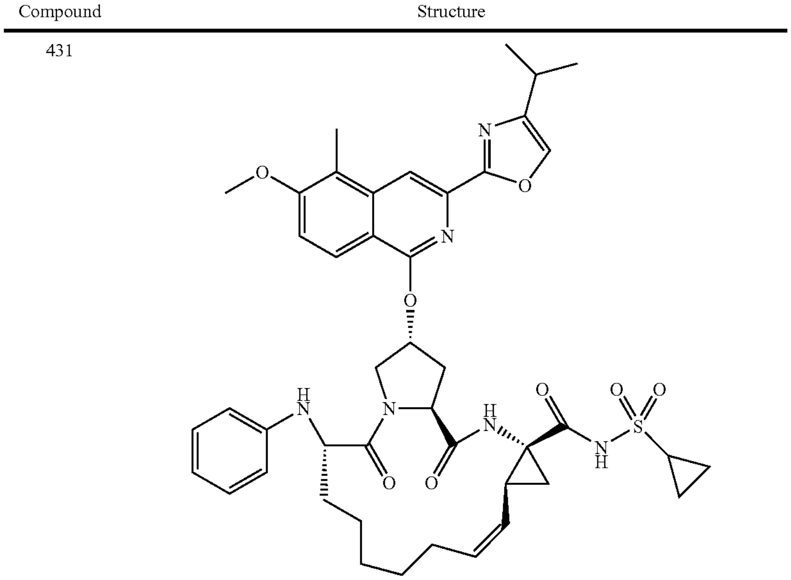 |
| 432 | 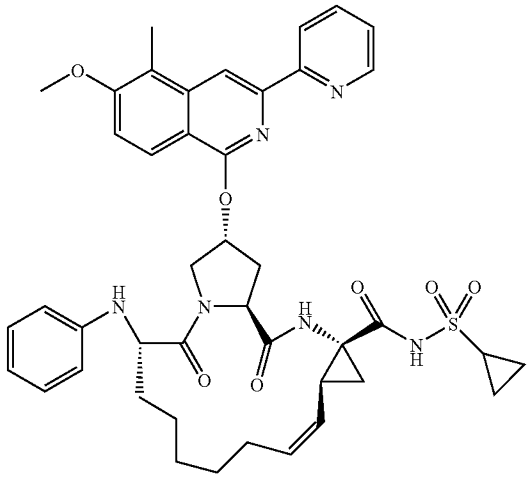 |
| 433 | 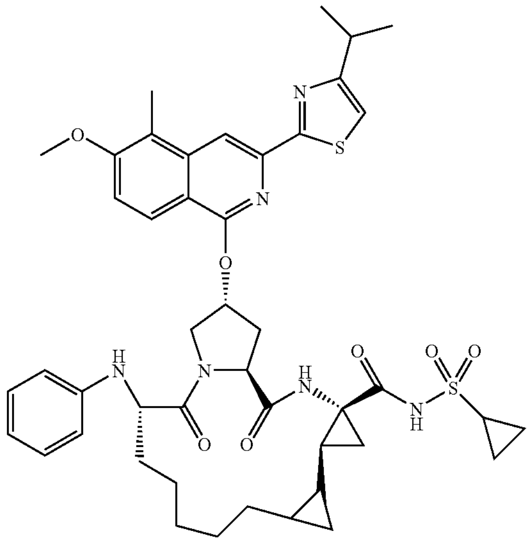 |

TABLE 1-continued
| Examples of compounds that can be prepared according to Examples 1-29 | |
|---|---|
| Compound | Structure |
| 434 | 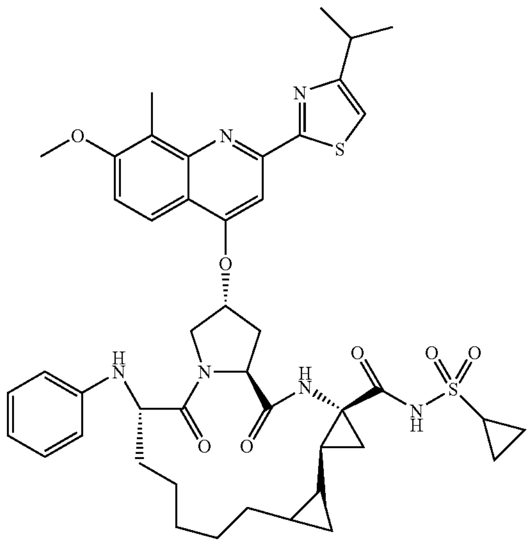 |
| 435 | 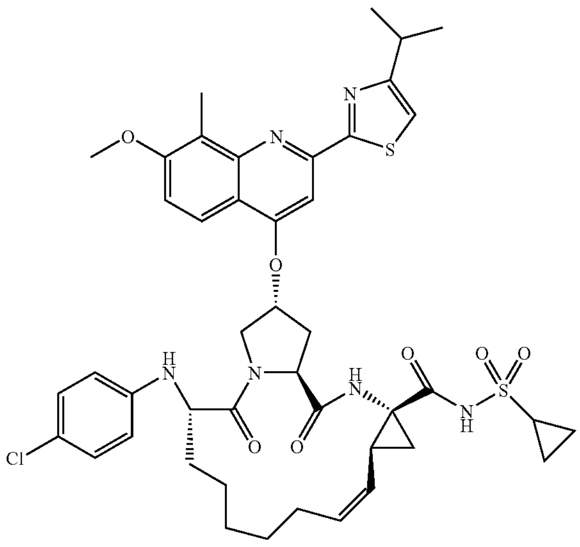 |

TABLE 1-continued
| Examples of compounds that can be prepared according to Examples 1-29 | |
|---|---|
| Compound | Structure |
| 436 | 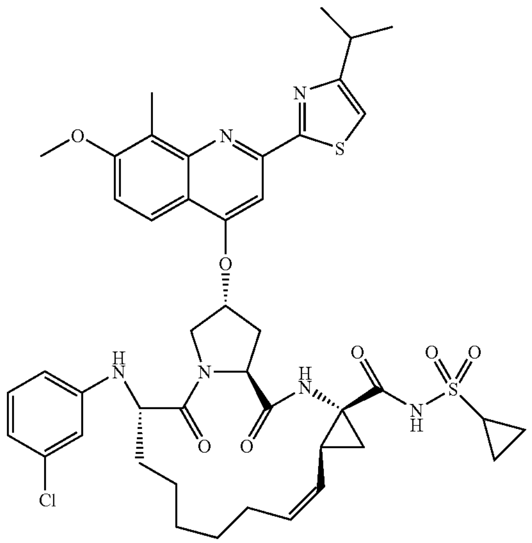 |
| 437 | 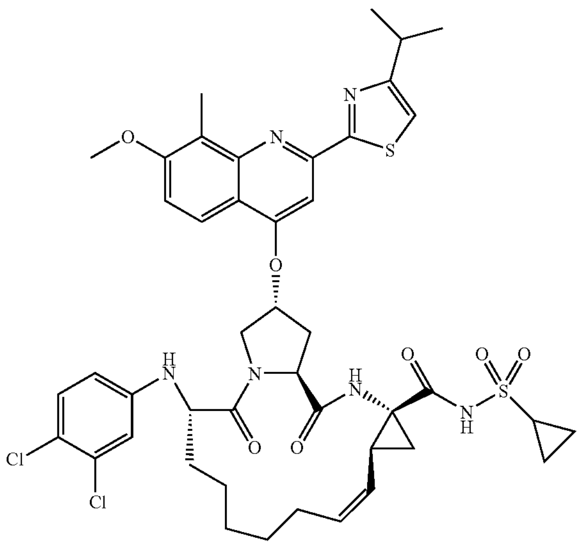 |

TABLE 1-continued
| Compound | Structure |
| --- | --- |
| Examples of compounds that can be prepared according to Examples 1-29 | |
| 438 | 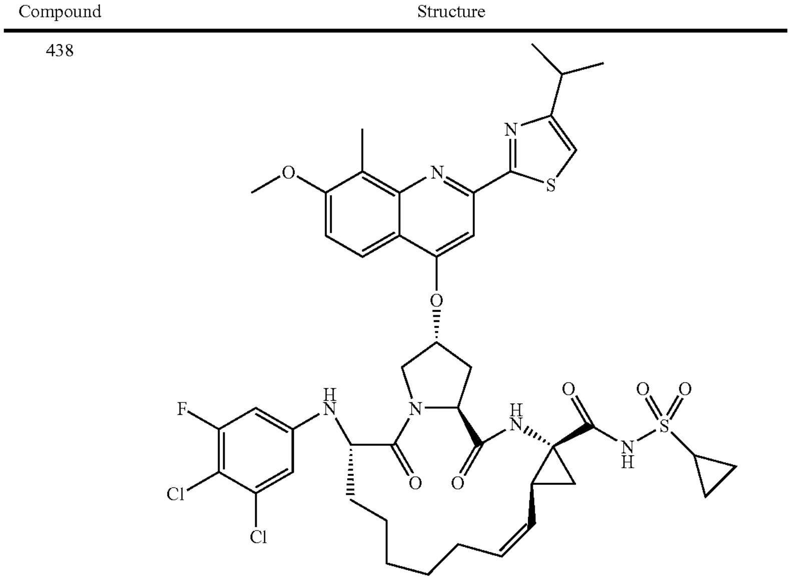 |
| 439 | 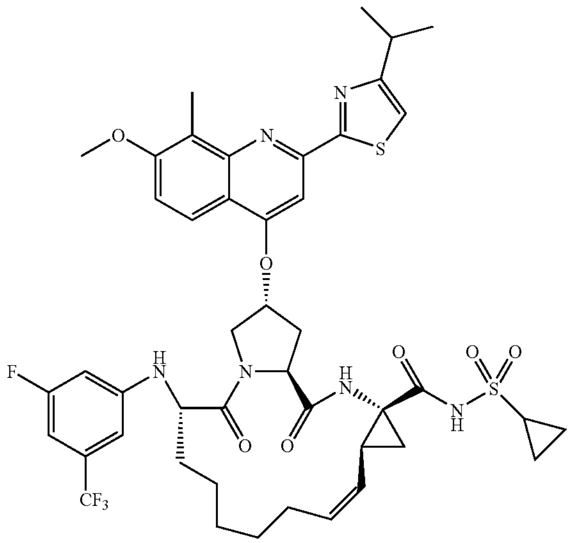 |

TABLE 1-continued
| Examples of compounds that can be prepared according to Examples 1-29 | |
|---|---|
| Compound | Structure |
| 440 | 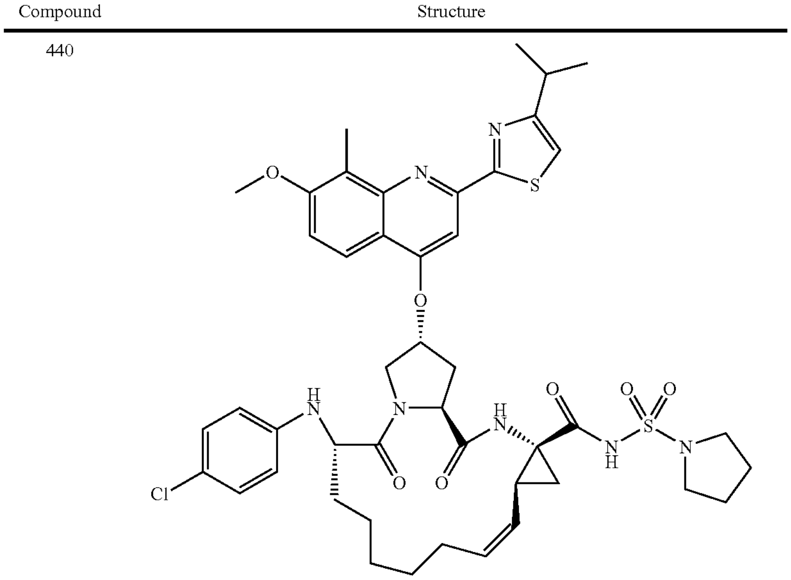 |
| 441 | 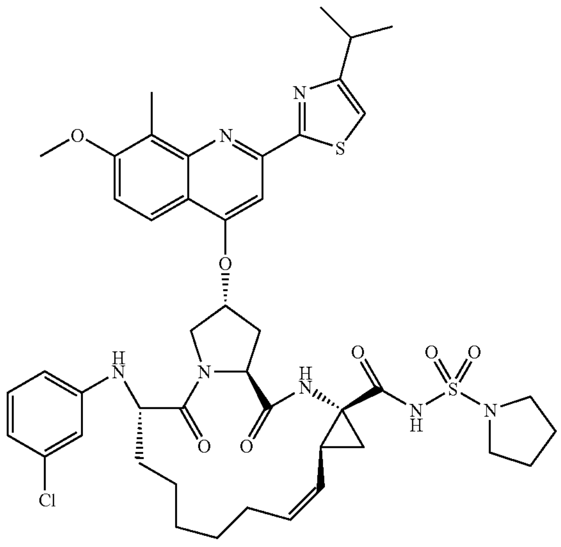 |

TABLE 1-continued
| Examples of compounds that can be prepared according to Examples 1-29 | |
|---|---|
| Compound | Structure |
| 442 | 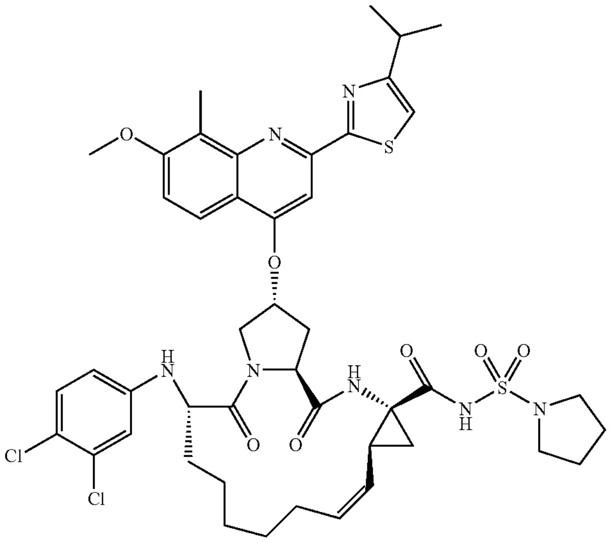 |
| 443 | 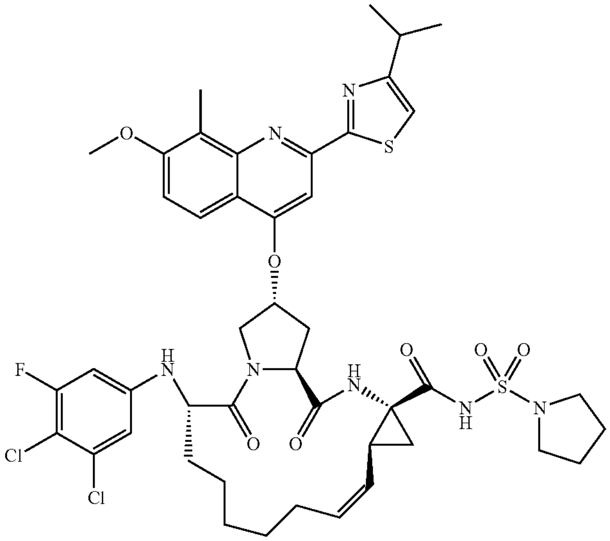 |
| 444 | 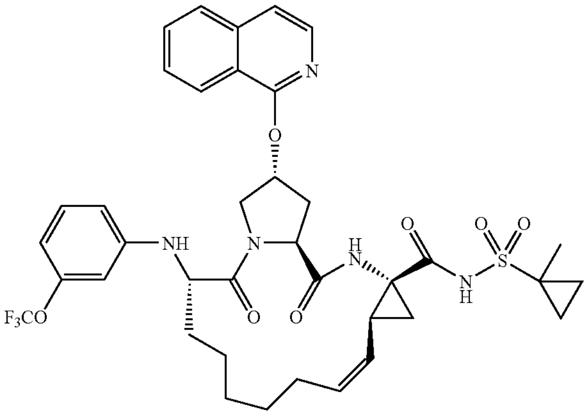 |

TABLE 1-continued
| Examples of compounds that can be prepared according to Examples 1-29 | |
|---|---|
| Compound | Structure |
| 445 | 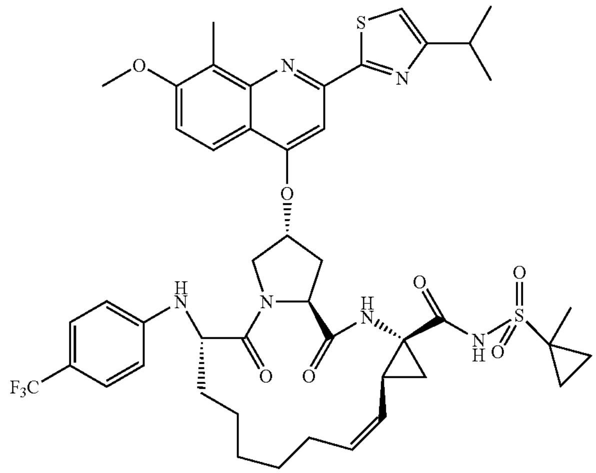 |
| 446 | 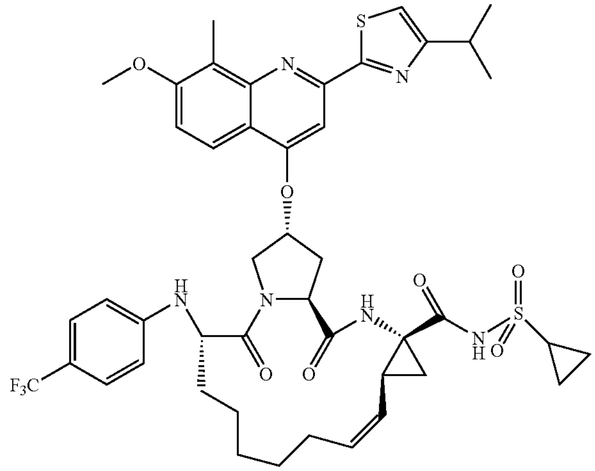 |
| 447 | 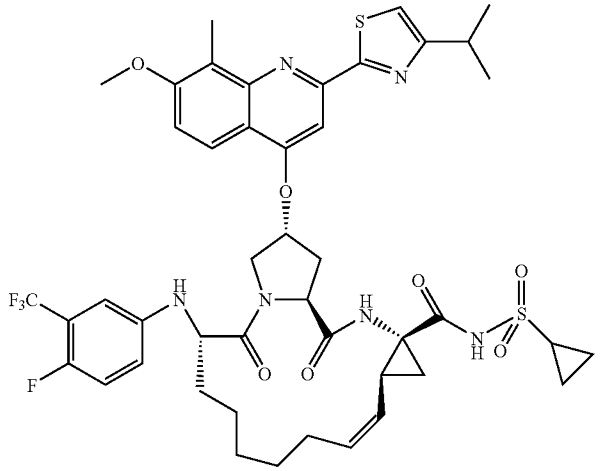 |

TABLE 1-continued
| Examples of compounds that can be prepared according to Examples 1-29 | |
|---|---|
| Compound | Structure |
| 448 | 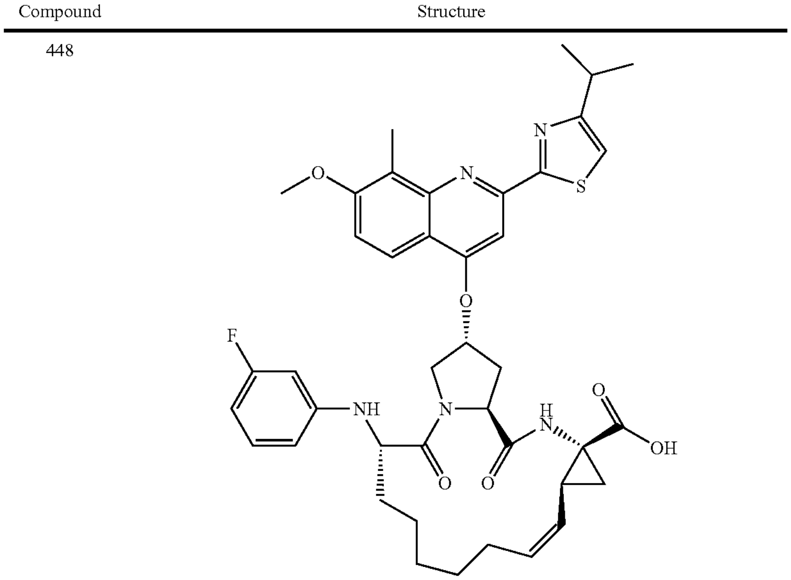 |
| 449 | 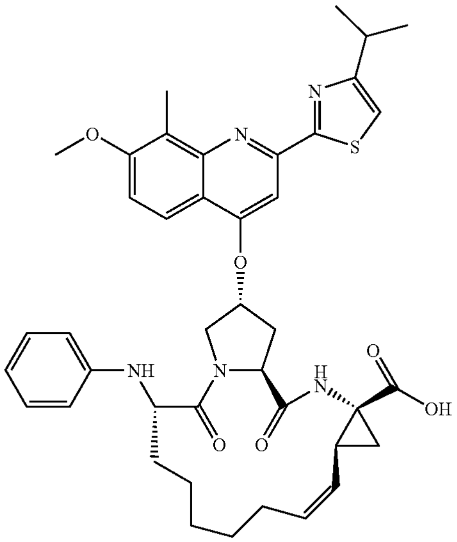 |

TABLE 1-continued
| Examples of compounds that can be prepared according to Examples 1-29 | |
|---|---|
| Compound | Structure |
| 450 | 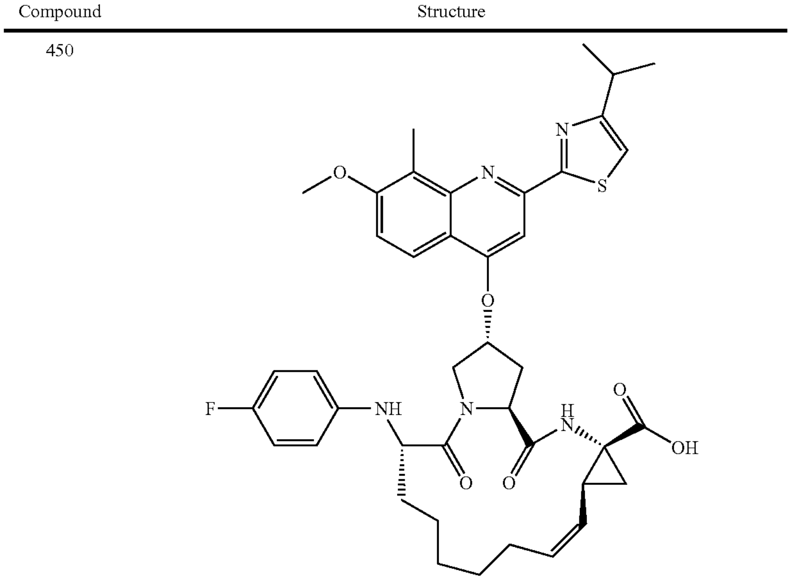 |
| 451 | 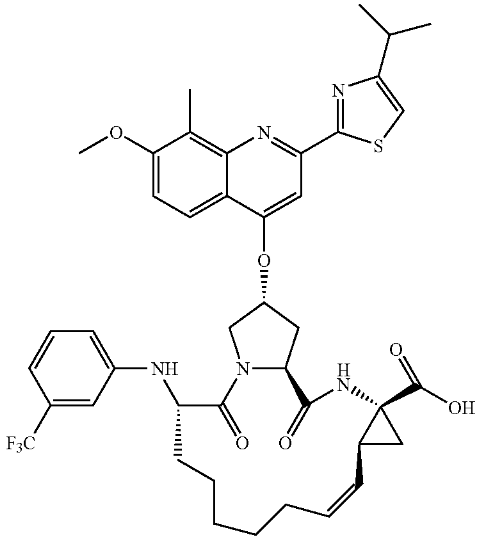 |

TABLE 1-continued
| Examples of compounds that can be prepared according to Examples 1-29 | |
|---|---|
| Compound | Structure |
| 452 | 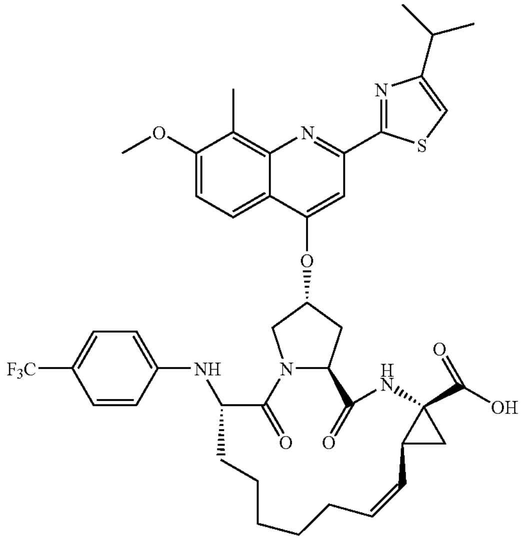 |
| 453 | 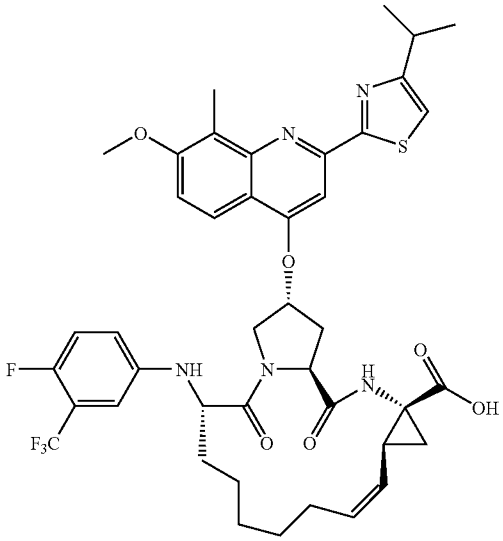 |

TABLE 1-continued
| Examples of compounds that can be prepared according to Examples 1-29 | |
|---|---|
| Compound | Structure |
| 454 | 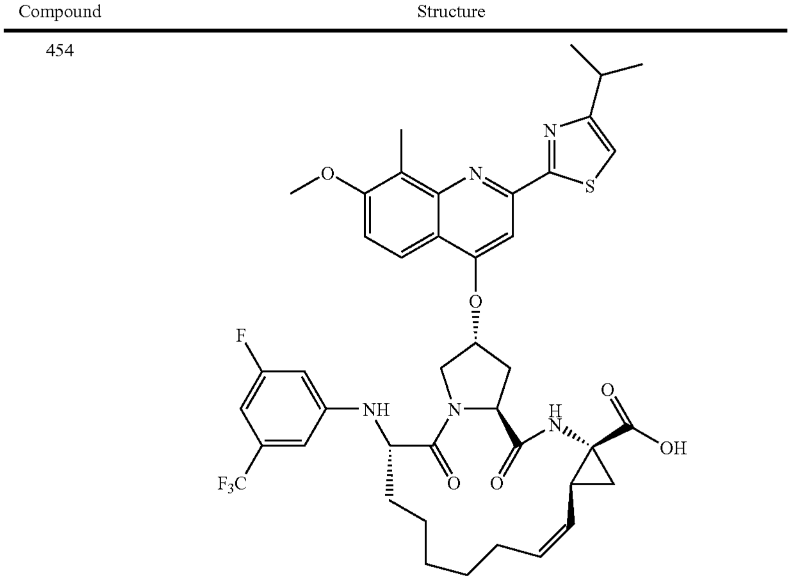 |
| 455 | 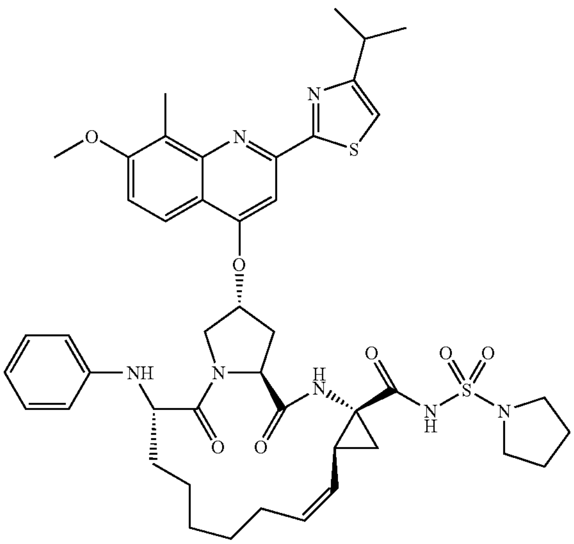 |

TABLE 1-continued
| Examples of compounds that can be prepared according to Examples 1-29 | |
|---|---|
| Compound | Structure |
| 456 | 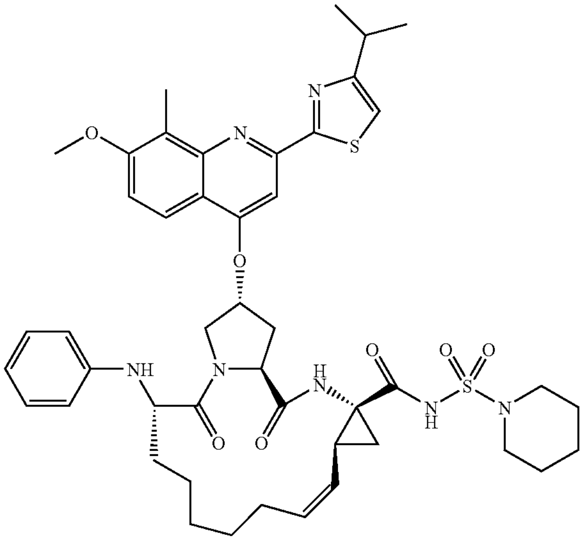 |
| 457 | 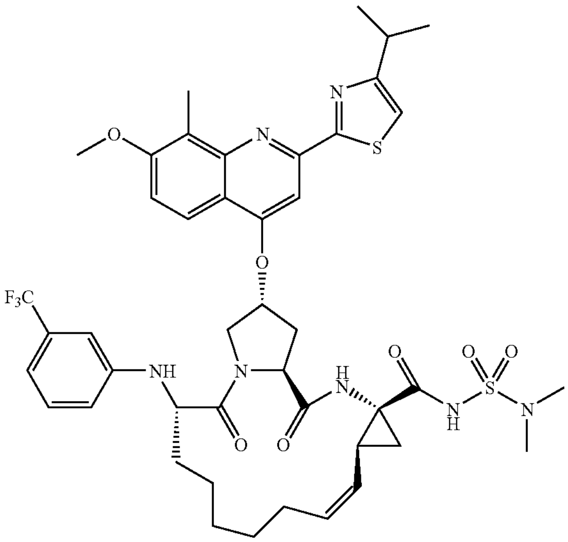 |

TABLE 1-continued
| Examples of compounds that can be prepared according to Examples 1-29 | |
|---|---|
| Compound | Structure |
| 458 | 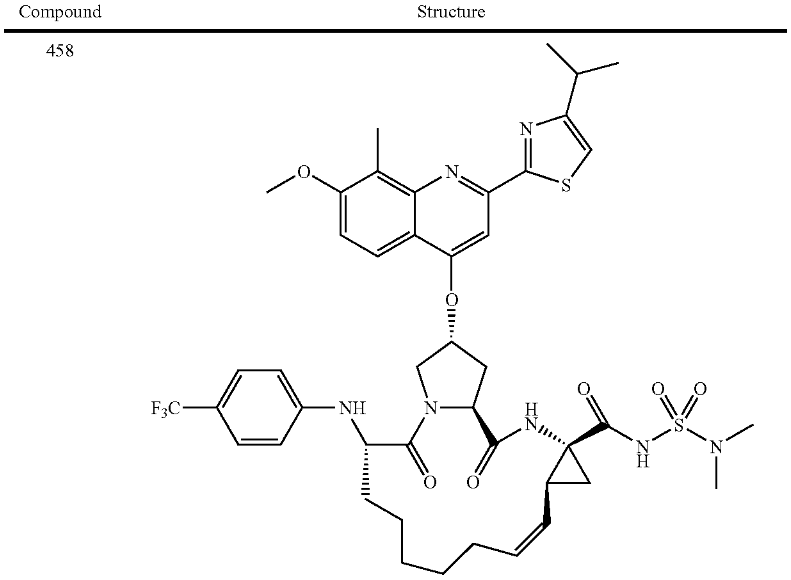 |
| 459 | 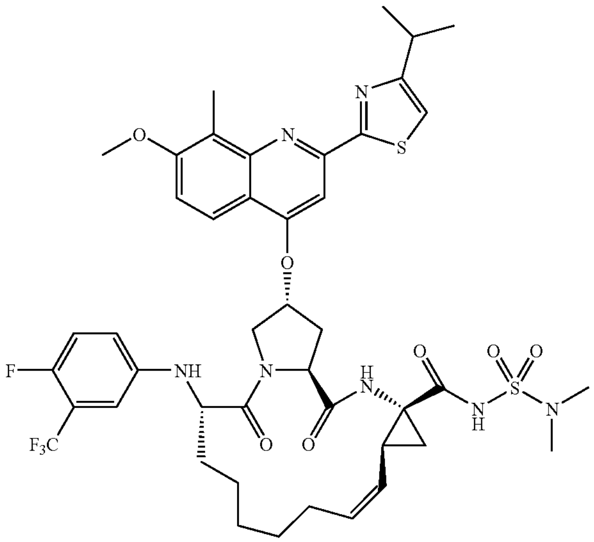 |

TABLE 1-continued
| Examples of compounds that can be prepared according to Examples 1-29 | |
|---|---|
| Compound | Structure |
| 460 | 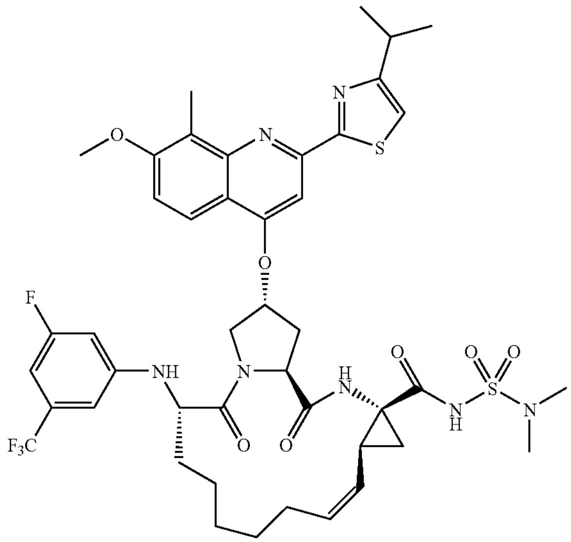 |
| 461 | 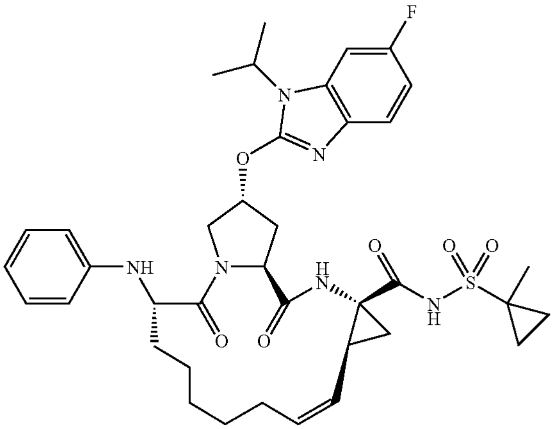 |
| 462 | 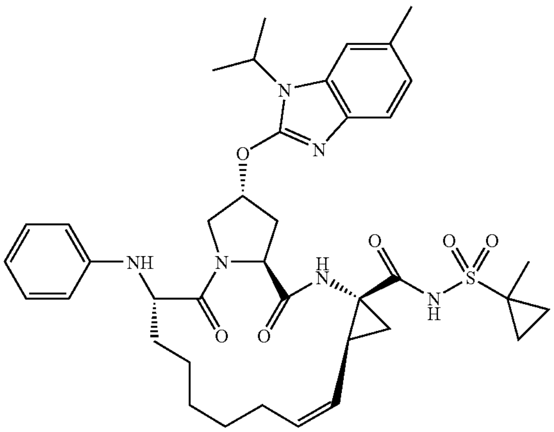 |

TABLE 1-continued
| Examples of compounds that can be prepared according to Examples 1-29 | |
|---|---|
| Compound | Structure |
| 463 | 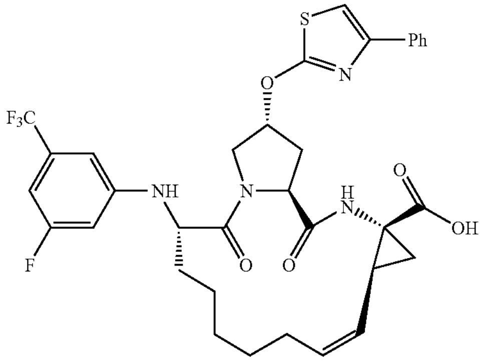 |
| 464 | 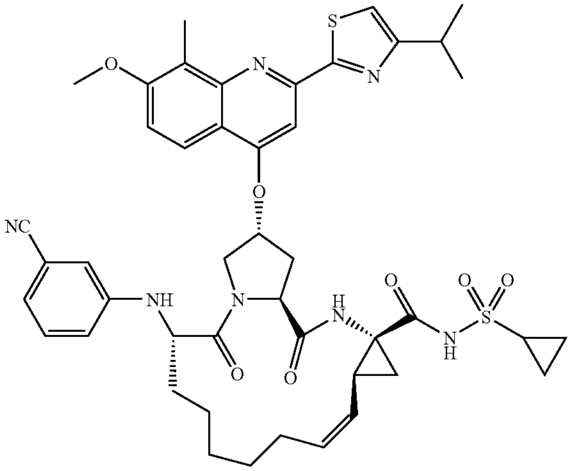 |
| 465 | 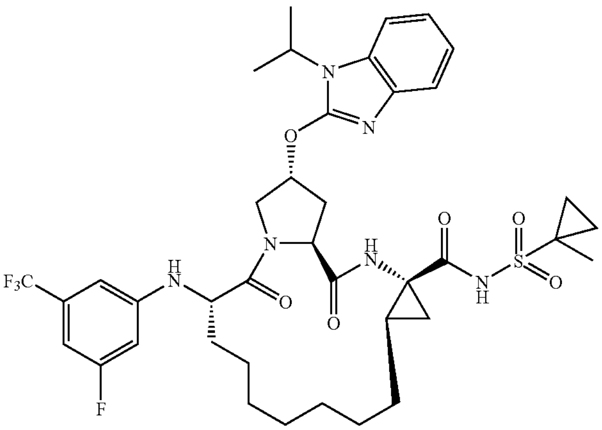 |

TABLE 1-continued
| Examples of compounds that can be prepared according to Examples 1-29 | |
|---|---|
| Compound | Structure |
| 466 | 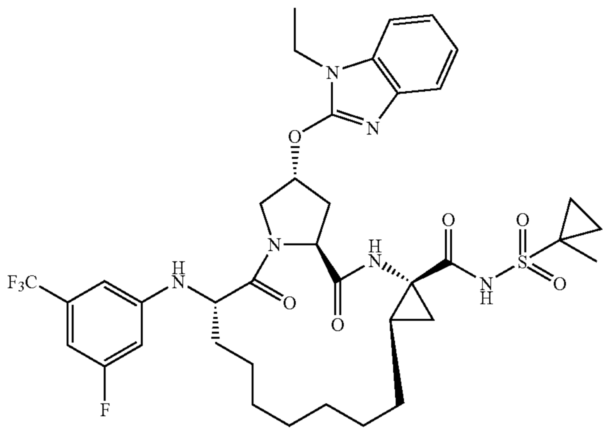 |
| 467 | 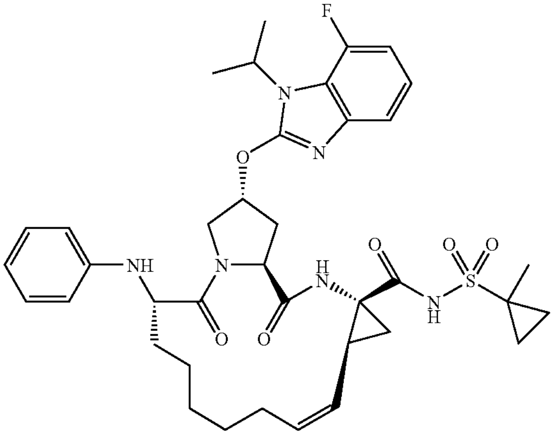 |
| 468 | 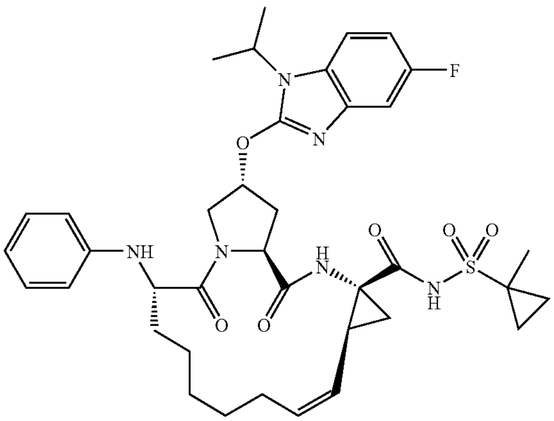 |

TABLE 1-continued
| Examples of compounds that can be prepared according to Examples 1-29 | |
|---|---|
| Compound | Structure |
| 469 | 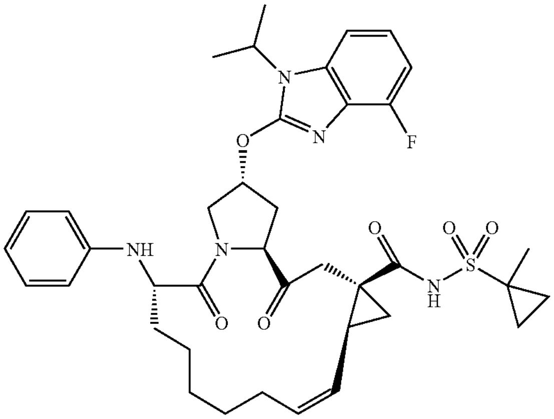 |
| 470 | 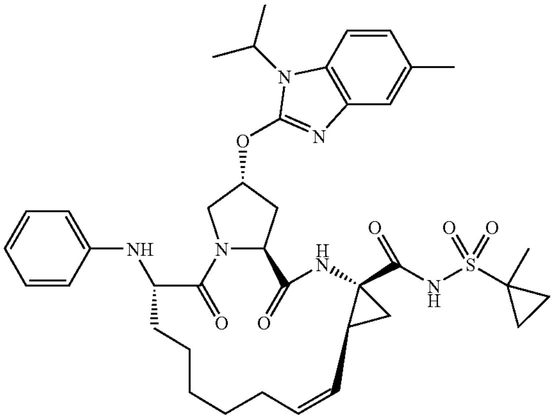 |
| 471 | 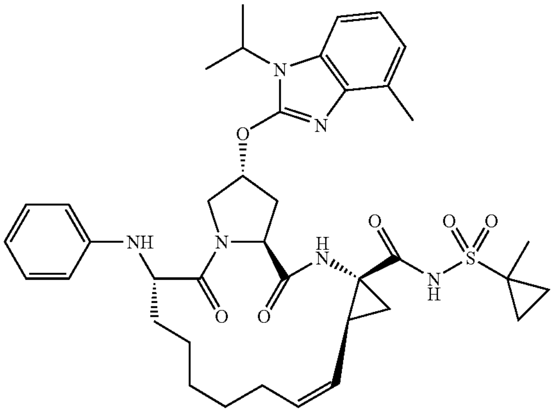 |

TABLE 1-continued
| Examples of compounds that can be prepared according to Examples 1-29 | |
|---|---|
| Compound | Structure |
| 472 | 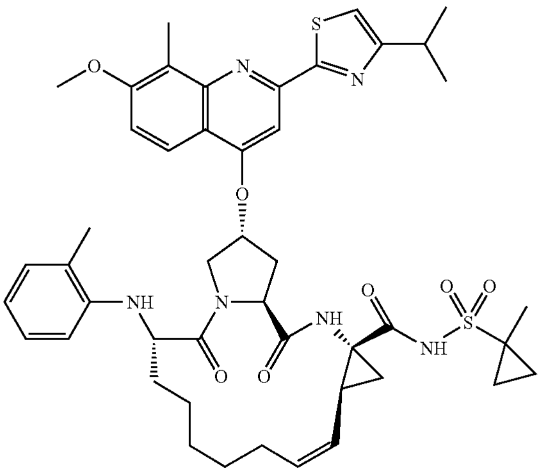 |
| 473 | 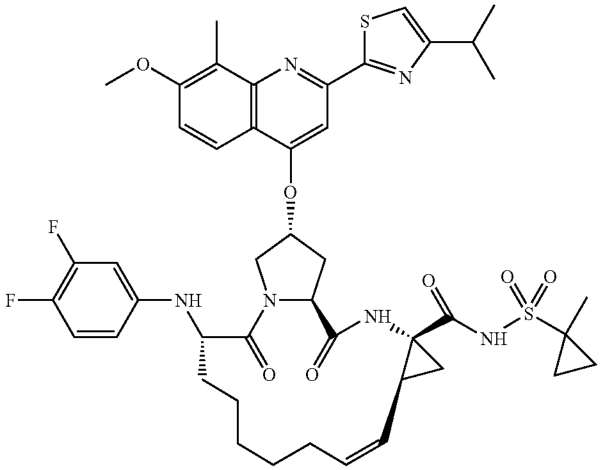 |
| 474 | 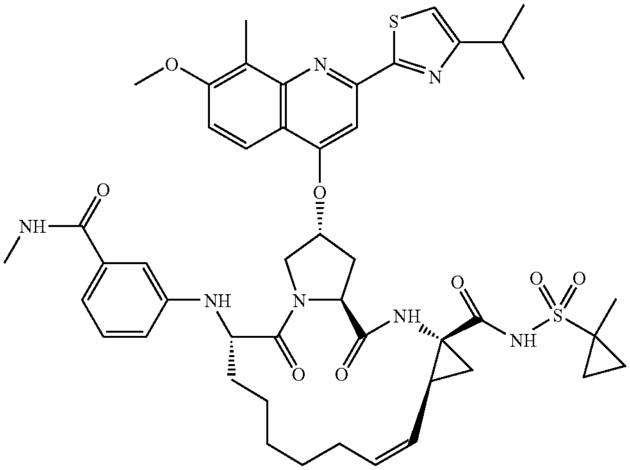 |

TABLE 1-continued
| Examples of compounds that can be prepared according to Examples 1-29 | |
|---|---|
| Compound | Structure |
| 475 | 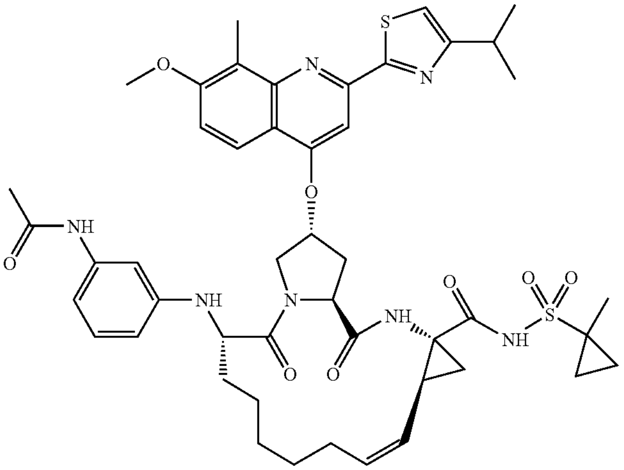 |
| 476 | 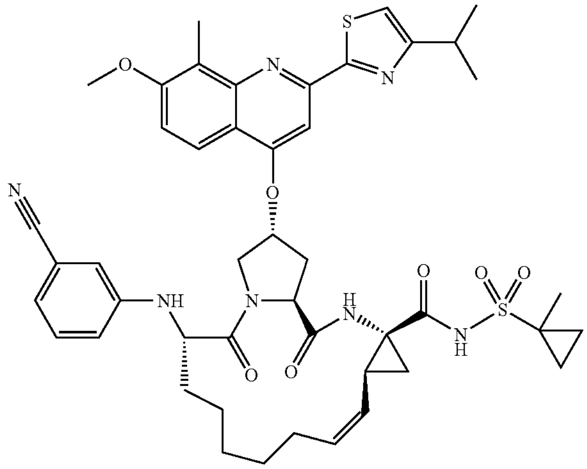 |
| 477 | 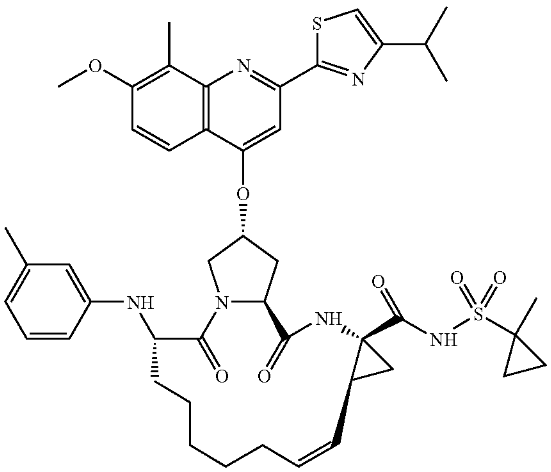 |

TABLE 1-continued
| Examples of compounds that can be prepared according to Examples 1-29 | |
|---|---|
| Compound | Structure |
| 478 | 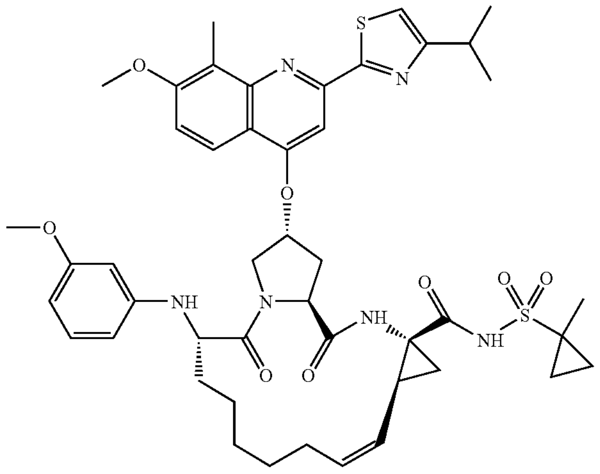 |
| 479 | 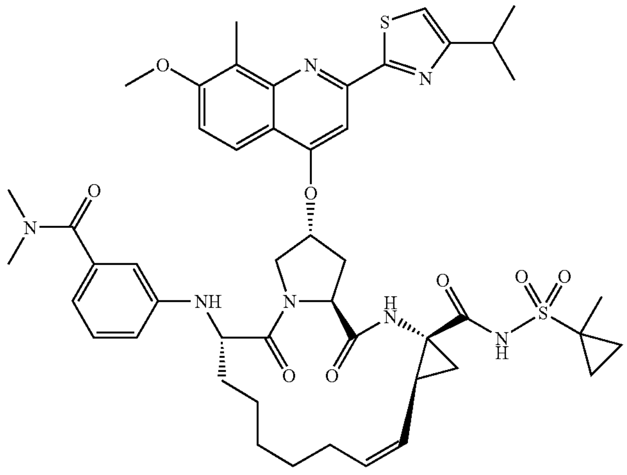 |
| 480 | 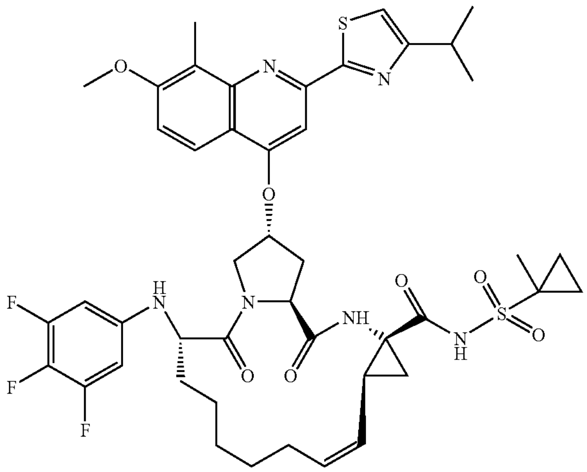 |

TABLE 1-continued
| Examples of compounds that can be prepared according to Examples 1-29 | |
|---|---|
| Compound | Structure |
| 481 | 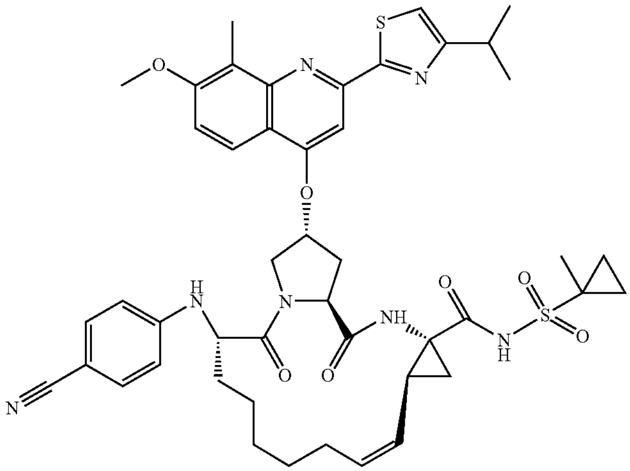 |
| 482 | 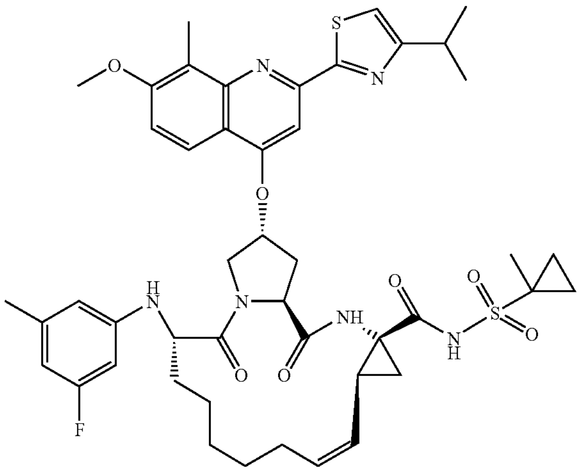 |
| 483 | 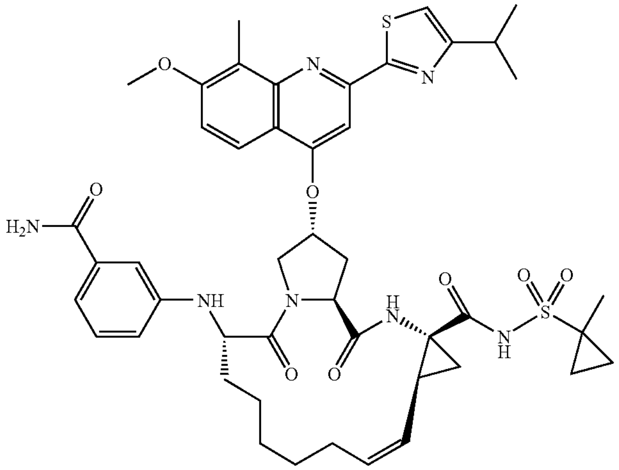 |

TABLE 1-continued
Examples of compounds that can be prepared according to Examples 1-29
| Compound | Structure |
| --- | --- |
| 484 | 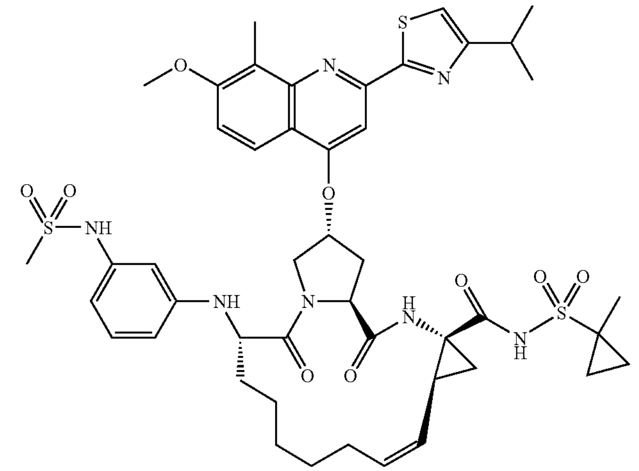 |
| 485 | 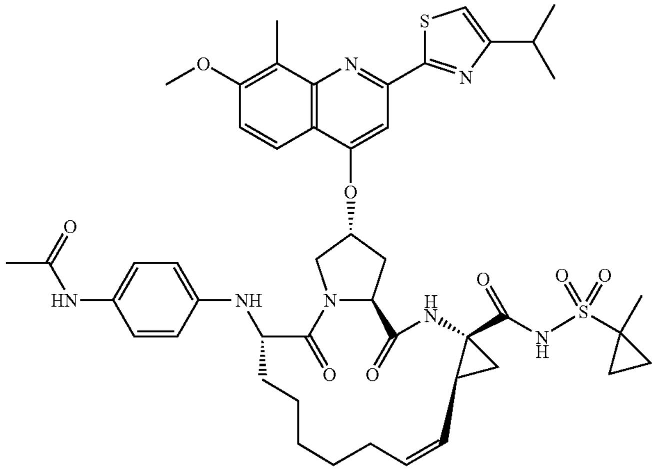 |
| 486 | 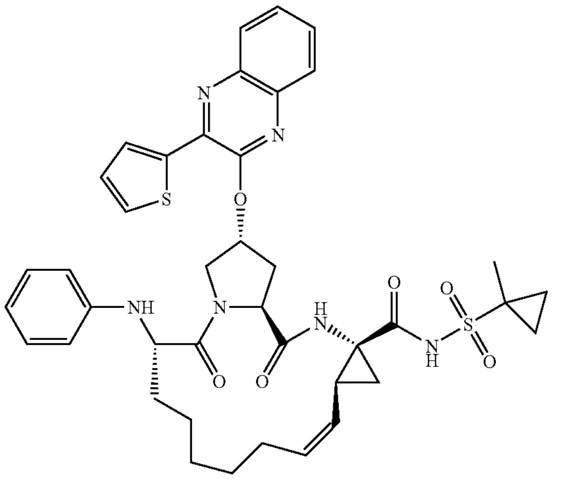 |

TABLE 1-continued
| Examples of compounds that can be prepared according to Examples 1-29 | |
|---|---|
| Compound | Structure |
| 487 | 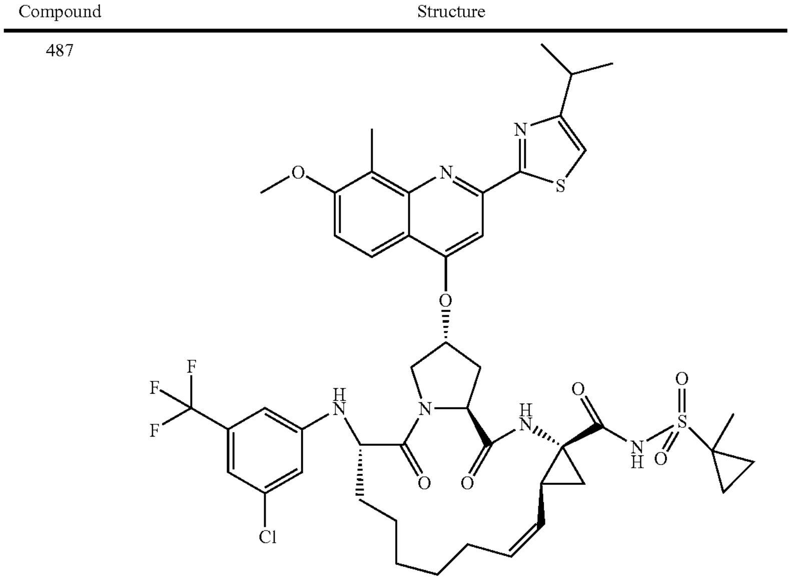 |
| 488 | 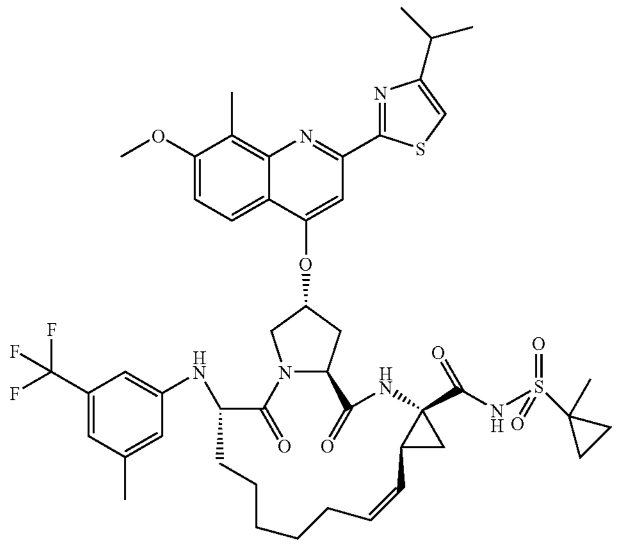 |

TABLE 1-continued
| Examples of compounds that can be prepared according to Examples 1-29 | |
|---|---|
| Compound | Structure |
| 489 | 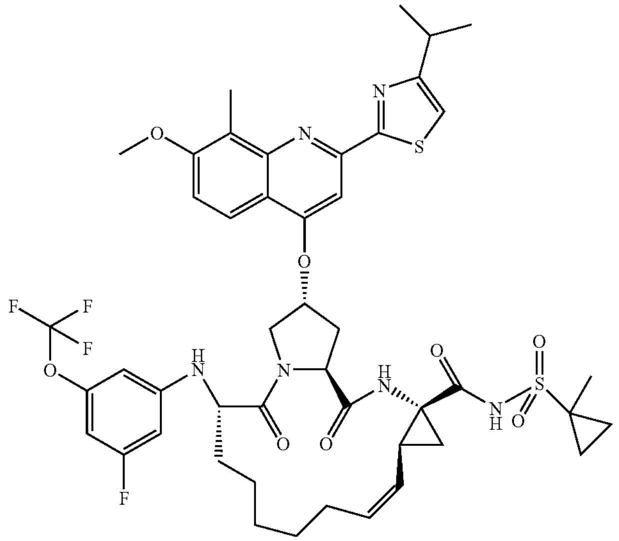 |
| 490 | 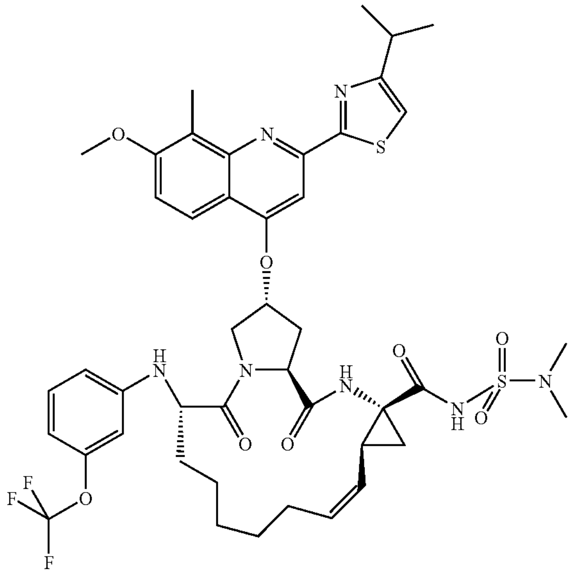 |
| 491 | 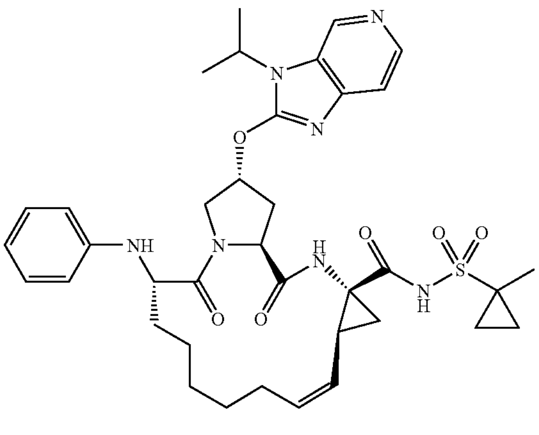 |

TABLE 1-continued

| Examples of compounds that can be prepared according to Examples 1-29 | |
|---|---|
| Compound | Structure |
| 492 | 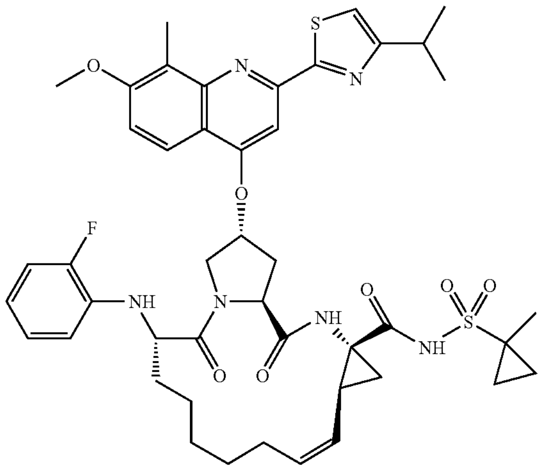 |

Preparation of NS3 Inhibitors: Section VII

Example 31-1

Synthesis of Compound 1001

Scheme XXIX

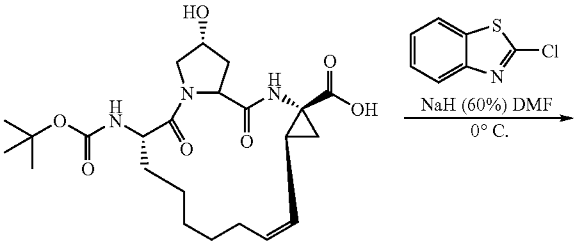

2

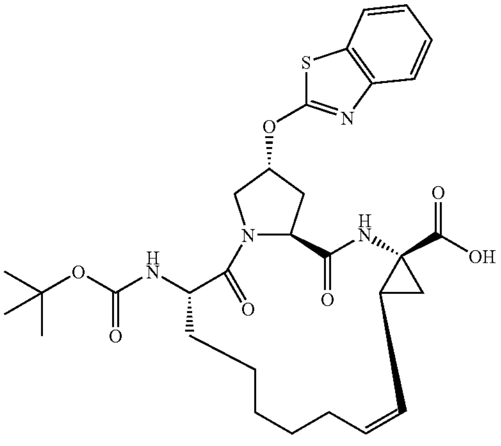

1001

General Method XA

To a solution of compound 2 (1 g, 2.2 mmol.) in 10 mL of dry DMF was added sodium hydride (0.53 g, 13.2 mmol.) at 0° C. The resulting mixture was stirred at this temperature for 1 h before the addition of 2-chloro-benzothiazole, the mixture was then allowed to slowly warm to room temperature and stirred overnight. The reaction was quenched by careful addition of methanol (10 mL) and water (30 mL). The resulting solution was stirred for 15 min, extracted with ethyl acetate, washed with brine, dried over $Na_2SO_4$, and concentrated under reduced pressure to afford a residue. The residue was purified by Prep-HPLC to afford compound 1001 as a white solid 0.78 g (yield 60.5%). $^1H$ NMR (400 MHz, DMSO-$d_6$) δ 12.22 (bra, 1 H), 8.61 (s, 2 H), 7.83 (d, J=7.6 Hz, 1 H), 7.67 (d, J=7.6 Hz, 1 H), 7.36 (t, J=7.2 Hz, 1 H), 7.24 (t, J=7.2 Hz, 1 H), 6.94 (d, J=6.8 Hz, 1 H), 5.74 (s, 1 H), 5.46 (q, J=8 Hz, 1 H), 5.25 (t, J=9.2 Hz, 1 H), 4.51 (d, J=12.8 Hz, 1 H), 4.41 (t, J=8 Hz, 1 H), 4.00 (t, J=10 Hz, 1 H), 3.87 (d, J=9.6 Hz, 1 H), 2.29-2.30 (m, 1 H), 2.14-2.16 (m, 1 H), 1.43-1.47 (m, 2 H), 1.29-1.14 (m, 16H). MS (ESI) m/e (M+H$^+$) 598.7.

Example 31-2
Synthesis of Compound 1002
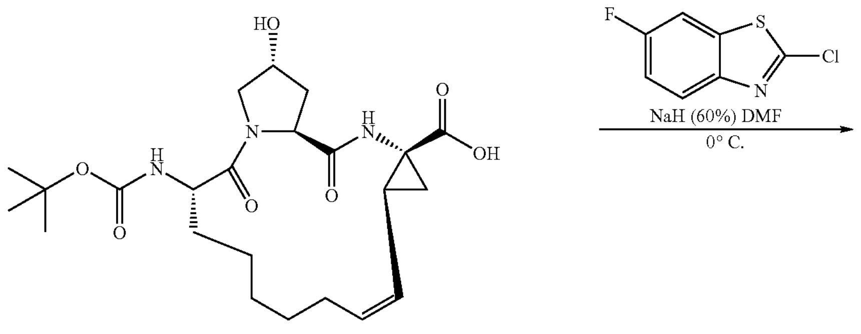
2
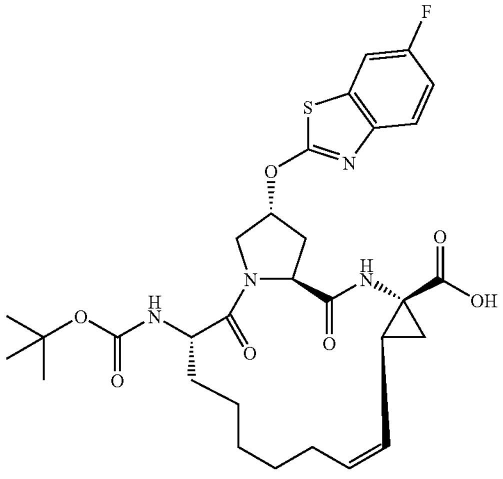
1002
The acid 1002 was prepared following General Method XA, and the yield was 65%. MS (ESI) m/e (M+H$^+$) 617.2.
Example 31-3
Synthesis of Compound 1003
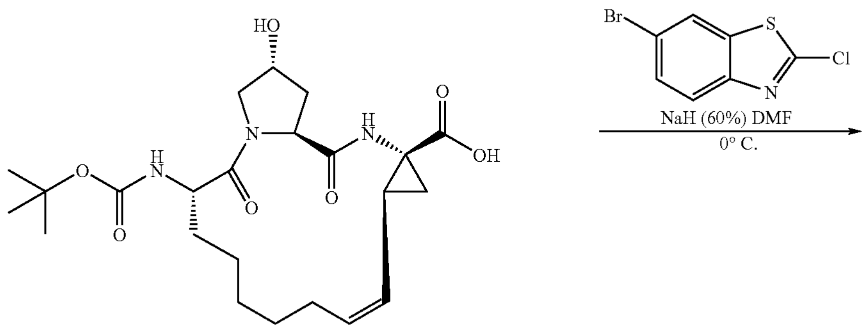
2

-continued
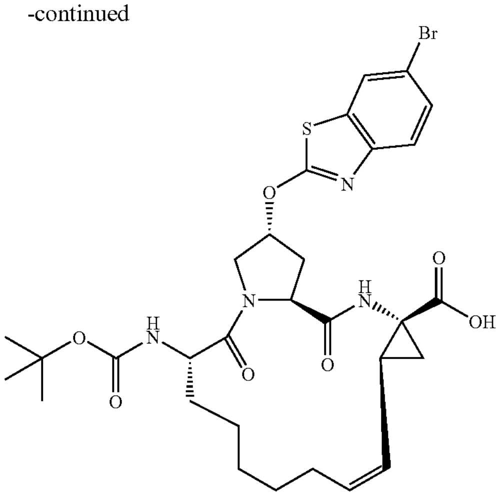
1003
The acid 1003 was prepared following General Method XA, and the yield was 65%. MS (ESI) m/e (M+H$^+$) 677.6.
Example 31-4
Synthesis of Compound 1004
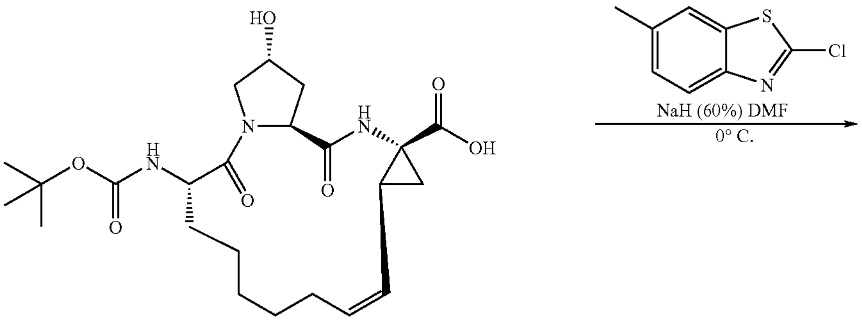
2
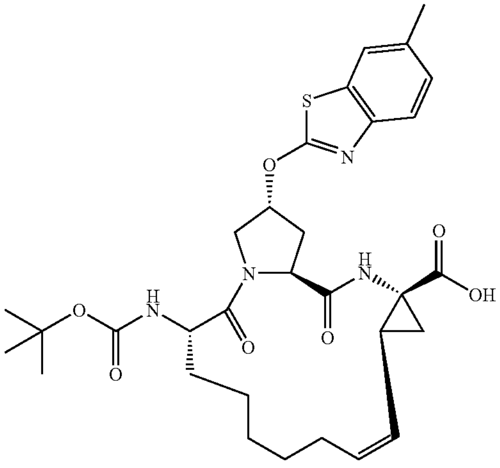
1004

The acid 1004 was prepared following General Method XA, and the yield was 50%. MS (ESI) m/e (M+H$^+$) 613.3.
Example 31-5
Synthesis of Compound 1005
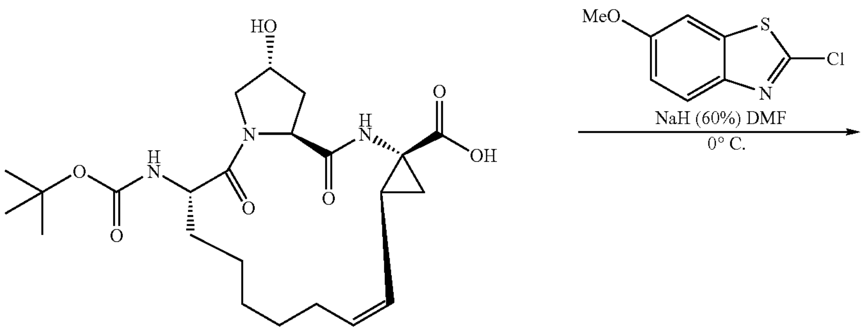
2
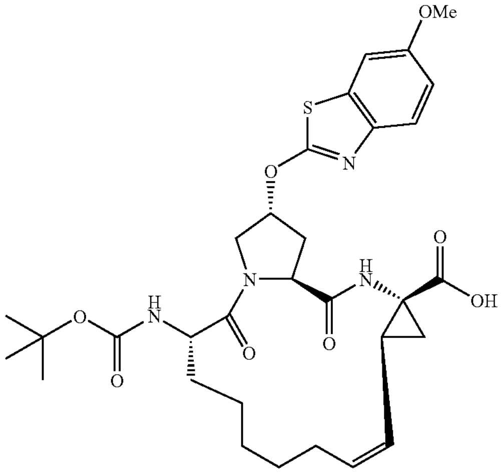
1005
The acid 1005 was prepared following General Method XA, and the yield was 51%, MS (ESI) m/e (M+H$^+$) 629.3.
Example 31-6
Synthesis of Compound 1006
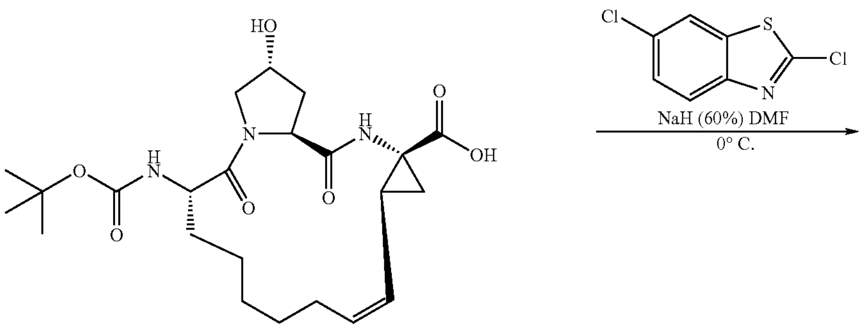
2

-continued
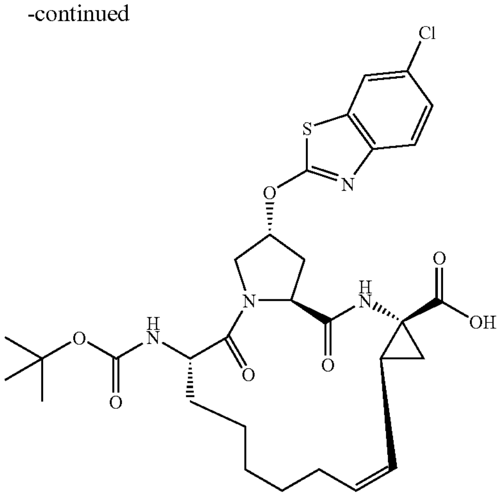
1006
The acid 1006 was prepared following General Method XA, and the yield was 41%, MS (ESI) m/e $(M+H^+)$ 633.
Example 32-1
Synthesis of Compound 1079
-continued
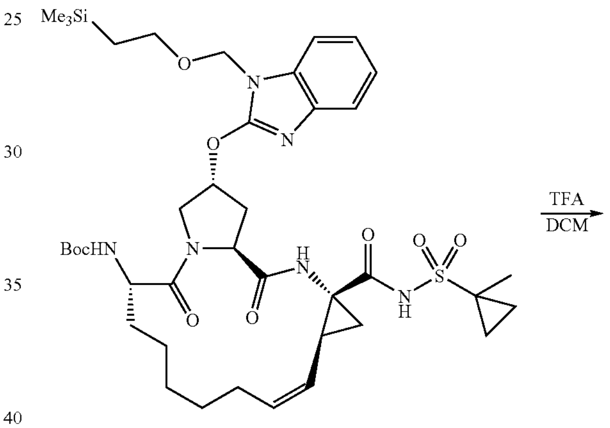
701
Scheme XXX
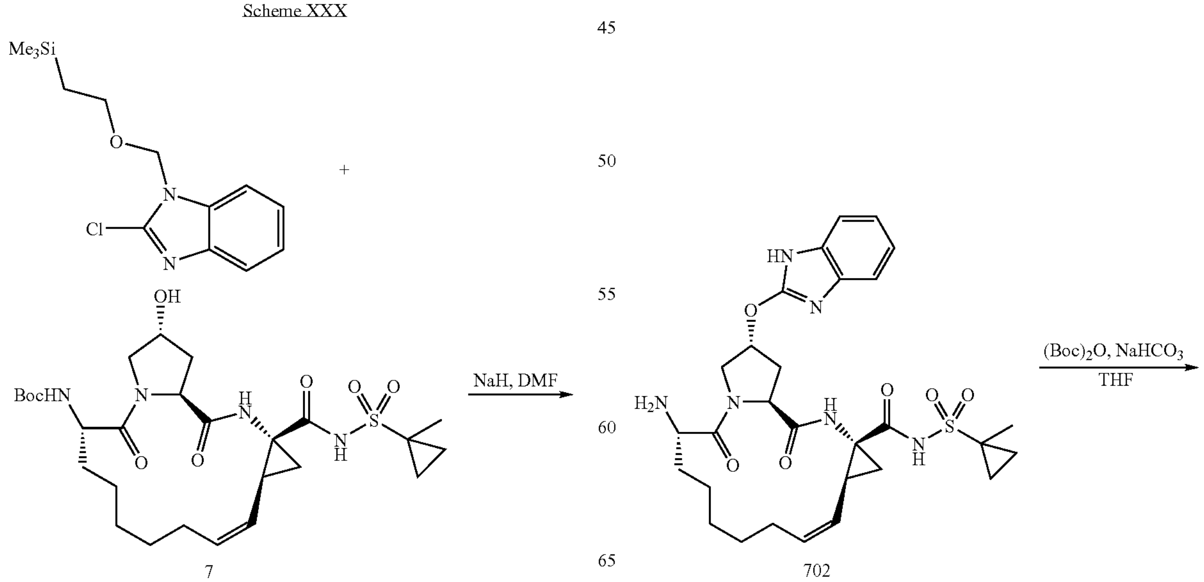
7
702

-continued

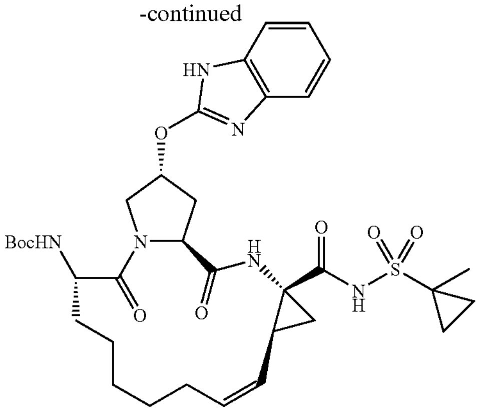

1079

Compound 1079 can be synthesized by the method of Scheme XXX. The benzimidazole can be introduced by use of a SEM protected benzimidazole, 1-((2-(trimethylsilyl)ethoxy)methyl)-2-chloro-1H-benzo[d]imidazole. The SEM protecting group can be introduced by treatment of 2-chloro-1H-benzo[d]imidazole with a base, such as sodium hydride, potassium hydride and the like, followed by addition of 2-(trimethylsilyl)ethoxymethyl chloride (SEMCl) thereby providing 1-((2-(trimethylsilyl)ethoxy)methyl)-2-chloro-1H-benzo[d]imidazole (1.13 g, 60.8%). The alcohol, compound 7, can be treated with a base, such as sodium hydride, potassium hydride, lithium hydride, cesium carbonate, sodium carbonate, potassium carbonate, potassium tert-butoxide, and the like, then reacted with 1-((2-(trimethylsilyl)ethoxy)methyl)-2-chloro-1H-benzo[d]imidazole to afford compound 701.The SEM and Boc groups can be removed under acidic conditions to afford compound 702. For example, the acid can be trifluoroacetic acid, hydrochloric acid, and the like. The Boc group can then be re-introduced by treatment of compound 702 with $(Boc)_2O$ in the presence of a base, such as cesium carbonate, sodium carbonate, potassium carbonate, sodium bicarbonate, potassium bicarbonate, and the like, to afford compound compound 1079.

Example 32-2

Synthesis of Compound 701

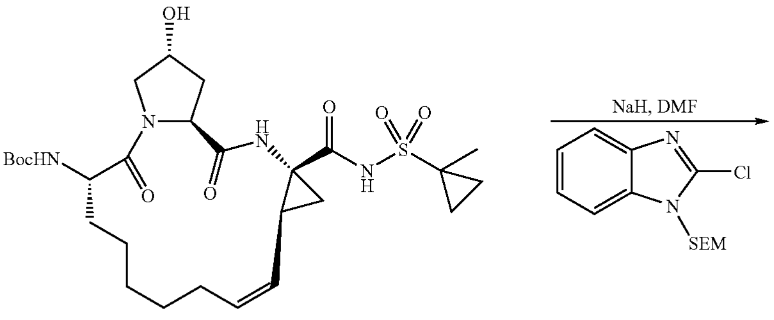

7

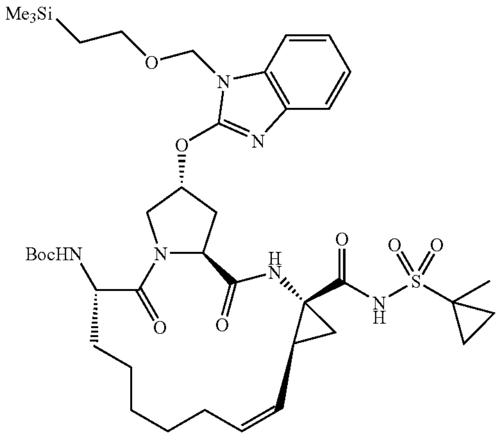

701

General Method XB

To a solution of compound 7 (300 mg, 0.515 mmol.) in 3 mL of dry DMF was added sodium hydride (60%, 204 mg, 5.1 mmol.) at 0° C. The resulting mixture was stirred at this temperature for 1 h, then 1-((2-(trimethylsilyl)ethoxy)methyl)-2-chloro-1H-benzo[d]imidazole (175 mg, 0.618 mmol.) was added. The reaction mixture was allowed to warm to room temperature and stirred overnight. The reaction was quenched with water and extracted with ethyl acetate (50 mL×3), washed with brine, dried over $Na_2SO_4$, concentrated to give a residue, which was purified by prep-TLC to give compound 701 as white solid (150 mg, yield 35.2%). MS (ESI) m/z $(M+H)^+$ 829.4.

Example 32-3

Synthesis of Compound 702

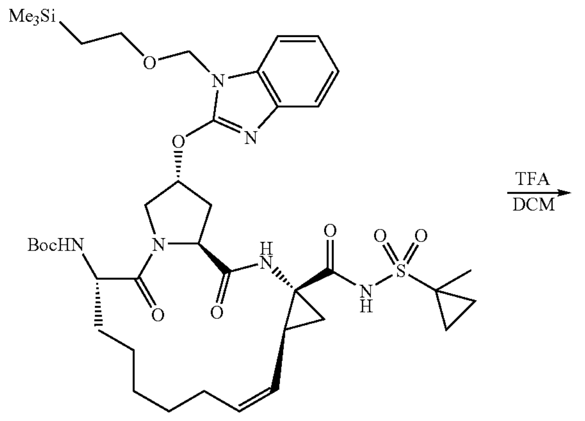

701

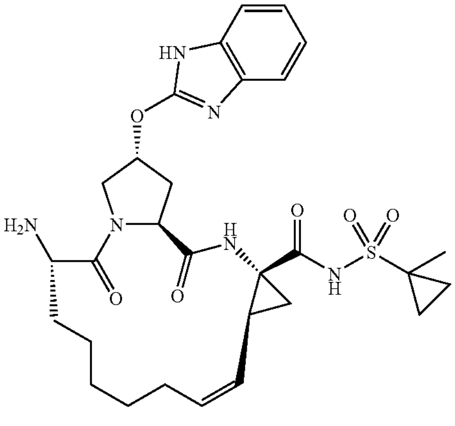

702

General Method XC

To a solution of compound 701 (60 mg, 0.072 mmol.) in dry DCM (2 mL) was added TFA (1 mL). The reaction mixture was stirred at room temperature for 3 h. LCMS analysis showed the reaction complete. The reaction mixture was concentrated to give crude compound 702 (40 mg, 93%), which was used without further purification.

Example 32-4

Synthesis of Compound 1079

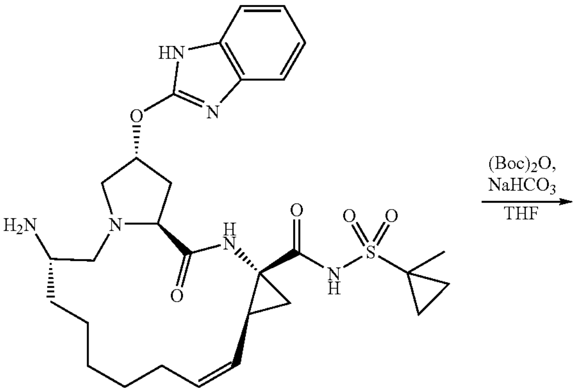

702

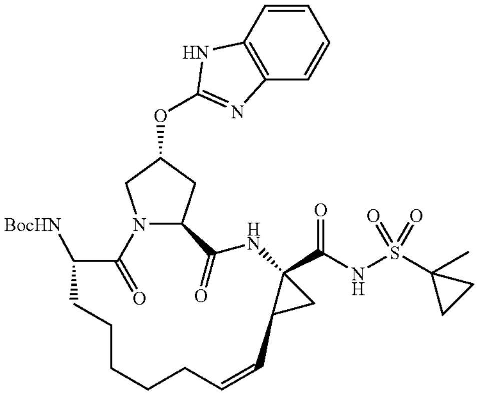

1079

General Method XD

To a solution of compound 702 (40 mg, 0.067 mmol.) in dry THF (2 mL) was added $NaHCO_3$ (16.9 mg, 0.261 mmol.) and followed by adding di-tert-butyl dicarbonate (34.6 mg, 0.201 mmol.). The reaction mixture was stirred at room temperature overnight. LCMS analysis showed the reaction complete. The reaction mixture was quenched with water and extracted with ethyl acetate (30 mL×3). The organic layer was dried over $Na_2SO_4$, concentrated and purified by prep-TLC to give compound 1079 (14.2 mg, 15%). MS (ESI) m/z $(M+H)^+$ 699.3.

Example 32-5

Synthesis of 1-((2-(trimethylsilyl)ethoxy)methyl)-2-chloro-1H-benzo[d]imidazole

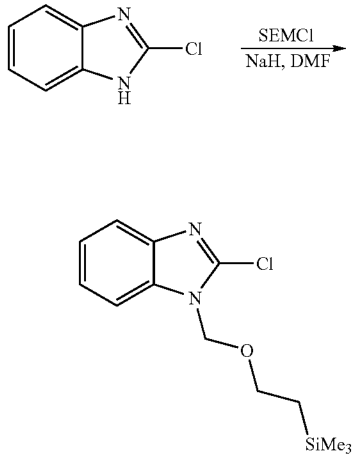

General Method XE

To a solution of 2-chloro-1H-benzo[d]imidazole (1 g, 6.6 mmol.) in dry DMF (10 mL) was added sodium hydride (60%, 0.26 g, 6.5 mmol.) at room temperature under nitrogen atmosphere. 2-(trimethylsilyl)ethoxymethyl chloride (SEMCl, 1.14 g, 6.8 mmol.) was added dropwise after the solution stirred for 1.5 h. The resulting mixture stirred overnight and then quenched with water and extracted with ethyl acetate (30 mL×3). The combined organic layers was washed with water, dried over sodium sulfate and concentrated to give a residue. The residue was purified by column chromatography to give 1-((2-(trimethylsilyl)ethoxy)methyl)-2-chloro-1H-benzo[d]imidazole (1.13 g, 60.8%).

Example 32-6

Synthesis of Compound 1077

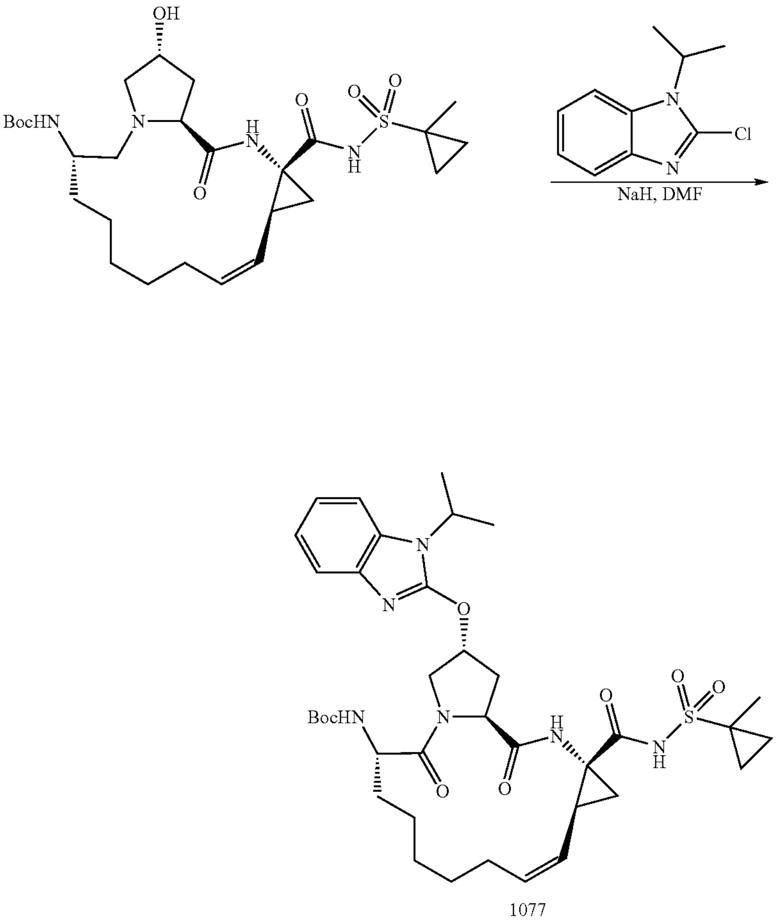

1077

General Method XF

To a suspension of NaH (60%, 62 mg, 1.54 mmol.) in 2 mL DMF was added compound 7 (150 mg, 0.257 mmol.) at 0° C. After the mixture was stirred for 2 h at 0-5° C., 2-chloro-1-isopropyl-benzimidazole (60 mg, 0.31 mmol.) was added, the resulting mixture was warmed to room temperature and stirred for 12 h. After completion of the reaction, the mixture was cooled by ice water, acidified by aq HCl (IN) to ~pH=5-6, then the mixture was extracted by ethyl acetate (30 mL×3), the organic layers were combined, washed by brine, dried over anhydrous sodium sulfate, the solvent was removed under reduced pressure, the residue was purified by prep-HPLC to afford compound 1077 (20 mg, 10.5%). MS (ESI) m/z $(M+H)^+$ 741.4.

Example 32-7

Synthesis of Compound 1007

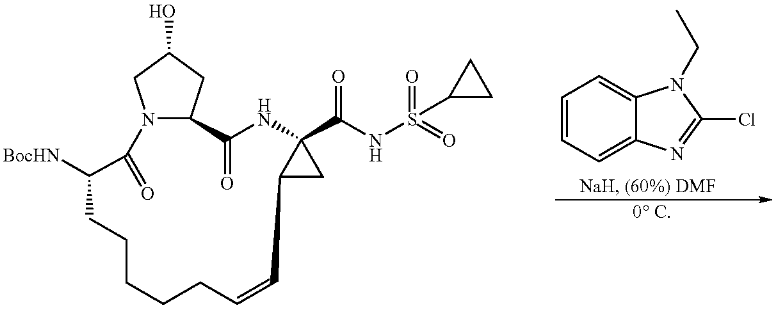

11

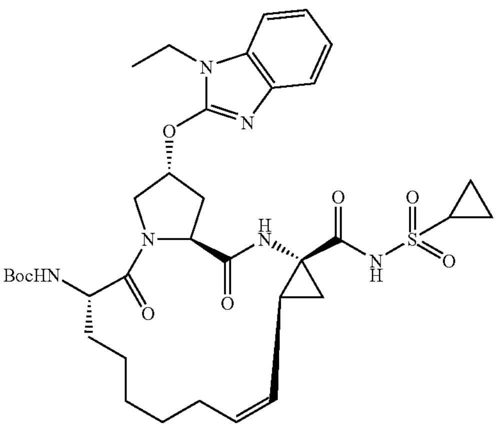

1007

The acylsulfonamide 1007 was prepared following General Method XF, and the yield was 45%, MS (ESI) m/e (M+H+) 713.

Example 33-1

Synthesis of Compound 1008

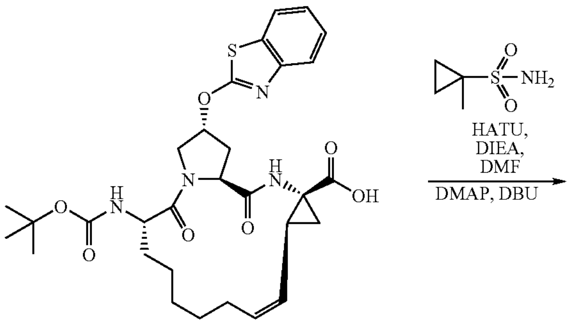

1001

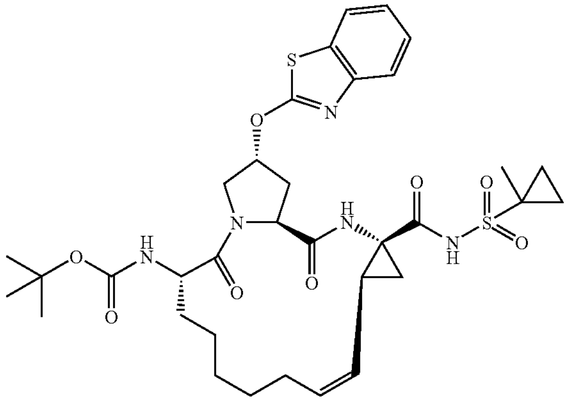

1008

General Method B

To a solution of compound 1001 (100 mg, 0.17 mmol.) in 5 mL of dry DMF was added HATU (226 mg, 0.6 mmol.) and DIEA (0.1 mL, 0.6 mmol.) at 20° C. The resulting mixture was stirred 1 h at the same temperature then treated with methylcyclopropanyl sulfonamide (45.9 mg, 0.34 mmol.), DMAP (104 mg, 0.85 mmol.), and DBU (0.1 mL, 0.85 mmol.). Subsequently, the resulting mixture was stirred overnight at 20° C. The reaction was quenched by adding EtOAc (20 mL), and washed with aqueous NaOAc buffer (pH 4, 2×15 mL), 5% aqueous $NaHCO_3$ (15 mL) and brine (20 mL). The organic layer was dried ($Na_2SO_4$), filtered, and concentrated to get a residue, which was purified by Prep-HPLC to give compound 1008 as a white solid 32 mg (yield 27%). MS (ESI) m/e (M+H+) 716.3.

Example 33-2

Synthesis of Compound 1009

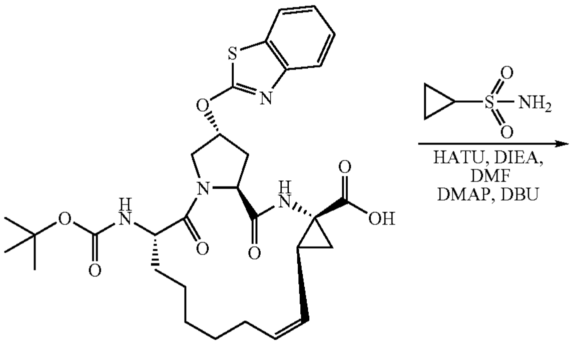

1001

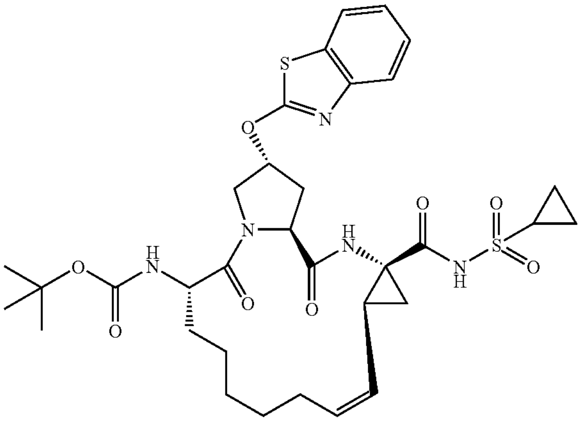

1009

The acylsulfonamide 1009 was prepared following General Method B, the pure product was isolated as a white solid. Yield=45.3%. MS (ESI) m/e (M+H$^+$) 702.3.
Example 33-3
Synthesis of Compound 1010
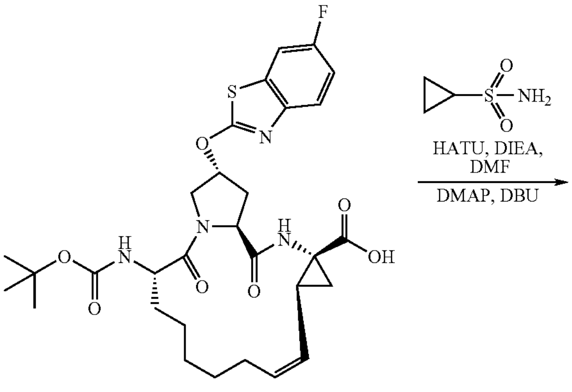
1002
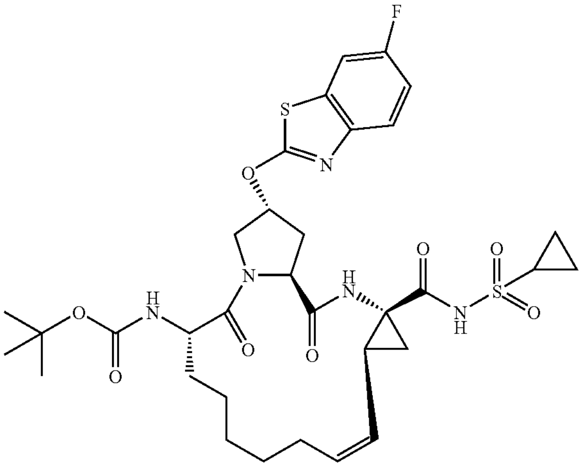
1010
The acylsulfonamide 1010 was prepared following General Method B, the pure product was isolated as a white solid. Yield=36%. MS (ESI) m/e (M+H$^+$) 720.3.
Example 33-4
Synthesis of Compound 1011
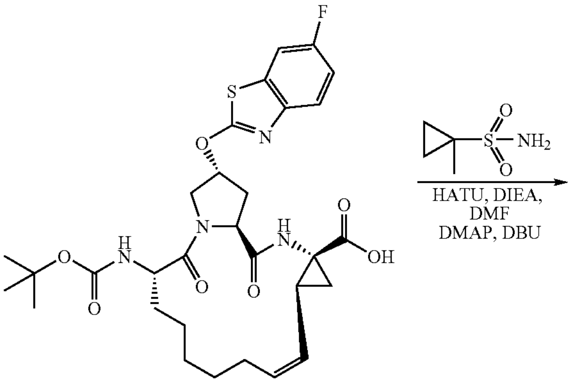
1002
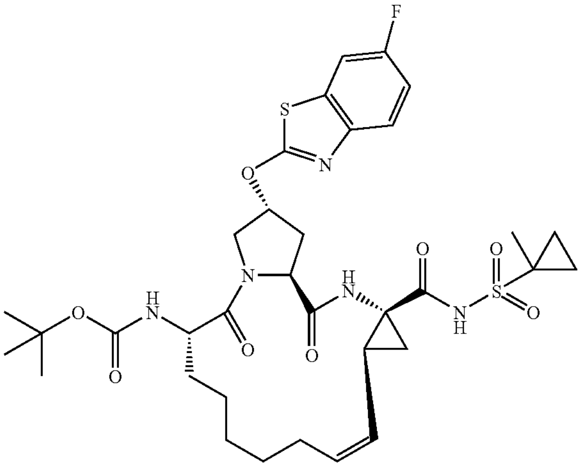
1011

The acylsulfonamide 1011 was prepared following General Method B, the pure product was isolated as a white solid. Yield=43%. MS (ESI) m/e (M+H$^+$) 734.3.
Example 33-5
Synthesis of Compound 1012
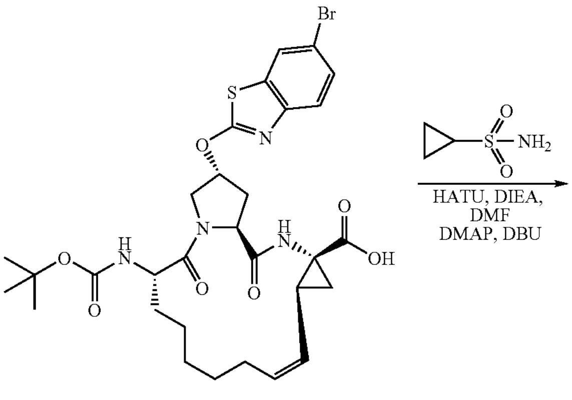
1003
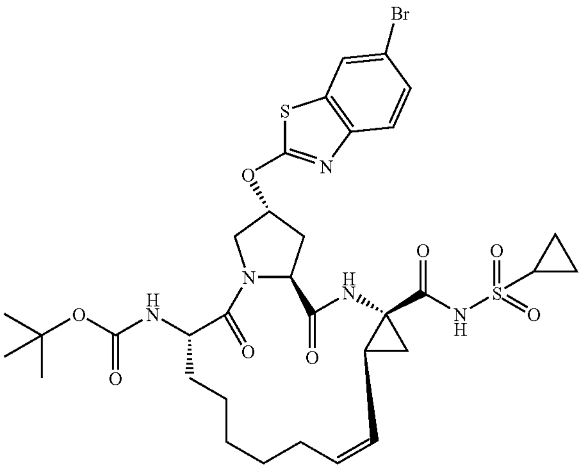
1012
The acylsulfonamide 1012 was prepared following General Method B, the pure product was isolated as a white solid. Yield=40%. MS (ESI) m/e (M+H$^+$) 780.8.
Example 33-6
Synthesis of Compound 1013
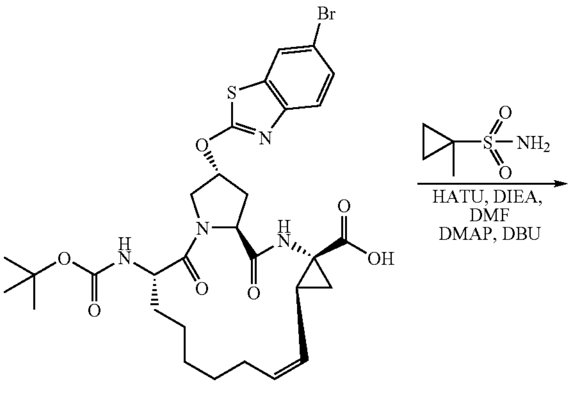
1003
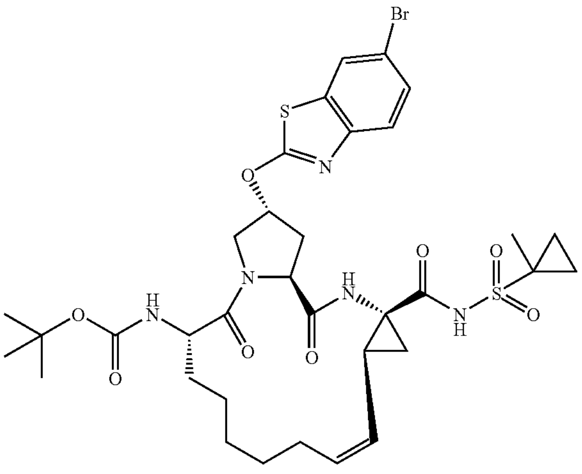
1013

The acylsulfonamide 1013 was prepared following General Method B, the pure product was isolated as a white solid. Yield=36%. MS (ESI) m/e (M+H$^+$) 794.8.
Example 33-7
Synthesis of Compound 1014
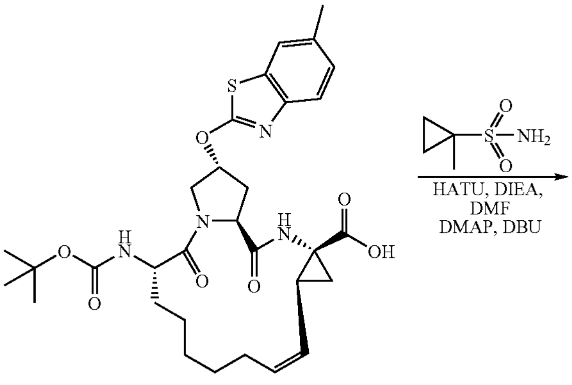
1004
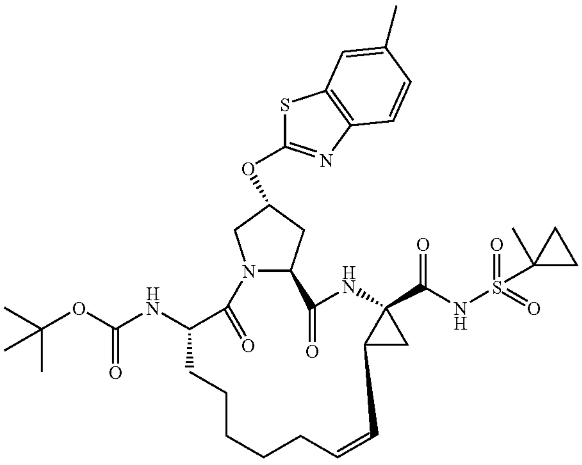
1014
The acylsulfonamide 1014 was prepared following General Method B, the pure product was isolated as a white solid. Yield=37%. MS (ESI) m/e (M+H$^+$) 730.3.
Example 33-8
Synthesis of Compound 1015
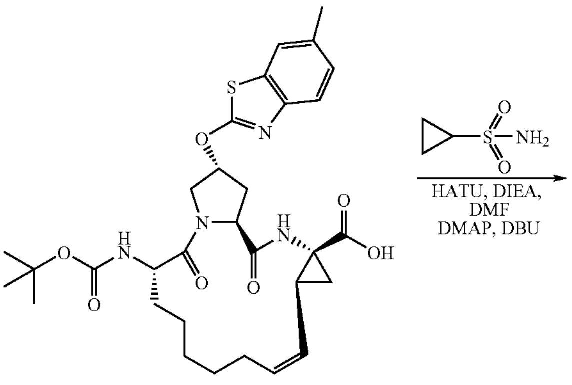
1004
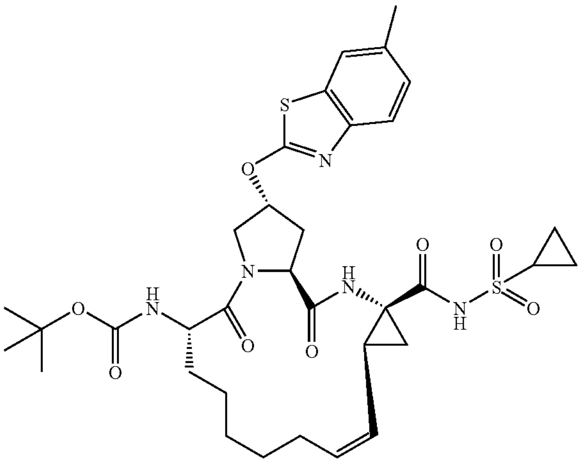
1015

The acylsulfonamide 1015 was prepared following General Method B, the pure product was isolated as a white solid. Yield=41%. MS (ESI) m/e (M+H$^+$) 716.3.
Example 33-9
Synthesis of Compound 1016
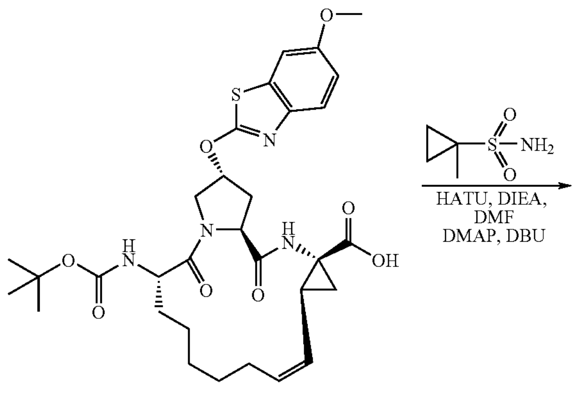
1005
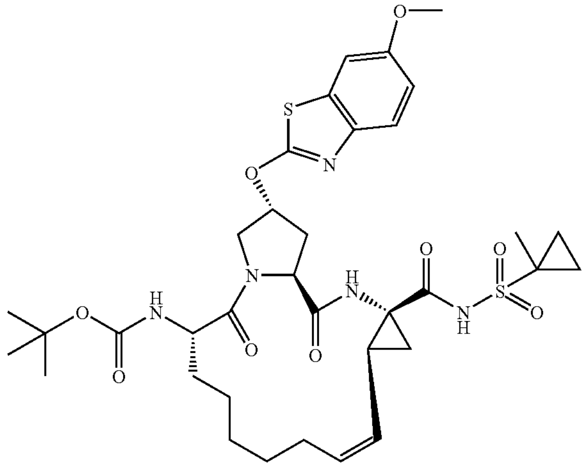
1016
The acylsulfonamide 1016 was prepared following General Method B, the pure product was isolated as a white solid. Yield=33%. MS (ESI) m/e (M+H$^+$) 746.3.
Example 33-10
Synthesis of Compound 1017
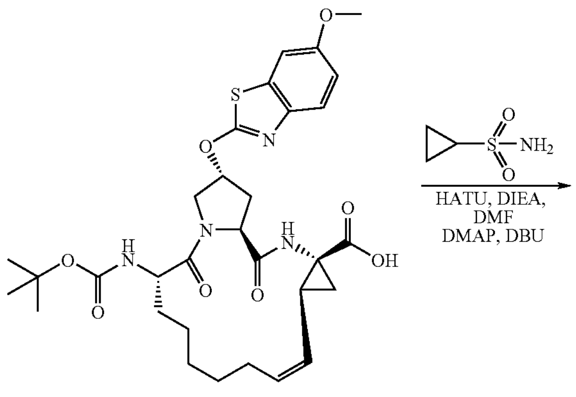
1005
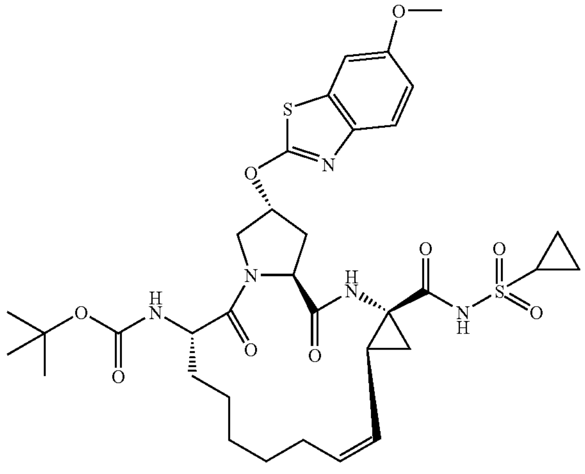
1017

The acylsulfonamide 1017 was prepared following General Method B, the pure product was isolated as a white solid. Yield=39%. MS (ESI) m/e (M+H$^+$) 742.3.
Example 33-11
Synthesis of Compound 1018
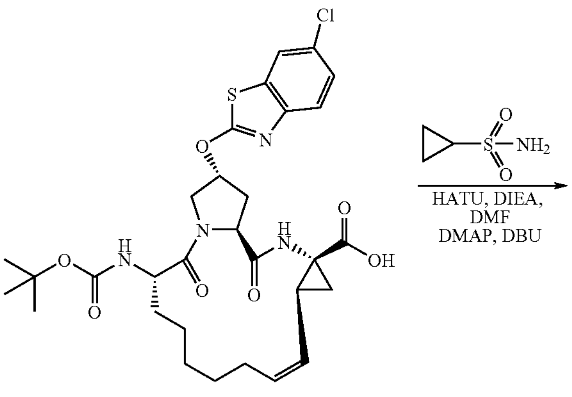
1006
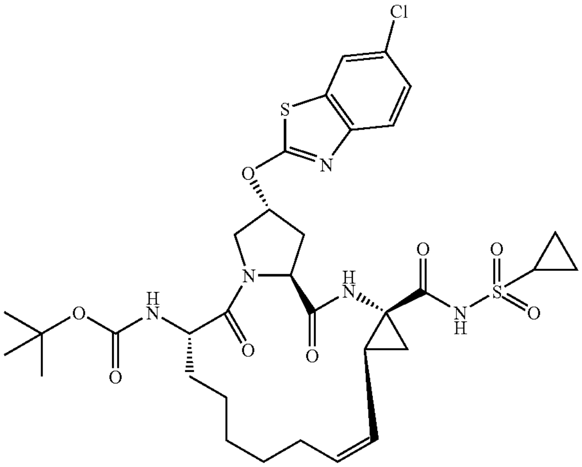
1018
The acylsulfonamide 1018 was prepared following General Method B, the pure product was isolated as a white solid. Yield=42%. MS (ESI) m/e (M+H$^+$) 736.
Example 33-12
Synthesis of Compound 1019
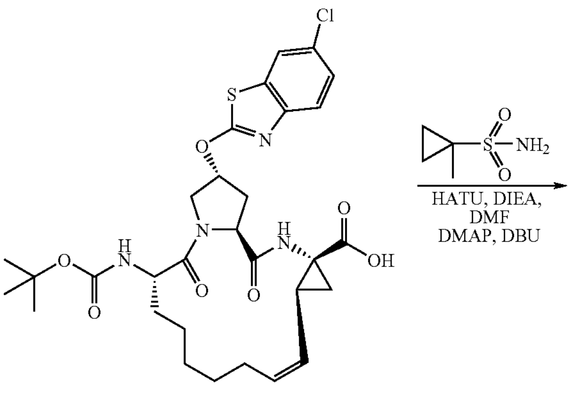
1006
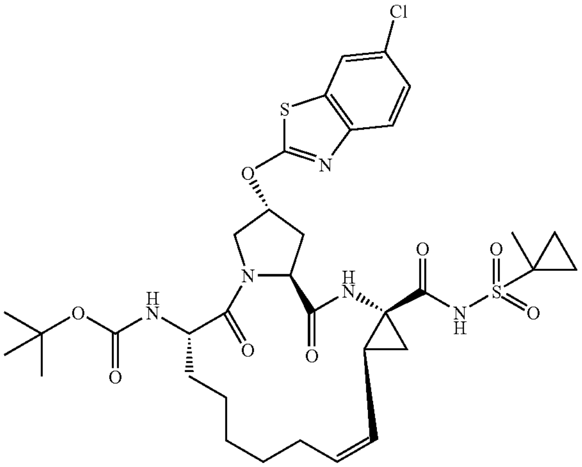
1019

The acylsulfonamide 1019 was prepared following General Method B, the pure product was isolated as a white solid. Yield=40%. MS (ESI) m/e (M+H$^+$) 742.3.

Example 34-1

Synthesis of Compound 7-E

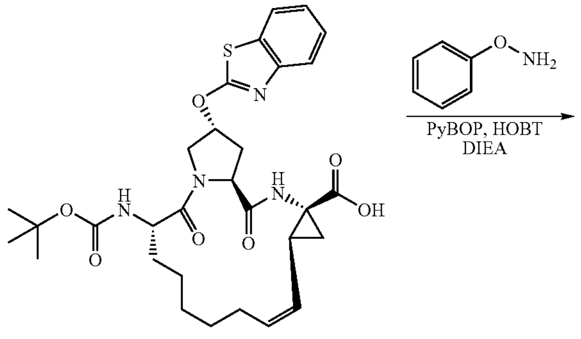

1001

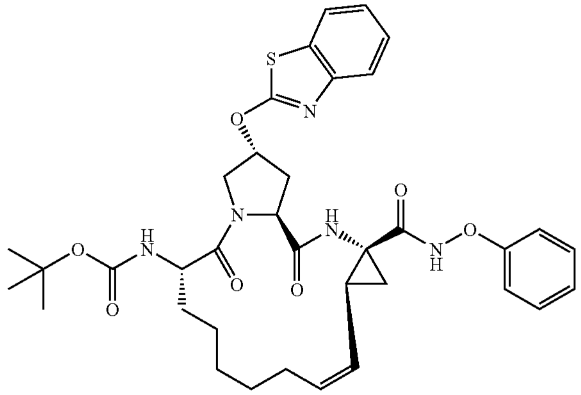

1020

General Method C

To a solution of compound 1001 (100 mg, 0.17 mmol.) in 5 mL of dry DMF was added PyBOP (177 mg, 0.34 mmol.) and HOBT (46 mg, 0.34 mmol.) at room temperature, the resulting mixture was stirred 2 h at the same temperature.

Subsequently, the stirring mixture was treated with O-phenylhydroxylamine hydrochloride (26.9 mg, 0.19 mmol.) and DIEA (88 mg, 0.68 mmol.), the resulting mixture was stirred overnight at rt. The reaction was quenched by adding water (20 mL) and extracted with ethyl acetate (3×15 mL). The combined organic layers were washed with brine, dried over $Na_2SO_4$, and concentrated to get a residue, which was purified by Prep-HPLC to give compound 1020 as white solid 50 mg (yield 32.5%). MS (ESI) m/e (M+H$^+$) 690.3.

Example 34-2

Synthesis of Compound 1021

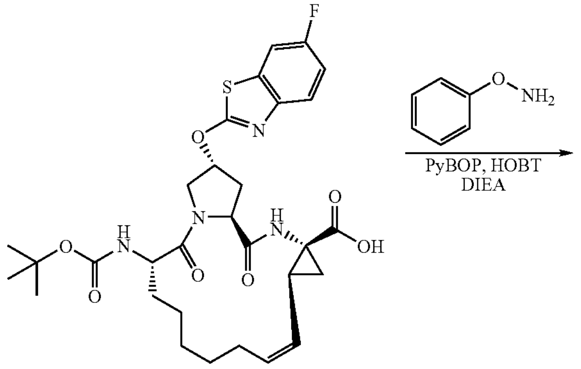

1002

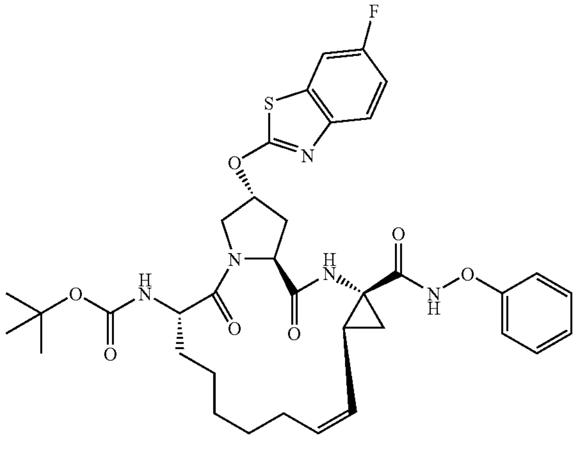

1021

The hydroxamate 1021 was prepared following General Method C, the pure product was isolated as a white solid. Yield=45.3%. MS (ESI) m/e (M+H$^+$) 708.3.
Example 34-3
Synthesis of Compound 1022
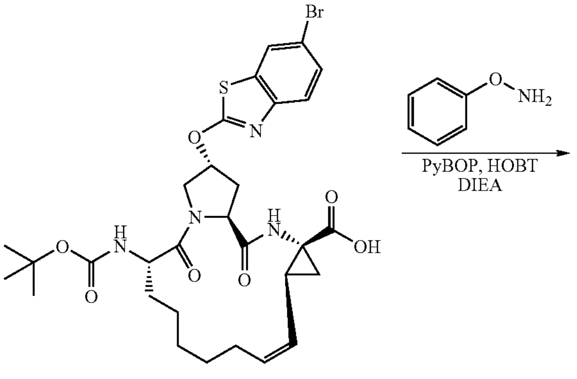
1003
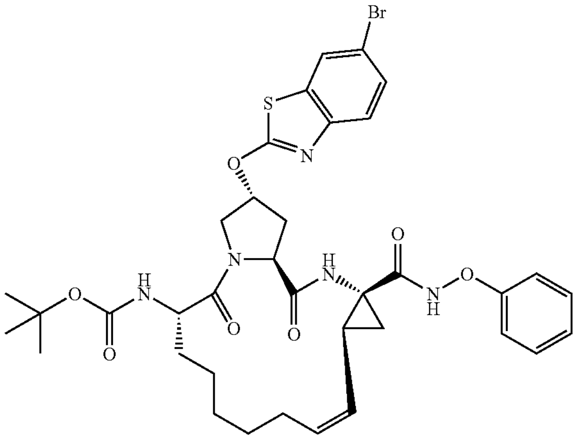
1022
The hydroxamate 1022 was prepared following General Method C, the pure product was isolated as a white solid. Yield=45.5%. MS (ESI) m/e (M+H$^+$) 768.7.
Example 34-4
Synthesis of Compound 1023
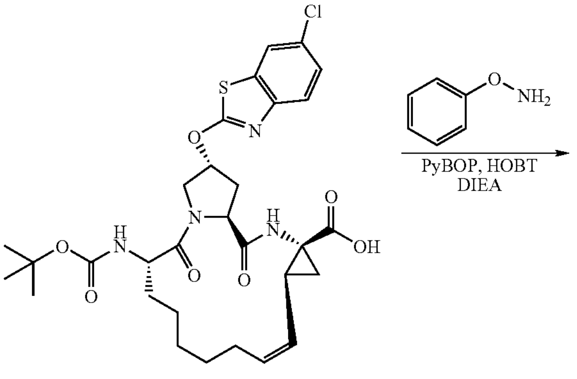
1006
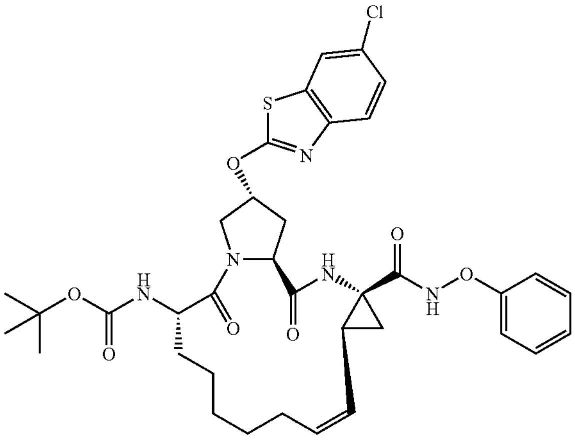
1023

The hydroxamate 1023 was prepared following General Method C, the pure product was isolated as a white solid. Yield=43.5%. MS (ESI) m/e ($M+H^+$) 724.

Example 34-5

Synthesis of Compound 1024

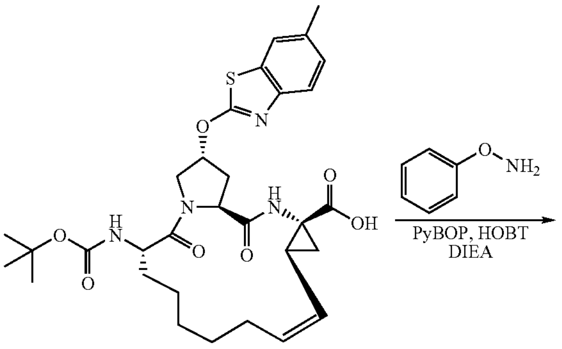

1004

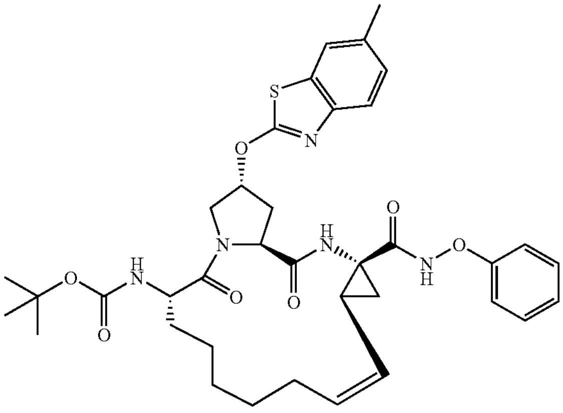

1024

The hydroxamate 1024 was prepared following General Method C, the pure product was isolated as a white solid. Yield=43.5%. MS (ESI) m/e ($M+H^+$) 704.3.

Example 34-6

Synthesis of Compound 1025

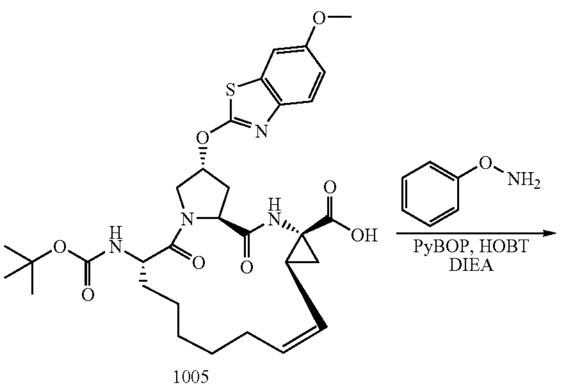

1005

-continued

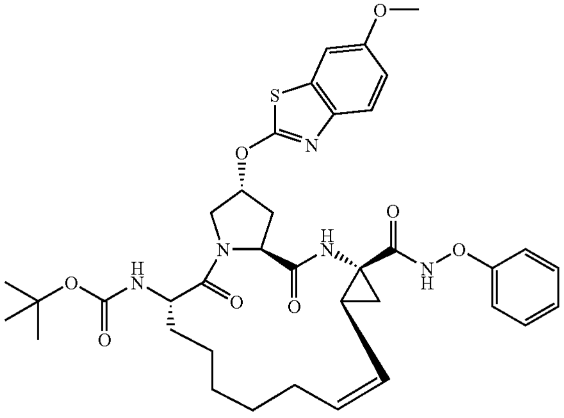

1025

The hydroxamate 1025 was prepared following General Method C, the pure product was isolated as a white solid. Yield=45.3%. MS (ESI) m/e ($M+H^+$) 720.3.

Example 35-1

Synthesis of Compound 1026

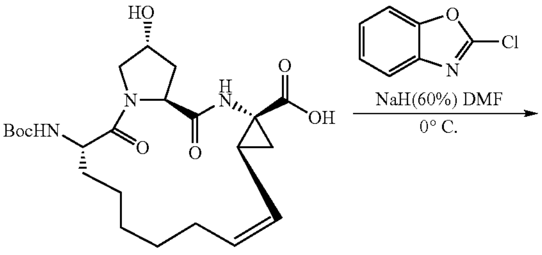

2

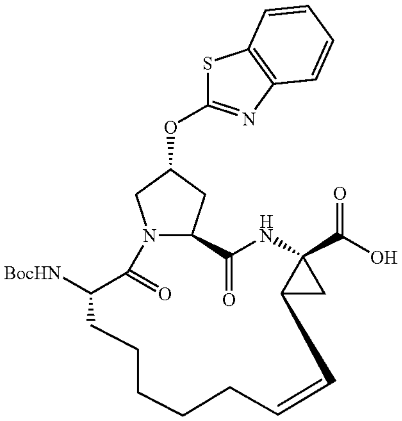

1026

The acid 1026 was prepared following General Method A, oxazole chloride was used in place of thiazole chloride. The isolated yield of the acid 1026 was 16%, MS (ESI) m/e (M+H+) 583.3.

Example 35-2

Synthesis of Compound 1027

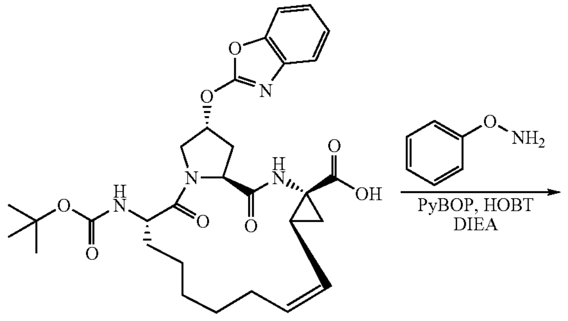

1026

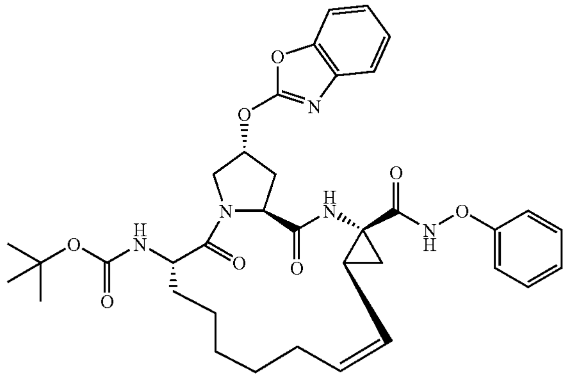

1027

The hydroxamate 1027 was prepared following General Method C, the pure product was isolated as a white solid. Yield=44.3%. MS (ESI) m/e (M+H+) 674.3.

Example 36-1

Synthesis of Compound 1028

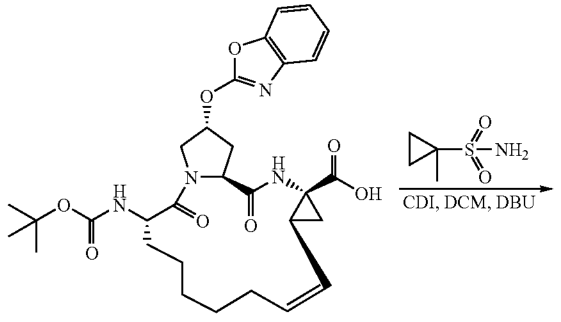

1026

-continued

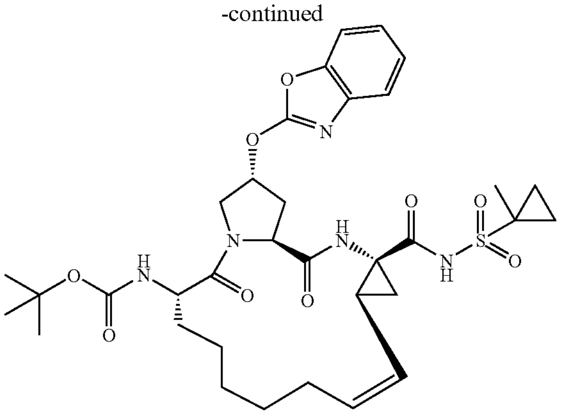

1028

General Method D

To a solution of compound 1026 (100 mg, 0.17 mmol.) in dry DCM (3 mL) was added CDI (55 mg, 0.34 mmol.) at 25° C., the mixture was stirred 1 h at the same temperature. Subsequently, the stirring mixture was treated with methyl-cyclopropanyl sulfonamide (46 mg, 0.34 mmol.) and DBU (0.1 mL, 0.85 mmol.), the resulting mixture was stirred overnight at 25° C. The solvent was removed to afford a residue which was purified by Prep-HPLC to afford 1028 as white solid 50 mg (yield 43%). MS (ESI) m/e (M+H+) 700.3.

Example 36-2

Synthesis of Compound 1029

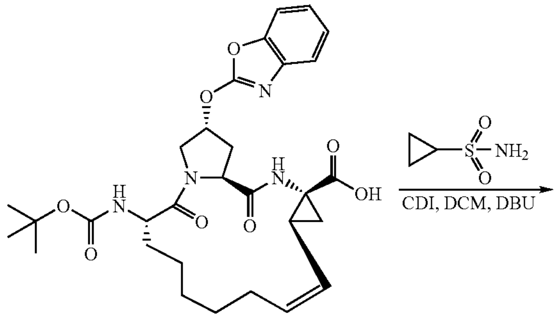

1026

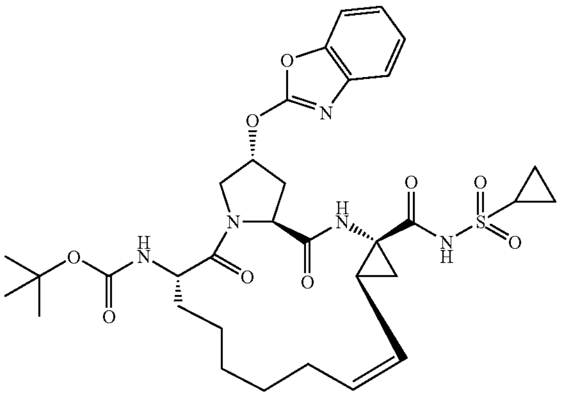

1029

The acylsulfonamide 1029 was prepared following General Method D, the pure product was isolated as a white solid. Yield is 17.3%. MS (ESI) m/e (M+H$^+$) 686.3.

Example 37-1

Synthesis of Compound 2

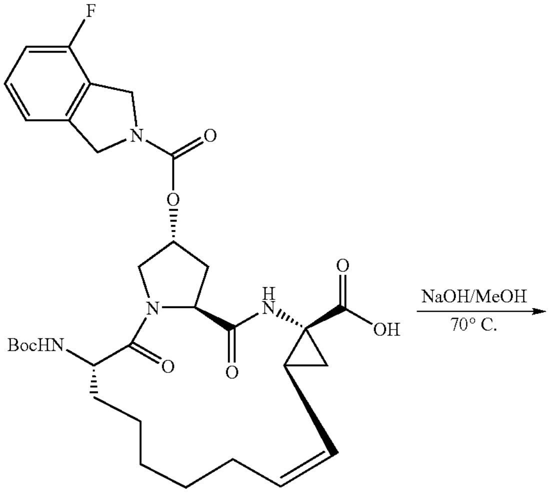

1

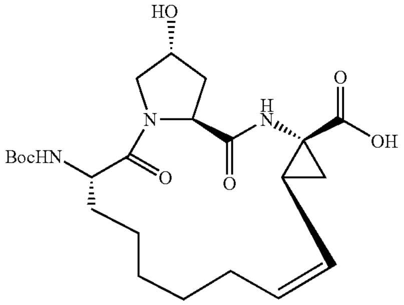

2

General Method E

To a solution of compound 1 (10 g, 15.9 mmol.) in methanol (100 mL) was added 100 mL of aqueous solution of NaOH (20%). The resulted mixture was stirred at 70° C. for 3 h. Concentrated hydrochloric acid was then added slowly at 5-10° C. until the pH was adjusted to 3-4. Methanol was removed under vacuum, and the resulting residue was partitioned between water (100 mL) and ethyl acetate (200 mL). The aqueous layer was extracted with ethyl acetate (3×200 mL). The combined organic layers were washed with brine, dried over $Na_2SO_4$, and concentrated under reduced pressure to afford compound 2, as a brown solid 6.5 g (yield 88%), which was used without further purification.

Preparation of NS3 Inhibitors: Section VIII

Example 39-1

Procedure for the Synthesis of 2-chloro benzoxazoles or 2-chloro benzothiazoles

Scheme XXXI

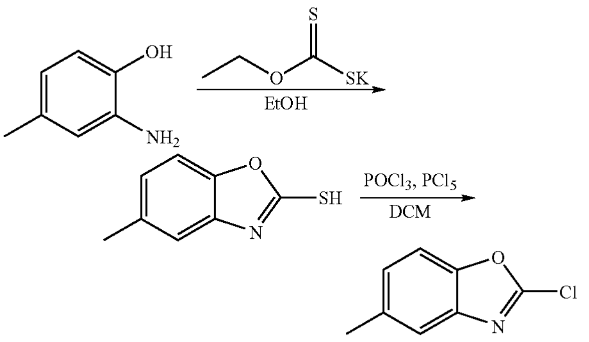

The synthetic intermediate 2-chloro-5-methylbenzo[d]oxazole can be prepared by the method shown in Scheme XXXI. 2-Amino-4-methyl-phenol can be treated with potassium ethyl xanthate in a solvent, such as ethanol, methanol and the like, to afford 5-methylbenzo[d]oxazole-2-thiol. 5-methylbenzo[d]oxazole-2-thiol can be treated with a chlorinating agent, such as $P(O)Cl_3$, $P(O)Cl_3$ with $PCl_5$, and the like, to afford 2-chloro-5-methylbenzo[d]oxazole.

General Procedure for Preparing 2-Thiol Benzoxazole or Benzothiazole Intermediates:

Potassium ethyl xanthate (4.4 g, 27.5 mmol.) was added to solution of 2-amino-4-methyl-phenol (2 g, 16.2 mmol.) in ethanol (40 mL). The reaction mixture was heated at reflux for 4 h then allowed to cool to rt. Upon cooling to rt the mixture was concentrated and the resulting residue was dissolved in water. Acetic acid was added until pH=5 and a white solid precipitated from the solution. The solid was collected by filtration, washed with water and dried to afford 5-methylbenzo[d]oxazole-2-thiol as a powder (2.4 g, 92.3%) which was used without further purification. MS (ESI) m/e (M+H$^+$) 166.

General Procedure for Preparing 2-Chloro Benzoxazole or Benzothiazole Intermediates:

To a suspension of 5-methylbenzo[d]oxazole-2-thiol (1.0 g, 6.1 mmol.) in $POCl_3$ (11.7 g, 76.4 mmol.) at room temperature was added $PCl_5$ (1.9 g, 9.15 mmol.) along with $CH_2Cl_2$ (10 mL). After 4 h of stirring at room temperature, the reaction mixture was concentrated to remove excess $POCl_3$, and the residue was treated with $Na_2CO_3$ solution until ~pH 8 was reached. The aqueous phase was extracted with $CH_2Cl_2$. The combined organic extracts were dried over $Na_2SO_4$, filtered and concentrated to afford 2-chloro-5-methylbenzo[d]oxazole (1.1 g crude product) which was used without further purification. MS (ESI) m/e (M+H$^+$) 168.

The following 2-chloro benzoxazole or 2-chloro benzothiazole intermediates were prepared following the same experimental procedure for making 2-chloro-5-methylbenzo[d]oxazole.

Example 40-1

Synthesis of Compound 1030

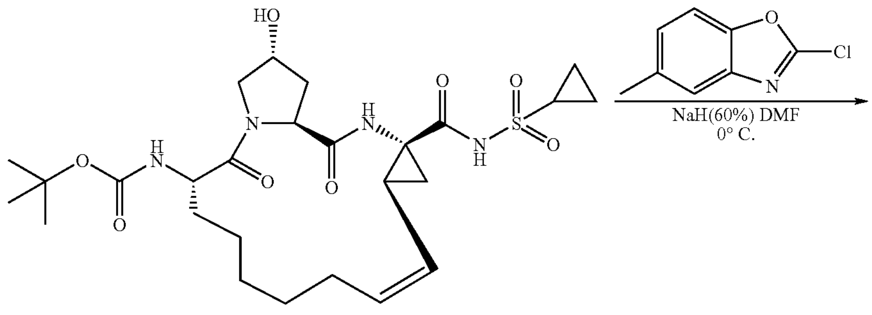

11

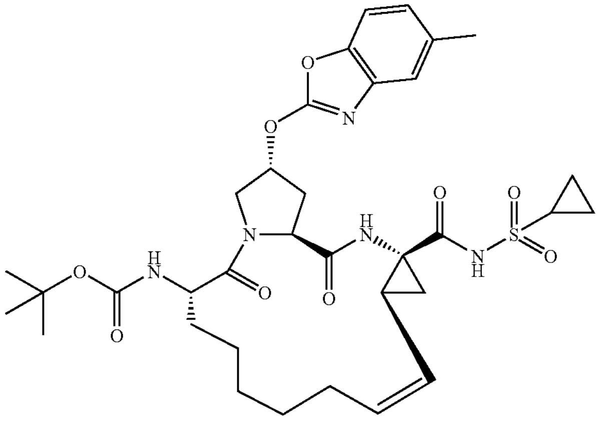

1030

General Method O

To a solution of compound 11 (100 mg, 0.176 mmol.) in 3 mL of dry DMF was added sodium hydride (42 mg, 10.3 mmol.) at 0° C. The resulting mixture was stirred at this temperature for 1 h before the addition of 2-chloro-5-methylbenzooxazole, and it was allowed to warm to room temperature slowly and stirred overnight. The reaction was quenched by careful addition of water (15 mL), extracted by ethyl acetate, backwashed with water, dried over $Na_2SO_4$, concentrated to afford a residue, which was purified by Prep-HPLC to give compound 1030 as white solid 5.3 mg (yield 4.3%). $^1H$ NMR (400 MHz, $CDCl_3$) δ 10.23 (bra, 1 H), 7.31 (s, 1 H), 7.20 (d, J=8.4 Hz, 1 H), 7.67 (d, J=7.6 Hz, 1 H), 6.85 (s, 1 H), 5.72 (m, 2 H), 5.67 (s, 1 H), 5.30 (t, J=9.4 Hz, 2 H), 4.65 (d, J=8 Hz, 1 H), 4.23 (t, J=9.2 Hz, 1 H), 4.51 (d, J=12.8 Hz, 1 H), 4.41 (t, J=8 Hz, 1 H), 4.23 (t, J=7.2 Hz, 1 H), 3.60 (d, J=11.6 Hz, 1 H), 2.90-2.95 (m, 1 H), 2.43 (s, 1 H), 1.70 (m, 1 H), 1.18-1.87 (m, 26 H), 1.0 (m, 1H). MS (ESI) m/e (M+H$^+$) 700.

Example 40-2

Synthesis of Compound 1031

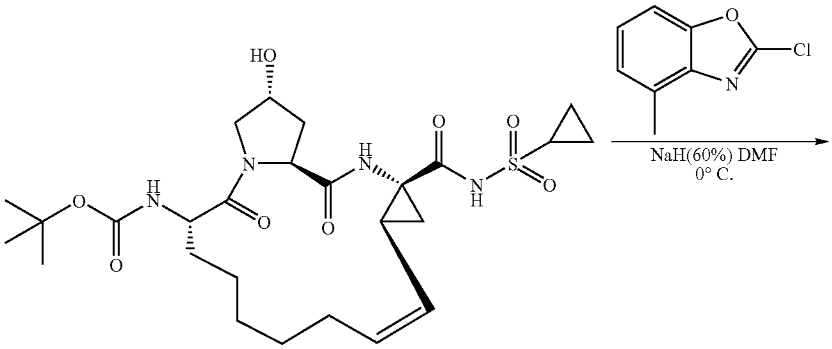

11

-continued
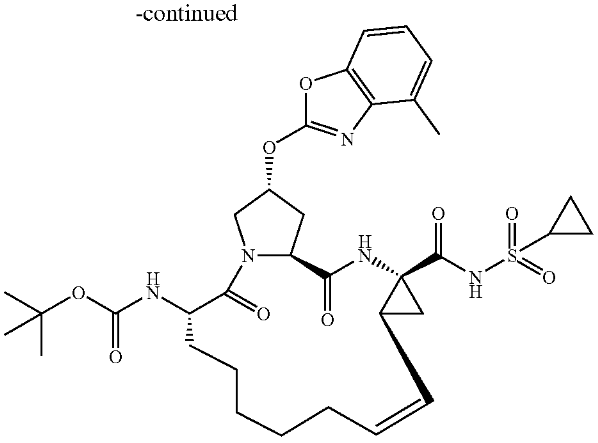
1031
Compound 1031 was prepared following General Method O, and the yield was 2%. MS (ESI) m/e $(M+H^+)$ 700.
Example 40-3
Synthesis of Compound 1032
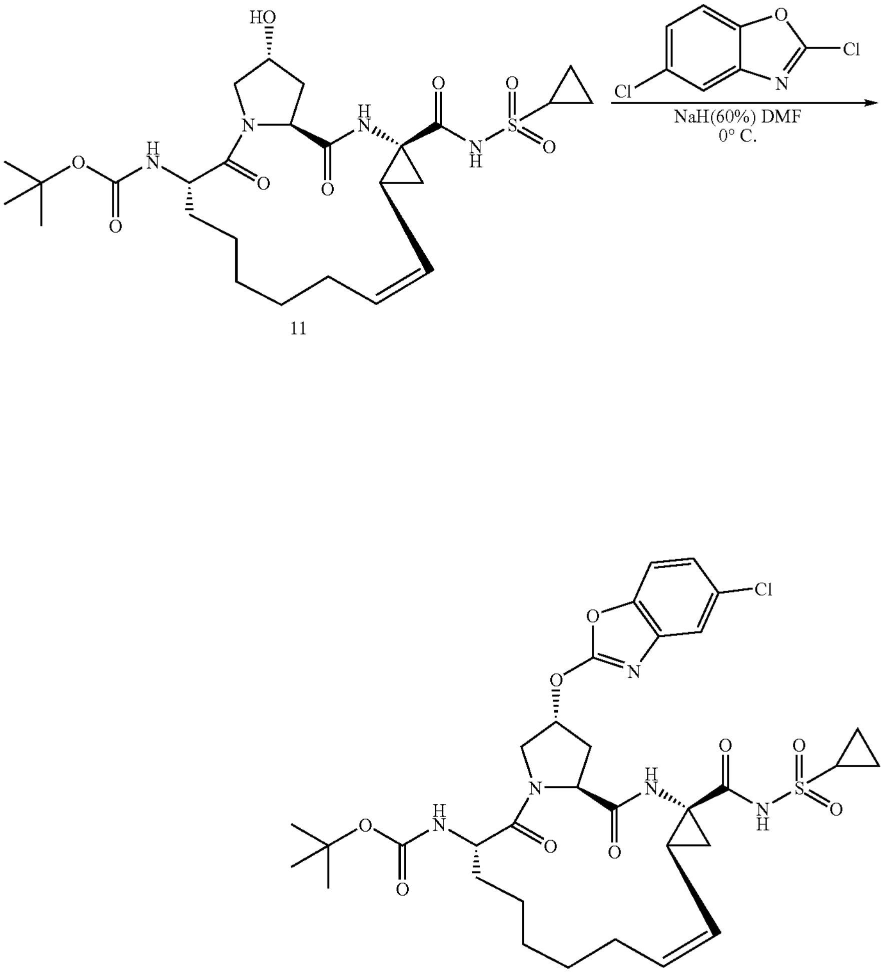
11
1032

Compound 1032 was prepared following General Method O. The pure product was purified by TLC to give white solid, and the yield was 18%. MS (ESI) m/e (M+H+) 720.
Example 40-4
Synthesis of Compound 1033
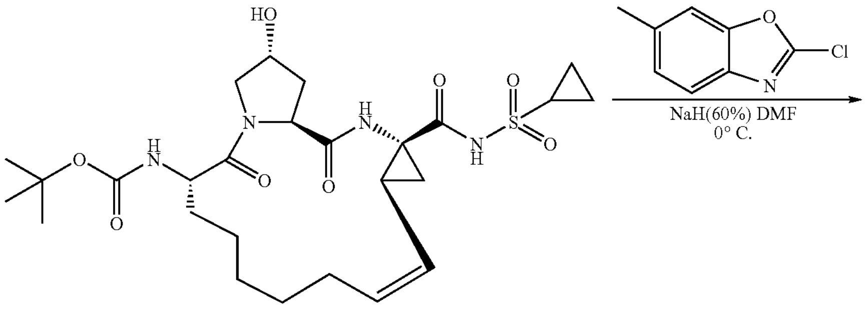
11
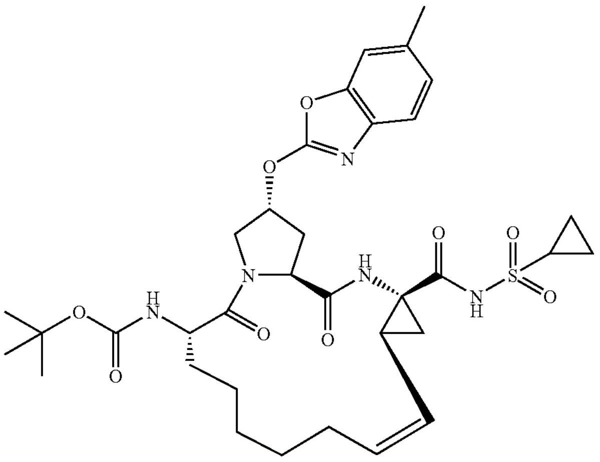
1033
Compound 1033 was prepared following General Method O. The pure product was isolated as a white solid, and the yield was 14%. MS (ESI) m/e (M+H+) 700.
Example 40-5
Synthesis of Compound 1034
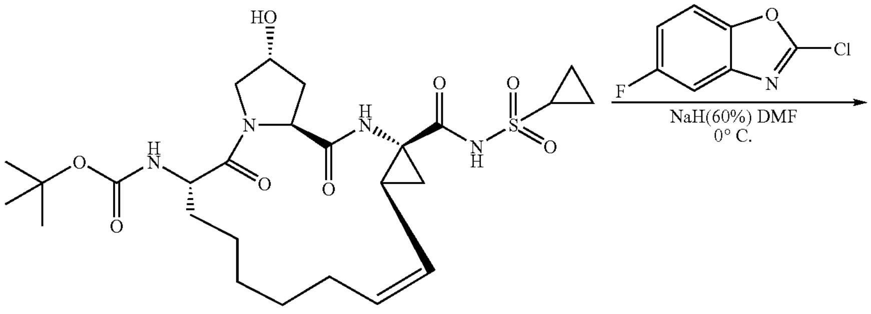
11

-continued
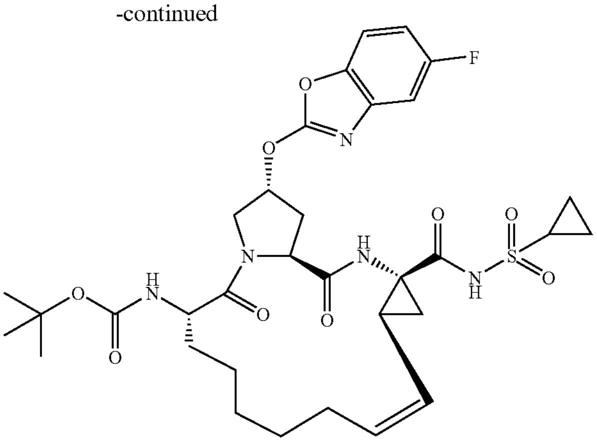
1034
Compound 1034 was prepared following General Method O. The pure product was isolated as a white solid, and the yield was 6%. MS (ESI) m/e (M+H$^+$) 704.
Example 40-6
Synthesis of Compound 1035
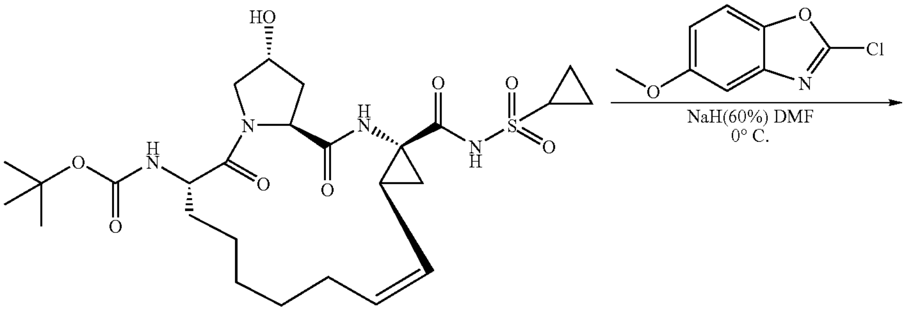
11
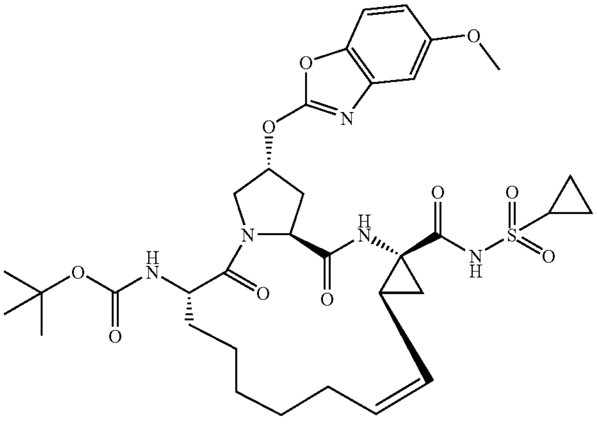
1035

Compound 1035 was prepared following General Method O. The pure product was isolated as a white solid, and the yield was 22%. MS (ESI) m/e (M+H$^+$) 716.
Example 40-7
Synthesis of Compound 1036
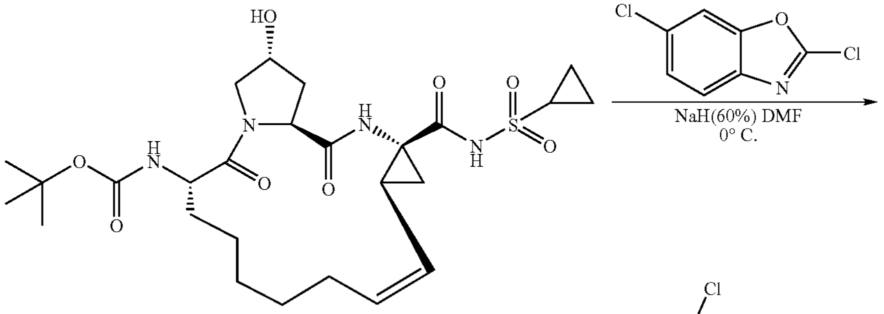
11
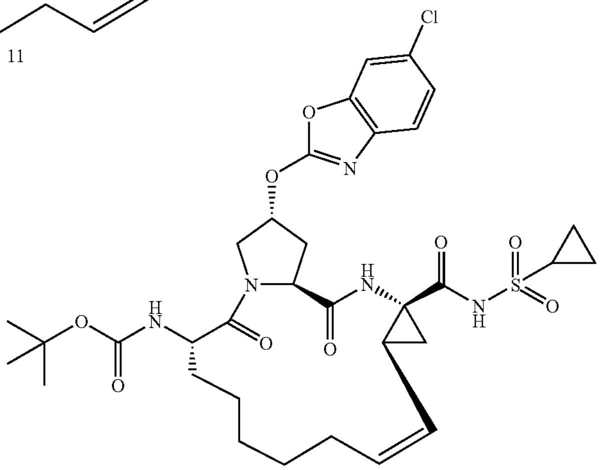
1036
Compound 1036 was prepared following General Method O. The pure product was isolated as a white solid, and the yield was 4%. MS (ESI) m/e (M+H$^+$) 720.
Example 40-8
Synthesis of Compound 1037
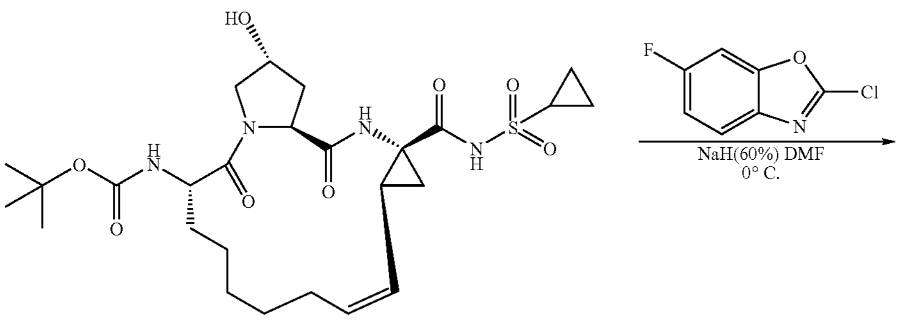
11

-continued
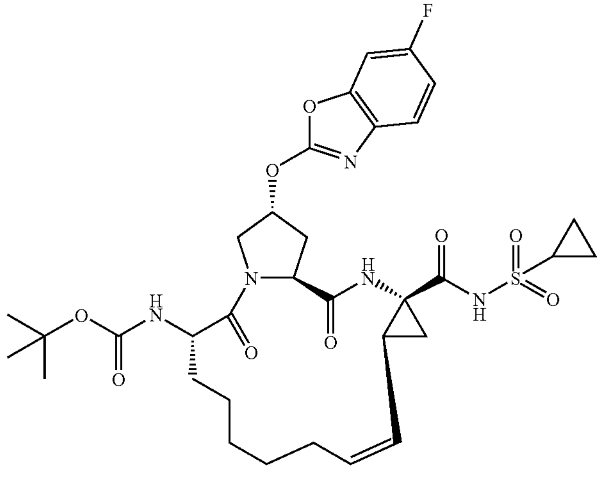
1037
Compound 1037 was prepared following General Method O. The pure product was isolated as a white solid, and the yield was 15%. MS (ESI) m/e (M+H$^+$) 704.
Example 40-9
Synthesis of Compound 1038
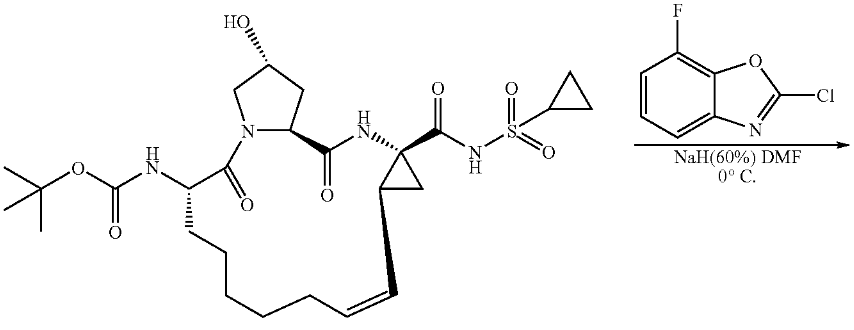
11
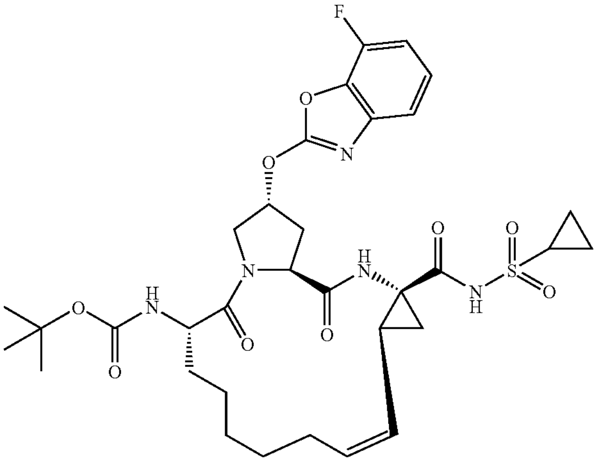
1038

Compound 1038 was prepared following General Method O. The pure product was isolated as a white solid, and the yield was 7%. MS (ESI) m/e (M+H$^+$) 704.
Example 40-10
Synthesis of Compound 1039
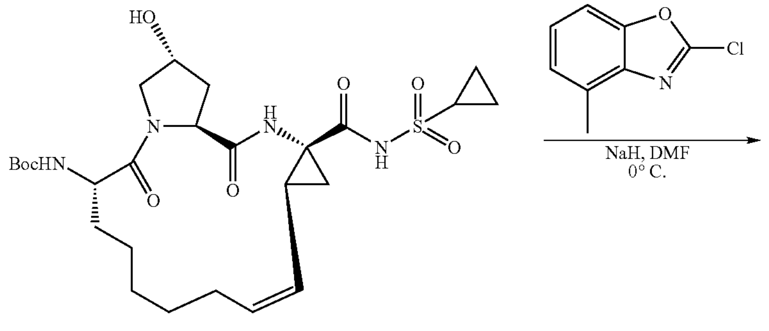
11
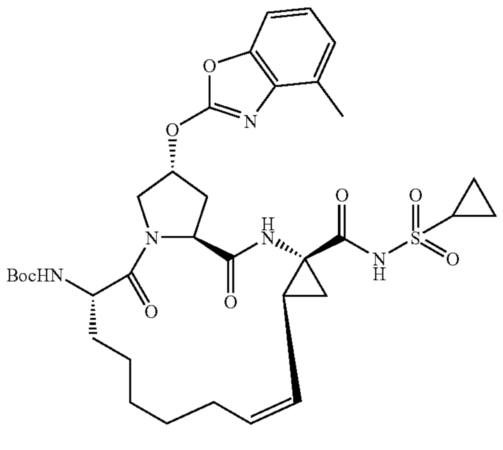
1039
Compound 1039 was prepared following General Method O. The pure product was isolated as a white solid, and the yield was 7%. MS (ESI) m/e (M+H$^+$) 716.
Example 40-11
Synthesis of Compound 1040
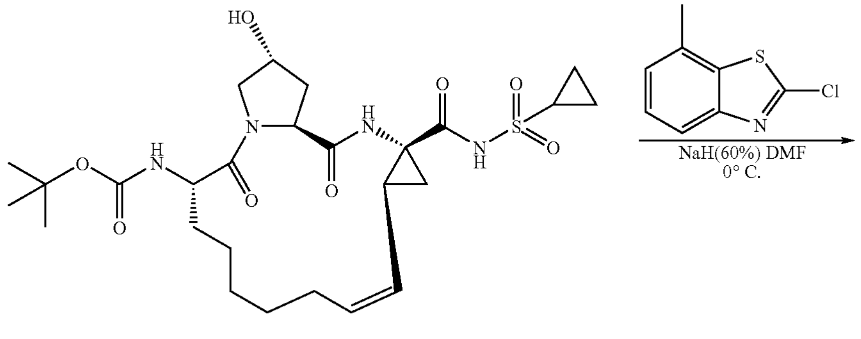
11

-continued
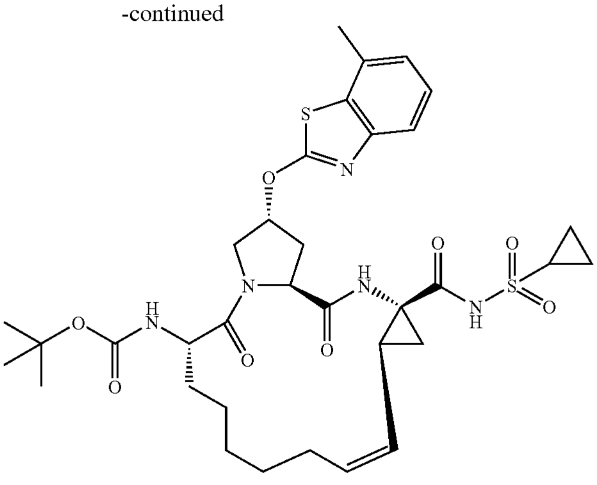
1040
Compound 1040 was prepared following General Method O. The pure product was isolated as a white solid, and the yield was 3%. MS (ESI) m/e (M+H$^+$) 716.
Example 41-1
Synthesis of Compound 1041
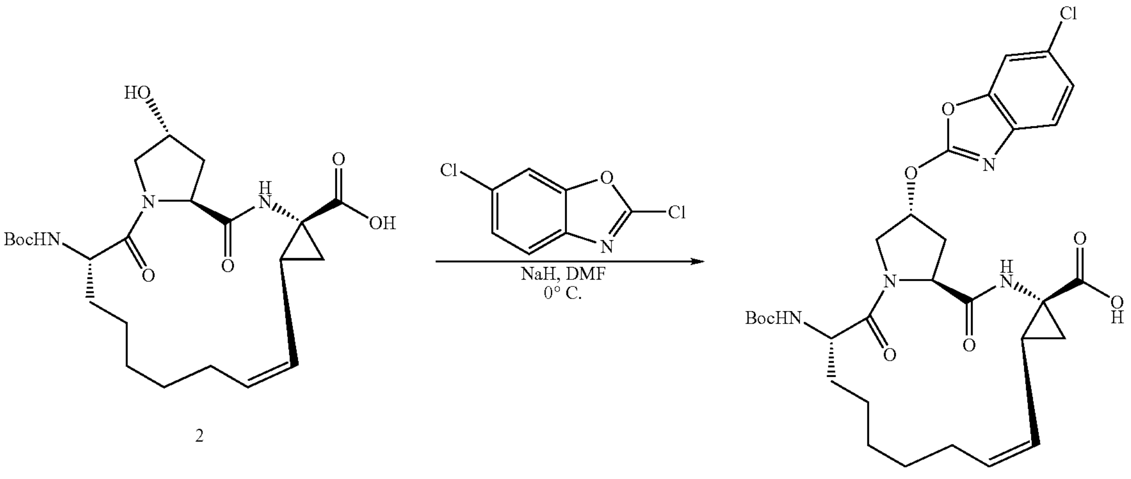
2
1041

General Method P

To a solution of compound 2 (200 mg, 0.35 mmol.) in 3 mL of dry DMF was added sodium hydride (84.5 mg, 2.11 mmol.) at 0° C. The resulting mixture was stirred at this temperature for 1 h before the addition of 2,6-Dichloro-benzoxazole, and it was allowed to warm to room temperature slowly and stirred overnight. The reaction was quenched by careful addition of water (20 mL). The aqueous layer was extracted by ethyl acetate, backwashed with water, dried over $Na_2SO_4$, concentrated to get a residue, which was purified by Prep-HPLC to give compound 1041 as white solid 12.8 mg (yield 6.0%), MS (ESI) m/e ($M+H^+$) 617.

Example 41-2

Synthesis of Compound 1042

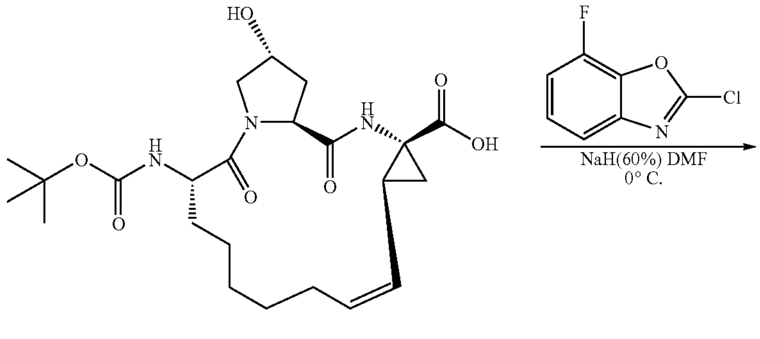

2

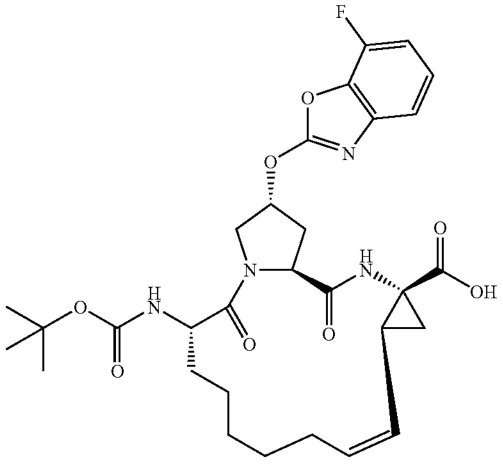

1042

Compound 1042 was prepared following General Method P. The pure product was isolated as a white solid, and the yield was 7%. MS (ESI) m/e (M+H$^+$) 601.
Example 41-3
Synthesis of Compound 1043
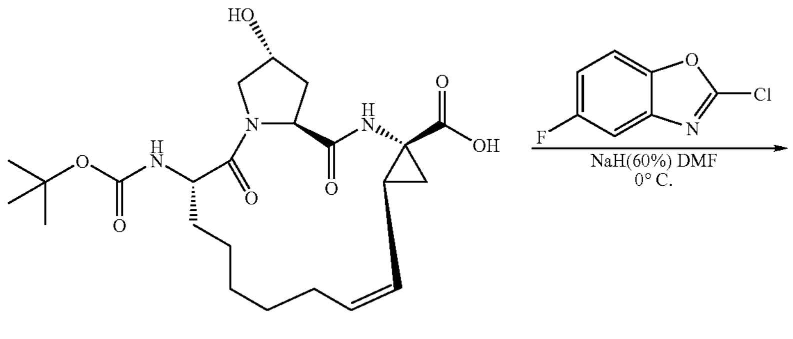
2
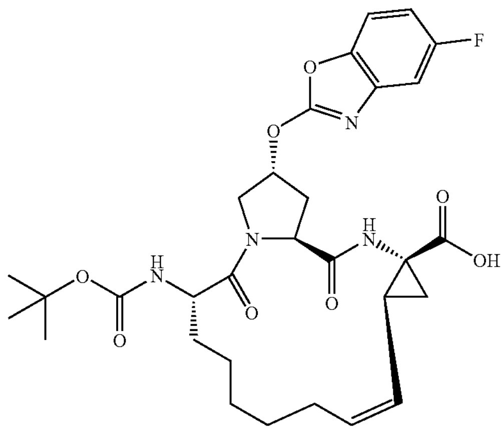
1043
Compound 1043 was prepared following General Method P, and the yield was 6%. MS (ESI) m/e (M+H$^+$) 601.
Example 41-4
Synthesis of Compound 1044
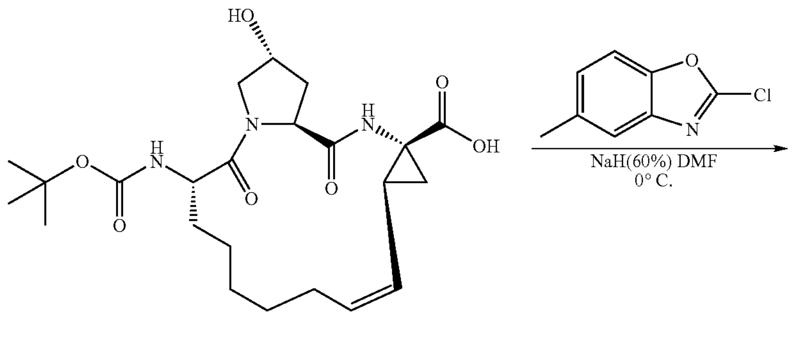
2

-continued
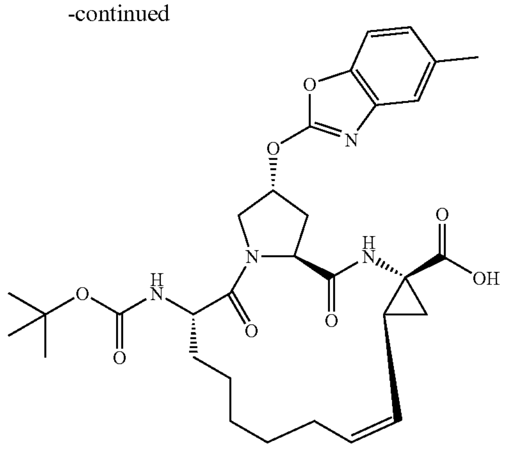
1044
Compound 1044 was prepared following General Method P, and the yield was 8%. MS (ESI) m/e ($M+H^+$) 597.
Example 41-5
Synthesis of Compound 1045
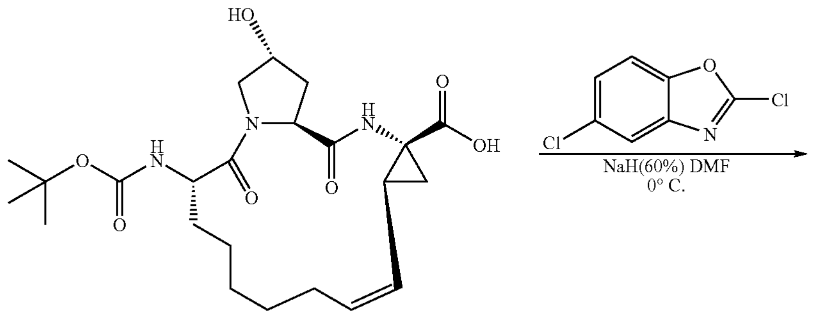
2
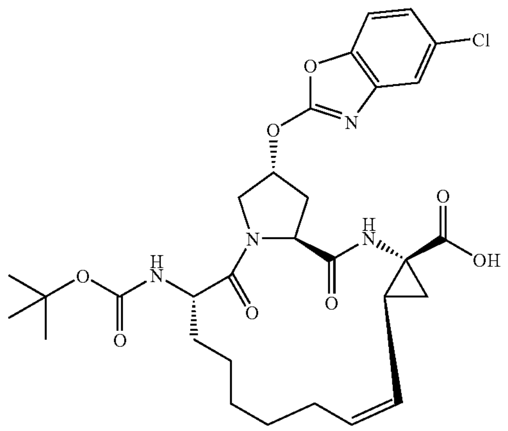
1045

Compound 1045 was prepared following General Method P. The crude product was used in the next step without further purification.

Example 42-1

Synthesis of Compound 1046

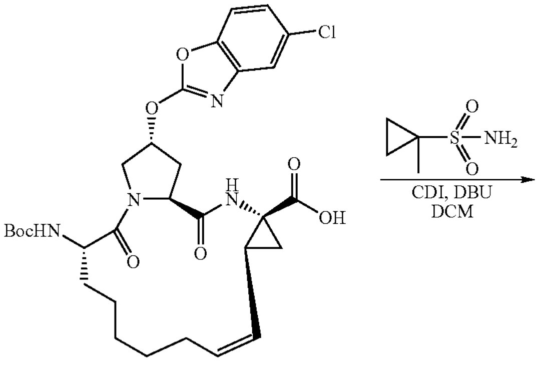

1045

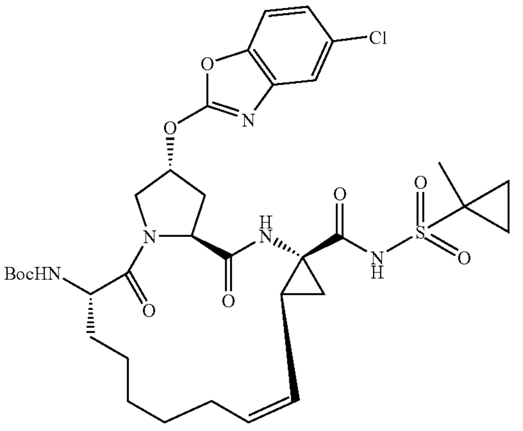

1046

General Method O

To a solution of compound 1045 (120 mg, 0.08 mmol.) which was used without further purification in dry DCM (3 mL) was added CDI (20 mg, 0.16 mmol.) at 25° C. The resulting mixture was stirred at same temperature for 1 h before the addition of methylcyclopropanyl sulfonamide (21.6 mg, 0.16 mmol.) and DBU (0.12 mL, 0.8 mmol.). The resulting mixture was stirred overnight at 25° C. then concentrated to get a residue, which was purified by Prep-HPLC to afford compound 1046 as white solid 7 mg (yield 3%). MS (ESI) m/e (M+H+) 734.2.

Example 43-1

Synthesis of Compound 1047

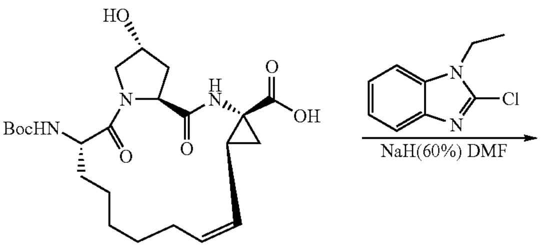

2

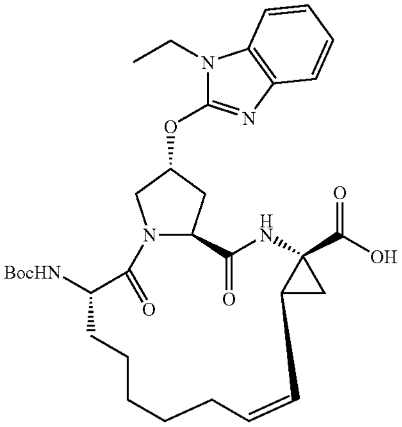

1047

General Method R

To a solution of compound 2 (300 mg, 0.65 mmol.) in 10 mL of dry DMF was added sodium hydride (155 mg 3.87 mmol.) at 0° C. The resulting mixture was stirred at this temperature for 1 h before the addition of 2-chloro-N-ethyl-benzoimdiazole (234 mg, 13 mmol.), and it was allowed to warm to room temperature slowly with ice bath and stir overnight. The reaction was quenched by adding methanol (10 mL) and water (30 mL). The resulting solution was stirred for 15 min, extract by ethyl acetate, washed with brine, dried over $Na_2SO_4$, concentrated to get a residue, which was purified by Prep-TLC to give compound 1047 as white solid 130 mg (yield 33%). MS (ESI) m/e $(M+H^+)$ 609.3.

Example 43-2

Synthesis of Compound 1048

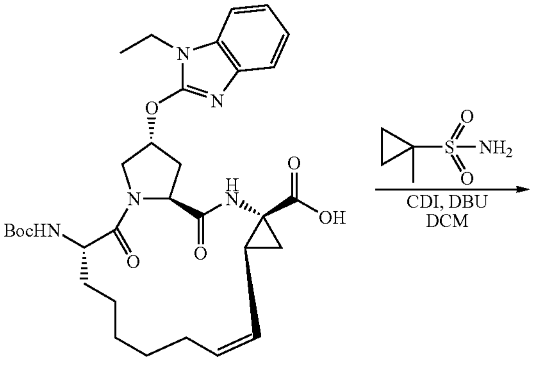

1047

-continued

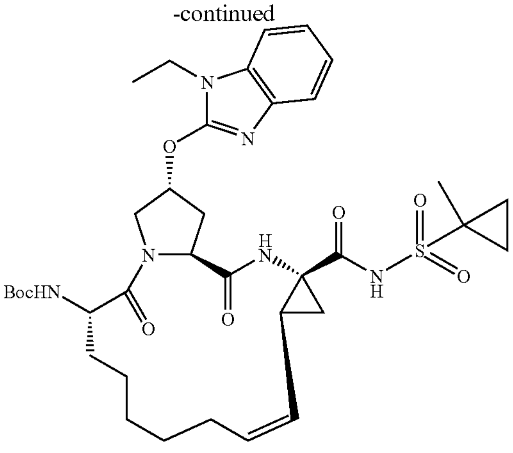

1048

General Method S

To a solution of compound 1047 (100 mg, 0.16 mmol.) in 3 mL of dry DCM was added CDI (54 mg, 0.32 mmol.) at 25° C. The resulting mixture was stirred at the same temperature for 1 h before the addition of methylcyclopropanyl sulfonamide (43 mg, 0.32 mmol.) and DBU (0.1 mL, 0.85 mmol.). The resulting mixture was stirred overnight at 25° C. The solvent was removed to afford residue. The residue was dissolved in ethyl acetate (20 mL), washed with 1N HCl, then aq. sat. $NaHCO_3$ and brine. The organic layer was dried over $Na_2SO_4$, filtered and concentrated to afford a residue. The crude residue was purified by Prep-TLC to afford 1048 as white solid 40 mg (yield 35%). MS (ESI) m/e $(M+H^+)$ 726.9.

Example 43-3

Synthesis of Compound 1049

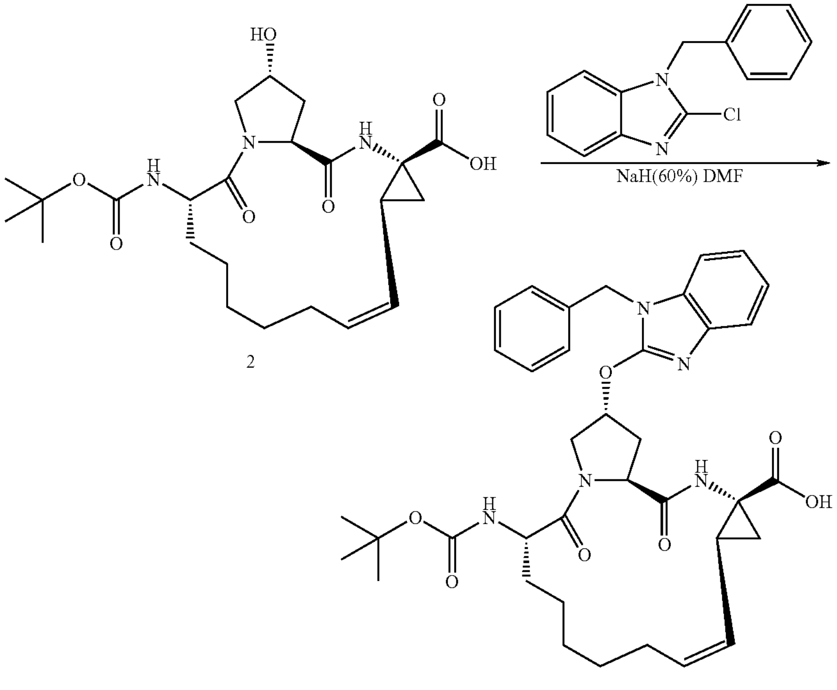

2

1049

Compound 1049 was prepared following General Method R, and the yield is 53%. MS (ESI) m/e (M+H$^+$) 671.3.

Example 43-4

Synthesis of Compound 1050

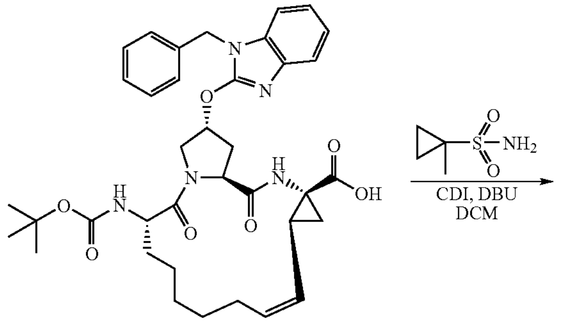

1049

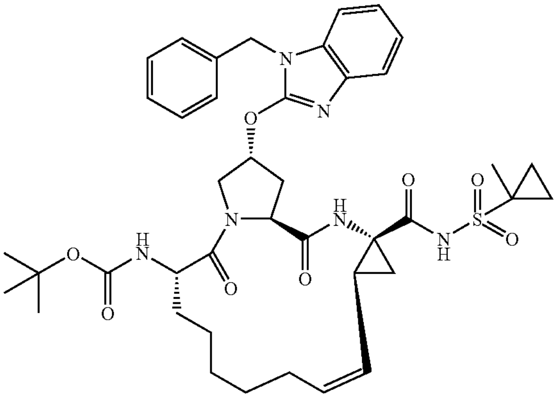

1050

Compound 1050 was prepared following General Method S, and the yield is 53%. MS (ESI) m/e (M+H$^+$) 789.0.

Example 43-5

Synthesis of Compound 1051

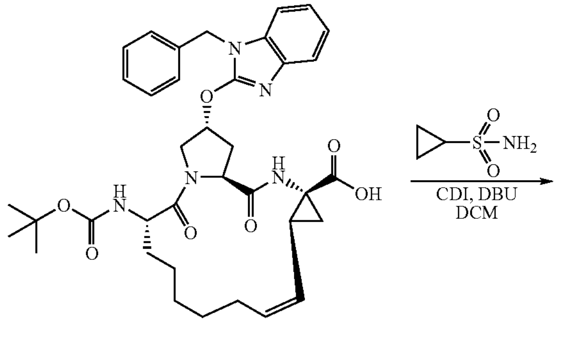

1049

-continued

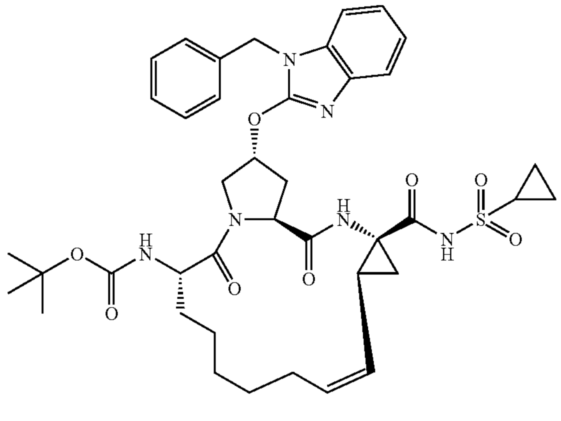

1051

Compound 1051 was prepared following General Method S, and the yield is 53%. MS (ESI) m/e (M+H$^+$) 774.3.

Example 43-6

Synthesis of 1080

1080

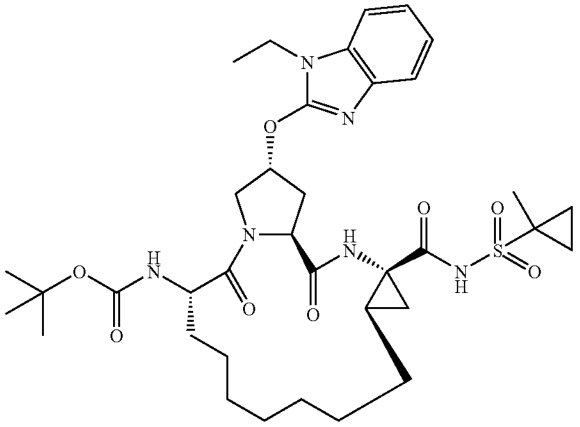

General Method XAX

To a solution of compound 1048 in ethyl acetate was added 5% Rh/$Al_2O_3$ (10 mol %). The reaction mixture was stirred at room temperature under 1 atm $H_2$ for 16 h. The reaction mixture was filtered, concentrated and purified by prep-HPLC to afford compound 1080 36 mg, (26% yield). MS (ESI) m/z $(M+H)^+$ 729.3.

Example 43-7

1081

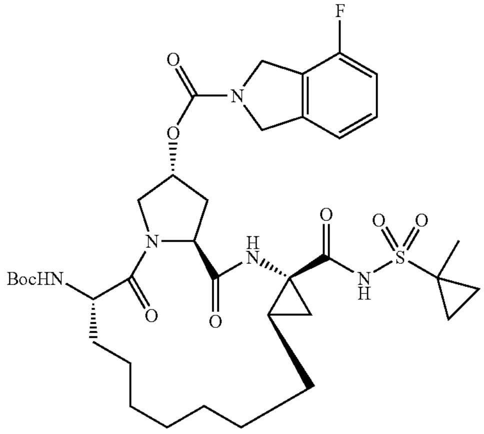

Compound 1081 was prepared in a manner analogous to General Method XAX to afford 170 mg (33% yield). MS (ESI) m/z $(M+H)^+$ 748.3.

Preparation of NS3 Inhibitors: Section IX

Example 44-1

1082

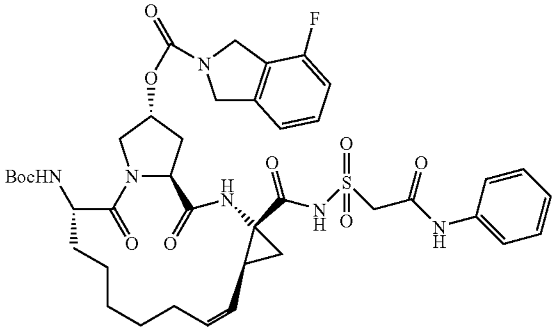

Compound 1082 was prepared in a manner analogous to General Method S, to afford 43.9 mg, 42%. MS (ESI) m/z $(M+H)^+$ 847.

Example 44-2

1083

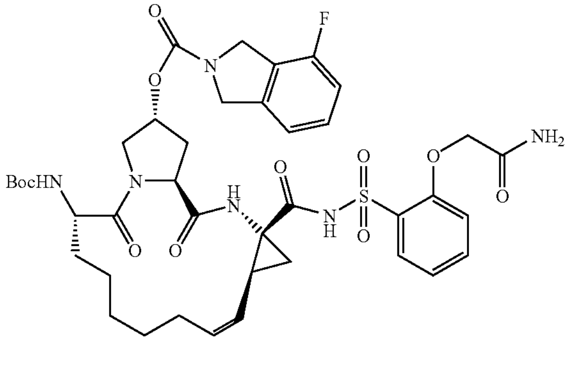

Compound 1083 was prepared in a manner analogous to General Method S, to afford 20 mg, 13%. MS (ESI) m/z $(M+H)^+$ 841.1.

Example 44-3

1084

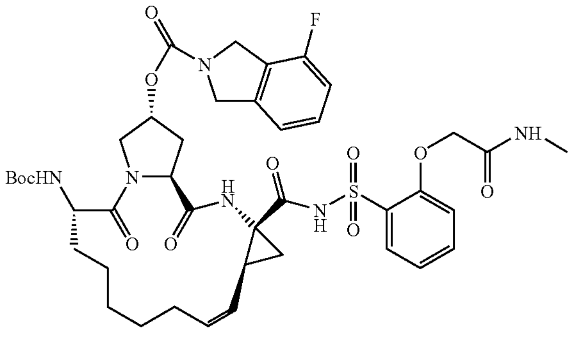

Compound 1084 was prepared in a manner analogous to General Method S, to afford 14.7 mg, 16%. MS (ESI) m/z $(M+H)^+$ 855.2.

Example 44-5

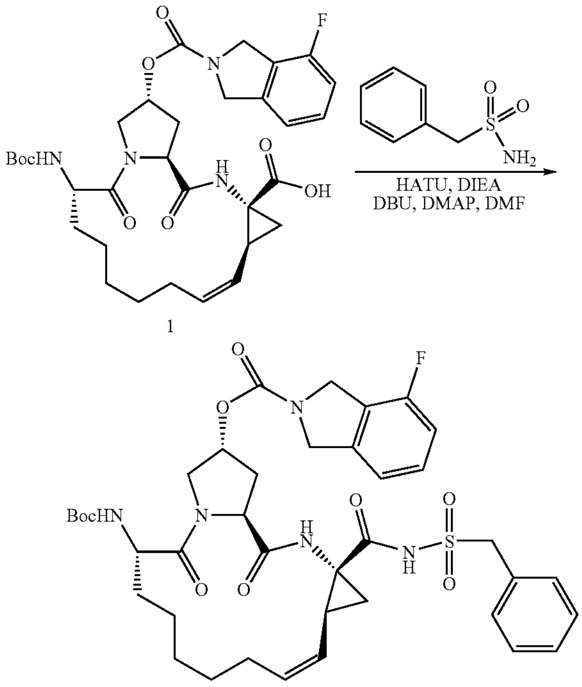

1

1086

General Method XBX

A solution of compound 1 (200 mg, 0.32 mmol.), HATU (182 mg, 0.48 mmol.) and DIEA (0.22 mL, 1.28 mmol.) in dry DMF was stirred for 1 h before the addition of a solution of benzylsulfonamide (200 mg, 1.28 mmol.), DMAP (156 mg, 1.28 mmol.), and DBU (0.19 mL, 1.28 mmol.) in dry DMF (1.5 mL). The mixture was stirred overnight. Then the mixture was diluted with brine and Ethyl acetate, the organic layers was separated, dried over anhydrous sodium sulfate, the residue was purified by prep-TLC to give compound 1086 (35.1 mg, 14%). MS (ESI) m/z $(M+H)^+$ 782.

Example 44-6

Scheme XXXII: Synthesis of Benzimidazole-dimethylsulfonamide Compounds

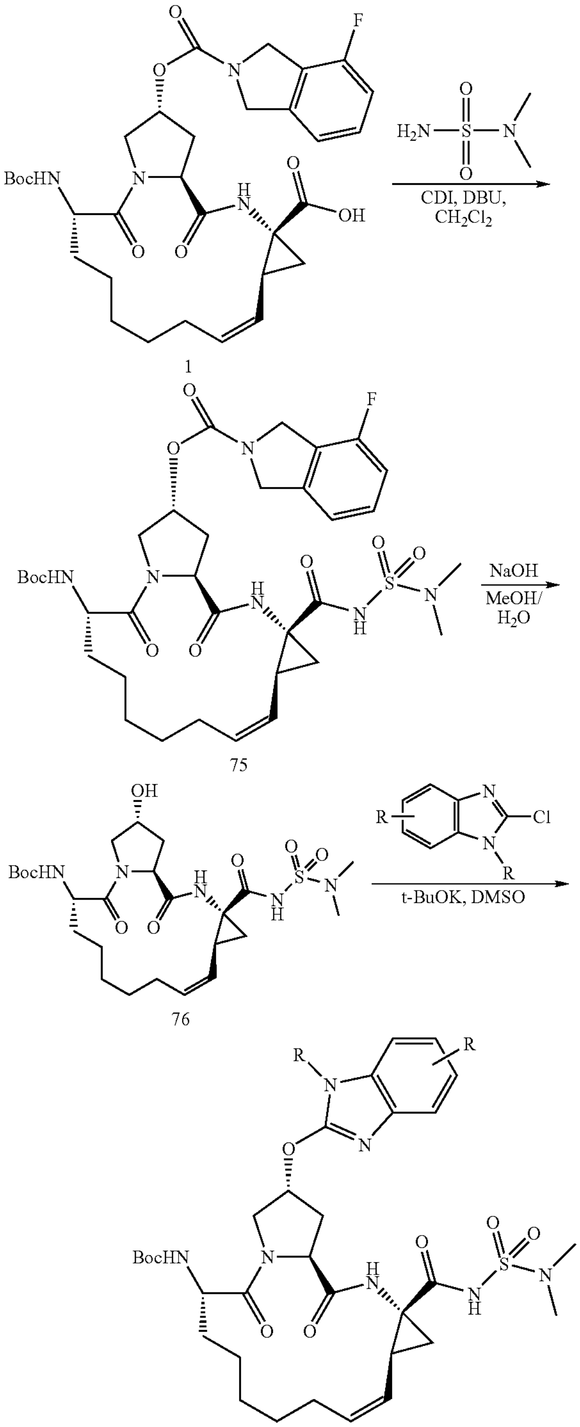

1, 75, 76, XVIII-A

Macrocycles of general structures XVIII-A can be synthesized according to the method of Scheme XXXII. Compound 1 can be coupled with dimethylsulfamide to afford compound 75. For example, the coupling reagents can be CDI, DCC, DIC, EDAC, HOSu, HOBt, HOAt, PyBOP, PyBrOP, HBTU, HATU, TBTU, combinations thereof, and the like. Subsequently, compound 75 can be treated under basic conditions to hydrolyse the isoindoline carbamate thereby providing alcohol 76. The alcohol, compound 76, can be reacted with an optionally substituted benzimidazole under basic conditions to afford a compound of general structure XVIII-A. For example, the base can be sodium hydride, potassium hydride, lithium hydride, cesium carbonate, sodium carbonate, potassium carbonate, potassium tert-butoxide, and the like.

Example 44-7

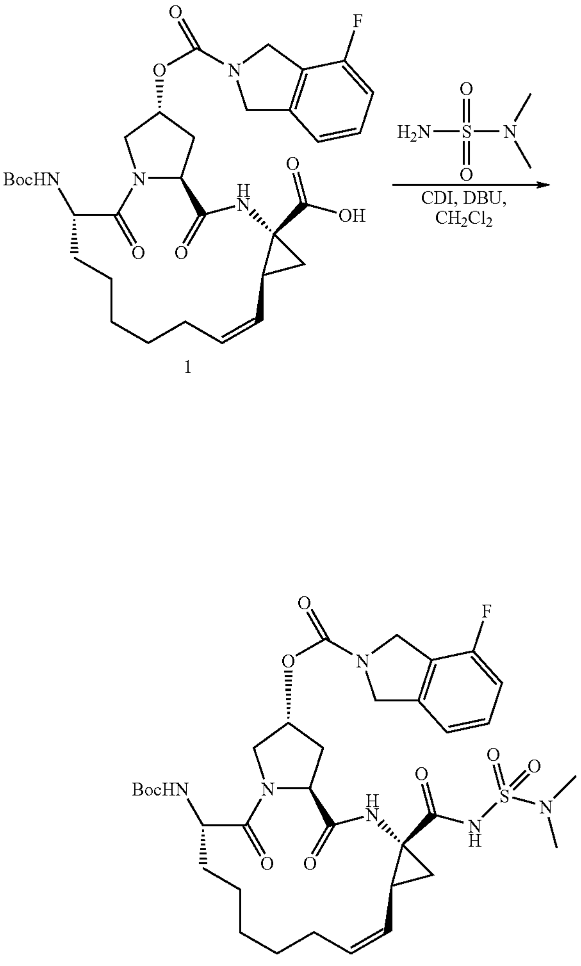

1

75

To a solution of compound 1 (1.5 g, 2.38 mmol.) in anhydrous dichloromethane was added CDI (1.56 g, 9.5 mmol.) under nitrogen protection. The resulting mixture was stirred at 35° C. for 2 h, then dimethylsulfamide (0.44 g, 3.57 mmol.) and DBU (2.89 g, 19.04 mmol.) was added, the resulting mixture was stirred at room temperature for another 12 h and the reaction was monitored by LC-MS. After completion of the reaction, the solvent was removed under reduced pressure. Then the residue was diluted with brine and Ethyl acetate, the organic layers was separated, dried over anhydrous sodium sulfate, filtered and concentrated to afford compound 75 (0.94 g, 55%).

Example 44-8

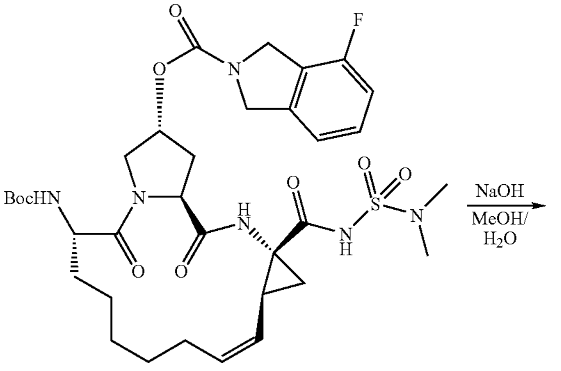

75

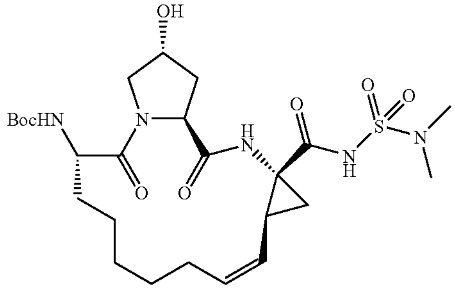

76

To a solution of compound 75 (1.4 g, 1.9 mmol) in 100 mL of methanol was added aq. NaOH (5 M, 11 mL), the resulting mixture was heated to 50° C. and stirred overnight, The reaction was monitored by LCMS. After completion of the reaction, the mixture was cooled by ice water, acidified by aq. HCl (2 M) to pH=4-5, then the mixture was extracted by ethyl acetate (50 mL×3), the organic layers were combined, washed by brine, dried over anhydrous sodium sulfate, the solvent was removed under reduced pressure, the crude compound 76 was used directly in the next step (0.89 g, 82%).

Example 44-9

General Procedure FFF

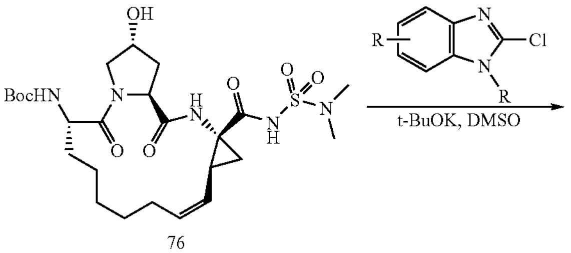

76

-continued

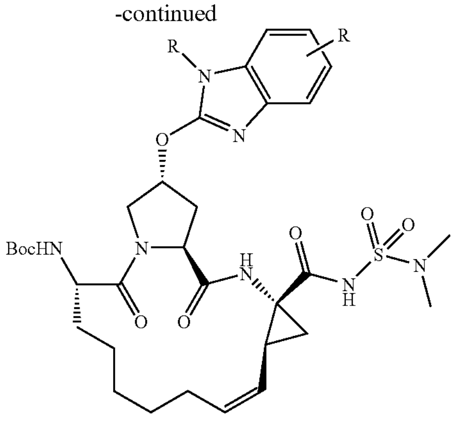

XVIII-A

To a solution of compound 76 (1.0 eq.) in 2 mL of DMSO was added t-BuOK (5 eq.) in portions at ambient temperature, then the mixture was stirred for 2 h at ambient temperature. After that, substituted 2-chlorobenzimidazole (1.2 eq.) was added, the resulting mixture was stirred at ambient temperature for 12 h, the reaction was monitored by LC-MS. After completion of the reaction, the mixture was cooled by ice water, acidified by aq. HCl (2 M) to pH=~8, then the mixture was extracted by ethyl acetate, the organic layers were combined, washed by brine, dried over anhydrous sodium sulfate, solvent was removed under reduced pressure, the crude product was purified by prep-HPLC to afford general compound XVIII-A.

Example 44-10

1129

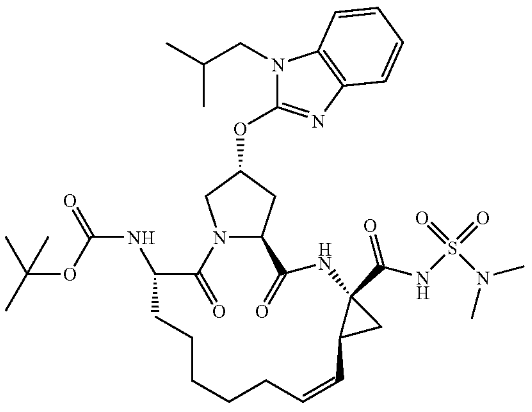

Compound 1129 was prepared in a manner analogous to General Procedure FFF, to afford 5.2 mg (8%). MS (ESI) m/z $(M+H)^+$ 744.4.

Example 44-11

1130

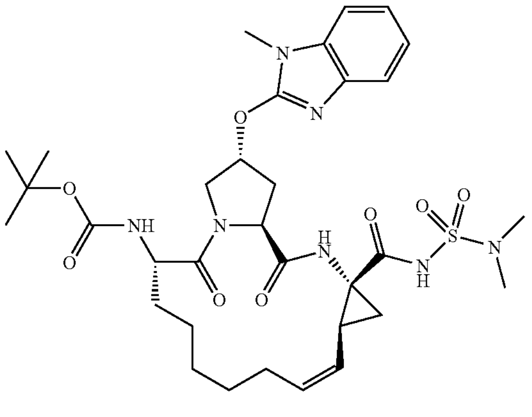

Compound 1130 was prepared in a manner analogous to General Procedure FFF, to afford 57.1 mg (23.3%). MS (ESI) m/z $(M+H)^+$ 701.9.

Example 44-12

1131

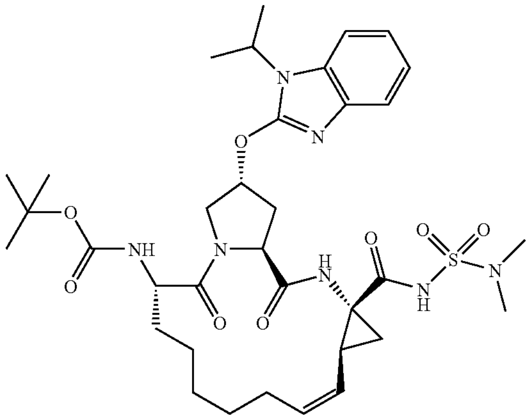

Compound 1131 was prepared in a manner analogous to General Procedure FFF, to afford 52.8 mg (20.7%). MS (ESI) m/z $(M+H)^+$ 730.5.

Example 44-13

1132

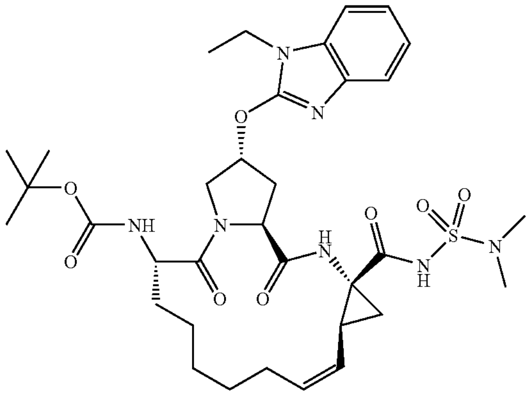

Compound 1132 was prepared in a manner analogous to General Procedure FFF, to afford 52.3 mg (38.0%). MS (ESI) m/z $(M+H)^+$ 716.5.

Example 44-14

1133

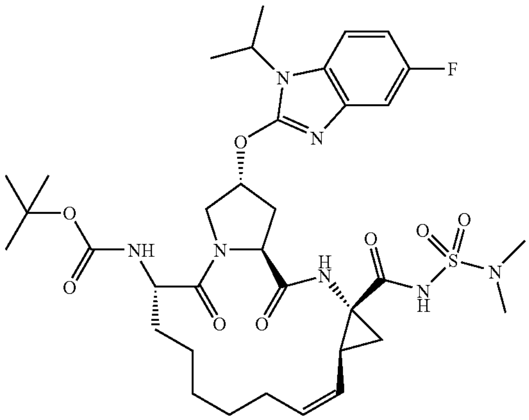

Compound 1111 was prepared in a manner analogous to General Procedure FFF, and the yield is 8%. MS (ESI) m/z $(M+H)^+$ 748.4.

Example 44-15

1134

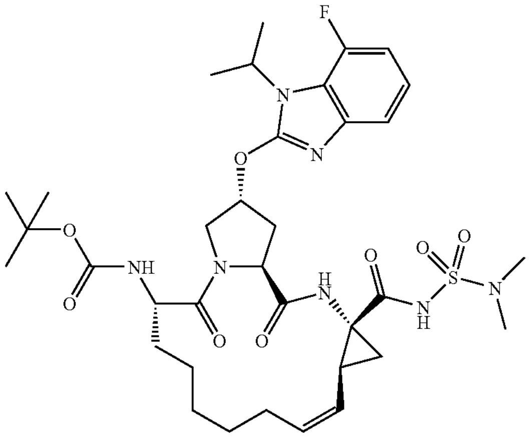

Compound 1134 was prepared in a manner analogous to General Procedure FFF, and the yield is 13.4%. $^1$H NMR (400 MHz, DMSO-$d_6$) δ 10.84 (s, 1H), 9.06 (s, 1 H), 7.37 (d, J=8 Hz, 1 H), 7.21 (s, 1 H), 7.12 (m, 1 H), 6.98 (t, J=8.2 Hz, 1 H), 5.80 (s, 1 H), 5.69 (m, 1 H), 5.14 (t, J=9 Hz, 1 H), 4.71 (m, 1 H), 4.33 (d, J=12 Hz, 1 H), 4.48 (t, J=4 Hz, 2 H), 4.08 (m, 1 H), 3.96 (d, J=4 Hz, 1 H), 2.79 (s, 6 H), 2.73 (s, 1 H), 2.33-2.47 (m, 2 H), 1.78 (m, 2 H), 1.25-1.62 (m, 26 H). MS (ESI) m/z $(M+H)^+$ 748.5.

1135

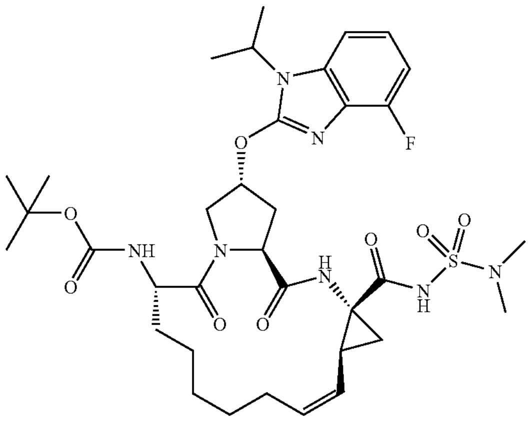

Example 44-16

Compound 1135 was prepared in a manner analogous to General Procedure FFF, and the yield is 8%. $^1H$ NMR (400 MHz, DMSO-$d_6$) δ 10.84 (s, 1 H), 9.06 (s, 1 H), 7.37 (d, J=8 Hz, 1 H), 7.21 (s, 1 H), 7.12 (m, 1 H), 6.98 (t, J=8.2 Hz, 1 H), 5.80 (s, 1H), 5.69 (m, 1 H), 5.14 (t, J=9 Hz, 1 H), 4.71 (m, 1 H), 4.33 (d, J=12 Hz, 1 H), 4.48 (t, J=4 Hz, 2 H), 4.08 (m, 1 H), 3.96 (d, J=4 Hz, 1 H), 2.79 (s, 6 H), 2.73 (s, 1 H), 2.33-2.47 (m, 2 H), 1.78 (m, 2 H), 1.25-1.62 (m, 26 H). MS (ESI) m/z $(M+H)^+$ 748.5.

Example 44-17

1136

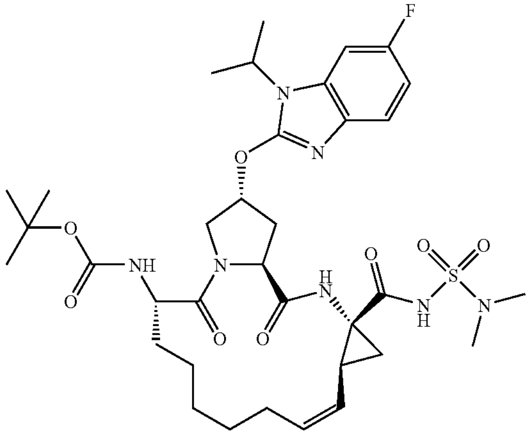

Compound 1136 was prepared in a manner analogous to General Procedure FFF, and the yield is 10%. MS (ESI) m/z $(M+H)^+$ 748.3.

Example 44-18

1137

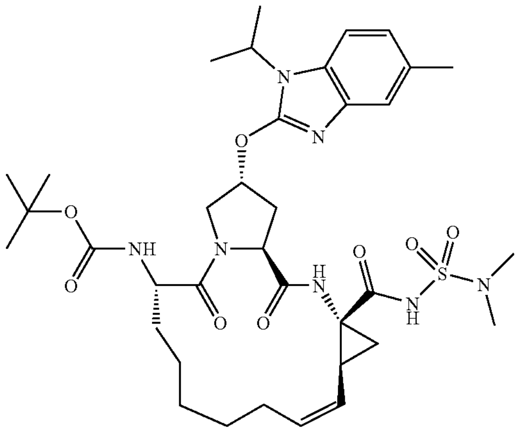

Compound 1137 was prepared in a manner analogous to General Procedure FFF, and the yield is 8.6%. MS (ESI) m/z $(M+H)^+$ 744.3.

Example 44-19

1138

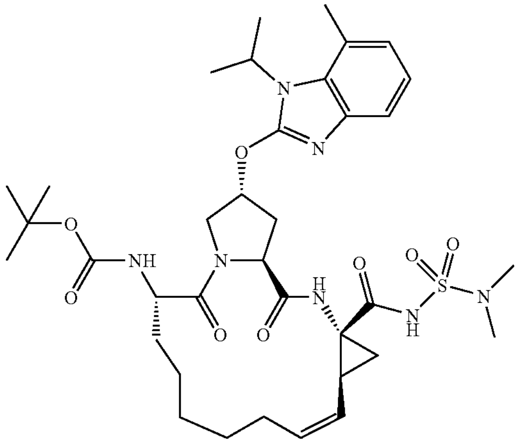

Compound 1138 was prepared in a manner analogous to General Procedure FFF, and the yield is 4.6%. $^1H$ NMR (400 MHz, DMSO-$d_6$) δ 10.80 (s, 1 H), 9.01 (s, 1 H), 7.24 (t, J=7.2 Hz, 1 H), 7.15 (m, 1 H), 6.97 (m, 1 H), 6.83 (d, J=7.2 Hz, 1 H), 5.70 (s, 1 H), 5.60 (m, 1 H), 5.08 (m, 1 H), 5.00 (m, 1 H), 4.51

(d, J=12 Hz, 1 H), 4.01 (m, 1 H), 3.90 (d, J=8 Hz, 1 H), 2.72 (s, 6 H), 2.67 (s, 1 H), 2.58 (s, 1 H), 1.00-1.72 (m, 32 H). MS (ESI) m/z $(M+H)^+$ 744.3.

Example 44-20

1139

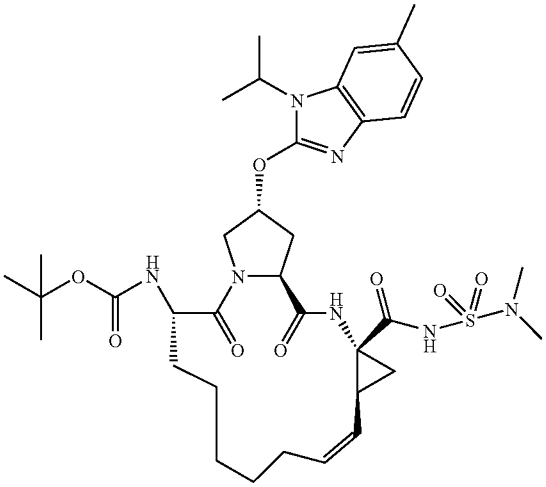

Compound 1139 was prepared in a manner analogous to General Procedure FFF, to afford 20 mg, 26.8%. MS (ESI) m/z $(M+H)^+$ 744.3.

Example 44-21

1140

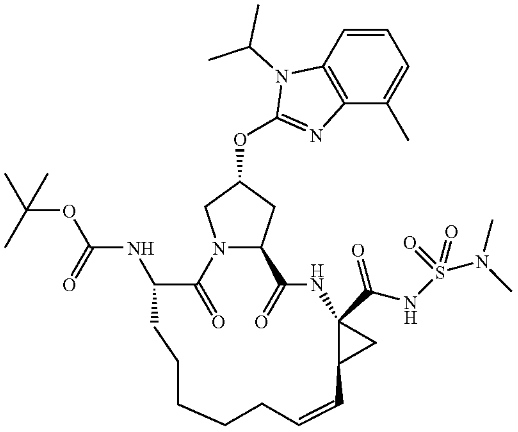

Compound 1140 was prepared in a manner analogous to General Procedure FFF, to afford 20 mg, 27.5%. MS (ESI) m/z $(M+H)^+$ 744.3.

Example 44-22

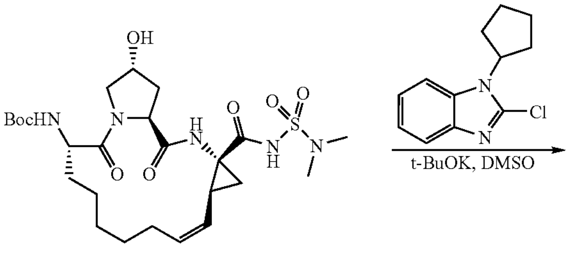

76

-continued

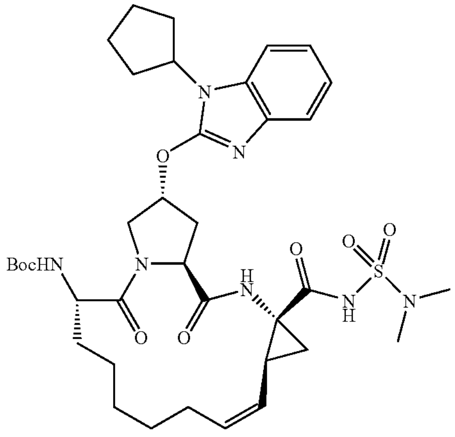

1141

Compound 1141 was prepared in a manner analogous to General Procedure FFF, to afford 64.8 mg, 21%. MS (ESI) m/z $(M+H)^+$ 755.9.

Example 44-23

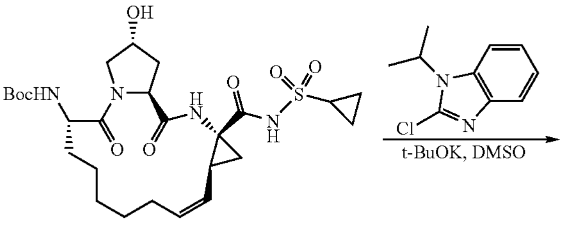

11

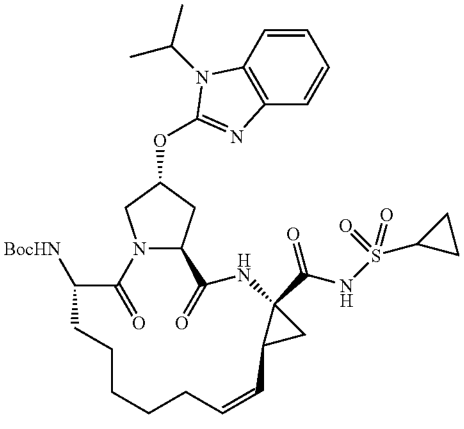

1142

Compound 1142w as prepared in a manner analogous to General Procedure FFF, to afford 60 mg, 21.8%. MS (ESI) m/z $(M+H)^+$ 727.2

Example 44-24

Scheme XXXIII

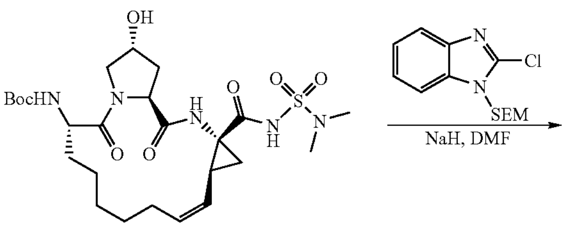

76

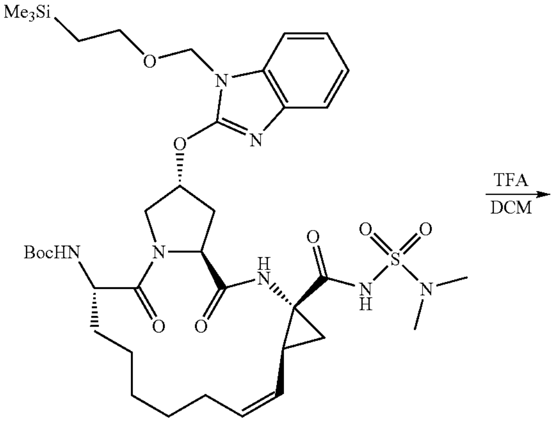

1143

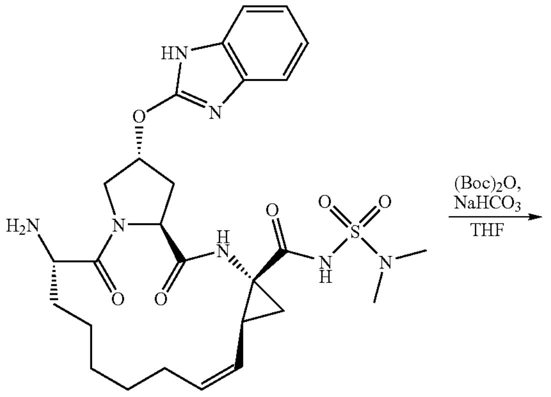

720

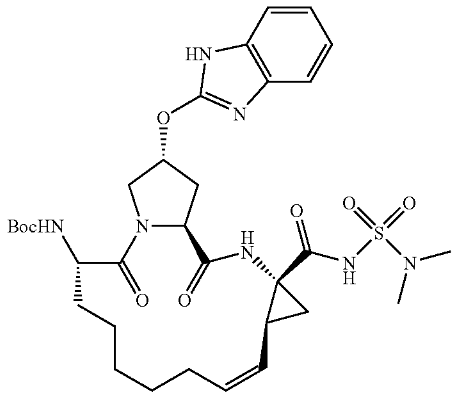

1144

Compound 1144 can be synthesized by the method of Scheme XXXIII. The alcohol, compound 76, can be treated with a base, such as sodium hydride, potassium hydride, lithium hydride, cesium carbonate, sodium carbonate, potassium carbonate, potassium tert-butoxide, and the like, then reacted with 1-((2-(trimethylsilyl)ethoxy)methyl)-2-chloro-1H-benzo[d]imidazole to afford compound 1143. The SEM and Boc groups can be removed under acidic conditions to afford compound 720. For example, the acid can be trifluoroacetic acid, hydrochloric acid, and the like. The Boc group can then be re-introduced by treatment of compound 720 with $(Boc)_2O$ in the presence of a base, such as cesium carbonate, sodium carbonate, potassium carbonate, sodium bicarbonate, potassium bicarbonate, and the like, to afford compound compound 1144.

Example 44-25

Synthesis of Compound 1143

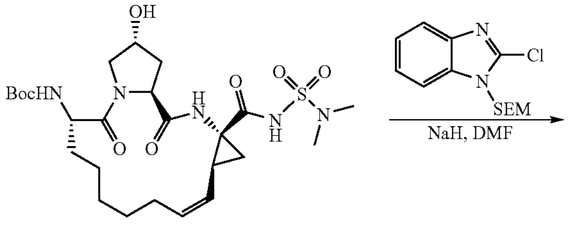

76

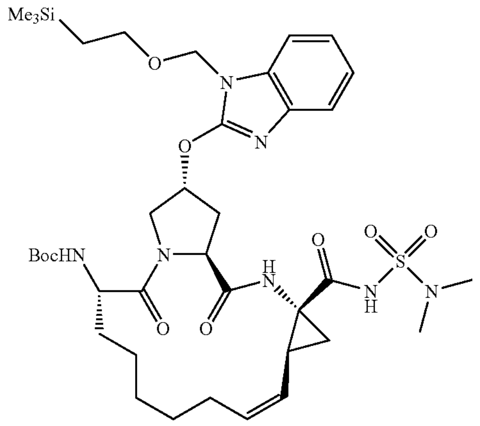

1143

General Method XCX

To a solution of compound 76 (300 mg, 0.515 mmol.) in 3 mL of dry DMF was added sodium hydride (60%, 204 mg, 5.1 mmol.) at 0° C. The resulting mixture was stirred at this temperature for 1 h. Then compound 7 (175 mg, 0.618 mmol.) was added. The reaction mixture was allowed to warm to room temperature and stirred overnight. The reaction was quenched with water and extracted with ethyl acetate (50 mL×3), washed with brine, dried over $Na_2SO_4$, concentrated to give a residue, which was purified by prep-TLC to give compound 1143 as white solid (150 mg, yield 35.2%). MS (ESI) m/z $(M+H)^+$ 818.

Example Example 44-26

Synthesis of Compound 720

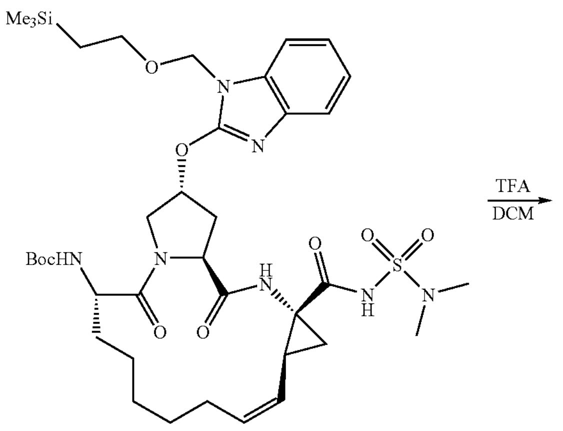

1143

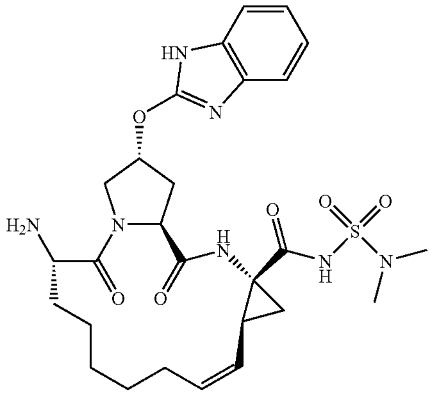

720

To a solution of compound 1143 (60 mg, 0.072 mmol.) in dry DCM (2 mL) was added TFA (1 mL). The reaction mixture was stirred at room temperature for 3 h. LCMS analysis showed the reaction complete. The reaction mixture was concentrated to give crude compound 720 (40 mg, 93%), which was used directly without further purification.

Example 44-27

Synthesis of Compound 1144

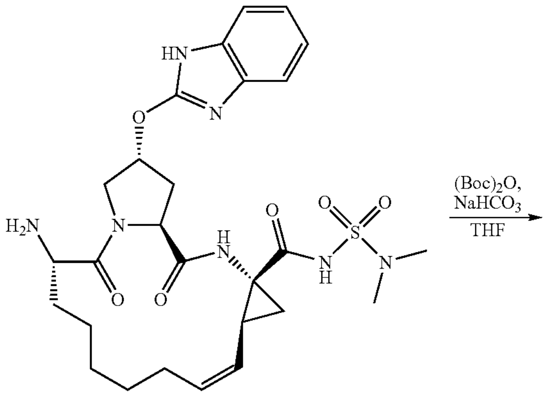

720

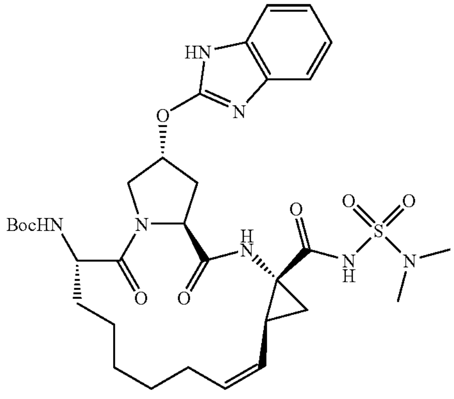

1144

To a solution of compound 720 (40 mg, 0.067 mmol.) in dry THF (2 mL) was added $NaHCO_3$ (16.9 mg, 0.261 mmol.) and followed by adding di-tert-butyl dicarbonate (34.6 mg, 0.201 mmol.). The reaction mixture was stirred at room temperature overnight. LCMS analysis showed the reaction complete. The reaction mixture was quenched with water and extracted with ethyl acetate (30 mL×3). The organic layer was dried over $Na_2SO_4$, concentrated and purified by prep-TLC to give compound 1144 (14.2 mg, 15%). MS (ESI) m/z $(M+H)^+$ 688.4.

Example 44-28

Synthesis of Compound 1145

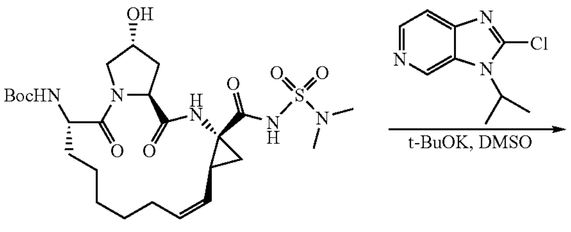

76

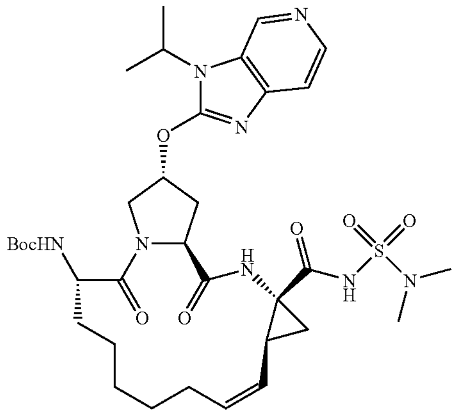

1145

To a solution of compound 76 (120 mg, 0.21 mmol.) in 2 mL of DMSO was added t-BuOK (118 mg, 1.05 mmol.). The resulting mixture was stirred at room temperature for 1.5 h before the addition of 2-chloro-3-isopropyl-3H-imidazo[4,5-c]pyridine (82 mg, 0.42 mmol.), and it was stirred overnight. The reaction was quenched with water (10 mL), extracted with ethyl acetate, washed with brine, dried over $Na_2SO_4$, concentrated to get a residue, which was purified by prep-HPLC to afford compound 1145 (55.1 mg, 36.0%). MS (ESI) m/z $(M+H)^+$ 731.1.

Example 44-29

Synthesis of 2-chloro-1-cyclopentyl-1H-benzo[d]imidazole

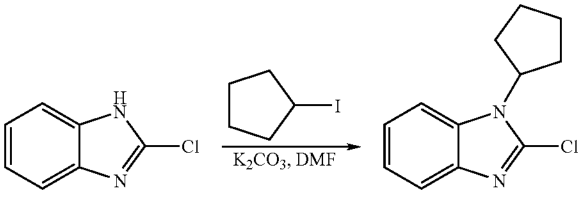

To a solution of 2-chloro-1H-benzo[d]imidazole (152 mg, 1.0 mmol.) in DMF was added $K_2CO_3$ (277 mg, 2.0 mmol.) and iodocyclopentane (295 mg, 1.5 mmol.). The reaction mixture was stirred at room temperature for 24 hours. The reaction mixture was poured into ice-water. The mixture was extracted with ethyl acetate (30 mL×3), washed with brine, dried over $Na_2SO_4$, concentrated to give a residue, which was purified by column chromatography to afford 2-chloro-1-cyclopentyl-1H-benzo[d]imidazole (130 mg, 59%). $^1H$ NMR (400 MHz, $CDCl_3$) δ 7.68~7.60 (m, 1 H), 7.39~7.30 (m, 1 H), 7.20~7.15 (m, 2 H), 5.04~4.90 (m, 1 H), 2.25~1.92 (m, 6 H), 1.85~1.70 (m, 2 H).

Example 44-30

Synthesis of 2-chloro-1-cyclopentyl-1H-benzo[d]imidazole

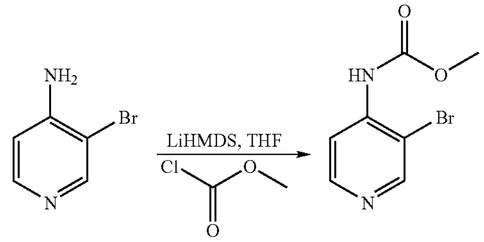

To a solution of compound 3-bromopyridin-4-amine (3 g, 17.4 mmol.) in 20 mL of anhydrous THF was added a solution of LiHMDS (1M in THF, 36.4 mL, 36.4 mmol) at 0° C. After stirring for 30 min, methyl chloroformate (2 g, 20.8 mmol) was added at 0° C. The reaction mixture was stirred at 0° C. for 2 hrs and then at r.t. overnight. The reaction was quenched with saturated aqueous ammonium chloride. The organic solvent was evaporated and the aqueous layer was extracted with ethyl acetate. The organic layers were dried over $Na_2SO_4$, concentrated. The crude product was purified by silica gel column chromatography (Petroleum ether:Ethyl acetate=1:2) to afford methyl 3-bromopyridin-4-ylcarbamate (2.34 g, 59%).

Example 44-31

Synthesis of 3-isopropyl-1H-imidazo[4,5-c]pyridin-2(3H)-one

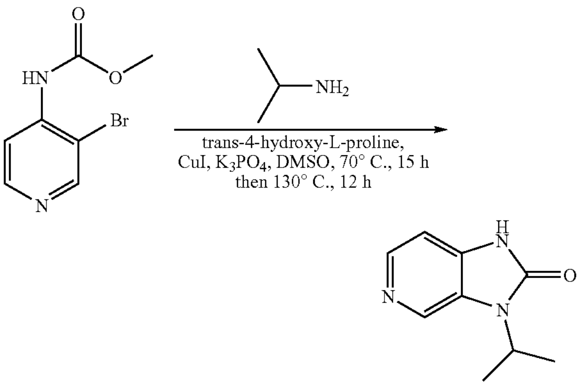

A sealed tube was charged with methyl 3-bromopyridin-4-ylcarbamate (1.76 g, 7.6 mmol.), CuI (290 mg, 1.52 mmol.), trans-4-hydroxy-L-proline (400 mg, 3.04 mmol.) and $K_3PO_4$ (3.2 g, 15.2 mmol.), evacuated and backfilled with argon. Isopropylamine (674 mg, 11.4 mmol.) and DMSO (15 mL) were added successively. The reaction mixture was stirred at 70° C. for 12 h and then at 130° C. for 12 h. The reaction mixture filtered and the filtrate was concentrated and purified by prep-HPLC to afford 3-isopropyl-1H-imidazo[4,5-c]pyridin-2(3H)-one (765 mg, 57%).

Example 44-32

Synthesis of 2-chloro-3-isopropyl-3H-imidazo[4,5-c]pyridine

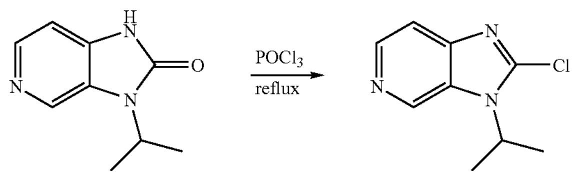

A mixture of 3-isopropyl-1H-imidazo[4,5-c]pyridin-2(3H)-one (0.5 g, 2.82 mmol.) in $POCl_3$ (5 mL) was refluxed for 16 hrs. Then the reaction mixture was poured into ice water and basified with $NH_4OH$ to pH=7~8. The mixture was extracted with ethyl acetate. The organic layer was dried over $Na_2SO_4$ and evaporated to afford crude 2-chloro-3-isopropyl-3H-imidazo[4,5-c]pyridine which was used directly for the next step (150 mg, 27%).

Example 45-1

Synthesis of Compound 1052

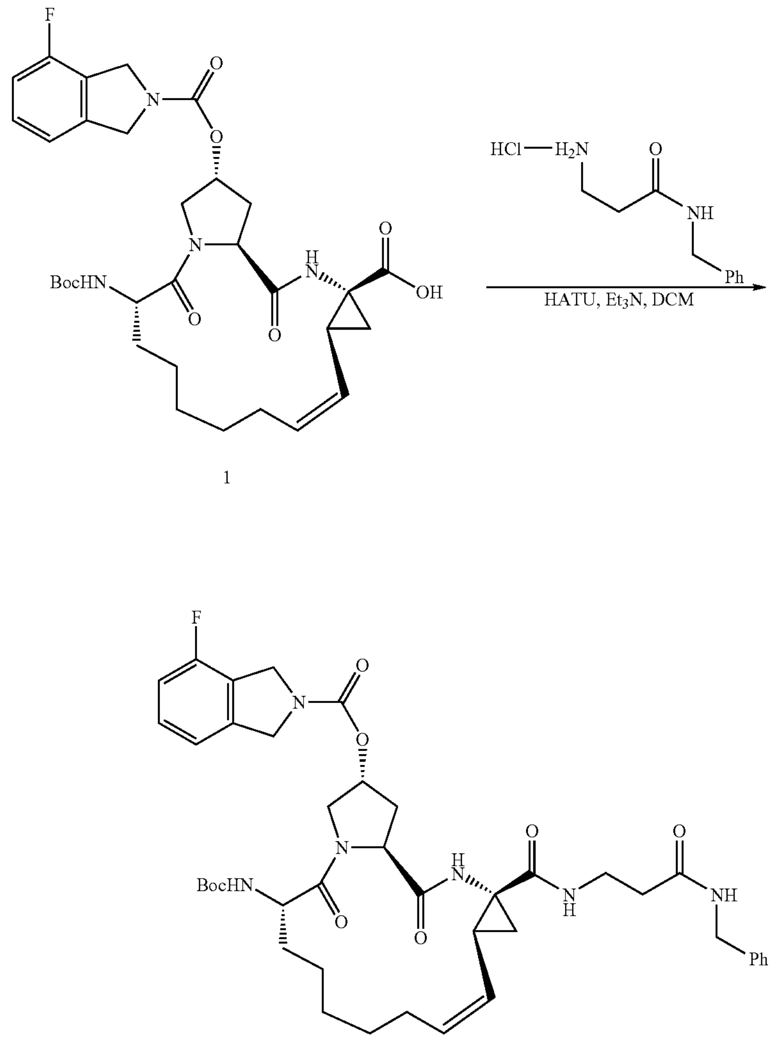

1

1052

General Method T

Compound 1 (100 mg, 0.16 mmol.), 3-amino-N-benzyl-propionamide hydrochloride (34 mg, 0.16 mmol.), and HATU (63 mg, 0.16 mmol.) were dissolved in DCM (5 mL). The stirring mixture was treated with $Et_3N$ (145 mg, 1.4 mmol.) and then stirred overnight. The organic solution was partitioned with water. The organic layer was washed with brine, dried over $Na_2SO_4$, filtered and concentrated. The crude product was purified on prep-TLC (DCM:MeOH 20:1) to afford compound 1052, as white solid (76 mg, yield 61%).

Example 45-2

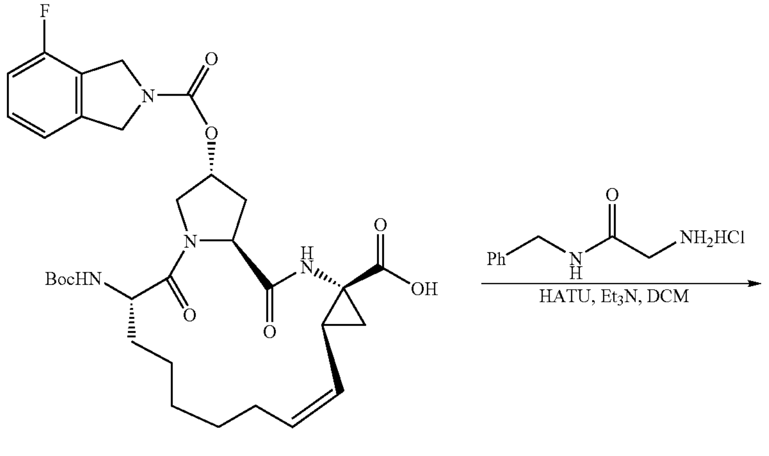

1

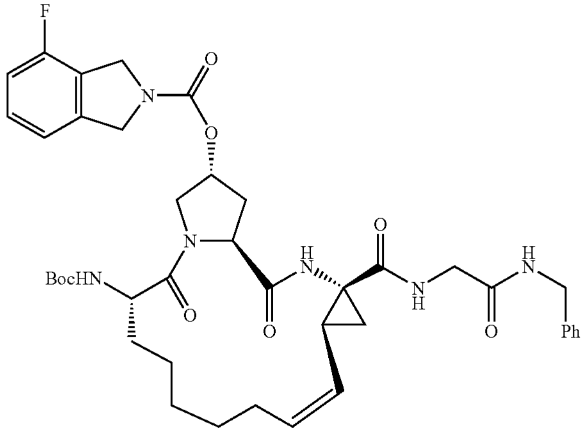

1053

Compound 1053 was prepared following General Method T, and the yield was 30%. MS (ESI) m/e ($M+H^+$) 775.

Example 45-3

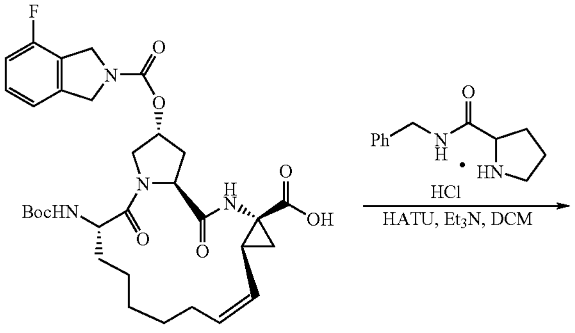

1

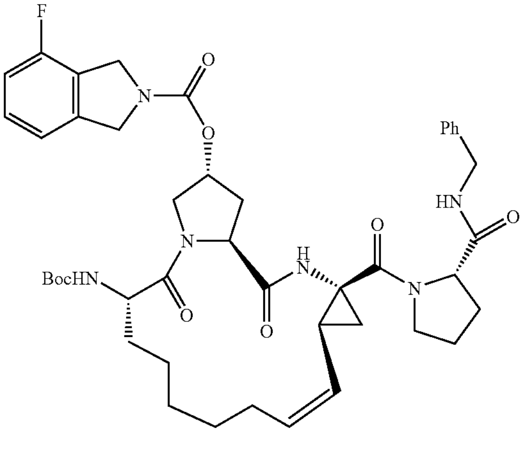

1054

Compound 1054 was prepared following General Method T, and the yield was 10%. MS (ESI) m/e ($M+H^+$) 815.

Example 45-4

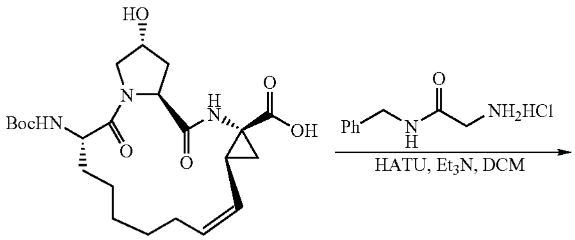

2

-continued

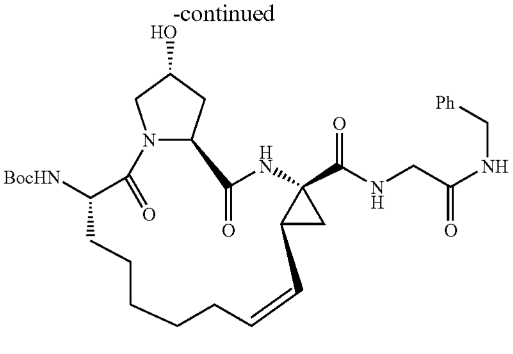

1055

Compound 1055 was prepared following General Method T, and the yield was 53.3%. MS (ESI) m/e ($M+H^+$) 612.

Example 45-5

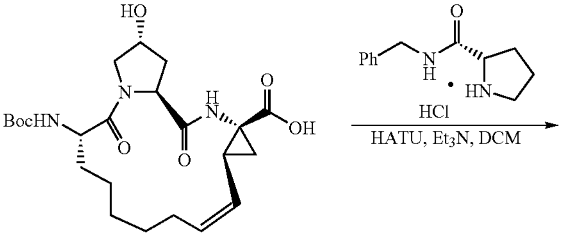

2

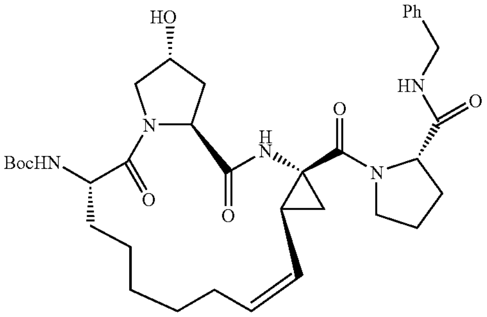

1056

Compound 1056 was prepared following General Method T, and the yield was 50%. MS (ESI) m/e ($M+H^+$) 652.

Example 45-6

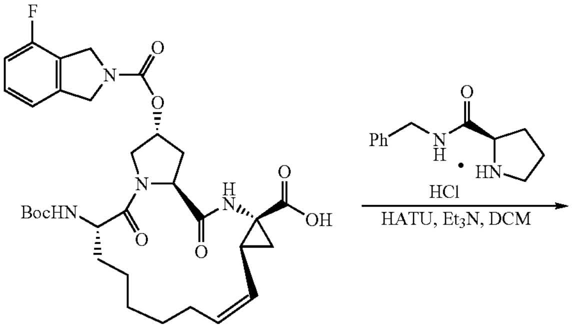

1

-continued

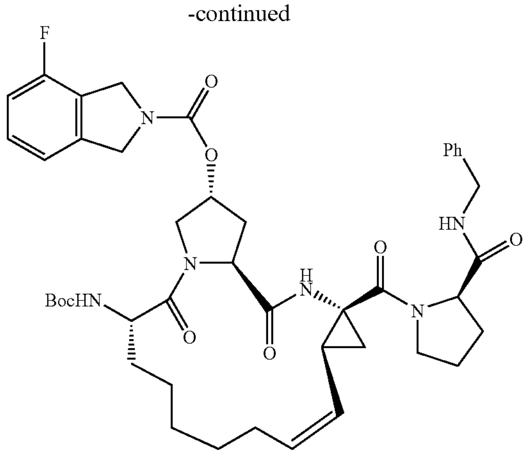

1057

Compound 1057 was prepared following General Method T, and the yield was 30%. MS (ESI) m/e (M+H$^+$) 815.41.

Example 45-7

Procedure for the Synthesis of 3-Amino-N-benzylpropionamide hydrochloride

Scheme XXXIV

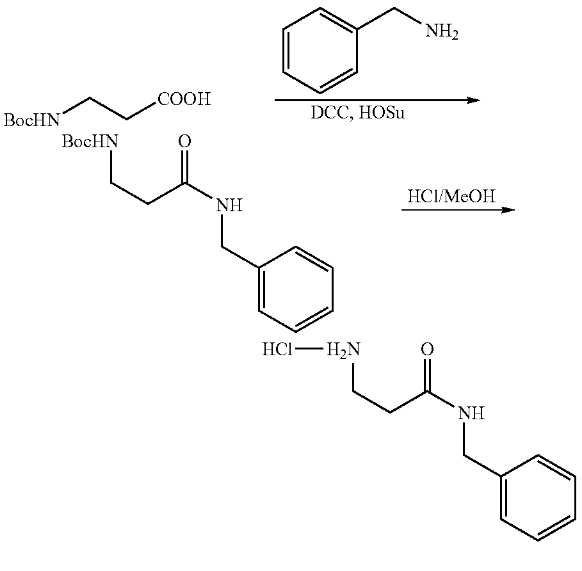

3-Amino-N-benzylpropionamide hydrochloride can be prepared by the method shown in Scheme XXXIV. 3-tert-Butoxycarbonylaminopropanoic acid can be coupled with benzylamine to provide 3-tert-butoxycarbonylamino-N-benzylpropionamide. For example, the coupling reagents can be CDI, DCC, DIC, EDAC, HOSu, HOBt, HOAt, PyBOP, PyBrOP, HBTU, HATU, TBTU, combinations thereof, and the like. The Boc group can then be removed under acidic conditions to afford 3-amino-N-benzylpropionamide hydrochloride. For example, the acid can be trifluoroacidic acid, hydrochloric acid, and the like.

A solution of 3-tert-butoxycarbonylaminopropanoic acid (2 g, 10.6 mmol.) and HOSu (1.22 g, 10.6 mmol.) in 40 mL DCM/Dioxane (2:1) was cooled in an ice bath. To this solution was added DCC (2.4 g, 11.6 mmol.), and the mixture was stirred at room temperature for 1 h. To the resulting mixture was added benzylamine (1.7 g, 15.8 mmol.), the mixture was stirred for 4 h at room temperature. The solid that formed in the mixture was removed by filtration and washed with EtOAc. The filtrate and washings were combined and washed with 1N HCl and saturated aqueous $NaHCO_3$. The organic layer was dried over $Na_2SO_4$, filtered and concentrated to afford 3-tert-butoxycarbonylamino-N-benzylpropionamide (2.4 g, 82%). 3-tert-Butoxycarbonylamino-N-benzylpropionamide was dissolved in cooled HCl/MeOH (20 mL) and the resulting mixture was stirred at room temperature for 1.5 h. The solvent was removed to afford 3-amino-N-benzylpropionamide hydrochloride (1.8 g, 100%).

Similar N-benzylamide amine hydrochlorides were prepared following the same experimental procedure of making 3-amino-N-benzylpropionamide hydrochloride.

Example 46-1

Synthesis of Compound 1058

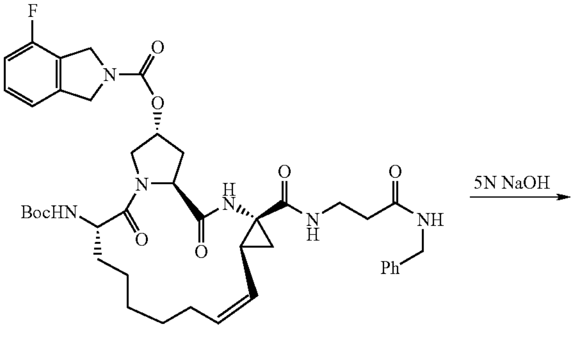

1052

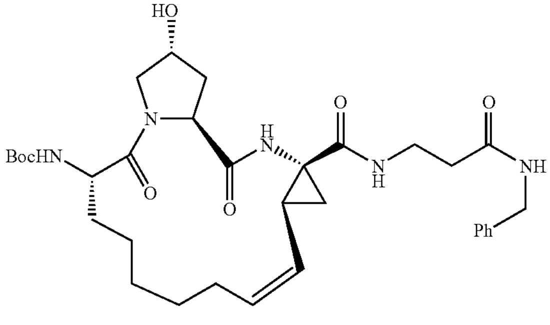

1058

General Method U

To a solution of compound 1052 (76 mg, 0.1 mmol.) in 2 mL MeOH, was added 5N NaOH (1 mL). The mixture was heated at 50° C. overnight. After cooling to room temperature, the pH was adjusted to ~4 with 2N HCl, and then extracted with EtOAc. The combined organic layer was washed with brine, dried over $Na_2SO_4$, filtered and concentrated under reduced pressure. The crude product was purified on prep-TLC (DCM:MeOH 20:1) to afford compound 1058, as a white solid (28 mg, yield 47%).

Example 46-2

Synthesis of Compound 1059

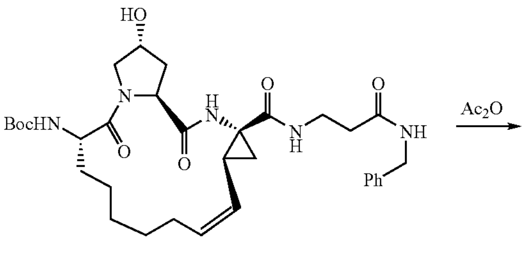

1058

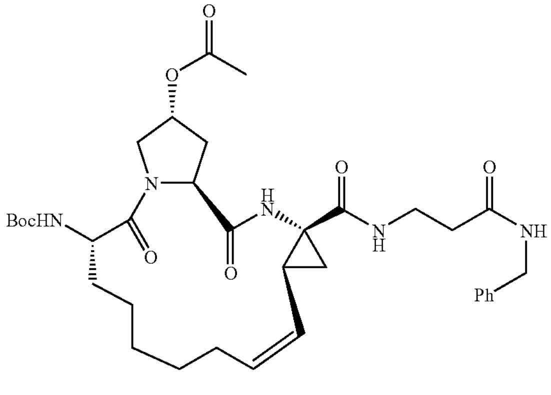

1059

General Method V

To a solution of compound 1058 (46 mg, 0.07 mmol.) in DCM (2 mL) were added $Ac_2O$ (15 mg, 0.14 mmol.) and $Et_3N$ (22 mg, 0.22 mmol.), the mixture was stirred at room temperature overnight. The organic solution was partitioned with water. The organic layer was washed with brine, dried over $Na_2SO_4$, filtered and concentrated. The crude product was purified on prep-TLC to afford compound 1059 as a white solid (27 mg, 56%). MS (ESI) m/e $(M+H^+)$ 668.2.

Example 46-3

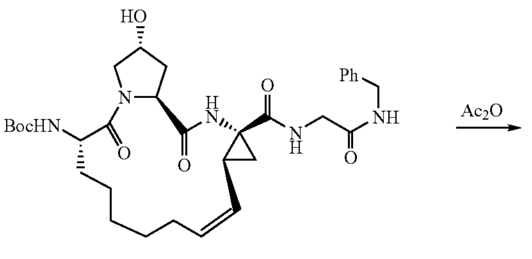

1055

-continued

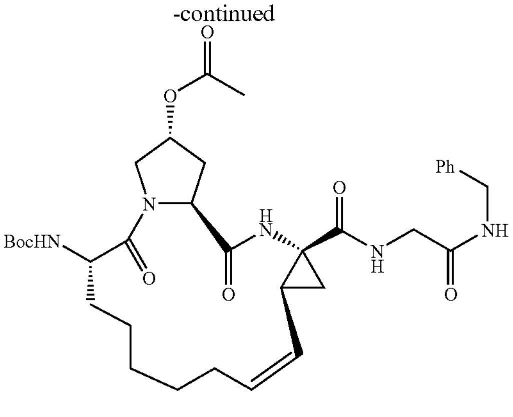

1060

Compound 1060 was prepared following General Method V, and the yield was 40%. MS (ESI) m/e $(M+H^+)$ 654.

Example 46-4

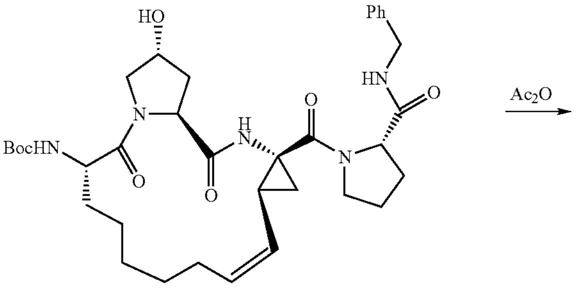

1056

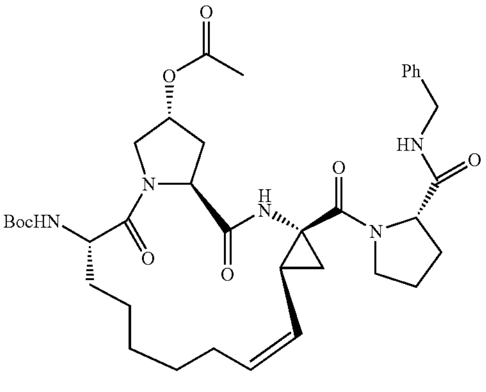

1061

Compound 1061 was prepared following General Method V, and the yield was 37.7%. MS (ESI) m/e ($M+H^+$) 694.

Example 46-5

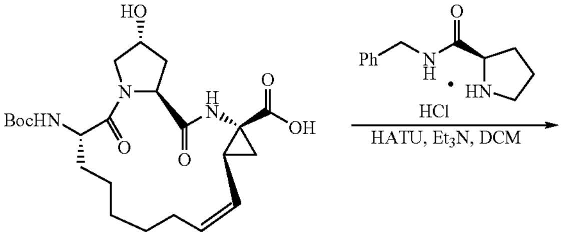

2

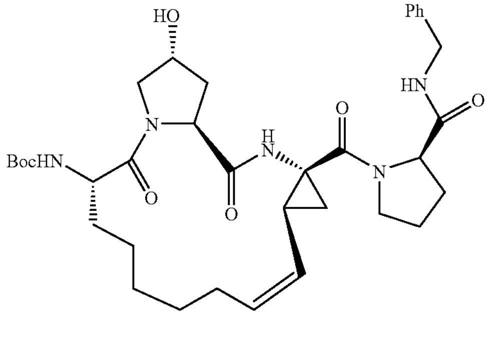

1087

Compound 1087 was prepared following General Method T, to afford 46 mg (43% yield). MS (ESI) m/z $(M+H)^+$ 652.3.

Example 46-6

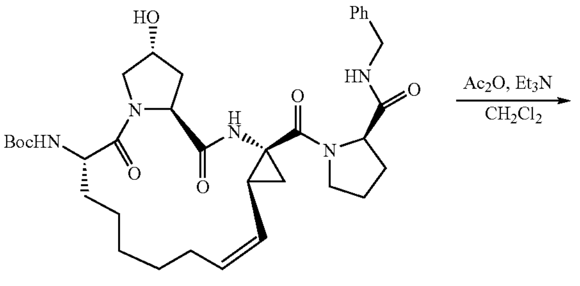

1087

-continued

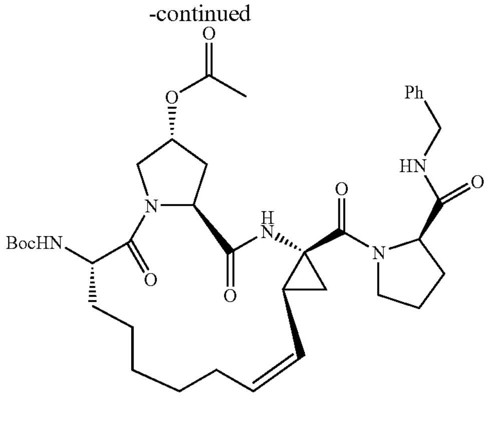

1088

Compound 1088 was prepared following General Method V, to afford 30 mg (28% yield). MS (ESI) m/z $(M+H)^+$ 694.1.

Example 47-1

Synthesis of Compound 1062

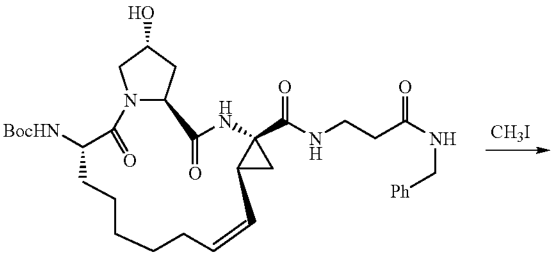

1058

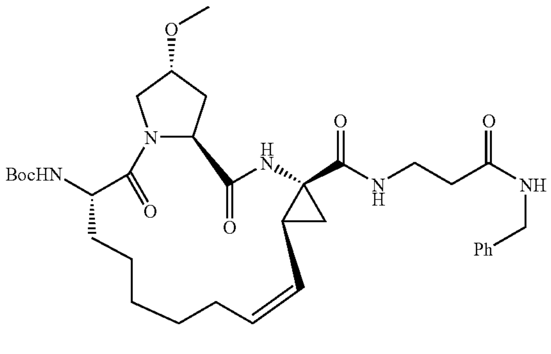

1062

General Method W

Compound 1058 was dissolved in DMF (1 mL), the resulting solution was treated with $CH_3I$ (18.5 mg, 0.13 mmol.) and the mixture cooled to 0° C. Subsequently, the mixture was treated with NaH (4.3 mg, 0.108 mmol.) and the mixture was stirred at room temperature overnight. The organic solution was partitioned with water and the aqueous layer was extracted with EtOAc, the combined organic layers were washed with brine, dried over $Na_2SO_4$, filtered and concentrated under reduced pressure. The crude product was purified on Prep-TLC (DCM:MeOH 20:1) to afford compound 1062, as white solid (20 mg, 28%). MS (ESI) m/e ($M+H^+$) 640.4.

Example 47-2

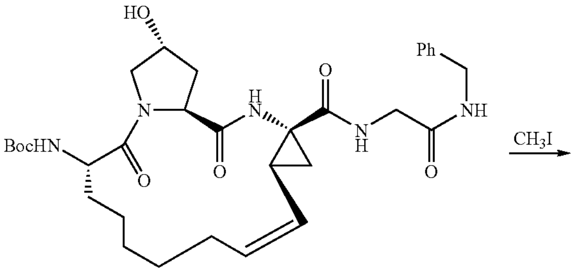

1055

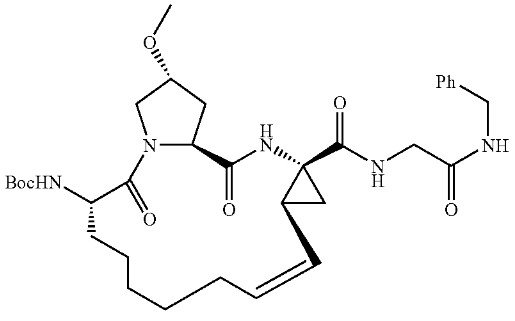

1063

Compound 1063 was prepared following General Method W, and the yield was 30%. MS (ESI) m/e ($M+H^+$) 626.

Example 47-3

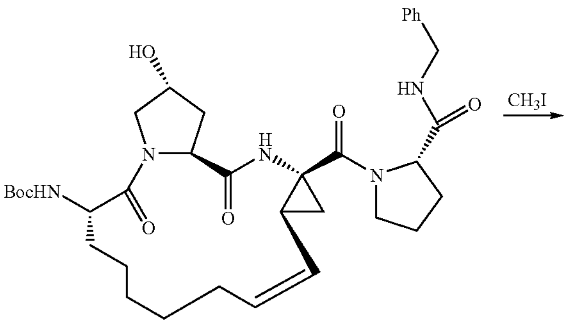

1056

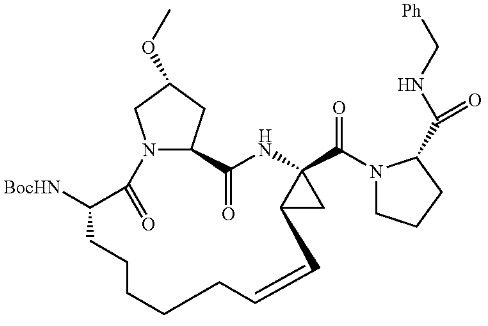

1064

Compound 1064 was prepared following General Method W, and the yield was 15%. MS (ESI) m/e ($M+H^+$) 666.

Example 47-4

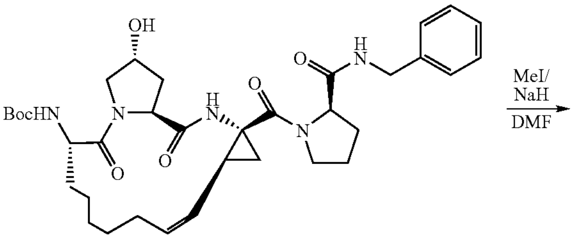

1087

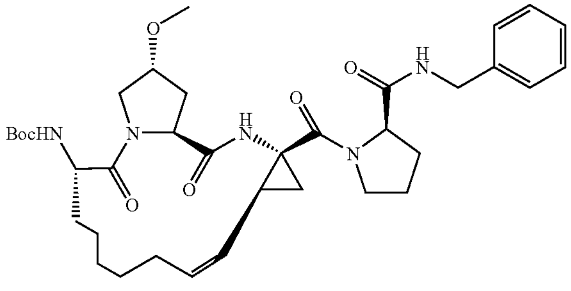

1089

Compound 1089 was prepared in a manner analogous to General Method W, to afford 8 mg (8% yield). MS (ESI) m/z $(M+H)^+$ 666.3.

Example 48-1

Synthesis of Compound 1065

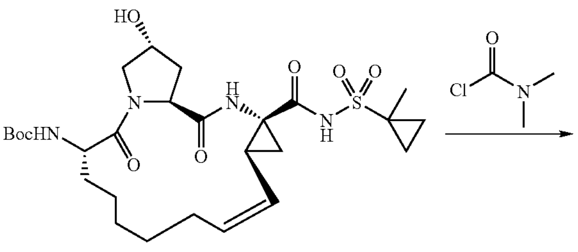

7

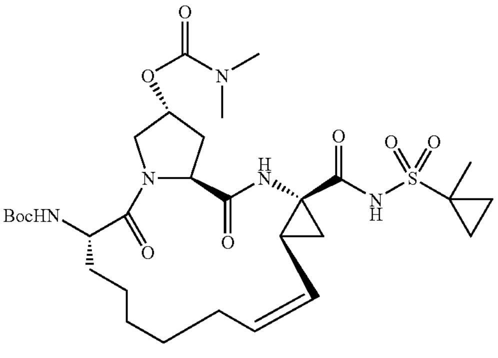

1065

General Method X

To a solution of compound 7 (50 mg, 0.08 mmol.) in THF (1 mL) at −10° C. was added NaH (6.4 mg, 0.16 mmol.). Subsequently, the stirring mixture was treated with dimethylcarbamic chloride (9 mg, 0.08 mmol.). The resultant mixture was stirred at room temperature overnight. The organic solution was partitioned with water and the aqueous layer was extracted with EtOAc, the combined organic layers were washed with brine, dried over $Na_2SO_4$, filtered and concentrated under reduced pressure. The crude product was purified on prep-TLC (DCM:MeOH 20:1) to afford compound 1065, as a white solid (21 mg, 37%). MS (ESI) m/e (M+H$^+$) 654.3.

Example 48-2

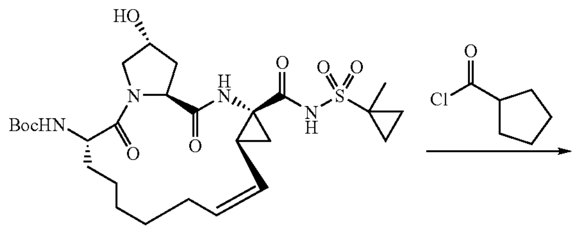

7

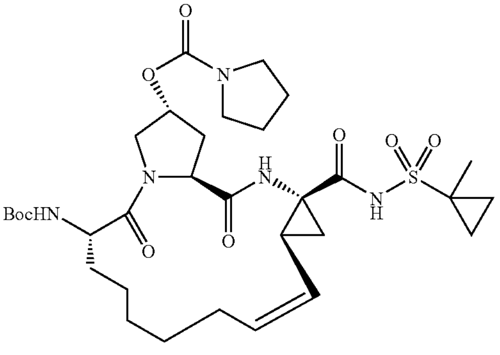

1072

Compound 1072 was prepared following General Method X, and the yield was 60%. MS (ESI) m/e (M+H$^+$) 680.3.

Example 48-3

Synthesis of Compound 1066

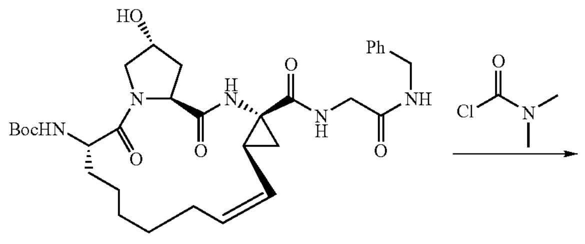

1055

-continued

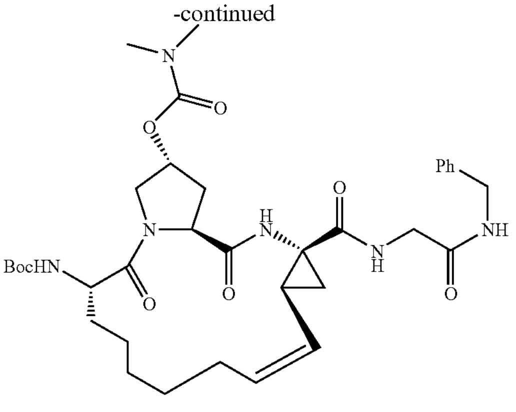

1066

Compound 1066 was prepared following General Method X, and the yield was 70%. MS (ESI) m/e (M+H$^+$) 683.

Example 48-4

Synthesis of Compound 1067

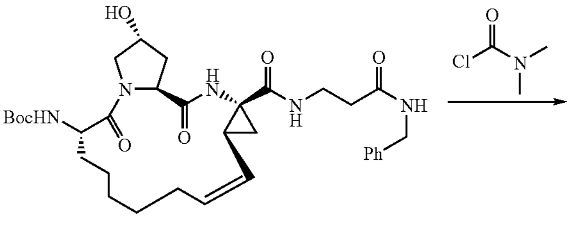

1058

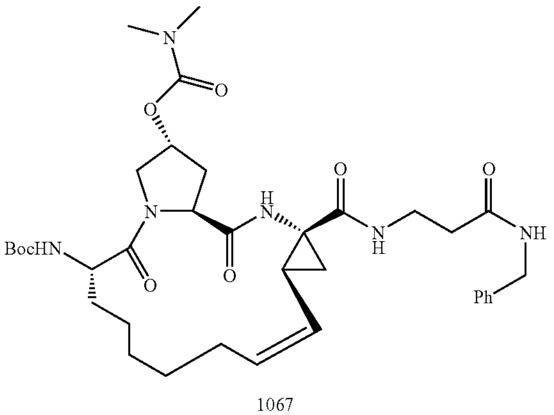

1067

Compound 1067 was prepared following General Method X, and the yield was 60%. MS (ESI) m/e ($M+H^+$) 697.4.

Example 48-5

Synthesis of Compound 1068

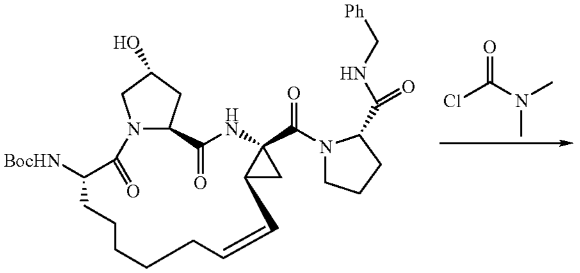

1056

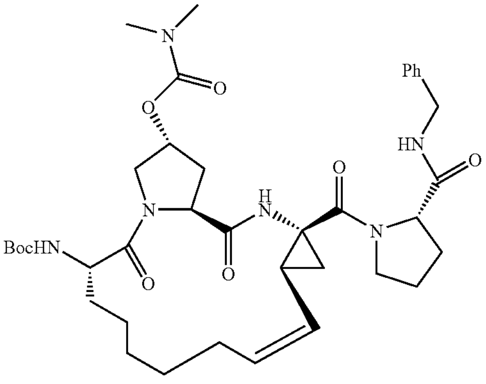

1068

Compound 1068 was prepared following General Method X, and the yield was 60%. MS (ESI) m/e ($M+H^+$) 723.

Example 48-6

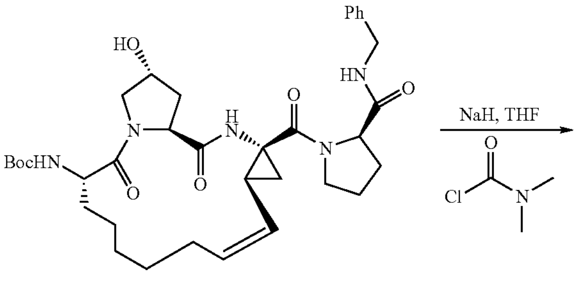

1087

-continued

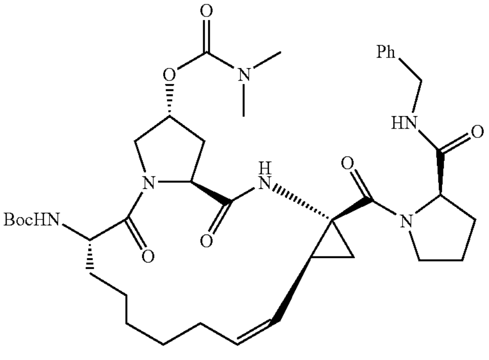

1090

Compound 1090 was prepared following General Method X, to afford 35 mg (32%). MS (ESI) m/z $(M+H)^+$ 723.2.

Example 49-1

Procedure for the Synthesis of Compound 1069

Scheme XXXV

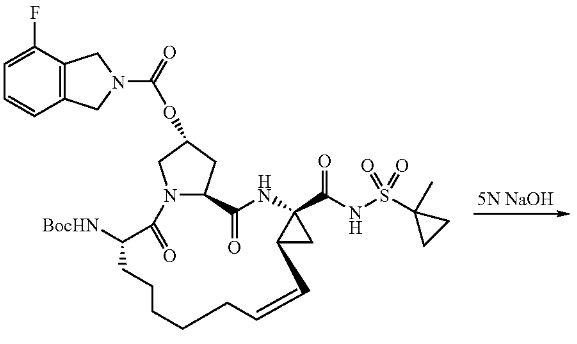

6

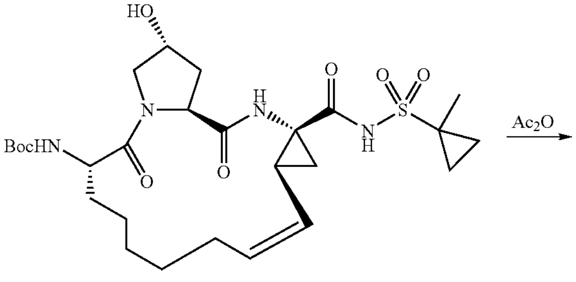

7

-continued

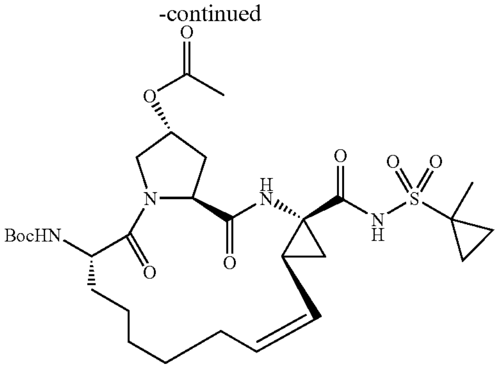

1069

Compound 1069 can be prepared according to the method of Scheme XXXV. Compound 6 can be treated with a base, such as sodium hydroxide, to afford compound 7. Compound 7 can be treated with an acylating agent, such as acetyl chloride, acetic anhydride and the like, to afford compound 1069.

Example 49-2

Synthesis of Compound 7

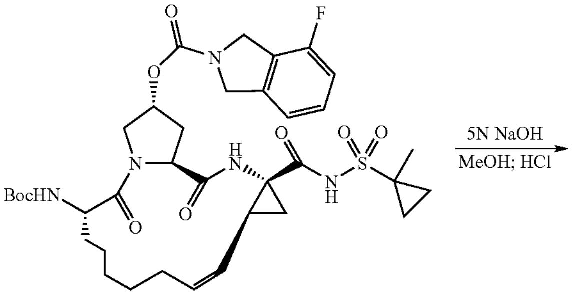

6

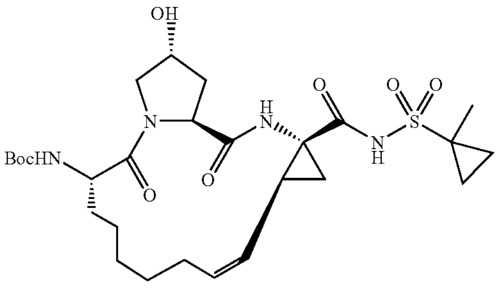

7

General Method Y

To a solution of compound 6 (1.0 g, 1.37 mmol.) in 20 mL of methanol was added 8.6 mL of 5M NaOH. The resulting mixture was stirred at 50° C. for 20 h. The solution was cooled down below 5° C. and acidified using diluted HCl and extracted. The crude material was purified by column chromatography to afford 0.58 g of 7 was obtained and the yield was 73%.

Example 49-3

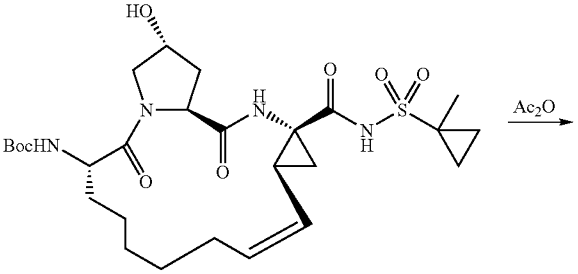

7

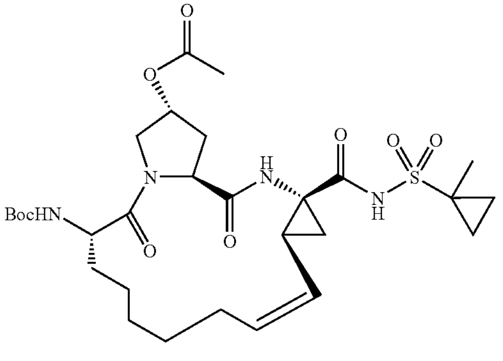

1069

Compound 1069 was prepared following General Method V, and the yield was 77%. MS (ESI) m/e ($M+H^+$) 583.2.

Example 49-4

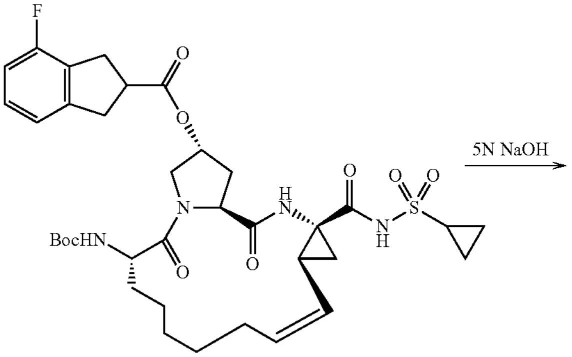

10

-continued

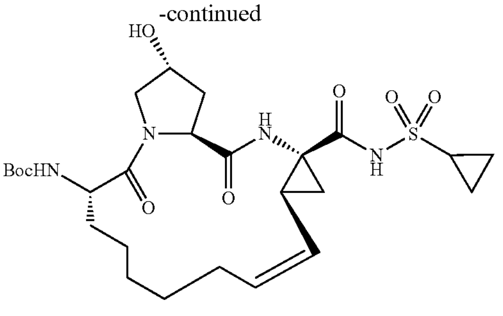

11

Compound 11 was prepared following General Method Y, and the yield was 70%. MS (ESI) m/e (M+H$^+$) 569.2.

Example 49-5

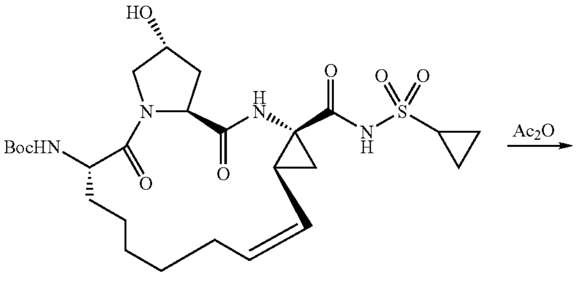

11

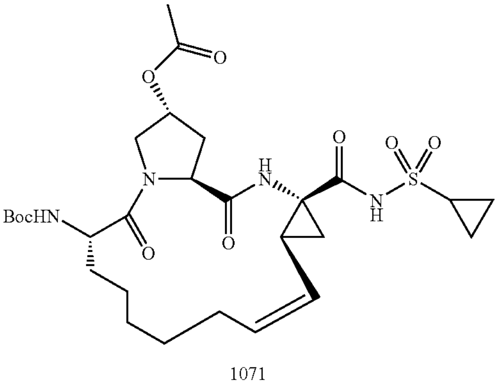

1071

Compound 1071 was prepared following General Method V, and the yield was 93%. MS (ESI) m/e (M+H$^+$) 611.2.

Example 49-6

Synthesis of Compound 1081

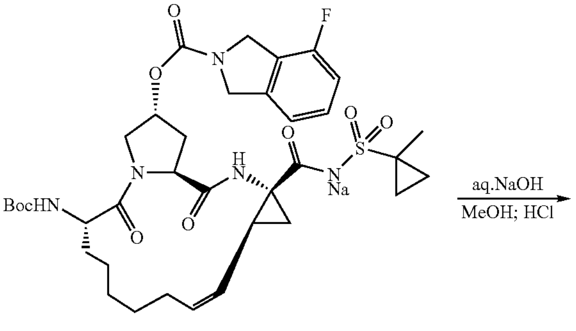

705

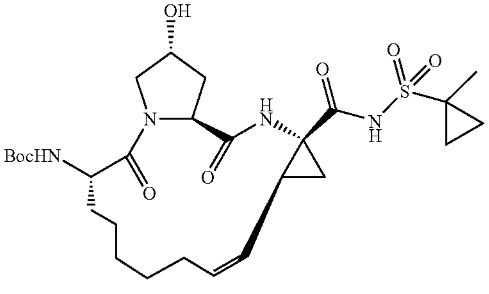

7

General Method VW

To a solution of compound 705 (2 g, 2.6 mmol.) in 100 mL methanol was added 15 mL of aq. NaOH solution (5 M), the resulting mixture was heated to 50° C. and stirred overnight. The reaction was monitored by LCMS. After completion of the reaction, The mixture was cooled by ice water, acidified by 2 M HCl to pH=~3-4, then the mixture was extracted by ethyl acetate (100 mL×3), the organic layers were combined, washed by brine, dried over anhydrous sodium sulfate, the solvent was removed under reduced pressure, the crude product compound 7 (1.5 g, 99%) was used directly in the next step. MS (ESI) m/z $(M+H)^+$ 583.1.

Example 49-7

Synthesis of Compound 1091

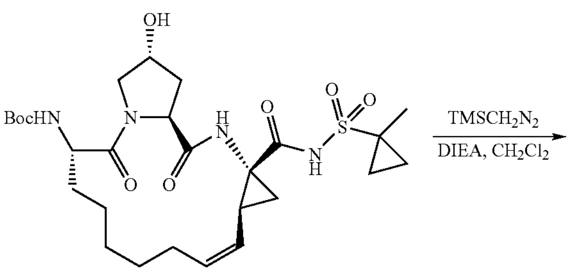

7

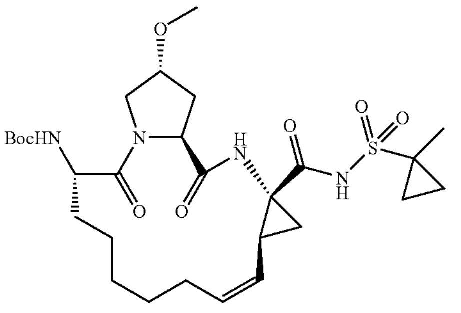

1091

General Method VX

To a solution of compound 7 (100 mg, 0.17 mmol.) and DIEA (0.1 mL) in 1 mL of $CH_2Cl_2$ was added a (trimethylsilyl)diazomethane solution (2.0 M in hexanes, 0.17 mL, 0.34 mmol.) at 0° C. After stirring for 3 h at 0° C., the mixture was concentrated in vacuo. The residue was purified by prep-HPLC to afford 1091 (4.2 mg, 4.1%). MS (ESI) m/z $(M+Na)^+$ 619.2.

Example 49-8

1092

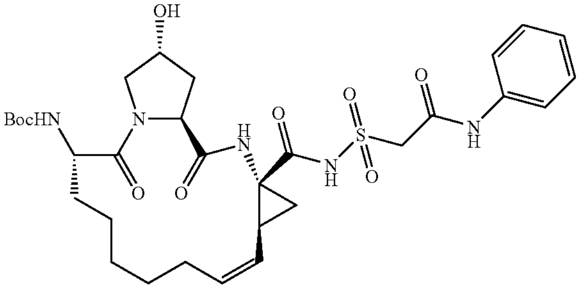

Compound 1092 was prepared in a manner analogous to General Method D, to afford 33.7 mg, 14%. MS (ESI) m/z $(M+H)^+$ 662.1.

Example 49-9

1093

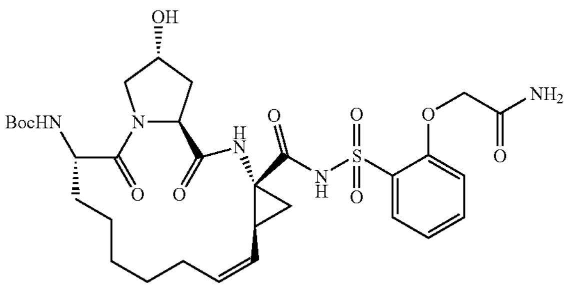

Compound 1093 was prepared in a manner analogous to General Method D, to afford 91.7 mg, 19.1%. MS (ESI) m/z $(M+H)^+$ 678.3.

Example 49-10

1094

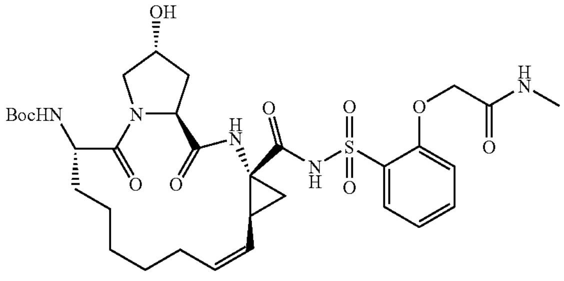

Compound 1094 was prepared in a manner analogous to General Method D, to afford 86.5 mg, 19.6%. MS (ESI) m/z $(M+H)^+$ 692.1.

Example 49-11

General Procedure for Preparation of Carbamates

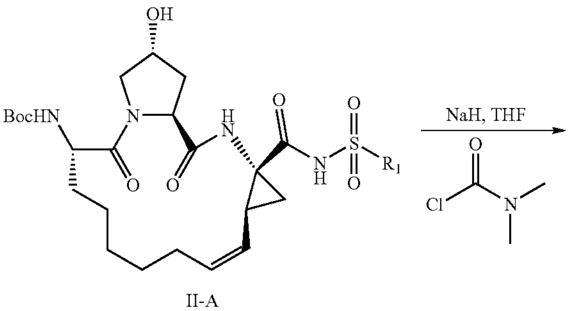

II-A

-continued

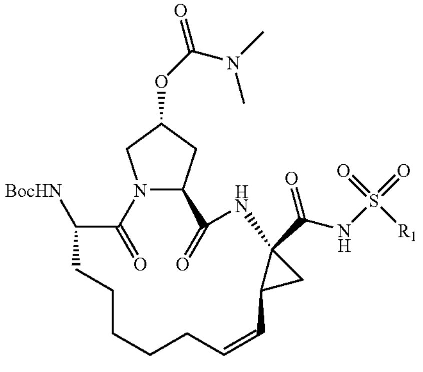

II-B

General Procedure VA

To a solution of a compound having the general structure II-A (1.0 eq.) in dry THF was added to NaH (10 eq.). The reaction mixture was stirred for 10 minutes. dimethylcarbamic chloride (1.1 eq.) was injected into flask at 0-5° C. The resulting solution was stirred overnight at room temperature. TLC analysis showed the reaction complete. The reaction mixture was poured into ice-water, and extracted with ethyl acetate (×3). The combined organic layer was dried over $Na_2SO_4$, concentrated. The residue was purified by prep-HPLC to afford a compound having the general structure II-B.

Example 49-12

1095

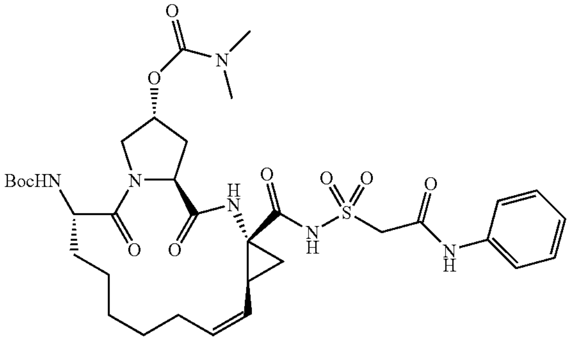

Compound 1095 was prepared in a manner analogous to General Procedure VA, to afford 20.9 mg, 31%. MS (ESI) m/z $(M+Na)^+$ 755.2.

Example 49-13

1096

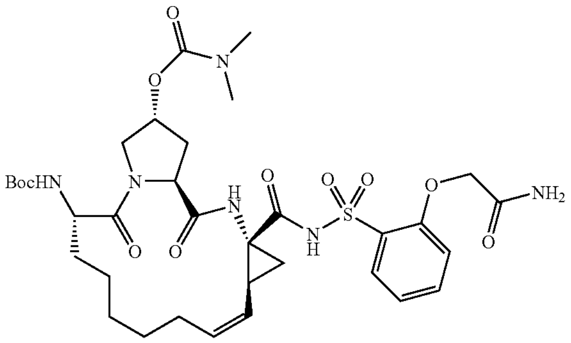

Compound 1096 was prepared in a manner analogous to General Procedure VA, to afford 41 mg, 46%. MS (ESI) m/z $(M+H)^+$ 749.2.

Example 49-14

1097

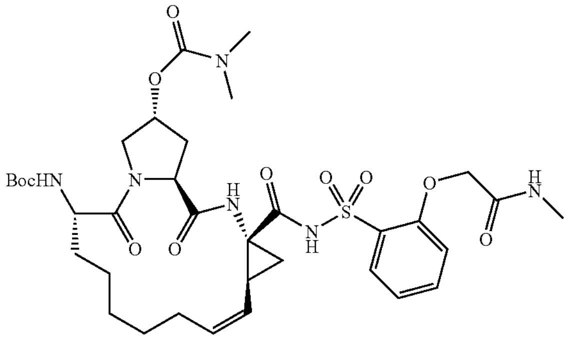

Compound 1097 was prepared in a manner analogous to General Procedure VA, to afford 42 mg, 50%. MS (ESI) m/z $(M+H)^+$ 763.2.

Example 49-15

General Procedure for Preparation of Esters

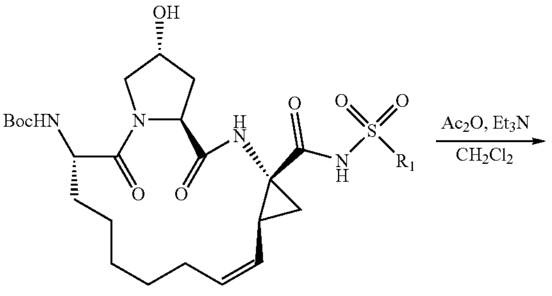

II-A

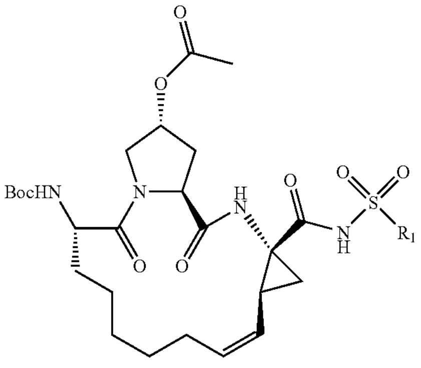

II-C

General Procedure VB

To a stirred solution of compound II-A (1 eq.) in $CH_2Cl_2$ was added triethylamine (6 eq.) and $Ac_2O$ (4 eq.). The mixture was stirred at room temperature overnight. TLC analysis showed the reaction complete. The mixture was quenched by adding water and extracted with EtOAc (×3). The combined organic layer was dried over $Na_2SO_4$, concentrated. The residue was purified by prep-HPLC to afford compound II-C.

Example 49-16

1098

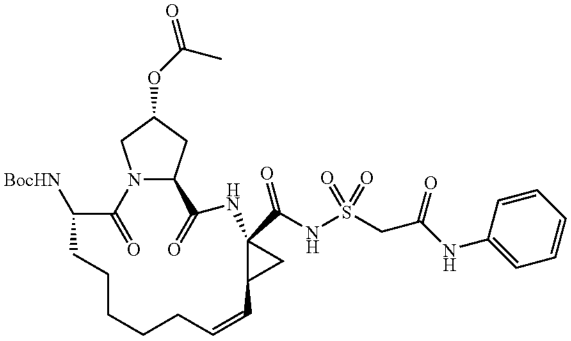

Compound 1098 was prepared in a manner analogous to General Procedure VB, to afford 26.2 mg, 41%. MS (ESI) m/z $(M+H)^+$ 704.1.

Example 49-17

Preparation of Compound 1099

Scheme XXXVI:

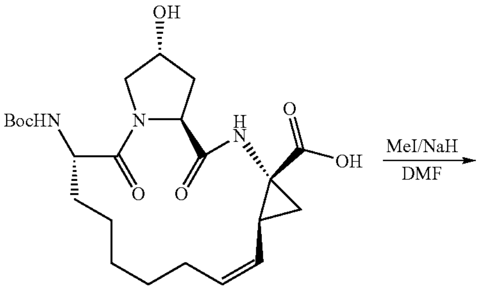

2

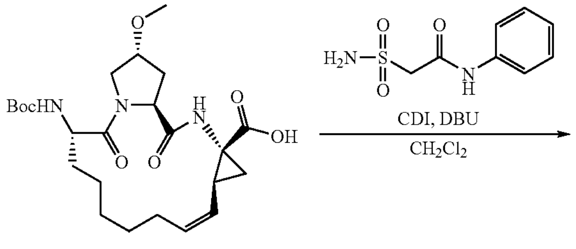

721

-continued

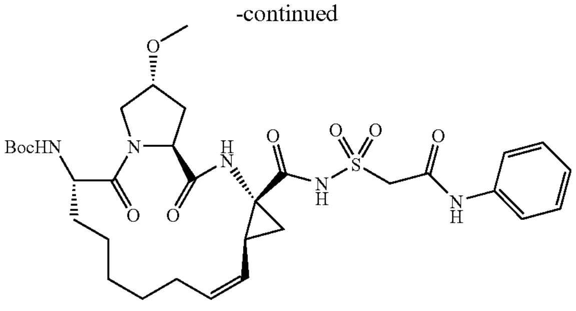

1099

Compound 1099 can be prepared according to Scheme XXXVI. Compound 2 can be treated with a methylating agent, such as methyl iodide, methyl triflate, dimethylsulfate, and the like, under basic condition to afford compound 721. For example, the base can be sodium hydride, potassium hydride, lithium hydride, cesium carbonate, sodium carbonate, potassium carbonate, and the like. Compound 721 can be coupled with 2-(sulfamoyl)-N-phenylacetamide to afford compound 1099. For example, the coupling reagents can be CDI, DCC, DIC, EDAC, HOSu, HOBt, HOAt, PyBOP, PyBrOP, HBTU, HATU, TBTU, combinations thereof, and the like.

Example 49-18

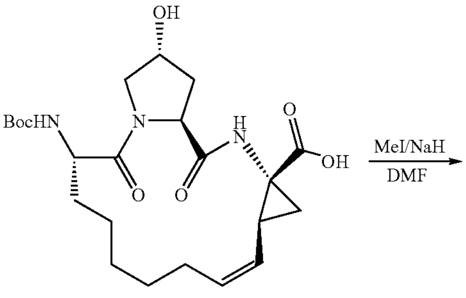

2

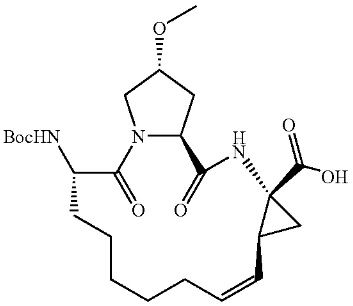

721

General Method VY

To a solution of compound 2 (200 mg, 0.21 mmol.) and MeI (28 μL, 0.5 mmol.) in 2 mL of DMF was added to NaH (60%, 34 mg, 0.84 mmol.) at −20° C. The reaction mixture was stirred for 30 minutes at −20° C. The resulting solution was allowed to warm to room temperature overnight. The mixture was neutralized with aq. HCl (1 N). The mixture was extracted with EtOAc (20 mL×3) and dried over $Na_2SO_4$, concentrated. The residue was purified with prep-HPLC to afford compound 721 (33 mg, 32%).

Example 49-19

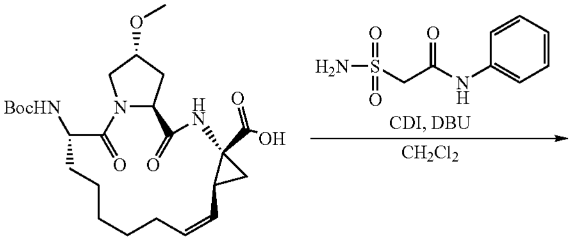

721

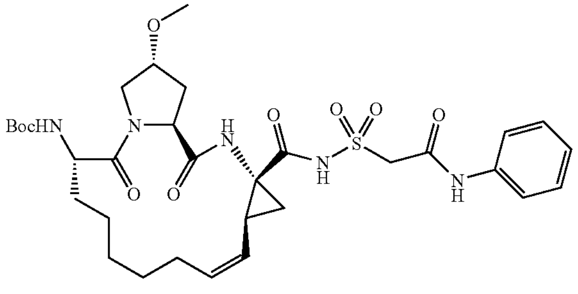

1099

Compound 1099 was prepared in a manner analogous to General Method VY, to afford 14.6 mg (29% yield) as white solid. MS (ESI) m/z $(M+Na)^+$ 698.3.

Example 50-1

Synthesis of (N-phenylaminocarbonyl)methanesulfonamide

Scheme XXXVII

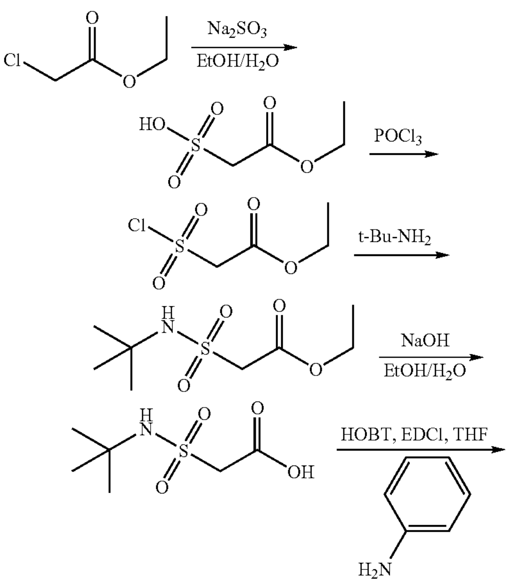

-continued

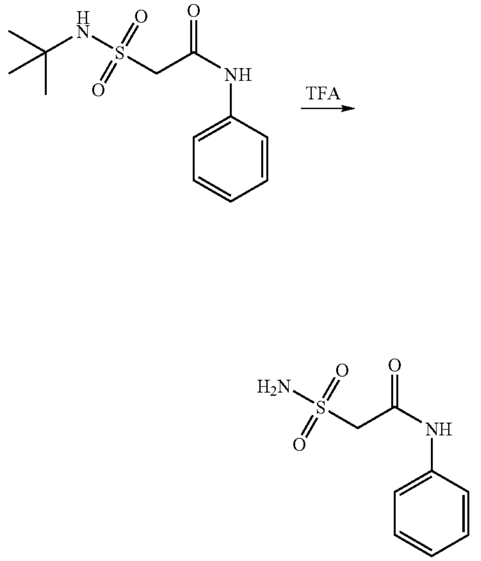

2-(Sulfamoyl)-N-phenylacetamide can be prepared according to the method of Scheme XXXVII. Ethyl 2-chloroacetate can be treated with $Na_2SO_3$ to afford (ethoxycarbonyl)methanesulfonic acid. The acid can be converted to an acid chloride by treating (ethoxycarbonyl)methanesulfonic acid with a chlorinating agent, such as phosphorus oxychloride and the like, thereby affording (ethoxycarbonyl)methanesulfonyl chloride. The acid chloride can be converted to a sulfonamide by treating (ethoxycarbonyl)methanesulfonyl chloride with tert-butylamine, thereby affording ethyl-2-(N-tert-butylsulfamoyl)acetate. The ester can be hydrolyzed under basic conditions, such as sodium hydroxide in ethanol and water, and the like, to afford 2-(N-tert-butylsulfamoyl) acetic acid. 2-(N-tert-Butylsulfamoyl)acetic acid can be coupled with aniline to afford 2-(N-tert-butylsulfamoyl)-N-phenylacetamide. For example, the coupling reagents can be CDI, DCC, DIC, EDAC, EDCI, HOSu, HOBt, HOAt, PyBOP, PyBrOP, HBTU, HATU, TBTU, combinations thereof, and the like. The tert-butyl can be removed under acidic conditions to afford 2-(sulfamoyl)-N-phenylacetamide. For example, the acid can be trifluoroacetic acid, hydrochloric acid, and the like.

Example 50-2

Preparation of (Ethoxycarbonyl)Methanesulfonic Acid

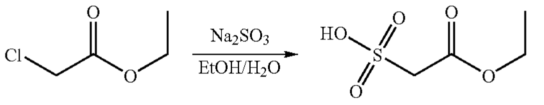

To a solution of $Na_2SO_3$ (10 g, 79 mmol.) in 50 mL of $H_2O$ was added a solution of ethyl 2-chloroacetate (12.7 mL, 119 mmol.) in 55 mL of EtOH. The mixture was heated at reflux for 6 h, after which time all the volatiles were removed by evaporation under reduced pressure. The concentrated materials were dried to afford crude (ethoxycarbonyl)methanesulfonic acid (13.3 g, 100%) used directly without purification.

Example 50-2

Preparation of (Ethoxycarbonyl)Methanesulfonyl Chloride

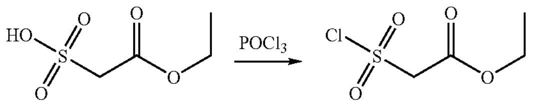

A mixture of (ethoxycarbonyl)methanesulfonic acid (10 g, 60 mmol.) and $POCl_3$ (45 mL) was heated at 125° C. for 5 h. The mixture was cooled and filtered, and excess $POCl_3$ was removed to give crude (ethoxycarbonyl)methanesulfonyl chloride (8.1 g, 80%) used directly without purification.

Example 50-3

Preparation of ethyl-2-(N-tert-butylsulfamoyl)acetate

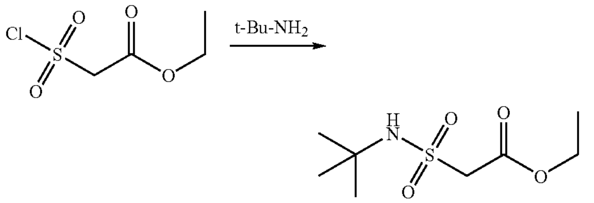

tert-Butylamine (7.9 mL, 75 mmol.) was dissolved in 50 mL of THF. The solution was cooled to −20° C. and (ethoxycarbonyl)methanesulfonyl chloride dissolved in 10 mL of THF was added slowly. The reaction mixture was allowed to warm to room temperature and stirred for 24 h. The mixture was filtered, and the filtrate concentrated in vacuo. The residue was purified by column chromatography (PE/EtOAc; 2:1) to afford ethyl-2-(N-tert-butylsulfamoyl)acetate (4.1 g, 43%).

Example 50-4

Preparation of 2-(N-tert-butylsulfamoyl)acetic acid

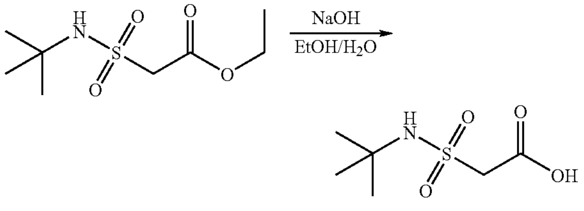

To a solution of ethyl-2-(N-tert-butylsulfamoyl)acetate (4 g, 17.9 mmol.) in 65 mL of EtOH and 13 mL of $H_2O$ at 0° C. was slowly added NaOH (3.6 g, 89.5 mmol.). The reaction was allowed to room temperature and stirred overnight. TLC analysis showed the reaction complete. The mixture was acidified to pH=5 with aq. HCl (1M). The resulting mixture was extracted with EtOAc (30 mL×3). The combined organic layer was dried over $Na_2SO_4$, concentrated to afford crude 2-(N-tert-butylsulfamoyl)acetic acid (2.4 g, 69%), which was used directly without purification.

Example 50-5

Preparation of 2-(N-tert-butylsulfamoyl)-N-phenylacetamide

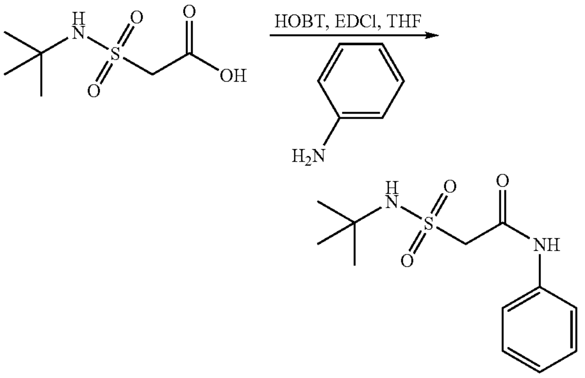

To a solution of compound 2-(N-tert-butylsulfamoyl)acetic acid (5 g, 25.6 mmol.) in dry THF (20 mL) was added HOBt (13.8 g, 102.4 mmol.) and EDCI (18.3 g, 102.4 mmol.). Then aniline (3.6 g, 38.4 mmol.) was added successively. The reaction mixture was stirred overnight at room temperature. TLC analysis showed the reaction complete. The mixture was quenched by adding water and extracted with EtOAc (30 mL×3). The combined organic layer was dried over $Na_2SO_4$, concentrated. The residue was purified by column chromatography (PE:EtOAc=2:1) to afford 2-(N-tert-butylsulfamoyl)-N-phenylacetamide (3.5 g, 51%).

Example 50-5

Preparation of 2-(sulfamoyl)-N-phenylacetamide

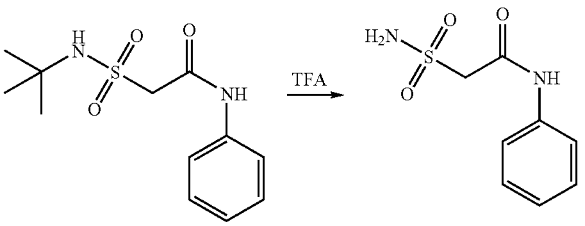

The solution of compound 2-(N-tert-butylsulfamoyl)-N-phenylacetamide (2.5 g, 9.2 mmol.) in 40 mL of TFA was stirred at room temperature overnight. TLC analysis showed the reaction complete. Excess TFA was removed in vacuo. The value of pH was adjusted to 7-8 with $NaHCO_3$. The mixture was extracted with EtOAc (30 mL×3). The combined organic layer was over $Na_2SO_4$, concentrated to afford compound 2-(sulfamoyl)-N-phenylacetamide (1.9 g, 96%), which was used directly without purification.

Example 50-6

Synthesis of 2-(2-sulfamoylphenoxy)acetamide

Scheme XXXVIII

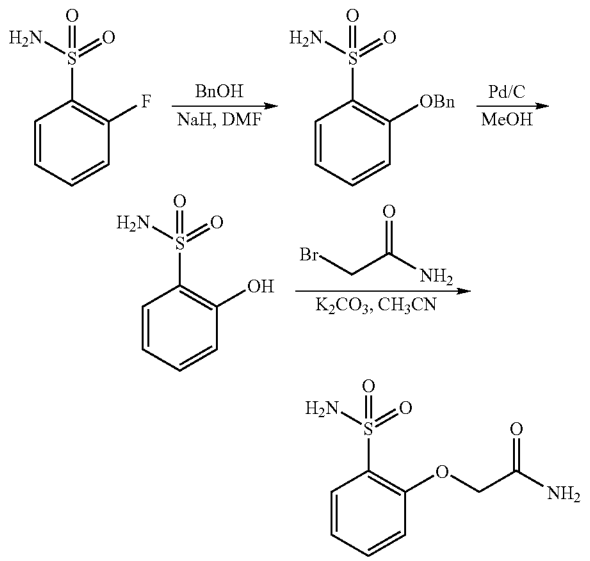

2-(2-Sulfamoylphenoxy)acetamide can be prepared according to the method of Scheme XXXVIII. 2-Sulfamoyl fluorobenzene can be reacted with benzyl alcohol under basic conditions to afford 1-(phenoxymethyl)-2-sulfamoylbenzene. For example, the base can be sodium hydride, potassium hydride, lithium hydride, cesium carbonate, sodium carbonate, potassium carbonate, and the like. The benzyl group of 1-(phenoxymethyl)-2-sulfamoylbenzene can be cleaved by hydrogenolysis to afford 1-(hydroxy)-2-sulfamoylbenzene. For example, the hydrogenolysis can be catalyzed using a catalyst, such as Pd/C in the presence of hydrogen or a hydrogen source. The hydrogen source can be formic acid, hydrazine, and the like. The phenoxy group of 1-(hydroxy)-2-sulfamoylbenzene can be alkylated with 2-bromoacetamide in the presence of a base, such as cesium carbonate, sodium carbonate, potassium carbonate, sodium bicarbonate, potassium bicarbonate, and the like, to afford 2-(2-sulfamoylphenoxy)acetamide.

Example 50-7

Preparation of 1-(phenoxymethyl)-2-sulfamoylbenzene

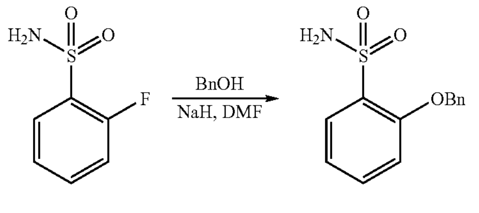

To a solution of benzyl alcohol (1 g, 8.6 mmol) in 10 mL of dry DMF was added to NaH (0.7 g, 17.1 mmol.) at 0° C. The reaction mixture was stirred at 0° C. for 30 min under $N_2$. To the resulting mixture was added 2-sulfamoyl fluorobenzene (1 g, 5.7 mmol.) in 20 mL of dry DMF. The reaction mixture was stirred at 80-90° C. for 3 hours. After cooling to r.t., the reaction mixture was poured into ice-water and neutralized with aq. HCl (2 M) to pH 7. The mixture was extracted with ethyl acetate (3×50 mL). The combined organic layer was over $Na_2SO_4$, filtered and concentrated to afford crude 1-(phenoxymethyl)-2-sulfamoylbenzene (1 g, 66.7%), which was used directly without further purification.

Example 50-8

Preparation of 1-(hydroxy)-2-sulfamoylbenzene

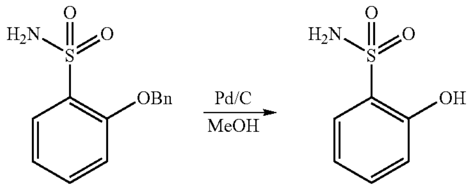

To a solution of crude 1-(phenoxymethyl)-2-sulfamoylbenzene (1.6 g, 6 mmol.) in 200 mL of methanol was added Pd/C (0.64 g). The reaction mixture was stirred at room temperature for 5 hours under $H_2$ with a pressure of 30 psi. After the material was consumed, the reaction mixture was filtered. The solvent was evaporated to give crude 1-(hydroxy)-2-sulfamoylbenzene (800 mg, 80%) which was used directly without purification.

Example 50-9

Preparation of 2-(2-sulfamoylphenoxy)acetamide

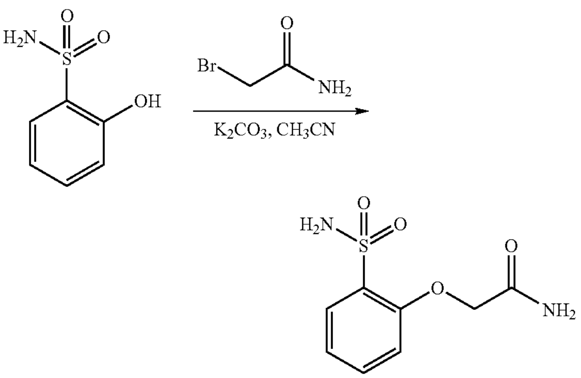

To a solution of crude 1-(hydroxy)-2-sulfamoylbenzene (400 mg, 2.4 mmol.) in 60 mL of acetonitrile was added 2-bromoacetamide (332 mg, 2.4 mmol.), $K_2CO_3$ (662 mg, 4.8 mmol.) and KI (400 mg, 2.4 mmol.). The reaction mixture was stirred at room temperature for 4 h. The reaction mixture was filtered, concentrated and purified by prep-TLC to afford 2-(2-sulfamoylphenoxy)acetamide (260 mg, 47%).

Example 50-10

Synthesis of 2-(2-Sulfamoylphenoxy)-N-methylacetamide

Scheme XXXIX

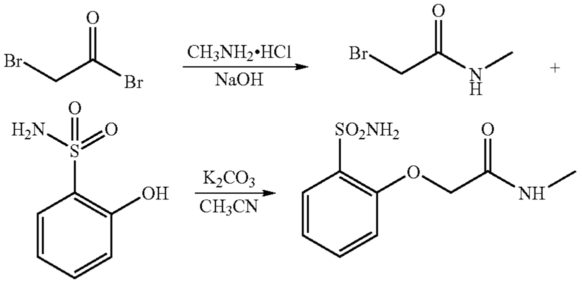

2-(2-Sulfamoylphenoxy)-N-methylacetamide can be prepared according to the method of Scheme XXXIX. Bromoacetyl bromide can be reacted methylamine hydrochloride in the presence of a base, such as sodium hydroxide to afford 2-bromo-N-methylacetamide. The phenoxy group of 1-(hydroxy)-2-sulfamoylbenzene can be alkylated with 2-bromo-N-methylacetamide in the presence of a base, such as cesium carbonate, sodium carbonate, potassium carbonate, sodium bicarbonate, potassium bicarbonate, and the like, to afford 2-(2-sulfamoylphenoxy)-N-methylacetamide.

Example 50-11

Synthesis of 2-Bromo-N-methylacetamide

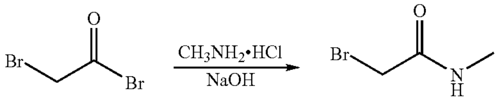

To a solution of NaOH (0.64 g, 16 mmol.) in 3 mL of water and 3 mL of DCM was added methylamine hydrochloride (0.51 g, 7.5 mmol.). To the mixture was added bromoacetyl bromide (1 g, 5 mmol.) in 3 mL of DCM at −10° C. The reaction mixture was stirred at −10° C. for 30 min, then at room temperature for 2 h. The organic layer was separated, washed with brine and dried over $Na_2SO_4$. The solvent was evaporated to give crude 2-bromo-N-methylacetamide (400 mg, 54%), which was used directly without purification.

Example 50-12

Synthesis of 2-(2-Sulfamoylphenoxy)-N-methylacetamide

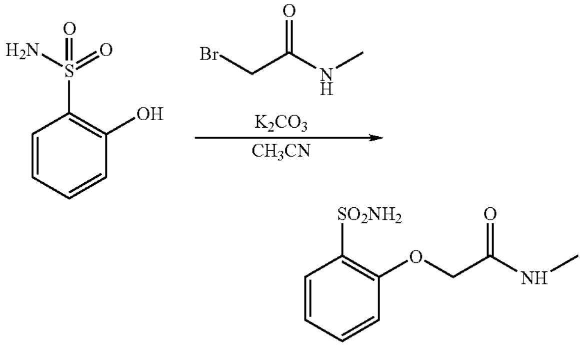

To a solution of crude 1-(hydroxy)-2-sulfamoylbenzene (400 mg, 2.4 mmol.) in 60 mL of acetonitrile was added 2-bromo-N-methylacetamide (332 mg, 2.4 mmol.), $K_2CO_3$ (662 mg, 4.8 mmol.) and KI (400 mg, 2.4 mmol.). The reaction mixture was stirred at room temperature for 4 h. The reaction mixture was filtered, concentrated and purified by prep-TLC to afford 2-(2-sulfamoylphenoxy)-N-methylacetamide (260 mg, 47%).

Preparation of NS3 Inhibitors: Section X

Example 51-1

Synthesis of Compound 707

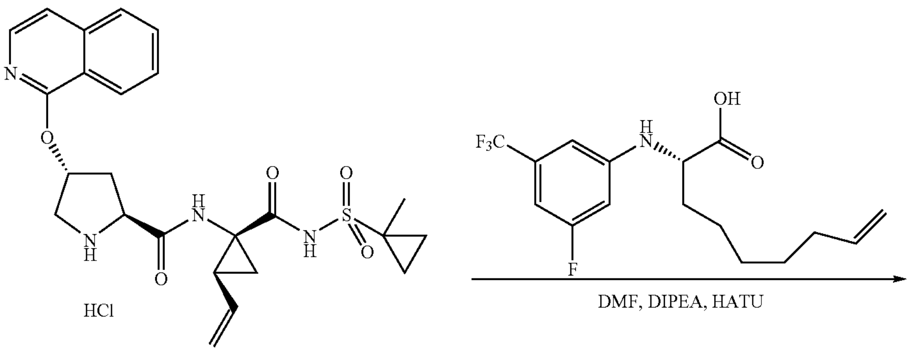

706

-continued

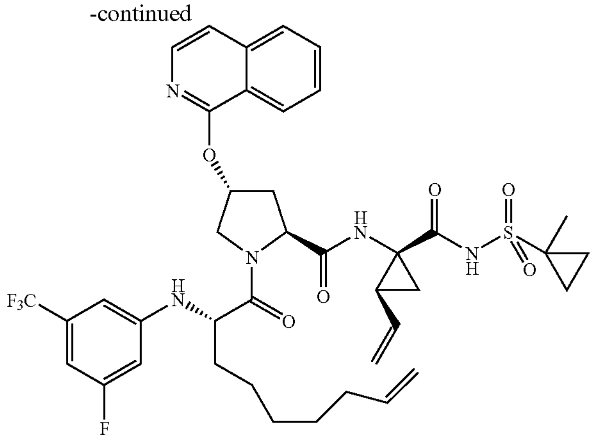

707

General Method Z

Deprotected heteroaryl ether intermediate 706 (HCl salt, 500 mg, 1.03 mmol., 1.0 eq.) and N,N-dimethylformamide (9 mL) were charged into a 25 mL round bottom flask under nitrogen. HATU (505 mg, 1.33 mmol., 1.3 eq.) and diisopropylethylamine (665 mg, 5.15 mmol., 5.0 eq.) were added and the reaction mixture stirred at ambient temperature for a further 15 minutes. (S)-2-(3-fluoro-5-(trifluoromethyl)phenylamino)non-8-enoic acid (376 mg, 1.13 mmol., 1.1 eq.) was added as a single portion and stirring was continued at ambient temperature for a further 15 hours. Monitoring the reaction extent by LCMS showed full consumption of the starting material. The solvent was removed under vacuum and the residue partitioned between dichloromethane (20 mL) and water (20 mL). The organic phase was washed with water (10 mL), brine (10 mL), dried over $Na_2SO_4$, filtered and concentrated to dryness. The residue was purified by flash column chromatography, using a heptanes:ethyl acetate gradient (from 95:5 to 50:50). After combining the relevant fractions and solvent removal, 531 mg (65%) of compound 707 was isolated as a yellow glassy solid. $^1$H NMR (500 MHz, $CDCl_3$) δ ppm 10.21 (br. s, 1 H) 8.06 (d, J=8.24 Hz, 1 H) 7.99 (d, J=5.95 Hz, 1 H) 7.78 (d, J=8.24 Hz, 1 H) 7.66-7.73 (m, 1 H) 7.54 (t, J=7.55 Hz, 1 H) 7.30 (d, J=5.80 Hz, 1 H) 6.87 (s, 1 H) 6.61 (d, J=8.39 Hz, 1 H) 6.58 (s, 1 H) 6.38 (d, J=10.83 Hz, 1 H) 6.04 (br. s, 1 H) 5.73-5.85 (m, 2 H) 5.24 (dd, J=17.17, 0.99 Hz, 1 H) 5.13 (dd, J=10.38, 1.22 Hz, 1 H) 5.08 (d, J=9.77 Hz, 1 H) 4.99 (dd, J=17.17, 1.75 Hz, 1 H) 4.94 (dt, J=10.19, 0.93 Hz, 1 H) 4.50 (t, J=8.39 Hz, 1 H) 4.05-4.17 (m, 3 H) 2.53-2.65 (m, 2 H) 2.02-2.09 (m, 4 H) 1.77-1.87 (m, 2 H) 1.68-1.75 (m, 2 H) 1.51 (s, 3 H) 1.44-1.49 (m, 2 H) 1.32-1.43 (m, 4 H) 0.82-0.96 (m, 3 H). LC-MS: purity 92% (UV), $t_R$ 2.79 min, m/z $[M+H]^+$ 800.35.

Example 51-1

Procedure for the Synthesis of Compound 1074

Scheme XXXX

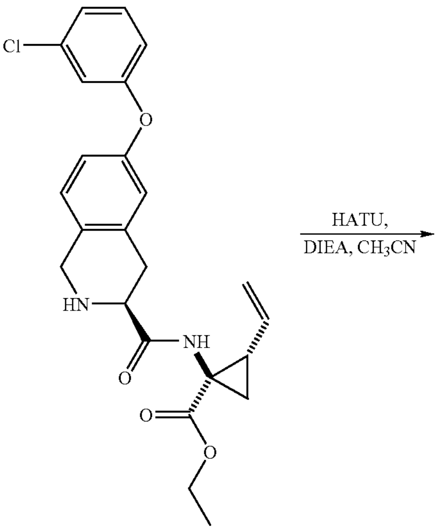

708

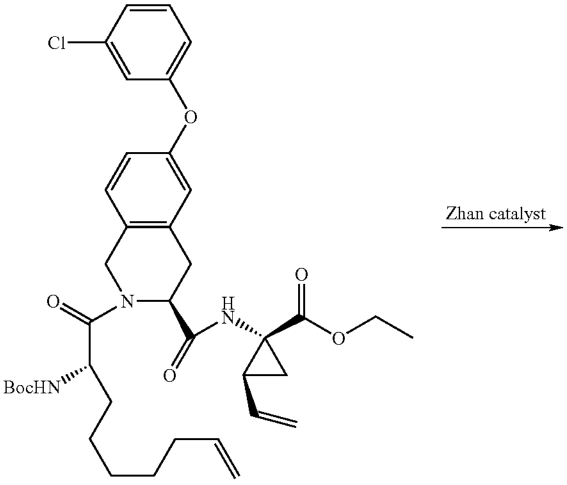

709

-continued

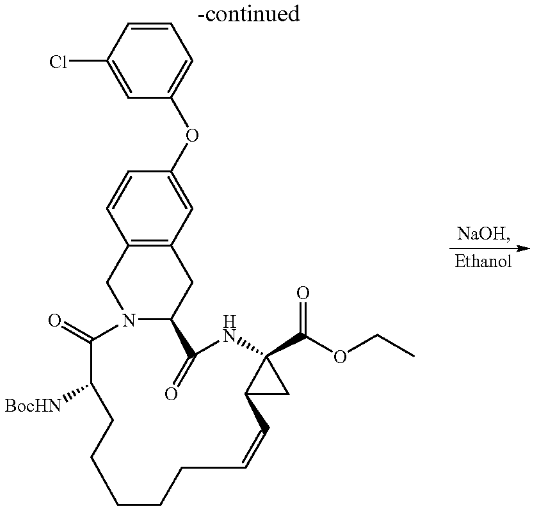

1073

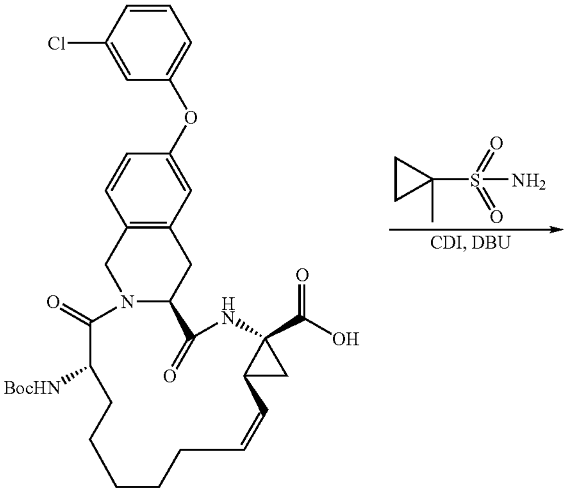

710

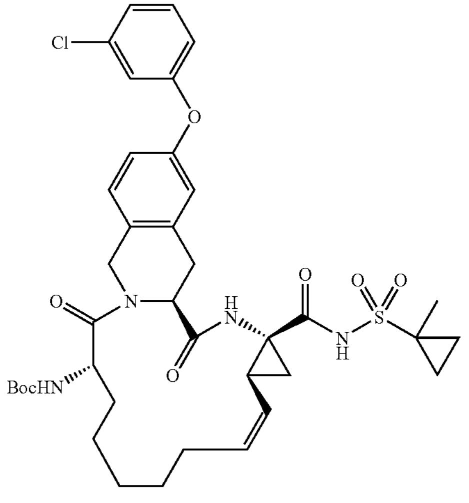

1074

Compound 1074 can be prepared according to the method of Scheme XXXX. Compound 708 can be coupled with (S)-2-(tert-butoxycarbonyl)aminonon-8-enoic acid to afford compound 709. For example, the coupling reagents can be CDI, DCC, DIC, EDAC, HOSu, HOBt, HOAt, PyBOP, PyBrOP, HBTU, HATU, TBTU, combinations thereof, and the like. Compound 709 can be cyclized using an olefin metathesis catalyst, such as a Schrock catalyst, a Grubb's catalyst, a Zhan catalyst, a Hoveyda catalyst, a Nolan catalyst, and the like. The ester of compound 709 can be hydrolyzed under basic conditions, such as sodium hydroxide in ethanol and optionally water, and the like, to afford compound 710. Compound 708 can be coupled with 1-methylcyclopropane-1-sulfonamide to afford compound 1074. For example, the coupling reagents can be CDI, DCC, DIC, EDAC, HOSu, HOBt, HOAt, PyBOP, PyBrOP, HBTU, HATU, TBTU, combinations thereof, and the like.

Example 51-2

Synthesis of Compound 709

709

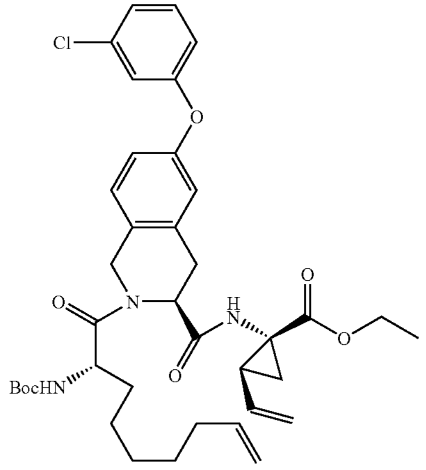

Compound 709 was prepared following General Method Z, and the yield is 78%. MS (ESI) m/e (M+H$^+$) 693.3.

Example 51-3

Synthesis of Compound 1073

1073

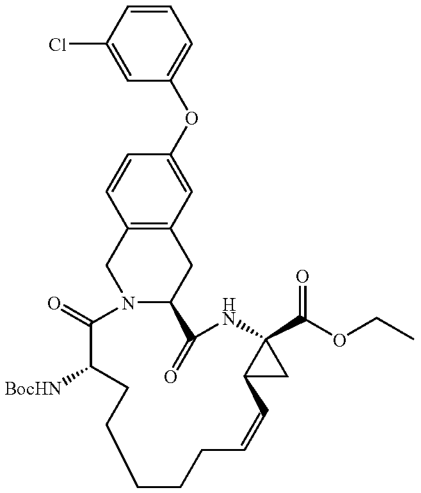

General Method AA

To a solution of compound 709 (200 mg, 0.288 mmol.) in 2 mL of anhydrous toluene was added Zhan catalyst (30 mg, 0.044 mmol.), this solution was stirred at 50° C. overnight. The reaction mixture was concentrated to give a residue, the crude product was purified by Prep-TLC to afford compound 1073 (70 mg, 37%) as white solid. MS (ESI) m/e (M+H$^+$) 665.3.

Example 51-4

Synthesis of Compound 1074

1074

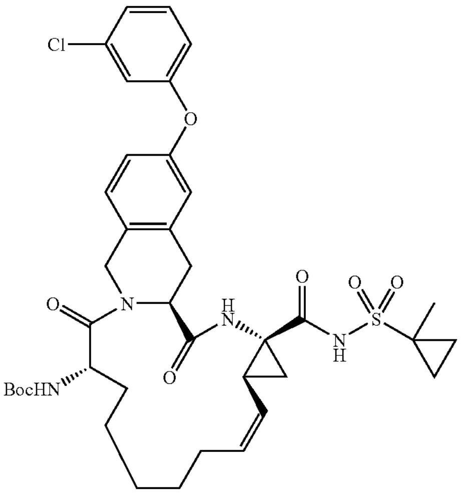

Compound 1074 was prepared following General Method S, and the yield is 18%. MS (ESI) m/e (M+H$^+$) 754.3.

Example 52-1

Synthesis of 2-phenyl-4-chloro-7-methoxy-quinoline

Scheme XXXXI

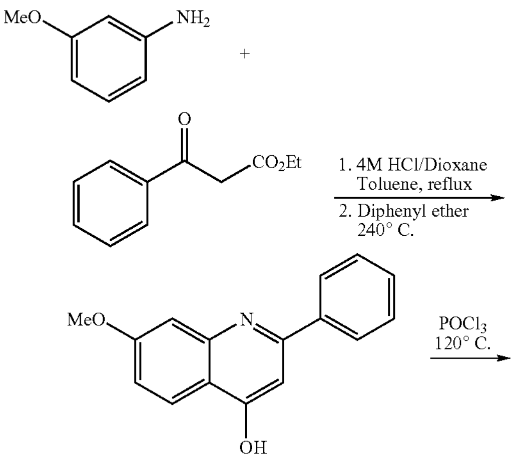

-continued

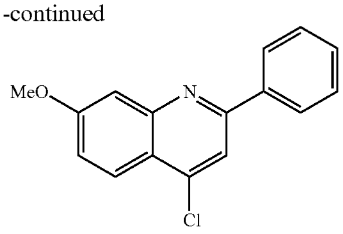

2-Phenyl-4-chloro-7-methoxy-quinoline can be prepared according to Scheme XXXXI. Ethyl benzoylacetate and m-anisidine can reacted together under thermal conditions to afford 2-phenyl-4-hydroxy-7-methoxy-quinoline in the presence of an acid, such as hydrochloric acid and the like. 2-Phenyl-4-hydroxy-7-methoxy-quinoline can be converted to 2-phenyl-4-chloro-7-methoxy-quinoline using a chlorinating agent. For example, the chlorinating can be $P(O)Cl_3$, $P(O)Cl_3$ with $PCl_5$, and the like.

Example 52-2

Synthesis of 2-phenyl-4-hydroxy-7-methoxy-quinoline

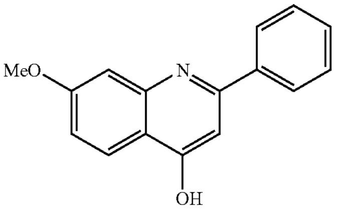

General Method BB

To a solution of ethyl benzoylacetate (10.00 g, 52.0 mmol., 1 eq) and m-anisidine (7.05 g, 57.2 mmol., 1.1 eq) in toluene (85 mL) was added 4M HCl in dioxane (0.520 mL, 2.08 mmol., 0.04 eq) drop wise. The reaction mixture was refluxed over night while ethanol and water were collected in a Dean and Stark's apparatus. The reaction mixture was left to cool to ambient temperature and the solvent removed under vacuum. The residue was suspended in diphenyl ether (28 mL) and the mixture was heated for 2 h at 240° C. The reaction mixture was then left to cool to ambient temperature and dichloromethane (55 mL) was added, leading to the precipitation of a yellow solid. Stirring was continued at ambient temperature for a further 30 min and the solid collected by filtration, rinsing the cake with a small amount of dichloromethane. The solid was transferred to a 100 ml round bottom flask and stirred with dichloromethane (50 mL) for another 45 min at ambient temperature. After filtration and drying under high vacuum, the title compound, 2-phenyl-4-hydroxy-7-methoxy-quinoline, was isolated as a pale yellow solid. Yield: 2.85 g (22%). $^1H$ NMR (250 MHz, DMSO-$d_6$) δ 11.54 (s, 1 H), 7.99 (d, J=8.91 Hz, 1 H), 7.73-7.90 (m, 2 H), 7.48-7.64 (m, 3H), 7.20 (d, J=2.32 Hz, 1 H), 6.94 (dd, J=2.34, 8.97 Hz, 1 H), 6.26 (s, 1 H), 3.86 (s, 3 H). LC-MS: purity 97% (ELS) 98% (UV), $t_R$ 1.52 min, m/z $[M+1]^+$ 252.10.

Example 52-2

Synthesis of 2-Phenyl-4-chloro-7-methoxy-quinoline

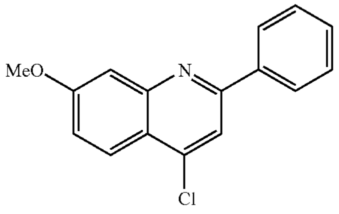

General Method CC

2-Phenyl-4-hydroxy-7-methoxy-quinoline (2.73 g, 10.9 mmol., 1 eq) was suspended in neat phosphorus oxychloride (30 mL). The reaction mixture was heated under reflux. After 2 h, LCMS analysis showed full conversion of the starting material. The reaction mixture was left to cool to ambient temperature and the solvent removed under vacuum. The residue was partitioned between ethyl acetate (100 mL) and 2M aqueous sodium hydroxide solution (80 mL). The mixture was stirred at ambient temperature for a further 10 min, and then the two layers were separated. The organic phase was washed with water (2×50 mL) and saturated aqueous sodium chloride solution (50 mL), dried over sodium sulfate, filtered and the solvent removed under vacuum. The obtained solid, 2-phenyl-4-chloro-7-methoxy-quinoline, was further dried under high vacuum for 2 h. Yield: 2.66 g (91%). $^1H$ NMR (250 MHz, DMSO-$d_6$) δ 8.25-8.35 (m, 2 H), 8.21 (s, 1 H), 8.09 (d, J=9.14 Hz, 1 H), 7.47-7.61 (m, 4 H), 7.38 (dd, J=2.55, 9.18 Hz, 1 H), 3.97 (s, 3 H). LC-MS: purity 100% (ELS) 100% (UV), $t_R$ 2.58 min, m/z $[M+1]^+$ 270.00

Example 53-1

Synthesis of Compound 1075

Scheme XXXXII

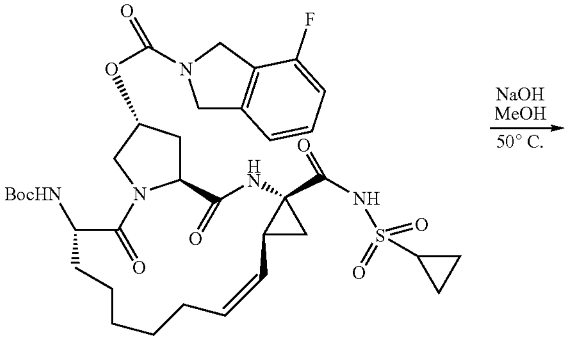

10

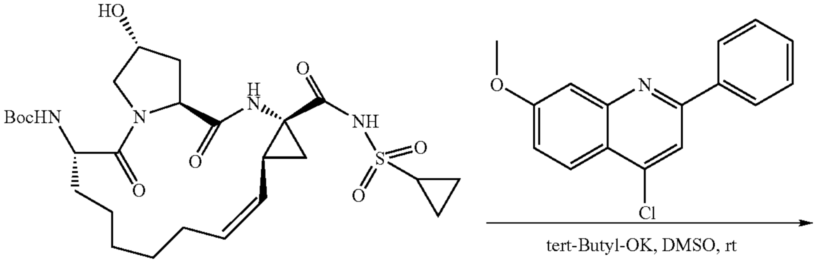

11

-continued

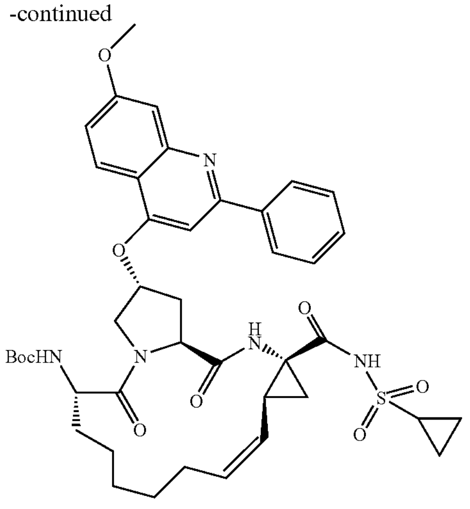

1075

Compound 1075 can be prepared according to Scheme XXXXII. Compound 10 can be treated with a base, such as sodium hydroxide, to hydrolyze the isoindoline carbamate, thereby affording compound 11. The alcohol, compound 11, can be treated with a base, such as sodium hydride, potassium hydride, lithium hydride, cesium carbonate, sodium carbonate, potassium carbonate, potassium tert-butoxide, and the like, then reacted with 2-phenyl-4-chloro-7-methoxy-quinoline to afford compound 1075.

Example 53-2

Synthesis of Compound 11

11

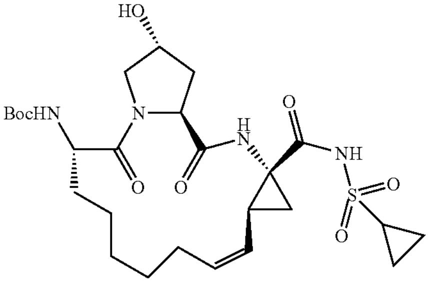

General Method DD

To a solution of the carbamate 10 (3.00 g, 4.10 mmol.) in 26 mL of methanol was added 26 mL of 5M aqueous sodium hydroxide. Precipitated material was not re-dissolved at 50° C. so further methanol (10 mL) was added. The resulting clear solution was stirred at 50° C. for 17 h when LCMS showed the reaction to be complete. The solution was cooled below 10° C. and 2M aqueous hydrochloric acid solution was added slowly until ~pH 4, much product had precipitated at this stage. The resulting gum and aqueous solution were stirred with ethyl acetate (30 mL) until all was in solution. The aqueous layer was further extracted with of ethyl acetate (3×30 mL). The combined organic layers were washed twice with brine, dried over $Na_2SO_4$, filtered and the solvent removed under vacuum to give beige solid (2.50 g) which was purified by flash column chromatography using a methanol/dichloromethane gradient (neat DCM to 5% MeOH in DCM). The relevant fractions were combined and the solvent removed under vacuum to afford compound 11 as a beige solid. Yield 1.98 g (85%). $^1H$ NMR (250 MHz, $CDCl_3$) δ 10.60 (br. s, 0.2 H), 10.46 (s, 0.8 H), 8.48 (br. s, 0.2 H), 7.74 (s, 0.8 H), 6.60 (br. s, 0.2 H), 5.56-5.81 (m, 1 H), 5.34 (m, 0.8 H), 4.85-5.03 (m, 1 H), 4.41-4.73 (m, 2 H), 4.28 (br. s, 1 H), 3.39-4.10 (m, 3 H), 2.73-2.98 (m, 1 H), 2.06-2.63 (m, 4H), 1.68-2.05 (m, 3 H), 1.20-1.67 (m, 17 H), 0.65-1.13 (m, 4 H). LC-MS: purity 100% (ELS) 99% (UV), $t_R$ 1.89 min, m/z $[M+Na]^+$ 591.

Example 53-3

Synthesis of 1075

1075

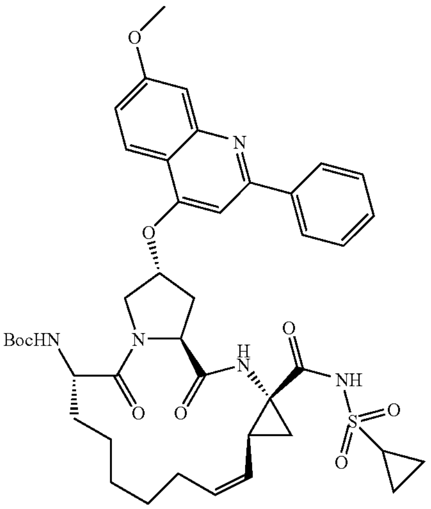

General Method EE

To a solution of compound 11 (1.00 g, 1.76 mmol., 1 eq) and 2-phenyl-4-chloro-7-methoxy-quinoline (0.520 g, 1.934 mmol., 1.1 eq) in dimethyl sulfoxide (20 mL) was added potassium tert-butoxide (0.790 g, 7.04 mmol., 4 eq) portion-wise. Stirring was continued at ambient temperature for 17 h. The reaction was monitored by LCMS showing complete disappearance of the starting material as well as partial N-butoxycarbonyl cleavage. The reaction mixture was cooled to 0° C. and quenched with water (10 mL). The resulting mixture was partitioned between ethyl acetate (40 mL) and water (30 mL). The organic phase was collected and the aqueous phase was further extracted with ethyl acetate (2×40 mL). The organic extracts were combined, washed with brine (50 mL), dried over sodium sulphate, filtered and the solvent was removed under vacuum. The residue was purified by flash column chromatography using a methanol/dichloromethane gradient (neat DCM to 2% MeOH in DCM). The relevant fractions were combined and the solvent removed under vacuum to afford compound 1075 as an off-white glassy solid. Yield 0.468 g (33%). $^1$H NMR (500 MHz, $CDCl_3$) δ 10.25 (br. s, 1 H), 7.98-8.10 (m, 3 H), 7.51-7.58 (m, 2 H), 7.45-7.50 (m, 1 H), 7.43 (d, J=2.02 Hz, 1 H), 7.03 (dd, J=2.50, 9.10 Hz, 1 H), 6.99 (s, 1 H), 6.94 (s, 1 H), 5.68 (q, J=8.83 Hz, 1 H), 5.37 (br. s, 1H), 5.13 (d, J=7.66 Hz, 1 H), 4.96 (t, J=9.38 Hz, 1 H), 4.77 (d, J=11.37 Hz, 1 H), 4.59 (t, J=7.93 Hz, 1 H), 4.52-4.64 (m, 1 H), 4.32 (ddd, J=3.07, 7.93, 10.73 Hz, 1 H), 4.04 (dd, J=3.30, 11.05 Hz, 1 H), 3.96 (s, 3 H), 2.82-2.94 (m, 1 H), 2.68-2.77 (m, 1 H), 2.62-2.68 (m, 1 H), 2.50-2.60 (m, 1 H), 2.33 (q, J=8.48 Hz, 1 H), 1.77-1.94 (m, 3 H), 1.54-1.70 (m, 2 H), 1.42-1.49 (m, 4 H), 1.36 (s, 9 H), 1.26-1.32 (m, 2 H), 1.01-1.16 (m, 2 H), 0.84-0.96 (m, 1 H). LC-MS: purity 96% (ELS) 99% (UV), $t_R$ 1.88 min, m/z $[M+1]^+$ 802.

Example 54-1

Synthesis of Compounds and 1078

Compound 1078 can be synthesized by one of the preceding methods:

1078

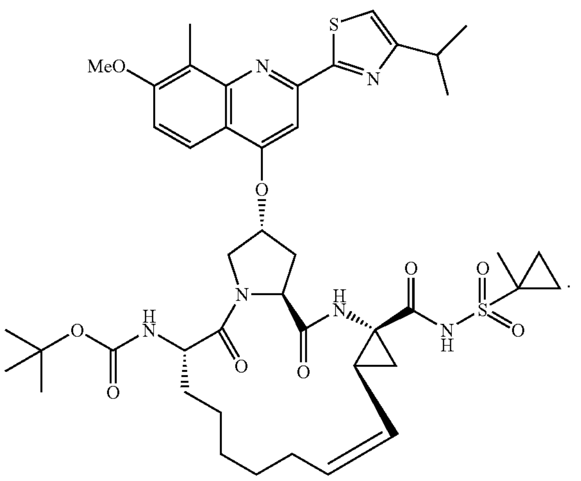

Example 55-1

Synthesis of N-aryl Amines

Scheme XXXXIII

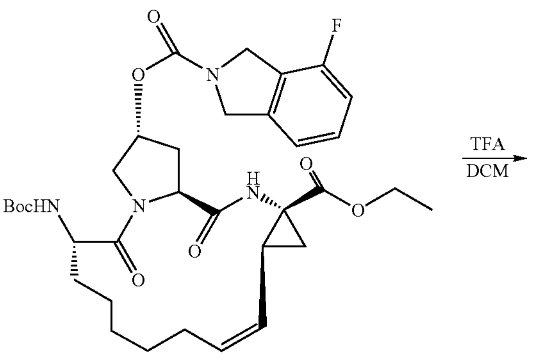

16

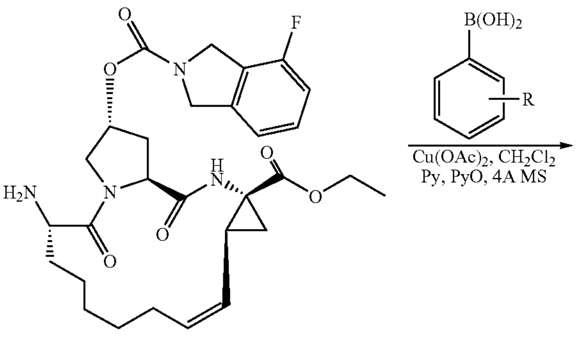

17

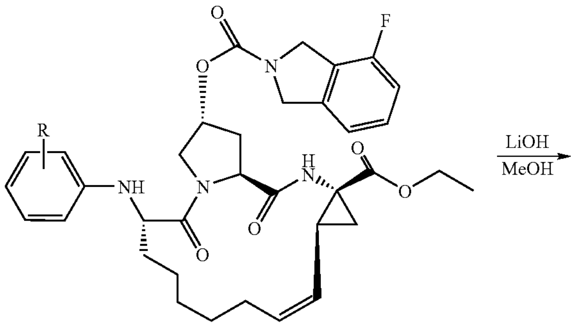

VII-A

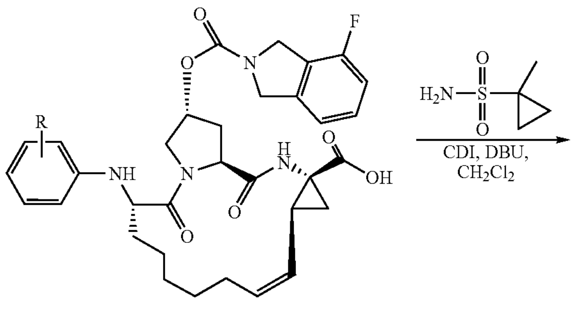

VII-B

-continued

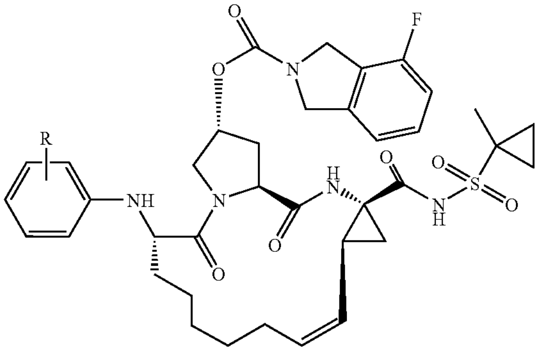

VII-C

Compounds having having the general structure VII-C can be synthesized as shown in Scheme XXXXIII. The isoindoline carbamate 16 can be treated with acid, for example TFA in DCM, to remove the Boc protecting group thereby providing compound 17. Compound 17 can be treated with an optionally substituted aryl boronic acids under $Cu^{2+}$-catalyzed conditions thereby providing a compound having the general structure VII-A. A compound having the general structure VII-A can be treated under basic conditions to hydrolyse the ethyl ester and the isoindoline carbamate thereby providing an acid having the general structure VII-B. The acid having the general structure VII-B can be coupled with 1-methylcyclopropane-1-sulfonamide to afford a compound having the general structure VII-C. For example, the coupling reagents can be CDI, DCC, DIC, EDAC, HOSu, HOBt, HOAt, PyBOP, PyBrOP, HBTU, HATU, TBTU, combinations thereof, and the like.

Example 55-2

Preparation of Compound 17

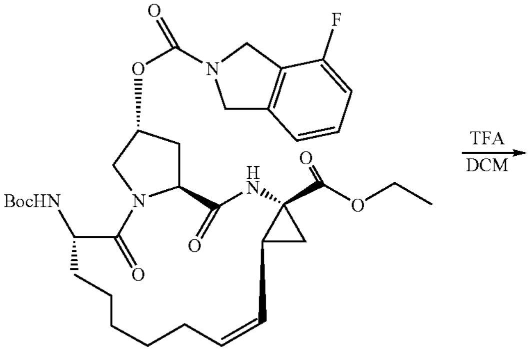

16

-continued

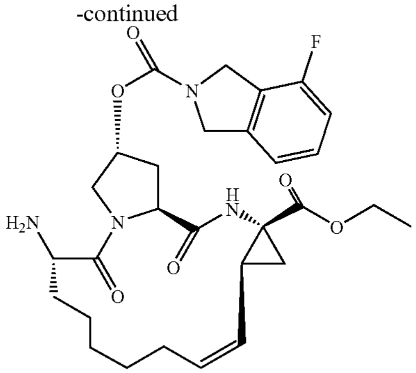

17

General Method XCX

To a solution of compound 16 (2 g, 3.0 mmol.) in dichloromethane (20 mL) was added 10 mL of trifluoroacetic acid, the resulting mixture was stirred at room temperature for 2 h, after that, the solvent was removed, the mixture was basified by aqueous $NaHCO_3$, extracted by ethyl acetate (3×100 mL), the organic layers were combined, washed by brine, dried over anhydrous sodium sulfate, the solvent was removed under reduced pressure, the crude compound 17 (1.6 g) was used directly in the next step.

Example 55-3

General Procedure for Preparation of Compounds of General Structure VII-A

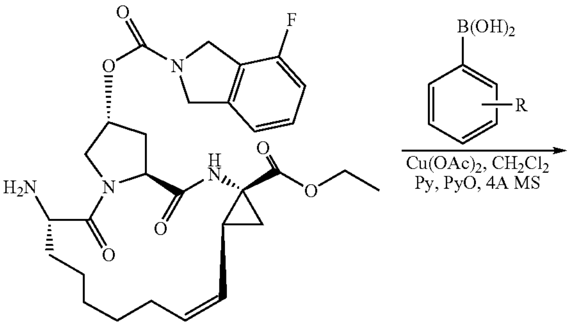

17

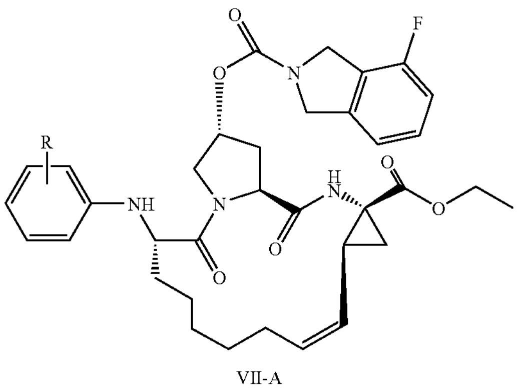

VII-A

General Procedure XA

A mixture of compound 17 (350 mg, 0.50 mmol.), optionally substituted phenylboronic acid (1.5 mmol.), $Cu(OAc)_2$ (188 mg, 1.0 mmol.), pyridine (316 mg, 4 mmol.), pyridine N-Oxide (47.5 mg, 0.5 mmol.) and molecular sieves 4 A in dichloromethane (10 mL) was stirred for 12 h at room temperature opening to the air. The reaction was monitored by LC-MS. After completion of the reaction, the reaction mixture was diluted with ethyl acetate (100 mL) and filtered. The filtrate was washed with brine, dried over anhydrous sodium sulfate, concentrated in vacuo. The residue was purified by prep-TLC (eluted with PE/EtOAc=1/1) to afford a compound of general structure VII-A. (yield 40-60%).

Example 55-4

General Procedure for Preparation of Compounds of General Structure VII-B

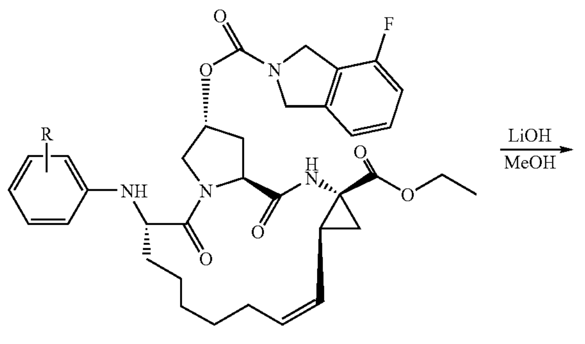

VII-A

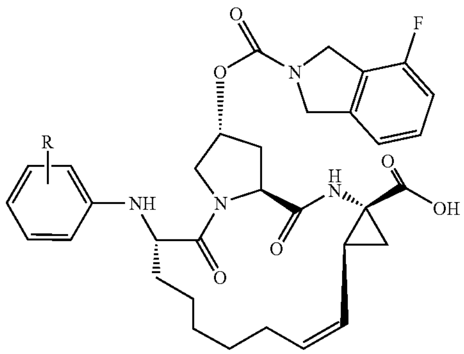

VII-B

General Procedure XB

To a solution of a compound of general structure VII-A (1 eq.) in methanol (10 mL) is added LiOH (30 eq.) and some water, the resulting mixture was stirred at room temperature overnight, after completion of the reaction, The mixture was cooled by ice water, acidified by aq. HCl (2 M) to pH=3-4, then the mixture was extracted by ethyl acetate (50 mL×3), the organic layers were combined, washed by brine, dried over anhydrous sodium sulfate, the solvent was removed under reduced pressure, the crude was purified by prep-TLC to provide a compound of general structure VII-B (EtOAc/Methanol=10:1) (yield 80-90%).

Example 55-5

General Procedure for Preparation of Compounds of General Structure VII-C

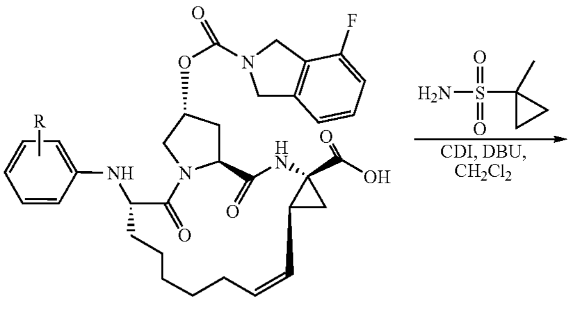

VII-B

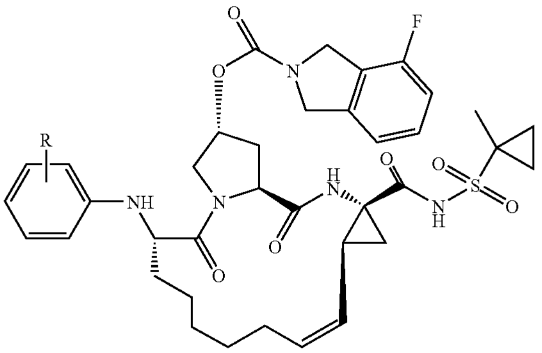

VII-C

General Procedure XC

To a solution of a compound of general structure VII-B (1 eq.) in anhydrous dichloromethane was added CDI (4 eq.) under nitrogen protection. The resulting mixture was stirred at 35° C. for 2 h, then 1-methylcyclopropane-1-sulfonamide (4 eq.) and DBU (8 eq.) was added, the resulting mixture was stirred at room temperature for another 12 h and the reaction was monitored by LCMS. After completion of the reaction, the solvent was removed under reduced pressure and the residue was purified by prep-HPLC to give the final compound of general structure VII-C (yield 6-40%).

Example 55-6

Synthesis of Compound 1100

1100

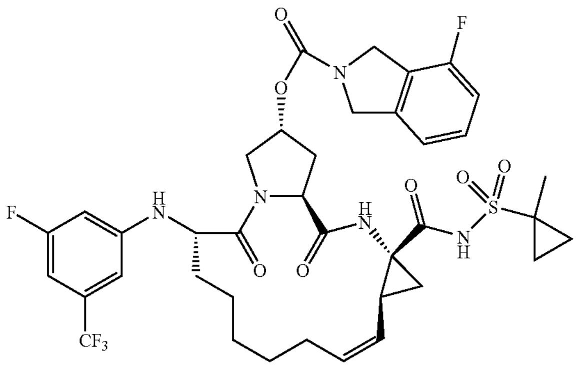

Compound 1100 was prepared in a manner analogous to General Procedure XC, to afford 140 mg (40% yield). MS (ESI) m/z $(M+H)^+$ 808.

Example 55-7

Synthesis of Compound 1101

1101

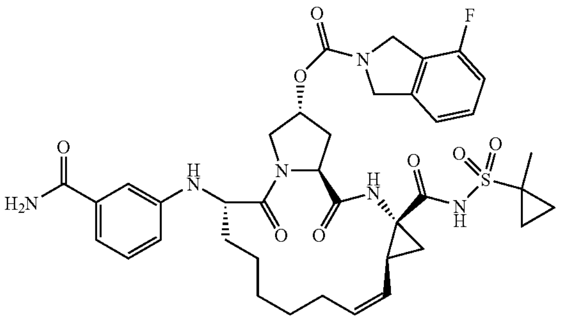

Compound 1101 was prepared in a manner analogous to General Procedure XC, to afford 5.4 mg (9% yield). MS (ESI) m/z $(M+H)^+$ 765.2.

Example 55-8

Synthesis of Compound 1102

1102

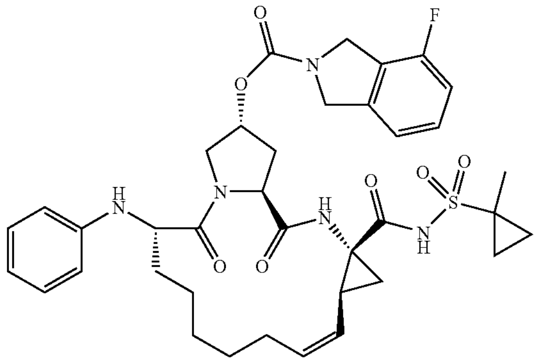

Compound 1102 was prepared in a manner analogous to General Procedure XC, to afford 26.4 mg (28% yield). MS (ESI) m/z $(M+H)^+$ 722.1.

Example 55-9

Synthesis of Compound 1103

1103

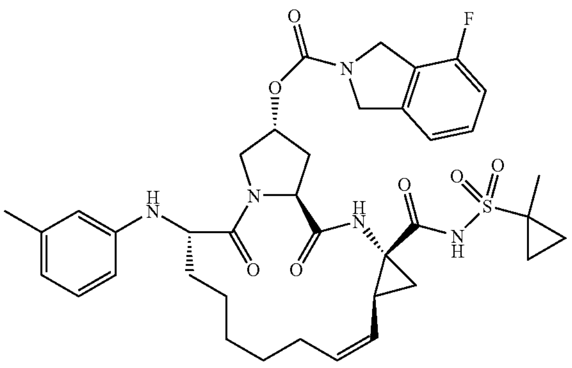

Compound 1103 was prepared in a manner analogous to General Procedure XC, to afford 36.1 mg (38% yield). MS (ESI) m/z $(M+H)^+$ 736.1.

Example 55-10

Synthesis of Compound 1104

1104

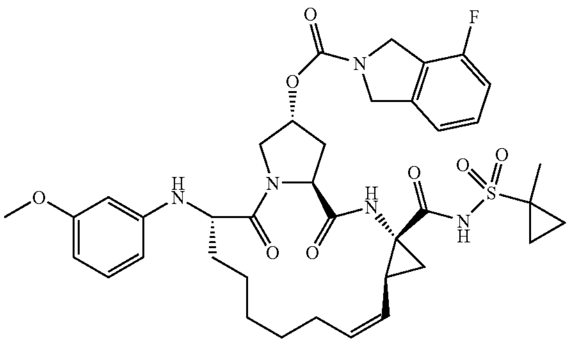

Compound 1104 was prepared in a manner analogous to General Procedure XC, to afford 22.7 mg (19% yield). MS (ESI) m/z $(M+H)^+$ 752.2.

Example 55-11

Synthesis of Compound 1105

1105

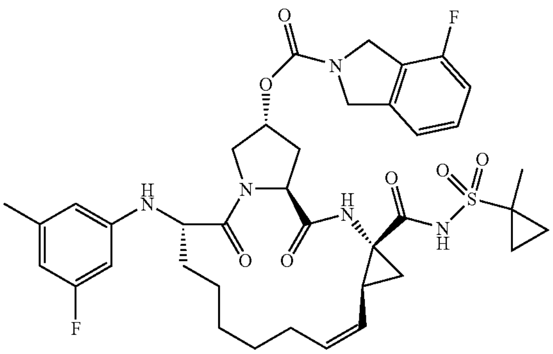

Compound 1105 was prepared in a manner analogous to General Procedure XC, to afford 22.5 mg (yield 19%). MS (ESI) m/z $(M+H)^+$ 754.2.

Example 55-12

Synthesis of Compound 1106 by General Procedure XC

1106

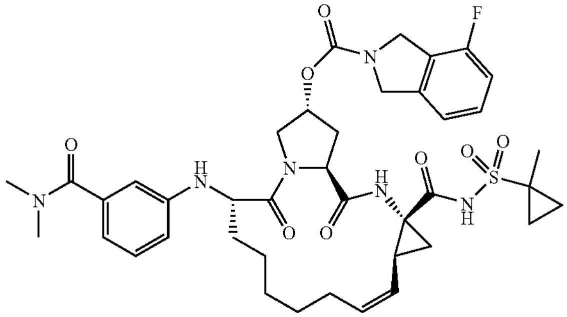

Compound 1106 was prepared in a manner analogous to General Procedure XC, to afford 5.5 mg (6% yield). MS (ESI) m/z $(M+H)^+$ 793.4.

Example 55-13

Synthesis of Compound 1107

1107

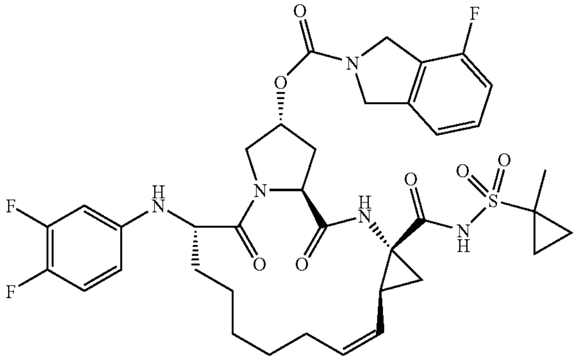

Compound 1107 was prepared in a manner analogous to General Procedure XC, to afford 5.2 mg (6% yield). MS (ESI) m/z $(M+H)^+$ 758.2.

Example 55-14

Synthesis of Compound 1108

1108

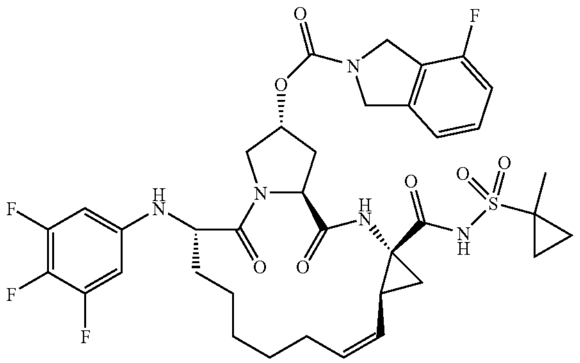

Compound 1108 was prepared in a manner analogous to General Procedure XC, to afford 5.6 mg (6% yield). MS (ESI) m/z $(M+Na)^+$ 798.2

Example 55-15

Synthesis of Compound 1109

1109

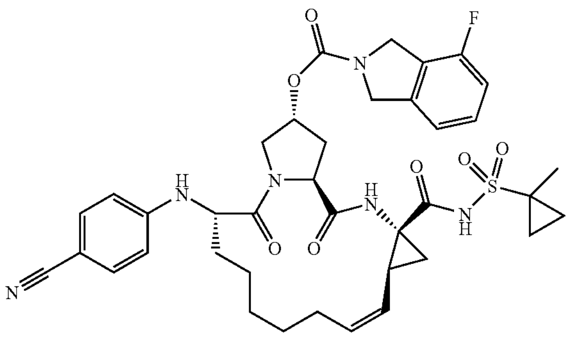

Compound 1109 was prepared in a manner analogous to General Procedure XC, to afford 20 mg (21% yield). MS (ESI) m/z $(M+H)^+$ 747.4.

Example 55-16

Synthesis of Compound 1110

1110

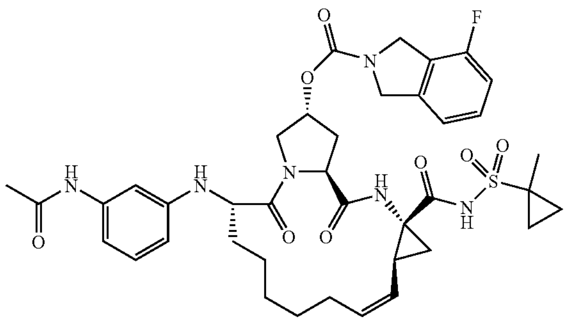

Compound 1110 was prepared in a manner analogous to General Procedure XC, to afford 41.3 mg (35% yield). MS (ESI) m/z $(M+Na)^+$ 801.5.

Example 55-17

Synthesis of Compound 1111

1111

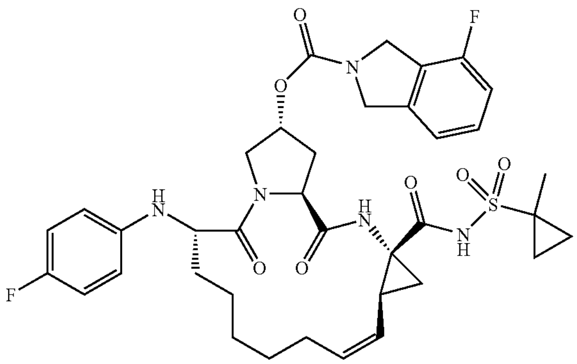

Compound 1111 was prepared in a manner analogous to General Procedure XC, to afford 5.4 mg (6% yield). MS (ESI) m/z $(M+H)^+$ 740.3.

Example 55-18

Synthesis of Compound 1112

1112

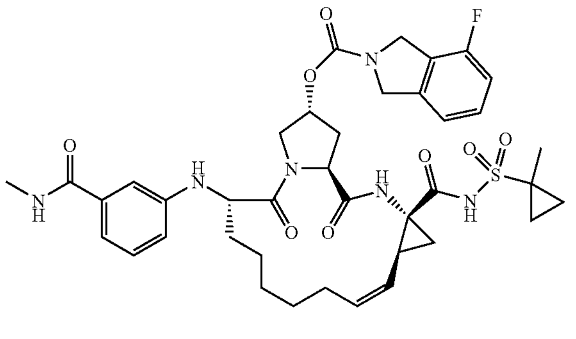

Compound 1112 was prepared in a manner analogous to General Procedure XC, to afford 5.4 mg (7% yield). MS (ESI) m/z $(M+H)^+$ 779.5.

Example 55-19

Synthesis of Compound 1113

1113

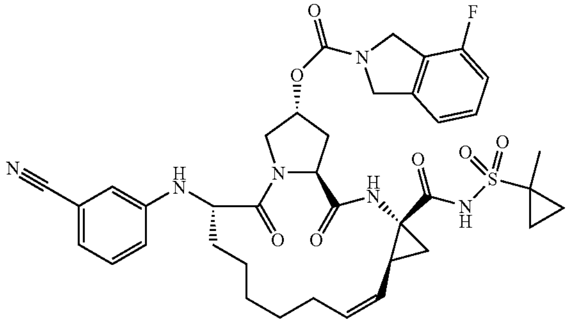

Compound 1113 was prepared in a manner analogous to General Procedure XC, to afford 6.5 mg, (11% yield). MS (ESI) m/z $(M+H)^+$ 747.3.

Example 55-20

Synthesis of Compound 1114

1114

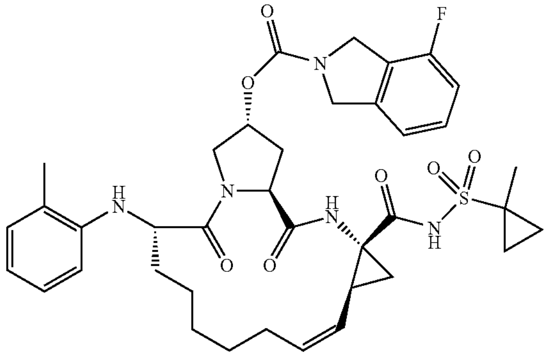

Compound 1114 was prepared in a manner analogous to General Procedure XC, to afford 30.1 mg (yield 36%). MS (ESI) m/z $(M+H)^+$ 736.

Example 55-21

Synthesis of Compound 1115

1115

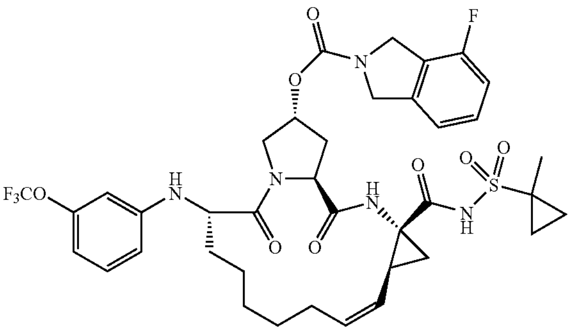

Compound 1115 was prepared in a manner analogous to General Procedure XC, to afford 5.6 mg (8% yield). MS (ESI) m/z $(M+H)^+$ 806.1.

Example 55-22

Synthesis of Compound 1116

1116

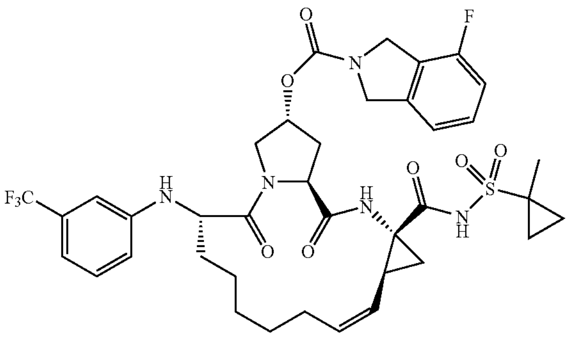

Compound 1116 was prepared in a manner analogous to General Procedure XC, to afford 5 mg (8.6% yield). MS (ESI) m/z $(M+H)^+$ 790.1.

Example 55-23

Synthesis of Compound 1117

1117

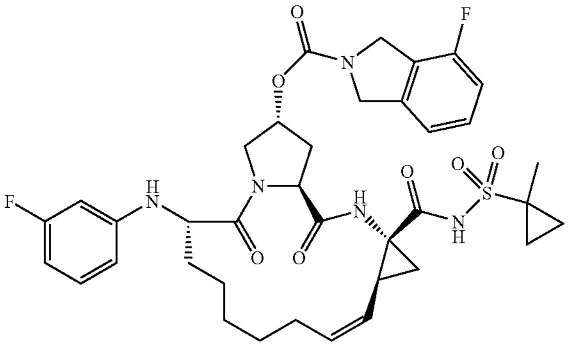

Compound 1117 was prepared in a manner analogous to General Procedure XC, to afford 5.1 mg (6% yield). MS (ESI) m/z $(M+H)^+$ 740.1.

Example 56-1

Synthesis of Compound 1128

Scheme XXXXIV

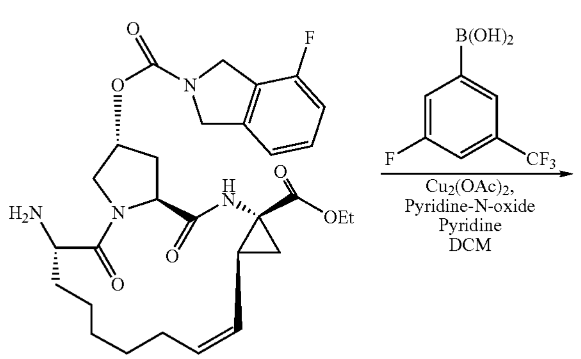

17

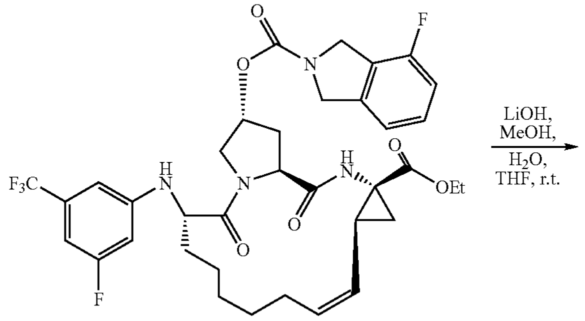

722

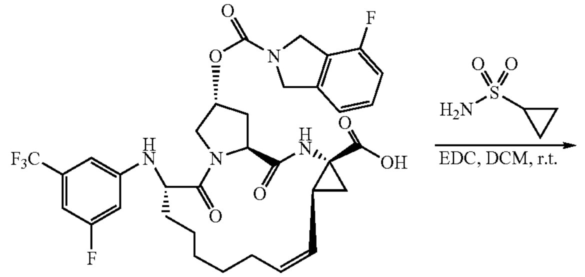

1070

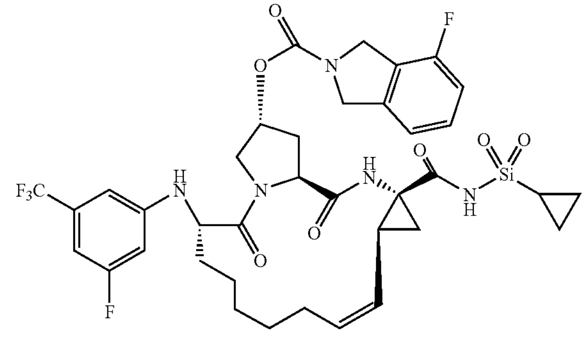

1128

Compound 1128 can be synthesized as shown in Scheme XXXXIV. Compound 17 can be treated with 3-fluoro-5-(trifluoromethyl)phenylboronic acid under $Cu^{2+}$-catalyzed conditions thereby providing compound 722. Compound 722 can be treated under basic conditions to hydrolyse the ethyl ester thereby providing compound 1070. For example, the base can be lithium hydroxide, sodium hydroxide, potassium hydroxide, and the like. Compound 1070 can be coupled with cyclopropane sulfonamide to afford compound 1128. For example, the coupling reagents can be CDI, DCC, DIC, EDAC, HOSu, HOBt, HOAt, PyBOP, PyBrOP, HBTU, HATU, TBTU, combinations thereof, and the like.

Example 56-2

722

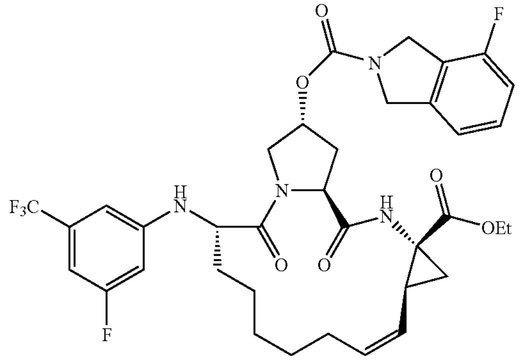

Copper (II) acetate (457 mg, 2.5 mmol, 1.4 eq.), pyridine (0.726 mL, 9.0 mmol, 5 eq.), pyridine-N-oxide (170 mg, 1.8 mmol, 1 eq.), 4 Å molecular sieves (700 mg) and dichloromethane (100 mL, previously saturated with air) were charged into reaction flask. Compound 17 (1 g, 1.8 mmol, 1 eq.) was added as a single portion and the reaction mixture was stirred for a further 5 min by when the initial light blue solution had turned dark blue. 3-fluoro-5-(trifluoromethyl) phenylboronic acid (370 mg, 1.8 mmol, 1 eq.) was added portion wise. The reaction mixture was stirred under an air atmosphere, at ambient temperature, for 72 hours. Water was added to the reaction mixture and the aqueous phase acidified to pH 5 with 1 M hydrochloric acid. The aqueous phase was further extracted with dichloromethane (100 mL). The organic layers were combined, washed with brine, dried over sodium sulfate and the solvent removed under vacuum to give 882 mg (68%) of the desired product as a brown foamy solid, which was used in the next step without further purification. LC-MS: 73% (UV), $t_R$ 2.61 min, m/z $[M+1]^+$ 719.35. $^1H$ NMR (250 MHz, $CDCl_3$) δ 6.82-7.16 (m, 3 H), 6.51-6.68 (m, 2 H), 6.40 (d, J=10.96 Hz, 1 H), 5.46-5.70 (m, 1 H), 5.34-5.47 (m, 1 H), 5.15-5.34 (m, 1 H), 5.01 (dd, J=4.26, 8.22 Hz, 1 H), 4.81-4.91 (m, 1 H), 4.76 (d, J=4.87 Hz, 2 H), 4.55-4.71 (m, 2 H), 4.37 (t, J=7.31 Hz, 1 H), 3.96-4.27 (m, 4H), 3.86 (d, J=10.66 Hz, 1 H), 2.69-2.96 (m, 1 H), 2.08-2.39 (m, 4 H), 1.86

(dd, J=5.48, 8.22 Hz, 3 H), 1.56 (dd, J=5.48, 9.75 Hz, 2 H), 1.33-1.48 (m, 3 H), 1.10-1.33 (m, 5 H).

Example 56-3

1070

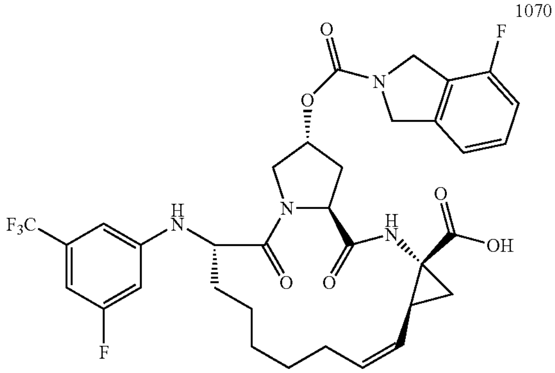

Compound 1070 (882 mg, 1.2 mmol., 1 eq.) and tetrahydrofuran (26 mL) were charged into reaction flask and the reaction mixture cooled on top of an ice bath for 5 minutes. Lithium hydroxide (128 mg, 3.06 mmol., 2.5 eq.) was dissolved in a mixture of water (26 mL) and methanol (13 mL) and the resulting solution was added dropwise to the reaction mixture. The reaction mixture was stirred at ambient temperature for a further 15 hours. LCMS analysis of a sample showed limited hydrolysis of the ester, so extra Lithium hydroxide (103 mg, 2 eq.) was added and the reaction mixture stirred for a further 24 hours. LCMS analysis showed good conversion of the ester to the acid (86%) but also formation of the 4-hydroxy-proline derivative by-product so the reaction was stopped. The reaction mixture volume was reduced by half in vacuo and acidified to pH 1 with 1M hydrochloric acid. The reaction mixture was then extracted with ethyl acetate. The organic extract was washed with brine, dried over sodium sulfate, filtered and the solvent removed under vacuum to give 688 mg (82%) of the desired product as brown solid. LC-MS: 46% (UV), 88% ELS, $t_R$ 2.37 min m/z [M+1]+691.30. $^1H$ NMR (500 MHz, $CDCl_3$) δ ppm 7.11-7.21 (m, 1 H) 6.87-7.00 (m, 2 H) 6.59-6.66 (m, 1 H) 6.52-6.60 (m, 1 H) 6.34-6.45 (m, 1 H) 5.52-5.65 (m, 1 H) 5.36-5.49 (m, 1 H) 5.16-5.31 (m, 1 H) 4.79-4.89 (m, 1 H) 4.57-4.80 (m, 5 H) 4.32-4.43 (m, 1 H) 3.98-4.05 (m, 1 H) 3.85-3.97 (m, 2 H) 2.73-2.89 (m, 1 H) 2.21-2.36 (m, 2 H) 1.88-2.03 (m, 1 H) 1.81-1.89 (m, 1 H) 1.69-1.79 (m, 1 H) 1.54-1.64 (m, 1 H) 1.33-1.52 (m, 2 H) 1.13-1.34 (m, 7 H).

Example 56-4

1128

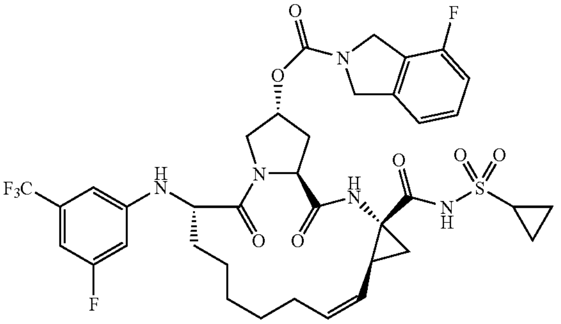

Compound 1070 (276 mg, 0.40 mmol., 1 eq.) and dichloromethane (8 mL) were charged into the reaction flask. EDC (159 mg, 0.83 mmol., 2.1 eq.) was added portion wise and the reaction mixture stirred at ambient temperature for 15 hours. The reaction mixture was diluted with dichloromethane (10 mL) washed with water (2×10 mL), dried over sodium sulfate, filtered and the solvent removed under vacuum. The residue was dissolved in dichloromethane (4 mL) and cyclopropylsulfonamide (111 mg, 0.92 mmol, 2.3 eq) and DBU (152 mg, 1.0 mmol, 2.5 eq.) were added. The reaction mixture was stirred at ambient temperature for a further 15 hours. LCMS analysis of a sample showed full consumption of the starting material. The reaction mixture was diluted with dichloromethane (10 mL) and then washed with 10% aqueous citric acid solution (2×10 mL) and brine (10 mL). The organic phase was dried over sodium sulfate, filtered and the solvent removed under vacuum to give 150 mg (48% crude, 68% pure by LCMS-UV) of product isolated as a brown solid. The solid was purified by preparative HPLC to give 5 mg (1.6% overall yield) of the desired product as a beige solid. LC-MS: purity 100% (UV), $t_R$ 5.21 min, m/z [M−H]-792.20. $^1H$ NMR (500 MHz, $CDCl_3$) δ 10.19-10.41 (m, 1 H), 7.31-7.43 (m, 1 H), 7.20-7.31 (m, 1 H), 6.87-7.10 (m, 2 H), 6.55-6.62 (m, 1 H), 6.47-6.55 (m, 1 H), 6.26-6.38 (m, 1 H), 5.63-5.80 (m, 1 H), 5.44-5.56 (m, 1 H), 4.95 (t, J=9.54 Hz, 1 H), 4.77 (d, J=10.27 Hz, 2 H), 4.51-4.70 (m, 3 H), 4.16-4.26 (m, 1 H), 3.95-4.09 (m, 2 H), 2.84-2.96 (m, 1H), 2.35-2.58 (m, 3 H), 2.21-2.33 (m, 1 H), 1.94-2.08 (m, 1 H), 1.79-1.93 (m, 2 H), 1.66-1.79 (m, 1 H), 1.36-1.61 (m, 6 H), 1.19-1.36 (m, 3 H), 1.01-1.17 (m, 2 H), 0.84-0.99 (m, 1 H).

Example 57-1

Synthesis of N-Aryl Amines

Scheme XXXXV

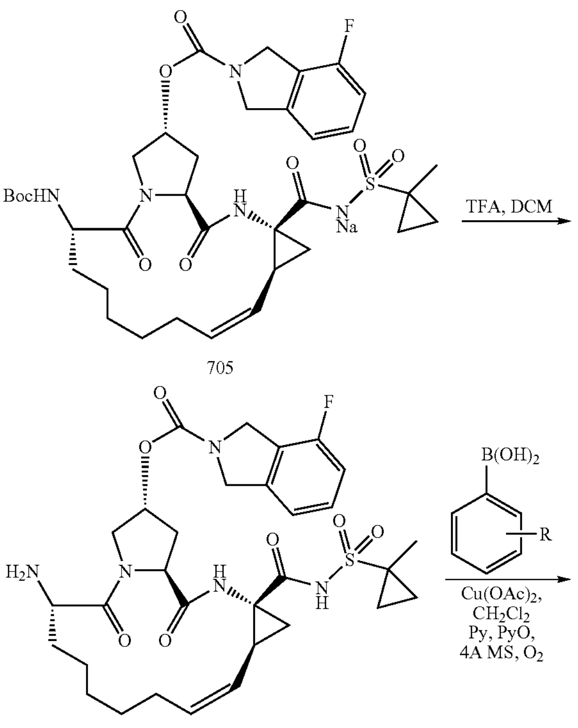

705

71

-continued

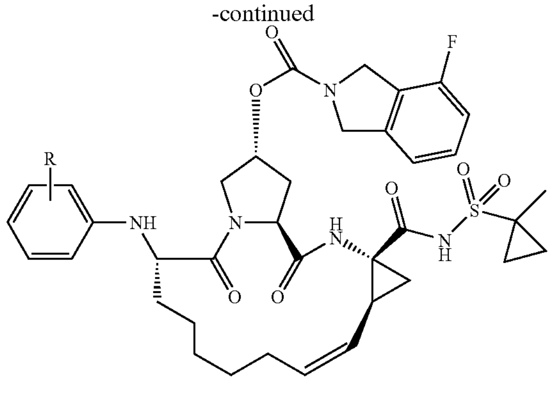

VIII-A

Compounds having having the general structure VIII-A can be synthesized as shown in Scheme XXXXV. Compound 705 can be treated with acid, for example TFA in DCM, to remove the Boc protecting group thereby providing compound 71. Compound 71 can be treated with an optionally substituted aryl boronic acid under $Cu^{2+}$-catalyzed conditions thereby providing a compound having the general structure VIII-A.

Example 57-2

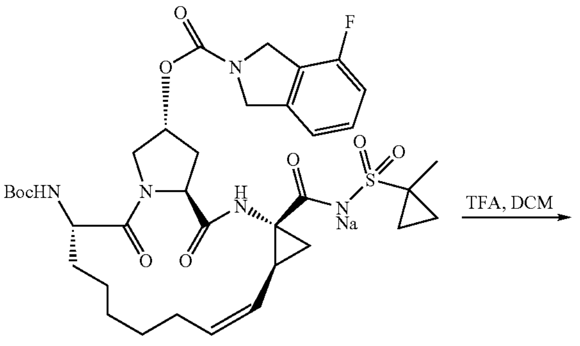

705

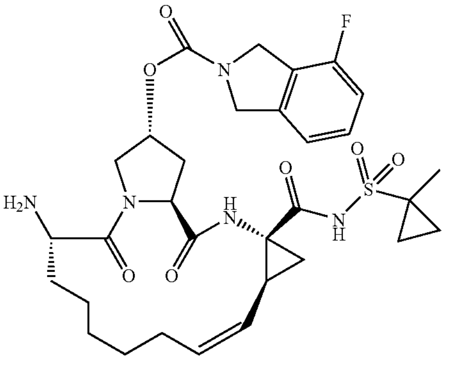

71

General Method XDX

To a solution of compound 705 (1 g, 1.34 mmol.) in dichloromethane (2 mL) was added 1 mL of trifluoroacetic acid, the resulting mixture was stirred at room temperature for 2 h, after that, the solvent was removed, the mixture was basified by aqueous $NaHCO_3$, extracted by ethyl acetate (50 mL×3), the organic layers were combined, washed by brine, dried over anhydrous sodium sulfate, the solvent was removed under reduced pressure, the crude compound 71 (0.86 g, 100%) was used directly in the next step.

Example 57-3

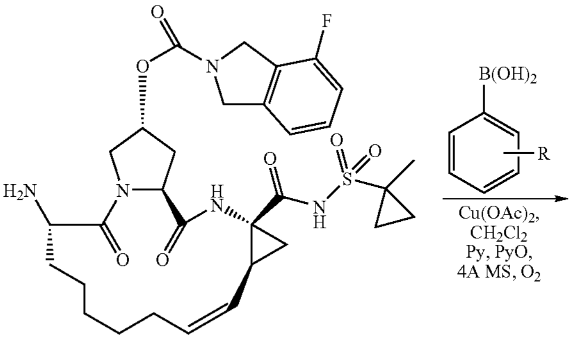

71

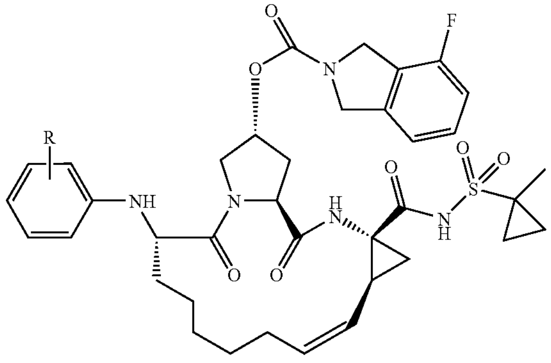

VIII-A

General Procedure XD

A mixture of compound 71 (1 eq.), optionally substituted phenyl boronic acid (3 eq), $Cu(OAc)_2$ (2 eq.), pyridine (10 eq.), pyridine N-Oxide (1 eq.) and molecular sieves 4 Å in dichloromethane (4 mL) was stirred at room temperature under oxygen atmosphere. The reaction was monitored by LC-MS. After completion of the reaction, the solid was removed by filtration, the solvent was removed and the crude mixture was purified by prep-TLC or prep-HPLC to give final compound VIII-A.

Example 57-4

1118

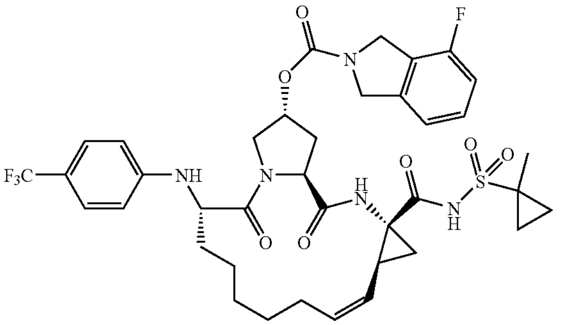

Compound 1118 was prepared in a manner analogous to General Procedure XD, to afford 22.7 mg (18.6% yield). MS (ESI) m/z $(M+H)^+$ 790.3.

Example 57-5

1119

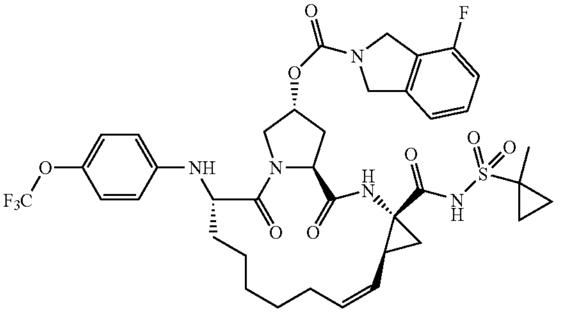

Compound 1119 was prepared in a manner analogous to General Procedure XD, to afford 12 mg (10% yield). MS (ESI) m/z $(M+H)^+$ 806.2.

Example 57-6

1120

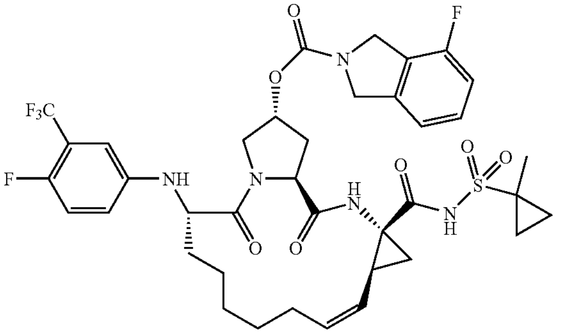

Compound 1120 was prepared in a manner analogous to General Procedure XD, to afford 12.5 mg (10% yield). MS (ESI) m/z $(M+H)^+$ 808.2.

Example 57-7

1121

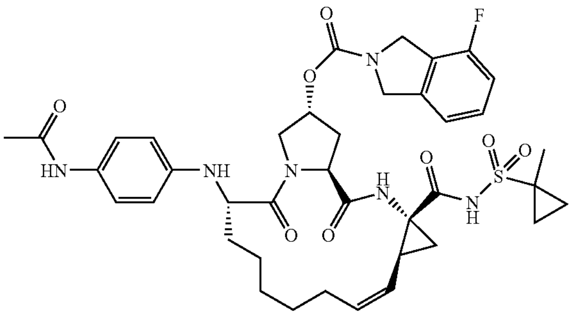

Compound 1121 was prepared in a manner analogous to General Procedure XD, to afford 21.2 mg (17% yield). MS (ESI) m/z $(M+H)^+$ 779.3.

Example 57-8

1122

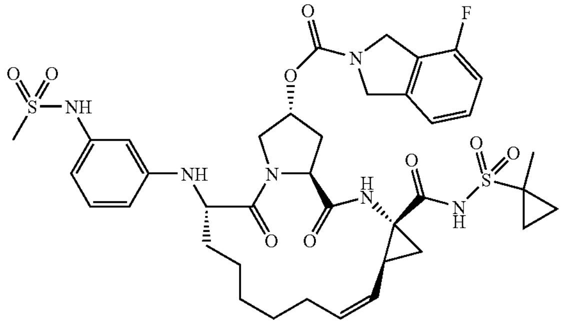

Compound 1122 was prepared in a manner analogous to General Procedure XD, to afford 11.1 mg (9% yield). MS (ESI) m/z $(M+H)^+$ 815.1.

Example 57-9

1123

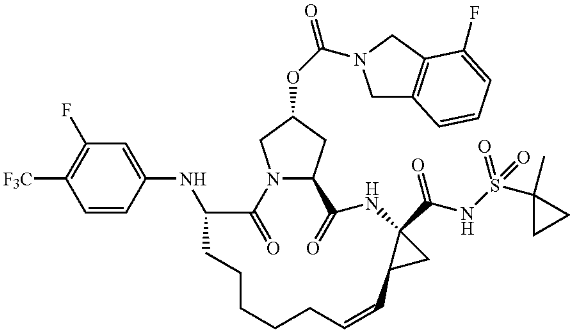

Compound 1123 was prepared in a manner analogous to General Procedure XD, to afford 11.2 mg (10% yield). MS (ESI) m z $(M+H)^+$ 808.4.

Example 57-10

1124

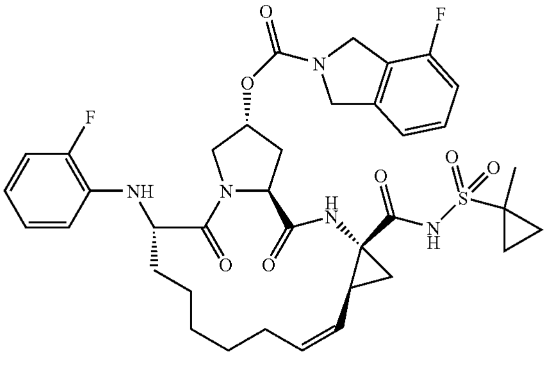

Compound 1124 was prepared in a manner analogous to General Procedure XD, to afford 2.7 mg (2.3% yield). MS (ESI) m/z $(M+H)^+$ 739.9.

Example 57-11

85

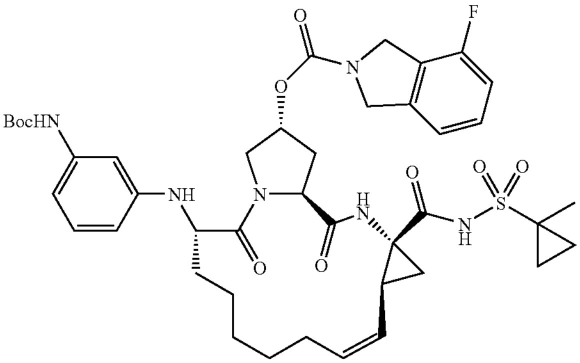

Compound 85 was prepared in a manner analogous to General Procedure XD, to afford 33 mg (25% yield).

Example 57-11

86

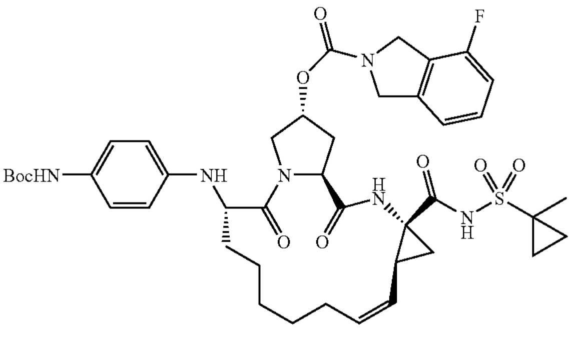

Compound 86 was prepared in a manner analogous to General Procedure XD, to afford 29 mg (15% yield).

Example 57-12

Scheme XXXXVI

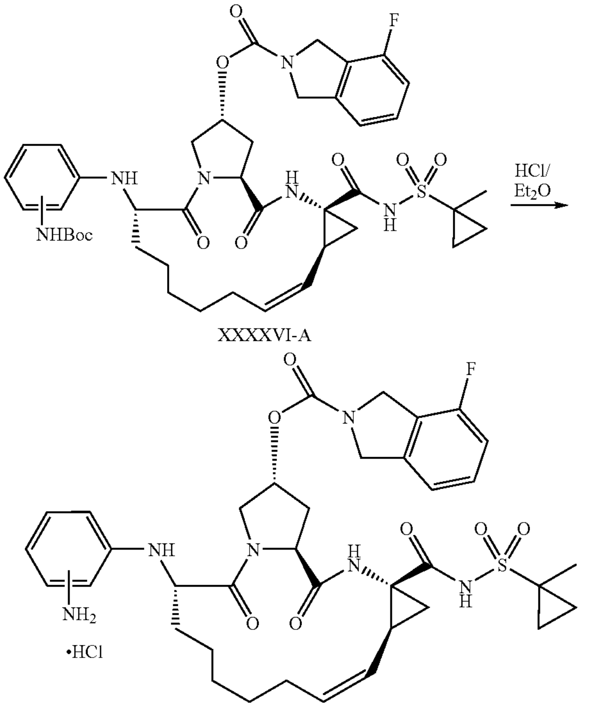

XXXXVI-A

XXXXVI-B

General Procedure XXD

The solution of a compound having the general structure XXXXVI-A in fresh $HCl/Et_2O$ (5 mL) was stirred at 0° C. protected by nitrogen for 1.5 h. The resulting mixture was dried by vacuum to give a compound having the general structure XXXXVI-B.

Example 57-12

Preparation of Compound 1146

1146

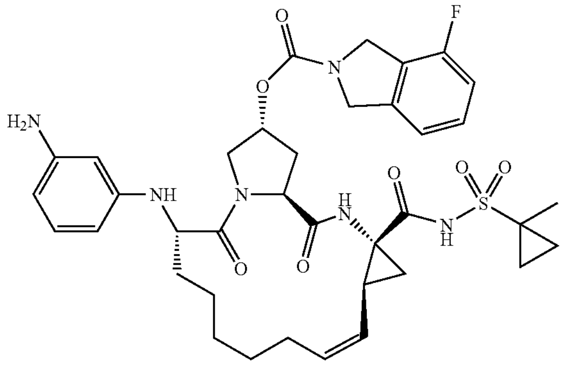

Compound 1146 was prepared in a manner analogous to General Procedure XXD, to afford 7.9 mg (45% yield). MS (ESI) m/z $(M+H)^+$ 736.7.

Example 57-13

Preparation of Compound 1147

1147

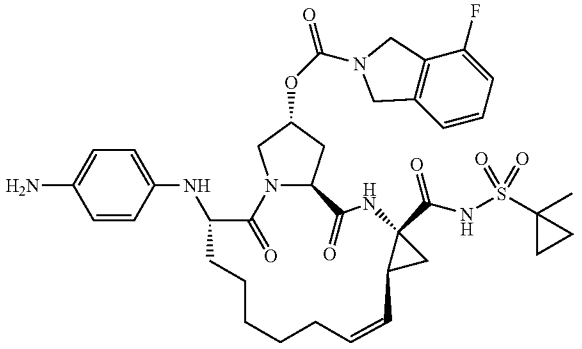

Compound 1147 was prepared in a manner analogous to General Procedure XXD, to afford 5.1 mg (49% yield). MS (ESI) m/z $(M+H)^+$ 736.8.

Example 58-1

Synthesis of N-Aryl Amines

Scheme XXXXVII

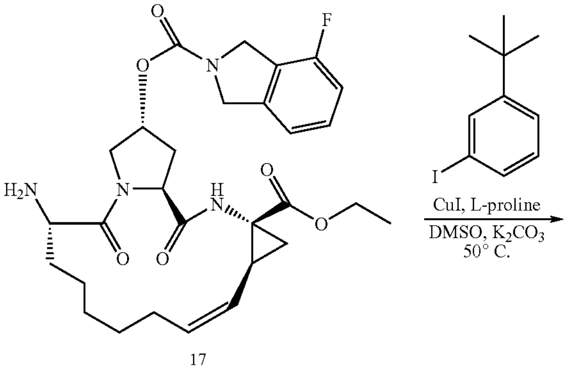

17

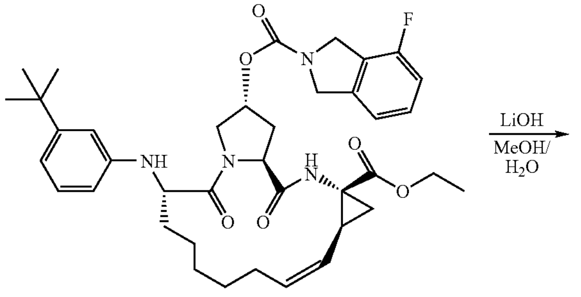

714

-continued

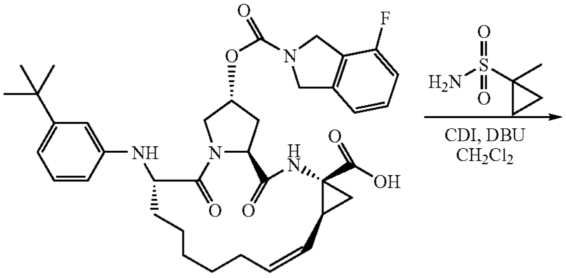

1125

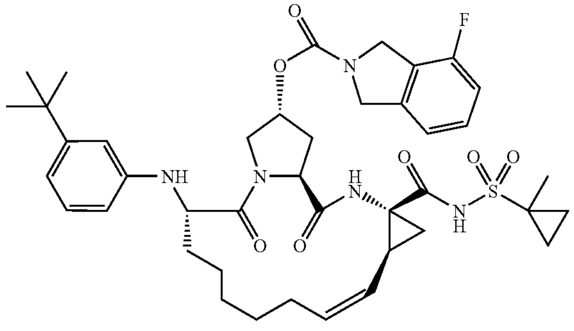

1126

Compound 1126 can be synthesized as shown in Scheme XXXXVII. Compound 17 can be treated with 1-tert-butyl-3-iodobenzene under copper catalyzed conditions, for example copper iodide and L-proline, thereby providing compound 714. Compound 714 can be treated under basic conditions to hydrolyse the ethyl ester thereby providing acid 1125. For example, the base can be lithium hydroxide, sodium hydroxide, potassium hydroxide, and the like. Finally, acid 1125 of can be coupled with 1-methylcyclopropane-1-sulfonamide to afford compound 1126. For example, the coupling reagents can be CDI, DCC, DIC, EDAC, HOSu, HOBt, HOAt, PyBOP, PyBrOP, HBTU, HATU, TBTU, combinations thereof, and the like.

Example 58-2

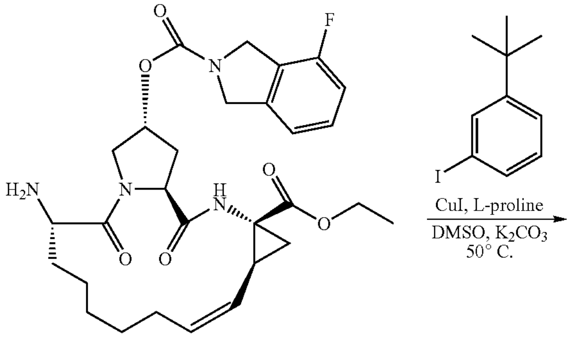

17

-continued

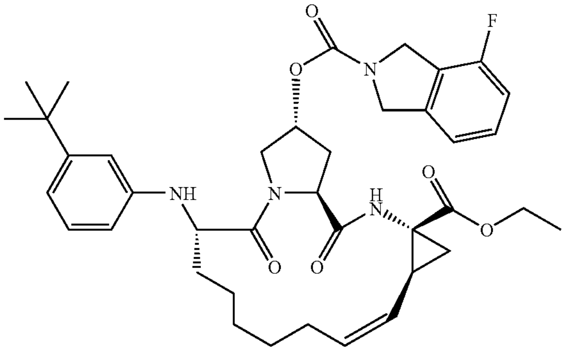

714

General Method XEX

A schlenk tube was charged with compound 17 (200 mg, 0.36 mmol.), CuI (13.7 mg, 0.072 mmol.), L-proline (16.6 mg, 0.144 mmol.) and $K_2CO_3$ (298.5 mg, 2.16 mmol.), evacuated and backfilled with argon. DMSO (2 mL) and 1-tert-butyl-3-iodobenzene (94 mg, 0.36 mmol.) were added successively. The resulting mixture was heated at 50° C. for 12 hours. LCMS monitored the reaction, after material was consumed, the reaction mixture was cooled to r.t. and diluted with ethyl acetate (100 mL), filtered. The organic layer was washed with brine, dried over $Na_2SO_4$, and concentrated in vacuo. The residue was purified with prep-TLC (petroleum ether:ethyl acetate=1:1) to afford compound 714 (30 mg, 12% yield).

Example 58-3

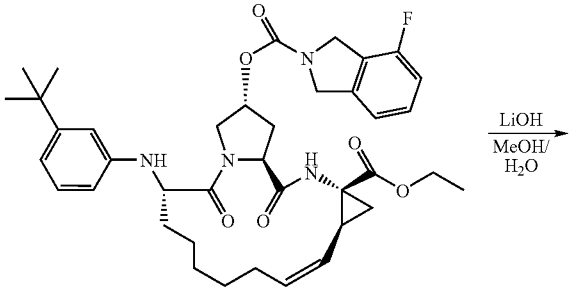

714

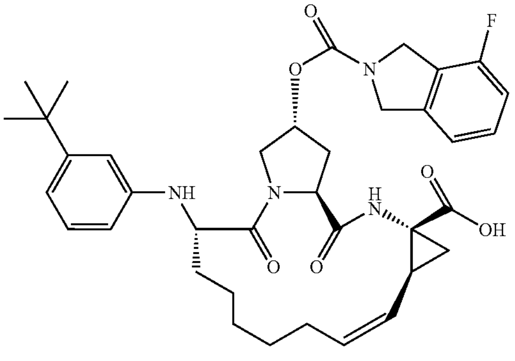

1125

General Method XFX

To a solution of compound 714 (30 mg, 0.043 mmol.) in methanol (5 mL) was added LiOH (30 mg, 1.29 mmol.) and water (0.5 mL), the resulting mixture was stirred at room temperature overnight. After completion of the reaction, the solvent was evaporated, the residue was acidified by aq. HCl (1 N) to pH=5-6, then the mixture was extracted by Ethyl acetate, the organic layers were combined, washed by brine, dried over anhydrous sodium sulfate, concentrated under reduced pressure, the residue was purified by prep-TLC (ethyl acetate/methanol=10:1) to afford compound 1125 (25 mg, 88%).

Example 58-3

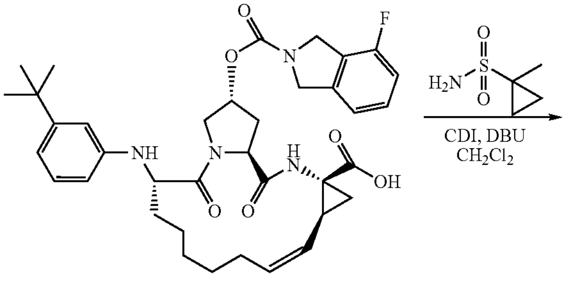

1125

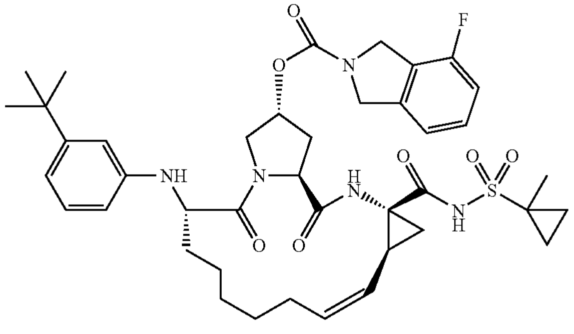

1126

Compound 1126 was prepared in a manner analogous to General Procedure XC, to afford 7 mg (24% yield). MS (ESI) m/z $(M+H)^+$ 778.4.

Example 58-4

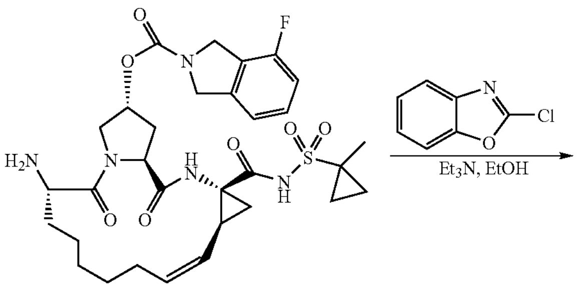

71

-continued

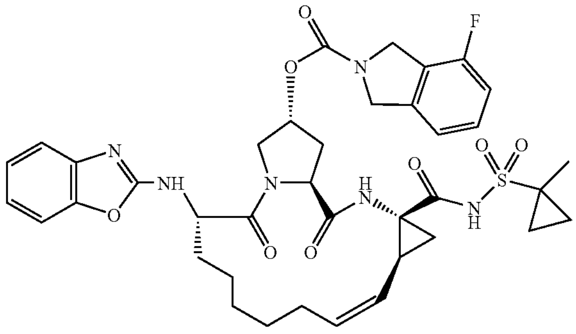

1127

General Method XGX

To a solution of compound 71 (86.5 mg, 0.13 mmol.) in ethanol (2 mL) was added triethylamine (39 mg, 0.39 mmol.) and 2-chlorobenzoxazole (24 mg, 0.15 mmol.), the resulting mixture was stirred at ambient temperature overnight, the reaction was monitored by LCMS. After completion of the reaction, the solvent was removed and the residue was purified by prep-TLC to afford compound 1127 (28.1 mg, 28%). MS (ESI) m/z $(M+H)^+$ 763.3.

Example 59-1

Synthesis of Compound 1085

Scheme XXXXVIII

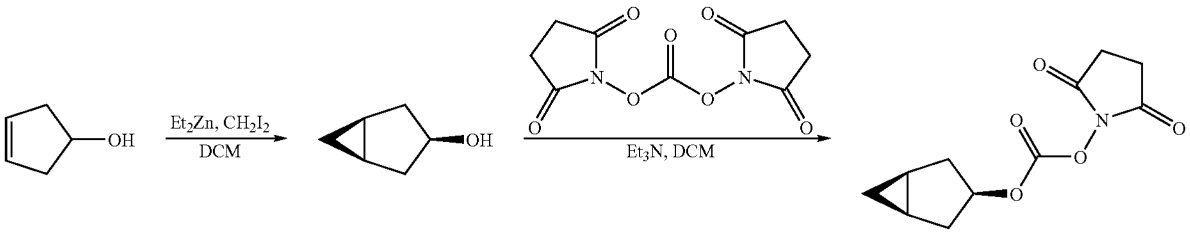

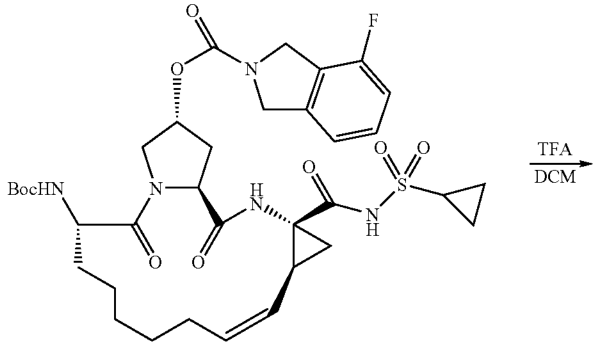

10

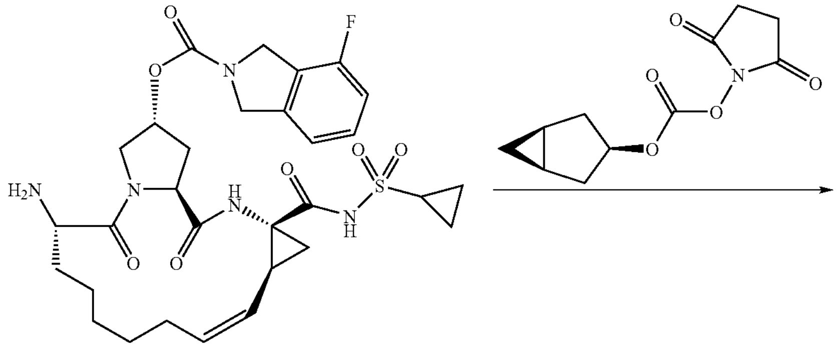

77

-continued

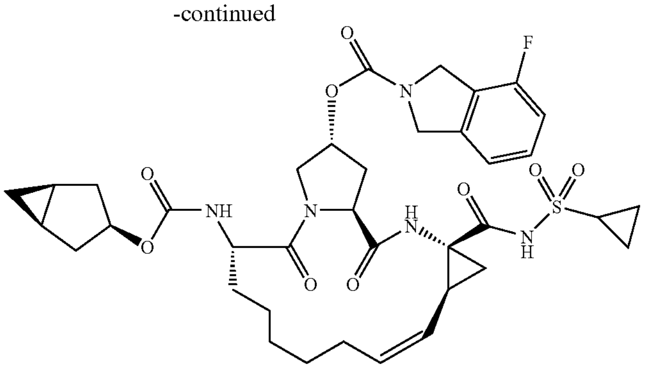

1085

Example 59-2

Preparation of bicyclo[3.1.0]hexan-3-ol

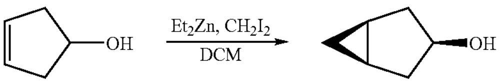

To a dry, nitrogen purged Schlenk tube were added anhydrous dichloromethane and $Et_2Zn$ solution in hexane (1.0 M, 10.2 mL, 10.2 mmol) at 0° C. Cyclopent-3-enol (0.25 mL, 2.97 mmol) was added dropwise. After the addition completion, the reaction mixture was allowed to stir until the evolution of gas had ceased. Diiodomethane (0.48 mL, 5.94 mmol) was then added dropwise slowly. The reaction was allowed to warm to room temperature and continued to stir overnight. The reaction was then diluted with $CH_2Cl_2$ and quenched with 2M HCl. The biphasic mixture was poured into a separatory funnel and the organic layer was collected. The solvent was removed under reduced pressure until 1 mL of material remained. The solution containing crude bicyclo[3.1.0]hexan-3-ol was used directly for the next step.

Example 59-3

Preparation of bicyclo[3.1.0]hexan-3-yl succinimidylcarbonate

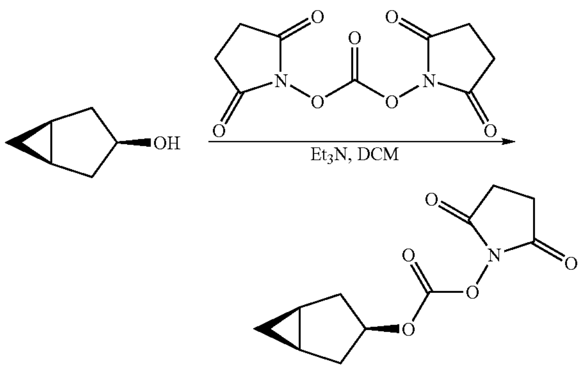

Anhydrous dichloromethane (1 mL) was added to the solution of crude bicyclo[3.1.0]hexan-3-ol (2.97 mmol.) from previous step followed by the dropwise addition of $Et_3N$ (0.88 mL, 6.11 mmol.). The reaction continued to stir at room temperature under nitrogen. Disuccinimidylcarbonate (988 mg, 3.86 mmol.) was added to the flask portionwise. The reaction was allowed to stir for 2 days. The reaction mixture was quenched with 1M HCl and washed with water. The desired material was extracted with $CH_2Cl_2$, and the combined organic layers were dried over $Na_2SO_4$. The solvent was removed under reduced pressure and the crude material was purified using prep-TLC (PE:EtOAc=3:1) to provide crude bicyclo[3.1.0]hexan-3-yl succinimidylcarbonate (210 mg, purity 50%).

Example 59-4

Preparation of Compound 1085

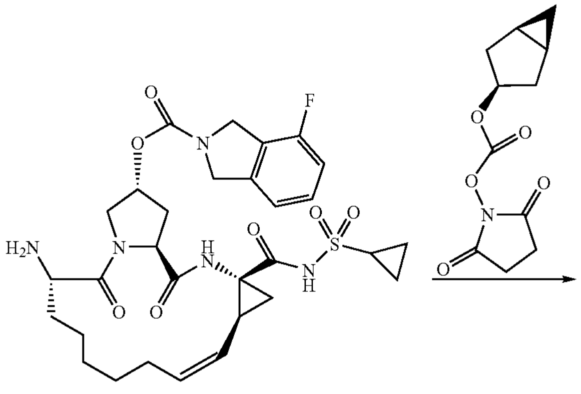

77

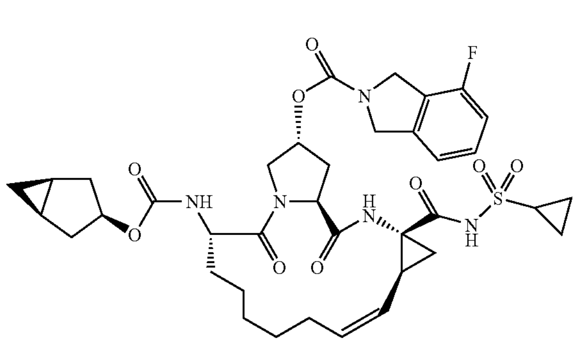

1085

Crude compound 77 (0.27 mmol.) was dissolved in EtOAc (2 mL) and saturated aqueous $NaHCO_3$ (3 mL). It was stirred vigorously. After 10 min, bicyclo[3.1.0]hexan-3-yl succinimidylcarbonate (78 mg, 0.33 mmol.) was added in one portion. After the resulting mixture was stirred for another 30 min, the organic layer was collected and washed with brine (5 mL), dried over $NaSO_4$, and concentrated. The residue was purified by prep-HPLC to afford compound 1085: 51.3 mg, yield 25%. MS (ESI) m/z $(M+H)^+$ 756.0.

Preparation of NS3 Inhibitors: Section XI

Example 60-1

Preparation of Phosphinates

Scheme XXXXIX (Stage 1)

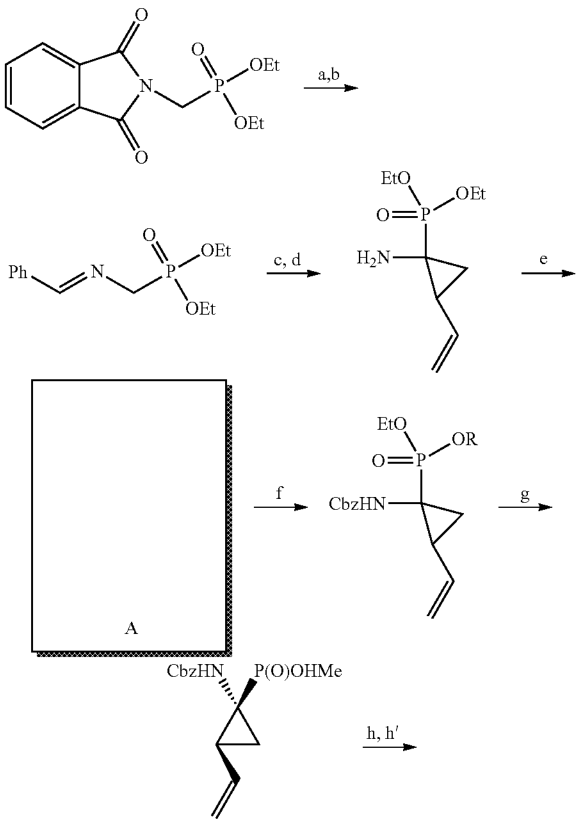

-continued

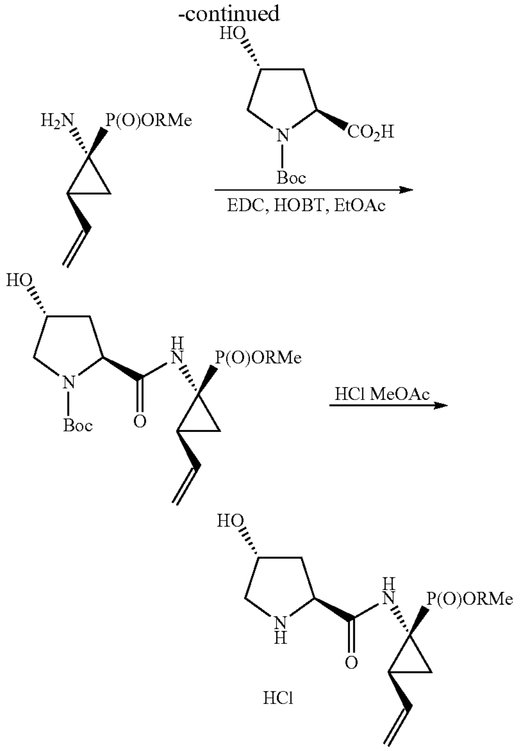

The dipeptide intermediate (product of Stage 1) may be prepared according to Scheme XXXXIX using the following reagents and conditions:

(a) $N_2H_4$, EtOH, rt;
(b) PhCHO, toluene, reflux;
(c) trans-1,4-dibromo-butene, CsOH, rt, DCM;
(d) HCl (aq), rt;
(e) CbzCl, $Na_2CO_3$, DCM, rt;
(f) NaI, Py, 110° C.; protection with a suitable phosphinate protecting group R (e.g., Me)
(g) $(COCl)_2$, DMF, 0° C.; then MeLi, −78° C., DCM;
(h) protection with a suitable phosphinate protecting group R
(h') TMSI, DCM, 0° C.

Scheme L (Stage 2)

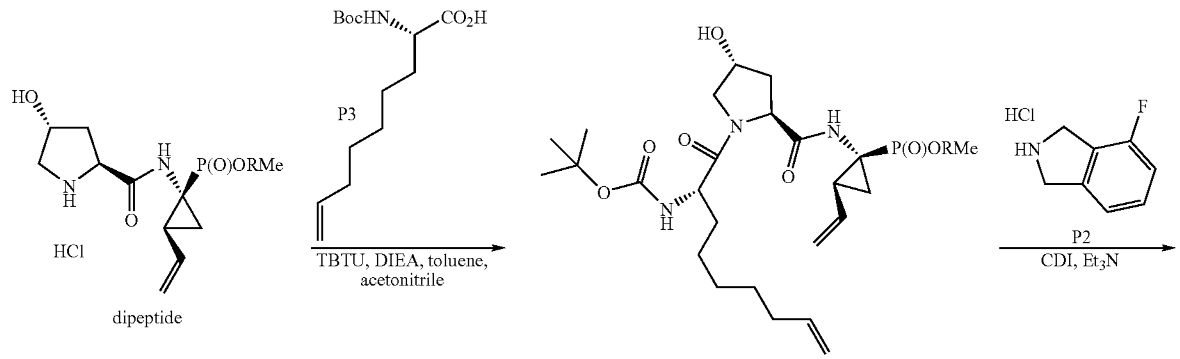

dipeptide tripeptide

-continued

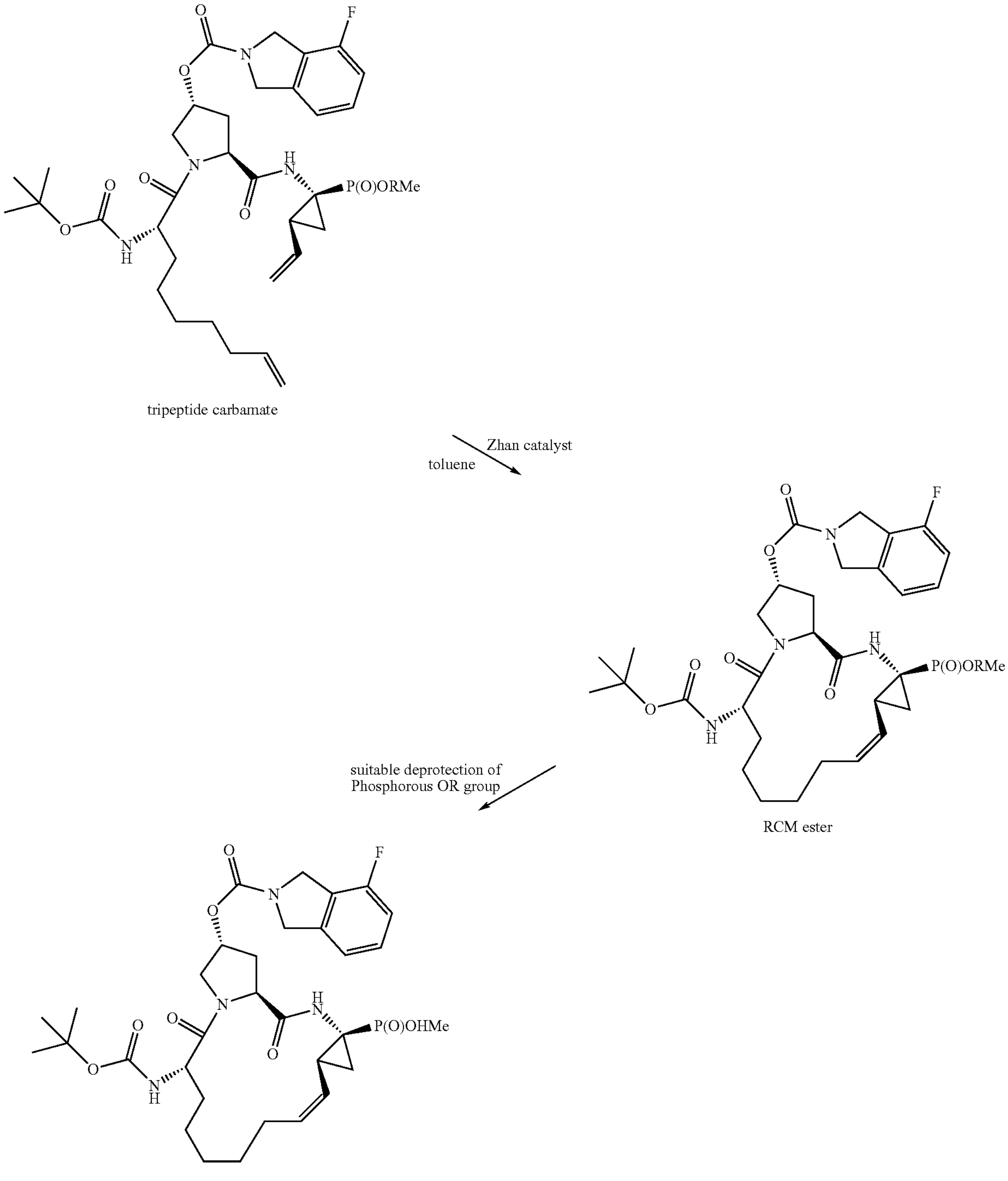

tripeptide carbamate

RCM ester

RCM carboxylic acid

The macrocycle product may be prepared from the dipeptide intermediate of Stage 1 according to Scheme L.

Example 60-2

Preparation of Phosphonates

Phosphonates may be prepared in a manner analogous to Schemes XXXXIX and L with the modification that intermediate A is deprotected to give the free amine and coupled to the proline to give a Boc-dipeptide diethyl phosphonate. The diethyl phosphonate can be carried through the remaining synthesis as the protected diethyl phosphonate then deprotected to give the final compound.

Example 61

Examples of NS3-NS4 Activity

NS3-NS4 inhibition activity can be determined using known assay methods. For example, NS3/NS4 complexes may be formed and inhibitory concentrations of test compounds determined as described in U.S. Patent Application Publication Number 2007/0054842 paragraph numbers 1497-1509, which is incorporated herein by reference in its entirety. Similarly, hepatitis C replicon $EC_{50}$ may be determined using known assay methods such as described in U.S. Patent Application Publication Number 2007/0054842 paragraph numbers 1510-1515. Assays may be conducted at ambient temperature (23° C.) in assay buffer containing 50 mM Tris-HCl, pH 7.5, 15% glycerol, 0.6 mM Lauryldimethylamine Oxide (LDAO), 25 µM NS4A peptide, and 10 mM Dithiothreitol (DTT).

Inhibition of NS3/NS4 activity was determined for several compounds exemplified herein and is presented in Tables 2 and 3.

TABLE 2

Examples NS3-NS4 activity.

| Compound | $EC_{50}$ nM | $IC_{50}$ nM |
|---|---|---|
| 101 | A | B |
| 110 | A | C |
| 119 | A | C |
| 123 | NA | B |
| 132 | NA | B |
| 157 | C | D |
| 164 | D | D |
| 197 | C | D |
| 213 | C | D |
| 214 | B | D |
| 217 | B | D |
| 218 | B | D |
| 220 | D | D |
| 221 | C | D |
| 222 | B | D |
| 223 | B | D |
| 226 | B | D |
| 227 | B | D |
| 229 | D | D |
| 230 | D | D |
| 231 | C | D |
| 235 | C | D |
| 242 | D | D |
| 243 | C | D |
| 244 | C | D |
| 253 | C | D |
| 309 | A | B |
| 315 | A | C |
| 316 | A | C |
| 317 | A | B |
| 318 | A | D |
| 319 | D | D |
| 320 | D | D |
| 321 | NA | C |
| 322 | NA | C |
| 323 | NA | D |
| 324 | NA | C |
| 325 | A | B |
| 326 | A | D |
| 327 | NA | C |
| 328 | C | D |
| 329 | NA | B |
| 330 | B | D |
| 331 | A | B |
| 332 | B | D |
| 333 | A | B |
| 334 | B | D |
| 335 | A | C |
| 336 | B | D |
| 337 | B | D |
| 338 | A | B |
| 339 | B | D |
| 340 | C | D |
| 341 | C | D |
| 342 | B | D |
| 343 | NA | B |
| 344 | NA | B |

TABLE 2-continued

Examples NS3-NS4 activity.

| Compound | $EC_{50}$ nM | $IC_{50}$ nM |
|---|---|---|
| 345 | C | D |
| 346 | D | D |
| 347 | D | D |
| 348 | B | D |
| 349 | C | D |
| 350 | B | D |
| 351 | B | D |
| 352 | C | D |
| 353 | B | D |
| 354 | B | D |
| 355 | D | D |
| 356 | D | D |
| 357 | NA | C |
| 358 | C | D |
| 359 | D | D |
| 360 | D | D |
| 361 | D | D |
| 362 | D | D |
| 363 | C | D |
| 364 | D | D |
| 365 | D | D |
| 369 | D | D |
| 374 | D | D |
| 375 | D | D |
| 376 | D | D |
| 377 | D | D |
| 378 | D | D |
| 379 | D | D |
| 380 | C | D |
| 381 | C | D |
| 388 | C | D |
| 391 | C | D |
| 392 | D | D |
| 393 | C | D |
| 395 | D | D |
| 396 | A | D |
| 401 | B | D |
| 402 | C | D |
| 407 | D | D |
| 409 | D | D |
| 411 | D | D |
| 412 | D | D |
| 415 | D | D |
| 417 | D | D |
| 439 | D | D |
| 444 | C | D |
| 445 | D | D |
| 446 | D | D |
| 447 | D | D |
| 448 | NA | D |
| 449 | C | D |
| 455 | D | D |
| 456 | C | D |
| 457 | D | D |
| 458 | C | D |
| 459 | D | D |
| 460 | D | D |
| 461 | C | D |
| 462 | C | D |
| 464 | D | D |
| 465 | B | D |
| 466 | B | D |
| 467 | C | D |
| 468 | D | D |
| 469 | D | D |
| 470 | C | D |
| 471 | C | D |
| 472 | C | D |
| 473 | D | D |
| 474 | D | D |
| 475 | D | D |
| 476 | D | D |
| 477 | D | D |
| 478 | B | D |
| 479 | D | D |
| 480 | C | D |

TABLE 2-continued

| Examples NS3-NS4 activity. | | |
|---|---|---|
| Compound | $EC_{50}$ nM | $IC_{50}$ nM |
| 481 | D | D |
| 482 | D | D |
| 483 | D | NA |
| 484 | C | NA |
| 485 | C | NA |
| 486 | C | D |
| 492 | C | D |

A indicates an $EC_{50}$ or $IC_{50}$ > 500 nM
B indicates an $EC_{50}$ or $IC_{50}$ between 75 and 500 nM
C indicates an $EC_{50}$ or $IC_{50}$ between 10 and 75 nM
D indicates an $EC_{50}$ or $IC_{50}$ of less than 10 nM
NA means the data is not available

TABLE 3

| Examples NS3-NS4 activity. | | |
|---|---|---|
| Compound Number | $IC_{50}$ | $EC_{50}$ |
| 701 | C | B |
| 1001 | B | A |
| 1007 | C | C |
| 1008 | C | C |
| 1009 | C | C |
| 1010 | C | B |
| 1011 | C | B |
| 1012 | C | C |
| 1013 | C | C |
| 1014 | C | C |
| 1015 | C | C |
| 1016 | C | B |
| 1017 | C | B |
| 1018 | C | B |
| 1019 | C | C |
| 1020 | B | NA |
| 1021 | B | NA |
| 1022 | A | NA |
| 1023 | A | NA |
| 1024 | A | NA |
| 1025 | A | NA |
| 1027 | A | A |
| 1028 | C | B |
| 1029 | C | B |
| 1030 | C | B |
| 1031 | C | B |
| 1032 | C | A |
| 1033 | C | B |
| 1034 | C | B |
| 1035 | C | A |
| 1036 | C | A |
| 1037 | C | A |
| 1038 | C | B |
| 1039 | C | C |
| 1040 | C | C |
| 1041 | A | NA |
| 1042 | B | NA |
| 1043 | B | NA |
| 1044 | A | NA |
| 1046 | C | A |
| 1048 | C | C |
| 1050 | C | B |
| 1051 | C | B |
| 1052 | A | A |
| 1053 | B | A |
| 1054 | A | NA |
| 1055 | A | NA |
| 1056 | A | NA |
| 1057 | A | A |
| 1058 | A | A |
| 1059 | A | NA |
| 1060 | A | NA |
| 1061 | A | A |
| 1062 | A | A |

TABLE 3-continued

| Examples NS3-NS4 activity. | | |
|---|---|---|
| Compound Number | $IC_{50}$ | $EC_{50}$ |
| 1063 | A | NA |
| 1064 | A | NA |
| 1065 | C | A |
| 1066 | A | NA |
| 1067 | A | NA |
| 1068 | A | NA |
| 1069 | C | A |
| 1071 | C | A |
| 1072 | C | A |
| 1075 | C | C |
| 1077 | C | C |
| 1078 | C | C |
| 1079 | C | A |
| 1080 | C | C |
| 1081 | C | C |
| 1082 | C | A |
| 1083 | C | A |
| 1084 | C | A |
| 1085 | C | C |
| 1086 | C | A |
| 1087 | A | NA |
| 1088 | A | NA |
| 1089 | A | NA |
| 1090 | A | NA |
| 1091 | A | A |
| 1092 | A | NA |
| 1093 | A | A |
| 1094 | A | A |
| 1095 | A | NA |
| 1097 | C | NA |
| 1098 | A | NA |
| 1099 | C | C |
| 1100 | C | C |
| 1101 | C | B |
| 1102 | C | C |
| 1103 | C | C |
| 1104 | C | C |
| 1105 | C | C |
| 1106 | C | B |
| 1107 | C | B |
| 1108 | C | B |
| 1109 | C | B |
| 1110 | C | B |
| 1111 | C | B |
| 1112 | C | A |
| 1113 | C | B |
| 1114 | C | B |
| 1115 | C | C |
| 1116 | C | C |
| 1117 | C | B |
| 1118 | C | A |
| 1119 | C | B |
| 1120 | C | C |
| 1121 | C | B |
| 1122 | C | B |
| 1123 | C | A |
| 1124 | C | B |
| 1126 | C | C |
| 1127 | C | B |
| 1128 | C | C |
| 1129 | C | C |
| 1130 | C | C |
| 1131 | C | C |
| 1132 | C | C |
| 1133 | C | C |
| 1134 | C | C |
| 1135 | C | C |
| 1136 | C | C |
| 1137 | C | C |
| 1138 | C | C |
| 1139 | C | C |
| 1140 | C | C |
| 1141 | C | C |
| 1142 | C | C |

TABLE 3-continued

| Examples NS3-NS4 activity. | | |
|---|---|---|
| Compound Number | $IC_{50}$ | $EC_{50}$ |
| 1143 | C | A |
| 1144 | C | A |
| 1145 | C | NA |

A indicates an $EC_{50}$ or $IC_{50}$ > 100 nM
B indicates an $EC_{50}$ or $IC_{50}$ between 10 and 100 nM
C indicates an $EC_{50}$ or $IC_{50}$ of less than 10 nM
NA means the data is not available Example 62-1

ITMN-191 Treatment Effect on HCV Viral Load (Comparative) Monotherapy

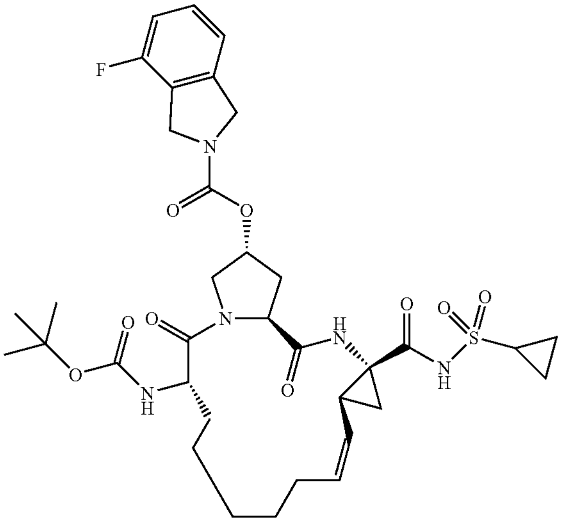

ITMN-191

The study was designed to provide the plasma pharmacokinetics (PK) of multiple ascending daily oral doses of ITMN-191 monotherapy and to evaluate the viral kinetics (VK) of multiple ascending daily oral doses of ITMN-191 monotherapy in patients, as measured by changes from Baseline in hepatitis C virus ribonucleic acid (HCV RNA) levels. The ITMN-191 was administered in the form of its sodium salt.

Proposed Dose Escalation:

In Part A and Part B, up to six cohorts (treatment arms) of 10 patients each were planned. In Part A, up to five cohorts of 10 treatment-naïve patients per cohort were planned to receive multiple ascending doses of study drug. Patients within each of the five cohorts were randomly assigned 8:2 to receive either ITMN-191 or placebo for 14 days. In Part B, one cohort of non-responder (NR) patients (Cohort 6) was planned to receive a single dose level of study drug for 14 days. Patients in Cohort 6 were randomly assigned 8:2 to receive either ITMN-191 (8 patients) or placebo (2 patients). Table S-1 provides the proposed cohorts and doses.

TABLE S-1

| Proposed Cohorts and Study Drug Doses (Active/Placebo) | | | | | |
|---|---|---|---|---|---|
| Cohort | Dose | Schedule | Total Daily Dose | No. of Patients Active/Placebo[a] | Patient Population |
| Part A (Treatment-Naïve) | | | | | |
| 1 | 100 mg | q12 h | 200 mg | 8/2 | Naïve |
| 2 | 100 mg | q8 h | 300 mg | 8/2 | Naïve |
| 3 | 200 mg | q12 h | 400 mg | 8/2 | Naïve |
| 4 | 200 mg | q8 h | 600 mg | 8/2 | Naïve |
| 5[b] | 300 mg | q8 h | 900 mg | 8/2 | Naïve |
| Part B (Nonresponder) | | | | | |
| 6[b] | 300 mg | q8 h | 900 mg | 8/2 | NR |

Notes:
q12 h = every 12 hours;
q8 h = every 8 hours.
Naïve = never previously received IFN-based monotherapy or combination therapy for their condition.
NR = nonresponders.
The number of patients excludes potential replacement patients.
[b]The total daily dose (TDD) was not to exceed 900 mg.

Number of Patients:

Planned enrollment: 60 patients (10 per cohort). Actual enrollment: 50 patients.

In Part A, there were 32 males and 8 females, ranging in age from 26 to 65 years old Patients who met all of the following criteria were eligible to participate in the study:

- Between 18 and 65 years of age, inclusive, at the time of dosing;
- History of chronic hepatitis C genotype 1, documented with HCV genotype and detectable HCV RNA levels at the Screening Visit;
- HCV Treatment History:
  - Part A: Treatment-naïve (i.e., had never received IFN-based monotherapy or combination therapy for their condition)
  - Part B: NR (nonresponders), defined as:
    - Previously treated with the combination of PEG-IFNα plus RBV; and
    - Failed to achieve a ≧2 $\log_{10}$ reduction in HCV RNA at Week 12, or detectable HCV RNA levels at Week 24 or beyond while on therapy;
- Liver biopsy or noninvasive (e.g., fibroscan) procedure in the past 2 years showing absence of cirrhosis; and
- At the Screening Visit, cardiac troponin values below the $99^{th}$ percentile based on assessment with both protocol-specified cardiac troponin immunoassays.

The treatment period consisted of 14 days of blinded study drug. In Part A, optional Standard of Care (SOC) consisting of PEG-IFN-α plus ribivarin (RBV) therapy was provided to treatment-naïve patients 24 hours after the last dose on Day 14. In Part B, NR patients were not permitted to start any additional HCV therapy before Day 44.

Part A (Treatment-Naive Patients):

Overall age ranged from 25 years to 65 years. Most of the treatment-naïve patients were male (80%) and European (90%). Median BMI ranged from 23.6 $kg/m^2$ to 26.9 $kg/m^2$, with an overall range of 19 $kg/m^2$ to 31 $kg/m^2$. The median duration since HCV diagnosis ranged from 2 years to 7.5 years, with an overall range of 1 year to 34 years. Median HCV RNA $\log_{10}$ levels ranged from 5.73 $\log_{10}$ IU/mL to 6.46

$log_{10}$ IU/mL. Median ALT levels ranged from 56 U/L to 74 U/L with an overall range of 26 U/L to 241 U/L.

Part B (NR Patients):

Overall age ranged from 25 years to 62 years. Of the 10 NR patients, 8 were male (ITMN-191), 2 were female (placebo), and 100% were European. Median BMI ranged from 23.5 kg/m$^2$ to 25.1 kg/m$^2$, with an overall range of 19 kg/m$^2$ to 30 kg/m$^2$. The median duration since HCV diagnosis ranged from 1 year to 9.5 years, with an overall range of 1 to 16 years. Median HCV RNA levels ranged from 6.47 $log_{10}$ IU/mL to 6.64 $log_{10}$ IU/mL, with an overall range of 5.98 $log_{10}$ IU/mL to 7.63 $log_{10}$ IU/mL. Median ALT levels ranged from 62.5 U/L to 75.5 U/L, with an overall range of 26 U/L to 152 U/L.

Patient Disposition

All patients completed 14 days of treatment (40 on ITMN-191 and 10 on placebo). During the 14-day dosing period, 3 treatment-naïve patients in the 200 mg q12h treatment arm received less than the assigned daily dose of blinded study drug dose (2 patients received 100 mg q12h of ITMN-191 during the entire 14 days, and 1 patient received 100 mg q12h of ITMN-191 during Day 1 through the first dose of Day 5 of the dosing period). Of the 50 enrolled patients, 49 completed through Day 44 (1 patient was lost to follow-up after Day 21), and 48 patients completed through Day 90. Among treatment-naïve patients, 31/40 initiated optional SOC treatment on Day 15, and among NR patients, 7/10 initiated optional SOC treatment on Day 44.

Efficacy was evaluated by $log_{10}$ reductions in HCV RNA levels and reductions in ALT values using the Efficacy-Evaluable Population, defined as those patients who received at least 90% of prescribed doses of assigned blinded study drug. Three patients in the treatment-naive 200 mg q12h cohort received less than the assigned randomized dose and were excluded from all efficacy analyses. The HCV RNA levels were determined by Roche COBAS Taqman HCV/HPS test, v2.0. This is a reverse transcriptase PCR method.

Viral Kinetics (VK)

Part A (Treatment-Naive Patients)

In the treatment-naïve patients, ITMN-191 treatment resulted in generally rapid, sustained (over the 14-day treatment period), dose-dependent reductions in HCV RNA levels, with median reductions of −3.12 $log_{10}$ IU/mL in the 200 mg q12h cohort and −3.76 $log_{10}$ IU/mL for the 200 mg q8h cohort at end of treatment (EOT) (Day 14). Similarly, median maximum reductions in HCV RNA levels in the 200 mg q12h and 200 mg q8h cohorts were −3.17 $log_{10}$ IU/mL and −3.90-$log_{10}$ IU/mL, respectively. Median ALT values declined from elevated Baseline levels in all ITMN-191 cohorts during study treatment, with the largest median EOT reduction of −37.5 U/L observed in the 200 mg q8h cohort.

Part B (NR Patients)

In the NR patients, 300 mg q8h of ITMN-191 treatment resulted in a median reduction of −2.46 $log_{10}$ IU/mL at EOT. The median maximum reduction in HCV RNA levels was −2.93 $log_{10}$ IU/mL. The median ALT value declined from an elevated Baseline level by −34.5 U/L at EOT.

Viral Resistance

In Parts A and B, rebound, plateau, and continuous decline of virologic response profiles were defined based on the HCV RNA level at end of treatment (EOT) relative to the nadir HCV RNA level. In general, patients experiencing virologic rebound (14/40 patients) and plateau (12/40 patients) were observed in the lower dose treatment arms, while the majority of patients (14/40 patients) experiencing a continual decline in HCV RNA level were observed in the upper dose treatment arms. The frequency of rebound for treatment-naïve patients (Part A) was higher in the 100 mg q2h treatment arm (4 patients) than in the higher dose treatment arms (2 to 3 patients). The frequency of rebound for NR patients (Part B) was the same (2 patients) as for the treatment-naïve patients in the 100 mg q8h treatment arm. However, there were no statistically significant differences in ITMN-191 AUC, $C_{max}$, or $C_\tau$ between rebound, plateau, and continual decline groups. At EOT, every patient classified as experiencing virologic rebound carried NS3 variants in which arginine at amino acid position 155 was replaced, at least in part, by lysine. Arginine substitution was observed 21 and 90 days following cessation of ITMN-191 administration in the majority of patients with amplifiable NS3 at those time points, indicating that NS3 bearing this substitution were genetically fit.

Conclusions:

ITMN-191 treatment provides a dose-dependent reduction in HCV RNA levels in treatment-naïve patients, with a daily dose of 200 mg q8h for 14 days providing the highest median reduction of HCV RNA levels of all the treatment arms. In the treatment-naïve cohorts (Part A) the median maximum post-Baseline $log_{10}$ reduction in HCV RNA in the 200 mg q12h and the 200 mg q8h cohorts are −3.17 $log_{10}$ IU/mL and −3.90 $log_{10}$ IU/mL, respectively during study drug treatment. In the single NR cohort (Part B), the 300 mg q12h dose results in a more modest median maximum post-Baseline change in HCV RNA of −2.93 $log_{10}$ IU/mL during study drug treatment. Virologic rebound occurred in 14 (35%) of the 40 ITMN-191 treated patients and was primarily associated with an R155K substitution in the NS3 protein coding sequence at end of treatment. ITMN-191 administration resulted in reductions in elevated Baseline ALT levels during 14 days of treatment in all cohorts.

TABLE 4

Viral Kinetic Assessments of Monotherapy Following 14 Days of Treatment.

| Group | N | Study Drug | Dose | Schedule | Total | (<43 IU/mL)[3] (%) |
|---|---|---|---|---|---|---|
| 1 | 10 | placebo | NA[1] | NA[1] | NA[1] | 0/10 (0%) |
| 2 | 8 | ITMN-191 | 100 mg | q8 h | 300 mg | 1/8 (13%) |
| 3 | 8 | ITMN-191 | 200 mg | q8 h | 600 mg | 1/8 (13%) |
| 4 | 8 | ITMN-191 | 100 mg | 12 h | 200 mg | 0/8 (0%) |
| 5 | 8 | ITMN-191 | 200 mg | q12 h | 400 mg | 0/5[2] (0%) |
| 6 | 8 | ITMN-191 | 300 mg | q12 h | 600 mg | 0/8 (0%) |

[1]NA = No Data: the placebo was given to two patients in each of the other patient groups
[2]Three patients removed from analysis for inconsistent dosing
[3]HCV RNA The data in Table 4 demonstrates in Group 2 (100 mg q8h) and Group 3 (200 mg q8h) that 13% of the patients in each group had HCV RNA lowered to levels below 43 IU/mL.

Example 62-2

ITMN-191 Treatment Effect on HCV Viral Load—Combination Therapy

Study Design:

This is a double-blind, placebo-controlled, multicenter study in treatment-naïve patients with chronic hepatitis C genotype 1 infection. All patients receive standard of care (SOC) treatment with PEG-IFN alfa-2a and weight-based ribavirin in accordance with the product labeling. In addition to this standard of care treatment, patients are randomized to receive either ITMN-191 or matching placebo, administered in the fed state, for 14 complete days, and a single dose on Day 15. PEG-IFN alfa-2a and ribavirin is provided from Day 0 and following the completion of study drug treatment on Day 15 through Day 44. No other HCV therapies are permitted prior to Day 44. All patients receive SOC and then are administered a pill containing either ITMN-191 or placebo. The ITMN-191 was administered in the form of its sodium salt.

Patients are admitted to a research facility and initiate PEG-IFN alfa-2a and ribavirin on Day O, Study drug (ITMN-191 or placebo) administration begins on Day 1 and continues to the morning of Day 15, and patients are discharged from the research facility on Day 16. Meals and activity levels are standardized across research facilities. Patients are contacted by telephone on Day 21 and return to the research facility for the Safety Follow-up Visit on Day 28 and the End of Study Visit on Day 44.

The initial ITMN-191 dose levels administered in this study resulted in exposures generally similar to those studied a completed multiple ascending dose study of ITMN-191 monotherapy (see Comparative Example 21-1 above).

Over the course of the study, blood samples are obtained for clinical laboratory analysis and for PK (pharmokinetics) and VK (viral kinetics). In addition, blood samples to assess VR (viral rebound) are obtained. To monitor potential cardiac toxicity, cardiac troponin are assessed every day during the treatment period.

Methods:

End of treatment (EOT) and nadir HCV RNA levels were used to define virologic rebound, continual decline, and plateau response patterns. NS3 protease domain was amplified and population sequenced by nested reverse transcription polymerase chain reaction (RT-PCR). Amplicons were cloned into a novel NS3 phenotyping vector and this plasmid used for clonal sequencing. The HCV RNA levels were determined by Roche COBAS Taqman HCV/HPS test, v2.0. This is a reverse transcriptase PCR method.

Results:

After 14 days of triple combination therapy, the median change in HCV RNA from baseline exceeded 5 logs in five of the six cohorts and was −5.5 log and −5.7 log in the best performing q12h and q8h cohorts, respectively. At the end of only 14 days of treatment, HCV RNA was below the limit of quantification (<25 IU/mL) in nearly three-quarters (71%, or 32 of 45) of patients at all doses and intervals who received treatment with ITMN-191 as summarized in Table 5. In all q12h and q8h cohorts of ITMN-191 in combination with SOC, reductions in HCV RNA occurred rapidly and there was no evidence of the viral rebound seen during during ITMN-191 monotherapy treatment (see Comparative Example 62-1 above).

The combination of ITMN-191 with SOC provides a much greater reduction in HCV RNA levels as compared to SOC alone, as evidenced by the median change of HCV RNA levels shown in Table 5. Further, the combination protocol prevents a viral rebound in all treatment groups, in contrast to patients treated with ITMN-191 alone where viral rebound was observed. This extraordinary and rapid reduction in HCV RNA was not seen in patients under SOC and placebo treatment. It was observed that at least 57% of the patients treated with the combination therapy obtained HCV RNA levels below 25 IU/mL. Further, it was observed that at least 13% of the patients treated with the combination therapy obtained HCV RNA levels below 9.3 IU/mL (detection limit of analysis method). Additionally, there was no viral rebound observed for any patients in the combination treatment groups.

Various trends are observed by comparing the earlier ITMN-191 monotherapy study (see Example 62-1) with the more recent combination study, as summarized in Table 5. The combination treatment provides (group 4 and group 6, Table 6) reduction of HCV RNA levels below 43 IU/mL in a significant percentage of the patients in each study group. This reduction is observed in the combination study where 100 mg of ITMN-191 was administered every 8 hours or 200 mg of ITMN-191 was administered every 8 hours. The baseline comparison can be seen in the placebo group (placebo alone) and the SOC treatment group (placebo with peginterferon alfa-2a and ribavirin) which did not show any patients with an HCV RNA level below 43 IU/mL after 14 days of treatment.

The superior virologic response of the combination therapy is evident by comparing the monotherapy cohorts to their corresponding combination therapy cohorts. The monotherapy cohort (group 3) where 100 mg of ITMN-191 was administered every 8 hours provided a reduction of HCV RNA levels below 43 IU/mL in 13% of patients after 14 days of treatment. In contrast, the corresponding cohort from the combination study where 100 mg of ITMN-191 was administered every 8 hours in combination with pegylated interferon-alfa and ribavirin provided a reduction of HCV RNA levels below 43 IU/mL in 75% of patients (group 4) after 14 days of treatment. The cohort from the monotherapy study where the amount of ITMN-191 was increased to 200 mg, again administered every 8 hours, provided a similar reduction of HCV RNA levels below 43 IU/mL in 13% of patients (group 5) after 14 days of treatment. Similar to the previous comparison, the corresponding cohort (group 6) where 200 mg of ITMN-191 was administered every 8 hours in combi-

TABLE 5

Viral Kinetic Assessments of Combination Therapy Following 14 Days of Treatment.

| N | Study Drug | Dose | Schedule | Total | Median Change[3] Log10 (IU/mL) | (<25 IU/mL)[4] (%) | (<9.3 IU/mL)[5] (%) |
|---|---|---|---|---|---|---|---|
| 12 | SOC[1] | SOC[1] | NA | NR | −2.0 | 1/12 (8.3%) | 0/12 (0%) |
| 8 | ITMN-191[2] | 100 mg | q8 h | 300 mg | −5.5 | 6/8 (75%) | 1/8 (13%) |
| 8 | ITMN-191[2] | 200 mg | q8 h | 600 mg | −5.7 | 7/8 (88%) | 4/8 (50%) |
| 7 | ITMN-191[2] | 300 mg | q8 h | 900 mg | −5.6 | 5/7 (71%) | 4/7 (57%) |
| 7 | ITMN-191[2] | 400 mg | q12 h | 800 mg | −4.7 | 4/7 (57%) | 1/7 (14%) |
| 8 | ITMN-191[2] | 600 mg | q12 h | 1200 mg | −5.4 | 6/8 (75%) | 1/8 (13%) |
| 7 | ITMN-191[2] | 900 mg | q12 h | 1800 mg | −5.5 | 4/7 (57%) | 1/7 (14%) |

[1]SOC is combination therapy of pegylated interferon-alfa with ribavirin. Dose and schedule is according to standard of care for individual patient.
[2]ITMN-191 in combination with SOC
[3]HCV RNA at EOT (End of Treatment) Median HCV RNA was at or below the lower limit of quantification at EOT
[4]Values below Limit of Quantification (LOQ) of 25 IU/mL were assigned value of 1.236 log10
[5]Values below Limit of Detection (LOD) of 9.3 IU/mL were assigned value of 0.667 log10 nation with pegylated interferon-alfa and ribavirin provided a reduction of HCV RNA levels below 43 IU/mL in 88% of patients after 14 days of treatment. Thus, the combination cohorts provide a superior reduction in HCV RNA levels in comparison to the monotherapy cohorts, as evidenced by the much greater percentage of patients with a reduction of HCV RNA levels in the blood.

TABLE 6

Comparison of Viral Kinetic Assessments Among Placebo, SOC, ITMN-191 Monotherapy and Combination Therapy Following 14 Days of Treatment.

| Group | N | Study Drug | Dose | Schedule | Total | (<43 IU/mL)[3] (%) |
|---|---|---|---|---|---|---|
| 1 | 10 | placebo | NA[1] | NA[1] | NA[1] | 0/10 (0%) |
| 2 | 12 | SOC | NA[2] | NA[2] | NA[2] | 0/10 (0%) |
| 3 | 8 | ITMN-191 | 100 mg | q8 h | 300 mg | 1/8 (13%) |
| 4 | 8 | ITMN-191 and SOC | 100 mg | q8 h | 300 mg | 6/8 (75%) |
| 5 | 8 | ITMN-191 | 200 mg | q8 h | 600 mg | 1/8 (13%) |
| 6 | 8 | ITMN-191 and SOC | 200 mg | q8 h | 600 mg | 7/8 (88%) |

[1]NA = No Data: the placebo was given to two patients in each of the other patient groups in the monotherapy study
[2]NA = No Data: the SOC (pegylated interferon-alfa with ribavirin) was provided to two patients in each of the other patient groups in the combination therapy study
[3]HCV RNA measured after 14 days of treatment

CONCLUSION

The combination of ITMN-191 with SOC provides, on average, reduction of HCV RNA in all patient cohorts that is greater than SOC alone. The reduction of HCV RNA is observed without viral rebound.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the structure of Formula II:

II

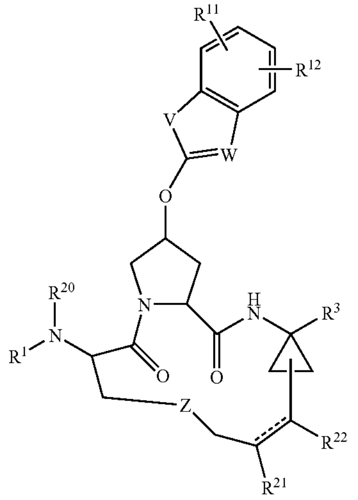

or a pharmaceutically acceptable salt thereof wherein:

(a) $R^1$ is $-(CR^5R^6)_nR^4$;

(b) n is 0;

(c) $R^3$ is $-C(O)NHS(O)_2R^9$, where $R^9$ is $-(CH_2)_qC_{3-7}$ cycloalkyl optionally substituted with one or more substituents each independently selected from the group consisting of halo, cyano, nitro, hydroxy, —COOH, $C_{1-6}$ alkyl, $-(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro;

(d) each m is separately 0, 1 or 2;

(e) each q is 0;

(f) each t is separately 0, 1 or 2;

(g) $R^4$ is aryl optionally substituted with one or more substituents each independently selected from the group consisting of halo, cyano, nitro, hydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, $-(CH_2)_qC_{3-7}$cy-

SEQUENCE LISTING

```
<160> NUMBER OF SEQ ID NOS: 1

<210> SEQ ID NO 1
<211> LENGTH: 12
<212> TYPE: PRT
<213> ORGANISM: Hepatitis C Virus

<400> SEQUENCE: 1

Asp Leu Glu Val Val Thr Ser Thr Trp Val Leu Val
 1               5                   10
```

cloalkyl, $C_{3-6}$ heterocycloalkyl, aryl, heteroaryl, ary loxy, arylthio, $C_{1-6}$ alkylthio, —N[$(CH_2)_p$OH][$(CH^2)_r$OH], —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —NHC(O) $OR^{2a}$, —$SO_mR^{2a}$, —NHS $(O)_2R^{2a}$, —$NR^{2a}[CH_2)_p$OH], —O[$(CH_2)_pNR^{3a}R^{3b}$], —S[$(CH_2)_pNR^{3a}R^{3b}$], —$(CH_2)_p$ $NR^{3a}R^{3b}$, —$(CH_2)_pR^{4a}$ and —$O(CH_2)_pR^{4a}$;

(h) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(i) each $R^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

(j) $R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

(k) each $R^{4a}$ is separately imidazolyl or pyrazolyl;

(l) each p is separately an integer selected from 1-6;

(m) each r is separately an integer selected from 1-6;

(n) $R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more sub stituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

(o) $R^{11}$ and $R^{12}$ are each separately selected from the group consisting of hydrogen, halo, cyano, nitro, hydroxy, cyanoamino, —SH, $C_{1-6}$ alkoxy, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —N[$(CH_2)_p$OH][$(CH_2)_r$OH], —$S(O)_2NR^7R^8$, —NHC (O)$NR^7R^8$, —$NHC(S)NR^7R^8$, —$C(O)NR^7R^8$, —$NR^7R^8$, —$C(O)R^{13}$, —$C(O)OR^{13}$, —$NHC(O)R^{13}$, $NHC(O)OR^{13}$, —$SO_mR^{13}$, —$NHS(O)_2R^{13}$, —$NR^{13}$ [$(CH_2)_p$OH], —O[$(CH_2)_pNR^{14}R^{15}$], —S[$(CH_2)_p$ $NR^{14}R^{15}$], —$(CH_2)_pNR^{14}R^{15}$, —$(CH_2)_pR^{16}$, —$O(CH_2)_pR^{16}$, and $C_{1-6}$ alkyl optionally substituted with up to 5 fluoro;

(p) $R^7$ and $R^8$ are each separately a hydrogen, or separately selected from the group consisting of $C_{1-6}$ alkyl, —$(CH_2)_qC_{3-7}$cycloalkyl, and phenyl, each optionally substituted with one or more substituents each independently selected from the group consisting of halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^7$ and $R^8$ are taken together with the nitrogen to which they are attached to form indolinyl, pyrrolidinyl, piperidinyl, piperazinyl, or morpholinyl;

(q) $R^{13}$ is selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{13}$ is a tetrahydrofuran ring linked through the $C_3$ or $C_4$ position of the tetrahydrofuran ring; or $R^{13}$ is a tetrahydropyran ring linked through the $C_4$ position of the tetrahydropyran ring;

(r) $R^{14}$ and $R^{15}$ are each separately selected from hydrogen and $C_{1-6}$ alkyl; or $R^{14}$ and $R^{15}$ are taken together with the nitrogen to which they are attached to form indolinyl, pyrrolidinyl, piperidinyl, piperazinyl, or morpholinyl;

(s) each $R^{16}$ is separately imidazolyl or pyrazolyl;

(t) V is selected from the group consisting of —(O)—, —S—, and —$NR^{15}$—;

(u) W is —N— or —$CR^{15}$—;

wherein $R^{15}$ is H, or selected from the group consisting of $C_{1-6}$ alkyl, $(CH_2)_qC_{3-7}$cycloalkyl, aryl, and heteroaryl, each optionally substituted with one or more sub stituents each independently selected from the group consisting of halo, cyano, nitro, $C_{1-6}$ alkyl, $C_{1-6}$ alkoxy, and phenyl;

(v) each u is separately 0, 1 or 2;

(w) Z is selected from the group consisting of

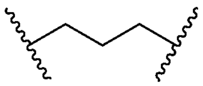,
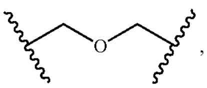,
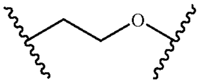,
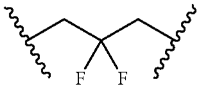,
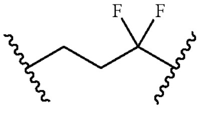,
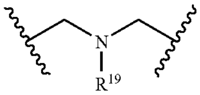,
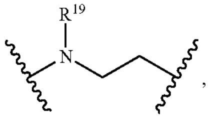,
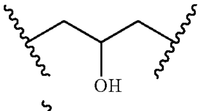, and
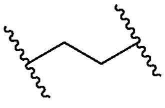;

(x) $R^{19}$ is hydrogen, $C_{1-6}$ alkyl optionally substituted with up to 5 fluoro, or —$SO_mR^{2a}$;

(y ) $R^{20}$ is hydrogen;

(z) $R^{21}$ and $R^{22}$ are each hydrogen; and (aa) the dashed line represents an optional double bond.

2. The compound of claim 1 having the structure:

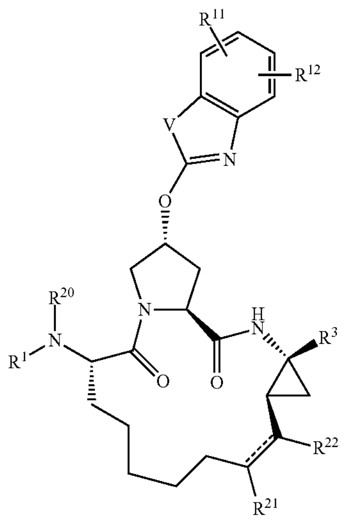

or a pharmaceutically acceptable salt thereof.

3. The compound of claim 1 or pharmaceutically acceptable salt thereof, wherein:

$R^4$ is aryl substituted with one or more substituents each independently selected from the group consisting of halo, cyano, nitro, hydroxy, cyanoamino, —SH, $C_{1-6}$ alkyl optionally substituted with up to 5 fluoro, and $C_{1-6}$ alkoxy optionally substituted with up to 5 fluoro;

n is 0; and $R^3$ is —C(O)NHS(O)$_2$R$^9$ where $R^9$ is $C_{3-7}$cycloalkyl optionally substituted with $C_{1-6}$ alkyl.

4. The compound of claim 3 or pharmaceutically acceptable salt thereof, wherein $R^4$ is aryl substituted with one or more substituents each independently selected from the group consisting of halo, $C_{1-6}$ alkyl optionally substituted with up to 5 fluoro, and $C_{1-6}$ alkoxy optionally substituted with up to 5 fluoro.

5. The compound of claim 4 or pharmaceutically acceptable salt thereof, wherein $R^4$ is aryl substituted with one or more substituents each independently selected from the group consisting of halo, and $C_{1-6}$ alkyl optionally substituted with up to 5 fluoro.

6. The compound of claim 5 or pharmaceutically acceptable salt thereof, wherein $R^4$ is aryl substituted with one or more substituents each independently selected from the group consisting of fluorine and $CF_3$.

7. The compound of claim 1 or pharmaceutically acceptable salt thereof, wherein:

n is 0;

$R^5$ and $R^6$ are each hydrogen;

$R^4$ is phenylor naphthyl, each optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen.

8. The compound of claim 1 or pharmaceutically acceptable salt thereof, wherein:

n is 0;

$R^5$ and $R^6$ are each hydrogen;

$R^4$ is phenyl optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen.

9. The compound of claim 1 or pharmaceutically acceptable salt thereof, wherein:

n is 0;

$R^5$ and $R^6$ are each hydrogen;

$R^4$ is phenyl substituted with one or more substituents each independently selected from the group consisting of halo and $C_{1-6}$ alkyl optionally substituted with up to 5 fluoro; and $R^{20}$ is hydrogen.

10. The compound of claim 1 or pharmaceutically acceptable salt thereof, wherein:

n is 0;

$R^5$ and $R^6$ are each hydrogen;

$R^4$ is phenyl substituted with one or more fluoro and optionally substituted with $CF_3$; and $R^{20}$ is hydrogen.

11. The compound of claim 1 or pharmaceutically acceptable salt thereof, wherein $R^{11}$ and $R^{12}$ are each separately selected from the group consisting of hydrogen, halo, $C_{1-6}$ alkyl optionally substituted with up to 5 fluoro, $C_{1-6}$ alkoxy, and —(CH$_2$)$_q$C$_{3-7}$cycloalkyl where q is 0.

12. The compound of claim 1 or pharmaceutically acceptable salt thereof, wherein Z is propyl.

13. The compound of claim 12 or pharmaceutically acceptable salt thereof, wherein $R^3$ is —C(O)NHS(O)$_2$R$^9$, where $R^9$ is $C_{3-7}$cycloalkyl optionally substituted with $C_{1-6}$ alkyl or $C_{1-6}$ alkoxy.

14. A compound having the structure of Formula V or VI:

(V)

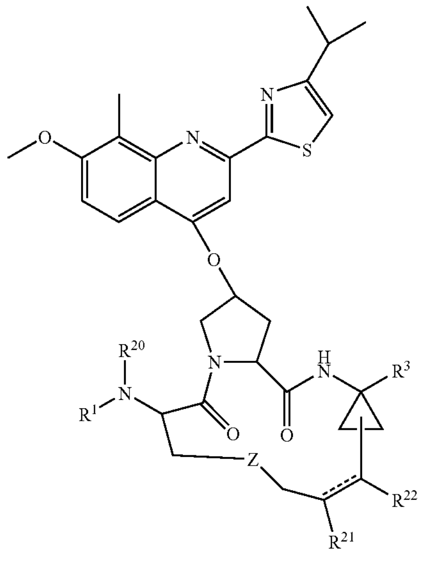

or

-continued (VI)

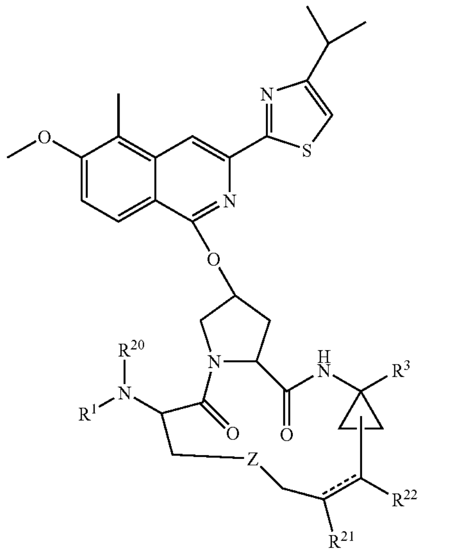

or a pharmaceutically acceptable salt thereof wherein:

(a) $R^1$ is —$(CR^5R^6)_nR^4$;

(b) n is 0;

(c) $R^4$ is aryl, optionally substituted with one or more substituents each independently selected from the group consisting of halo, cyano, nitro, ydroxy, cyanoamino, —SH, $C_{1-6}$ alkyl optionally substituted with up to 5 fluoro, $C_{1-6}$ alkoxy optionally substituted with up to 5 fluoro, $C_{2-6}$ alkenyl, $C_{2-6}$ alkynyl, —$(CH_2)_qC_{3-7}$cycloalkyl, $C_{3-6}$ heterocycloalkyl, aryl, heteroaryl, aryloxy, arylthio, $C_{1-6}$ alkylthio, —$N[(CH_2)_pOH][(CH_2)_rOH]$, —$S(O)_2NR^{1a}R^{1b}$, —$NHC(O)NR^{1a}R^{1b}$, —$NHC(S)NR^{1a}R^{1b}$, —$C(O)NR^{1a}R^{1b}$, —$NR^{1a}R^{1b}$, —$C(O)R^{2a}$, —$C(O)OR^{2a}$, —$NHC(O)R^{2a}$, —$NHC(O)OR^{2a}$, —$SO_mR^{2a}$, —$NHS(O)_2R^{2a}$, —$NR^{2a}[(CH_2)_pOH]$, —$O[(CH_2)_pNR^{3a}R^{3b}]$, —$S[(CH_2)_pNR^{3a}R^{3b}]$, —$(CH_2)_p NR^{3a}R^{3b}$, —$(CH_2)_pR^{4a}$ and —$O(CH_2)_pR^{4a}$;

(d) $R^{1a}$ and $R^{1b}$ are each separately a hydrogen atom, or separately selected from the group consisting of $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_qC_{3-7}$cycloalkyl, $C_{2-6}$ alkenyl, hydroxy-$C_{1-6}$ alkyl, $C_{1-6}$ alkyl optionally substituted with up to 5 fluoro, and $C_{1-6}$ alkoxy optionally substituted with up to 5 fluoro; or $R^{1a}$ and $R^{1b}$ are taken together with the nitrogen to which they are attached to form indolinyl, pyrrolidinyl, piperidinyl, piperazinyl, or morpholinyl;

(e) each $^{2a}$ is separately selected from the group consisting of $C_{1-6}$ alkyl, $C_{3-7}$ cycloalkyl, and $C_{6\ or\ 10}$ aryl, each optionally substituted with one or more substituents each independently selected from the group consisting of halo, cyano, nitro, hydroxy, $C_{1-6}$ alkyl, $C_{2-6}$ alkenyl, —$(CH_2)_qC_{3-7}$cycloalkyl, $C_{1-6}$ alkoxy, phenyl, and hydroxy-$C_{1-6}$ alkyl; or $R^{2a}$ is a tetrahydrofuran ring linked through the $C_3$ or $C_4$ position of the tetrahydrofuran ring; or $R^{2a}$ is a tetrahydropyran ring linked through the $C_4$ position of the tetrahydropyran ring;

(f) $R^{3a}$ and $R^{3b}$ are each separately selected from the group consisting of hydrogen and $C_{1-6}$ alkyl; or $R^{3a}$ and $R^{3b}$ are taken together with the nitrogen to which they are attached to form indolinyl, pyrrolidinyl, piperidinyl, piperazinyl, or morpholinyl;

(g) each $R^{4a}$ is separately imidazolyl or pyrazolyl;

(h) each m is separately 0, 1 or 2;

(i) each p is separately an integer selected from 1-6;

(j) each q is 0;

(k) each r is separately an integer selected from 1-6;

(l) $R^3$ is —$C(O)NHS(O)_2R^9$, where $R^9$ is —$(CH_2)_qC_{3-7}$cycloalkyl, optionally substituted with one or more substituents each independently selected from the group consisting of halo, cyano, nitro, hydroxy, —COOH, $C_{1-6}$ alkyl, —$(CH_2)_tC_{3-7}$cycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, and $C_{1-6}$ alkoxy optionally substituted with up to 5 fluoro;

(m) each t is separately 0, 1 or 2;

(n) $R^5$ and $R^6$ are each separately a hydrogen, or separately selected from the group consisting of alkyl and arylalkyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro; or $R^5$ and $R^6$ are taken together with the carbon to which they are attached to form a $C_{3-7}$ cycloalkyl, optionally substituted with one or more sub stituents each independently selected from the group consisting of halo, cyano, nitro, hydroxy, $C_{1-6}$ alkyl, —$(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

(o) each u is separately 0, 1 or 2;

(p) Z is selected from the group consisting of

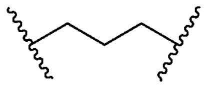, 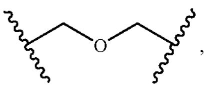,

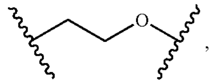, 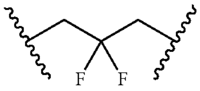,

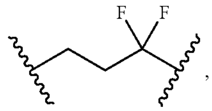, 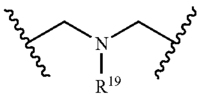,

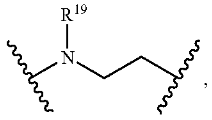, 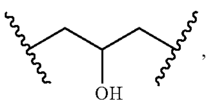, and

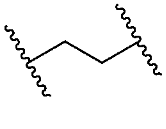;

(q) $R^{19}$ is hydrogen, $C_{1-6}$ alkyl optionally substituted with up to 5 fluoro, or —$SO_mR^{2a}$;

(r) $R^{20}$ is hydrogen;

(s) $R^{21}$ and $R^{22}$ are each hydrogen; and (t) the dashed line represents an optional double bond.

15. The compound of claim 14 or pharmaceutically acceptable salt thereof, wherein:

n is 0;

$R^5$ and $R^6$ are each hydrogen;

$R^4$ is phenyl or naphthyl, each optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen.

16. The compound of claim 14 or pharmaceutically acceptable salt thereof, wherein:

n is 0;

$R^5$ and $R^6$ are each hydrogen;

$R^4$ is phenyl optionally substituted with one or more substituents each independently selected from the group consisting of halo, cyano, phenyl, $C_{1-6}$ alkyl optionally substituted with up to 5 fluoro, and $C_{1-6}$ alkoxy optionally substituted with up to 5 fluoro; and $R^{20}$ is hydrogen.

17. The compound of claim 14 or pharmaceutically acceptable salt thereof, wherein:

n is 0;

$R^5$ and $R^6$ are each hydrogen;

$R^4$ is phenyl substituted with one or more substituents each independently selected from the group consisting of halo and $C_{1-6}$ alkyl optionally substituted with up to 5 fluoro; and $R^{20}$ is hydrogen.

18. The compound of claim 14 or pharmaceutically acceptable salt thereof, wherein:

n is 0;

$R^5$ and $R^6$ are each hydrogen;

$R^4$ is phenyl substituted with one or more fluoro and optionally substituted with $CF_3$; and $R^{20}$ is hydrogen.

19. The compound of claim 14 or pharmaceutically acceptable salt thereof, wherein Z is propyl.

20. The compound of claim 19 or pharmaceutically acceptable salt thereof, wherein $R^3$ is —C(O)NHS(O)$_2$R$^9$, where $R^9$ is $C_{3-7}$cycloalkyl optionally substituted with $C_{1-6}$ alkyl or $C_{1-6}$ alkoxy.

21. A compound selected from the group consisting of:

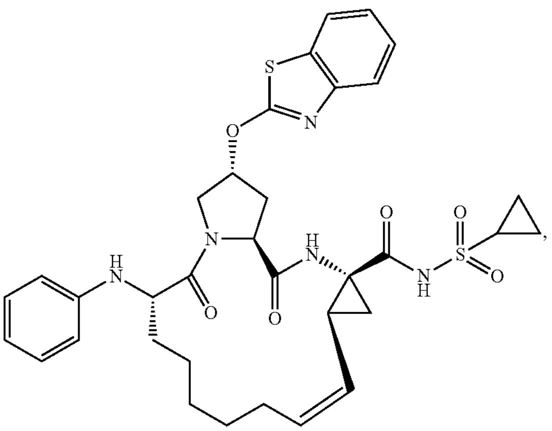

,

-continued

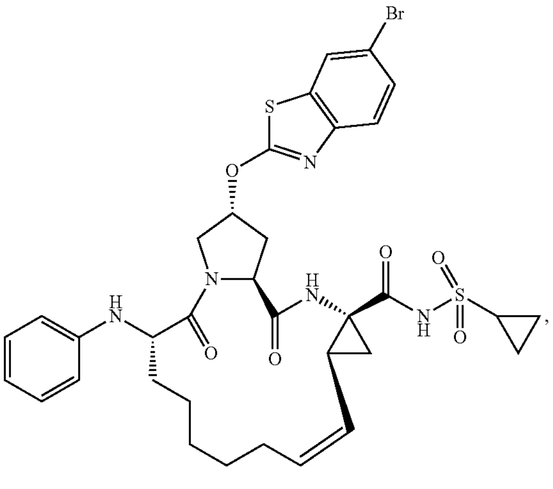

,

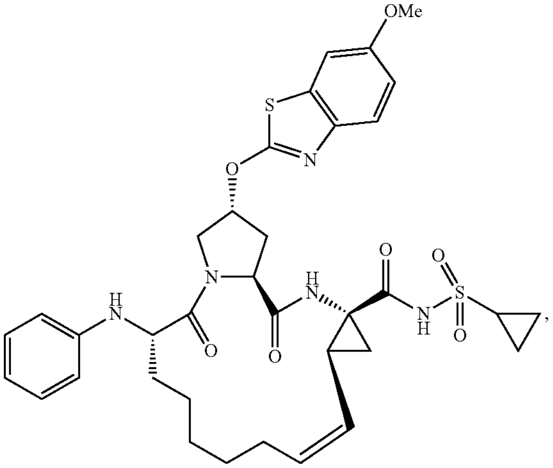

,

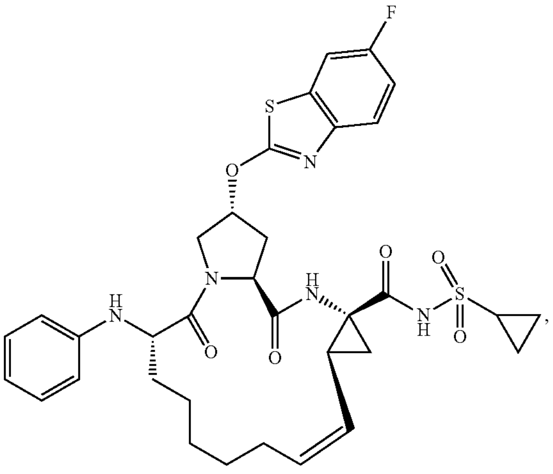

,

-continued
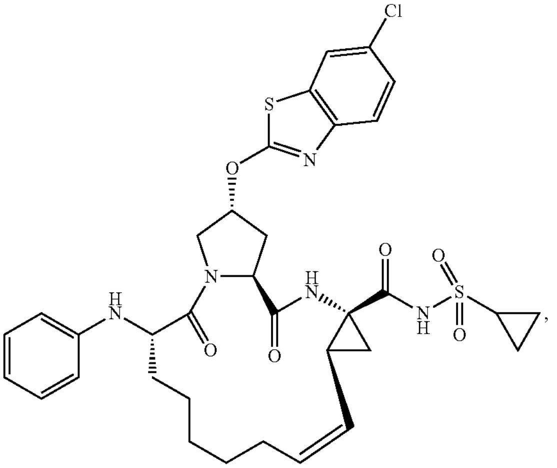
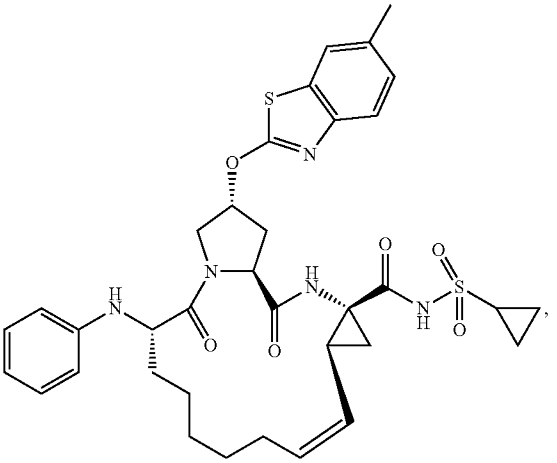
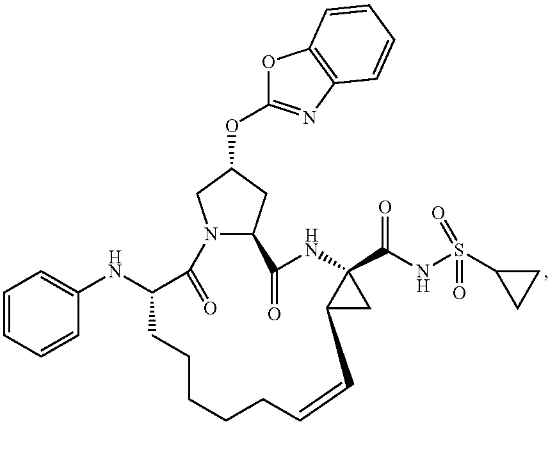
-continued
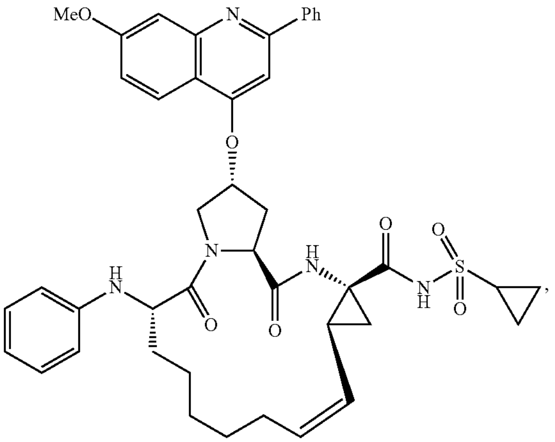
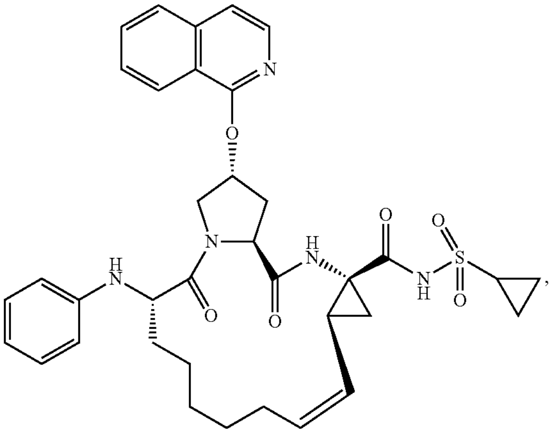
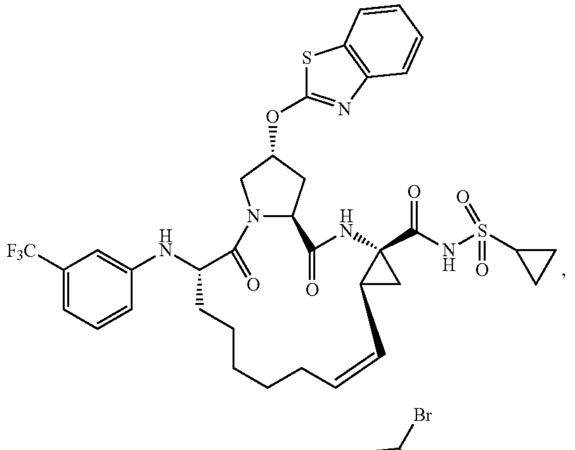
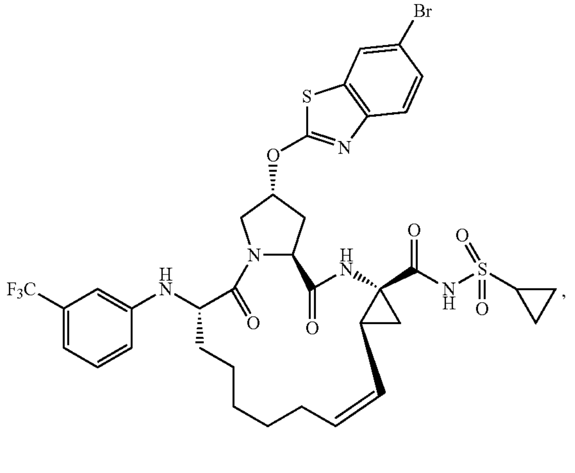

-continued
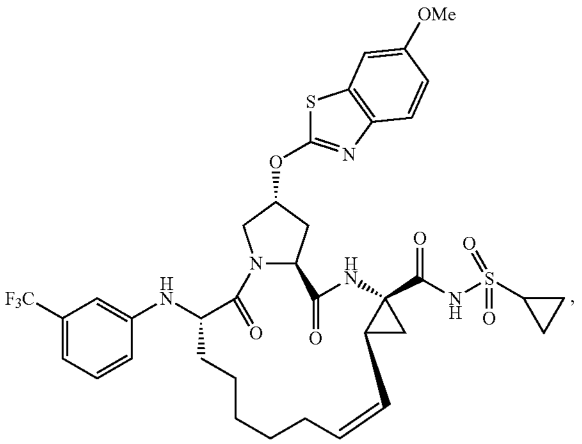
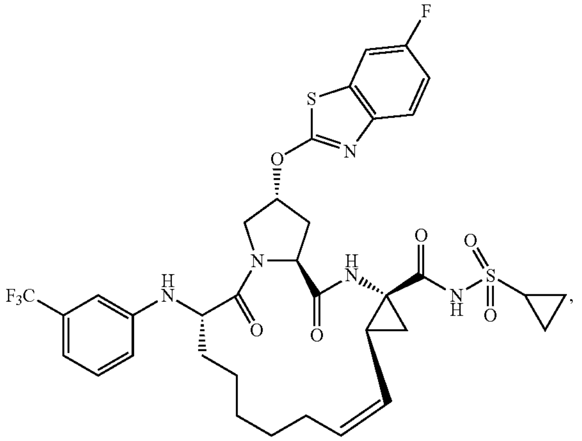
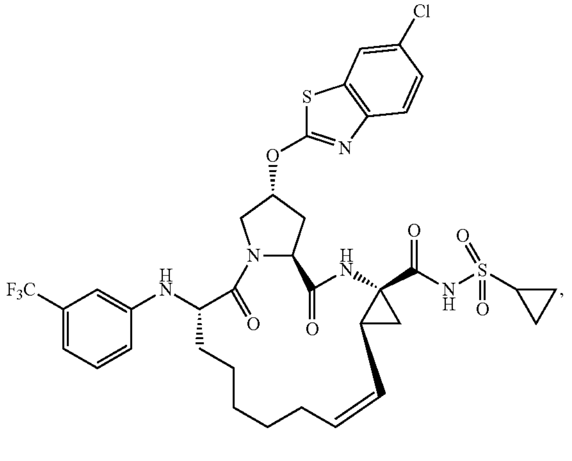
-continued
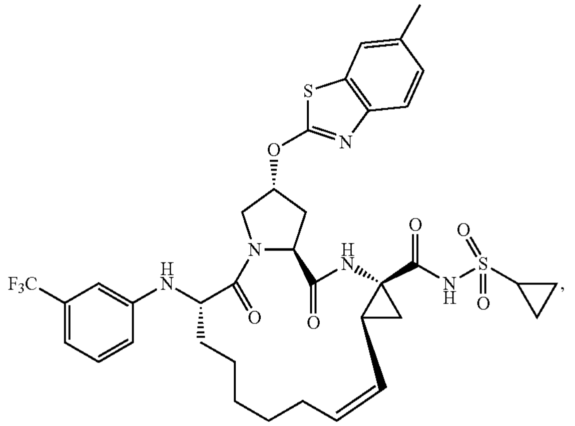
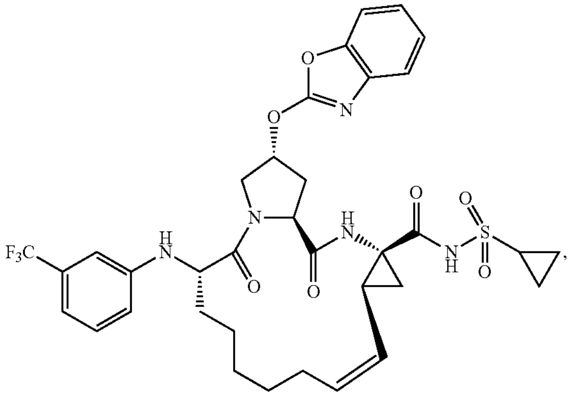
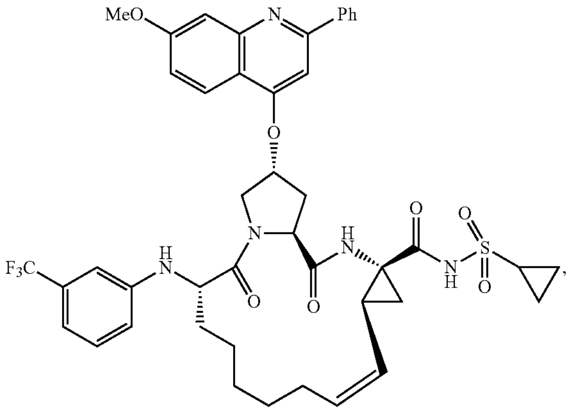
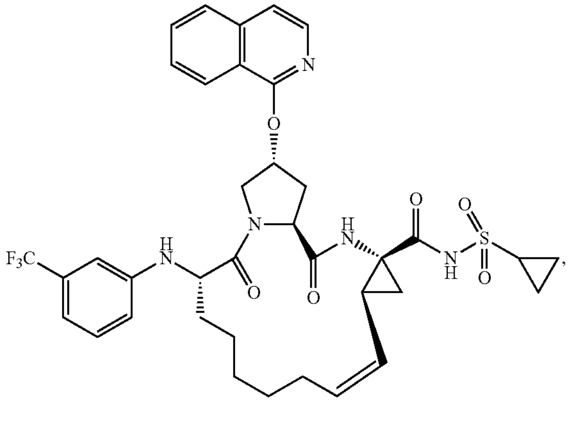

-continued
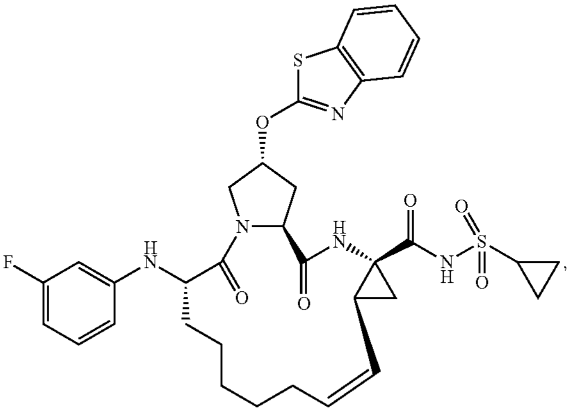
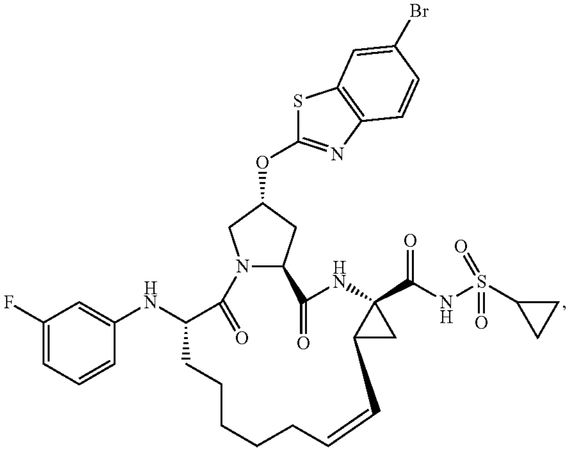
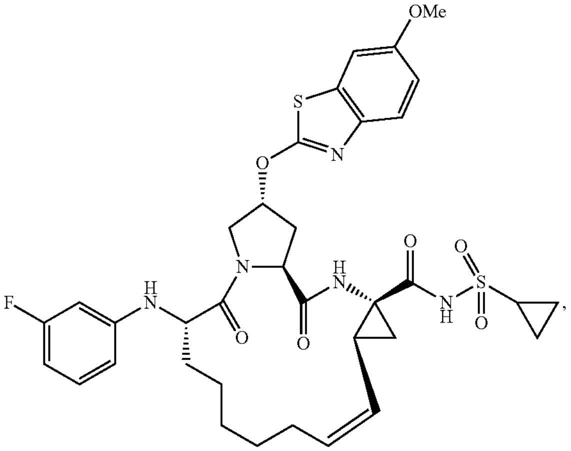
-continued
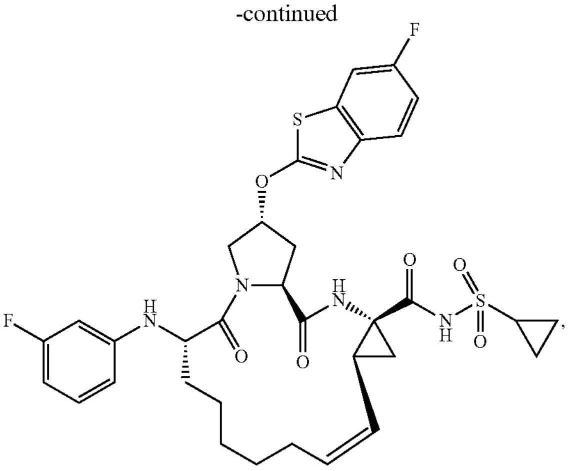
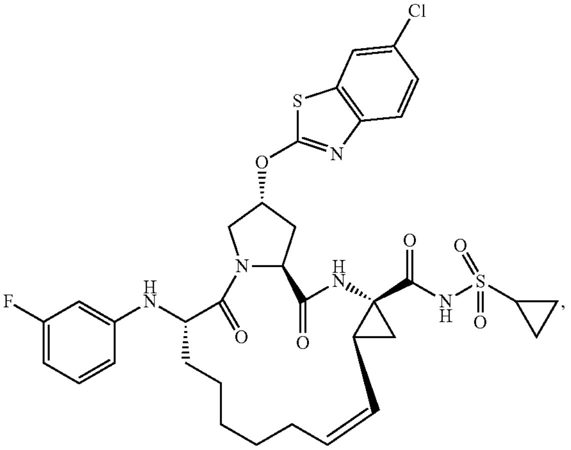
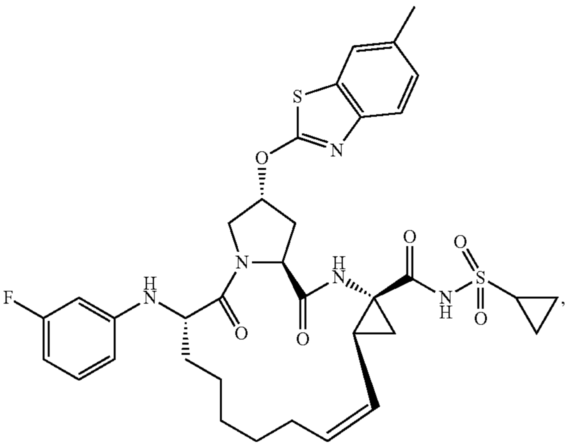

-continued
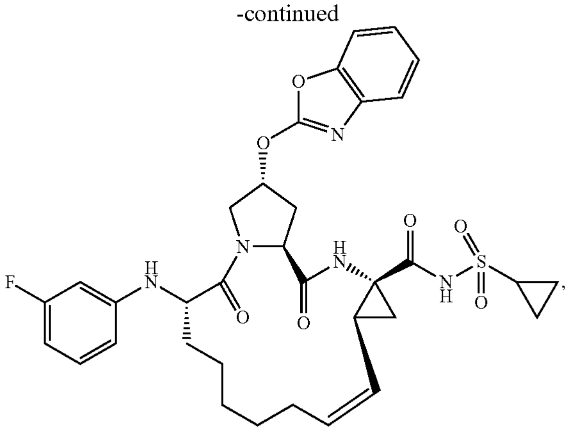
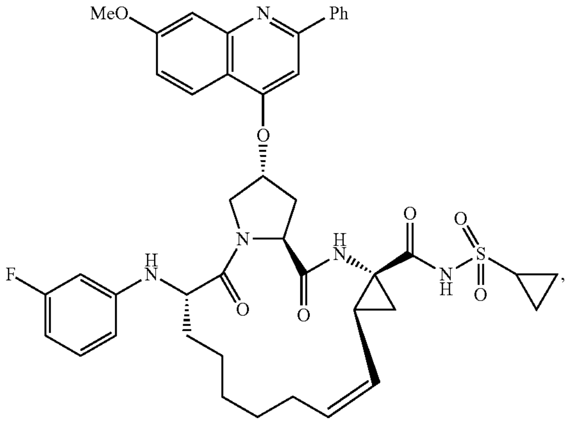
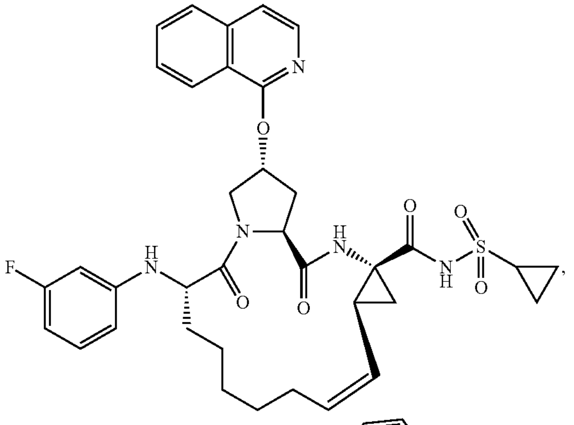
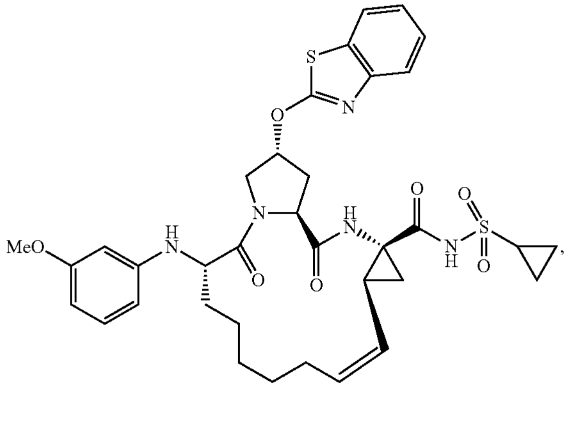
-continued
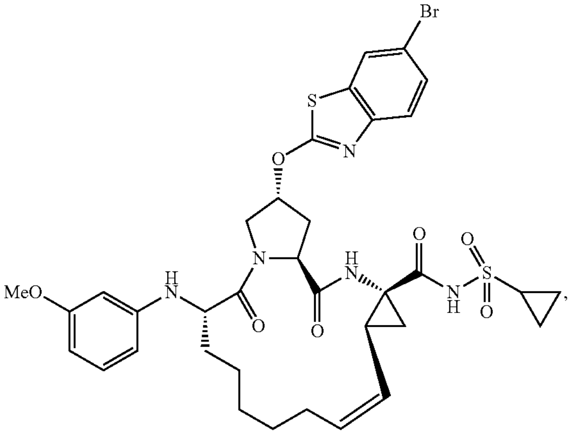
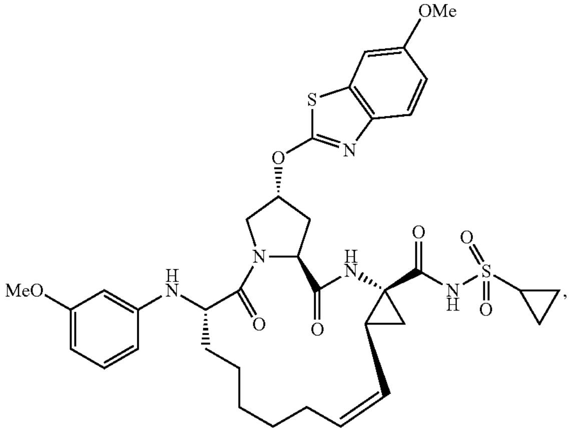
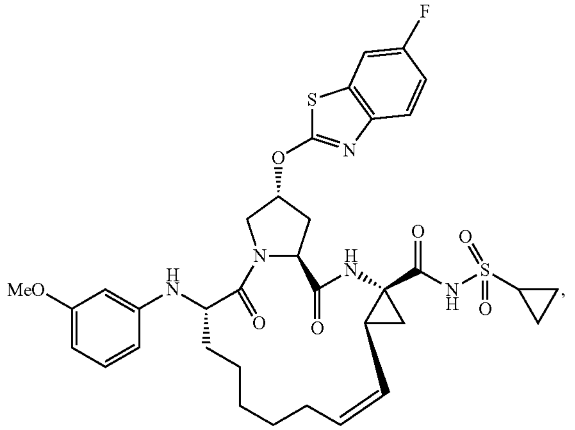
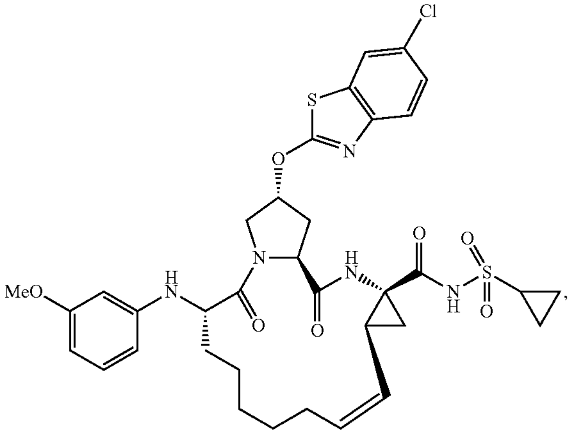

-continued
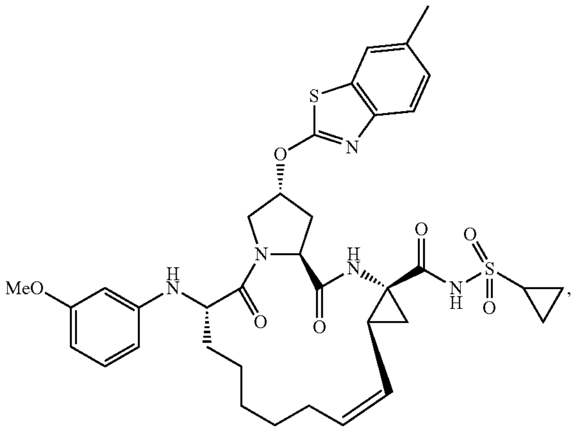
,
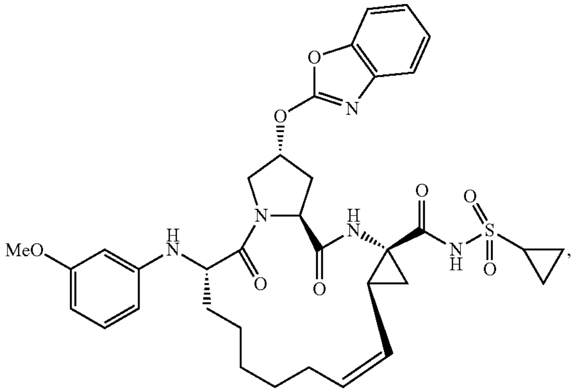
,
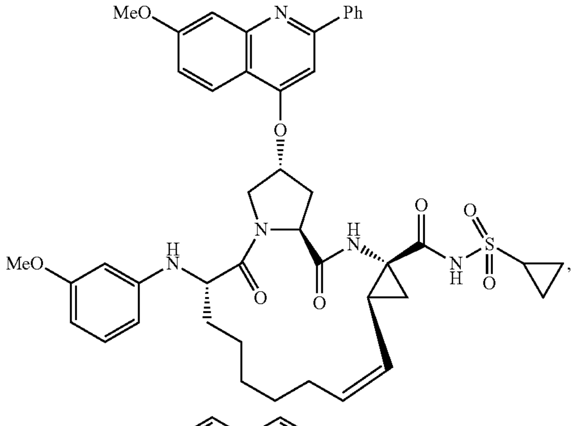
,
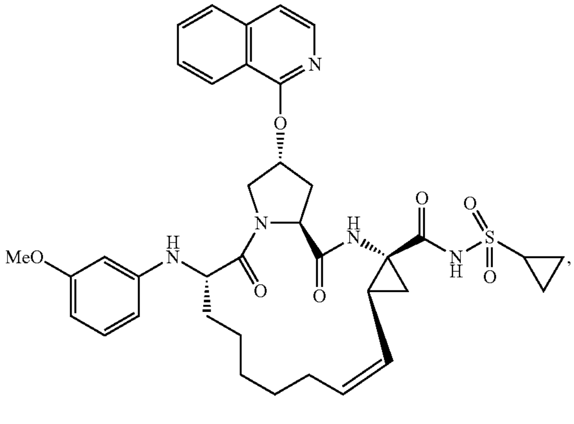
,
-continued
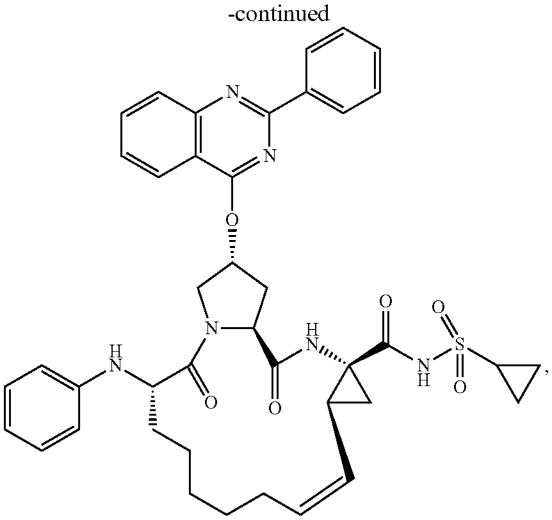
,
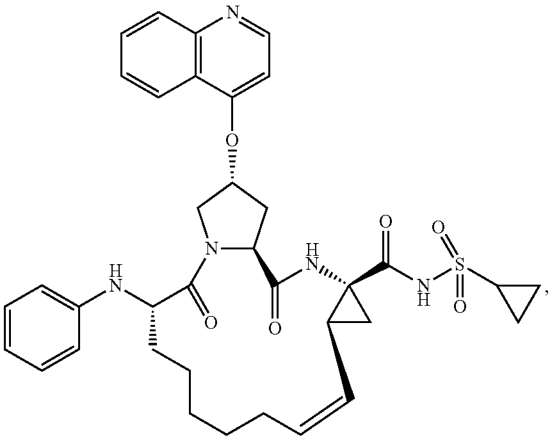
,
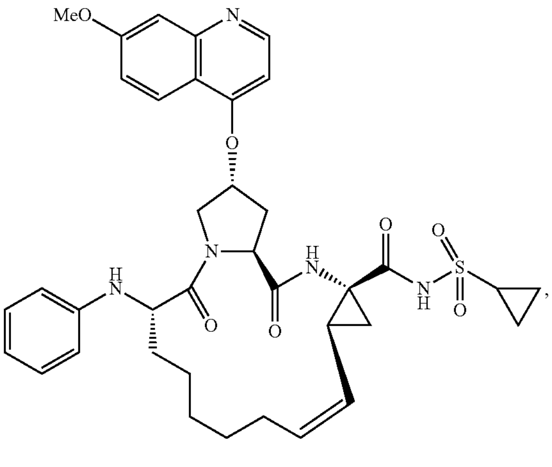
, -continued
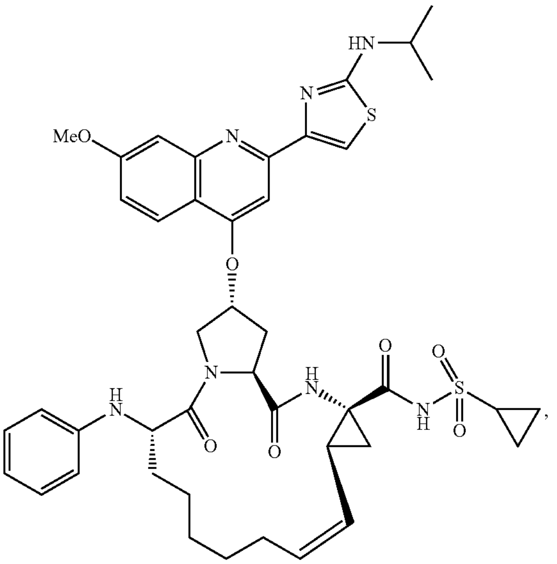
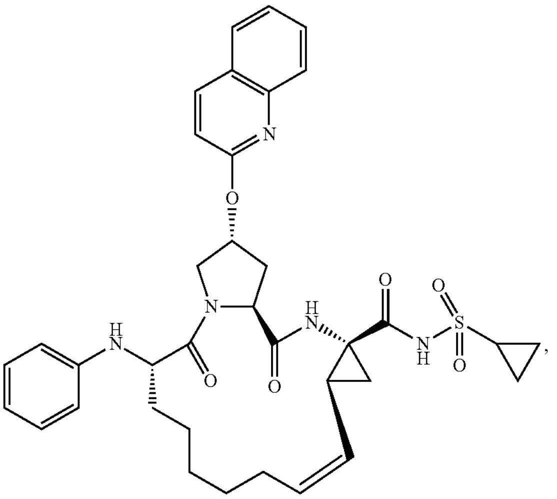
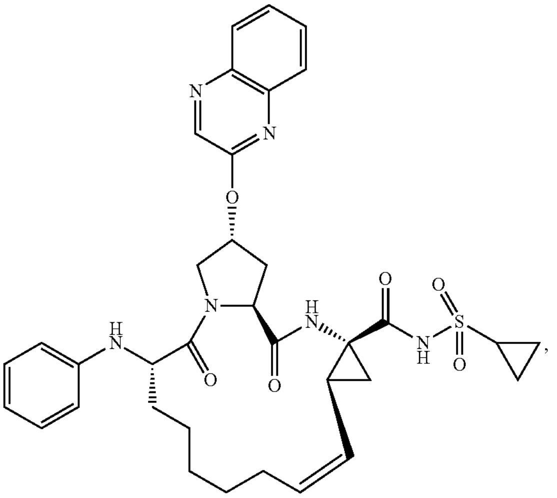
-continued
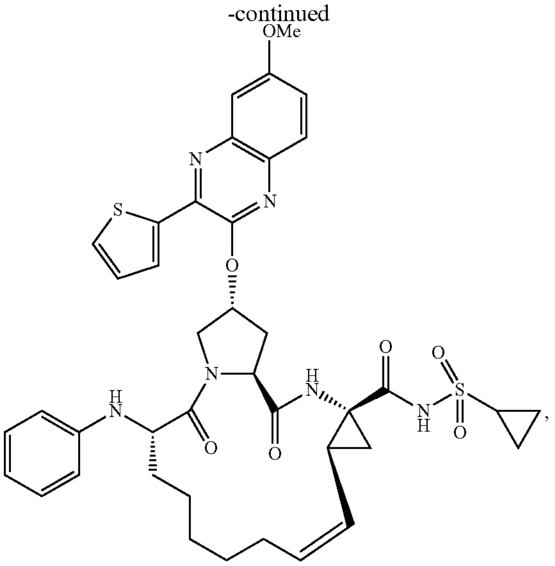
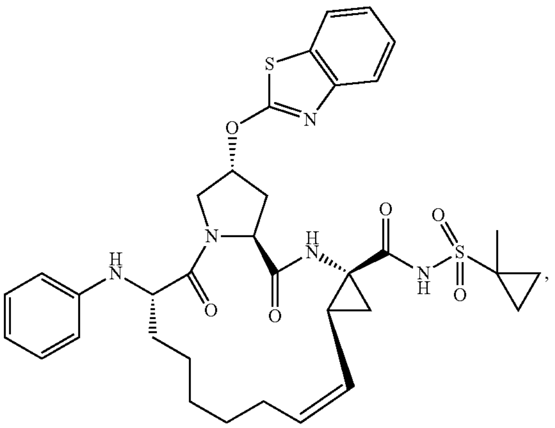
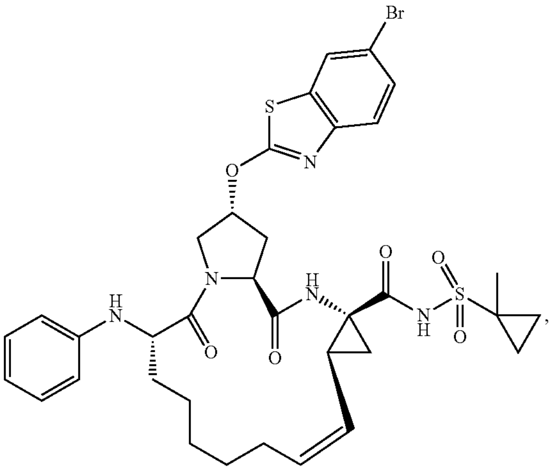

-continued
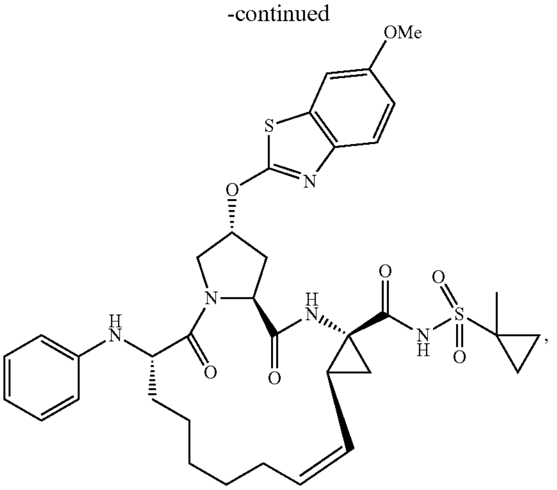
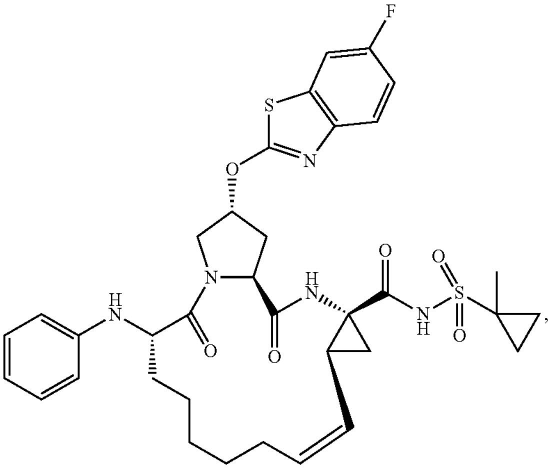
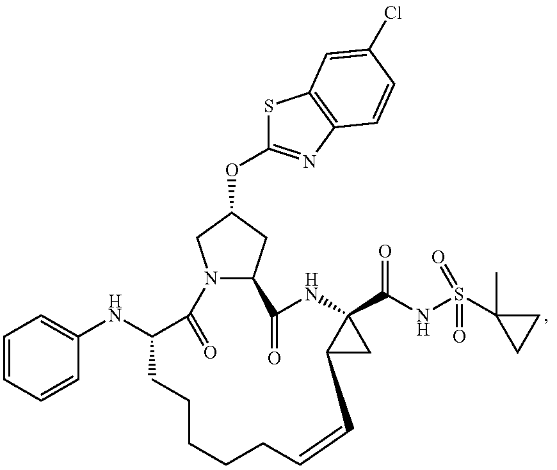
-continued
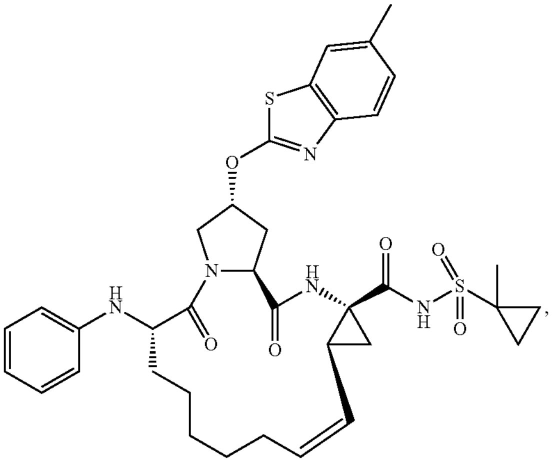
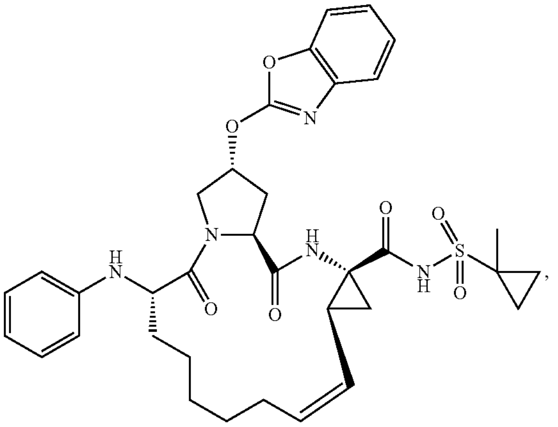
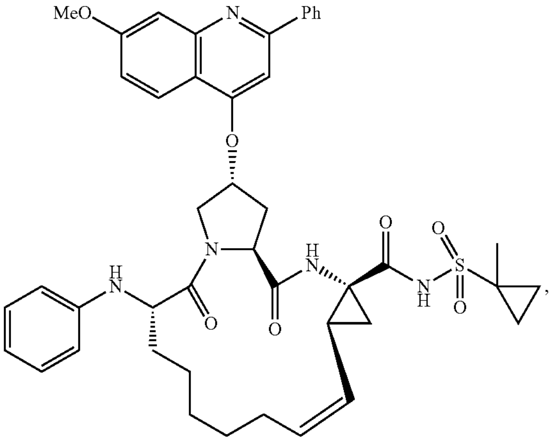

-continued
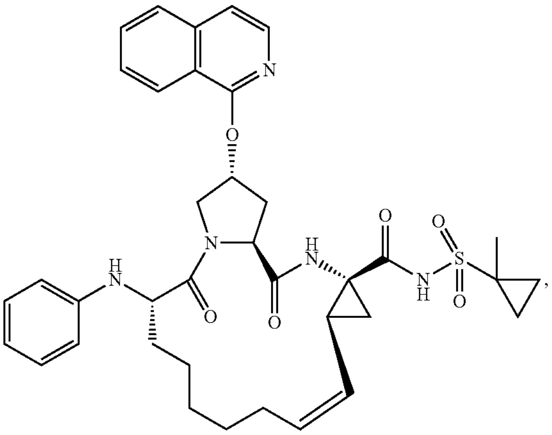
,
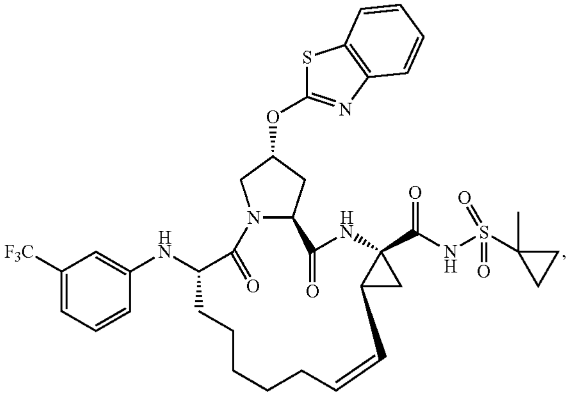
,
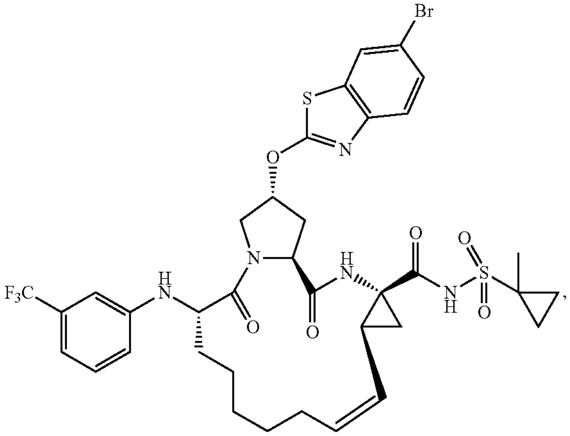
,
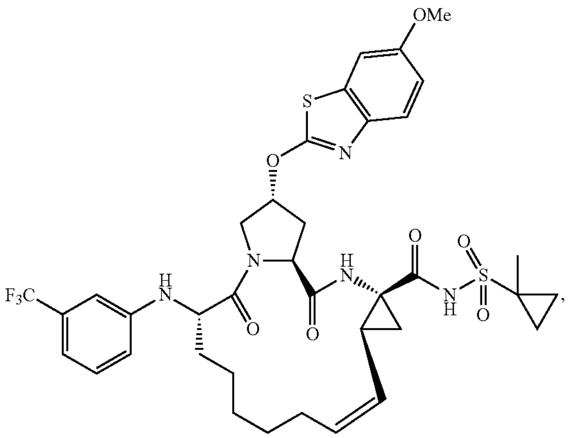
,
-continued
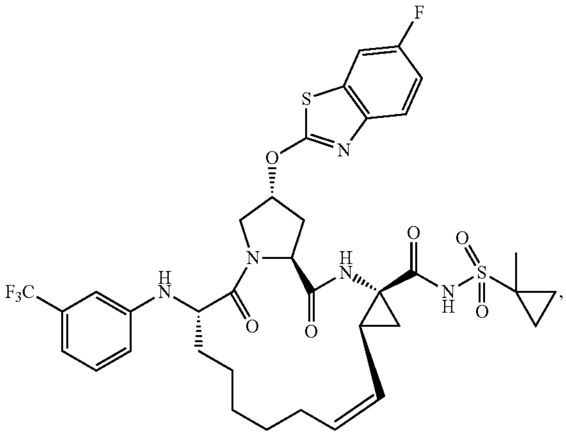
,
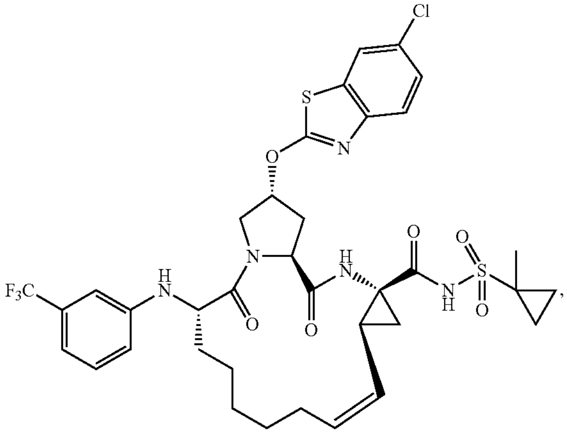
,
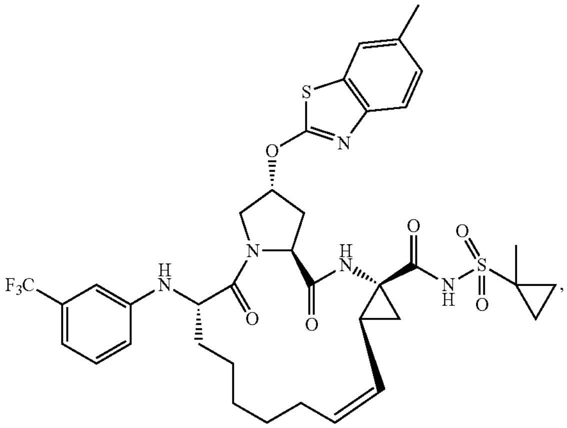
,
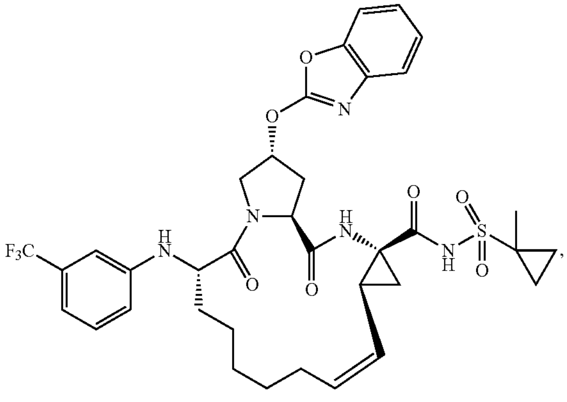
, -continued
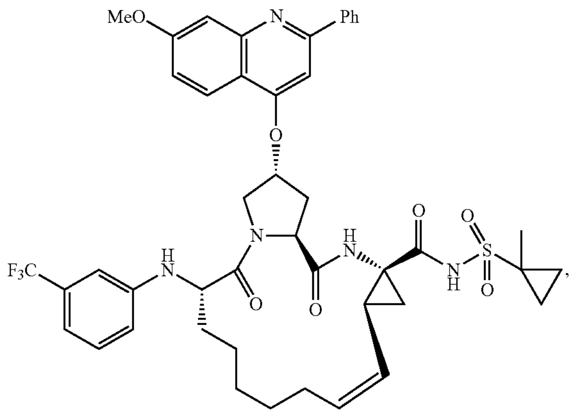
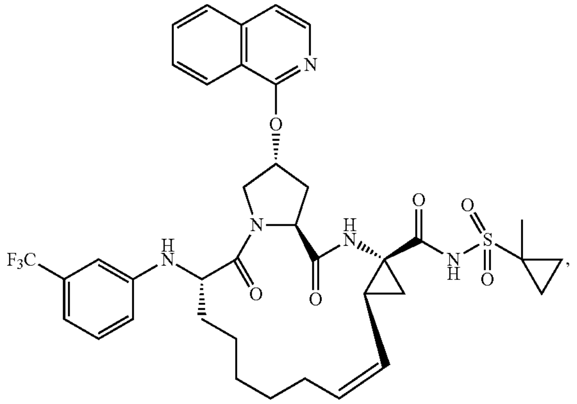
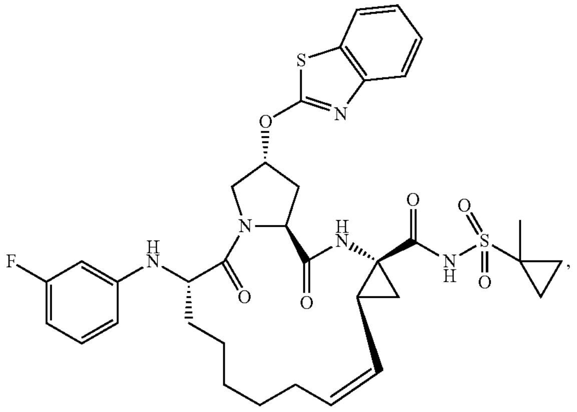
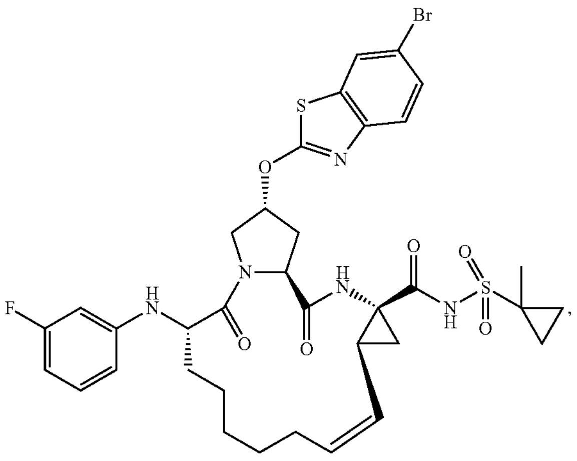
-continued
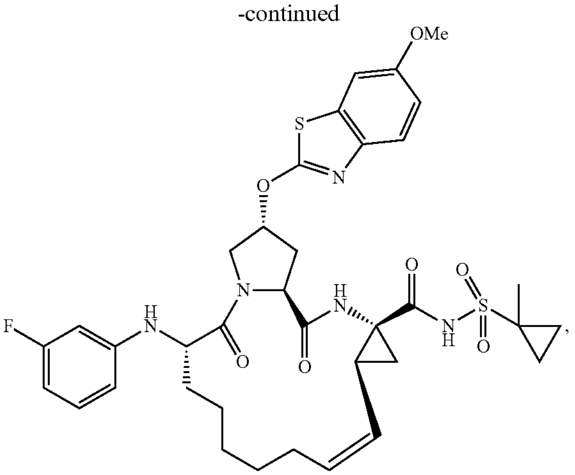
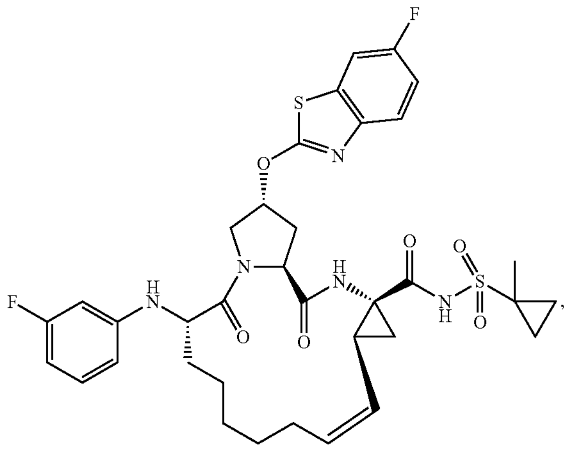
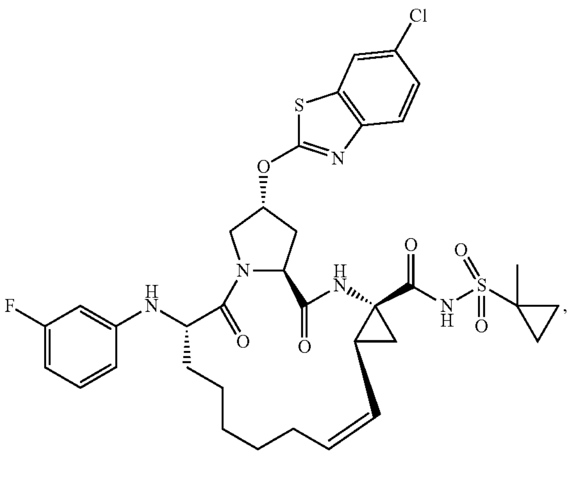

-continued
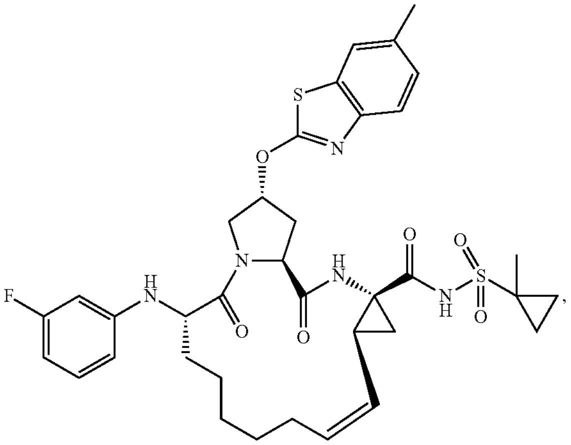
,
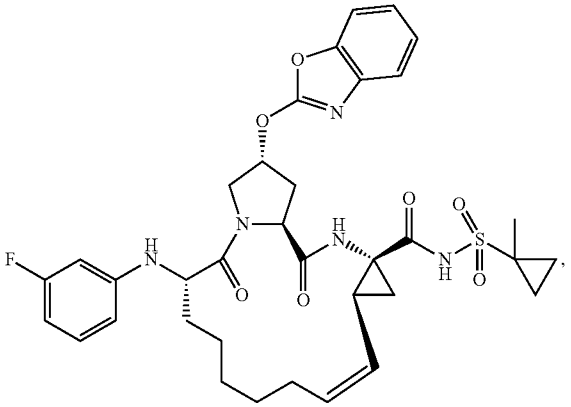
,
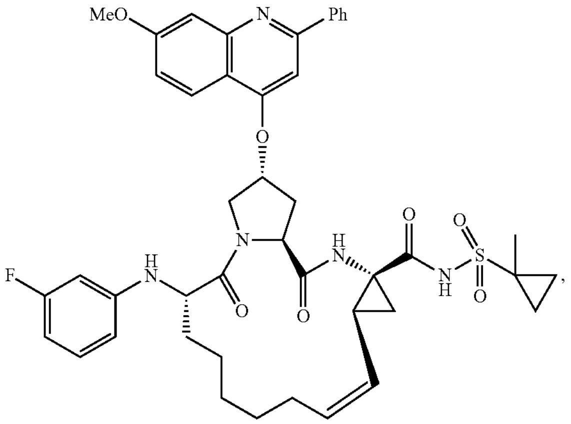
,
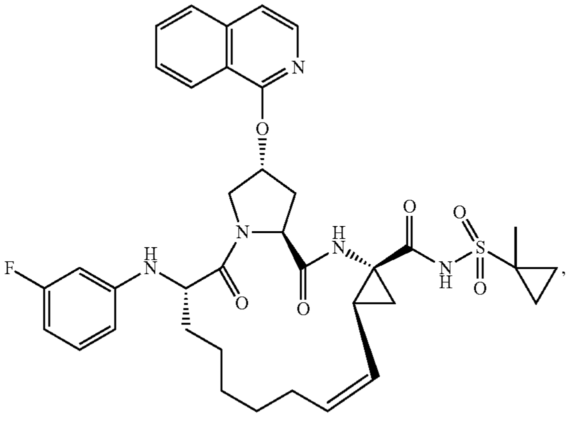
,
-continued
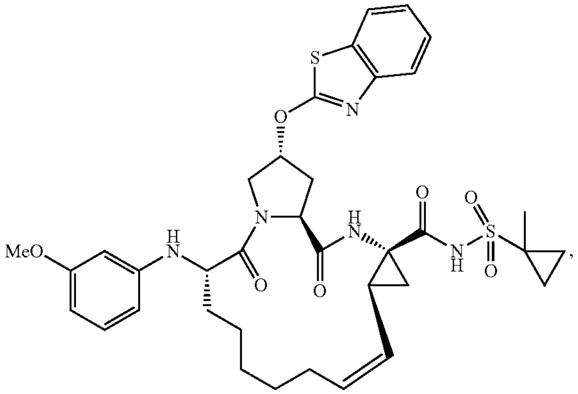
,
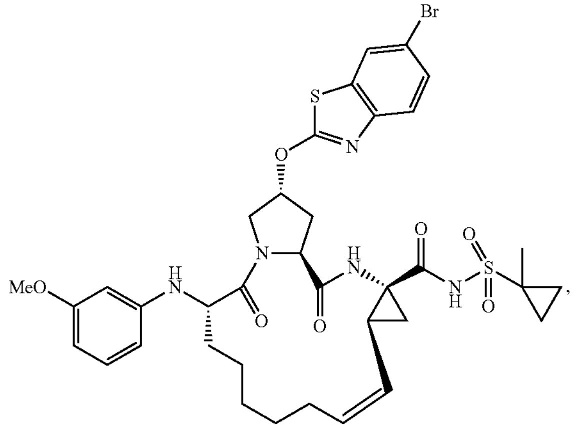
,
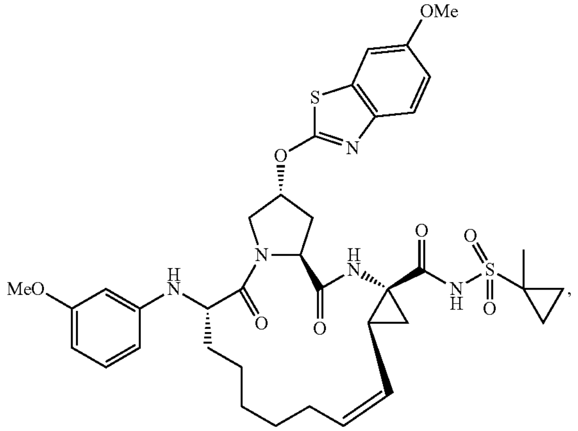
,
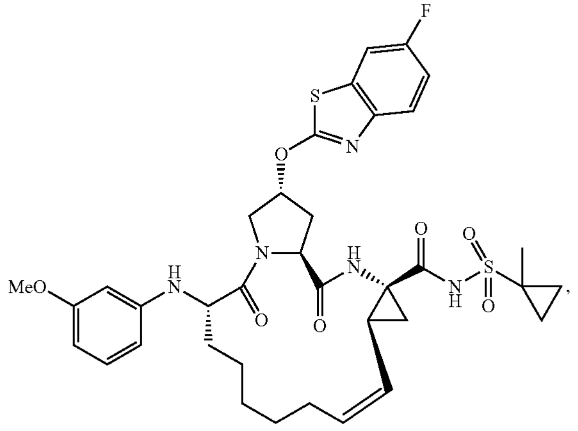
, -continued
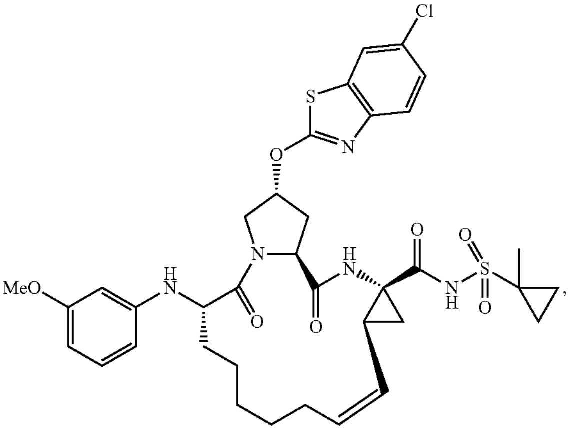
,
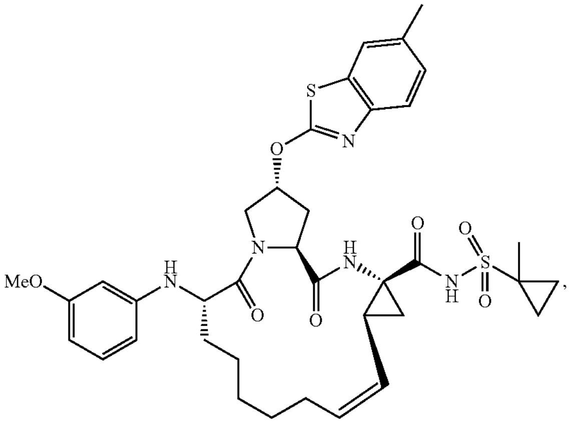
,
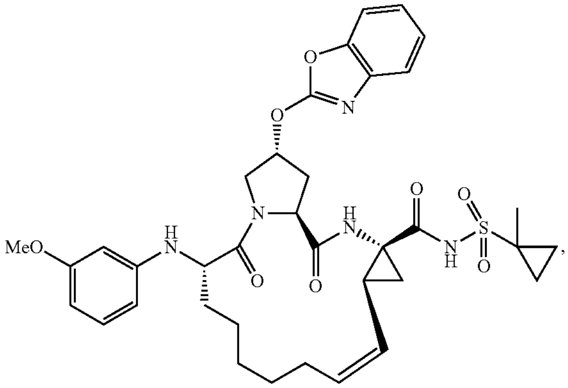
,
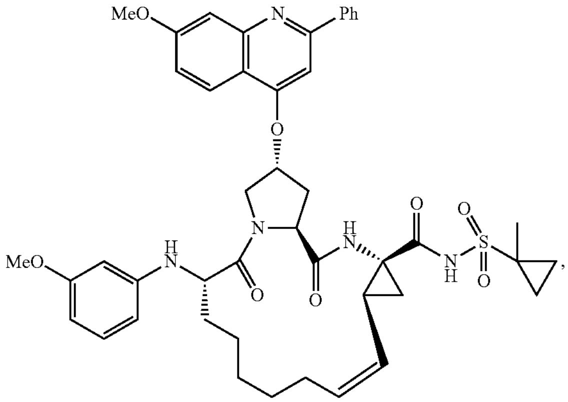
,
-continued
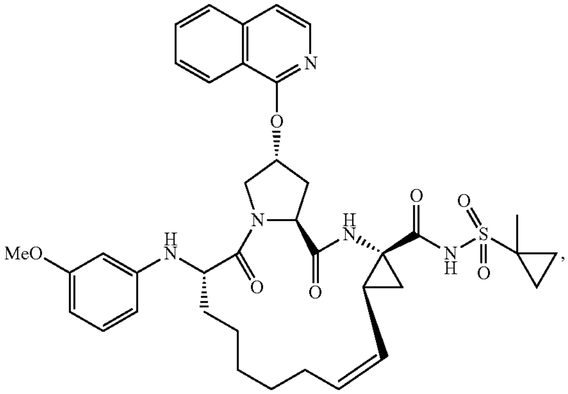
,
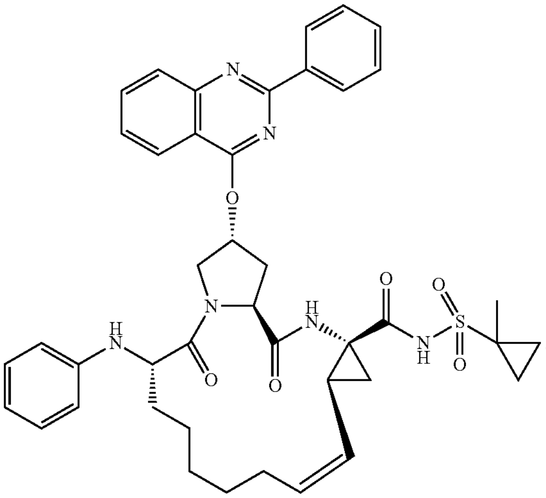
,
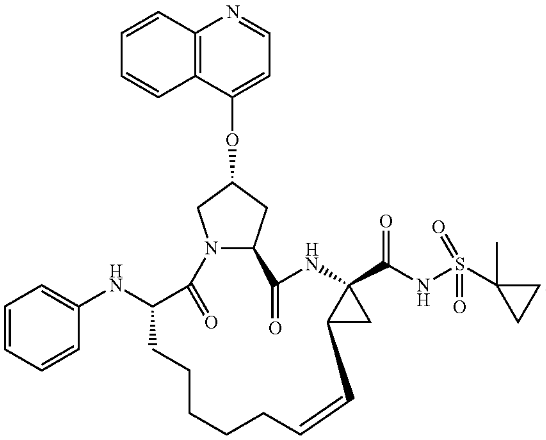
, -continued
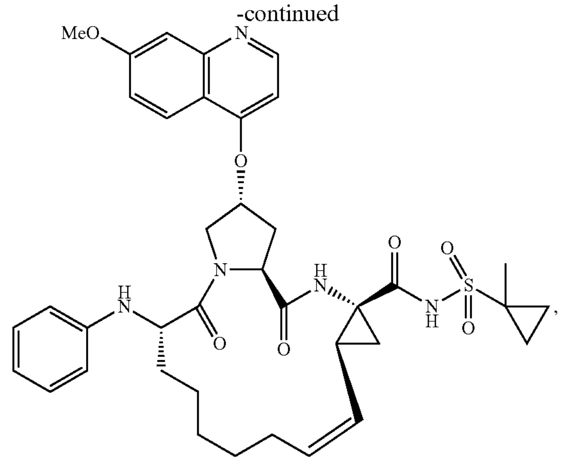
,
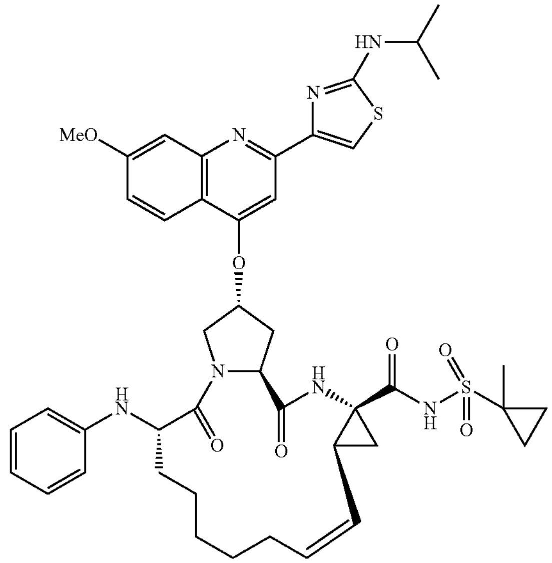
,
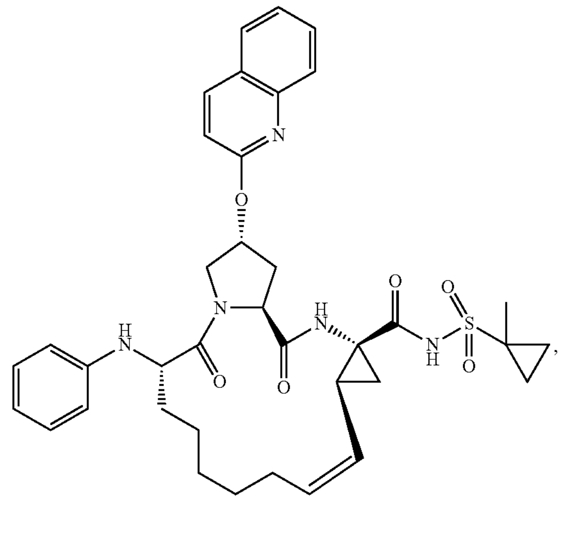
,
-continued
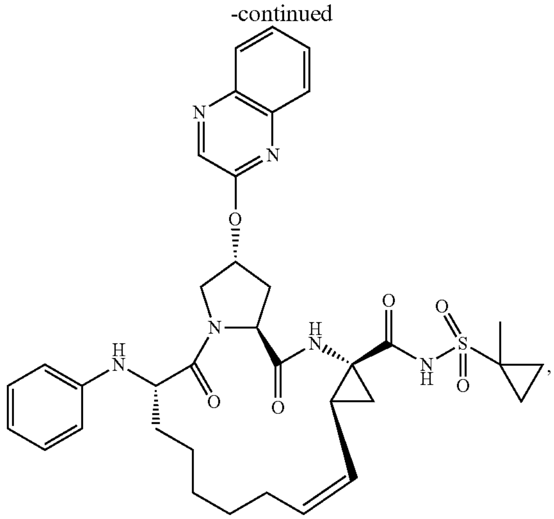
,
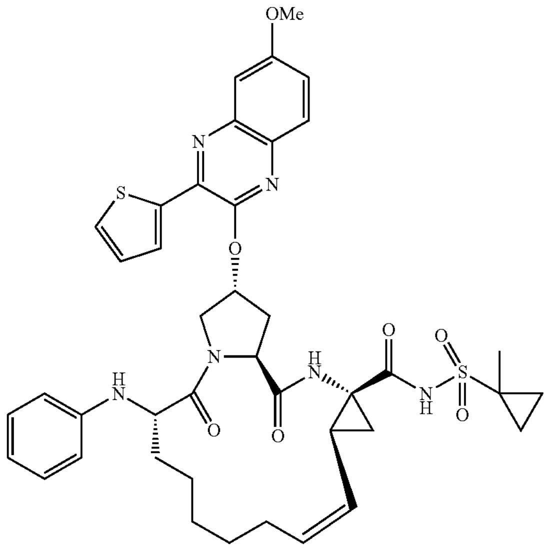
,
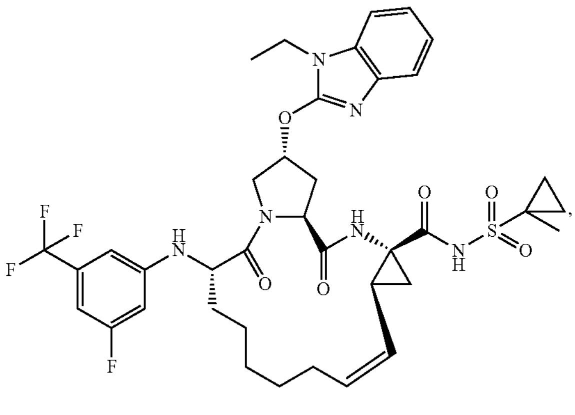
, -continued
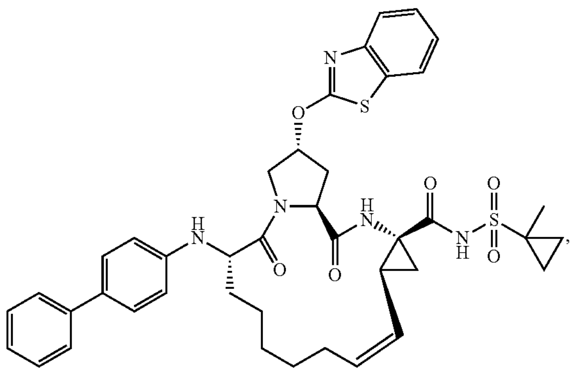,
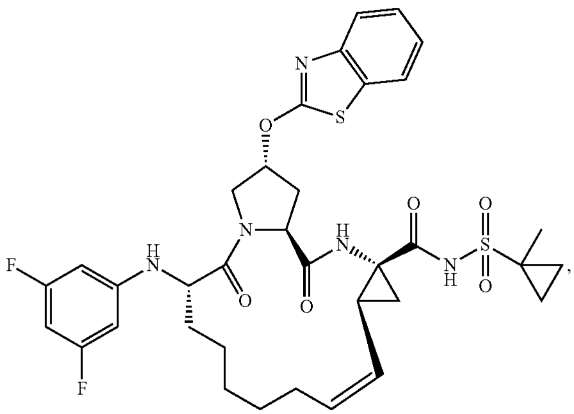
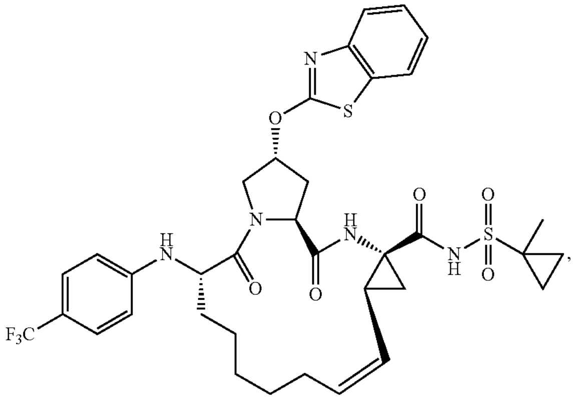,
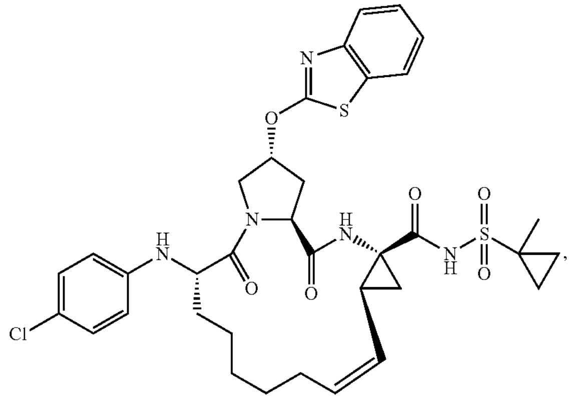,
-continued
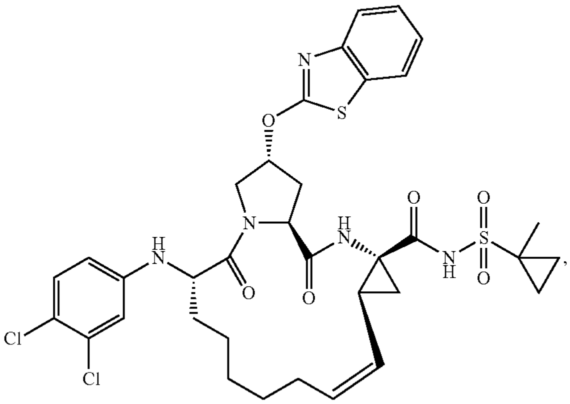,
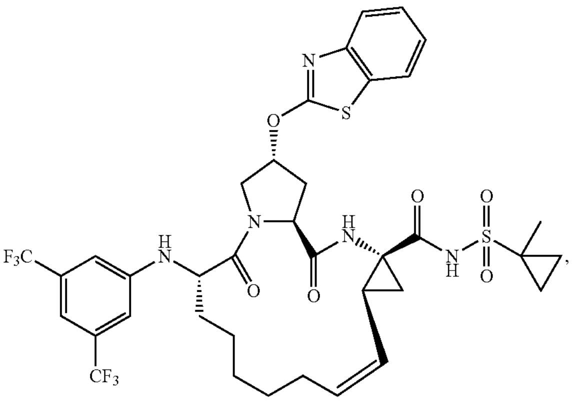,
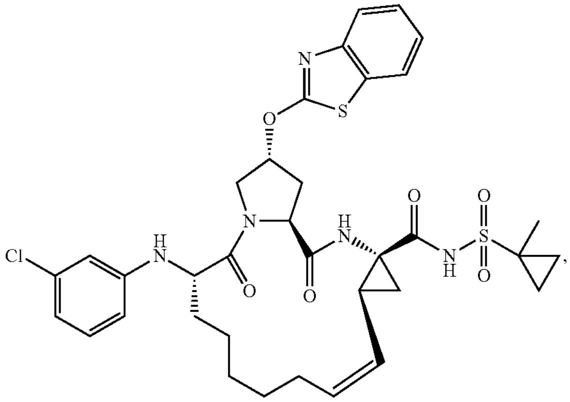,
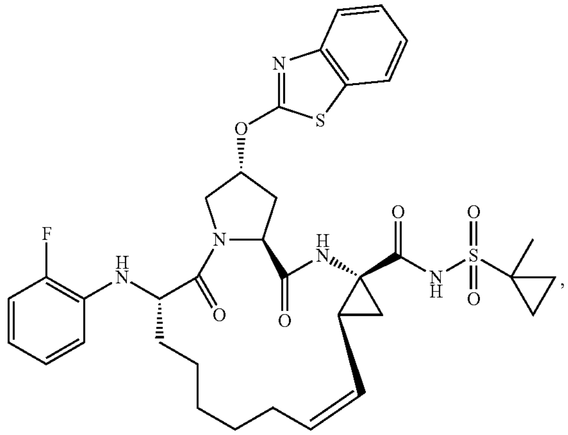, -continued
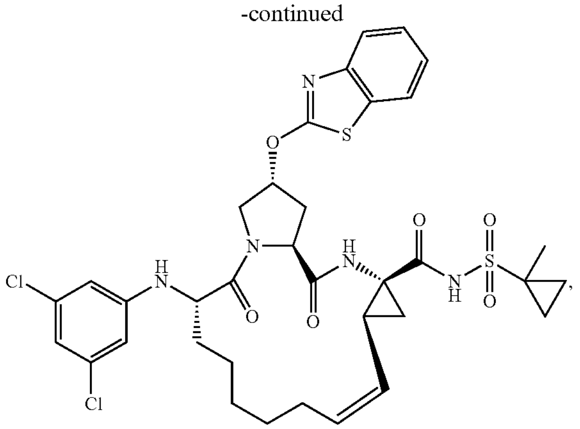
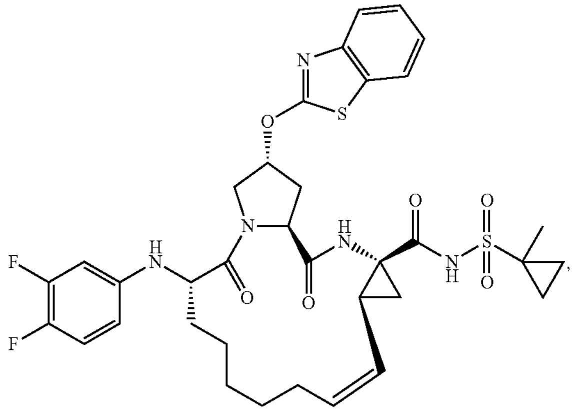
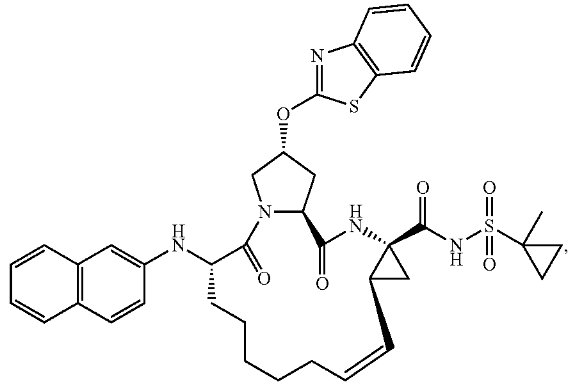
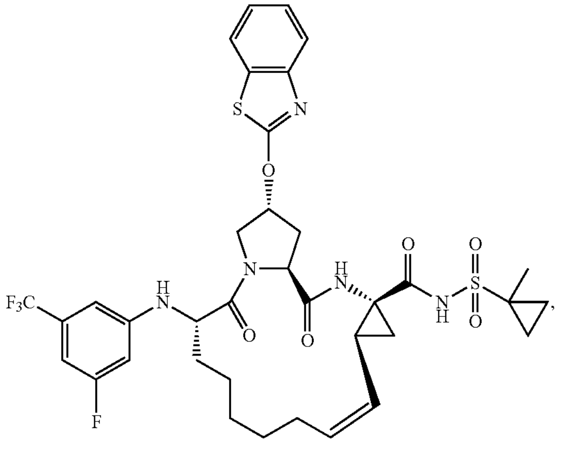
-continued
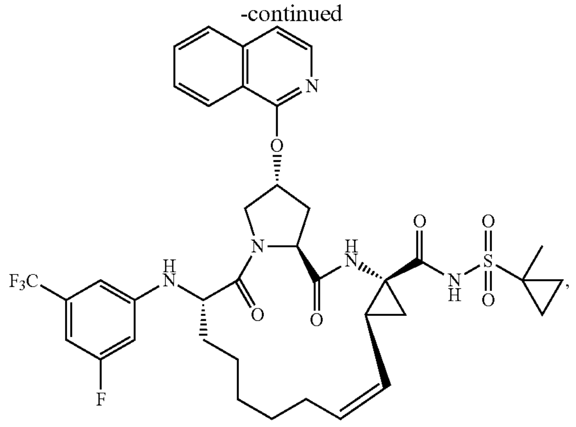
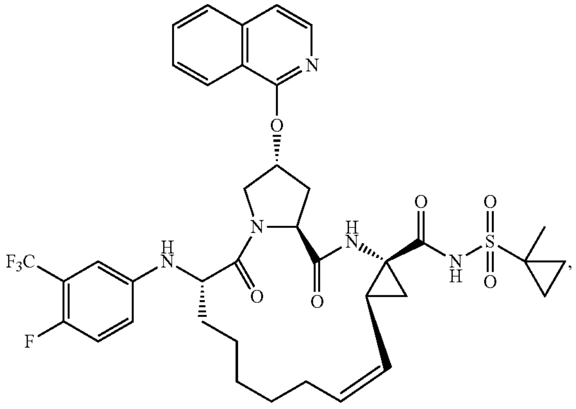
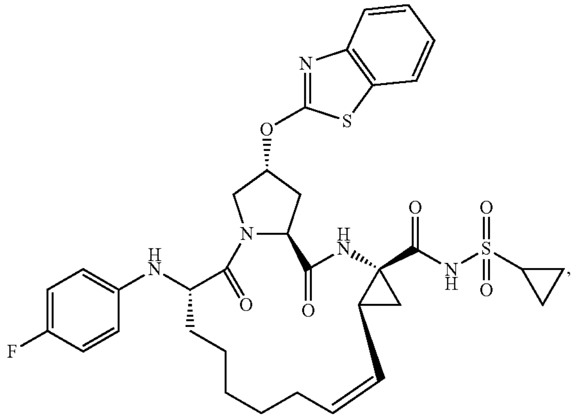
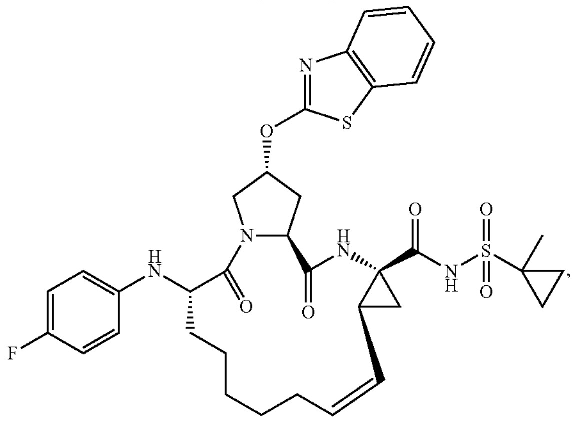

-continued
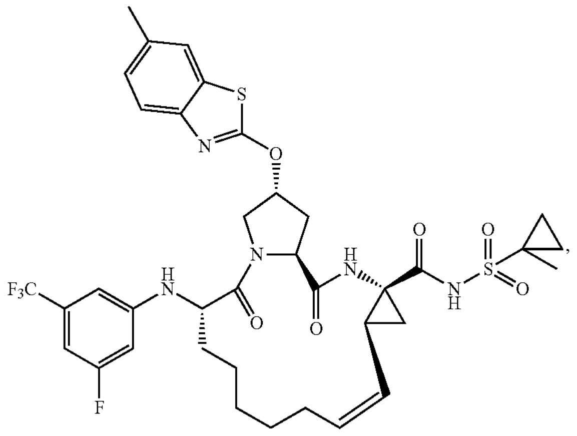
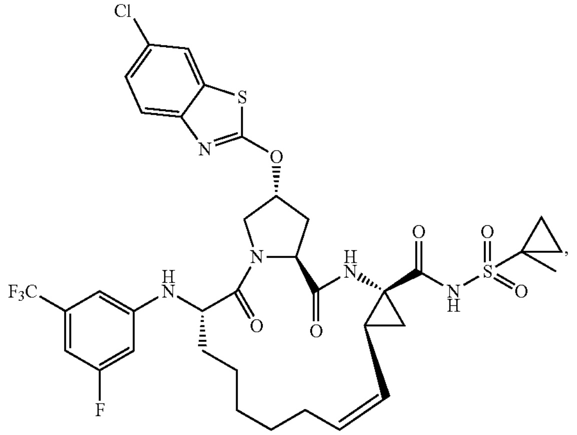
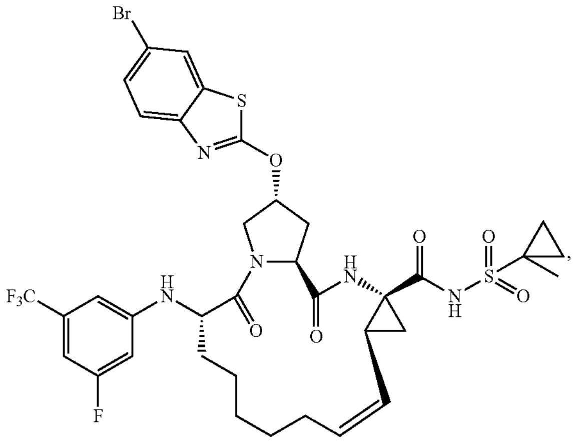
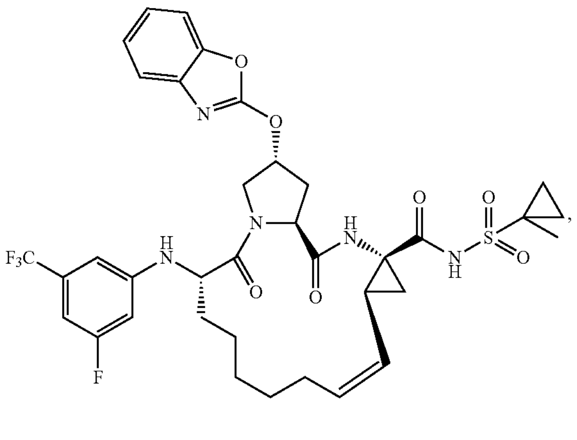
-continued
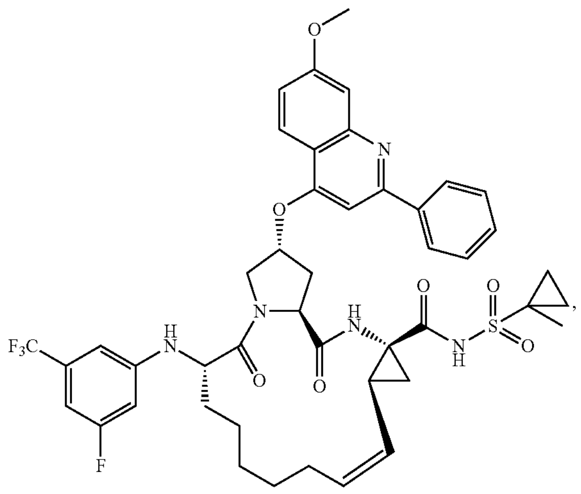
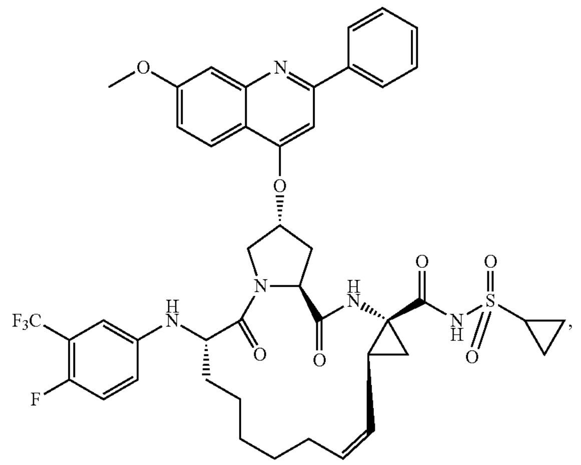
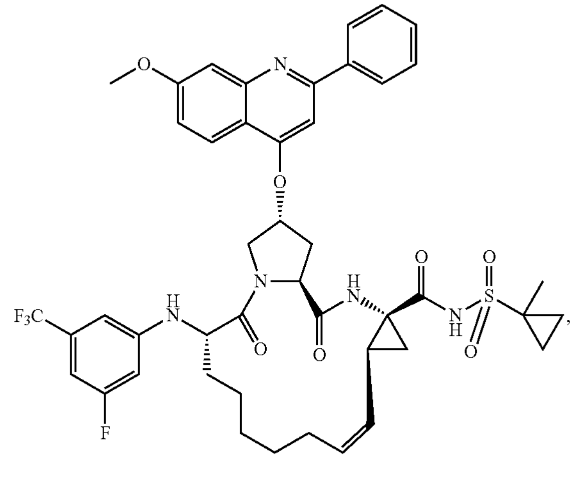

-continued
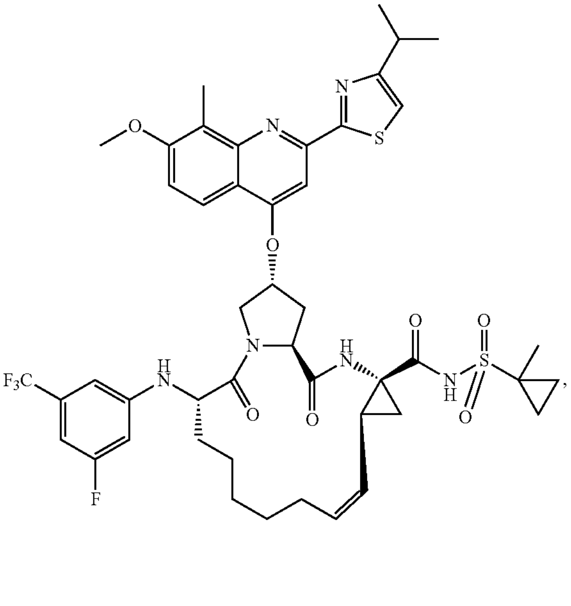
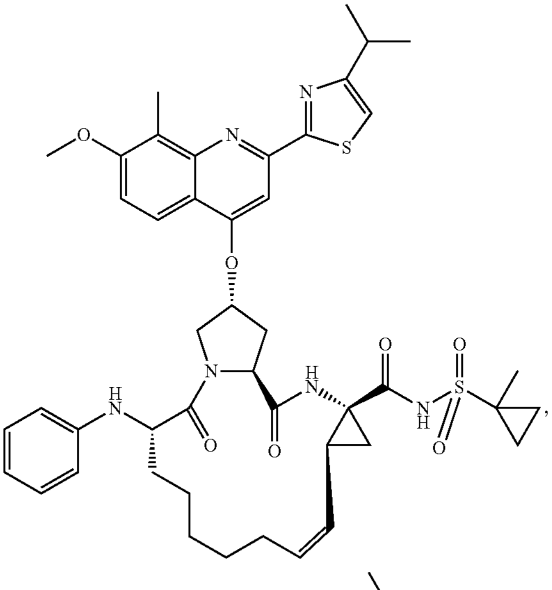
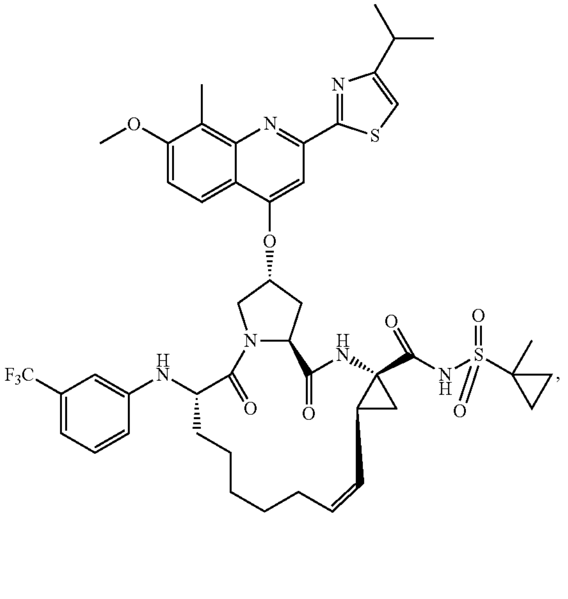
-continued
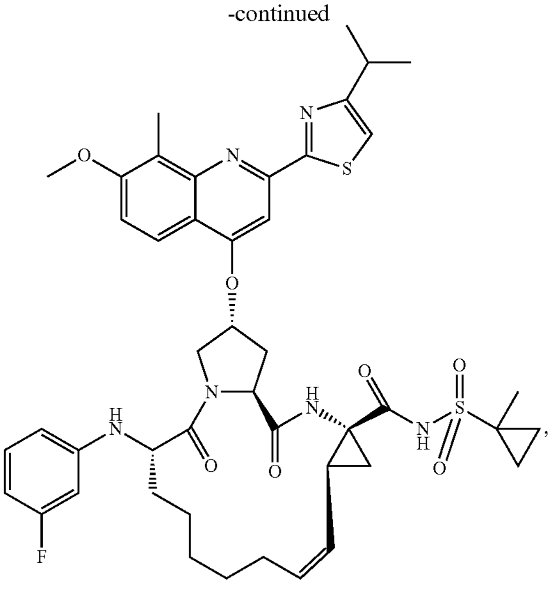
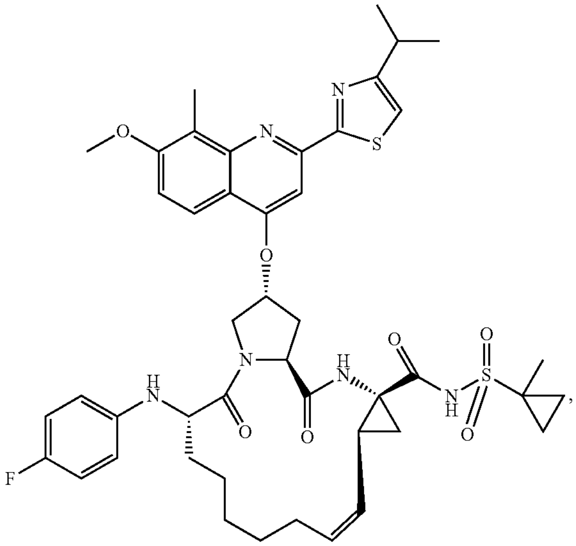
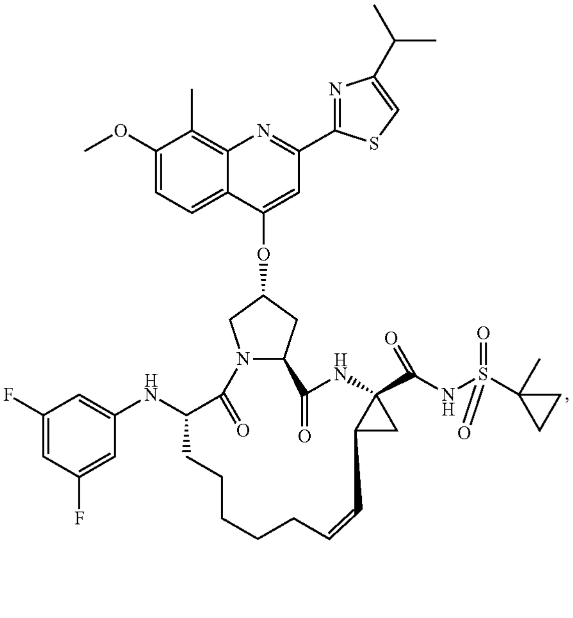

-continued
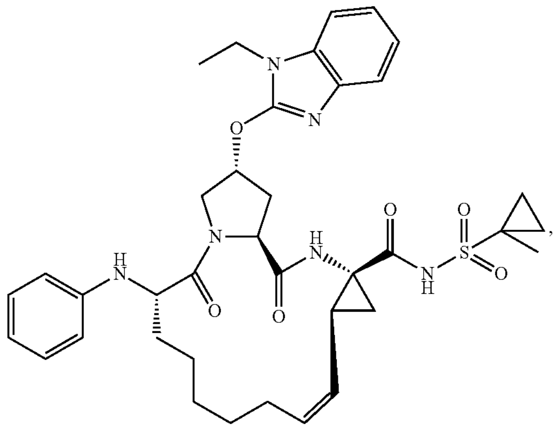
,
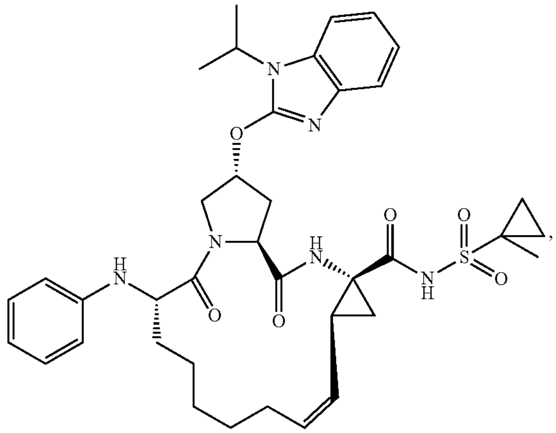
,
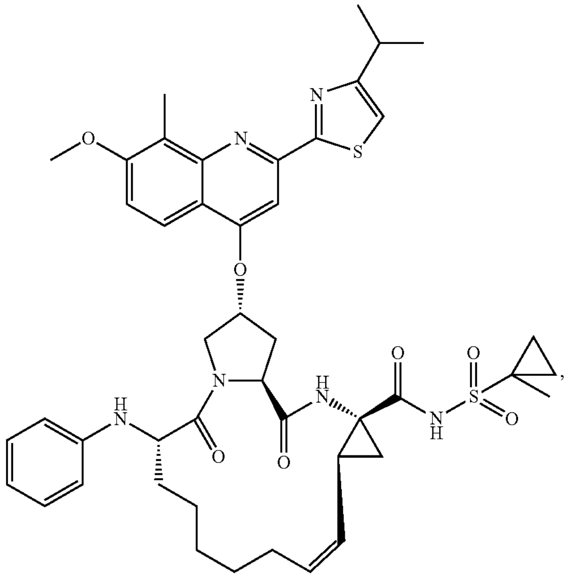
,
-continued
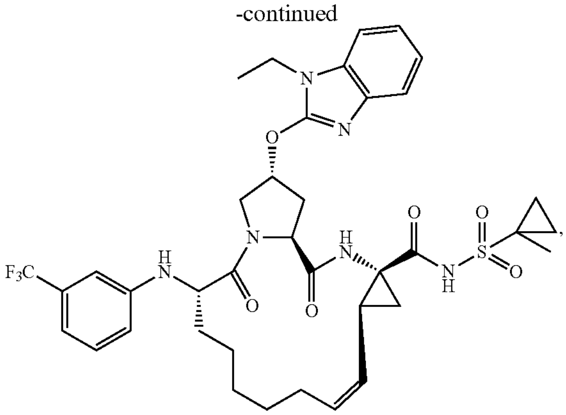
,
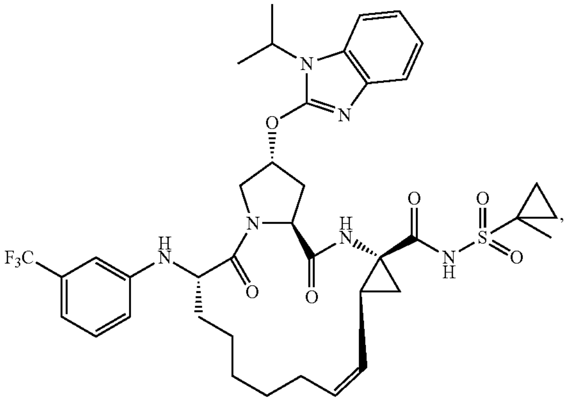
,
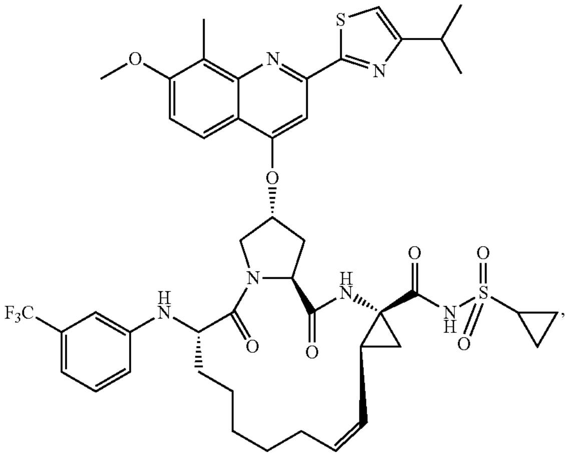
,
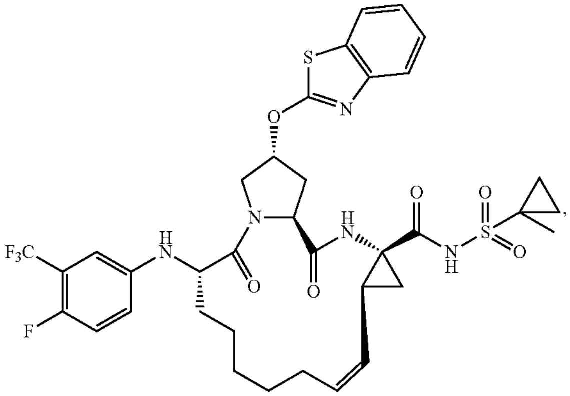
, -continued
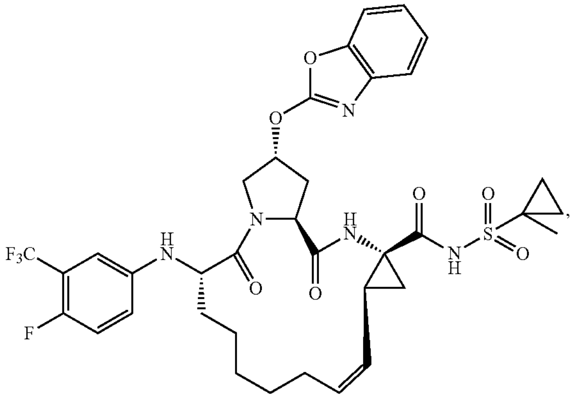
,
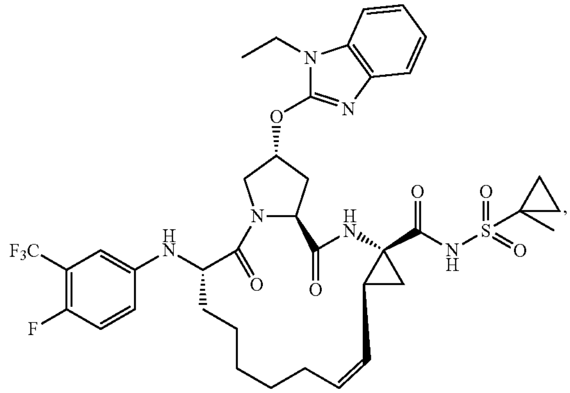
,
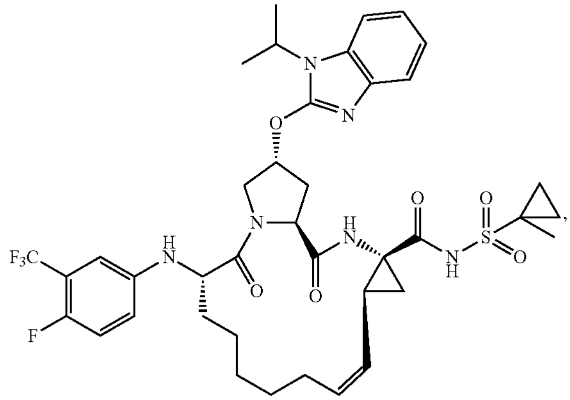
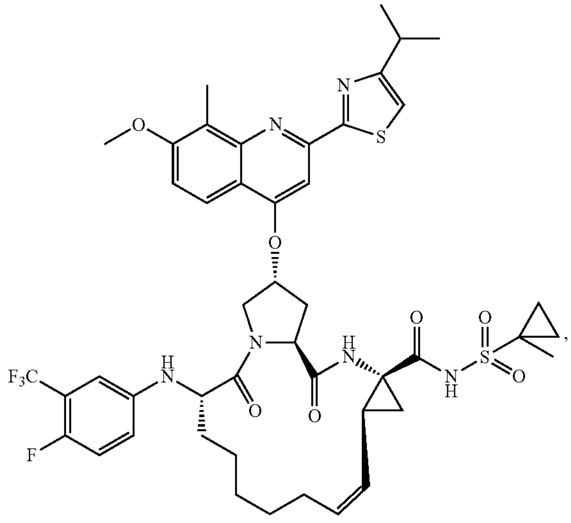
,
-continued
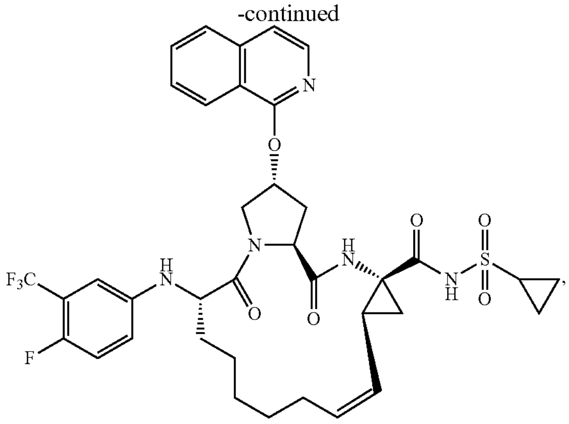
,
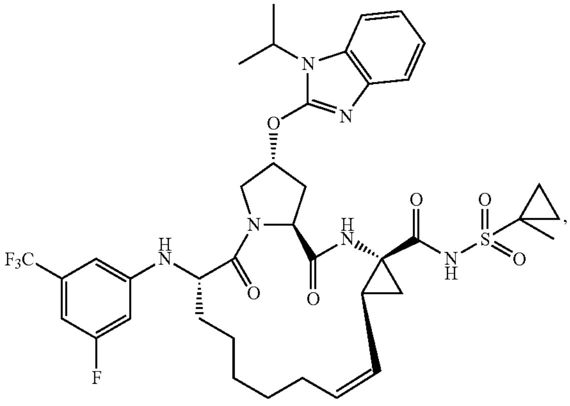
,
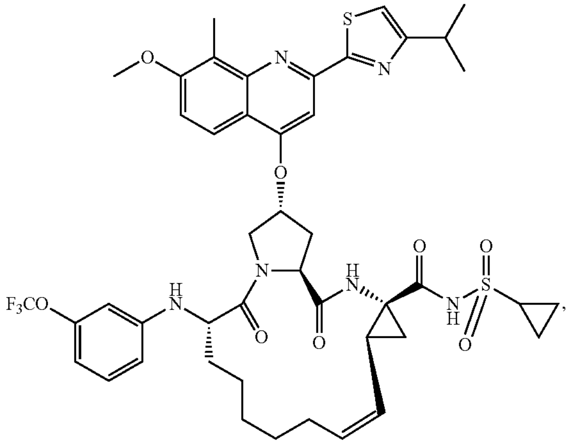
,

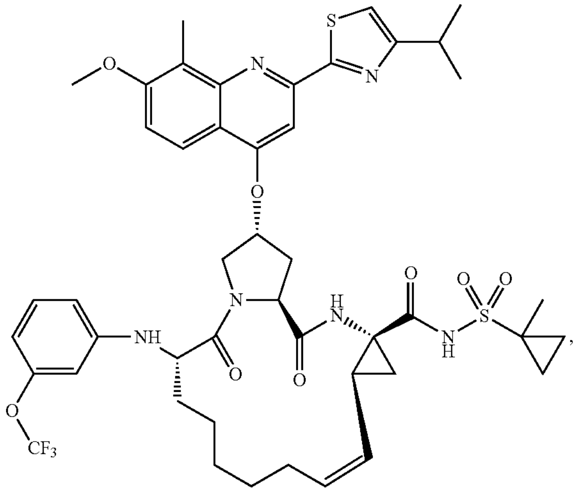
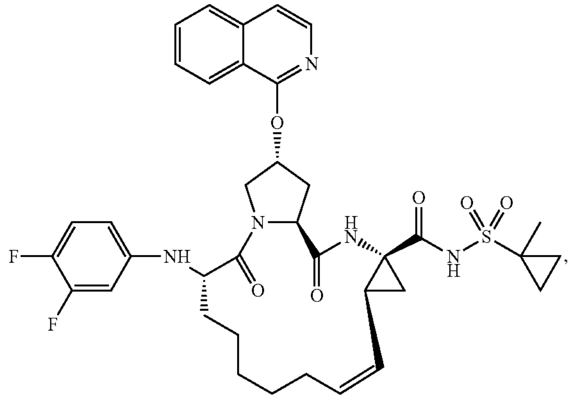
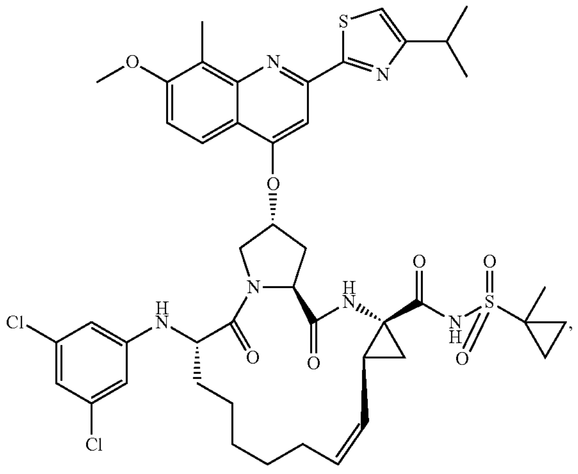
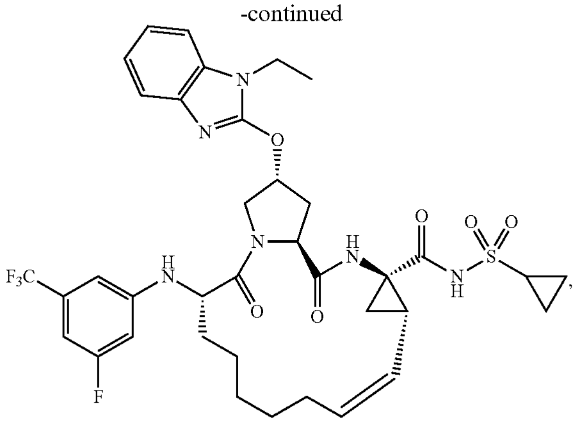
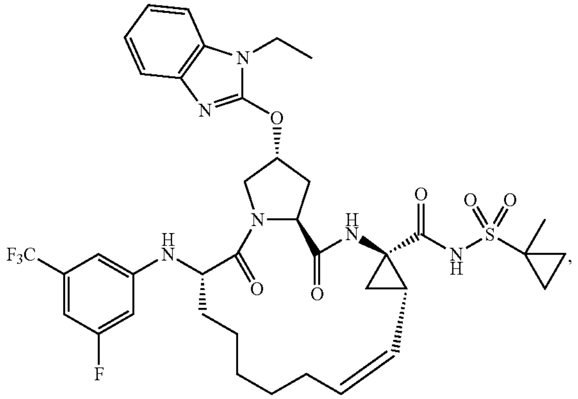
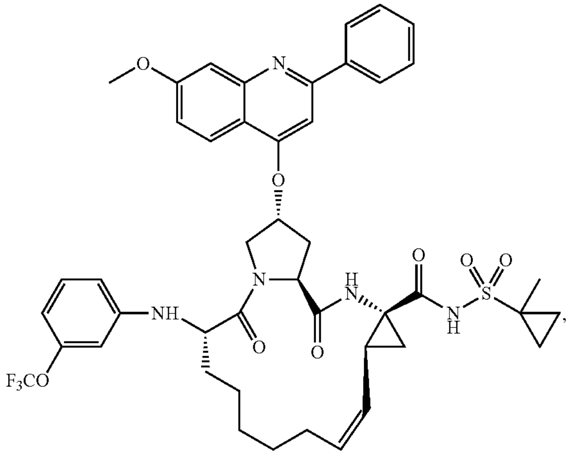
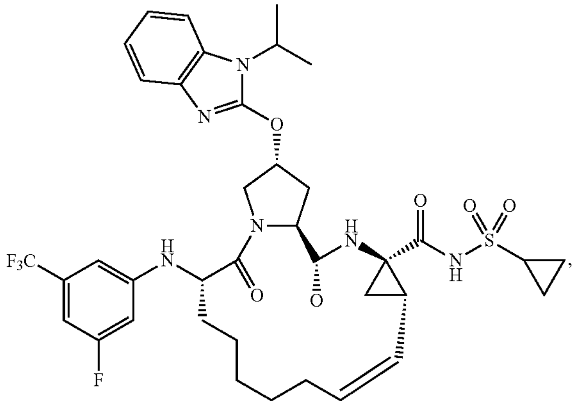

-continued
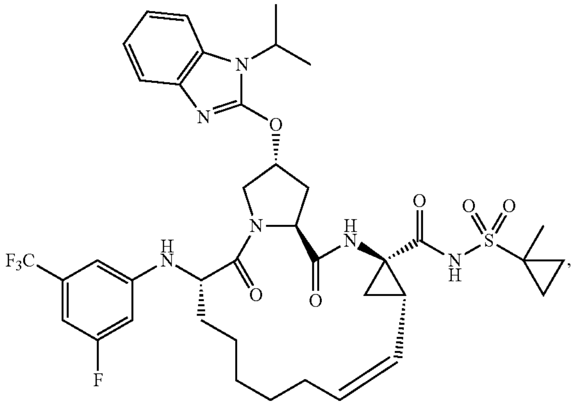
,
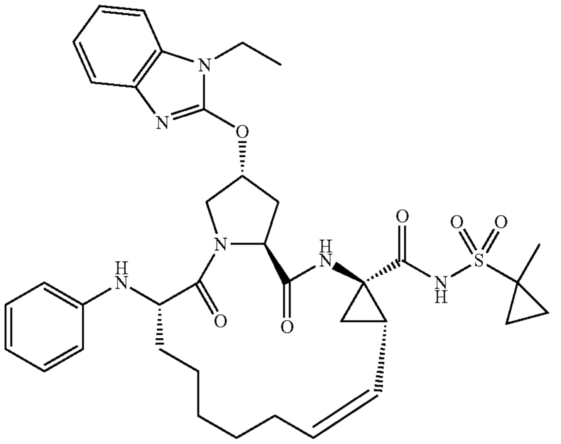
,
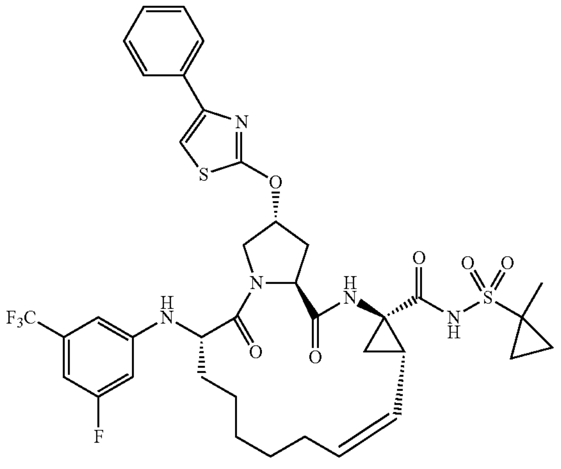
,
-continued
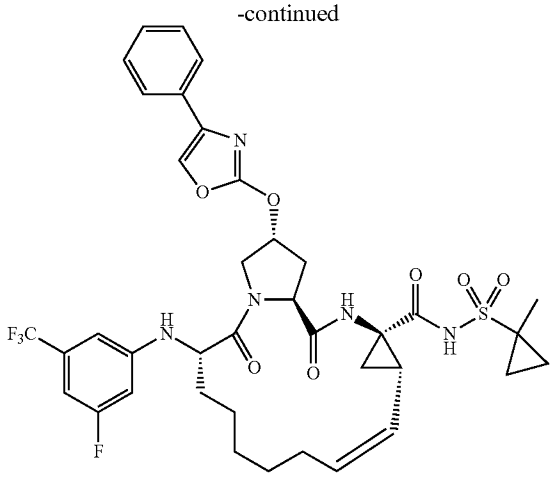
,
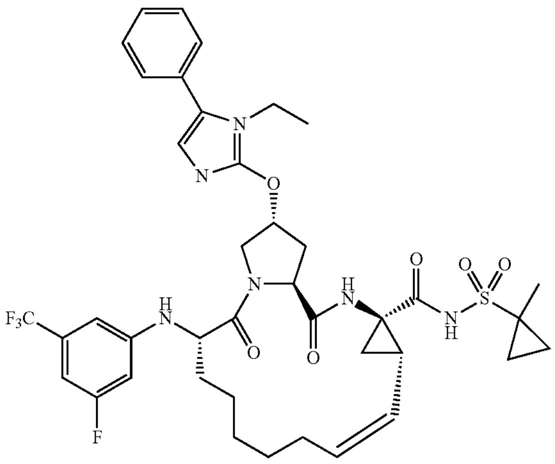
,
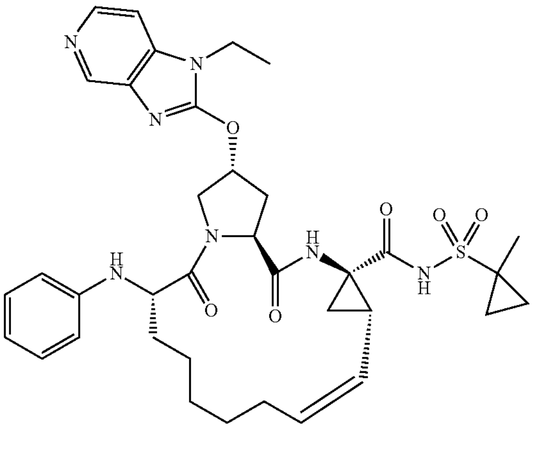
, -continued
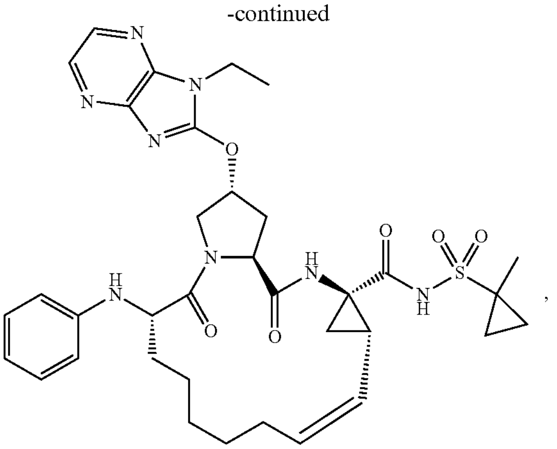
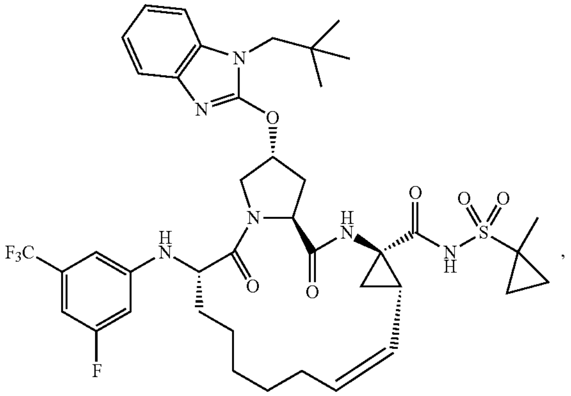
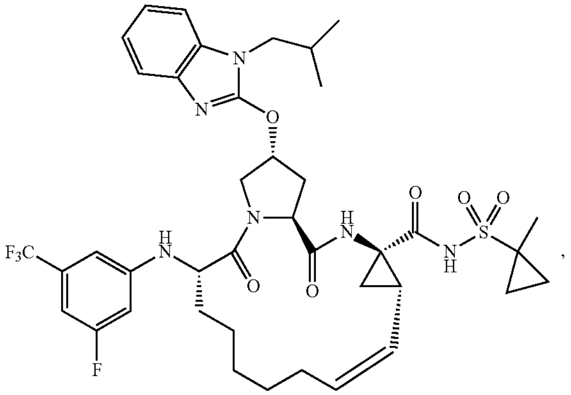
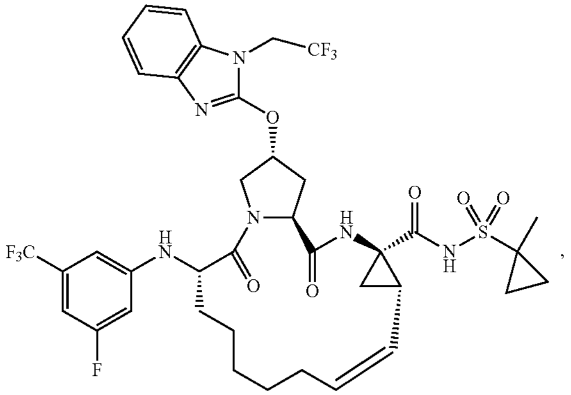
-continued
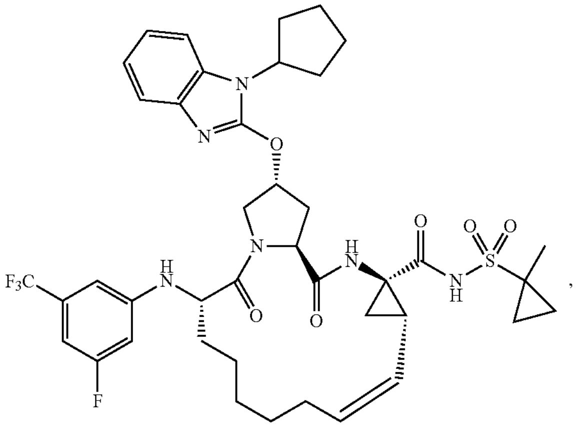
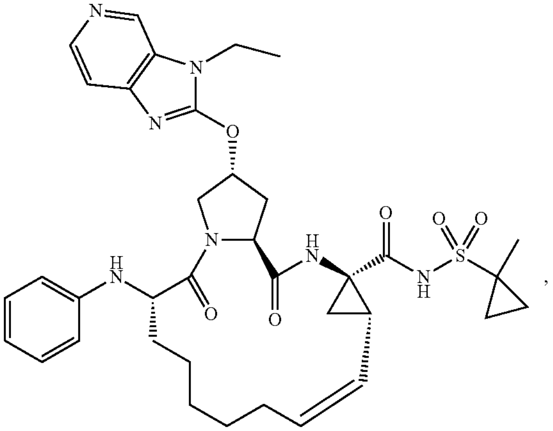
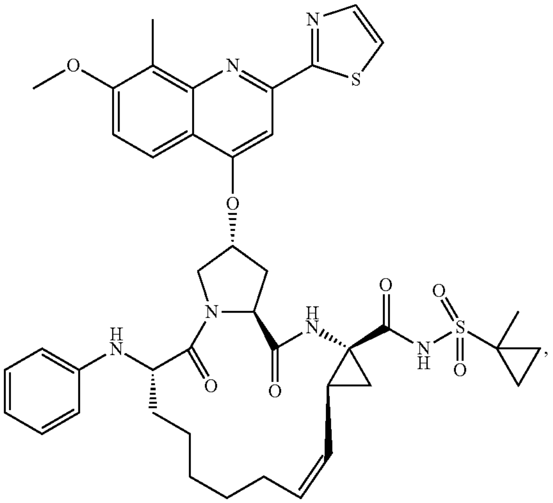

-continued
-continued
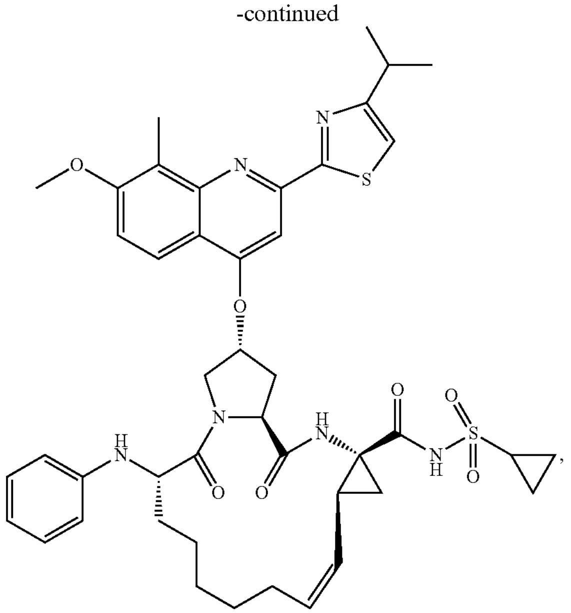
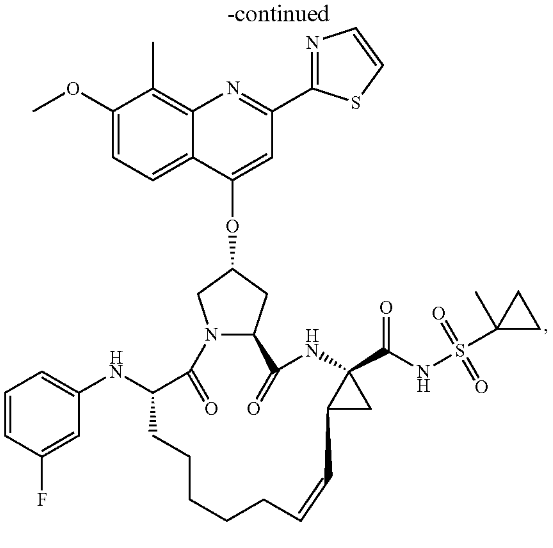
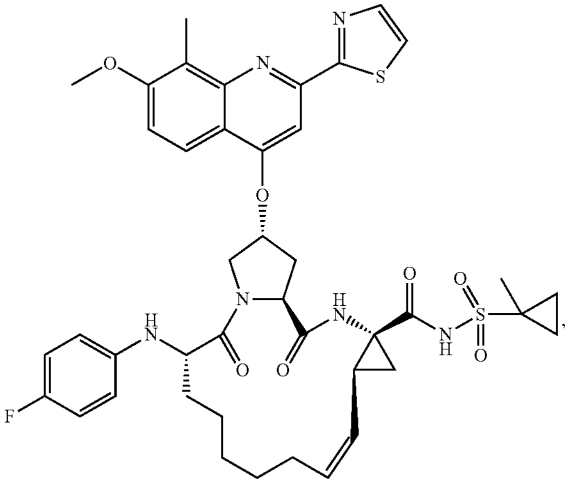
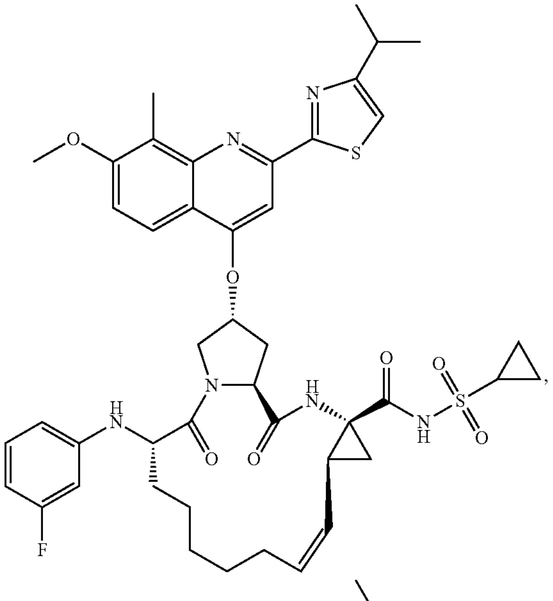
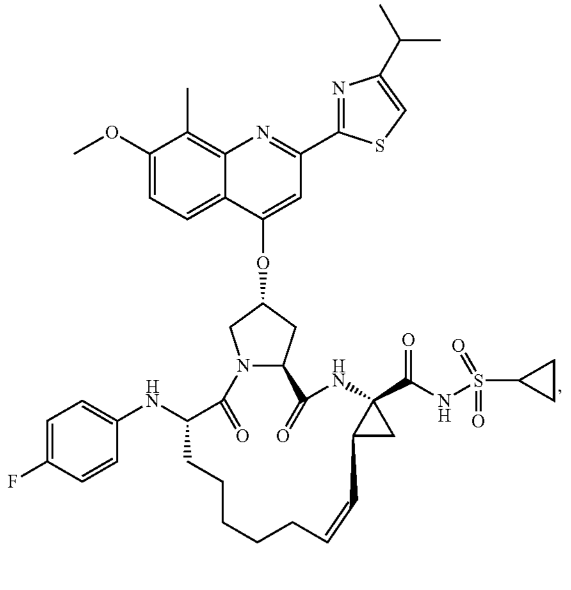
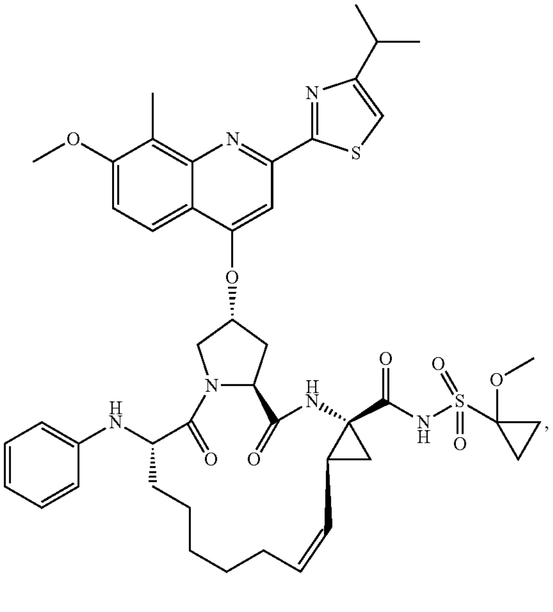

-continued
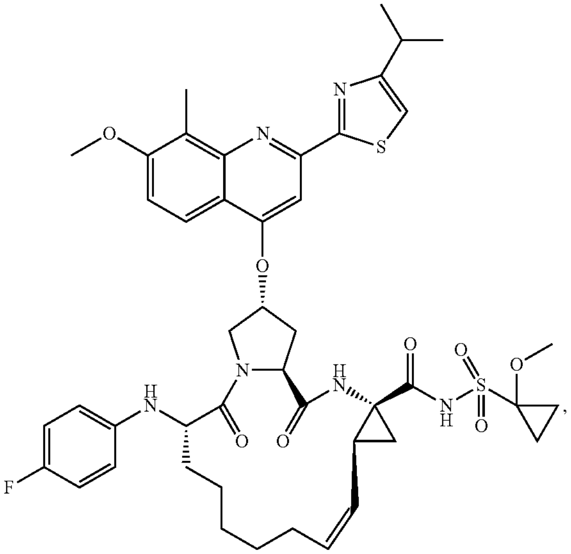
,
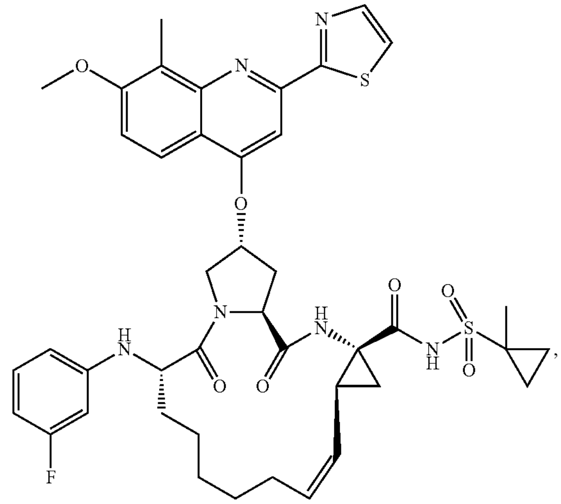
,
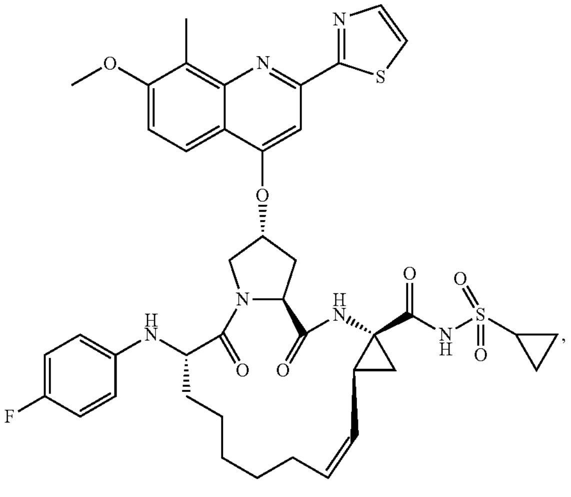
,
-continued
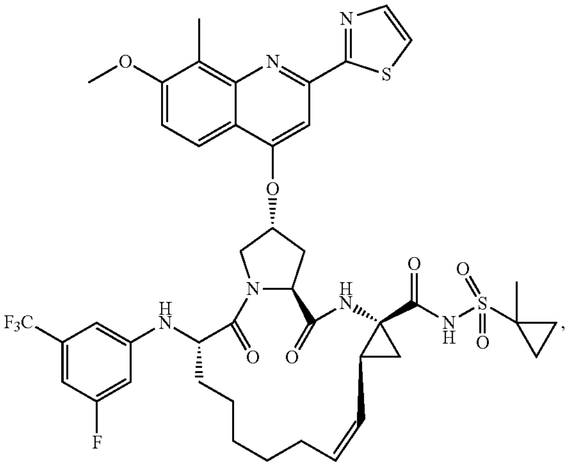
,
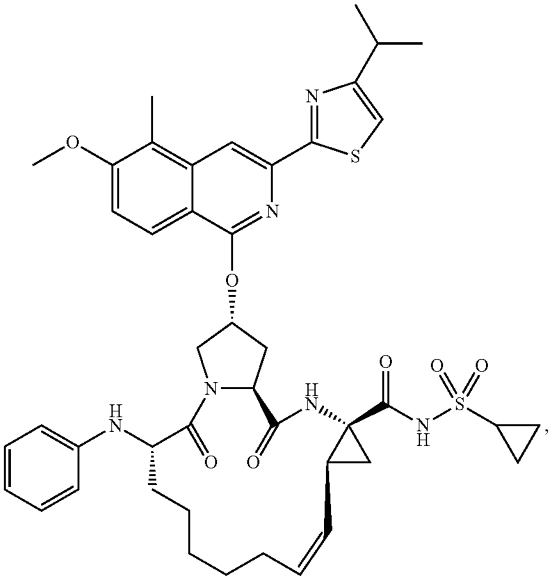
,
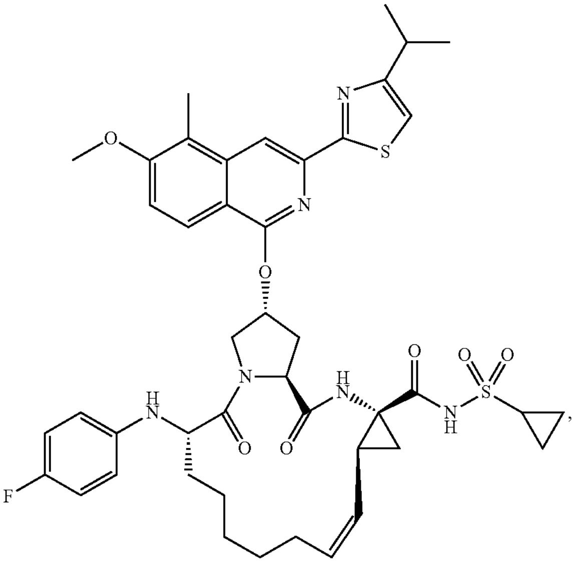
, -continued
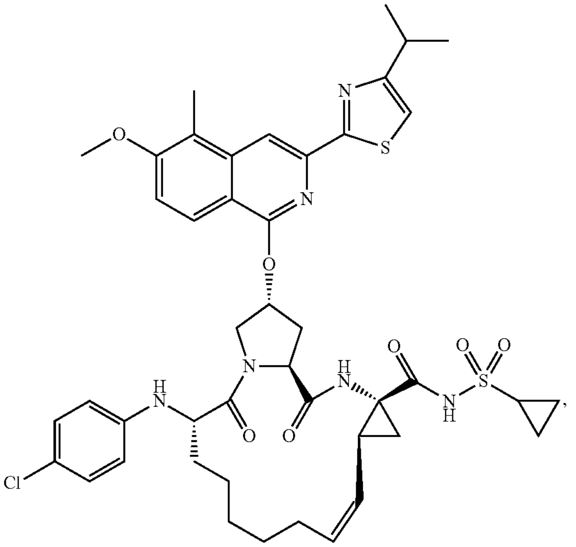
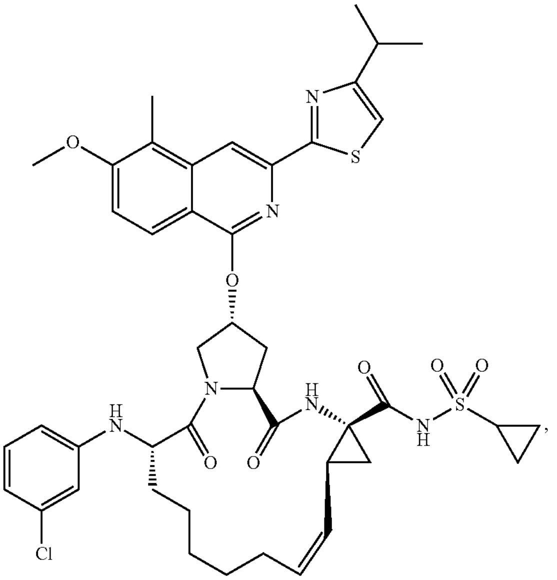
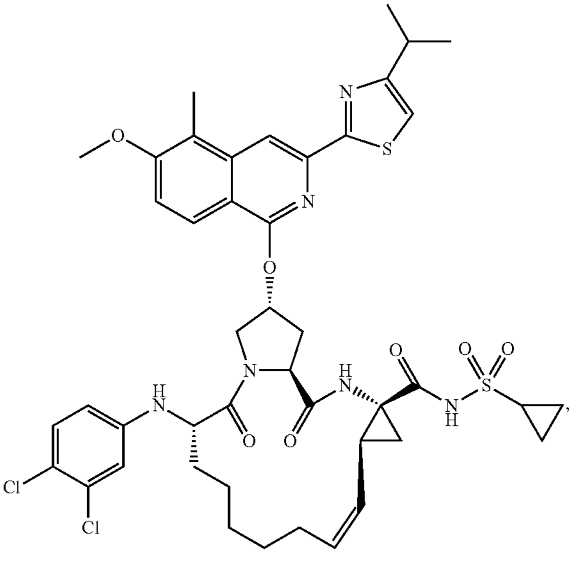
-continued
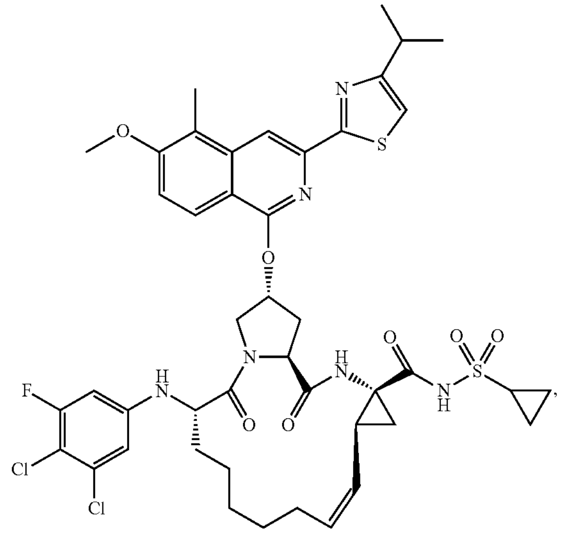
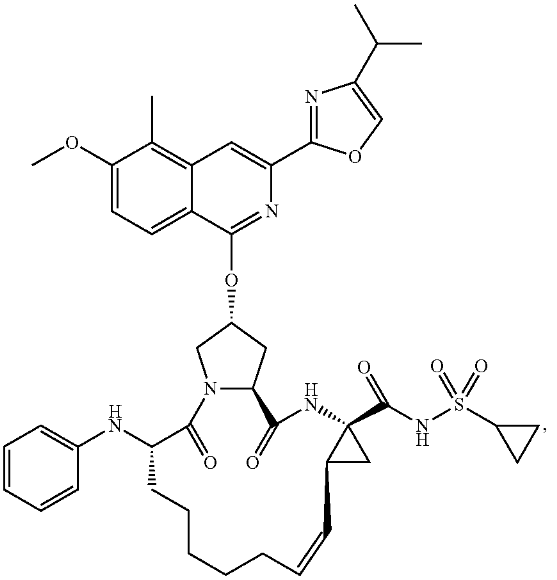
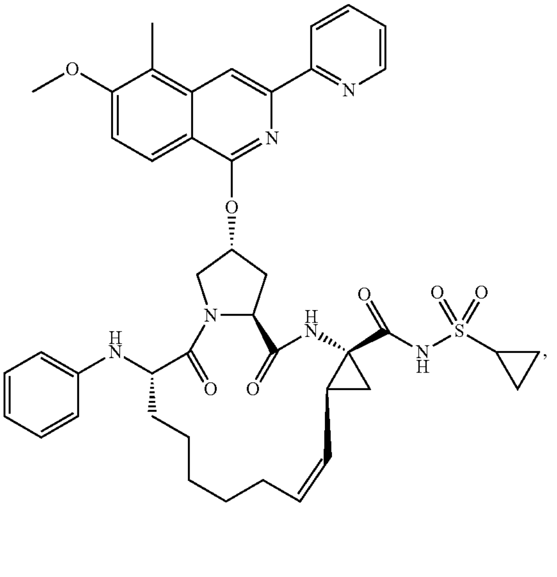

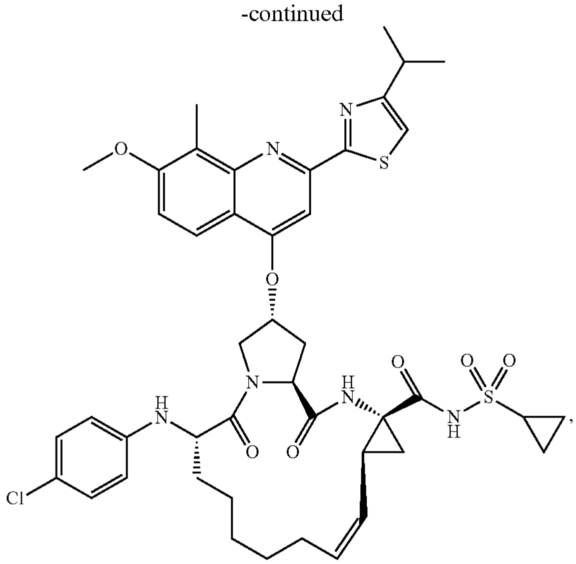
,
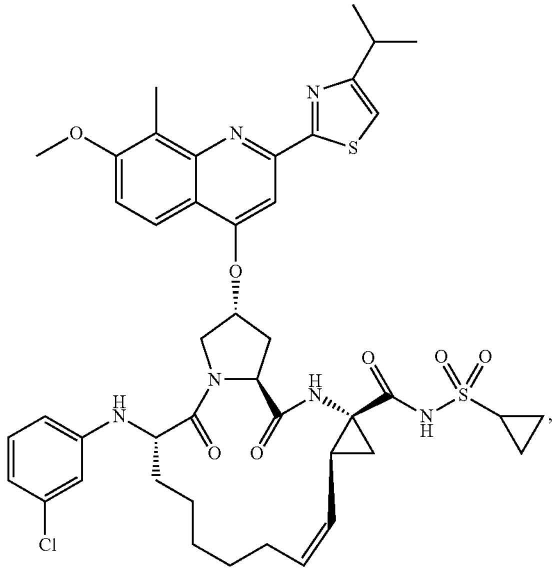
,
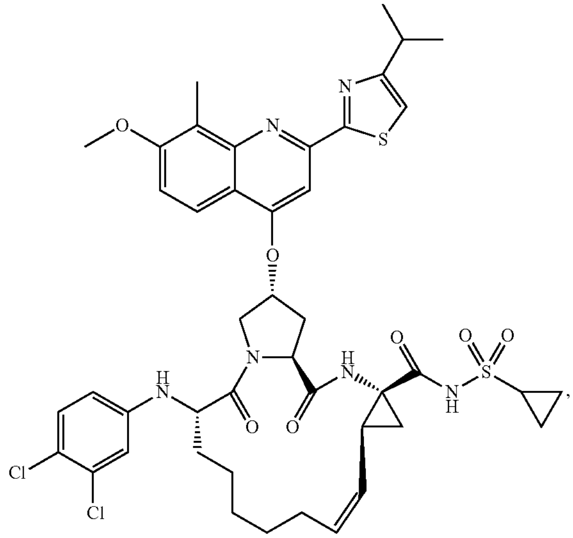
,
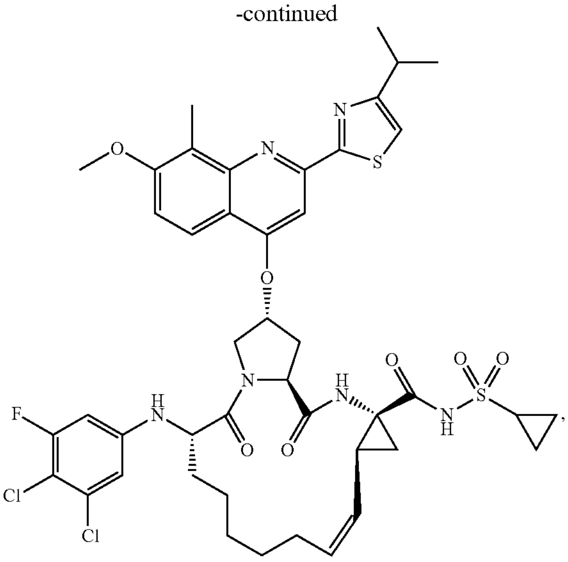
,
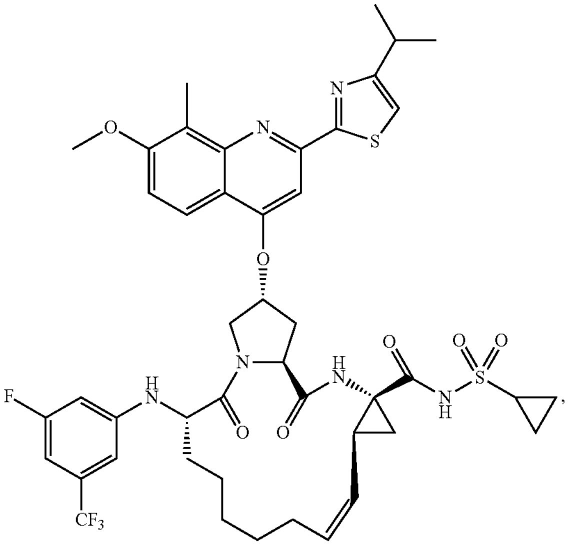
,
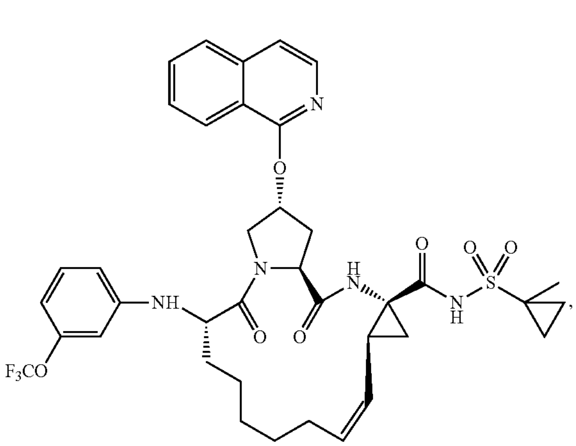
, -continued
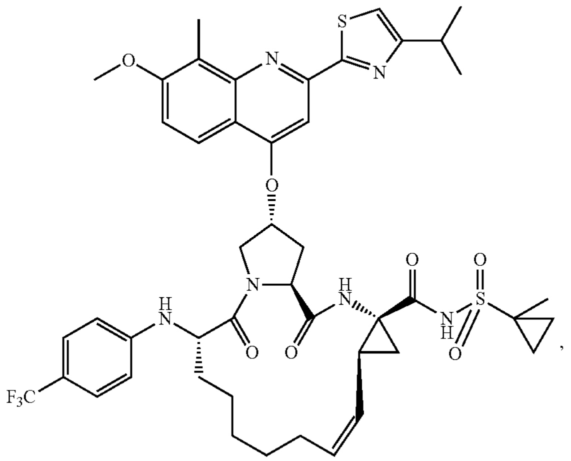
,
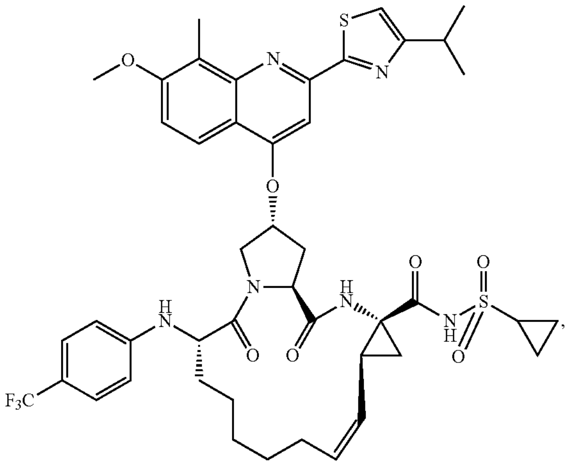
,
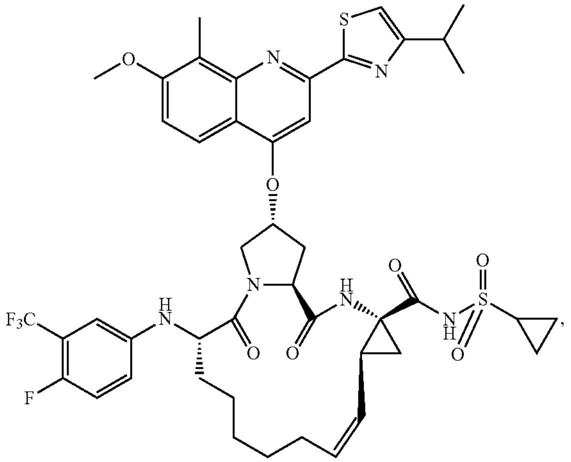
,
-continued
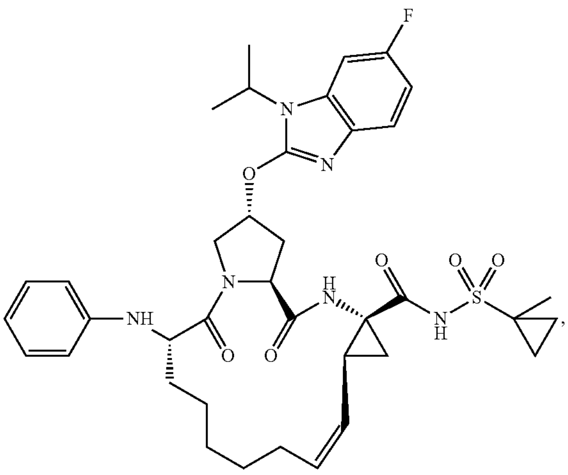
,
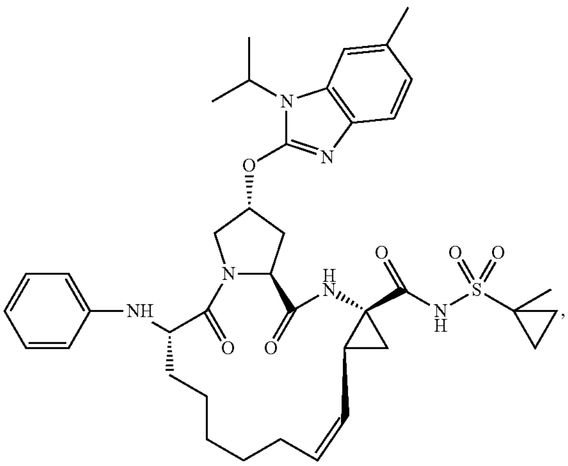
,
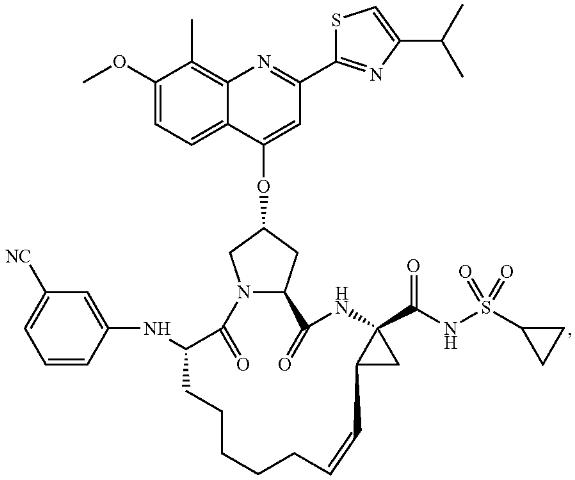
, -continued
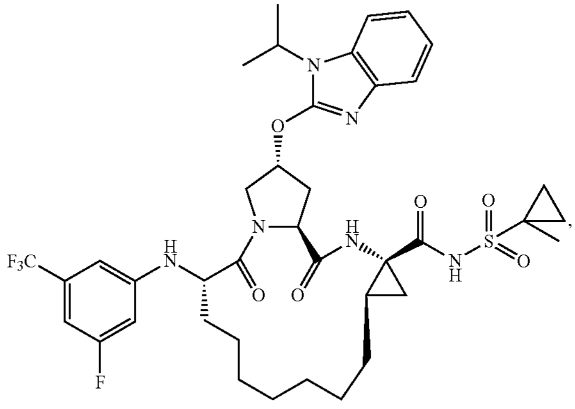
,
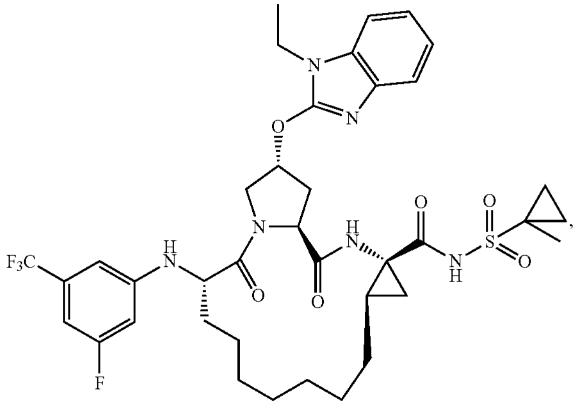
,
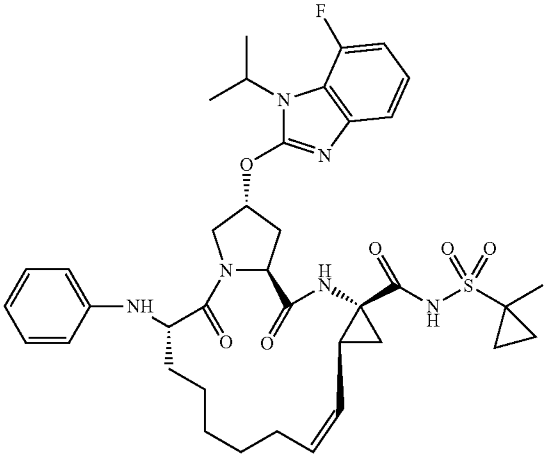
,
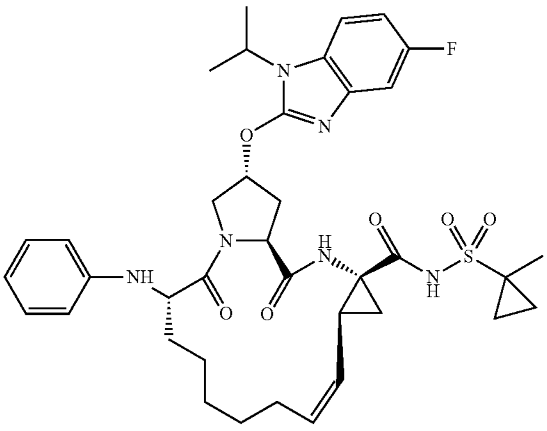
,
-continued
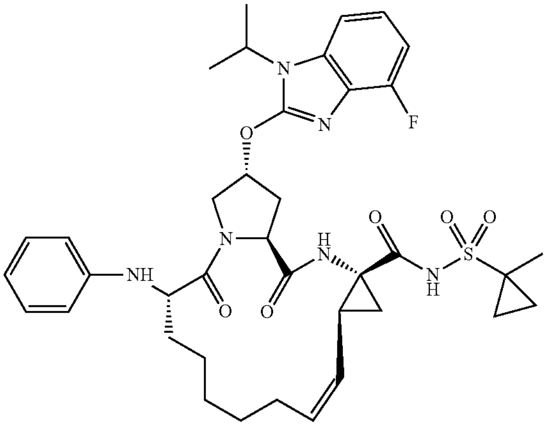
,
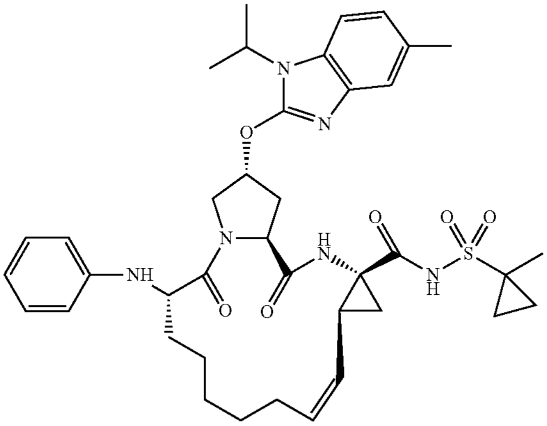
,
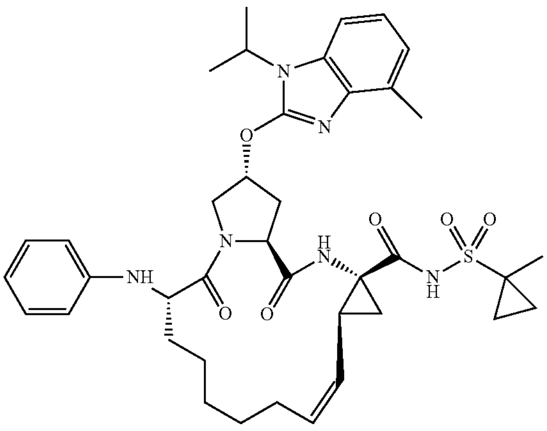
, -continued
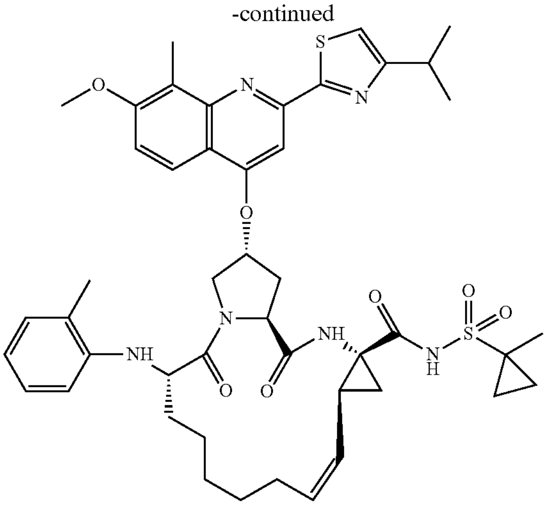
,
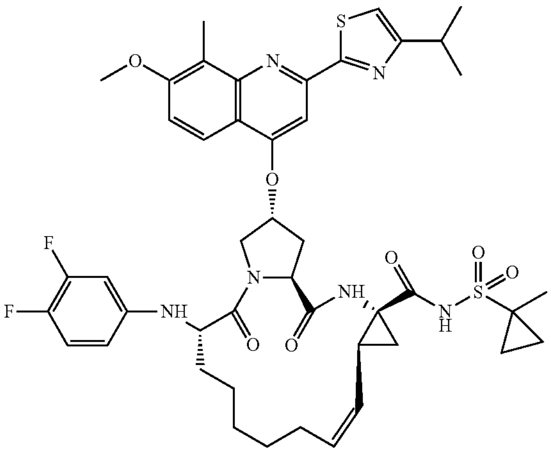
,
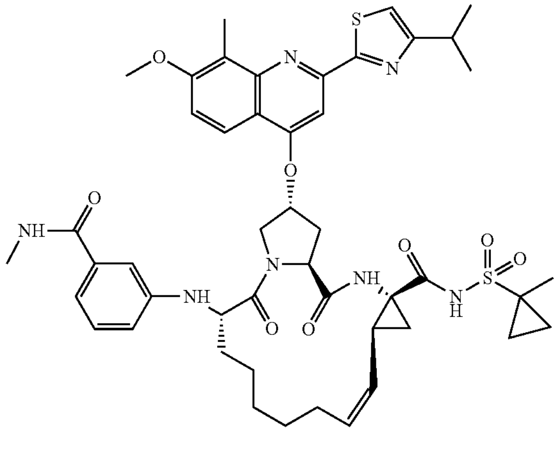
,
-continued
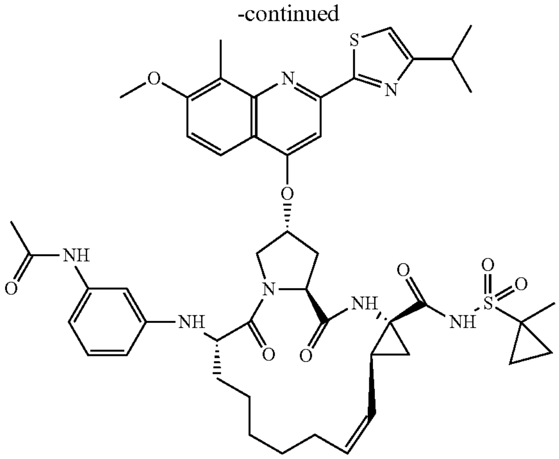
,
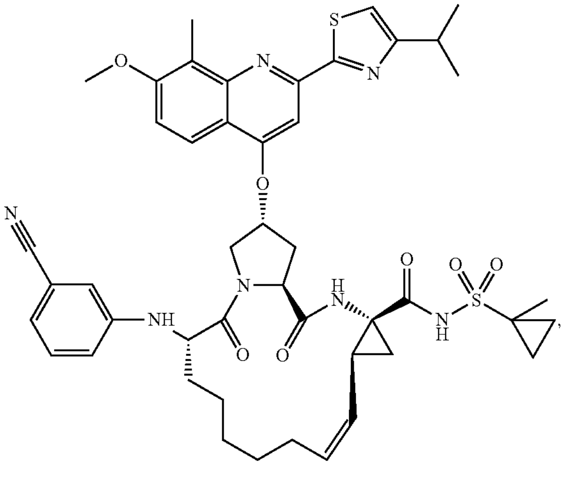
,
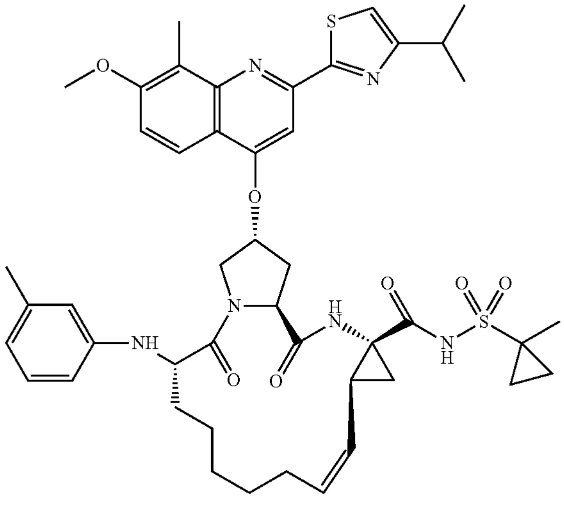
, -continued
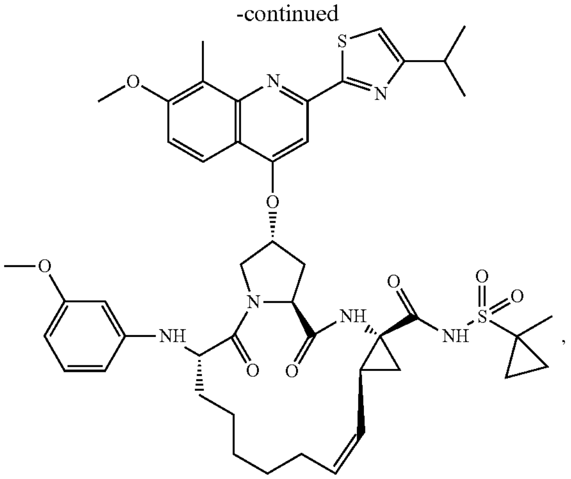
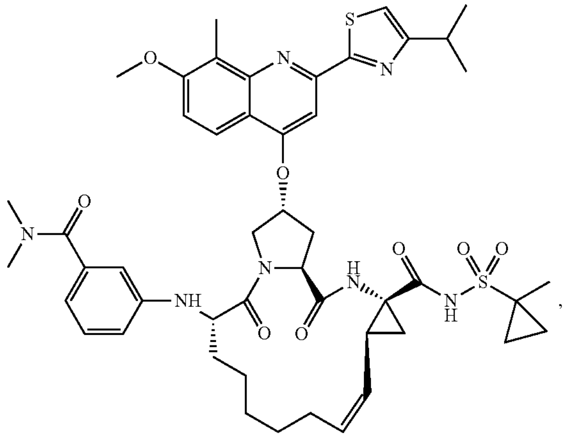
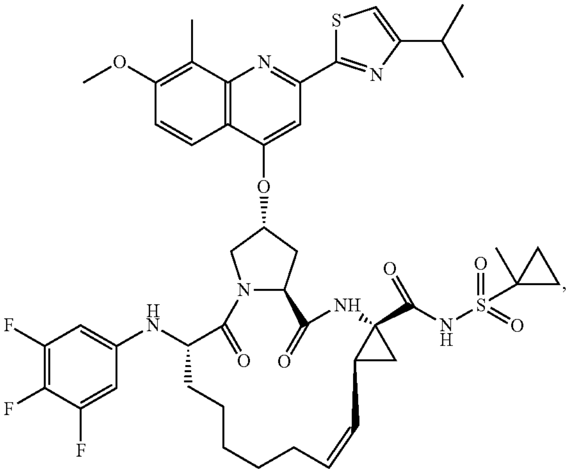
-continued
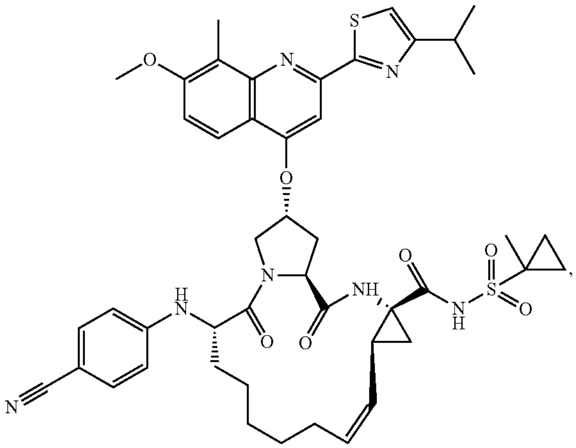
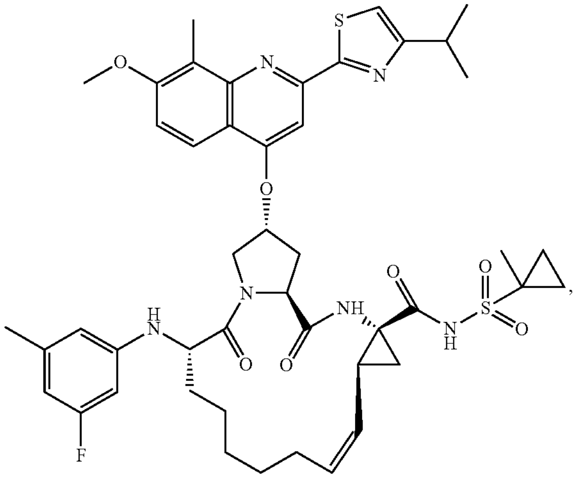
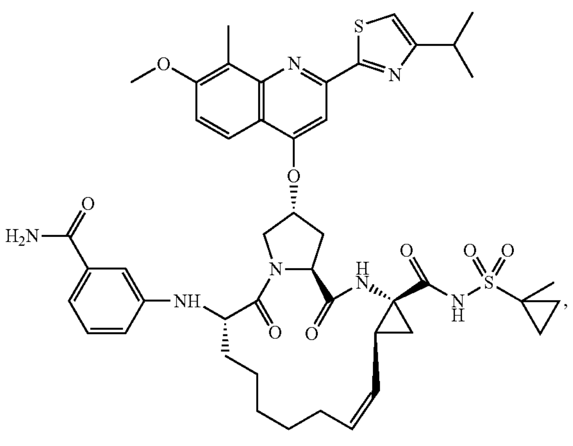

-continued
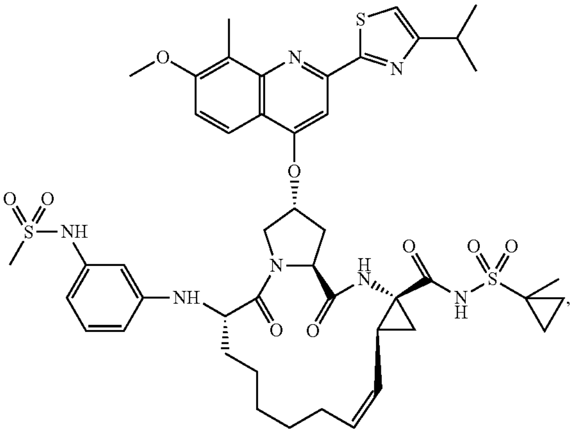
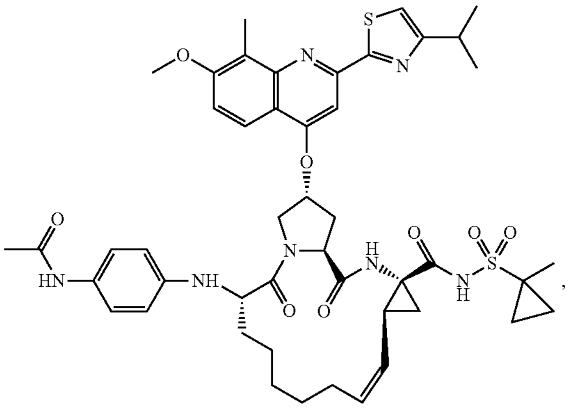
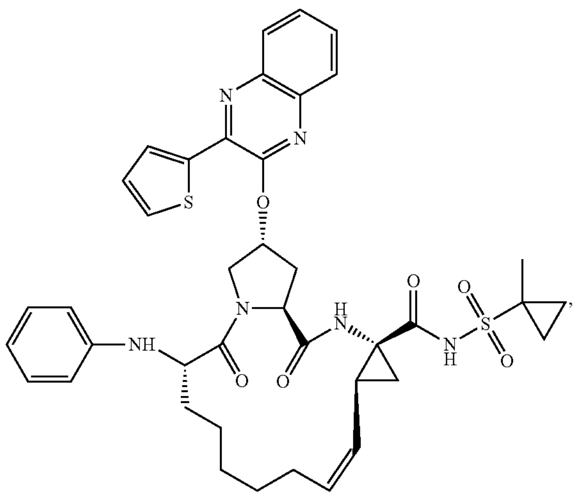
-continued
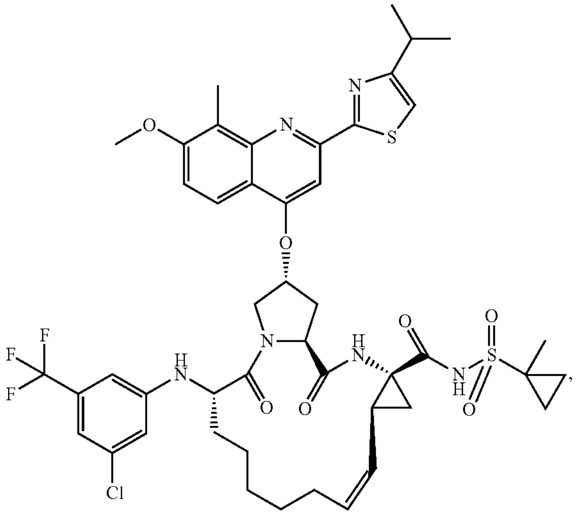
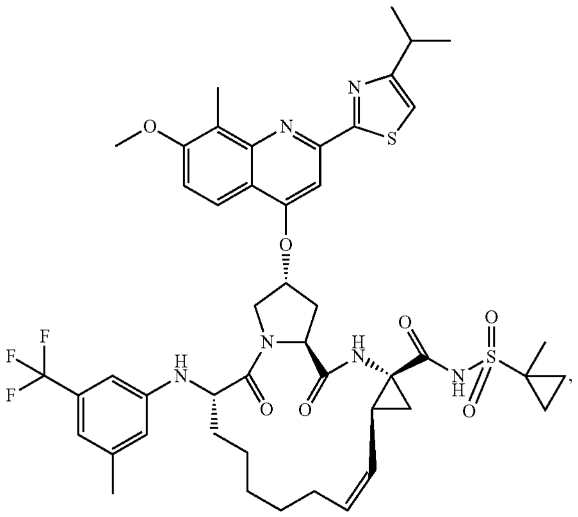
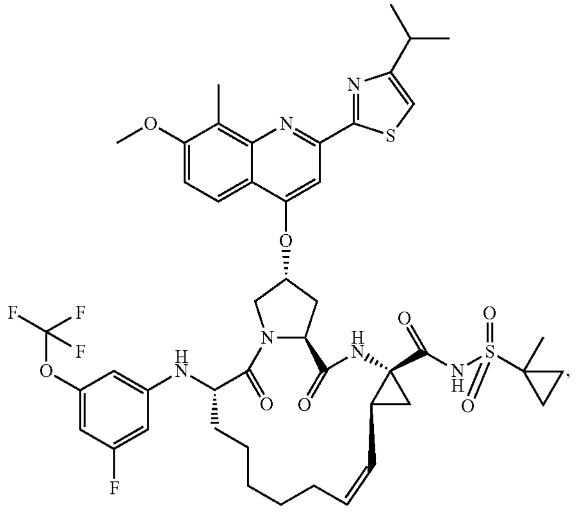

-continued
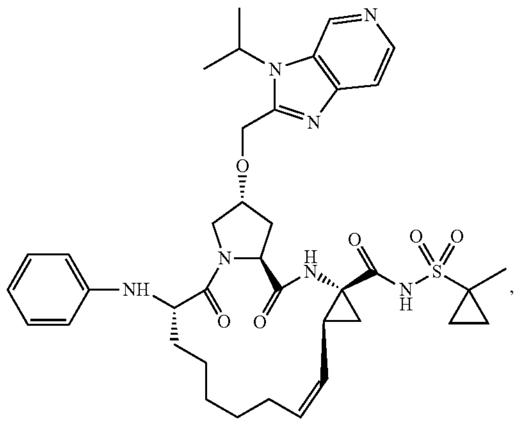
, and
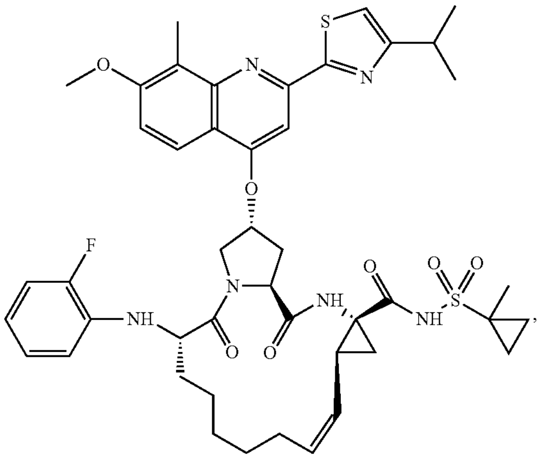
,
and pharmaceutically acceptable salts of the foregoing.
22. A compound selected from the group consisting of:
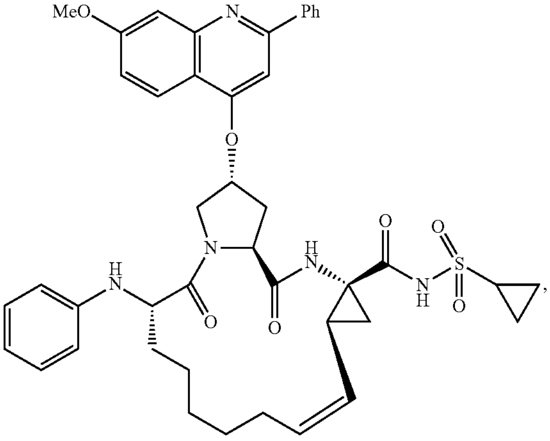
,
-continued
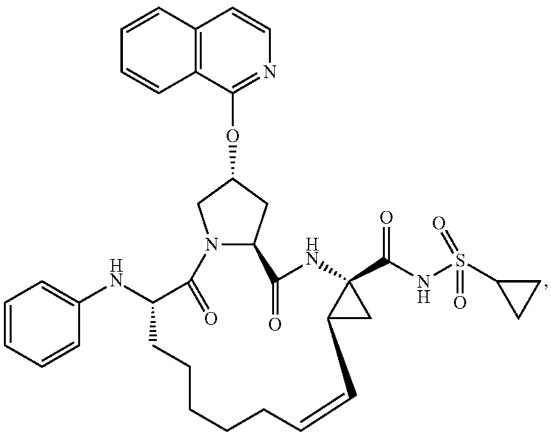
,
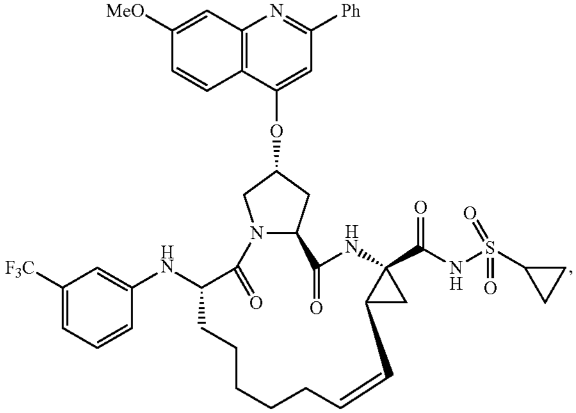
,
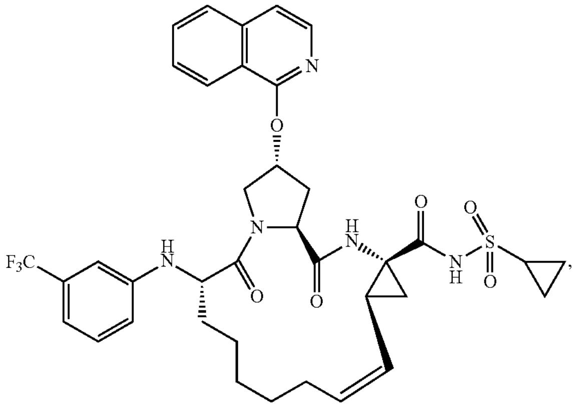
,
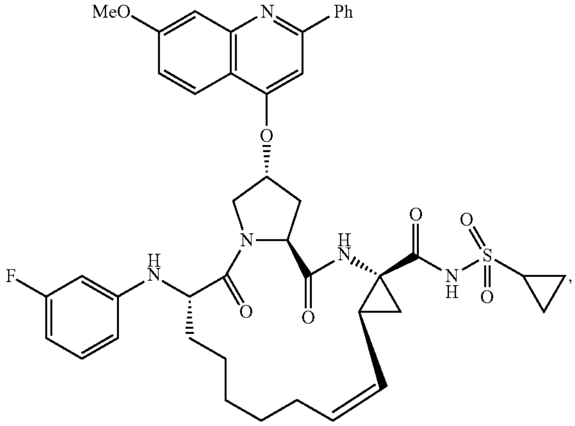
, -continued
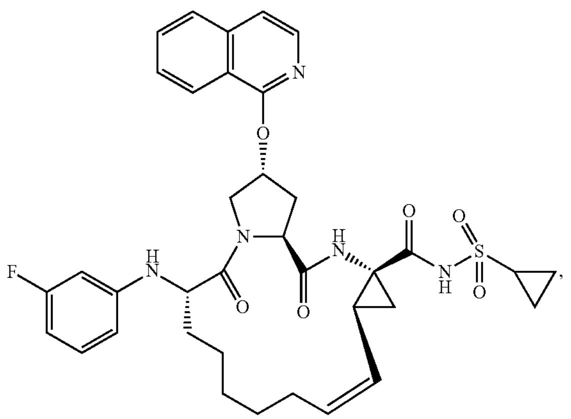
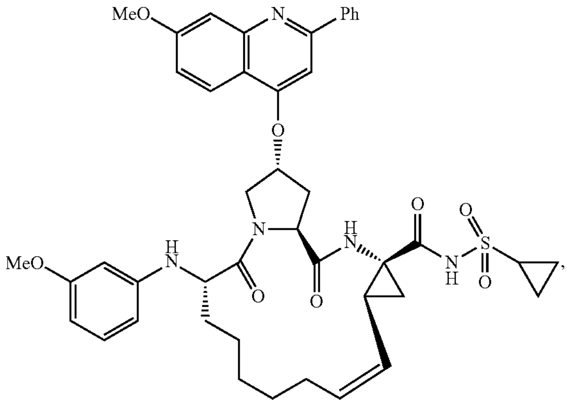
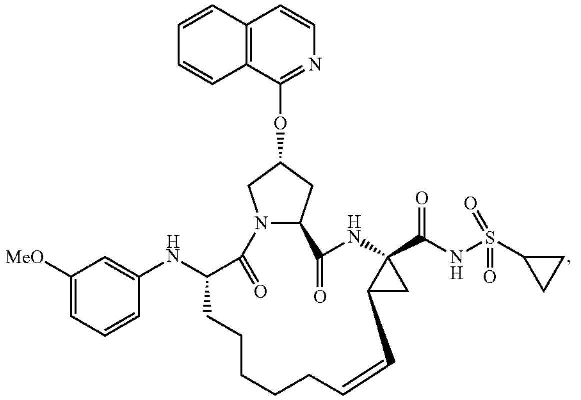
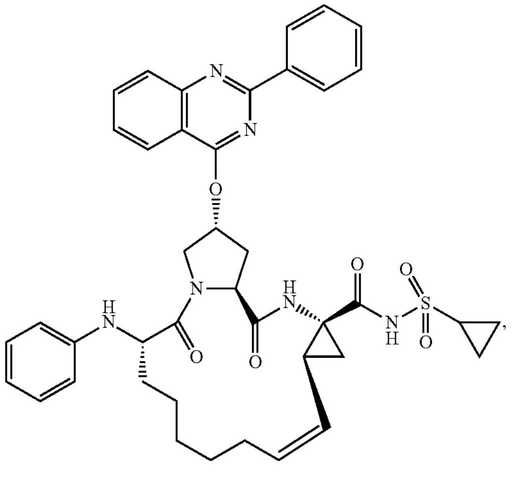
-continued
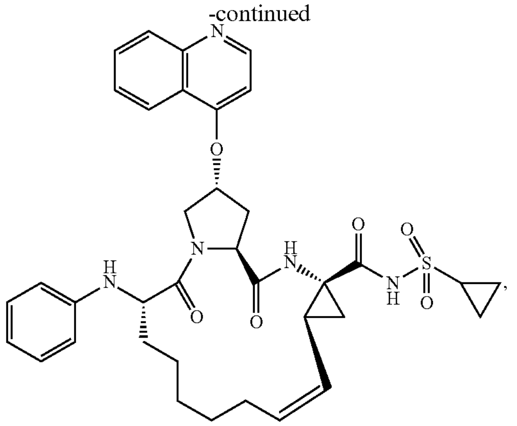
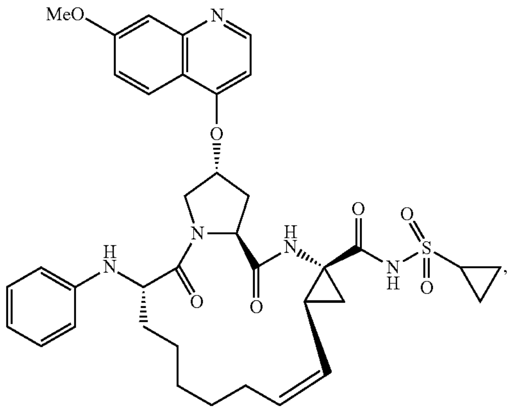
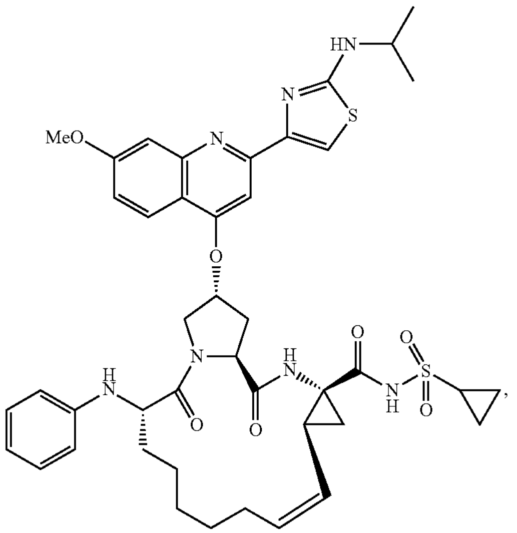

-continued
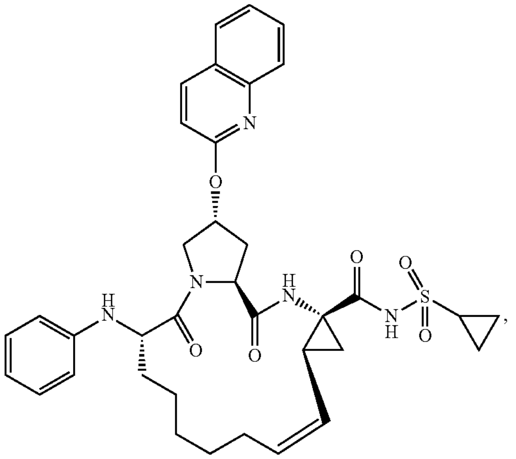
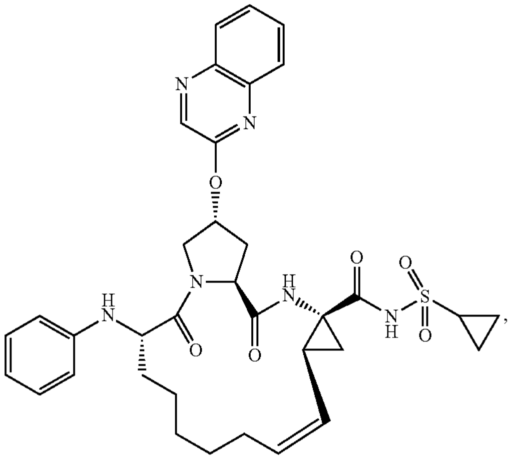
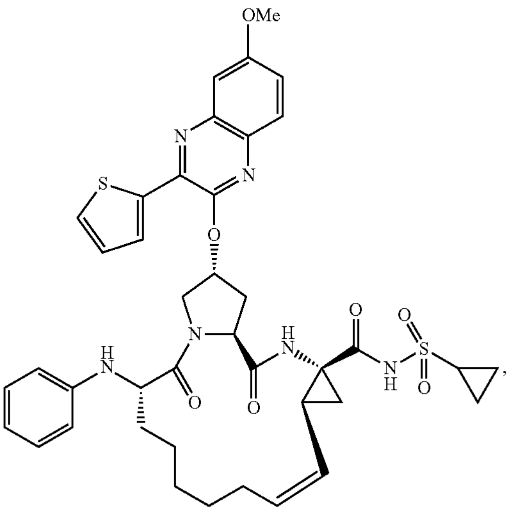
-continued
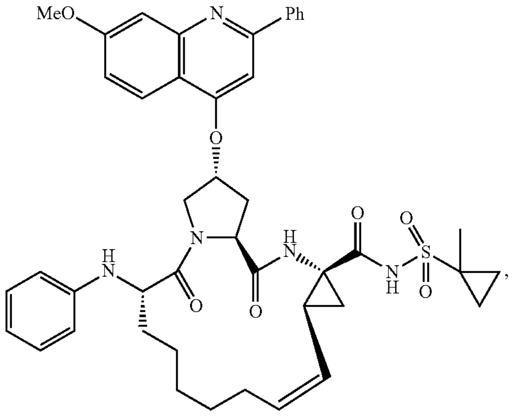
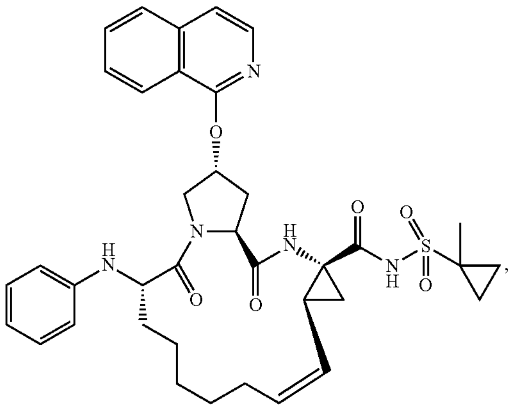
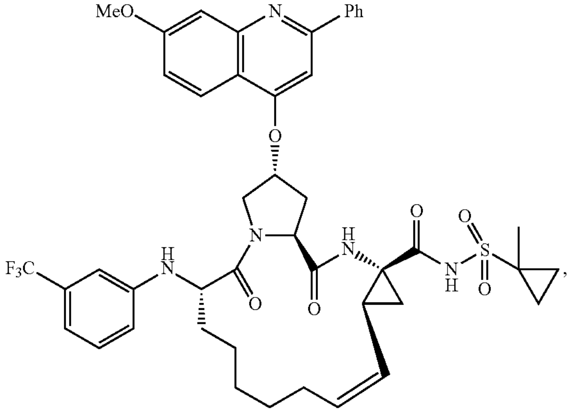
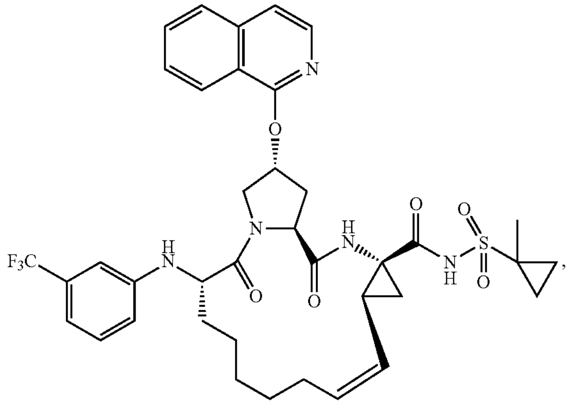

-continued
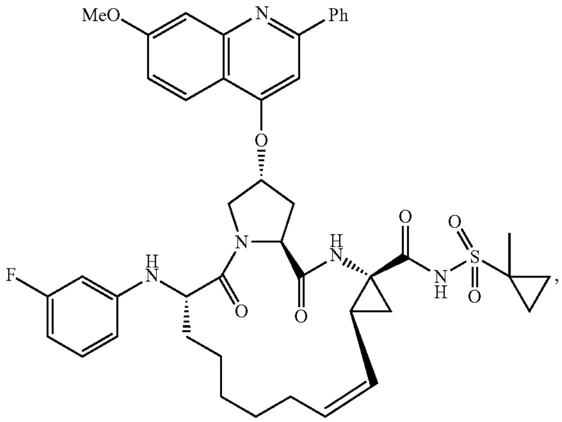
,
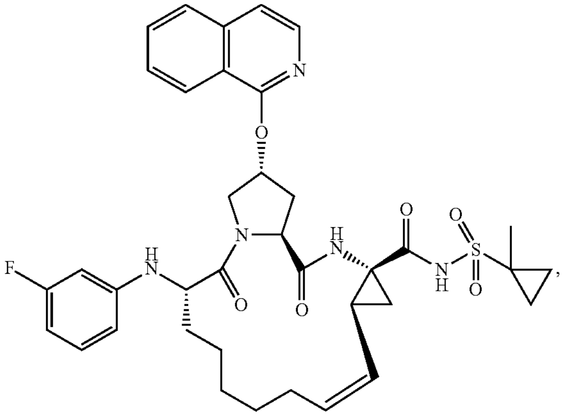
,
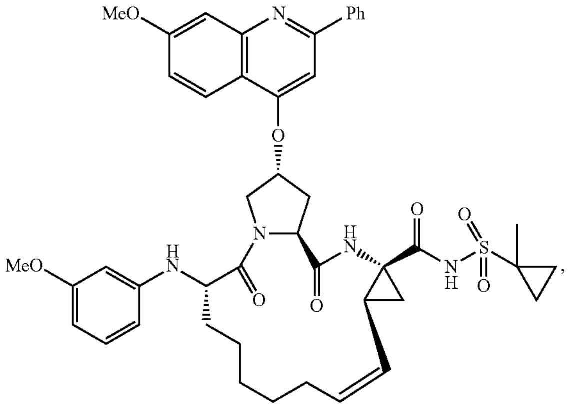
,
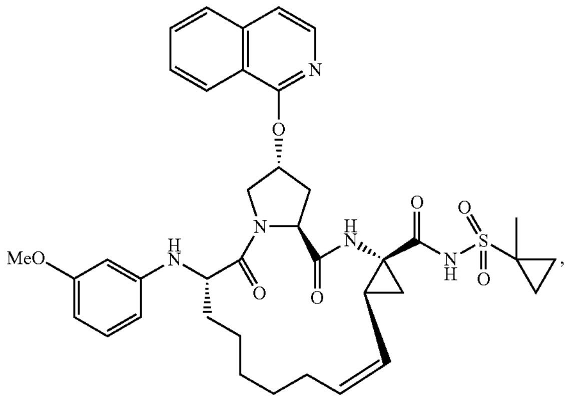
,
-continued
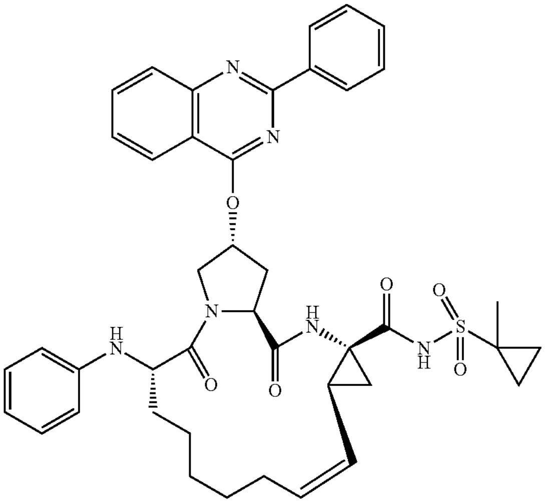
,
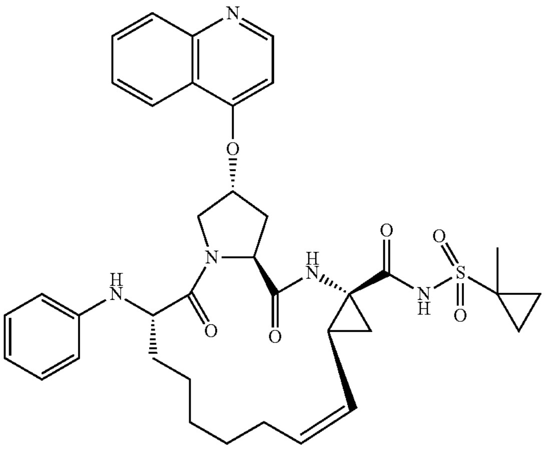
,
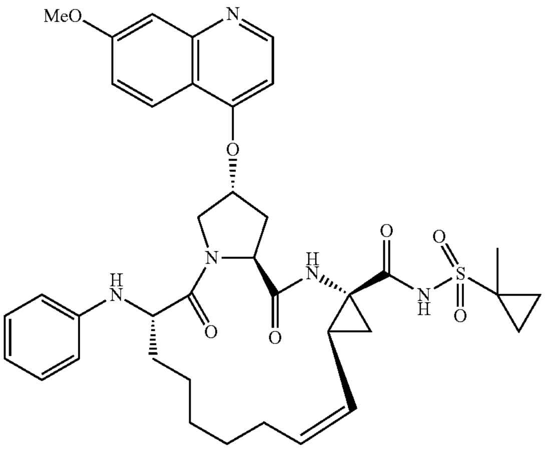
, -continued
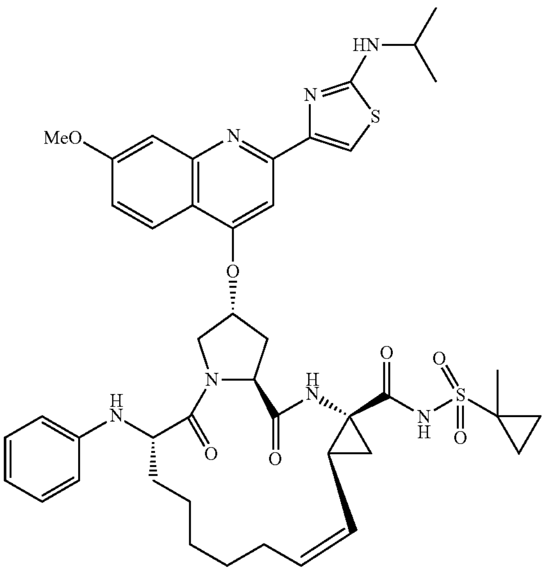
,
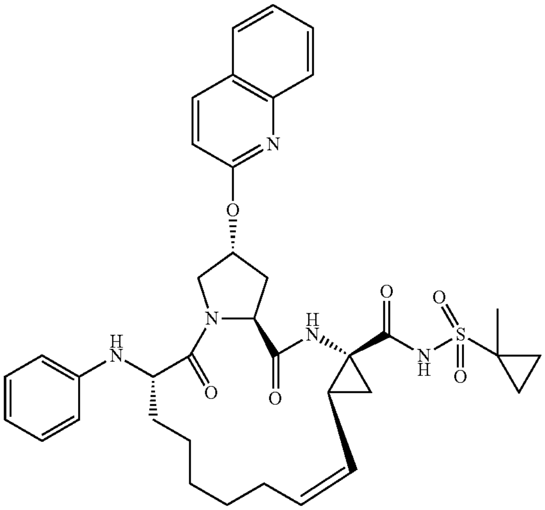
,
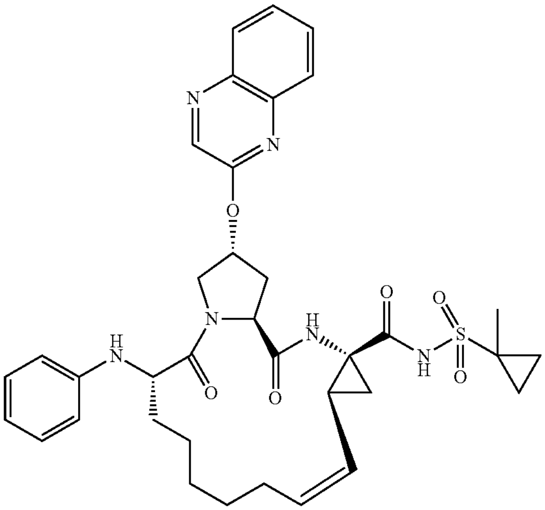
,
-continued
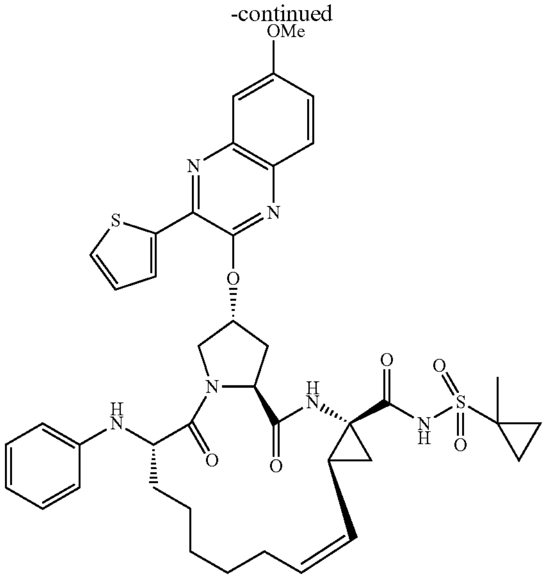
,
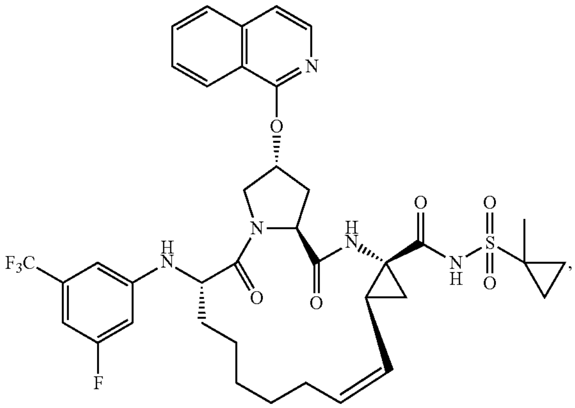
,
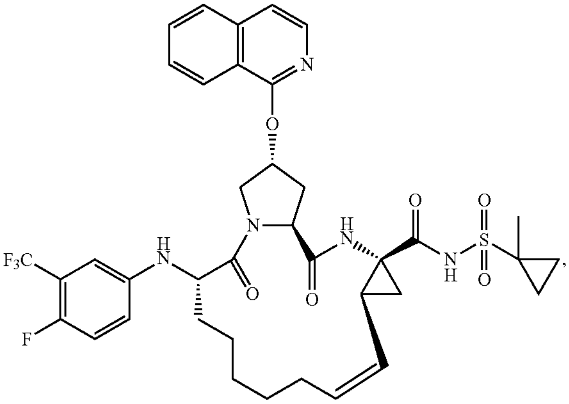
, -continued
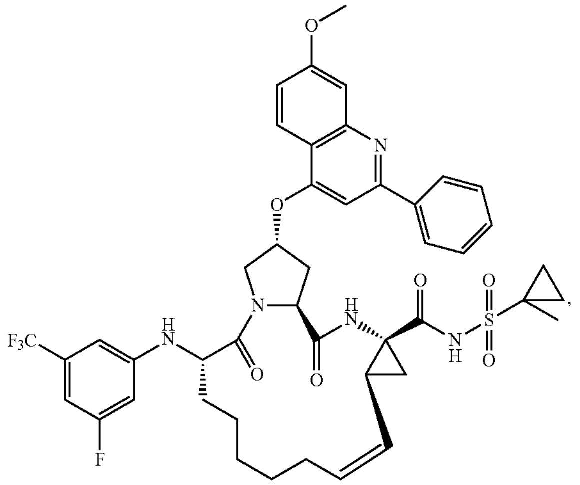
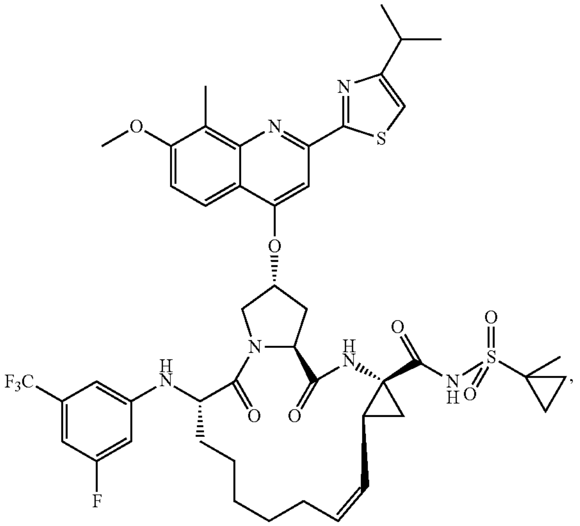
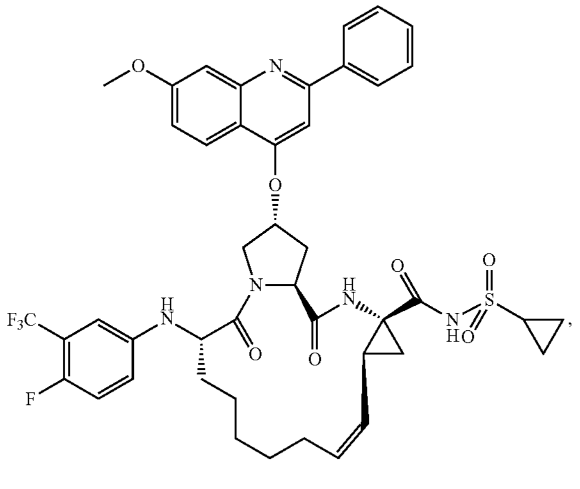
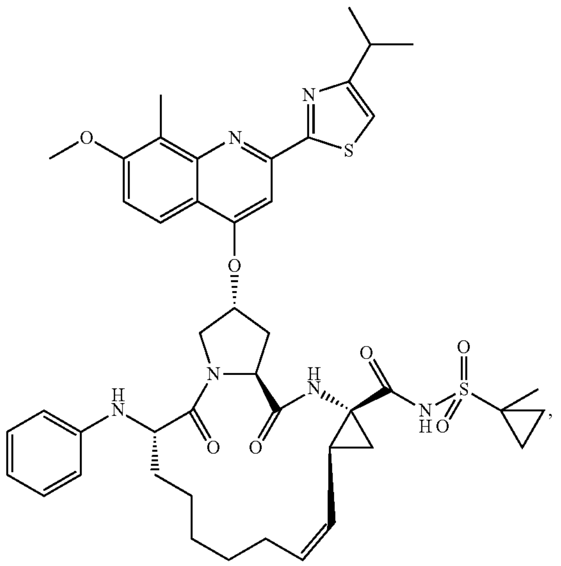
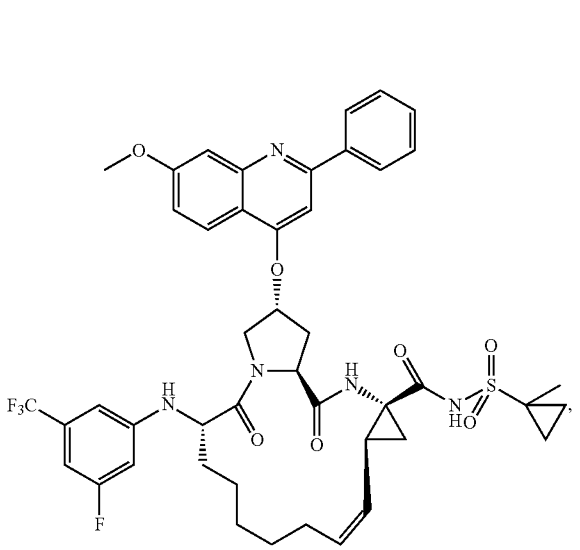
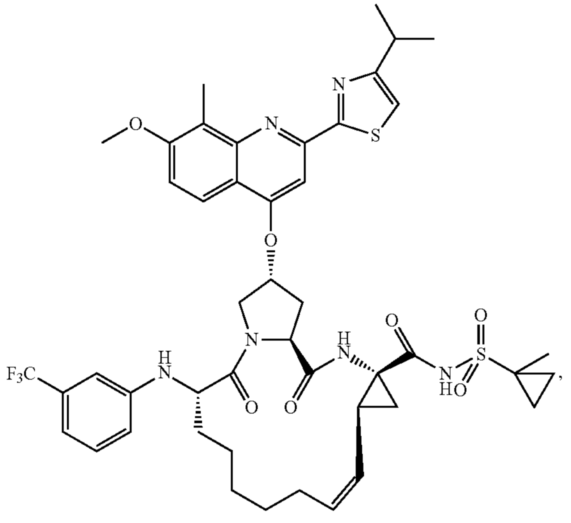
-continued -continued
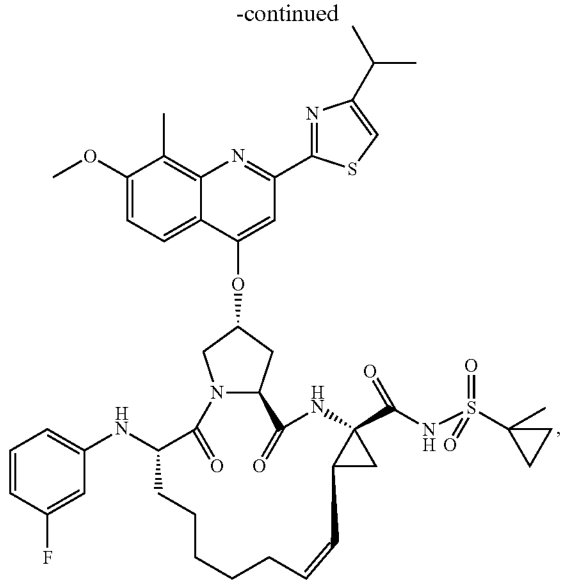
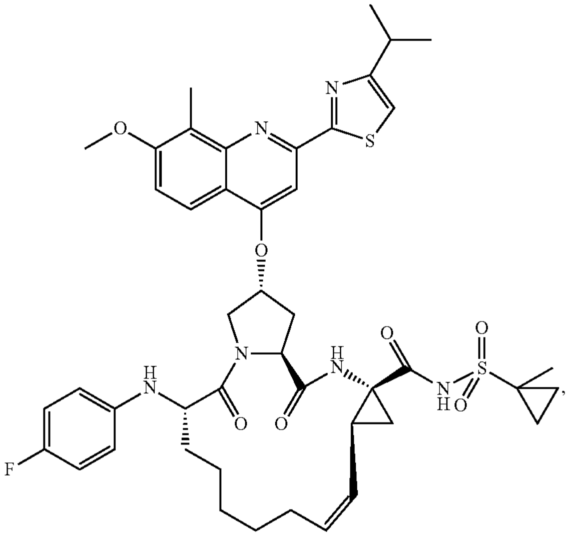
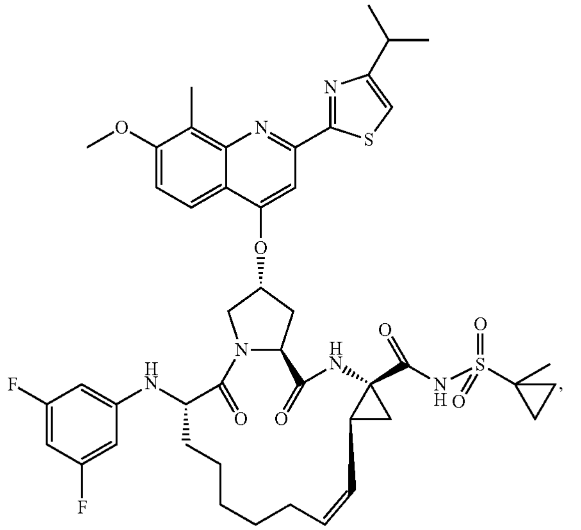
-continued
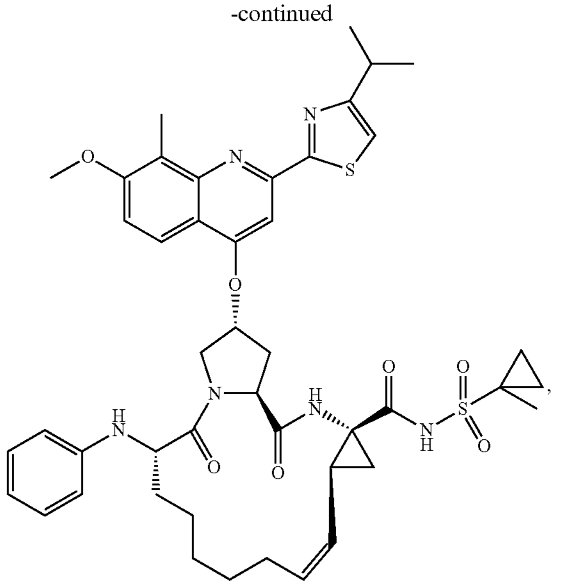
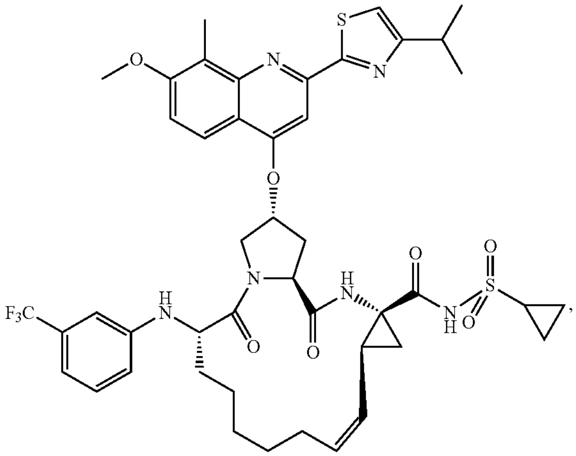
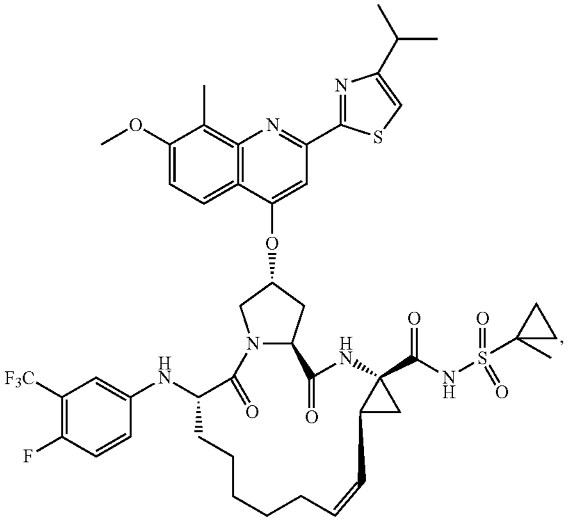

-continued
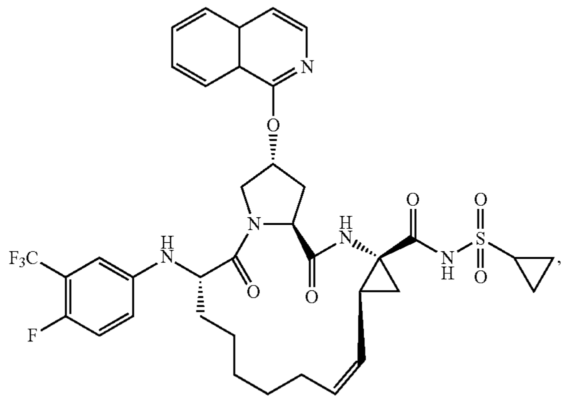
,
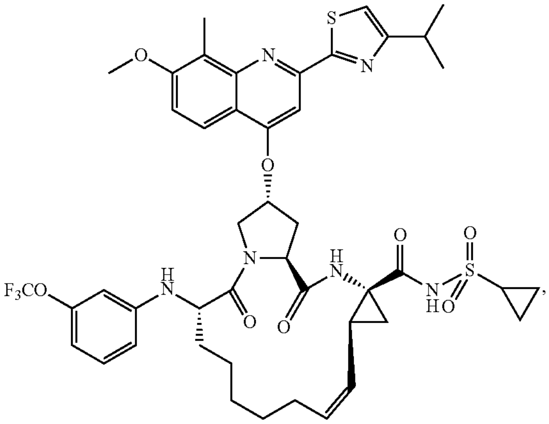
,
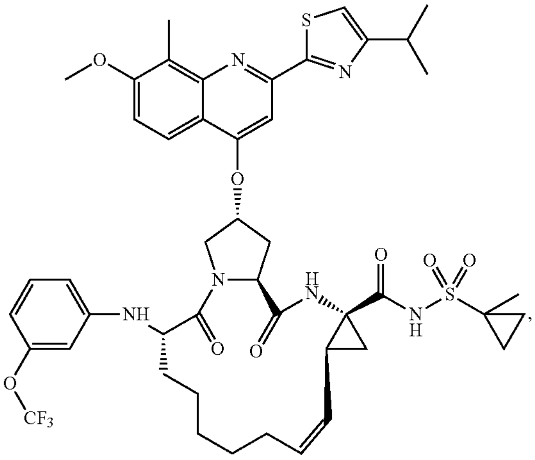
,
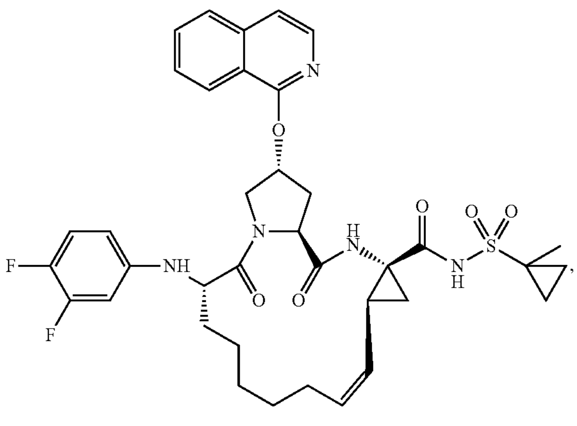
,
-continued
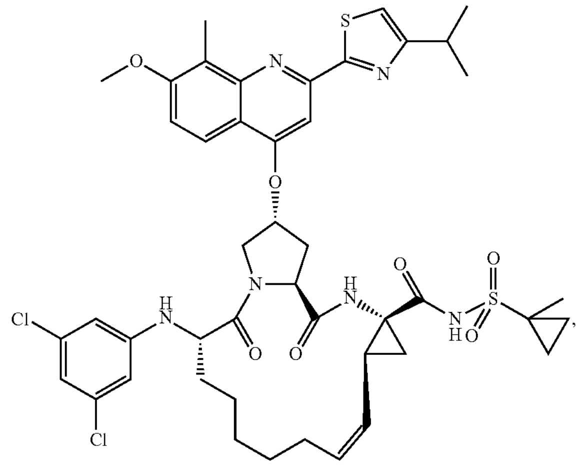
,
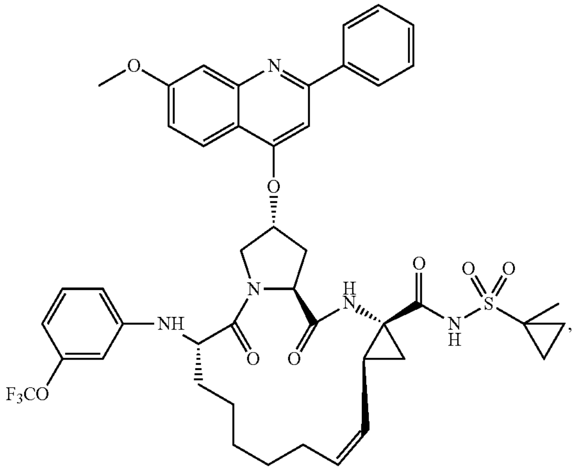
,
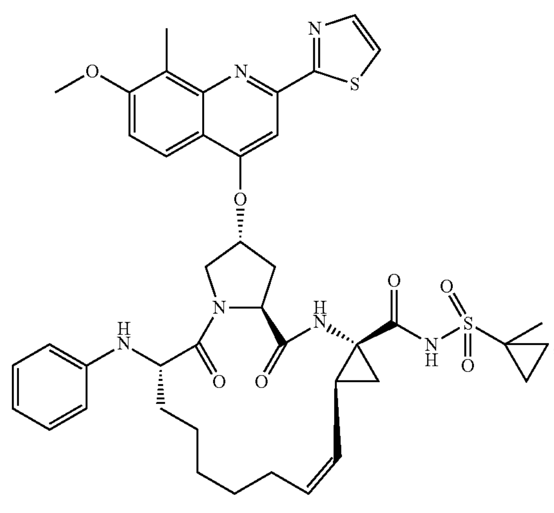
, -continued
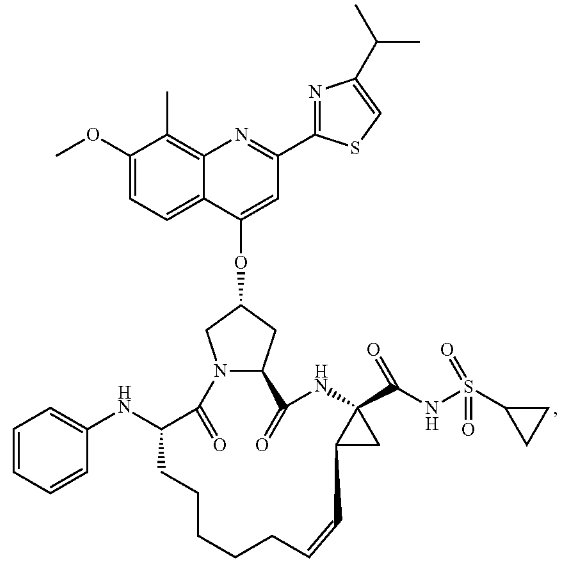
,
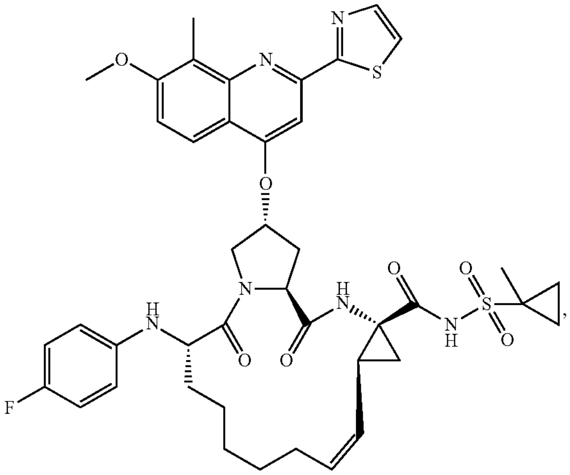
,
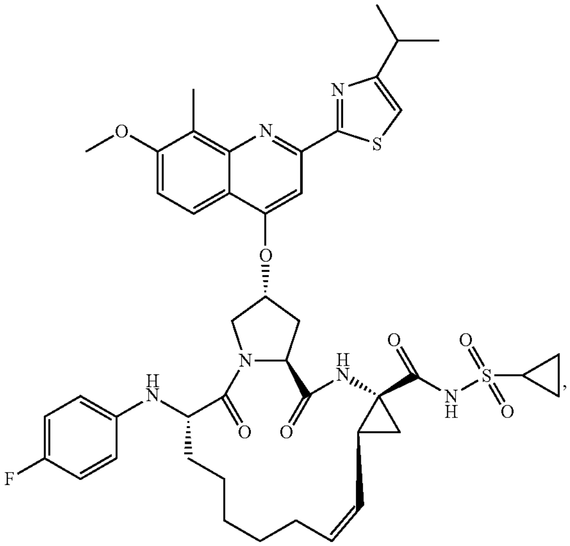
,
-continued
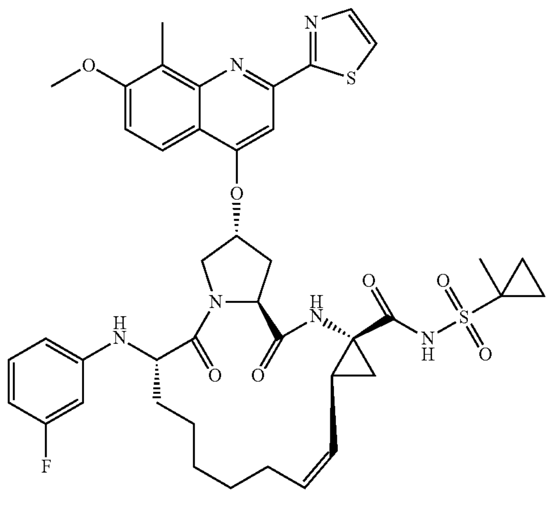
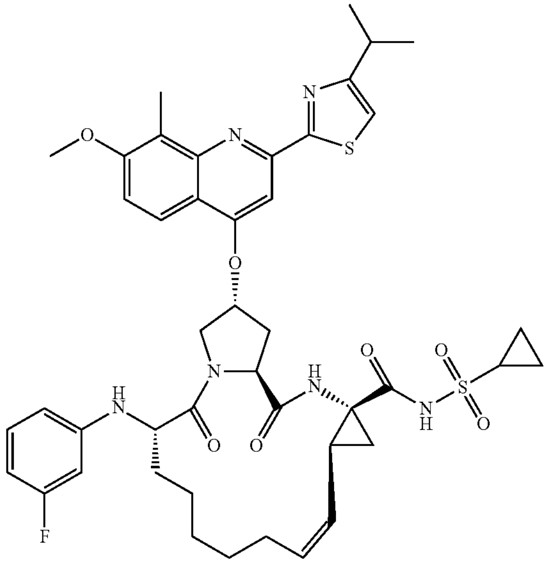
,
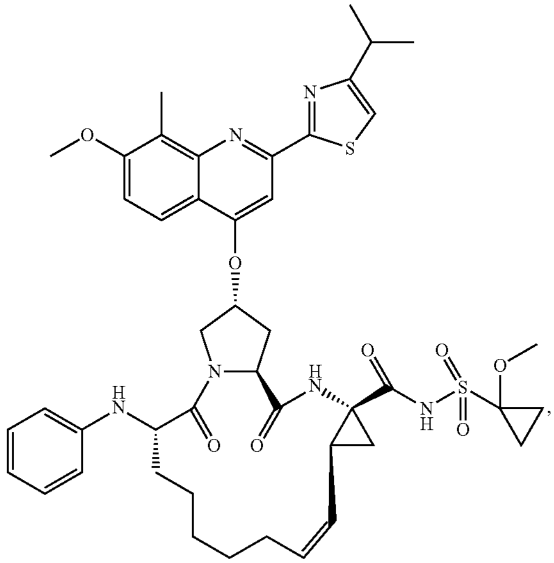
, -continued
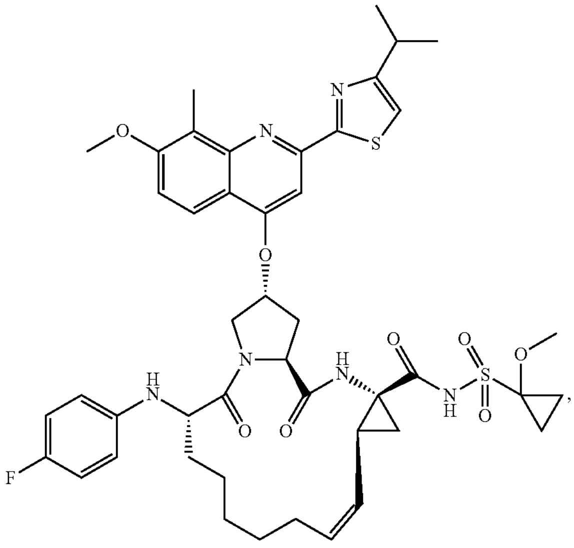
,
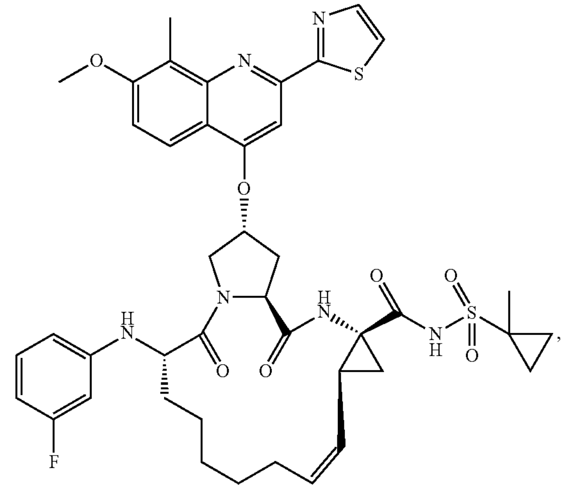
,
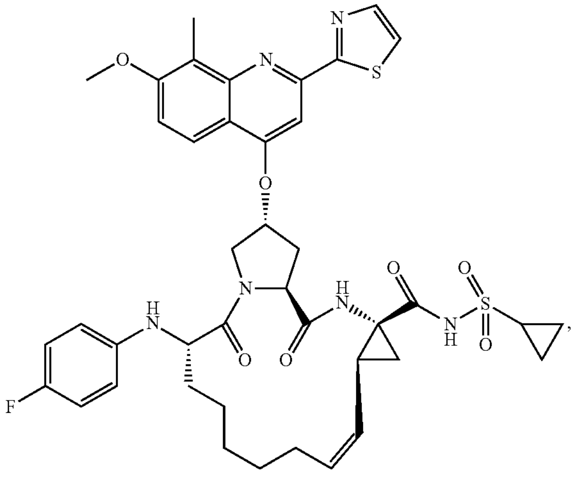
,
-continued
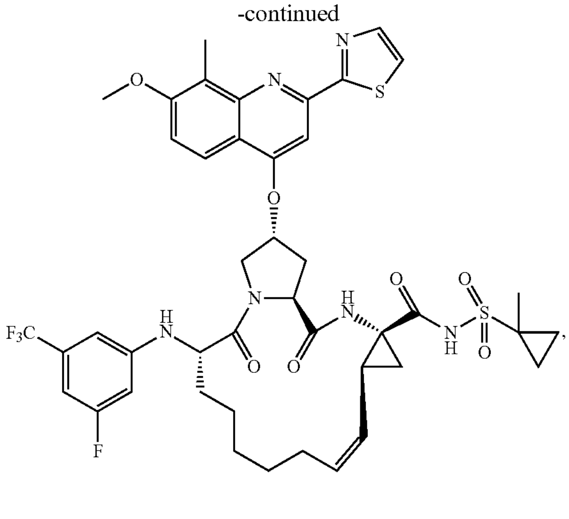
,
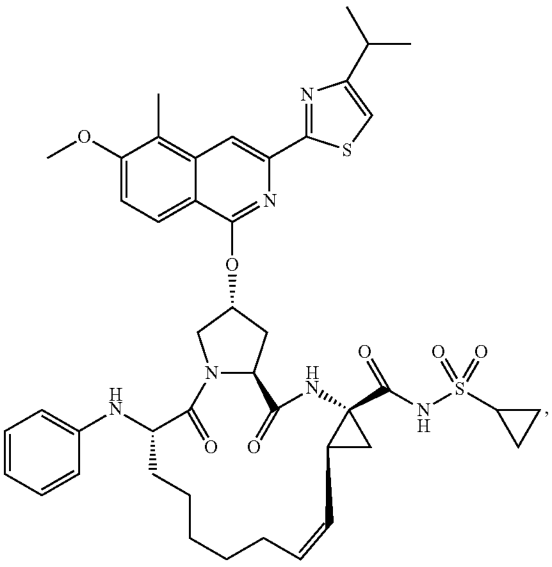
,
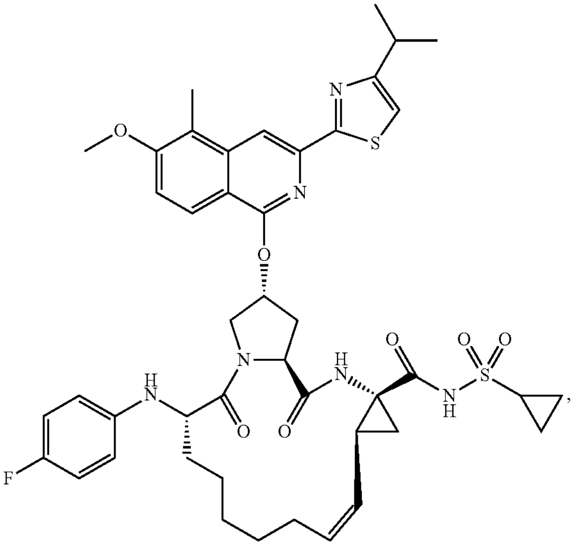
, -continued
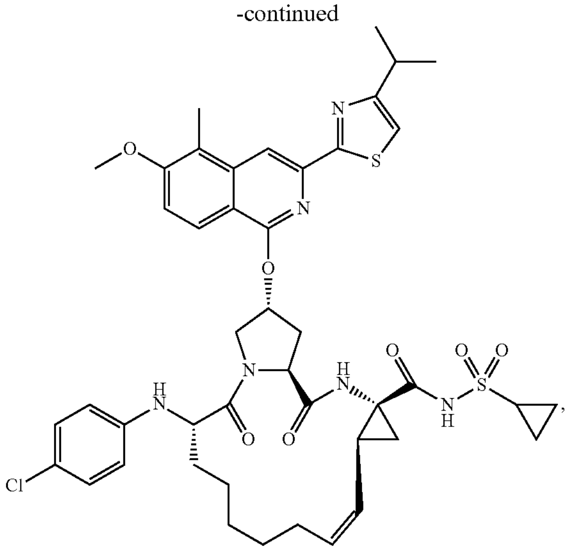
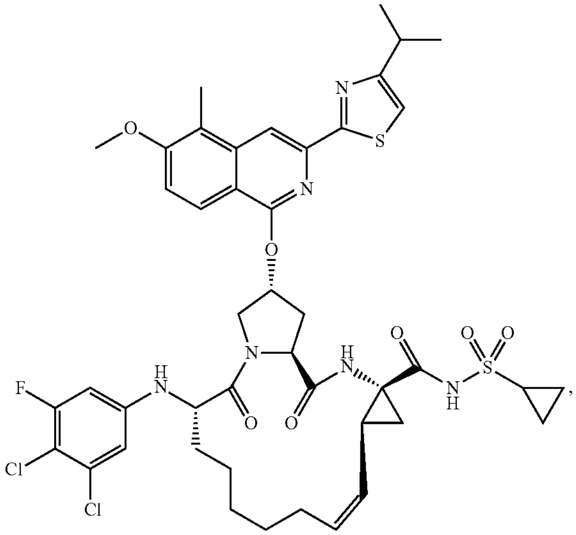
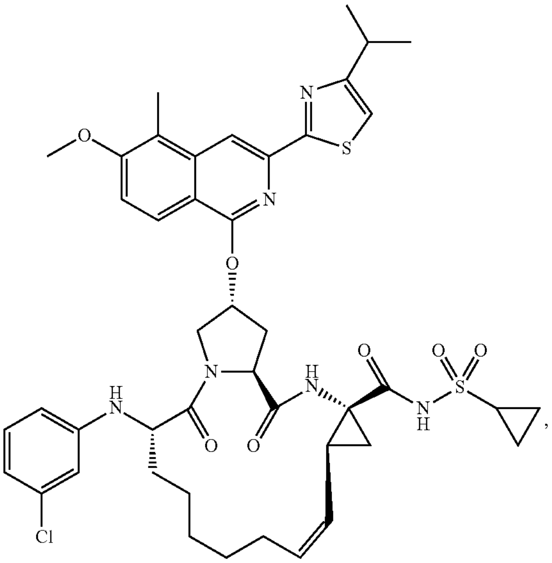
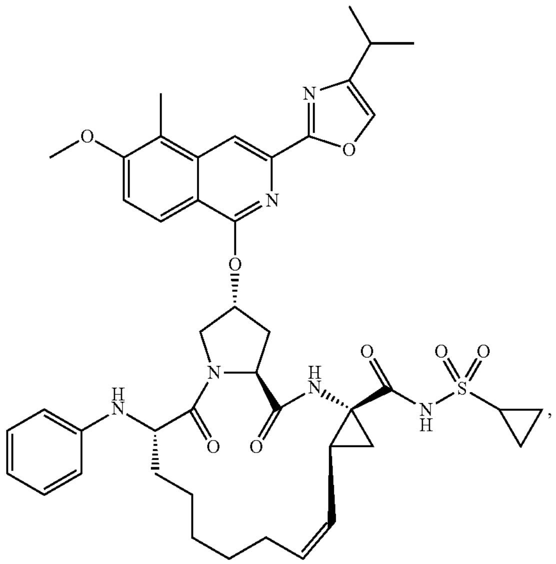
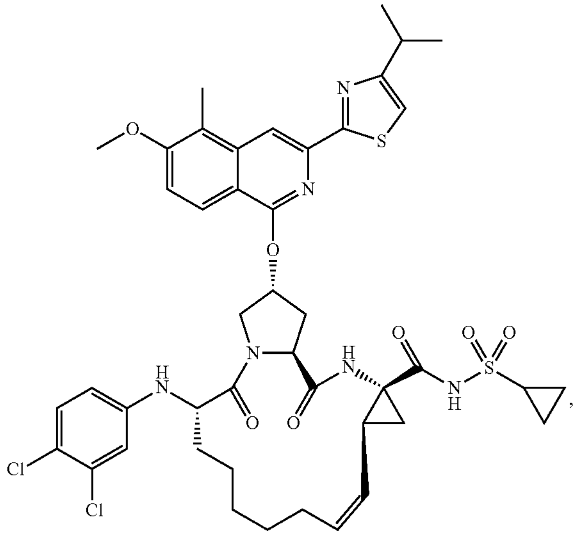
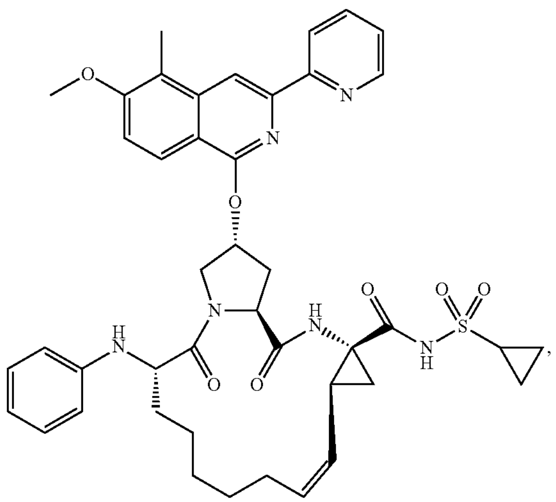

-continued
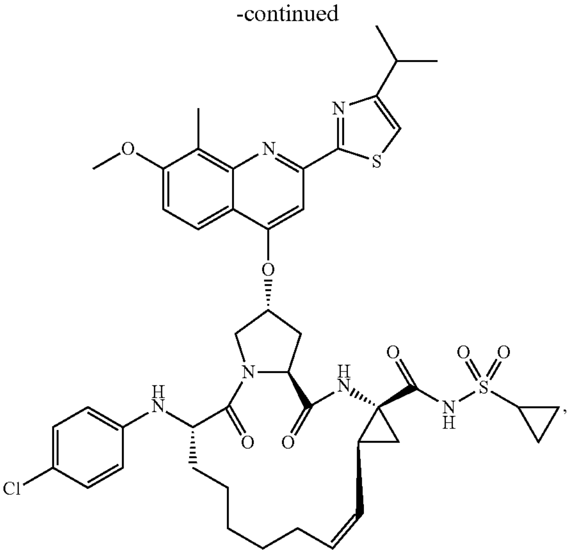
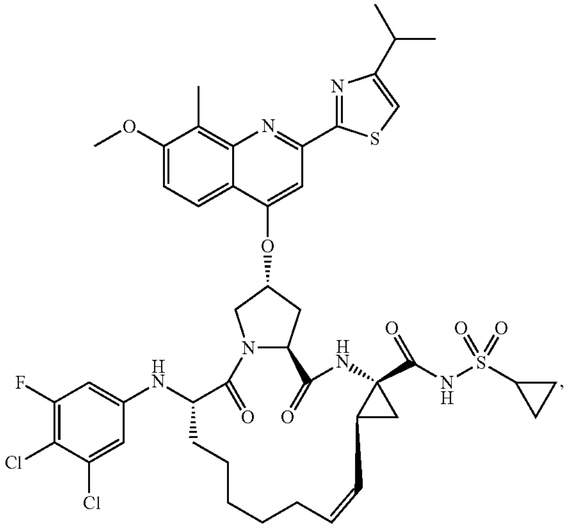
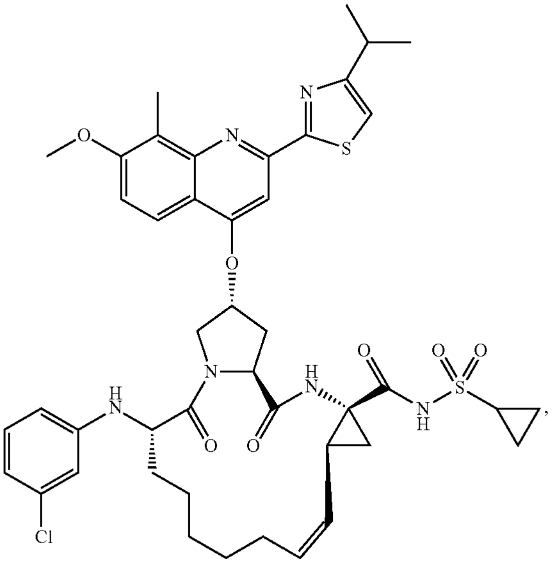
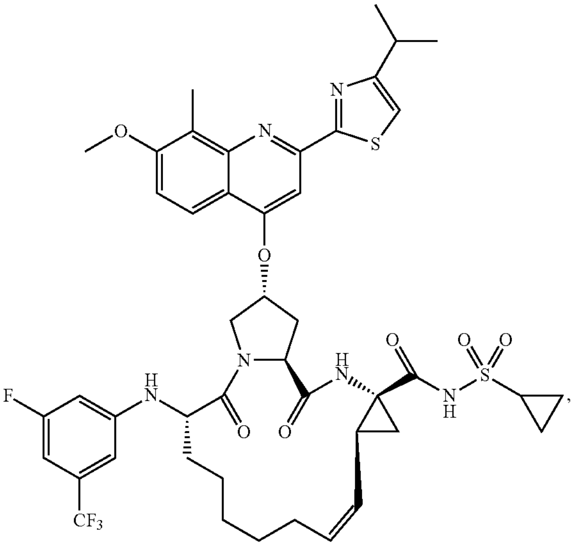
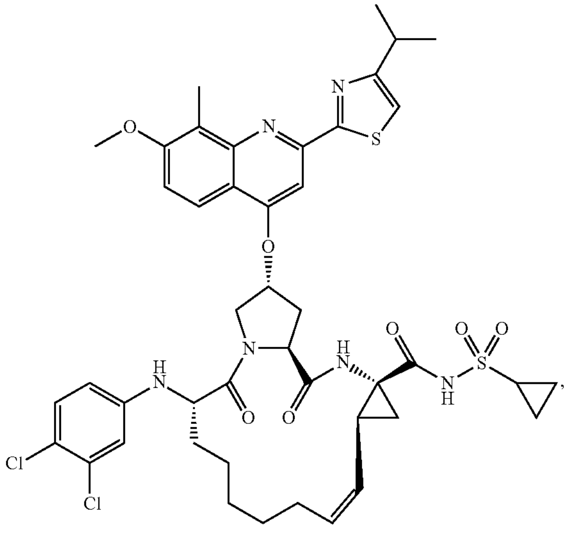
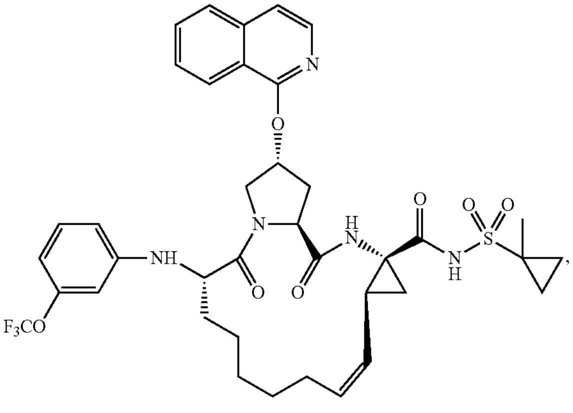

-continued
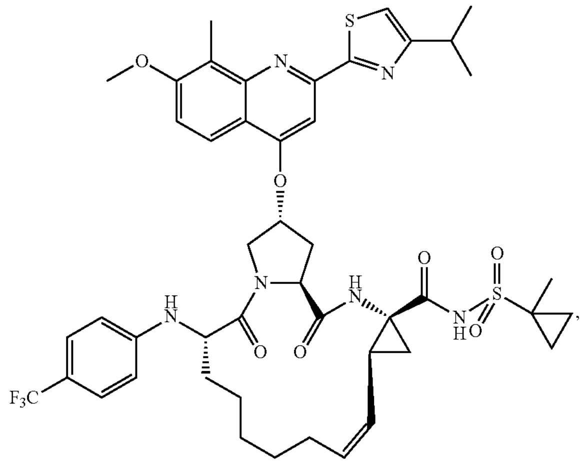
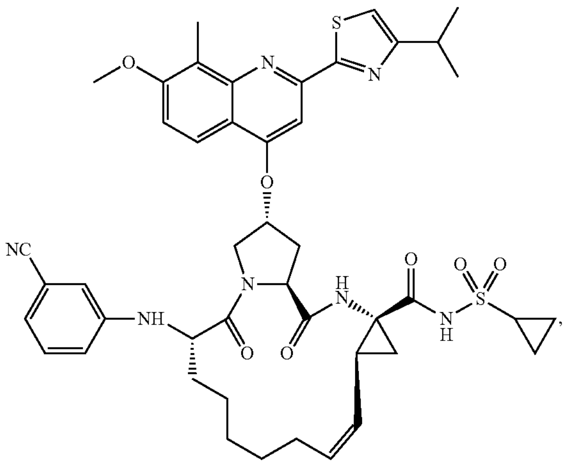
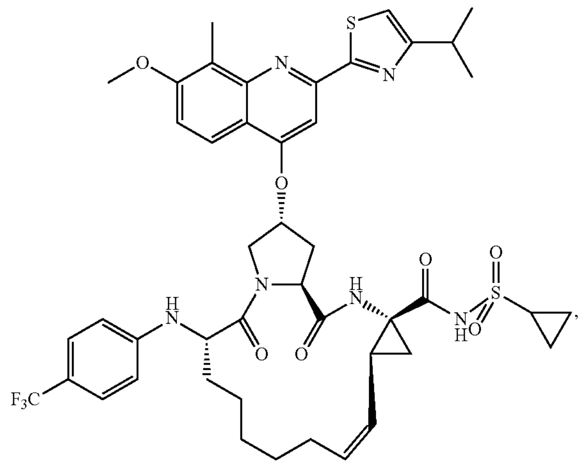
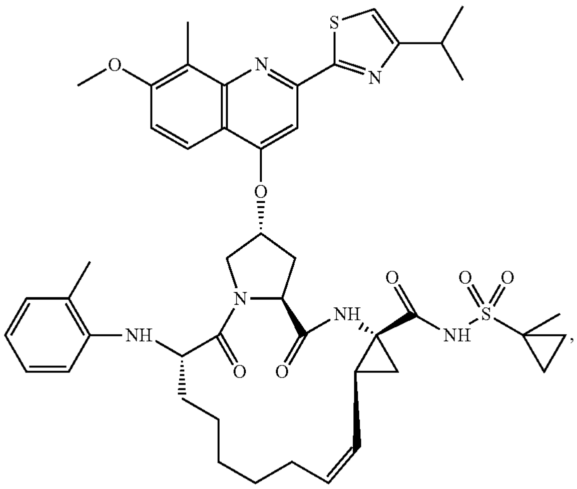
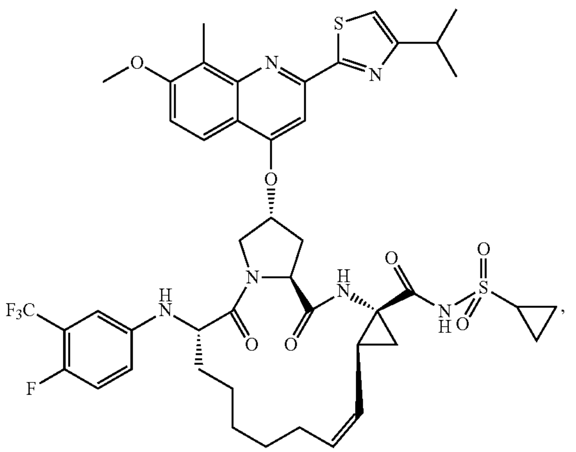
-continued
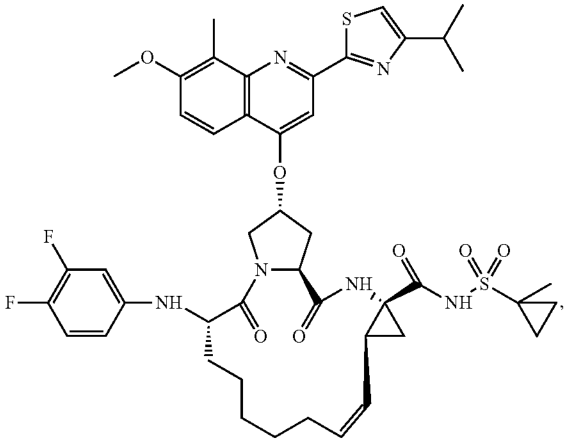

-continued
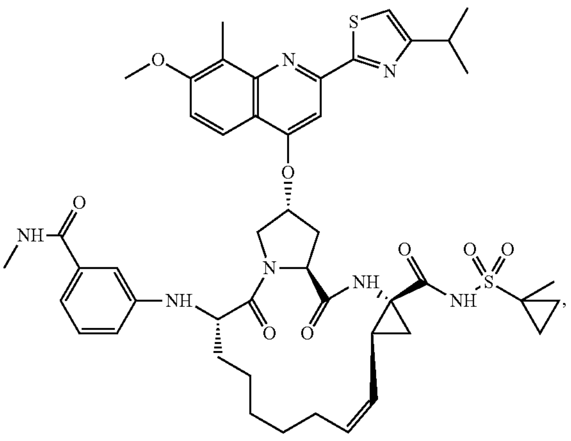
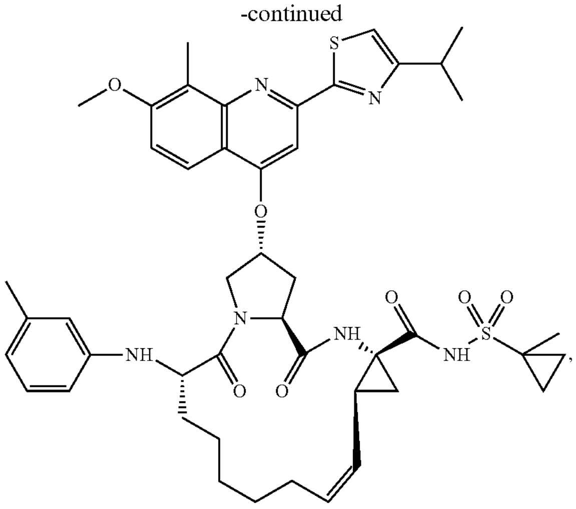
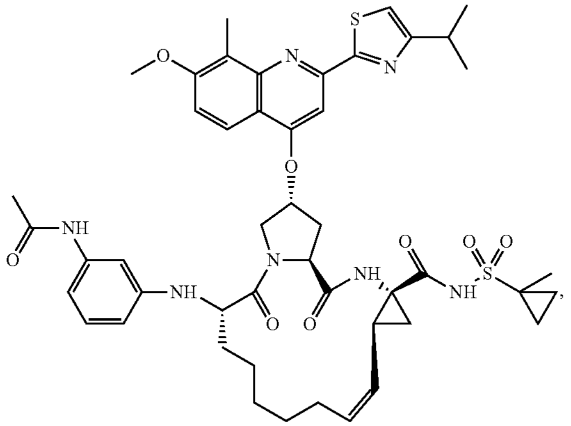
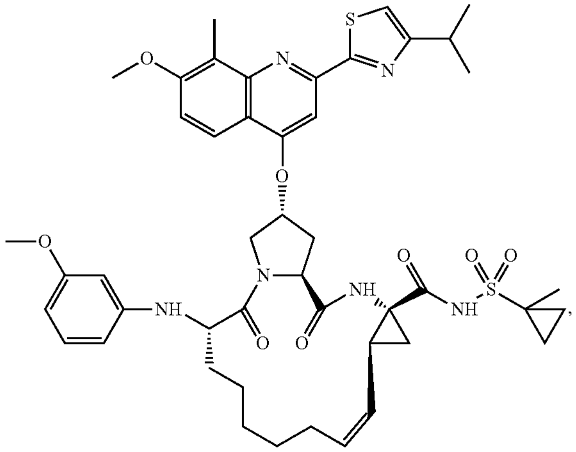
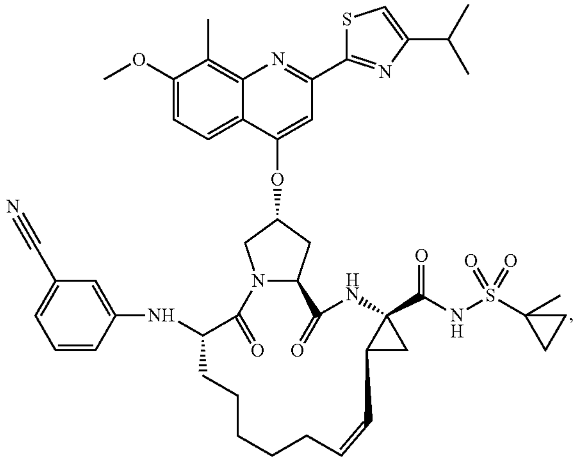
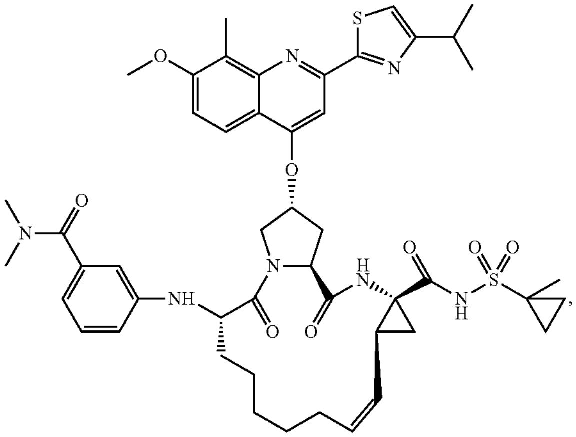

-continued
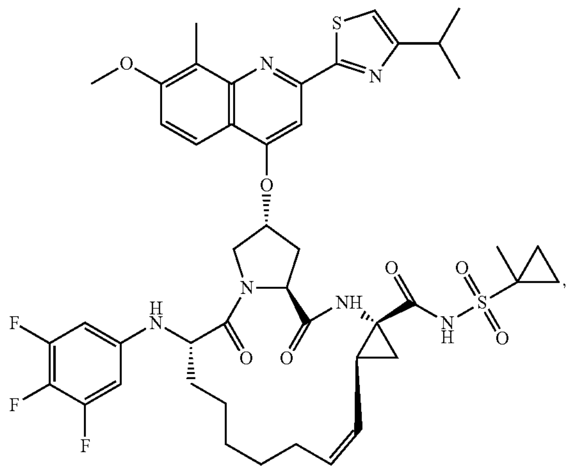
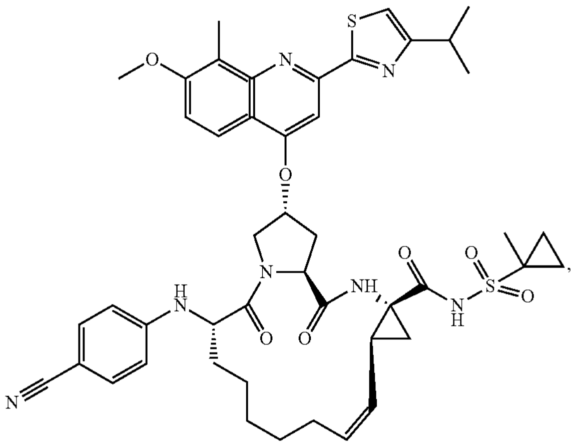
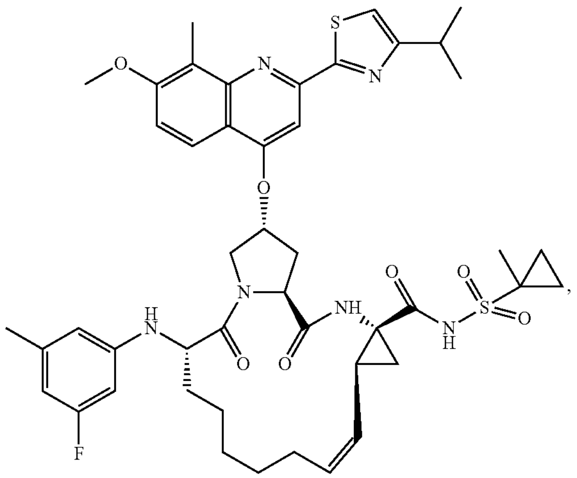
-continued
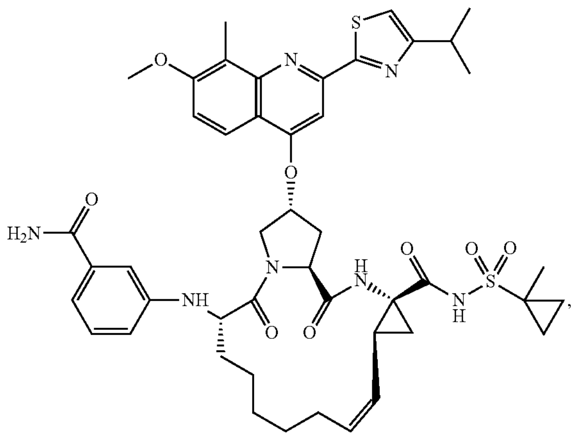
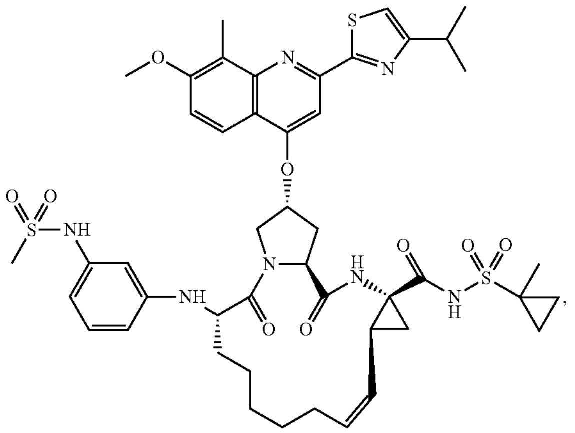
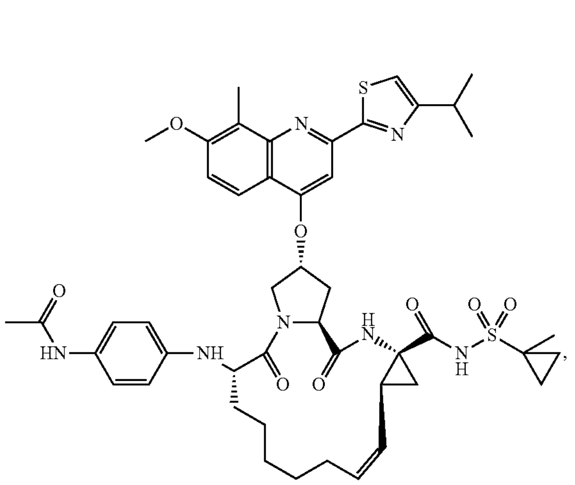

-continued
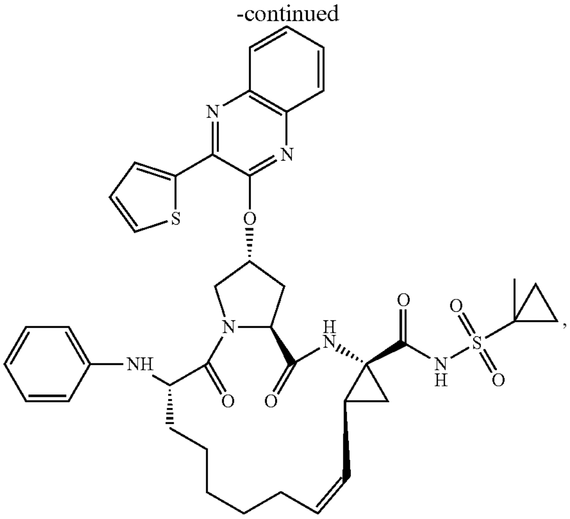,
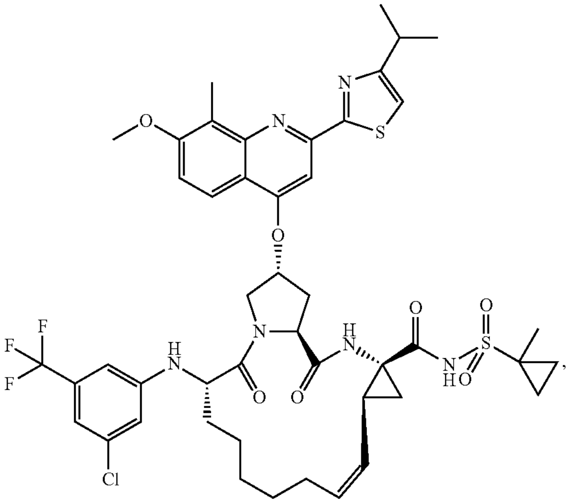,
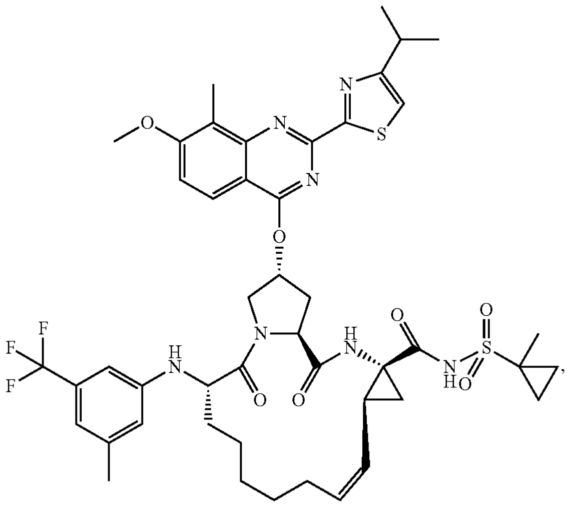,
-continued
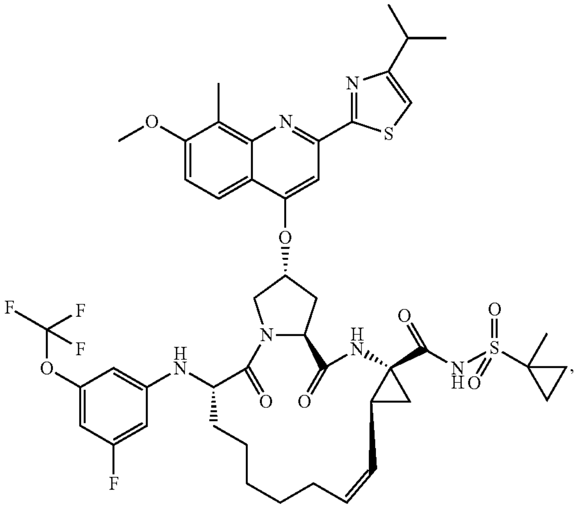,
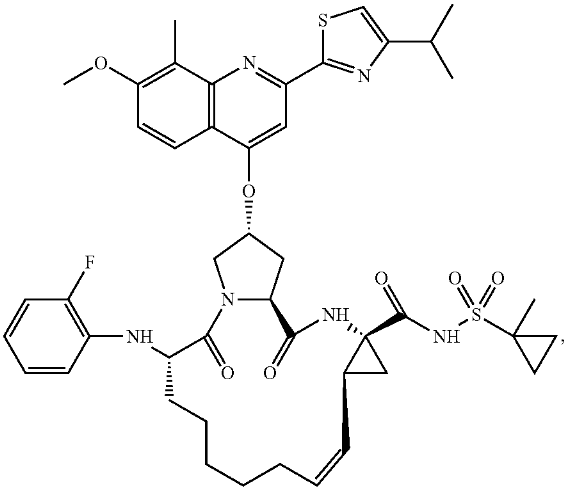,
and pharmaceutically acceptable salts of the foregoing.
23. A pharmaceutical composition comprising a pharmaceutically acceptable excipient and a compound of claim 14 or pharmaceutically acceptable salt thereof. ,
24. A compound of the following formula:
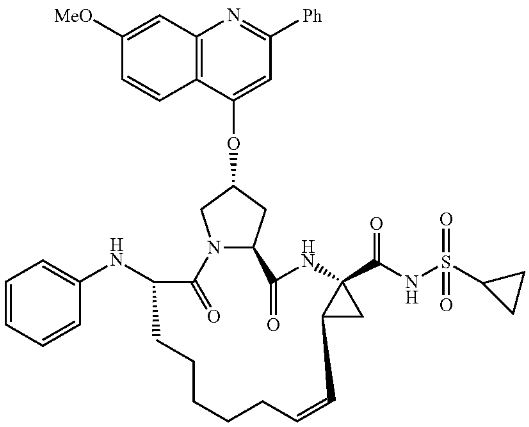
or a pharmaceutically acceptable salt thereof.

25. A compound of the following formula:

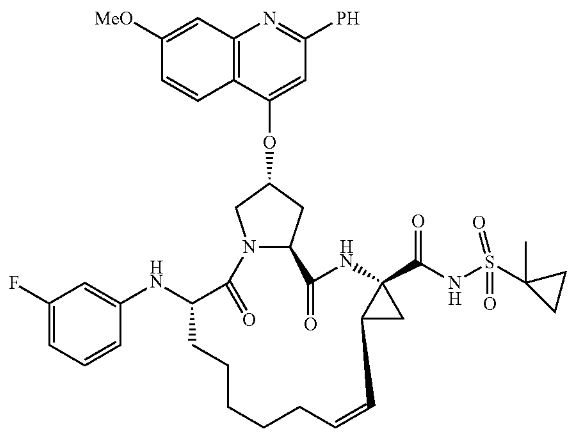

or pharmaceutically acceptable salt thereof.

26. The compound of claim 14, of the following formula:

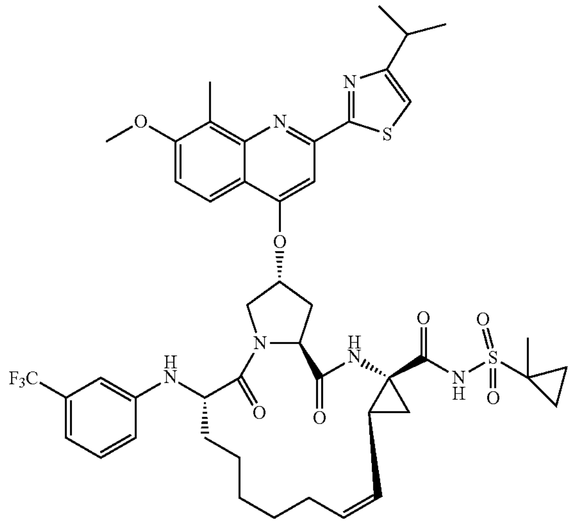

or pharmaceutically acceptable salt thereof.

27. A compound of the following formula:

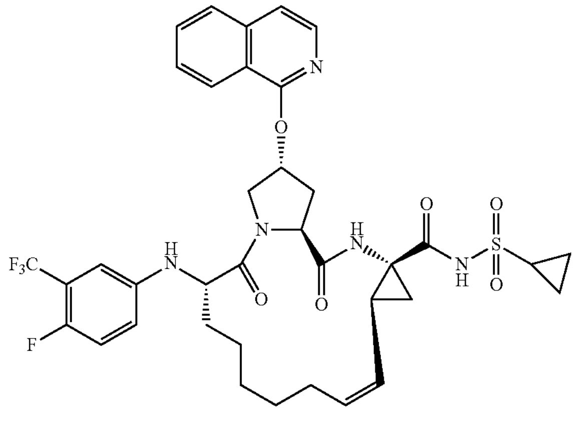

or a pharmaceutically acceptable salt thereof.

28. A compound of the following formula:

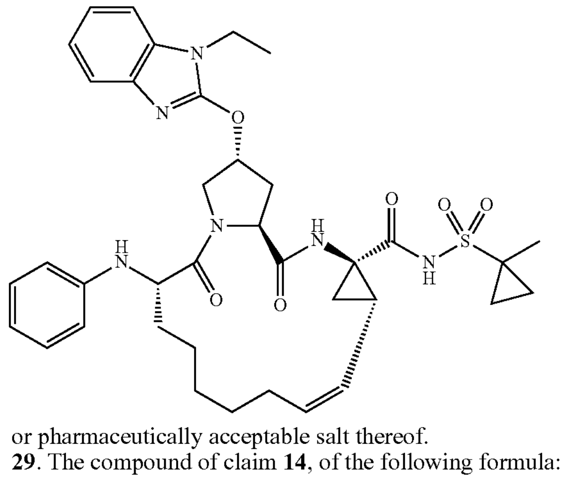

or pharmaceutically acceptable salt thereof.

29. The compound of claim 14, of the following formula:

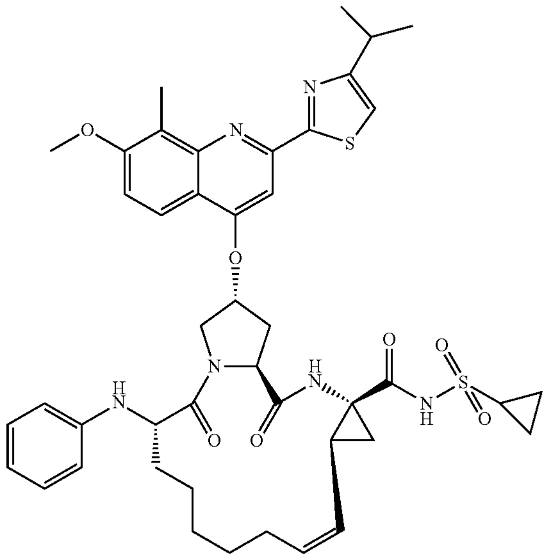

or pharmaceutically acceptable salt thereof.

30. The compound of claim 14, of the following formula:

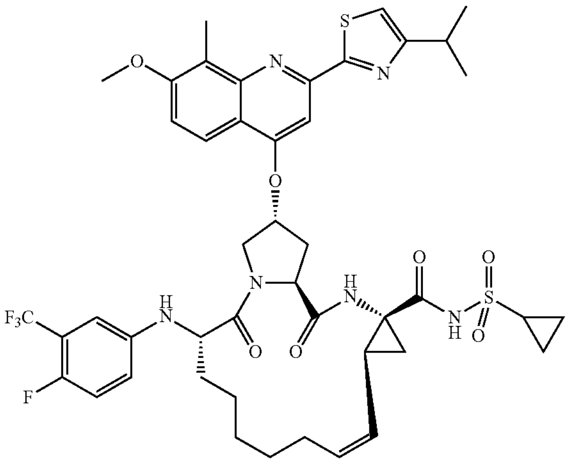

or pharmaceutically acceptable salt thereof.

31. The compound of claim 14, of the following formula:

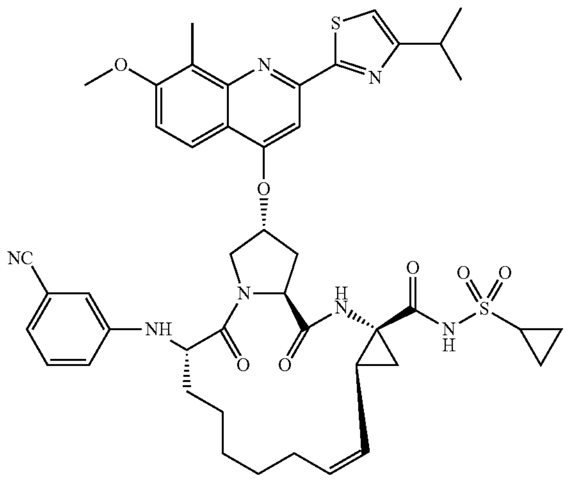

or pharmaceutically acceptable salt thereof.

32. A compound of the following formula:

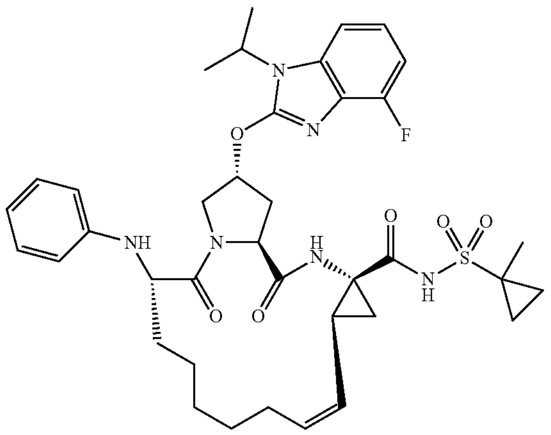

or pharmaceutically acceptable salt thereof.

33. The compound of claim 14, of the following formula:

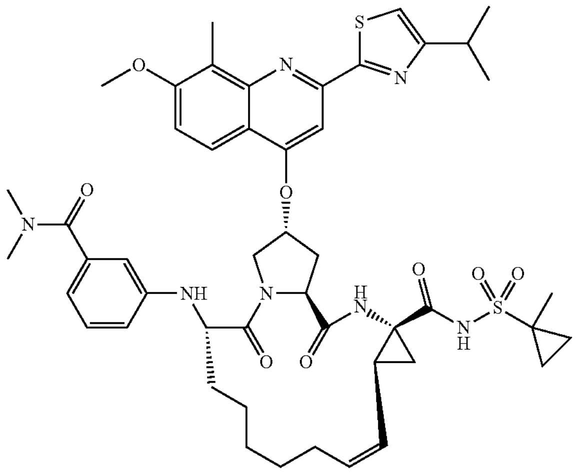

or pharmaceutically acceptable salt thereof.

34. A compound of the following formula:

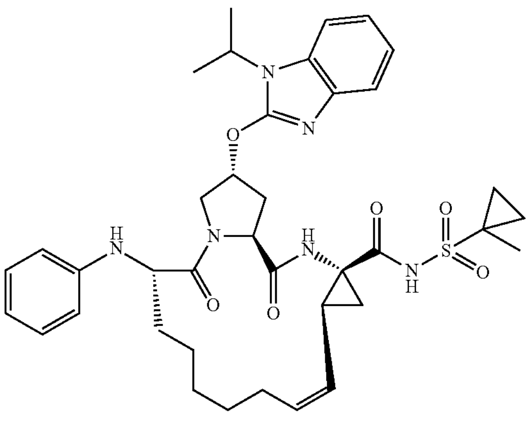

or pharmaceutically acceptable salt thereof.

35. A compound of the following formula:

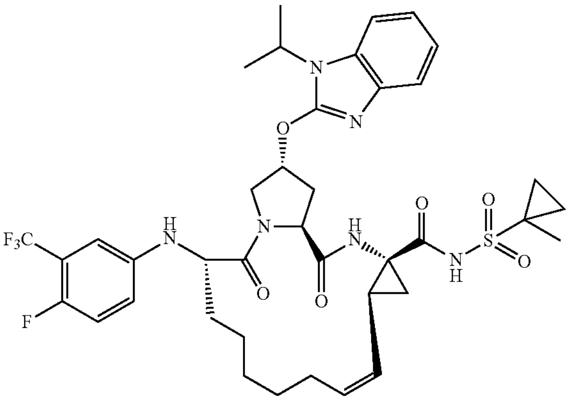

or pharmaceutically acceptable salt thereof.

36. A compound of the following formula:

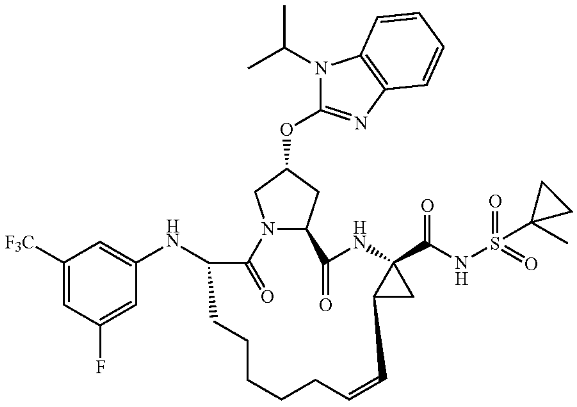

or pharmaceutically acceptable salt thereof.

37. A compound of the following formula:

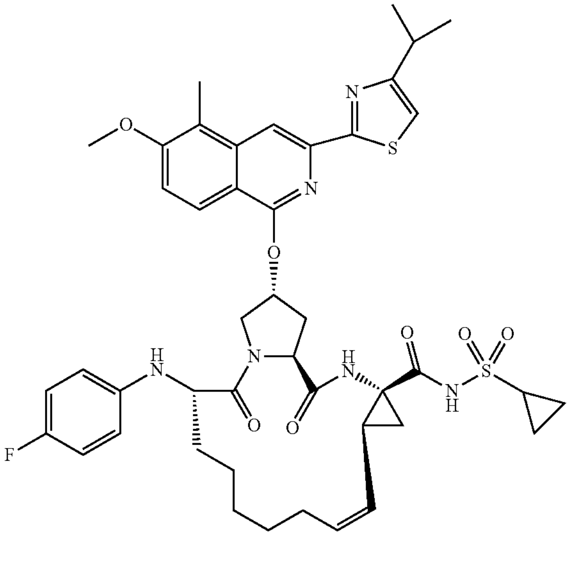

or pharmaceutically acceptable salt thereof.

38. A compound of the following formula:

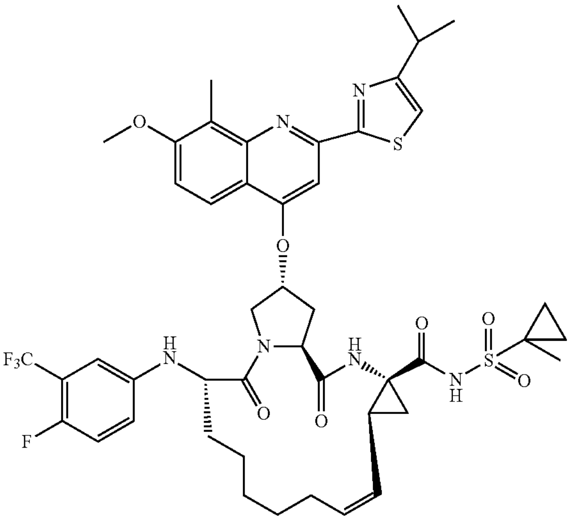

or pharmaceutically acceptable salt thereof.

39. A compound of the following formula:

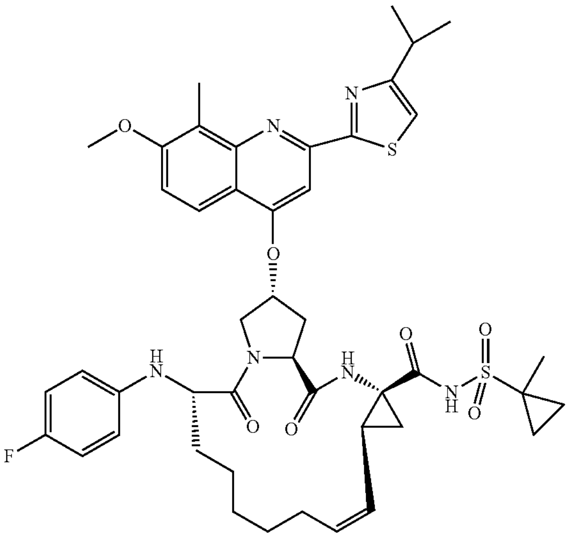

or pharmaceutically acceptable salt thereof.

40. A pharmaceutical composition comprising a pharmaceutically acceptable excipient and a compound of claim 1 or pharmaceutically acceptable salt thereof.

* * * * *